US012790385B2

(12) United States Patent
Wong

(10) Patent No.: US 12,790,385 B2
(45) Date of Patent: Nov. 10, 2026

(54) METHODS FOR STIMULATING PROLIFERATION OR DIFFERENTIATION OF AN IMMUNE CELL WITH A MULTI-CHAIN CHIMERIC POLYPEPTIDE

(71) Applicant: ImmunityBio, Inc., San Diego, CA (US)

(72) Inventor: Hing Wong, Miramar, FL (US)

(73) Assignee: ImmunityBio, Inc., San Diego, CA (US)

( * ) Notice: Subject to any disclaimer, the term of this patent is extended or adjusted under 35 U.S.C. 154(b) by 705 days.

(21) Appl. No.: 18/345,670

(22) Filed: Jun. 30, 2023

(65) Prior Publication Data

US 2023/0398151 A1 Dec. 14, 2023

Related U.S. Application Data

(62) Division of application No. 16/557,822, filed on Aug. 30, 2019, now Pat. No. 11,730,762.

(60) Provisional application No. 62/881,088, filed on Jul. 31, 2019, provisional application No. 62/881,039, filed on Jul. 31, 2019, provisional application No. 62/817,244, filed on Mar. 12, 2019, provisional application No. 62/817,230, filed on Mar. 12, 2019, provisional application No. 62/817,241, filed on Mar. 12, 2019, provisional application No. 62/816,683, filed on Mar. 11, 2019, provisional application No. 62/749,506, filed on Oct. 23, 2018, provisional application No. 62/749,007, filed on Oct. 22, 2018, provisional application No. 62/746,832, filed on Oct. 17, 2018, provisional application No. 62/724,969, filed on Aug. 30, 2018, provisional application No. 62/725,010, filed on Aug. 30, 2018, provisional application No. 62/725,038, filed on Aug. 30, 2018, provisional application No. 62/725,043, filed on Aug. 30, 2018.

(51) Int. Cl.

| | |
|---|---|
| ***A61K 40/11*** | (2025.01) |
| ***A61K 40/10*** | (2025.01) |
| ***A61K 40/15*** | (2025.01) |
| ***A61K 40/42*** | (2025.01) |
| ***C07K 14/705*** | (2006.01) |
| ***C07K 14/715*** | (2006.01) |
| ***C07K 16/22*** | (2006.01) |
| ***C07K 16/24*** | (2006.01) |
| ***C07K 16/28*** | (2006.01) |
| ***C07K 16/46*** | (2006.01) |

(52) U.S. Cl.

CPC .......... *C07K 14/7155* (2013.01); *A61K 40/10* (2025.01); *A61K 40/15* (2025.01); *A61K 40/4229* (2025.01); *C07K 14/70503* (2013.01); *C07K 16/22* (2013.01); *C07K 16/244* (2013.01); *C07K 16/2863* (2013.01); *C07K 16/468* (2013.01); *A61K 2239/31* (2023.05); *A61K 2239/48* (2023.05); *A61K 2239/57* (2023.05); *C07K 2317/24* (2013.01); *C07K 2317/52* (2013.01); *C07K 2317/569* (2013.01); *C07K 2317/622* (2013.01)

(58) Field of Classification Search

None

See application file for complete search history.

(56) References Cited

U.S. PATENT DOCUMENTS

| | | | |
|---|---|---|---|
| 6,117,980 | A | 9/2000 | Gonzalez et al. |
| 7,452,537 | B2 | 11/2008 | Bauer et al. |
| 7,482,436 | B2 | 1/2009 | Sugimura et al. |
| 7,488,802 | B2 | 2/2009 | Collins et al. |
| 7,521,051 | B2 | 4/2009 | Collins et al. |
| 7,612,181 | B2 | 11/2009 | Wu et al. |
| 7,691,380 | B2 | 4/2010 | Thorpe et al. |
| 7,723,482 | B2 | 5/2010 | Soulillou et al. |
| 7,968,094 | B2 | 6/2011 | Jiao et al. |
| 8,007,795 | B2 | 8/2011 | Jiao et al. |
| 8,133,485 | B2 | 3/2012 | Levi-Schaffer et al. |
| 8,217,149 | B2 | 7/2012 | Irving et al. |
| 8,258,268 | B2 | 9/2012 | Wu et al. |
| 8,475,792 | B2 | 7/2013 | Dall'Acqua et al. |
| 8,552,156 | B2 | 10/2013 | Takayanagi et al. |
| 8,586,714 | B2 | 11/2013 | Ghayur et al. |
| 8,716,450 | B2 | 5/2014 | Ghayur et al. |
| 8,722,855 | B2 | 5/2014 | Ghayur et al. |
| 8,735,546 | B2 | 5/2014 | Ghayur et al. |

(Continued)

FOREIGN PATENT DOCUMENTS

| | | |
|---|---|---|
| CN | 1844150 | 10/2006 |
| CN | 101653603 | 2/2010 |

(Continued)

OTHER PUBLICATIONS

Wells (1990). Biochemistry 29:8509-8517.*
Ngo et al. (1994). The Protein Folding Problem and Tertiary Structure Prediction, pp. 492-495.*
Skolnick et al.(2000). Trends in Biotech. 18(1):34-39.*
[No Author Listed], "CN Br-activated Sepharose 4 Fast Flow," 1999, Affinity Chromatography, 4 pages.

(Continued)

*Primary Examiner* — Christine J Saoud
*Assistant Examiner* — Jon M Lockard
(74) *Attorney, Agent, or Firm* — Sheridan Ross P.C.

(57) ABSTRACT

The present disclosure relates to the field of biotechnology, and more specifically, to single-chain and multi-chain chimeric polypeptides having a linker domain positioned between two target-binding domains that are useful for a variety of applications including, without limitation, stimulating an immune cell, inducing or increasing proliferation of an immune cell, inducing differentiation of an immune cell, or treating a subject in need thereof (e.g., a subject having cancer or an aging-related disease or condition).

40 Claims, 123 Drawing Sheets

Specification includes a Sequence Listing.

(56) References Cited

U.S. PATENT DOCUMENTS

| | | | |
|---|---|---|---|
| 8,741,604 | B2 | 6/2014 | Campbell et al. |
| 8,753,640 | B2 | 6/2014 | Wu et al. |
| 8,759,494 | B2 | 6/2014 | Bachmann et al. |
| 8,822,645 | B2 | 9/2014 | Ghayur et al. |
| 9,035,026 | B2 | 5/2015 | Hoffmann et al. |
| 9,067,997 | B2 | 6/2015 | Romagne et al. |
| 9,085,623 | B2 | 7/2015 | Rother et al. |
| 9,090,684 | B2 | 7/2015 | Borras et al. |
| 9,226,962 | B2 | 1/2016 | Le Gall et al. |
| 9,238,084 | B2 | 1/2016 | Liu et al. |
| 9,273,136 | B2 | 3/2016 | Rader et al. |
| 9,371,395 | B2 | 6/2016 | Takahashi et al. |
| 9,441,034 | B2 | 9/2016 | Sivakumar et al. |
| 9,505,843 | B2 | 11/2016 | Kim et al. |
| 9,617,345 | B2 | 4/2017 | Berne et al. |
| 9,701,758 | B2 | 7/2017 | Cooper et al. |
| 11,401,324 | B2 | 8/2022 | Wong |
| 11,518,792 | B2 | 12/2022 | Wong |
| 11,672,826 | B2 | 6/2023 | Wong |
| 11,730,762 | B2 | 8/2023 | Wong |
| 11,738,052 | B2 | 8/2023 | Wong |
| 12,018,071 | B2 | 6/2024 | Wong |
| 12,024,545 | B2 | 7/2024 | Wong et al. |
| 12,516,112 | B2 | 1/2026 | Wong |
| 2001/0044427 | A1 | 11/2001 | Mazel et al. |
| 2003/0124678 | A1 | 7/2003 | Epstein et al. |
| 2003/0219441 | A1 | 11/2003 | Thorpe et al. |
| 2005/0014224 | A1 | 1/2005 | Collins et al. |
| 2006/0159655 | A1 | 7/2006 | Collins et al. |
| 2007/0160579 | A1 | 7/2007 | Schmitz et al. |
| 2008/0025979 | A1 | 1/2008 | Honjo et al. |
| 2009/0148942 | A1 | 6/2009 | McDonagh et al. |
| 2012/0171197 | A1 | 7/2012 | Eriksson et al. |
| 2012/0264920 | A1 | 10/2012 | Wang et al. |
| 2013/0274446 | A1 | 10/2013 | Kumagai et al. |
| 2014/0242077 | A1 | 8/2014 | Choi |
| 2015/0218274 | A1 | 8/2015 | Sabatos-Peyton et al. |
| 2015/0259429 | A1 | 9/2015 | Benaroch et al. |
| 2016/0175397 | A1 | 6/2016 | Umana et al. |
| 2016/0340413 | A1 | 11/2016 | Duerner et al. |
| 2016/0367664 | A1 | 12/2016 | Wang et al. |
| 2017/0051063 | A1 | 2/2017 | Baum et al. |
| 2017/0198042 | A1 | 7/2017 | Williams et al. |
| 2017/0283499 | A1 | 10/2017 | Delhem et al. |
| 2018/0200366 | A1 | 7/2018 | Wong |
| 2019/0078082 | A1 | 3/2019 | Amorese et al. |
| 2019/0092846 | A1 | 3/2019 | Ibebunjo et al. |
| 2019/0177406 | A1 | 6/2019 | Ledbetter et al. |
| 2019/0315850 | A1 | 10/2019 | Bedinger et al. |
| 2020/0071374 | A1 | 3/2020 | Wong |
| 2020/0123607 | A1 | 4/2020 | Serrano Marugan et al. |
| 2020/0190174 | A1 | 6/2020 | Wong |
| 2020/0392221 | A1 | 12/2020 | Van Snick et al. |
| 2020/0399358 | A1 | 12/2020 | Shapiro et al. |
| 2021/0060064 | A1 | 3/2021 | Wong |
| 2021/0061897 | A1 | 3/2021 | Ledbetter et al. |
| 2021/0070825 | A1 | 3/2021 | Wong |
| 2021/0070826 | A1 | 3/2021 | Wong |
| 2021/0100840 | A1 | 4/2021 | Wong et al. |
| 2021/0137981 | A1 | 5/2021 | Wong |
| 2021/0268022 | A1 | 9/2021 | Wong et al. |
| 2021/0277054 | A1 | 9/2021 | Wong et al. |
| 2021/0338724 | A1 | 11/2021 | Wong |
| 2021/0355204 | A1 | 11/2021 | Bedinger et al. |
| 2021/0403545 | A1 | 12/2021 | Van Snick et al. |
| 2022/0073578 | A1 | 3/2022 | Wong et al. |
| 2023/0023389 | A1 | 1/2023 | Wong |
| 2023/0039157 | A1 | 2/2023 | Wong |
| 2023/0128292 | A1 | 4/2023 | Wong |
| 2023/0174666 | A1 | 6/2023 | Wong et al. |
| 2023/0272027 | A1 | 8/2023 | Wong |
| 2023/0372399 | A1 | 11/2023 | Wong |
| 2023/0372444 | A1 | 11/2023 | Wong et al. |
| 2023/0381238 | A1 | 11/2023 | Wong |
| 2023/0398151 | A1 | 12/2023 | Wong |
| 2024/0124543 | A1 | 4/2024 | Wong |
| 2024/0124544 | A1 | 4/2024 | Wong |
| 2024/0132561 | A1 | 4/2024 | Wong |
| 2025/0066500 | A1 | 2/2025 | Wong |

FOREIGN PATENT DOCUMENTS

| | | |
|---|---|---|
| CN | 101965364 | 2/2011 |
| CN | 102153653 | 8/2011 |
| CN | 106255703 | 12/2016 |
| CN | 109513003 | 3/2019 |
| EP | 1245676 | 10/2002 |
| EP | 1719528 | 11/2006 |
| EP | 2537933 | 12/2012 |
| EP | 3029069 | 6/2016 |
| EP | 3348276 | 7/2018 |
| JP | 2005-124568 | 5/2005 |
| JP | 2008-536487 | 9/2008 |
| JP | 2009-512433 | 3/2009 |
| JP | 4361133 | 8/2009 |
| KR | 2016/0127688 | 11/2016 |
| KR | 101778439 | 9/2017 |
| WO | WO 1995/015341 | 6/1995 |
| WO | WO 1996/001653 | 1/1996 |
| WO | WO 2001/083755 | 11/2001 |
| WO | WO 2002/083152 | 10/2002 |
| WO | WO 2003/037911 | 5/2003 |
| WO | WO 2003/104425 | 12/2003 |
| WO | WO 2004/076488 | 9/2004 |
| WO | WO 2006/096828 | 9/2006 |
| WO | WO 2006/097743 | 9/2006 |
| WO | WO 2006/119897 | 11/2006 |
| WO | WO 2008/096158 | 8/2008 |
| WO | WO 2011/127324 | 10/2011 |
| WO | WO 2012/040323 | 3/2012 |
| WO | WO 2012/120125 | 9/2012 |
| WO | WO 2012/170470 | 12/2012 |
| WO | WO 2012/175222 | 12/2012 |
| WO | WO 2012/175692 | 12/2012 |
| WO | WO 2013/068946 | 5/2013 |
| WO | WO 2014/007513 | 1/2014 |
| WO | WO 2014/026054 | 2/2014 |
| WO | WO 2014/095808 | 6/2014 |
| WO | WO 2014/130635 | 8/2014 |
| WO | WO 2014/159531 | 10/2014 |
| WO | WO 2015/089881 | 6/2015 |
| WO | WO 2016/106221 | 6/2016 |
| WO | WO 2016/154585 | 9/2016 |
| WO | WO 2016/166348 | 10/2016 |
| WO | WO 2017/053748 | 3/2017 |
| WO | WO 2017/083612 | 5/2017 |
| WO | WO 2017/149538 | 9/2017 |
| WO | WO 2017/189526 | 11/2017 |
| WO | WO 2018/067825 | 4/2018 |
| WO | WO 2018/075989 | 4/2018 |
| WO | WO 2018/129007 | 7/2018 |
| WO | WO 2018/158350 | 9/2018 |
| WO | WO 2018/183169 | 10/2018 |
| WO | WO 2018/165208 | 12/2018 |
| WO | WO 2019/046313 | 3/2019 |
| WO | WO 2020/0047299 | 3/2020 |
| WO | WO 2020/047333 | 3/2020 |
| WO | WO 2020/047462 | 3/2020 |
| WO | WO 2020/047473 | 3/2020 |
| WO | WO 2021/163369 | 8/2021 |

OTHER PUBLICATIONS

Bartscht et al., "Dasatinib blocks transcriptional and promigratory responses to transforming growth factor-beta in pancreatic adenocarcinoma cells through inhibition of Smad signalling: implications for in vivo mode of action," Molecular Cancer, Dec. 2015, 14(199):1-12.

Bird et al., "TGFβ inhibition restores a regenerative response in acute liver injury by suppressing paracrine senescence," Science translational medicine, Aug. 15, 2018, 10(454):eaan 1230, 15 pages.

(56) References Cited

OTHER PUBLICATIONS

Brämer et al., "Membrane adsorber for the fast purification of a monoclonal antibody using protein a chromatography," Membranes, Nov. 27, 2019, 9(12):159, 15 pages.

Cai et al., "Quercetin inhibits transforming growth factor β1-induced epithelial-mesenchymal transition in human retinal pigment epithelial cells via the Smad pathway, " Drug design, development and therapy, Dec. 6, 2018, 12:4149-4161.

Chabannon et al., "Manufacturing natural killer cells as medicinal products," Frontiers in Immunology, Nov. 15, 2016, 7(504): 1-9.

Chen et al., "A novel idea for establishing Parkinson's disease mouse model by intranasal administration of paraquat" Neurological Research, 43(4):267-277, 2021.

Fernando et al., "Targeting tumor endothelial marker 8 in the tumor vasculature of colorectal carcinomas in mice, " Cancer research, Jun. 15, 2009, 69(12):5126-5132.

Guha et al., "Affinity purification of human tissue factor: interaction of factor VII and tissue factor in detergent micelles," Proceedings of the National Academy of Sciences, Jan. 1986, 83(2):299-302.

Hélie et al., "Application of the Protein Maker as a platform purification system for therapeutic antibody research and development," Computational and Structural Biotechnology Journal, Jan. 1, 2016, 14:238-244.

Igarashi et al., "VEGF-C and TGF-β reciprocally regulate mesenchymal stem cell commitment to differentiation into lymphatic endothelial or osteoblastic phenotypes," International journal of molecular medicine, Apr. 1, 2016, 37(4):1005-1013.

Infante-Duarte et al., "New developments in understanding and treating neuroinflammation" Journal of Molecular Medicine, 86:975-985, Sep. 2008.

info.gbiosciences.com [Online], "G-Biosciences, The Basics of Affinity Purification/Affinity Chromatography," Jul. 31, 2018, retrieved on Apr. 18, 2023, retrieved from URL<https://info.gbiosciences.com/blog/the-basics-of-affinity-purification/affinity-chromatography?utm_campaign=G-Bio+Search+Ads&utm_term=&utm_source=adwords&utm_medium=ppc&hsa_src=g&hsa_ver-3&hsa_cam=737902488&hsa_kw=&hsa_ad=621736020174&hsa_tgt=dsa-460355902483&hsa_mt=&hsa_acc-6752996364&hsa_grp=92226101427&hsanet-adwords&gclid=CjwKCAjw_ihBhADEiwAXEazJvXifVFgeRGV_W99XbY72eRROhWnHtdd695ydPgyh8qdvTwd9ikGIRoCdecQAvD_BwE>, 5 pages.

International Search Report and Written Opinion in International Appln. No. PCT/US2023/065745, mailed on Jun. 26, 2023, 14 pages.

Janeway et al., "The interaction of the antibody molecule with specific antigen" In Immunobiology: The Immune System in Health and Disease, 5th edition, 5 pages, 2001.

Klingemann et al., "Natural killer cells for immunotherapy-advantages of the NK-92 cell line over blood NK cells," Frontiers in immunology, Mar. 14, 2016, 7(91): 1-7.

Kozlowska et al., "Adoptive transfer of osteoclast-expanded natural killer cells for immunotherapy targeting cancer stem-like cells in humanized mice," Cancer Immunology, Immunotherapy, Jul. 2016, 65:835-845.

Matsuura et al., "Pole test is a useful method for evaluating the mouse movement disorder caused by striatal dopamine depletion" Journal of neuroscience methods, 73(1):45-48, 1997.

Mortier et al., "Soluble interleukin-15 receptor α (IL-15Rα)-sushi as a selective and potent agonist of IL-15 action through IL-15Rβ/γ: hyperagonist IL-15• IL-15Rα fusion proteins," Journal of Biological Chemistry, Jan. 20, 2006, 281(3):1612-1619.

Putnam et al., "Clinical grade manufacturing of human alloantigen-reactive regulatory T cells for use in transplantation," American journal of transplantation, Nov. 1, 2013, 13(11):3010-3020.

Reddy et al., "Linkers in the structural biology of protein-protein interactions" Protein science, 22(2):153-167, 2013.

Ross et al., "Signaling and function of interleukin-2 in T lymphocytes" Annual review of immunology, 36:411-433, 2018.

ThermoFisher.com [Online], "Covalent Immobilization of Affinity Ligands," 2018, retrieved on Apr. 18, 2023, retrieved from <URLhttps://www.thermofisher.com/us/en/home/life-science/protein-biology/protein-biology-learning-center/protein-biology-resource-library/pierce-protein-methods/covalent-immobilization-affinity-ligands.html>, 13 pages.

Uppendahl et al., "Natural killer cell-based immunotherapy in gynecologic malignancy: a review," Frontiers in immunology, Jan. 5, 2018, 8(1825): 1-15.

Urh et al., "Affinity chromatography: general methods," Methods in enzymology, Jan. 1, 2009, 463: 23 pages.

Van Bockstaele et al., "The development of nanobodies for therapeutic applications" Current opinion in investigational drugs, 10(11):1212-1224, 2009.

Veluchamy et al., "The rise of allogeneic natural killer cells as a platform for cancer immunotherapy: recent innovations and future developments," Frontiers in immunology, May 31, 2017, 8(631): 1-20.

Wong et al., "Interleukin-15: Interleukin-15 receptor a scaffold for creation of multivalent targeted immune molecules," Protein Engineering, Design & Selection, Apr. 1, 2011, 24(4):373-383.

Zhou, "Emerging mechanisms and applications of low-dose IL-2 therapy in autoimmunity," Cytokine & Growth Factor Reviews, Jun. 30, 2022, 67: 80-88.

U.S. Appl. No. 16/556,040, filed Aug. 29, 2019, Wong.

U.S. Appl. No. 16/557,822, filed Aug. 30, 2019, Wong.

U.S. Appl. No. 16/557,875, filed Aug. 30, 2019, Wong.

Abbott et al., "Genomic organization, exact localization, and tissue expression of the human CD26 (dipeptidyl peptidase IV) gene," Immunogentics, Sep. 1994, 40(5):331-338.

Abdul-Aziz et al., "Acute myeloid leukemia induces protumoral p16INK4a-driven senescence in the bone marrow microenvironment," Blood, Jan. 31, 2019, 133(5):446-456.

Aertgeerts et al., "Crystal structure of human dipeptidyl peptidase IV in complex with a decapeptide reveals details on substrate specificity and tetrahedral intermediate formation," Protein Science, Feb. 2004, 13(2):412-421.

Ait-Oufella et al., "Natural regulatory T cells control the development of atherosclerosis in mice," Nature Medicine, Feb. 5, 2006, 12:178-180.

Akbari, et al., "Design, expression and evaluation of a novel humanized single chain antibody against epidermal growth factor receptor (EGFR)," Protein Expr. Purif., 2016, 127:8-15.

Ali et al., "Regulatory T cells in skin," Immunology, Jul. 12, 2017, 152(3):372-381.

Angevin et al., "First-in-human phase 1 of YS110, a monoclonal antibody directed against CD26 in advanced CD26-expressing cancers," British Journal of Cancer, Mar. 14, 2017, 116(9):1126-1134.

Bachelet et al., "Mast Cell Costimulation by CD226/CD112 (DNAM-1/Nectin-2) A Novel Interface in the Allergic Process," Journal of Biological Chemistry, Sep. 15, 2006, 281(37):27190-6.

Baker et al., "Chronic treatment with the beta(2)-adrenoceptor agonist prodrug BRL-47672 impairs rat skeletal muscle function by inducing a comprehensive shift to a faster muscle phenotype," J Pharmacol Exp Ther., Oct. 2006, 319(1):439-446.

Baker et al., "Effects of conjugated linoleic acid (CLA) on tissue composition parameters in a murine cachexia model," The FASEB Journal, Mar. 2006, 20(4), 2 pages (Abstract Only).

Baker, et al., "Clearance of p16Ink4a-positive senescent cells delays ageing-associated disorders," Nature, 2011, 479(7372): 232-236.

Bennett et al., "Erratum: Killing the old: cell senescence in atherosclerosis," Nature Reviews Cardiology, Jan. 12, 2017, 14(3):132.

Bennett et al., "Killing the old: cell senescence in atherosclerosis," Nature Reviews Cardiology, Dec. 12, 2016, 14(1):8-9, 2 pages.

Bentebibel et al., "A First-in-Human Study and Biomarker Analysis of NKTR-214, a Novel IL2Raf Biased Cytokine, in Patients with Advanced or Metastatic Solid Tumors," Cancer Discovery, Jun. 2019, 9(6):711-721.

Berry et al., "Cancer Anorexia and Cachexia: Screening in an Ambulatory Infusion Service and Nutrition Consultation," Clin J Oncol Nurs., 2018, 22(1):63-68.

(56) References Cited

OTHER PUBLICATIONS

Bhat et al., "Astrocyte Senescence as a Component of Alzheimer's Disease, " PLoS One, Sep. 12, 2012, 7(9):e45069, 10 pages.
Biran et al., "Senescent cells communicate via intercellular protein transfer," Genes & Development, Apr. 8, 2015, 29(8):791-802, 13 pages.
Borea et al., "Pharmacology of Adenosine Receptors: The State of the Art," Physiological Reviews, May 30, 2018, 98(3):1591-1625.
Borgerding et al., "B-lymphoma cells escape rituximab-triggered elimination by NK cells through increased HLA class I expression," Experimental Hematology, Mar. 1, 2010, 38(3):213-21.
Bork, "Powers and Pitfalls in Sequence Analysis: The 70% Hurdle," Genome Research, 2000, 10:398-400.
Bourgeois et al., "Regulation of cellular senescence via the FOXO4-p53 axis," FEBS Lett., 2018, 592(12): 2083-2097.
Bowie et al., "Deciphering the Message in Protein Sequences: Tolerance to Amino Acid Substitutions," Science, 1990, 247:1306-1310.
Boyman et al., "IL-7/Anti-IL-7 mAb Complexes Restore T Cell Development and Induce Homeostatic T Cell Expansion without Lymphopenia," The Journal of Immunology, Jun. 1, 2008, 180:7265-7275.
Boyman et al., "Selective Stimulation of T Cell Subsets with Antibody-Cytokine Immune Complexes," Science, Mar. 31, 2006, 311(5769):1924-1927.
Brennan et al., "Structural determination of lipid antigens captured at the CD1d-T-cell receptor interface," PNAS, 2017, 114(31):8348-8353.
Brighton et al., "Clearance of senescent decidual cells by uterine natural killer cells in cycling human endometrium," Elife, Dec. 11, 2017, 6:e31274, 23 pages.
Brooks et al., "Combined inhibition of PD1 and CD96 checkpoints improves survival in a resectable murine model of pancreatic cancer," European Journal of Cancer, Jul. 1, 2016, 61:S189, 1 page.
Broxmeyer et al., "Modulation of Hematopoietic Chemokine Effects In Vitro and In Vivo by DPP-4/CD26," Stem Cells and Development, Mar. 4, 2016, 25(8):575-585.
Brunstein et al., "Infusion of Ex Vivo Expanded T Regulatory Cells in Adults Transplanted with Umbilical Cord Blood: Safety Profile and Detection Kinetics," Blood, Jan. 20, 2011, 117(3):1061-1070.
Brunstein et al., "Umbilical cord blood-derived T regulatory cells to prevent GVHD:kinetics, toxicity profile, and clinical effect," Blood, Feb. 25, 2016, 127(8):1044-1051.
Buhling et al., "Functional role of CD26 on human B lymphocytes," Immunology Letters, Feb. 1995, 45(1-2):47-51.
Burgess et al., "Possible Dissociation of the Heparin-binding and Mitogenic Activities of Heparin-binding (Acidic Fibroblast) GrowthFactor-1 from its Receptor-binding Activities by Site-directed Mutagenesis of a Single Lysine Residue," J. Cell Biol., 1990, 111:2129-2138.
Bussian et al., "Clearance of senescent glial cells prevents tau-dependent pathology and cognitive decline," Nature, Sep. 19, 2018, 562(7728):578-582, 21 pages.
Cai et al., "Chibby suppresses aerobic glycolysis and proliferation of nasopharyngeal carcinoma via the Wnt/β-catenin-Lin28/let7-PDK1 cascade," Journal of Experimental & Clinical Cancer Research, Dec. 1, 2018, 37(1):104.
Cao et al., "Expression and characterization of recombinant humanized anti-HER2 single-chain antibody in Pichia pastoris for targeted cancer therapy," Biotechnology Letters, Jul. 1, 2015, 37(7):1347-54.
Cao, "Self-regulation and cross-regulation of pattern-recognition receptor signaling in health and disease," Nature Reviews Immunology, Dec. 29, 2015, 16(1):35-50.
Carr et al., "NK Cell-Mediated Lysis of Autologous HCMV-Infected Skin Fibroblasts is Highly Variable among NK Cell Clones and Polyclonal NK Cell Lines," Clinical Immunology, Nov. 2002, 105(2):126-140.
Catania et al., "The tumor-targeting immunocytokine F16-IL2 in combination with doxorubicin: dose escalation in patients with advanced solid tumors and expansion into patients with metastatic breast cancer," Cell Adhesion and Migration, Jan.-Apr. 2015, 9(1-2):14-21.
Cavinato et al., "Molecular mechanisms of UVB-induced senescence of dermal fibroblasts and its relevance for photoaging of the human skin," Experimental Gerontology. Aug. 2017, 94:78-82.
Chalan et al., "Expression of Lectin-Like Transcript 1, the Ligand for CD161, in Rheumatoid Arthritis, " PLoS ONE, 2015, 10(7):e0132436.
Chambers et al., "Can blocking inflammation enhance immunity during aging?," Journal of Allergy and Clinical Immunology, May 2020, 145(5):1323-1331.
Chan et al., "Molecular mechanisms of natural killer cell activation in response to cellular stress," Cell Death & Differentiation, Jan. 2014, 21(1):5-14.
Chance et al., "A simple and rapid assay of oxidative phosphorylation," Nature, Jun. 1955, 175(4469):1120-1121.
Chandrudu et al., "Chemical methods for peptide and protein production," Molecules, 2013, 18(4):4373-4388.
Chang et al., "Association Between Sarcopenia and Cognitive Impairment: A Systematic Review and Meta-Analysis," J Am Med Dir Assoc., Dec. 1, 2016, 17(12):1164e7-1164e15, 9 pages.
Chang et al., "The dock and lock method: a novel platform technology for building multivalent, multifunctional structures of defined composition with retained bioactivity," Clinical cancer research, Sep. 15, 2007, 13(18):5586s-5591s.
Chattopadyhay et al., "Structural Basis of Inducible Costimulator Ligand Costimulatory Function: Determination of the Cell Surface Oligomeric State and Functional Mapping of the Receptor Binding Site of the Protein1," J Immunol., 2006, 3920-3929.
Chen et al., "Circulating levels of resistin and risk of type 2 diabetes in men and women: results from two prospective cohorts," Diabetes Care, Feb. 2009, 32(2):329-334.
Chen et al., "Sterile inflammation: sensing and reacting to damage," Nature Reviews Immunology, Nov. 19, 2010, 10(12):826-837.
Chichili et al., "Linkers in the structural biology of protein-protein interactions," Protein Science, Feb. 2013, 22(2):153-67.
Childs et al., "Senescent cells: an emerging target for diseases of ageing," Nature Reviews Drug Discovery, Jul. 21, 2017, 16(10):718-735, 18 pages.
Childs et al., "Senescent intimal foam cells are deleterious at all stages of atherosclerosis," Science, Oct. 28, 2016, 354(6311):472-477.
Chinta, et al., "Cellular senescence is induced by the environmental neurotoxin paraquat and bontributes to neuropathology linked to Parkinson's Disease," Cell Rep., 2018, 22(4): 930-940.
Chong et al., "CD36 initiates the secretory phenotype during the establishment of cellular senescence," EMBO Rep., May 18, 2018, 19(6):e45274, 13 pages.
Ciaglia et al., "Recognition by natural killer cells of N6-isopentenyladensoine-treated human glioma cell lines, " Int. J. Cancer, 2018 142(1): 176-190.
Cichocki et al., "GSK3 inhibition drives maturation of NK cells and enhances their antitumor activity," Cancer Research, Oct. 15, 2017, 77(20):5664-75.
Cifaldi et al., "Boosting Natural Killer Cell-Based Immunotherapy with Anticancer Drugs: a Perspective," Trends Molecular Medicine, Dec. 2017, 23(12):1156-1175, 20 pages.
Cipriani et al., "Hippocampal Radial Glial Subtypes and Their Neurogenic Potential in Human Fetuses and Healthy and Alzheimer's Disease Adults," Cerebral Cortex, May 2, 2018, 28(7):2458-2478, 21 pages.
Clayton et al.,"Soluble T Cell Immunoglobulin Mucin Domain 3 is Shed from CD8 T Cells by the Sheddase ADAM10, Is Increased in Plasma during Untreated HIV Infection, and Correlates with HIV Disease Progression," J Viral., 2015, 89(7):3723-3736.
Collado et al., "Senescence in tumours: evidence from mice and humans," Nature Reviews Cancer, Jan. 2010, 10(1):51-57.
Conarello et al., "Mice lacking dipeptidyl peptidase IV are protected against obesity and insulin resistance," Proc. Natl. Acad. Sci. U.S.A., May 27, 2003, 100(11):6825-6830.

(56) References Cited

OTHER PUBLICATIONS

Conlon et al., "Abstract CT082: Phase (Ph) I/Ib study of NIZ985 with and without spartalizumab (PDR001) in patients (pts) with metastatic/unresectable solid tumors," Cancer Res. 79(13 Suppl.):CT082, Jul. 1, 2019, 2 pages.
Coppe et al., "Tumor Suppressor and Aging Biomarker p16INK4a Induces Cellular Senescence without the Associated Inflammatory Secretory Phenotype," Journal of Biological Chemistry, Oct. 21, 2011, 286(42): 36396-36403.
Cosgrove et al., "Usher protein functions in hair cells and photoreceptors," Int J Biochem Cell Biol., Jan. 2014, 46:80-89.
Cosman et al., "ULBPs, novel MHC class I-related molecules, bind to CMV glycoprotein UL16 and stimulate NK cytotoxicity through the NKG2D receptor," Immunity, Feb. 1, 2001, 14(2):123-33.
Costa et al., "Targeting the epidermal growth factor receptor can counteract the inhibition of natural killer cell function exerted by colorectal tumor-associated fibroblasts," Frontiers in Immunology, May 29, 2018, 9:1150, 14 pages.
Crews et al., "Molecular mechanisms of neurodegeneration in Alzheimer's disease," Human Molecular Genetics, Apr. 22, 2010, 19(R1):R12-R20, 9 pages.
Cromie et al., "Nanobodies and their use in GPCR drug discovery," Current Topics in Medicinal Chemistry, Dec. 1, 2015, 15(24):2543-57.
Czaja et al., "A comprehensive analysis of the binding of anti-KIR antibodies to activating KIRs," Genes and Immunity, Jan. 2014, 15(1), 15 pages.
Da Silva et al., "Dipeptidylpeptidase 4 inhibition enhances lymphocyte trafficking, improving both naturally occurring tumor immunity and immunotherapy," Nature Immunology, Jun. 15, 2015, 16(8):850-858, 11 pages.
Dall'Era et al., "Adoptive Regulatory T Cell Therapy in a Patient with Systemic Lupus Erythematosus," Arthritis Rheumatology, Mar. 2019, 71(3):431-440.
De Crescenzo et al., "Engineering TGF-β Traps: Artificially Dimerized Receptor Ectodomains as High-affinity Blockers of TGF-β Action," Transforming Growth Factor-β in Cancer Therapy, vol. II, 2008, Humana Press, 671-84.
De Genst et al., "Antibody repertoire development in camelids," Developmental & Comparative Immunology, Jan. 1, 2006, 30(1-2):187-98.
De Meyer et al., "Nanobody-based products as research and diagnostic tools," Trends in Biotechnology, May 1, 2014, 32(5):263-70.
De Stefano et al., "Establishing pathological cut-offs of brain atrophy rates in multiple sclerosis," Journal of Neurology, Neurosurgery, and Psychiatry, Jan. 2016, 87(1):93-99.
Deacon, "Physiology and Pharmacology of DPP-4 in Glucose Homeostasis and the Treatment of Type 2 Diabetes," Frontiers in Endocrinology, Feb. 2019, 10:80, 14 pages.
Deaglio et al., "Adenosine generation catalyzed by CD39 and CD73 expressed on regulatory T cells mediates immune suppression," Journal of Experimental Medicine, May 14, 2007, 204(6):1257-1265.
Demaria et al., "An Essential Role for Senescent Cellsin Optimal Wound Healing through Secretion of PDGF-AA," Developmental Cell, Dec. 22, 2014, 31(6):722-733.
Deyev et al., "Design of multivalent complexes using the barnase• barstar module," Nature Biotechnology, Dec. 2003, 21(12):1486-92.
Di Ianni et al., "Tregs prevent GVHD and promote immune reconstitution inHLA-haploidentical transplantation," Blood, Apr. 7, 2011, 117(14):3921-3928.
Dietel et al., "Decreased numbers of regulatory T cells are associated with human atherosclerotic lesion vulnerability and inversely correlate with infiltrated mature dendritic cells," Atherosclerosis, Sep. 2013, 230:92-99.
DiGiammarino et al., "Design and generation of DVD-Ig™ molecules for dual-specific targeting," Therapeutic Proteins: Methods and Protocols, Methods in Molecular Biology, 2012, Humana Press, Totowa, NJ., 899:145-516.
Dikov et al., "New fluorescent method for the histochemical detection of tripeptidyl peptidase I using glycyl-1-proly1-1-met-2-anthraquinonyl hydrazide as substrate," Cellular and Molecular Biology, Jan. 1, 2004, 50 Online Pub: OL565-568, 1 page (Abstract Only).
Dimri et al., "A biomarker that identifies senescent human cells in culture and in aging skin in vivo," Proceedings of the National Academy of Sciences, Sep. 29, 1995, 92(20):9363-9367.
Dinarello, "Interleukin 1 and interleukin 18 as mediators of inflammation and the aging process," The American Journal of Clinical Nutrition, Feb. 1, 2006, 83(2):447S-455S.
Docagne et al., "A soluble transforming growth factor-β (TGF-β) type I receptor mimics TGF-β responses," Journal of Biological Chemistry, Dec. 7, 2001, 276(49):46243-50.
Dong et al., "Characterization of adenosine deaminase binding to human CD26 on T cells and its biologic role in immune response," Journal of Immunology, Feb. 15, 1996, 156(4):1349-1355.
Dong et al., "Determination of adenosine deaminase binding domain on CD26 and its immunoregulatory effect on T cell activation," Journal of Immunology, Dec. 15, 1997, 159(12):6070-6076.
Dong et al., "Loss of methylation at theIFNGpromoter and CNS-1 is associated with the development of functional IFN-γ memory in human CD4+T lymphocytes," European Journal of Immunology, 2013, 43(3), 793-804.
Dou et al., "Cytoplasmic chromatin triggers inflammation in senescence and cancer," Nature, Oct. 4, 2017, 550(7676):402-406, 21 pages.
Drees et al., "Soluble production of a biologically active single-chain antibody against murine PD-L1 in *Escherichia coli*, " Protein Express. Purif., 2014, 94:60-66.
Dubois et al., "Preassociation of IL-15 with IL-15Rα-IgG1-Fc Enhances its Activity on Proliferation of NK and CD8+/CD44high T Cells and its Antitumor Action," The Journal of Immunology, Feb. 15, 2008, 180:2099-2106.
Edwardraja et al., "Redesigning of anti-c-met single chain Fv antibody for the cytoplasmic folding and its structural analysis," Biotechnology and Bioengineering, Jun. 15, 2010, 106(3):367-75.
Eisenhut et al., "Ion Channels in Inflammation," Pflugers Archive, Jan. 29, 2011, 461(4):401-421.
Elgueta et al., "Molecular mechanism and function of CD40/CD40L engagement in the immune system," Immunological Reviews, 2009, 229(1):152-172 doi.org/10.1111/j.1600-065X.2009.00782.x.
Elpek et al., "Mature natural killer cells with phenotypic and functional alterations accumulate upon sustained stimulation with IL-15/IL-15Rα complexes," Proceedings of the National Academy of Science, Dec. 14, 2010, 107: 21647-21652.
Engel et al., "The crystal structure of dipeptidyl peptidase IV (CD26) reveals its functional regulation and enzymatic mechanism," Proc. Natl. Acad. Sci. U.S.A., Apr. 29, 2003, 100(9):5063-5068.
Epardaud et al., "Interleukin-15/Interleukin-15RA Complexes Promote Destruction of Established Tumors by Reviving Tumor-Resident CD8+ T Cells, " Cancer Research 68: Apr. 15, 2008, 2972-2983.
Esensten et al., "Regulatory T-cell therapy for autoimmune and autoinflammatory diseases: The next frontier," The Journal of Allergy and Clinical Immunology, Dec. 1, 2018, 142(6):1710-1718.
Farr et al., "Targeting cellular senescence prevents age-related bone loss in mice," Nat. Med., 2017, 23(9): 1072-1079.
Fehniger et al., "A Phase 1 Trial of CNDO-109-Activated Natural Killer Cells in Patients with High-Risk Acute Myeloid Leukemia," Biology of Blood and Marrow Transplantation, Aug. 2018, 24(8):1581-1589.
Feng et al., "The yin and yang functions of extracellular ATP and adenosine in tumor immunity," Cancer Cell International, Apr. 7, 2020, 20:110, 11 pages.
Ferreira et al., "Next-generation regulatory T cell therapy," Nature Reviews Drug Discovery, Sep. 20, 2019, 18(10):749-769, 21 pages.
Ferrucci et al., "The origins of age-related proinflammatory state," Blood, Mar. 15, 2005, 105(6):2294-2299.
Finkelman et al., "Anti-cytokine antibodies as carrier proteins. Prolongation of in vivo effects of exogenous cytokines by injection

(56) References Cited

OTHER PUBLICATIONS of cytokine-anti-cytokine antibody complexes," The Journal of Immunology, Aug. 1, 1993, 151:1235-1244.
Finkelstein et al., "Obesity and Severe Obesity Forecasts Through 2030," American Journal of Preventative Medicine, Jun. 2012, 42(6):563-570.
Ford et al., "TREM and TREM-like receptors in inflammation and disease," Current Opinion in Immunology, Feb. 21, 2009, 21(1):38-46.
Franceschi et al., "Inflamm-aging. An evolutionary perspective on immunosenescence," Annals of the New York Academy of Sciences, Jun. 2000, 908:244-254.
Frutoso et al., "Emergence of NK Cell Hyporesponsiveness after Two IL-15 Stimulation Cycles," Journal of Immunology, May 30, 2018, 201: 493-506.
Ganesh et al., "TGF-β Inhibition and Immunotherapy: Checkmate," Immunity, Apr. 17, 2018, 48(4):626-628.
Garber, "Bispecific antibodies rise again," Nat. Rev. Drug Discov., 2014, 13:799-801.
Gaulton et al., "Characterization of a monoclonal rat anti-mouse interleukin 2 (IL-2) receptor antibody and its use in the biochemical characterization of the murine IL-2 receptor," Clinical Immunology and Immunopathology, Jul. 1, 1985, 36(1):18-29.
Gejima et al., "Human single-chain Fv (scFv) antibody specific to human IL-6 with the inhibitory activity on IL-6-signaling," Human Antibodies, Jan. 1, 2002, 11(4):121-9.
Geng et al., "A novel anti-TNF scFv constructed with human antibody frameworks and antagonistic peptides," Immunol. Res. 62(3):377-385, 2015.
Georgilis et al., "PTBP1-Mediated Alternative Splicing Regulates the Inflammatory Secretome and the Pro-tumorigenic Effects of Senescent Cells," Cancer Cell, Jul. 9, 2018, 34(1):85-102.
Ghosh et al., "The Senescence-Associated Secretory Phenotype: Critical Effector in SkinCancer and Aging," Journal of Investigative Dermatology, Nov. 2016, 136(11):2133-2139.
Gibbs et al., "Identification of the factor VIIa binding site on tissue factor by homologous loop swap and alanine scanning mutagenesis," Biochemistry, Nov. 1, 1994, 33(47):14003-10.
Gong et al., "DAMP-sensing receptors in sterile inflammation and inflammatory diseases," Nature Reviews Immunology, Sep. 26, 2019, 20(2):95-112.
Gorrell et al., "Expression of the rat CD26 Antigen (dipeptidyl peptidase IV) on subpopulations of rat lymphocytes," Cellular Immunology, Apr. 15, 1991, 134(1):205-215.
Greenspan et al., "Defining epitopes: Its not as easy as it seems," Nature Biotechnology, 1999, 17:936-937.
Grupp et al., "Chimeric Antigen Receptor-Modified T Cells for Acute Lymphoid Leukemia," The New England Journal of Medicine, Apr. 18, 2013, 368(16):1509-1518.
Gu et al., "Human CD39hi regulatory T cells present stronger stability and function under inflammatory conditions," Cellular and Molecular Immunology, Jul. 4, 2016, 14(6):521-528.
Guo et al., "Immunobiology of the IL-15-IL-15R complex as an antitumor and antiviral agent," 2017, Cytokine & Growth Factor Reviews, 38:10-21.
Gutschmidt et al., "A quantitative histochemical study of dipeptidyl peptidase Iv (Dpp Iv)," Histochemistry, 1981, 73(2):285-304.
Haile et al., "Soluble CD80 Restores T Cell Activation and Overcomes Tumor Cell Programmed Death Ligand 1-Mediated Immune Suppression," J. Immunol., 2013, 191(5):2829-2836.
Hayflick et al., "The serial cultivation of human diploid cell strains," Experimental Cell Research, Dec. 1961, 25:585-621.
He et al., "Senescence in Health and Disease," Cell, Jun. 1, 2017, 169(6):1000-1011.
Hebbar et al., "Detection of circulating soluble CD28 in patients with systemic lupus erythematosus, primary Sjögren's syndrome and systemic sclerosis," Clinical & Experimental Immunology, May 2004, 136(2):388-92.
Helfrich et al., "A rapid and versatile method for harnessing scFv antibody fragments with varous biological effector functions," Journal of Immunological methods, 2000, 237(1-2):131-145.
Helman et al., "Effects of ageing and senescence on pancreatic β-cell function," Diabetes Obes Metab., Sep. 2016, 18(Suppl. 1):58-62.
Heneka et al., "Inflammasome signaling in brain function and neurodegenerative disease," Nature Reviews Neuroscience, Sep. 11, 2018, 19(10):610-621.
Heneka et al., "NLRP3 is activated in Alzheimer's disease and contributes to pathology in APP/PS1 mice, " Nature, Jan. 31, 2013, 493(7434):674-678, 8 pages.
Heng et al., "G Protein-Coupled Receptors Revisited: Therapeutic Applications Inspired by Synthetic Biology," Annual Review of Pharmacology and Toxicology, Jan. 2014, 54:227-249.
Heng et al., "Multiple soluble TGF-β receptors in addition to soluble endoglin are elevated in preeclamptic serum and they synergistically inhibit TGF-B signalling." Placenta, 2017 57: 320 (1 page).
Highfill et al., "Overcoming Challenges in Process Development of Cellular Therapies," Current Hematologic Malignancy Reports, Jul. 6, 2019, 14(4):269-277, 9 pages.
Hoare et al., "The Power Behind the Throne: Senescence and the Hallmarks of Cancer," Annual Review of Cancer Biology, 2018, 2:175-194.
Hoffmann et al., "Large-scale in vitro expansion of polyclonal human CD4+CD25high regulatory T Cells," Blood, Aug. 2004, 104(3):895-903.
Hollande et al., "Inhibition of the dipeptidyl peptidase DPP4 (CD26) reveals IL-33-dependent eosinophil-mediated control of tumor growth," Nature Immunology, Feb. 18, 2019, 20(3):257-264.
Hombach et al., "Generation of the single chain antibody fragment conserves the idiotypic profile of the anti-CD30 monoclonal antibody HRS3," Scandinavian Journal of Immunology, Nov. 1998, 48(5):497-501.
Hu et al., "Discovery of a novel IL-15 based protein with improved developability and efficacy for cancer immunotherapy," Scientific Reports, 2018, 8:7675, 11 pages.
Huang et al., "Substrate recognition by tissue factor-factor VIIa Evidence for interaction of residues Lys165 and Lys166 of tissue factor with the 4-carboxyglutamate-rich domain of factor X," Journal of Biological Chemistry, Sep. 6, 1996, 271(36):21752-7.
Huang et al., "Targeting the vasculature of colorectal carcinoma with a fused protein of (RGD) 3-tTF" The Scientific World Journal, 2013(637086): 1-11, 2013.
Hudak et al., "Glycocalyx engineering reveals a Siglec-based mechanism for NK cell immunoevasion," Nature Chemical Biology, Jan. 2014, 10(1), 20 pages.
Hudson et al., "Targeting RAGE Signaling in Inflammatory Disease," Annual Review of Medicine, Jan. 2018, 69:349-364, 16 pages.
Huell et al., "Interleukin-6 is present in early stages of plaque formation and is restricted to the brains of Alzheimer's disease patients," Acta Neuropathologica, Nov. 1995, 89(6):544-551.
Hughes et al., "Transfer of a TCR gene derived from a patient with a marked antitumor response conveys highly active T-cell effector functions," Hum. Gene Ther., 2005, 16:457-72.
Hui et al., "Butyrate inhibit collagen-induced arthritis via Treg/IL-10/Th17 axis," International immunopharmacology, Mar. 1, 2019, 68: Abstract 1 page.
Hynes et al., "In vitro analysis of cell metabolism using a long-decay pH-sensitive lanthanide probe and extracellular acidification assay," Analytical biochemistry, Jul. 1, 2009, 390(1):21-28.
Iannello et al., "p53-dependent chemokine production by senescent tumor cells supports NKG2D-dependent tumor elimination by natural killer cells," Journal of Experimental Medicine, Sep. 23, 2013, 210(10):2057-69.
Iihoshi et al., "Aclarubicin, an anthracycline anti-cancer drug, fluorescently contrasts mitochondria and reduces the oxygen consumption rate in living human cells," Toxicology Letters, Aug. 5, 2017, 277:109-114, 22 pages.
International Preliminary Report on Patentability in International Appln. No. PCT/US2019/048881, dated Mar. 11, 2021, 7 pages.

(56) References Cited

OTHER PUBLICATIONS

International Preliminary Report on Patentability in International Appln. No. PCT/US2019/048930, dated Mar. 11, 2021, 9 pages.
International Preliminary Report on Patentability in International Appln. No. PCT/US2019/049142, dated Mar. 11, 2021, 11 pages.
International Preliminary Report on Patentability in International Appln. No. PCT/US2019/049158, dated Mar. 11, 2021, 8 pages.
International Preliminary Report on Patentability in International Appln. No. PCT/US2020/035598, mailed Dec. 6, 2022, 7 pages.
International Preliminary Report on Patentability in International Appln. No. PCT/US2020/038717, dated Dec. 30, 2021, 9 pages.
International Preliminary Report on Patentability in International Appln. No. PCT/US2021/017620, dated Aug. 25, 2022, 12 pages.
International Preliminary Report on Patentability in International Appln. No. PCT/US2021/017621, dated Aug. 25, 2022, 8 pages.
International Preliminary Report on Patentability in International Appln. No. PCT/US2021/017714, dated Aug. 25, 2022, 12 pages.
International Preliminary Report on Patentability in International Appln. No. PCT/US2021/029920, dated Nov. 10, 2022, 11 pages.
International Preliminary Report on Patentability in International Appln. No. PCT/US2021/035285, mailed Dec. 15, 2022, 7 pages.
International Search Report and Written Opinion in International Appln. No. PCT/US2019/048881, dated Nov. 9, 2019, 16 pages.
International Search Report and Written Opinion in International Appln. No. PCT/US2019/048930, dated Nov. 20, 2019, 18 pages.
International Search Report and Written Opinion in International Appln. No. PCT/US2019/049142, dated Jun. 23, 2020, 20 pages.
International Search Report and Written Opinion in International Appln. No. PCT/US2019/049158, dated Jan. 20, 2020, 17 pages.
International Search Report and Written Opinion in International Appln. No. PCT/US2020/035598, dated Feb. 18, 2021, 12 pages.
International Search Report and Written Opinion in International Appln. No. PCT/US2020/038717, dated Oct. 16, 2020, 17 pages.
International Search Report and Written Opinion in International Appln. No. PCT/US2021/017620, dated Aug. 6, 2021, 22 pages.
International Search Report and Written Opinion in International Appln. No. PCT/US2021/017621, dated Jun. 9, 2021, 15 pages.
International Search Report and Written Opinion in International Appln. No. PCT/US2021/017714, dated Aug. 27, 2021, 22 pages.
International Search Report and Written Opinion in International Appln. No. PCT/US2021/029920, dated Oct. 6, 2021, 21 pages.
International Search Report and Written Opinion in International Appln. No. PCT/US2021/035285, dated Oct. 18, 2021, 14 pages.
Inzucchi et al., "New Drugs for the Treatment of Diabetes, Part II: Incretin-Based Therapy and Beyond, " Circulation, Jan. 29, 2008, 117(4):574-584, 21 pages.
Jain et al., "Mitochondrial Reactive Oxygen Species Regulate Transforming Growth Factor-β Signaling," Journal of Biological Chemistry, Jan. 11, 2013, 288(2):770-777.
Jakob et al., "Structure reveals function of the dual variable domain immunoglobulin (DVD-Ig™) molecule," Mabs, May 1, 2013, Taylor & Francis, 5(3):358-63.
Janeway, "Approaching the Asymptote? Evolution and Revolution in Immunology," Cold Spring Harbor Symposia on Quantitative Biology, 1989, 54 Pt 1:1-13.
Jeannin et al., "Soluble CD86 is a Costimulatory Moleculefor Human T Lymphocytes," Immunity, 2000, 13(3):303-312.
Jeon et al., "Local clearance of senescent cells attenuates the development of post-traumatic osteoarthritis and creates a pro-regenerative environment," Nat Med., Jun. 2017, 23(6):775-781.
Jin et al., "Novel Insights Into the NLRP3 Inflammasome in Atherosclerosis," Journal of the American Heart Association, Jun. 11, 2019, 8(12):e012219, 12 pages.
Justice et al., "Senolytics in idiopathic pulmonary fibrosis: Results from a first-in-human, open-label, pilot study," EBioMedicine, Feb. 2019, 40:554-563.
Kain et al., "The identification of the endogenous ligands of natural killer T cells reveals the presence of mammalian α-linked glycosylceramides," Immunity, Oct. 16, 2014, 41(4):543-54.
Karin et al., "Senescent cell turnover slows with age providing an explanation for the Gompertz law," Nature Communications, Dec. 2, 2019, 10:5495, 9 pages.
Karkera et al., "The anti-interleukin-6 antibody siltuximab down-regulates genes implicated in tumorigenesis in prostate cancer patients from a phase I study," The Prostate, Feb. 14, 2011, 71(13):1455-1465.
Katsuumi et al., "Vascular Senescence in Cardiovascular and Metabolic Diseases," Frontiers in Cardiovascular Medicine, Mar. 5, 2018, 5:18, 13 pages.
Kellner et al., "Enhancing natural killer cell-mediated lysis of lymphoma cells by combining therapeutic antibodies with CD20-specific immunoligands engaging NKG2D or NKp30," Oncoimmunology, Jan. 2, 2016, 5(1):e1058459, 12 pages.
Kijanka et al., "Nanobody-based cancer therapy of solid tumors," Nanomedicine, Jan. 2015, 10(1):161-74.
Kim et al., "Experimental malaria infection triggers early expansion of natural killer cells," Infection and Immunity, Dec. 1, 2008, 76(12):5873-82.
Kim et al., "Identification of senescent cell surface targetable protein DPP4," Genes & Development, 2017, 31(15):1529-1534.
Kim et al., "Insulin resistance, inflammation, and nonalcoholic fatty liver disease in non-obese adults without metabolic syndrome components," Hepatol Int., Jun. 2013, 7(2):586-591.
Kim et al., "SCAMP4 enhances the senescent cell secretome," Genes & Development, 2018, 32(13-14):909-914.
Kirchhofer et al., "The tissue factor region that interacts with substrates factor IX and factor X," Biochemistry, Jun. 27, 2000, 39(25):7380-7.
Kirkland et al., "Cellular Senescence: A Translational Perspective," EBioMedicine, Jul. 2017, 21:21-28.
Klein et al., "Cergutuzumab amunaleukin (CEA-IL2v), a CEA-targeted IL-2 variant- based immunocytokine for combination cancer immunotherapy: Overcoming limitations of aldesleukin and conventional IL-2-based immunocytokines," Oncoimmunology, 2017 6(3):e1277306, 15 pages.
Klein et al., "Design and characterization of structured protein linkers with differing flexibilities," Protein Engineering, Design & Selection, 2014, 27(10):325-30.
Klemann et al., "Cut to the chase: a review of CD26/dipeptidyl peptidase-4's (DPP4) entanglement in the immune system," Clinical and Experimental Immunology, Feb. 25, 2016, 185(1):1-21.
Klingenberg et al., "Depletion of FOXP3+ regulatory T cells promotes hypercholesterolemia and atherosclerosis," The Journal of Clinical Investigation, Feb. 15, 2013, 123:1323-1334.
Kondo et al., "Requirements for the functional expression of OX40 ligand on human activated CD4+ and CD8+ T cells," Human Immunology, 2007, 68(7):563-571.
Kovaleva et al., "Shark variable new antigen receptor biologics—a novel technology platform for therapeutic drug development," Expert Opinion on Biological Therapy, Oct. 1, 2014, 14(10):1527-39.
Krah et al., "Single-domain antibodies for biomedical applications," Immunopharmacology and Immunotoxicology, Jan. 2, 2016, 38(1):21-8.
Kritsilis et al., "Ageing, Cellular Senescence and Neurodegenerative Disease," International Journal of Molecular Sciences, Sep. 27, 2018, 19(10):2937, 37 pages.
Krizhanovsky et al., "Senescence of activated stellate cells limits liver fibrosis," Cell, Aug. 22, 2008, 134(4):657-67.
Kumagai et al., "Monitoring of glutamate-induced excitotoxicity by mitochondrial oxygen consumption," Synapse, Jan. 2019, 73(1):e22067, 24 Pages.
Kuyinu et al., "Animal models of osteoarthritis: classification, update, and measurement of outcomes," J Orthop Surg Res., Feb. 2, 2016, 11:19, 27 pages.
Lambeir et al., "Dipeptidyl-Peptidase IV from Bench to Bedside: An Update on Structural Properties, Functions, and Clinical Aspects of the Enzyme DPP IV," Critical Reviews in Clinical Laboratory Sciences, Sep. 29, 2003, 40(3):209-294.
Lamkanfi et al., "Mechanisms and Functions of Inflammasomes," Cell, May 22, 2014, 157(5):1013-1022.

(56) References Cited

OTHER PUBLICATIONS

Lansigan et al., "DI-Leu16-IL2, an Anti-CD20-Interleukin-2 Immunocytokine, is Safe and Active in Patients with Relapsed and Refractory B-Cell Lymphoma: A Report of Maximum Tolerated Dose, Optimal Biologic Dose, and Recommended Phase 2 Dose," Blood, Dec. 2, 2016, 128(22):620, 3 pages (Abstract Only).
Latz et al., "Activation and regulation of the inflammasomes," Nature Reviews Immunology, May 24, 2013, 13(6):397-411.
Latz et al., "NLRP3 inflammasome activation in inflammaging," Seminars in Immunology, Dec. 2018, 40:61-73, 13 pages.
Lau et al., "RNA-associated autoantigens activate B cells by combined B cell antigen receptor/Toll-like receptor 7 engagement," The Journal of Experimental Medicine, Oct. 31, 2005, 202(9):1171-1177.
Lazar et al., "Transforming Growth Factor Alpha: Mutation of Aspartic Acid 47 and Leucine 48 Results in Different Biological Activities," Mol. Cell. Biol., 1988, 8:1247-1252.
Li et al., "A Novel I L2-based Irrmunotherapeutic Protein Prevents the Development of Atherosclerosis in ApoE-/mice and LDLR-/-mice," Journal of Immunology, May 1, 2020, 204(1):Supplement (Abstract Only), 2 pages.
Li et al., "Adoptive transfer of natural killer cells in combination with chemotherapy improves outcomes of patients with locally advanced colon carcinoma," Cytotherapy, Jan. 2018, 20(1):134-148, 15 pages.
Li et al., "Lipid metabolism fuels cancer's spread," Cell metabolism, Feb. 7, 2017, 25(2):228-230.
Li et al., "The cGAS-cGAMP-STING pathway connects DNA damage to inflammation, senescence, and cancer," Journal of Experimental Medicine, Apr. 5, 2018, 215(5):1287-1299.
Li et al., "Transforming Growth Factor-β Regulation of Immune Responses," Annu. Rev. Immunol., 2006, 24:99-146.
Liton et al., "Cellular senescence in the glaucomatous outflow pathway," Experimental Gerontology, Aug.-Sep. 2005, 40(8-9):745-748.
Liu et al., "A Novel Fusion of ALT-803 (IL-15 Superagonist) with an Antibody Demonstrates Antigen-specific Antitumor Responses," Journal of Biological Chemistry, 2016, 291(46):23869-23881.
Liu et al., "Evaluation of the biological activities of the IL-15 superagonist complex, ALT-803, following intravenous versus subcutaneous administration in murine models," Cytokine, Jul. 2018, 107: 105-112, 8 pages.
Loster et al., "The Cysteine-Rich Region of Dipeptidyl Peptidase IV (CD 26) is the Collagen Binding Site," Biochemical and Biophysical Research Communications, Dec. 5, 1995, 217(1):341-348.
Lu et al., "Molecular basis of binding between novel human coronavirus MERS-CoV and its receptor CD26," Nature, Jul. 7, 2013, 500(7461):227-231.
Lujambio et al., "Non-Cell-Autonomous Tumor Suppression by p53," Cell, Apr. 11, 2013, 153(2):449-460.
Maeda et al., "Original Ligand for LTβR is LIGHT: Insight into Evolution of the LT/LTBR System," J Immunol., 2018, 201(1):202-214.
Maganto-García et al., "Dynamic Changes in Regulatory T Cells are Linked to Levels of Diet-Induced Hypercholesterolemia," Circulation, Jun. 20, 2011, 124:185-195.
Mandelboim et al., "Recognition of haemagglutinins on virus-infected cells by NKp46 activates lysis by human NK cells," Nature, Feb. 2001, 409(6823):1055.
Marguet et al., "Enhanced insulin secretion and improved glucose tolerance in mice lacking CD26," Proc. Natl. Acad. Sci. U.S.A., Jun. 6, 2000, 97(12):6874-6879.
Martelli et al., "HLA-haploidentical transplantation with regulatory and conventionalT-cell adoptive immunotherapy prevents acute leukemia relapse," Blood, Jul. 24, 2014, 124(4):638-644.
Masoumi et al., "The role of hypoxia as the driving force for non-erythroid production of globin chains in preeclamptic placentas," Placenta. 2017;57:320.
McCarron et al., "TGF-β prevents T follicular helper cell accumulation and B cell autoreactivity," J Clin Invest., 2014, 124(10):4375-4386.
McHugh et al., "Senescence and aging: Causes, consequences, and therapeutic avenues," Journal of Cellular Biology, Nov. 7, 2017, 217(1):65-77.
Mehta et al., "Why do trials for Alzheimer's disease drugs keep failing? A discontinued drug perspective for 2010-2015," Expert Opinion on Investigational Drugs, May 2017, 26(6):735-739.
Melk et al., "Expression of p16INK4a and other cell cycle regulator and senescence associated genes in aging human kidney, " Kidney Int., Feb. 2004, 65(2):510-520.
Melk et al., "Senescence of renal cells: molecular basis and clinical implications," Nephrology Dialysis Transplantation, Dec. 2003, 18(12):2474-2478.
Menshawy et al., "CD58; leucocyte function adhesion-3 (LFA-3) could be used as a differentiating marker between immune and non-immune thyroid disorders," Comparative Clinical Pathology, 2018, 27(3), 721-727.
Mentlein et al., "Dipeptidyl-peptidase IV (CD26)-role in the inactivation of regulatory peptides," Regulatory Peptides, Nov. 30, 1999, 85(1):9-24.
Miah et al., "KIR2DL4 differentially signals downstream functions in human NK cells through distinct structural modules," The Journal of Immunology, Mar. 1, 2008, 180(5):2922-32.
Michelet et al., "Metabolic reprogramming of natural killer cells in obesity limits antitumor responses," Nature Immunology, Nov. 12, 2018, 19(12):1330-1340.
Mikayama et al., "Molecular cloning and functional expression of a cDNA encoding glycosylation-inhibiting factor," Proc. Natl. Acad. Sci. USA, Nov. 1, 1993, 90(21):10056-10060.
Milanovic et al., "Senescence-associated reprogramming promotes cancer stemness," Nature, Dec. 20, 2017, 553(7686):96-100.
Milanovic et al., "The Senescence-Stemness Alliance—A Cancer-Hijacked Regeneration Principle," Trends in Cellular Biology, Dec. 2018, 28(12):1049-1061, 13 pages.
Miller et al., "Soluble CD70: a novel immunotherapeutic agent for experimental glioblastoma," J Neurosurg., 2010, 113(2):280-285.
Miller et al., "Successful adoptive transfer and in vivo expansion of human haploidentical NK cells in patients with cancer," Blood, Apr. 15, 2005, 105(8):3051-3057.
Minamino et al., "A crucial role for adipose tissue p53 in the regulation of insulin resistance," Nature Medicine, Aug. 30, 2009, 15(9):1082-1087.
Mitterberger et al., "Adipogenic Differentiation is Impaired in Replicative Senescent Human Subcutaneous Adipose-Derived Stromal/Progenitor Cells," The Journals of Gerontology: Series A, Biological Sciences and Medical Sciences, Jan. 2014, 69(1):13-24.
Miyazaki et al., "Abstract 3265: NKTR-255, a polymer-conjugated IL-15 enhances anti-tumor NK cell responses and synergizes with monoclonal antibodies to provide long-term survival in human lymphoma model," Proceedings: AACR Annual Meeting 2019, Atlanta, GA, Mar. 29-Apr. 3, 2019, 1 page.
Moesta et al., "Targeting CD39 in cancer," Nature Reviews Immunology, Jul. 29, 2020, 20(12):739-755, 17 pages.
Moiseeva et al., "Metformin inhibits the senescence-associated secretory phenotype by interfering with IKK/NF-κB activation," Aging Cell, Mar. 23, 2013, 12(3):489-498.
Molema et al., "The use of bispecific antibodies in tumor cell and tumor vasculature directed immunotherapy," Journal of Controlled Release, 2000, 64(1-3):229-239.
Molgora et al., "Regulatory role of IL-1R8 in immunity and disease," Frontiers in Immunology, Apr. 20, 2016, 7:149.
Mookerjee et al., "Measurement and Analysis of Extracellular Acid Production to Determine Glycolytic Rate," Journal of Visualized Experiments : Jove, Dec. 2015, (106):e53464, 9 Pages.
Moore et al., "Macrophages in atherosclerosis: a dynamic balance," Nature Reviews Immunology, Sep. 2, 2013, 13:709-721, 13 pages.
Moreno et al., "Molecular Evidence of Adenosine Deaminase Linking Adenosine A2A Receptor and CD26 Proteins," Frontiers in Pharmacology, Feb. 15, 2018, 9:106, 18 pages.
Moretta et al., "CD69-mediated pathway of lymphocyte activation: anti-CD69 monoclonal antibodies trigger the cytolytic activity of

(56) References Cited

OTHER PUBLICATIONS different lymphoid effector cells with the exception of cytolytic T lymphocytes expressing T cell receptor alpha/beta, " Journal of Experimental Medicine, Dec. 1, 1991, 174(6):1393-8.
Mujić-Delić et al., "GPCR-targeting nanobodies: attractive research tools, diagnostics, and therapeutics," Trends in Pharmacological Sciences, May 1, 2014, 35(5):247-55.
Muller et al., "Antibody fusions with immunomodulatory proteins for cancer therapy," Pharmacology and Therapeutics, 2015, 154:57-66.
Mulvihill et al., "Pharmacology, Physiology, and Mechanisms of Action of Dipeptidyl Peptidase-4 Inhibitors," Endocrine Reviews, Dec. 1, 2014, 35(6):992-1019.
Munoz-Espin et al., "Cellular senescence: from physiology to pathology," Nature Reviews Molecular Cellular Biology, Jun. 23, 2014, 15(7):482-496.
Munoz-Espin et al., "Programmed Cell Senescence during Mammalian Embryonic Development," Cell, Nov. 21, 2013, 155(5):1104-1118.
Musi et al., "Tau protein aggregation is associated with cellular senescence in the brain," Aging Cell, Aug. 20, 2018, 17(6):e12840, 13 pages.
Must et al., "The Disease Burden Associated with Overweight and Obesity," Endotext, Feingold et al. (eds.), South Dartmouth, MA, 2000, 35 pages.
Muyldermans et al., "Recognition of antigens by single-domain antibody fragments: the superfluous luxury of paired domains," Trends in Biochemical Sciences, Apr. 1, 2001, 26(4):230-5.
Muyldermans, "Nanobodies: natural single-domain antibodies," Annual Review of Biochemistry, Jun. 2, 2013, 82:775-97.
Muyldermans, "Single domain camel antibodies: current status," Reviews in Molecular Biotechnology, Jun. 1, 2001, 74(4):277-302.
Myung et al., "Evidence of DNA damage in Alzheimer disease: phosphorylation of histone H2AX in astrocytes," Age, Apr. 23, 2008, 30(4):209-215.
Nag et al., "Soluble MHC II-peptide complexes induce antigen-specific apoptosis in T cells, " Cellular Immunology, May 25, 1996, 170(1):25-33.
Nayyar et al., "Overcoming Resistance to Natural Killer Cell Based Immunotherapies for Solid Tumors," Frontiers in Oncology, 2019, 9: 28 pages.
Nelson et al., "A senescent cell bystander effect: senescence-induced senescence," Aging Cell, Feb. 9, 2012, 11(2):345-349.
Nilsson et al., "Targeted delivery of tissue factor to the ED-B domain of fibronectin, a marker of angiogenesis, mediates the infarction of solid tumors in mice," Cancer Research, American Association for Cancer Researc, Proceddings: AACR 107th Annual Meeting, 2016, Apr. 16-20, 2016, New Orleans, LA 61(2):711-716.
Nishida et al., "CD26 is a potential therapeutic target by humanized monoclonal antibody for the treatment of multiple myeloma," Blood Cancer Journal, Oct. 22, 2018, 8(11):99, 17 pages.
O'Sullivan et al., "Natural Killer Cell Memory," Immunity, Oct. 20, 2015, 43(4):634-645.
Oberle et al., "Rapid Suppression of Cytokine Transcription in Human CD4+CD25-T Cells by CD4+Foxp3+ Regulatory T Cells: Independence of IL-2 Consumption, TGF-β, and Various Inhibitors of TCR Signaling, " The Journal of Immunology, Sep. 15, 2007, 179(6):3578-3587.
Ogrodnik et al., "Cellular senescence drives age-dependent hepatic steatosis," Nat Commun. Jun. 13, 2017;8:15691, 12 pages.
Ogrodnik et al., "Obesity-Induced Cellular Senescence Drives Anxiety and Impairs Neurogenesis," Cell Metabolism, May 2019, 29(5):1061-1077, 25 pages.
Ohnuma et al., "Blockade of CD26-mediated T cell costimulation with soluble caveolin-1-Ig fusion protein induces anergy in CD4+T cells," Biochemical and Biophysics Research Communications, Aug. 21, 2009, 386(2):327-332.
Ohnuma et al., "CD26 Mediates Dissociation of Tollip and IRAK-1 from Caveolin-1 and Induces Upregulation of CD86 on Antigen-Presenting Cells," Molecular and Cellular Biology, Sep. 1, 2005, 25(17):7743-7757.
Ohnuma et al., "CD26 up-regulates expression of CD86 on antigen-presenting cells by means of caveolin-1," Proc. Natl. Acad. Sci. U.S.A., Sep. 28, 2004, 101(39):14186-14191.
Ohnuma et al., "Role of CD26/dipeptidyl peptidase IV in human T cell activation and function," Frontiers in Bioscience, Jan. 1, 2008, 13:2299-2310.
Ohnuma et al., "Soluble CD26/Dipeptidyl Peptidase IV Induces T Cell Proliferation Through CD86 Up-Regulation on APCs," Journal of Immunology, Dec. 15, 2001, 167(12):6745-6755.
Ovadya et al., "Strategies targeting cellular senescence," The Journal of Clinical Investigation, Apr. 2, 2018, 128(4):1247-54.
Owicki et al., "Biosensors based on the energy metabolism of living cells: the physical chemistry and cell biology of extracellular acidification," Biosensors and Bioelectronics, Jan. 1, 1992, 7(4):255-272.
Padutsch et al., "Superior Treg-Expanding Properties of a Novel Dual-Acting Cytokine Fusion Protein," Frontiers in Pharmacology, Dec. 18, 2019, 10:1490, 10 pages.
Palmer et al., "Cellular Senescence in Type 2 Diabetes: A Therapeutic Opportunity," Diabetes, Jul. 2015, 64(7):2289-2298.
Parker et al., "Design, production, and characterization of a single-chain variable fragment (ScFv) derived from the prostate specific membrane antigen (PSMA) monoclonal antibody J591," Protein Expression and Purification, Jun. 1, 2013, 89(2):136-45.
Peipp et al., "HER2-specific immunoligands engaging NKp30 or NKp80 trigger NK-cell-mediated lysis of tumor cells and enhance antibody-dependent cell-mediated cytotoxicity," Oncotarget, Oct. 13, 2015, 6(31):32075.
Pittayapruek et al., "Role of Matrix Metalloproteinases in Photoaging and Photocarcinogenesis," International Journal of Molecular Sciences, 2016, 17(6):868, 20 pages.
Price et al., "Comparison of collagenase-cleaved articular cartilage collagen in mice in the naturally occurring STR/ort model of osteoarthritis and in collagen-induced arthritis," Osteoarthritis Cartilage, Mar. 2002, 10(3):172-179.
Priyanka et al., "Linkers in the structural biology of protein-protein interactions," Protein Sci., 2013, 22(2):153-167.
Purohit et al., "Smad3-dependent regulation of type I collagen in human dermal fibroblasts: Impact on human skin connective tissue aging," Journal of Dermatological Science, Jul. 2016, 83(1):80-83.
Qin et al., "Critical Role of P2Y12 Receptor in Regulation of Th17 Differentiation and Experimental Autoimmune Encephalomyelitis Pathogenesis," The Journal of Immunology, Jul. 1, 2017, 199(1):72-81.
Rafei et al., "Off-the-shelf virus specific T-cells for therapy of adenovirus disease in immunosuppressed patients," Journal of Clinical Oncology, May 26, 2019, 37(15 Suppl.):7008, 2 pages.
Rahbarizadeh et al., "Nanobody; an old concept and new vehicle for immunotargeting," Immunological Investigations, Jan. 1, 2011, 40(3):299-338.
Raj et al., "Adenosine Deaminase Acts as a Natural Antagonist for Dipeptidyl Peptidase 4-Mediated Entry of the Middle East Respiratory Syndrome Coronavirus," Journal of Virology, Feb. 2014, 88(3):1834-1838, 7 pages.
Ranganathan et al., "Pinpointing the putative heparin/sialic acid-binding residues in the 'sushi' domain 7 of factor H: a molecular modeling study," Biocomputing 2000, 1999, 155-67.
Rao et al., "Purification and characterization of rabbit tissue factor," Thrombosis Research, Oct. 1, 1989, 56(1):109-118.
Rasmussen et al., "Crystal structure of human dipeptidyl peptidase IV/CD26 in complex with a substrate analog," Nature Structural and Molecular Biology, 2003, 10(1):19-25.
Raz et al., "Efficacy and safety of the dipeptidyl peptidase-4 inhibitor sitagliptin as monotherapy in patients with type 2 diabetes mellitus," Diabetologia, Sep. 26, 2006, 49(11):2564-2571.
Resta et al., "Ecto-enzyme and signaling functions of lymphocyte CD 7 3," Immunological Reviews, 1998, 161:95-109.

(56) References Cited

OTHER PUBLICATIONS

Rhein et al., "Characterization of Human and Murine T-Cell Immunoglobulin Mucin Domain 4 (TIM-4) IgV Domain Residues Critical for Ebola Virus Entry," J Viral., 2016, 90(13):6097-6111.

Rippmann et al., "Fusion of the Tissue Factor Extracellular Domain to a Tumor Stromaspecific Single-Chain Fragment Variable Antibody Results in an Antigen-Specific Coagulation-Promoting Molecule," Biochemical Journal, 2000, 349(3):805-812.

Rittie et al., "Natural and Sun-Induced Aging of Human Skin," Cold Spring Harbor Perspective in Medicine, 2015, 5(1):a015370, 15 pages.

Rocha et al., "A novel immunofluorescent assay to investigate oxidative phosphorylation deficiency in mitochondrial myopathy: understanding mechanisms and improving diagnosis," Scientific reports, Oct. 15, 2015, 5:15037, 17 Pages.

Rodier et al., "Persistent DNA damage signaling triggers senescence-associated inflammatory cytokine secretion," Nature Cell Biology, Jul. 13, 2009, 11(8): 15 pages.

Rogge et al., "Antibodies to the IL-12 receptor β2 chain mark human Th1 but not Th2 cells in vitro and in vivo," The Journal of Immunology, Apr. 1, 1999, 162(7):3926-32.

Roh et al., "Damage-Associated Molecular Patterns in Inflammatory Diseases," Immune Network, Aug. 2018, 18(4):e27, 14 pages.

Romano et al., "Past, Present, and Future of Regulatory T Cell Therapy in Transplantation and Autoimmunity," Frontiers in Immunology, Jan. 1, 2019, 10:43, 14 pages.

Romee et al., "Cytokine activation induces human memory-like NK cells," Blood, Dec. 6, 2012, 120(24):4751-4760.

Rossi et al., "Complex and defined biostructures with the dock-and-lock method," Trends in Pharmacological Sciences, Sep. 1, 2012, 33(9):474-81.

Rossi et al., "Stably tethered multifunctional structures of defined composition made by the dock and lock method for use in cancer targeting," Proceedings of the National Academy of Sciences, May 2, 2006, 103(18):6841-6.

Rubinstein et al., "Converting IL-15 to a superagonist by binding to soluble IL-15Rα," Proceedings of the National Academy of Sciences U.S.A., Jun. 13, 2006, 103(24):9166-9171.

Ruf et al., "Cofactor residues lysine 165 and 166 are critical for protein substrate recognition by the tissue factor-factor VIIa protease complex," Journal of Biological Chemistry, Mar. 25, 1992, 267(9):6375-81.

Ruf et al., "Tissue factor residues 157-167 are required for efficient proteolytic activation of factor X and factor VII," Journal of Biological Chemistry, Nov. 5, 1992, 267(31):22206-10.

Ruscetti et al., "NK cell-mediated cytotoxicity contributes to tumor control by a cytostatic drug combination," Science, Dec. 21, 2018, 362(6421):1416-1422, 8 pages.

Sagiv et al., "Granule exocytosis mediates immune surveillance of senescent cells," Oncogene, 2013, 32(15):1971-1977.

Sakaguchi et al., "Regulatory T Cells and Human Disease," Annual Review of Immunology, Apr. 26, 2020, 38:541-566.

Sakaguchi et al., "Regulatory T Cells and Immune Tolerance," Cell, May 30, 2008, 133(5):775-787.

Sakaguchi et al., "Regulatory T cells: how do they suppress immune responses?" International Immunology, Sep. 7, 2009, 21(10):1105-1111.

Sakamoto et al., "Phase I clinical trial of autologous NK cell therapy using novel expansion method in patients with advanced digestive cancer," Journal of Translational Medicine, Aug. 25, 2015, 13:277, 13 pages.

Sakamuri et al., "Measurement of respiratory function in isolated cardiac mitochondria using Seahorse XFe24 Analyzer: applications for aging research," Geroscience, Jun. 1, 2018, 40(3):347-356.

Salminen et al., "Emerging role of NF-κB signaling in the induction of senescence-associated secretory phenotype (SASP)," Cellular Signaling, Apr. 2012, 24(4):835-845.

Sandusky et al., "Regulation of 2B4 (CD244)-mediated NK cell activation by ligand-induced receptor modulation," European Journal of Immunology, Dec. 2006, 36(12):3268-76.

Sato et al., "Recombinant soluble murine IL-4 receptor can inhibit or enhance IgE responses in vivo," The Journal of Immunology, Apr. 1, 1993, 150:2717-2723.

Schafer et al., "Cellular senescence mediates fibrotic pulmonary disease," Nat Commun., Feb. 2017, 8:14532, 11 pages.

Schullek et al., "Key ligand interface residues in tissue factor contribute independently to factor VIIa binding," Journal of Biological Chemistry, Jul. 29, 1994, 269(30):19399-403.

Schwoppe et al., "Tissue-factor fusion proteins induce occlusion of tumor vessels," Thrombosis Research, Apr. 1, 2010, 125:S143-S150.

Seo et al., "Positive Feedback Loop between Plasminogen Activator Inhibitor-1 and Transforming Growth Factor-Beta1 during Renal Fibrosis in Diabetes," American Journal of Nephrology, Sep. 25, 2009, 30:481-490.

Sharkey et al., "Improved Therapeutic Results by Pretargeted Radioimmunotherapy of Non-Hodgkin's Lymphoma with a New Recombinant, Trivalent, Anti-CD20, Bispecific Antibody," Cancer Research, Jul. 1, 2008, 68(13):5282-90.

Sharma et al., "Regulatory T Cells License Macrophage Pro Resolving Functions During Atherosclerosis Regression," Circulation Research, Apr. 27, 2020, 127:335-353.

Smith et al., "Antigen Nature and Complexity Influence Human Antibody Light Chain Usage and Specificity," Vaccine, 2016, 34(25): 2813-2820.

Smith et al., "Development and evaluation of an optimal human single-chain variable fragment-derived BCMA-targeted CAR T cell vector," Molecular Therapy, Jun. 6, 2018, 26(6):1447-56.

Soerensen et al., "Safety, PK/PD, and anti-tumor activity of RO6874281, an engineered variant of interleukin-2 (IL-2v) targeted to tumor-associated fibroblasts via binding to fibroblast activation protein (FAP)," Journal of Clinical Oncology, Jun. 1, 2018, 36(No. 15 Suppl.):e15155, 2 pages.

Sondel et al., "Combination Therapy with Interleukin-2 and Antitumor Monoclonal Antibodies," Cancer Journal from Scientific American, Jan. 1, 1997, 3(Suppl. 1):S121-S127.

Sone et al., "Pancreatic beta cell senescence contributes to the pathogenesis of type 2 diabetes in high-fat diet-induced diabetic mice," Diabetologia, 2005, 48(1):58-67.

Song et al., "IL-12/IL-18-preactivated donor NK cells enhance GVL effects and mitigate GvHD after allogeneic hematopoietic stem cell transplantation," European Journal of Immunology, Apr. 2018, 48(4):670-682.

Soriani et al., "ATM-ATR-dependent up-regulation of DNAM-1 and NKG2D ligands on multiple myeloma cells by therapeutic agents results in enhanced NK-cell susceptibility and is associated with a senescent phenotype," Blood, Apr. 9, 2009, 113(15):3503-11.

Sousa-Victor et al., "Geroconversion of aged muscle stem cells under regenerative pressure," Cell Cycle, Oct. 15, 2014, 13(20):3183-3190.

Spiess et al., "Alternative molecular formats and therapeutic applications for bispecific antibodies," Molecular Immunology, Oct. 1, 2015, 67(2):95-106.

Stoklasek et al., "Combined IL-15/IL-15Rα Immunotherapy Maximizes IL-15 Activity In Vivo," The Journal of Immunology, Nov. 1, 2006, 177(9):6072-6080.

Storer et al., "Senescence is a Developmental Mechanism that Contributes to Embryonic Growth and Patterning," Cell, Nov. 21, 2013, 155(5):1119-1130.

Stryer, Biochemistry Fourth Edition, W. H. Freeman and Company, New York, 1995, pp. 18-23, 8 pages.

Swanson et al., "The NLRP3 inflammasome: molecular activation and regulation to therapeutics, " Nature Reviews Immunology, Apr. 29, 2019, 19(8):477-489, 13 pages.

Szalay et al., "Cutting edge: anti-CD1 monoclonal antibody treatment reverses the production patterns of TGF-β2 and Th1 cytokines and ameliorates listeriosis in mice," The Journal of Immunology, Jun. 15, 1999, 162(12):6955-8.

Tahara-Hanaoka et al., "Functional characterization of DNAM-1 (CD226) interaction with its ligands PVR (CD155) and nectin-2 (PRR-2/CD112)," International Immunology, Apr. 1, 2004, 16(4):533-8.

(56) References Cited

OTHER PUBLICATIONS

Takahashi et al., "Downregulation of cytoplasmic DNases is implicated in cytoplasmic DNA accumulation and SASP in senescent cells," Nature Communications, Mar. 28, 2018, 9:1249, 12 pages.
Takahashi et al., "Simple and inexpensive technique for measuring oxygen consumption rate in adherent cultured cells," The Journal of Physiological Sciences, Nov. 2017, 67(6):731-737.
Takeda et al., "Phase I study of YS110, a recombinant humanized monoclonal antibody to CD26, in Japanese patients with advanced malignant pleural mesothelioma," Lung Cancer, Nov. 2019, 137:64-70.
Tam et al., "Methods and strategies of peptide ligation," Peptide Science: Original Research on Biomolecules, 2001, 60(3):194-205.
Tanaka et al., "Cloning and functional expression of the T cell activation antigen CD26," Journal of Immunology, Jul. 15, 1992, 149(2):481-486.
Tang et al., "The Foxp3+ regulatory T cell: a jack of all trades, master of regulation," Nature Immunology, Feb. 19, 2008, 9(3):239-244.
Teissier et al., "The receptor for advanced glycation end-products (RAGE) is an important pattern recognition receptor (PRR) for inflammaging," Biogerontology, Apr. 9, 2019, 20(3):279-301, 23 pages.
Teng et al., "Structural assessment of the effects of amino acid substitutions on protein stability and protein proteininteraction," International journal of computational biology and drug design, Feb. 7, 2011, 3(4):334-349.
Theil et al., "Adoptive transfer of allogeneic regulatory T cells into patients with chronic graft-versus-host disease," Cytotherapy, Apr. 2015, 17(4):473-486, 14 pages.
Thonhoff et al., "Expanded autologous regulatory T-lymphocyte infusions in ALS," Neurology Neuroimmunology Neuroinflammation, May 18, 2018, 5(4):e465, 8 pages.
Tobin et al., "NK cells in childhood obesity are activated, metabolically stressed, and functionally deficient," JCI Insight, Dec. 21, 2017, 2(24):e94939, 9 pages.
Tomala et al., "In Vivo Expansion of Activated Naive CD8+ T Cells and NK Cells Driven by Complexes of IL-2 and Anti-IL-2 Monoclonal Antibody as Novel Approach of Cancer Immunotherapy," The Journal of Immunology, Oct. 15, 2009, 183:4904-4912.
Tominaga et al., "TGF-β Signaling in Cellular Senescence and Aging-Related Pathology," International Journal of Molecular Sciences, Oct. 10, 2019, 20(20):5002, 18 pages.
Trevani et al., "Extracellular acidification induces human neutrophil activation," The Journal of Immunology, Apr. 15, 1999, 162(8):4849-4857.
Tse et al., "ABT-263: A Potent and Orally Bioavailable Bcl-2 Family Inhibitor," Cancer Research, May 2008, 68(9):3421-3428.
Uryga et al., "Ageing induced vascular smooth muscle cell senescence in atherosclerosis," Journal of Physiology, Apr. 15, 2016, 594(8):2115-2124.
Vaishampayan et al., "A phase I trial of ALKS 4230, an engineered cytokine activator of NK and effector T cells, in patients with advanced solid tumors," Journal of Clinical Oncology, 2017, 35(15 Suppl.):TPS3111, 4 pages (Abstract Only).
Van Audenhove et al., "Nanobodies as versatile tools to understand, diagnose, visualize and treat cancer," EBioMedicine, Jun. 1, 2016, 8:40-8.
Van den Bergh et al., "IL-15 receptor alpha as the magic wand to boost the success of IL-15 antitumor therapies: The upswing of IL-15 transpresentation," Pharmacology and Therapeutics, 2017, 170:73-79.
Van Deursen, "The role of senescent cells in ageing," Nature, May 21, 2014, 509(7501):439-446.
Vankadari et al., "Emerging COVID-19 coronavirus: glycan shield and structure prediction of spike glycoprotein and its interaction with human CD26," Emerging Microbes and Infection, Mar. 17, 2020, 9(1):601-604.
Vidarsson et al., "IgG subclasses and allotypes: from structure to effector functions," Frontiers in immunology, Oct. 20, 2014, 5:520, 17 Pages.
Vincke et al., "Introduction to heavy chain antibodies and derived Nanobodies," Single Domain Antibodies, Humana Press, Totowa, NJ, 2012, pp. 15-26.
Voelker et al., "Anti-TGF-β1 Antibody Therapy in Patients with Diabetic Nephropathy," J Am Soc Nephrol., 2017, 28:953-962.
Voet et al., Biochemistry, John Wiley & Sons, Inc., 1990, pp. 126-128 and 228- 234, 12 pages.
Von Kobbe, "Cellular senescence: a view throughout organismal life," Cellular and Molecular Life Sciences, Jul. 20, 2018, 75:3553-3567, 15 pages.
Waaijer et al., "Do senescence markers correlate in vitro and in situ within individual human donors?," Aging Feb. 2018, 10(2):278-289.
Wallace et al., "B lymphocytes confer immune tolerance via cell surface GARP-TGF-β complex," JCI Insight., 2018, 3(7):e99863, 19 pages.
Walsh et al., "Inflammasomes in the CNS," Nature Reviews Neuroscience, Jan. 8, 2014, 15(2):84-97, 14 pages.
Wang et al., A New Recombinant Single Chain Trispecific Antibody Recruits T Lymphocytes to Kill CEA (Carcinoma Embryonic Antigen) Positive Tumor Cells In Vitro Efficiently, Journal of Biochemisty, 2004, 135(4):555-565.
Wang et al., "Biomarkers of Cellular Senescence and Skin Aging," Frontiers in Genetics, Aug. 23, 2018, 9:247, 14 pages.
Wang et al., "Loss of lamin B1 is a biomarker to quantify cellular senescence in photoaged skin," Scientific Reports, Nov. 15, 2017, 7(1):15678, 8 pages.
Wang et al., "Recombinant human CD137L for cancer immunotherapy: effects of different fusions and linkers on its activity," Cancer Immunol Immunother., 2012, 61(4):489-495.
Washburn et al., "A potential role for shed soluble major histocompatibility class I molecules as modulators of neurite outgrowth," PLoS One, Mar. 31, 2011, 6(3):e18439.
Weber et al., "Specific low-affinity recognition of major histocompatibility complex plus peptide by soluble T-cell receptor," Nature, Apr. 1992, 356(6372):793.
Weihermann et al., "Elastin structure and its involvement in skin photoageing," International Journal of Cosmetic Science, Jun. 2017, 39(3):241-247.
Weihofen et al., "Crystal Structure of CD26/Dipeptidyl-peptidase IV in Complex with Adenosine Deaminase Reveals a Highly Amphiphilic Interface," Journal of Biological Chemistry, Oct. 2004, 279(41):43330-43335.
Weiner et al., "Antibody-based immunotherapy of cancer," Cell, Mar. 16, 2012, 148(6):1081-4.
Weiss et al., "Formyl-Peptide Receptors in Infection, Inflammation, and Cancer," Trends in Immunology, Oct. 2018, 39(10):815-829, 15 pages.
Wesolowski et al., "Single domain antibodies: promising experimental and therapeutic tools in infection and immunity," Medical Microbiology and Immunology. Aug. 1, 2009, 198(3):157-74.
Wiemann et al., "Hepatocyte telomere shortening and senescence are general markers of human liver cirrhosis," The FASEB Journal, Jul. 2002, 16(9):935-942.
Wilchek et al., "Essentials of biorecognition: The (strept) avidin-biotin system as a model for protein-protein and protein-ligand interaction," Immunology letters, Feb. 28, 2006, 103(1): Abstract 2 pages.
Wiley et al., "Mitochondrial Dysfunction Induces Senescence with a Distinct Secretory Phenotype," Cell Metabolism, Feb. 9, 2016, 23(2):303-314.
Witkowsa et al., "Soluble intercellular adhesion molecule-1 (sICAM-1): an overview," Eur Cytokine Netw. 2004, 15(2):91-98.
Xiong et al., "Maternal uterine NK cell-activating receptor KIR2DS1 enhances placentation," The Journal of Clinical Investigation, Oct. 1, 2013, 123(10):4264-72.
Xu et al., "Celecoxib attenuates cachectic events in mice by modulating the expression of vascular endothelial growth factor," Mol Med Rep., Jan. 2015, 11(1):289-294.

(56) References Cited

OTHER PUBLICATIONS

Xu et al., "JAK inhibition alleviates the cellular senescence-associated secretory phenotype and frailty in old age," Proceedings of the National Academy of Sciences U.S.A., Nov. 17, 2015, 112(46):E6301-6310, 10 pages.
Xu et al., "Senolytics improve physical function and increase lifespan in old age," Nature Medicine, Aug. 2018, 24(8):1246, 15 pages.
Xu et al., "Transplanted senescent cells induce an osteoarthritis-like condition in mice," The Journals of Gerontology: Series A, Jun. 1, 2017, 72(6):780-5.
Yamamoto et al., "Measurement of glucose uptake in cultured cells," Curr Protoc Pharmacol, Dec. 2011, Chapter 12:12.14.1-12.14.22.
Yamazaki et al., "Vascular Cell Senescence Contributes to Blood-Brain Barrier Breakdown," Stroke, Feb. 16, 2016, 47(4):1068-1077, 15 pages.
Yan et al., "Obesity- and aging-induced excess of central transforming growth factor-β potentiates diabetic development via an RNA stress response," Nature Medicine, Aug. 3, 2014, 20:1001-1008, 9 pages.
Yanai et al., "Cellular senescence-like features of lung fibroblasts derived from idiopathic pulmonary fibrosis patients," Aging (Albany NY), Sep. 2015, 7(9):664-672.
Yigit et al., "A combination of an anti-SLAMF6 antibody and ibrutinib efficiently abrogates expansion of chronic lymphocytic leukemia cells," Oncotarget, May 3, 2016, 7(18):26346.
Yousefzadeh et al., "An aged immune system drives senescence and ageing of solid organs," Nature, May 12, 2021, 594:100-105, 34 pages.
Yu et al., "Targeting the Senescence-Overriding Cooperative Activity of Structurally Unrelated H3K9 Demethylases in Melanoma," Cancer Cell, Feb. 12, 2018, 33(2):322-336, 23 pages.
Yu et al., "The dipeptidyl peptidase IV family in cancer and cell biology," FEBS Journal, Feb. 5, 2010, 277(5):1126-1144.
Yun et al., "Recurrent turnover of senescent cells during regeneration of a complex structure," Elife, May 5, 2015, 4:e05505, 16 pages.
Yung et al., "A selective transforming growth factor-β ligand trap attenuates pulmonary hypertension," American Journal of Respiratory and Critical Care Medicine, Nov. 1, 2016, 194(9):1140-51.
Zhang et al., "AAED1 modulates proliferation and glycolysis in gastric cancer," Oncology Reports, Aug. 1, 2018, 40(2):1156-1164.
Zhang et al., "Depletion of NK cells improves cognitive function in the Alzheimer disease mouse model, " The Journal of Immunology, Jul. 15, 2020, 205(2): 10pages.
Zhang et al., "The bone anabolic effects of irisin are through preferential stimulation of aerobic glycolysis," Bone, Sep. 1, 2018, 114:150-160.
Zhao et al., "Histone Deacetylase-3 Modification of MicroRNA-31 Promotes Cell Proliferation and Aerobic Glycolysis in Breast Cancer and is Predictive of Poor Prognosis, " Journal of breast cancer, Jun. 1, 2018, 21(2):112-123.
Zheng et al., "Acquisition of Suppressive Function by Activated Human CD4+CD25-T Cells is Associated with the Expression of CTLA-4 not FoxP3," The Journal of Immunology, Aug. 1, 2008, 181(3):1683-1691.
Zhong et al., "A Potential Role for Dendritic Cell/Macrophage-Expressing DPP4 in Obesity-Induced Visceral Inflammation," Diabetes, Jan. 2013, 62(1):149-157.
Zhou et al., "A novel chimeric antigen receptor redirecting T-cell specificity towards CD26cancer cells," Leukemia, Apr. 2020, 35(1):119-129, 11 pages.
Zhu et al., "New agents that target senescent cells: the flavone, fisetin, and the BCL-XL inhibitors, A1331852 and A1155463," Aging (Albany NY), Mar. 2017, 9(3):955-963.
Zhu et al., "Novel Human Interleukin-15 Agonists," The Journal of Immunology, Sep. 15, 2009, 183(6):3598-3607.
Zou et al., "2-NBDG as a fluorescent indicator for direct glucose uptake measurement," Journal of biochemical and biophysical methods, Sep. 30, 2005, 64(3):207-215.
Zwaagstra et al., "Engineering and therapeutic application of single-chain bivalent TGF-β family traps," Molecular Cancer Therapeutics, Jul. 1, 2012, 11(7):1477-87.
Shen et al., "Engineering peptide linkers for scFv immunosensors," Anal Chem., Mar. 2008, 80(6):1910-1917.
U.S. Appl. No. 19/389,881, filed Nov. 14, 2025, Wong.
U.S. Appl. No. 19/551,027, filed Feb. 26, 2026, Wong et al.
Auerbach et al., "Angiogenesis assays: problems and pitfalls," Cancer and Metastasis Reviews, 2000, vol. 19, pp. 167-172.
Beans, "Targeting metastasis to halt cancer's spread," Proceedings of the National Academy of Sciences, 2018, vol. 115(50), pp. 12539-12543.
Brown et al., Tolerance to Single, but Not Multiple, Amino Acid Replacements in Antibody VH CDR2, Journal of Immunology, May 1996, vol. 156(9), pp. 3285-3291.
Chen et al., "Fusion protein linkers: Property, design and functionality," Advanced Drug Delivery Reviews, Oct. 15, 2013, Fol. 65(10), pp. 1357-1369.
Chen et al., "A novel idea for establishing Parkinson's disease mouse model by intranasal administration of paraquat," Neurological Research, 2021, 43(4):267-277, 11 pages.
Christiansen et al., "Biological impediments to monoclonal antibody-based cancer immunotherapy," Molecular Cancer Therapeutics, 2004, vol. 3, pp. 1493-1501.
Gao et al., "Natural killer and natural killer T cells in liver fibrosis," Biochimica et Biophysica Acta, 2013, vol. 1832, pp. 1061-1069.
GE Healthcare, "Affinity Chromatography, Vol. 3: Specific Groups of Biomolecules, " Handbooks for GE Healthcare Life Sciences, 2016, 153 pages.
Goebel et al., "Structural biology of the TGF-β family," Experimental Biology and Medicine, 2019, vol. 244, pp. 1530-1546.
Gravanis et al., "The changing world of cancer drug development: the regulatory bodies' perspective," Chinese Clinical Oncology, 2014, vol. 3, pp. 1-5.
Gura, "Systems for identifying new drugs are often faulty," Science, 1997, vol. 278(5340), pp. 1041-1042.
Hait, "Anticancer drug development: the grand challenges," Nature Reviews/Drug Discovery, 2010, vol. 9, pp. 253-254.
Heppner et al., "Tumor heterogeneity: biological implications and therapeutic consequences," Cancer Metastasis Review, 1983, vol. 2, pp. 5-23.
Jain, "Barriers to drug delivery in solid tumors," Scientific American, Jul. 1994, pp. 58-65.
Kajdaniuk et al., Transforming growth factor β1 (TGF β1) in physiology and pathology, Endokrynol Polska, 2013, vol. 65(5), pp. 384-396.
Kulmanov et al., "DeepGO: predicting protein functions from sequence and interactions using a deep ontology-aware classifier," Bioinformatics, 2018, vol. 34(4), pp. 660-668.
Miosge et al., "Comparison of predicted and actual consequences of missense mutations," Proceedings of the National Academy of Sciences USA, Sep. 15, 2015, vol. 112(37), pp. E5189-E5198.
Ng et al., "Stimulation of Natural Killer Cell-Mediated Tumor Immunity by an IL 15/TGFβ-Neutralizing Fusion Protein," Cancer Research, Oct. 1, 2016, vol. 76(19), pp. 5683-5695.
Prasad et al., "Molecular determinants involved in differential behavior between soluble tissue factor and full-length tissue factor towards factor VIIa," Phys. Chem. Chem. Phys., 2017, vol. 19, pp. 22230-22242.
Quatromoni et al., "The timing of TGF-β inhibition affects the generation of antigen-specific CD8+ T Cells," BMC Immunology, 2013, vol. 14(30), 16 pages.
Radaev et al., Ternary Complex of Transforming Growth Factor-β1 Reveals Isoform-specific Ligand Recognition and Receptor Recruitment in the Superfamily, Journal of Biological Chemistry, May 7, 2010, vol. 285(19), pp. 14806-14814.
Ring et al., "Mechanistic and structural insight into the functional dichotomy between IL-2 and IL-15," (Nature immunology, Dec. 2012, vol. 13(12), pp. 1187-1195.
Sporn et al., "Chemoprevention of Cancer," Carcinogenesis, 2000, vol. 21(3), pp. 525-530.
Topp et al., "Antibody transport in cultured tumor cell layers," Journal of Controlled Release, 1998, vol. 53, pp. 15-23.
Vadivel et al., Structural biology of factor VIIa/tissue factor initiated coagulation, Frontiers in Bioscience, Jun. 1, 2012, vol. 17, pp. 2476-2494.

(56) References Cited

OTHER PUBLICATIONS

Vajdos et al., "Comprehensive Functional Maps of the Antigen-binding Site of an Anti-ErbB2 Antibody Obtained with Shotgun Scanning Mutagenesis," Journal of Molecular Biology, Jul. 5, 2002, vol. 320(2), pp. 415-428.
Zhang et al., "TGF-β Family Signaling in the Control of Cell Proliferation and Survival," (Cold Spring Harbor Perspective in Biology, Apr. 3, 2017, vol. 9(4), a022145).
Zhou et al., "One-Way Allosteric Communication between the Two Disulfide Bonds in Tissue Factor," Biophysical Journal, Jan. 10, 2017, vol. 112, pp. 78-86.

* cited by examiner

SEQUENCE LISTING

```
Sequence total quantity: 198
SEQ ID NO: 1            moltype = AA  length = 219
FEATURE                 Location/Qualifiers
REGION                  1..219
                        note = soluble human tissue factor domain
source                  1..219
                        mol_type = protein
                        organism = Homo sapiens
SEQUENCE: 1
SGTTNTVAAY NLTWKSTNFK TILEWEPKPV NQVYTVQIST KSGDWKSKCF YTTDTECDLT  60
DEIVKDVKQT YLARVFSYPA GNVESTGSAG EPLYENSPEF TPYLETNLGQ PTIQSFEQVG  120
TKVNVTVEDE RTLVRRNNTF LSLRDVFGKD LIYTLYYWKS SSSGKKTAKT NTNEFLIDVD  180
KGENYCFSVQ AVIPSRTVNR KSTDSPVECM GQEKGEFRE                         219

SEQ ID NO: 2            moltype = DNA  length = 657
FEATURE                 Location/Qualifiers
misc_feature            1..657
                        note = Soluble Human Tissue Factor Domain
```

```
source                  1..657
                        mol_type = unassigned DNA
                        organism = Homo sapiens
SEQUENCE: 2
agcggcacaa ccaacacagt cgctgcctat aacctcactt ggaagagcac caacttcaaa  60
accatcctcg aatgggaacc caaacccgtt aaccaagttt acaccgtgca gatcagcacc  120
aagtccggcg actggaagtc caaatgtttc tataccaccg acaccgagtg cgatctcacc  180
gatgagatcg tgaaagatgt gaaacagacc tacctcgccc gggtgtttag ctaccccgcc  240
ggcaatgtgg agagcactgg ttccgctggc gagcctttat acgagaacag ccccgaattt  300
acccccttacc tcgagaccaa tttaggacag cccaccatcc aaagctttga gcaagttggc  360
acaaaggtga atgtgacagt ggaggacgag cggactttag tgcggcggaa caacaccttt  420
ctcagcctcc gggatgtgtt cggcaaagat ttaatctaca cactgtatta ctggaagtcc  480
tcttcctccg gcaagaagac agctaaaacc aacacaaacg agtttttaat cgacgtggat  540
aaaggcgaaa actactgttt cagcgtgcaa gctgtgatcc cctcccggac cgtgaatagg  600
aaaagcaccg atagccccgt tgagtgcatg ggccaagaaa agggcgagtt ccgggag     657

SEQ ID NO: 3            moltype = AA  length = 223
FEATURE                 Location/Qualifiers
REGION                  1..223
                        note = Soluble Mouse Tissue Factor domain
source                  1..223
                        mol_type = protein
                        organism = Mus musculus
SEQUENCE: 3
AGIPEKAFNL TWISTDFKTI LEWQPKPTNY TYTVQISDRS RNWKNKCFST TDTECDLTDE  60
IVKDVTWAYE AKVLSVPRRN SVHGDGDQLV IHGEEPPFTN APKFLPYRDT NLGQPVIQQF  120
EQDGRKLNVV VKDSLTLVRK NGTFLTLRQV FGKDLGYIIT YRKGSSTGKK TNITNTNEFS  180
IDVEEGVSYC FFVQAMIFSR KTNQNSPGSS TVCTEQWKSF LGE                223

SEQ ID NO: 4            moltype = AA  length = 224
FEATURE                 Location/Qualifiers
REGION                  1..224
                        note = Soluble rat Tissue Factor domain
source                  1..224
                        mol_type = protein
                        organism = Rattus rattus
SEQUENCE: 4
AGTPPGKAFN LTWISTDFKT ILEWQPKPTN YTYTVQISDR SRNWKYKCTG TTDTECDLTD  60
EIVKDVNWTY EARVLSVPWR NSTHGKETLF GTHGEEPPFT NARKFLPYRD TKIGQPVIQK  120
YEQGGTKLKV TVKDSFTLVR KNGTFLTLRQ VFGNDLGYIL TYRKDSSTGR KTNTTHTNEF  180
LIDVEKGVSY CFFAQAVIFS RKTNHKSPES ITKCTEQWKS VLGE               224

SEQ ID NO: 5            moltype = AA  length = 219
FEATURE                 Location/Qualifiers
REGION                  1..219
                        note = Mutant Soluble Human Tissue Factor Domain
source                  1..219
                        mol_type = protein
                        organism = Homo sapiens
SEQUENCE: 5
SGTTNTVAAY NLTWKSTNFA TALEWEPKPV NQVYTVQIST KSGDWKSKCF YTTDTECALT  60
DEIVKDVKQT YLARVFSYPA GNVESTGSAG EPLYENSPEF TPYLETNLGQ PTIQSFEQVG  120
TKVNVTVEDE RTLVARNNTA LSLRDVFGKD LIYTLYYWKS SSSGKKTAKT NTNEFLIDVD  180
KGENYCFSVQ AVIPSRTVNR KSTDSPVECM GQEKGEFRE                     219

SEQ ID NO: 6            moltype = AA  length = 219
FEATURE                 Location/Qualifiers
REGION                  1..219
                        note = Mutant Soluble Human Tissue Factor Domain
source                  1..219
                        mol_type = protein
                        organism = Homo sapiens
SEQUENCE: 6
SGTTNTVAAY NLTWKSTNFA TALEWEPKPV NQVYTVQIST KSGDAKSKCF YTTDTECALT  60
DEIVKDVKQT YLARVFSYPA GNVESTGSAG EPLAENSPEF TPYLETNLGQ PTIQSFEQVG  120
TKVNVTVEDE RTLVARNNTA LSLRDVFGKD LIYTLYYWKS SSSGKKTAKT NTNEFLIDVD  180
KGENYCFSVQ AVIPSRTVNR KSTDSPVECM GQEKGEFRE                     219

SEQ ID NO: 7            moltype = AA  length = 15
FEATURE                 Location/Qualifiers
REGION                  1..15
                        note = Description of Artificial Sequence: Synthetic linker
                         sequence
source                  1..15
                        mol_type = protein
                        organism = synthetic construct
SEQUENCE: 7
GGGGSGGGGS GGGGS                                                   15
```

```
SEQ ID NO: 8            moltype = DNA  length = 45
FEATURE                 Location/Qualifiers
misc_feature            1..45
                        note = Description of Artificial Sequence: Synthetic linker
                         sequence
source                  1..45
                        mol_type = other DNA
                        organism = synthetic construct
SEQUENCE: 8
ggcggtggag gatccggagg aggtggctcc ggcggcggag gatct                  45

SEQ ID NO: 9            moltype = AA  length = 8
FEATURE                 Location/Qualifiers
REGION                  1..8
                        note = Description of Artificial Sequence: Synthetic linker
                         sequence
source                  1..8
                        mol_type = protein
                        organism = synthetic construct
SEQUENCE: 9
GGGSGGGS                                                           8

SEQ ID NO: 10           moltype = AA  length = 65
FEATURE                 Location/Qualifiers
REGION                  1..65
                        note = sushi domain from an alpha chain of IL-15 receptor
                         alpha (IL15Ralpha)
source                  1..65
                        mol_type = protein
                        organism = Homo sapiens
SEQUENCE: 10
ITCPPPMSVE HADIWVKSYS LYSRERYICN SGFKRKAGTS SLTECVLNKA TNVAHWTTPS  60
LKCIR                                                              65

SEQ ID NO: 11           moltype = DNA  length = 195
FEATURE                 Location/Qualifiers
misc_feature            1..195
                        note = sushi domain from an alpha chain of IL-15 receptor
                         alpha (IL15Ralpha)
source                  1..195
                        mol_type = unassigned DNA
                        organism = Homo sapiens
SEQUENCE: 11
attacatgcc cccctcccat gagcgtggag cacgccgaca tctgggtgaa gagctatagc  60
ctctacagcc gggagaggta tatctgtaac agcggcttca agaggaaggc cggcaccagc  120
agcctcaccg agtgcgtgct gaataaggct accaacgtgg ctcactggac aacaccctct  180
ttaaagtgca tccgg                                                   195

SEQ ID NO: 12           moltype = DNA  length = 723
FEATURE                 Location/Qualifiers
misc_feature            1..723
                        note = Description of Artificial Sequence: Synthetic
                         anti-CD3 scFv sequence
source                  1..723
                        mol_type = other DNA
                        organism = synthetic construct
SEQUENCE: 12
cagatcgtgc tgacccaaag ccccgccatc atgagcgcta gccccggtga gaaggtgacc  60
atgacatgct ccgcttccag ctccgtgtcc tacatgaact ggtatcagca gaaaagcgga  120
accagcccca aaaggtggat ctacgacacc agcaagctgg cctccggagt gcccgctcat  180
ttccggggct ctggatccgg caccagctac tctttaacca tttccggcat ggaagctgaa  240
gacgctgcca cctactattg ccagcaatgg agcagcaacc ccttcacatt cggatctggc  300
accaagctcg aaatcaatcg tggaggaggt ggcagcggcg gcggtggatc cggcggagga  360
ggaagccaag ttcaactcca gcagagcggc gctgaactgg cccggcccgg cgcctccgtc  420
aagatgagct gcaaggcttc cggctataca tttactcgtt acacaatgca ttgggtcaag  480
cagaggcccg gtcaaggttt agagtggatc ggatatatca acccttcccg gggctacacc  540
aactataacc aaaagttcaa ggataaagcc actttaacca ctgacaagag ctcctccacc  600
gcctacatgc agctgtcctc tttaaccagc gaggactccg ctgtttacta ctgcgctagg  660
tattacgacg accactactg tttagactat tggggacaag gtaccacttt aaccgtcagc  720
agc                                                                723

SEQ ID NO: 13           moltype = DNA  length = 708
FEATURE                 Location/Qualifiers
misc_feature            1..708
                        note = Description of Artificial Sequence: Synthetic
                         anti-CD28 scFv sequence
source                  1..708
                        mol_type = other DNA
                        organism = synthetic construct
```

```
SEQUENCE: 13
gtccagctgc agcagagcgg acccgaactc gtgaaacccg gtgcttccgt gaaaatgtct  60
tgtaaggcca gcggatacac cttcacctcc tatgtgatcc agtgggtcaa acagaagccc  120
ggacaaggtc tcgagtggat cggcagcatc aacccttaca acgactatac caaatacaac  180
gagaagttta agggaaaggc tactttaacc tccgacaaaa gctccatcac agcctacatg  240
gagttcagct ctttaacatc cgaggacagc gctctgtact attgcgcccg gtggggcgac  300
ggcaattact ggggacgggg cacaacactg accgtgagca gcggaggcgg aggctccggc  360
ggaggcggat ctggcggtgg cggctccgac atcgagatga cccagtcccc cgctatcatg  420
tccgcctctt taggcgagcg ggtcacaatg acttgtacag cctcctccag cgtctcctcc  480
tcctacttcc attggtacca acagaaaccc ggaagctccc ctaaactgtg catctacagc  540
accagcaatc tcgccagcgg cgtgcccct aggttttccg gaagcggaag caccagctac  600
tctttaacca tctcctccat ggaggctgag gatgccgcca cctacttttg tcaccagtac  660
caccggtccc ccaccttcgg aggcggcacc aaactggaga caaagagg             708

SEQ ID NO: 14          moltype = DNA  length = 15
FEATURE                Location/Qualifiers
misc_feature           1..15
                       note = Description of Artificial Sequence: Synthetic
                        sequencing primer C186-IFNG135F
source                 1..15
                       mol_type = other DNA
                       organism = synthetic construct
SEQUENCE: 14
ggtgggtata atggg                                                  15

SEQ ID NO: 15          moltype = DNA  length = 25
FEATURE                Location/Qualifiers
misc_feature           1..25
                       note = Description of Artificial Sequence: Synthetic
                        sequencing primer C54-IFNG261F
source                 1..25
                       mol_type = other DNA
                       organism = synthetic construct
SEQUENCE: 15
attattttat tttaaaaaat ttgtg                                       25

SEQ ID NO: 16          moltype = AA  length = 119
FEATURE                Location/Qualifiers
REGION                 1..119
                       note = Description of Artificial Sequence: Synthetic
                        anti-CD3 scFv heavy chain variable domain sequence
source                 1..119
                       mol_type = protein
                       organism = synthetic construct
SEQUENCE: 16
QVQLQQSGAE LARPGASVKM SCKASGYTFT RYTMHWVKQR PGQGLEWIGY INPSRGYTNY  60
NQKFKDKATL TTDKSSSTAY MQLSSLTSED SAVYYCARYY DDHYCLDYWG QGTTLTVSS   119

SEQ ID NO: 17          moltype = AA  length = 107
FEATURE                Location/Qualifiers
REGION                 1..107
                       note = Description of Artificial Sequence: Synthetic
                        anti-CD3 scFv light chain variable domain sequence
source                 1..107
                       mol_type = protein
                       organism = synthetic construct
SEQUENCE: 17
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINR               107

SEQ ID NO: 18          moltype = DNA  length = 357
FEATURE                Location/Qualifiers
misc_feature           1..357
                       note = Description of Artificial Sequence: Synthetic
                        anti-CD3 scFv heavy chain variable domain sequence
source                 1..357
                       mol_type = other DNA
                       organism = synthetic construct
SEQUENCE: 18
caagttcagc tccagcaaag cggcgccgaa ctcgctcggc ccggcgcttc cgtgaagatg  60
tcttgtaagg cctccggcta taccttcacc cggtacacaa tgcactgggt caagcaacgg  120
cccggtcaag gtttagagtg gattggctat atcaacccct cccggggcta taccaactac  180
aaccagaagt tcaaggacaa agccaccctc accaccgaca agtccagcag caccgcttac  240
atgcagctga gctctttaac atccgaggat tccgccgtgt actactgcgc tcggtactac  300
gacgatcatt actgcctcga ttactggggc caaggtacca ccttaacagt ctcctcc    357
```

```
SEQ ID NO: 19          moltype = DNA  length = 321
FEATURE                Location/Qualifiers
misc_feature           1..321
                       note = Description of Artificial Sequence: Synthetic
                        anti-CD3 scFv light chain variable domain sequence
source                 1..321
                       mol_type = other DNA
                       organism = synthetic construct
SEQUENCE: 19
cagatcgtgc tgacccagtc ccccgctatt atgagcgcta gccccggtga aaaggtgact  60
atgacatgca gcgccagctc ttccgtgagc tacatgaact ggtatcagca gaagtccggc  120
accagcccta aaaggtggat ctacgacacc agcaagctgg ccagcggcgt ccccgctcac  180
tttcggggct ccggctccgg aacaagctac tctctgacca tcagcggcat ggaagccgag  240
gatgccgcta cctattactg tcagcagtgg agctccaacc ccttcacctt tggatccggc  300
accaagctcg agattaatcg t                                            321

SEQ ID NO: 20          moltype = AA  length = 241
FEATURE                Location/Qualifiers
REGION                 1..241
                       note = Description of Artificial Sequence: Synthetic
                        anti-CD3 scFv sequence
source                 1..241
                       mol_type = protein
                       organism = synthetic construct
SEQUENCE: 20
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINRGGG GSGGGGSGGG  120
GSQVQLQQSG AELARPGASV KMSCKASGYT FTRYTMHWVK QRPGQGLEWI GYINPSRGYT  180
NYNQKFKDKA TLTTDKSSST AYMQLSSLTS EDSAVYYCAR YYDDHYCLDY WGQGTTLTVS  240
S                                                                  241

SEQ ID NO: 21          moltype = DNA  length = 723
FEATURE                Location/Qualifiers
misc_feature           1..723
                       note = Description of Artificial Sequence: Synthetic
                        anti-CD3 scFv sequence
source                 1..723
                       mol_type = other DNA
                       organism = synthetic construct
SEQUENCE: 21
cagatcgtgc tgacccagtc ccccgctatt atgagcgcta gccccggtga aaaggtgact  60
atgacatgca gcgccagctc ttccgtgagc tacatgaact ggtatcagca gaagtccggc  120
accagcccta aaaggtggat ctacgacacc agcaagctgg ccagcggcgt ccccgctcac  180
tttcggggct ccggctccgg aacaagctac tctctgacca tcagcggcat ggaagccgag  240
gatgccgcta cctattactg tcagcagtgg agctccaacc ccttcacctt tggatccggc  300
accaagctcg agattaatcg tggaggcgga ggtagcggag gaggcggatc cggcggtgga  360
ggtagccaag ttcagctcca gcaaagcggc gccgaactcg ctcggcccgg cgcttccgtg  420
aagatgtctt gtaaggcctc cggctatacc ttcacccggt acacaatgca ctgggtcaag  480
caacggcccg gtcaaggttt agagtggatt ggctatatca acccctcccg gggctatacc  540
aactacaacc agaagttcaa ggacaaagcc accctcacca ccgacaagtc cagcagcacc  600
gcttacatgc agctgagctc tttaacatcc gaggattccg ccgtgtacta ctgcgctcgg  660
tactacgacg atcattactg cctcgattac tggggccaag gtaccacctt aacagtctcc  720
tcc                                                                723

SEQ ID NO: 22          moltype = AA  length = 107
FEATURE                Location/Qualifiers
REGION                 1..107
                       note = Description of Artificial Sequence: Synthetic
                        anti-CD28 scFv heavy chain variable domain sequence
source                 1..107
                       mol_type = protein
                       organism = synthetic construct
SEQUENCE: 22
DIEMTQSPAI MSASLGERVT MTCTASSSVS SSYFHWYQQK PGSSPKLCIY STSNLASGVP  60
PRFSGSGSTS YSLTISSMEA EDAATYFCHQ YHRSPTFGGG TKLETKR                107

SEQ ID NO: 23          moltype = AA  length = 114
FEATURE                Location/Qualifiers
REGION                 1..114
                       note = Description of Artificial Sequence: Synthetic
                        anti-CD28 scFv light chain variable domain sequence
source                 1..114
                       mol_type = protein
                       organism = synthetic construct
SEQUENCE: 23
VQLQQSGPEL VKPGASVKMS CKASGYTFTS YVIQWVKQKP GQGLEWIGSI NPYNDYTKYN  60
EKFKGKATLT SDKSSITAYM EFSSLTSEDS ALYYCARWGD GNYWGRGTTL TVSS        114
```

```
SEQ ID NO: 24          moltype = DNA  length = 321
FEATURE                Location/Qualifiers
misc_feature           1..321
                       note = Description of Artificial Sequence: Synthetic
                        anti-CD28 scFv heavy chain variable domain sequence
source                 1..321
                       mol_type = other DNA
                       organism = synthetic construct
SEQUENCE: 24
gacatcgaga tgacacagtc ccccgctatc atgagcgcct ctttaggaga acgtgtgacc  60
atgacttgta cagcttcctc cagcgtgagc agctcctatt tccactggta ccagcagaaa  120
cccggctcct cccctaaact gtgtatctac tccacaagca atttagctag cggcgtgcct  180
cctcgtttta gcggctccgg cagcacctct tactctttaa ccattagctc tatggaggcc  240
gaagatgccg ccacatactt ttgccatcag taccaccggt cccctacctt tggcggaggc  300
acaaagctgg agaccaagcg g                                            321

SEQ ID NO: 25          moltype = DNA  length = 342
FEATURE                Location/Qualifiers
misc_feature           1..342
                       note = Description of Artificial Sequence: Synthetic
                        anti-CD28 scFv light chain variable domain sequence
source                 1..342
                       mol_type = other DNA
                       organism = synthetic construct
SEQUENCE: 25
gtgcagctgc agcagtccgg acccgaactg gtcaagcccg gtgcctccgt gaaaatgtct  60
tgtaaggctt ctggctacac ctttacctcc tacgtcatcc aatgggtgaa gcagaagccc  120
ggtcaaggtc tcgagtggat cggcagcatc aatccctaca acgattacac caagtataac  180
gaaaagttta agggcaaggc cactctgaca agcgacaaga gctccattac cgcctacatg  240
gagttttcct ctttaacttc tgaggactcc gctttatact attgcgctcg ttggggcgat  300
ggcaattatt ggggccgggg aactacttta acagtgagct cc                     342

SEQ ID NO: 26          moltype = AA  length = 236
FEATURE                Location/Qualifiers
REGION                 1..236
                       note = Description of Artificial Sequence: Synthetic
                        anti-CD28 scFv sequence
source                 1..236
                       mol_type = protein
                       organism = synthetic construct
SEQUENCE: 26
VQLQQSGPEL VKPGASVKMS CKASGYTFTS YVIQWVKQKP GQGLEWIGSI NPYNDYTKYN  60
EKFKGKATLT SDKSSITAYM EFSSLTSEDS ALYYCARWGD GNYWGRGTTL TVSSGGGGSG  120
GGGSGGGGSD IEMTQSPAIM SASLGERVTM TCTASSSVSS SYFHWYQQKP GSSPKLCIYS  180
TSNLASGVPP RFSGSGSTSY SLTISSMEAE DAATYFCHQY HRSPTFGGGT KLETKR      236

SEQ ID NO: 27          moltype = DNA  length = 708
FEATURE                Location/Qualifiers
misc_feature           1..708
                       note = Description of Artificial Sequence: Synthetic
                        anti-CD28 scFv sequence
source                 1..708
                       mol_type = other DNA
                       organism = synthetic construct
SEQUENCE: 27
gtgcagctgc agcagtccgg acccgaactg gtcaagcccg gtgcctccgt gaaaatgtct  60
tgtaaggctt ctggctacac ctttacctcc tacgtcatcc aatgggtgaa gcagaagccc  120
ggtcaaggtc tcgagtggat cggcagcatc aatccctaca acgattacac caagtataac  180
gaaaagttta agggcaaggc cactctgaca agcgacaaga gctccattac cgcctacatg  240
gagttttcct ctttaacttc tgaggactcc gctttatact attgcgctcg ttggggcgat  300
ggcaattatt ggggccgggg aactacttta acagtgagct ccggcggcgg cggaagcgga  360
ggtggaggat ctggcggtgg aggcagcgac atcgagatga cacagtcccc cgctatcatg  420
agcgcctctt taggagaacg tgtgaccatg acttgtacag cttcctccag cgtgagcagc  480
tcctatttcc actggtacca gcagaaaccc ggctcctccc ctaaactgtg tatctactcc  540
acaagcaatt tagctagcgg cgtgcctcct cgttttagcg gctccggcag cacctcttac  600
tctttaacca ttagctctat ggaggccgaa gatgccgcca catacttttg ccatcagtac  660
caccggtccc ctacctttgg cggaggcaca aagctggaga ccaagcgg               708

SEQ ID NO: 28          moltype = AA  length = 133
FEATURE                Location/Qualifiers
REGION                 1..133
                       note = Human Soluble IL-2
source                 1..133
                       mol_type = protein
                       organism = Homo sapiens
SEQUENCE: 28
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133
```

```
SEQ ID NO: 29          moltype = AA  length = 133
FEATURE                Location/Qualifiers
REGION                 1..133
                       note = Human Soluble IL-3
source                 1..133
                       mol_type = protein
                       organism = Homo sapiens
SEQUENCE: 29
APMTQTTPLK TSWVNCSNMI DEIITHLKQP PLPLLDFNNL NGEDQDILME NNLRRPNLEA  60
FNRAVKSLQN ASAIESILKN LLPCLPLATA APTRHPIHIK DGDWNEFRRK LTFYLKTLEN  120
AQAQQTTLSL AIF                                                    133

SEQ ID NO: 30          moltype = DNA  length = 22
FEATURE                Location/Qualifiers
misc_feature           1..22
                       note = Description of Artificial Sequence: Synthetic
                        sequencing primer IFNG127F
source                 1..22
                       mol_type = other DNA
                       organism = synthetic construct
SEQUENCE: 30
atggtatagg tgggtataat gg                                          22

SEQ ID NO: 31          moltype = AA  length = 79
FEATURE                Location/Qualifiers
REGION                 1..79
                       note = Human Soluble IL-8
source                 1..79
                       mol_type = protein
                       organism = Homo sapiens
SEQUENCE: 31
EGAVLPRSAK ELRCQCIKTY SKPFHPKFIK ELRVIESGPH CANTEIIVKL SDGRELCLDP  60
KENWVQRVVE KFLKRAENS                                              79

SEQ ID NO: 32          moltype = AA  length = 160
FEATURE                Location/Qualifiers
REGION                 1..160
                       note = Human Soluble IL-10
source                 1..160
                       mol_type = protein
                       organism = Homo sapiens
SEQUENCE: 32
SPGQGTQSEN SCTHFPGNLP NMLRDLRDAF SRVKTFFQMK DQLDNLLLKE SLLEDFKGYL  60
GCQALSEMIQ FYLEEVMPQA ENQDPDIKAH VNSLGENLKT LRLRLRRCHR FLPCENKSKA  120
VEQVKNAFNK LQEKGIYKAM SEFDIFINYI EAYMTMKIRN                       160

SEQ ID NO: 33          moltype = AA  length = 306
FEATURE                Location/Qualifiers
REGION                 1..306
                       note = Human Soluble IL-12beta (p40)
source                 1..306
                       mol_type = protein
                       organism = Homo sapiens
SEQUENCE: 33
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCS                                                            306

SEQ ID NO: 34          moltype = DNA  length = 918
FEATURE                Location/Qualifiers
misc_feature           1..918
                       note = Human Soluble IL-12beta (p40)
source                 1..918
                       mol_type = unassigned DNA
                       organism = Homo sapiens
SEQUENCE: 34
atttgggaac tgaagaagga cgtctacgtg gtcgaactgg actggtatcc cgatgctccc  60
ggcgaaatgg tggtgctcac ttgtgacacc cccgaagaag acggcatcac ttggaccctc  120
gatcagagca gcgaggtgct gggctccgga aagaccctca caatccaagt taaggagttc  180
ggagacgctg gccaatacac atgccacaag ggaggcgagg tgctcagcca ttccttatta  240
ttattacaca agaaggaaga cggaatctgg tccaccgaca ttttaaaaga tcagaaggag  300
cccaagaata agaccttttt aaggtgtgag gccaaaaact acagcggtcg tttcacttgt  360
tggtggctga ccaccatttc caccgattta accttctccg tgaaaagcag ccggggaagc  420
tccgaccctc aaggtgtgac atgtggagcc gctaccctca gcgctgagag ggttcgtggc  480
gataacaagg aatacgagta cagcgtggag tgccaagaag atagcgcttg tcccgctgcc  540
```

```
gaagaatctt tacccattga ggtgatggtg gacgccgtgc acaaactcaa gtacgagaac  600
tacacctcct ccttctttat ccgggacatc attaagcccg atcctcctaa gaatttacag  660
ctgaagcctc tcaaaaatag ccggcaagtt gaggtctctt gggaatatcc cgacacttgg  720
agcacacccc acagctactt ctctttaacc ttttgtgtgc aagttcaagg taaaagcaag  780
cgggagaaga aagaccgggt gtttaccgac aaaaccagcg ccaccgtcat ctgtcggaag  840
aacgcctcca tcagcgtgag ggctcaagat cgttattact ccagcagctg gtccgagtgg  900
gccagcgtgc cttgttcc                                                918

SEQ ID NO: 35          moltype = AA  length = 197
FEATURE                Location/Qualifiers
REGION                 1..197
                       note = Human Soluble IL-12alpha (p35)
source                 1..197
                       mol_type = protein
                       organism = Homo sapiens
SEQUENCE: 35
RNLPVATPDP GMFPCLHHSQ NLLRAVSNML QKARQTLEFY PCTSEEIDHE DITKDKTSTV  60
EACLPLELTK NESCLNSRET SFITNGSCLA SRKTSFMMAL CLSSIYEDLK MYQVEFKTMN  120
AKLLMDPKRQ IFLDQNMLAV IDELMQALNF NSETVPQKSS LEEPDFYKTK IKLCILLHAF  180
RIRAVTIDRV MSYLNAS                                                 197

SEQ ID NO: 36          moltype = DNA  length = 591
FEATURE                Location/Qualifiers
misc_feature           1..591
                       note = Human Soluble IL-12alpha (p35)
source                 1..591
                       mol_type = unassigned DNA
                       organism = Homo sapiens
SEQUENCE: 36
cgtaacctcc ccgtggctac ccccgatccc ggaatgttcc cttgtttaca ccacagccag  60
aatttactga gggccgtgag caacatgctg cagaaagcta ggcagacttt agaattttac  120
ccttgcacca gcgaggagat cgaccatgaa gatatcacca aggacaagac atccaccgtg  180
gaggcttgtt tacctctgga gctgacaaag aacgagtctt gtctcaactc tcgtgaaacc  240
agcttcatca caaatggctc ttgtttagct tcccggaaga cctcctttat gatggcttta  300
tgcctcagct ccatctacga ggatttaaag atgtaccaag tggagttcaa gaccatgaac  360
gccaagctgc tcatggaccc taaacggcag atctttttag accagaacat gctggctgtg  420
attgatgagc tgatgcaagc tttaaacttc aactccgaga ccgtccctca gaagtcctcc  480
ctcgaggagc ccgattttta caagacaaag atcaaactgt gcattttact ccacgccttt  540
aggatccggg ccgtgaccat tgaccgggtc atgagctatt taaacgccag c           591

SEQ ID NO: 37          moltype = AA  length = 518
FEATURE                Location/Qualifiers
REGION                 1..518
                       note = Human Soluble IL-12
source                 1..518
                       mol_type = protein
                       organism = Homo sapiens
SEQUENCE: 37
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNAS                          518

SEQ ID NO: 38          moltype = DNA  length = 1554
FEATURE                Location/Qualifiers
misc_feature           1..1554
                       note = Human Soluble IL-12
source                 1..1554
                       mol_type = unassigned DNA
                       organism = Homo sapiens
SEQUENCE: 38
atttgggaac tgaagaagga cgtctacgtg gtcgaactgg actggtatcc cgatgctccc  60
ggcgaaatgg tggtgctcac ttgtgacacc cccgaagaag acggcatcac ttggaccctc  120
gatcagagca gcgaggtgct gggctccgga aagaccctca caatccaagt taaggagttc  180
ggagacgctg gccaatacac atgccacaag ggaggcgagg tgctcagcca ttccttatta  240
ttattacaca agaaggaaga cggaatctgg tccaccgaca ttttaaaaga tcagaaggag  300
cccaagaata agaccttttt aaggtgtgag gccaaaaact acagcggtcg tttcacttgt  360
tggtggctga ccaccatttc caccgattta accttctccg tgaaaagcag ccggggaagc  420
tccgaccctc aaggtgtgac atgtggagcc gctaccctca gcgctgagag ggttcgtggc  480
gataacaagg aatacgagta cagcgtggag tgccaagaag atagcgcttg tcccgctgcc  540
gaagaatctt tacccattga ggtgatggtg gacgccgtgc acaaactcaa gtacgagaac  600
tacacctcct ccttctttat ccgggacatc attaagcccg atcctcctaa gaatttacag  660
ctgaagcctc tcaaaaatag ccggcaagtt gaggtctctt gggaatatcc cgacacttgg  720
agcacacccc acagctactt ctctttaacc ttttgtgtgc aagttcaagg taaaagcaag  780
```

```
cgggagaaga aagaccgggt gtttaccgac aaaaccagcg ccaccgtcat ctgtcggaag  840
aacgcctcca tcagcgtgag ggctcaagat cgttattact ccagcagctg gtccgagtgg  900
gccagcgtgc cttgttccgg cggtggagga tccggaggag gtggctccgg cggcggagga  960
tctcgtaacc tccccgtggc tacccccgat cccggaatgt tcccttgttt acaccacagc  1020
cagaatttac tgagggccgt gagcaacatg ctgcagaaag ctaggcagac tttagaattt  1080
tacccttgca ccagcgagga gatcgaccat gaagatatca ccaaggacaa gacatccacc  1140
gtggaggctt gtttacctct ggagctgaca aagaacgagt cttgtctcaa ctctcgtgaa  1200
accagcttca tcacaaatgg ctcttgttta gcttcccgga agacctcctt tatgatggct  1260
ttatgcctca gctccatcta cgaggattta aagatgtacc aagtggagtt caagaccatg  1320
aacgccaagc tgctcatgga ccctaaacgg cagatctttt tagaccagaa catgctggct  1380
gtgattgatg agctgatgca agctttaaac ttcaactccg agaccgtccc tcagaagtcc  1440
tccctcgagg agcccgattt ttacaagaca aagatcaaac tgtgcatttt actccacgcc  1500
tttaggatcc gggccgtgac cattgaccgg gtcatgagct atttaaacgc cagc        1554

SEQ ID NO: 39          moltype = AA  length = 114
FEATURE                Location/Qualifiers
REGION                 1..114
                       note = Human Soluble IL-15
source                 1..114
                       mol_type = protein
                       organism = Homo sapiens
SEQUENCE: 39
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 40          moltype = AA  length = 132
FEATURE                Location/Qualifiers
REGION                 1..132
                       note = Human Soluble IL-17
source                 1..132
                       mol_type = protein
                       organism = Homo sapiens
SEQUENCE: 40
GITIPRNPGC PNSEDKNFPR TVMVNLNIHN RNTNTNPKRS SDYYNRSTSP WNLHRNEDPE  60
RYPSVIWEAK CRHLGCINAD GNVDYHMNSV PIQQEILVLR REPPHCPNSF RLEKILVSVG  120
CTCVTPIVHH VA                                                      132

SEQ ID NO: 41          moltype = AA  length = 157
FEATURE                Location/Qualifiers
REGION                 1..157
                       note = Human Soluble IL-18
source                 1..157
                       mol_type = protein
                       organism = Homo sapiens
SEQUENCE: 41
YFGKLESKLS VIRNLNDQVL FIDQGNRPLF EDMTDSDCRD NAPRTIFIIS MYKDSQPRGM  60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                           157

SEQ ID NO: 42          moltype = DNA  length = 471
FEATURE                Location/Qualifiers
misc_feature           1..471
                       note = Human Soluble IL-18
source                 1..471
                       mol_type = unassigned DNA
                       organism = Homo sapiens
SEQUENCE: 42
tacttcggca aactggaatc caagctgagc gtgatccgga atttaaacga ccaagttctg  60
tttatcgatc aaggtaaccg gcctctgttc gaggacatga ccgactccga ttgccgggac  120
aatgcccccc ggaccatctt cattatctcc atgtacaagg acagccagcc ccggggcatg  180
gctgtgacaa ttagcgtgaa gtgtgagaaa atcagcactt tatcttgtga gaacaagatc  240
atctccttta aggaaatgaa ccccccgat aacatcaagg acaccaagtc cgatatcatc  300
ttcttccagc ggtccgtgcc cggtcacgat aacaagatgc agttcgaatc ctcctcctac  360
gagggctact ttttagcttg tgaaaaggag agggatttat tcaagctgat cctcaagaag  420
gaggacgagc tgggcgatcg ttccatcatg ttcaccgtcc aaaacgagga t           471

SEQ ID NO: 43          moltype = DNA  length = 26
FEATURE                Location/Qualifiers
misc_feature           1..26
                       note = Description of Artificial Sequence: Synthetic
                        sequencing primer IFNG355R-bio
source                 1..26
                       mol_type = other DNA
                       organism = synthetic construct
SEQUENCE: 43
caatatacta cacctcctct aactac                                       26

SEQ ID NO: 44          moltype = AA  length = 17
FEATURE                Location/Qualifiers
```

```
REGION                  1..17
                        note = Description of Artificial Sequence: Synthetic signal
                         sequence
source                  1..17
                        mol_type = protein
                        organism = synthetic construct
SEQUENCE: 44
MGVKVLFALI CIAVAEA                                                  17

SEQ ID NO: 45           moltype = AA  length = 352
FEATURE                 Location/Qualifiers
REGION                  1..352
                        note = Human Soluble PDGF-DD
source                  1..352
                        mol_type = protein
                        organism = Homo sapiens
SEQUENCE: 45
RDTSATPQSA SIKALRNANL RRDESNHLTD LYRRDETIQV KGNGYVQSPR FPNSYPRNLL  60
LTWRLHSQEN TRIQLVFDNQ FGLEEAENDI CRYDFVEVED ISETSTIIRG RWCGHKEVPP  120
RIKSRTNQIK ITFKSDDYFV AKPGFKIYYS LLEDFQPAAA SETNWESVTS SISGVSYNSP  180
SVTDPTLIAD ALDKKIAEFD TVEDLLKYFN PESWQEDLEN MYLDTPRYRG RSYHDRKSKV  240
DLDRLNDDAK RYSCTPRNYS VNIREELKLA NVVFFPRCLL VQRCGGNCGC GTVNWRSCTC  300
NSGKTVKKYH EVLQFEPGHI KRRGRAKTMA LVDIQLDHHE RCDCICSSRP PR          352

SEQ ID NO: 46           moltype = AA  length = 248
FEATURE                 Location/Qualifiers
REGION                  1..248
                        note = Human Soluble SCF
source                  1..248
                        mol_type = protein
                        organism = Homo sapiens
SEQUENCE: 46
EGICRNRVTN NVKDVTKLVA NLPKDYMITL KYVPGMDVLP SHCWISEMVV QLSDSLTDLL  60
DKFSNISEGL SNYSIIDKLV NIVDDLVECV KENSSKDLKK SFKSPEPRLF TPEEFFRIFN  120
RSIDAFKDFV VASETSDCVV SSTLSPEKDS RVSVTKPFML PPVAASSLRN DSSSSNRKAK  180
NPPGDSSLHW AAMALPALFS LIIGFAFGAL YWKKRQPSLT RAVENIQINE EDNEISMLQE  240
KEREFQEV                                                            248

SEQ ID NO: 47           moltype = AA  length = 209
FEATURE                 Location/Qualifiers
REGION                  1..209
                        note = Human Soluble FLT3L
source                  1..209
                        mol_type = protein
                        organism = Homo sapiens
SEQUENCE: 47
TQDCSFQHSP ISSDFAVKIR ELSDYLLQDY PVTVASNLQD EELCGGLWRL VLAQRWMERL  60
KTVAGSKMQG LLERVNTEIH FVTKCAFQPP PSCLRFVQTN ISRLLQETSE QLVALKPWIT  120
RQNFSRCLEL QCQPDSSTLP PPWSPRPLEA TAPTAPQPPL LLLLLLPVGL LLLAAAWCLH  180
WQRTRRRTPR PGEQVPPVPS PQDLLLVEH                                     209

SEQ ID NO: 48           moltype = AA  length = 360
FEATURE                 Location/Qualifiers
REGION                  1..360
                        note = Human Soluble MICA
source                  1..360
                        mol_type = protein
                        organism = Homo sapiens
SEQUENCE: 48
EPHSLRYNLT VLSWDGSVQS GFLTEVHLDG QPFLRCDRQK CRAKPQGQWA EDVLGNKTWD  60
RETRDLTGNG KDLRMTLAHI KDQKEGLHSL QEIRVCEIHE DNSTRSSQHF YYDGELFLSQ  120
NLETKEWTMP QSSRAQTLAM NVRNFLKEDA MKTKTHYHAM HADCLQELRR YLKSGVVLRR  180
TVPPMVNVTR SEASEGNITV TCRASGFYPW NITLSWRQDG VSLSHDTQQW GDVLPDGNGT  240
YQTWVATRIC QGEEQRFTCY MEHSGNHSTH PVPSGKVLVL QSHWQTFHVS AVAAAAIFVI  300
IIFYVRCCKK KTSAAEGPEL VSLQVLDQHP VGTSDHRDAT QLGFQPLMSD LGSTGSTEGA  360

SEQ ID NO: 49           moltype = AA  length = 361
FEATURE                 Location/Qualifiers
REGION                  1..361
                        note = Human Soluble MICB
source                  1..361
                        mol_type = protein
                        organism = Homo sapiens
SEQUENCE: 49
AEPHSLRYNL MVLSQDESVQ SGFLAEGHLD GQPFLRYDRQ KRRAKPQGQW AEDVLGAKTW  60
DTETEDLTEN GQDLRRTLTH IKDQKGGLHS LQEIRVCEIH EDSSTRGSRH FYYDGELFLS  120
QNLETQESTV PQSSRAQTLA MNVTNFWKED AMKTKTHYRA MQADCLQKLQ RYLKSGVAIR  180
RTVPPMVNVT CSEVSEGNIT VTCRASSFYP RNITLTWRQD GVSLSHNTQQ WGDVLPDGNG  240
```

```
TYQTWVATRI RQGEEQRFTC YMEHSGNHGT HPVPSGKVLV LQSQRTDFPY VSAAMPCFVI  300
IIILCVPCCK KKTSAAEGPE LVSLQVLDQH PVGTGDHRDA AQLGFQPLMS ATGSTGSTEG  360
A                                                                  361

SEQ ID NO: 50           moltype = AA  length = 190
FEATURE                 Location/Qualifiers
REGION                  1..190
                        note = Human Soluble ULBP1
source                  1..190
                        mol_type = protein
                        organism = Homo sapiens
SEQUENCE: 50
WVDTHCLCYD FIITPKSRPE PQWCEVQGLV DERPFLHYDC VNHKAKAFAS LGKKVNVTKT  60
WEEQTETLRD VVDFLKGQLL DIQVENLIPI EPLTLQARMS CEHEAHGHGR GSWQFLFNGQ  120
KFLLFDSNNR KWTALHPGAK KMTEKWEKNR DVTMFFQKIS LGDCKMWLEE FLMYWEQMLD  180
PTKPPSLAPG                                                         190

SEQ ID NO: 51           moltype = AA  length = 191
FEATURE                 Location/Qualifiers
REGION                  1..191
                        note = Human Soluble ULBP2
source                  1..191
                        mol_type = protein
                        organism = Homo sapiens
SEQUENCE: 51
GRADPHSLCY DITVIPKFRP GPRWCAVQGQ VDEKTFLHYD CGNKTVTPVS PLGKKLNVTT  60
AWKAQNPVLR EVVDILTEQL RDIQLENYTP KEPLTLQARM SCEQKAEGHS SGSWQFSFDG  120
QIFLLFDSEK RMWTTVHPGA RKMKEKWEND KVVAMSFHYF SMGDCIGWLE DFLMGMDSTL  180
EPSAGAPLAM S                                                       191

SEQ ID NO: 52           moltype = AA  length = 188
FEATURE                 Location/Qualifiers
REGION                  1..188
                        note = Human Soluble ULBP3
source                  1..188
                        mol_type = protein
                        organism = Homo sapiens
SEQUENCE: 52
DAHSLWYNFT IIHLPRHGQQ WCEVQSQVDQ KNFLSYDCGS DKVLSMGHLE EQLYATDAWG  60
KQLEMLREVG QRLRLELADT ELEDFTPSGP LTLQVRMSCE CEADGYIRGS WQFSFDGRKF  120
LLFDSNNRKW TVVHAGARRM KEKWEKDSGL TTFFKMVSMR DCKSWLRDFL MHRKKRLEPT  180
APPTMAPG                                                           188

SEQ ID NO: 53           moltype = AA  length = 233
FEATURE                 Location/Qualifiers
REGION                  1..233
                        note = Human Soluble ULBP4
source                  1..233
                        mol_type = protein
                        organism = Homo sapiens
SEQUENCE: 53
HSLCFNFTIK SLSRPGQPWC EAQVFLNKNL FLQYNSDNNM VKPLGLLGKK VYATSTWGEL  60
TQTLGEVGRD LRMLLCDIKP QIKTSDPSTL QVEMFCQREA ERCTGASWQF ATNGEKSLLF  120
DAMNMTWTVI NHEASKIKET WKKDRGLEKY FRKLSKGDCD HWLREFLGHW EAMPEPTVSP  180
VNASDIHWSS SSLPDRWIIL GAFILLVLMG IVLICVWWQN GEWQAGLWPL RTS          233

SEQ ID NO: 54           moltype = AA  length = 193
FEATURE                 Location/Qualifiers
REGION                  1..193
                        note = Human Soluble ULBP5
source                  1..193
                        mol_type = protein
                        organism = Homo sapiens
SEQUENCE: 54
GLADPHSLCY DITVIPKFRP GPRWCAVQGQ VDEKTFLHYD CGSKTVTPVS PLGKKLNVTT  60
AWKAQNPVLR EVVDILTEQL LDIQLENYIP KEPLTLQARM SCEQKAEGHG SGSWQLSFDG  120
QIFLLFDSEN RMWTTVHPGA RKMKEKWEND KDMTMSFHYI SMGDCTGWLE DFLMGMDSTL  180
EPSAGAPPTM SSG                                                     193

SEQ ID NO: 55           moltype = AA  length = 193
FEATURE                 Location/Qualifiers
REGION                  1..193
                        note = Human Soluble ULBP6
source                  1..193
                        mol_type = protein
                        organism = Homo sapiens
SEQUENCE: 55
RRDDPHSLCY DITVIPKFRP GPRWCAVQGQ VDEKTFLHYD CGNKTVTPVS PLGKKLNVTM  60
AWKAQNPVLR EVVDILTEQL LDIQLENYTP KEPLTLQARM SCEQKAEGHS SGSWQFSIDG  120
```

```
QTFLLFDSEK RMWTTVHPGA RKMKEKWEND KDVAMSFHYI SMGDCIGWLE DFLMGMDSTL  180
EPSAGAPLAM SSG                                                    193

SEQ ID NO: 56          moltype = AA  length = 136
FEATURE                Location/Qualifiers
REGION                 1..136
                       note = soluble TGFbetaRII receptor
source                 1..136
                       mol_type = protein
                       organism = Homo sapiens
SEQUENCE: 56
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPD                                                 136

SEQ ID NO: 57          moltype = DNA  length = 408
FEATURE                Location/Qualifiers
misc_feature           1..408
                       note = soluble TGFbetaRII receptor
source                 1..408
                       mol_type = unassigned DNA
                       organism = Homo sapiens
SEQUENCE: 57
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcacgatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgat              408

SEQ ID NO: 58          moltype =   length =
SEQUENCE: 58
000

SEQ ID NO: 59          moltype =   length =
SEQUENCE: 59
000

SEQ ID NO: 60          moltype = AA  length = 287
FEATURE                Location/Qualifiers
REGION                 1..287
                       note = soluble TGFbetaRII receptor
source                 1..287
                       mol_type = protein
                       organism = Homo sapiens
SEQUENCE: 60
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPD               287

SEQ ID NO: 61          moltype = DNA  length = 861
FEATURE                Location/Qualifiers
misc_feature           1..861
                       note = soluble TGFbetaRII receptor
source                 1..861
                       mol_type = unassigned DNA
                       organism = Homo sapiens
SEQUENCE: 61
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcacgatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgcaca  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga c                                           861

SEQ ID NO: 62          moltype = AA  length = 18
FEATURE                Location/Qualifiers
```

```
REGION                  1..18
                        note = Description of Artificial Sequence: Synthetic signal
                         sequence
source                  1..18
                        mol_type = protein
                        organism = synthetic construct
SEQUENCE: 62
MKWVTFISLL FLFSSAYS                                                 18

SEQ ID NO: 63           moltype = DNA  length = 54
FEATURE                 Location/Qualifiers
misc_feature            1..54
                        note = Description of Artificial Sequence: Synthetic signal
                         sequence
source                  1..54
                        mol_type = other DNA
                        organism = synthetic construct
SEQUENCE: 63
atgaaatggg tgacctttat ttctttactg ttcctcttta gcagcgccta ctcc        54

SEQ ID NO: 64           moltype = DNA  length = 54
FEATURE                 Location/Qualifiers
misc_feature            1..54
                        note = Description of Artificial Sequence: Synthetic signal
                         sequence
source                  1..54
                        mol_type = other DNA
                        organism = synthetic construct
SEQUENCE: 64
atgaagtggg tcacatttat ctctttactg ttcctcttct ccagcgccta cagc        54

SEQ ID NO: 65           moltype = DNA  length = 54
FEATURE                 Location/Qualifiers
misc_feature            1..54
                        note = Description of Artificial Sequence: Synthetic signal
                         sequence
source                  1..54
                        mol_type = other DNA
                        organism = synthetic construct
SEQUENCE: 65
atgaaatggg tgacctttat ttctttactg ttcctcttta gcagcgccta ctcc        54

SEQ ID NO: 66           moltype = AA  length = 16
FEATURE                 Location/Qualifiers
REGION                  1..16
                        note = Description of Artificial Sequence: Synthetic signal
                         sequence
source                  1..16
                        mol_type = protein
                        organism = synthetic construct
SEQUENCE: 66
MKCLLYLAFL FLGVNC                                                   16

SEQ ID NO: 67           moltype = AA  length = 58
FEATURE                 Location/Qualifiers
REGION                  1..58
                        note = Description of Artificial Sequence: Synthetic signal
                         sequence
source                  1..58
                        mol_type = protein
                        organism = synthetic construct
SEQUENCE: 67
MGQIVTMFEA LPHIIDEVIN IVIIVLIIIT SIKAVYNFAT CGILALVSFL FLAGRSCG    58

SEQ ID NO: 68           moltype = AA  length = 97
FEATURE                 Location/Qualifiers
REGION                  1..97
                        note = Description of Artificial Sequence: Synthetic signal
                         sequence
source                  1..97
                        mol_type = protein
                        organism = synthetic construct
SEQUENCE: 68
MPNHQSGSPT GSSDLLLSGK KQRPHLALRR KRRREMRKIN RKVRRMNLAP IKEKTAWQHL  60
QALISEAEEV LKTSQTPQNS LTLFLALLSV LGPPVTG                            97
```

```
SEQ ID NO: 69           moltype = AA  length = 30
FEATURE                 Location/Qualifiers
REGION                  1..30
                        note = Description of Artificial Sequence: Synthetic signal
                         sequence
source                  1..30
                        mol_type = protein
                        organism = synthetic construct
SEQUENCE: 69
MDSKGSSQKG SRLLLLLVVS NLLLCQGVVS                                      30

SEQ ID NO: 70           moltype = AA  length = 15
FEATURE                 Location/Qualifiers
REGION                  1..15
                        note = Description of Artificial Sequence: Synthetic AviTag
                         sequence
source                  1..15
                        mol_type = protein
                        organism = synthetic construct
SEQUENCE: 70
GLNDIFEAQK IEWHE                                                      15

SEQ ID NO: 71           moltype = AA  length = 26
FEATURE                 Location/Qualifiers
REGION                  1..26
                        note = Description of Artificial Sequence: Synthetic
                         calmodulin-tag sequence
source                  1..26
                        mol_type = protein
                        organism = synthetic construct
SEQUENCE: 71
KRRWKKNFIA VSAANRFKKI SSSGAL                                          26

SEQ ID NO: 72           moltype = AA  length = 6
FEATURE                 Location/Qualifiers
REGION                  1..6
                        note = Description of Artificial Sequence: Synthetic
                         polyglutamate tag sequence
source                  1..6
                        mol_type = protein
                        organism = synthetic construct
SEQUENCE: 72
EEEEEE                                                                6

SEQ ID NO: 73           moltype = AA  length = 13
FEATURE                 Location/Qualifiers
REGION                  1..13
                        note = Description of Artificial Sequence: Synthetic E-tag
                         sequence
source                  1..13
                        mol_type = protein
                        organism = synthetic construct
SEQUENCE: 73
GAPVPYPDPL EPR                                                        13

SEQ ID NO: 74           moltype = AA  length = 8
FEATURE                 Location/Qualifiers
REGION                  1..8
                        note = Description of Artificial Sequence: Synthetic
                         FLAG-tag sequence
source                  1..8
                        mol_type = protein
                        organism = synthetic construct
SEQUENCE: 74
DYKDDDDK                                                              8

SEQ ID NO: 75           moltype = AA  length = 9
FEATURE                 Location/Qualifiers
REGION                  1..9
                        note = Description of Artificial Sequence: Synthetic HA-tag
                         sequence
source                  1..9
                        mol_type = protein
                        organism = synthetic construct
SEQUENCE: 75
YPYDVPDYA                                                             9

SEQ ID NO: 76           moltype = AA  length = 5
```

```
FEATURE                 Location/Qualifiers
REGION                  1..5
                        note = Description of Artificial Sequence: Synthetic
                         his-tag sequence
source                  1..5
                        mol_type = protein
                        organism = synthetic construct
SEQUENCE: 76
HHHHH                                                                       5

SEQ ID NO: 77           moltype = AA  length = 6
FEATURE                 Location/Qualifiers
REGION                  1..6
                        note = Description of Artificial Sequence: Synthetic
                         his-tag sequence
source                  1..6
                        mol_type = protein
                        organism = synthetic construct
SEQUENCE: 77
HHHHHH                                                                      6

SEQ ID NO: 78           moltype = AA  length = 7
FEATURE                 Location/Qualifiers
REGION                  1..7
                        note = Description of Artificial Sequence: Synthetic
                         his-tag sequence
source                  1..7
                        mol_type = protein
                        organism = synthetic construct
SEQUENCE: 78
HHHHHHH                                                                     7

SEQ ID NO: 79           moltype = AA  length = 8
FEATURE                 Location/Qualifiers
REGION                  1..8
                        note = Description of Artificial Sequence: Synthetic
                         his-tag sequence
source                  1..8
                        mol_type = protein
                        organism = synthetic construct
SEQUENCE: 79
HHHHHHHH                                                                    8

SEQ ID NO: 80           moltype = AA  length = 9
FEATURE                 Location/Qualifiers
REGION                  1..9
                        note = Description of Artificial Sequence: Synthetic
                         his-tag sequence
source                  1..9
                        mol_type = protein
                        organism = synthetic construct
SEQUENCE: 80
HHHHHHHHH                                                                   9

SEQ ID NO: 81           moltype = AA  length = 10
FEATURE                 Location/Qualifiers
REGION                  1..10
                        note = Description of Artificial Sequence: Synthetic
                         his-tag sequence
source                  1..10
                        mol_type = protein
                        organism = synthetic construct
SEQUENCE: 81
HHHHHHHHHH                                                                  10

SEQ ID NO: 82           moltype = AA  length = 10
FEATURE                 Location/Qualifiers
REGION                  1..10
                        note = Description of Artificial Sequence: Synthetic
                         myc-tag sequence
source                  1..10
                        mol_type = protein
                        organism = synthetic construct
SEQUENCE: 82
EQKLISEEDL                                                                  10
```

```
SEQ ID NO: 83           moltype = AA  length = 18
FEATURE                 Location/Qualifiers
REGION                  1..18
                        note = Description of Artificial Sequence: Synthetic NE-tag
                         sequence
source                  1..18
                        mol_type = protein
                        organism = synthetic construct
SEQUENCE: 83
TKENPRSNQE ESYDDNES                                                   18

SEQ ID NO: 84           moltype = AA  length = 15
FEATURE                 Location/Qualifiers
REGION                  1..15
                        note = Description of Artificial Sequence: Synthetic S-tag
                         sequence
source                  1..15
                        mol_type = protein
                        organism = synthetic construct
SEQUENCE: 84
KETAAAKFER QHMDS                                                      15

SEQ ID NO: 85           moltype = AA  length = 38
FEATURE                 Location/Qualifiers
REGION                  1..38
                        note = Description of Artificial Sequence: Synthetic
                         SBP-tag sequence
source                  1..38
                        mol_type = protein
                        organism = synthetic construct
SEQUENCE: 85
MDEKTTGWRG GHVVEGLAGE LEQLRARLEH HPQGQREP                             38

SEQ ID NO: 86           moltype = AA  length = 13
FEATURE                 Location/Qualifiers
REGION                  1..13
                        note = Description of Artificial Sequence: Synthetic Softag
                         1 sequence
source                  1..13
                        mol_type = protein
                        organism = synthetic construct
SEQUENCE: 86
SLAELLNAGL GGS                                                        13

SEQ ID NO: 87           moltype = AA  length = 8
FEATURE                 Location/Qualifiers
REGION                  1..8
                        note = Description of Artificial Sequence: Synthetic Softag
                         3 sequence
source                  1..8
                        mol_type = protein
                        organism = synthetic construct
SEQUENCE: 87
TQDPSRVG                                                              8

SEQ ID NO: 88           moltype = AA  length = 12
FEATURE                 Location/Qualifiers
REGION                  1..12
                        note = Description of Artificial Sequence: Synthetic
                         Spot-tag sequence
source                  1..12
                        mol_type = protein
                        organism = synthetic construct
SEQUENCE: 88
PDRVRAVSHW SS                                                         12

SEQ ID NO: 89           moltype = AA  length = 8
FEATURE                 Location/Qualifiers
REGION                  1..8
                        note = Description of Artificial Sequence: Synthetic
                         Strep-tag sequence
source                  1..8
                        mol_type = protein
                        organism = synthetic construct
SEQUENCE: 89
WSHPQFEK                                                              8

SEQ ID NO: 90           moltype = AA  length = 6
```

```
FEATURE                Location/Qualifiers
REGION                 1..6
                       note = Description of Artificial Sequence: Synthetic TC tag
                        sequence
source                 1..6
                       mol_type = protein
                       organism = synthetic construct
SEQUENCE: 90
CCPGCC                                                                     6

SEQ ID NO: 91          moltype = AA  length = 10
FEATURE                Location/Qualifiers
REGION                 1..10
                       note = Description of Artificial Sequence: Synthetic Ty tag
                        sequence
source                 1..10
                       mol_type = protein
                       organism = synthetic construct
SEQUENCE: 91
EVHTNQDPLD                                                                 10

SEQ ID NO: 92          moltype = AA  length = 14
FEATURE                Location/Qualifiers
REGION                 1..14
                       note = Description of Artificial Sequence: Synthetic V5 tag
                        sequence
source                 1..14
                       mol_type = protein
                       organism = synthetic construct
SEQUENCE: 92
GKPIPNPLLG LDST                                                            14

SEQ ID NO: 93          moltype = AA  length = 11
FEATURE                Location/Qualifiers
REGION                 1..11
                       note = Description of Artificial Sequence: Synthetic
                        VSV-tag sequence
source                 1..11
                       mol_type = protein
                       organism = synthetic construct
SEQUENCE: 93
YTDIEMNRLG K                                                               11

SEQ ID NO: 94          moltype = AA  length = 8
FEATURE                Location/Qualifiers
REGION                 1..8
                       note = Description of Artificial Sequence: Synthetic Xpress
                        tag sequence
source                 1..8
                       mol_type = protein
                       organism = synthetic construct
SEQUENCE: 94
DLYDDDDK                                                                   8

SEQ ID NO: 95          moltype =   length =
SEQUENCE: 95
000

SEQ ID NO: 96          moltype = AA  length = 220
FEATURE                Location/Qualifiers
REGION                 1..220
                       note = wildtype human IgG1 Fc region
source                 1..220
                       mol_type = protein
                       organism = Homo sapiens
SEQUENCE: 96
PCPAPELLGG PSVFLFPPKP KDTLMISRTP EVTCVVVDVS HEDPEVKFNW YVDGVEVHNA  60
KTKPREEQYN STYRVVSVLT VLHQDWLNGK EYKCKVSNKA LPAPIEKTIS KAKGQPREPQ  120
VYTLPPSRDE LTKNQVSLTC LVKGFYPSDI AVEWESNGQP ENNYKTTPPV LDSDGSFFLY  180
SKLTVDKSRW QQGNVFSCSV MHEALHNHYT QKSLSLSPGK                        220

SEQ ID NO: 97          moltype = AA  length = 216
FEATURE                Location/Qualifiers
REGION                 1..216
                       note = Wildtype Human IgG2 Fc region
source                 1..216
                       mol_type = protein
                       organism = Homo sapiens
```

```
SEQUENCE: 97
APPVAGPSVF LFPPKPKDTL MISRTPEVTC VVVDVSHEDP EVQFNWYVDG VEVHNAKTKP  60
REEQFNSTFR VVSVLTVVHQ DWLNGKEYKC KVSNKGLPAP IEKTISKTKG QPREPQVYTL  120
PPSREEMTKN QVSLTCLVKG FYPSDISVEW ESNGQPENNY KTTPPMLDSD GSFFLYSKLT  180
VDKSRWQQGN VFSCSVMHEA LHNHYTQKSL SLSPGK                           216

SEQ ID NO: 98          moltype = AA  length = 217
FEATURE                Location/Qualifiers
REGION                 1..217
                       note = Wildtype Human IgG3 Fc
source                 1..217
                       mol_type = protein
                       organism = Homo sapiens
SEQUENCE: 98
APELLGGPSV FLFPPKPKDT LMISRTPEVT CVVVDVSHED PEVQFKWYVD GVEVHNAKTK  60
PREEQYNSTF RVVSVLTVLH QDWLNGKEYK CKVSNKALPA PIEKTISKTK GQPREPQVYT  120
LPPSREEMTK NQVSLTCLVK GFYPSDIAVE WESSGQPENN YNTTPPMLDS DGSFFLYSKL  180
TVDKSRWQQG NIFSCSVMHE ALHNRFTQKS LSLSPGK                          217

SEQ ID NO: 99          moltype = AA  length = 217
FEATURE                Location/Qualifiers
REGION                 1..217
                       note = Wildtype Human IgG4 Fc
source                 1..217
                       mol_type = protein
                       organism = Homo sapiens
SEQUENCE: 99
APEFLGGPSV FLFPPKPKDT LMISRTPEVT CVVVDVSQED PEVQFNWYVD GVEVHNAKTK  60
PREEQFNSTY RVVSVLTVLH QDWLNGKEYK CKVSNKGLPS SIEKTISKAK GQPREPQVYT  120
LPPSQEEMTK NQVSLTCLVK GFYPSDIAVE WESNGQPENN YKTTPPVLDS DGSFFLYSRL  180
TVDKSRWQEG NVFSCSVMHE ALHNHYTQKS LSLSLGK                          217

SEQ ID NO: 100         moltype = AA  length = 696
FEATURE                Location/Qualifiers
REGION                 1..696
                       note = Description of Artificial Sequence: Synthetic
                        anti-CD3scFv/TF/anti-CD28scFv sequence
source                 1..696
                       mol_type = protein
                       organism = synthetic construct
SEQUENCE: 100
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINRGGG GSGGGGSGGG  120
GSQVQLQQSG AELARPGASV KMSCKASGYT FTRYTMHWVK QRPGQGLEWI GYINPSRGYT  180
NYNQKFKDKA TLTTDKSSST AYMQLSSLTS EDSAVYYCAR YYDDHYCLDY WGQGTTLTVS  240
SSGTTNTVAA YNLTWKSTNF KTILEWEPKP VNQVYTVQIS TKSGDWKSKC FYTTDTECDL  300
TDEIVKDVKQ TYLARVFSYP AGNVESTGSA GEPLYENSPE FTPYLETNLG QPTIQSFEQV  360
GTKVNVTVED ERTLVRRNNT FLSLRDVFGK DLIYTLYYWK SSSSGKKTAK TNTNEFLIDV  420
DKGENYCFSV QAVIPSRTVN RKSTDSPVEC MGQEKGEFRE VQLQQSGPEL VKPGASVKMS  480
CKASGYTFTS YVIQWVKQKP GQGLEWIGSI NPYNDYTKYN EKFKGKATLT SDKSSITAYM  540
EFSSLTSEDS ALYYCARWGD GNYWGRGTTL TVSSGGGGSG GGGSGGGGSD IEMTQSPAIM  600
SASLGERVTM TCTASSSVSS SYFHWYQQKP GSSPKLCIYS TSNLASGVPP RFSGSGSTSY  660
SLTISSMEAE DAATYFCHQY HRSPTFGGGT KLETKR                           696

SEQ ID NO: 101         moltype = DNA  length = 2088
FEATURE                Location/Qualifiers
misc_feature           1..2088
                       note = Description of Artificial Sequence: Synthetic
                        anti-CD3scFv/TF/anti-CD28scFv sequence
source                 1..2088
                       mol_type = other DNA
                       organism = synthetic construct
SEQUENCE: 101
cagatcgtgc tgacccaaag ccccgccatc atgagcgcta gccccggtga gaaggtgacc  60
atgacatgct ccgcttccag ctccgtgtcc tacatgaact ggtatcagca gaaaagcgga  120
accagcccca aaaggtggat ctacgacacc agcaagctgg cctccggagt gcccgctcat  180
ttccggggct ctggatccgg caccagctac tctttaacca tttccggcat ggaagctgaa  240
gacgctgcca cctactattg ccagcaatgg agcagcaacc ccttcacatt cggatctggc  300
accaagctcg aaatcaatcg tggaggaggt ggcagcggcg gcggtggatc cggcggagga  360
ggaagccaag ttcaactcca gcagagcggc gctgaactgg cccggcccgg cgcctccgtc  420
aagatgagct gcaaggcttc cggctataca tttactcgtt acacaatgca ttgggtcaag  480
cagaggcccg gtcaaggttt agagtggatc ggatatatca acccttcccg gggctacacc  540
aactataacc aaaagttcaa ggataaagcc actttaacca ctgacaagag ctcctccacc  600
gcctacatgc agctgtcctc tttaaccagc gaggactccg ctgtttacta ctgcgctagg  660
tattacgacg accactactg tttagactat tggggacaag gtaccacttt aaccgtcagc  720
agctccggca ccaccaatac cgtggccgct tataacctca catggaagag caccaacttc  780
aagacaattc tggaatggga acccaagccc gtcaatcaag tttacaccgt gcagatctcc  840
accaaatccg gagactggaa gagcaagtgc ttctacacaa cagacaccga gtgtgattta  900
accgacgaaa tcgtcaagga cgtcaagcaa acctatctgg ctcgggtctt ttcctacccc  960
```

```
gctggcaatg tcgagtccac cggctccgct ggcgagcctc tctacgagaa ttcccccgaa  1020
ttcacccctt atttagagac caatttaggc cagcctacca tccagagctt cgagcaagtt  1080
ggcaccaagg tgaacgtcac cgtcgaggat gaaaggactt tagtgcggcg gaataacaca  1140
tttttatccc tccgggatgt gttcggcaaa gacctcatct acacactgta ctattggaag  1200
tccagctcct ccggcaaaaa gaccgctaag accaacacca acgagttttt aattgacgtg  1260
gacaaaggcg agaactactg cttcagcgtg caagccgtga tcccttctcg taccgtcaac  1320
cggaagagca cagattcccc cgttgagtgc atgggccaag aaaagggcga gttccgggag  1380
gtccagctgc agcagagcgg acccgaactc gtgaaacccg gtgcttccgt gaaaatgtct  1440
tgtaaggcca gcggatacac cttcacctcc tatgtgatcc agtgggtcaa acagaagccc  1500
ggacaaggtc tcgagtggat cggcagcatc aacccttaca acgactatac caaatacaac  1560
gagaagttta agggaaaggc tactttaacc tccgacaaaa gctccatcac agcctacatg  1620
gagttcagct ctttaacatc cgaggacagc gctctgtact attgcgcccg gtggggcgac  1680
ggcaattact ggggacgggg cacaacactg accgtgagca gcggaggcgg aggctccggc  1740
ggaggcggat ctggcggtgg cggctccgac atcgagatga cccagtcccc cgctatcatg  1800
tccgcctctt taggcgagcg ggtcacaatg acttgtacag cctcctccag cgtctcctcc  1860
tcctacttcc attggtacca acagaaaccc ggaagctccc ctaaactgtg catctacagc  1920
accagcaatc tcgccagcgg cgtgcccccct aggttttccg gaagcggaag caccagctac  1980
tctttaacca tctcctccat ggaggctgag gatgccgcca cctacttttg tcaccagtac  2040
caccggtccc ccaccttcgg aggcggcacc aaactggaga caaagagg              2088

SEQ ID NO: 102          moltype = AA  length = 714
FEATURE                 Location/Qualifiers
REGION                  1..714
                        note = Description of Artificial Sequence: Synthetic
                         anti-CD3scFv/TF/anti-CD28scFv sequence
source                  1..714
                        mol_type = protein
                        organism = synthetic construct
SEQUENCE: 102
MKWVTFISLL FLFSSAYSQI VLTQSPAIMS ASPGEKVTMT CSASSSVSYM NWYQQKSGTS  60
PKRWIYDTSK LASGVPAHFR GSGSGTSYSL TISGMEAEDA ATYYCQQWSS NPFTFGSGTK  120
LEINRGGGGS GGGGSGGGGS QVQLQQSGAE LARPGASVKM SCKASGYTFT RYTMHWVKQR  180
PGQGLEWIGY INPSRGYTNY NQKFKDKATL TTDKSSSTAY MQLSSLTSED SAVYYCARYY  240
DDHYCLDYWG QGTTLTVSSS GTTNTVAAYN LTWKSTNFKT ILEWEPKPVN QVYTVQISTK  300
SGDWKSKCFY TTDTECDLTD EIVKDVKQTY LARVFSYPAG NVESTGSAGE PLYENSPEFT  360
PYLETNLGQP TIQSFEQVGT KVNVTVEDER TLVRRNNTFL SLRDVFGKDL IYTLYYWKSS  420
SSGKKTAKTN TNEFLIDVDK GENYCFSVQA VIPSRTVNRK STDSPVECMG QEKGEFREVQ  480
LQQSGPELVK PGASVKMSCK ASGYTFTSYV IQWVKQKPGQ GLEWIGSINP YNDYTKYNEK  540
FKGKATLTSD KSSITAYMEF SSLTSEDSAL YYCARWGDGN YWGRGTTLTV SSGGGGSGGG  600
GSGGGGSDIE MTQSPAIMSA SLGERVTMTC TASSSVSSSY FHWYQQKPGS SPKLCIYSTS  660
NLASGVPPRF SGSGSTSYSL TISSMEAEDA ATYFCHQYHR SPTFGGGTKL ETKR        714

SEQ ID NO: 103          moltype = DNA  length = 2142
FEATURE                 Location/Qualifiers
misc_feature            1..2142
                        note = Description of Artificial Sequence: Synthetic
                         anti-CD3scFv/TF/anti-CD28scFv sequence
source                  1..2142
                        mol_type = other DNA
                        organism = synthetic construct
SEQUENCE: 103
atgaagtggg tgaccttcat cagcttatta tttttattca gctccgccta ttcccagatc  60
gtgctgaccc aaagccccgc catcatgagc gctagccccg gtgagaaggt gaccatgaca  120
tgctccgctt ccagctccgt gtcctacatg aactggtatc agcagaaaag cggaaccagc  180
cccaaaaggt ggatctacga caccagcaag ctggcctccg gagtgcccgc tcatttccgg  240
ggctctggat ccggcaccag ctactcttta accatttccg gcatggaagc tgaagacgct  300
gccacctact attgccagca atggagcagc aacccctca cattcggatc tggcaccaag  360
ctcgaaatca atcgtggagg aggtggcagc ggcggcggtg gatccggcgg aggaggaagc  420
caagttcaac tccagcagag cggcgctgaa ctggcccggc ccggcgcctc cgtcaagatg  480
agctgcaagg cttccggcta tacatttact cgttacacaa tgcattgggt caagcagagg  540
cccggtcaag gtttagagtg gatcggatat atcaaccctt cccggggcta caccaactat  600
aaccaaaagt tcaaggataa agccacttta accactgaca agagctcctc caccgcctac  660
atgcagctgt cctctttaac cagcgaggac tccgctgttt actactgcgc taggtattac  720
gacgaccact actgtttaga ctattgggga caaggtacca ctttaaccgt cagcagctcc  780
ggcaccacca ataccgtggc cgcttataac ctcacatgga agagcaccaa cttcaagaca  840
attctggaat gggaacccaa gcccgtcaat caagtttaca ccgtgcagat ctccaccaaa  900
tccggagact ggaagagcaa gtgcttctac acaacagaca ccgagtgtga tttaaccgac  960
gaaatcgtca aggacgtcaa gcaaacctat ctggctcggg tcttttccta ccccgctggc  1020
aatgtcgagt ccaccggctc cgctggcgag cctctctacg agaattcccc cgaattcacc  1080
ccttatttag agaccaattt aggccagcct accatccaga gcttcgagca agttggcacc  1140
aaggtgaacg tcaccgtcga ggatgaaagg actttagtgc ggcggaataa cacattttta  1200
tccctccggg atgtgttcgg caaagacctc atctacacac tgtactattg gaagtccagc  1260
tcctccggca aaaagaccgc taagaccaac accaacgagt ttttaattga cgtggacaaa  1320
ggcgagaact actgcttcag cgtgcaagcc gtgatccctt ctcgtaccgt caaccggaag  1380
agcacagatt cccccgttga gtgcatgggc caagaaaagg gcgagttccg ggaggtccag  1440
ctgcagcaga gcggacccga actcgtgaaa cccggtgctt ccgtgaaaat gtcttgtaag  1500
gccagcggat acaccttcac ctcctatgtg atccagtggg tcaaacagaa gcccggacaa  1560
ggtctcgagt ggatcggcag catcaaccct tacaacgact ataccaaata caacgagaag  1620
tttaagggaa aggctacttt aacctccgac aaaagctcca tcacagccta catggagttc  1680
```

```
agctctttaa catccgagga cagcgctctg tactattgcg cccggtgggg cgacggcaat  1740
tactggggac ggggcacaac actgaccgtg agcagcggag gcggaggctc cggcggaggc  1800
ggatctggcg gtggcggctc cgacatcgag atgacccagt cccccgctat catgtccgcc  1860
tctttaggcg agcgggtcac aatgacttgt acagcctcct ccagcgtctc ctcctcctac  1920
ttccattggt accaacagaa acccggaagc tcccctaaac tgtgcatcta cagcaccagc  1980
aatctcgcca gcggcgtgcc ccctaggttt tccggaagcg gaagcaccag ctactcttta  2040
accatctcct ccatggaggc tgaggatgcc gccacctact tttgtcacca gtaccaccgg  2100
tcccccacct tcggaggcgg caccaaactg gagacaaaga gg                     2142

SEQ ID NO: 104          moltype = DNA  length = 399
FEATURE                 Location/Qualifiers
misc_feature            1..399
                        note = IL-2
source                  1..399
                        mol_type = unassigned DNA
                        organism = Homo sapiens
SEQUENCE: 104
gcacctactt caagttctac aaagaaaaca cagctacaac tggagcattt actgctggat  60
ttacagatga ttttgaatgg aattaataat tacaagaatc ccaaactcac caggatgctc  120
acatttaagt tttacatgcc caagaaggcc acagaactga aacatcttca gtgtctagaa  180
gaagaactca aacctctgga ggaagtgcta aatttagctc aaagcaaaaa ctttcactta  240
agacccaggg acttaatcag caatatcaac gtaatagttc tggaactaaa gggatctgaa  300
acaacattca tgtgtgaata tgctgatgag acagcaacca ttgtagaatt tctgaacaga  360
tggattacct tttgtcaaag catcatctca acactaact                         399

SEQ ID NO: 105          moltype = DNA  length = 399
FEATURE                 Location/Qualifiers
misc_feature            1..399
                        note = IL-2
source                  1..399
                        mol_type = unassigned DNA
                        organism = Homo sapiens
SEQUENCE: 105
gcccccacct cctcctccac caagaagacc cagctgcagc tggagcattt actgctggat  60
ttacagatga ttttaaacgg catcaacaac tacaagaacc ccaagctgac tcgtatgctg  120
accttcaagt tctacatgcc caagaaggcc accgagctga agcatttaca gtgtttagag  180
gaggagctga agcccctcga ggaggtgctg aatttagccc agtccaagaa tttccattta  240
aggccccggg atttaatcag caacatcaac gtgatcgttt tagagctgaa gggctccgag  300
accaccttca tgtgcgagta cgccgacgag accgccacca tcgtggagtt tttaaatcgt  360
tggatcacct tctgccagtc catcatctcc actttaacc                         399

SEQ ID NO: 106          moltype = AA  length = 485
FEATURE                 Location/Qualifiers
REGION                  1..485
                        note = Description of Artificial Sequence: Synthetic
                         IL-2/TF/IL-2 sequence
source                  1..485
                        mol_type = protein
                        organism = synthetic construct
SEQUENCE: 106
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGTTNTV AAYNLTWKST NFKTILEWEP KPVNQVYTVQ ISTKSGDWKS  180
KCFYTTDTEC DLTDEIVKDV KQTYLARVFS YPAGNVESTG SAGEPLYENS PEFTPYLETN  240
LGQPTIQSFE QVGTKVNVTV EDERTLVRRN NTFLSLRDVF GKDLIYTLYY WKSSSSGKKT  300
AKTNTNEFLI DVDKGENYCF SVQAVIPSRT VNRKSTDSPV ECMGQEKGEF REAPTSSSTK  360
KTQLQLEHLL LDLQMILNGI NNYKNPKLTR MLTFKFYMPK KATELKHLQC LEEELKPLEE  420
VLNLAQSKNF HLRPRDLISN INVIVLELKG SETTFMCEYA DETATIVEFL NRWITFCQSI  480
ISTLT                                                              485

SEQ ID NO: 107          moltype = DNA  length = 1455
FEATURE                 Location/Qualifiers
misc_feature            1..1455
                        note = Description of Artificial Sequence: Synthetic
                         IL-2/TF/IL-2 sequence
source                  1..1455
                        mol_type = other DNA
                        organism = synthetic construct
SEQUENCE: 107
gcccccacct cctcctccac caagaagacc cagctgcagc tggagcattt actgctggat  60
ttacagatga ttttaaacgg catcaacaac tacaagaacc ccaagctgac tcgtatgctg  120
accttcaagt tctacatgcc caagaaggcc accgagctga agcatttaca gtgtttagag  180
gaggagctga agcccctcga ggaggtgctg aatttagccc agtccaagaa tttccattta  240
aggccccggg atttaatcag caacatcaac gtgatcgttt tagagctgaa gggctccgag  300
accaccttca tgtgcgagta cgccgacgag accgccacca tcgtggagtt tttaaatcgt  360
tggatcacct tctgccagtc catcatctcc actttaacca gcggcacaac caacacagtc  420
gctgcctata acctcacttg gaagagcacc aacttcaaaa ccatcctcga atgggaaccc  480
aaacccgtta accaagttta caccgtgcag atcagcacca agtccggcga ctggaagtcc  540
aaatgtttct ataccaccga caccgagtgc gatctcaccg atgagatcgt gaaagatgtg  600
```

```
aaacagacct acctcgcccg ggtgtttagc taccccgccg gcaatgtgga gagcactggt  660
tccgctggcg agcctttata cgagaacagc cccgaattta ccccttacct cgagaccaat  720
ttaggacagc ccaccatcca aagctttgag caagttggca caaaggtgaa tgtgacagtg  780
gaggacgagc ggactttagt gcggcggaac aacacctttc tcagcctccg ggatgtgttc  840
ggcaaagatt taatctacac actgtattac tggaagtcct cttcctccgg caagaagaca  900
gctaaaacca acacaaacga gtttttaatc gacgtggata aaggcgaaaa ctactgtttc  960
agcgtgcaag ctgtgatccc ctcccggacc gtgaatagga aaagcaccga tagccccgtt  1020
gagtgcatgg gccaagaaaa gggcgagttc cgggaggcac ctacttcaag ttctacaaag  1080
aaaacacagc tacaactgga gcatttactg ctggatttac agatgatttt gaatggaatt  1140
aataattaca agaatcccaa actcaccagg atgctcacat ttaagtttta catgcccaag  1200
aaggccacag aactgaaaca tcttcagtgt ctagaagaag aactcaaacc tctggaggaa  1260
gtgctaaatt tagctcaaag caaaaacttt cacttaagac ccagggactt aatcagcaat  1320
atcaacgtaa tagttctgga actaaaggga tctgaaacaa cattcatgtg tgaatatgct  1380
gatgagacag caaccattgt agaatttctg aacagatgga ttaccttttg tcaaagcatc  1440
atctcaacac taact                                                  1455

SEQ ID NO: 108          moltype = AA  length = 503
FEATURE                 Location/Qualifiers
REGION                  1..503
                        note = Description of Artificial Sequence: Synthetic
                         IL-2/TF/IL-2 sequence
source                  1..503
                        mol_type = protein
                        organism = synthetic construct
SEQUENCE: 108
MKWVTFISLL FLFSSAYSAP TSSSTKKTQL QLEHLLLDLQ MILNGINNYK NPKLTRMLTF  60
KFYMPKKATE LKHLQCLEEE LKPLEEVLNL AQSKNFHLRP RDLISNINVI VLELKGSETT  120
FMCEYADETA TIVEFLNRWI TFCQSIISTL TSGTTNTVAA YNLTWKSTNF KTILEWEPKP  180
VNQVYTVQIS TKSGDWKSKC FYTTDTECDL TDEIVKDVKQ TYLARVFSYP AGNVESTGSA  240
GEPLYENSPE FTPYLETNLG QPTIQSFEQV GTKVNVTVED ERTLVRRNNT FLSLRDVFGK  300
DLIYTLYYWK SSSSGKKTAK TNTNEFLIDV DKGENYCFSV QAVIPSRTVN RKSTDSPVEC  360
MGQEKGEFRE APTSSSTKKT QLQLEHLLLD LQMILNGINN YKNPKLTRML TFKFYMPKKA  420
TELKHLQCLE EELKPLEEVL NLAQSKNFHL RPRDLISNIN VIVLELKGSE TTFMCEYADE  480
TATIVEFLNR WITFCQSIIS TLT                                         503

SEQ ID NO: 109          moltype = DNA  length = 1509
FEATURE                 Location/Qualifiers
misc_feature            1..1509
                        note = Description of Artificial Sequence: Synthetic
                         IL-2/TF/IL-2 sequence
source                  1..1509
                        mol_type = other DNA
                        organism = synthetic construct
SEQUENCE: 109
atgaagtggg tgaccttcat cagcctgctg ttcctgttct ccagcgccta ctccgccccc  60
acctcctcct ccaccaagaa gacccagctg cagctggagc atttactgct ggatttacag  120
atgattttaa acggcatcaa caactacaag aaccccaagc tgactcgtat gctgaccttc  180
aagttctaca tgcccaagaa ggccaccgag ctgaagcatt tacagtgttt agaggaggag  240
ctgaagcccc tcgaggaggt gctgaattta gcccagtcca agaatttcca tttaaggccc  300
cgggatttaa tcagcaacat caacgtgatc gttttagagc tgaagggctc cgagaccacc  360
ttcatgtgcg agtacgccga cgagaccgcc accatcgtgg agtttttaaa tcgttggatc  420
accttctgcc agtccatcat ctccacttta accagcggca caaccaacac agtcgctgcc  480
tataacctca cttggaagag caccaacttc aaaaccatcc tcgaatggga acccaaaccc  540
gttaaccaag tttacaccgt gcagatcagc accaagtccg gcgactggaa gtccaaatgt  600
ttctatacca ccgacaccga gtgcgatctc accgatgaga tcgtgaaaga tgtgaaacag  660
acctacctcg cccgggtgtt tagctacccc gccggcaatg tggagagcac tggttccgct  720
ggcgagcctt tatacgagaa cagccccgaa tttacccctt acctcgagac caatttagga  780
cagcccacca tccaaagctt tgagcaagtt ggcacaaagg tgaatgtgac agtggaggac  840
gagcggactt tagtgcggcg gaacaacacc tttctcagcc tccgggatgt gttcggcaaa  900
gatttaatct acacactgta ttactggaag tcctcttcct ccggcaagaa gacagctaaa  960
accaacacaa acgagttttt aatcgacgtg gataaaggcg aaaactactg tttcagcgtg  1020
caagctgtga tcccctcccg gaccgtgaat aggaaaagca ccgatagccc cgttgagtgc  1080
atgggccaag aaaagggcga gttccgggag gcacctactt caagttctac aaagaaaaca  1140
cagctacaac tggagcattt actgctggat ttacagatga ttttgaatgg aattaataat  1200
tacaagaatc ccaaactcac caggatgctc acatttaagt tttacatgcc caagaaggcc  1260
acagaactga aacatcttca gtgtctagaa gaagaactca aacctctgga ggaagtgcta  1320
aatttagctc aaagcaaaaa ctttcactta agacccaggg acttaatcag caatatcaac  1380
gtaatagttc tggaactaaa gggatctgaa acaacattca tgtgtgaata tgctgatgag  1440
acagcaacca ttgtagaatt tctgaacaga tggattacct tttgtcaaag catcatctca  1500
acactaact                                                         1509

SEQ ID NO: 110          moltype = DNA  length = 342
FEATURE                 Location/Qualifiers
misc_feature            1..342
                        note = IL-15
source                  1..342
                        mol_type = unassigned DNA
                        organism = Homo sapiens
```

```
SEQUENCE: 110
aactgggtga acgtcatcag cgatttaaag aagatcgaag atttaattca gtccatgcat  60
atcgacgcca ctttatacac agaatccgac gtgcacccct cttgtaaggt gaccgccatg  120
aaatgttttt tactggagct gcaagttatc tctttagaga gcggagacgc tagcatccac  180
gacaccgtgg agaatttaat cattttagcc aataactctt tatccagcaa cggcaacgtg  240
acagagtccg gctgcaagga gtgcgaagag ctggaggaga agaacatcaa ggagtttctg  300
caatcctttg tgcacattgt ccagatgttc atcaatacct cc                    342

SEQ ID NO: 111          moltype = DNA  length = 342
FEATURE                 Location/Qualifiers
misc_feature            1..342
                        note = IL-15
source                  1..342
                        mol_type = unassigned DNA
                        organism = Homo sapiens
SEQUENCE: 111
aactgggtga acgtgatcag cgatttaaag aagatcgagg atttaatcca gagcatgcac  60
atcgacgcca ctctgtacac tgagagcgac gtgcacccta gctgcaaggt gactgccatg  120
aagtgctttt tactggagct gcaagttatc tctttagaga gcggcgatgc cagcatccac  180
gacactgtgg agaatttaat cattttagcc aacaactctt taagcagcaa cggcaacgtg  240
acagagagcg gctgcaagga gtgcgaggag ctggaggaga agaacatcaa ggagttttta  300
cagagcttcg tgcacatcgt gcagatgttc atcaacacta gc                    342

SEQ ID NO: 112          moltype = AA  length = 447
FEATURE                 Location/Qualifiers
REGION                  1..447
                        note = Description of Artificial Sequence: Synthetic
                         IL-15/TF/IL-15 sequence
source                  1..447
                        mol_type = protein
                        organism = synthetic construct
SEQUENCE: 112
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTSSGTTNT  120
VAAYNLTWKS TNFKTILEWE PKPVNQVYTV QISTKSGDWK SKCFYTTDTE CDLTDEIVKD  180
VKQTYLARVF SYPAGNVEST GSAGEPLYEN SPEFTPYLET NLGQPTIQSF EQVGTKVNVT  240
VEDERTLVRR NNTFLSLRDV FGKDLIYTLY YWKSSSSGKK TAKTNTNEFL IDVDKGENYC  300
FSVQAVIPSR TVNRKSTDSP VECMGQEKGE FRENWVNVIS DLKKIEDLIQ SMHIDATLYT  360
ESDVHPSCKV TAMKCFLLEL QVISLESGDA SIHDTVENLI ILANNSLSSN GNVTESGCKE  420
CEELEEKNIK EFLQSFVHIV QMFINTS                                     447

SEQ ID NO: 113          moltype = DNA  length = 1341
FEATURE                 Location/Qualifiers
misc_feature            1..1341
                        note = Description of Artificial Sequence: Synthetic
                         IL-15/TF/IL-15 sequence
source                  1..1341
                        mol_type = other DNA
                        organism = synthetic construct
SEQUENCE: 113
aactgggtga acgtgatcag cgatttaaag aagatcgagg atttaatcca gagcatgcac  60
atcgacgcca ctctgtacac tgagagcgac gtgcacccta gctgcaaggt gactgccatg  120
aagtgctttt tactggagct gcaagttatc tctttagaga gcggcgatgc cagcatccac  180
gacactgtgg agaatttaat cattttagcc aacaactctt taagcagcaa cggcaacgtg  240
acagagagcg gctgcaagga gtgcgaggag ctggaggaga agaacatcaa ggagttttta  300
cagagcttcg tgcacatcgt gcagatgttc atcaacacta gcagcggcac aaccaacaca  360
gtcgctgcct ataacctcac ttggaagagc accaacttca aaaccatcct cgaatgggaa  420
cccaaacccg ttaaccaagt ttacaccgtg cagatcagca ccaagtccgg cgactggaag  480
tccaaatgtt tctataccac cgacaccgag tgcgatctca ccgatgagat cgtgaaagat  540
gtgaaacaga cctacctcgc ccgggtgttt agctaccccg ccggcaatgt ggagagcact  600
ggttccgctg gcgagccttt atacgagaac agccccgaat ttacccctta cctcgagacc  660
aatttaggac agcccaccat ccaaagcttt gagcaagttg gcacaaaggt gaatgtgaca  720
gtggaggacg agcggacttt agtgcggcgg aacaacacct ttctcagcct ccgggatgtg  780
ttcggcaaag atttaatcta cactgtat tactggaagt cctcttcctc cggcaagaag  840
acagctaaaa ccaacacaaa cgagttttta atcgacgtgg ataaaggcga aaactactgt  900
ttcagcgtgc aagctgtgat cccctcccgg accgtgaata ggaaaagcac cgatagcccc  960
gttgagtgca tgggccaaga aaagggcgag ttccgggaga actgggtgaa cgtcatcagc  1020
gatttaaaga agatcgaaga tttaattcag tccatgcata tcgacgccac tttatacaca  1080
gaatccgacg tgcacccctc ttgtaaggtg accgccatga aatgtttttt actggagctg  1140
caagttatct ctttagagag cggagacgct agcatccacg acaccgtgga gaatttaatc  1200
attttagcca ataactcttt atccagcaac ggcaacgtga cagagtccgg ctgcaaggag  1260
tgcgaagagc tggaggagaa gaacatcaag gagtttctgc aatcctttgt gcacattgtc  1320
cagatgttca tcaatacctc c                                           1341

SEQ ID NO: 114          moltype = AA  length = 465
FEATURE                 Location/Qualifiers
REGION                  1..465
                        note = Description of Artificial Sequence: Synthetic
                         IL-15/TF/IL-15 sequence
```

```
source                  1..465
                        mol_type = protein
                        organism = synthetic construct
SEQUENCE: 114
MKWVTFISLL FLFSSAYSNW VNVISDLKKI EDLIQSMHID ATLYTESDVH PSCKVTAMKC  60
FLLELQVISL ESGDASIHDT VENLIILANN SLSSNGNVTE SGCKECEELE EKNIKEFLQS  120
FVHIVQMFIN TSSGTTNTVA AYNLTWKSTN FKTILEWEPK PVNQVYTVQI STKSGDWKSK  180
CFYTTDTECD LTDEIVKDVK QTYLARVFSY PAGNVESTGS AGEPLYENSP EFTPYLETNL  240
GQPTIQSFEQ VGTKVNVTVE DERTLVRRNN TFLSLRDVFG KDLIYTLYYW KSSSSGKKTA  300
KTNTNEFLID VDKGENYCFS VQAVIPSRTV NRKSTDSPVE CMGQEKGEFR ENWVNVISDL  360
KKIEDLIQSM HIDATLYTES DVHPSCKVTA MKCFLLELQV ISLESGDASI HDTVENLIIL  420
ANNSLSSNGN VTESGCKECE ELEEKNIKEF LQSFVHIVQM FINTS                465

SEQ ID NO: 115          moltype = DNA  length = 1395
FEATURE                 Location/Qualifiers
misc_feature            1..1395
                        note = Description of Artificial Sequence: Synthetic
                         IL-15/TF/IL-15 sequence
source                  1..1395
                        mol_type = other DNA
                        organism = synthetic construct
SEQUENCE: 115
atgaagtggg tgaccttcat cagcctgctg ttcctgttct ccagcgccta ctccaactgg  60
gtgaacgtga tcagcgattt aaagaagatc gaggatttaa tccagagcat gcacatcgac  120
gccactctgt acactgagag cgacgtgcac cctagctgca aggtgactgc catgaagtgc  180
tttttactgg agctgcaagt tatctcttta gagagcggcg atgccagcat ccacgacact  240
gtggagaatt taatcatttt agccaacaac tctttaagca gcaacggcaa cgtgacagag  300
agcggctgca aggagtgcga ggagctggag gagaagaaca tcaaggagtt tttacagagc  360
ttcgtgcaca tcgtgcagat gttcatcaac actagcagcg gcacaaccaa cacagtcgct  420
gcctataacc tcacttggaa gagcaccaac ttcaaaacca tcctcgaatg ggaacccaaa  480
cccgttaacc aagtttacac cgtgcagatc agcaccaagt ccggcgactg gaagtccaaa  540
tgtttctata ccaccgacac cgagtgcgat ctcaccgatg agatcgtgaa agatgtgaaa  600
cagacctacc tcgcccgggt gtttagctac cccgccggca atgtggagag cactggttcc  660
gctggcgagc ctttatacga gaacagcccc gaatttaccc cttacctcga gaccaattta  720
ggacagccca ccatccaaag ctttgagcaa gttggcacaa aggtgaatgt gacagtggag  780
gacgagcgga ctttagtgcg gcggaacaac acctttctca gcctccggga tgtgttcggc  840
aaagatttaa tctacacact gtattactgg aagtcctctt cctccggcaa gaagacagct  900
aaaaccaaca caaacgagtt tttaatcgac gtggataaag gcgaaaacta ctgtttcagc  960
gtgcaagctg tgatcccctc ccggaccgtg aataggaaaa gcaccgatag ccccgttgag  1020
tgcatgggcc aagaaaaggg cgagttccgg gagaactggg tgaacgtcat cagcgattta  1080
aagaagatcg aagatttaat tcagtccatg catatcgacg ccactttata cacagaatcc  1140
gacgtgcacc cctcttgtaa ggtgaccgcc atgaaatgtt ttttactgga gctgcaagtt  1200
atctctttag agagcggaga cgctagcatc cacgacaccg tggagaattt aatcatttta  1260
gccaataact ctttatccag caacggcaac gtgacagagt ccggctgcaa ggagtgcgaa  1320
gagctggagg agaagaacat caaggagttt ctgcaatcct ttgtgcacat tgtccagatg  1380
ttcatcaata cctcc                                                  1395

SEQ ID NO: 116          moltype = AA  length = 490
FEATURE                 Location/Qualifiers
REGION                  1..490
                        note = Description of Artificial Sequence: Synthetic
                         IL-18/TF/IL-15:IL-12/IL-15RalphaSu sequence
source                  1..490
                        mol_type = protein
                        organism = synthetic construct
SEQUENCE: 116
YFGKLESKLS VIRNLNDQVL FIDQGNRPLF EDMTDSDCRD NAPRTIFIIS MYKDSQPRGM  60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNEDSGT TNTVAAYNLT WKSTNFKTIL  180
EWEPKPVNQV YTVQISTKSG DWKSKCFYTT DTECDLTDEI VKDVKQTYLA RVFSYPAGNV  240
ESTGSAGEPL YENSPEFTPY LETNLGQPTI QSFEQVGTKV NVTVEDERTL VRRNNTFLSL  300
RDVFGKDLIY TLYYWKSSSS GKKTAKTNTN EFLIDVDKGE NYCFSVQAVI PSRTVNRKST  360
DSPVECMGQE KGEFRENWVN VISDLKKIED LIQSMHIDAT LYTESDVHPS CKVTAMKCFL  420
LELQVISLES GDASIHDTVE NLIILANNSL SSNGNVTESG CKECEELEEK NIKEFLQSFV  480
HIVQMFINTS                                                       490

SEQ ID NO: 117          moltype = DNA  length = 1470
FEATURE                 Location/Qualifiers
misc_feature            1..1470
                        note = Description of Artificial Sequence: Synthetic
                         IL-18/TF/IL-15:IL-12/IL-15RalphaSu sequence
source                  1..1470
                        mol_type = other DNA
                        organism = synthetic construct
SEQUENCE: 117
tacttcggca aactggaatc caagctgagc gtgatccgga atttaaacga ccaagttctg  60
tttatcgatc aaggtaaccg gcctctgttc gaggacatga ccgactccga ttgccgggac  120
aatgcccccc ggaccatctt cattatctcc atgtacaagg acagccagcc ccggggcatg  180
gctgtgacaa ttagcgtgaa gtgtgagaaa atcagcactt tatcttgtga gaacaagatc  240
```

```
atctccttta aggaaatgaa cccccccgat aacatcaagg acaccaagtc cgatatcatc  300
ttcttccagc ggtccgtgcc cggtcacgat aacaagatgc agttcgaatc ctcctcctac  360
gagggctact ttttagcttg tgaaaaggag agggatttat tcaagctgat cctcaagaag  420
gaggacgagc tgggcgatcg ttccatcatg ttcaccgtcc aaaacgagga tagcggcaca  480
accaacacag tcgctgccta taacctcact tggaagagca ccaacttcaa aaccatcctc  540
gaatgggaac ccaaacccgt taaccaagtt tacaccgtgc agatcagcac caagtccggc  600
gactggaagt ccaaatgttt ctataccacc gacaccgagt gcgatctcac cgatgagatc  660
gtgaaagatg tgaaacagac ctacctcgcc cgggtgttta gctaccccgc cggcaatgtg  720
gagagcactg gttccgctgg cgagccttta tacgagaaca gccccgaatt tacccccttac  780
ctcgagacca atttaggaca gcccaccatc caaagctttg agcaagttgg cacaaaggtg  840
aatgtgacag tggaggacga gcggacttta gtgcggcgga acaacacctt tctcagcctc  900
cgggatgtgt tcggcaaaga tttaatctac acactgtatt actggaagtc ctcttcctcc  960
ggcaagaaga cagctaaaac caacacaaac gagtttttaa tcgacgtgga taaaggcgaa  1020
aactactgtt tcagcgtgca agctgtgatc ccctcccgga ccgtgaatag gaaaagcacc  1080
gatagccccg ttgagtgcat gggccaagaa aagggcgagt tccgggagaa ctgggtgaac  1140
gtcatcagcg atttaaagaa gatcgaagat ttaattcagt ccatgcatat cgacgccact  1200
ttatacacag aatccgacgt gcacccctct tgtaaggtga ccgccatgaa atgtttttta  1260
ctggagctgc aagttatctc tttagagagc ggagacgcta gcatccacga caccgtggag  1320
aatttaatca ttttagccaa taactcttta tccagcaacg gcaacgtgac agagtccggc  1380
tgcaaggagt gcgaagagct ggaggagaag aacatcaagg agtttctgca atcctttgtg  1440
cacattgtcc agatgttcat caatacctcc                                 1470

SEQ ID NO: 118         moltype = AA  length = 508
FEATURE                Location/Qualifiers
REGION                 1..508
                       note = Description of Artificial Sequence: Synthetic
                        IL-18/TF/IL-15:IL-12/IL-15RalphaSu sequence
source                 1..508
                       mol_type = protein
                       organism = synthetic construct
SEQUENCE: 118
MKWVTFISLL FLFSSAYSYF GKLESKLSVI RNLNDQVLFI DQGNRPLFED MTDSDCRDNA  60
PRTIFIISMY KDSQPRGMAV TISVKCEKIS TLSCENKIIS FKEMNPPDNI KDTKSDIIFF  120
QRSVPGHDNK MQFESSSYEG YFLACEKERD LFKLILKKED ELGDRSIMFT VQNEDSGTTN  180
TVAAYNLTWK STNFKTILEW EPKPVNQVYT VQISTKSGDW KSKCFYTTDT ECDLTDEIVK  240
DVKQTYLARV FSYPAGNVES TGSAGEPLYE NSPEFTPYLE TNLGQPTIQS FEQVGTKVNV  300
TVEDERTLVR RNNTFLSLRD VFGKDLIYTL YYWKSSSSGK KTAKTNTNEF LIDVDKGENY  360
CFSVQAVIPS RTVNRKSTDS PVECMGQEKG EFRENWVNVI SDLKKIEDLI QSMHIDATLY  420
TESDVHPSCK VTAMKCFLLE LQVISLESGD ASIHDTVENL IILANNSLSS NGNVTESGCK  480
ECEELEEKNI KEFLQSFVHI VQMFINTS                                   508

SEQ ID NO: 119         moltype = DNA  length = 1524
FEATURE                Location/Qualifiers
misc_feature           1..1524
                       note = Description of Artificial Sequence: Synthetic
                        IL-18/TF/IL-15:IL-12/IL-15RalphaSu sequence
source                 1..1524
                       mol_type = other DNA
                       organism = synthetic construct
SEQUENCE: 119
atgaagtggg tcacatttat ctctttactg ttcctcttct ccagcgccta cagctacttc  60
ggcaaactgg aatccaagct gagcgtgatc cggaatttaa acgaccaagt tctgtttatc  120
gatcaaggta accggcctct gttcgaggac atgaccgact ccgattgccg ggacaatgcc  180
ccccggacca tcttcattat ctccatgtac aaggacagcc agccccgggg catggctgtg  240
acaattagcg tgaagtgtga gaaaatcagc actttatctt gtgagaacaa gatcatctcc  300
tttaaggaaa tgaacccccc cgataacatc aaggacacca agtccgatat catcttcttc  360
cagcggtccg tgcccggtca cgataacaag atgcagttcg aatcctcctc ctacgagggc  420
tactttttag cttgtgaaaa ggagagggat ttattcaagc tgatcctcaa gaaggaggac  480
gagctgggcg atcgttccat catgttcacc gtccaaaacg aggatagcgg cacaaccaac  540
acagtcgctg cctataacct cacttggaag agcaccaact tcaaaaccat cctcgaatgg  600
gaacccaaac ccgttaacca agtttacacc gtgcagatca gcaccaagtc cggcgactgg  660
aagtccaaat gtttctatac caccgacacc gagtgcgatc tcaccgatga gatcgtgaaa  720
gatgtgaaac agacctacct cgcccgggtg tttagctacc ccgccggcaa tgtggagagc  780
actggttccg ctggcgagcc tttatacgag aacagccccg aatttacccc ttacctcgag  840
accaatttag gacagcccac catccaaagc tttgagcaag ttggcacaaa ggtgaatgtg  900
acagtggagg acgagcggac tttagtgcgg cggaacaaca cctttctcag cctccgggat  960
gtgttcggca aagatttaat ctacacactg tattactgga agtcctcttc ctccggcaag  1020
aagacagcta aaaccaacac aaacgagttt ttaatcgacg tggataaagg cgaaaactac  1080
tgtttcagcg tgcaagctgt gatcccctcc cggaccgtga ataggaaaag caccgatagc  1140
cccgttgagt gcatgggcca agaaaagggc gagttccggg agaactgggt gaacgtcatc  1200
agcgatttaa agaagatcga agatttaatt cagtccatgc atatcgacgc cactttatac  1260
acagaatccg acgtgcaccc ctcttgtaag gtgaccgcca tgaaatgttt tttactggag  1320
ctgcaagtta tctctttaga gagcggagac gctagcatcc acgacaccgt ggagaattta  1380
atcattttag ccaataactc tttatccagc aacggcaacg tgacagagtc cggctgcaag  1440
gagtgcgaag agctggagga gaagaacatc aaggagtttc tgcaatcctt tgtgcacatt  1500
gtccagatgt tcatcaatac ctcc                                       1524

SEQ ID NO: 120         moltype = AA  length = 583
FEATURE                Location/Qualifiers
```

```
REGION                  1..583
                        note = Description of Artificial Sequence: Synthetic
                         IL-12/IL-15RalphaSu sequence
source                  1..583
                        mol_type = protein
                        organism = synthetic construct
SEQUENCE: 120
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASIT CPPPMSVEHA DIWVKSYSLY  540
SRERYICNSG FKRKAGTSSL TECVLNKATN VAHWTTPSLK CIR                  583

SEQ ID NO: 121          moltype = DNA  length = 1749
FEATURE                 Location/Qualifiers
misc_feature            1..1749
                        note = Description of Artificial Sequence: Synthetic
                         IL-12/IL-15RalphaSu sequence
source                  1..1749
                        mol_type = other DNA
                        organism = synthetic construct
SEQUENCE: 121
atttgggaac tgaagaagga cgtctacgtg gtcgaactgg actggtatcc cgatgctccc  60
ggcgaaatgg tggtgctcac ttgtgacacc cccgaagaag acggcatcac ttggaccctc  120
gatcagagca gcgaggtgct gggctccgga aagaccctca caatccaagt taaggagttc  180
ggagacgctg gccaatacac atgccacaag ggaggcgagg tgctcagcca ttccttatta  240
ttattacaca agaaggaaga cggaatctgg tccaccgaca ttttaaaaga tcagaaggag  300
cccaagaata agaccttttt aaggtgtgag gccaaaaact acagcggtcg tttcacttgt  360
tggtggctga ccaccatttc caccgattta accttctccg tgaaaagcag ccggggaagc  420
tccgaccctc aaggtgtgac atgtggagcc gctaccctca gcgctgagag ggttcgtggc  480
gataacaagg aatacgagta cagcgtggag tgccaagaag atagcgcttg tcccgctgcc  540
gaagaatctt tacccattga ggtgatggtg gacgccgtgc acaaactcaa gtacgagaac  600
tacacctcct ccttctttat ccgggacatc attaagcccg atcctcctaa gaatttacag  660
ctgaagcctc tcaaaaatag ccggcaagtt gaggtctctt gggaatatcc cgacacttgg  720
agcacacccc acagctactt ctctttaacc ttttgtgtgc aagttcaagg taaaagcaag  780
cgggagaaga aagaccgggt gtttaccgac aaaaccagcg ccaccgtcat ctgtcggaag  840
aacgcctcca tcagcgtgag ggctcaagat cgttattact ccagcagctg gtccgagtgg  900
gccagcgtgc cttgttccgg cggtggagga tccggaggag gtggctccgg cggcggagga  960
tctcgtaacc tccccgtggc tacccccgat cccggaatgt tcccttgttt acaccacagc  1020
cagaatttac tgagggccgt gagcaacatg ctgcagaaag ctaggcagac tttagaattt  1080
tacccttgca ccagcgagga gatcgaccat gaagatatca ccaaggacaa gacatccacc  1140
gtggaggctt gtttacctct ggagctgaca aagaacgagt cttgtctcaa ctctcgtgaa  1200
accagcttca tcacaaatgg ctcttgttta gcttcccgga agacctcctt tatgatggct  1260
ttatgcctca gctccatcta cgaggattta aagatgtacc aagtggagtt caagaccatg  1320
aacgccaagc tgctcatgga ccctaaacgg cagatctttt tagaccagaa catgctggct  1380
gtgattgatg agctgatgca agctttaaac ttcaactccg agaccgtccc tcagaagtcc  1440
tccctcgagg agcccgattt ttacaagaca aagatcaaac tgtgcatttt actccacgcc  1500
tttaggatcc gggccgtgac cattgaccgg gtcatgagct atttaaacgc cagcattaca  1560
tgccccccctc ccatgagcgt ggagcacgcc gacatctggg tgaagagcta tagcctctac  1620
agccgggaga ggtatatctg taacagcggc ttcaagagga aggccggcac cagcagcctc  1680
accgagtgcg tgctgaataa ggctaccaac gtggctcact ggacaacacc ctctttaaag  1740
tgcatccgg                                                        1749

SEQ ID NO: 122          moltype = AA  length = 601
FEATURE                 Location/Qualifiers
REGION                  1..601
                        note = Description of Artificial Sequence: Synthetic
                         IL-12/IL-15RalphaSu sequence
source                  1..601
                        mol_type = protein
                        organism = synthetic construct
SEQUENCE: 122
MKWVTFISLL FLFSSAYSIW ELKKDVYVVE LDWYPDAPGE MVVLTCDTPE EDGITWTLDQ  60
SSEVLGSGKT LTIQVKEFGD AGQYTCHKGG EVLSHSLLLL HKKEDGIWST DILKDQKEPK  120
NKTFLRCEAK NYSGRFTCWW LTTISTDLTF SVKSSRGSSD PQGVTCGAAT LSAERVRGDN  180
KEYEYSVECQ EDSACPAAEE SLPIEVMVDA VHKLKYENYT SSFFIRDIIK PDPPKNLQLK  240
PLKNSRQVEV SWEYPDTWST PHSYFSLTFC VQVQGKSKRE KKDRVFTDKT SATVICRKNA  300
SISVRAQDRY YSSSWSEWAS VPCSGGGGSG GGGSGGGGSR NLPVATPDPG MFPCLHHSQN  360
LLRAVSNMLQ KARQTLEFYP CTSEEIDHED ITKDKTSTVE ACLPLELTKN ESCLNSRETS  420
FITNGSCLAS RKTSFMMALC LSSIYEDLKM YQVEFKTMNA KLLMDPKRQI FLDQNMLAVI  480
DELMQALNFN SETVPQKSSL EEPDFYKTKI KLCILLHAFR IRAVTIDRVM SYLNASITCP  540
PPMSVEHADI WVKSYSLYSR ERYICNSGFK RKAGTSSLTE CVLNKATNVA HWTTPSLKCI  600
R                                                                601
```

-continued

```
SEQ ID NO: 123          moltype = DNA  length = 1803
FEATURE                 Location/Qualifiers
misc_feature            1..1803
                        note = Description of Artificial Sequence: Synthetic
                         IL-12/IL-15RalphaSu sequence
source                  1..1803
                        mol_type = other DNA
                        organism = synthetic construct
SEQUENCE: 123
atgaaatggg tgacctttat ttctttactg ttcctcttta gcagcgccta ctccatttgg  60
gaactgaaga aggacgtcta cgtggtcgaa ctggactggt atcccgatgc tcccggcgaa  120
atggtggtgc tcacttgtga cacccccgaa gaagacggca tcacttggac cctcgatcag  180
agcagcgagg tgctgggctc cggaaagacc ctcacaatcc aagttaagga gttcggagac  240
gctggccaat acacatgcca caagggaggc gaggtgctca gccattcctt attattatta  300
cacaagaagg aagacggaat ctggtccacc gacattttaa aagatcagaa ggagcccaag  360
aataagacct ttttaaggtg tgaggccaaa aactacagcg gtcgtttcac ttgttggtgg  420
ctgaccacca tttccaccga tttaaccttc tccgtgaaaa gcagccgggg aagctccgac  480
cctcaaggtg tgacatgtgg agccgctacc ctcagcgctg agagggttcg tggcgataac  540
aaggaatacg agtacagcgt ggagtgccaa gaagatagcg cttgtcccgc tgccgaagaa  600
tctttaccca ttgaggtgat ggtggacgcc gtgcacaaac tcaagtacga gaactacacc  660
tcctccttct ttatccggga catcattaag cccgatcctc ctaagaattt acagctgaag  720
cctctcaaaa atagccggca agttgaggtc tcttgggaat atcccgacac ttggagcaca  780
ccccacagct acttctcttt aaccttttgt gtgcaagttc aaggtaaaag caagcgggag  840
aagaaagacc gggtgtttac cgacaaaacc agcgccaccg tcatctgtcg gaagaacgcc  900
tccatcagcg tgagggctca agatcgttat tactccagca gctggtccga gtgggccagc  960
gtgccttgtt ccggcggtgg aggatccgga ggaggtggct ccggcggcgg aggatctcgt  1020
aacctccccg tggctacccc cgatcccgga atgttccctt gtttacacca cagccagaat  1080
ttactgaggg ccgtgagcaa catgctgcag aaagctaggc agactttaga attttaccct  1140
tgcaccagcg aggagatcga ccatgaagat atcaccaagg acaagacatc caccgtggag  1200
gcttgtttac ctctggagct gacaaagaac gagtcttgtc tcaactctcg tgaaaccagc  1260
ttcatcacaa atggctcttg tttagcttcc cggaagacct cctttatgat ggctttatgc  1320
ctcagctcca tctacgagga tttaaagatg taccaagtgg agttcaagac catgaacgcc  1380
aagctgctca tggaccctaa acggcagatc tttttagacc agaacatgct ggctgtgatt  1440
gatgagctga tgcaagcttt aaacttcaac tccgagaccg tccctcagaa gtcctccctc  1500
gaggagcccg atttttacaa gacaaagatc aaactgtgca ttttactcca cgcctttagg  1560
atccgggccg tgaccattga ccgggtcatg agctatttaa acgccagcat tacatgcccc  1620
cctcccatga gcgtggagca cgccgacatc tgggtgaaga gctatagcct ctacagccgg  1680
gagaggtata tctgtaacag cggcttcaag aggaaggccg gcaccagcag cctcaccgag  1740
tgcgtgctga ataaggctac caacgtggct cactggacaa caccctcttt aaagtgcatc  1800
cgg                                                                1803

SEQ ID NO: 124          moltype = AA  length = 133
FEATURE                 Location/Qualifiers
REGION                  1..133
                        note = IL-21
source                  1..133
                        mol_type = protein
                        organism = Homo sapiens
SEQUENCE: 124
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDS                                                     133

SEQ ID NO: 125          moltype = DNA  length = 399
FEATURE                 Location/Qualifiers
misc_feature            1..399
                        note = IL-21
source                  1..399
                        mol_type = unassigned DNA
                        organism = Homo sapiens
SEQUENCE: 125
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcc                         399

SEQ ID NO: 126          moltype = AA  length = 466
FEATURE                 Location/Qualifiers
REGION                  1..466
                        note = Description of Artificial Sequence: Synthetic 21t15
                         sequence
source                  1..466
                        mol_type = protein
                        organism = synthetic construct
```

```
SEQUENCE: 126
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSSGTTNTV AAYNLTWKST NFKTILEWEP KPVNQVYTVQ ISTKSGDWKS  180
KCFYTTDTEC DLTDEIVKDV KQTYLARVFS YPAGNVESTG SAGEPLYENS PEFTPYLETN  240
LGQPTIQSFE QVGTKVNVTV EDERTLVRRN NTFLSLRDVF GKDLIYTLYY WKSSSSGKKT  300
AKTNTNEFLI DVDKGENYCF SVQAVIPSRT VNRKSTDSPV ECMGQEKGEF RENWVNVISD  360
LKKIEDLIQS MHIDATLYTE SDVHPSCKVT AMKCFLLELQ VISLESGDAS IHDTVENLII  420
LANNSLSSNG NVTESGCKEC EELEEKNIKE FLQSFVHIVQ MFINTS                466

SEQ ID NO: 127          moltype = DNA  length = 1398
FEATURE                 Location/Qualifiers
misc_feature            1..1398
                        note = Description of Artificial Sequence: Synthetic 21t15
                         sequence
source                  1..1398
                        mol_type = other DNA
                        organism = synthetic construct
SEQUENCE: 127
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcct ccggcaccac caataccgtg  420
gccgcttata acctcacatg gaagagcacc aacttcaaga caattctgga atgggaaccc  480
aagcccgtca atcaagttta caccgtgcag atctccacca aatccggaga ctggaagagc  540
aagtgcttct acacaacaga caccgagtgt gatttaaccg acgaaatcgt caaggacgtc  600
aagcaaacct atctggctcg ggtcttttcc taccccgctg gcaatgtcga gtccaccggc  660
tccgctggcg agcctctcta cgagaattcc cccgaattca ccccttattt agagaccaat  720
ttaggccagc ctaccatcca gagcttcgag caagttggca ccaaggtgaa cgtcaccgtc  780
gaggatgaaa ggactttagt gcggcggaat aacacatttt tatccctccg ggatgtgttc  840
ggcaaagacc tcatctacac actgtactat tggaagtcca gctcctccgg caaaaagacc  900
gctaagacca acaccaacga gtttttaatt gacgtggaca aaggcgagaa ctactgcttc  960
agcgtgcaag ccgtgatccc ttctcgtacc gtcaaccgga agagcacaga ttcccccgtt  1020
gagtgcatgg gccaagaaaa gggcgagttc cgggagaact gggtgaacgt catcagcgat  1080
ttaaagaaga tcgaagattt aattcagtcc atgcatatcg acgccacttt atacacagaa  1140
tccgacgtgc acccctcttg taaggtgacc gccatgaaat gtttttttact ggagctgcaa  1200
gttatctctt tagagagcgg agacgctagc atccacgaca ccgtggagaa tttaatcatt  1260
ttagccaata actctttatc cagcaacggc aacgtgacag agtccggctg caaggagtgc  1320
gaagagctgg aggagaagaa catcaaggag tttctgcaat cctttgtgca cattgtccag  1380
atgttcatca atacctcc                                             1398

SEQ ID NO: 128          moltype = AA  length = 484
FEATURE                 Location/Qualifiers
REGION                  1..484
                        note = Description of Artificial Sequence: Synthetic 21t15
                         sequence
source                  1..484
                        mol_type = protein
                        organism = synthetic construct
SEQUENCE: 128
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SSGTTNTVAA YNLTWKSTNF KTILEWEPKP  180
VNQVYTVQIS TKSGDWKSKC FYTTDTECDL TDEIVKDVKQ TYLARVFSYP AGNVESTGSA  240
GEPLYENSPE FTPYLETNLG QPTIQSFEQV GTKVNVTVED ERTLVRRNNT FLSLRDVFGK  300
DLIYTLYYWK SSSSGKKTAK TNTNEFLIDV DKGENYCFSV QAVIPSRTVN RKSTDSPVEC  360
MGQEKGEFRE NWVNVISDLK KIEDLIQSMH IDATLYTESD VHPSCKVTAM KCFLLELQVI  420
SLESGDASIH DTVENLIILA NNSLSSNGNV TESGCKECEE LEEKNIKEFL QSFVHIVQMF  480
INTS                                                            484

SEQ ID NO: 129          moltype = DNA  length = 1452
FEATURE                 Location/Qualifiers
misc_feature            1..1452
                        note = Description of Artificial Sequence: Synthetic 21t15
                         sequence
source                  1..1452
                        mol_type = other DNA
                        organism = synthetic construct
SEQUENCE: 129
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
```

```
ctgtcctcca ggacccacgg ctccgaggac tcctccggca ccaccaatac cgtggccgct  480
tataacctca catggaagag caccaacttc aagacaattc tggaatggga acccaagccc  540
gtcaatcaag tttacaccgt gcagatctcc accaaatccg gagactggaa gagcaagtgc  600
ttctacacaa cagacaccga gtgtgattta accgacgaaa tcgtcaagga cgtcaagcaa  660
acctatctgg ctcgggtctt ttcctacccc gctggcaatg tcgagtccac cggctccgct  720
ggcgagcctc tctacgagaa ttcccccgaa ttcacccctt atttagagac caatttaggc  780
cagcctacca tccagagctt cgagcaagtt ggcaccaagg tgaacgtcac cgtcgaggat  840
gaaaggactt tagtgcggcg gaataacaca tttttatccc tccgggatgt gttcggcaaa  900
gacctcatct acacactgta ctattggaag tccagctcct ccggcaaaaa gaccgctaag  960
accaacacca acgagttttt aattgacgtg gacaaaggcg agaactactg cttcagcgtg  1020
caagccgtga tcccttctcg taccgtcaac cggaagagca cagattcccc cgttgagtgc  1080
atgggccaag aaaagggcga gttccgggag aactgggtga acgtcatcag cgatttaaag  1140
aagatcgaag atttaattca gtccatgcat atcgacgcca ctttatacac agaatccgac  1200
gtgcacccct cttgtaaggt gaccgccatg aaatgttttt tactggagct gcaagttatc  1260
tctttagaga gcggagacgc tagcatccac gacaccgtgg agaatttaat catttttagcc  1320
aataactctt tatccagcaa cggcaacgtg acagagtccg gctgcaagga gtgcgaagag  1380
ctggaggaga agaacatcaa ggagtttctg caatcctttg tgcacattgt ccagatgttc  1440
atcaatacct cc                                                    1452

SEQ ID NO: 130         moltype = AA  length = 352
FEATURE                Location/Qualifiers
REGION                 1..352
                       note = Description of Artificial Sequence: Synthetic TGFRs
                        sequence
source                 1..352
                       mol_type = protein
                       organism = synthetic construct
SEQUENCE: 130
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IR          352

SEQ ID NO: 131         moltype = DNA  length = 1056
FEATURE                Location/Qualifiers
misc_feature           1..1056
                       note = Description of Artificial Sequence: Synthetic TGFRs
                        sequence
source                 1..1056
                       mol_type = other DNA
                       organism = synthetic construct
SEQUENCE: 131
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcacgatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgcaca  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga catcacgtgt cctcctccta tgtccgtgga acacgcagac  900
atctgggtca agagctacag cttgtactcc agggagcggt acatttgtaa ctctggtttc  960
aagcgtaaag ccggcacgtc cagcctgacg gagtgcgtgt tgaacaaggc cacgaatgtc  1020
gcccactgga caaccccag tctcaaatgt attaga                           1056

SEQ ID NO: 132         moltype = AA  length = 370
FEATURE                Location/Qualifiers
REGION                 1..370
                       note = Description of Artificial Sequence: Synthetic TGFRs
                        sequence
source                 1..370
                       mol_type = protein
                       organism = synthetic construct
SEQUENCE: 132
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR                                                        370
```

```
SEQ ID NO: 133          moltype = DNA  length = 1110
FEATURE                 Location/Qualifiers
misc_feature            1..1110
                        note = Description of Artificial Sequence: Synthetic TGFRs
                         sequence
source                  1..1110
                        mol_type = other DNA
                        organism = synthetic construct
SEQUENCE: 133
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcac gatcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg cacaatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gacctttttc  840
atgtgctcct gcagcagcga cgaatgcaac gacaatatca tctttagcga ggaatacaat  900
accagcaacc ccgacatcac gtgtcctcct cctatgtccg tggaacacgc agacatctgg  960
gtcaagagct acagcttgta ctccagggag cggtacattt gtaactctgg tttcaagcgt  1020
aaagccggca cgtccagcct gacggagtgc gtgttgaaca aggccacgaa tgtcgcccac  1080
tggacaaccc ccagtctcaa atgtattaga                                  1110

SEQ ID NO: 134          moltype = DNA  length = 399
FEATURE                 Location/Qualifiers
misc_feature            1..399
                        note = IL-21
source                  1..399
                        mol_type = unassigned DNA
                        organism = Homo sapiens
SEQUENCE: 134
caaggtcaag atcgccacat gattagaatg cgtcaactta tagatattgt tgatcagctg  60
aaaaattatg tgaatgactt ggtccctgaa tttctgccag ctccagaaga tgtagagaca  120
aactgtgagt ggtcagcttt ttcctgtttt cagaaggccc aactaaagtc agcaaataca  180
ggaaacaatg aaaggataat caatgtatca attaaaaagc tgaagaggaa accaccttcc  240
acaaatgcag ggagaagaca gaaacacaga ctaacatgcc cttcatgtga ttcttatgag  300
aaaaaaccac ccaaagaatt cctagaaaga ttcaaatcac ttctccaaaa gatgattcat  360
cagcatctgt cctctagaac acacggaagt gaagattcc                        399

SEQ ID NO: 135          moltype = AA  length = 152
FEATURE                 Location/Qualifiers
REGION                  1..152
                        note = IL-7
source                  1..152
                        mol_type = protein
                        organism = Homo sapiens
SEQUENCE: 135
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EH                               152

SEQ ID NO: 136          moltype = DNA  length = 456
FEATURE                 Location/Qualifiers
misc_feature            1..456
                        note = IL-7
source                  1..456
                        mol_type = unassigned DNA
                        organism = Homo sapiens
SEQUENCE: 136
gattgtgata ttgaaggtaa agatggcaaa caatatgaga gtgttctaat ggtcagcatc  60
gatcaattat tggacagcat gaaagaaatt ggtagcaatt gcctgaataa tgaatttaac  120
ttttttaaaa gacatatctg tgatgctaat aaggaaggta tgtttttatt ccgtgctgct  180
cgcaagttga ggcaatttct taaaatgaat agcactggtg attttgatct ccacttatta  240
aaagtttcag aaggcacaac aatactgttg aactgcactg gccaggttaa aggaagaaaa  300
ccagctgccc tgggtgaagc ccaaccaaca aagagtttgg aagaaaataa atctttaaag  360
gaacagaaaa aactgaatga cttgtgtttc ctaaagagac tattacaaga gataaaaact  420
tgttggaata aaattttgat gggcactaaa gaacac                           456

SEQ ID NO: 137          moltype = AA  length = 217
FEATURE                 Location/Qualifiers
```

```
REGION                  1..217
                        note = Description of Artificial Sequence: Synthetic 7s
                         sequence
source                  1..217
                        mol_type = protein
                        organism = synthetic construct
SEQUENCE: 137
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EHITCPPPMS VEHADIWVKS YSLYSRERYI  180
CNSGFKRKAG TSSLTECVLN KATNVAHWTT PSLKCIR                          217

SEQ ID NO: 138          moltype = DNA  length = 651
FEATURE                 Location/Qualifiers
misc_feature            1..651
                        note = Description of Artificial Sequence: Synthetic 7s
                         sequence
source                  1..651
                        mol_type = other DNA
                        organism = synthetic construct
SEQUENCE: 138
gattgtgata ttgaaggtaa agatggcaaa caatatgaga gtgttctaat ggtcagcatc  60
gatcaattat tggacagcat gaaagaaatt ggtagcaatt gcctgaataa tgaatttaac  120
ttttttaaaa gacatatctg tgatgctaat aaggaaggta tgtttttatt ccgtgctgct  180
cgcaagttga ggcaatttct taaaatgaat agcactggtg attttgatct ccacttatta  240
aaagtttcag aaggcacaac aatactgttg aactgcactg gccaggttaa aggaagaaaa  300
ccagctgccc tgggtgaagc ccaaccaaca aagagtttgg aagaaaataa atctttaaag  360
gaacagaaaa aactgaatga cttgtgtttc ctaaagagac tattacaaga gataaaaact  420
tgttggaata aaattttgat gggcactaaa gaacacatca cgtgccctcc ccccatgtcc  480
gtggaacacg cagacatctg ggtcaagagc tacagcttgt actccaggga gcggtacatt  540
tgtaactctg gtttcaagcg taaagccggc acgtccagcc tgacggagtg cgtgttgaac  600
aaggccacga atgtcgccca ctggacaacc cccagtctca aatgcattag a           651

SEQ ID NO: 139          moltype = AA  length = 234
FEATURE                 Location/Qualifiers
REGION                  1..234
                        note = Description of Artificial Sequence: Synthetic 7s
                         sequence
source                  1..234
                        mol_type = protein
                        organism = synthetic construct
SEQUENCE: 139
MGVKVLFALI CIAVAEADCD IEGKDGKQYE SVLMVSIDQL LDSMKEIGSN CLNNEFNFFK  60
RHICDANKEG MFLFRAARKL RQFLKMNSTG DFDLHLLKVS EGTTILLNCT GQVKGRKPAA  120
LGEAQPTKSL EENKSLKEQK KLNDLCFLKR LLQEIKTCWN KILMGTKEHI TCPPPMSVEH  180
ADIWVKSYSL YSRERYICNS GFKRKAGTSS LTECVLNKAT NVAHWTTPSL KCIR        234

SEQ ID NO: 140          moltype = DNA  length = 702
FEATURE                 Location/Qualifiers
misc_feature            1..702
                        note = Description of Artificial Sequence: Synthetic 7s
                         sequence
source                  1..702
                        mol_type = other DNA
                        organism = synthetic construct
SEQUENCE: 140
atgggagtga aagttctttt tgcccttatt tgtattgctg tggccgaggc cgattgtgat  60
attgaaggta aagatggcaa acaatatgag agtgttctaa tggtcagcat cgatcaatta  120
ttggacagca tgaaagaaat tggtagcaat tgcctgaata atgaatttaa ctttttttaaa  180
agacatatct gtgatgctaa taaggaaggt atgtttttat tccgtgctgc tcgcaagttg  240
aggcaatttc ttaaaatgaa tagcactggt gattttgatc tccacttatt aaaagtttca  300
gaaggcacaa caatactgtt gaactgcact ggccaggtta aaggaagaaa accagctgcc  360
ctgggtgaag cccaaccaac aaagagtttg gaagaaaata aatctttaaa ggaacagaaa  420
aaactgaatg acttgtgttt cctaaagaga ctattacaag agataaaaac ttgttggaat  480
aaaattttga tgggcactaa agaacacatc acgtgccctc cccccatgtc cgtggaacac  540
gcagacatct gggtcaagag ctacagcttg tactccaggg agcggtacat ttgtaactct  600
ggtttcaagc gtaaagccgg cacgtccagc ctgacggagt gcgtgttgaa caaggccacg  660
aatgtcgccc actggacaac ccccagtctc aaatgcatta ga                    702

SEQ ID NO: 141          moltype = AA  length = 485
FEATURE                 Location/Qualifiers
REGION                  1..485
                        note = Description of Artificial Sequence: Synthetic 7t15
                         sequence
source                  1..485
                        mol_type = protein
                        organism = synthetic construct
```

```
SEQUENCE: 141
DCDIEGKDGK QYESVLMVSI DQLLDSMKEI GSNCLNNEFN FFKRHICDAN KEGMFLFRAA  60
RKLRQFLKMN STGDFDLHLL KVSEGTTILL NCTGQVKGRK PAALGEAQPT KSLEENKSLK  120
EQKKLNDLCF LKRLLQEIKT CWNKILMGTK EHSGTTNTVA AYNLTWKSTN FKTILEWEPK  180
PVNQVYTVQI STKSGDWKSK CFYTTDTECD LTDEIVKDVK QTYLARVFSY PAGNVESTGS  240
AGEPLYENSP EFTPYLETNL GQPTIQSFEQ VGTKVNVTVE DERTLVRRNN TFLSLRDVFG  300
KDLIYTLYYW KSSSSGKKTA KTNTNEFLID VDKGENYCFS VQAVIPSRTV NRKSTDSPVE  360
CMGQEKGEFR ENWVNVISDL KKIEDLIQSM HIDATLYTES DVHPSCKVTA MKCFLLELQV  420
ISLESGDASI HDTVENLIIL ANNSLSSNGN VTESGCKECE ELEEKNIKEF LQSFVHIVQM  480
FINTS                                                        485

SEQ ID NO: 142          moltype = DNA  length = 1455
FEATURE                 Location/Qualifiers
misc_feature            1..1455
                        note = Description of Artificial Sequence: Synthetic 7t15
                         sequence
source                  1..1455
                        mol_type = other DNA
                        organism = synthetic construct
SEQUENCE: 142
gattgcgaca tcgagggcaa ggacggcaag cagtacgaga gcgtgctgat ggtgtccatc  60
gaccagctgc tggacagcat gaaggagatc ggctccaact gcctcaacaa cgagttcaac  120
ttcttcaagc ggcacatctg cgacgccaac aaggagggca tgttcctgtt cagggccgcc  180
aggaaactgc ggcagttcct gaagatgaac tccaccggcg acttcgacct gcacctgctg  240
aaggtgtccg agggcaccac catcctgctg aactgcaccg gacaggtgaa gggccggaaa  300
cctgctgctc tgggagaggc ccaacccacc aagagcctgg aggagaacaa gtccctgaag  360
gagcagaaga agctgaacga cctgtgcttc ctgaagaggc tgctgcagga gatcaagacc  420
tgctggaaca agatcctgat gggcaccaag gagcatagcg gcacaaccaa cacagtcgct  480
gcctataacc tcacttggaa gagcaccaac ttcaaaacca tcctcgaatg ggaacccaaa  540
cccgttaacc aagtttacac cgtgcagatc agcaccaagt ccggcgactg gaagtccaaa  600
tgtttctata ccaccgacac cgagtgcgat ctcaccgatg agatcgtgaa agatgtgaaa  660
cagacctacc tcgcccgggt gtttagctac cccgccggca atgtggagag cactggttcc  720
gctggcgagc ctttatacga gaacagcccc gaatttaccc cttacctcga gaccaattta  780
ggacagccca ccatccaaag ctttgagcaa gttggcacaa aggtgaatgt gacagtggag  840
gacgagcgga ctttagtgcg gcggaacaac acctttctca gcctccggga tgtgttcggc  900
aaagatttaa tctacacact gtattactgg aagtcctctt cctccggcaa gaagacagct  960
aaaaccaaca caaacgagtt tttaatcgac gtggataaag gcgaaaacta ctgtttcagc  1020
gtgcaagctg tgatcccctc ccggaccgtg aataggaaaa gcaccgatag ccccgttgag  1080
tgcatgggcc aagaaaaggg cgagttccgg gagaactggg tgaacgtcat cagcgattta  1140
aagaagatcg aagatttaat tcagtccatg catatcgacg ccactttata cacagaatcc  1200
gacgtgcacc cctcttgtaa ggtgaccgcc atgaaatgtt ttttactgga gctgcaagtt  1260
atctctttag agagcggaga cgctagcatc cacgacaccg tggagaattt aatcatttta  1320
gccaataact ctttatccag caacggcaac gtgacagagt ccggctgcaa ggagtgcgaa  1380
gagctggagg agaagaacat caaggagttt ctgcaatcct ttgtgcacat tgtccagatg  1440
ttcatcaata cctcc                                             1455

SEQ ID NO: 143          moltype = AA  length = 503
FEATURE                 Location/Qualifiers
REGION                  1..503
                        note = Description of Artificial Sequence: Synthetic 7t15
                         sequence
source                  1..503
                        mol_type = protein
                        organism = synthetic construct
SEQUENCE: 143
MKWVTFISLL FLFSSAYSDC DIEGKDGKQY ESVLMVSIDQ LLDSMKEIGS NCLNNEFNFF  60
KRHICDANKE GMFLFRAARK LRQFLKMNST GDFDLHLLKV SEGTTILLNC TGQVKGRKPA  120
ALGEAQPTKS LEENKSLKEQ KKLNDLCFLK RLLQEIKTCW NKILMGTKEH SGTTNTVAAY  180
NLTWKSTNFK TILEWEPKPV NQVYTVQIST KSGDWKSKCF YTTDTECDLT DEIVKDVKQT  240
YLARVFSYPA GNVESTGSAG EPLYENSPEF TPYLETNLGQ PTIQSFEQVG TKVNVTVEDE  300
RTLVRRNNTF LSLRDVFGKD LIYTLYYWKS SSSGKKTAKT NTNEFLIDVD KGENYCFSVQ  360
AVIPSRTVNR KSTDSPVECM GQEKGEFREN WVNVISDLKK IEDLIQSMHI DATLYTESDV  420
HPSCKVTAMK CFLLELQVIS LESGDASIHD TVENLIILAN NSLSSNGNVT ESGCKECEEL  480
EEKNIKEFLQ SFVHIVQMFI NTS                                    503

SEQ ID NO: 144          moltype = DNA  length = 1509
FEATURE                 Location/Qualifiers
misc_feature            1..1509
                        note = Description of Artificial Sequence: Synthetic 7t15
                         sequence
source                  1..1509
                        mol_type = other DNA
                        organism = synthetic construct
SEQUENCE: 144
atgaagtggg tgaccttcat cagcctgctg ttcctgttct ccagcgccta ctccgattgc  60
gacatcgagg gcaaggacgg caagcagtac gagagcgtgc tgatggtgtc catcgaccag  120
ctgctggaca gcatgaagga gatcggctcc aactgcctca acaacgagtt caacttcttc  180
aagcggcaca tctgcgacgc caacaaggag ggcatgttcc tgttcagggc cgccaggaaa  240
ctgcggcagt tcctgaagat gaactccacc ggcgacttcg acctgcacct gctgaaggtg  300
```

```
tccgagggca ccaccatcct gctgaactgc accggacagg tgaagggccg gaaacctgct  360
gctctgggag aggcccaacc caccaagagc ctggaggaga acaagtccct gaaggagcag  420
aagaagctga acgacctgtg cttcctgaag aggctgctgc aggagatcaa gacctgctgg  480
aacaagatcc tgatgggcac caaggagcat agcggcacaa ccaacacagt cgctgcctat  540
aacctcactt ggaagagcac caacttcaaa accatcctcg aatgggaacc caaacccgtt  600
aaccaagttt acaccgtgca gatcagcacc aagtccggcg actggaagtc caaatgtttc  660
tataccaccg acaccgagtg cgatctcacc gatgagatcg tgaaagatgt gaaacagacc  720
tacctcgccc gggtgtttag ctaccccgcc ggcaatgtgg agagcactgg ttccgctggc  780
gagcctttat acgagaacag ccccgaattt accccttacc tcgagaccaa tttaggacag  840
cccaccatcc aaagctttga gcaagttggc acaaaggtga atgtgacagt ggaggacgag  900
cggactttag tgcggcggaa caacaccttt ctcagcctcc gggatgtgtt cggcaaagat  960
ttaatctaca cactgtatta ctggaagtcc tcttcctccg gcaagaagac agctaaaacc  1020
aacacaaacg agtttttaat cgacgtggat aaaggcgaaa actactgttt cagcgtgcaa  1080
gctgtgatcc cctcccggac cgtgaatagg aaaagcaccg atagccccgt tgagtgcatg  1140
ggccaagaaa agggcgagtt ccgggagaac tgggtgaacg tcatcagcga tttaaagaag  1200
atcgaagatt taattcagtc catgcatatc gacgccactt tatacacaga atccgacgtg  1260
cacccctctt gtaaggtgac cgccatgaaa tgttttttac tggagctgca agttatctct  1320
ttagagagcg gagacgctag catccacgac accgtggaga atttaatcat tttagccaat  1380
aactctttat ccagcaacgg caacgtgaca gagtccggct gcaaggagtg cgaagagctg  1440
gaggagaaga acatcaagga gtttctgcaa tcctttgtgc acattgtcca gatgttcatc  1500
aatacctcc                                                          1509

SEQ ID NO: 145          moltype = AA  length = 198
FEATURE                 Location/Qualifiers
REGION                  1..198
                        note = Description of Artificial Sequence: Synthetic 21s
                         sequence
source                  1..198
                        mol_type = protein
                        organism = synthetic construct
SEQUENCE: 145
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSITCPPPM SVEHADIWVK SYSLYSRERY ICNSGFKRKA GTSSLTECVL  180
NKATNVAHWT TPSLKCIR                                                198

SEQ ID NO: 146          moltype = DNA  length = 594
FEATURE                 Location/Qualifiers
misc_feature            1..594
                        note = Description of Artificial Sequence: Synthetic 21s
                         sequence
source                  1..594
                        mol_type = other DNA
                        organism = synthetic construct
SEQUENCE: 146
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcca ttacatgccc ccctcccatg  420
agcgtggagc acgccgacat ctgggtgaag agctatagcc tctacagccg ggagaggtat  480
atctgtaaca gcggcttcaa gaggaaggcc ggcaccagca gcctcaccga gtgcgtgctg  540
aataaggcta ccaacgtggc tcactggaca acaccctctt taaagtgcat ccgg        594

SEQ ID NO: 147          moltype = AA  length = 216
FEATURE                 Location/Qualifiers
REGION                  1..216
                        note = Description of Artificial Sequence: Synthetic 21s
                         sequence
source                  1..216
                        mol_type = protein
                        organism = synthetic construct
SEQUENCE: 147
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SITCPPPMSV EHADIWVKSY SLYSRERYIC  180
NSGFKRKAGT SSLTECVLNK ATNVAHWTTP SLKCIR                            216

SEQ ID NO: 148          moltype = DNA  length = 648
FEATURE                 Location/Qualifiers
misc_feature            1..648
                        note = Description of Artificial Sequence: Synthetic 21s
                         sequence
source                  1..648
                        mol_type = other DNA
                        organism = synthetic construct
```

```
SEQUENCE: 148
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctcccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tccattacat gcccccctcc catgagcgtg  480
gagcacgccg acatctgggt gaagagctat agcctctaca gccgggagag gtatatctgt  540
aacagcggct tcaagaggaa ggccggcacc agcagcctca ccgagtgcgt gctgaataag  600
gctaccaacg tggctcactg gacaacaccc tctttaaagt gcatccgg  648

SEQ ID NO: 149          moltype = AA  length = 108
FEATURE                 Location/Qualifiers
REGION                  1..108
                        note = Description of Artificial Sequence: Synthetic CD16
                         scfv light chain variable domain sequence
source                  1..108
                        mol_type = protein
                        organism = synthetic construct
SEQUENCE: 149
SELTQDPAVS VALGQTVRIT CQGDSLRSYY ASWYQQKPGQ APVLVIYGKN NRPSGIPDRF  60
SGSSSGNTAS LTITGAQAED EADYYCNSRD SSGNHVVFGG GTKLTVGH  108

SEQ ID NO: 150          moltype = DNA  length = 324
FEATURE                 Location/Qualifiers
misc_feature            1..324
                        note = Description of Artificial Sequence: Synthetic CD16
                         scfv light chain variable domain sequence
source                  1..324
                        mol_type = other DNA
                        organism = synthetic construct
SEQUENCE: 150
tccgagctga cccaggaccc tgctgtgtcc gtggctctgg gccagaccgt gaggatcacc  60
tgccagggcg actccctgag gtcctactac gcctcctggt accagcagaa gcccggccag  120
gctcctgtgc tggtgatcta cggcaagaac aacaggccct ccggcatccc tgacaggttc  180
tccggatcct cctccggcaa caccgcctcc ctgaccatca caggcgctca ggccgaggac  240
gaggctgact actactgcaa ctccagggac tcctccggca accatgtggt gttcggcggc  300
ggcaccaagc tgaccgtggg ccat  324

SEQ ID NO: 151          moltype = AA  length = 117
FEATURE                 Location/Qualifiers
REGION                  1..117
                        note = Description of Artificial Sequence: Synthetic CD16
                         scfv heavy chain variable domain sequence
source                  1..117
                        mol_type = protein
                        organism = synthetic construct
SEQUENCE: 151
EVQLVESGGG VVRPGGSLRL SCAASGFTFD DYGMSWVRQA PGKGLEWVSG INWNGGSTGY  60
ADSVKGRFTI SRDNAKNSLY LQMNSLRAED TAVYYCARGR SLLFDYWGQG TLVTVSR  117

SEQ ID NO: 152          moltype = DNA  length = 351
FEATURE                 Location/Qualifiers
misc_feature            1..351
                        note = Description of Artificial Sequence: Synthetic CD16
                         scfv heavy chain variable domain sequence
source                  1..351
                        mol_type = other DNA
                        organism = synthetic construct
SEQUENCE: 152
gaggtgcagc tggtggagtc cggaggagga gtggtgaggc ctggaggctc cctgaggctg  60
agctgtgctg cctccggctt caccttcgac gactacggca tgtcctgggt gaggcaggct  120
cctggaaagg gcctggagtg ggtgtccggc atcaactgga acggcggatc caccggctac  180
gccgattccg tgaagggcag gttcaccatc agcagggaca acgccaagaa ctccctgtac  240
ctgcagatga actccctgag ggccgaggac accgccgtgt actactgcgc caggggcagg  300
tccctgctgt tcgactactg gggacagggc accctggtga ccgtgtccag g  351

SEQ ID NO: 153          moltype = AA  length = 823
FEATURE                 Location/Qualifiers
REGION                  1..823
                        note = Description of Artificial Sequence: Synthetic 12s16
                         sequence
source                  1..823
                        mol_type = protein
                        organism = synthetic construct
```

```
SEQUENCE: 153
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNASIT CPPPMSVEHA DIWVKSYSLY  540
SRERYICNSG FKRKAGTSSL TECVLNKATN VAHWTTPSLK CIRSELTQDP AVSVALGQTV  600
RITCQGDSLR SYYASWYQQK PGQAPVLVIY GKNNRPSGIP DRFSGSSSGN TASLTITGAQ  660
AEDEADYYCN SRDSSGNHVV FGGGTKLTVG HGGGGSGGGG SGGGGSEVQL VESGGGVVRP  720
GGSLRLSCAA SGFTFDDYGM SWVRQAPGKG LEWVSGINWN GGSTGYADSV KGRFTISRDN  780
AKNSLYLQMN SLRAEDTAVY YCARGRSLLF DYWGQGTLVT VSR                   823

SEQ ID NO: 154          moltype = DNA  length = 2469
FEATURE                 Location/Qualifiers
misc_feature            1..2469
                        note = Description of Artificial Sequence: Synthetic 12s16
                         sequence
source                  1..2469
                        mol_type = other DNA
                        organism = synthetic construct
SEQUENCE: 154
atttgggaac tgaagaagga cgtctacgtg gtcgaactgg actggtatcc cgatgctccc  60
ggcgaaatgg tggtgctcac ttgtgacacc cccgaagaag acggcatcac ttggaccctc  120
gatcagagca gcgaggtgct gggctccgga aagaccctca caatccaagt taaggagttc  180
ggagacgctg gccaatacac atgccacaag ggaggcgagg tgctcagcca ttccttatta  240
ttattacaca agaaggaaga cggaatctgg tccaccgaca ttttaaaaga tcagaaggag  300
cccaagaata agacctttt aaggtgtgag gccaaaaact acagcggtcg tttcacttgt  360
tggtggctga ccaccatttc caccgattta accttctccg tgaaaagcag ccggggaagc  420
tccgaccctc aaggtgtgac atgtggagcc gctaccctca gcgctgagag ggttcgtggc  480
gataacaagg aatacgagta cagcgtggag tgccaagaag atagcgcttg tcccgctgcc  540
gaagaatctt tacccattga ggtgatggtg gacgccgtgc acaaactcaa gtacgagaac  600
tacacctcct ccttctttat ccgggacatc attaagcccg atcctcctaa gaatttacag  660
ctgaagcctc tcaaaaatag ccggcaagtt gaggtctctt gggaatatcc cgacacttgg  720
agcacacccc acagctactt ctctttaacc ttttgtgtgc aagttcaagg taaaagcaag  780
cgggagaaga aagaccgggt gtttaccgac aaaaccagcg ccaccgtcat ctgtcggaag  840
aacgcctcca tcagcgtgag ggctcaagat cgttattact ccagcagctg gtccgagtgg  900
gccagcgtgc cttgttccgg cggtggagga tccggaggag gtggctccgg cggcggagga  960
tctcgtaacc tccccgtggc tacccccgat cccggaatgt tcccttgttt acaccacagc  1020
cagaatttac tgagggccgt gagcaacatg ctgcagaaag ctaggcagac tttagaattt  1080
tacccttgca ccagcgagga gatcgaccat gaagatatca ccaaggacaa gacatccacc  1140
gtggaggctt gtttacctct ggagctgaca aagaacgagt cttgtctcaa ctctcgtgaa  1200
accagcttca tcacaaatgg ctcttgttta gcttcccgga agacctcctt tatgatggct  1260
ttatgcctca gctccatcta cgaggattta aagatgtacc aagtggagtt caagaccatg  1320
aacgccaagc tgctcatgga ccctaaacgg cagatctttt tagaccagaa catgctggct  1380
gtgattgatg agctgatgca agctttaaac ttcaactccg agaccgtccc tcagaagtcc  1440
tccctcgagg agcccgattt ttacaagaca aagatcaaac tgtgcatttt actccacgcc  1500
tttaggatcc gggccgtgac cattgaccgg gtcatgagct atttaaacgc cagcattaca  1560
tgccccccctc ccatgagcgt ggagcacgcc gacatctggg tgaagagcta tagcctctac  1620
agccgggaga ggtatatctg taacagcggc ttcaagagga aggccggcac cagcagcctc  1680
accgagtgcg tgctgaataa ggctaccaac gtggctcact ggacaacacc ctctttaaag  1740
tgcatccggt ccgagctgac ccaggaccct gctgtgtccg tggctctggg ccagaccgtg  1800
aggatcacct gccagggcga ctccctgagg tcctactacg cctcctggta ccagcagaag  1860
cccggccagg ctcctgtgct ggtgatctac ggcaagaaca acaggccctc cggcatccct  1920
gacaggttct ccggatcctc ctccggcaac accgcctccc tgaccatcac aggcgctcag  1980
gccgaggacg aggctgacta ctactgcaac tccagggact cctccggcaa ccatgtggtg  2040
ttcggcggcg gcaccaagct gaccgtgggc catggcggcg gcggctccgg aggcggcggc  2100
agcggcggag gaggatccga ggtgcagctg gtggagtccg gaggaggagt ggtgaggcct  2160
ggaggctccc tgaggctgag ctgtgctgcc tccggcttca ccttcgacga ctacggcatg  2220
tcctgggtga ggcaggctcc tggaaagggc ctggagtggg tgtccggcat caactggaac  2280
ggcggatcca ccggctacgc cgattccgtg aagggcaggt tcaccatcag cagggacaac  2340
gccaagaact ccctgtacct gcagatgaac tccctgaggg ccgaggacac cgccgtgtac  2400
tactgcgcca ggggcaggtc cctgctgttc gactactggg gacagggcac cctggtgacc  2460
gtgtccagg                                                         2469

SEQ ID NO: 155          moltype = AA  length = 841
FEATURE                 Location/Qualifiers
REGION                  1..841
                        note = Description of Artificial Sequence: Synthetic 12s16
                         sequence
source                  1..841
                        mol_type = protein
                        organism = synthetic construct
SEQUENCE: 155
MKWVTFISLL FLFSSAYSIW ELKKDVYVVE LDWYPDAPGE MVVLTCDTPE EDGITWTLDQ  60
SSEVLGSGKT LTIQVKEFGD AGQYTCHKGG EVLSHSLLLL HKKEDGIWST DILKDQKEPK  120
```

```
NKTFLRCEAK NYSGRFTCWW LTTISTDLTF SVKSSRGSSD PQGVTCGAAT LSAERVRGDN  180
KEYEYSVECQ EDSACPAAEE SLPIEVMVDA VHKLKYENYT SSFFIRDIIK PDPPKNLQLK  240
PLKNSRQVEV SWEYPDTWST PHSYFSLTFC VQVQGKSKRE KKDRVFTDKT SATVICRKNA  300
SISVRAQDRY YSSSWSEWAS VPCSGGGGSG GGGSGGGGSR NLPVATPDPG MFPCLHHSQN  360
LLRAVSNMLQ KARQTLEFYP CTSEEIDHED ITKDKTSTVE ACLPLELTKN ESCLNSRETS  420
FITNGSCLAS RKTSFMMALC LSSIYEDLKM YQVEFKTMNA KLLMDPKRQI FLDQNMLAVI  480
DELMQALNFN SETVPQKSSL EEPDFYKTKI KLCILLHAFR IRAVTIDRVM SYLNASITCP  540
PPMSVEHADI WVKSYSLYSR ERYICNSGFK RKAGTSSLTE CVLNKATNVA HWTTPSLKCI  600
RSELTQDPAV SVALGQTVRI TCQGDSLRSY YASWYQQKPG QAPVLVIYGK NNRPSGIPDR  660
FSGSSSGNTA SLTITGAQAE DEADYYCNSR DSSGNHVVFG GGTKLTVGHG GGGSGGGGSG  720
GGGSEVQLVE SGGGVVRPGG SLRLSCAASG FTFDDYGMSW VRQAPGKGLE WVSGINWNGG  780
STGYADSVKG RFTISRDNAK NSLYLQMNSL RAEDTAVYYC ARGRSLLFDY WGQGTLVTVS  840
R                                                                841

SEQ ID NO: 156          moltype = DNA  length = 2523
FEATURE                 Location/Qualifiers
misc_feature            1..2523
                        note = Description of Artificial Sequence: Synthetic 12s16
                         sequence
source                  1..2523
                        mol_type = other DNA
                        organism = synthetic construct
SEQUENCE: 156
atgaaatggg tgacctttat ttctttactg ttcctcttta gcagcgccta ctccatttgg  60
gaactgaaga aggacgtcta cgtggtcgaa ctggactggt atcccgatgc tcccggcgaa  120
atggtggtgc tcacttgtga cacccccgaa gaagacggca tcacttggac cctcgatcag  180
agcagcgagg tgctgggctc cggaaagacc ctcacaatcc aagttaagga gttcggagac  240
gctggccaat acacatgcca caagggaggc gaggtgctca gccattcctt attattatta  300
cacaagaagg aagacggaat ctggtccacc gacattttaa aagatcagaa ggagcccaag  360
aataagacct ttttaaggtg tgaggccaaa aactacagcg gtcgtttcac ttgttggtgg  420
ctgaccacca tttccaccga tttaaccttc tccgtgaaaa gcagccgggg aagctccgac  480
cctcaaggtg tgacatgtgg agccgctacc ctcagcgctg agagggttcg tggcgataac  540
aaggaatacg agtacagcgt ggagtgccaa gaagatagcg cttgtcccgc tgccgaagaa  600
tctttaccca ttgaggtgat ggtggacgcc gtgcacaaac tcaagtacga gaactacacc  660
tcctccttct ttatccggga catcattaag cccgatcctc ctaagaattt acagctgaag  720
cctctcaaaa atagccggca agttgaggtc tcttgggaat atcccgacac ttggagcaca  780
ccccacagct acttctcttt aacctttgt gtgcaagttc aaggtaaaag caagcgggag  840
aagaaagacc gggtgtttac cgacaaaacc agcgccaccg tcatctgtcg gaagaacgcc  900
tccatcagcg tgagggctca agatcgttat tactccagca gctggtccga gtgggccagc  960
gtgccttgtt ccggcggtgg aggatccgga ggaggtggct ccggcggcgg aggatctcgt  1020
aacctccccg tggctacccc cgatcccgga atgttccctt gtttacacca cagccagaat  1080
ttactgaggg ccgtgagcaa catgctgcag aaagctaggc agactttaga attttaccct  1140
tgcaccagcg aggagatcga ccatgaagat atcaccaagg acaagacatc caccgtggag  1200
gcttgtttac ctctggagct gacaaagaac gagtcttgtc tcaactctcg tgaaaccagc  1260
ttcatcacaa atggctcttg tttagcttcc cggaagacct cctttatgat ggctttatgc  1320
ctcagctcca tctacgagga tttaaagatg taccaagtgg agttcaagac catgaacgcc  1380
aagctgctca tggaccctaa acggcagatc tttttagacc agaacatgct ggctgtgatt  1440
gatgagctga tgcaagcttt aaacttcaac tccgagaccg tccctcagaa gtcctccctc  1500
gaggagcccg atttttacaa gacaaagatc aaactgtgca ttttactcca cgcctttagg  1560
atccgggccg tgaccattga ccgggtcatg agctatttaa acgccagcat tacatgcccc  1620
cctcccatga gcgtggagca cgccgacatc tgggtgaaga gctatagcct ctacagccgg  1680
gagaggtata tctgtaacag cggcttcaag aggaaggccg gcaccagcag cctcaccgag  1740
tgcgtgctga ataaggctac caacgtggct cactggacaa caccctcttt aaagtgcatc  1800
cggtccgagc tgacccagga ccctgctgtg tccgtggctc tgggccagac cgtgaggatc  1860
acctgccagg gcgactccct gaggtcctac tacgcctcct ggtaccagca gaagcccggc  1920
caggctcctg tgctggtgat ctacggcaag aacaacaggc cctccggcat ccctgacagg  1980
ttctccggat cctcctccgg caacaccgcc tccctgacca tcacaggcgc tcaggccgag  2040
gacgaggctg actactactg caactccagg gactcctccg gcaaccatgt ggtgttcggc  2100
ggcggcacca agctgaccgt gggccatggc ggcggcggct ccggaggcgg cggcagcggc  2160
ggaggaggat ccgaggtgca gctggtggag tccggaggag gagtggtgag gcctggaggc  2220
tccctgaggc tgagctgtgc tgcctccggc ttcaccttcg acgactacgg catgtcctgg  2280
gtgaggcagg ctcctggaaa gggcctggag tgggtgtccg gcatcaactg gaacggcgga  2340
tccaccggct acgccgattc cgtgaagggc aggttcacca tcagcaggga caacgccaag  2400
aactccctgt acctgcagat gaactccctg agggccgagg acaccgccgt gtactactgc  2460
gccaggggca ggtccctgct gttcgactac tggggacagg gcaccctggt gaccgtgtcc  2520
agg                                                              2523

SEQ ID NO: 157          moltype = AA  length = 438
FEATURE                 Location/Qualifiers
REGION                  1..438
                        note = Description of Artificial Sequence: Synthetic 16s21
                         sequence
source                  1..438
                        mol_type = protein
                        organism = synthetic construct
SEQUENCE: 157
SELTQDPAVS VALGQTVRIT CQGDSLRSYY ASWYQQKPGQ APVLVIYGKN NRPSGIPDRF  60
SGSSSGNTAS LTITGAQAED EADYYCNSRD SSGNHVVFGG GTKLTVGHGG GGSGGGGSGG  120
GGSEVQLVES GGGVVRPGGS LRLSCAASGF TFDDYGMSWV RQAPGKGLEW VSGINWNGGS  180
```

```
TGYADSVKGR FTISRDNAKN SLYLQMNSLR AEDTAVYYCA RGRSLLFDYW GQGTLVTVSR  240
ITCPPPMSVE HADIWVKSYS LYSRERYICN SGFKRKAGTS SLTECVLNKA TNVAHWTTPS  300
LKCIRQGQDR HMIRMRQLID IVDQLKNYVN DLVPEFLPAP EDVETNCEWS AFSCFQKAQL  360
KSANTGNNER IINVSIKKLK RKPPSTNAGR RQKHRLTCPS CDSYEKKPPK EFLERFKSLL  420
QKMIHQHLSS RTHGSEDS                                               438

SEQ ID NO: 158         moltype = DNA  length = 1314
FEATURE                Location/Qualifiers
misc_feature           1..1314
                       note = Description of Artificial Sequence: Synthetic 16s21
                        sequence
source                 1..1314
                       mol_type = other DNA
                       organism = synthetic construct
SEQUENCE: 158
tccgagctga cccaggaccc tgctgtgtcc gtggctctgg gccagaccgt gaggatcacc  60
tgccagggcg actccctgag gtcctactac gcctcctggt accagcagaa gcccggccag  120
gctcctgtgc tggtgatcta cggcaagaac aacaggccct ccggcatccc tgacaggttc  180
tccggatcct cctccggcaa caccgcctcc ctgaccatca caggcgctca ggccgaggac  240
gaggctgact actactgcaa ctccagggac tcctccggca accatgtggt gttcggcggc  300
ggcaccaagc tgaccgtggg ccatggcggc ggcggctccg gaggcggcgg cagcggcgga  360
ggaggatccg aggtgcagct ggtggagtcc ggaggaggag tggtgaggcc tggaggctcc  420
ctgaggctga gctgtgctgc ctccggcttc accttcgacg actacggcat gtcctgggtg  480
aggcaggctc ctggaaaggg cctggagtgg gtgtccggca tcaactggaa cggcggatcc  540
accggctacg ccgattccgt gaagggcagg ttcaccatca gcagggacaa cgccaagaac  600
tccctgtacc tgcagatgaa ctccctgagg gccgaggaca ccgccgtgta ctactgcgcc  660
aggggcaggt ccctgctgtt cgactactgg ggacagggca ccctggtgac cgtgtccagg  720
attacatgcc cccctcccat gagcgtggag cacgccgaca tctgggtgaa gagctatagc  780
ctctacagcc gggagaggta tatctgtaac agcggcttca agaggaaggc cggcaccagc  840
agcctcaccg agtgcgtgct gaataaggct accaacgtgg ctcactggac aacaccctct  900
ttaaagtgca tccggcaggg ccaggacagg cacatgatcc ggatgaggca gctcatcgac  960
atcgtcgacc agctgaagaa ctacgtgaac gacctggtgc ccgagtttct gcctgccccc  1020
gaggacgtgg agaccaactg cgagtggtcc gccttctcct gctttcagaa ggcccagctg  1080
aagtccgcca acaccggcaa caacgagcgg atcatcaacg tgagcatcaa gaagctgaag  1140
cggaagcctc cctccacaaa cgccggcagg aggcagaagc acaggctgac ctgccccagc  1200
tgtgactcct acgagaagaa gccccccaag gagttcctgg agaggttcaa gtccctgctg  1260
cagaagatga tccatcagca cctgtcctcc aggacccacg gctccgagga ctcc        1314

SEQ ID NO: 159         moltype = AA  length = 456
FEATURE                Location/Qualifiers
REGION                 1..456
                       note = Description of Artificial Sequence: Synthetic 16s21
                        sequence
source                 1..456
                       mol_type = protein
                       organism = synthetic construct
SEQUENCE: 159
MKWVTFISLL FLFSSAYSSE LTQDPAVSVA LGQTVRITCQ GDSLRSYYAS WYQQKPGQAP  60
VLVIYGKNNR PSGIPDRFSG SSSGNTASLT ITGAQAEDEA DYYCNSRDSS GNHVVFGGGT  120
KLTVGHGGGG SGGGGSGGGG SEVQLVESGG GVVRPGGSLR LSCAASGFTF DDYGMSWVRQ  180
APGKGLEWVS GINWNGGSTG YADSVKGRFT ISRDNAKNSL YLQMNSLRAE DTAVYYCARG  240
RSLLFDYWGQ GTLVTVSRIT CPPPMSVEHA DIWVKSYSLY SRERYICNSG FKRKAGTSSL  300
TECVLNKATN VAHWTTPSLK CIRQGQDRHM IRMRQLIDIV DQLKNYVNDL VPEFLPAPED  360
VETNCEWSAF SCFQKAQLKS ANTGNNERII NVSIKKLKRK PPSTNAGRRQ KHRLTCPSCD  420
SYEKKPPKEF LERFKSLLQK MIHQHLSSRT HGSEDS                            456

SEQ ID NO: 160         moltype = DNA  length = 1368
FEATURE                Location/Qualifiers
misc_feature           1..1368
                       note = Description of Artificial Sequence: Synthetic 16s21
                        sequence
source                 1..1368
                       mol_type = other DNA
                       organism = synthetic construct
SEQUENCE: 160
atgaagtggg tgaccttcat cagcctgctg ttcctgttct ccagcgccta ctcctccgag  60
ctgacccagg accctgctgt gtccgtggct ctgggccaga ccgtgaggat cacctgccag  120
ggcgactccc tgaggtccta ctacgcctcc tggtaccagc agaagcccgg ccaggctcct  180
gtgctggtga tctacggcaa gaacaacagg ccctccggca tccctgacag gttctccgga  240
tcctcctccg gcaacaccgc ctccctgacc atcacaggcg ctcaggccga ggacgaggct  300
gactactact gcaactccag ggactcctcc ggcaaccatg tggtgttcgg cggcggcacc  360
aagctgaccg tgggccatgg cggcggcggc tccggaggcg gcggcagcgg cggaggagga  420
tccgaggtgc agctggtgga gtccggagga ggagtggtga ggcctggagg ctccctgagg  480
ctgagctgtg ctgcctccgg cttcaccttc gacgactacg gcatgtcctg ggtgaggcag  540
gctcctggaa agggcctgga gtgggtgtcc ggcatcaact ggaacggcgg atccaccggc  600
tacgccgatt ccgtgaaggg caggttcacc atcagcaggg acaacgccaa gaactccctg  660
tacctgcaga tgaactccct gagggccgag gacaccgccg tgtactactg cgccaggggc  720
aggtccctgc tgttcgacta ctggggacag ggcaccctgg tgaccgtgtc caggattaca  780
tgcccccctc ccatgagcgt ggagcacgcc gacatctggg tgaagagcta tagcctctac  840
```

```
agccgggaga ggtatatctg taacagcggc ttcaagagga aggccggcac cagcagcctc  900
accgagtgcg tgctgaataa ggctaccaac gtggctcact ggacaacacc ctctttaaag  960
tgcatccggc agggccagga caggcacatg atccggatga ggcagctcat cgacatcgtc  1020
gaccagctga agaactacgt gaacgacctg gtgcccgagt ttctgcctgc cccgaggac  1080
gtggagacca actgcgagtg gtccgccttc tcctgctttc agaaggccca gctgaagtcc  1140
gccaacaccg gcaacaacga gcggatcatc aacgtgagca tcaagaagct gaagcggaag  1200
cctccctcca caaacgccgg caggaggcag aagcacaggc tgacctgccc cagctgtgac  1260
tcctacgaga agaagccccc caaggagttc ctggagaggt tcaagtccct gctgcagaag  1320
atgatccatc agcacctgtc ctccaggacc cacggctccg aggactcc               1368

SEQ ID NO: 161         moltype = AA  length = 620
FEATURE                Location/Qualifiers
REGION                 1..620
                       note = Description of Artificial Sequence: Synthetic
                        TGFRt15 sequence
source                 1..620
                       mol_type = protein
                       organism = synthetic construct
SEQUENCE: 161
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDSGT TNTVAAYNLT  300
WKSTNFKTIL EWEPKPVNQV YTVQISTKSG DWKSKCFYTT DTECDLTDEI VKDVKQTYLA  360
RVFSYPAGNV ESTGSAGEPL YENSPEFTPY LETNLGQPTI QSFEQVGTKV NVTVEDERTL  420
VRRNNTFLSL RDVFGKDLIY TLYYWKSSSS GKKTAKTNTN EFLIDVDKGE NYCFSVQAVI  480
PSRTVNRKST DSPVECMGQE KGEFRENWVN VISDLKKIED LIQSMHIDAT LYTESDVHPS  540
CKVTAMKCFL LELQVISLES GDASIHDTVE NLIILANNSL SSNGNVTESG CKECEELEEK  600
NIKEFLQSFV HIVQMFINTS                                            620

SEQ ID NO: 162         moltype = DNA  length = 1860
FEATURE                Location/Qualifiers
misc_feature           1..1860
                       note = Description of Artificial Sequence: Synthetic
                        TGFRt15 sequence
source                 1..1860
                       mol_type = other DNA
                       organism = synthetic construct
SEQUENCE: 162
atccccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cagcggcaca accaacacag tcgctgccta taacctcact  900
tggaagagca ccaacttcaa aaccatcctc gaatgggaac ccaaacccgt taaccaagtt  960
tacaccgtgc agatcagcac caagtccggc gactggaagt ccaaatgttt ctataccacc  1020
gacaccgagt gcgatctcac cgatgagatc gtgaaagatg tgaaacagac ctacctcgcc  1080
cgggtgttta gctaccccgc cggcaatgtg gagagcactg gttccgctgg cgagccttta  1140
tacgagaaca gccccgaatt taccccttac ctcgagacca atttaggaca gcccaccatc  1200
caaagctttg agcaagttgg cacaaaggtg aatgtgacag tggaggacga gcggacttta  1260
gtgcggcgga acaacacctt tctcagcctc cgggatgtgt tcggcaaaga tttaatctac  1320
acactgtatt actggaagtc ctcttcctcc ggcaagaaga cagctaaaac caacacaaac  1380
gagtttttaa tcgacgtgga taaaggcgaa aactactgtt tcagcgtgca agctgtgatc  1440
cctcccgga ccgtgaatag gaaaagcacc gatagccccg ttgagtgcat gggccaagaa  1500
aagggcgagt tccgggagaa ctgggtgaac gtcatcagcg atttaaagaa gatcgaagat  1560
ttaattcagt ccatgcatat cgacgccact ttatacacag aatccgacgt gcacccctct  1620
tgtaaggtga ccgccatgaa atgtttttta ctggagctgc aagttatctc tttagagagc  1680
ggagacgcta gcatccacga caccgtggag aatttaatca ttttagccaa taactcttta  1740
tccagcaacg gcaacgtgac agagtccggc tgcaaggagt gcgaagagct ggaggagaag  1800
aacatcaagg agtttctgca atcctttgtg cacattgtcc agatgttcat caatacctcc  1860

SEQ ID NO: 163         moltype = AA  length = 638
FEATURE                Location/Qualifiers
REGION                 1..638
                       note = Description of Artificial Sequence: Synthetic
                        TGFRt15 sequence
```

```
source                  1..638
                        mol_type = protein
                        organism = synthetic construct
SEQUENCE: 163
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDSGTTN TVAAYNLTWK STNFKTILEW EPKPVNQVYT VQISTKSGDW KSKCFYTTDT  360
ECDLTDEIVK DVKQTYLARV FSYPAGNVES TGSAGEPLYE NSPEFTPYLE TNLGQPTIQS  420
FEQVGTKVNV TVEDERTLVR RNNTFLSLRD VFGKDLIYTL YYWKSSSSGK KTAKTNTNEF  480
LIDVDKGENY CFSVQAVIPS RTVNRKSTDS PVECMGQEKG EFRENWVNVI SDLKKIEDLI  540
QSMHIDATLY TESDVHPSCK VTAMKCFLLE LQVISLESGD ASIHDTVENL IILANNSLSS  600
NGNVTESGCK ECEELEEKNI KEFLQSFVHI VQMFINTS                        638

SEQ ID NO: 164          moltype = DNA  length = 1914
FEATURE                 Location/Qualifiers
misc_feature            1..1914
                        note = Description of Artificial Sequence: Synthetic
                         TGFRt15 sequence
source                  1..1914
                        mol_type = other DNA
                        organism = synthetic construct
SEQUENCE: 164
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gacctttttc  840
atgtgctcct gcagcagcga cgaatgcaac gacaatatca tctttagcga ggaatacaat  900
accagcaacc ccgacagcgg cacaaccaac acagtcgctg cctataacct cacttggaag  960
agcaccaact tcaaaaccat cctcgaatgg gaacccaaac ccgttaacca agtttacacc  1020
gtgcagatca gcaccaagtc cggcgactgg aagtccaaat gtttctatac caccgacacc  1080
gagtgcgatc tcaccgatga gatcgtgaaa gatgtgaaac agacctacct cgcccgggtg  1140
tttagctacc ccgccggcaa tgtggagagc actggttccg ctggcgagcc tttatacgag  1200
aacagccccg aatttacccc ttacctcgag accaatttag gacagcccac catccaaagc  1260
tttgagcaag ttggcacaaa ggtgaatgtg acagtggagg acgagcggac tttagtgcgg  1320
cggaacaaca cctttctcag cctccgggat gtgttcggca aagatttaat ctacacactg  1380
tattactgga agtcctcttc ctccggcaag aagacagcta aaaccaacac aaacgagttt  1440
ttaatcgacg tggataaagg cgaaaactac tgtttcagcg tgcaagctgt gatcccctcc  1500
cggaccgtga ataggaaaag caccgatagc cccgttgagt gcatgggcca agaaaagggc  1560
gagttccggg agaactgggt gaacgtcatc agcgatttaa agaagatcga agatttaatt  1620
cagtccatgc atatcgacgc cactttatac acagaatccg acgtgcaccc ctcttgtaag  1680
gtgaccgcca tgaaatgttt tttactggag ctgcaagtta tctctttaga gagcggagac  1740
gctagcatcc acgacaccgt ggagaattta atcattttag ccaataactc tttatccagc  1800
aacggcaacg tgacagagtc cggctgcaag gagtgcgaag agctggagga gaagaacatc  1860
aaggagtttc tgcaatcctt tgtgcacatt gtccagatgt tcatcaatac ctcc        1914

SEQ ID NO: 165          moltype = AA  length = 184
FEATURE                 Location/Qualifiers
REGION                  1..184
                        note = Description of Artificial Sequence: Synthetic CD137L
                         sequence
source                  1..184
                        mol_type = protein
                        organism = synthetic construct
SEQUENCE: 165
REGPELSPDD PAGLLDLRQG MFAQLVAQNV LLIDGPLSWY SDPGLAGVSL TGGLSYKEDT  60
KELVVAKAGV YYVFFQLELR RVVAGEGSGS VSLALHLQPL RSAAGAAALA LTVDLPPASS  120
EARNSAFGFQ GRLLHLSAGQ RLGVHLHTEA RARHAWQLTQ GATVLGLFRV TPEIPAGLPS  180
PRSE                                                             184

SEQ ID NO: 166          moltype = DNA  length = 552
FEATURE                 Location/Qualifiers
misc_feature            1..552
                        note = Description of Artificial Sequence: Synthetic CD137L
                         sequence
```

```
source                  1..552
                        mol_type = other DNA
                        organism = synthetic construct
SEQUENCE: 166
cgcgagggtc ccgagctttc gcccgacgat cccgccggcc tcttggacct gcggcagggc  60
atgtttgcgc agctggtggc ccaaaatgtt ctgctgatcg atgggcccct gagctggtac  120
agtgacccag gcctggcagg cgtgtccctg acgggggcc tgagctacaa agaggacacg  180
aaggagctgg tggtggccaa ggctggagtc tactatgtct tctttcaact agagctgcgg  240
cgcgtggtgg ccggcgaggg ctcaggctcc gtttcacttg cgctgcacct gcagccactg  300
cgctctgctg ctggggccgc cgccctggct ttgaccgtgg acctgccacc cgcctcctcc  360
gaggctcgga actcggcctt cggtttccag ggccgcttgc tgcacctgag tgccggccag  420
cgcctgggcg tccatcttca cactgaggcc agggcacgcc atgcctggca gcttacccag  480
ggcgccacag tcttgggact cttccgggtg acccccgaaa tcccagccgg actcccttca  540
ccgaggtcgg aa                                                    552

SEQ ID NO: 167          moltype = AA  length = 165
FEATURE                 Location/Qualifiers
REGION                  1..165
                        note = Description of Artificial Sequence: Synthetic CD137L
                         (short version) sequence
source                  1..165
                        mol_type = protein
                        organism = synthetic construct
SEQUENCE: 167
DPAGLLDLRQ GMFAQLVAQN VLLIDGPLSW YSDPGLAGVS LTGGLSYKED TKELVVAKAG  60
VYYVFFQLEL RRVVAGEGSG SVSLALHLQP LRSAAGAAAL ALTVDLPPAS SEARNSAFGF  120
QGRLLHLSAG QRLGVHLHTE ARARHAWQLT QGATVLGLFR VTPEI                165

SEQ ID NO: 168          moltype = DNA  length = 495
FEATURE                 Location/Qualifiers
misc_feature            1..495
                        note = Description of Artificial Sequence: Synthetic CD137L
                         (short version) sequence
source                  1..495
                        mol_type = other DNA
                        organism = synthetic construct
SEQUENCE: 168
gatcccgccg gcctcttgga cctgcggcag ggcatgtttg cgcagctggt ggcccaaaat  60
gttctgctga tcgatgggcc cctgagctgg tacagtgacc caggcctggc aggcgtgtcc  120
ctgacggggg gcctgagcta caaagaggac acgaaggagc tggtggtggc caaggctgga  180
gtctactatg tcttctttca actagagctg cggcgcgtgg tggccggcga gggctcaggc  240
tccgtttcac ttgcgctgca cctgcagcca ctgcgctctg ctgctggggc cgccgccctg  300
gctttgaccg tggacctgcc acccgcctcc tccgaggctc ggaactcggc cttcggtttc  360
cagggccgct tgctgcacct gagtgccggc cagcgcctgg gcgtccatct tcacactgag  420
gccagggcac gccatgcctg gcagcttacc cagggcgcca cagtcttggg actcttccgg  480
gtgacccccg aaatc                                                 495

SEQ ID NO: 169          moltype = AA  length = 397
FEATURE                 Location/Qualifiers
REGION                  1..397
                        note = Description of Artificial Sequence: Synthetic
                         21s137L sequence
source                  1..397
                        mol_type = protein
                        organism = synthetic construct
SEQUENCE: 169
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSITCPPPM SVEHADIWVK SYSLYSRERY ICNSGFKRKA GTSSLTECVL  180
NKATNVAHWT TPSLKCIRGG GGSGGGGSGG GGSREGPELS PDDPAGLLDL RQGMFAQLVA  240
QNVLLIDGPL SWYSDPGLAG VSLTGGLSYK EDTKELVVAK AGVYYVFFQL ELRRVVAGEG  300
SGSVSLALHL QPLRSAAGAA ALALTVDLPP ASSEARNSAF GFQGRLLHLS AGQRLGVHLH  360
TEARARHAWQ LTQGATVLGL FRVTPEIPAG LPSPRSE                          397

SEQ ID NO: 170          moltype = DNA  length = 1191
FEATURE                 Location/Qualifiers
misc_feature            1..1191
                        note = Description of Artificial Sequence: Synthetic
                         21s137L sequence
source                  1..1191
                        mol_type = other DNA
                        organism = synthetic construct
SEQUENCE: 170
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
```

```
cagcacctgt cctccaggac ccacggctcc gaggactcca ttacatgccc ccctcccatg  420
agcgtggagc acgccgacat ctgggtgaag agctatagcc tctacagccg ggagaggtat  480
atctgtaaca gcggcttcaa gaggaaggcc ggcaccagca gcctcaccga gtgcgtgctg  540
aataaggcta ccaacgtggc tcactggaca acaccctctt taaagtgcat ccggggcggt  600
ggaggatccg gaggaggtgg ctccggcggc ggaggatctc gcgagggtcc cgagctttcg  660
cccgacgatc ccgccggcct cttggacctg cggcagggca tgtttgcgca gctggtggcc  720
caaaatgttc tgctgatcga tggcccctg agctggtaca gtgacccagg cctggcaggc  780
gtgtccctga cgggggcct gagctacaaa gaggacacga aggagctggt ggtggccaag  840
gctggagtct actatgtctt ctttcaacta gagctgcggc gcgtggtggc cggcgagggc  900
tcaggctccg tttcacttgc gctgcacctg cagccactgc gctctgctgc tggggccgcc  960
gccctggctt tgaccgtgga cctgccaccc gcctcctccg aggctcggaa ctcggccttc  1020
ggtttccagg gccgcttgct gcacctgagt gccggccagc gcctgggcgt ccatcttcac  1080
actgaggcca gggcacgcca tgcctggcag cttacccagg gcgccacagt cttgggactc  1140
ttccgggtga cccccgaaat cccagccgga ctcccttcac cgaggtcgga a           1191

SEQ ID NO: 171          moltype = AA  length = 415
FEATURE                 Location/Qualifiers
REGION                  1..415
                        note = Description of Artificial Sequence: Synthetic
                         21s137L sequence
source                  1..415
                        mol_type = protein
                        organism = synthetic construct
SEQUENCE: 171
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SITCPPPMSV EHADIWVKSY SLYSRERYIC  180
NSGFKRKAGT SSLTECVLNK ATNVAHWTTP SLKCIRGGGG SGGGGSGGGG SREGPELSPD  240
DPAGLLDLRQ GMFAQLVAQN VLLIDGPLSW YSDPGLAGVS LTGGLSYKED TKELVVAKAG  300
VYYVFFQLEL RRVVAGEGSG SVSLALHLQP LRSAAGAAAL ALTVDLPPAS SEARNSAFGF  360
QGRLLHLSAG QRLGVHLHTE ARARHAWQLT QGATVLGLFR VTPEIPAGLP SPRSE       415

SEQ ID NO: 172          moltype = DNA  length = 1245
FEATURE                 Location/Qualifiers
misc_feature            1..1245
                        note = Description of Artificial Sequence: Synthetic
                         21s137L sequence
source                  1..1245
                        mol_type = other DNA
                        organism = synthetic construct
SEQUENCE: 172
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tccattacat gccccctcc catgagcgtg  480
gagcacgccg acatctgggt gaagagctat agcctctaca gccgggagag gtatatctgt  540
aacagcggct tcaagaggaa ggccggcacc agcagcctca ccgagtgcgt gctgaataag  600
gctaccaacg tggctcactg gacaacaccc tctttaaagt gcatccgggg cggtggagga  660
tccggaggag gtggctccgg cggcggagga tctcgcgagg gtcccgagct ttcgcccgac  720
gatcccgccg gcctcttgga cctgcggcag ggcatgtttg cgcagctggt ggcccaaaat  780
gttctgctga tcgatgggcc cctgagctgg tacagtgacc caggcctggc aggcgtgtcc  840
ctgacggggg gcctgagcta caaagaggac acgaaggagc tggtggtggc caaggctgga  900
gtctactatg tcttctttca actagagctg cggcgcgtgg tggccggcga gggctcaggc  960
tccgtttcac ttgcgctgca cctgcagcca ctgcgctctg ctgctggggc cgccgccctg  1020
gctttgaccg tggacctgcc acccgcctcc tccgaggctc ggaactcggc cttcggtttc  1080
cagggccgct tgctgcacct gagtgccggc cagcgcctgg gcgtccatct tcacactgag  1140
gccagggcac gccatgcctg gcagcttacc cagggcgcca cagtcttggg actcttccgg  1200
gtgacccccg aaatcccagc cggactccct tcaccgaggt cggaa                  1245

SEQ ID NO: 173          moltype = AA  length = 378
FEATURE                 Location/Qualifiers
REGION                  1..378
                        note = Description of Artificial Sequence: Synthetic
                         21s137L (short version) sequence
source                  1..378
                        mol_type = protein
                        organism = synthetic construct
SEQUENCE: 173
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDSITCPPPM SVEHADIWVK SYSLYSRERY ICNSGFKRKA GTSSLTECVL  180
NKATNVAHWT TPSLKCIRGG GGSGGGGSGG GGSDPAGLLD LRQGMFAQLV AQNVLLIDGP  240
LSWYSDPGLA GVSLTGGLSY KEDTKELVVA KAGVYYVFFQ LELRRVVAGE GSGSVSLALH  300
LQPLRSAAGA AALALTVDLP PASSEARNSA FGFQGRLLHL SAGQRLGVHL HTEARARHAW  360
QLTQGATVLG LFRVTPEI                                                378
```

```
SEQ ID NO: 174          moltype = DNA  length = 1134
FEATURE                 Location/Qualifiers
misc_feature            1..1134
                        note = Description of Artificial Sequence: Synthetic
                         21s137L (short version) sequence
source                  1..1134
                        mol_type = other DNA
                        organism = synthetic construct
SEQUENCE: 174
cagggccagg acaggcacat gatccggatg aggcagctca tcgacatcgt cgaccagctg  60
aagaactacg tgaacgacct ggtgcccgag tttctgcctg cccccgagga cgtggagacc  120
aactgcgagt ggtccgcctt ctcctgcttt cagaaggccc agctgaagtc cgccaacacc  180
ggcaacaacg agcggatcat caacgtgagc atcaagaagc tgaagcggaa gcctccctcc  240
acaaacgccg gcaggaggca gaagcacagg ctgacctgcc ccagctgtga ctcctacgag  300
aagaagcccc ccaaggagtt cctggagagg ttcaagtccc tgctgcagaa gatgatccat  360
cagcacctgt cctccaggac ccacggctcc gaggactcca ttacatgccc ccctcccatg  420
agcgtggagc acgccgacat ctgggtgaag agctatagcc tctacagccg ggagaggtat  480
atctgtaaca gcggcttcaa gaggaaggcc ggcaccagca gcctcaccga gtgcgtgctg  540
aataaggcta ccaacgtggc tcactggaca acaccctctt taaagtgcat ccggggcggt  600
ggaggatccg gaggaggtgg ctccggcggc ggaggatctg atcccgccgg cctcttggac  660
ctgcggcagg gcatgtttgc gcagctggtg gcccaaaatg ttctgctgat cgatgggccc  720
ctgagctggt acagtgaccc aggcctggca ggcgtgtccc tgacgggggg cctgagctac  780
aaagaggaca cgaaggagct ggtggtggcc aaggctggag tctactatgt cttctttcaa  840
ctagagctgc ggcgcgtggt ggccggcgag ggctcaggct ccgtttcact tgcgctgcac  900
ctgcagccac tgcgctctgc tgctggggcc gccgccctgg ctttgaccgt ggacctgcca  960
cccgcctcct ccgaggctcg gaactcggcc ttcggtttcc agggccgctt gctgcacctg  1020
agtgccggcc agcgcctggg cgtccatctt cacactgagg ccagggcacg ccatgcctgg  1080
cagcttaccc agggcgccac agtcttggga ctcttccggg tgacccccga aatc        1134

SEQ ID NO: 175          moltype = AA  length = 396
FEATURE                 Location/Qualifiers
REGION                  1..396
                        note = Description of Artificial Sequence: Synthetic
                         21s137L (short version) sequence
source                  1..396
                        mol_type = protein
                        organism = synthetic construct
SEQUENCE: 175
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SITCPPPMSV EHADIWVKSY SLYSRERYIC  180
NSGFKRKAGT SSLTECVLNK ATNVAHWTTP SLKCIRGGGG SGGGGSGGGG SDPAGLLDLR  240
QGMFAQLVAQ NVLLIDGPLS WYSDPGLAGV SLTGGLSYKE DTKELVVAKA GVYYVFFQLE  300
LRRVVAGEGS GSVSLALHLQ PLRSAAGAAA LALTVDLPPA SSEARNSAFG FQGRLLHLSA  360
GQRLGVHLHT EARARHAWQL TQGATVLGLF RVTPEI                            396

SEQ ID NO: 176          moltype = DNA  length = 1188
FEATURE                 Location/Qualifiers
misc_feature            1..1188
                        note = Description of Artificial Sequence: Synthetic
                         21s137L (short version) sequence
source                  1..1188
                        mol_type = other DNA
                        organism = synthetic construct
SEQUENCE: 176
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tccattacat gcccccctcc catgagcgtg  480
gagcacgccg acatctgggt gaagagctat agcctctaca gccgggagag gtatatctgt  540
aacagcggct tcaagaggaa ggccggcacc agcagcctca ccgagtgcgt gctgaataag  600
gctaccaacg tggctcactg gacaacaccc tctttaaagt gcatccgggg cggtggagga  660
tccggaggag gtggctccgg cggcggagga tctgatcccg ccggcctctt ggacctgcgg  720
cagggcatgt ttgcgcagct ggtggcccaa aatgttctgc tgatcgatgg gcccctgagc  780
tggtacagtg acccaggcct ggcaggcgtg tccctgacgg ggggcctgag ctacaaagag  840
gacacgaagg agctggtggt ggccaaggct ggagtctact atgtcttctt tcaactagag  900
ctgcggcgcg tggtggccgg cgagggctca ggctccgttt cacttgcgct gcacctgcag  960
ccactgcgct ctgctgctgg ggccgccgcc ctggctttga ccgtggacct gccacccgcc  1020
tcctccgagg ctcggaactc ggccttcggt ttccagggcc gcttgctgca cctgagtgcc  1080
ggccagcgcc tgggcgtcca tcttcacact gaggccaggg cacgccatgc ctggcagctt  1140
acccagggcg ccacagtctt gggactcttc cgggtgaccc ccgaaatc              1188

SEQ ID NO: 177          moltype = AA  length = 485
FEATURE                 Location/Qualifiers
```

```
REGION                  1..485
                        note = Description of Artificial Sequence: Synthetic
                         TGFRs21 sequence
source                  1..485
                        mol_type = protein
                        organism = synthetic construct
SEQUENCE: 177
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IRQGQDRHMI  360
RMRQLIDIVD QLKNYVNDLV PEFLPAPEDV ETNCEWSAFS CFQKAQLKSA NTGNNERIIN  420
VSIKKLKRKP PSTNAGRRQK HRLTCPSCDS YEKKPPKEFL ERFKSLLQKM IHQHLSSRTH  480
GSEDS                                                            485

SEQ ID NO: 178          moltype = DNA  length = 1455
FEATURE                 Location/Qualifiers
misc_feature            1..1455
                        note = Description of Artificial Sequence: Synthetic
                         TGFRs21 sequence
source                  1..1455
                        mol_type = other DNA
                        organism = synthetic construct
SEQUENCE: 178
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cattacatgc ccccctccca tgagcgtgga gcacgccgac  900
atctgggtga agagctatag cctctacagc cgggagaggt atatctgtaa cagcggcttc  960
aagaggaagg ccggcaccag cagcctcacc gagtgcgtgc tgaataaggc taccaacgtg  1020
gctcactgga caacaccctc tttaaagtgc atccggcagg gccaggacag gcacatgatc  1080
cggatgaggc agctcatcga catcgtcgac cagctgaaga actacgtgaa cgacctggtg  1140
cccgagtttc tgcctgcccc cgaggacgtg gagaccaact gcgagtggtc cgccttctcc  1200
tgctttcaga aggcccagct gaagtccgcc aacaccggca acaacgagcg gatcatcaac  1260
gtgagcatca agaagctgaa gcggaagcct ccctccacaa acgccggcag gaggcagaag  1320
cacaggctga cctgccccag ctgtgactcc tacgagaaga agccccccaa ggagttcctg  1380
gagaggttca agtccctgct gcagaagatg atccatcagc acctgtcctc caggacccac  1440
ggctccgagg actcc                                                 1455

SEQ ID NO: 179          moltype = AA  length = 503
FEATURE                 Location/Qualifiers
REGION                  1..503
                        note = Description of Artificial Sequence: Synthetic
                         TGFRs21 sequence
source                  1..503
                        mol_type = protein
                        organism = synthetic construct
SEQUENCE: 179
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR QGQDRHMIRM RQLIDIVDQL KNYVNDLVPE FLPAPEDVET NCEWSAFSCF  420
QKAQLKSANT GNNERIINVS IKKLKRKPPS TNAGRRQKHR LTCPSCDSYE KKPPKEFLER  480
FKSLLQKMIH QHLSSRTHGS EDS                                        503

SEQ ID NO: 180          moltype = DNA  length = 1509
FEATURE                 Location/Qualifiers
misc_feature            1..1509
                        note = Description of Artificial Sequence: Synthetic
                         TGFRs21 sequence
source                  1..1509
                        mol_type = other DNA
                        organism = synthetic construct
```

```
SEQUENCE: 180
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt ttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gacctttttc  840
atgtgctcct gcagcagcga cgaatgcaac gacaatatca tctttagcga ggaatacaat  900
accagcaacc ccgacattac atgcccccct cccatgagcg tggagcacgc cgacatctgg  960
gtgaagagct atagcctcta cagccgggag aggtatatct gtaacagcgg cttcaagagg  1020
aaggccggca ccagcagcct caccgagtgc gtgctgaata aggctaccaa cgtggctcac  1080
tggacaacac cctctttaaa gtgcatccgg cagggccagg acaggcacat gatccggatg  1140
aggcagctca tcgacatcgt cgaccagctg aagaactacg tgaacgacct ggtgcccgag  1200
tttctgcctg cccccgagga cgtggagacc aactgcgagt ggtccgcctt ctcctgcttt  1260
cagaaggccc agctgaagtc cgccaacacc ggcaacaacg agcggatcat caacgtgagc  1320
atcaagaagc tgaagcggaa gcctccctcc acaaacgccg gcaggaggca gaagcacagg  1380
ctgacctgcc ccagctgtga ctcctacgag aagaagcccc ccaaggagtt cctggagagg  1440
ttcaagtccc tgctgcagaa gatgatccat cagcacctgt cctccaggac ccacggctcc  1500
gaggactcc                                                          1509

SEQ ID NO: 181          moltype = AA  length = 592
FEATURE                 Location/Qualifiers
REGION                  1..592
                        note = Description of Artificial Sequence: Synthetic
                         TGFRs16 sequence
source                  1..592
                        mol_type = protein
                        organism = synthetic construct
SEQUENCE: 181
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IRSELTQDPA  360
VSVALGQTVR ITCQGDSLRS YYASWYQQKP GQAPVLVIYG KNNRPSGIPD RFSGSSSGNT  420
ASLTITGAQA EDEADYYCNS RDSSGNHVVF GGGTKLTVGH GGGGSGGGGS GGGGSEVQLV  480
ESGGGVVRPG GSLRLSCAAS GFTFDDYGMS WVRQAPGKGL EWVSGINWNG GSTGYADSVK  540
GRFTISRDNA KNSLYLQMNS LRAEDTAVYY CARGRSLLFD YWGQGTLVTV SR          592

SEQ ID NO: 182          moltype = DNA  length = 1776
FEATURE                 Location/Qualifiers
misc_feature            1..1776
                        note = Description of Artificial Sequence: Synthetic
                         TGFRs16 sequence
source                  1..1776
                        mol_type = other DNA
                        organism = synthetic construct
SEQUENCE: 182
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cattacatgc ccccctccca tgagcgtgga gcacgccgac  900
atctgggtga agagctatag cctctacagc cgggagaggt atatctgtaa cagcggcttc  960
aagaggaagg ccggcaccag cagcctcacc gagtgcgtgc tgaataaggc taccaacgtg  1020
gctcactgga caacaccctc tttaaagtgc atccggtccg agctgaccca ggaccctgct  1080
gtgtccgtgg ctctgggcca gaccgtgagg atcacctgcc agggcgactc cctgaggtcc  1140
tactacgcct cctggtacca gcagaagccc ggccaggctc ctgtgctggt gatctacggc  1200
aagaacaaca ggccctccgg catccctgac aggttctccg gatcctcctc cggcaacacc  1260
gcctccctga ccatcacagg cgctcaggcc gaggacgagg ctgactacta ctgcaactcc  1320
```

```
agggactcct ccggcaacca tgtggtgttc ggcggcggca ccaagctgac cgtgggccat  1380
ggcggcggcg gctccggagg cggcggcagc ggcggaggag gatccgaggt gcagctggtg  1440
gagtccggag gaggagtggt gaggcctgga ggctccctga ggctgagctg tgctgcctcc  1500
ggcttcacct tcgacgacta cggcatgtcc tgggtgaggc aggctcctgg aaagggcctg  1560
gagtgggtgt ccggcatcaa ctggaacggc ggatccaccg gctacgccga ttccgtgaag  1620
ggcaggttca ccatcagcag ggacaacgcc aagaactccc tgtacctgca gatgaactcc  1680
ctgagggccg aggacaccgc cgtgtactac tgcgccaggg gcaggtccct gctgttcgac  1740
tactggggac agggcaccct ggtgaccgtg tccagg                           1776

SEQ ID NO: 183         moltype = AA  length = 610
FEATURE                Location/Qualifiers
REGION                 1..610
                       note = Description of Artificial Sequence: Synthetic
                        TGFRs16 sequence
source                 1..610
                       mol_type = protein
                       organism = synthetic construct
SEQUENCE: 183
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR SELTQDPAVS VALGQTVRIT CQGDSLRSYY ASWYQQKPGQ APVLVIYGKN  420
NRPSGIPDRF SGSSSGNTAS LTITGAQAED EADYYCNSRD SSGNHVVFGG GTKLTVGHGG  480
GGSGGGGSGG GGSEVQLVES GGGVVRPGGS LRLSCAASGF TFDDYGMSWV RQAPGKGLEW  540
VSGINWNGGS TGYADSVKGR FTISRDNAKN SLYLQMNSLR AEDTAVYYCA RGRSLLFDYW  600
GQGTLVTVSR                                                        610

SEQ ID NO: 184         moltype = DNA  length = 1830
FEATURE                Location/Qualifiers
misc_feature           1..1830
                       note = Description of Artificial Sequence: Synthetic
                        TGFRs16 sequence
source                 1..1830
                       mol_type = other DNA
                       organism = synthetic construct
SEQUENCE: 184
atgaagtggg tgaccttcat cagcctgctg ttcctgttct ccagcgccta ctccatcccc  60
ccccatgtgc aaaagagcgt gaacaacgat atgatcgtga ccgacaacaa cggcgccgtg  120
aagtttcccc agctctgcaa gttctgcgat gtcaggttca gcacctgcga taatcagaag  180
tcctgcatgt ccaactgcag catcacctcc atctgcgaga agccccaaga agtgtgcgtg  240
gccgtgtggc ggaaaaatga cgagaacatc accctggaga ccgtgtgtca cgaccccaag  300
ctcccttatc acgacttcat tctggaggac gctgcctccc ccaaatgcat catgaaggag  360
aagaagaagc ccggagagac cttctttatg tgttcctgta gcagcgacga gtgtaacgac  420
aacatcatct tcagcgaaga gtacaacacc agcaaccctg atggaggtgg cggatccgga  480
ggtggaggtt ctggtggagg tgggagtatt cctccccacg tgcagaagag cgtgaataat  540
gacatgatcg tgaccgataa caatggcgcc gtgaaatttc cccagctgtg caaattctgc  600
gatgtgaggt tttccacctg cgacaaccag aagtcctgta tgagcaactg ctccatcacc  660
tccatctgtg agaagcctca ggaggtgtgc gtggctgtct ggcggaagaa tgacgagaat  720
atcaccctgg aaaccgtctg ccacgatccc aagctgccct accacgattt catcctggaa  780
gacgccgcca gccctaagtg catcatgaaa gagaaaaaga agcctggcga gacctttttc  840
atgtgctcct gcagcagcga cgaatgcaac gacaatatca tctttagcga ggaatacaat  900
accagcaacc ccgacattac atgccccccct cccatgagcg tggagcacgc cgacatctgg  960
gtgaagagct atagcctcta cagccgggag aggtatatct gtaacagcgg cttcaagagg  1020
aaggccggca ccagcagcct caccgagtgc gtgctgaata aggctaccaa cgtggctcac  1080
tggacaacac cctctttaaa gtgcatccgg tccgagctga cccaggaccc tgctgtgtcc  1140
gtggctctgg gccagaccgt gaggatcacc tgccagggcg actccctgag gtcctactac  1200
gcctcctggt accagcagaa gcccggccag gctcctgtgc tggtgatcta cggcaagaac  1260
aacaggccct ccggcatccc tgacaggttc tccggatcct cctccggcaa caccgcctcc  1320
ctgaccatca caggcgctca ggccgaggac gaggctgact actactgcaa ctccagggac  1380
tcctccggca accatgtggt gttcggcggc ggcaccaagc tgaccgtggg ccatggcggc  1440
ggcggctccg gaggcggcgg cagcggcgga ggaggatccg aggtgcagct ggtggagtcc  1500
ggaggaggag tggtgaggcc tggaggctcc ctgaggctga gctgtgctgc ctccggcttc  1560
accttcgacg actacggcat gtcctgggtg aggcaggctc ctggaaaggg cctggagtgg  1620
gtgtccggca tcaactggaa cggcggatcc accggctacg ccgattccgt gaagggcagg  1680
ttcaccatca gcagggacaa cgccaagaac tccctgtacc tgcagatgaa ctccctgagg  1740
gccgaggaca ccgccgtgta ctactgcgcc aggggcaggt ccctgctgtt cgactactgg  1800
ggacagggca ccctggtgac cgtgtccagg                                  1830

SEQ ID NO: 185         moltype = AA  length = 551
FEATURE                Location/Qualifiers
REGION                 1..551
                       note = Description of Artificial Sequence: Synthetic
                        TGFRs137L sequence
source                 1..551
                       mol_type = protein
                       organism = synthetic construct
```

```
SEQUENCE: 185
IPPHVQKSVN NDMIVTDNNG AVKFPQLCKF CDVRFSTCDN QKSCMSNCSI TSICEKPQEV  60
CVAVWRKNDE NITLETVCHD PKLPYHDFIL EDAASPKCIM KEKKKPGETF FMCSCSSDEC  120
NDNIIFSEEY NTSNPDGGGG SGGGGSGGGG SIPPHVQKSV NNDMIVTDNN GAVKFPQLCK  180
FCDVRFSTCD NQKSCMSNCS ITSICEKPQE VCVAVWRKND ENITLETVCH DPKLPYHDFI  240
LEDAASPKCI MKEKKKPGET FFMCSCSSDE CNDNIIFSEE YNTSNPDITC PPPMSVEHAD  300
IWVKSYSLYS RERYICNSGF KRKAGTSSLT ECVLNKATNV AHWTTPSLKC IRGGGGSGGG  360
GSGGGGSREG PELSPDDPAG LLDLRQGMFA QLVAQNVLLI DGPLSWYSDP GLAGVSLTGG  420
LSYKEDTKEL VVAKAGVYYV FFQLELRRVV AGEGSGSVSL ALHLQPLRSA AGAAALALTV  480
DLPPASSEAR NSAFGFQGRL LHLSAGQRLG VHLHTEARAR HAWQLTQGAT VLGLFRVTPE  540
IPAGLPSPRS E                                                       551

SEQ ID NO: 186         moltype = DNA  length = 1653
FEATURE                Location/Qualifiers
misc_feature           1..1653
                       note = Description of Artificial Sequence: Synthetic
                        TGFRs137L sequence
source                 1..1653
                       mol_type = other DNA
                       organism = synthetic construct
SEQUENCE: 186
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga cattacatgc ccccctccca tgagcgtgga gcacgccgac  900
atctgggtga agagctatag cctctacagc cgggagaggt atatctgtaa cagcggcttc  960
aagaggaagg ccggcaccag cagcctcacc gagtgcgtgc tgaataaggc taccaacgtg  1020
gctcactgga caacaccctc tttaaagtgc atccggggcg gtggaggatc cggaggaggt  1080
ggctccggcg gcggaggatc tcgcgagggt cccgagcttt cgcccgacga tcccgccggc  1140
ctcttggacc tgcggcaggg catgtttgcg cagctggtgg cccaaaatgt tctgctgatc  1200
gatgggcccc tgagctggta cagtgaccca ggcctggcag gcgtgtccct gacgggggc  1260
ctgagctaca aagaggacac gaaggagctg gtggtggcca aggctggagt ctactatgtc  1320
ttctttcaac tagagctgcg gcgcgtggtg gccggcgagg gctcaggctc cgtttcactt  1380
gcgctgcacc tgcagccact gcgctctgct gctggggccg ccgccctggc tttgaccgtg  1440
gacctgccac ccgcctcctc cgaggctcgg aactcggcct tcggtttcca gggccgcttg  1500
ctgcacctga gtgccggcca gcgcctgggc gtccatcttc acactgaggc cagggcacgc  1560
catgcctggc agcttaccca gggcgccaca gtcttgggac tcttccgggt gacccccgaa  1620
atcccagccg gactcccttc accgaggtcg gaa                              1653

SEQ ID NO: 187         moltype = AA  length = 569
FEATURE                Location/Qualifiers
REGION                 1..569
                       note = Description of Artificial Sequence: Synthetic
                        TGFRs137L sequence
source                 1..569
                       mol_type = protein
                       organism = synthetic construct
SEQUENCE: 187
MKWVTFISLL FLFSSAYSIP PHVQKSVNND MIVTDNNGAV KFPQLCKFCD VRFSTCDNQK  60
SCMSNCSITS ICEKPQEVCV AVWRKNDENI TLETVCHDPK LPYHDFILED AASPKCIMKE  120
KKKPGETFFM CSCSSDECND NIIFSEEYNT SNPDGGGGSG GGGSGGGGSI PPHVQKSVNN  180
DMIVTDNNGA VKFPQLCKFC DVRFSTCDNQ KSCMSNCSIT SICEKPQEVC VAVWRKNDEN  240
ITLETVCHDP KLPYHDFILE DAASPKCIMK EKKKPGETFF MCSCSSDECN DNIIFSEEYN  300
TSNPDITCPP PMSVEHADIW VKSYSLYSRE RYICNSGFKR KAGTSSLTEC VLNKATNVAH  360
WTTPSLKCIR GGGGSGGGGS GGGGSREGPE LSPDDPAGLL DLRQGMFAQL VAQNVLLIDG  420
PLSWYSDPGL AGVSLTGGLS YKEDTKELVV AKAGVYYVFF QLELRRVVAG EGSGSVSLAL  480
HLQPLRSAAG AAALALTVDL PPASSEARNS AFGFQGRLLH LSAGQRLGVH LHTEARARHA  540
WQLTQGATVL GLFRVTPEIP AGLPSPRSE                                    569

SEQ ID NO: 188         moltype = DNA  length = 1707
FEATURE                Location/Qualifiers
misc_feature           1..1707
                       note = Description of Artificial Sequence: Synthetic
                        TGFRs137L sequence
source                 1..1707
                       mol_type = other DNA
                       organism = synthetic construct
```

SEQUENCE: 188
atgaagtggg tgaccttcat cagcctgctg ttcctgttct ccagcgccta ctccatcccc 60
ccccatgtgc aaaagagcgt gaacaacgat atgatcgtga ccgacaacaa cggcgccgtg 120
aagtttcccc agctctgcaa gttctgcgat gtcaggttca gcacctgcga taatcagaag 180
tcctgcatgt ccaactgcag catcacctcc atctgcgaga agccccaaga agtgtgcgtg 240
gccgtgtggc ggaaaaatga cgagaacatc accctggaga ccgtgtgtca cgaccccaag 300
ctcccttatc acgacttcat tctggaggac gctgcctccc ccaaatgcat catgaaggag 360
aagaagaagc ccggagagac cttctttatg tgttcctgta gcagcgacga gtgtaacgac 420
aacatcatct tcagcgaaga gtacaacacc agcaaccctg atggaggtgg cggatccgga 480
ggtggaggtt ctggtggagg tgggagtatt cctccccacg tgcagaagag cgtgaataat 540
gacatgatcg tgaccgataa caatggcgcc gtgaaatttc cccagctgtg caaattctgc 600
gatgtgaggt tttccacctg cgacaaccag aagtcctgta tgagcaactg ctccatcacc 660
tccatctgtg agaagcctca ggaggtgtgc gtggctgtct ggcggaagaa tgacgagaat 720
atcaccctgg aaaccgtctg ccacgatccc aagctgccct accacgattt catcctggaa 780
gacgccgcca gccctaagtg catcatgaaa gagaaaaaga agcctggcga gacctttttc 840
atgtgctcct gcagcagcga cgaatgcaac gacaatatca tctttagcga ggaatacaat 900
accagcaacc ccgacattac atgcccccct cccatgagcg tggagcacgc cgacatctgg 960
gtgaagagct atagcctcta cagccgggag aggtatatct gtaacagcgg cttcaagagg 1020
aaggccggca ccagcagcct caccgagtgc gtgctgaata aggctaccaa cgtggctcac 1080
tggacaacac cctctttaaa gtgcatccgg ggcggtggag gatccggagg aggtggctcc 1140
ggcggcggag gatctcgcga gggtcccgag ctttcgcccg acgatcccgc cggcctcttg 1200
gacctgcggc agggcatgtt tgcgcagctg gtggcccaaa atgttctgct gatcgatggg 1260
cccctgagct ggtacagtga cccaggcctg gcaggcgtgt ccctgacggg gggcctgagc 1320
tacaaagagg acacgaagga gctggtggtg gccaaggctg gagtctacta tgtcttcttt 1380
caactagagc tgcggcgcgt ggtggccggc gagggctcag gctccgtttc acttgcgctg 1440
cacctgcagc cactgcgctc tgctgctggg gccgccgccc tggctttgac cgtggacctg 1500
ccacccgcct cctccgaggc tcggaactcg gccttcggtt tccagggccg cttgctgcac 1560
ctgagtgccg gccagcgcct gggcgtccat cttcacactg aggccagggc acgccatgcc 1620
tggcagctta cccagggcgc cacagtcttg ggactcttcc gggtgacccc cgaaatccca 1680
gccggactcc cttcaccgag gtcggaa 1707

SEQ ID NO: 189 moltype = DNA length = 720
FEATURE Location/Qualifiers
misc_feature 1..720
note = Description of Artificial Sequence: Synthetic 18s sequence
source 1..720
mol_type = other DNA
organism = synthetic construct SEQUENCE: 189
atgaagtggg tcacatttat ctctttactg ttcctcttct ccagcgccta cagctacttc 60
ggcaaactgg aatccaagct gagcgtgatc cggaatttaa acgaccaagt tctgtttatc 120
gatcaaggta accggcctct gttcgaggac atgaccgact ccgattgccg ggacaatgcc 180
ccccggacca tcttcattat ctccatgtac aaggacagcc agccccgggg catggctgtg 240
acaattagcg tgaagtgtga gaaaatcagc actttatctt gtgagaacaa gatcatctcc 300
tttaaggaaa tgaacccccc cgataacatc aaggacacca agtccgatat catcttcttc 360
cagcggtccg tgcccggtca cgataacaag atgcagttcg aatcctcctc ctacgagggc 420
tactttttag cttgtgaaaa ggagagggat ttattcaagc tgatcctcaa gaaggaggac 480
gagctgggcg atcgttccat catgttcacc gtccaaaacg aggatattac atgcccccct 540
cccatgagcg tggagcacgc cgacatctgg gtgaagagct atagcctcta cagccgggag 600
aggtatatct gtaacagcgg cttcaagagg aaggccggca ccagcagcct caccgagtgc 660
gtgctgaata aggctaccaa cgtggctcac tggacaacac cctctttaaa gtgcatccgg 720

SEQ ID NO: 190 moltype = DNA length = 2607
FEATURE Location/Qualifiers
misc_feature 1..2607
note = Description of Artificial Sequence: Synthetic 12t15 sequence
source 1..2607
mol_type = other DNA
organism = synthetic construct SEQUENCE: 190
atgaaatggg tgacctttat ttctttactg ttcctcttta gcagcgccta ctccatttgg 60
gaactgaaga aggacgtcta cgtggtcgaa ctggactggt atcccgatgc tcccggcgaa 120
atggtggtgc tcacttgtga cacccccgaa gaagacggca tcacttggac cctcgatcag 180
agcagcgagg tgctgggctc cggaaagacc ctcacaatcc aagttaagga gttcggagac 240
gctggccaat acacatgcca caagggaggc gaggtgctca gccattcctt attattatta 300
cacaagaagg aagacggaat ctggtccacc gacattttaa aagatcagaa ggagcccaag 360
aataagacct ttttaaggtg tgaggccaaa aactacagcg gtcgtttcac ttgttggtgg 420
ctgaccacca tttccaccga tttaaccttc tccgtgaaaa gcagccgggg aagctccgac 480
cctcaaggtg tgacatgtgg agccgctacc ctcagcgctg agagggttcg tggcgataac 540
aaggaatacg agtacagcgt ggagtgccaa gaagatagcg cttgtcccgc tgccgaagaa 600
tctttaccca ttgaggtgat ggtggacgcc gtgcacaaac tcaagtacga gaactacacc 660
tcctccttct ttatccggga catcattaag cccgatcctc ctaagaattt acagctgaag 720
cctctcaaaa atagccggca agttgaggtc tcttgggaat atcccgacac ttggagcaca 780
ccccacagct acttctcttt aaccttttgt gtgcaagttc aaggtaaaag caagcgggag 840
aagaaagacc gggtgtttac cgacaaaacc agcgccaccg tcatctgtcg gaagaacgcc 900
tccatcagcg tgagggctca agatcgttat tactccagca gctggtccga gtgggccagc 960
gtgccttgtt ccggcggtgg aggatccgga ggaggtggct ccggcggcgg aggatctcgt 1020

```
aacctccccg tggctacccc cgatcccgga atgttccctt gtttacacca cagccagaat  1080
ttactgaggg ccgtgagcaa catgctgcag aaagctaggc agactttaga attttaccct  1140
tgcaccagcg aggagatcga ccatgaagat atcaccaagg acaagacatc caccgtggag  1200
gcttgtttac ctctggagct gacaaagaac gagtcttgtc tcaactctcg tgaaaccagc  1260
ttcatcacaa atggctcttg tttagcttcc cggaagacct cctttatgat ggctttatgc  1320
ctcagctcca tctacgagga tttaaagatg taccaagtgg agttcaagac catgaacgcc  1380
aagctgctca tggaccctaa acggcagatc tttttagacc agaacatgct ggctgtgatt  1440
gatgagctga tgcaagcttt aaacttcaac tccgagaccg tccctcagaa gtcctccctc  1500
gaggagcccg atttttacaa gacaaagatc aaactgtgca ttttactcca cgcctttagg  1560
atccgggccg tgaccattga ccgggtcatg agctatttaa acgccagcag cggcacaacc  1620
aacacagtcg ctgcctataa cctcacttgg aagagcacca acttcaaaac catcctcgaa  1680
tgggaaccca aacccgttaa ccaagtttac accgtgcaga tcagcaccaa gtccggcgac  1740
tggaagtcca aatgtttcta taccaccgac accgagtgcg atctcaccga tgagatcgtg  1800
aaagatgtga aacagaccta cctcgcccgg gtgtttagct accccgccgg caatgtggag  1860
agcactggtt ccgctggcga gcctttatac gagaacagcc ccgaatttac cccttacctc  1920
gagaccaatt taggacagcc caccatccaa agctttgagc aagttggcac aaaggtgaat  1980
gtgacagtgg aggacgagcg gactttagtg cggcggaaca acacctttct cagcctccgg  2040
gatgtgttcg gcaaagattt aatctacaca ctgtattact ggaagtcctc ttcctccggc  2100
aagaagacag ctaaaaccaa cacaaacgag tttttaatcg acgtggataa aggcgaaaac  2160
tactgtttca gcgtgcaagc tgtgatcccc tcccggaccg tgaataggaa aagcaccgat  2220
agccccgttg agtgcatggg ccaagaaaag ggcgagttcc gggagaactg ggtgaacgtc  2280
atcagcgatt taaagaagat cgaagattta attcagtcca tgcatatcga cgccactttta  2340
tacacagaat ccgacgtgca cccctcttgt aaggtgaccg ccatgaaatg tttttttactg  2400
gagctgcaag ttatctcttt agagagcgga gacgctagca tccacgacac cgtggagaat  2460
ttaatcattt tagccaataa ctctttatcc agcaacggca acgtgacaga gtccggctgc  2520
aaggagtgcg aagagctgga ggagaagaac atcaaggagt ttctgcaatc ctttgtgcac  2580
attgtccaga tgttcatcaa tacctcc                                    2607
```

```
SEQ ID NO: 191         moltype = AA  length = 240
FEATURE                Location/Qualifiers
REGION                 1..240
                       note = Description of Artificial Sequence: Synthetic 18s
                        sequence
source                 1..240
                       mol_type = protein
                       organism = synthetic construct
SEQUENCE: 191
MKWVTFISLL FLFSSAYSYF GKLESKLSVI RNLNDQVLFI DQGNRPLFED MTDSDCRDNA  60
PRTIFIISMY KDSQPRGMAV TISVKCEKIS TLSCENKIIS FKEMNPPDNI KDTKSDIIFF  120
QRSVPGHDNK MQFESSSYEG YFLACEKERD LFKLILKKED ELGDRSIMFT VQNEDITCPP  180
PMSVEHADIW VKSYSLYSRE RYICNSGFKR KAGTSSLTEC VLNKATNVAH WTTPSLKCIR  240
```

```
SEQ ID NO: 192         moltype = AA  length = 869
FEATURE                Location/Qualifiers
REGION                 1..869
                       note = Description of Artificial Sequence: Synthetic 12t15
                        sequence
source                 1..869
                       mol_type = protein
                       organism = synthetic construct
SEQUENCE: 192
MKWVTFISLL FLFSSAYSIW ELKKDVYVVE LDWYPDAPGE MVVLTCDTPE EDGITWTLDQ  60
SSEVLGSGKT LTIQVKEFGD AGQYTCHKGG EVLSHSLLLL HKKEDGIWST DILKDQKEPK  120
NKTFLRCEAK NYSGRFTCWW LTTISTDLTF SVKSSRGSSD PQGVTCGAAT LSAERVRGDN  180
KEYEYSVECQ EDSACPAAEE SLPIEVMVDA VHKLKYENYT SSFFIRDIIK PDPPKNLQLK  240
PLKNSRQVEV SWEYPDTWST PHSYFSLTFC VQVQGKSKRE KKDRVFTDKT SATVICRKNA  300
SISVRAQDRY YSSSWSEWAS VPCSGGGGSG GGGSGGGGSR NLPVATPDPG MFPCLHHSQN  360
LLRAVSNMLQ KARQTLEFYP CTSEEIDHED ITKDKTSTVE ACLPLELTKN ESCLNSRETS  420
FITNGSCLAS RKTSFMMALC LSSIYEDLKM YQVEFKTMNA KLLMDPKRQI FLDQNMLAVI  480
DELMQALNFN SETVPQKSSL EEPDFYKTKI KLCILLHAFR IRAVTIDRVM SYLNASSGTT  540
NTVAAYNLTW KSTNFKTILE WEPKPVNQVY TVQISTKSGD WKSKCFYTTD TECDLTDEIV  600
KDVKQTYLAR VFSYPAGNVE STGSAGEPLY ENSPEFTPYL ETNLGQPTIQ SFEQVGTKVN  660
VTVEDERTLV RRNNTFLSLR DVFGKDLIYT LYYWKSSSSG KKTAKTNTNE FLIDVDKGEN  720
YCFSVQAVIP SRTVNRKSTD SPVECMGQEK GEFRENWVNV ISDLKKIEDL IQSMHIDATL  780
YTESDVHPSC KVTAMKCFLL ELQVISLESG DASIHDTVEN LIILANNSLS SNGNVTESGC  840
KECEELEEKN IKEFLQSFVH IVQMFINTS                                  869
```

```
SEQ ID NO: 193         moltype = DNA  length = 1452
FEATURE                Location/Qualifiers
misc_feature           1..1452
                       note = Description of Artificial Sequence: Synthetic
                        IL-21/TF mutant/IL-15 construct sequence
source                 1..1452
                       mol_type = other DNA
                       organism = synthetic construct
SEQUENCE: 193
atgaagtggg tgaccttcat cagcctgctg ttcctgttct ccagcgccta ctcccagggc  60
caggacaggc acatgatccg gatgaggcag ctcatcgaca tcgtcgacca gctgaagaac  120
tacgtgaacg acctggtgcc cgagtttctg cctgcccccg aggacgtgga gaccaactgc  180
```

```
gagtggtccg ccttctcctg ctttcagaag gcccagctga agtccgccaa caccggcaac  240
aacgagcgga tcatcaacgt gagcatcaag aagctgaagc ggaagcctcc ctccacaaac  300
gccggcagga ggcagaagca caggctgacc tgccccagct gtgactccta cgagaagaag  360
ccccccaagg agttcctgga gaggttcaag tccctgctgc agaagatgat ccatcagcac  420
ctgtcctcca ggacccacgg ctccgaggac tcctccggca ccaccaatac cgtggccgct  480
tataacctca catggaagag caccaacttc gcgacagctc tggaatggga acccaagccc  540
gtcaatcaag tttacaccgt gcagatctcc accaaatccg gagactggaa gagcaagtgc  600
ttctacacaa cagacaccga gtgtgcttta accgacgaaa tcgtcaagga cgtcaagcaa  660
acctatctgg ctcgggtctt ttcctacccc gctggcaatg tcgagtccac cggctccgct  720
ggcgagcctc tctacgagaa ttcccccgaa ttcacccctt atttagagac caatttaggc  780
cagcctacca tccagagctt cgagcaagtt ggcaccaagg tgaacgtcac cgtcgaggat  840
gaaaggactt tagtggcgcg gaataacaca gctttatccc tccgggatgt gttcggcaaa  900
gacctcatct acacactgta ctattggaag tccagctcct ccggcaaaaa gaccgctaag  960
accaacacca acgagttttt aattgacgtg gacaaaggcg agaactactg cttcagcgtg  1020
caagccgtga tcccttctcg taccgtcaac cggaagagca cagattcccc cgttgagtgc  1080
atgggccaag aaaagggcga gttccgggag aactgggtga acgtcatcag cgatttaaag  1140
aagatcgaag atttaattca gtccatgcat atcgacgcca ctttatacac agaatccgac  1200
gtgcacccct cttgtaaggt gaccgccatg aaatgttttt tactggagct gcaagttatc  1260
tctttagaga gcggagacgc tagcatccac gacaccgtgg agaatttaat cattttagcc  1320
aataactctt tatccagcaa cggcaacgtg acagagtccg gctgcaagga gtgcgaagag  1380
ctggaggaga agaacatcaa ggagtttctg caatcctttg tgcacattgt ccagatgttc  1440
atcaatacct cc                                                      1452

SEQ ID NO: 194         moltype = AA  length = 484
FEATURE                Location/Qualifiers
REGION                 1..484
                       note = Description of Artificial Sequence: Synthetic
                        IL-21/TF mutant/IL-15 construct sequence
source                 1..484
                       mol_type = protein
                       organism = synthetic construct
SEQUENCE: 194
MKWVTFISLL FLFSSAYSQG QDRHMIRMRQ LIDIVDQLKN YVNDLVPEFL PAPEDVETNC  60
EWSAFSCFQK AQLKSANTGN NERIINVSIK KLKRKPPSTN AGRRQKHRLT CPSCDSYEKK  120
PPKEFLERFK SLLQKMIHQH LSSRTHGSED SSGTTNTVAA YNLTWKSTNF ATALEWEPKP  180
VNQVYTVQIS TKSGDWKSKC FYTTDTECAL TDEIVKDVKQ TYLARVFSYP AGNVESTGSA  240
GEPLYENSPE FTPYLETNLG QPTIQSFEQV GTKVNVTVED ERTLVARNNT ALSLRDVFGK  300
DLIYTLYYWK SSSSGKKTAK TNTNEFLIDV DKGENYCFSV QAVIPSRTVN RKSTDSPVEC  360
MGQEKGEFRE NWVNVISDLK KIEDLIQSMH IDATLYTESD VHPSCKVTAM KCFLLELQVI  420
SLESGDASIH DTVENLIILA NNSLSSNGNV TESGCKECEE LEEKNIKEFL QSFVHIVQMF  480
INTS                                                               484

SEQ ID NO: 195         moltype = DNA  length = 2142
FEATURE                Location/Qualifiers
misc_feature           1..2142
                       note = Description of Artificial Sequence: Synthetic
                        alphaCD28scFv/TF/alphaCD3scFv sequence
source                 1..2142
                       mol_type = other DNA
                       organism = synthetic construct
SEQUENCE: 195
atgaaatggg tcaccttcat ctctttactg tttttattta gcagcgccta cagcgtgcag  60
ctgcagcagt ccggacccga actggtcaag cccggtgcct ccgtgaaaat gtcttgtaag  120
gcttctggct acacctttac ctcctacgtc atccaatggg tgaagcagaa gcccggtcaa  180
ggtctcgagt ggatcggcag catcaatccc tacaacgatt acaccaagta taacgaaaag  240
tttaagggca aggccactct gacaagcgac aagagctcca ttaccgccta catggagttt  300
tcctctttaa cttctgagga ctccgcttta tactattgcg ctcgttgggg cgatggcaat  360
tattggggcc ggggaactac tttaacagtg agctccggcg gcggcggaag cggaggtgga  420
ggatctggcg gtggaggcag cgacatcgag atgacacagt cccccgctat catgagcgcc  480
tctttaggag aacgtgtgac catgacttgt acagcttcct ccagcgtgag cagctcctat  540
ttccactggt accagcagaa acccggctcc tcccctaaac tgtgtatcta ctccacaagc  600
aatttagcta gcggcgtgcc tcctcgtttt agcggctccg gcagcacctc ttactcttta  660
accattagct ctatggaggc cgaagatgcc gccacatact tttgccatca gtaccaccgg  720
tcccctacct ttggcggagg cacaaagctg gagaccaagc ggagcggcac caccaacaca  780
gtggccgcct acaatctgac ttggaaatcc accaacttca agaccatcct cgagtgggag  840
cccaagcccg ttaatcaagt ttataccgtg cagatttcca ccaagagcgg cgactggaaa  900
tccaagtgct tctataccac agacaccgag tgcgatctca ccgacgagat cgtcaaagac  960
gtgaagcaga catatttagc tagggtgttc tcctaccccg ctggaaacgt ggagagcacc  1020
ggatccgctg gagagccttt atacgagaac tcccccgaat tcacccccta tctggaaacc  1080
aatttaggcc agcccaccat ccagagcttc gaacaagttg gcacaaaggt gaacgtcacc  1140
gtcgaagatg agaggacttt agtgcggagg aacaatacat ttttatcctt acgtgacgtc  1200
ttcggcaagg atttaatcta cacactgtat tactggaagt ctagctcctc cggcaagaag  1260
accgccaaga ccaataccaa cgaattttta attgacgtgg acaagggcga gaactactgc  1320
ttctccgtgc aagctgtgat cccctcccgg acagtgaacc ggaagtccac cgactccccc  1380
gtggagtgca tgggccaaga gaagggagag tttcgtgagc agatcgtgct gacccagtcc  1440
cccgctatta tgagcgctag ccccggtgaa aaggtgacta tgacatgcag cgccagctct  1500
tccgtgagct acatgaactg gtatcagcag aagtccggca ccagccctaa aaggtggatc  1560
tacgacacca gcaagctggc cagcggcgtc cccgctcact ttcggggctc cggctccgga  1620
acaagctact ctctgaccat cagcggcatg gaagccgagg atgccgctac ctattactgt  1680
```

```
cagcagtgga gctccaaccc cttcaccttt ggatccggca ccaagctcga gattaatcgt  1740
ggaggcggag gtagcggagg aggcggatcc ggcggtggag gtagccaagt tcagctccag  1800
caaagcggcg ccgaactcgc tcggcccggc gcttccgtga agatgtcttg taaggcctcc  1860
ggctatacct tcacccggta cacaatgcac tgggtcaagc aacggcccgg tcaaggttta  1920
gagtggattg gctatatcaa cccctcccgg ggctatacca actacaacca gaagttcaag  1980
gacaaagcca ccctcaccac cgacaagtcc agcagcaccg cttacatgca gctgagctct  2040
ttaacatccg aggattccgc cgtgtactac tgcgctcggt actacgacga tcattactgc  2100
ctcgattact ggggccaagg taccacctta acagtctcct cc                    2142
```

```
SEQ ID NO: 196          moltype = AA  length = 714
FEATURE                 Location/Qualifiers
REGION                  1..714
                        note = Description of Artificial Sequence: Synthetic
                         alphaCD28scFv/TF/alphaCD3scFv sequence
source                  1..714
                        mol_type = protein
                        organism = synthetic construct
SEQUENCE: 196
MKWVTFISLL FLFSSAYSVQ LQQSGPELVK PGASVKMSCK ASGYTFTSYV IQWVKQKPGQ  60
GLEWIGSINP YNDYTKYNEK FKGKATLTSD KSSITAYMEF SSLTSEDSAL YYCARWGDGN  120
YWGRGTTLTV SSGGGGSGGG GSGGGGSDIE MTQSPAIMSA SLGERVTMTC TASSSVSSSY  180
FHWYQQKPGS SPKLCIYSTS NLASGVPPRF SGSGSTSYSL TISSMEAEDA ATYFCHQYHR  240
SPTFGGGTKL ETKRSGTTNT VAAYNLTWKS TNFKTILEWE PKPVNQVYTV QISTKSGDWK  300
SKCFYTTDTE CDLTDEIVKD VKQTYLARVF SYPAGNVEST GSAGEPLYEN SPEFTPYLET  360
NLGQPTIQSF EQVGTKVNVT VEDERTLVRR NNTFLSLRDV FGKDLIYTLY YWKSSSSGKK  420
TAKTNTNEFL IDVDKGENYC FSVQAVIPSR TVNRKSTDSP VECMGQEKGE FREQIVLTQS  480
PAIMSASPGE KVTMTCSASS SVSYMNWYQQ KSGTSPKRWI YDTSKLASGV PAHFRGSGSG  540
TSYSLTISGM EAEDAATYYC QQWSSNPFTF GSGTKLEINR GGGGSGGGGS GGGGSQVQLQ  600
QSGAELARPG ASVKMSCKAS GYTFTRYTMH WVKQRPGQGL EWIGYINPSR GYTNYNQKFK  660
DKATLTTDKS SSTAYMQLSS LTSEDSAVYY CARYYDDHYC LDYWGQGTTL TVSS        714
```

```
SEQ ID NO: 197          moltype = DNA  length = 456
FEATURE                 Location/Qualifiers
misc_feature            1..456
                        note = Description of Artificial Sequence: Synthetic IL-7
                         sequence
source                  1..456
                        mol_type = other DNA
                        organism = synthetic construct
SEQUENCE: 197
gattgcgaca tcgagggcaa ggacggcaag cagtacgaga gcgtgctgat ggtgtccatc  60
gaccagctgc tggacagcat gaaggagatc ggctccaact gcctcaacaa cgagttcaac  120
ttcttcaagc ggcacatctg cgacgccaac aaggagggca tgttcctgtt cagggccgcc  180
aggaaactgc ggcagttcct gaagatgaac tccaccggcg acttcgacct gcacctgctg  240
aaggtgtccg agggcaccac catcctgctg aactgcaccg gacaggtgaa gggccggaaa  300
cctgctgctc tgggagaggc ccaacccacc aagagcctgg aggagaacaa gtccctgaag  360
gagcagaaga agctgaacga cctgtgcttc ctgaagaggc tgctgcagga gatcaagacc  420
tgctggaaca agatcctgat gggcaccaag gagcat                          456
```

```
SEQ ID NO: 198          moltype = DNA  length = 861
FEATURE                 Location/Qualifiers
misc_feature            1..861
                        note = Description of Artificial Sequence: Synthetic
                         TGFbetaRII receptor sequence
source                  1..861
                        mol_type = other DNA
                        organism = synthetic construct
SEQUENCE: 198
atcccccccc atgtgcaaaa gagcgtgaac aacgatatga tcgtgaccga caacaacggc  60
gccgtgaagt ttccccagct ctgcaagttc tgcgatgtca ggttcagcac ctgcgataat  120
cagaagtcct gcatgtccaa ctgcagcatc acctccatct gcgagaagcc ccaagaagtg  180
tgcgtggccg tgtggcggaa aaatgacgag aacatcaccc tggagaccgt gtgtcacgac  240
cccaagctcc cttatcacga cttcattctg gaggacgctg cctcccccaa atgcatcatg  300
aaggagaaga agaagcccgg agagaccttc tttatgtgtt cctgtagcag cgacgagtgt  360
aacgacaaca tcatcttcag cgaagagtac aacaccagca accctgatgg aggtggcgga  420
tccggaggtg gaggttctgg tggaggtggg agtattcctc cccacgtgca gaagagcgtg  480
aataatgaca tgatcgtgac cgataacaat ggcgccgtga aatttcccca gctgtgcaaa  540
ttctgcgatg tgaggttttc cacctgcgac aaccagaagt cctgtatgag caactgctcc  600
atcacctcca tctgtgagaa gcctcaggag gtgtgcgtgg ctgtctggcg gaagaatgac  660
gagaatatca ccctggaaac cgtctgccac gatcccaagc tgccctacca cgatttcatc  720
ctggaagacg ccgccagccc taagtgcatc atgaaagaga aaaagaagcc tggcgagacc  780
tttttcatgt gctcctgcag cagcgacgaa tgcaacgaca atatcatctt tagcgaggaa  840
tacaatacca gcaaccccga c                                          861
```

METHODS FOR STIMULATING PROLIFERATION OR DIFFERENTIATION OF AN IMMUNE CELL WITH A MULTI-CHAIN CHIMERIC POLYPEPTIDE

CROSS-REFERENCE TO RELATED APPLICATIONS

This application is a divisional application of U.S. patent application Ser. No. 16/557,822, filed Aug. 30, 2019, now U.S. Pat. No. 11,730,762, which claims priority to: U.S. Patent Application Ser. No. 62/816,683, filed Mar. 11, 2019; U.S. Patent Application Ser. No. 62/725,038, filed Aug. 30, 2018; U.S. Patent Application Ser. No. 62/817,244, filed Mar. 12, 2019; U.S. Patent Application Ser. No. 62/881,039, filed Jul. 31, 2019; U.S. Patent Application Ser. No. 62/724,969, filed Aug. 30, 2018; U.S. Patent Application Ser. No. 62/817,230, filed Mar. 12, 2019; U.S. Patent Application Ser. No. 62/725,043, filed Aug. 30, 2018; U.S. Patent Application Ser. No. 62/725,010, filed Aug. 30, 2018; U.S. Patent Application Ser. No. 62/749,007, filed Oct. 22, 2018; U.S. Patent Application Ser. No. 62/746,832, filed Oct. 17, 2018; U.S. Patent Application Ser. No. 62/749,506, filed Oct. 23, 2018; U.S. Patent Application Ser. No. 62/817,241, filed Mar. 12, 2019; and U.S. Patent Application Ser. No. 62/881,088, filed Jul. 31, 2019, each of which is incorporated hereby reference in its entirety.

SEQUENCE LISTING

This application contains a Sequence Listing that has been submitted electronically as an XML file named "47039-0012002_SL_ST26.XML". The XML file, created on Jun. 30, 2023, is 356,266 bytes in size. The material in the XML file is hereby incorporated by reference in its entirety.

TECHNICAL FIELD

The present disclosure relates to the field of biotechnology, and more specifically, to single-chain and multi-chain chimeric polypeptides having a linker domain positioned between two target-binding domains that are useful for a variety of applications.

BACKGROUND

Adoptive immunotherapy or cellular therapy requires the culture of immune cells obtained from a subject in vivo (and optionally genetic manipulation of the immune cells to express a chimeric antigen receptor or a T-cell receptor) before administration back into the subject. A sufficient number of immune cells is necessary in order to provide a therapeutic effect in the subject. In many examples, immune cells obtained from a subject need to be cultured for three or more weeks before a therapeutically effective number of immune cells can be obtained. In addition, many methods of culturing immune cells obtained from a subject in vitro require a layer of feeder cells, which requires subsequent purification or isolation of the immune cells before administration back to the subject.

SUMMARY

The present invention is based on the discovery that single-chain and multi-chain chimeric polypeptides having a linker domain positioned between two target-binding domains are effective in stimulating an immune cell, inducing or increasing proliferation of an immune cell, inducing differentiation of an immune cell, or treating a subject in need thereof (e.g., a subject having cancer or an aging-related disease or condition). The present invention is also based on the discovery that the multi-chain chimeric polypeptides described herein promote the metabolism of the immune cells by increasing their aerobic glycolysis (Warburg Effect), oxidative phosphorylation, and mitochondrial reserve respiratory capacity to support their differentiation to effector cells and to enhance their effector-cell function(s).

In some aspects, provided herein are methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, under conditions that allow for the activation and proliferation of the natural killer cell or the T cell, wherein the first target-binding domain and the second target-binding domain are each independently selected from the group consisting of: a soluble interleukin, soluble cytokine protein, or soluble cell surface protein, an antigen-binding domain, a soluble interleukin receptor, soluble cytokine receptor, or soluble cell surface receptor, and ligands of co-stimulatory molecules. In some embodiments, the first target-binding domain and the linker domain directly abut each other. In some embodiments, the single-chain chimeric polypeptide further includes a linker sequence between the first target-binding domain and the linker domain. In some embodiments, the linker domain and the second target-binding domain directly abut each other. In some embodiments, the single-chain chimeric polypeptide further includes a linker sequence between the linker domain and the second target-binding domain. In some embodiments, the first target-binding domain and the second target-binding domain directly abut each other. In some embodiments, the single-chain chimeric polypeptide further includes a linker sequence between the first target-binding domain and the second target-binding domain. In some embodiments, the second target-binding domain and the linker domain directly abut each other. In some embodiments, the single-chain chimeric polypeptide further includes a linker sequence between the second target-binding domain and the linker domain. In some embodiments, the first target-binding domain and the second target-binding domain bind specifically to the same antigen. In some embodiments, the first target-binding domain and the second target-binding domain bind specifically to the same epitope. In some embodiments, the first target-binding domain and the second target-binding domain comprise the same amino acid sequence. In some embodiments, the first target-binding domain and the second target-binding domain bind specifically to different antigens. In some embodiments, one or both of the first target-binding domain and the second target-binding domain is an antigen-binding domain. In some embodiments, the first target-binding domain and the second target-binding domain are each an antigen-binding domain. In some embodiments, antigen-binding domain comprises a scFv or a single domain antibody.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, one or both of the first target-binding domain and the second target-binding domain bind to a target selected from the group consisting of: CD16a, CD28, CD3, CD33, CD20, CD19, CD22, CD52, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, one or both of the first target-binding domain and the second target-binding domain is a soluble interleukin or cytokine protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or both of the first target-binding domain and the second target-binding domain is a soluble interleukin or cytokine receptor. In some embodiments, the soluble interleukin or cytokine receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28. In some embodiments, one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, the linker domain is a soluble tissue factor domain. In some embodiments, the soluble tissue factor domain is a soluble human tissue factor domain. In some embodiments, the soluble human tissue factor domain comprises a sequence that is at least 80% identical to SEQ ID NO: 1. In some embodiments, the soluble human tissue factor domain comprises a sequence that is at least 90% identical to SEQ ID NO: 1. In some embodiments, the soluble human tissue factor domain comprises a sequence that is at least 95% identical to SEQ ID NO: 1. In some embodiments, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding Factor VIIa. In some embodiments, the soluble tissue factor domain does not convert inactive Factor X into Factor Xa. In some embodiments, the single-chain chimeric polypeptide does not stimulate blood coagulation in a mammal.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, the IgG1 antibody construct includes at least one antigen-binding domain that binds specifically to the soluble tissue factor domain. In some embodiments, the linker domain is selected from the group consisting of: a kappa chain and a lambda chain. In some embodiments, the IgG1 antibody construct is a monoclonal IgG1 antibody, where both of the antigen-binding domains in the monoclonal IgG1 antibody bind specifically to the linker domain. In some embodiments, the IgG1 antibody construct is a bispecific IgG1 antibody, where one of the two antigen-binding domains in the bispecific IgG1 antibody binds specifically to the linker domain. In some embodiments, the single-chain chimeric polypeptide further includes one or more additional target-binding domains at its N- and/or C-terminus. In some embodiments, the single-chain chimeric polypeptide includes one or more additional target-binding domains at its N-terminus. In some embodiments, one or more additional target-binding domains directly abuts the first target-binding domain, the second target-binding domain, or the linker domain. In some embodiments, the single-chain chimeric polypeptide further includes a linker sequence between one of the at least one additional target-binding domains and the first target-binding domain, the second target-binding domain, or the linker domain. In some embodiments, the single-chain chimeric polypeptide includes one or more additional target-binding domains at its C-terminus. In some embodiments, one of the one or more additional target-binding domains directly abuts the first target-binding domain, the second target-binding domain, or the linker domain. In some embodiments, the single-chain chimeric polypeptide further includes a linker sequence between one of the at least one additional target-binding domains and the first target-binding domain, the second target-binding domain, or the linker domain. In some embodiments, the single-chain chimeric polypeptide includes one or more additional target binding domains at its N-terminus and the C-terminus. In some embodiments, one of the one or more additional target-binding domains at the N-terminus directly abuts the first target-binding domain, the second target-binding domain, or the linker domain. In some embodiments, the single-chain chimeric polypeptide further includes a linker sequence between one of the one or more additional target-binding domains at the N-terminus and the first target-binding domain, the second target-binding domain, or the linker domain. In some embodiments, one of the one or more additional target-binding domains at the C-terminus directly abuts the first target-binding domain, the second target-binding domain, or the linker domain. In some embodiments, the single-chain chimeric polypeptide further includes a linker sequence between one of the one or more additional target-binding domains at the C-terminus and the first target-binding domain, the second target-binding domain, or the linker domain.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each comprise the same amino acid sequence. In some embodiments, the first target-binding domain, the second target-binding domain, and the one or more additional target-binding domains bind specifically to different antigens. In some embodiments, one or more of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain. In some embodiments, the antigen-binding domain comprises a scFv or a single domain antibody.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or more of the first target-binding domain, the second target-binding domain, and the one or more additional target-binding domains is a soluble interleukin, soluble cytokine protein, or soluble cell surface protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, wherein one or more of the first target-binding domain, the second target-binding domain, and the one or more additional target-binding domains is a soluble interleukin or cytokine receptor. In some embodiments, the soluble interleukin or cytokine receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28. In some embodiments, one or more of the first target-binding domain, the second target-binding domain, and the one or more additional target-binding domains is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, the single-chain chimeric polypeptide further comprises a signal sequence at its N-terminal end. In some embodiments, the single-chain chimeric polypeptide lacks a signal sequence at its N-terminal end. In some embodiments, the single-chain chimeric polypeptide further comprises a peptide tag positioned at the N-terminal end or the C-terminal end of the single-chain chimeric polypeptide. In some embodiments, the single-chain chimeric polypeptide further includes a signal sequence at its N-terminal end. In some embodiments, the single-chain chimeric polypeptide lacks a signal sequence at its N-terminal end.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, the contacting step is performed for a period of about 2 hours to about 20 days. In some embodiments, the contacting step is performed for a period of about 1 day to about 15 days. In some embodiments, the liquid culture medium is a serum-free liquid culture medium. In some embodiments, the liquid culture medium is a chemically-defined liquid culture medium. In some embodiments, the liquid culture medium comprises the single-chain chimeric polypeptide and the IgG1 antibody construct at a molar ratio of about 0.5:1 to about 2:1. In some embodiments, the liquid culture medium comprises the single-chain chimeric polypeptide and the IgG1 antibody construct at a molar ratio of about 0.8:1 to about 1.2:1.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, the NK cell or T cell was previously obtained from a subject. In some embodiments, the method further includes obtaining the NK cell or T cell from the subject prior to the contacting step. In some embodiments, the NK cell or T cell has previously been genetically modified to express a chimeric antigen receptor or a recombinant T-cell receptor. In some embodiments, the method further includes, after the contacting step, introducing into the NK cell or the T cell a nucleic acid encoding a chimeric antigen-receptor or a recombinant T-cell receptor. In some embodiments, the method further includes, before the contacting step, introducing into the NK cell or the T cell a nucleic acid encoding a chimeric antigen-receptor or a recombinant T-cell receptor. In some embodiments, the method further includes, after the contacting step, isolating the NK cell or the T cell. In some embodiments, after the contacting step, the NK cell or the T cell has an increased level of expression or secretion of one or more proteins selected from the group consisting of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step.

In some embodiments of methods of promoting the activation and proliferation of a natural killer cell or a T cell that include contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, the method further includes, after the contacting step, administering the NK cell or the T cell to a subject in need thereof. In some embodiments, the subject has been identified or diagnosed as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been diagnosed or identified as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

In some aspects, provided herein are activated NK cell or T cells produced by any of the methods described herein that employ single-chain chimeric polypeptides. In some aspects, provided herein are pharmaceutical compositions that include such activated NK cells or T cell. In some aspects, provided herein are kits that include such pharmaceutical compositions. In some aspects, provided herein are methods of killing a cancer cell, an infected cell, or a senescent cell in a subject in need thereof that include administering to the subject a therapeutically effective amount of the activated NK cell or the activated T cell produced by any of the methods described herein that employ single-chain chimeric polypeptides or the pharmaceutical composition that include such NK cells or T cell. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been identified or diagnosed as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments, the methods of killing a cancer cell, an infected cell, or a senescent cell in a subject in need thereof include administering to the subject a therapeutically effective amount of the activated NK cell or the activated T cell produced by any of the methods described herein that employ single-chain chimeric polypeptides or the pharmaceutical composition that includes such activated NK cells or T cells. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been identified or diagnosed as having an aging-related disease or condition. In some embodiments, the subject has been identified or diagnosed as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the subject has been diagnosed or identified as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

In some aspects, provided herein are kits that include (i) a single-chain chimeric polypeptide including a first target-binding domain, a linker domain, and a second target-binding domain, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules; and (ii) an IgG1 antibody construct including at least one antigen-binding domain that binds specifically to the linker domain. In some embodiments, the first target-binding domain and the linker domain directly abut each other. In some embodiments, the single-chain chimeric polypeptide further comprises a linker sequence between the first target-binding domain and the linker domain. In some embodiments, the linker domain and the second target-binding domain directly abut each other. In some embodiments, the single-chain chimeric polypeptide further includes a linker sequence between the linker domain and the second target-binding domain. In some embodiments, the first target-binding domain and the second target-binding domain directly abut each other. In some embodiments, the single-chain chimeric polypeptide further includes a linker sequence between the first target-binding domain and the second target-binding domain. In some embodiments, the second target-binding domain and the linker domain directly abut each other. In some embodiments, the single-chain chimeric polypeptide further includes a linker sequence between the second target-binding domain and the linker domain. In some embodiments, the first target-binding domain and the second target-binding domain bind specifically to the same antigen. In some embodiments, the first target-binding domain and the second target-binding domain bind specifically to the same epitope. In some embodiments, the first target-binding domain and the second target-binding domain comprise the same amino acid sequence. In some embodiments, the first target-binding domain and the second target-binding domain bind specifically to different antigens. In some embodiments, one or both of the first target-binding domain and the second target-binding domain is an antigen-binding domain. In some embodiments, the first target-binding domain and the second target-binding domain are each an antigen-binding domain. In some embodiments, the antigen-binding domain comprises a scFv or a single domain antibody.

In some embodiments of kits that include a single-chain chimeric polypeptide and an IgG1 antibody construct, one or both of the first target-binding domain and the second target-binding domain bind to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or both of the first target-binding domain and the second target-binding domain is a soluble interleukin, soluble cytokine protein, or soluble cell surface protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or both of the first target-binding domain and the second target-binding domain is a soluble interleukin receptor, soluble cytokine receptor, or soluble cell surface receptor. In some embodiments, the soluble interleukin receptor, soluble cytokine receptor, or soluble cell surface receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28. In some embodiments, one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of kits that include a single-chain chimeric polypeptide and an IgG1 antibody construct, the linker domain is a soluble tissue factor domain. In some embodiments, the soluble tissue factor domain is a soluble human tissue factor domain. In some embodiments, the soluble human tissue factor domain includes a sequence that is at least 80% identical to SEQ ID NO: 1. In some embodiments, the soluble human tissue factor domain includes a sequence that is at least 90% identical to SEQ ID NO: 1. In some embodiments, the soluble human tissue factor domain includes a sequence that is at least 95% identical to SEQ ID NO: 1. In some embodiments, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding Factor VIIa. In some embodiments, the soluble tissue factor domain does not convert inactive Factor X into Factor Xa. In some embodiments, the single-chain chimeric polypeptide does not stimulate blood coagulation in a mammal.

In some embodiments of kits that include a single-chain chimeric polypeptide and an IgG1 antibody construct, the IgG1 antibody construct includes at least one antigen-binding domain that binds specifically to the soluble tissue factor domain. In some embodiments, the linker domain is selected from the group consisting of: a kappa chain and a lambda chain. In some embodiments, the IgG1 antibody construct is a monoclonal IgG1 antibody, where both antigen-binding domains in the monoclonal IgG1 antibody bind specifically to the linker domain. In some embodiments, the IgG1 antibody construct is a bispecific IgG1 antibody, where one of the two antigen-binding domains in the bispecific IgG1 antibody binds specifically to the linker domain.

In some embodiments of kits that include a single-chain chimeric polypeptide and an IgG1 antibody construct, the single-chain chimeric polypeptide further includes one or more additional target-binding domains at its N- and/or C-terminus. In some embodiments, the single-chain chimeric polypeptide includes one or more additional target-binding domains at its N-terminus. In some embodiments, the one or more additional target-binding domains directly abuts the first target-binding domain, the second target-binding domain, or the linker domain. In some embodiments, the single-chain chimeric polypeptide further includes a linker sequence between one of the at least one additional target-binding domains and the first target-binding domain, the second target-binding domain, or the linker domain. In some embodiments, the single-chain chimeric polypeptide includes one or more additional target-binding domains at its C-terminus. In some embodiments, one of the one or more additional target-binding domains directly abuts the first target-binding domain, the second target-binding domain, or the linker domain. In some embodiments, the single-chain chimeric polypeptide further includes a linker sequence between one of the at least one additional target-binding domains and the first target-binding domain, the second target-binding domain, or the linker domain. In some embodiments, the single-chain chimeric polypeptide includes one or more additional target binding domains at its N-terminus and the C-terminus. In some embodiments, one of the one or more additional target-binding domains at the N-terminus directly abuts the first target-binding domain, the second target-binding domain, or the linker domain. In some embodiments, the single-chain chimeric polypeptide further includes a linker sequence between one of the one or more additional target-binding domains at the N-terminus and the first target-binding domain, the second target-binding domain, or the linker domain. In some embodiments, one of the one or more additional target-binding domains at the C-terminus directly abuts the first target-binding domain, the second target-binding domain, or the linker domain. In some embodiments, the single-chain chimeric polypeptide further includes a linker sequence between one of the one or more additional target-binding domains at the C-terminus and the first target-binding domain, the second target-binding domain, or the linker domain.

In some embodiments of kits that include a single-chain chimeric polypeptide and an IgG1 antibody construct, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence. In some embodiments, the first target-binding domain, the second target-binding domain, and the one or more additional target-binding domains bind specifically to different antigens. In some embodiments, one or more of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain. In some embodiments, the antigen-binding domain includes a scFv or a single domain antibody.

In some embodiments of kits that include a single-chain chimeric polypeptide and an IgG1 antibody construct, one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or more of the first target-binding domain, the second target-binding domain, and the one or more additional target-binding domains is a soluble interleukin, soluble cytokine protein, or soluble cell surface protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or more of the first target-binding domain, the second target-binding domain, and the one or more additional target-binding domains is a soluble interleukin receptor, soluble cytokine receptor, or soluble cell surface receptor. In some embodiments, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28. In some embodiments, one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1. In some embodiments, the single-chain chimeric polypeptide further includes a peptide tag positioned at the N-terminal end or the C-terminal end of the single-chain chimeric polypeptide. In some embodiments, the single-chain chimeric polypeptide further includes a signal sequence at its N-terminal end. In some embodiments, the single-chain chimeric polypeptide lacks a signal sequence at its N-terminal end.

In some aspects, provided herein are methods of promoting the activation and proliferation of a natural killer cell or a T cell that include contacting a natural killer cell or a T cell in a liquid culture medium including: (1) an effective amount of a multi-chain chimeric polypeptide that includes: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, wherein the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain, under conditions that allow for the activation and proliferation of the natural killer cell or the T cell. In some embodiments, the first target-binding domain and the linker domain directly abut each other in the first chimeric polypeptide. In some embodiments, the first chimeric polypeptide further includes a linker sequence between the first target-binding domain and the linker domain in the first chimeric polypeptide. In some embodiments, the linker domain and the first domain of the pair of affinity domains directly abut each other in the first chimeric polypeptide. In some embodiments, the first chimeric polypeptide further includes a linker sequence between the linker domain and the first domain of the pair of affinity domains in the first chimeric polypeptide. In some embodiments, the second domain of the pair of affinity domains and the second target-binding domain directly abut each other in the second chimeric polypeptide. In some embodiments, the second chimeric polypeptide further includes a linker sequence between the second domain of the pair of affinity domains and the second target-binding domain in the second chimeric polypeptide. In some embodiments, the first target-binding domain and the second target-binding domain bind specifically to the same antigen. In some embodiments, the first target-binding domain and the second target-binding domain bind specifically to the same epitope. In some embodiments, the first target-binding domain and the second target-binding domain include the same amino acid sequence. In some embodiments, the first target-binding domain and the second target-binding domain bind specifically to different antigens. In some embodiments, one or both of the first target-binding domain and the second target-binding domain is an antigen-binding domain. In some embodiments, the first target-binding domain and the second target-binding domain are each antigen-binding domains. In some embodiments, the antigen-binding domain includes a scFv or a single domain antibody.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or both of the first target-binding domain and the second target-binding domain is a soluble interleukin or cytokine protein. one or both of the first target-binding domain and the second target-binding domain is a soluble interleukin, soluble cytokine protein, or soluble cell surface protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or both of the first target-binding domain and the second target-binding domain is a soluble interleukin receptor, soluble cytokine receptor, or soluble cell surface receptor. In some embodiments, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28. In some embodiments, one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the first chimeric polypeptide further includes one or more additional target-binding domain(s), where at least one of the one or more target-binding domain(s) is positioned between the linker domain and the first domain of the pair of affinity domains. In some embodiments, the first chimeric polypeptide further includes a linker sequence between the linker domain and the at least one of the one or more target antigen-binding domain(s), and/or a linker sequence between the at least one of the one or more target antigen-binding domain(s) and the first domain of the pair of affinity domains. In some embodiments, the first chimeric polypeptide further includes one or more additional target-binding domains at the N-terminal and/or C-terminal end of the first chimeric polypeptide. In some embodiments, at least one of the one or more additional target-binding domains directly abuts the first domain of the pair of affinity domains in the first chimeric polypeptide. In some embodiments, the first chimeric polypeptide further includes a linker sequence between the at least one of the one or more additional target-binding domains and the first domain of the pair of affinity domains. In some embodiments, the at least one of the one or more additional target-binding domains directly abuts the first target-binding domain in the first chimeric polypeptide. In some embodiments, the first chimeric polypeptide further includes a linker sequence between the at least one of the one or more additional target-binding domains and the first target-binding domain. In some embodiments, at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide. In some embodiments, the at least one additional target-binding domain of the one or more additional target-binding domains disposed at the N-terminus directly abuts the first target-binding domain or the first domain of the pair of affinity domains in the first chimeric polypeptide. In some embodiments, the first chimeric polypeptide further includes a linker sequence disposed between the at least one additional target-binding domain and the first target-binding domain or the first domain of the pair of affinity domains in the first chimeric polypeptide. In some embodiments, the at least one additional target-binding domain of the one or more additional target-binding domains disposed at the C-terminus directly abuts the first target-binding domain or the first domain of the pair of affinity domains in the first chimeric polypeptide. In some embodiments, the first chimeric polypeptide further includes a linker sequence disposed between the at least one additional target-binding domain and the first target-binding domain or the first domain of the pair of affinity domains in the first chimeric polypeptide. In some embodiments, the at least one of the one or more additional target-binding domains positioned between the linker domain and the first domain of the pair of affinity domains, directly abuts the linker domain and/or the first domain of the pair of affinity domains. In some embodiments, the first chimeric polypeptide further includes a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the second chimeric polypeptide further includes one or more additional target-binding domains at the N-terminal end and/or the C-terminal end of the second chimeric polypeptide. In some embodiments, at least one of the one or more additional target-binding domains directly abuts the second domain of the pair of affinity domains in the second chimeric polypeptide. In some embodiments, the second chimeric polypeptide further includes a linker sequence between at least one of the one or more additional target-binding domains and the second domain of the pair of affinity domains in the second chimeric polypeptide. In some embodiments, at least one of the one or more additional target-binding domains directly abuts the second target-binding domain in the second chimeric polypeptide. In some embodiments, the second chimeric polypeptide further includes a linker sequence between at least one of the one or more additional target-binding domains and the second target-binding domain in the second chimeric polypeptide.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each comprise the same amino acid sequence. In some embodiments, first target-binding domain, the second target-binding domain, and the one or more additional target-binding domains bind specifically to different antigens. In some embodiments, one or more of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain. In some embodiments, the antigen-binding domain includes a scFv.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28. In some embodiments, one or more of the first target-binding domain, the second target-binding domain, and the one or more additional target-binding domains is a soluble interleukin, soluble cytokine protein, or soluble cell surface protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or more of the first target-binding domain, the second target-binding domain, and the one or more additional target-binding domains is a soluble interleukin receptor, soluble cytokine receptor, or soluble cell surface receptor. In some embodiments, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28. In some embodiments, the first chimeric polypeptide further comprises a peptide tag at the N-terminal end or the C-terminal end of the first chimeric polypeptide. In some one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1. In some embodiments, the first chimeric polypeptide further comprises a peptide tag at the N-terminal end or the C-terminal end of the second chimeric polypeptide. In some embodiments, the second chimeric polypeptide further comprises a peptide tag at the N-terminal end or the C-terminal end of the second chimeric polypeptide.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the linker domain is a soluble tissue factor domain. In some embodiments, the soluble tissue factor domain is a soluble human tissue factor domain. In some embodiments, the soluble human tissue factor domain includes a sequence that is at least 80% identical to SEQ ID NO: 1. In some embodiments, the soluble human tissue factor domain includes a sequence that is at least 90% identical to SEQ ID NO: 1. In some embodiments, the soluble human tissue factor domain includes a sequence that is at least 95% identical to SEQ ID NO: 1. In some embodiments, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding to Factor VIIa. In some embodiments, the soluble tissue factor domain does not convert inactive Factor X into Factor Xa. In some embodiments, the multi-chain chimeric polypeptide does not stimulate blood coagulation in a mammal.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the IgG1 antibody construct includes at least one antigen-binding domain that binds specifically to the soluble tissue factor domain. In some embodiments, the linker domain is selected from the group consisting of: a kappa chain and a lambda chain. In some embodiments, the IgG1 antibody construct is a monoclonal IgG1 antibody, where both antigen-binding domains in the monoclonal IgG1 antibody bind specifically to the linker domain. In some embodiments, the IgG1 antibody construct is a bispecific IgG1 antibody, where one of the two antigen-binding domains in the bispecific IgG1 antibody binds specifically to the linker domain.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the pair of affinity domains is a sushi domain from an alpha chain of human IL-15 receptor (IL15Rα) and a soluble IL-15. In some embodiments, the soluble IL15 has a D8N or D8A amino acid substitution. In some embodiments, the human IL15Rα is a mature full-length IL15Rα. In some embodiments, the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25. In some embodiments, the first chimeric polypeptide and/or the second chimeric polypeptide further includes a signal sequence at its N-terminal end. In some embodiments, the first chimeric polypeptide and/or the second chimeric polypeptide lacks a signal sequence at its N-terminal end.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the contacting step is performed for a period of about 2 hours to about 20 days. In some embodiments, the contacting step is performed for a period of about 1 day to about 15 days. In some embodiments, the liquid culture medium is a serum-free liquid culture medium. In some embodiments, the liquid culture medium is a chemically-defined liquid culture medium. In some embodiments, the liquid culture medium comprises the multi-chain chimeric polypeptide and the IgG1 antibody construct at a molar ratio of about 0.5:1 to about 2:1. In some embodiments, the liquid culture medium comprises the multi-chain chimeric polypeptide and the IgG1 antibody construct at a molar ratio of about 0.8:1 to about 1.2:1. In some embodiments, the NK cell or T cell was previously obtained from a subject. In some embodiments, the method further includes obtaining the NK cell or T cell from the subject prior to the contacting step. In some embodiments, the NK cell or T cell has previously been genetically modified to express a chimeric antigen receptor or a recombinant T-cell receptor. In some embodiments, the method further includes, after the contacting step, introducing into the NK cell or the T cell a nucleic acid encoding a chimeric antigen-receptor or a recombinant T-cell receptor. In some embodiments, the method further includes, before the contacting step, introducing into the NK cell or the T cell a nucleic acid encoding a chimeric antigen-receptor or a recombinant T-cell receptor. In some embodiments, the method further includes, after the contacting step, isolating the NK cell or the T cell. In some embodiments, after the contacting step, the NK cell or the T cell has an increased level of expression or secretion of one or more proteins selected from the group consisting of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step. In some embodiments, the method further includes, after the contacting step, administering the NK cell or the T cell to a subject in need thereof.

In some embodiments of methods of promoting the activation and proliferation of a natural killer cell or a T cell that include contacting a natural killer cell or a T cell in a liquid culture medium that includes first and second chimeric polypeptides and an IgG1 antibody construct that includes at least one antigen-binding domain that binds specifically to a linker domain in one chimeric polypeptide, the subject has been identified or diagnosed as having an age-related disease or condition. In some embodiments, the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been diagnosed or identified as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

In some aspects, provided herein are activated NK cell or T cells produced by any of the methods described herein that employ multi-chain chimeric polypeptides. In some aspects, provided herein are pharmaceutical compositions that include such activated NK cells or T cell. In some aspects, provided herein are kits that include such pharmaceutical compositions. In some aspects, provided herein are methods of killing a cancer cell, an infected cell, or a senescent cell in a subject in need thereof that include administering to the subject a therapeutically effective amount of the activated NK cell or the activated T cell produced by any of the methods described herein that employ multi-chain chimeric polypeptides or the pharmaceutical composition that include such NK cells or T cell. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been identified or diagnosed as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments, the methods of killing a cancer cell, an infected cell, or a senescent cell in a subject in need thereof include administering to the subject a therapeutically effective amount of the activated NK cell or the activated T cell produced by any of the methods described herein that employ multi-chain chimeric polypeptides or the pharmaceutical composition that includes such activated NK cells or T cells. In some embodiments, the subject has been identified or diagnosed as having a cancer. In some embodiments, the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, the subject has been identified or diagnosed as having an aging-related disease or condition. In some embodiments, the subject has been identified or diagnosed as having an aging-related disease or condition. In some embodiments, the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some embodiments, the subject has been diagnosed or identified as having an infectious disease. In some embodiments, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

In some aspects, provided herein are kits that include: 1) a multi-chain chimeric polypeptide that includes: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, wherein the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain. In some embodiments, the first target-binding domain and the linker domain directly abut each other in the first chimeric polypeptide. In some embodiments, the first chimeric polypeptide further includes a linker sequence between the first target-binding domain and the linker domain in the first chimeric polypeptide. In some embodiments, the linker domain and the first domain of the pair of affinity domains directly abut each other in the first chimeric polypeptide. In some embodiments, the first chimeric polypeptide further includes a linker sequence between the linker domain and the first domain of the pair of affinity domains in the first chimeric polypeptide. In some embodiments, the second domain of the pair of affinity domains and the second target-binding domain directly abut each other in the second chimeric polypeptide. In some embodiments, the second chimeric polypeptide further includes a linker sequence between the second domain of the pair of affinity domains and the second target-binding domain in the second chimeric polypeptide. In some embodiments, the first target-binding domain and the second target-binding domain bind specifically to the same antigen. In some embodiments, the first target-binding domain and the second target-binding domain bind specifically to the same epitope. In some embodiments, the first target-binding domain and the second target-binding domain include the same amino acid sequence. In some embodiments, the first target-binding domain and the second target-binding domain bind specifically to different antigens. In some embodiments, one or both of the first target-binding domain and the second target-binding domain is an antigen-binding domain. In some embodiments, the first target-binding domain and the second target-binding domain are each antigen-binding domains. In some embodiments, the antigen-binding domain includes a scFv or a single domain antibody.

In some embodiments of kits that include a multi-chain chimeric polypeptide and an IgG1 antibody construct, one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28. In some embodiments, one or both of the first target-binding domain and the second target-binding domain is a soluble interleukin, soluble cytokine protein, or soluble cell surface protein. In some embodiments, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or both of the first target-binding domain and the second target-binding domain is a soluble interleukin receptor, soluble cytokine receptor, or soluble cell surface receptor. In some embodiments, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28. In some embodiments, one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of kits that include a multi-chain chimeric polypeptide and an IgG1 antibody construct, the first chimeric polypeptide further includes one or more additional target-binding domain(s), where at least one of the one or more target-binding domain(s) is positioned between the linker domain and the first domain of the pair of affinity domains. In some embodiments, the first chimeric polypeptide further includes a linker sequence between the linker domain and the at least one of the one or more target antigen-binding domain(s), and/or a linker sequence between the at least one of the one or more target antigen-binding domain(s) and the first domain of the pair of affinity domains. In some embodiments, the first chimeric polypeptide further includes one or more additional target-binding domains at the N-terminal and/or C-terminal end of the first chimeric polypeptide. In some embodiments, at least one of the one or more additional target-binding domains directly abuts the first domain of the pair of affinity domains in the first chimeric polypeptide. In some embodiments, the first chimeric polypeptide further includes a linker sequence between the at least one of the one or more additional target-binding domains and the first domain of the pair of affinity domains. In some embodiments, the at least one of the one or more additional target-binding domains directly abuts the first target-binding domain in the first chimeric polypeptide. In some embodiments, the first chimeric polypeptide further includes a linker sequence between the at least one of the one or more additional target-binding domains and the first target-binding domain. In some embodiments, at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide. In some embodiments, the at least one additional target-binding domain of the one or more additional target-binding domains disposed at the N-terminus directly abuts the first target-binding domain or the first domain of the pair of affinity domains in the first chimeric polypeptide. In some embodiments, the first chimeric polypeptide further includes a linker sequence disposed between the at least one additional target-binding domain and the first target-binding domain or the first domain of the pair of affinity domains in the first chimeric polypeptide. In some embodiments, the at least one additional target-binding domain of the one or more additional target-binding domains disposed at the C-terminus directly abuts the first target-binding domain or the first domain of the pair of affinity domains in the first chimeric polypeptide. In some embodiments, the first chimeric polypeptide further includes a linker sequence disposed between the at least one additional target-binding domain and the first target-binding domain or the first domain of the pair of affinity domains in the first chimeric polypeptide. In some embodiments, the at least one of the one or more additional target-binding domains positioned between the linker domain and the first domain of the pair of affinity domains, directly abuts the linker domain and/or the first domain of the pair of affinity domains. In some embodiments, the first chimeric polypeptide further includes a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

In some embodiments of kits that include a multi-chain chimeric polypeptide and an IgG1 antibody construct, the second chimeric polypeptide further includes one or more additional target-binding domains at the N-terminal end or the C-terminal end of the second chimeric polypeptide. In some embodiments, at least one of the one or more additional target-binding domains directly abuts the second domain of the pair of affinity domains in the second chimeric polypeptide. In some embodiments, the second chimeric polypeptide further includes a linker sequence between at least one of the one or more additional target-binding domains and the second domain of the pair of affinity domains in the second chimeric polypeptide. In some embodiments, at least one of the one or more additional target-binding domains directly abuts the second target-binding domain in the second chimeric polypeptide. In some embodiments, the second chimeric polypeptide further includes a linker sequence between at least one of the one or more additional target-binding domains and the second target-binding domain in the second chimeric polypeptide.

In some embodiments of kits that include a multi-chain chimeric polypeptide and an IgG1 antibody construct, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some two or more of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence. In some embodiments, the first target-binding domain, the second target-binding domain, and the one or more additional target-binding domains bind specifically to different antigens. In some embodiments, one or more of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain. In some embodiments, the antigen-binding domain includes a scFv.

In some embodiments of kits that include a multi-chain chimeric polypeptide and an IgG1 antibody construct, one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28. In some embodiments, one or more of the first target-binding domain, the second target-binding domain, and the one or more additional target-binding domains is a soluble interleukin, soluble cytokine protein, or soluble cell surface protein. In some embodiments, the soluble interleukin, soluble cytokine protein, or soluble cell surface receptor is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein. In some embodiments, one or more of the first target-binding domain, the second target-binding domain, and the one or more additional target-binding domains is a soluble interleukin receptor, soluble cytokine receptor, or soluble cell surface receptor. In some embodiments, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28. In some embodiments, one or both of the first target-binding domain and the second target-binding domain is a ligand of a co-stimulatory molecule. In some embodiments, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of kits that include a multi-chain chimeric polypeptide and an IgG1 antibody construct, the linker domain is a soluble tissue factor domain. In some embodiments, the soluble tissue factor domain is a soluble human tissue factor domain. In some embodiments, the soluble human tissue factor domain includes a sequence that is at least 80% identical to SEQ ID NO: 1. In some embodiments, the soluble human tissue factor domain includes a sequence that is at least 90% identical to SEQ ID NO: 1. In some embodiments, the soluble human tissue factor domain includes a sequence that is at least 95s % identical to SEQ ID NO: 1. In some embodiments, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the soluble tissue factor domain is not capable of binding to Factor VIIa. In some embodiments, the soluble tissue factor domain does not convert inactive Factor X into Factor Xa. In some embodiments, the multi-chain chimeric polypeptide does not stimulate blood coagulation in a mammal.

In some embodiments of kits that include a multi-chain chimeric polypeptide and an IgG1 antibody construct, the IgG1 antibody construct includes at least one antigen-binding domain that binds specifically to the soluble tissue factor domain. In some embodiments, the linker domain is selected from the group consisting of: a kappa chain and a lambda chain. In some embodiments, the IgG1 antibody construct is a monoclonal IgG1 antibody, where both antigen-binding domains in the monoclonal IgG1 antibody bind specifically to the linker domain. In some embodiments, the IgG1 antibody construct is a bispecific IgG1 antibody, where one of the two antigen-binding domains in the bispecific IgG1 antibody binds specifically to the linker domain.

In some embodiments of kits that include a multi-chain chimeric polypeptide and an IgG1 antibody construct, the pair of affinity domains is a sushi domain from an alpha chain of human IL-15 receptor (IL15Rα) and a soluble IL-15. In some embodiments, the soluble IL15 has a D8N or D8A amino acid substitution. In some embodiments, the human IL15Rα is a mature full-length IL15Rα. In some embodiments, the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25. In some embodiments, the first chimeric polypeptide and/or the second chimeric polypeptide further include a signal sequence at its N-terminal end. In some embodiments, the first chimeric polypeptide and/or the second chimeric polypeptide lacks a signal sequence at its N-terminal end. In some embodiments, the first chimeric polypeptide and/or the second chimeric polypeptide further include a signal sequence at its N-terminal end. In some embodiments, the first chimeric polypeptide and/or the second chimeric polypeptide lacks a signal sequence at its N-terminal end.

Also provided herein are methods of increasing the glucose consumption of an immune cell that include: contacting an immune cell in a liquid culture medium including an effective amount of (i) a single-chain chimeric polypeptide including a first target-binding domain, a linker domain, and a second target-binding domain, and optionally (ii) an IgG1 antibody construct that includes at least one antigen-binding domain that binds specifically to the linker domain, under conditions that allow for glucose consumption in the immune cell, where the first target-binding domain and the second target-binding domain are each independently selected from the group of: a soluble interleukin, soluble cytokine protein, or soluble cell surface protein, an antigen-binding domain, a soluble interleukin receptor, soluble cytokine receptor, or soluble cell surface receptor, and ligands of co-stimulatory molecules.

Also provided herein are methods of increasing the oxidative phosphorylation of an immune cell that include: contacting an immune cell in a liquid culture medium including an effective amount of (i) a single-chain chimeric polypeptide including a first target-binding domain, a linker domain, and a second target-binding domain, and optionally (ii) an IgG1 antibody construct that includes at least one antigen-binding domain that binds specifically to the linker domain, under conditions that allow for oxidative phosphorylation in the immune cell, where the first target-binding domain and the second target-binding domain are each independently selected from the group of: a soluble interleukin, soluble cytokine protein, or soluble cell surface protein, an antigen-binding domain, a soluble interleukin receptor, soluble cytokine receptor, or soluble cell surface receptor, and ligands of co-stimulatory molecules.

Also provided herein are methods of increasing the aerobic glycolysis of an immune cell that include: contacting an immune cell in a liquid culture medium including an effective amount of (i) a single-chain chimeric polypeptide including a first target-binding domain, a linker domain, and a second target-binding domain, and optionally (ii) an IgG1 antibody construct that includes at least one antigen-binding domain that binds specifically to the linker domain, under conditions that allow for aerobic glycolysis in the immune cell, where the first target-binding domain and the second target-binding domain are each independently selected from the group of: a soluble interleukin, soluble cytokine protein, or soluble cell surface protein, an antigen-binding domain, a soluble interleukin receptor, soluble cytokine receptor, or soluble cell surface receptor, and ligands of co-stimulatory molecules.

Also provided herein are methods of increasing the extracellular acidification rate (ECAR) of an immune cell that include: contacting an immune cell in a liquid culture medium including an effective amount of (i) a single-chain chimeric polypeptide including a first target-binding domain, a linker domain, and a second target-binding domain, and optionally (ii) an IgG1 antibody construct that includes at least one antigen-binding domain that binds specifically to the linker domain, under conditions that allow for extracellular acidification by the immune cell, where the first target-binding domain and the second target-binding domain are each independently selected from the group of: a soluble interleukin, soluble cytokine protein, or soluble cell surface protein, an antigen-binding domain, a soluble interleukin receptor, soluble cytokine receptor, or soluble cell surface receptor, and ligands of co-stimulatory molecules.

Also provided herein are methods of increasing the mitochondrial oxygen consumption rate of an immune cell that include: contacting an immune cell in a liquid culture medium including an effective amount of (i) a single-chain chimeric polypeptide including a first target-binding domain, a linker domain, and a second target-binding domain, and optionally (ii) an IgG1 antibody construct that includes at least one antigen-binding domain that binds specifically to the linker domain, under conditions that allow for mitochondrial oxygen consumption rate by the immune cell, where the first target-binding domain and the second target-binding domain are each independently selected from the group of: a soluble interleukin, soluble cytokine protein, or soluble cell surface protein, an antigen-binding domain, a soluble interleukin receptor, soluble cytokine receptor, or soluble cell surface receptor, and ligands of co-stimulatory molecules.

In some embodiments of any of the methods described herein, the liquid culture medium includes the single-chain chimeric polypeptide and the IgG1 antibody construct. In some embodiments of any of the methods described herein, the IgG1 antibody construct is a monoclonal IgG1 antibody, where both of the antigen-binding domains in the monoclonal IgG1 antibody bind specifically to the linker domain. In some embodiments of any of the methods described herein, the IgG1 antibody construct is a bispecific IgG1 antibody, where one of the two antigen-binding domains in the bispecific IgG1 antibody binds specifically to the linker domain.

In some embodiments of any of the methods described herein, the contacting step is performed for a period of about 2 hours to about 20 days (e.g., about 1 day to about 15 days). In some embodiments of any of the methods described herein, the liquid culture medium is a serum-free liquid culture medium. In some embodiments of any of the methods described herein, the liquid culture medium is a chemically-defined liquid culture medium. In some embodiments of any of the methods described herein, the liquid culture medium includes serum. In some embodiments of any of the methods described herein, the liquid culture medium includes the single-chain chimeric polypeptide and the IgG1 antibody construct at a molar ratio of about 0.5:1 to about 2:1 (e.g., about 0.8:1 to about 1.2:1).

In some embodiments of any of the methods described herein, the first target-binding domain and the linker domain directly abut each other. In some embodiments of any of the methods described herein, the single-chain chimeric polypeptide further comprises a linker sequence between the first target-binding domain and the linker domain. In some embodiments of any of the methods described herein, the linker domain and the second target-binding domain directly abut each other. In some embodiments of any of the methods described herein, the single-chain chimeric polypeptide further includes a linker sequence between the linker domain and the second target-binding domain. In some embodiments of any of the methods described herein, the first target-binding domain and the second target-binding domain directly abut each other.

In some embodiments of any of the methods described herein, the single-chain chimeric polypeptide further includes a linker sequence between the first target-binding domain and the second target-binding domain. In some embodiments of any of the methods described herein, the second target-binding domain and the linker domain directly abut each other. In some embodiments of any of the methods described herein, the single-chain chimeric polypeptide further includes a linker sequence between the second target-binding domain and the linker domain.

In some embodiments of any of the methods described herein, the first target-binding domain and the second target-binding domain bind specifically to the same antigen. In some embodiments of any of the methods described herein, the first target-binding domain and the second target-binding domain bind specifically to the same epitope. In some embodiments of any of the methods described herein, the first target-binding domain and the second target-binding domain include the same amino acid sequence. In some embodiments of any of the methods described herein, the first target-binding domain and the second target-binding domain bind specifically to different antigens.

In some embodiments of any of the methods described herein, one or both of the first target-binding domain and the second target-binding domain is an antigen-binding domain. In some embodiments of any of the methods described herein, the first target-binding domain and the second target-binding domain are each an antigen-binding domain. In some embodiments of any of the methods described herein, the antigen-binding domain includes a scFv or a single domain antibody.

In some embodiments of any of the methods described herein, one or both of the first target-binding domain and the second target-binding domain bind to a target selected from the group of: CD16a, CD28, CD3, CD33, CD20, CD19, CD22, CD52, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the methods described herein, one or both of the first target-binding domain and the second target-binding domain is a soluble interleukin, soluble cytokine protein, or soluble cell surface protein. In some embodiments of any of the methods described herein, the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

In some embodiments of any of the methods described herein, one or both of the first target-binding domain and the second target-binding domain is a soluble interleukin receptor, soluble cytokine receptor, or soluble cell surface receptor. In some embodiments of any of the methods described herein, the soluble interleukin receptor, soluble cytokine receptor, or soluble cell surface receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

In some embodiments of any of the methods described herein, the linker domain is a soluble tissue factor domain. In some embodiments of any of the methods described herein, the soluble tissue factor domain is a soluble human tissue factor domain. In some embodiments of any of the methods described herein, the soluble human tissue factor domain comprises a sequence that is at least 80% identical, at least 90% identical, or at least 95% identical to SEQ ID NO: 1. In some embodiments of any of the methods described herein, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein.

In some embodiments of any of the methods described herein, the soluble tissue factor domain is not capable of binding Factor VIIa. In some embodiments of any of the methods described herein, the soluble tissue factor domain does not convert inactive Factor X into Factor Xa. In some embodiments of any of the methods described herein, the single-chain chimeric polypeptide does not stimulate blood coagulation in a mammal. In some embodiments of any of the methods described herein, the IgG1 antibody construct includes at least one antigen-binding domain that binds specifically to the soluble tissue factor domain. In some embodiments of any of the methods described herein, the linker domain is selected from the group of: a kappa chain and a lambda chain. In some embodiments of any of the methods described herein, the IgG1 antibody construct is a monoclonal IgG1 antibody, where both of the antigen-binding domains in the monoclonal IgG1 antibody bind specifically to the linker domain. In some embodiments of any of the methods described herein, the IgG1 antibody construct is a bispecific IgG1 antibody, where one of the two antigen-binding domains in the bispecific IgG1 antibody binds specifically to the linker domain.

In some embodiments of any of the methods described herein, the single-chain chimeric polypeptide further includes one or more additional target-binding domains at its N- and/or C-terminus. In some embodiments of any of the methods described herein, the single-chain chimeric polypeptide includes one or more additional target-binding domains at its N-terminus. In some embodiments of any of the methods described herein, one or more additional target-binding domains directly abuts the first target-binding domain, the second target-binding domain, or the linker domain. In some embodiments of any of the methods described herein, the single-chain chimeric polypeptide further includes a linker sequence between one of the at least one additional target-binding domains and the first target-binding domain, the second target-binding domain, or the linker domain.

In some embodiments of any of the methods described herein, the single-chain chimeric polypeptide includes one or more additional target-binding domains at its C-terminus. In some embodiments of any of the methods described herein, one of the one or more additional target-binding domains directly abuts the first target-binding domain, the second target-binding domain, or the linker domain. In some embodiments of any of the methods described herein, the single-chain chimeric polypeptide further includes a linker sequence between one of the at least one additional target-binding domains and the first target-binding domain, the second target-binding domain, or the linker domain.

In some embodiments of any of the methods described herein, the single-chain chimeric polypeptide includes one or more additional target binding domains at its N-terminus and the C-terminus. In some embodiments of any of the methods described herein, one of the one or more additional target-binding domains at the N-terminus directly abuts the first target-binding domain, the second target-binding domain, or the linker domain. In some embodiments of any of the methods described herein, the single-chain chimeric polypeptide further includes a linker sequence between one of the one or more additional target-binding domains at the N-terminus and the first target-binding domain, the second target-binding domain, or the linker domain. In some embodiments of any of the methods described herein, one of the one or more additional target-binding domains at the C-terminus directly abuts the first target-binding domain, the second target-binding domain, or the linker domain. In some embodiments of any of the methods described herein, the single-chain chimeric polypeptide further includes a linker sequence between one of the one or more additional target-binding domains at the C-terminus and the first target-binding domain, the second target-binding domain, or the linker domain.

In some embodiments of any of the methods described herein, two or more of the first target-binding domain, the second target-binding domain, and the one or more additional target-binding domains bind specifically to the same antigen. In some embodiments of any of the methods described herein, two or more of the first target-binding domain, the second target-binding domain, and the one or more additional target-binding domains bind specifically to the same epitope. In some embodiments of any of the methods described herein, two or more of the first target-binding domain, the second target-binding domain, and the one or more additional target-binding domains include the same amino acid sequence. In some embodiments of any of the methods described herein, the first target-binding domain, the second target-binding domain, and the one or more additional target-binding domains each bind specifically to the same antigen. In some embodiments of any of the methods described herein, the first target-binding domain, the second target-binding domain, and the one or more additional target-binding domains each bind specifically to the same epitope. In some embodiments of any of the methods described herein, the first target-binding domain, the second target-binding domain, and the one or more additional target-binding domains each include the same amino acid sequence. In some embodiments of any of the methods described herein, the first target-binding domain, the second target-binding domain, and the one or more additional target-binding domains bind specifically to different antigens.

In some embodiments of any of the methods described herein, one or more of the first target-binding domain, the second target-binding domain, and the one or more target-binding domains is an antigen-binding domain. In some embodiments of any of the methods described herein, the first target-binding domain, the second target-binding domain, and the one or more additional target-binding domains are each an antigen-binding domain. In some embodiments of any of the methods described herein, the antigen-binding domain includes a scFv or a single domain antibody.

In some embodiments of any of the methods described herein, one or more of the first target-binding domain, the second target-binding domain, and the one or more target-binding domains bind specifically to a target selected from the group of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the methods described herein, one or more of the first target-binding domain, the second target-binding domain, and the one or more additional target-binding domains is a soluble interleukin, soluble cytokine protein, or soluble cell surface protein. In some embodiments of any of the methods described herein, the soluble interleukin, soluble cytokine protein, or soluble cell surface protein is selected from the group of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

In some embodiments of any of the methods described herein, one or more of the first target-binding domain, the second target-binding domain, and the one or more additional target-binding domains is a soluble interleukin receptor, soluble cytokine receptor, or soluble cell surface receptor. In some embodiments of any of the methods described herein, the soluble interleukin, soluble cytokine receptor, or soluble cell surface receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

In some embodiments of any of the methods described herein, one or more of the first target-binding domain, the second target-binding domain, and the one or more additional target-binding domains is a ligand of a co-stimulatory molecule. In some embodiments of any of the methods described herein, the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

In some embodiments of any of the methods described herein, the single-chain chimeric polypeptide further includes a peptide tag positioned at the N-terminal end or the C-terminal end of the single-chain chimeric polypeptide. In some embodiments of any of the methods described herein, the immune cell was previously obtained from a subject. Some embodiments of any of the methods described herein further include obtaining the immune cell from the subject prior to the contacting step. In some embodiments of any of the methods described herein, the immune cell has previously been genetically modified to express a chimeric antigen receptor or a recombinant T-cell receptor. Some embodiments of any of the methods described herein further include, after the contacting step, introducing into the immune cell a nucleic acid encoding a chimeric antigen-receptor or a recombinant T-cell receptor. Some embodiments of any of the methods described herein further include, before the contacting step, introducing into the immune cell a nucleic acid encoding a chimeric antigen-receptor or a recombinant T-cell receptor. Some embodiments of any of the methods described herein further include, after the contacting step, isolating the immune cell. In some embodiments of any of the methods described herein, after the contacting step, the immune cell has an increased level of expression or secretion of one or more proteins selected from the group of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step. administering the immune cell to a subject in need thereof.

In some embodiments of any of the methods described herein, the subject has been identified or diagnosed as having an age-related disease or condition. In some embodiments of any of the methods described herein, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been diagnosed or identified as having an infectious disease. In some embodiments of any of the methods described herein, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Also provided herein are activated immune cells produced by any of the methods described herein. Also provided herein are pharmaceutical compositions that include any of the activated immune cells produced by any of the methods described herein. Also provided herein are kits that include a pharmaceutical composition including any of the activated immune cells described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein. In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been identified or diagnosed as having an aging-related disease or condition. In some embodiments of any of the methods described herein, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Also provided herein are methods of treating a subject in need thereof that include administering to the subject a therapeutically effective amount of any of the activated immune cells described herein produced by any of the methods described herein or any of the pharmaceutical compositions described herein. In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CMIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been identified or diagnosed as having an aging-related disease or condition. In some embodiments of any of the methods described herein, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments of any of the methods described herein, the subject has been diagnosed or identified as having an infectious disease. In some embodiments of any of the methods described herein, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Also provided herein are methods of increasing the glucose consumption of an immune cell that include: contacting an immune cell in a liquid culture medium including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain, under conditions that allow for glucose consumption in the immune cell.

Also provided herein are methods of increasing the oxidative phosphorylation of an immune cell that include: contacting an immune cell in a liquid culture medium including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain, under conditions that allow for oxidative phosphorylation in the immune cell.

Also provided herein are methods of increasing the aerobic glycolysis of an immune cell that include: contacting an immune cell in a liquid culture medium including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain, under conditions that allow for aerobic glycolysis in the immune cell.

Also provided herein are methods of increasing the extracellular acidification rate (ECAR) of an immune cell that include: contacting an immune cell in a liquid culture medium including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain, under conditions that allow for extracellular acidification by the immune cell.

Also provided herein are methods of increasing the mitochondrial oxygen consumption rate of an immune cell that include: contacting an immune cell in a liquid culture medium including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain, under conditions that allow for mitochondrial oxygen consumption rate by the immune cell.

In some embodiments of any of the methods described herein, the liquid culture medium includes the single-chain chimeric polypeptide and the IgG1 antibody construct. In some embodiments of any of the methods described herein, the IgG1 antibody construct is a monoclonal IgG1 antibody, where both of the antigen-binding domains in the monoclonal IgG1 antibody bind specifically to the linker domain. In some embodiments of any of the methods described herein, the IgG1 antibody construct is a bispecific IgG1 antibody, where one of the two antigen-binding domains in the bispecific IgG1 antibody binds specifically to the linker domain. In some embodiments of any of the methods described herein, the contacting step is performed for a period of about 2 hours to about 20 days (e.g., about 1 day to about 15 days).

In some embodiments of any of the methods described herein, the liquid culture medium is a serum-free liquid culture medium. In some embodiments of any of the methods described herein, the liquid culture medium is a chemically-defined liquid culture medium. In some embodiments of any of the methods described herein, the liquid culture medium includes serum. In some embodiments of any of the methods described herein, the liquid culture medium includes the single-chain chimeric polypeptide and the IgG1 antibody construct at a molar ratio of about 0.5:1 to about 2:1 (e.g., about 0.8:1 to about 1.2:1).

In some embodiments of any of the methods described herein, the first target-binding domain and the linker domain directly abut each other in the first chimeric polypeptide. In some embodiments of any of the methods described herein, the first chimeric polypeptide further includes a linker sequence between the first target-binding domain and the linker domain in the first chimeric polypeptide. In some embodiments of any of the methods described herein, the linker domain and the first domain of the pair of affinity domains directly abut each other in the first chimeric polypeptide. In some embodiments of any of the methods described herein, the first chimeric polypeptide further comprises a linker sequence between the linker domain and the first domain of the pair of affinity domains in the first chimeric polypeptide. In some embodiments of any of the methods described herein, the second domain of the pair of affinity domains and the second target-binding domain directly abut each other in the second chimeric polypeptide. In some embodiments of any of the methods described herein, the second chimeric polypeptide further includes a linker sequence between the second domain of the pair of affinity domains and the second target-binding domain in the second chimeric polypeptide.

In some embodiments of any of the methods described herein, the first target-binding domain and the second target-binding domain bind specifically to the same antigen. In some embodiments of any of the methods described herein, the first target-binding domain and the second target-binding domain bind specifically to the same epitope. In some embodiments of any of the methods described herein, the first target-binding domain and the second target-binding domain include the same amino acid sequence. In some embodiments of any of the methods described herein, the first target-binding domain and the second target-binding domain bind specifically to different antigens.

In some embodiments of any of the methods described herein, one or both of the first target-binding domain and the second target-binding domain is an antigen-binding domain. In some embodiments of any of the methods described herein, the first target-binding domain and the second target-binding domain are each antigen-binding domains. In some embodiments of any of the methods described herein, the antigen-binding domain comprises a scFv or a single domain antibody. In some embodiments of any of the methods described herein, one or both of the first target-binding domain and the second target-binding domain bind specifically to a target selected from the group of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the methods described herein, one or both of the first target-binding domain and the second target-binding domain is a soluble interleukin, soluble cytokine protein, or soluble cell surface protein. In some embodiments of any of the methods described herein, the soluble interleukin, soluble cytokine protein, or soluble cell surface protein is selected from the group of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

In some embodiments of any of the methods described herein, one or both of the first target-binding domain and the second target-binding domain is a soluble interleukin receptor, soluble cytokine receptor, or soluble cell surface receptor. In some embodiments of any of the methods described herein, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

In some embodiments of any of the methods described herein, the first chimeric polypeptide further includes one or more additional target-binding domain(s), where at least one of the one or more target-binding domain(s) is positioned between the linker domain and the first domain of the pair of affinity domains. In some embodiments of any of the methods described herein, the first chimeric polypeptide further includes a linker sequence between the linker domain and the at least one of the one or more target antigen-binding domain(s), and/or a linker sequence between the at least one of the one or more target antigen-binding domain(s) and the first domain of the pair of affinity domains.

In some embodiments of any of the methods described herein, the first chimeric polypeptide further comprises one or more additional target-binding domains at the N-terminal and/or C-terminal end of the first chimeric polypeptide. In some embodiments of any of the methods described herein, at least one of the one or more additional target-binding domains directly abuts the first domain of the pair of affinity domains in the first chimeric polypeptide. In some embodiments of any of the methods described herein, the first chimeric polypeptide further includes a linker sequence between the at least one of the one or more additional target-binding domains and the first domain of the pair of affinity domains. In some embodiments of any of the methods described herein, the at least one of the one or more additional target-binding domains directly abuts the first target-binding domain in the first chimeric polypeptide. In some embodiments of any of the methods described herein, the first chimeric polypeptide further includes a linker sequence between the at least one of the one or more additional target-binding domains and the first target-binding domain. In some embodiments of any of the methods described herein, at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide. In some embodiments of any of the methods described herein, the at least one additional target-binding domain of the one or more additional target-binding domains disposed at the N-terminus directly abuts the first target-binding domain or the first domain of the pair of affinity domains in the first chimeric polypeptide. In some embodiments of any of the methods described herein, the first chimeric polypeptide further includes a linker sequence disposed between the at least one additional target-binding domain and the first target-binding domain or the first domain of the pair of affinity domains in the first chimeric polypeptide. In some embodiments of any of the methods described herein, the at least one additional target-binding domain of the one or more additional target-binding domains disposed at the C-terminus directly abuts the first target-binding domain or the first domain of the pair of affinity domains in the first chimeric polypeptide. In some embodiments of any of the methods described herein, the first chimeric polypeptide further includes a linker sequence disposed between the at least one additional target-binding domain and the first target-binding domain or the first domain of the pair of affinity domains in the first chimeric polypeptide. In some embodiments of any of the methods described herein, the at least one of the one or more additional target-binding domains positioned between the linker domain and the first domain of the pair of affinity domains, directly abuts the linker domain and/or the first domain of the pair of affinity domains. In some embodiments of any of the methods described herein, the first chimeric polypeptide further includes a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

In some embodiments of any of the methods described herein, the second chimeric polypeptide further includes one or more additional target-binding domains at the N-terminal end and/or the C-terminal end of the second chimeric polypeptide. In some embodiments of any of the methods described herein, at least one of the one or more additional target-binding domains directly abuts the second domain of the pair of affinity domains in the second chimeric polypeptide. In some embodiments of any of the methods described herein, the second chimeric polypeptide further includes a linker sequence between at least one of the one or more additional target-binding domains and the second domain of the pair of affinity domains in the second chimeric polypeptide. In some embodiments of any of the methods described herein, at least one of the one or more additional target-binding domains directly abuts the second target-binding domain in the second chimeric polypeptide. In some embodiments of any of the methods described herein, the second chimeric polypeptide further includes a linker sequence between at least one of the one or more additional target-binding domains and the second target-binding domain in the second chimeric polypeptide.

In some embodiments of any of the methods described herein, two or more of the first target-binding domain, the second target-binding domain, and the one or more additional target-binding domains bind specifically to the same antigen. In some embodiments of any of the methods described herein, two or more of the first target-binding domain, the second target-binding domain, and the one or more additional target-binding domains bind specifically to the same epitope. In some embodiments of any of the methods described herein, two or more of the first target-binding domain, the second target-binding domain, and the one or more additional target-binding domains include the same amino acid sequence. In some embodiments of any of the methods described herein, the first target-binding domain, the second target-binding domain, and the one or more additional target-binding domains each bind specifically to the same antigen. In some embodiments of any of the methods described herein, the first target-binding domain, the second target-binding domain, and the one or more additional target-binding domains each bind specifically to the same epitope. In some embodiments of any of the methods described herein, the first target-binding domain, the second target-binding domain, and the one or more additional target-binding domains each include the same amino acid sequence. In some embodiments of any of the methods described herein, the first target-binding domain, the second target-binding domain, and the one or more additional target-binding domains bind specifically to different antigens.

In some embodiments of any of the methods described herein, one or more of the first target-binding domain, the second target-binding domain, and the one or more target-binding domains is an antigen-binding domain. In some embodiments of any of the methods described herein, the first target-binding domain, the second target-binding domain, and the one or more additional target-binding domains are each an antigen-binding domain. In some embodiments of any of the methods described herein, the antigen-binding domain comprises a scFv.

In some embodiments of any of the methods described herein, one or more of the first target-binding domain, the second target-binding domain, and the one or more target-binding domains bind specifically to a target selected from the group of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

In some embodiments of any of the methods described herein, one or more of the first target-binding domain, the second target-binding domain, and the one or more additional target-binding domains is a soluble interleukin, soluble cytokine protein, or soluble cell surface protein. In some embodiments of any of the methods described herein, the soluble interleukin, soluble cytokine protein, or soluble cell surface protein is selected from the group of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

In some embodiments of any of the methods described herein, one or more of the first target-binding domain, the second target-binding domain, and the one or more additional target-binding domains is a soluble interleukin receptor, soluble cytokine receptor, or soluble cell surface receptor. In some embodiments of any of the methods described herein, the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

In some embodiments of any of the methods described herein, the first chimeric polypeptide further includes a peptide tag at the N-terminal end or the C-terminal end of the first chimeric polypeptide. In some embodiments of any of the methods described herein, the second chimeric polypeptide further includes a peptide tag at the N-terminal end or the C-terminal end of the second chimeric polypeptide.

In some embodiments of any of the methods described herein, the linker domain is a soluble tissue factor domain. In some embodiments of any of the methods described herein, the soluble tissue factor domain is a soluble human tissue factor domain. In some embodiments of any of the methods described herein, the soluble human tissue factor domain includes a sequence that is at least 80% identical, at least 90% identical, or at least 95% identical to SEQ ID NO: 1. In some embodiments of any of the methods described herein, the soluble human tissue factor domain does not include one or more of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods described herein, the soluble human tissue factor domain does not include any of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments of any of the methods described herein, the soluble tissue factor domain is not capable of binding to Factor VIIa. In some embodiments of any of the methods described herein, the soluble tissue factor domain does not convert inactive Factor X into Factor Xa. In some embodiments of any of the methods described herein, the multi-chain chimeric polypeptide does not stimulate blood coagulation in a mammal. In some embodiments of any of the methods described herein, the IgG1 antibody construct includes at least one antigen-binding domain that binds specifically to the soluble tissue factor domain. In some embodiments of any of the methods described herein, the linker domain is selected from the group of: a kappa chain and a lambda chain. In some embodiments of any of the methods described herein, the IgG1 antibody construct is a monoclonal IgG1 antibody, where both antigen-binding domains in the monoclonal IgG1 antibody bind specifically to the linker domain. In some embodiments of any of the methods described herein, the IgG1 antibody construct is a bispecific IgG1 antibody, where one of the two antigen-binding domains in the bispecific IgG1 antibody binds specifically to the linker domain.

In some embodiments of any of the methods described herein, the pair of affinity domains is a sushi domain from an alpha chain of human IL-15 receptor (IL15Rα) and a soluble IL-15. In some embodiments of any of the methods described herein, the soluble IL15 has a D8N or D8A amino acid substitution. In some embodiments of any of the methods described herein, the human IL15Rα is a mature full-length IL15Rα. In some embodiments of any of the methods described herein, the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

In some embodiments of any of the methods described herein, the first chimeric polypeptide and/or the second chimeric polypeptide further includes a signal sequence at its N-terminal end. In some embodiments of any of the methods described herein, the first chimeric polypeptide and/or the second chimeric polypeptide lacks a signal sequence at its N-terminal end.

In some embodiments of any of the methods described herein, the immune cell was previously obtained from a subject. Some embodiments of any of the methods described herein further include obtaining the immune cell from the subject prior to the contacting step. In some embodiments of any of the methods described herein, the immune cell has previously been genetically modified to express a chimeric antigen receptor or a recombinant T-cell receptor. Some embodiments of any of the methods described herein further include, after the contacting step, introducing into the immune cell a nucleic acid encoding a chimeric antigen-receptor or a recombinant T-cell receptor. Some embodiments of any of the methods described herein further include, before the contacting step, introducing into the immune cell a nucleic acid encoding a chimeric antigen-receptor or a recombinant T-cell receptor. Some embodiments of any of the methods described herein further include, after the contacting step, isolating the immune cell. In some embodiments of any of the methods described herein, after the contacting step, the immune cell has an increased level of expression or secretion of one or more proteins selected from the group of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step. Some embodiments of any of the methods described herein further include, after the contacting step, administering the immune cell to a subject in need thereof.

In some embodiments of any of the methods described herein, the subject has been identified or diagnosed as having an age-related disease or condition. In some embodiments of any of the methods described herein, the age-related disease or condition is selected from the consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been diagnosed or identified as having an infectious disease. In some embodiments of any of the methods described herein, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Also provided herein are activated immune cells produced using any of the methods described herein. Also pharmaceutical compositions that include any of the activated immune cells described herein produced by any of the methods described herein. Also provided herein are kits that include any of the pharmaceutical compositions described herein that include any of the activated immune cells described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced using any of the methods described herein or any of the pharmaceutical compositions described herein.

In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been identified or diagnosed as having an aging-related disease or condition. In some embodiments of any of the methods described herein, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Also provided herein are methods of treating a subject in need thereof that include administering to the subject a therapeutically effective amount of any of the activated immune cells described herein produced by any of the methods described herein or any of the pharmaceutical compositions described herein. In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been identified or diagnosed as having an aging-related disease or condition. In some embodiments of any of the methods described herein, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments of any of the methods described herein, the subject has been diagnosed or identified as having an infectious disease. In some embodiments of any of the methods described herein, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

In some embodiments of any of the methods or kits described herein, the soluble human tissue factor domain does not stimulate blood coagulation. In some embodiments of any of the methods or kits described herein, the soluble tissue factor domain comprises or consists of a sequence from a wildtype soluble human tissue factor (or any sequence therefrom).

Also provided herein are methods of inducing differentiation of an immune cell into a memory or memory-like immune cell that include contacting an immune cell in a liquid culture medium including: (1) an effective amount of a multi-chain chimeric polypeptide comprising: (a) a first chimeric polypeptide including: (i) a first target-binding domain; (ii) a linker domain; and (iii) a first domain of a pair of affinity domains;

(b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains; and (2) an effective amount of an IgG1 antibody construct including at least one antigen-binding domain that binds specifically to the linker domain.

Also provided herein are methods of inducing differentiation of an immune cell into a memory or memory-like immune cell that include contacting an immune cell in a liquid culture medium including an effective amount of (i) a single-chain chimeric polypeptide including a first target-binding domain, a linker domain, and a second target-binding domain, and (ii) an IgG1 antibody construct that includes at least one antigen-binding domain that binds specifically to the linker domain.

In some embodiments of any of the methods described herein, the immune cell was previously obtained from a subject. In some embodiments of any of the methods described herein, the immune cell is selected from the group c of: an immature thymocyte, a periperhal blood Treg cell, a Th17 cell, a Th22 cell, a Th9 cell, a Th2 cell, a Th1 cell, a Th3 cell, λδ T cell, an αβ T cell, a tumor-infiltrating T cell, a $CD8^{+}$ T cell, a $CD4^{+}$ T cell, a natural killer T cell, a mast cell, a macrophage, a neutrophil, a dendritic cell, a basophil, an eosinophil, and a natural killer cell. In some embodiments of any of the methods described herein, the immune cell has previously been genetically modified to express a chimeric antigen receptor or a recombinant T-cell receptor.

Some embodiments of any of the methods described herein further include, after the contacting step, introducing into the immune cell a nucleic acid encoding a chimeric antigen-recpetor or a recombinant T-cell receptor. Some embodiments of any of the methods described herein further include administering to the immune cell to a subject in need thereof.

As used herein, the term "chimeric" refers to a polypeptide that includes amino acid sequences (e.g., domains) originally derived from two different sources (e.g., two different naturally-occurring proteins, e.g., from the same or different species). For example, a chimeric polypeptide can include domains from at least two different naturally occurring human proteins. In some examples, a chimeric polypeptide can include a domain that is a synthetic sequence (e.g., a scFv) and a domain that is derived from a naturally-occurring protein (e.g., a naturally-occurring human protein). In some embodiments, a chimeric polypeptide can include at least two different domains that are synthetic sequences (e.g., two different scFvs).

An "antigen-binding domain" is one or more protein domain(s) (e.g., formed from amino acids from a single polypeptide or formed from amino acids from two or more polypeptides (e.g., the same or different polypeptides) that is capable of specifically binding to one or more different antigen(s). In some examples, an antigen-binding domain can bind to an antigen or epitope with specificity and affinity similar to that of naturally-occurring antibodies. In some embodiments, the antigen-binding domain can be an antibody or a fragment thereof. In some embodiments, an antigen-binding domain can include an alternative scaffold. Non-limiting examples of antigen-binding domains are described herein. Additional examples of antigen-binding domains are known in the art.

A "soluble tissue factor domain" refers to a polypeptide having at least 70% identity (e.g., at least 75% identity, at least 80% identity, at least 85% identity, at least 90% identity, at least 95% identity, at least 99% identity, or 100% identical) to a segment of a wildtype mammalian tissue factor protein (e.g., a wildtype human tissue factor protein) that lacks the transmembrane domain and the intracellular domain. Non-limiting examples of soluble tissue factor domains are described herein.

The term "soluble interleukin protein" is used herein to refer to a mature and secreted interleukin protein or a biologically active fragment thereof. In some examples, a soluble interleukin protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble interleukin proteins are described herein.

The term "soluble cytokine protein" is used herein to refer to a mature and secreted cytokine protein or a biologically active fragment thereof. In some examples, a soluble cytokine protein can include a sequence that is at least 70% identical, at least 75% identical, at least 80% identical, at least 85% identical, at least 90% identical, at least 95% identical, at least 99% identical, or 100% identical to a wildtype mature and secreted mammalian interleukin protein (e.g., a wildtype human interleukin protein) and retains its biological activity. Non-limiting examples of soluble cytokine proteins are described herein.

The term "soluble interleukin receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble interleukin receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype interleukin receptor and retains its ability to specifically bind to one or more of its natural ligands, but lacks its transmembrane domain (and optionally, further lacks its intracellular domain). Non-limiting examples of soluble interleukin receptors are described herein.

The term "soluble cytokine receptor" is used herein in the broadest sense to refer to a polypeptide that lacks a transmembrane domain (and optionally an intracellular domain) that is capable of binding one or more of its natural ligands (e.g., under physiological conditions, e.g., in phosphate buffered saline at room temperature). For example, a soluble cytokine receptor can include a sequence that is at least 70% identical (e.g., at least 75% identical, at least 80% identical, at least 85% identical, at least 90% identical, at least 95% identical, at least 99% identical, or 100% identical) to an extracellular domain of wildtype cytokine receptor and retains its ability to specifically bind to one or more of its natural ligands, but lacks its transmembrane domain (and optionally, further lacks its intracellular domain). Non-limiting examples of soluble cytokine receptors are described herein.

The term "ligand of a co-stimulatory molecule" is used herein in the broadest sense to refer to a polypeptide that is capable of binding and activating a co-stimulatory receptor molecule on an immune cell (e.g., under physiological conditions, e.g., in phosphate buffered saline at room temperature). For example, a ligand of a co-stimulatory molecule can include a sequence that is at least 70% identical (e.g., at least 75% identical, at least 80% identical, at least 85% identical, at least 90% identical, at least 95% identical, at least 99% identical, or 100% identical) to a ligand of a co-stimulatory molecule that retains its ability to specifically bind to one or more of its natural receptors. Non-limiting examples of ligands of co-stimulatory molecules are described herein.

The term "antibody" is used herein in its broadest sense and includes certain types of immunoglobulin molecules that include one or more antigen-binding domains that specifically bind to an antigen or epitope. An antibody specifically includes, e.g., intact antibodies (e.g., intact immunoglobulins), antibody fragments, and multi-specific antibodies. One example of an antigen-binding domain is an antigen-binding domain formed by a VH-VL dimer. Additional examples of an antibody are described herein. Additional examples of an antibody are known in the art.

"Affinity" refers to the strength of the sum total of non-covalent interactions between an antigen-binding site and its binding partner (e.g., an antigen or epitope). Unless indicated otherwise, as used herein, "affinity" refers to intrinsic binding affinity, which reflects a 1:1 interaction between members of an antigen-binding domain and an antigen or epitope. The affinity of a molecule X for its partner Y can be represented by the dissociation equilibrium constant ($K_D$). The kinetic components that contribute to the dissociation equilibrium constant are described in more detail below. Affinity can be measured by common methods known in the art, including those described herein. Affinity can be determined, for example, using surface plasmon resonance (SPR) technology (e.g., BIACORE®) or biolayer interferometry (e.g., FORTEBIO®). Additional methods for determining the affinity for an antigen-binding domain and its corresponding antigen or epitope are known in the art.

A "single-chain polypeptide" as used herein to refers to a single protein chain.

The term "pair of affinity domains" is two different protein domain(s) that bind specifically to each other with a $K_D$ of less than of less than $1\times10^{-7}$M (e.g., less than $1\times10^{-8}$ M, less than $1\times10^{-9}$ M, less than $1\times10^{-10}$ M, or less than $1\times10^{-11}$ M). In some examples, a pair of affinity domains can be a pair of naturally-occurring proteins. In some embodiments, a pair of affinity domains can be a pair of synthetic proteins. Non-limiting examples of pairs of affinity domains are described herein.

The term "epitope" means a portion of an antigen that specifically binds to an antigen-binding domain. Epitopes can, e.g., consist of surface-accessible amino acid residues and/or sugar side chains and may have specific three-dimensional structural characteristics, as well as specific charge characteristics. Conformational and non-conformational epitopes are distinguished in that the binding to the former but not the latter may be lost in the presence of denaturing solvents. An epitope may comprise amino acid residues that are directly involved in the binding, and other amino acid residues, which are not directly involved in the binding. Methods for identifying an epitope to which an antigen-binding domain binds are known in the art.

An "immune effector cell" refers to a cell of the immune system of a mammal that is capable, directly or indirectly, of recognizing and/or causing cytostasis or cell death of a pathogenic cell (e.g., a cancer cell) in the mammal. Non-limiting examples of immune effector cells include macrophages, natural killer cells, T-lymphocytes (e.g., cytotoxic T-lymphocytes and T-helper cells), neutrophils, monocytes, and eosinophils. Additional examples of immune effector cells are known in the art.

The term "treatment" means to ameliorate at least one symptom of a disorder. In some examples, the disorder being treated is cancer and to ameliorate at least one symptom of cancer includes reducing aberrant proliferation, gene expression, signaling, translation, and/or secretion of factors. Generally, the methods of treatment include administering a therapeutically effective amount of composition that reduces at least one symptom of a disorder to a subject who is in need of, or who has been determined to be in need of such treatment.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF DRAWINGS

FIG. 94A shows binding affinity of TGFRt15-16s21 with CHO cells expressing human CD16b. FIG. 94B shows binding affinity of 7t15-21s with CHO cells expressing human CD16b.

FIG. 113A shows spleen weight in mice treated with TGFRt15-TGFRs as compared to PBS control. FIG. 113B shows the percentage of CD4+ T cells, CD8+ T cells, and NK cells in mice treated with TGFRt15-TGFRs as compared to PBS control.

FIG. 114A shows spleen weight of mice treated with TGFRt15-TGFRs at 16, 24, 48, 72, and 92 hours after treatment. FIG. 114B shows the percentages of immune cells in mice treated with TGFRt15-TGFRs at 16, 24, 48, 72, and 92 hours after treatment.

FIGS. 115A and 115B show Ki67 and Granzyme B expression in mice treated with TGFRt15-TGFRs over time.

FIG. 119A shows a schematic of the treatment regimen. FIG. 119B shows tumor volume over time following saline treatment, chemotherapy (DTX), or chemotherapy (DTX), TGFRt15-TGFRs and TA99 (anti-TRP1 antibody) combination treatment. FIG. 119C shows peripheral blood analysis using fluorescently labeled antibodies against NK1.1. FIG. 119D shows peripheral blood analysis using fluorescently labeled antibodies against CD8. FIG. 119E shows peripheral blood analysis using fluorescently labeled antibodies against CD4.

FIG. 122 is a line graph showing the chromatographic profile of 7t15-21s137L (long version) protein containing cell culture supernatant following binding and elution on anti-TF antibody resin.

FIG. 123 shows the analytical SEC profile of 7t15-21s137L (long version).

FIG. 124 shows binding of 7t15-21s137L (short version) to CD137L (4.1BBL)

Figure 125A:
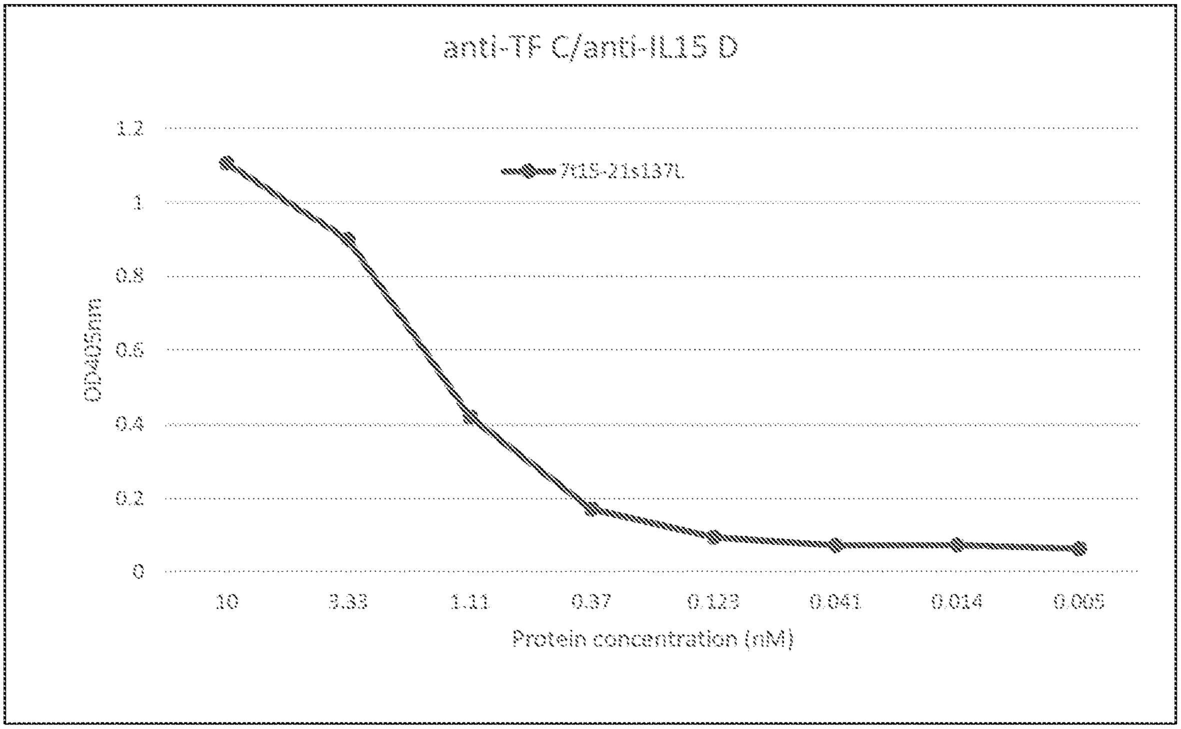
Figure 125B:
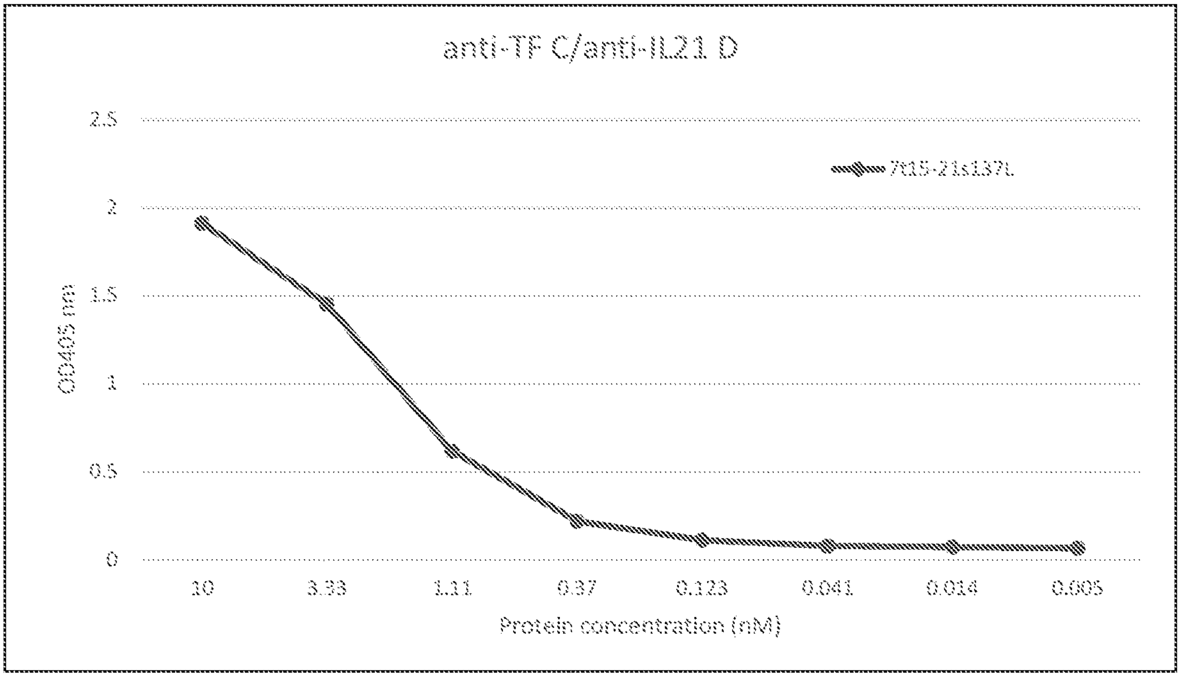
Figure 125C:
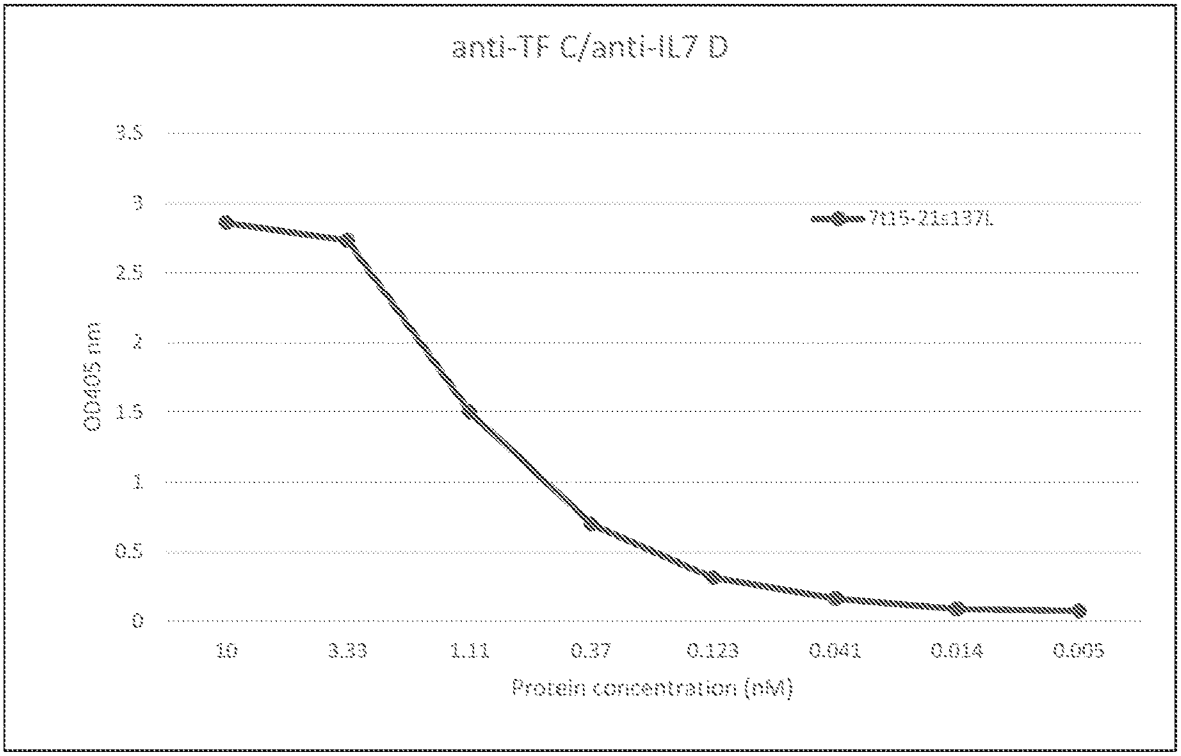

FIGS. 125A-125C show detection of IL15, IL21, and IL7 in 7t15-21s137L (short version) with ELISA. FIG. 125A shows detection of IL15 in 7t15-21s137L (short version) with ELISA. FIG. 125B shows detection of IL21 in 7t15-21s137L (short version) with ELISA.

FIG. 125C shows detection of IL7 in 7t15-21s137L (short version) with ELISA.

Figure 126:
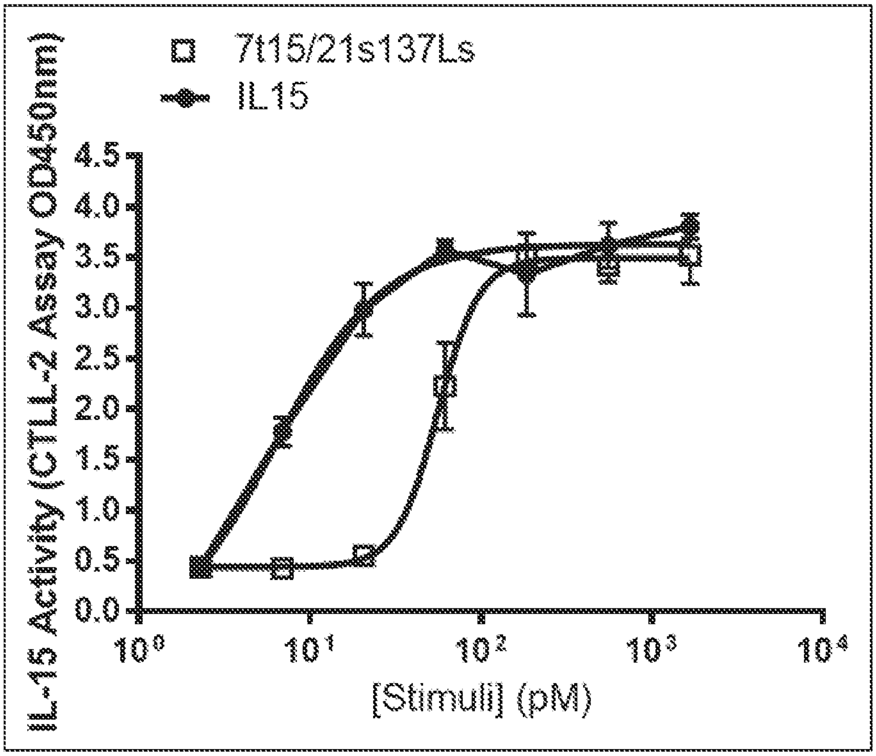

FIG. 126 shows results from a CTLL-2 cell proliferation assay.

Figure 127:
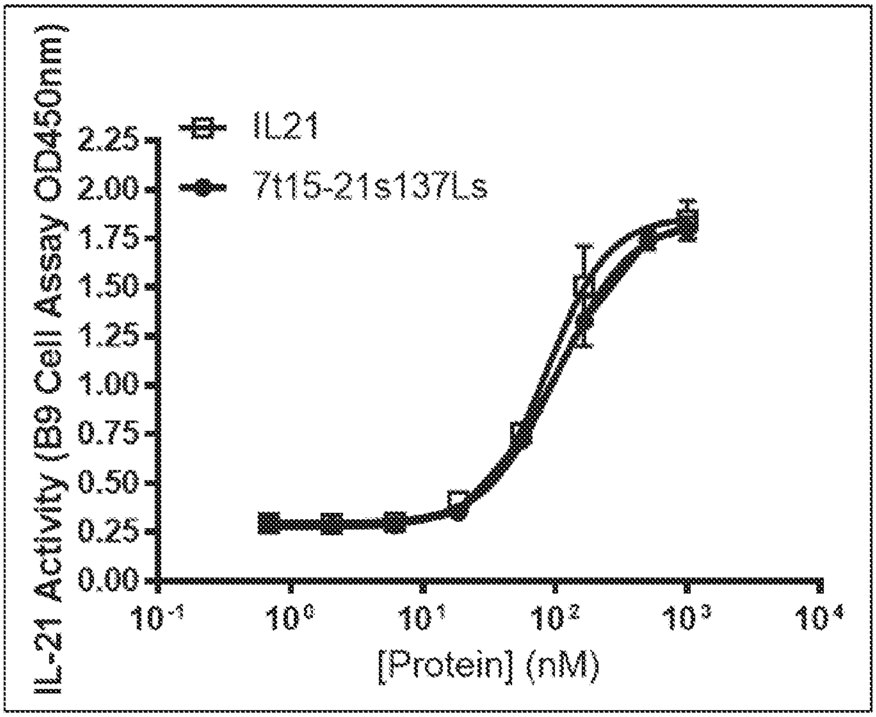

FIG. 127 shows the activity of 7t15-1s137L (short version) in promoting IL21R containing B9 cell proliferation.

Figure 128:
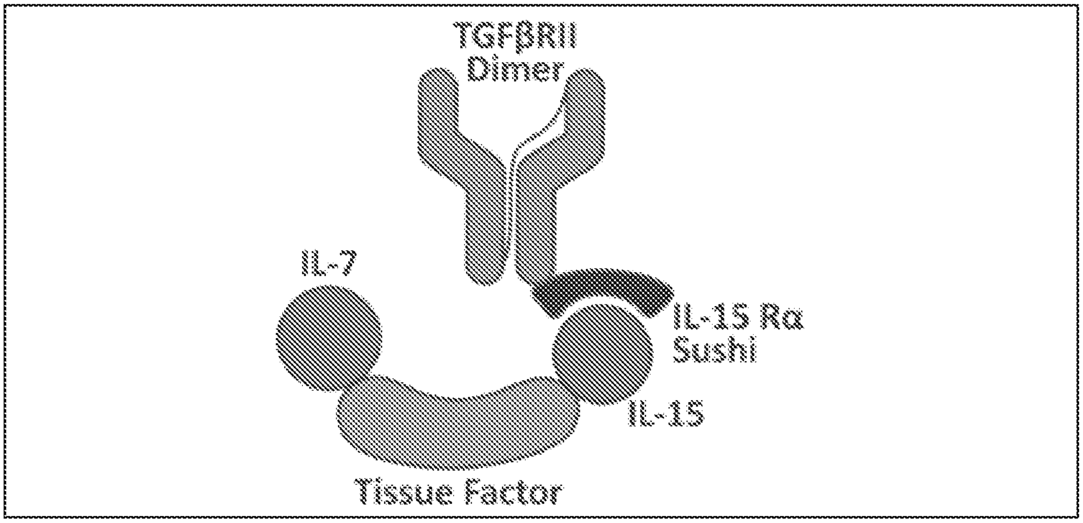

FIG. 128 shows a schematic of the 7t15-TGFRs construct.

Figure 129:
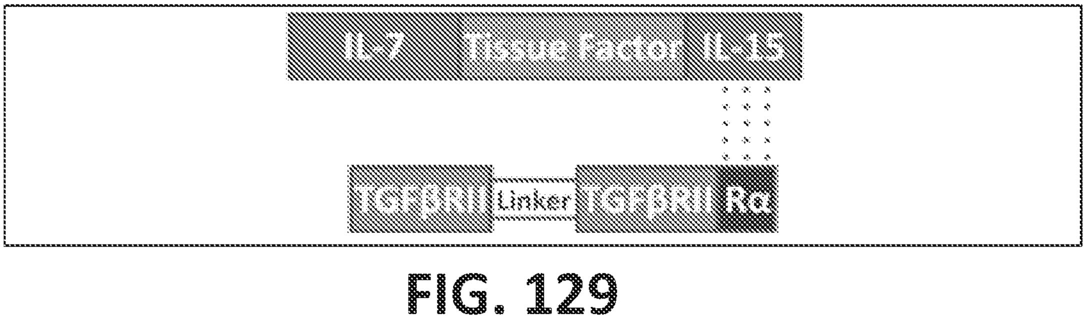

FIG. 129 shows an additional schematic of the 7t15-TGFRs construct.

Figure 130:
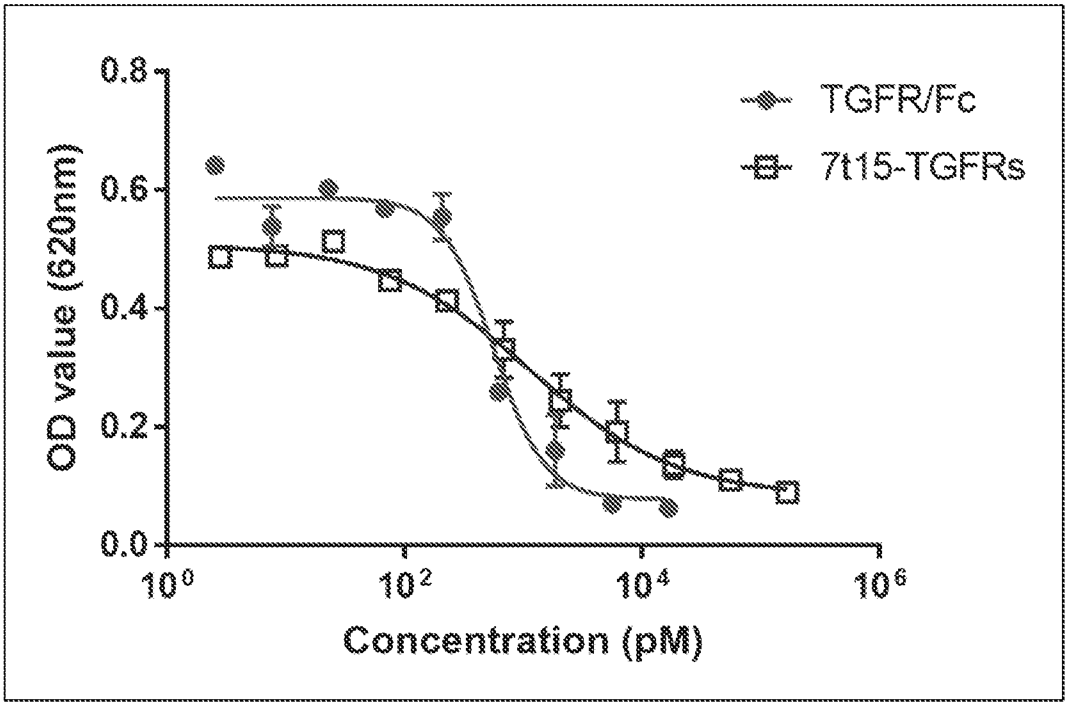

FIG. 130 shows results of TGFβ1 inhibition by 7t15-TGFRs and TGFR-Fc.

Figure 131A:
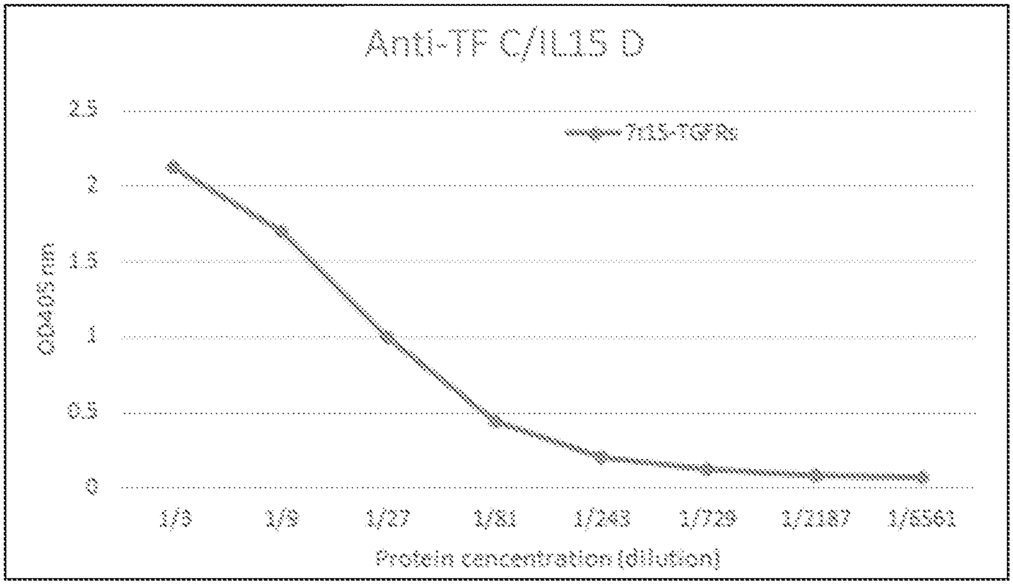
Figure 131B:
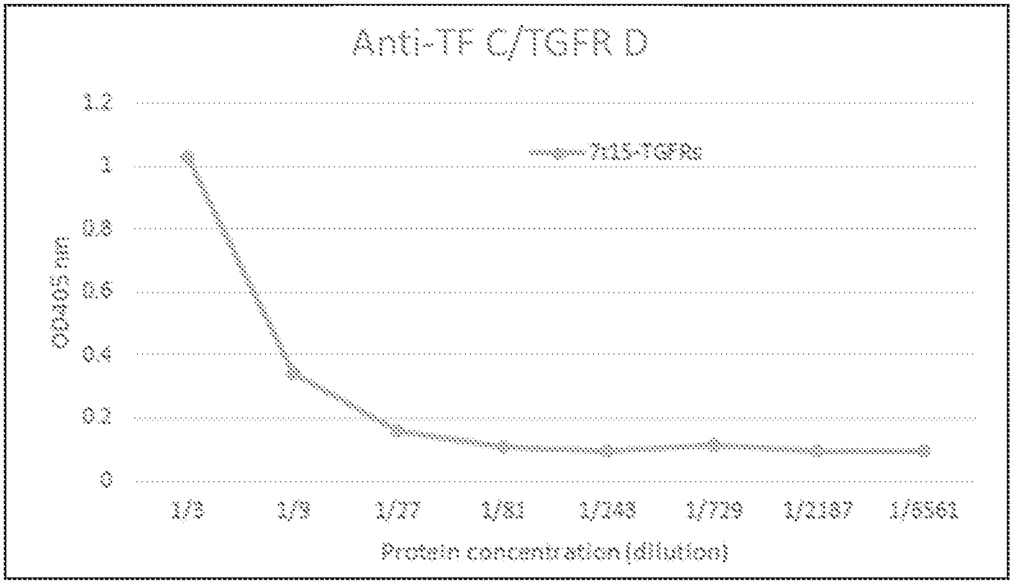
Figure 131C:
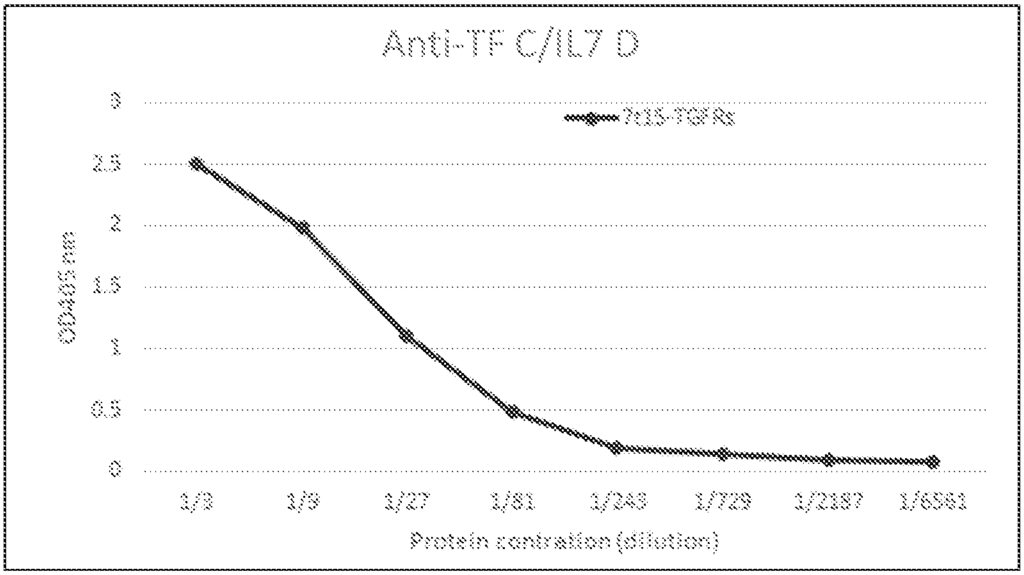

FIGS. 131A-131C show detection of IL-15, TGFβRII, and IL-7 in 7t15-TGFRs with ELISA.

Figure 132:
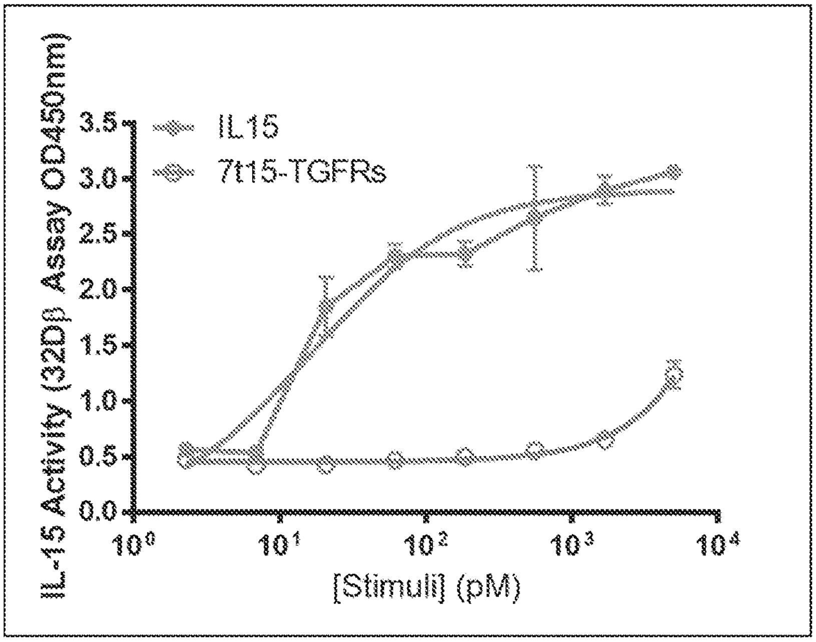

FIG. 132 shows results of 32Dβ cell proliferation assay with 7t15-TGFRs or recombinant IL-15.

Figure 133:
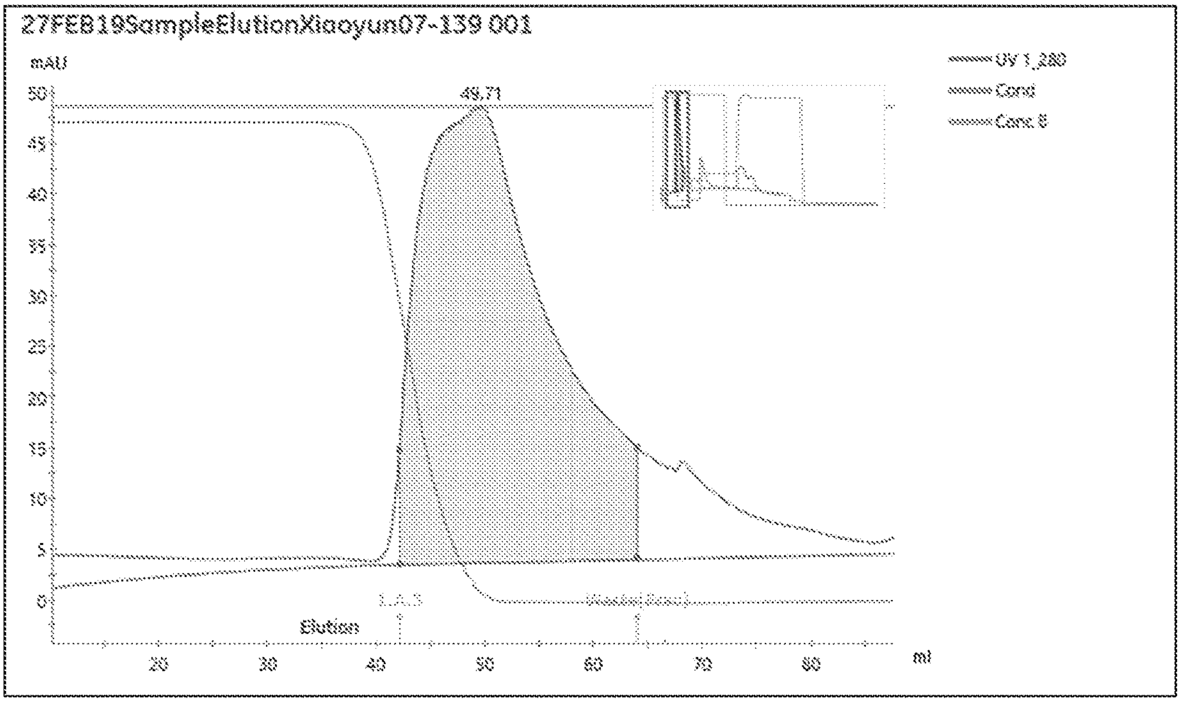

FIG. 133 is a line graph showing the chromatographic profile of 7t15-TGFRs protein containing cell culture supernatant following binding and elution on anti-TF antibody resin.

Figure 134:
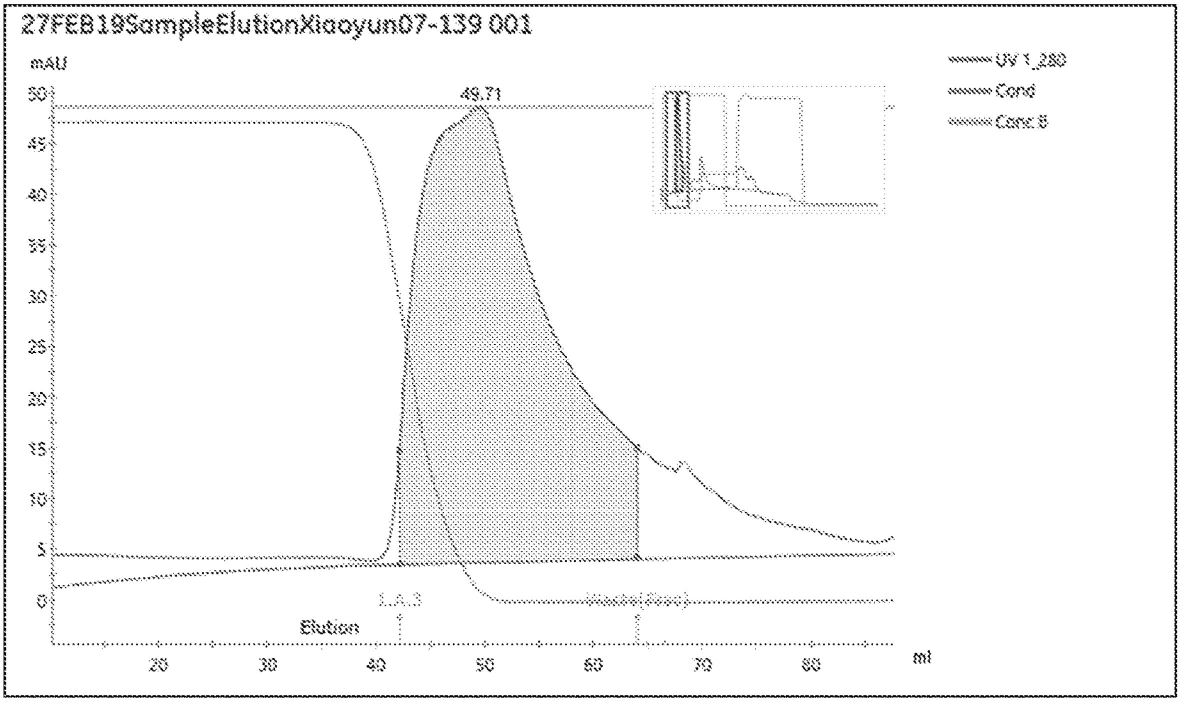

FIG. 134 shows 7t15-TGFRs before and after deglycosylation as analyzed using reduced SDS-PAGE.

Figure 135:
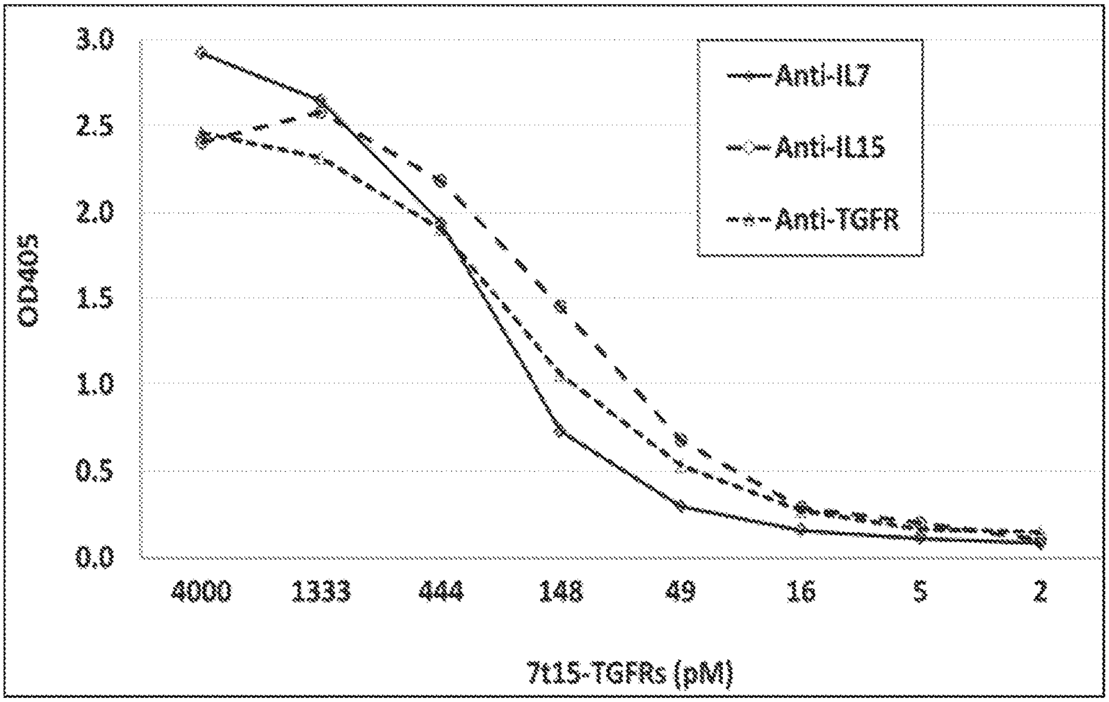

FIG. 135 shows ELISA detection of IL-7, IL-15 and TGFβRII in the 7t15-TGFRs protein.

Figure 136A:
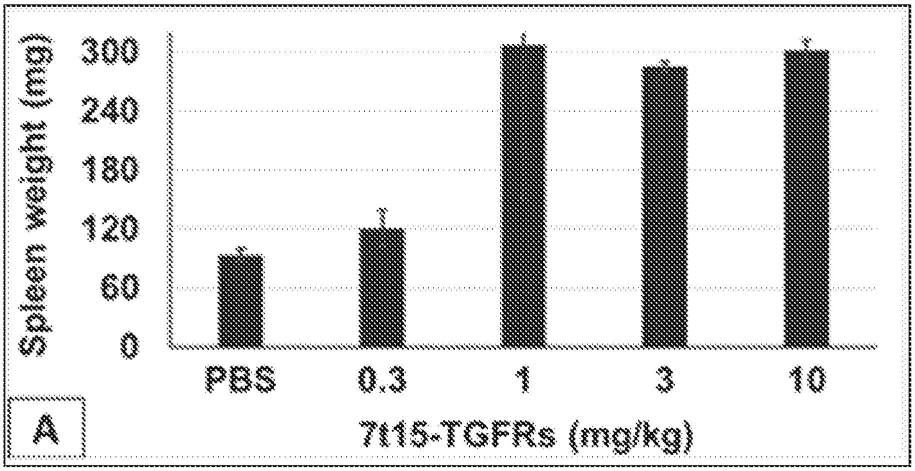
Figure 136B:
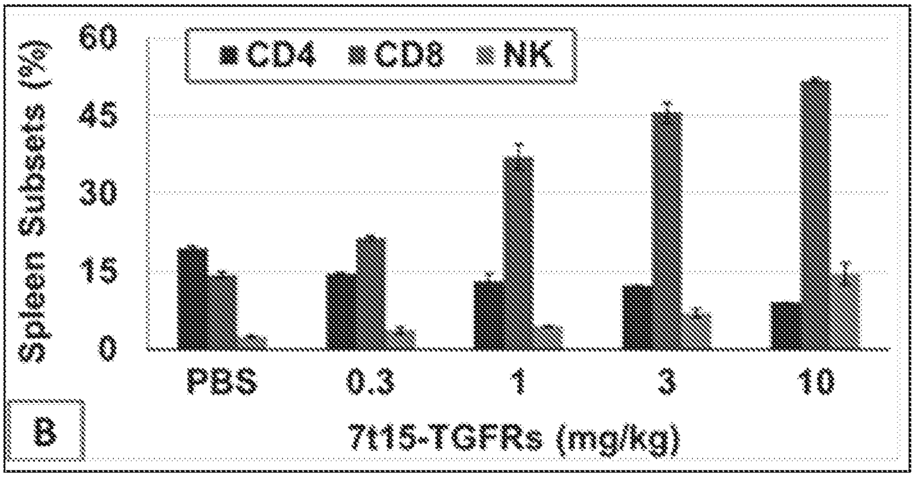

FIGS. 136A and 136B show spleen weight and the percentages of immune cell types in 7t15-TGFRs-treated and control-treated mice. FIG. 136A shows spleen weight in mice treated with 7t15-TGFRs at various dosages, as compared to PBS control. FIG. 136B shows the percentage of $CD4^+$ T cells, $CD8^+$ T cells, and NK cells in mice treated with 7t15-TGFRs at various dosages, as compared to PBS control.

Figure 137A:
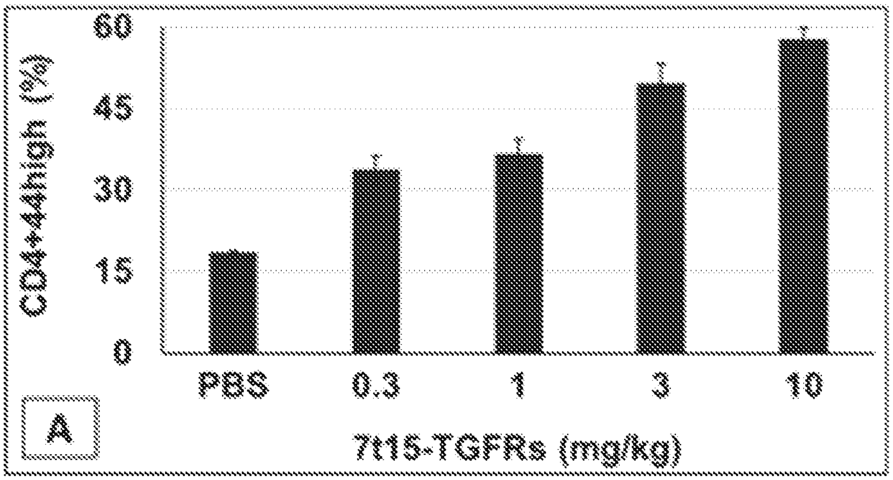
Figure 137B:
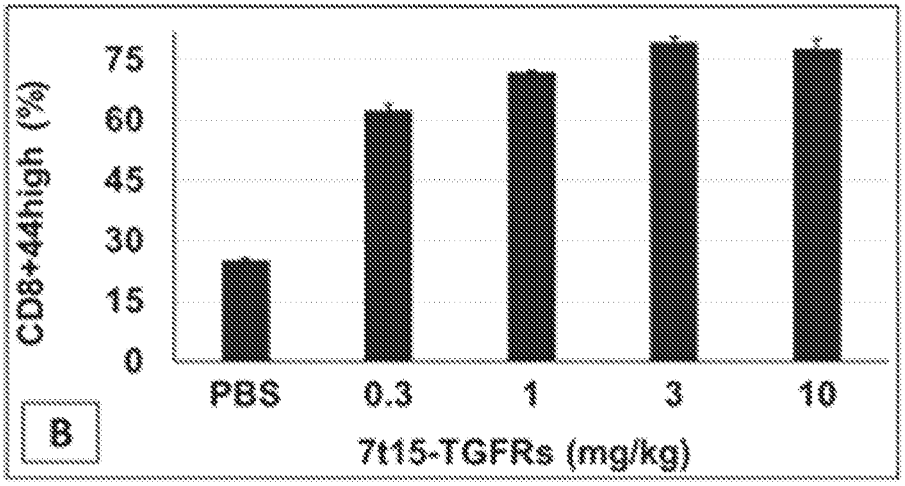

FIGS. 137A and 137B show upregulation of CD44 expression of $CD4^+$ and $CD8^+$ T cells by 7t15-TGFRs in C57BL/6 mice.

Figure 138A:
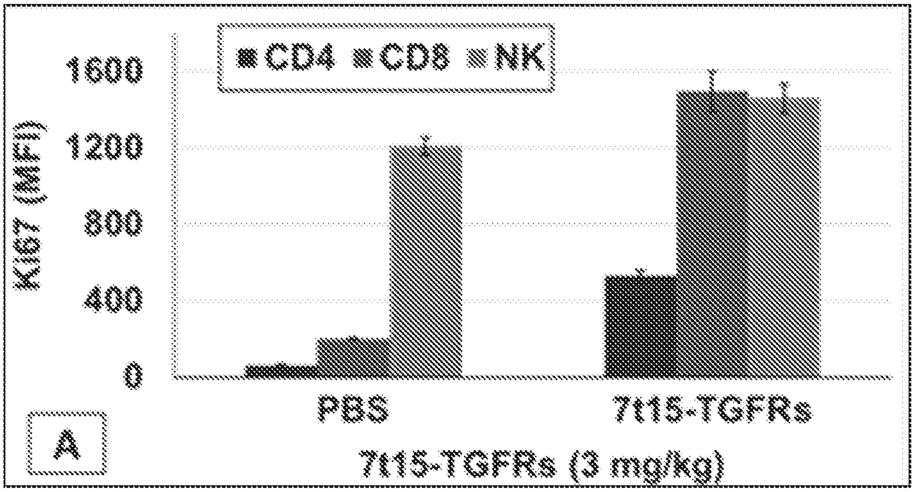
Figure 138B:
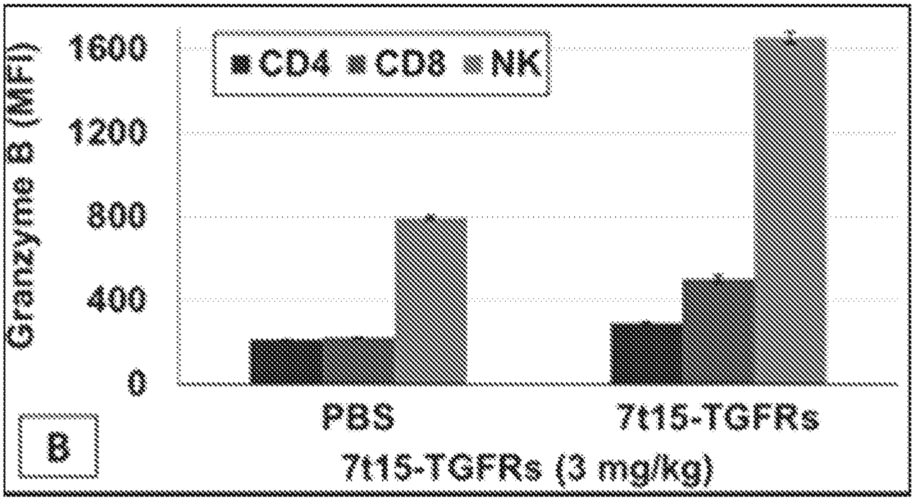

FIGS. 138A and 138B show upregulation of Ki67 expression and Granzyme B expression of $CD8^+$ T cells and NK Cells by 7t15-TGFRs in C57BL/6 mice.

Figure 139:
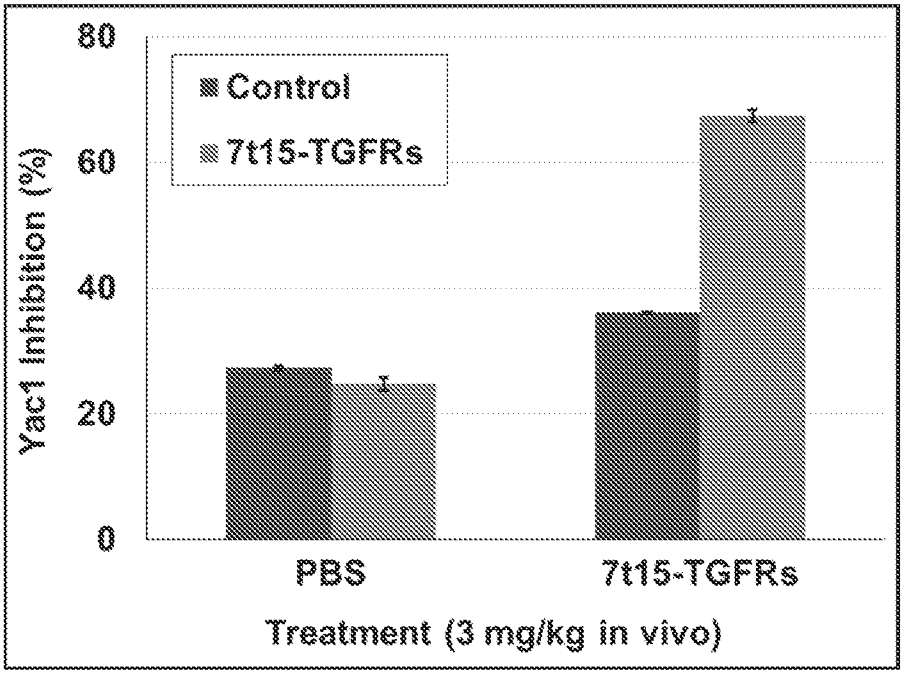

FIG. 139 shows enhancement of cytotoxicity of splenocytes by 7t15-TGFRs in C57BL/6 mice.

Figure 140:
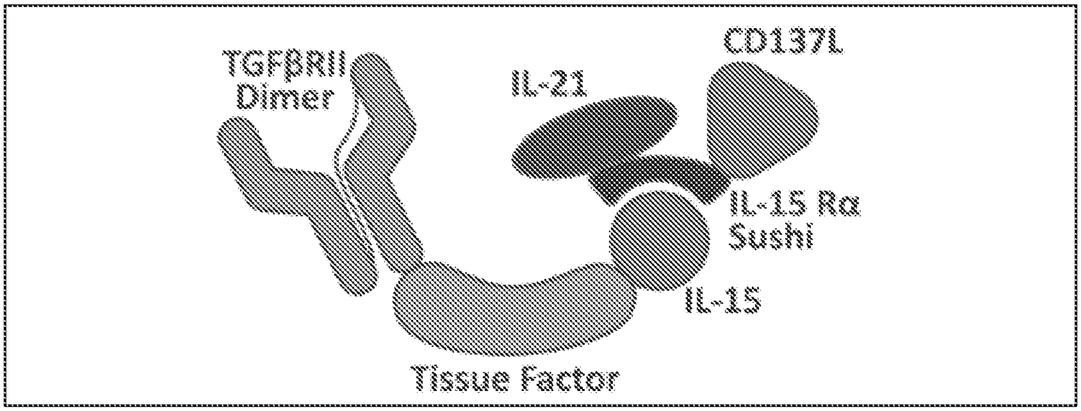

FIG. 140 shows a schematic of the TGFRt15-21s137L construct.

Figure 141:
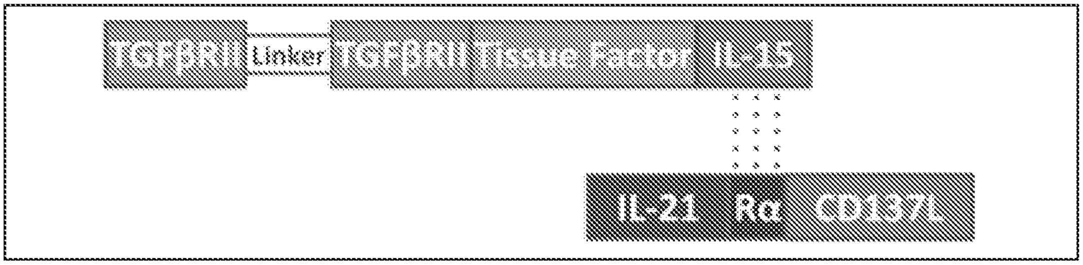

FIG. 141 shows an additional schematic of the TGFRt15-21s137L construct.

Figure 142:
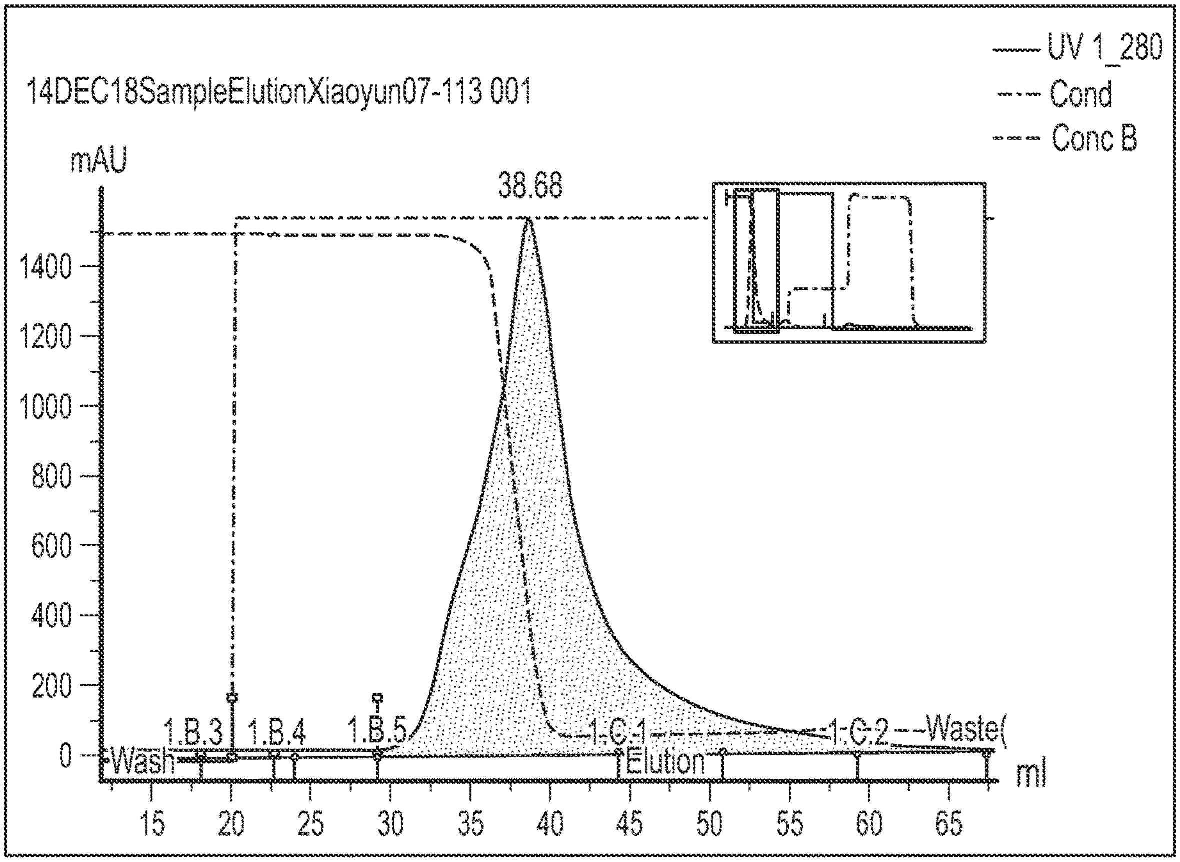

FIG. 142 is a line graph showing the chromatographic profile of TGFRt15-21s137L protein containing cell culture supernatant following binding and elution on anti-TF antibody resin.

Figure 143:
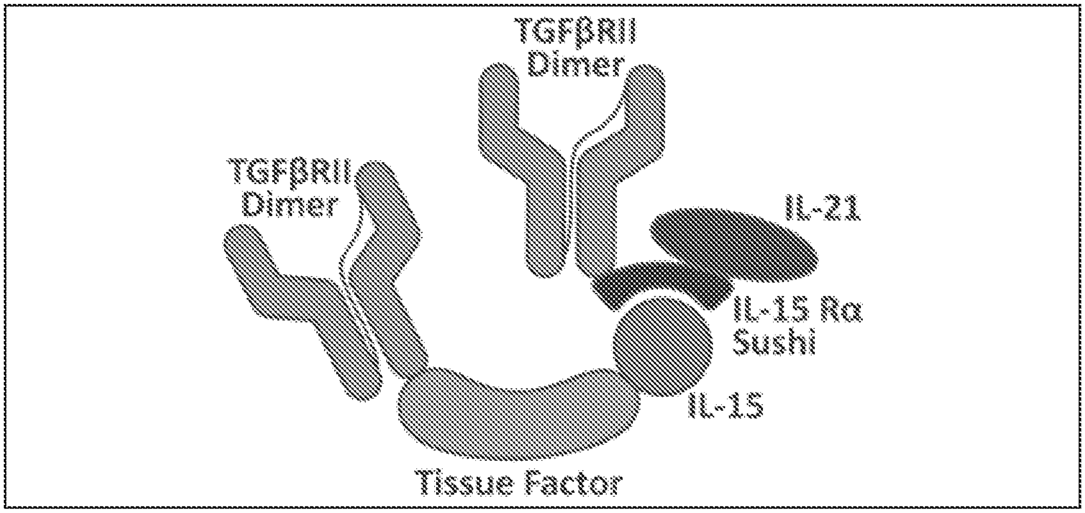

FIG. 143 shows a schematic of the TGFRt15-TGFRs21 construct.

Figure 144:
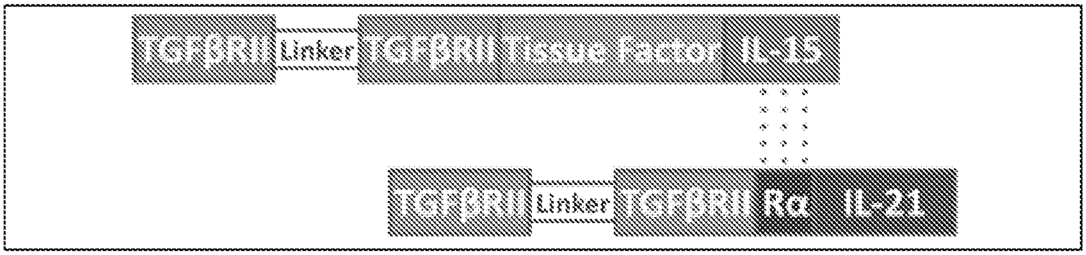

FIG. 144 shows an additional schematic of the TGFRt15-TGFRs21 construct.

Figure 145:
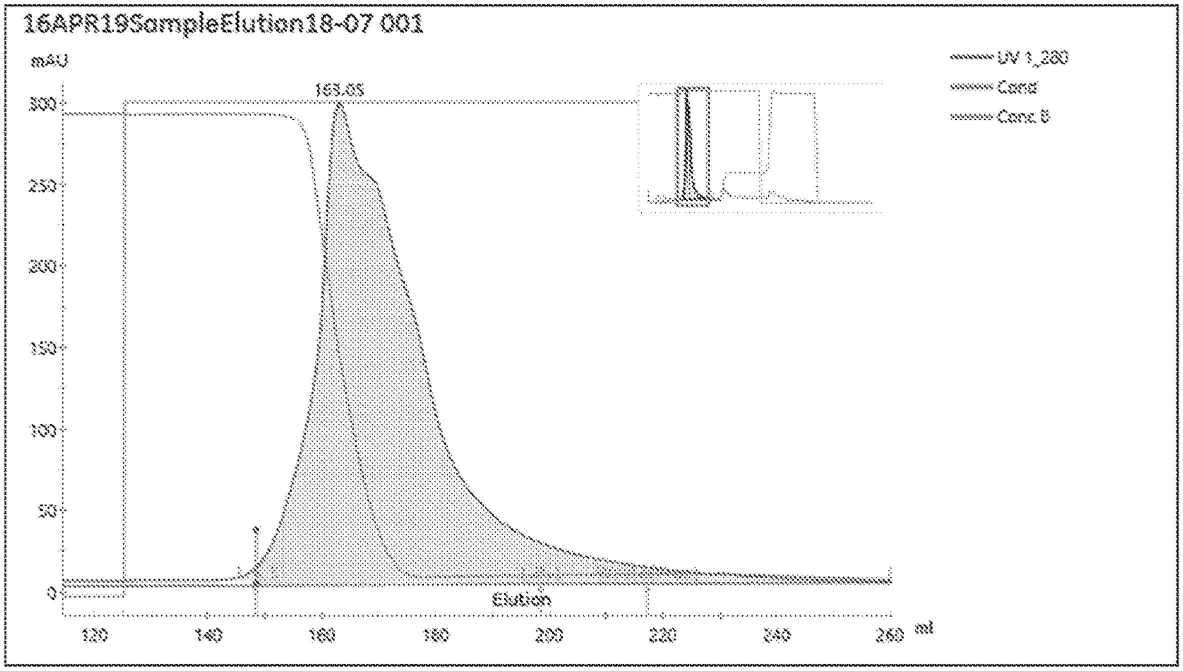

FIG. 145 is a line graph showing the chromatographic profile of TGFRt15-TGFRs21 protein containing cell culture supernatant following binding and elution on anti-TF antibody resin.

Figure 146:
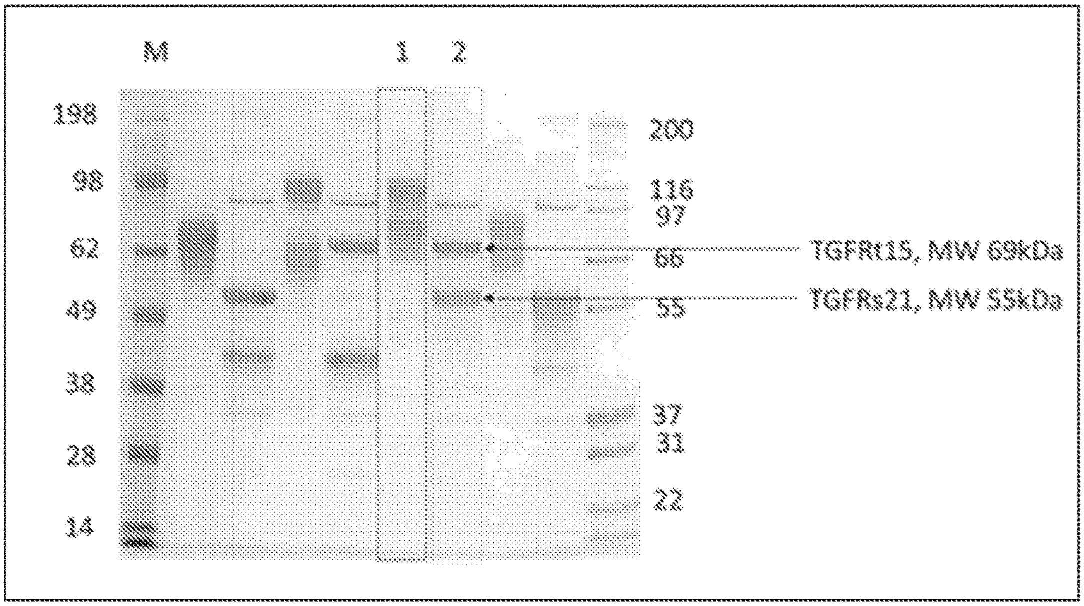

FIG. 146 shows TGFRt15-TGFRs21 before and after deglycosylation as analyzed by reduced SDS-PAGE.

Figure 147A:
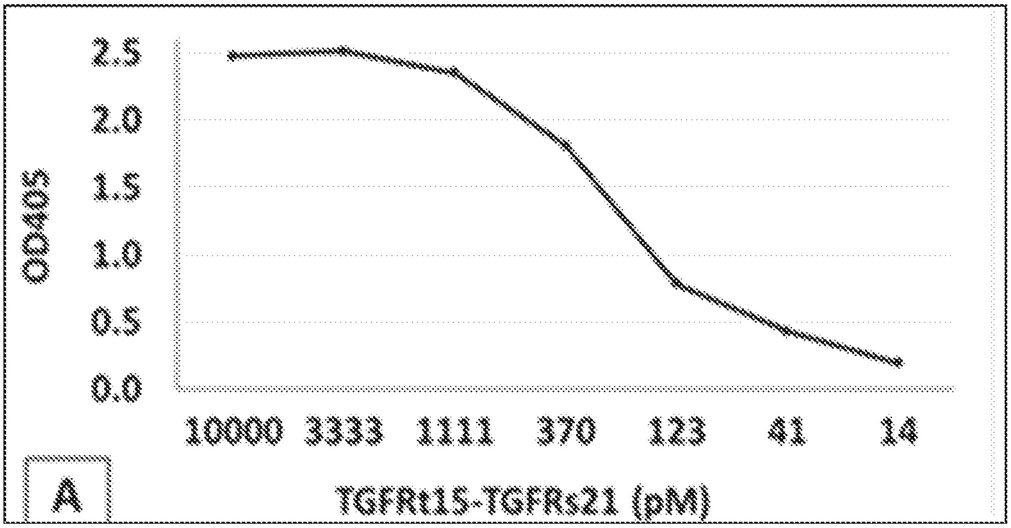
Figure 147B:
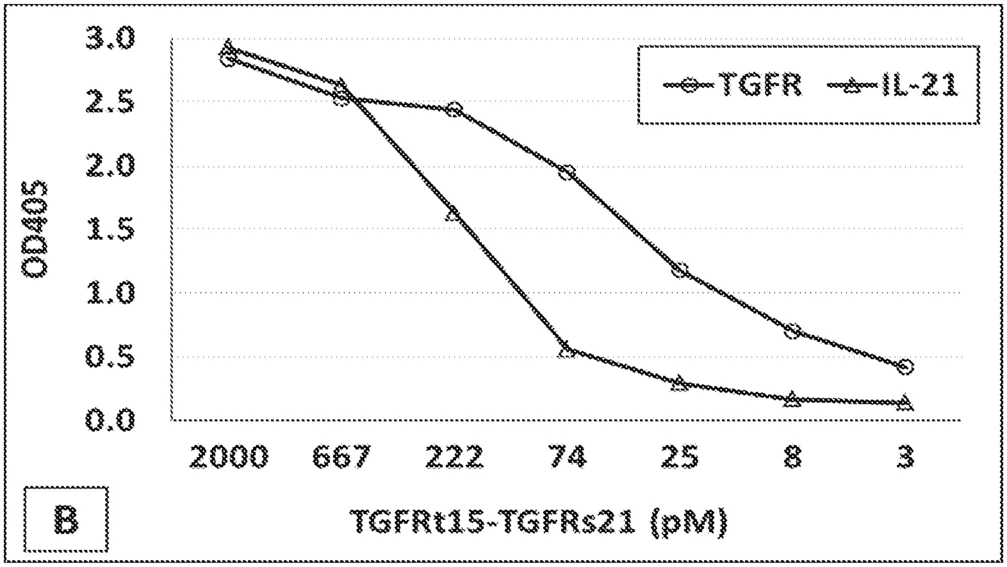

FIGS. 147A and 147B show detection of components of TGFRt15-TGFRs21 using ELISA.

Figure 148A:
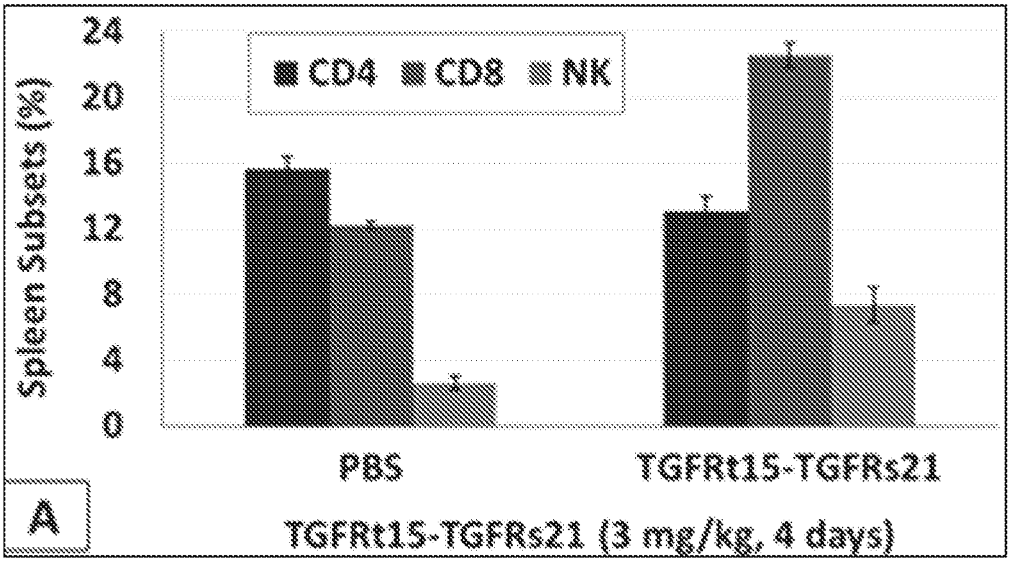
Figure 148B:
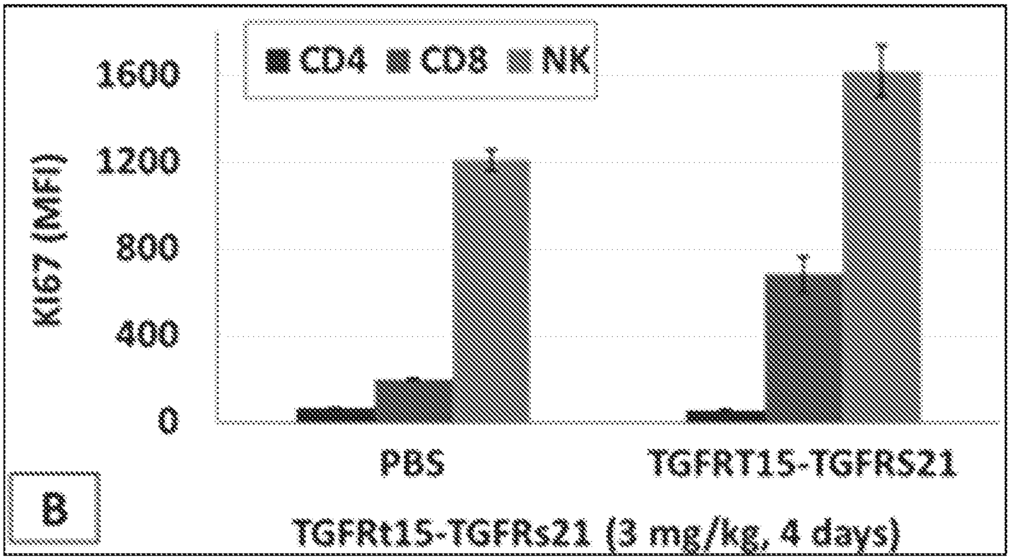

FIGS. 148A and 148B show the percentages and proliferation of CD4+ T cells, CD8+ T cells, and natural killer (NK) cells present in the spleen of control-treated and TGFRt15-TGFRs21-treated mice.

Figure 149:
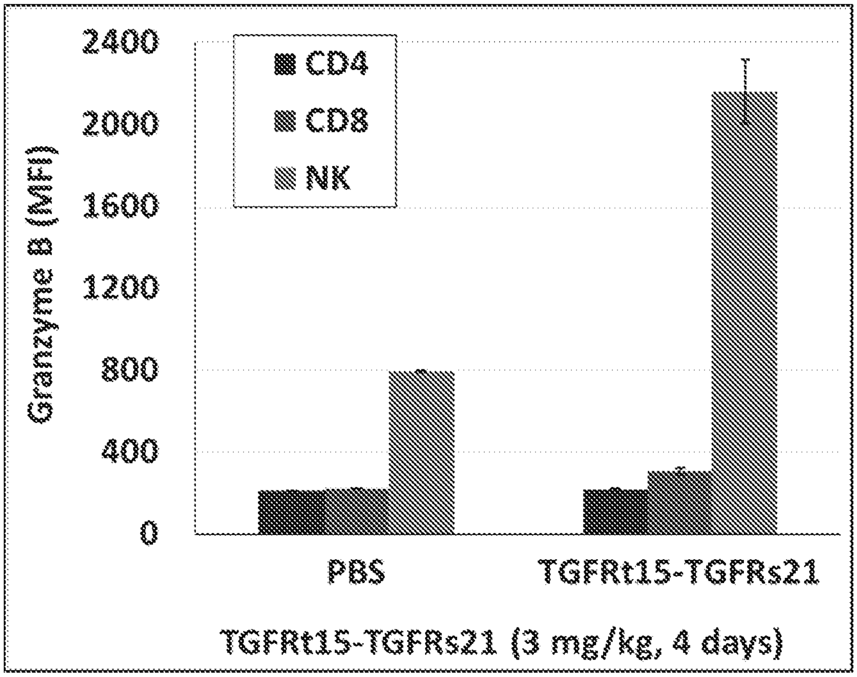

FIG. 149 shows upregulation of Granzyme B expression of splenocytes in mice treated with TGFRt15-TGFRs21.

Figure 150:
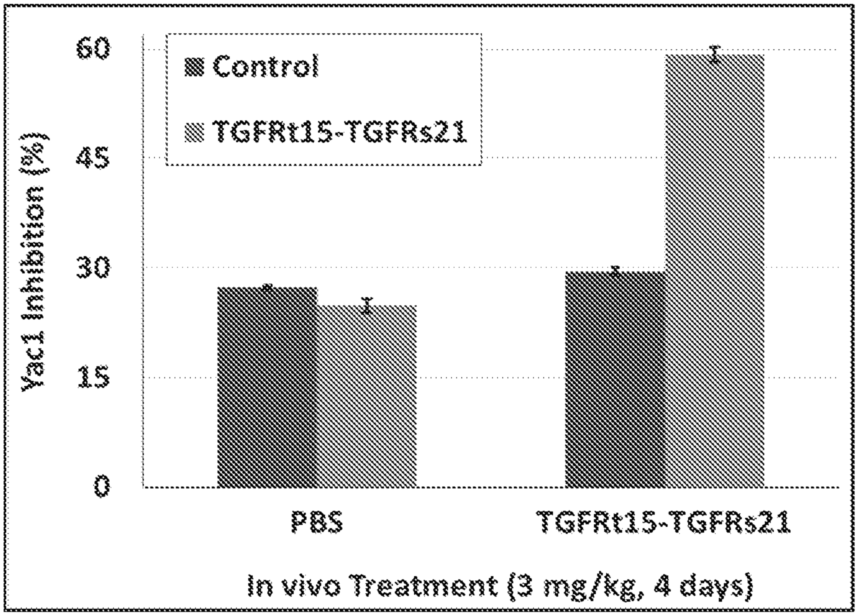

FIG. 150 shows enhancement of cytotoxicity of splenocytes by TGFRt15-TGFRs21 in C57BL/6 Mice.

Figure 151:
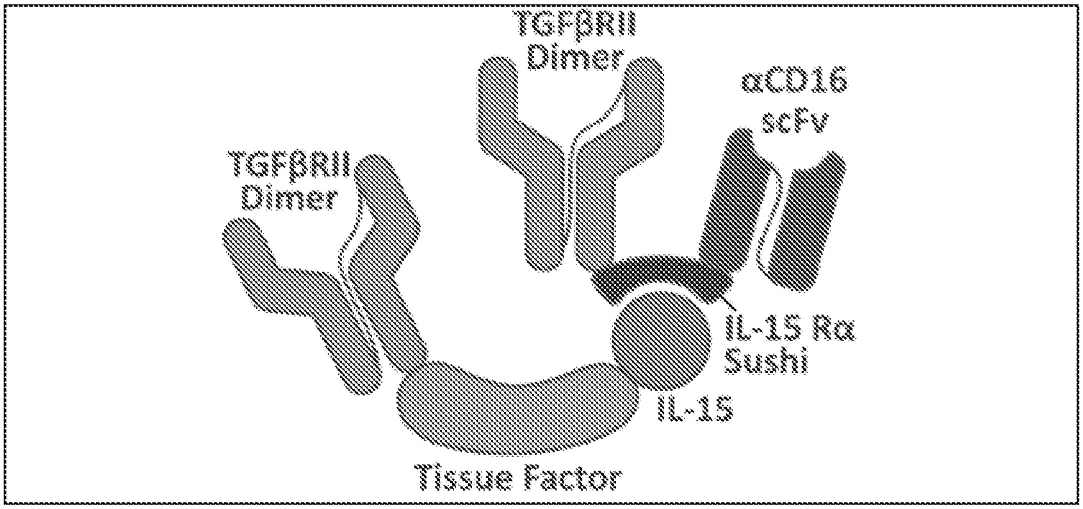

FIG. 151 shows a schematic of the TGFRt15-TGFRs16 construct.

Figure 152:
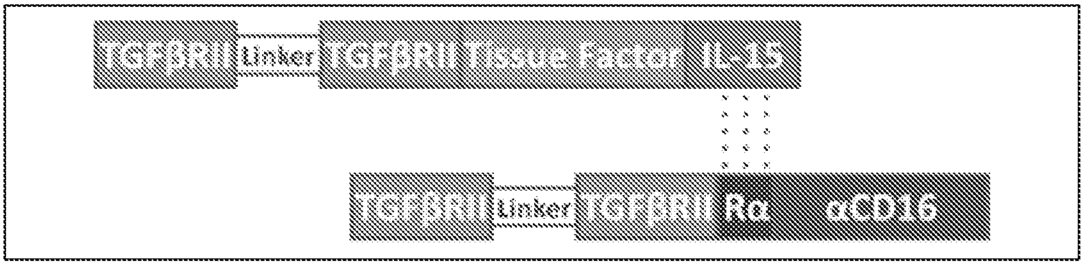

FIG. 152 shows an additional schematic of the TGFRt15-TGFRs16 construct.

Figure 153:
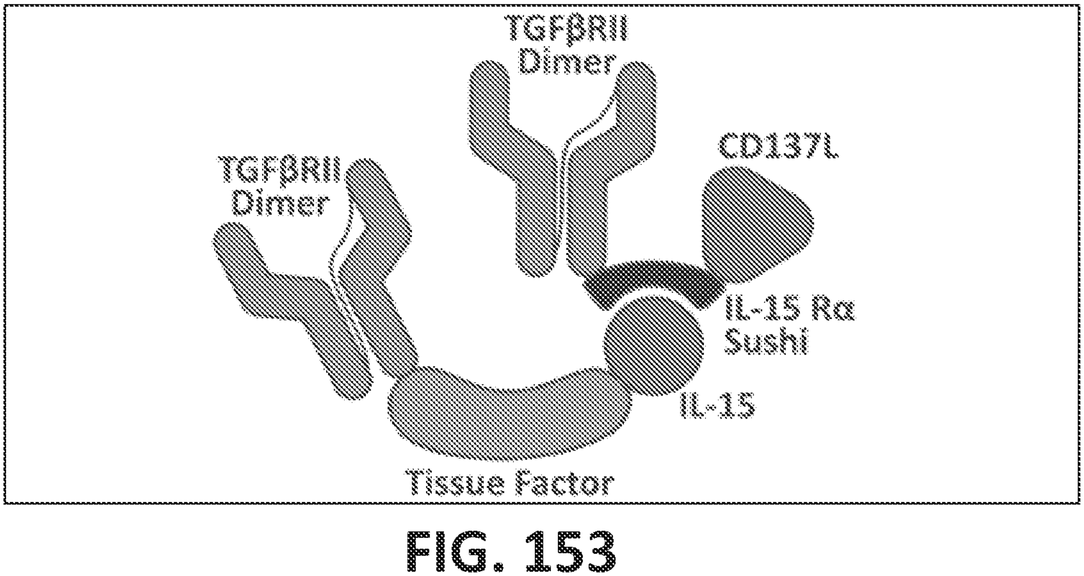

FIG. 153 shows a schematic of the TGFRt15-TGFRs137L construct.

Figure 154:
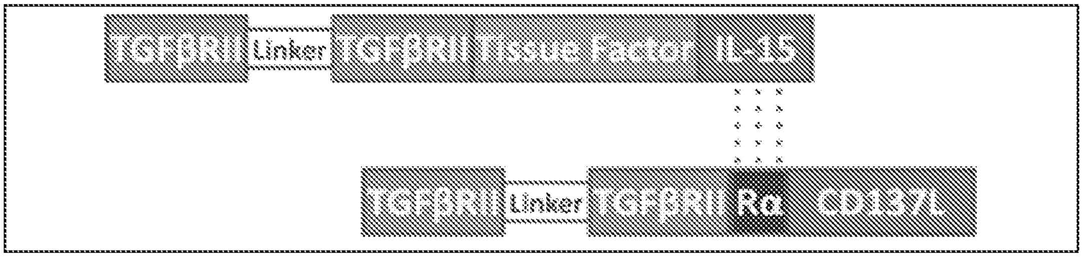

FIG. 154 shows an additional schematic of the TGFRt15-TGFRs137L construct.

Figure 155:
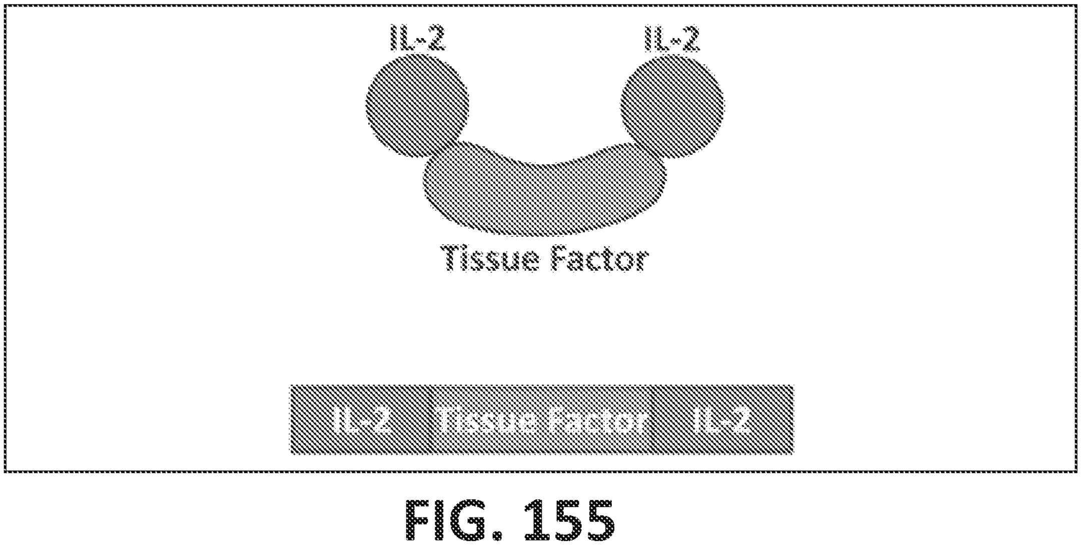

FIG. 155 are schematic diagrams of an exemplary 2t2 single-chain chimeric polypeptide.

Figure 156:
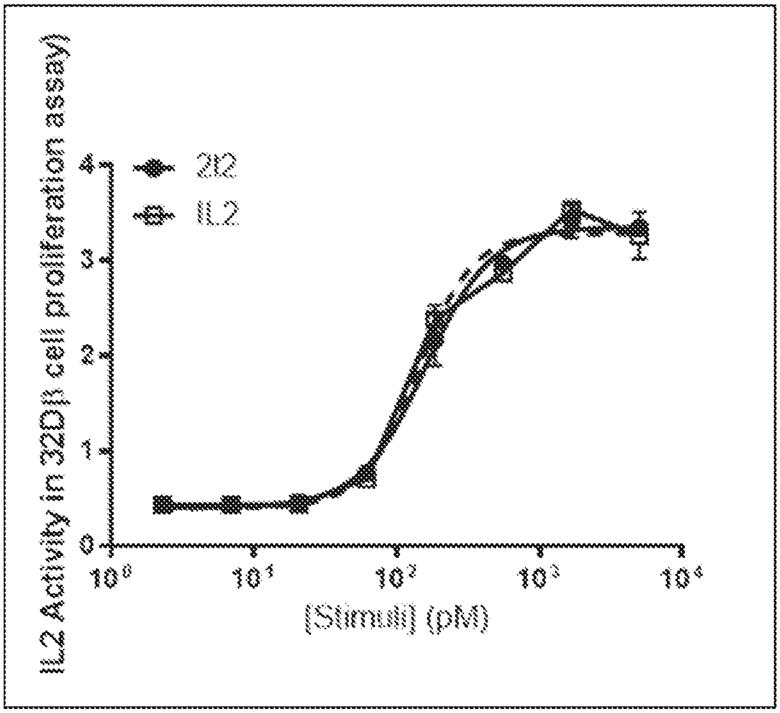

FIG. 156 shows IL-2 activity in 2t2 as compared to recombinant IL-2 using a 32Dβ cell proliferation assay.

Figure 157:
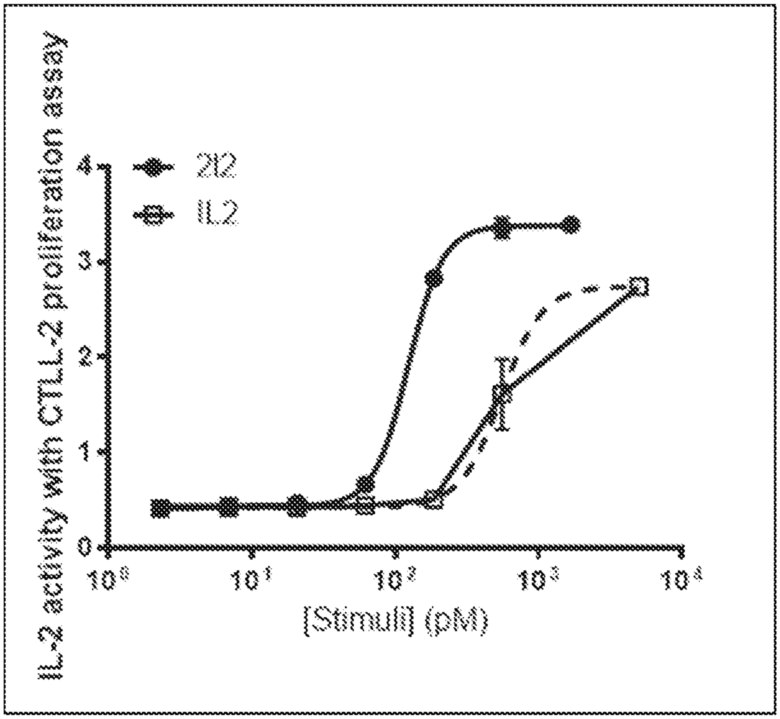

FIG. 157 shows IL-2 activity in 2t2 as compared to recombinant IL-2 using a CTLL-2 cell proliferation assay.

Figure 158:
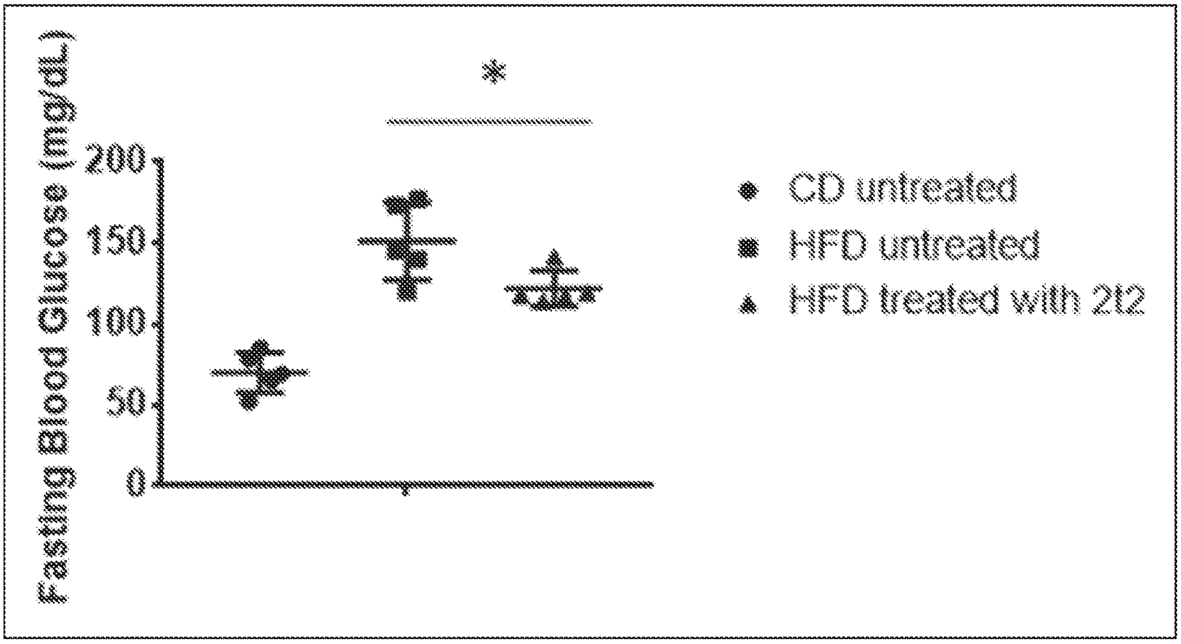

FIG. 158 shows the fasting blood glucose levels in $ApoE^{-/-}$ mice fed with standard chow or a high fat diet and treated with a PBS control (untreated) or with 2t2.

Figure 159:
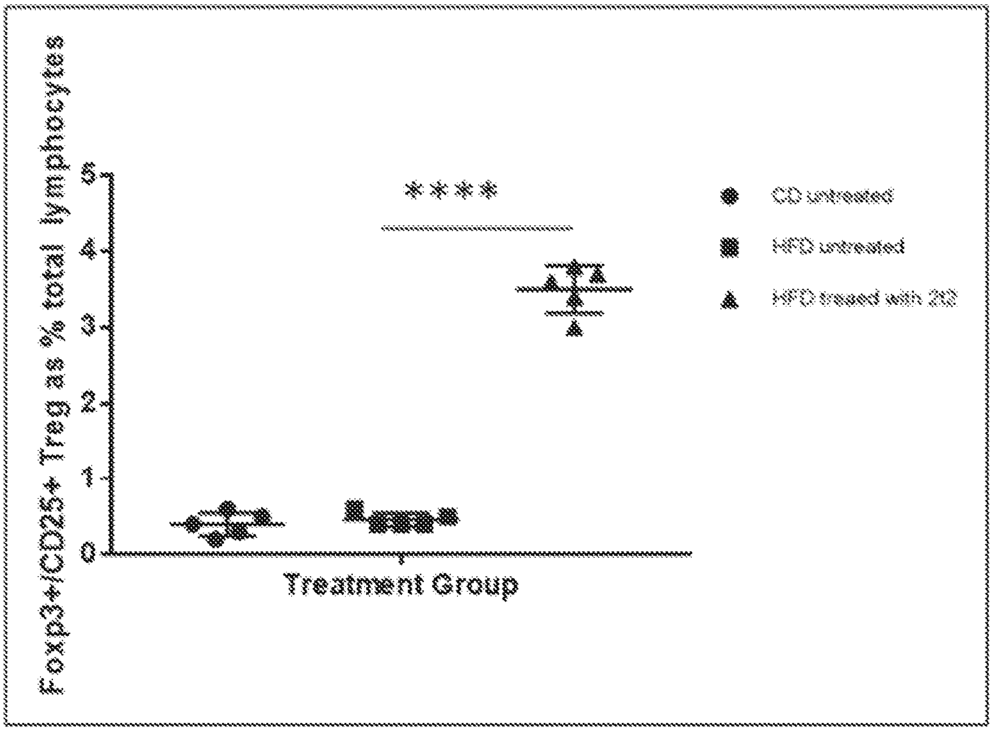

FIG. 159 shows the ratio of $CD4^+CD25^+FoxP3^+$ T regulatory cells in blood lymphocytes from $ApoE^{-/-}$ mice fed with standard chow or a high fat diet and treated with a PBS control (untreated) or with 2t2.

Figure 160:
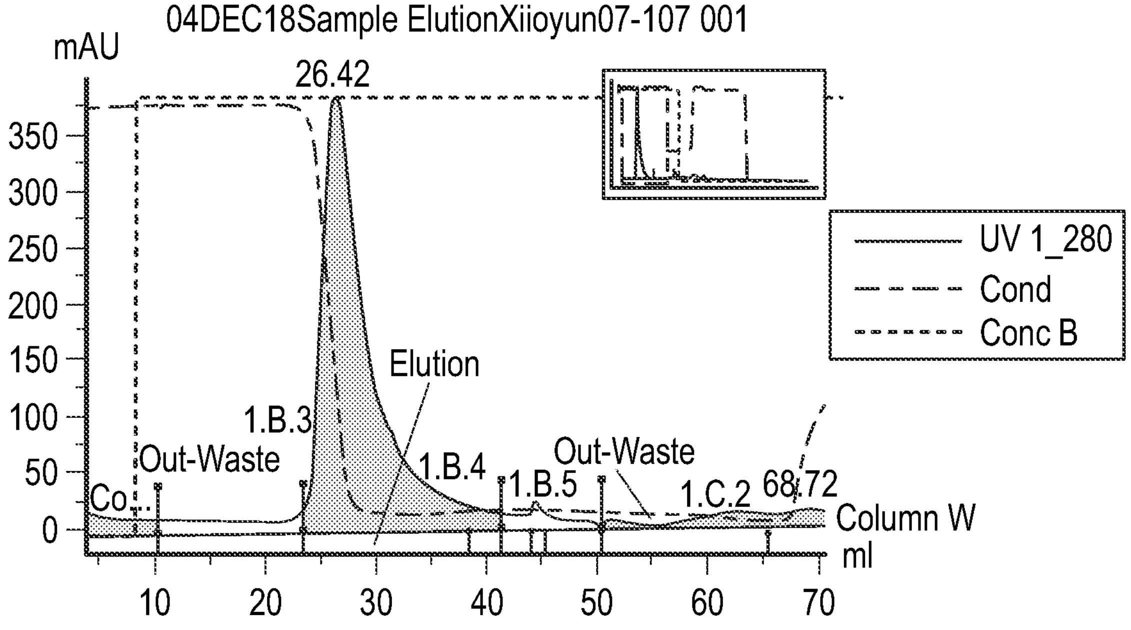

FIG. 160 is a line graph showing the chromatographic profile of 2t2 protein containing cell culture supernatant following binding and elution on anti-TF antibody resin.

Figure 161:
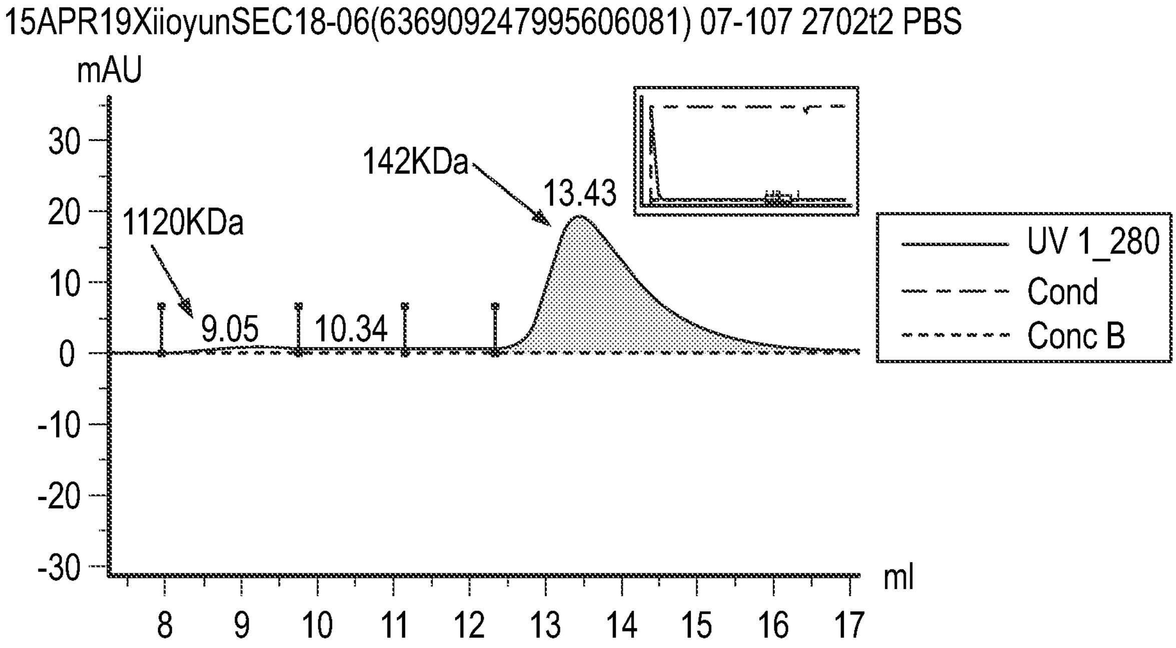

FIG. 161 shows an analytical SEC profile of 2t2.

Figure 162A:
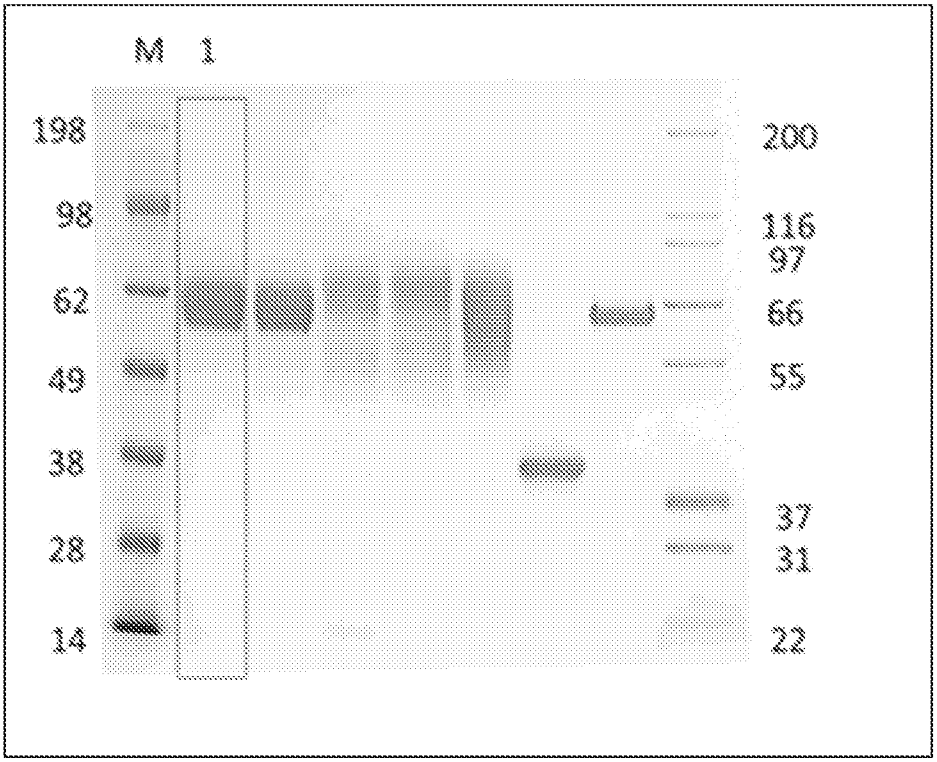
Figure 162B:
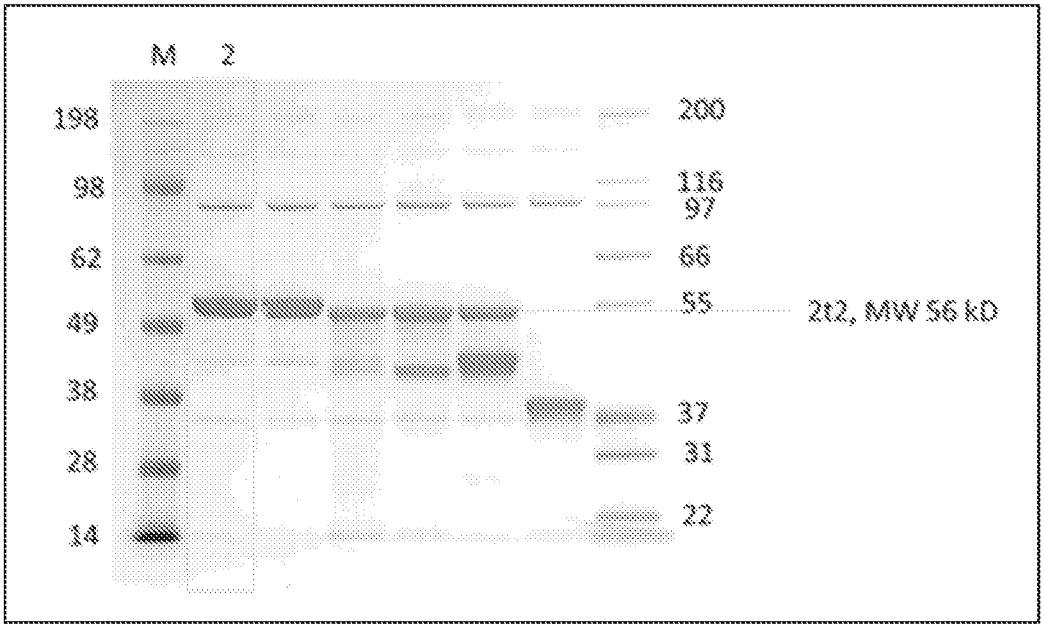

FIGS. 162A and 162B show reduced SDS-PAGE analysis of 2t2 before and after deglycosylation. FIG. 162A shows reduced SDS-PAGE analysis of 2t2 before deglycosylation.

FIG. 162B shows reduced SDS-PAGE analysis of 2t2 after deglycosylation.

Figure 163A:
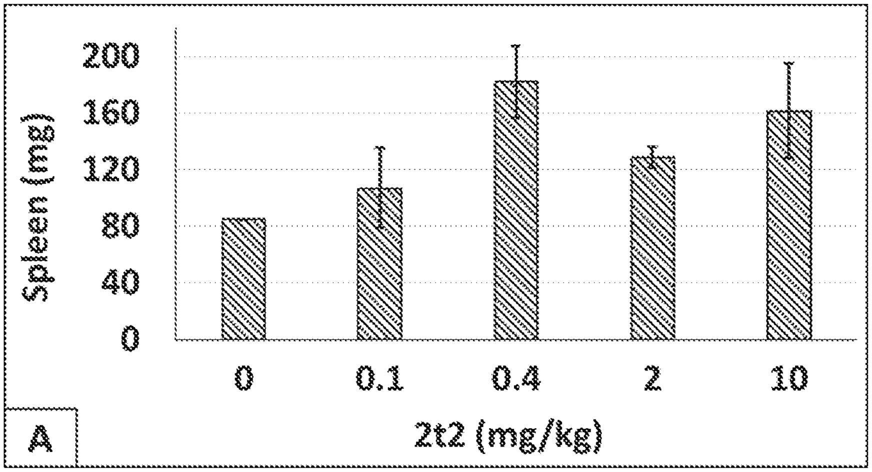
Figure 163B:
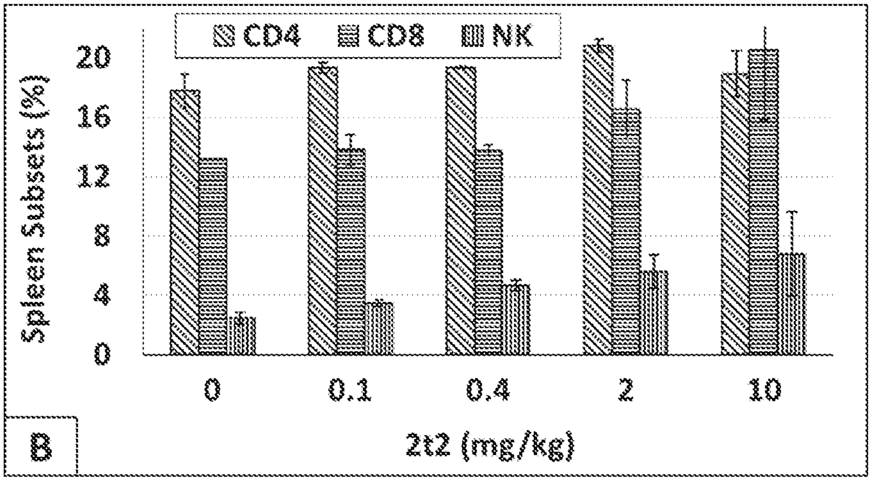

FIGS. 163A and 163B show results of immunostimulation in C57BL/6 mice using 2t2. FIG. 163A shows spleen weight following treatment with 2t2. FIG. 163B shows the percentages of immune cell types following 2t2 treatment.

Figure 164:
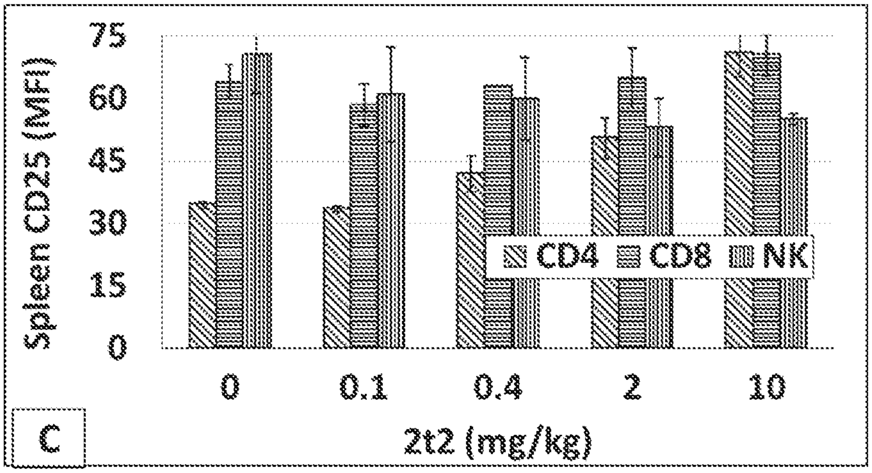

FIG. 164 shows upregulation of CD25 expression of CD4+ T cells in mice treated with 2t2.

Figure 165:
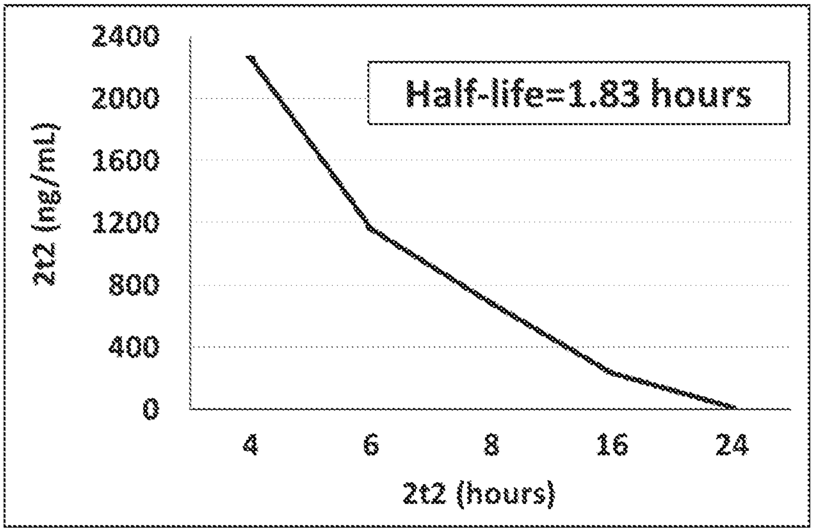

FIG. 165 shows the pharmacokinetics of 2t2 in C57BL/6 mice.

Figure 166A:
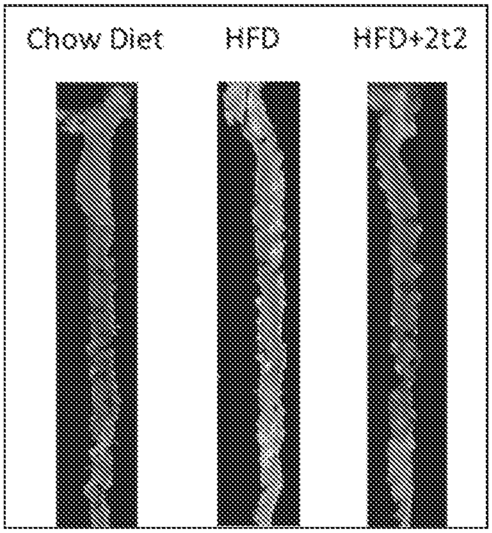
Figure 166B:
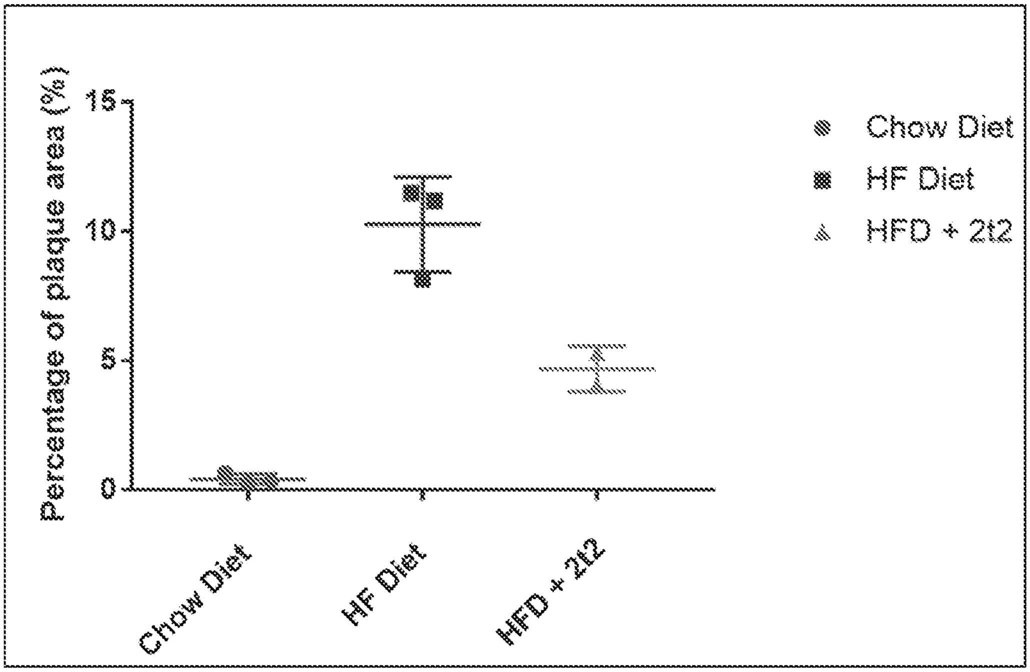

FIGS. 166A and 166B show effects of 2t2 in attenuating the formation of high fat-induced atherosclerotic plaques in $ApoE^{-/-}$ mice. FIG. 166A shows a representative view of atherosclerotic plaques from $ApoE^{-/-}$ mice fed with standard chow or a high fat diet and treated with either PBS control or 2t2. FIG. 166B shows the results of quantitative analysis of atherosclerotic plaques of each group.

Figure 167:
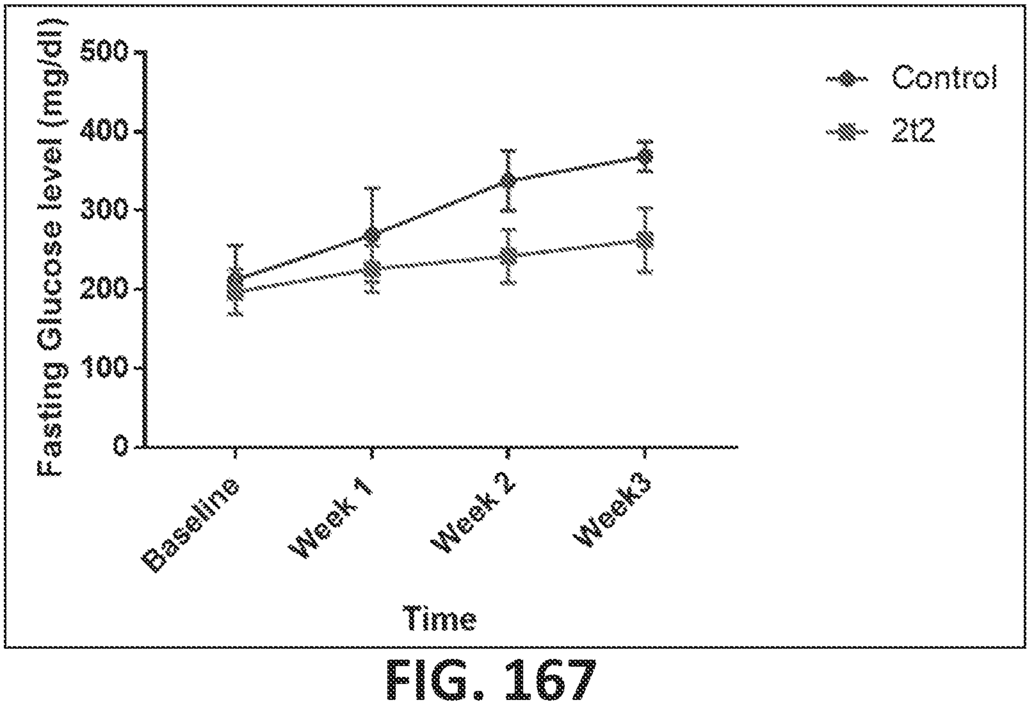

FIG. 167 shows fasting glucose levels in 2t2 treated-mice as compared to control-treated mice.

Figure 168:
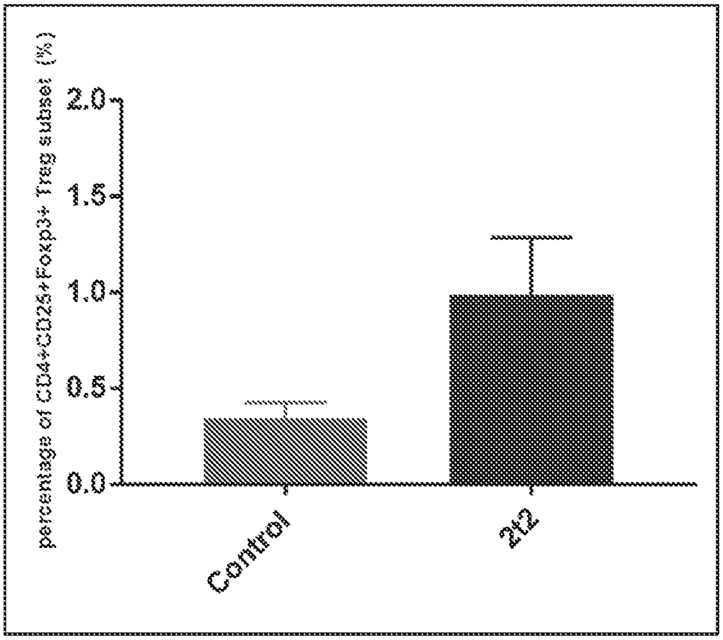

FIG. 168 shows the percentage of $CD4^{+}CD25^{+}FoxP3^{+}$ Tregs in blood lymphocytes from mice treated with 2t2 and control-treated mice.

Figure 169:
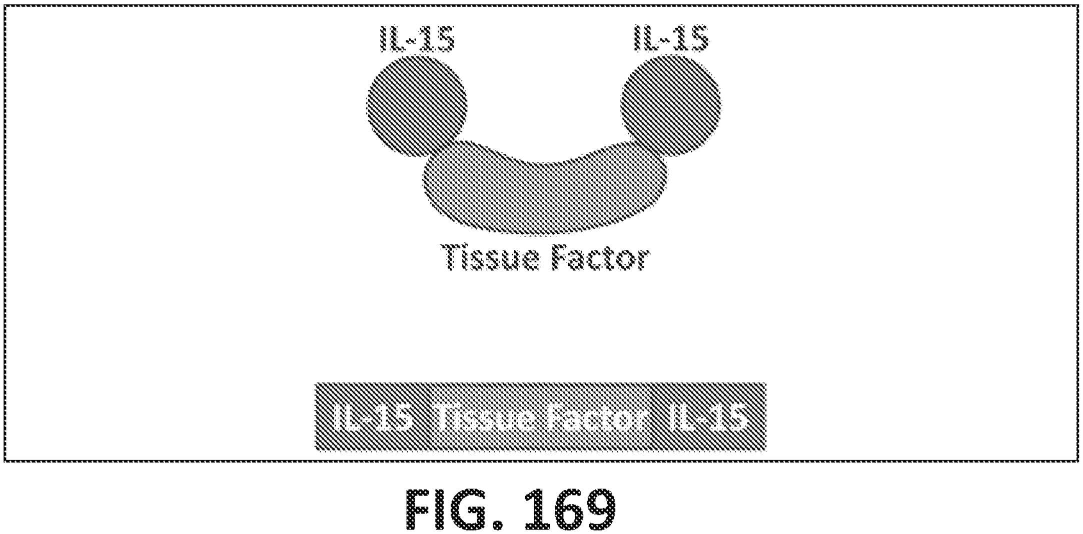

FIG. 169 are schematic diagrams of an exemplary 15t15 single-chain chimeric polypeptide.

Figure 170:
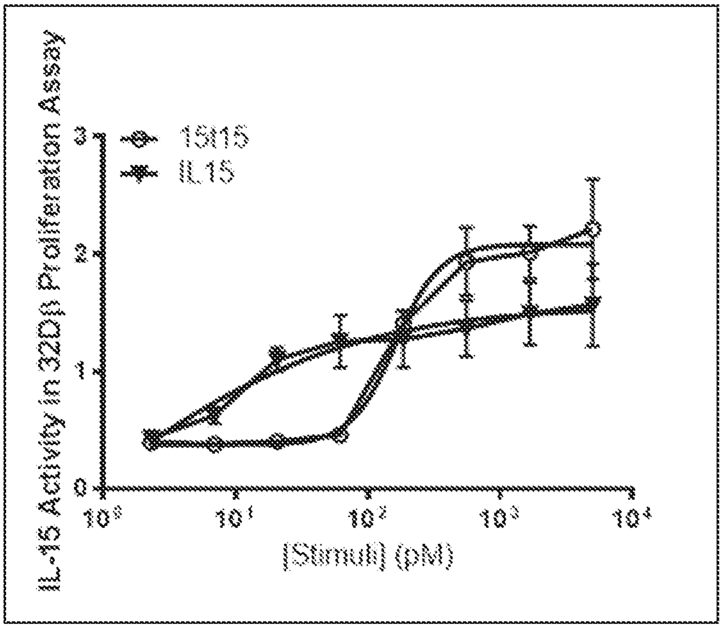

FIG. 170 shows the IL-15 activity of 15t15 as compared to recombinant IL-15 in a 32Dβ cell proliferation assay.

Figure 171:
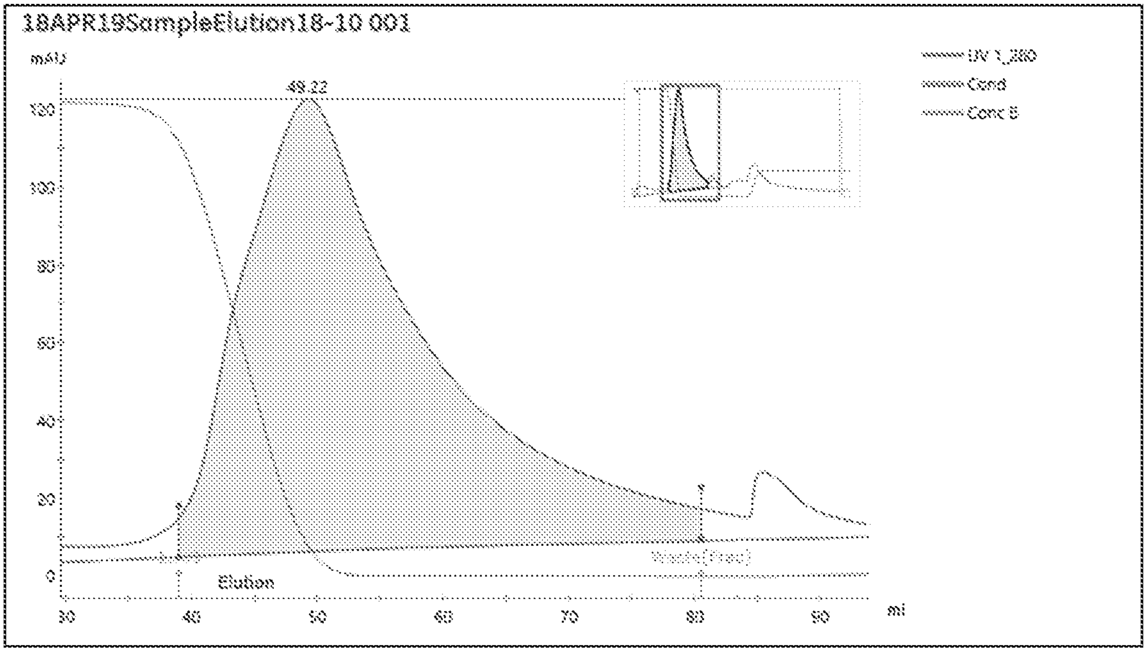

FIG. 171 is a line graph showing the chromatographic profile of 15t15 protein containing cell culture supernatant following binding and elution on anti-TF resin.

Figure 172A:
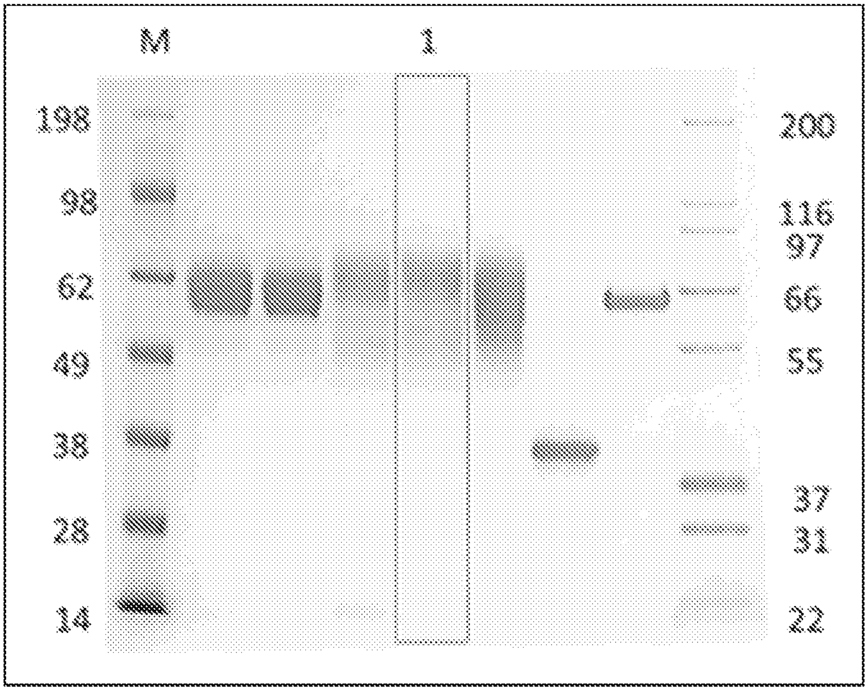
Figure 172B:
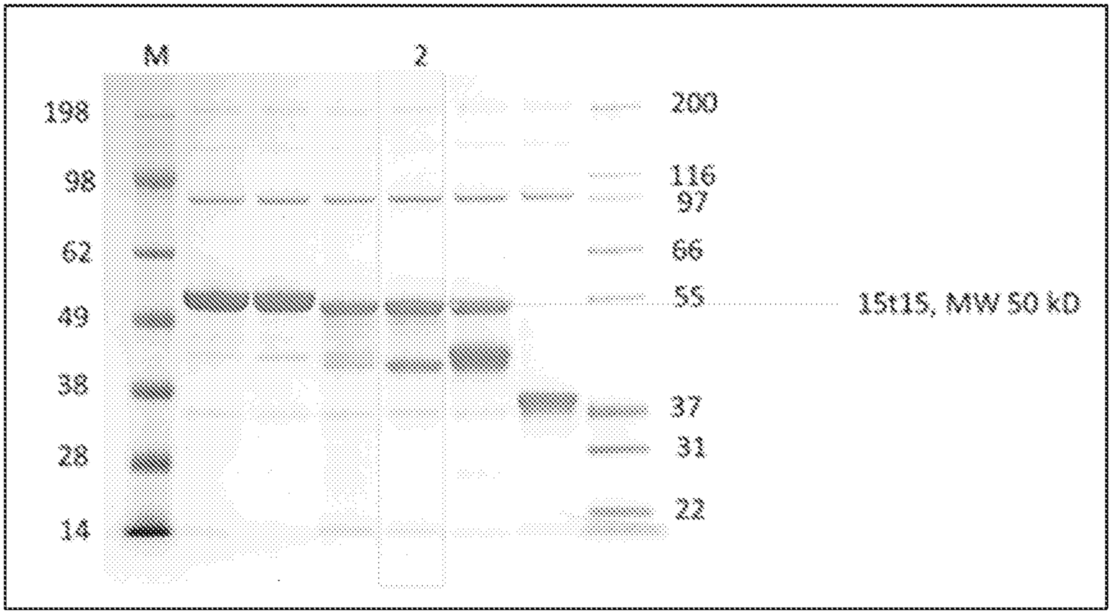

FIGS. 172A and 172B show reduced SDS-PAGE analysis of 15t15 before and after deglycosylation. FIG. 172A shows reduced SDS-PAGE analysis of 15t15 before deglycosylation. FIG. 172B shows reduced SDS-PAGE analysis of 15t15 after deglycosylation.

Figure 173:
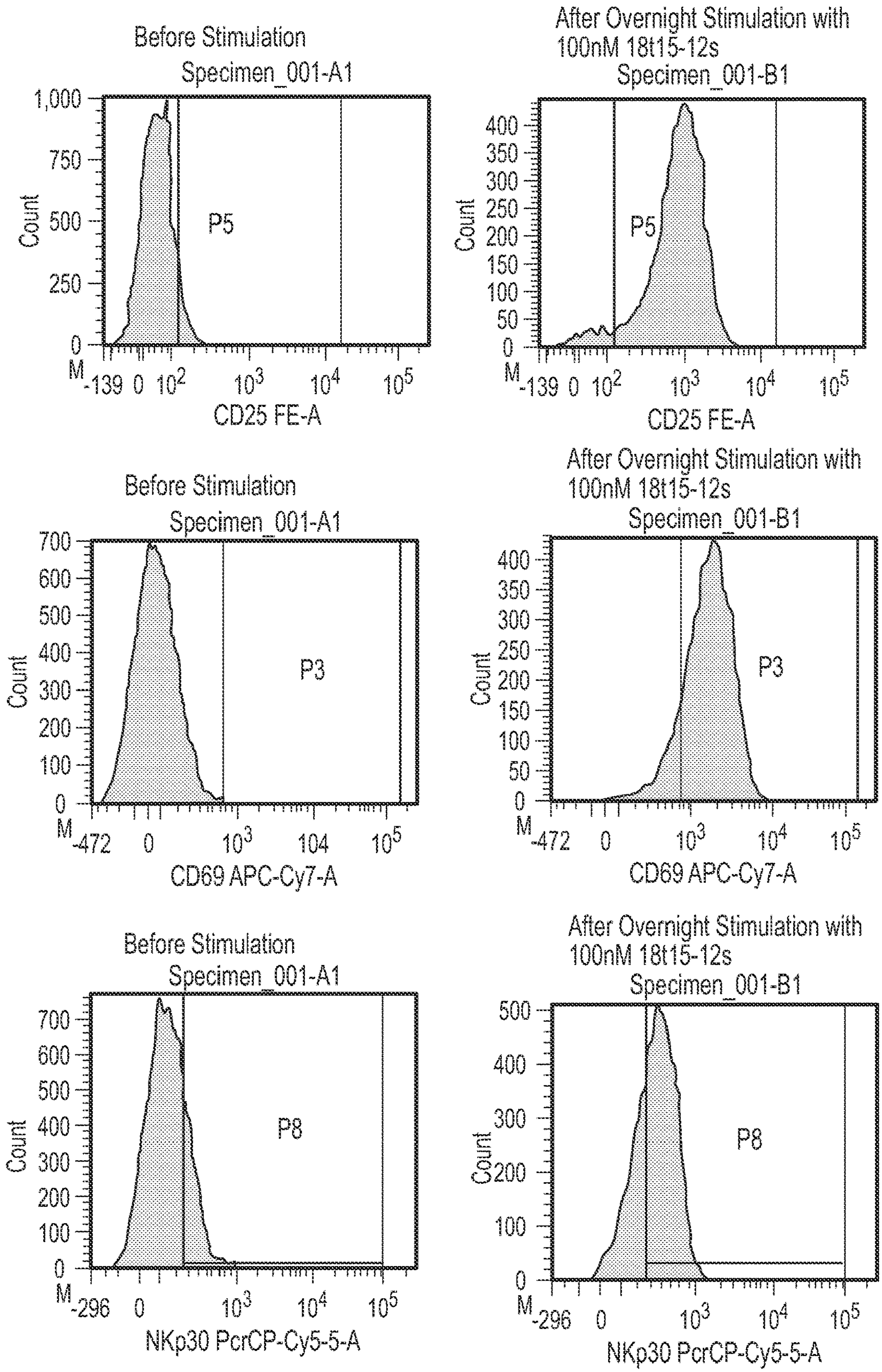
Figure 173:
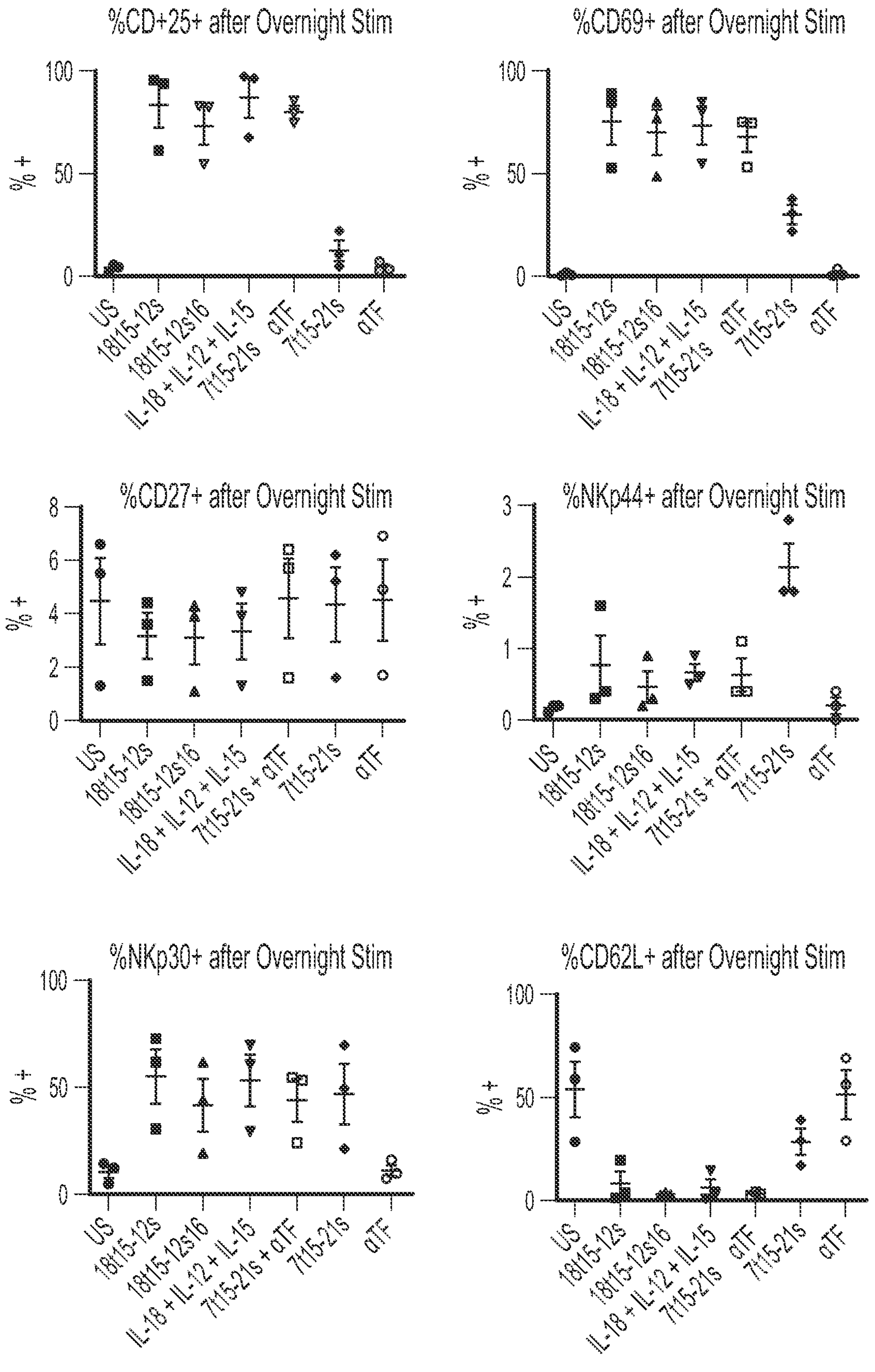

FIG. 173 is a set of histograms and a set of graphs showing the change in the surface phenotype of NK cells after stimulation with 18t15-12s, 18t15-12s16, and 7t15-21s+anti-TF antibody.

Figure 174:
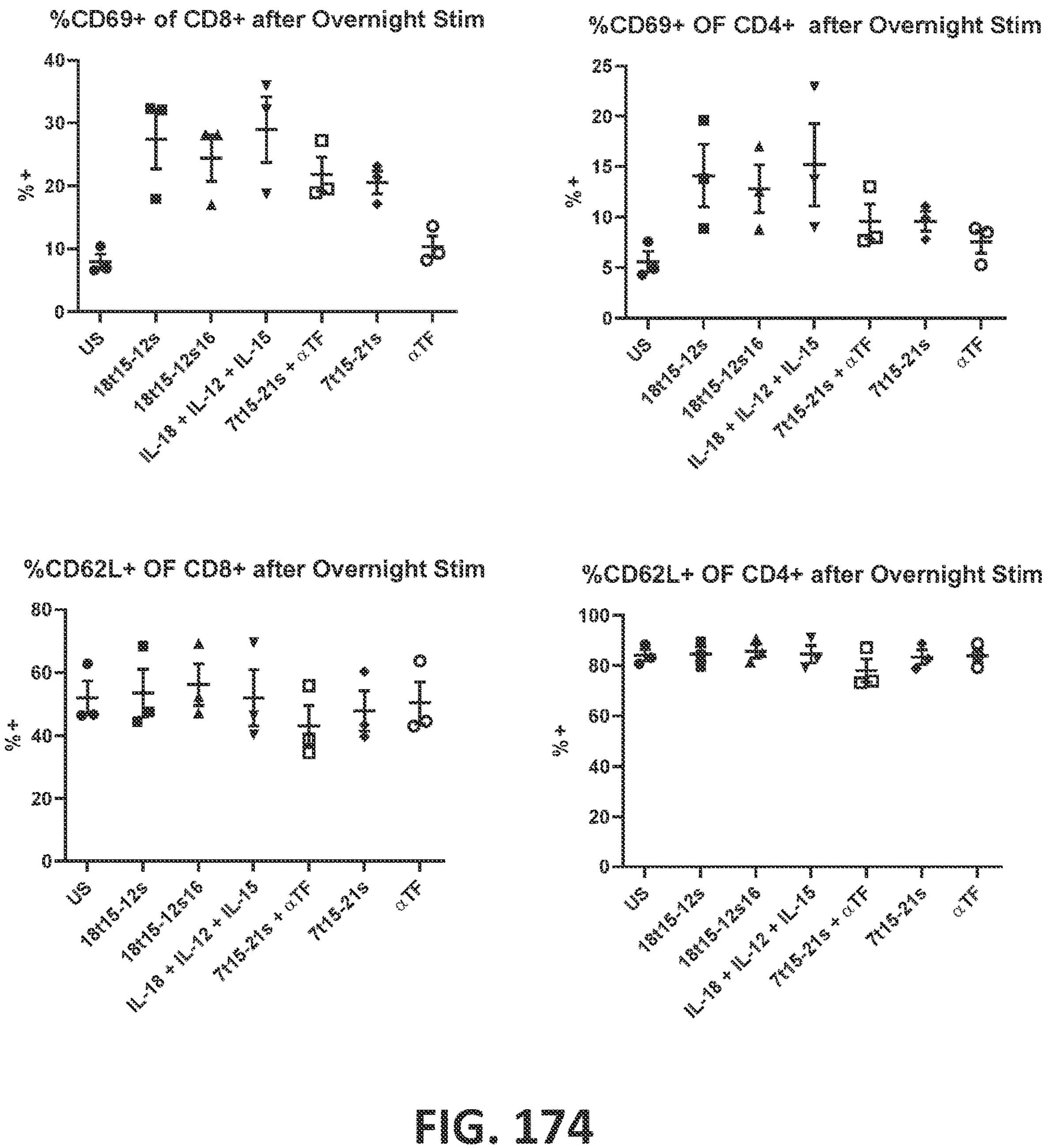

FIG. 174 is a set of graphs showing changes in the surface phenotype of lymphocyte populations after stimulation with 18t15-12s; 18t15-12s16; a mixture of single cytokines rhIL15, rhIL18, and rhIL-12; 7t15-21s+anti-TF antibody; 7t15-21s; or anti-TF antibody.

Figure 175:
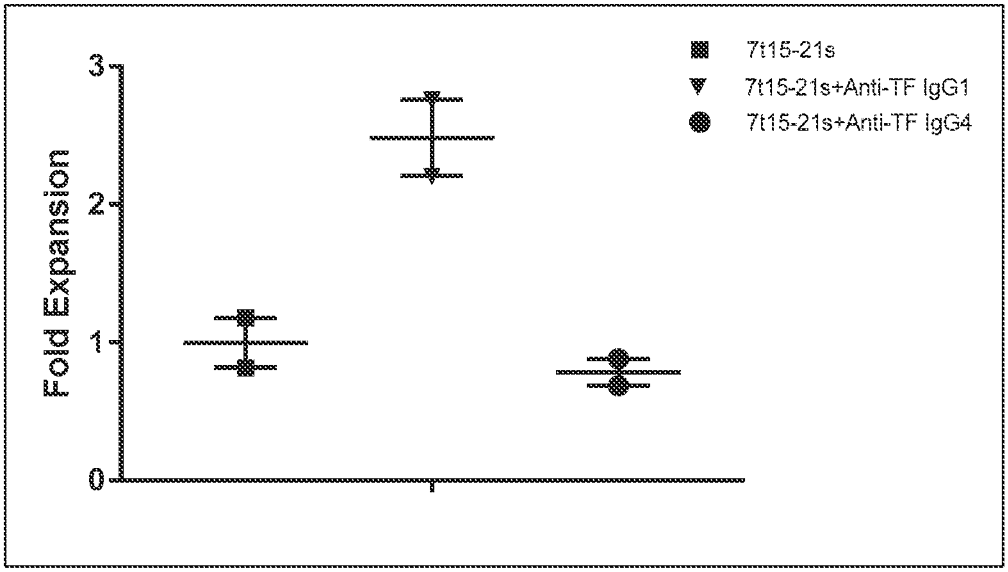

FIG. 175 is a graph of the increase in proliferation of NK cells in vitro after stimulation with a multi-chain construct alone or in the presence of anti-TF IgG1 or anti-TF IgG4.

Figure 176:
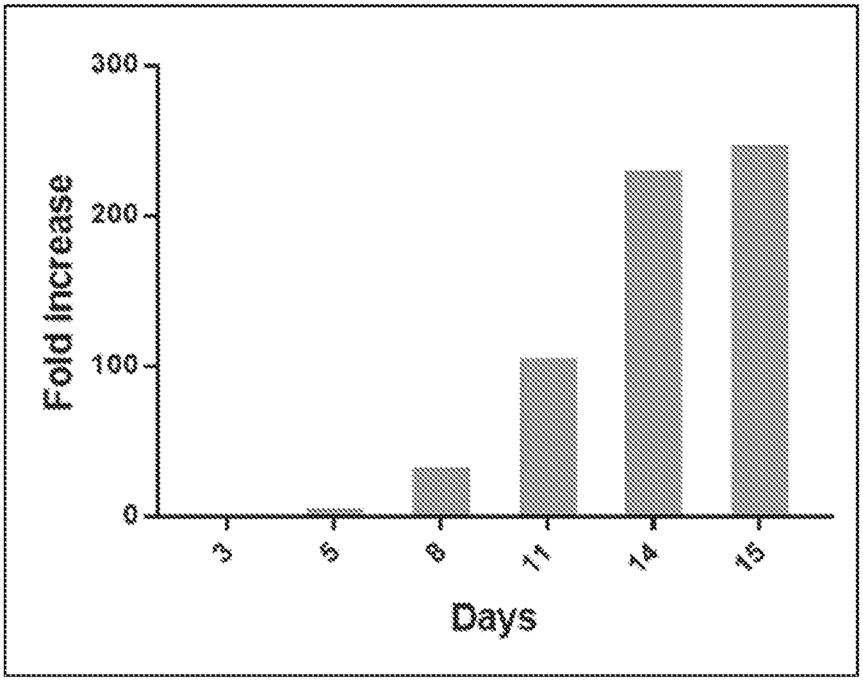

FIG. 176 is a graph of the increase in proliferation over time of NK cells in vitro after stimulation with the combination of 7t15-21s and anti-TF antibody.

Figure 177:
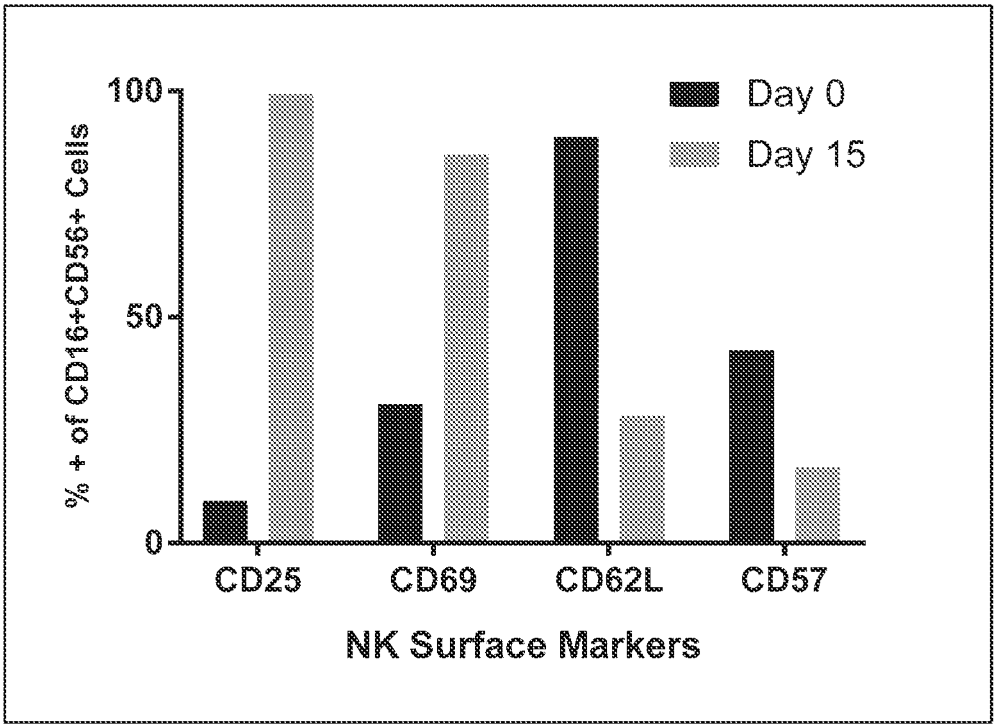

FIG. 177 is a graph of the changes in surface phenotype on 7t15-21s+anti-TF antibody-expanded NK cells.

Figure 178:
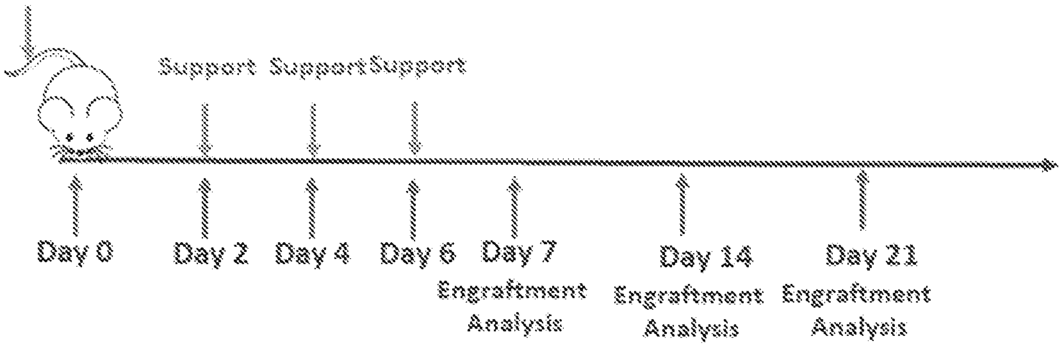
Figure 178:
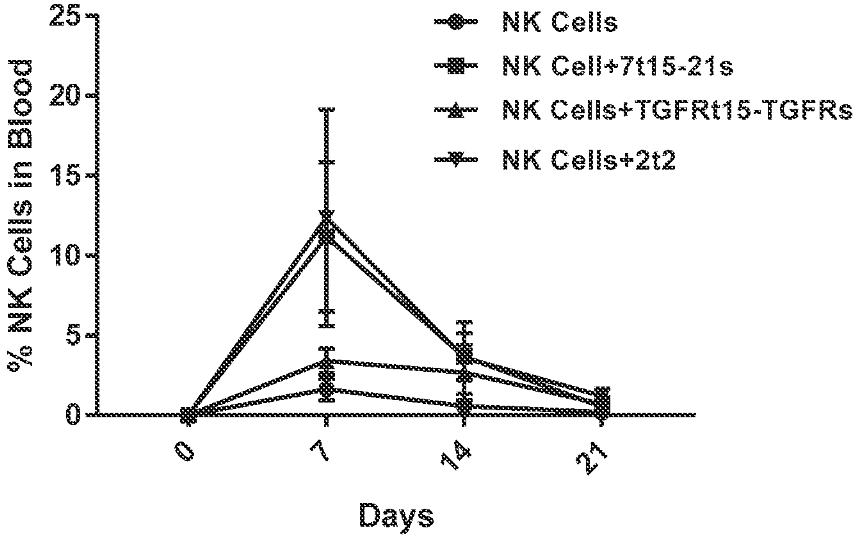

FIG. 178 is a schematic and a set of graphs showing the persistence of 7t15-21s and anti-TF antibody-expanded NK cells in NSG mice following treatment with 7t15-21, TGFRt15-TGFRs or 2t2.

Figure 179A:
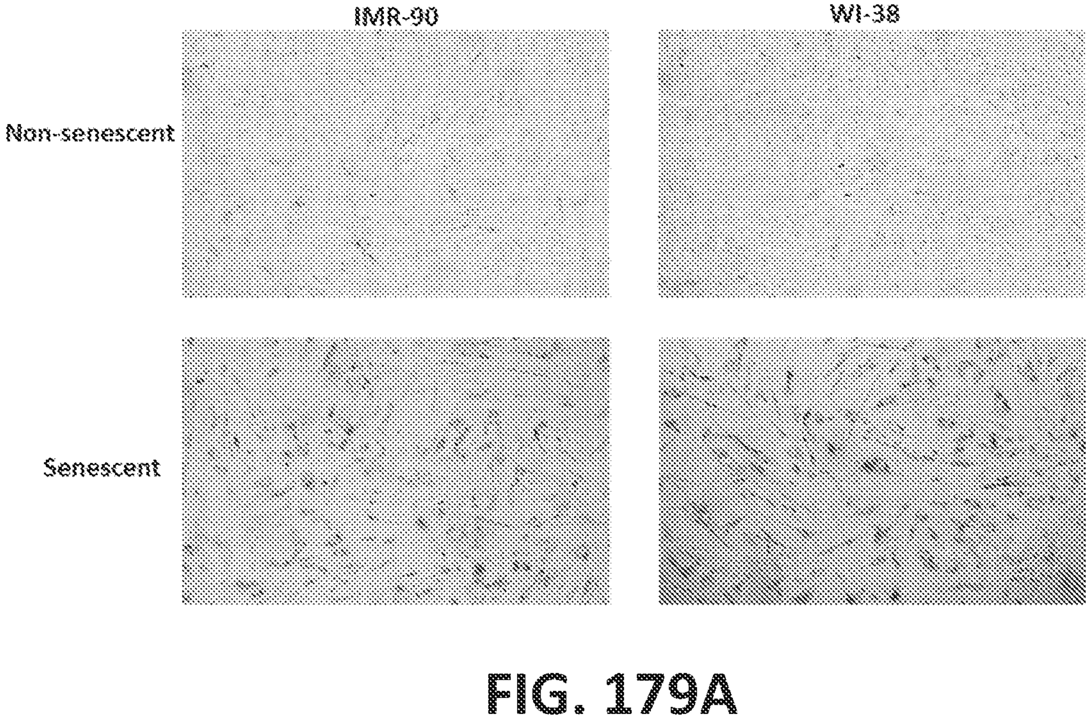
Figure 179B:
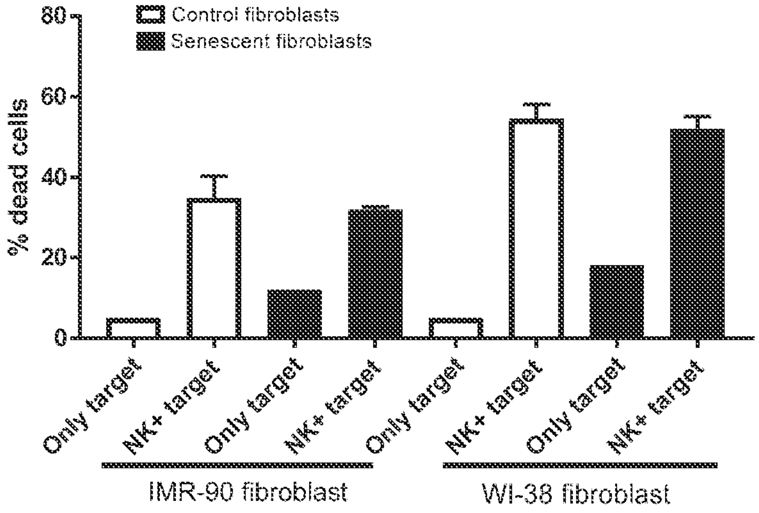

FIGS. 179A and 179B is a set of images and a set of graphs showing killing of chemically-induced senescent human fibroblasts by 7t15-21s+anti-TF antibody-expanded NK cells.

Figure 180A:
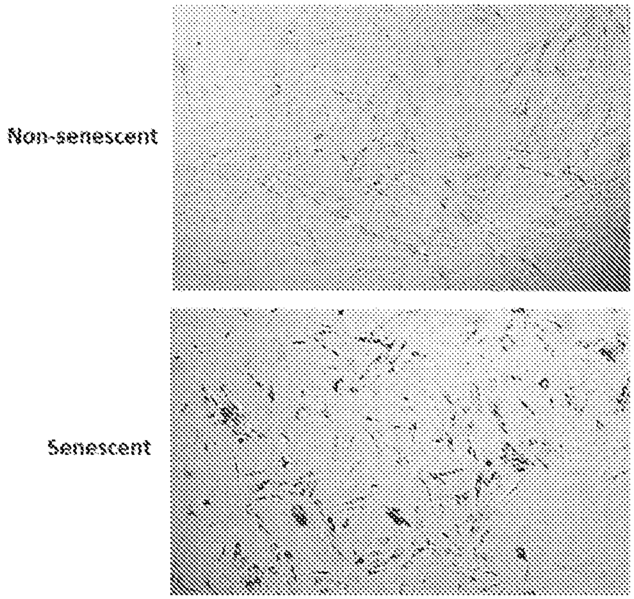
Figure 180B:
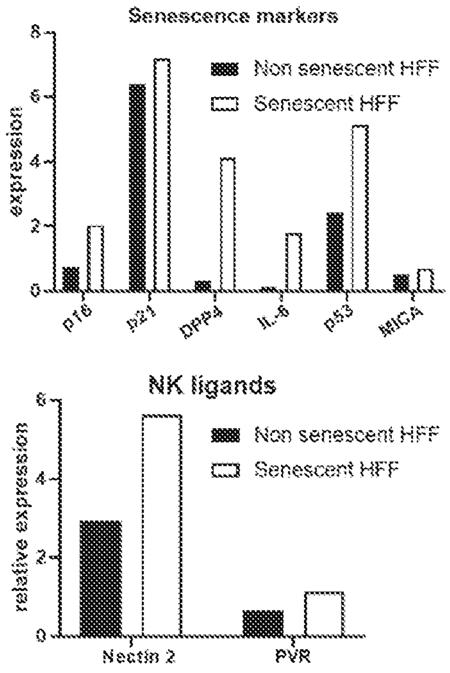
Figure 180C:
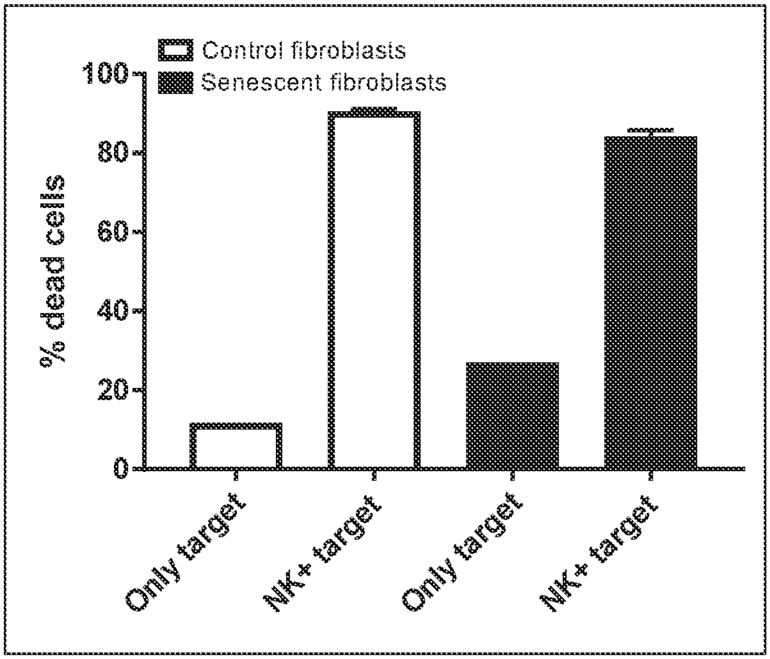

FIG. 180A-180C is a set of images and a set of graphs showing killing of UV-induced senescent human fibroblast by 7t15-21s+anti-TF antibody-expanded NK cells.

Figure 181:
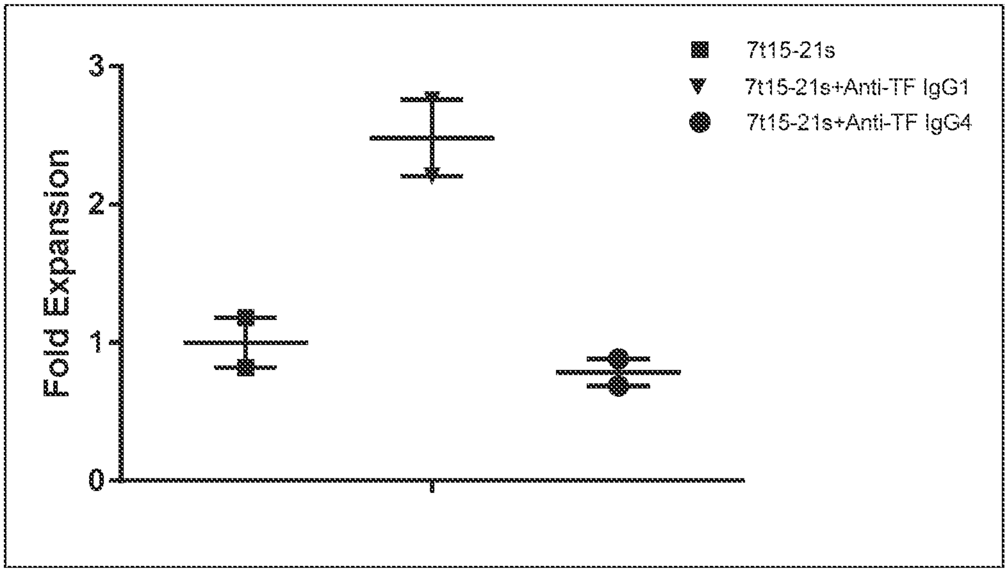

FIG. 181 shows proliferation of NK cells upon stimulation with 7t15-21s, 7t15-21s+anti-TF antibody (IgG1), or 7t15-21s+anti-TF antibody (IgG4).

Figure 182:
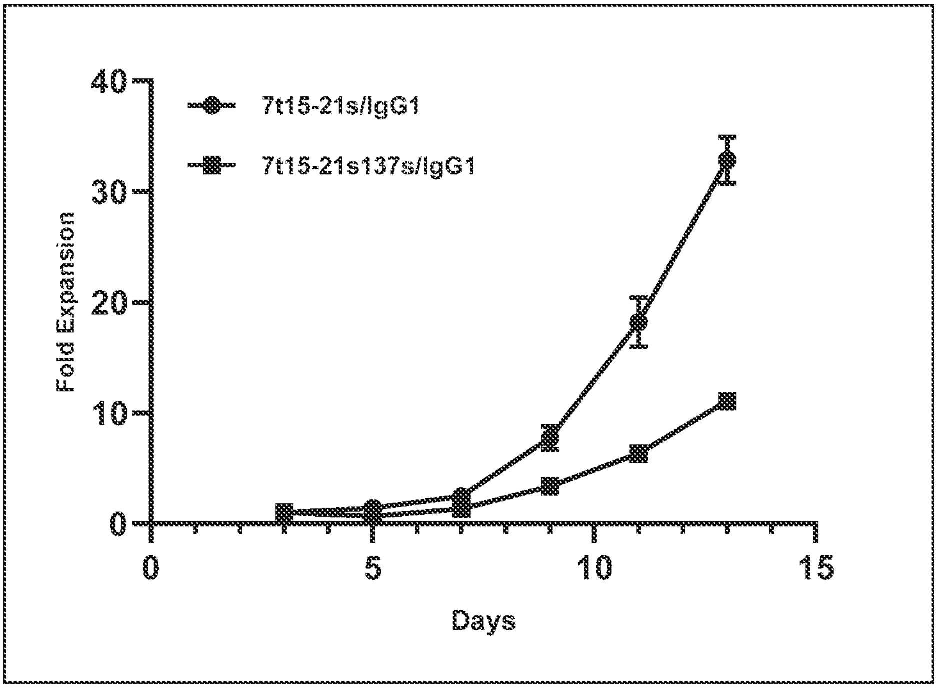

FIG. 182 shows NK cell expansion induced by the 7t15-21s+anti-TF antibody (IgG1) and by the 7t15-21s137L (short version)+anti-TF antibody (IgG1).

Figure 183:
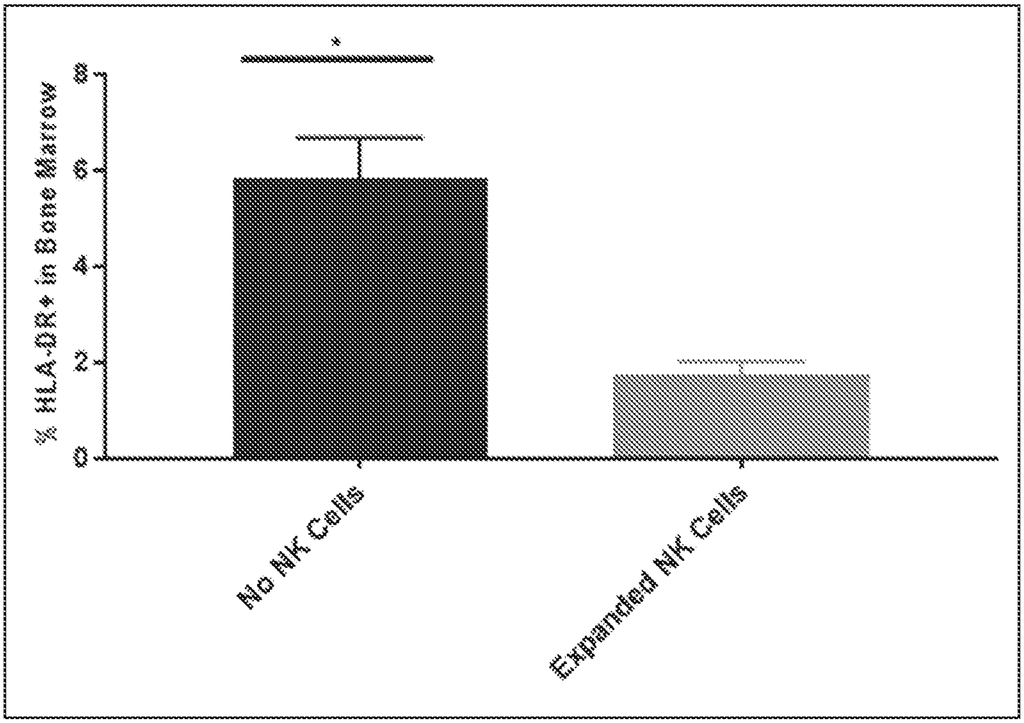

FIG. 183 shows clearance of Daudi tumor cells in NSG mice upon treatment with NK cells activated by the 7t15-21s and anti-TF antibody (IgG1) complex.

Figures 184A, 184B, 184C, 184D, 184E:
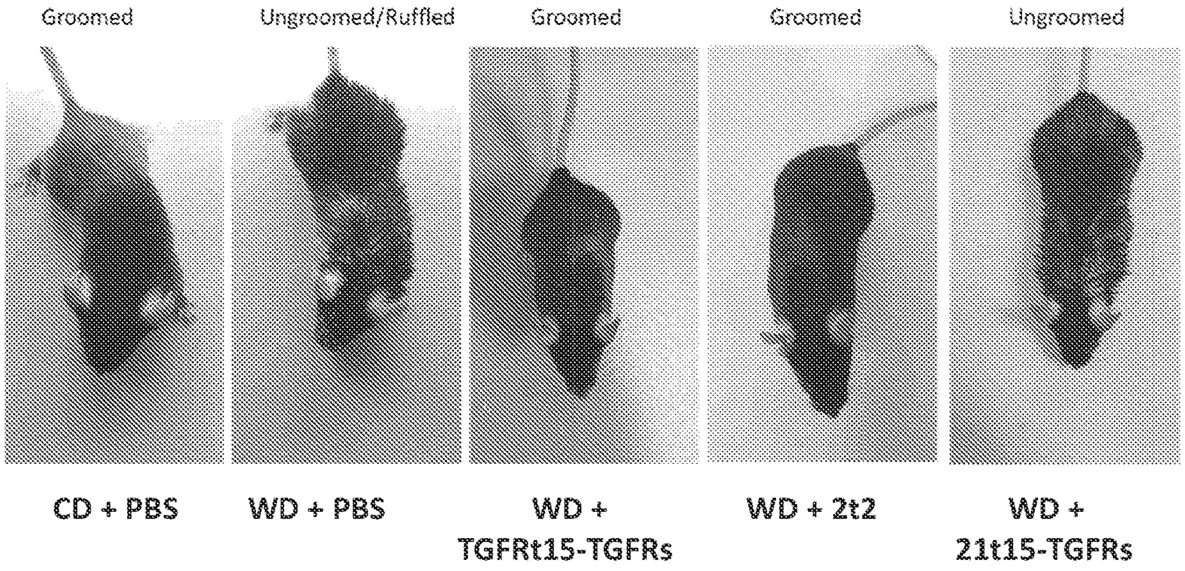

FIGS. 184A-184E show improvement of skin texture in $ApoE^{-/-}$ mice fed with a Western diet and treated with 2t2 or TGFRt15-TGFRs. FIG. 184A is a representative picture of a chow diet-fed $ApoE^{-/-}$ mouse taken one week after PBS treatment. FIG. 184B is a representative picture of a Western diet-fed $ApoE^{-/-}$ mouse taken one week after PBS treatment. FIG. 184C shows a representative picture of a Western diet-fed $ApoE^{-/-}$ mouse taken one week after TGFRt15-TGFRs treatment. FIG. 184D shows a representative picture of a Western diet-fed $ApoE^{-/-}$ mouse taken one week after 2t2 treatment. FIG. 184E shows a representative picture of a Western diet-fed $ApoE^{-/-}$ mouse taken one week after treatment with 21t15-TGFRs.

Figure 185:
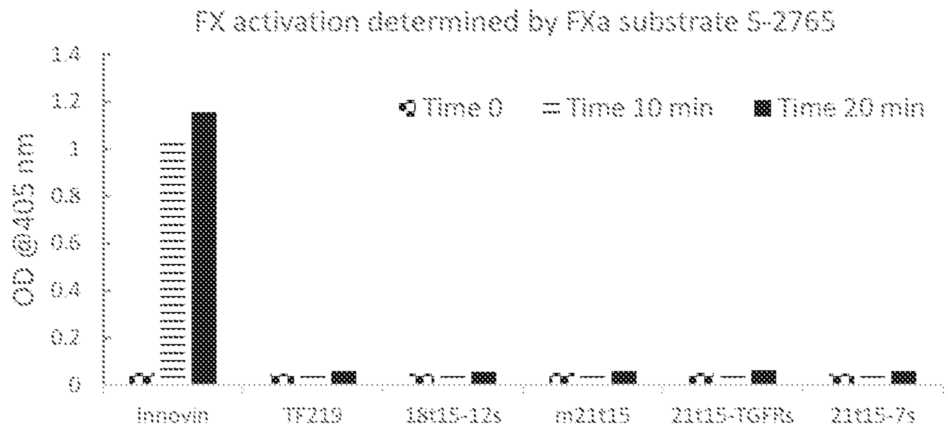

FIG. 185 shows a graph of Factor X (FX) activation following treatment with single-chain or multi-chain chimeric polypeptides.

Figure 186:
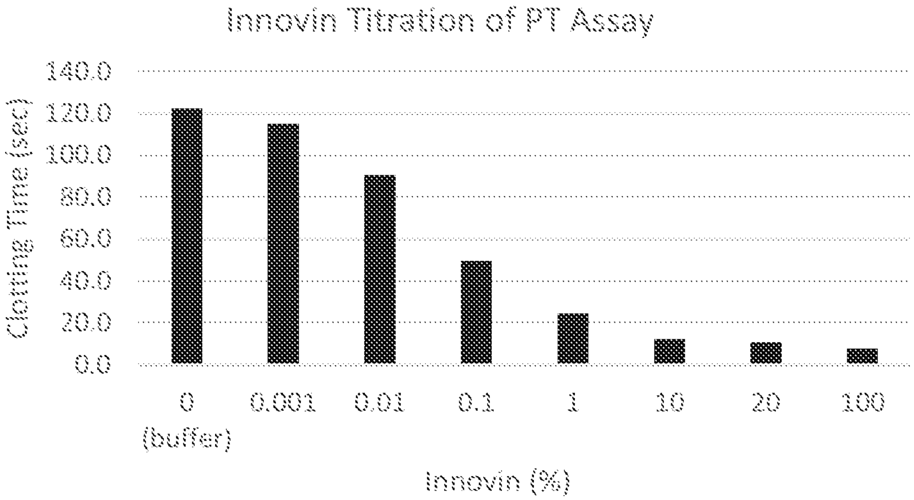

FIG. 186 shows clotting time for a buffer with varying concentrations of Innovin in a prothrombin time (PT) test.

Figure 187:
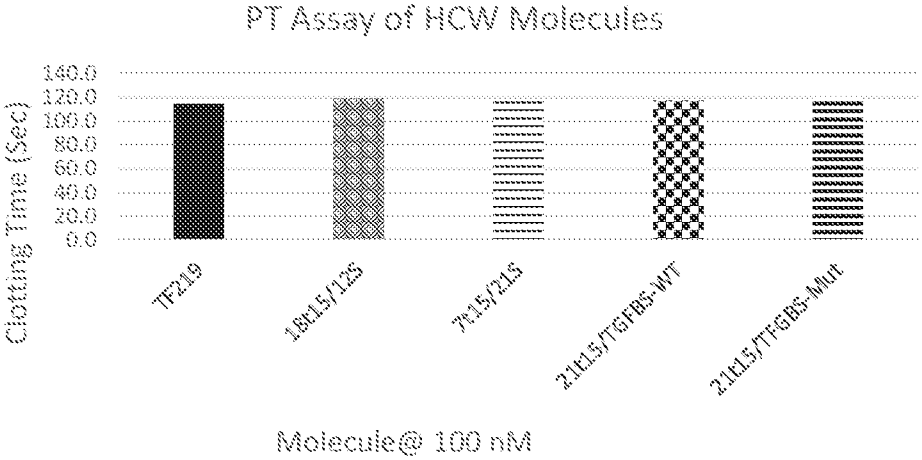

FIG. 187 shows clotting time for multi-chain chimeric polypeptides in a PT Assay.

Figure 188:
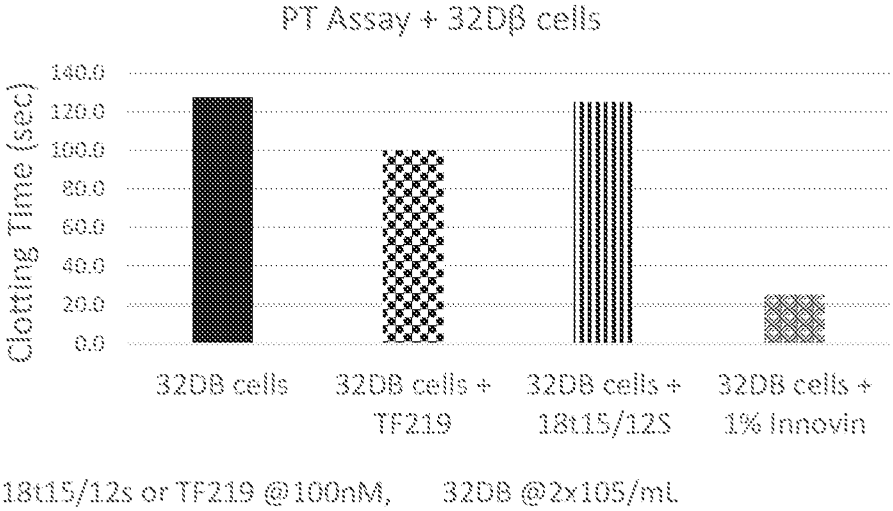

FIG. 188 shows clotting time of the multi-chain chimeric polypeptides in a PT assay when mixed with 32DB cells.

Figure 189:
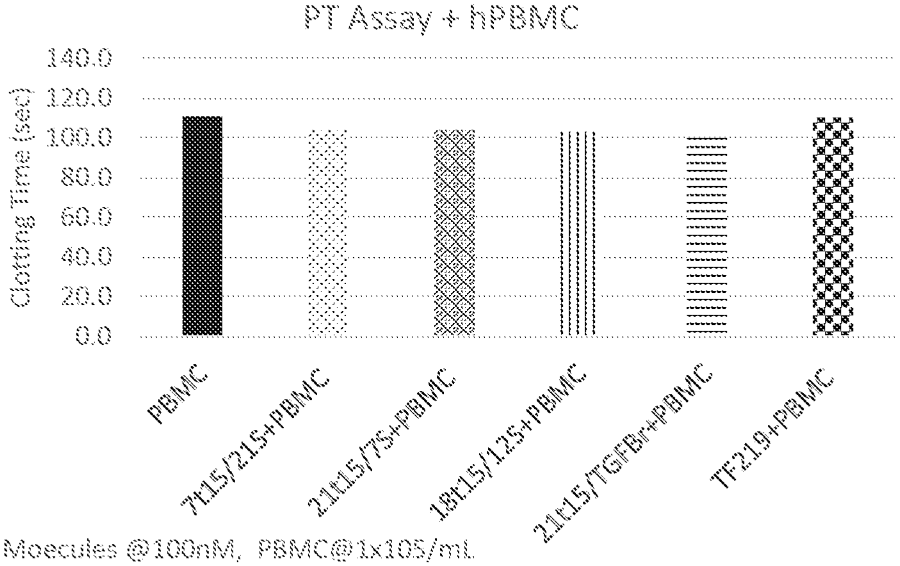

FIG. 189 shows clotting time of multi-chain chimeric polypeptides in a PT assay when mixed with human PBMC.

Figure 190:
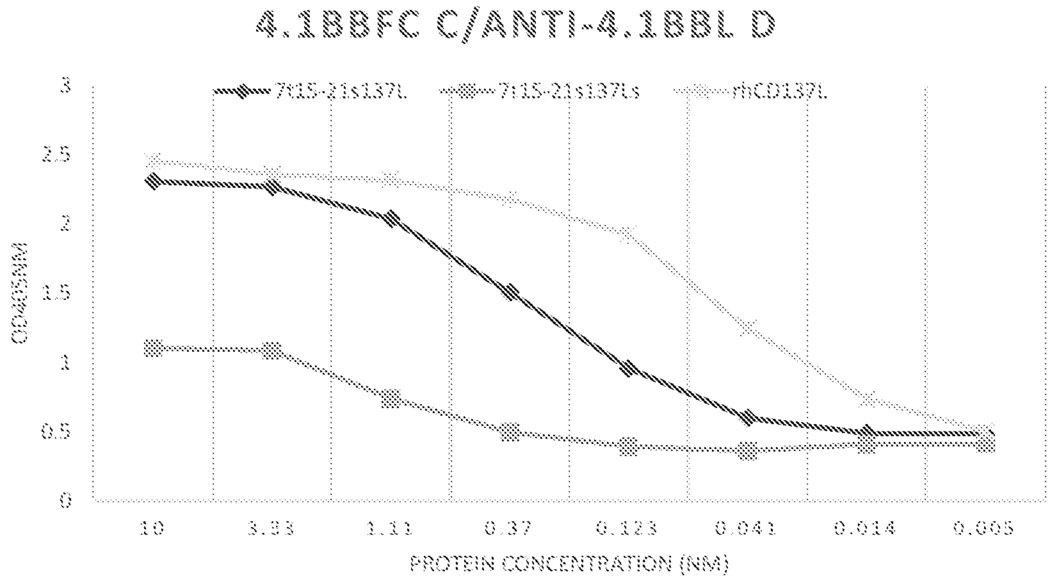
Figure 191A:
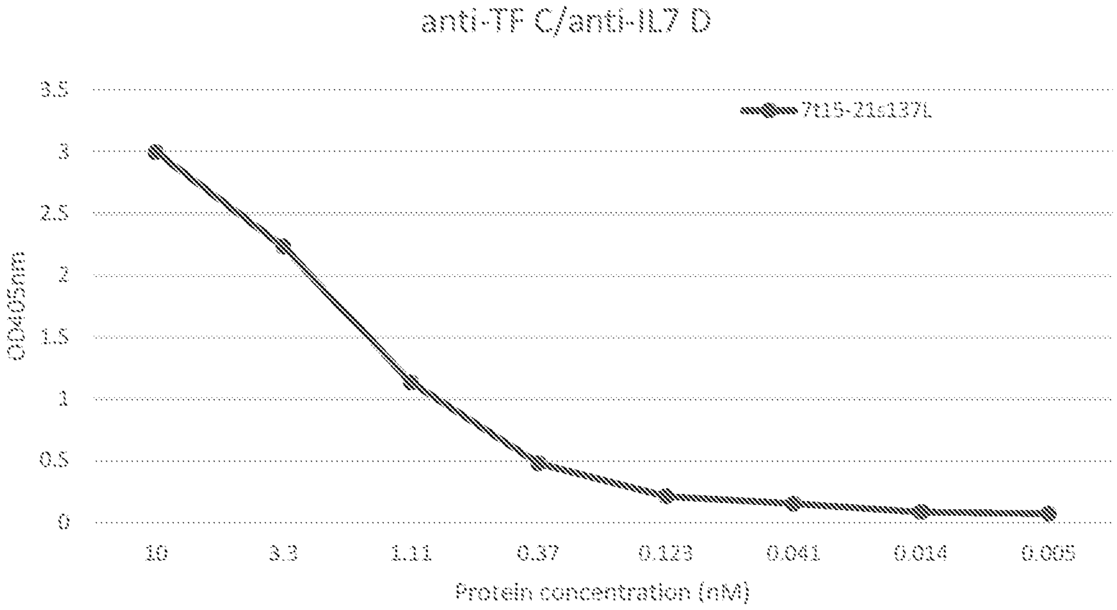
Figure 191B:
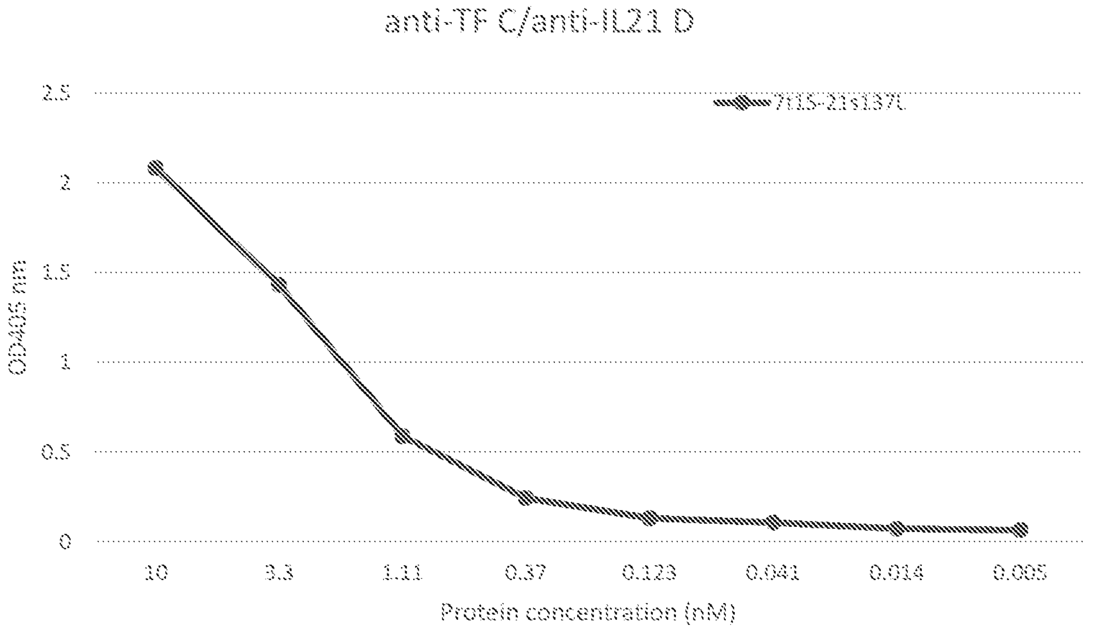
Figure 191C:
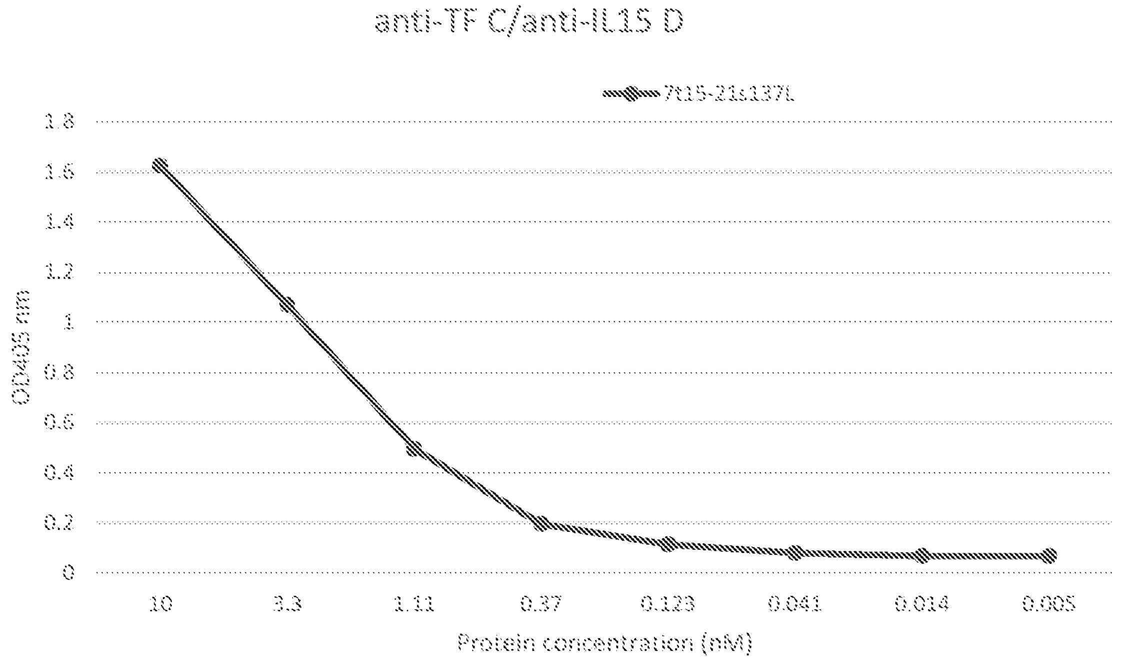
Figure 191D:
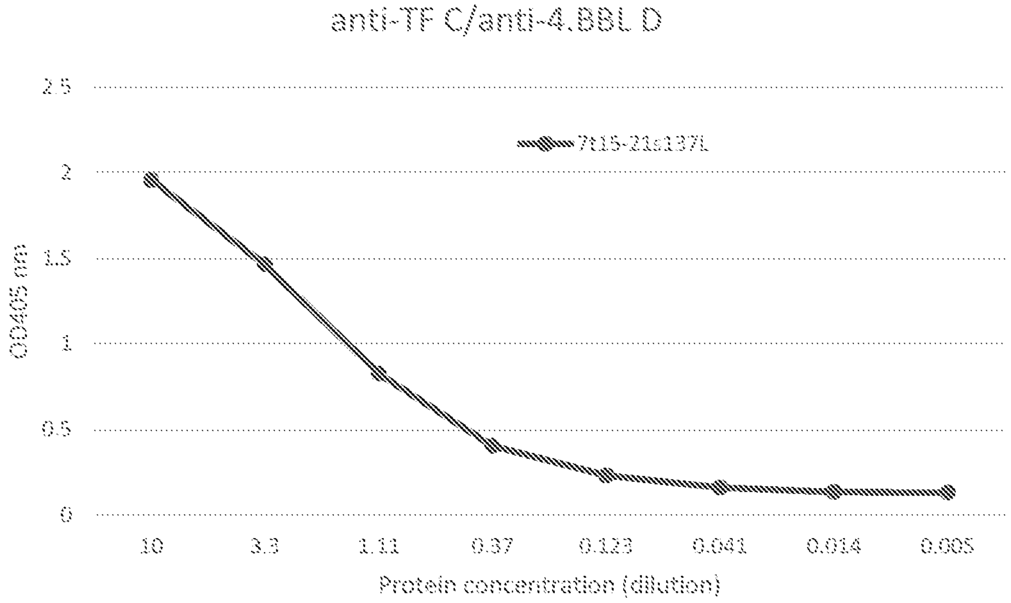

FIG. 190 shows binding of 7t15-21s137L (long version) and 7t15-21s137L (short version) to CD137 (4.1BB).

FIG. 191A-191D show detection of IL7, IL21, IL15, and 4.1BBL in 7t15-21s137L (long version) by the respective antibodies using ELISA.

Figure 192:
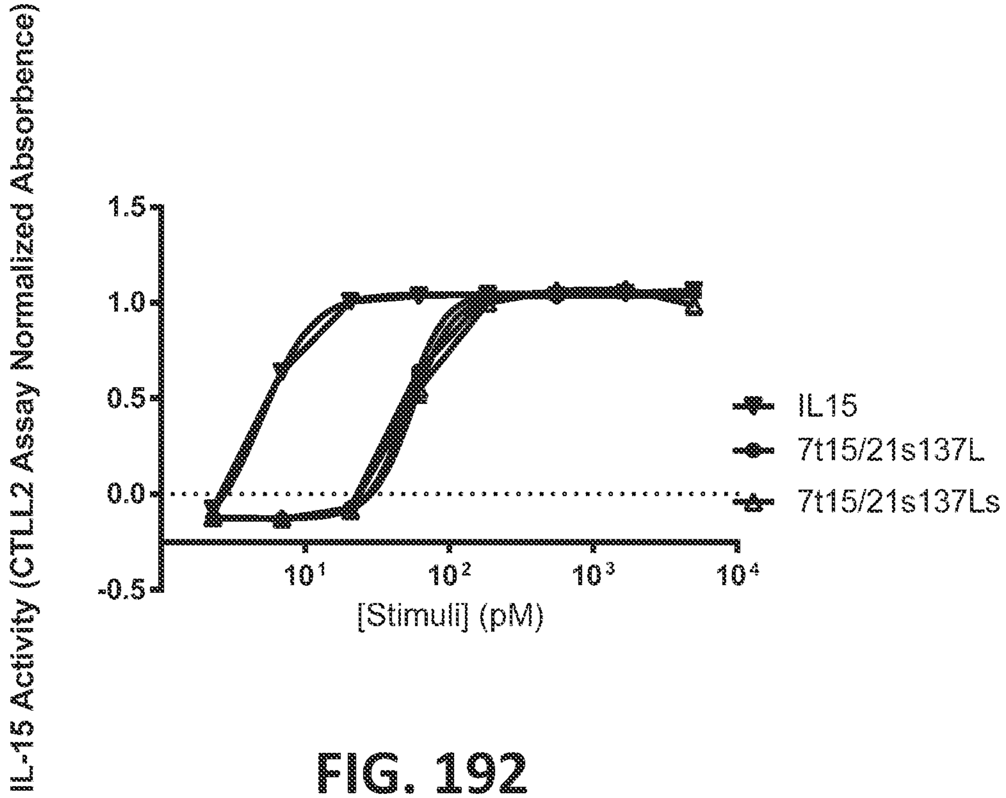

FIG. 192 shows IL-15 activity of 7t15-21s137L (long version) and 7t15-21s137L (short version) as evaluated by a IL2Rαβγ-containing CTLL2 cell proliferation assay.

Figure 193A:
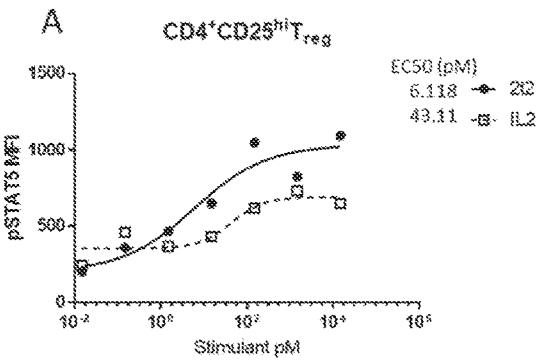
Figure 193B:
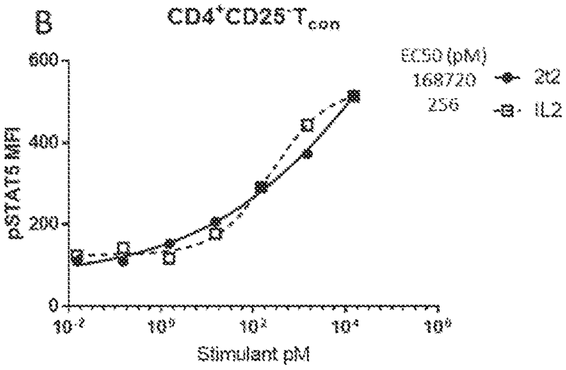
Figure 193C:
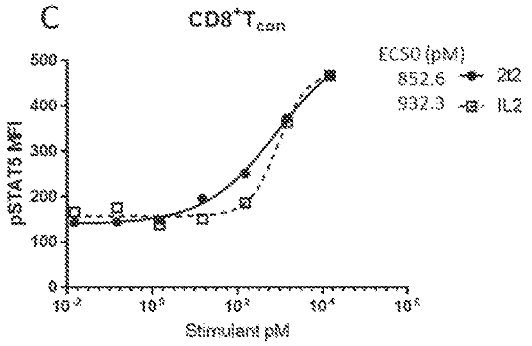

FIG. 193A-193C show human blood lymphocyte pStat5a responses in $CD4+CD25^{hi}T_{reg}$ cells, $CD4^{+}CD25^{-}$ $T_{con}$ cells, or in $CD8^{+}$ $T_{con}$ cells in response to 2t2 or IL2 treatment. FIG. 193A shows pSTAT5 responses in $CD4^{+}CD25^{+}$ $T_{reg}$ cells. FIG. 193B shows pSTAT5 responses in $CD4^{+}CD25^{-}$ $T_{con}$ cells. FIG. 193C shows pSTAT5 responses in $CD8^{+}$ $T_{con}$ cells.

Figure 194:
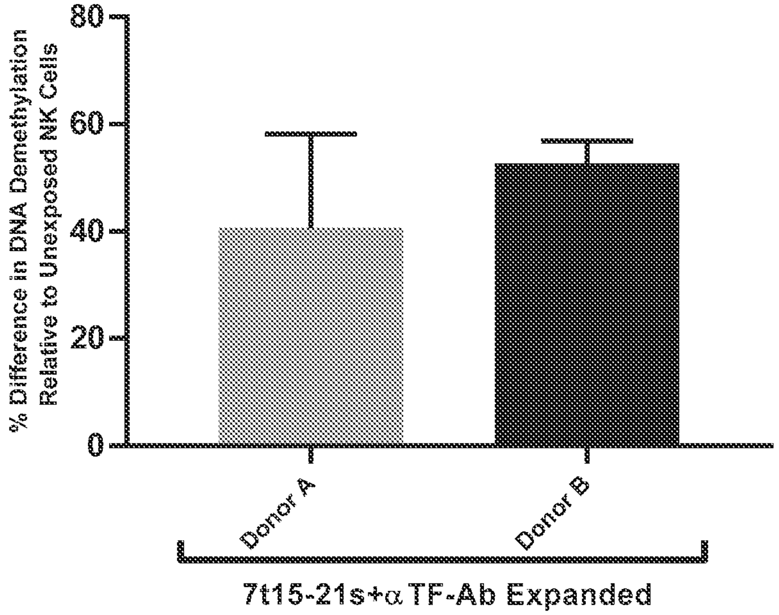

FIG. 194 is a graph showing the percentage different in DNA demethylation in NK cells (relative to unexposed NK cells) from two different donors following expansion with 7t15-21s+anti-tissue factor (TF)-antibody (IgG1) (50 nM).

DETAILED DESCRIPTION

Provided herein are a variety of single-chain and multi-chain chimeric polypeptides, methods of using them, and kits including them. In some embodiments, the single-chain and multi-chain chimeric polypeptides include a linker domain positioned between two target-binding domains. In some embodiments, the linker domain is or includes a soluble tissue factor domain. In some embodiments, the linker domain can be recognized by a cognate IgG1 antibody (e.g., a monoclonal antibody). In some embodiments, a single-chain or multi-chain chimeric polypeptide provided herein can be used to stimulate an immune cell, induce or increase proliferation of an immune cell, induce differentiation of an immune cell, or treat a subject in need thereof (e.g., a subject having cancer or an aging-related disease or condition).

Single Chain Chimeric Polypeptides

Some embodiments of any of the methods described herein include the use of any of the single chain chimeric polypeptides described herein. Some embodiments of any of the kits described herein include any of the single-chain chimeric polypeptides described herein. The single-chain chimeric polypeptides provided herein include a first target-binding domain, a linker domain, and a second target-binding domain, where the first target-binding domain and the second target-binding domain are each independently selected from the group consisting of a soluble interleukin or cytokine protein, an antigen-binding domain, and a soluble interleukin or cytokine receptor, and ligands of co-stimulatory molecules.

In some examples of any of the single-chain chimeric polypeptides described herein, the single-chain chimeric polypeptide can have a total length of about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids, about 360 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 950 amino acids to about 1000 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids.

In some embodiments of any of the single-chain chimeric polypeptides described herein, the first target-binding domain (e.g., any of the exemplary target-binding domains described herein or known in the art) and the linker domain (e.g., any of the exemplary linker described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the linker domain (e.g., any of the exemplary linker domains described herein). In some embodiments of any of the single-chain chimeric polypeptides described herein, the linker domain (e.g., any of the exemplary linker domains described herein) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the linker domain (e.g., any of the exemplary linker domains described herein) and the second target-binding domain (e.g., any of the exemplary target-binding domains described herein or known in the art).

In some embodiments of any of the single-chain chimeric polypeptides described herein, the first target-binding domain (e.g., any of the exemplary target-binding domains described herein or known in the art) and the second target-binding domain (e.g., any of the exemplary target-binding domains described herein or known in the art) directly abut each other. In some embodiments of any of the single-chain chimeric polypeptides described herein, the single-chain chimeric polypeptide further comprises a linker sequence (e.g., any of the exemplary linker sequences described herein or known in the art) between the first target-binding domain (e.g., any of the exemplary target-binding domains described herein or known in the art) and the second target-binding domain (e.g., any of the exemplary target-binding domains described herein or known in the art). In some embodiments of any of the single-chain chimeric polypeptides described herein, the second target-binding domain (e.g., any of the exemplary target-binding domains described herein or known in the art) and the linker domain (e.g., any of the exemplary linker domains described herein) directly abut each other. In some embodiments of any of the single-chain chimeric polypeptides described herein, the single-chain chimeric polypeptide further comprises a linker sequence (e.g., any of the exemplary linker sequences described herein or known in the art) between the second target-binding domain (e.g., any of the exemplary target-binding domains described herein or known in the art) and the linker domain (e.g., any of the exemplary linker domains described herein or known in the art).

Non-limiting aspects of these chimeric polypeptides, nucleic acids, vectors, cells, and methods are described below, and can be used in any combination without limitation. Additional aspects of these chimeric polypeptides, nucleic acids, vectors, cells, and methods are known in the art.

Multi-Chain Chimeric Polypeptides

Some embodiments of any of the methods described herein include the use of any of the multi-chain chimeric polypeptides described herein. Some embodiments of any of the kits described herein include any of the multi-chain chimeric polypeptides described herein.

The multi-chain chimeric polypeptides provided herein include: (a) a first chimeric polypeptide including: (i) a first target-binding domain; (ii) a linker domain; and (iii) a first domain of a pair of affinity domains; and (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains.

Figure 1:
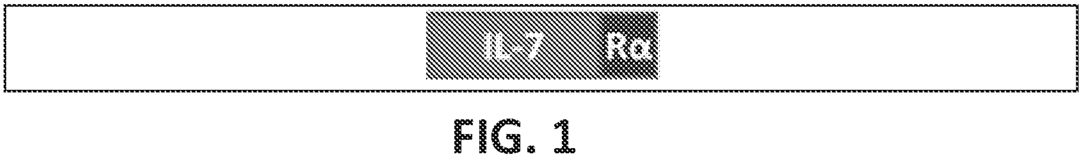
FIG. 1 shows a schematic diagram of an exemplary IL-7/IL-15RαSu DNA construct.
Figure 2:
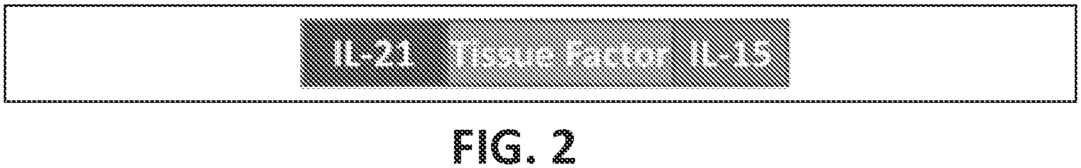
FIG. 2 shows a schematic diagram of an exemplary IL-21/TF/IL-15 DNA construct.

In some examples of any of the multi-chain chimeric polypeptides described herein the total length of first chimeric polypeptide and/or the second chimeric polypeptide can each independently be about 50 amino acids to about 3000 amino acids, about 50 amino acids to about 2500 amino acids, about 50 amino acids to about 2000 amino acids, about 50 amino acids to about 1500 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 480 amino acids, about 50 amino acids to about 460 amino acids, about 50 amino acids to about 440 amino acids, about 50 amino acids to about 420 amino acids, about 50 amino acids to about 400 amino acids, about 50 amino acids to about 380 amino acids, about 50 amino acids to about 360 amino acids, about 50 amino acids to about 340 amino acids, about 50 amino acids to about 320 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 150 amino acids, about 50 amino acids to about 100 amino acids, about 100 amino acids to about 3000 amino acids, about 100 amino acids to about 2500 amino acids, about 100 amino acids to about 2000 amino acids, about 100 amino acids to about 1500 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 480 amino acids, about 100 amino acids to about 460 amino acids, about 100 amino acids to about 440 amino acids, about 100 amino acids to about 420 amino acids, about 100 amino acids to about 400 amino acids, about 100 amino acids to about 380 amino acids, about 100 amino acids to about 360 amino acids, about 100 amino acids to about 340 amino acids, about 100 amino acids to about 320 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 150 amino acids, about 150 amino acids to about 3000 amino acids, about 150 amino acids to about 2500 amino acids, about 150 amino acids to about 2000 amino acids, about 150 amino acids to about 1500 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 480 amino acids, about 150 amino acids to about 460 amino acids, about 150 amino acids to about 440 amino acids, about 150 amino acids to about 420 amino acids, about 150 amino acids to about 400 amino acids, about 150 amino acids to about 380 amino acids, about 150 amino acids to about 360 amino acids, about 150 amino acids to about 340 amino acids, about 150 amino acids to about 320 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 200 amino acids to about 3000 amino acids, about 200 amino acids to about 2500 amino acids, about 200 amino acids to about 2000 amino acids, about 200 amino acids to about 1500 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 480 amino acids, about 200 amino acids to about 460 amino acids, about 200 amino acids to about 440 amino acids, about 200 amino acids to about 420 amino acids, about 200 amino acids to about 400 amino acids, about 200 amino acids to about 380 amino acids, about 200 amino acids to about 360 amino acids, about 200 amino acids to about 340 amino acids, about 200 amino acids to about 320 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 3000 amino acids, about 220 amino acids to about 2500 amino acids, about 220 amino acids to about 2000 amino acids, about 220 amino acids to about 1500 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 480 amino acids, about 220 amino acids to about 460 amino acids, about 220 amino acids to about 440 amino acids, about 220 amino acids to about 420 amino acids, about 220 amino acids to about 400 amino acids, about 220 amino acids to about 380 amino acids, about 220 amino acids to about 360 amino acids, about 220 amino acids to about 340 amino acids, about 220 amino acids to about 320 amino acids, about 220 amino acids to about 300 amino acids, about 220 amino acids to about 280 amino acids, about 220 amino acids to about 260 amino acids, about 220 amino acids to about 240 amino acids, about 240 amino acids to about 3000 amino acids, about 240 amino acids to about 2500 amino acids, about 240 amino acids to about 2000 amino acids, about 240 amino acids to about 1500 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 480 amino acids, about 240 amino acids to about 460 amino acids, about 240 amino acids to about 440 amino acids, about 240 amino acids to about 420 amino acids, about 240 amino acids to about 400 amino acids, about 240 amino acids to about 380 amino acids, about 240 amino acids to about 360 amino acids, about 240 amino acids to about 340 amino acids, about 240 amino acids to about 320 amino acids, about 240 amino acids to about 300 amino acids, about 240 amino acids to about 280 amino acids, about 240 amino acids to about 260 amino acids, about 260 amino acids to about 3000 amino acids, about 260 amino acids to about 2500 amino acids, about 260 amino acids to about 2000 amino acids, about 260 amino acids to about 1500 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 480 amino acids, about 260 amino acids to about 460 amino acids, about 260 amino acids to about 440 amino acids, about 260 amino acids to about 420 amino acids, about 260 amino acids to about 400 amino acids, about 260 amino acids to about 380 amino acids, about 260 amino acids to about 360 amino acids, about 260 amino acids to about 340 amino acids, about 260 amino acids to about 320 amino acids, about 260 amino acids to about 300 amino acids, about 260 amino acids to about 280 amino acids, about 280 amino acids to about 3000 amino acids, about 280 amino acids to about 2500 amino acids, about 280 amino acids to about 2000 amino acids, about 280 amino acids to about 1500 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 480 amino acids, about 280 amino acids to about 460 amino acids, about 280 amino acids to about 440 amino acids, about 280 amino acids to about 420 amino acids, about 280 amino acids to about 400 amino acids, about 280 amino acids to about 380 amino acids, about 280 amino acids to about 360 amino acids, about 280 amino acids to about 340 amino acids, about 280 amino acids to about 320 amino acids, about 280 amino acids to about 300 amino acids, about 300 amino acids to about 3000 amino acids, about 300 amino acids to about 2500 amino acids, about 300 amino acids to about 2000 amino acids, about 300 amino acids to about 1500 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 480 amino acids, about 300 amino acids to about 460 amino acids, about 300 amino acids to about 440 amino acids, about 300 amino acids to about 420 amino acids, about 300 amino acids to about 400 amino acids, about 300 amino acids to about 380 amino acids, about 300 amino acids to about 360 amino acids, about 300 amino acids to about 340 amino acids, about 300 amino acids to about 320 amino acids, about 320 amino acids to about 3000 amino acids, about 320 amino acids to about 2500 amino acids, about 320 amino acids to about 2000 amino acids, about 320 amino acids to about 1500 amino acids, about 320 amino acids to about 1000 amino acids, about 320 amino acids to about 950 amino acids, about 320 amino acids to about 900 amino acids, about 320 amino acids to about 850 amino acids, about 320 amino acids to about 800 amino acids, about 320 amino acids to about 750 amino acids, about 320 amino acids to about 700 amino acids, about 320 amino acids to about 650 amino acids, about 320 amino acids to about 600 amino acids, about 320 amino acids to about 550 amino acids, about 320 amino acids to about 500 amino acids, about 320 amino acids to about 480 amino acids, about 320 amino acids to about 460 amino acids, about 320 amino acids to about 440 amino acids, about 320 amino acids to about 420 amino acids, about 320 amino acids to about 400 amino acids, about 320 amino acids to about 380 amino acids, about 320 amino acids to about 360 amino acids, about 320 amino acids to about 340 amino acids, about 340 amino acids to about 3000 amino acids, about 340 amino acids to about 2500 amino acids, about 340 amino acids to about 2000 amino acids, about 340 amino acids to about 1500 amino acids, about 340 amino acids to about 1000 amino acids, about 340 amino acids to about 950 amino acids, about 340 amino acids to about 900 amino acids, about 340 amino acids to about 850 amino acids, about 340 amino acids to about 800 amino acids, about 340 amino acids to about 750 amino acids, about 340 amino acids to about 700 amino acids, about 340 amino acids to about 650 amino acids, about 340 amino acids to about 600 amino acids, about 340 amino acids to about 550 amino acids, about 340 amino acids to about 500 amino acids, about 340 amino acids to about 480 amino acids, about 340 amino acids to about 460 amino acids, about 340 amino acids to about 440 amino acids, about 340 amino acids to about 420 amino acids, about 340 amino acids to about 400 amino acids, about 340 amino acids to about 380 amino acids, about 340 amino acids to about 360 amino acids, about 360 amino acids to about 3000 amino acids, about 360 amino acids to about 2500 amino acids, about 360 amino acids to about 2000 amino acids, about 360 amino acids to about 1500 amino acids, about 360 amino acids to about 1000 amino acids, about 360 amino acids to about 950 amino acids, about 360 amino acids to about 900 amino acids, about 360 amino acids to about 850 amino acids, about 360 amino acids to about 800 amino acids, about 360 amino acids to about 750 amino acids, about 360 amino acids to about 700 amino acids, about 360 amino acids to about 650 amino acids, about 360 amino acids to about 600 amino acids, about 360 amino acids to about 550 amino acids, about 360 amino acids to about 500 amino acids, about 360 amino acids to about 480 amino acids, about 360 amino acids to about 460 amino acids, about 360 amino acids to about 440 amino acids, about 360 amino acids to about 420 amino acids, about 360 amino acids to about 400 amino acids, about 360 amino acids to about 380 amino acids, about 380 amino acids to about 3000 amino acids, about 380 amino acids to about 2500 amino acids, about 380 amino acids to about 2000 amino acids, about 380 amino acids to about 1500 amino acids, about 380 amino acids to about 1000 amino acids, about 380 amino acids to about 950 amino acids, about 380 amino acids to about 900 amino acids, about 380 amino acids to about 850 amino acids, about 380 amino acids to about 800 amino acids, about 380 amino acids to about 750 amino acids, about 380 amino acids to about 700 amino acids, about 380 amino acids to about 650 amino acids, about 380 amino acids to about 600 amino acids, about 380 amino acids to about 550 amino acids, about 380 amino acids to about 500 amino acids, about 380 amino acids to about 480 amino acids, about 380 amino acids to about 460 amino acids, about 380 amino acids to about 440 amino acids, about 380 amino acids to about 420 amino acids, about 380 amino acids to about 400 amino acids, about 400 amino acids to about 3000 amino acids, about 400 amino acids to about 2500 amino acids, about 400 amino acids to about 2000 amino acids, about 400 amino acids to about 1500 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 480 amino acids, about 400 amino acids to about 460 amino acids, about 400 amino acids to about 440 amino acids, about 400 amino acids to about 420 amino acids, about 420 amino acids to about 3000 amino acids, about 420 amino acids to about 2500 amino acids, about 420 amino acids to about 2000 amino acids, about 420 amino acids to about 1500 amino acids, about 420 amino acids to about 1000 amino acids, about 420 amino acids to about 950 amino acids, about 420 amino acids to about 900 amino acids, about 420 amino acids to about 850 amino acids, about 420 amino acids to about 800 amino acids, about 420 amino acids to about 750 amino acids, about 420 amino acids to about 700 amino acids, about 420 amino acids to about 650 amino acids, about 420 amino acids to about 600 amino acids, about 420 amino acids to about 550 amino acids, about 420 amino acids to about 500 amino acids, about 420 amino acids to about 480 amino acids, about 420 amino acids to about 460 amino acids, about 420 amino acids to about 440 amino acids, about 440 amino acids to about 3000 amino acids, about 440 amino acids to about 2500 amino acids, about 440 amino acids to about 2000 amino acids, about 440 amino acids to about 1500 amino acids, about 440 amino acids to about 1000 amino acids, about 440 amino acids to about 950 amino acids, about 440 amino acids to about 900 amino acids, about 440 amino acids to about 850 amino acids, about 440 amino acids to about 800 amino acids, about 440 amino acids to about 750 amino acids, about 440 amino acids to about 700 amino acids, about 440 amino acids to about 650 amino acids, about 440 amino acids to about 600 amino acids, about 440 amino acids to about 550 amino acids, about 440 amino acids to about 500 amino acids, about 440 amino acids to about 480 amino acids, about 440 amino acids to about 460 amino acids, about 460 amino acids to about 3000 amino acids, about 460 amino acids to about 2500 amino acids, about 460 amino acids to about 2000 amino acids, about 460 amino acids to about 1500 amino acids, about 460 amino acids to about 1000 amino acids, about 460 amino acids to about 950 amino acids, about 460 amino acids to about 900 amino acids, about 460 amino acids to about 850 amino acids, about 460 amino acids to about 800 amino acids, about 460 amino acids to about 750 amino acids, about 460 amino acids to about 700 amino acids, about 460 amino acids to about 650 amino acids, about 460 amino acids to about 600 amino acids, about 460 amino acids to about 550 amino acids, about 460 amino acids to about 500 amino acids, about 460 amino acids to about 480 amino acids, about 480 amino acids to about 3000 amino acids, about 480 amino acids to about 2500 amino acids, about 480 amino acids to about 2000 amino acids, about 480 amino acids to about 1500 amino acids, about 480 amino acids to about 1000 amino acids, about 480 amino acids to about 950 amino acids, about 480 amino acids to about 900 amino acids, about 480 amino acids to about 850 amino acids, about 480 amino acids to about 800 amino acids, about 480 amino acids to about 750 amino acids, about 480 amino acids to about 700 amino acids, about 480 amino acids to about 650 amino acids, about 480 amino acids to about 600 amino acids, about 480 amino acids to about 550 amino acids, about 480 amino acids to about 500 amino acids, about 500 amino acids to about 3000 amino acids, about 500 amino acids to about 2500 amino acids, about 500 amino acids to about 2000 amino acids, about 500 amino acids to about 1500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 3000 amino acids, about 550 amino acids to about 2500 amino acids, about 550 amino acids to about 2000 amino acids, about 550 amino acids to about 1500 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 3000 amino acids, about 600 amino acids to about 2500 amino acids, about 600 amino acids to about 2000 amino acids, about 600 amino acids to about 1500 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 3000 amino acids, about 650 amino acids to about 2500 amino acids, about 650 amino acids to about 2000 amino acids, about 650 amino acids to about 1500 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 3000 amino acids, about 700 amino acids to about 2500 amino acids, about 700 amino acids to about 2000 amino acids, about 700 amino acids to about 1500 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 3000 amino acids, about 750 amino acids to about 2500 amino acids, about 750 amino acids to about 2000 amino acids, about 750 amino acids to about 1500 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 3000 amino acids, about 800 amino acids to about 2500 amino acids, about 800 amino acids to about 2000 amino acids, about 800 amino acids to about 1500 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 3000 amino acids, about 850 amino acids to about 2500 amino acids, about 850 amino acids to about 2000 amino acids, about 850 amino acids to about 1500 amino acids, about 850 amino acids to about 1000 amino acids, about 850 amino acids to about 950 amino acids, about 850 amino acids to about 900 amino acids, about 900 amino acids to about 3000 amino acids, about 900 amino acids to about 2500 amino acids, about 900 amino acids to about 2000 amino acids, about 900 amino acids to about 1500 amino acids, about 900 amino acids to about 1000 amino acids, about 900 amino acids to about 950 amino acids, about 950 amino acids to about 3000 amino acids, about 950 amino acids to about 2500 amino acids, about 950 amino acids to about 2000 amino acids, about 950 amino acids to about 1500 amino acids, about 950 amino acids to about 1000 amino acids, about 1000 amino acids to about 3000 amino acids, about 1000 amino acids to about 2500 amino acids, about 1000 amino acids to about 2000 amino acids, about 1000 amino acids to about 1500 amino acids, about 1500 amino acids to about 3000 amino acids, about 1500 amino acids to about 2500 amino acids, about 1500 amino acids to about 2000 amino acids, about 2000 amino acids to about 3000 amino acids, about 2000 amino acids to about 2500 amino acids, or about 2500 amino acids to about 3000 amino acids. Diagrams of exemplary multi-chain chimeric polypeptides provided herein are depicted in FIGS. 1 and 2.

In some embodiments of any of the multi-chain chimeric polypeptides described herein, the first target-binding domain (e.g., any of the first target-binding domains described herein) and the linker domain (e.g., any of the exemplary linker domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the first target-binding domain (e.g., any of the exemplary first target-binding domains described herein) and the linker domain (e.g., any of the exemplary linker domains described herein) in the first chimeric polypeptide.

In some embodiments of any of the multi-chain chimeric polypeptides described herein, the linker domain (e.g., any of the exemplary linker domains described herein) and the first domain of the pair of affinity domains (e.g., any of the exemplary first domains of any of the exemplary pairs of affinity domains described herein) directly abut each other in the first chimeric polypeptide. In some embodiments of any of the multi-chain chimeric polypeptides described herein, the first chimeric polypeptide further comprises a linker sequence (e.g., any of the exemplary linker sequences described herein or known in the art) between the linker domain (e.g., any of the exemplary linker domains described herein) and the first domain of the pair of affinity domains (e.g., any of the exemplary first domains of any of the exemplary pairs of affinity domains described herein) in the first chimeric polypeptide.

In some embodiments of any of the multi-chain chimeric polypeptides described herein, the second domain of the pair of affinity domains (e.g., any of the exemplary second domains of any of the exemplary pairs of affinity domains described herein) and the second target-binding domain (e.g., any of the exemplary second target-binding domains described herein) directly abut each other in the second chimeric polypeptide. In some embodiments of any of the multi-chain chimeric polypeptides described herein, the second chimeric polypeptide further comprises a linker sequence (e.g., any of the exemplary linker sequences described herein or known in the art) between the second domain of the pair of affinity domains (e.g., any of the exemplary second domains of any of the exemplary pairs of affinity domains described herein) and the second target-binding domain (e.g., any of the exemplary second target-binding domains described herein) in the second chimeric polypeptide.

Tissue Factor

Human tissue factor is a 263 amino-acid transmembrane protein containing three domains: (1) a 219-amino acid N-terminal extracellular domain (residues 1-219); (2) a 22-amino acid transmembrane domain (residues 220-242); and (3) a 21-amino acid cytoplasmic C-terminal tail (residues 242-263) ((UniProtKB Identifier Number: P13726). The cytoplasmic tail contains two phosphorylation sites at $Ser^{253}$ and $Ser^{258}$, and one S-palmitoylation site at $Cys^{245}$. Deletion or mutation of the cytoplasmic domain was not found to affect tissue factor coagulation activity. Tissue factor has one S-palmitoylation site in the intracellular domain of the protein at $Cys^{245}$ The $Cys^{245}$ is located at the amino acid terminus of the intracellular domain and close to the membrane surface. The tissue factor transmembrane domain is composed of a single-spanning α-helix.

The extracellular domain of tissue factor, composed of two fibronectin type III domains, is connected to the transmembrane domain through a six-amino acid linker. This linker provides conformational flexibility to decouple the tissue factor extracellular domain from its transmembrane and cytoplasmic domains. Each tissue factor fibronectin type III module is composed of two overlapping β sheets with the top sheet domain containing three antiparallel β-strands and the bottom sheet containing four β-strands. The β-strands are connected by β-loops between strand βA and βB, βC and βD, and βE and βF, all of which are conserved in conformation in the two modules. There are three short α-helix segments connecting the β-strands. A unique feature of tissue factor is a 17-amino acid β-hairpin between strand β10 and strand β11, which is not a common element of the fibronectin superfamily. The N-terminal domain also contains a 12 amino acid loop between β6F and β7G that is not present in the C-terminal domain and is unique to tissue factor. Such a fibronectin type III domain structure is a feature of the immunoglobulin-like family of protein folds and is conserved among a wide variety of extracellular proteins.

The zymogen FVII is rapidly converted to FVIIa by limited proteolysis once it binds to tissue to form the active tissue factor-FVIIa complex. The FVIIa, which circulates as an enzyme at a concentration of approximately 0.1 nM (1% of plasma FVII), can also bind directly to tissue factor. The allosteric interaction between tissue factor and FVIIa on the tissue factor-FVIIa complex greatly increases the enzymatic activity of FVIIa: an approximate 20- to 100-fold increase in the rate of hydrolysis of small, chromogenic peptidyl substrates, and nearly a million-fold increase in the rate of activation of the natural macromolecular substrates FIX and FX. In concert with allosteric activation of the active site of FVIIa upon binding to tissue factor, the formation of tissue factor-FVIIa complex on phospholipid bilayer (i.e., upon exposure of phosphatidyl-L-serine on membrane surfaces) increases the rate of FIX or FX activation, in a $Ca^{2+}$-dependent manner, an additional 1,000-fold. The roughly million-fold overall increase in FX activation by tissue factor-FVIIa-phospholipid complex relative to free FVIIa is a critical regulatory point for the coagulation cascade.

FVII is a ~50 kDa, single-chain polypeptide consisting of 406 amino acid residues, with an N-terminal γ-carboxyglutamate-rich (GLA) domain, two epidermal growth factor-like domains (EGF1 and EFG2), and a C-terminal serine protease domain. FVII is activated to FVIIa by a specific proteolytic cleavage of the $Ile\text{-}^{154}\text{-}Arg^{152}$ bond in the short linker region between the EGF2 and the protease domain. This cleavage results in the light and heavy chains being held together by a single disulfide bond of $Cys^{135}$ and $Cys^{262}$. FVIIa binds phospholipid membrane in a $Ca^{2+}$-dependent manner through its N-terminal GLA-domain. Immediately C-terminal to the GLA domain is an aromatic stack and two EGF domains. The aromatic stack connects the GLA to EGF1 domain which binds a single $Ca^{2+}$ ion. Occupancy of this $Ca^{2+}$-binding site increases FVIIa amidolytic activity and tissue factor association. The catalytic triad consist of $His^{193}$, $Asp^{242}$, and $Ser^{344}$, and binding of a single $Ca^{2+}$ ion within the FVIIa protease domain is critical for its catalytic activity. Proteolytic activation of FVII to FVIIa frees the newly formed amino terminus at $Ile^{153}$ to fold back and be inserted into the activation pocket forming a salt bridge with the carboxylate of $Asp^{343}$ to generate the oxyanion hole. Formation of this salt bridge is critical for FVIIa activity. However, oxyanion hole formation does not occur in free FVIIa upon proteolytic activation. As a result, FVIIa circulates in a zymogen-like state that is poorly recognized by plasma protease inhibitors, allowing it to circulate with a half-life of approximately 90 minutes.

Tissue factor-mediated positioning of the FVIIa active site above the membrane surface is important for FVIIa towards cognate substrates. Free FVIIa adopts a stable, extended structure when bound to the membrane with its active site positioned ~80 Å above the membrane surface. Upon FVIIa binding to tissue factor, the FVa active site is repositioned ~6 Å closer to the membrane. This modulation may aid in a proper alignment of the FVIIa catalytic triad with the target substrate cleavage site. Using GLA-domainless FVIIa, it has been shown that the active site was still positioned a similar distance above the membrane, demonstrating that tissue factor is able to fully support FVIIa active site positioning even in the absence of FVIIa-membrane interaction. Additional data showed that tissue factor supported full FVIIa proteolytic activity as long as the tissue factor extracellular domain was tethered in some way to the membrane surface. However, raising the active site of FVIIa greater than 80A above the membrane surface greatly reduced the ability of the tissue factor-FVIIa complex to activate FX but did not diminish tissue factor-FVIIa amidolytic activity.

Alanine scanning mutagenesis has been used to assess the role of specific amino acid side chains in the tissue factor extracellular domain for interaction with FVIIa (Gibbs et al., *Biochemistry* 33(47): 14003-14010, 1994; Schullek et al., *J Biol Chem* 269(30): 19399-19403, 1994). Alanine substitution identified a limited number of residue positions at which alanine replacements cause 5- to 10-fold lower affinity for FVIIa binding. Most of these residue side chains were found to be well-exposed to solvent in the crystal structure, concordant with macromolecular ligand interaction. The FVIIa ligand-binding site is located over an extensive region at the boundary between the two modules. In the C-module, residues $Arg^{135}$ and $Phe^{140}$ located on the protruding B-C loop provide an independent contact with FVIIa. $Leu^{133}$ is located at the base of the fingerlike structure and packed into the cleft between the two modules. This provides continuity to a major cluster of important binding residues consisting of $Lys^{20}$, $Thr^{60}$, $Asp^{58}$, and $Ile^{22}$. $Thr^{60}$ is only partially solvent-exposed and may play a local structural role rather than making a significant contact with ligand. The binding site extends onto the concave side of the intermodule angle involving $Glu^{24}$ and $Gln^{110}$, and potentially the more distant residue $Val^{207}$. The binding region extends from Asp58 onto a convex surface area formed by $Lys^{48}$, $Lys^{46}$, $Gln^{37}$, $Asp^{44}$, and $Trp^{45}$. $Trp^{45}$ and $Asp^{44}$ do not interact independently with FVIIa, indicating that the mutational effect at the $Trp^{45}$ position may reflect a structural importance of this side chain for the local packing of the adjacent $Asp^{44}$ and $Gln^{37}$ side chain. The interactive area further includes two surface-exposed aromatic residues, $Phe^{76}$ and $Tyr^{78}$, which form part of the hydrophobic cluster in the N-module.

The known physiologic substrates of tissue factor-FVIIa are FVII, FIX, and FX and certain proteinase-activated receptors. Mutational analysis has identified a number of residues that, when mutated, support full FVIIa amidolytic activity towards small peptidyl substrates but are deficient in their ability to support macromolecular substrate (i.e., FVII, FIX, and FX) activation (Ruf et al., *J Biol Chem* 267(31): 22206-22210, 1992; Ruf et al., *J Biol Chem* 267(9): 6375-6381, 1992; Huang et al., *J Biol Chem* 271(36): 21752-21757, 1996; Kirchhofer et al., *Biochemistry* 39(25): 7380-7387, 2000). The tissue factor loop region at residues 159-165, and residues in or adjacent to this flexible loop have been shown to be critical for the proteolytic activity of the tissue factor-FVIIa complex. This defines the proposed substrate-binding exosite region of tissue factor that is quite distant from the FVIIa active site. A substitution of the glycine residue by a marginally bulkier residue alanine, significantly impairs tissue factor-FVIIa proteolytic activity. This suggests that the flexibility afforded by glycine is critical for the loop of residues 159-165 for tissue factor macromolecular substrate recognition.

The residues $Lys^{165}$ and $Lys^{166}$ have also been demonstrated to be important for substrate recognition and binding. Mutation of either of these residues to alanine results in a significant decrease in the tissue factor co-factor function. $Lys^{165}$ and $Lys^{166}$ face away from each other, with $Lys^{165}$ pointing towards FVIIa in most tissue factor-FVIIa structures, and $Lys^{166}$ pointing into the substrate binding exosite region in the crystal structure. Putative salt bridge formation between $Lys^{165}$ of and $Gla^{35}$ of FVIIa would support the notion that tissue factor interaction with the GLA domain of FVIIa modulates substrate recognition. These results suggest that the C-terminal portion of the tissue factor ectodomain directly interacts with the GLA-domain, the possible adjacent EGF1 domains, of FIX and FX, and that the presence of the FVIIa GLA-domain may modulate these interactions either directly or indirectly.

Exemplary Linker Domains and IgG1 Antibody Constructs

In some examples of any of the methods, compositions, or kits described herein, the linker domain can be or include any antigen that is recognized by a cognate IgG1 antibody (e.g., a monoclonal antibody). IgG1 antibodies are distinguished from other IgG classes of antibodies by their constant region, particularly in hinge regions and upper CH2 domains (see, e.g., Vadarsson et al., IgG Subclasses and Allotypes: From Structure to Effector Functions, Front Immunol., 5, Article 520, 2014). Human IgG1 is the only known IgG subclass which binds to human CD16a and activates the signaling of human CD16a.

Any of a variety of linker domains can be used in the single-chain chimeric polypeptides and multi-chain chimeric polypeptides provided herein. In certain embodiments, a linker domain is recognized by an antibody (e.g., an IgG1 antibody) or antibody fragment. In some embodiments, the linker domain is a kappa light chain of an antibody that is recognized by a cognate anti-kappa light chain IgG1 antibody. In some embodiments, the linker domain is a lambda light chain of an antibody that is recognized by a cognate anti-lambda light chain human IgG1 antibody. A variety of kappa light chains and lambda light chains are known in the art (see, e.g., Smith et al., Antigen Nature and Complexity Influence Human Antibody Light Chain Usage and Specificity, Vaccine, 34(25): 2813-2820, 2016). In some embodiments, the linker domain is or comprises a human polypeptide (e.g., a human kappa light chain of an antibody or a human lambda light chain of an antibody) that is recognized by a cognate human IgG1 antibody (e.g., a monoclonal antibody). In some embodiments, the cognate human IgG1 antibody includes at least two antigen-binding domains, and each antigen-binding domain binds specifically to the linker domain. In some embodiments, the cognate human IgG1 antibody includes at least two antigen-binding domains, and only a subset (e.g., one) of the antigen-binding domains bind specifically to the linker domain. In some embodiments, a linker domain can be any of the soluble tissue factor domains described herein.

In some embodiments of any of the methods, compositions, and kits described herein, an IgG1 antibody construct can be an IgG1 antibody (e.g., a monoclonal or a polyclonal IgG1 antibody that binds specifically to the linker domain). In some embodiments of any of the methods, compositions, and kits described herein, an IgG1 antibody construct can be an antibody or an antibody fragment that includes an IgG1 Fc region (e.g., a human IgG1 Fc region) and that binds specifically to the linker domain. As is known in the art, the IgG1 Fc region binds to CD16a (FcRgammaIII) (e.g., human CD16a) and induces its intracellular signaling. In some embodiments, an IgG1 antibody construct can be a single chain or a multi-chain polypeptide that includes an Fc region that is capable of binding specifically to CD16a (FcRgammaIII) (e.g., human CD16a) and is capable of inducing its intracellular signaling in a natural killer cell (e.g., a human natural killer cell), and specifically binds to the linker domain. In some embodiments, an IgG1 antibody construct can be a single chain or a multi-chain polypeptide that includes an Fc region that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, or at least 99% identical) to a wildtype IgG1 Fc domain (e.g., a wildtype human IgG1 Fc domain, e.g., SEQ ID NO: 96) and is capable of binding specifically to CD16a (FcRgammaIII) (e.g., human CD16a), and is capable of inducing its intracellular signaling in a natural killer cell (e.g., a human natural killer cell), and specifically binds to the linker domain. In some embodiments of any of the methods, compositions, or kits described herein, the IgG1 antibody construct can be an antibody or antibody fragment that specifically binds to the linker domain and includes a non-IgG1 Fc region (e.g., an IgG2, IgG3, or IgG4 Fc region) that has been altered (e.g., by substituting 1, 2, 3, 4, 5, 6, 7, 8, 9, 10, 11, 12, 13, 14, 15, 16, 17, 18, 19, or 20 amino acids in the wildtype non-IgG1 Fc region) such that the non-IgG1 Fc region is capable of binding to CD16a (FcRgammaIII) (e.g., human CD16a) and inducing its intracellular signaling in a natural killer cell (e.g., a human natural killer cell). In some embodiments of any of the methods, compositions, or kits described herein, the IgG1 antibody construct binds specifically to the linker domain and includes a non-human Fc region (e.g., a Fc region from a non-human antibody) that has been altered (e.g., by substituting 1, 2, 3, 4, 5, 6, 7, 8, 9, 10, 11, 12, 13, 14, 15, 16, 17, 18, 19, or 20 amino acids in the wildtype non-human Fc region) such that the non-human Fc region is capable of binding to human CD16a (human FcRgammaIII) and inducing its intracellular signaling in a natural killer cell (e.g., a human natural killer cell).

```
Wildtype Human IgG1 Fc Region
                                        (SEQ ID NO: 96)
PCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSN

KALPAPIEKTISKAKGQPREPQVYTLPPSRDELTKNQVSLTCLVKGFYP

SDIAVEWESNGQPENNYKTTPPVLDSDGSFFLYSKLTVDKSRWQQGNVF

SCSVMHEALHNHYTQKSLSLSPGK

Wildtype Human IgG2 Fc Region
                                        (SEQ ID NO: 97)
APPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLP

APIEKTISKTKGQPREPQVYTLPPSREEMTKNQVSLTCLVKGFYPSDIS

VEWESNGQPENNYKTTPPMLDSDGSFFLYSKLTVDKSRWQQGNVFSCSV

MHEALHNHYTQKSLSLSPGK

Wildtype Human IgG3 Fc Region
                                        (SEQ ID NO: 98)
APELLGGPSVFLFPPKPKDTLMISRTPEVTCVVVDVSHEDPEVQFKWYV

DGVEVHNAKTKPREEQYNSTFRVVSVLTVLHQDWLNGKEYKCKVSNKAL

PAPIEKTISKTKGQPREPQVYTLPPSREEMTKNQVSLTCLVKGFYPSDI

AVEWESSGQPENNYNTTPPMLDSDGSFFLYSKLTVDKSRWQQGNIFSCS

VMHEALHNRFTQKSLSLSPGK
```

-continued

Wildtype Human IgG4 Fc Region (SEQ ID NO: 99)

APEFLGGPSVFLFPPKPKDTLMISRTPEVTCVVVDVSQEDPEVQFNWYV

DGVEVHNAKTKPREEQFNSTYRVVSVLTVLHQDWLNGKEYKCKVSNKGL

PSSIEKTISKAKGQPREPQVYTLPPSQEEMTKNQVSLTCLVKGFYPSDI

AVEWESNGQPENNYKTTPPVLDSDGSFFLYSRLTVDKSRWQEGNVFSCS

VMHEALHNHYTQKSLSLSLGK

In some embodiments, the linker domain can have a total length of about 20 amino acids to about 220 amino acids, about 20 amino acids to about 215 amino acids, about 20 amino acids to about 210 amino acids, about 20 amino acids to about 205 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids, about 30 amino acids to about 220 amino acids, about 30 amino acids to about 215 amino acids, about 30 amino acids to about 210 amino acids, about 30 amino acids to about 205 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 60 amino acids, about 30 amino acids to about 50 amino acids, about 30 amino acids to about 40 amino acids, about 40 amino acids to about 220 amino acids, about 40 amino acids to about 215 amino acids, about 40 amino acids to about 210 amino acids, about 40 amino acids to about 205 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 60 amino acids, about 40 amino acids to about 50 amino acids, about 50 amino acids to about 220 amino acids, about 50 amino acids to about 215 amino acids, about 50 amino acids to about 210 amino acids, about 50 amino acids to about 205 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 60 amino acids, about 60 amino acids to about 220 amino acids, about 60 amino acids to about 215 amino acids, about 60 amino acids to about 210 amino acids, about 60 amino acids to about 205 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 70 amino acids to about 220 amino acids, about 70 amino acids to about 215 amino acids, about 70 amino acids to about 210 amino acids, about 70 amino acids to about 205 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 80 amino acids to about 220 amino acids, about 80 amino acids to about 215 amino acids, about 80 amino acids to about 210 amino acids, about 80 amino acids to about 205 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 90 amino acids to about 220 amino acids, about 90 amino acids to about 215 amino acids, about 90 amino acids to about 210 amino acids, about 90 amino acids to about 205 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 100 amino acids to about 220 amino acids, about 100 amino acids to about 215 amino acids, about 100 amino acids to about 210 amino acids, about 100 amino acids to about 205 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 110 amino acids to about 220 amino acids, about 110 amino acids to about 215 amino acids, about 110 amino acids to about 210 amino acids, about 110 amino acids to about 205 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 220 amino acids, about 115 amino acids to about 215 amino acids, about 115 amino acids to about 210 amino acids, about 115 amino acids to about 205 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 220 amino acids, about 120 amino acids to about 215 amino acids, about 120 amino acids to about 210 amino acids, about 120 amino acids to about 205 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 220 amino acids, about 125 amino acids to about 215 amino acids, about 125 amino acids to about 210 amino acids, about 125 amino acids to about 205 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 220 amino acids, about 130 amino acids to about 215 amino acids, about 130 amino acids to about 210 amino acids, about 130 amino acids to about 205 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 220 amino acids, about 135 amino acids to about 215 amino acids, about 135 amino acids to about 210 amino acids, about 135 amino acids to about 205 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 220 amino acids, about 140 amino acids to about 215 amino acids, about 140 amino acids to about 210 amino acids, about 140 amino acids to about 205 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 220 amino acids, about 145 amino acids to about 215 amino acids, about 145 amino acids to about 210 amino acids, about 145 amino acids to about 205 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 220 amino acids, about 150 amino acids to about 215 amino acids, about 150 amino acids to about 210 amino acids, about 150 amino acids to about 205 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 220 amino acids, about 155 amino acids to about 215 amino acids, about 155 amino acids to about 210 amino acids, about 155 amino acids to about 205 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 220 amino acids, about 160 amino acids to about 215 amino acids, about 160 amino acids to about 210 amino acids, about 160 amino acids to about 205 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 220 amino acids, about 165 amino acids to about 215 amino acids, about 165 amino acids to about 210 amino acids, about 165 amino acids to about 205 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 220 amino acids, about 170 amino acids to about 215 amino acids, about 170 amino acids to about 210 amino acids, about 170 amino acids to about 205 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 220 amino acids, about 175 amino acids to about 215 amino acids, about 175 amino acids to about 210 amino acids, about 175 amino acids to about 205 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 220 amino acids, about 180 amino acids to about 215 amino acids, about 180 amino acids to about 210 amino acids, about 180 amino acids to about 205 amino acids, about 180 amino acids to about 200 amino acids, about 180 amino acids to about 195 amino acids, about 180 amino acids to about 190 amino acids, about 180 amino acids to about 185 amino acids, about 185 amino acids to about 220 amino acids, about 185 amino acids to about 215 amino acids, about 185 amino acids to about 210 amino acids, about 185 amino acids to about 205 amino acids, about 185 amino acids to about 200 amino acids, about 185 amino acids to about 195 amino acids, about 185 amino acids to about 190 amino acids, about 190 amino acids to about 220 amino acids, about 190 amino acids to about 215 amino acids, about 190 amino acids to about 210 amino acids, about 190 amino acids to about 205 amino acids, about 190 amino acids to about 200 amino acids, about 190 amino acids to about 195 amino acids, about 195 amino acids to about 220 amino acids, about 195 amino acids to about 215 amino acids, about 195 amino acids to about 210 amino acids, about 195 amino acids to about 205 amino acids, about 195 amino acids to about 200 amino acids, about 200 amino acids to about 220 amino acids, about 200 amino acids to about 215 amino acids, about 200 amino acids to about 210 amino acids, about 200 amino acids to about 205 amino acids, about 205 amino acids to about 220 amino acids, about 205 amino acids to about 215 amino acids, about 205 amino acids to about 210 amino acids, about 210 amino acids to about 220 amino acids, about 210 amino acids to about 215 amino acids, or about 215 amino acids to about 220 amino acids.

Soluble Tissue Factor Domain

In some examples of any of the methods, compositions, or kits described herein, the linker domain can be a soluble tissue factor domain. In some embodiments, the soluble tissue factor domain can be a wildtype tissue factor polypeptide lacking the signal sequence, the transmembrane domain, and the intracellular domain. In some examples, the soluble tissue factor domain can be a tissue factor mutant, wherein a wildtype tissue factor polypeptide lacking the signal sequence, the transmembrane domain, and the intracellular domain, and has been further modified at selected amino acids. In some examples, the soluble tissue factor domain can be a soluble human tissue factor domain. In some examples, the soluble tissue factor domain can be a soluble mouse tissue factor domain. In some examples, the soluble tissue factor domain can be a soluble rat tissue factor domain. Non-limiting examples of soluble human tissue factor domains, a mouse soluble tissue factor domain, a rat soluble tissue factor domain, and mutant soluble tissue factor domains are shown below.

```
Exemplary Soluble Human Tissue Factor Domain
                                   (SEQ ID NO: 1)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE
```

```
Exemplary Nucleic Acid Encoding Soluble Human
Tissue Factor Domain
                                   (SEQ ID NO: 2)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG
```

```
Exemplary Soluble Mouse Tissue Factor Domain
                                   (SEQ ID NO: 3)
AGIPEKAFNLTWISTDFKTILEWQPKPTNYTYTVQISDRSRNWKNKCFS

TTDTECDLTDEIVKDVTWAYEAKVLSVPRRNSVHGDGDQLVIHGEEPPF

TNAPKFLPYRDTNLGQPVIQQFEQDGRKLNVVVKDSLTLVRKNGTFLTL

RQVFGKDLGYIITYRKGSSTGKKTNITNTNEFSIDVEEGVSYCFFVQAM

IFSRKTNQNSPGSSTVCTEQWKSFLGE
```

```
Exemplary Soluble Rat Tissue Factor Domain
                                   (SEQ ID NO: 4)
AGTPPGKAFNLTWISTDFKTILEWQPKPTNYTYTVQISDRSRNWKYKCT

GTTDTECDLTDEIVKDVNWTYEARVLSVPWRNSTHGKETLFGTHGEEPP

FTNARKFLPYRDTKIGQPVIQKYEQGGTKLKVTVKDSFTLVRKNGTFLT

LRQVFGNDLGYILTYRKDSSTGRKTNTTHTNEFLIDVEKGVSYCFFAQA

VIFSRKTNHKSPESITKCTEQWKSVLGE
```

```
Exemplary Mutant Soluble Human Tissue Factor
Domain
                                   (SEQ ID NO: 5)
SGTTNTVAAYNLTWKSTNFATALEWEPKPVNQVYTVQISTKSGDWKSKC

FYTTDTECALTDEIVKDVKQTYLARVFSYPAGNVESTGSAGEPLYENSP

EFTPYLETNLGQPTIQSFEQVGTKVNVTVEDERTLVARNNTALSLRDVF

GKDLIYTLYYWKSSSSGKKTAKTNTNEFLIDVDKGENYCFSVQAVIPSR

TVNRKSTDSPVECMGQEKGEFRE
```

-continued

Exemplary Mutant Soluble Human Tissue Factor Domain (SEQ ID NO: 6)

SGTTNTVAAYNLTWKSTNFATALEWEPKPVNQVYTVQISTKSGDAKSKC

FYTTDTECALTDEIVKDVKQTYLARVFSYPAGNVESTGSAGEPLAENSP

EFTPYLETNLGQPTIQSFEQVGTKVNVTVEDERTLVARNNTALSLRDVF

GKDLIYTLYYWKSSSSGKKTAKTNTNEFLIDVDKGENYCFSVQAVIPSR

TVNRKSTDSPVECMGQEKGEFRE

In some embodiments, a soluble tissue factor domain can include a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 1, 3, 4, 5, or 6. In some embodiments, a soluble tissue factor domain can include a sequence of SEQ ID NO: 1, 3, 4, 5, or 6 with one to twenty amino acids (e.g., 2, 3, 4, 5, 6, 7, 8, 9, 10, 11, 12, 13, 14, 15, 16, 17, 18, 19, or 20) amino acids removed from its N-terminus and/or one to twenty amino acids (e.g., 2, 3, 4, 5, 6, 7, 8, 9, 10, 11, 12, 13, 14, 15, 16, 17, 18, 19, or 20) amino acids removed from its C-terminus.

As will be appreciated by those of skill in the art, mutation of amino acids that are conserved between different mammalian species is more likely to decrease the activity and/or structural stability of the protein, while mutation of amino acids that are not conserved between different mammalian species is less likely to decrease the activity and/or structural stability of the protein.

In some examples, the soluble tissue factor domain is not capable of binding to Factor VIIa. In some examples, the soluble tissue factor domain does not convert inactive Factor X into Factor Xa. In some embodiments, the single-chain chimeric polypeptide does not stimulate blood coagulation in a mammal.

In some examples, the soluble tissue factor domain can be a soluble human tissue factor domain. In some embodiments, the soluble tissue factor domain can be a soluble mouse tissue factor domain. In some embodiments, the soluble tissue factor domain can be a soluble rat tissue factor domain.

In some examples, the soluble tissue factor domain does not include one or more (e.g., two, three, four, five, six or seven) of: a lysine at an amino acid position that corresponds to amino acid position 20 of mature wildtype human tissue factor protein; an isoleucine at an amino acid position that corresponds to amino acid position 22 of mature wildtype human tissue factor protein; a tryptophan at an amino acid position that corresponds to amino acid position 45 of mature wildtype human tissue factor protein; an aspartic acid at an amino acid position that corresponds to amino acid position 58 of mature wildtype human tissue factor protein; a tyrosine at an amino acid position that corresponds to amino acid position 94 of mature wildtype human tissue factor protein; an arginine at an amino acid position that corresponds to amino acid position 135 of mature wildtype human tissue factor protein; and a phenylalanine at an amino acid position that corresponds to amino acid position 140 of mature wildtype human tissue factor protein. In some embodiments, the mutant soluble tissue factor possesses the amino acid sequence of SEQ ID NO: 5 or SEQ ID NO: 6.

In some examples, the soluble tissue factor domain can be encoded by a nucleic acid including a sequence that is at least 70% identical, at least 72% identical, at least 74% identical, at least 76% identical, at least 78% identical, at least 80% identical, at least 82% identical, at least 84% identical, at least 86% identical, at least 88% identical, at least 90% identical, at least 92% identical, at least 94% identical, at least 96% identical, at least 98% identical, at least 99% identical, or 100% identical to SEQ ID NO: 2.

In some embodiments, the soluble tissue factor domain can have a total length of about amino acids to about 220 amino acids, about 20 amino acids to about 215 amino acids, about amino acids to about 210 amino acids, about 20 amino acids to about 205 amino acids, about amino acids to about 200 amino acids, about 20 amino acids to about 195 amino acids, about amino acids to about 190 amino acids, about 20 amino acids to about 185 amino acids, about amino acids to about 180 amino acids, about 20 amino acids to about 175 amino acids, about amino acids to about 170 amino acids, about 20 amino acids to about 165 amino acids, about amino acids to about 160 amino acids, about 20 amino acids to about 155 amino acids, about amino acids to about 150 amino acids, about 20 amino acids to about 145 amino acids, about amino acids to about 140 amino acids, about 20 amino acids to about 135 amino acids, about amino acids to about 130 amino acids, about 20 amino acids to about 125 amino acids, about amino acids to about 120 amino acids, about 20 amino acids to about 115 amino acids, about amino acids to about 110 amino acids, about 20 amino acids to about 105 amino acids, about amino acids to about 100 amino acids, about 20 amino acids to about 95 amino acids, about amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 60 amino acids, about 20 amino acids to about 50 amino acids, about 20 amino acids to about 40 amino acids, about 20 amino acids to about 30 amino acids, about 30 amino acids to about 220 amino acids, about 30 amino acids to about 215 amino acids, about 30 amino acids to about 210 amino acids, about 30 amino acids to about 205 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 60 amino acids, about 30 amino acids to about 50 amino acids, about 30 amino acids to about 40 amino acids, about 40 amino acids to about 220 amino acids, about 40 amino acids to about 215 amino acids, about 40 amino acids to about 210 amino acids, about 40 amino acids to about 205 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 60 amino acids, about 40 amino acids to about 50 amino acids, about 50 amino acids to about 220 amino acids, about 50 amino acids to about 215 amino acids, about 50 amino acids to about 210 amino acids, about 50 amino acids to about 205 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 60 amino acids, about 60 amino acids to about 220 amino acids, about 60 amino acids to about 215 amino acids, about 60 amino acids to about 210 amino acids, about 60 amino acids to about 205 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 70 amino acids to about 220 amino acids, about 70 amino acids to about 215 amino acids, about 70 amino acids to about 210 amino acids, about 70 amino acids to about 205 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 80 amino acids to about 220 amino acids, about 80 amino acids to about 215 amino acids, about 80 amino acids to about 210 amino acids, about 80 amino acids to about 205 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 90 amino acids to about 220 amino acids, about 90 amino acids to about 215 amino acids, about 90 amino acids to about 210 amino acids, about 90 amino acids to about 205 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 100 amino acids to about 220 amino acids, about 100 amino acids to about 215 amino acids, about 100 amino acids to about 210 amino acids, about 100 amino acids to about 205 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 110 amino acids to about 220 amino acids, about 110 amino acids to about 215 amino acids, about 110 amino acids to about 210 amino acids, about 110 amino acids to about 205 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 220 amino acids, about 115 amino acids to about 215 amino acids, about 115 amino acids to about 210 amino acids, about 115 amino acids to about 205 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 220 amino acids, about 120 amino acids to about 215 amino acids, about 120 amino acids to about 210 amino acids, about 120 amino acids to about 205 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 220 amino acids, about 125 amino acids to about 215 amino acids, about 125 amino acids to about 210 amino acids, about 125 amino acids to about 205 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 220 amino acids, about 130 amino acids to about 215 amino acids, about 130 amino acids to about 210 amino acids, about 130 amino acids to about 205 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 220 amino acids, about 135 amino acids to about 215 amino acids, about 135 amino acids to about 210 amino acids, about 135 amino acids to about 205 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 220 amino acids, about 140 amino acids to about 215 amino acids, about 140 amino acids to about 210 amino acids, about 140 amino acids to about 205 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 220 amino acids, about 145 amino acids to about 215 amino acids, about 145 amino acids to about 210 amino acids, about 145 amino acids to about 205 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 220 amino acids, about 150 amino acids to about 215 amino acids, about 150 amino acids to about 210 amino acids, about 150 amino acids to about 205 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 220 amino acids, about 155 amino acids to about 215 amino acids, about 155 amino acids to about 210 amino acids, about 155 amino acids to about 205 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 220 amino acids, about 160 amino acids to about 215 amino acids, about 160 amino acids to about 210 amino acids, about 160 amino acids to about 205 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 220 amino acids, about 165 amino acids to about 215 amino acids, about 165 amino acids to about 210 amino acids, about 165 amino acids to about 205 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 220 amino acids, about 170 amino acids to about 215 amino acids, about 170 amino acids to about 210 amino acids, about 170 amino acids to about 205 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 220 amino acids, about 175 amino acids to about 215 amino acids, about 175 amino acids to about 210 amino acids, about 175 amino acids to about 205 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 220 amino acids, about 180 amino acids to about 215 amino acids, about 180 amino acids to about 210 amino acids, about 180 amino acids to about 205 amino acids, about 180 amino acids to about 200 amino acids, about 180 amino acids to about 195 amino acids, about 180 amino acids to about 190 amino acids, about 180 amino acids to about 185 amino acids, about 185 amino acids to about 220 amino acids, about 185 amino acids to about 215 amino acids, about 185 amino acids to about 210 amino acids, about 185 amino acids to about 205 amino acids, about 185 amino acids to about 200 amino acids, about 185 amino acids to about 195 amino acids, about 185 amino acids to about 190 amino acids, about 190 amino acids to about 220 amino acids, about 190 amino acids to about 215 amino acids, about 190 amino acids to about 210 amino acids, about 190 amino acids to about 205 amino acids, about 190 amino acids to about 200 amino acids, about 190 amino acids to about 195 amino acids, about 195 amino acids to about 220 amino acids, about 195 amino acids to about 215 amino acids, about 195 amino acids to about 210 amino acids, about 195 amino acids to about 205 amino acids, about 195 amino acids to about 200 amino acids, about 200 amino acids to about 220 amino acids, about 200 amino acids to about 215 amino acids, about 200 amino acids to about 210 amino acids, about 200 amino acids to about 205 amino acids, about 205 amino acids to about 220 amino acids, about 205 amino acids to about 215 amino acids, about 205 amino acids to about 210 amino acids, about 210 amino acids to about 220 amino acids, about 210 amino acids to about 215 amino acids, or about 215 amino acids to about 220 amino acids.

Linker Sequences

In some embodiments, the linker sequence can be a flexible linker sequence. Non-limiting examples of linker sequences that can be used are described in Klein et al., Protein Engineering, Design & Selection Vol. 27, No. 10, pp. 325-330, 2014; Priyanka et al., Protein Sci., 2013 February; 22(2):153-167. In some examples, the linker sequence is a synthetic linker sequence.

In some embodiments of any of the single-chain chimeric polypeptides or any of the multi-chain chimeric polypeptides described herein, the polypeptide can include one, two, three, four, five, six, seven, eight, nine, or ten linker sequence(s) (e.g., the same or different linker sequences, e.g., any of the exemplary linker sequences described herein or known in the art). In some embodiments of any of the single-chain chimeric polypeptides or any of the multi-chain chimeric polypeptides described herein, the polypeptide can include one, two, three, four, five, six, seven, eight, nine, or ten linker sequence(s) (e.g., the same or different linker sequences, e.g., any of the exemplary linker sequences described herein or known in the art).

In some embodiments, a linker sequence can have a total length of 1 amino acid to about 100 amino acids, 1 amino acid to about 90 amino acids, 1 amino acid to about 80 amino acids, 1 amino acid to about 70 amino acids, 1 amino acid to about 60 amino acids, 1 amino acid to about 50 amino acids, 1 amino acid to about 45 amino acids, 1 amino acid to about 40 amino acids, 1 amino acid to about 35 amino acids, 1 amino acid to about 30 amino acids, 1 amino acid to about amino acids, 1 amino acid to about 24 amino acids, 1 amino acid to about 22 amino acids, 1 amino acid to about 20 amino acids, 1 amino acid to about 18 amino acids, 1 amino acid to about 16 amino acids, 1 amino acid to about 14 amino acids, 1 amino acid to about 12 amino acids, 1 amino acid to about 10 amino acids, 1 amino acid to about 8 amino acids, 1 amino acid to about 6 amino acids, 1 amino acid to about 4 amino acids, about 2 amino acids to about 100 amino acids, about 2 amino acids to about 90 amino acids, about 2 amino acids to about 80 amino acids, about 2 amino acids to about 70 amino acids, about 2 amino acids to about 60 amino acids, about 2 amino acids to about 50 amino acids, about 2 amino acids to about 45 amino acids, about 2 amino acids to about 40 amino acids, about 2 amino acids to about 35 amino acids, about 2 amino acids to about 30 amino acids, about 2 amino acids to about 25 amino acids, about 2 amino acids to about 24 amino acids, about 2 amino acids to about 22 amino acids, about 2 amino acids to about 20 amino acids, about 2 amino acids to about 18 amino acids, about 2 amino acids to about 16 amino acids, about 2 amino acids to about 14 amino acids, about 2 amino acids to about 12 amino acids, about 2 amino acids to about 10 amino acids, about 2 amino acids to about 8 amino acids, about 2 amino acids to about 6 amino acids, about 2 amino acids to about 4 amino acids, about 4 amino acids to about 100 amino acids, about 4 amino acids to about 90 amino acids, about 4 amino acids to about 80 amino acids, about 4 amino acids to about 70 amino acids, about 4 amino acids to about 60 amino acids, about 4 amino acids to about 50 amino acids, about 4 amino acids to about 45 amino acids, about 4 amino acids to about 40 amino acids, about 4 amino acids to about 35 amino acids, about 4 amino acids to about 30 amino acids, about 4 amino acids to about 25 amino acids, about 4 amino acids to about 24 amino acids, about 4 amino acids to about 22 amino acids, about 4 amino acids to about 20 amino acids, about 4 amino acids to about 18 amino acids, about 4 amino acids to about 16 amino acids, about 4 amino acids to about 14 amino acids, about 4 amino acids to about 12 amino acids, about 4 amino acids to about 10 amino acids, about 4 amino acids to about 8 amino acids, about 4 amino acids to about 6 amino acids, about 6 amino acids to about 100 amino acids, about 6 amino acids to about 90 amino acids, about 6 amino acids to about 80 amino acids, about 6 amino acids to about 70 amino acids, about 6 amino acids to about 60 amino acids, about 6 amino acids to about 50 amino acids, about 6 amino acids to about 45 amino acids, about 6 amino acids to about 40 amino acids, about 6 amino acids to about 35 amino acids, about 6 amino acids to about 30 amino acids, about 6 amino acids to about 25 amino acids, about 6 amino acids to about 24 amino acids, about 6 amino acids to about 22 amino acids, about 6 amino acids to about 20 amino acids, about 6 amino acids to about 18 amino acids, about 6 amino acids to about 16 amino acids, about 6 amino acids to about 14 amino acids, about 6 amino acids to about 12 amino acids, about 6 amino acids to about 10 amino acids, about 6 amino acids to about 8 amino acids, about 8 amino acids to about 100 amino acids, about 8 amino acids to about 90 amino acids, about 8 amino acids to about 80 amino acids, about 8 amino acids to about 70 amino acids, about 8 amino acids to about 60 amino acids, about 8 amino acids to about 50 amino acids, about 8 amino acids to about 45 amino acids, about 8 amino acids to about 40 amino acids, about 8 amino acids to about 35 amino acids, about 8 amino acids to about 30 amino acids, about 8 amino acids to about 25 amino acids, about 8 amino acids to about 24 amino acids, about 8 amino acids to about 22 amino acids, about 8 amino acids to about 20 amino acids, about 8 amino acids to about 18 amino acids, about 8 amino acids to about 16 amino acids, about 8 amino acids to about 14 amino acids, about 8 amino acids to about 12 amino acids, about 8 amino acids to about 10 amino acids, about 10 amino acids to about 100 amino acids, about 10 amino acids to about 90 amino acids, about 10 amino acids to about 80 amino acids, about 10 amino acids to about 70 amino acids, about 10 amino acids to about 60 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 24 amino acids, about 10 amino acids to about 22 amino acids, about 10 amino acids to about 20 amino acids, about 10 amino acids to about 18 amino acids, about 10 amino acids to about 16 amino acids, about 10 amino acids to about 14 amino acids, about 10 amino acids to about 12 amino acids, about 12 amino acids to about 100 amino acids, about 12 amino acids to about 90 amino acids, about 12 amino acids to about 80 amino acids, about 12 amino acids to about 70 amino acids, about 12 amino acids to about 60 amino acids, about 12 amino acids to about 50 amino acids, about 12 amino acids to about 45 amino acids, about 12 amino acids to about 40 amino acids, about 12 amino acids to about 35 amino acids, about 12 amino acids to about 30 amino acids, about 12 amino acids to about 25 amino acids, about 12 amino acids to about 24 amino acids, about 12 amino acids to about 22 amino acids, about 12 amino acids to about 20 amino acids, about 12 amino acids to about 18 amino acids, about 12 amino acids to about 16 amino acids, about 12 amino acids to about 14 amino acids, about 14 amino acids to about 100 amino acids, about 14 amino acids to about 90 amino acids, about 14 amino acids to about 80 amino acids, about 14 amino acids to about 70 amino acids, about 14 amino acids to about 60 amino acids, about 14 amino acids to about 50 amino acids, about 14 amino acids to about 45 amino acids, about 14 amino acids to about 40 amino acids, about 14 amino acids to about 35 amino acids, about 14 amino acids to about 30 amino acids, about 14 amino acids to about 25 amino acids, about 14 amino acids to about 24 amino acids, about 14 amino acids to about 22 amino acids, about 14 amino acids to about 20 amino acids, about 14 amino acids to about 18 amino acids, about 14 amino acids to about 16 amino acids, about 16 amino acids to about 100 amino acids, about 16 amino acids to about 90 amino acids, about 16 amino acids to about 80 amino acids, about 16 amino acids to about 70 amino acids, about 16 amino acids to about 60 amino acids, about 16 amino acids to about 50 amino acids, about 16 amino acids to about 45 amino acids, about 16 amino acids to about 40 amino acids, about 16 amino acids to about 35 amino acids, about 16 amino acids to about 30 amino acids, about 16 amino acids to about 25 amino acids, about 16 amino acids to about 24 amino acids, about 16 amino acids to about 22 amino acids, about 16 amino acids to about 20 amino acids, about 16 amino acids to about 18 amino acids, about 18 amino acids to about 100 amino acids, about 18 amino acids to about 90 amino acids, about 18 amino acids to about 80 amino acids, about 18 amino acids to about 70 amino acids, about 18 amino acids to about 60 amino acids, about 18 amino acids to about 50 amino acids, about 18 amino acids to about 45 amino acids, about 18 amino acids to about 40 amino acids, about 18 amino acids to about 35 amino acids, about 18 amino acids to about 30 amino acids, about 18 amino acids to about 25 amino acids, about 18 amino acids to about 24 amino acids, about 18 amino acids to about 22 amino acids, about 18 amino acids to about 20 amino acids, about 20 amino acids to about 100 amino acids, about 20 amino acids to about 90 amino acids, about 20 amino acids to about 80 amino acids, about 20 amino acids to about 70 amino acids, about 20 amino acids to about 60 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 20 amino acids to about 24 amino acids, about 20 amino acids to about 22 amino acids, about 22 amino acids to about 100 amino acids, about 22 amino acids to about 90 amino acids, about 22 amino acids to about 80 amino acids, about 22 amino acids to about 70 amino acids, about 22 amino acids to about 60 amino acids, about 22 amino acids to about 50 amino acids, about 22 amino acids to about 45 amino acids, about 22 amino acids to about 40 amino acids, about 22 amino acids to about 35 amino acids, about 22 amino acids to about 30 amino acids, about 22 amino acids to about 25 amino acids, about 22 amino acids to about 24 amino acids, about 25 amino acids to about 100 amino acids, about 25 amino acids to about 90 amino acids, about 25 amino acids to about 80 amino acids, about 25 amino acids to about 70 amino acids, about 25 amino acids to about 60 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 100 amino acids, about 30 amino acids to about 90 amino acids, about 30 amino acids to about 80 amino acids, about 30 amino acids to about 70 amino acids, about 30 amino acids to about 60 amino acids, about 30 amino acids to about 50 amino acids, about 30 amino acids to about 45 amino acids, about 30 amino acids to about 40 amino acids, about 30 amino acids to about 35 amino acids, about 35 amino acids to about 100 amino acids, about 35 amino acids to about 90 amino acids, about 35 amino acids to about 80 amino acids, about 35 amino acids to about 70 amino acids, about 35 amino acids to about 60 amino acids, about 35 amino acids to about 50 amino acids, about 35 amino acids to about 45 amino acids, about 35 amino acids to about 40 amino acids, about 40 amino acids to about 100 amino acids, about 40 amino acids to about 90 amino acids, about 40 amino acids to about 80 amino acids, about 40 amino acids to about 70 amino acids, about 40 amino acids to about 60 amino acids, about 40 amino acids to about 50 amino acids, about 40 amino acids to about 45 amino acids, about 45 amino acids to about 100 amino acids, about 45 amino acids to about 90 amino acids, about 45 amino acids to about 80 amino acids, about 45 amino acids to about 70 amino acids, about 45 amino acids to about 60 amino acids, about 45 amino acids to about 50 amino acids, about 50 amino acids to about 100 amino acids, about 50 amino acids to about 90 amino acids, about 50 amino acids to about 80 amino acids, about 50 amino acids to about 70 amino acids, about 50 amino acids to about 60 amino acids, about 60 amino acids to about 100 amino acids, about 60 amino acids to about 90 amino acids, about 60 amino acids to about 80 amino acids, about 60 amino acids to about 70 amino acids, about 70 amino acids to about 100 amino acids, about 70 amino acids to about 90 amino acids, about 70 amino acids to about 80 amino acids, about 80 amino acids to about 100 amino acids, about 80 amino acids to about 90 amino acids, or about 90 amino acids to about 100 amino acids.

In some embodiments, the linker sequence is rich in glycine (Gly or G) residues. In some embodiments, the linker sequence is rich in serine (Ser or S) residues. In some embodiments, the linker sequence is rich in glycine and serine residues. In some embodiments, the linker sequence has one or more glycine-serine residue pairs (GS), e.g., 1, 2, 3, 4, 5, 6, 7, 8, 9, or 10 or more GS pairs. In some embodiments, the linker sequence has one or more Gly-Gly-Gly-Ser (GGGS) sequences, e.g., 1, 2, 3, 4, 5, 6, 7, 8, 9, or 10 or more GGGS sequences. In some embodiments, the linker sequence has one or more Gly-Gly-Gly-Gly-Ser (GGGGS) sequences, e.g., 1, 2, 3, 4, 5, 6, 7, 8, 9, or 10 or more GGGGS sequences. In some embodiments, the linker sequence has one or more Gly-Gly-Ser-Gly (GGSG) sequences, e.g., 1, 2, 3, 4, 5, 6, 7, 8, 9, or 10 or more GGSG sequences.

In some embodiments, the linker sequence can comprise or consist of GGGGSGGGGSGGGGS (SEQ ID NO: 7). In some embodiments, the linker sequence can be encoded by a nucleic acid comprising or consisting of:

```
                                      (SEQ ID NO: 8)
GGCGGTGGAGGATCCGGAGGAGGTGGCTCCGGCGGCGGAGGATCT.
```

In some embodiments, the linker sequence can comprise or consist of: GGGSGGGS (SEQ ID NO: 9).

Target-Binding Domains

In some embodiments of any of the single-chain chimeric polypeptides or any of the multi-chain chimeric polypeptides described herein, the first target-binding domain, the second target-binding domain, and/or the additional one or more target-binding domains can be an antigen-binding domain (e.g., any of the exemplary antigen-binding domains described herein or known in the art), a soluble interleukin or cytokine protein (e.g., any of the exemplary soluble interleukin proteins or soluble cytokine proteins described herein or known in the art), a soluble interleukin or cytokine receptor (e.g., any of the exemplary soluble interleukin receptors or soluble cytokine receptors described herein or known in the art), and ligands of co-stimulatory molecules (e.g., any of the exemplary ligands of co-stimulatory molecules described herein or known in the art).

In some embodiments of any of the single-chain chimeric polypeptides or any of the multi-chain chimeric polypeptides described herein, one or more of the first target-binding domain (e.g., any of the exemplary first target binding domains described herein or known in the art), the second target-binding domain (e.g., any of the exemplary second target binding domains described herein or known in the art), and the one or more additional target binding domains can each, independently, bind specifically to a target selected from the group of: CD16a, CD28, CD3 (e.g., one or more of CD3α, CD3β, CD3δ, CD3ε, and CD3γ), CD33, CD20, CD19, CD22, CD40, CD47, CD52, CD70, CD80, CD86, CD123, CD137, CD272, IL-1R, IL-1, VEGF, IL-6R, IL-4, IL-10, PDL-1, PDL-2, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, B7-H4, HVEM, EPCAM, BCMA, P-cadherin, CEACAM5, VISTA, a UL16-binding protein, HLA-DR, DLL4, TYRO3, AXL, MER, CD122, CD155, PDGF-DD, ILT3, ILT4, TIGIT, MHCII, LAG3, OX40, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the single-chain chimeric polypeptides or any of the multi-chain chimeric polypeptides described herein, the first target-binding domain, the second target-binding domain, and/or the one or more additional target-binding domains, can be a soluble interleukin, soluble cytokine protein, or soluble cell surface protein. In some examples, the soluble interleukin, soluble cytokine protein, or soluble cell surface protein is selected from the group of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

In some embodiments of any of the single-chain chimeric polypeptides or any of the multi-chain chimeric polypeptides described herein, the first target-binding domain, the second target-binding domain, and/or the one or more additional target-binding domains, can be a soluble interleukin receptor, a soluble cytokine receptor, or a soluble cell surface receptor. In some examples, the soluble interleukin receptor, the soluble cytokine receptor, or the soluble cell surface receptor is soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

In some embodiments of any of the single-chain chimeric polypeptides or any of the multi-chain chimeric polypeptides described herein, the first target-binding domain, the second target-binding domain, and/or the one or more additional target-binding domains, can be a ligand of a co-stimulatory molecule. Non-limiting examples of ligands of a co-stimulatory molecule include soluble CD80, soluble CD86, soluble CD40, soluble ICOSL, soluble CD70, soluble OX40L, soluble 4-1BBL, soluble GITRL, soluble LIGHT, soluble TIM3, soluble TIM4, soluble ICAM1, soluble LFA3, soluble CD1d, or soluble LLT-1.

In some embodiments of any of the single-chain chimeric polypeptides or any of the multi-chain chimeric polypeptides described herein, the first target-binding domain, the second target-binding domain, and/or the one or more additional target-binding domains can each independent have a total number of amino acids of about 5 amino acids to about 1000 amino acids, about 5 amino acids to about 950 amino acids, about 5 amino acids to about 900 amino acids, about 5 amino acids to about 850 amino acids, about 5 amino acids to about 800 amino acids, about 5 amino acids to about 750 amino acids, about 5 amino acids to about 700 amino acids, about 5 amino acids to about 650 amino acids, about 5 amino acids to about 600 amino acids, about 5 amino acids to about 550 amino acids, about 5 amino acids to about 500 amino acids, about 5 amino acids to about 450 amino acids, about 5 amino acids to about 400 amino acids, about 5 amino acids to about 350 amino acids, about 5 amino acids to about 300 amino acids, about 5 amino acids to about 280 amino acids, about 5 amino acids to about 260 amino acids, about 5 amino acids to about 240 amino acids, about 5 amino acids to about 220 amino acids, about 5 amino acids to about 200 amino acids, about 5 amino acids to about 195 amino acids, about 5 amino acids to about 190 amino acids, about 5 amino acids to about 185 amino acids, about 5 amino acids to about 180 amino acids, about 5 amino acids to about 175 amino acids, about 5 amino acids to about 170 amino acids, about 5 amino acids to about 165 amino acids, about 5 amino acids to about 160 amino acids, about 5 amino acids to about 155 amino acids, about 5 amino acids to about 150 amino acids, about 5 amino acids to about 145 amino acids, about 5 amino acids to about 140 amino acids, about 5 amino acids to about 135 amino acids, about 5 amino acids to about 130 amino acids, about 5 amino acids to about 125 amino acids, about 5 amino acids to about 120 amino acids, about 5 amino acids to about 115 amino acids, about 5 amino acids to about 110 amino acids, about 5 amino acids to about 105 amino acids, about 5 amino acids to about 100 amino acids, about 5 amino acids to about 95 amino acids, about 5 amino acids to about 90 amino acids, about 5 amino acids to about 85 amino acids, about 5 amino acids to about 80 amino acids, about 5 amino acids to about 75 amino acids, about amino acids to about 70 amino acids, about 5 amino acids to about 65 amino acids, about 5 amino acids to about 60 amino acids, about 5 amino acids to about 55 amino acids, about 5 amino acids to about 50 amino acids, about 5 amino acids to about 45 amino acids, about 5 amino acids to about 40 amino acids, about 5 amino acids to about 35 amino acids, about 5 amino acids to about 30 amino acids, about 5 amino acids to about 25 amino acids, about 5 amino acids to about 20 amino acids, about 5 amino acids to about 15 amino acids, about 5 amino acids to about 10 amino acids, about 10 amino acids to about 1000 amino acids, about 10 amino acids to about 950 amino acids, about 10 amino acids to about 900 amino acids, about 10 amino acids to about 850 amino acids, about 10 amino acids to about 800 amino acids, about 10 amino acids to about 750 amino acids, about 10 amino acids to about 700 amino acids, about 10 amino acids to about 650 amino acids, about 10 amino acids to about 600 amino acids, about 10 amino acids to about 550 amino acids, about 10 amino acids to about 500 amino acids, about 10 amino acids to about 450 amino acids, about 10 amino acids to about 400 amino acids, about 10 amino acids to about 350 amino acids, about 10 amino acids to about 300 amino acids, about 10 amino acids to about 280 amino acids, about 10 amino acids to about 260 amino acids, about 10 amino acids to about 240 amino acids, about 10 amino acids to about 220 amino acids, about 10 amino acids to about 200 amino acids, about 10 amino acids to about 195 amino acids, about 10 amino acids to about 190 amino acids, about 10 amino acids to about 185 amino acids, about 10 amino acids to about 180 amino acids, about 10 amino acids to about 175 amino acids, about 10 amino acids to about 170 amino acids, about 10 amino acids to about 165 amino acids, about 10 amino acids to about 160 amino acids, about 10 amino acids to about 155 amino acids, about 10 amino acids to about 150 amino acids, about 10 amino acids to about 145 amino acids, about 10 amino acids to about 140 amino acids, about 10 amino acids to about 135 amino acids, about 10 amino acids to about 130 amino acids, about 10 amino acids to about 125 amino acids, about 10 amino acids to about 120 amino acids, about 10 amino acids to about 115 amino acids, about 10 amino acids to about 110 amino acids, about 10 amino acids to about 105 amino acids, about 10 amino acids to about 100 amino acids, about 10 amino acids to about 95 amino acids, about 10 amino acids to about 90 amino acids, about 10 amino acids to about 85 amino acids, about 10 amino acids to about 80 amino acids, about 10 amino acids to about 75 amino acids, about 10 amino acids to about 70 amino acids, about 10 amino acids to about 65 amino acids, about 10 amino acids to about 60 amino acids, about 10 amino acids to about 55 amino acids, about 10 amino acids to about 50 amino acids, about 10 amino acids to about 45 amino acids, about 10 amino acids to about 40 amino acids, about 10 amino acids to about 35 amino acids, about 10 amino acids to about 30 amino acids, about 10 amino acids to about 25 amino acids, about 10 amino acids to about 20 amino acids, about 10 amino acids to about 15 amino acids, about 15 amino acids to about 1000 amino acids, about 15 amino acids to about 950 amino acids, about 15 amino acids to about 900 amino acids, about 15 amino acids to about 850 amino acids, about 15 amino acids to about 800 amino acids, about 15 amino acids to about 750 amino acids, about 15 amino acids to about 700 amino acids, about 15 amino acids to about 650 amino acids, about 15 amino acids to about 600 amino acids, about 15 amino acids to about 550 amino acids, about 15 amino acids to about 500 amino acids, about 15 amino acids to about 450 amino acids, about 15 amino acids to about 400 amino acids, about 15 amino acids to about 350 amino acids, about 15 amino acids to about 300 amino acids, about 15 amino acids to about 280 amino acids, about 15 amino acids to about 260 amino acids, about 15 amino acids to about 240 amino acids, about 15 amino acids to about 220 amino acids, about 15 amino acids to about 200 amino acids, about 15 amino acids to about 195 amino acids, about 15 amino acids to about 190 amino acids, about 15 amino acids to about 185 amino acids, about 15 amino acids to about 180 amino acids, about 15 amino acids to about 175 amino acids, about 15 amino acids to about 170 amino acids, about 15 amino acids to about 165 amino acids, about 15 amino acids to about 160 amino acids, about 15 amino acids to about 155 amino acids, about 15 amino acids to about 150 amino acids, about 15 amino acids to about 145 amino acids, about 15 amino acids to about 140 amino acids, about 15 amino acids to about 135 amino acids, about 15 amino acids to about 130 amino acids, about 15 amino acids to about 125 amino acids, about 15 amino acids to about 120 amino acids, about 15 amino acids to about 115 amino acids, about 15 amino acids to about 110 amino acids, about 15 amino acids to about 105 amino acids, about 15 amino acids to about 100 amino acids, about 15 amino acids to about 95 amino acids, about 15 amino acids to about 90 amino acids, about 15 amino acids to about 85 amino acids, about 15 amino acids to about 80 amino acids, about 15 amino acids to about 75 amino acids, about 15 amino acids to about 70 amino acids, about 15 amino acids to about 65 amino acids, about 15 amino acids to about 60 amino acids, about 15 amino acids to about 55 amino acids, about 15 amino acids to about 50 amino acids, about 15 amino acids to about 45 amino acids, about 15 amino acids to about 40 amino acids, about 15 amino acids to about 35 amino acids, about 15 amino acids to about 30 amino acids, about 15 amino acids to about 25 amino acids, about 15 amino acids to about 20 amino acids, about 20 amino acids to about 1000 amino acids, about 20 amino acids to about 950 amino acids, about 20 amino acids to about 900 amino acids, about 20 amino acids to about 850 amino acids, about 20 amino acids to about 800 amino acids, about 20 amino acids to about 750 amino acids, about 20 amino acids to about 700 amino acids, about 20 amino acids to about 650 amino acids, about 20 amino acids to about 600 amino acids, about 20 amino acids to about 550 amino acids, about 20 amino acids to about 500 amino acids, about 20 amino acids to about 450 amino acids, about 20 amino acids to about 400 amino acids, about 20 amino acids to about 350 amino acids, about 20 amino acids to about 300 amino acids, about 20 amino acids to about 280 amino acids, about 20 amino acids to about 260 amino acids, about 20 amino acids to about 240 amino acids, about 20 amino acids to about 220 amino acids, about 20 amino acids to about 200 amino acids, about 20 amino acids to about 195 amino acids, about 20 amino acids to about 190 amino acids, about 20 amino acids to about 185 amino acids, about 20 amino acids to about 180 amino acids, about 20 amino acids to about 175 amino acids, about 20 amino acids to about 170 amino acids, about 20 amino acids to about 165 amino acids, about 20 amino acids to about 160 amino acids, about 20 amino acids to about 155 amino acids, about 20 amino acids to about 150 amino acids, about 20 amino acids to about 145 amino acids, about 20 amino acids to about 140 amino acids, about 20 amino acids to about 135 amino acids, about 20 amino acids to about 130 amino acids, about 20 amino acids to about 125 amino acids, about 20 amino acids to about 120 amino acids, about 20 amino acids to about 115 amino acids, about 20 amino acids to about 110 amino acids, about 20 amino acids to about 105 amino acids, about 20 amino acids to about 100 amino acids, about 20 amino acids to about 95 amino acids, about 20 amino acids to about 90 amino acids, about 20 amino acids to about 85 amino acids, about 20 amino acids to about 80 amino acids, about 20 amino acids to about 75 amino acids, about 20 amino acids to about 70 amino acids, about 20 amino acids to about 65 amino acids, about 20 amino acids to about 60 amino acids, about 20 amino acids to about 55 amino acids, about 20 amino acids to about 50 amino acids, about 20 amino acids to about 45 amino acids, about 20 amino acids to about 40 amino acids, about 20 amino acids to about 35 amino acids, about 20 amino acids to about 30 amino acids, about 20 amino acids to about 25 amino acids, about 25 amino acids to about 1000 amino acids, about 25 amino acids to about 950 amino acids, about 25 amino acids to about 900 amino acids, about 25 amino acids to about 850 amino acids, about 25 amino acids to about 800 amino acids, about 25 amino acids to about 750 amino acids, about 25 amino acids to about 700 amino acids, about 25 amino acids to about 650 amino acids, about 25 amino acids to about 600 amino acids, about 25 amino acids to about 550 amino acids, about 25 amino acids to about 500 amino acids, about 25 amino acids to about 450 amino acids, about 25 amino acids to about 400 amino acids, about 25 amino acids to about 350 amino acids, about 25 amino acids to about 300 amino acids, about 25 amino acids to about 280 amino acids, about 25 amino acids to about 260 amino acids, about 25 amino acids to about 240 amino acids, about 25 amino acids to about 220 amino acids, about 25 amino acids to about 200 amino acids, about 25 amino acids to about 195 amino acids, about 25 amino acids to about 190 amino acids, about 25 amino acids to about 185 amino acids, about 25 amino acids to about 180 amino acids, about 25 amino acids to about 175 amino acids, about 25 amino acids to about 170 amino acids, about 25 amino acids to about 165 amino acids, about 25 amino acids to about 160 amino acids, about 25 amino acids to about 155 amino acids, about 25 amino acids to about 150 amino acids, about 25 amino acids to about 145 amino acids, about 25 amino acids to about 140 amino acids, about 25 amino acids to about 135 amino acids, about 25 amino acids to about 130 amino acids, about 25 amino acids to about 125 amino acids, about 25 amino acids to about 120 amino acids, about 25 amino acids to about 115 amino acids, about 25 amino acids to about 110 amino acids, about 25 amino acids to about 105 amino acids, about 25 amino acids to about 100 amino acids, about 25 amino acids to about 95 amino acids, about 25 amino acids to about 90 amino acids, about 25 amino acids to about 85 amino acids, about 25 amino acids to about 80 amino acids, about 25 amino acids to about 75 amino acids, about 25 amino acids to about 70 amino acids, about 25 amino acids to about 65 amino acids, about 25 amino acids to about 60 amino acids, about 25 amino acids to about 55 amino acids, about 25 amino acids to about 50 amino acids, about 25 amino acids to about 45 amino acids, about 25 amino acids to about 40 amino acids, about 25 amino acids to about 35 amino acids, about 25 amino acids to about 30 amino acids, about 30 amino acids to about 1000 amino acids, about 30 amino acids to about 950 amino acids, about 30 amino acids to about 900 amino acids, about 30 amino acids to about 850 amino acids, about 30 amino acids to about 800 amino acids, about 30 amino acids to about 750 amino acids, about 30 amino acids to about 700 amino acids, about 30 amino acids to about 650 amino acids, about 30 amino acids to about 600 amino acids, about 30 amino acids to about 550 amino acids, about 30 amino acids to about 500 amino acids, about 30 amino acids to about 450 amino acids, about 30 amino acids to about 400 amino acids, about 30 amino acids to about 350 amino acids, about 30 amino acids to about 300 amino acids, about 30 amino acids to about 280 amino acids, about 30 amino acids to about 260 amino acids, about 30 amino acids to about 240 amino acids, about 30 amino acids to about 220 amino acids, about 30 amino acids to about 200 amino acids, about 30 amino acids to about 195 amino acids, about 30 amino acids to about 190 amino acids, about 30 amino acids to about 185 amino acids, about 30 amino acids to about 180 amino acids, about 30 amino acids to about 175 amino acids, about 30 amino acids to about 170 amino acids, about 30 amino acids to about 165 amino acids, about 30 amino acids to about 160 amino acids, about 30 amino acids to about 155 amino acids, about 30 amino acids to about 150 amino acids, about 30 amino acids to about 145 amino acids, about 30 amino acids to about 140 amino acids, about 30 amino acids to about 135 amino acids, about 30 amino acids to about 130 amino acids, about 30 amino acids to about 125 amino acids, about 30 amino acids to about 120 amino acids, about 30 amino acids to about 115 amino acids, about 30 amino acids to about 110 amino acids, about 30 amino acids to about 105 amino acids, about 30 amino acids to about 100 amino acids, about 30 amino acids to about 95 amino acids, about 30 amino acids to about 90 amino acids, about 30 amino acids to about 85 amino acids, about 30 amino acids to about 80 amino acids, about 30 amino acids to about 75 amino acids, about 30 amino acids to about 70 amino acids, about 30 amino acids to about 65 amino acids, about 30 amino acids to about 60 amino acids, about 30 amino acids to about 55 amino acids, about 30 amino acids to about 50 amino acids, about 30 amino acids to about 45 amino acids, about 30 amino acids to about 40 amino acids, about 30 amino acids to about 35 amino acids, about 35 amino acids to about 1000 amino acids, about 35 amino acids to about 950 amino acids, about 35 amino acids to about 900 amino acids, about 35 amino acids to about 850 amino acids, about 35 amino acids to about 800 amino acids, about 35 amino acids to about 750 amino acids, about 35 amino acids to about 700 amino acids, about 35 amino acids to about 650 amino acids, about 35 amino acids to about 600 amino acids, about 35 amino acids to about 550 amino acids, about 35 amino acids to about 500 amino acids, about 35 amino acids to about 450 amino acids, about 35 amino acids to about 400 amino acids, about 35 amino acids to about 350 amino acids, about 35 amino acids to about 300 amino acids, about 35 amino acids to about 280 amino acids, about 35 amino acids to about 260 amino acids, about 35 amino acids to about 240 amino acids, about 35 amino acids to about 220 amino acids, about 35 amino acids to about 200 amino acids, about 35 amino acids to about 195 amino acids, about 35 amino acids to about 190 amino acids, about 35 amino acids to about 185 amino acids, about 35 amino acids to about 180 amino acids, about 35 amino acids to about 175 amino acids, about 35 amino acids to about 170 amino acids, about 35 amino acids to about 165 amino acids, about 35 amino acids to about 160 amino acids, about 35 amino acids to about 155 amino acids, about 35 amino acids to about 150 amino acids, about 35 amino acids to about 145 amino acids, about 35 amino acids to about 140 amino acids, about 35 amino acids to about 135 amino acids, about 35 amino acids to about 130 amino acids, about 35 amino acids to about 125 amino acids, about 35 amino acids to about 120 amino acids, about 35 amino acids to about 115 amino acids, about 35 amino acids to about 110 amino acids, about 35 amino acids to about 105 amino acids, about 35 amino acids to about 100 amino acids, about 35 amino acids to about 95 amino acids, about 35 amino acids to about 90 amino acids, about 35 amino acids to about 85 amino acids, about 35 amino acids to about 80 amino acids, about 35 amino acids to about 75 amino acids, about 35 amino acids to about 70 amino acids, about 35 amino acids to about 65 amino acids, about 35 amino acids to about 60 amino acids, about 35 amino acids to about 55 amino acids, about 35 amino acids to about 50 amino acids, about 35 amino acids to about 45 amino acids, about 35 amino acids to about 40 amino acids, about 40 amino acids to about 1000 amino acids, about 40 amino acids to about 950 amino acids, about 40 amino acids to about 900 amino acids, about 40 amino acids to about 850 amino acids, about 40 amino acids to about 800 amino acids, about 40 amino acids to about 750 amino acids, about 40 amino acids to about 700 amino acids, about 40 amino acids to about 650 amino acids, about 40 amino acids to about 600 amino acids, about 40 amino acids to about 550 amino acids, about 40 amino acids to about 500 amino acids, about 40 amino acids to about 450 amino acids, about 40 amino acids to about 400 amino acids, about 40 amino acids to about 350 amino acids, about 40 amino acids to about 300 amino acids, about 40 amino acids to about 280 amino acids, about 40 amino acids to about 260 amino acids, about 40 amino acids to about 240 amino acids, about 40 amino acids to about 220 amino acids, about 40 amino acids to about 200 amino acids, about 40 amino acids to about 195 amino acids, about 40 amino acids to about 190 amino acids, about 40 amino acids to about 185 amino acids, about 40 amino acids to about 180 amino acids, about 40 amino acids to about 175 amino acids, about 40 amino acids to about 170 amino acids, about 40 amino acids to about 165 amino acids, about 40 amino acids to about 160 amino acids, about 40 amino acids to about 155 amino acids, about 40 amino acids to about 150 amino acids, about 40 amino acids to about 145 amino acids, about 40 amino acids to about 140 amino acids, about 40 amino acids to about 135 amino acids, about 40 amino acids to about 130 amino acids, about 40 amino acids to about 125 amino acids, about 40 amino acids to about 120 amino acids, about 40 amino acids to about 115 amino acids, about 40 amino acids to about 110 amino acids, about 40 amino acids to about 105 amino acids, about 40 amino acids to about 100 amino acids, about 40 amino acids to about 95 amino acids, about 40 amino acids to about 90 amino acids, about 40 amino acids to about 85 amino acids, about 40 amino acids to about 80 amino acids, about 40 amino acids to about 75 amino acids, about 40 amino acids to about 70 amino acids, about 40 amino acids to about 65 amino acids, about 40 amino acids to about 60 amino acids, about 40 amino acids to about 55 amino acids, about 40 amino acids to about 50 amino acids, about 40 amino acids to about 45 amino acids, about 45 amino acids to about 1000 amino acids, about 45 amino acids to about 950 amino acids, about 45 amino acids to about 900 amino acids, about 45 amino acids to about 850 amino acids, about 45 amino acids to about 800 amino acids, about 45 amino acids to about 750 amino acids, about 45 amino acids to about 700 amino acids, about 45 amino acids to about 650 amino acids, about 45 amino acids to about 600 amino acids, about 45 amino acids to about 550 amino acids, about 45 amino acids to about 500 amino acids, about 45 amino acids to about 450 amino acids, about 45 amino acids to about 400 amino acids, about 45 amino acids to about 350 amino acids, about 45 amino acids to about 300 amino acids, about 45 amino acids to about 280 amino acids, about 45 amino acids to about 260 amino acids, about 45 amino acids to about 240 amino acids, about 45 amino acids to about 220 amino acids, about 45 amino acids to about 200 amino acids, about 45 amino acids to about 195 amino acids, about 45 amino acids to about 190 amino acids, about 45 amino acids to about 185 amino acids, about 45 amino acids to about 180 amino acids, about 45 amino acids to about 175 amino acids, about 45 amino acids to about 170 amino acids, about 45 amino acids to about 165 amino acids, about 45 amino acids to about 160 amino acids, about 45 amino acids to about 155 amino acids, about 45 amino acids to about 150 amino acids, about 45 amino acids to about 145 amino acids, about 45 amino acids to about 140 amino acids, about 45 amino acids to about 135 amino acids, about 45 amino acids to about 130 amino acids, about 45 amino acids to about 125 amino acids, about 45 amino acids to about 120 amino acids, about 45 amino acids to about 115 amino acids, about 45 amino acids to about 110 amino acids, about 45 amino acids to about 105 amino acids, about 45 amino acids to about 100 amino acids, about 45 amino acids to about 95 amino acids, about 45 amino acids to about 90 amino acids, about 45 amino acids to about 85 amino acids, about 45 amino acids to about 80 amino acids, about 45 amino acids to about 75 amino acids, about 45 amino acids to about 70 amino acids, about 45 amino acids to about 65 amino acids, about 45 amino acids to about 60 amino acids, about 45 amino acids to about 55 amino acids, about 45 amino acids to about 50 amino acids, about 50 amino acids to about 1000 amino acids, about 50 amino acids to about 950 amino acids, about 50 amino acids to about 900 amino acids, about 50 amino acids to about 850 amino acids, about 50 amino acids to about 800 amino acids, about 50 amino acids to about 750 amino acids, about 50 amino acids to about 700 amino acids, about 50 amino acids to about 650 amino acids, about 50 amino acids to about 600 amino acids, about 50 amino acids to about 550 amino acids, about 50 amino acids to about 500 amino acids, about 50 amino acids to about 450 amino acids, about 50 amino acids to about 400 amino acids, about 50 amino acids to about 350 amino acids, about 50 amino acids to about 300 amino acids, about 50 amino acids to about 280 amino acids, about 50 amino acids to about 260 amino acids, about 50 amino acids to about 240 amino acids, about 50 amino acids to about 220 amino acids, about 50 amino acids to about 200 amino acids, about 50 amino acids to about 195 amino acids, about 50 amino acids to about 190 amino acids, about 50 amino acids to about 185 amino acids, about 50 amino acids to about 180 amino acids, about 50 amino acids to about 175 amino acids, about 50 amino acids to about 170 amino acids, about 50 amino acids to about 165 amino acids, about 50 amino acids to about 160 amino acids, about 50 amino acids to about 155 amino acids, about 50 amino acids to about 150 amino acids, about 50 amino acids to about 145 amino acids, about 50 amino acids to about 140 amino acids, about 50 amino acids to about 135 amino acids, about 50 amino acids to about 130 amino acids, about 50 amino acids to about 125 amino acids, about 50 amino acids to about 120 amino acids, about 50 amino acids to about 115 amino acids, about 50 amino acids to about 110 amino acids, about 50 amino acids to about 105 amino acids, about 50 amino acids to about 100 amino acids, about 50 amino acids to about 95 amino acids, about 50 amino acids to about 90 amino acids, about 50 amino acids to about 85 amino acids, about 50 amino acids to about 80 amino acids, about 50 amino acids to about 75 amino acids, about 50 amino acids to about 70 amino acids, about 50 amino acids to about 65 amino acids, about 50 amino acids to about 60 amino acids, about 50 amino acids to about 55 amino acids, about 55 amino acids to about 1000 amino acids, about 55 amino acids to about 950 amino acids, about 55 amino acids to about 900 amino acids, about 55 amino acids to about 850 amino acids, about 55 amino acids to about 800 amino acids, about 55 amino acids to about 750 amino acids, about 55 amino acids to about 700 amino acids, about 55 amino acids to about 650 amino acids, about 55 amino acids to about 600 amino acids, about 55 amino acids to about 550 amino acids, about 55 amino acids to about 500 amino acids, about 55 amino acids to about 450 amino acids, about 55 amino acids to about 400 amino acids, about 55 amino acids to about 350 amino acids, about 55 amino acids to about 300 amino acids, about 55 amino acids to about 280 amino acids, about 55 amino acids to about 260 amino acids, about 55 amino acids to about 240 amino acids, about 55 amino acids to about 220 amino acids, about 55 amino acids to about 200 amino acids, about 55 amino acids to about 195 amino acids, about 55 amino acids to about 190 amino acids, about 55 amino acids to about 185 amino acids, about 55 amino acids to about 180 amino acids, about 55 amino acids to about 175 amino acids, about 55 amino acids to about 170 amino acids, about 55 amino acids to about 165 amino acids, about 55 amino acids to about 160 amino acids, about 55 amino acids to about 155 amino acids, about 55 amino acids to about 150 amino acids, about 55 amino acids to about 145 amino acids, about 55 amino acids to about 140 amino acids, about 55 amino acids to about 135 amino acids, about 55 amino acids to about 130 amino acids, about 55 amino acids to about 125 amino acids, about 55 amino acids to about 120 amino acids, about 55 amino acids to about 115 amino acids, about 55 amino acids to about 110 amino acids, about 55 amino acids to about 105 amino acids, about 55 amino acids to about 100 amino acids, about 55 amino acids to about 95 amino acids, about 55 amino acids to about 90 amino acids, about 55 amino acids to about 85 amino acids, about 55 amino acids to about 80 amino acids, about 55 amino acids to about 75 amino acids, about 55 amino acids to about 70 amino acids, about 55 amino acids to about 65 amino acids, about 55 amino acids to about 60 amino acids, about 60 amino acids to about 1000 amino acids, about 60 amino acids to about 950 amino acids, about 60 amino acids to about 900 amino acids, about 60 amino acids to about 850 amino acids, about 60 amino acids to about 800 amino acids, about 60 amino acids to about 750 amino acids, about 60 amino acids to about 700 amino acids, about 60 amino acids to about 650 amino acids, about 60 amino acids to about 600 amino acids, about 60 amino acids to about 550 amino acids, about 60 amino acids to about 500 amino acids, about 60 amino acids to about 450 amino acids, about 60 amino acids to about 400 amino acids, about 60 amino acids to about 350 amino acids, about 60 amino acids to about 300 amino acids, about 60 amino acids to about 280 amino acids, about 60 amino acids to about 260 amino acids, about 60 amino acids to about 240 amino acids, about 60 amino acids to about 220 amino acids, about 60 amino acids to about 200 amino acids, about 60 amino acids to about 195 amino acids, about 60 amino acids to about 190 amino acids, about 60 amino acids to about 185 amino acids, about 60 amino acids to about 180 amino acids, about 60 amino acids to about 175 amino acids, about 60 amino acids to about 170 amino acids, about 60 amino acids to about 165 amino acids, about 60 amino acids to about 160 amino acids, about 60 amino acids to about 155 amino acids, about 60 amino acids to about 150 amino acids, about 60 amino acids to about 145 amino acids, about 60 amino acids to about 140 amino acids, about 60 amino acids to about 135 amino acids, about 60 amino acids to about 130 amino acids, about 60 amino acids to about 125 amino acids, about 60 amino acids to about 120 amino acids, about 60 amino acids to about 115 amino acids, about 60 amino acids to about 110 amino acids, about 60 amino acids to about 105 amino acids, about 60 amino acids to about 100 amino acids, about 60 amino acids to about 95 amino acids, about 60 amino acids to about 90 amino acids, about 60 amino acids to about 85 amino acids, about 60 amino acids to about 80 amino acids, about 60 amino acids to about 75 amino acids, about 60 amino acids to about 70 amino acids, about 60 amino acids to about 65 amino acids, about 65 amino acids to about 1000 amino acids, about 65 amino acids to about 950 amino acids, about 65 amino acids to about 900 amino acids, about 65 amino acids to about 850 amino acids, about 65 amino acids to about 800 amino acids, about 65 amino acids to about 750 amino acids, about 65 amino acids to about 700 amino acids, about 65 amino acids to about 650 amino acids, about 65 amino acids to about 600 amino acids, about 65 amino acids to about 550 amino acids, about 65 amino acids to about 500 amino acids, about 65 amino acids to about 450 amino acids, about 65 amino acids to about 400 amino acids, about 65 amino acids to about 350 amino acids, about 65 amino acids to about 300 amino acids, about 65 amino acids to about 280 amino acids, about 65 amino acids to about 260 amino acids, about 65 amino acids to about 240 amino acids, about 65 amino acids to about 220 amino acids, about 65 amino acids to about 200 amino acids, about 65 amino acids to about 195 amino acids, about 65 amino acids to about 190 amino acids, about 65 amino acids to about 185 amino acids, about 65 amino acids to about 180 amino acids, about 65 amino acids to about 175 amino acids, about 65 amino acids to about 170 amino acids, about 65 amino acids to about 165 amino acids, about 65 amino acids to about 160 amino acids, about 65 amino acids to about 155 amino acids, about 65 amino acids to about 150 amino acids, about 65 amino acids to about 145 amino acids, about 65 amino acids to about 140 amino acids, about 65 amino acids to about 135 amino acids, about 65 amino acids to about 130 amino acids, about 65 amino acids to about 125 amino acids, about 65 amino acids to about 120 amino acids, about 65 amino acids to about 115 amino acids, about 65 amino acids to about 110 amino acids, about 65 amino acids to about 105 amino acids, about 65 amino acids to about 100 amino acids, about 65 amino acids to about 95 amino acids, about 65 amino acids to about 90 amino acids, about 65 amino acids to about 85 amino acids, about 65 amino acids to about 80 amino acids, about 65 amino acids to about 75 amino acids, about 65 amino acids to about 70 amino acids, about 70 amino acids to about 1000 amino acids, about 70 amino acids to about 950 amino acids, about 70 amino acids to about 900 amino acids, about 70 amino acids to about 850 amino acids, about 70 amino acids to about 800 amino acids, about 70 amino acids to about 750 amino acids, about 70 amino acids to about 700 amino acids, about 70 amino acids to about 650 amino acids, about 70 amino acids to about 600 amino acids, about 70 amino acids to about 550 amino acids, about 70 amino acids to about 500 amino acids, about 70 amino acids to about 450 amino acids, about 70 amino acids to about 400 amino acids, about 70 amino acids to about 350 amino acids, about 70 amino acids to about 300 amino acids, about 70 amino acids to about 280 amino acids, about 70 amino acids to about 260 amino acids, about 70 amino acids to about 240 amino acids, about 70 amino acids to about 220 amino acids, about 70 amino acids to about 200 amino acids, about 70 amino acids to about 195 amino acids, about 70 amino acids to about 190 amino acids, about 70 amino acids to about 185 amino acids, about 70 amino acids to about 180 amino acids, about 70 amino acids to about 175 amino acids, about 70 amino acids to about 170 amino acids, about 70 amino acids to about 165 amino acids, about 70 amino acids to about 160 amino acids, about 70 amino acids to about 155 amino acids, about 70 amino acids to about 150 amino acids, about 70 amino acids to about 145 amino acids, about 70 amino acids to about 140 amino acids, about 70 amino acids to about 135 amino acids, about 70 amino acids to about 130 amino acids, about 70 amino acids to about 125 amino acids, about 70 amino acids to about 120 amino acids, about 70 amino acids to about 115 amino acids, about 70 amino acids to about 110 amino acids, about 70 amino acids to about 105 amino acids, about 70 amino acids to about 100 amino acids, about 70 amino acids to about 95 amino acids, about 70 amino acids to about 90 amino acids, about 70 amino acids to about 85 amino acids, about 70 amino acids to about 80 amino acids, about 70 amino acids to about 75 amino acids, about 75 amino acids to about 1000 amino acids, about 75 amino acids to about 950 amino acids, about 75 amino acids to about 900 amino acids, about 75 amino acids to about 850 amino acids, about 75 amino acids to about 800 amino acids, about 75 amino acids to about 750 amino acids, about 75 amino acids to about 700 amino acids, about 75 amino acids to about 650 amino acids, about 75 amino acids to about 600 amino acids, about 75 amino acids to about 550 amino acids, about 75 amino acids to about 500 amino acids, about 75 amino acids to about 450 amino acids, about 75 amino acids to about 400 amino acids, about 75 amino acids to about 350 amino acids, about 75 amino acids to about 300 amino acids, about 75 amino acids to about 280 amino acids, about 75 amino acids to about 260 amino acids, about 75 amino acids to about 240 amino acids, about 75 amino acids to about 220 amino acids, about 75 amino acids to about 200 amino acids, about 75 amino acids to about 195 amino acids, about 75 amino acids to about 190 amino acids, about 75 amino acids to about 185 amino acids, about 75 amino acids to about 180 amino acids, about 75 amino acids to about 175 amino acids, about 75 amino acids to about 170 amino acids, about 75 amino acids to about 165 amino acids, about 75 amino acids to about 160 amino acids, about 75 amino acids to about 155 amino acids, about 75 amino acids to about 150 amino acids, about 75 amino acids to about 145 amino acids, about 75 amino acids to about 140 amino acids, about 75 amino acids to about 135 amino acids, about 75 amino acids to about 130 amino acids, about 75 amino acids to about 125 amino acids, about 75 amino acids to about 120 amino acids, about 75 amino acids to about 115 amino acids, about 75 amino acids to about 110 amino acids, about 75 amino acids to about 105 amino acids, about 75 amino acids to about 100 amino acids, about 75 amino acids to about 95 amino acids, about 75 amino acids to about 90 amino acids, about 75 amino acids to about 85 amino acids, about 75 amino acids to about 80 amino acids, about 80 amino acids to about 1000 amino acids, about 80 amino acids to about 950 amino acids, about 80 amino acids to about 900 amino acids, about 80 amino acids to about 850 amino acids, about 80 amino acids to about 800 amino acids, about 80 amino acids to about 750 amino acids, about 80 amino acids to about 700 amino acids, about 80 amino acids to about 650 amino acids, about 80 amino acids to about 600 amino acids, about 80 amino acids to about 550 amino acids, about 80 amino acids to about 500 amino acids, about 80 amino acids to about 450 amino acids, about 80 amino acids to about 400 amino acids, about 80 amino acids to about 350 amino acids, about 80 amino acids to about 300 amino acids, about 80 amino acids to about 280 amino acids, about 80 amino acids to about 260 amino acids, about 80 amino acids to about 240 amino acids, about 80 amino acids to about 220 amino acids, about 80 amino acids to about 200 amino acids, about 80 amino acids to about 195 amino acids, about 80 amino acids to about 190 amino acids, about 80 amino acids to about 185 amino acids, about 80 amino acids to about 180 amino acids, about 80 amino acids to about 175 amino acids, about 80 amino acids to about 170 amino acids, about 80 amino acids to about 165 amino acids, about 80 amino acids to about 160 amino acids, about 80 amino acids to about 155 amino acids, about 80 amino acids to about 150 amino acids, about 80 amino acids to about 145 amino acids, about 80 amino acids to about 140 amino acids, about 80 amino acids to about 135 amino acids, about 80 amino acids to about 130 amino acids, about 80 amino acids to about 125 amino acids, about 80 amino acids to about 120 amino acids, about 80 amino acids to about 115 amino acids, about 80 amino acids to about 110 amino acids, about 80 amino acids to about 105 amino acids, about 80 amino acids to about 100 amino acids, about 80 amino acids to about 95 amino acids, about 80 amino acids to about 90 amino acids, about 80 amino acids to about 85 amino acids, about 85 amino acids to about 1000 amino acids, about 85 amino acids to about 950 amino acids, about 85 amino acids to about 900 amino acids, about 85 amino acids to about 850 amino acids, about 85 amino acids to about 800 amino acids, about 85 amino acids to about 750 amino acids, about 85 amino acids to about 700 amino acids, about 85 amino acids to about 650 amino acids, about 85 amino acids to about 600 amino acids, about 85 amino acids to about 550 amino acids, about 85 amino acids to about 500 amino acids, about 85 amino acids to about 450 amino acids, about 85 amino acids to about 400 amino acids, about 85 amino acids to about 350 amino acids, about 85 amino acids to about 300 amino acids, about 85 amino acids to about 280 amino acids, about 85 amino acids to about 260 amino acids, about 85 amino acids to about 240 amino acids, about 85 amino acids to about 220 amino acids, about 85 amino acids to about 200 amino acids, about 85 amino acids to about 195 amino acids, about 85 amino acids to about 190 amino acids, about 85 amino acids to about 185 amino acids, about 85 amino acids to about 180 amino acids, about 85 amino acids to about 175 amino acids, about 85 amino acids to about 170 amino acids, about 85 amino acids to about 165 amino acids, about 85 amino acids to about 160 amino acids, about 85 amino acids to about 155 amino acids, about 85 amino acids to about 150 amino acids, about 85 amino acids to about 145 amino acids, about 85 amino acids to about 140 amino acids, about 85 amino acids to about 135 amino acids, about 85 amino acids to about 130 amino acids, about 85 amino acids to about 125 amino acids, about 85 amino acids to about 120 amino acids, about 85 amino acids to about 115 amino acids, about 85 amino acids to about 110 amino acids, about 85 amino acids to about 105 amino acids, about 85 amino acids to about 100 amino acids, about 85 amino acids to about 95 amino acids, about 85 amino acids to about 90 amino acids, about 90 amino acids to about 1000 amino acids, about 90 amino acids to about 950 amino acids, about 90 amino acids to about 900 amino acids, about 90 amino acids to about 850 amino acids, about 90 amino acids to about 800 amino acids, about 90 amino acids to about 750 amino acids, about 90 amino acids to about 700 amino acids, about 90 amino acids to about 650 amino acids, about 90 amino acids to about 600 amino acids, about 90 amino acids to about 550 amino acids, about 90 amino acids to about 500 amino acids, about 90 amino acids to about 450 amino acids, about 90 amino acids to about 400 amino acids, about 90 amino acids to about 350 amino acids, about 90 amino acids to about 300 amino acids, about 90 amino acids to about 280 amino acids, about 90 amino acids to about 260 amino acids, about 90 amino acids to about 240 amino acids, about 90 amino acids to about 220 amino acids, about 90 amino acids to about 200 amino acids, about 90 amino acids to about 195 amino acids, about 90 amino acids to about 190 amino acids, about 90 amino acids to about 185 amino acids, about 90 amino acids to about 180 amino acids, about 90 amino acids to about 175 amino acids, about 90 amino acids to about 170 amino acids, about 90 amino acids to about 165 amino acids, about 90 amino acids to about 160 amino acids, about 90 amino acids to about 155 amino acids, about 90 amino acids to about 150 amino acids, about 90 amino acids to about 145 amino acids, about 90 amino acids to about 140 amino acids, about 90 amino acids to about 135 amino acids, about 90 amino acids to about 130 amino acids, about 90 amino acids to about 125 amino acids, about 90 amino acids to about 120 amino acids, about 90 amino acids to about 115 amino acids, about 90 amino acids to about 110 amino acids, about 90 amino acids to about 105 amino acids, about 90 amino acids to about 100 amino acids, about 90 amino acids to about 95 amino acids, about 95 amino acids to about 1000 amino acids, about 95 amino acids to about 950 amino acids, about 95 amino acids to about 900 amino acids, about 95 amino acids to about 850 amino acids, about 95 amino acids to about 800 amino acids, about 95 amino acids to about 750 amino acids, about 95 amino acids to about 700 amino acids, about 95 amino acids to about 650 amino acids, about 95 amino acids to about 600 amino acids, about 95 amino acids to about 550 amino acids, about 95 amino acids to about 500 amino acids, about 95 amino acids to about 450 amino acids, about 95 amino acids to about 400 amino acids, about 95 amino acids to about 350 amino acids, about 95 amino acids to about 300 amino acids, about 95 amino acids to about 280 amino acids, about 95 amino acids to about 260 amino acids, about 95 amino acids to about 240 amino acids, about 95 amino acids to about 220 amino acids, about 95 amino acids to about 200 amino acids, about 95 amino acids to about 195 amino acids, about 95 amino acids to about 190 amino acids, about 95 amino acids to about 185 amino acids, about 95 amino acids to about 180 amino acids, about 95 amino acids to about 175 amino acids, about 95 amino acids to about 170 amino acids, about 95 amino acids to about 165 amino acids, about 95 amino acids to about 160 amino acids, about 95 amino acids to about 155 amino acids, about 95 amino acids to about 150 amino acids, about 95 amino acids to about 145 amino acids, about 95 amino acids to about 140 amino acids, about 95 amino acids to about 135 amino acids, about 95 amino acids to about 130 amino acids, about 95 amino acids to about 125 amino acids, about 95 amino acids to about 120 amino acids, about 95 amino acids to about 115 amino acids, about 95 amino acids to about 110 amino acids, about 95 amino acids to about 105 amino acids, about 95 amino acids to about 100 amino acids, about 100 amino acids to about 1000 amino acids, about 100 amino acids to about 950 amino acids, about 100 amino acids to about 900 amino acids, about 100 amino acids to about 850 amino acids, about 100 amino acids to about 800 amino acids, about 100 amino acids to about 750 amino acids, about 100 amino acids to about 700 amino acids, about 100 amino acids to about 650 amino acids, about 100 amino acids to about 600 amino acids, about 100 amino acids to about 550 amino acids, about 100 amino acids to about 500 amino acids, about 100 amino acids to about 450 amino acids, about 100 amino acids to about 400 amino acids, about 100 amino acids to about 350 amino acids, about 100 amino acids to about 300 amino acids, about 100 amino acids to about 280 amino acids, about 100 amino acids to about 260 amino acids, about 100 amino acids to about 240 amino acids, about 100 amino acids to about 220 amino acids, about 100 amino acids to about 200 amino acids, about 100 amino acids to about 195 amino acids, about 100 amino acids to about 190 amino acids, about 100 amino acids to about 185 amino acids, about 100 amino acids to about 180 amino acids, about 100 amino acids to about 175 amino acids, about 100 amino acids to about 170 amino acids, about 100 amino acids to about 165 amino acids, about 100 amino acids to about 160 amino acids, about 100 amino acids to about 155 amino acids, about 100 amino acids to about 150 amino acids, about 100 amino acids to about 145 amino acids, about 100 amino acids to about 140 amino acids, about 100 amino acids to about 135 amino acids, about 100 amino acids to about 130 amino acids, about 100 amino acids to about 125 amino acids, about 100 amino acids to about 120 amino acids, about 100 amino acids to about 115 amino acids, about 100 amino acids to about 110 amino acids, about 100 amino acids to about 105 amino acids, about 105 amino acids to about 1000 amino acids, about 105 amino acids to about 950 amino acids, about 105 amino acids to about 900 amino acids, about 105 amino acids to about 850 amino acids, about 105 amino acids to about 800 amino acids, about 105 amino acids to about 750 amino acids, about 105 amino acids to about 700 amino acids, about 105 amino acids to about 650 amino acids, about 105 amino acids to about 600 amino acids, about 105 amino acids to about 550 amino acids, about 105 amino acids to about 500 amino acids, about 105 amino acids to about 450 amino acids, about 105 amino acids to about 400 amino acids, about 105 amino acids to about 350 amino acids, about 105 amino acids to about 300 amino acids, about 105 amino acids to about 280 amino acids, about 105 amino acids to about 260 amino acids, about 105 amino acids to about 240 amino acids, about 105 amino acids to about 220 amino acids, about 105 amino acids to about 200 amino acids, about 105 amino acids to about 195 amino acids, about 105 amino acids to about 190 amino acids, about 105 amino acids to about 185 amino acids, about 105 amino acids to about 180 amino acids, about 105 amino acids to about 175 amino acids, about 105 amino acids to about 170 amino acids, about 105 amino acids to about 165 amino acids, about 105 amino acids to about 160 amino acids, about 105 amino acids to about 155 amino acids, about 105 amino acids to about 150 amino acids, about 105 amino acids to about 145 amino acids, about 105 amino acids to about 140 amino acids, about 105 amino acids to about 135 amino acids, about 105 amino acids to about 130 amino acids, about 105 amino acids to about 125 amino acids, about 105 amino acids to about 120 amino acids, about 105 amino acids to about 115 amino acids, about 105 amino acids to about 110 amino acids, about 110 amino acids to about 1000 amino acids, about 110 amino acids to about 950 amino acids, about 110 amino acids to about 900 amino acids, about 110 amino acids to about 850 amino acids, about 110 amino acids to about 800 amino acids, about 110 amino acids to about 750 amino acids, about 110 amino acids to about 700 amino acids, about 110 amino acids to about 650 amino acids, about 110 amino acids to about 600 amino acids, about 110 amino acids to about 550 amino acids, about 110 amino acids to about 500 amino acids, about 110 amino acids to about 450 amino acids, about 110 amino acids to about 400 amino acids, about 110 amino acids to about 350 amino acids, about 110 amino acids to about 300 amino acids, about 110 amino acids to about 280 amino acids, about 110 amino acids to about 260 amino acids, about 110 amino acids to about 240 amino acids, about 110 amino acids to about 220 amino acids, about 110 amino acids to about 200 amino acids, about 110 amino acids to about 195 amino acids, about 110 amino acids to about 190 amino acids, about 110 amino acids to about 185 amino acids, about 110 amino acids to about 180 amino acids, about 110 amino acids to about 175 amino acids, about 110 amino acids to about 170 amino acids, about 110 amino acids to about 165 amino acids, about 110 amino acids to about 160 amino acids, about 110 amino acids to about 155 amino acids, about 110 amino acids to about 150 amino acids, about 110 amino acids to about 145 amino acids, about 110 amino acids to about 140 amino acids, about 110 amino acids to about 135 amino acids, about 110 amino acids to about 130 amino acids, about 110 amino acids to about 125 amino acids, about 110 amino acids to about 120 amino acids, about 110 amino acids to about 115 amino acids, about 115 amino acids to about 1000 amino acids, about 115 amino acids to about 950 amino acids, about 115 amino acids to about 900 amino acids, about 115 amino acids to about 850 amino acids, about 115 amino acids to about 800 amino acids, about 115 amino acids to about 750 amino acids, about 115 amino acids to about 700 amino acids, about 115 amino acids to about 650 amino acids, about 115 amino acids to about 600 amino acids, about 115 amino acids to about 550 amino acids, about 115 amino acids to about 500 amino acids, about 115 amino acids to about 450 amino acids, about 115 amino acids to about 400 amino acids, about 115 amino acids to about 350 amino acids, about 115 amino acids to about 300 amino acids, about 115 amino acids to about 280 amino acids, about 115 amino acids to about 260 amino acids, about 115 amino acids to about 240 amino acids, about 115 amino acids to about 220 amino acids, about 115 amino acids to about 200 amino acids, about 115 amino acids to about 195 amino acids, about 115 amino acids to about 190 amino acids, about 115 amino acids to about 185 amino acids, about 115 amino acids to about 180 amino acids, about 115 amino acids to about 175 amino acids, about 115 amino acids to about 170 amino acids, about 115 amino acids to about 165 amino acids, about 115 amino acids to about 160 amino acids, about 115 amino acids to about 155 amino acids, about 115 amino acids to about 150 amino acids, about 115 amino acids to about 145 amino acids, about 115 amino acids to about 140 amino acids, about 115 amino acids to about 135 amino acids, about 115 amino acids to about 130 amino acids, about 115 amino acids to about 125 amino acids, about 115 amino acids to about 120 amino acids, about 120 amino acids to about 1000 amino acids, about 120 amino acids to about 950 amino acids, about 120 amino acids to about 900 amino acids, about 120 amino acids to about 850 amino acids, about 120 amino acids to about 800 amino acids, about 120 amino acids to about 750 amino acids, about 120 amino acids to about 700 amino acids, about 120 amino acids to about 650 amino acids, about 120 amino acids to about 600 amino acids, about 120 amino acids to about 550 amino acids, about 120 amino acids to about 500 amino acids, about 120 amino acids to about 450 amino acids, about 120 amino acids to about 400 amino acids, about 120 amino acids to about 350 amino acids, about 120 amino acids to about 300 amino acids, about 120 amino acids to about 280 amino acids, about 120 amino acids to about 260 amino acids, about 120 amino acids to about 240 amino acids, about 120 amino acids to about 220 amino acids, about 120 amino acids to about 200 amino acids, about 120 amino acids to about 195 amino acids, about 120 amino acids to about 190 amino acids, about 120 amino acids to about 185 amino acids, about 120 amino acids to about 180 amino acids, about 120 amino acids to about 175 amino acids, about 120 amino acids to about 170 amino acids, about 120 amino acids to about 165 amino acids, about 120 amino acids to about 160 amino acids, about 120 amino acids to about 155 amino acids, about 120 amino acids to about 150 amino acids, about 120 amino acids to about 145 amino acids, about 120 amino acids to about 140 amino acids, about 120 amino acids to about 135 amino acids, about 120 amino acids to about 130 amino acids, about 120 amino acids to about 125 amino acids, about 125 amino acids to about 1000 amino acids, about 125 amino acids to about 950 amino acids, about 125 amino acids to about 900 amino acids, about 125 amino acids to about 850 amino acids, about 125 amino acids to about 800 amino acids, about 125 amino acids to about 750 amino acids, about 125 amino acids to about 700 amino acids, about 125 amino acids to about 650 amino acids, about 125 amino acids to about 600 amino acids, about 125 amino acids to about 550 amino acids, about 125 amino acids to about 500 amino acids, about 125 amino acids to about 450 amino acids, about 125 amino acids to about 400 amino acids, about 125 amino acids to about 350 amino acids, about 125 amino acids to about 300 amino acids, about 125 amino acids to about 280 amino acids, about 125 amino acids to about 260 amino acids, about 125 amino acids to about 240 amino acids, about 125 amino acids to about 220 amino acids, about 125 amino acids to about 200 amino acids, about 125 amino acids to about 195 amino acids, about 125 amino acids to about 190 amino acids, about 125 amino acids to about 185 amino acids, about 125 amino acids to about 180 amino acids, about 125 amino acids to about 175 amino acids, about 125 amino acids to about 170 amino acids, about 125 amino acids to about 165 amino acids, about 125 amino acids to about 160 amino acids, about 125 amino acids to about 155 amino acids, about 125 amino acids to about 150 amino acids, about 125 amino acids to about 145 amino acids, about 125 amino acids to about 140 amino acids, about 125 amino acids to about 135 amino acids, about 125 amino acids to about 130 amino acids, about 130 amino acids to about 1000 amino acids, about 130 amino acids to about 950 amino acids, about 130 amino acids to about 900 amino acids, about 130 amino acids to about 850 amino acids, about 130 amino acids to about 800 amino acids, about 130 amino acids to about 750 amino acids, about 130 amino acids to about 700 amino acids, about 130 amino acids to about 650 amino acids, about 130 amino acids to about 600 amino acids, about 130 amino acids to about 550 amino acids, about 130 amino acids to about 500 amino acids, about 130 amino acids to about 450 amino acids, about 130 amino acids to about 400 amino acids, about 130 amino acids to about 350 amino acids, about 130 amino acids to about 300 amino acids, about 130 amino acids to about 280 amino acids, about 130 amino acids to about 260 amino acids, about 130 amino acids to about 240 amino acids, about 130 amino acids to about 220 amino acids, about 130 amino acids to about 200 amino acids, about 130 amino acids to about 195 amino acids, about 130 amino acids to about 190 amino acids, about 130 amino acids to about 185 amino acids, about 130 amino acids to about 180 amino acids, about 130 amino acids to about 175 amino acids, about 130 amino acids to about 170 amino acids, about 130 amino acids to about 165 amino acids, about 130 amino acids to about 160 amino acids, about 130 amino acids to about 155 amino acids, about 130 amino acids to about 150 amino acids, about 130 amino acids to about 145 amino acids, about 130 amino acids to about 140 amino acids, about 130 amino acids to about 135 amino acids, about 135 amino acids to about 1000 amino acids, about 135 amino acids to about 950 amino acids, about 135 amino acids to about 900 amino acids, about 135 amino acids to about 850 amino acids, about 135 amino acids to about 800 amino acids, about 135 amino acids to about 750 amino acids, about 135 amino acids to about 700 amino acids, about 135 amino acids to about 650 amino acids, about 135 amino acids to about 600 amino acids, about 135 amino acids to about 550 amino acids, about 135 amino acids to about 500 amino acids, about 135 amino acids to about 450 amino acids, about 135 amino acids to about 400 amino acids, about 135 amino acids to about 350 amino acids, about 135 amino acids to about 300 amino acids, about 135 amino acids to about 280 amino acids, about 135 amino acids to about 260 amino acids, about 135 amino acids to about 240 amino acids, about 135 amino acids to about 220 amino acids, about 135 amino acids to about 200 amino acids, about 135 amino acids to about 195 amino acids, about 135 amino acids to about 190 amino acids, about 135 amino acids to about 185 amino acids, about 135 amino acids to about 180 amino acids, about 135 amino acids to about 175 amino acids, about 135 amino acids to about 170 amino acids, about 135 amino acids to about 165 amino acids, about 135 amino acids to about 160 amino acids, about 135 amino acids to about 155 amino acids, about 135 amino acids to about 150 amino acids, about 135 amino acids to about 145 amino acids, about 135 amino acids to about 140 amino acids, about 140 amino acids to about 1000 amino acids, about 140 amino acids to about 950 amino acids, about 140 amino acids to about 900 amino acids, about 140 amino acids to about 850 amino acids, about 140 amino acids to about 800 amino acids, about 140 amino acids to about 750 amino acids, about 140 amino acids to about 700 amino acids, about 140 amino acids to about 650 amino acids, about 140 amino acids to about 600 amino acids, about 140 amino acids to about 550 amino acids, about 140 amino acids to about 500 amino acids, about 140 amino acids to about 450 amino acids, about 140 amino acids to about 400 amino acids, about 140 amino acids to about 350 amino acids, about 140 amino acids to about 300 amino acids, about 140 amino acids to about 280 amino acids, about 140 amino acids to about 260 amino acids, about 140 amino acids to about 240 amino acids, about 140 amino acids to about 220 amino acids, about 140 amino acids to about 200 amino acids, about 140 amino acids to about 195 amino acids, about 140 amino acids to about 190 amino acids, about 140 amino acids to about 185 amino acids, about 140 amino acids to about 180 amino acids, about 140 amino acids to about 175 amino acids, about 140 amino acids to about 170 amino acids, about 140 amino acids to about 165 amino acids, about 140 amino acids to about 160 amino acids, about 140 amino acids to about 155 amino acids, about 140 amino acids to about 150 amino acids, about 140 amino acids to about 145 amino acids, about 145 amino acids to about 1000 amino acids, about 145 amino acids to about 950 amino acids, about 145 amino acids to about 900 amino acids, about 145 amino acids to about 850 amino acids, about 145 amino acids to about 800 amino acids, about 145 amino acids to about 750 amino acids, about 145 amino acids to about 700 amino acids, about 145 amino acids to about 650 amino acids, about 145 amino acids to about 600 amino acids, about 145 amino acids to about 550 amino acids, about 145 amino acids to about 500 amino acids, about 145 amino acids to about 450 amino acids, about 145 amino acids to about 400 amino acids, about 145 amino acids to about 350 amino acids, about 145 amino acids to about 300 amino acids, about 145 amino acids to about 280 amino acids, about 145 amino acids to about 260 amino acids, about 145 amino acids to about 240 amino acids, about 145 amino acids to about 220 amino acids, about 145 amino acids to about 200 amino acids, about 145 amino acids to about 195 amino acids, about 145 amino acids to about 190 amino acids, about 145 amino acids to about 185 amino acids, about 145 amino acids to about 180 amino acids, about 145 amino acids to about 175 amino acids, about 145 amino acids to about 170 amino acids, about 145 amino acids to about 165 amino acids, about 145 amino acids to about 160 amino acids, about 145 amino acids to about 155 amino acids, about 145 amino acids to about 150 amino acids, about 150 amino acids to about 1000 amino acids, about 150 amino acids to about 950 amino acids, about 150 amino acids to about 900 amino acids, about 150 amino acids to about 850 amino acids, about 150 amino acids to about 800 amino acids, about 150 amino acids to about 750 amino acids, about 150 amino acids to about 700 amino acids, about 150 amino acids to about 650 amino acids, about 150 amino acids to about 600 amino acids, about 150 amino acids to about 550 amino acids, about 150 amino acids to about 500 amino acids, about 150 amino acids to about 450 amino acids, about 150 amino acids to about 400 amino acids, about 150 amino acids to about 350 amino acids, about 150 amino acids to about 300 amino acids, about 150 amino acids to about 280 amino acids, about 150 amino acids to about 260 amino acids, about 150 amino acids to about 240 amino acids, about 150 amino acids to about 220 amino acids, about 150 amino acids to about 200 amino acids, about 150 amino acids to about 195 amino acids, about 150 amino acids to about 190 amino acids, about 150 amino acids to about 185 amino acids, about 150 amino acids to about 180 amino acids, about 150 amino acids to about 175 amino acids, about 150 amino acids to about 170 amino acids, about 150 amino acids to about 165 amino acids, about 150 amino acids to about 160 amino acids, about 150 amino acids to about 155 amino acids, about 155 amino acids to about 1000 amino acids, about 155 amino acids to about 950 amino acids, about 155 amino acids to about 900 amino acids, about 155 amino acids to about 850 amino acids, about 155 amino acids to about 800 amino acids, about 155 amino acids to about 750 amino acids, about 155 amino acids to about 700 amino acids, about 155 amino acids to about 650 amino acids, about 155 amino acids to about 600 amino acids, about 155 amino acids to about 550 amino acids, about 155 amino acids to about 500 amino acids, about 155 amino acids to about 450 amino acids, about 155 amino acids to about 400 amino acids, about 155 amino acids to about 350 amino acids, about 155 amino acids to about 300 amino acids, about 155 amino acids to about 280 amino acids, about 155 amino acids to about 260 amino acids, about 155 amino acids to about 240 amino acids, about 155 amino acids to about 220 amino acids, about 155 amino acids to about 200 amino acids, about 155 amino acids to about 195 amino acids, about 155 amino acids to about 190 amino acids, about 155 amino acids to about 185 amino acids, about 155 amino acids to about 180 amino acids, about 155 amino acids to about 175 amino acids, about 155 amino acids to about 170 amino acids, about 155 amino acids to about 165 amino acids, about 155 amino acids to about 160 amino acids, about 160 amino acids to about 1000 amino acids, about 160 amino acids to about 950 amino acids, about 160 amino acids to about 900 amino acids, about 160 amino acids to about 850 amino acids, about 160 amino acids to about 800 amino acids, about 160 amino acids to about 750 amino acids, about 160 amino acids to about 700 amino acids, about 160 amino acids to about 650 amino acids, about 160 amino acids to about 600 amino acids, about 160 amino acids to about 550 amino acids, about 160 amino acids to about 500 amino acids, about 160 amino acids to about 450 amino acids, about 160 amino acids to about 400 amino acids, about 160 amino acids to about 350 amino acids, about 160 amino acids to about 300 amino acids, about 160 amino acids to about 280 amino acids, about 160 amino acids to about 260 amino acids, about 160 amino acids to about 240 amino acids, about 160 amino acids to about 220 amino acids, about 160 amino acids to about 200 amino acids, about 160 amino acids to about 195 amino acids, about 160 amino acids to about 190 amino acids, about 160 amino acids to about 185 amino acids, about 160 amino acids to about 180 amino acids, about 160 amino acids to about 175 amino acids, about 160 amino acids to about 170 amino acids, about 160 amino acids to about 165 amino acids, about 165 amino acids to about 1000 amino acids, about 165 amino acids to about 950 amino acids, about 165 amino acids to about 900 amino acids, about 165 amino acids to about 850 amino acids, about 165 amino acids to about 800 amino acids, about 165 amino acids to about 750 amino acids, about 165 amino acids to about 700 amino acids, about 165 amino acids to about 650 amino acids, about 165 amino acids to about 600 amino acids, about 165 amino acids to about 550 amino acids, about 165 amino acids to about 500 amino acids, about 165 amino acids to about 450 amino acids, about 165 amino acids to about 400 amino acids, about 165 amino acids to about 350 amino acids, about 165 amino acids to about 300 amino acids, about 165 amino acids to about 280 amino acids, about 165 amino acids to about 260 amino acids, about 165 amino acids to about 240 amino acids, about 165 amino acids to about 220 amino acids, about 165 amino acids to about 200 amino acids, about 165 amino acids to about 195 amino acids, about 165 amino acids to about 190 amino acids, about 165 amino acids to about 185 amino acids, about 165 amino acids to about 180 amino acids, about 165 amino acids to about 175 amino acids, about 165 amino acids to about 170 amino acids, about 170 amino acids to about 1000 amino acids, about 170 amino acids to about 950 amino acids, about 170 amino acids to about 900 amino acids, about 170 amino acids to about 850 amino acids, about 170 amino acids to about 800 amino acids, about 170 amino acids to about 750 amino acids, about 170 amino acids to about 700 amino acids, about 170 amino acids to about 650 amino acids, about 170 amino acids to about 600 amino acids, about 170 amino acids to about 550 amino acids, about 170 amino acids to about 500 amino acids, about 170 amino acids to about 450 amino acids, about 170 amino acids to about 400 amino acids, about 170 amino acids to about 350 amino acids, about 170 amino acids to about 300 amino acids, about 170 amino acids to about 280 amino acids, about 170 amino acids to about 260 amino acids, about 170 amino acids to about 240 amino acids, about 170 amino acids to about 220 amino acids, about 170 amino acids to about 200 amino acids, about 170 amino acids to about 195 amino acids, about 170 amino acids to about 190 amino acids, about 170 amino acids to about 185 amino acids, about 170 amino acids to about 180 amino acids, about 170 amino acids to about 175 amino acids, about 175 amino acids to about 1000 amino acids, about 175 amino acids to about 950 amino acids, about 175 amino acids to about 900 amino acids, about 175 amino acids to about 850 amino acids, about 175 amino acids to about 800 amino acids, about 175 amino acids to about 750 amino acids, about 175 amino acids to about 700 amino acids, about 175 amino acids to about 650 amino acids, about 175 amino acids to about 600 amino acids, about 175 amino acids to about 550 amino acids, about 175 amino acids to about 500 amino acids, about 175 amino acids to about 450 amino acids, about 175 amino acids to about 400 amino acids, about 175 amino acids to about 350 amino acids, about 175 amino acids to about 300 amino acids, about 175 amino acids to about 280 amino acids, about 175 amino acids to about 260 amino acids, about 175 amino acids to about 240 amino acids, about 175 amino acids to about 220 amino acids, about 175 amino acids to about 200 amino acids, about 175 amino acids to about 195 amino acids, about 175 amino acids to about 190 amino acids, about 175 amino acids to about 185 amino acids, about 175 amino acids to about 180 amino acids, about 180 amino acids to about 1000 amino acids, about 180 amino acids to about 950 amino acids, about 180 amino acids to about 900 amino acids, about 180 amino acids to about 850 amino acids, about 180 amino acids to about 800 amino acids, about 180 amino acids to about 750 amino acids, about 180 amino acids to about 700 amino acids, about 180 amino acids to about 650 amino acids, about 180 amino acids to about 600 amino acids, about 180 amino acids to about 550 amino acids, about 180 amino acids to about 500 amino acids, about 180 amino acids to about 450 amino acids, about 180 amino acids to about 400 amino acids, about 180 amino acids to about 350 amino acids, about 180 amino acids to about 300 amino acids, about 180 amino acids to about 280 amino acids, about 180 amino acids to about 260 amino acids, about 180 amino acids to about 240 amino acids, about 180 amino acids to about 220 amino acids, about 180 amino acids to about 200 amino acids, about 180 amino acids to about 195 amino acids, about 180 amino acids to about 190 amino acids, about 180 amino acids to about 185 amino acids, about 185 amino acids to about 1000 amino acids, about 185 amino acids to about 950 amino acids, about 185 amino acids to about 900 amino acids, about 185 amino acids to about 850 amino acids, about 185 amino acids to about 800 amino acids, about 185 amino acids to about 750 amino acids, about 185 amino acids to about 700 amino acids, about 185 amino acids to about 650 amino acids, about 185 amino acids to about 600 amino acids, about 185 amino acids to about 550 amino acids, about 185 amino acids to about 500 amino acids, about 185 amino acids to about 450 amino acids, about 185 amino acids to about 400 amino acids, about 185 amino acids to about 350 amino acids, about 185 amino acids to about 300 amino acids, about 185 amino acids to about 280 amino acids, about 185 amino acids to about 260 amino acids, about 185 amino acids to about 240 amino acids, about 185 amino acids to about 220 amino acids, about 185 amino acids to about 200 amino acids, about 185 amino acids to about 195 amino acids, about 185 amino acids to about 190 amino acids, about 190 amino acids to about 1000 amino acids, about 190 amino acids to about 950 amino acids, about 190 amino acids to about 900 amino acids, about 190 amino acids to about 850 amino acids, about 190 amino acids to about 800 amino acids, about 190 amino acids to about 750 amino acids, about 190 amino acids to about 700 amino acids, about 190 amino acids to about 650 amino acids, about 190 amino acids to about 600 amino acids, about 190 amino acids to about 550 amino acids, about 190 amino acids to about 500 amino acids, about 190 amino acids to about 450 amino acids, about 190 amino acids to about 400 amino acids, about 190 amino acids to about 350 amino acids, about 190 amino acids to about 300 amino acids, about 190 amino acids to about 280 amino acids, about 190 amino acids to about 260 amino acids, about 190 amino acids to about 240 amino acids, about 190 amino acids to about 220 amino acids, about 190 amino acids to about 200 amino acids, about 190 amino acids to about 195 amino acids, about 195 amino acids to about 1000 amino acids, about 195 amino acids to about 950 amino acids, about 195 amino acids to about 900 amino acids, about 195 amino acids to about 850 amino acids, about 195 amino acids to about 800 amino acids, about 195 amino acids to about 750 amino acids, about 195 amino acids to about 700 amino acids, about 195 amino acids to about 650 amino acids, about 195 amino acids to about 600 amino acids, about 195 amino acids to about 550 amino acids, about 195 amino acids to about 500 amino acids, about 195 amino acids to about 450 amino acids, about 195 amino acids to about 400 amino acids, about 195 amino acids to about 350 amino acids, about 195 amino acids to about 300 amino acids, about 195 amino acids to about 280 amino acids, about 195 amino acids to about 260 amino acids, about 195 amino acids to about 240 amino acids, about 195 amino acids to about 220 amino acids, about 195 amino acids to about 200 amino acids, about 200 amino acids to about 1000 amino acids, about 200 amino acids to about 950 amino acids, about 200 amino acids to about 900 amino acids, about 200 amino acids to about 850 amino acids, about 200 amino acids to about 800 amino acids, about 200 amino acids to about 750 amino acids, about 200 amino acids to about 700 amino acids, about 200 amino acids to about 650 amino acids, about 200 amino acids to about 600 amino acids, about 200 amino acids to about 550 amino acids, about 200 amino acids to about 500 amino acids, about 200 amino acids to about 450 amino acids, about 200 amino acids to about 400 amino acids, about 200 amino acids to about 350 amino acids, about 200 amino acids to about 300 amino acids, about 200 amino acids to about 280 amino acids, about 200 amino acids to about 260 amino acids, about 200 amino acids to about 240 amino acids, about 200 amino acids to about 220 amino acids, about 220 amino acids to about 1000 amino acids, about 220 amino acids to about 950 amino acids, about 220 amino acids to about 900 amino acids, about 220 amino acids to about 850 amino acids, about 220 amino acids to about 800 amino acids, about 220 amino acids to about 750 amino acids, about 220 amino acids to about 700 amino acids, about 220 amino acids to about 650 amino acids, about 220 amino acids to about 600 amino acids, about 220 amino acids to about 550 amino acids, about 220 amino acids to about 500 amino acids, about 220 amino acids to about 450 amino acids, about 220 amino acids to about 400 amino acids, about 220 amino acids to about 350 amino acids, about 220 amino acids to about 300 amino acids, about 220 amino acids to about 280 amino acids, about 220 amino acids to about 260 amino acids, about 220 amino acids to about 240 amino acids, about 240 amino acids to about 1000 amino acids, about 240 amino acids to about 950 amino acids, about 240 amino acids to about 900 amino acids, about 240 amino acids to about 850 amino acids, about 240 amino acids to about 800 amino acids, about 240 amino acids to about 750 amino acids, about 240 amino acids to about 700 amino acids, about 240 amino acids to about 650 amino acids, about 240 amino acids to about 600 amino acids, about 240 amino acids to about 550 amino acids, about 240 amino acids to about 500 amino acids, about 240 amino acids to about 450 amino acids, about 240 amino acids to about 400 amino acids, about 240 amino acids to about 350 amino acids, about 240 amino acids to about 300 amino acids, about 240 amino acids to about 280 amino acids, about 240 amino acids to about 260 amino acids, about 260 amino acids to about 1000 amino acids, about 260 amino acids to about 950 amino acids, about 260 amino acids to about 900 amino acids, about 260 amino acids to about 850 amino acids, about 260 amino acids to about 800 amino acids, about 260 amino acids to about 750 amino acids, about 260 amino acids to about 700 amino acids, about 260 amino acids to about 650 amino acids, about 260 amino acids to about 600 amino acids, about 260 amino acids to about 550 amino acids, about 260 amino acids to about 500 amino acids, about 260 amino acids to about 450 amino acids, about 260 amino acids to about 400 amino acids, about 260 amino acids to about 350 amino acids, about 260 amino acids to about 300 amino acids, about 260 amino acids to about 280 amino acids, about 280 amino acids to about 1000 amino acids, about 280 amino acids to about 950 amino acids, about 280 amino acids to about 900 amino acids, about 280 amino acids to about 850 amino acids, about 280 amino acids to about 800 amino acids, about 280 amino acids to about 750 amino acids, about 280 amino acids to about 700 amino acids, about 280 amino acids to about 650 amino acids, about 280 amino acids to about 600 amino acids, about 280 amino acids to about 550 amino acids, about 280 amino acids to about 500 amino acids, about 280 amino acids to about 450 amino acids, about 280 amino acids to about 400 amino acids, about 280 amino acids to about 350 amino acids, about 280 amino acids to about 300 amino acids, about 300 amino acids to about 1000 amino acids, about 300 amino acids to about 950 amino acids, about 300 amino acids to about 900 amino acids, about 300 amino acids to about 850 amino acids, about 300 amino acids to about 800 amino acids, about 300 amino acids to about 750 amino acids, about 300 amino acids to about 700 amino acids, about 300 amino acids to about 650 amino acids, about 300 amino acids to about 600 amino acids, about 300 amino acids to about 550 amino acids, about 300 amino acids to about 500 amino acids, about 300 amino acids to about 450 amino acids, about 300 amino acids to about 400 amino acids, about 300 amino acids to about 350 amino acids, about 350 amino acids to about 1000 amino acids, about 350 amino acids to about 950 amino acids, about 350 amino acids to about 900 amino acids, about 350 amino acids to about 850 amino acids, about 350 amino acids to about 800 amino acids, about 350 amino acids to about 750 amino acids, about 350 amino acids to about 700 amino acids, about 350 amino acids to about 650 amino acids, about 350 amino acids to about 600 amino acids, about 350 amino acids to about 550 amino acids, about 350 amino acids to about 500 amino acids, about 350 amino acids to about 450 amino acids, about 350 amino acids to about 400 amino acids, about 400 amino acids to about 1000 amino acids, about 400 amino acids to about 950 amino acids, about 400 amino acids to about 900 amino acids, about 400 amino acids to about 850 amino acids, about 400 amino acids to about 800 amino acids, about 400 amino acids to about 750 amino acids, about 400 amino acids to about 700 amino acids, about 400 amino acids to about 650 amino acids, about 400 amino acids to about 600 amino acids, about 400 amino acids to about 550 amino acids, about 400 amino acids to about 500 amino acids, about 400 amino acids to about 450 amino acids, about 450 amino acids to about 1000 amino acids, about 450 amino acids to about 950 amino acids, about 450 amino acids to about 900 amino acids, about 450 amino acids to about 850 amino acids, about 450 amino acids to about 800 amino acids, about 450 amino acids to about 750 amino acids, about 450 amino acids to about 700 amino acids, about 450 amino acids to about 650 amino acids, about 450 amino acids to about 600 amino acids, about 450 amino acids to about 550 amino acids, about 450 amino acids to about 500 amino acids, about 500 amino acids to about 1000 amino acids, about 500 amino acids to about 950 amino acids, about 500 amino acids to about 900 amino acids, about 500 amino acids to about 850 amino acids, about 500 amino acids to about 800 amino acids, about 500 amino acids to about 750 amino acids, about 500 amino acids to about 700 amino acids, about 500 amino acids to about 650 amino acids, about 500 amino acids to about 600 amino acids, about 500 amino acids to about 550 amino acids, about 550 amino acids to about 1000 amino acids, about 550 amino acids to about 950 amino acids, about 550 amino acids to about 900 amino acids, about 550 amino acids to about 850 amino acids, about 550 amino acids to about 800 amino acids, about 550 amino acids to about 750 amino acids, about 550 amino acids to about 700 amino acids, about 550 amino acids to about 650 amino acids, about 550 amino acids to about 600 amino acids, about 600 amino acids to about 1000 amino acids, about 600 amino acids to about 950 amino acids, about 600 amino acids to about 900 amino acids, about 600 amino acids to about 850 amino acids, about 600 amino acids to about 800 amino acids, about 600 amino acids to about 750 amino acids, about 600 amino acids to about 700 amino acids, about 600 amino acids to about 650 amino acids, about 650 amino acids to about 1000 amino acids, about 650 amino acids to about 950 amino acids, about 650 amino acids to about 900 amino acids, about 650 amino acids to about 850 amino acids, about 650 amino acids to about 800 amino acids, about 650 amino acids to about 750 amino acids, about 650 amino acids to about 700 amino acids, about 700 amino acids to about 1000 amino acids, about 700 amino acids to about 950 amino acids, about 700 amino acids to about 900 amino acids, about 700 amino acids to about 850 amino acids, about 700 amino acids to about 800 amino acids, about 700 amino acids to about 750 amino acids, about 750 amino acids to about 1000 amino acids, about 750 amino acids to about 950 amino acids, about 750 amino acids to about 900 amino acids, about 750 amino acids to about 850 amino acids, about 750 amino acids to about 800 amino acids, about 800 amino acids to about 1000 amino acids, about 800 amino acids to about 950 amino acids, about 800 amino acids to about 900 amino acids, about 800 amino acids to about 850 amino acids, about 850 amino acids to about 1000 amino acids, about 850 amino acids to about 950 amino acids, about 850 amino acids to about 900 amino acids, about 900 amino acids to about 1000 amino acids, about 900 amino acids to about 950 amino acids, or about 950 amino acids to about 1000 amino acids.

Any of the target-binding domains described herein can bind to its target with a dissociation equilibrium constant ($K_D$) of less than $1\times10^{-7}$M, less than $1\times10^{-8}$ M, less than $1\times10^{-9}$ M, less than $1\times10^{-10}$ M, less than $1\times10^{-11}$ M, less than $1\times10^{-12}$M, or less than $1\times10^{-13}$ M. In some embodiments, the antigen-binding protein constructs provided herein can bind to an identifying antigen with a $K_D$ of about $1\times10^{-3}$ M to about $1\times10^{-5}$ M, about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, or about $1\times10^{-9}$ M to about $1\times10^{-11}$ M (inclusive).

Any of the target-binding domains described herein can bind to its target with a $K_D$ of between about 1 pM to about 30 nM (e.g., about 1 pM to about 25 nM, about 1 pM to about 20 nM, about 1 pM to about 15 nM, about 1 pM to about 10 nM, about 1 pM to about 5 nM, about 1 pM to about 2 nM, about 1 pM to about 1 nM, about 1 pM to about 950 pM, about 1 pM to about 900 pM, about 1 pM to about 850 pM, about 1 pM to about 800 pM, about 1 pM to about 750 pM, about 1 pM to about 700 pM, about 1 pM to about 650 pM, about 1 pM to about 600 pM, about 1 pM to about 550 pM, about 1 pM to about 500 pM, about 1 pM to about 450 pM, about 1 pM to about 400 pM, about 1 pM to about 350 pM, about 1 pM to about 300 pM, about 1 pM to about 250 pM, about 1 pM to about 200 pM, about 1 pM to about 150 pM, about 1 pM to about 100 pM, about 1 pM to about 90 pM, about 1 pM to about 80 pM, about 1 pM to about 70 pM, about 1 pM to about 60 pM, about 1 pM to about 50 pM, about 1 pM to about 40 pM, about 1 pM to about 30 pM, about 1 pM to about 20 pM, about 1 pM to about 10 pM, about 1 pM to about 5 pM, about 1 pM to about 4 pM, about 1 pM to about 3 pM, about 1 pM to about 2 pM, about 2 pM to about 30 nM, about 2 pM to about 25 nM, about 2 pM to about 20 nM, about 2 pM to about 15 nM, about 2 pM to about 10 nM, about 2 pM to about 5 nM, about 2 pM to about 2 nM, about 2 pM to about 1 nM, about 2 pM to about 950 pM, about 2 pM to about 900 pM, about 2 pM to about 850 pM, about 2 pM to about 800 pM, about 2 pM to about 750 pM, about 2 pM to about 700 pM, about 2 pM to about 650 pM, about 2 pM to about 600 pM, about 2 pM to about 550 pM, about 2 pM to about 500 pM, about 2 pM to about 450 pM, about 2 pM to about 400 pM, about 2 pM to about 350 pM, about 2 pM to about 300 pM, about 2 pM to about 250 pM, about 2 pM to about 200 pM, about 2 pM to about 150 pM, about 2 pM to about 100 pM, about 2 pM to about 90 pM, about 2 pM to about 80 pM, about 2 pM to about 70 pM, about 2 pM to about 60 pM, about 2 pM to about 50 pM, about 2 pM to about 40 pM, about 2 pM to about 30 pM, about 2 pM to about 20 pM, about 2 pM to about 10 pM, about 2 pM to about 5 pM, about 2 pM to about 4 pM, about 2 pM to about 3 pM, about 5 pM to about 30 nM, about 5 pM to about 25 nM, about 5 pM to about 20 nM, about 5 pM to about 15 nM, about 5 pM to about 10 nM, about 5 pM to about 5 nM, about 5 pM to about 2 nM, about 5 pM to about 1 nM, about 5 pM to about 950 pM, about 5 pM to about 900 pM, about 5 pM to about 850 pM, about 5 pM to about 800 pM, about 5 pM to about 750 pM, about 5 pM to about 700 pM, about 5 pM to about 650 pM, about 5 pM to about 600 pM, about 5 pM to about 550 pM, about 5 pM to about 500 pM, about 5 pM to about 450 pM, about 5 pM to about 400 pM, about 5 pM to about 350 pM, about 5 pM to about 300 pM, about 5 pM to about 250 pM, about 5 pM to about 200 pM, about 5 pM to about 150 pM, about 5 pM to about 100 pM, about 5 pM to about 90 pM, about 5 pM to about 80 pM, about 5 pM to about 70 pM, about 5 pM to about 60 pM, about 5 pM to about 50 pM, about 5 pM to about 40 pM, about 5 pM to about 30 pM, about 5 pM to about 20 pM, about 5 pM to about 10 pM, about 10 pM to about 30 nM, about 10 pM to about 25 nM, about 10 pM to about 20 nM, about 10 pM to about 15 nM, about 10 pM to about 10 nM, about pM to about 5 nM, about 10 pM to about 2 nM, about 10 pM to about 1 nM, about 10 pM to about 950 pM, about 10 pM to about 900 pM, about 10 pM to about 850 pM, about 10 pM to about 800 pM, about 10 pM to about 750 pM, about 10 pM to about 700 pM, about 10 pM to about 650 pM, about 10 pM to about 600 pM, about 10 pM to about 550 pM, about 10 pM to about 500 pM, about 10 pM to about 450 pM, about 10 pM to about 400 pM, about 10 pM to about 350 pM, about 10 pM to about 300 pM, about 10 pM to about 250 pM, about 10 pM to about 200 pM, about 10 pM to about 150 pM, about 10 pM to about 100 pM, about 10 pM to about 90 pM, about 10 pM to about 80 pM, about 10 pM to about 70 pM, about 10 pM to about 60 pM, about 10 pM to about 50 pM, about 10 pM to about 40 pM, about 10 pM to about 30 pM, about 10 pM to about 20 pM, about 15 pM to about 30 nM, about 15 pM to about 25 nM, about pM to about 20 nM, about 15 pM to about 15 nM, about 15 pM to about 10 nM, about 15 pM to about 5 nM, about 15 pM to about 2 nM, about 15 pM to about 1 nM, about 15 pM to about 950 pM, about 15 pM to about 900 pM, about 15 pM to about 850 pM, about 15 pM to about 800 pM, about 15 pM to about 750 pM, about 15 pM to about 700 pM, about 15 pM to about 650 pM, about 15 pM to about 600 pM, about 15 pM to about 550 pM, about 15 pM to about 500 pM, about 15 pM to about 450 pM, about 15 pM to about 400 pM, about 15 pM to about 350 pM, about 15 pM to about 300 pM, about 15 pM to about 250 pM, about 15 pM to about 200 pM, about 15 pM to about 150 pM, about 15 pM to about 100 pM, about 15 pM to about 90 pM, about 15 pM to about 80 pM, about 15 pM to about 70 pM, about 15 pM to about 60 pM, about pM to about 50 pM, about 15 pM to about 40 pM, about 15 pM to about 30 pM, about 15 pM to about 20 pM, about 20 pM to about 30 nM, about 20 pM to about 25 nM, about 20 pM to about 20 nM, about 20 pM to about 15 nM, about 20 pM to about 10 nM, about 20 pM to about 5 nM, about 20 pM to about 2 nM, about 20 pM to about 1 nM, about 20 pM to about 950 pM, about 20 pM to about 900 pM, about 20 pM to about 850 pM, about 20 pM to about 800 pM, about 20 pM to about 750 pM, about 20 pM to about 700 pM, about 20 pM to about 650 pM, about 20 pM to about 600 pM, about 20 pM to about 550 pM, about 20 pM to about 500 pM, about 20 pM to about 450 pM, about 20 pM to about 400 pM, about 20 pM to about 350 pM, about 20 pM to about 300 pM, about 20 pM to about 250 pM, about 20 pM to about 20 pM, about 200 pM to about 150 pM, about 20 pM to about 100 pM, about 20 pM to about 90 pM, about 20 pM to about 80 pM, about 20 pM to about 70 pM, about 20 pM to about 60 pM, about pM to about 50 pM, about 20 pM to about 40 pM, about 20 pM to about 30 pM, about 30 pM to about 30 nM, about 30 pM to about 25 nM, about 30 pM to about 30 nM, about 30 pM to about 15 nM, about 30 pM to about 10 nM, about 30 pM to about 5 nM, about 30 pM to about 2 nM, about 30 pM to about 1 nM, about 30 pM to about 950 pM, about 30 pM to about 900 pM, about 30 pM to about 850 pM, about 30 pM to about 800 pM, about 30 pM to about 750 pM, about 30 pM to about 700 pM, about 30 pM to about 650 pM, about 30 pM to about 600 pM, about 30 pM to about 550 pM, about 30 pM to about 500 pM, about 30 pM to about 450 pM, about 30 pM to about 400 pM, about 30 pM to about 350 pM, about 30 pM to about 300 pM, about 30 pM to about 250 pM, about 30 pM to about 200 pM, about 30 pM to about 150 pM, about 30 pM to about 100 pM, about 30 pM to about 90 pM, about 30 pM to about 80 pM, about pM to about 70 pM, about 30 pM to about 60 pM, about 30 pM to about 50 pM, about 30 pM to about 40 pM, about 40 pM to about 30 nM, about 40 pM to about 25 nM, about 40 pM to about 30 nM, about 40 pM to about 15 nM, about 40 pM to about 10 nM, about 40 pM to about 5 nM, about 40 pM to about 2 nM, about 40 pM to about 1 nM, about 40 pM to about 950 pM, about 40 pM to about 900 pM, about 40 pM to about 850 pM, about 40 pM to about 800 pM, about 40 pM to about 750 pM, about 40 pM to about 700 pM, about 40 pM to about 650 pM, about 40 pM to about 600 pM, about 40 pM to about 550 pM, about 40 pM to about 500 pM, about 40 pM to about 450 pM, about 40 pM to about 400 pM, about 40 pM to about 350 pM, about 40 pM to about 300 pM, about 40 pM to about 250 pM, about 40 pM to about 200 pM, about 40 pM to about 150 pM, about 40 pM to about 100 pM, about 40 pM to about 90 pM, about 40 pM to about 80 pM, about 40 pM to about 70 pM, about 40 pM to about 60 pM, about pM to about 50 pM, about 50 pM to about 30 nM, about 50 pM to about 25 nM, about 50 pM to about 30 nM, about 50 pM to about 15 nM, about 50 pM to about 10 nM, about 50 pM to about 5 nM, about 50 pM to about 2 nM, about 50 pM to about 1 nM, about 50 pM to about 950 pM, about 50 pM to about 900 pM, about 50 pM to about 850 pM, about 50 pM to about 800 pM, about 50 pM to about 750 pM, about 50 pM to about 700 pM, about 50 pM to about 650 pM, about 50 pM to about 600 pM, about 50 pM to about 550 pM, about 50 pM to about 500 pM, about 50 pM to about 450 pM, about 50 pM to about 400 pM, about 50 pM to about 350 pM, about 50 pM to about 300 pM, about 50 pM to about 250 pM, about 50 pM to about 200 pM, about 50 pM to about 150 pM, about 50 pM to about 100 pM, about 50 pM to about 90 pM, about 50 pM to about 80 pM, about 50 pM to about 70 pM, about 50 pM to about 60 pM, about 60 pM to about 30 nM, about 60 pM to about 25 nM, about 60 pM to about 30 nM, about 60 pM to about 15 nM, about 60 pM to about 10 nM, about 60 pM to about 5 nM, about 60 pM to about 2 nM, about 60 pM to about 1 nM, about 60 pM to about 950 pM, about 60 pM to about 900 pM, about 60 pM to about 850 pM, about 60 pM to about 800 pM, about 60 pM to about 750 pM, about 60 pM to about 700 pM, about 60 pM to about 650 pM, about 60 pM to about 600 pM, about 60 pM to about 550 pM, about 60 pM to about 500 pM, about 60 pM to about 450 pM, about 60 pM to about 400 pM, about 60 pM to about 350 pM, about 60 pM to about 300 pM, about 60 pM to about 250 pM, about 60 pM to about 200 pM, about 60 pM to about 150 pM, about 60 pM to about 100 pM, about 60 pM to about 90 pM, about 60 pM to about 80 pM, about 60 pM to about 70 pM, about 70 pM to about 30 nM, about 70 pM to about 25 nM, about 70 pM to about 30 nM, about 70 pM to about 15 nM, about 70 pM to about 10 nM, about 70 pM to about 5 nM, about 70 pM to about 2 nM, about 70 pM to about 1 nM, about 70 pM to about 950 pM, about 70 pM to about 900 pM, about 70 pM to about 850 pM, about 70 pM to about 800 pM, about 70 pM to about 750 pM, about 70 pM to about 700 pM, about 70 pM to about 650 pM, about 70 pM to about 600 pM, about 70 pM to about 550 pM, about 70 pM to about 500 pM, about 70 pM to about 450 pM, about 70 pM to about 400 pM, about 70 pM to about 350 pM, about 70 pM to about 300 pM, about 70 pM to about 250 pM, about 70 pM to about 200 pM, about 70 pM to about 150 pM, about 70 pM to about 100 pM, about 70 pM to about 90 pM, about 70 pM to about 80 pM, about 80 pM to about 30 nM, about 80 pM to about 25 nM, about 80 pM to about 30 nM, about 80 pM to about 15 nM, about 80 pM to about 10 nM, about 80 pM to about 5 nM, about 80 pM to about 2 nM, about 80 pM to about 1 nM, about 80 pM to about 950 pM, about 80 pM to about 900 pM, about 80 pM to about 850 pM, about 80 pM to about 800 pM, about 80 pM to about 750 pM, about 80 pM to about 700 pM, about 80 pM to about 650 pM, about 80 pM to about 600 pM, about 80 pM to about 550 pM, about 80 pM to about 500 pM, about 80 pM to about 450 pM, about 80 pM to about 400 pM, about 80 pM to about 350 pM, about 80 pM to about 300 pM, about 80 pM to about 250 pM, about 80 pM to about 200 pM, about 80 pM to about 150 pM, about 80 pM to about 100 pM, about 80 pM to about 90 pM, about 90 pM to about 30 nM, about 90 pM to about 25 nM, about 90 pM to about 30 nM, about 90 pM to about 15 nM, about 90 pM to about 10 nM, about 90 pM to about 5 nM, about 90 pM to about 2 nM, about 90 pM to about 1 nM, about 90 pM to about 950 pM, about 90 pM to about 900 pM, about 90 pM to about 850 pM, about 90 pM to about 800 pM, about 90 pM to about 750 pM, about 90 pM to about 700 pM, about 90 pM to about 650 pM, about 90 pM to about 600 pM, about 90 pM to about 550 pM, about 90 pM to about 500 pM, about 90 pM to about 450 pM, about 90 pM to about 400 pM, about 90 pM to about 350 pM, about 90 pM to about 300 pM, about 90 pM to about 250 pM, about 90 pM to about 200 pM, about 90 pM to about 150 pM, about 90 pM to about 100 pM, about 100 pM to about 30 nM, about 100 pM to about 25 nM, about 100 pM to about 30 nM, about 100 pM to about 15 nM, about 100 pM to about 10 nM, about 100 pM to about 5 nM, about 100 pM to about 2 nM, about 100 pM to about 1 nM, about 100 pM to about 950 pM, about 100 pM to about 900 pM, about 100 pM to about 850 pM, about 100 pM to about 800 pM, about 100 pM to about 750 pM, about 100 pM to about 700 pM, about 100 pM to about 650 pM, about 100 pM to about 600 pM, about 100 pM to about 550 pM, about 100 pM to about 500 pM, about 100 pM to about 450 pM, about 100 pM to about 400 pM, about 100 pM to about 350 pM, about 100 pM to about 300 pM, about 100 pM to about 250 pM, about 100 pM to about 200 pM, about 100 pM to about 150 pM, about 150 pM to about 30 nM, about 150 pM to about 25 nM, about 150 pM to about 30 nM, about 150 pM to about 15 nM, about 150 pM to about 10 nM, about 150 pM to about 5 nM, about 150 pM to about 2 nM, about 150 pM to about 1 nM, about 150 pM to about 950 pM, about 150 pM to about 900 pM, about 150 pM to about 850 pM, about 150 pM to about 800 pM, about 150 pM to about 750 pM, about 150 pM to about 700 pM, about 150 pM to about 650 pM, about 150 pM to about 600 pM, about 150 pM to about 550 pM, about 150 pM to about 500 pM, about 150 pM to about 450 pM, about 150 pM to about 400 pM, about 150 pM to about 350 pM, about 150 pM to about 300 pM, about 150 pM to about 250 pM, about 150 pM to about 200 pM, about 200 pM to about 30 nM, about 200 pM to about 25 nM, about 200 pM to about 30 nM, about 200 pM to about 15 nM, about 200 pM to about 10 nM, about 200 pM to about 5 nM, about 200 pM to about 2 nM, about 200 pM to about 1 nM, about 200 pM to about 950 pM, about 200 pM to about 900 pM, about 200 pM to about 850 pM, about 200 pM to about 800 pM, about 200 pM to about 750 pM, about 200 pM to about 700 pM, about 200 pM to about 650 pM, about 200 pM to about 600 pM, about 200 pM to about 550 pM, about 200 pM to about 500 pM, about 200 pM to about 450 pM, about 200 pM to about 400 pM, about 200 pM to about 350 pM, about 200 pM to about 300 pM, about 200 pM to about 250 pM, about 300 pM to about 30 nM, about 300 pM to about 25 nM, about 300 pM to about 30 nM, about 300 pM to about 15 nM, about 300 pM to about 10 nM, about 300 pM to about 5 nM, about 300 pM to about 2 nM, about 300 pM to about 1 nM, about 300 pM to about 950 pM, about 300 pM to about 900 pM, about 300 pM to about 850 pM, about 300 pM to about 800 pM, about 300 pM to about 750 pM, about 300 pM to about 700 pM, about 300 pM to about 650 pM, about 300 pM to about 600 pM, about 300 pM to about 550 pM, about 300 pM to about 500 pM, about 300 pM to about 450 pM, about 300 pM to about 400 pM, about 300 pM to about 350 pM, about 400 pM to about 30 nM, about 400 pM to about 25 nM, about 400 pM to about nM, about 400 pM to about 15 nM, about 400 pM to about 10 nM, about 400 pM to about 5 nM, about 400 pM to about 2 nM, about 400 pM to about 1 nM, about 400 pM to about 950 pM, about 400 pM to about 900 pM, about 400 pM to about 850 pM, about 400 pM to about 800 pM, about 400 pM to about 750 pM, about 400 pM to about 700 pM, about 400 pM to about 650 pM, about 400 pM to about 600 pM, about 400 pM to about 550 pM, about 400 pM to about 500 pM, about 500 pM to about 30 nM, about 500 pM to about 25 nM, about 500 pM to about 30 nM, about 500 pM to about 15 nM, about 500 pM to about 10 nM, about 500 pM to about 5 nM, about 500 pM to about 2 nM, about 500 pM to about 1 nM, about 500 pM to about 950 pM, about 500 pM to about 900 pM, about 500 pM to about 850 pM, about 500 pM to about 800 pM, about 500 pM to about 750 pM, about 500 pM to about 700 pM, about 500 pM to about 650 pM, about 500 pM to about 600 pM, about 500 pM to about 550 pM, about 600 pM to about 30 nM, about 600 pM to about 25 nM, about 600 pM to about 30 nM, about 600 pM to about 15 nM, about 600 pM to about 10 nM, about 600 pM to about 5 nM, about 600 pM to about 2 nM, about 600 pM to about 1 nM, about 600 pM to about 950 pM, about 600 pM to about 900 pM, about 600 pM to about 850 pM, about 600 pM to about 800 pM, about 600 pM to about 750 pM, about 600 pM to about 700 pM, about 600 pM to about 650 pM, about 700 pM to about 30 nM, about 700 pM to about 25 nM, about 700 pM to about 30 nM, about 700 pM to about 15 nM, about 700 pM to about 10 nM, about 700 pM to about 5 nM, about 700 pM to about 2 nM, about 700 pM to about 1 nM, about 700 pM to about 950 pM, about 700 pM to about 900 pM, about 700 pM to about 850 pM, about 700 pM to about 800 pM, about 700 pM to about 750 pM, about 800 pM to about 30 nM, about 800 pM to about 25 nM, about 800 pM to about 30 nM, about 800 pM to about 15 nM, about 800 pM to about 10 nM, about 800 pM to about 5 nM, about 800 pM to about 2 nM, about 800 pM to about 1 nM, about 800 pM to about 950 pM, about 800 pM to about 900 pM, about 800 pM to about 850 pM, about 900 pM to about 30 nM, about 900 pM to about 25 nM, about 900 pM to about 30 nM, about 900 pM to about 15 nM, about 900 pM to about 10 nM, about 900 pM to about 5 nM, about 900 pM to about 2 nM, about 900 pM to about 1 nM, about 900 pM to about 950 pM, about 1 nM to about 30 nM, about 1 nM to about 25 nM, about 1 nM to about 20 nM, about 1 nM to about 15 nM, about 1 nM to about 10 nM, about 1 nM to about 5 nM, about 2 nM to about 30 nM, about 2 nM to about 25 nM, about 2 nM to about nM, about 2 nM to about 15 nM, about 2 nM to about 10 nM, about 2 nM to about 5 nM, about 4 nM to about 30 nM, about 4 nM to about 25 nM, about 4 nM to about 20 nM, about 4 nM to about 15 nM, about 4 nM to about 10 nM, about 4 nM to about 5 nM, about 5 nM to about nM, about 5 nM to about 25 nM, about 5 nM to about 20 nM, about 5 nM to about 15 nM, about 5 nM to about 10 nM, about 10 nM to about 30 nM, about 10 nM to about 25 nM, about 10 nM to about 20 nM, about 10 nM to about 15 nM, about 15 nM to about 30 nM, about 15 nM to about 25 nM, about 15 nM to about 20 nM, about 20 nM to about 30 nM, and about 20 nM to about 25 nM).

Any of the target-binding domains described herein can bind to its target with a $K_D$ of between about 1 nM to about 10 nM (e.g., about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 10 nM, about 5 nM to about 9 nM, about 5 nM to about 8 nM, about 5 nM to about 7 nM, about 5 nM to about 6 nM, about 6 nM to about 10 nM, about 6 nM to about 9 nM, about 6 nM to about 8 nM, about 6 nM to about 7 nM, about 7 nM to about 10 nM, about 7 nM to about 9 nM, about 7 nM to about 8 nM, about 8 nM to about 10 nM, about 8 nM to about 9 nM, and about 9 nM to about 10 nM).

A variety of different methods known in the art can be used to determine the $K_D$ values of any of the antigen-binding protein constructs described herein (e.g., an electrophoretic mobility shift assay, a filter binding assay, surface plasmon resonance, and a biomolecular binding kinetics assay, etc.).

Antigen-Binding Domains

In some embodiments of any of the single-chain chimeric polypeptides or any of the multi-chain chimeric polypeptides described herein, the first target-binding domain and the second target-binding domain bind specifically to the same antigen. In some embodiments of any of the single-chain chimeric polypeptides or any of the multi-chain chimeric polypeptides described herein, the first target-binding domain and the second target-binding domain bind specifically to the same epitope. In some embodiments of any of the single-chain chimeric polypeptides or any of the multi-chain chimeric polypeptides, the first target-binding domain and the second target-binding domain include the same amino acid sequence.

In some embodiments of any of the single-chain chimeric polypeptides or any of the multi-chain chimeric polypeptides described herein, the first target-binding domain and the second target-binding domain bind specifically to different antigens.

In some embodiments of any of the single-chain chimeric polypeptides or any of the multi-chain chimeric polypeptides described herein, one or both of the first target-binding domain and the second target-binding domain is an antigen-binding domain. In some embodiments of any of the single-chain chimeric polypeptides or any of the multi-chain chimeric polypeptides described herein, the first target-binding domain and the second target-binding domain are each an antigen-binding domain.

In some embodiments of any of the single-chain chimeric polypeptides or any of the multi-chain chimeric polypeptides described herein, the antigen-binding domain includes or is a scFv or a single domain antibody (e.g., a $V_HH$ or a $V_{NAR}$ domain).

In some examples, an antigen-binding domain (e.g., any of the antigen-binding domains described herein) can bind specifically to any one of CD16a (see, e.g., those described in U.S. Pat. No. 9,035,026), CD28 (see, e.g., those described in U.S. Pat. No. 7,723,482), CD3 (see, e.g., those described in U.S. Pat. No. 9,226,962), CD33 (see, e.g., those described in U.S. Pat. No. 8,759,494), CD20 (see, e.g., those described in WO 2014/026054), CD19 (see, e.g., those described in U.S. Pat. No. 9,701,758), CD22 (see, e.g., those described in WO 2003/104425), CD123 (see, e.g., those described in WO 2014/130635), IL-1R (see, e.g., those described in U.S. Pat. No. 8,741,604), IL-1 (see, e.g., those described in WO 2014/095808), VEGF (see, e.g., those described in U.S. Pat. No. 9,090,684), IL-6R (see, e.g., those described in U.S. Pat. No. 7,482,436), IL-4 (see, e.g., those described in U.S. Patent Application Publication No. 2012/0171197), IL-10 (see, e.g., those described in U.S. Patent Application Publication No. 2016/0340413), PDL-1 (see, e.g., those described in Drees et al., *Protein Express. Purif* 94:60-66, 2014), TIGIT (see, e.g., those described in U.S. Patent Application Publication No. 2017/0198042), PD-1 (see, e.g., those described in U.S. Pat. No. 7,488,802), TIM3 (see, e.g., those described in U.S. Pat. No. 8,552,156), CTLA4 (see, e.g., those described in WO 2012/120125), MICA (see, e.g., those described in WO 2016/154585), MICB (see, e.g., those described in U.S. Pat. No. 8,753,640), IL-6 (see, e.g., those described in Gejima et al., *Human Antibodies* 11(4): 121-129, 2002), IL-8 (see, e.g., those described in U.S. Pat. No. 6,117,980), TNFα (see, e.g., those described in Geng et al., *Immunol. Res.* 62(3):377-385, 2015), CD26a (see, e.g., those described in WO 2017/189526), CD36 (see, e.g., those described in U.S. Patent Application Publication No. 2015/0259429), ULBP2 (see, e.g., those described in U.S. Pat. No. 9,273,136), CD30 (see, e.g., those described in Homach et al., *Scand. J. Immunol.* 48(5):497-501, 1998), CD200 (see, e.g., those described in U.S. Pat. No. 9,085,623), IGF-1R (see, e.g., those described in U.S. Patent Application Publication No. 2017/0051063), MUC4AC (see, e.g., those described in WO 2012/170470), MUCSAC (see, e.g., those described in U.S. Pat. No. 9,238,084), Trop-2 (see, e.g., those described in WO 2013/068946), CMET (see, e.g., those described in Edwardraja et al., *Biotechnol. Bioeng.* 106(3):367-375, 2010), EGFR (see, e.g., those described in Akbari et al., *Protein Expr. Purif* 127:8-15, 2016), HER1 (see, e.g., those described in U.S. Patent Application Publication No. 2013/0274446), HER2 (see, e.g., those described in Cao et al., *Biotechnol. Lett.* 37(7):1347-1354, 2015), HER3 (see, e.g., those described in U.S. Pat. No. 9,505,843), PSMA (see, e.g., those described in Parker et al., *Protein Expr. Purif.* 89(2):136-145, 2013), CEA (see, e.g., those described in WO 1995/015341), B7H3 (see, e.g., those described in U.S. Pat. No. 9,371,395), EPCAM (see, e.g., those described in WO 2014/159531), BCMA (see, e.g., those described in Smith et al., *Mol. Ther.* 26(6):1447-1456, 2018), P-cadherin (see, e.g., those described in U.S. Pat. No. 7,452,537), CEACAM5 (see, e.g., those described in U.S. Pat. No. 9,617,345), a UL16-binding protein (see, e.g., those described in WO 2017/083612), HLA-DR (see, e.g., Pistillo et al., *Exp. Clin. Immunogenet.* 14(2):123-130, 1997), DLL4 (see, e.g., those described in WO 2014/007513), TYRO3 (see, e.g., those described in WO 2016/166348), AXL (see, e.g., those described in WO 2012/175692), MER (see, e.g., those described in WO 2016/106221), CD122 (see, e.g., those described in U.S. Patent Application Publication No. 2016/0367664), CD155 (see, e.g., those described in WO 2017/149538), and PDGF-DD (see, e.g., those described in U.S. Pat. No. 9,441,034). The antigen-binding domains present in any of the single-chain chimeric polypeptides or any of the multi-chain polypeptides described herein are each independently selected from the group consisting of: a VHH domain, a VNAR domain, and a scFv.

In some embodiments, the first target binding domain, the second target-binding domain, and/or one or more of the one or more additional antigen-binding domains can be an anti-CD3 scFv. In some embodiments, the anti-CD3 scFv can include a heavy chain variable domain including a sequence that is at least 70% identical (e.g., at least 75% identical, at least 80% identical, at least 85% identical, at least 90% identical, at least 95% identical, at least 99% identical, or 100% identical) to QVQLQQSGAELARP-GASVKMSCKASGYTFTRYTMHWVKQRPGQGLEWI-GYINPSRGY TNYNQKFKDKATLTTDKSSSTAYMQL SSLT SEDSAVYYCARYYDDHYCLDYWGQGTT LTVSS (SEQ ID NO: 16) and/or a light chain variable domain including a sequence that is at least 70% identical (e.g., at least 75% identical, at least 80% identical, at least 85% identical, at least 90% identical, at least 95% identical, at least 99% identical, or 100% identical) to

```
                                    (SEQ ID NO: 17)
QIVLTQSPAIMSASPGEKVTMTCSASSSVSYMNWYQQKSGTSPKRWIYD

TSKLASGVPAHFRGSGSGTSYSLTISGMEAEDAATYYCQQWSSNPFTFG

SGTKLEINR.
```

In some embodiments, a scFv (e.g., any of the scFvs described herein) can include a linker sequence (e.g., any of the exemplary linker sequences described herein or known in the art) between the heavy chain variable domain and the light chain variable domain. In some embodiments, the anti-CD3 scFv can include a heavy chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to CAAGTTCAGCTCCAGCAAAGCGGCGC-CGAACTCGCTCGGCCCGGCGCTTCCGTGAA GATGTCTTGTAAGGCCTCCGGCTATACCTT-CACCCGGTACACAATGCACTGGGTCAA GCAACGGCCCGGTCAAGGTTTAGAGTGGATTGGC-TATATCAACCCCTCCCGGGGCTA TACCAACTA-CAACCAGAAGTTCAAGGACAAAGCCACCCTCAC-CACCGACAAGTCCA GCAGCACCGCTTACATGCAGCTGAGCTCTTTAA-CATCCGAGGATTCCGCCGTGTACT ACTGCGCTCGGTACTACGACGATCATTACTGCCTC-GATTACTGGGGCCAAGGTACCA CCT-TAACAGTCTCCTCC (SEQ ID NO: 18), and/or a light chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to

```
                                    (SEQ ID NO: 19)
CAGATCGTGCTGACCCAGTCCCCCGCTATTATGAGCGCTAGCCCCGGTG

AAAAGGTGACTATGACATGCAGCGCCAGCTCTTCCGTGAGCTACATGAA

CTGGTATCAGCAGAAGTCCGGCACCAGCCCTAAAAGGTGGATCTACGAC

ACCAGCAAGCTGGCCAGCGGCGTCCCCGCTCACTTTCGGGGCTCCGGCT

CCGGAACAAGCTACTCTCTGACCATCAGCGGCATGGAAGCCGAGGATGC

CGCTACCTATTACTGTCAGCAGTGGAGCTCCAACCCCTTCACCTTTGGA

TCCGGCACCAAGCTCGAGATTAATCGT.
```

In some embodiments, an anti-CD3 scFv can include a sequence that is at least 70% identical (e.g., at least 75% identical, at least 80% identical, at least 85% identical, at least 90% identical, at least 95% identical, at least 99% identical, or 100% identical) to QIVLTQSPAIMSASPGEKVTMTCSASSSVSYMNWYQQKSGTSPKRWIYDTSKLASGVPA HFRGSGSGTSYSLTISGMEAEDAATYYCQQW SSNPFTFGSGTKLEINRGGGGSGGGGSG GGGSQVQLQQ SGAELARPGASVKMSCKASGYTFTRYTMHWVKQRPGQGLEWIGYINP SRGYTNYNQKFKDKATLTTDKSSSTAYMQLSSLTSEDSAVYYCARYYDDHYCLDYWG QGTTLTVSS (SEQ ID NO: 20). In some embodiments, an anti-CD3 scFv can include the six CDRs present in SEQ ID NO: 20.

In some embodiments, an anti-CD3 scFv can include a sequence encoded by a nucleic acid sequence that is at least 70% identical (e.g., at least 75% identical, at least 80% identical, at least 85% identical, at least 90% identical, at least 95% identical, at least 99% identical, or 100% identical) to (SEQ ID NO: 21)
CAGATCGTGCTGACCCAGTCCCCCGCTATTATGAGCGCTAGCCCCGGTG

AAAAGGTGACTATGACATGCAGCGCCAGCTCTTCCGTGAGCTACATGAA

CTGGTATCAGCAGAAGTCCGGCACCAGCCCTAAAAGGTGGATCTACGAC

ACCAGCAAGCTGGCCAGCGGCGTCCCCGCTCACTTTCGGGGCTCCGGCT

CCGGAACAAGCTACTCTCTGACCATCAGCGGCATGGAAGCCGAGGATGC

CGCTACCTATTACTGTCAGCAGTGGAGCTCCAACCCCTTCACCTTTGGA

TCCGGCACCAAGCTCGAGATTAATCGTGGAGGCGGAGGTAGCGGAGGAG

GCGGATCCGGCGGTGGAGGTAGCCAAGTTCAGCTCCAGCAAAGCGGCGC

CGAACTCGCTCGGCCCGGCGCTTCCGTGAAGATGTCTTGTAAGGCCTCC

GGCTATACCTTCACCCGGTACACAATGCACTGGGTCAAGCAACGGCCCG

GTCAAGGTTTAGAGTGGATTGGCTATATCAACCCCTCCCGGGGCTATAC

CAACTACAACCAGAAGTTCAAGGACAAAGCCACCCTCACCACCGACAAG

TCCAGCAGCACCGCTTACATGCAGCTGAGCTCTTTAACATCCGAGGATT

CCGCCGTGTACTACTGCGCTCGGTACTACGACGATCATTACTGCCTCGA

TTACTGGGGCCAAGGTACCACCTTAACAGTCTCCTCC.

In some embodiments, the first target binding domain, the second target-binding domain, and/or one or more of the one or more additional antigen-binding domains can be an anti-CD28 scFv. In some embodiments, the anti-CD28 scFv can include a heavy chain variable domain including a sequence that is at least 70% identical (e.g., at least 75% identical, at least 80% identical, at least 85% identical, at least 90% identical, at least 95% identical, at least 99% identical, or 100% identical) to (SEQ ID NO: 22)
DIEMTQSPAIMSASLGERVTMTCTASSSVSSSYFHWYQQKPGSSPKLCI

YSTSNLASGVPPRFSGSGSTSYSLTISSMEAEDAATYFCHQYHRSPTFG

GGTKLETKR and/or a light chain variable domain including a sequence that is at least 70% identical (e.g., at least 75% identical, at least 80% identical, at least 85% identical, at least 90% identical, at least 95% identical, at least 99% identical, or 100% identical) to VQLQQSGPELVKPGASVKMSCKASGYTFT SYVIQWVKQKPGQGLEWIGSINPYNDYTK YNEKFKGKATLTSDKSSITAYMEFSSLTSEDSALYYCARWGDGNYWGRGTTLTVSS (SEQ ID NO: 23). In some embodiments, the anti-CD28 scFv can include a heavy chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to GACATCGAGATGACACAGTCCCCCGCTATCATGAGCGCCTCTTTAGGAGAACGTGTG ACCATGACTTGTACAGCTTCCTCCAGCGTGAGCAGCTCCTATTTCCACTGGTACCAG CAGAAACCCGGCTCCTCCCCTAAACTGTGTATCTACTCCACAAGCAATTTAGCTAGC GGCGTGCCTCCTCGTTTTAGCGGCTCCGGCAGCACCTCTTACTCTTTAACCATTAGCT CTATGGAGGCCGAAGATGCCGCCACATACTTTTGCCATCAGTACCACCGGTCCCCTA CCTTTGGCGGAGGCACAAAGCTGGAGACCAAGCGG (SEQ ID NO: 24), and/or a light chain variable domain encoded by a nucleic acid including a sequence that is at least 70% identical (e.g., at least 75% identical, at least 80% identical, at least 85% identical, at least 90% identical, at least 95% identical, at least 99% identical, or 100% identical) to (SEQ ID NO: 25)
GTGCAGCTGCAGCAGTCCGGACCCGAACTGGTCAAGCCCGGTGCCTCCG

TGAAAATGTCTTGTAAGGCTTCTGGCTACACCTTTACCTCCTACGTCAT

CCAATGGGTGAAGCAGAAGCCCGGTCAAGGTCTCGAGTGGATCGGCAGC

ATCAATCCCTACAACGATTACACCAAGTATAACGAAAAGTTTAAGGGCA

AGGCCACTCTGACAAGCGACAAGAGCTCCATTACCGCCTACATGGAGTT

TTCCTCTTTAACTTCTGAGGACTCCGCTTTATACTATTGCGCTCGTTGG

GGCGATGGCAATTATTGGGGCCGGGGAACTACTTTAACAGTGAGCTCC.

In some embodiments, an anti-CD28 scFv can include a sequence that is at least 70% identical (e.g., at least 75% identical, at least 80% identical, at least 85% identical, at least 90% identical, at least 95% identical, at least 99% identical, or 100% identical) to VQLQQSGPELVKPGASVKMSCKASGYTFTSYVIQWVKQKPGQGLEWIGSINPYNDYTK YNEKFKGKATLTSDKSSITAYMEFSSLTSEDSALYYCARWGDGNYWGRGTTLTVSSGG GGSGGGGSGGGGSDIEMTQSPAIMSASLGERVTMTCTASSSVSSSYFHWYQQKPGSSPK LCIYSTSNLASGVPPRFSGSGSTSYSLTISSMEAEDAATYFCHQYHRSPTFGGGTKLETKR (SEQ ID NO: 26). In some embodiments, an anti-CD28 scFv can include the six CDRs present in SEQ ID NO: 26.

In some embodiments, an anti-CD28 scFv can include a sequence encoded by a nucleic acid sequence that is at least 70% identical (e.g., at least 75% identical, at least 80% identical, at least 85% identical, at least 90% identical, at least 95% identical, at least 99% identical, or 100% identical) to (SEQ ID NO: 27)
GTGCAGCTGCAGCAGTCCGGACCCGAACTGGTCAAGCCCGGTGCCTCCG

TGAAAATGTCTTGTAAGGCTTCTGGCTACACCTTTACCTCCTACGTCAT

CCAATGGGTGAAGCAGAAGCCCGGTCAAGGTCTCGAGTGGATCGGCAGC

-continued

```
ATCAATCCCTACAACGATTACACCAAGTATAACGAAAAGTTTAAGGGCA

AGGCCACTCTGACAAGCGACAAGAGCTCCATTACCGCCTACATGGAGTT

TTCCTCTTTAACTTCTGAGGACTCCGCTTTATACTATTGCGCTCGTTGG

GGCGATGGCAATTATTGGGGCCGGGGAACTACTTTAACAGTGAGCTCCG

GCGGCGGCGGAAGCGGAGGTGGAGGATCTGGCGGTGGAGGCAGCGACAT

CGAGATGACACAGTCCCCCGCTATCATGAGCGCCTCTTTAGGAGAACGT

GTGACCATGACTTGTACAGCTTCCTCCAGCGTGAGCAGCTCCTATTTCC

ACTGGTACCAGCAGAAACCCGGCTCCTCCCCTAAACTGTGTATCTACTC

CACAAGCAATTTAGCTAGCGGCGTGCCTCCTCGTTTTAGCGGCTCCGGC

AGCACCTCTTACTCTTTAACCATTAGCTCTATGGAGGCCGAAGATGCCG

CCACATACTTTTGCCATCAGTACCACCGGTCCCCTACCTTTGGCGGAGG

CACAAAGCTGGAGACCAAGCGG.
```

In some embodiments, any of the antigen-binding domains described herein is a BiTe, a $(scFv)_2$, a nanobody, a nanobody-HSA, a DART, a TandAb, a scDiabody, a scDiabody-CH3, scFv-CH-CL-scFv, a HSAbody, scDiabody-HAS, or a tandem-scFv. Additional examples of antigen-binding domains that can be used in any of the single-chain chimeric polypeptides or multi-chain chimeric polypeptides described herein are known in the art.

A VHH domain is a single monomeric variable antibody domain that can be found in camelids. A VNAR domain is a single monomeric variable antibody domain that can be found in cartilaginous fish. Non-limiting aspects of VHH domains and VNAR domains are described in, e.g., Cromie et al., *Curr. Top. Med. Chem.* 15:2543-2557, 2016; De Genst et al., *Dev. Comp. Immunol.* 30:187-198, 2006; De Meyer et al., *Trends Biotechnol.* 32:263-270, 2014; Kijanka et al., *Nanomedicine* 10:161-174, 2015; Kovaleva et al., *Expert. Opin. Biol. Ther.* 14:1527-1539, 2014; Krah et al., *Immunopharmacol. Immunotoxicol.* 38:21-28, 2016; Mujic-Delic et al., *Trends Pharmacol. Sci.* 35:247-255, 2014; Muyldermans, *J. Biotechnol.* 74:277-302, 2001; Muyldermans et al., *Trends Biochem. Sci.* 26:230-235, 2001; Muyldermans, *Ann. Rev. Biochem.* 82:775-797, 2013; Rahbarizadeh et al., *Immunol. Invest.* 40:299-338, 2011; Van Audenhove et al., *EBioMedicine* 8:40-48, 2016; Van Bockstaele et al., *Curr Opin. Investig. Drugs* 10:1212-1224, 2009; Vincke et al., *Methods Mol. Biol.* 911:15-26, 2012; and Wesolowski et al., *Med. Microbiol. Immunol.* 198:157-174, 2009.

In some embodiments, each of the antigen-binding domains in the single-chain chimeric polypeptides or multi-chain chimeric polypeptides described herein are both VHH domains, or at least one antigen-binding domain is a VHH domain. In some embodiments, each of the antigen-binding domains in the single-chain chimeric polypeptides or multi-chain chimeric polypeptides described herein are both VNAR domains, or at least one antigen-binding domain is a VNAR domain. In some embodiments, each of the antigen-binding domains in the single-chain chimeric polypeptides or multi-chain chimeric polypeptides described herein are both scFv domains, or at least one antigen-binding domain is a scFv domain. DARTs are described in, e.g., Garber, *Nature Reviews Drug Discovery* 13:799-801, 2014.

In some embodiments of any of the antigen-binding domains described herein, the antigen-binding domain can bind to an antigen selected from the group consisting of: a protein, a carbohydrate, a lipid, and a combination thereof.

Additional examples and aspects of antigen-binding domains are known in the art.

Soluble Interleukin or Cytokine Protein

In some embodiments of any of the single-chain chimeric polypeptides or multi-chain chimeric polypeptides described herein, one or both of the first target-binding domain and the second target-binding domain can be a soluble interleukin protein, soluble cytokine protein, or soluble cell surface protein. In some embodiments, the soluble interleukin, soluble cytokine protein, or soluble cell surface protein is selected from the group of: IL-2, IL-3, IL-7, IL-8, IL-10, IL-12, IL-15, IL-17, IL-18, IL-21, PDGF-DD, SCF, FLT3L, MICA, MICB, and a ULP16-binding protein (e.g., ULBP1, ULBP2, ULBP3, ULBP4, ULPB5, or ULBP6. Non-limiting examples of soluble IL-2, IL-3, IL-7, IL-8, IL-10, IL-15, IL-17, IL-18, IL-21, PDGF-DD, SCF and FLT3L.

```
Human Soluble IL-2
                                                  (SEQ ID NO: 28)
APTSSSTKKT QLQLEHLLLD LQMILNGINN YKNPKLTRML

TFKFYMPKKA TELKHLQCLE EELKPLEEVL NLAQSKNFHL

RPRDLISNIN VIVLELKGSE TTFMCEYADE TATIVEFLNR

WITFCQSIIS TLT

Human Soluble IL-3
                                                  (SEQ ID NO: 29)
APMTQTTPLKT SWVNCSNMID EIITHLKQPP LPLLDFNNLN

GEDQDILMEN NLRRPNLEAF NRAVKSLQNA SAIESILKNL

LPCLPLATAA PTRHPIHIKD GDWNEFRRKL TFYLKTLENA

QAQQTTLSLA IF

Human Soluble IL-8
                                                  (SEQ ID NO: 31)
EGAVLPRSAK ELRCQCIKTY SKPFHPKFIK ELRVIESGPH

CANTEIIVKL SDGRELCLDP KENWVQRVVE KFLKRAENS

Human Soluble IL-10
                                                  (SEQ ID NO: 32)
SPGQGTQSENSC THFPGNLPNM LRDLRDAFSR VKTFFQMKDQ

LDNLLLKESL LEDFKGYLGC QALSEMIQFY LEEVMPQAEN

QDPDIKAHVN SLGENLKTLR LRLRRCHRFL PCENKSKAVE

QVKNAFNKLQ EKGIYKAMSE FDIFINYIEA YMTMKIRN

Human Soluble IL-12β (p40)
                                                  (SEQ ID NO: 33)
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS

Nucleic Acid Encoding Human Soluble IL-12β (p40)
                                                  (SEQ ID NO: 34)
ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC
```

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

AAGGAGCCCAAGAATAAGACCTTTTTAAGGTGTGAGGCCAAAAACTACA

GCGGTCGTTTCACTTGTTGGTGGCTGACCACCATTTCCACCGATTTAAC

CTTCTCCGTGAAAAGCAGCCGGGGAAGCTCCGACCCTCAAGGTGTGACA

TGTGGAGCCGCTACCCTCAGCGCTGAGAGGGTTCGTGGCGATAACAAGG

AATACGAGTACAGCGTGGAGTGCCAAGAAGATAGCGCTTGTCCCGCTGC

CGAAGAATCTTTACCCATTGAGGTGATGGTGGACGCCGTGCACAAACTC

AAGTACGAGAACTACACCTCCTCCTTCTTTATCCGGGACATCATTAAGC

CCGATCCTCCTAAGAATTTACAGCTGAAGCCTCTCAAAAATAGCCGGCA

AGTTGAGGTCTCTTGGGAATATCCCGACACTTGGAGCACACCCCACAGC

TACTTCTCTTTAACCTTTTGTGTGCAAGTTCAAGGTAAAAGCAAGCGGG

AGAAGAAAGACCGGGTGTTTACCGACAAAACCAGCGCCACCGTCATCTG

TCGGAAGAACGCCTCCATCAGCGTGAGGGCTCAAGATCGTTATTACTCC

AGCAGCTGGTCCGAGTGGGCCAGCGTGCCTTGTTCC

Human Soluble IL-12α (p35)

(SEQ ID NO: 35)

RNLPVATPDPGMFPCLHHSQNLLRAVSNMLQKARQTLEFYPCTSEEIDH

EDITKDKTSTVEACLPLELTKNESCLNSRETSFITNGSCLASRKTSFMM

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

S

Nucleic Acid Encoding Human Soluble IL-12α (p35)

(SEQ ID NO: 36)

CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC

Exemplary Human Soluble IL-12

(SEQ ID NO: 37)

IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCSGGGGSGGGGSGGGGSRNLPVATPDPGMFPCLHHSQNL

LRAVSNMLQKARQTLEFYPCTSEEIDHEDITKDKTSTVEACLPLELTKN

ESCLNSRETSFITNGSCLASRKTSFMMALCLSSIYEDLKMYQVEFKTMN

AKLLMDPKRQIFLDQNMLAVIDELMQALNFNSETVPQKSSLEEPDFYKT

KIKLCILLHAFRIRAVTIDRVMSYLNAS

Nucleic Acid Encoding Exemplary Human Soluble IL-12

(SEQ ID NO: 38)

ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

AAGGAGCCCAAGAATAAGACCTTTTTAAGGTGTGAGGCCAAAAACTACA

GCGGTCGTTTCACTTGTTGGTGGCTGACCACCATTTCCACCGATTTAAC

CTTCTCCGTGAAAAGCAGCCGGGGAAGCTCCGACCCTCAAGGTGTGACA

TGTGGAGCCGCTACCCTCAGCGCTGAGAGGGTTCGTGGCGATAACAAGG

AATACGAGTACAGCGTGGAGTGCCAAGAAGATAGCGCTTGTCCCGCTGC

CGAAGAATCTTTACCCATTGAGGTGATGGTGGACGCCGTGCACAAACTC

AAGTACGAGAACTACACCTCCTCCTTCTTTATCCGGGACATCATTAAGC

CCGATCCTCCTAAGAATTTACAGCTGAAGCCTCTCAAAAATAGCCGGCA

AGTTGAGGTCTCTTGGGAATATCCCGACACTTGGAGCACACCCCACAGC

TACTTCTCTTTAACCTTTTGTGTGCAAGTTCAAGGTAAAAGCAAGCGGG

AGAAGAAAGACCGGGTGTTTACCGACAAAACCAGCGCCACCGTCATCTG

TCGGAAGAACGCCTCCATCAGCGTGAGGGCTCAAGATCGTTATTACTCC

AGCAGCTGGTCCGAGTGGGCCAGCGTGCCTTGTTCCGGCGGTGGAGGAT

CCGGAGGAGGTGGCTCCGGCGGCGGAGGATCTCGTAACCTCCCCGTGGC

TACCCCCGATCCCGGAATGTTCCCTTGTTTACACCACAGCCAGAATTTA

CTGAGGGCCGTGAGCAACATGCTGCAGAAAGCTAGGCAGACTTTAGAAT

TTTACCCTTGCACCAGCGAGGAGATCGACCATGAAGATATCACCAAGGA

CAAGACATCCACCGTGGAGGCTTGTTTACCTCTGGAGCTGACAAAGAAC

GAGTCTTGTCTCAACTCTCGTGAAACCAGCTTCATCACAAATGGCTCTT

GTTTAGCTTCCCGGAAGACCTCCTTTATGATGGCTTTATGCCTCAGCTC

CATCTACGAGGATTTAAAGATGTACCAAGTGGAGTTCAAGACCATGAAC

GCCAAGCTGCTCATGGACCCTAAACGGCAGATCTTTTTAGACCAGAACA

TGCTGGCTGTGATTGATGAGCTGATGCAAGCTTTAAACTTCAACTCCGA

GACCGTCCCTCAGAAGTCCTCCCTCGAGGAGCCCGATTTTTACAAGACA

AAGATCAAACTGTGCATTTTACTCCACGCCTTTAGGATCCGGGCCGTGA

CCATTGACCGGGTCATGAGCTATTTAAACGCCAGC

-continued

Human Soluble IL-15

(SEQ ID NO: 39)

NWVNVISDLKKI EDLIQSMHID ATLYTESDVH PSCKVTAMKC

FLLELQVISL ESGDASIHDT VENLIILANN SLSSNGNVTE

SGCKECEELE EKNIKEFLQS FVHIVQMFIN TS

Soluble IL-17

(SEQ ID NO: 40)

GITIPRN PGCPNSEDKN FPRTVMVNLN IHNRNTNTNP

KRSSDYYNRS TSPWNLHRNE DPERYPSVIW EAKCRHLGCI

NADGNVDYHM NSVPIQQEIL VLRREPPHCP NSFRLEKILV

SVGCTCVTPI VHHVA

Soluble IL-18

(SEQ ID NO: 41)

YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNED

Nucleic Acid Encoding Human Soluble IL-18

(SEQ ID NO: 42)

TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT

Human Soluble PDGF-DD (SEQ ID NO: 45)

RDTSATPQSASI KALRNANLRR DESNHLTDLY RRDETIQVKG

NGYVQSPRFP NSYPRNLLLT WRLHSQENTR IQLVFDNQFG

LEEAENDICR YDFVEVEDIS ETSTIIRGRW CGHKEVPPRI

KSRTNQIKIT FKSDDYFVAK PGFKIYYSLL EDFQPAAASE

TNWESVTSSI SGVSYNSPSV TDPTLIADAL DKKIAEFDTV

EDLLKYFNPE SWQEDLENMY LDTPRYRGRS YHDRKSKVDL

DRLNDDAKRY SCTPRNYSVN IREELKLANV VFFPRCLLVQ

RCGGNCGCGT VNWRSCTCNS GKTVKKYHEV LQFEPGHIKR

RGRAKTMALV DIQLDHHERC DCICSSRPPR

Human Soluble SCF (SEQ ID NO: 46)

EGICRNRVTNNVKDV TKLVANLPKD YMITLKYVPG MDVLPSHCWI

SEMVVQLSDS LTDLLDKFSN ISEGLSNYSI IDKLVNIVDD

LVECVKENSS KDLKKSFKSP EPRLFTPEEF FRIFNRSIDA

FKDFVVASET SDCVVSSTLS PEKDSRVSVT KPFMLPPVAA

-continued

SSLRNDSSSS NRKAKNPPGD SSLHWAAMAL PALFSLIIGF

AFGALYWKKR QPSLTRAVEN IQINEEDNEI SMLQEKEREF QEV

Human Soluble FLT3L (SEQ ID NO: 47)

tqdcsfqhspissd favkirelsd yllqdypvtv asnlqdeelc gglwrlvlaq rwmerlktva gskmqgller vnteihfvtk cafqpppscl rfvqtnisrl lqetseqlva lkpwitrqnf srclelqcqp dsstlpppws prpleatapt apqppllll l llpvgllll a aawclhwqrt rrrtprpgeq vppvpspqdl llveh Exemplary soluble cell surface proteins include soluble MICA, MICB, and a ULP16 binding protein (e.g., ULBP1, ULBP2, ULBP3, ULBP4, ULBP5, or ULBP6). Exemplary sequences for soluble MICA, MICB, ULBP1, ULBP2, ULBP3, ULBP4, ULBP5, and ULBP6 are listed below.

Human Soluble MICA (SEQ ID NO: 48)

ephslry nitvlswdgs vqsgfltevh ldgqpflrcd rqkcrakpqg qwaedvlgnk twdretrdlt gngkdlrmtl ahikdqkegl hslqeirvce ihednstrss qhfyydgelf lsqnletkew tmpqssraqt lamnvrnflk edamktkthy hamhadclqe lrrylksgvv lrrtvppmvn vtrseasegn itvtcrasgf ypwnitlswr qdgvslshdt qqwgdvlpdg ngtyqtwvat ricqgeeqrf tcymehsgnh sthpvpsgkv lvlqshwqtf hvsavaaaai fviiifyvrc ckkktsaaeg pelvslqvld qhpvgtsdhr datqlgfqpl msdlgstgst ega Human Soluble MICB (SEQ ID NO: 49)

aephslry nlmvlsqdes vqsgflaegh ldgqpflryd rqkrrakpqg qwaedvlgak twdtetedlt engqdlrrtl thikdqkggl hslqeirvce ihedsstrgs rhfyydgelf lsqnletqes tvpqssraqt lamnvtnfwk edamktkthy ramqadclqk lqrylksgva irrtvppmvn vtcsevsegn itvtcrassf yprnitltwr qdgvslshnt qqwgdvlpdg ngtyqtwvat rirqgeeqrf tcymehsgnh gthpvpsgkv lvlqsqrtdf pyvsaampcf viiiilcvpc ckkktsaaeg pelvslqvld qhpvgtgdhr daaqlgfqpl msatgstgst ega Human Soluble ULBP1

(SEQ ID NO: 50)

wvdthclcydfiit pksrpepqwc evqglvderp flhydcvnhk akafaslgkk vnvtktweeq tetlrdvvdf lkgqlldiqv enlipieplt lqarmscehe ahghgrgswq flfngqkfll fdsnnrkwta lhpgakkmte kweknrdvtm ffqkislgdc kmwleeflmy weqmldptkp pslapg -continued Human SolubleULBP2

(SEQ ID NO: 51)

gradphslcyditvi pkfrpgprwc avqgqvdekt flhydcgnkt vtpvsplgkk lnvttawkaq npvlrevvdi lteqlrdiql enytpkeplt lqarmsceqk aeghssgswq fsfdgqifll fdsekrmwtt vhpgarkmke kwendkvvam sfhyfsmgdc igwledflmg mdstlepsag aplams Human Soluble ULBP3

(SEQ ID NO: 52)

dahslwynfti ihlprhgqqw cevqsqvdqk nflsydcgsd kvlsmghlee qlyatdawgk qlemlrevgq rlrleladte ledftpsgpl tlqvrmscec eadgyirgsw qfsfdgrkfl lfdsnnrkwt vvhagarrmk ekwekdsglt tffkmvsmrd ckswlrdflm hrkkrlepta pptmapg Human Soluble ULBP4

(SEQ ID NO: 53)

hslcfnftik slsrpgqpwc eaqvflnknl flqynsdnnm vkplgllgkk vyatstwgel tqtlgevgrd lrmllcdikp qiktsdpstl qvemfcgrea erctgaswqf atngeksllf damnmtwtvi nheaskiket wkkdrgleky frklskgdcd hwlreflghw eampeptvsp vnasdihwss sslpdrwiil gafillvlmg ivlicvwwqn gewqaglwpl rts Human Soluble ULBP5

(SEQ ID NO: 54)

gladp hslcyditvi pkfrpgprwc avqgqvdekt flhydcgskt vtpvsplgkk lnvttawkaq npvlrevvdi lteqlldiql enyipkeplt lqarmsceqk aeghgsgswq lsfdgqifll fdsenrmwtt vhpgarkmke kwendkdmtm sfhyismgdc tgwledflmg mdstlepsag apptmssg Human Soluble ULBP6

(SEQ ID NO: 55)

rrddp hslcyditvi pkfrpgprwc avqgqvdekt flhydcgnkt vtpvsplgkk lnvtmawkaq npvlrevvdi lteqlldiql enytpkeplt lqarmsceqk aeghssgswq fsidgqtfll fdsekrmwtt vhpgarkmke kwendkdvam sfhyismgdc igwledflmg mdstlepsag aplamssg In some embodiments, a soluble IL-12 protein can include a first sequence that is at least 70% identical (e.g., at least 75% identical, at least 80% identical, at least 85% identical, at least 90% identical, at least 95% identical, at least 99% identical, or 100% identical) to SEQ ID NO: 33, and a second sequence that is at least 70% identical (e.g., at least 75% identical, at least 80% identical, at least 85% identical, at least 90% identical, at least 95% identical, at least 99% identical, or 100% identical) to SEQ ID NO: 35. In some embodiments, the soluble IL-12 can further include a linker sequence (e.g., any of the exemplary linker sequences described herein or known in the art) between the first sequence and the second sequence.

In some embodiments, a soluble IL-12 protein is encoded by a first nucleic acid encoding a first sequence at least 70% identical (e.g., at least 75% identical, at least 80% identical, at least 85% identical, at least 90% identical, at least 95% identical, at least 99% identical, or 100% identical) to SEQ ID NO: 34, and a second nucleic acid sequence encoding a second sequence that is at least 70% identical (e.g., at least 75% identical, at least 80% identical, at least 85% identical, at least 90% identical, at least 95% identical, at least 99% identical, or 100% identical) to SEQ ID NO: 36. In some embodiments, the nucleic acid encoding a soluble IL-12 protein further includes a nucleic acid sequence encoding a linker sequence (e.g., any of the exemplary linker sequences described herein or known in the art) between the first nucleic acid and the second nucleic acid.

In some embodiments, a soluble IL-12 protein includes a sequence that is at least 70% identical (e.g., at least 75% identical, at least 80% identical, at least 85% identical, at least 90% identical, at least 95% identical, at least 99% identical, or 100% identical) to SEQ ID NO: 37. In some embodiments, a soluble IL-12 protein is encoded by a nucleic acid including a sequence at least 70% identical (e.g., at least 75% identical, at least 80% identical, at least 85% identical, at least 90% identical, at least 95% identical, at least 99% identical, or 100% identical) to SEQ ID NO: 38.

In some embodiments, a soluble IL-18 protein can include a sequence that is at least 70% identical (e.g., at least 75% identical, at least 80% identical, at least 85% identical, at least 90% identical, at least 95% identical, at least 99% identical, or 100% identical) to SEQ ID NO: 41. In some embodiments, a soluble IL-18 protein is encoded by a nucleic acid including a sequence at least 70% identical (e.g., at least 75% identical, at least 80% identical, at least 85% identical, at least 90% identical, at least 95% identical, at least 99% identical, or 100% identical) to SEQ ID NO: 42.

Additional examples of soluble interleukin proteins and soluble cytokine proteins are known in the art.

Soluble Interleukin or Cytokine Receptor

In some embodiments of any of the single-chain chimeric polypeptides or multi-chain chimeric polypeptides described herein, one or both of the first target-binding domain and the second target-binding domain is a soluble interleukin receptor or a soluble cytokine receptor. In some embodiments, the soluble receptor is a soluble TGF-β receptor II (TGF-β RII) (see, e.g., those described in Yung et al., *Am. J Resp. Crit. Care Med.* 194(9):1140-1151, 2016), a soluble TGF-β RIII (see, e.g., those described in Heng et al., *Placenta* 57:320, 2017), a soluble NKG2D (see, e.g., Cosman et al., *Immunity* 14(2):123-133, 2001; Costa et al., *Front. Immunol.*, Vol. 9, Article 1150, May 29, 2018; doi: 10.3389/fimmu.2018.01150), a soluble NKp30 (see, e.g., Costa et al., *Front. Immunol.*, Vol. 9, Article 1150, May 29, 2018; doi: 10.3389/fimmu.2018.01150), a soluble NKp44 (see, e.g., those described in Costa et al., *Front. Immunol.*, Vol. 9, Article 1150, May 29, 2018; doi: 10.3389/fimmu.2018.01150), a soluble NKp46 (see, e.g., Mandelboim et al., *Nature* 409:1055-1060, 2001; Costa et al., *Front. Immunol.*, Vol. 9, Article 1150, May 29, 2018; doi: 10.3389/fimmu.2018.01150), a soluble DNAM-1 (see, e.g., those described in Costa et al., *Front. Immunol.*, Vol. 9, Article 1150, May 29, 2018; doi: 10.3389/fimmu.2018.01150), a scMHCI (see, e.g., those described in Washburn et al., *PLoS One* 6(3):e18439, 2011), a scMHCII (see, e.g., those described in Bishwajit et al., *Cellular Immunol.* 170(1):25-33, 1996), a scTCR (see, e.g., those described in Weber et al., *Nature* 356(6372):793-796, 1992), a soluble CD155 (see, e.g., those described in Tahara-Hanaoka et al., *Int. Immunol.* 16(4):533-538, 2004), or a soluble CD28 (see, e.g., Hebbar et al., *Clin. Exp. Immunol.* 136:388-392, 2004).

In some embodiments, a soluble TGFβ RII receptor can include a first sequence that is at least 70% identical (e.g., at least 75% identical, at least 80% identical, at least 85% identical, at least 90% identical, at least 95% identical, at least 99% identical, or 100% identical) to IPPHVQKSVNNDMIVTDNNGAVKFPQLCKFCDVRF STCDNQKSCMSNCSITSICEKPQEV CVAVWRKNDEN-ITLETVCHDPKLPYHDFILEDAASPKCI-MKEKKKPGETFFMCSCSSDE CNDNIIFSEEYNTSNPD (SEQ ID NO: 56), and a second sequence that is at least 70% identical (e.g., at least 75% identical, at least 80% identical, at least 85% identical, at least 90% identical, at least 95% identical, at least 99% identical, or 100% identical) to IPPHVQKSVNNDMIVTDNNGAVKFPQLCKFCDVRF-STCDNQKSCMSNCSITSICEKPQEV CVAVWRKNDEN-ITLETVCHDPKLPYHDFILEDAASPKCI-MKEKKKPGETFFMCSCSSDE CNDNIIFSEEYNTSNPD (SEQ ID NO: 56). In some embodiments, the soluble TGF-β RII receptor can further include a linker sequence (e.g., any of the exemplary linker sequences described herein or known in the art) between the first sequence and the second sequence.

In some embodiments, a soluble TGF-β RII receptor is encoded by a first nucleic acid encoding a first sequence at least 70% identical (e.g., at least 75% identical, at least 80% identical, at least 85% identical, at least 90% identical, at least 95% identical, at least 99% identical, or 100% identical) to ATCCCCCCCCATGTGCAAAAGAGCGT-GAACAACGATATGATCGTGACCGACAACAA CGGCGCCGT-GAAGTTTCCCCAGCTCTGCAAGTTCTGC-GATGTCAGGTTCAGCACCTG CGA-TAATCAGAAGTCCTGCATGTCCAACTGCACGATC-ACCTCCATCTGCGAGAAGCC CCAAGAAGTGTGCGTGGCCGTGTGGCG-GAAAAATGACGAGAACATCACCCTGGAGA CCGTGTGTCACGACCCCAAGCTCCCTTAT-CACGACTTCATTCTGGAGGACGCTGCCT CCCC-CAAATGCATCATGAAGGAGAAGAAGAAGCCCG-GAGAGACCTTCTTTATGTGT TCCTGTAGCAGCGACGAGTGTAACGACAACAT-CATCTTCAGCGAAGAGTACAACAC CAGCAACCCT-GAT (SEQ ID NO: 57), and a second nucleic acid sequence encoding a second sequence that is at least 70% identical (e.g., at least 75% identical, at least 80% identical, at least 85% identical, at least 90% identical, at least 95% identical, at least 99% identical, or 100% identical) to ATCCCCCCC-CATGTGCAAAAGAGCGTGAACAACGATAT-GATCGTGACCGACAACAA CGGCGCCGT-GAAGTTTCCCCAGCTCTGCAAGTTCTGCGATGTC-AGGTTCAGCACCTG CGATAATCAGAAGTCCTG-CATGTCCAACTGCACGATCACCTC-CATCTGCGAGAAGCC CCAAGAAGTGTGCGTGGCCGTGTGGCG-GAAAAATGACGAGAACATCACCCTGGAGA CCGTGTGTCACGACCCCAAGCTCCCTTAT-CACGACTTCATTCTGGAGGACGCTGCCT CCCC-CAAATGCATCATGAAGGAGAAGAAGAAGCCCG-GAGAGACCTTCTTTATGTGT TCCTGTAGCAGCGACGAGTGTAACGACAACAT-CATCTTCAGCGAAGAGTACAACAC CAGCAACCCT-GAT (SEQ ID NO: 57). In some embodiments, the nucleic acid encoding a soluble TGF-β RII receptor further includes a nucleic acid sequence encoding a linker sequence (e.g., any of the exemplary linker sequences described herein or known in the art) between the first nucleic acid and the second nucleic acid.

In some embodiments, a soluble TGF-β RII receptor includes a sequence that is at least 70% identical (e.g., at least 75% identical, at least 80% identical, at least 85% identical, at least 90% identical, at least 95% identical, at least 99% identical, or 100% identical) to IPPHVQKSVNNDMIVTDNNGAVKFPQLCKFCDVRF STCDNQKSCMSNCSITSICEKPQEV CVAVWRKNDEN-ITLETVCHDPKLPYHDFILEDAASPKCI-MKEKKKPGETFFMCSCSSDE CNDNIIF SEEYNTSNPDGGGGSGGGGSGGGGSIP-PHVQKSVNNDMIVTDNNGAVKFPQL CKFCDVRF STCDNQKSCMSNCSIT SICEKPQEVCVAVWRKNDEN-ITLETVCHDPKLPYH DFILEDAASPKCI-MKEKKKPGETFFMCSCSSDECNDNIIFSEEYNTSNPD (SEQ ID NO: 60). In some embodiments, a soluble TGF-β RII receptor is encoded by a nucleic acid including a sequence at least 70% identical (e.g., at least 75% identical, at least 80% identical, at least 85% identical, at least 90% identical, at least 95% identical, at least 99% identical, or 100% identical) to (SEQ ID NO: 61)
```
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCACG
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCACAATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC.
```

Additional examples of soluble interleukin receptors and soluble cytokine receptors are known in the art.

Ligands of Co-Stimulatory Molecules

In some embodiments of any of the single-chain chimeric polypeptides or multi-chain chimeric polypeptides described herein, one or both of the first target-binding domain and the second target-binding domain is a ligand of a co-stimulatory molecule. In some embodiments, the ligand of a co-stimulatory molecule is a soluble CD80 (see, e.g., those described in Haile et al., *J Immunol.* 2013 Sep. 1; 191(5):2829-36, and those described WO2004/076488 A1), a soluble CD86 (see, e.g., those described in Jeannin et al., *Immunity.* 2000 September; 13(3):303-12, and those described in WO 2004/076488 A1), a soluble CD40 (see, e.g., those described in Elgueta et al., *Immunological Reviews,* 229(1), doi.org/

10.1111/j.1600-065X.2009.00782.x, and those described in WO 2001/083755 A2), a soluble ICOSL (see, e.g., those described in Chattopadyhay et al., *J. Immunol.*, Sep. 15, 2006, 177 (6) 3920-3929), a soluble CD70 (see, e.g., those described in Miller et al., *J. Neurosurg.*, 2010 August; 113(2):280-5, and those described in US 2009/0148942 A1), a soluble OX40L (see, e.g., those described in Kondo et al., *Hum. Immunol.*, 2007 July; 68(7):563-71. Epub 2007 Apr. 13), a soluble 4-1BBL (see, e.g., those described in Wang et al., *Cancer Immunol Immunother.*, 2012 April; 61(4):489-95), a soluble GITRL (see, e.g., those described in Stone et al., *J. Virol.*, 2006 February; 80(4):1762-72), a soluble LIGHT (see, e.g., those described in Maeda et al., *J. Immunol.*, 2018 Jul. 1; 201(1):202-214), a soluble TIM3 (see, e.g., those described in Clayton et al., *J. Virol.*, 2015 April; 89(7):3723-36), a soluble TIM4 (see, e.g., those described in Rhein et al., *J. Virol.*, 2016 Jun. 10; 90(13):6097-6111), soluble a ICAM1 (see, e.g., those described in Witkowsa and Borawska, Eur Cytokine Netw. 2004 April-June; 15(2):91-8), a soluble LFA3 (see, e.g., those described in Menshawy et al., *Comparative ClinicalPathology*, 27(3), 721-727, doi.org/10.1007/s00580-018-2657-x), a soluble CD1d (see, e.g., those described in Brennan et al., *PNAS*, Aug. 1, 2017 114 (31) 8348-8353), or a soluble LLT-1 (see, e.g., those described in Chalan et al., PLoS ONE, 10(7), e0132436, doi.org/10.1371/journal.pone.0132436).

In some embodiments, a soluble CD80, a soluble CD86, a soluble CD40, a soluble ICOSL, a soluble CD70, a soluble OX40L, a soluble 4-1BBL, a soluble GITRL, a soluble LIGHT, a soluble TIM3, a soluble TIM4, a soluble ICAM1, a soluble LFA3, a soluble CD1d, or a soluble LLT-1 can include a sequence that is at least 70% identical (e.g., at least 75% identical, at least 80% identical, at least 85% identical, at least 90% identical, at least 95% identical, at least 99% identical, or 100% identical) to the wild type sequence.

Additional examples of ligands of a co-stimulatory molecules are known in the art.

Additional Antigen-Binding Domains

Some embodiments of any of the single-chain chimeric polypeptides or multi-chain chimeric polypeptides described herein can further include one or more (e.g., two, three, four, five, six, seven, eight, nine, or ten) additional target-binding domains (e.g., any of the exemplary target-binding domains described herein or known in the art) at its N- and/or C-terminus.

In some embodiments, the single-chain chimeric polypeptide or multi-chain chimeric polypeptide can include one or more (e.g., two, three, four, five, six, seven, eight, nine, or ten) additional target-binding domains (e.g., any of the exemplary target-binding domains described herein or known in the art) at its N-terminus. In some embodiments, one of the one or more additional target-binding domains (e.g., any of the exemplary target-binding domains described herein or known in the art) at the N-terminus of the single-chain chimeric polypeptide or multi-chain chimeric polypeptide can directly abut the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains described herein). In some embodiments, the single-chain chimeric polypeptide or multi-chain chimeric polypeptide further includes a linker sequence (e.g., any of the exemplary linker sequences described herein or known in the art) between one of the at least one additional target-binding domains (e.g., any of the exemplary target-binding domains described herein or known in the art) at the N-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains described herein).

In some embodiments of any of the single-chain chimeric polypeptides or multi-chain chimeric polypeptide described herein, the polypeptide includes one or more (e.g., two, three, four, five, six, seven, eight, nine, or ten) additional target-binding domains (e.g., any of the exemplary target-binding domains described herein or known in the art) at its C-terminus. In some embodiments, one of the one or more additional target-binding domains (e.g., any of the exemplary target-binding domains described herein or known in the art) at the C-terminus of the single-chain chimeric polypeptide or the multi-chain chimeric polypeptide directly abuts the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains described herein or known in the art). In some embodiments, the single-chain chimeric polypeptide or multi-chain chimeric polypeptide further comprises a linker sequence (e.g., any of the exemplary linker sequences described herein or known in the art) between one of the at least one additional target-binding domains (e.g., any of the exemplary target-binding domains described herein or known in the art) at the C-terminus of the single-chain chimeric polypeptide and the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains described herein).

In some embodiments of any of the single-chain chimeric polypeptides or multi-chain chimeric polypeptides described herein, the polypeptide comprises one or more (e.g., two, three, four, five, six, seven, eight, nine, or ten) additional target binding domains (e.g., any of the exemplary target-binding domains described herein or known in the art) at its N-terminus and its C-terminus. In some embodiments, one of the one or more additional antigen binding domains (e.g., any of the exemplary target-binding domains described herein or known in the art) at the N-terminus of the single-chain chimeric polypeptide or the multi-chain chimeric polypeptide directly abuts the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains described herein). In some embodiments, the single-chain chimeric polypeptide or multi-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the N-terminus and the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains). In some embodiments, one of the one or more additional antigen binding domains (e.g., any of the exemplary target-binding domains described herein or known in the art) at the C-terminus directly abuts the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains). In some embodiments, the single-chain chimeric polypeptide or multi-chain chimeric polypeptide further includes a linker sequence (e.g., any of the exemplary linker sequences described herein or known in the art) between one of the one or more additional antigen-binding domains (e.g., any of the exemplary target-binding domains described herein or known in the art) at the C-terminus and the first target-binding domain (e.g., any of the exemplary target-binding domains described herein or known in the art), the second target-binding domain (e.g., any of the exemplary target-binding domains described herein or known in the art), or the linker domain (e.g., any of the exemplary linker domains described herein).

In some embodiments of any of the single-chain chimeric polypeptides or multi-chain chimeric polypeptides described herein, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same antigen. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) bind specifically to the same epitope. In some embodiments, two or more (e.g., three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) include the same amino acid sequence.

In some embodiments of any of the single-chain chimeric polypeptides or multi-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same antigen. In some embodiments, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) each bind specifically to the same epitope. In some embodiments, the first target-binding domain, the second target-binding domain, and the one or more (e.g., two, three, four, five, six, seven, eight, nine, or ten) additional target-binding domains each comprise the same amino acid sequence.

In some embodiments of any of the single-chain chimeric polypeptides or multi-chain chimeric polypeptides described herein, the first target-binding domain (e.g., any of the exemplary target-binding domains described herein or known in the art), the second target-binding domain (e.g., any of the exemplary target-binding domains described herein or known in the art), and the one or more (e.g., two, three, four, five, six, seven, eight, nine, or ten) additional target-binding domains (e.g., any of the exemplary target-binding domains described herein or known in the art) bind specifically to different antigens.

In some embodiments of any of the single-chain chimeric polypeptides or multi-chain chimeric polypeptides described herein, one or more of the first target-binding domain, the second target-binding domain, and the one or more target-binding domains is an antigen-binding domain (e.g., any of the exemplary antigen-binding domains described herein or known in the art). In some embodiments of any of the single-chain chimeric polypeptides or multi-chain chimeric polypeptides described herein, the first target-binding domain, the second target-binding domain, and the one or more additional target-binding domains are each an antigen-binding domain (e.g., any of the exemplary antigen-binding domains described herein or known in the art). In some embodiments, the antigen-binding domain can include a scFv or a single domain antibody.

In some embodiments of any of the single-chain chimeric polypeptides or multi-chain chimeric polypeptides described herein, one or more (e.g., two, three, four, five, six, seven, eight, nine, or ten) of the first target-binding domain (e.g., any of the exemplary target-binding domains described herein or known in the art), the second target-binding domain (e.g., any of the exemplary target-binding domains described herein or known in the art), and the one or more target-binding domains (e.g., any of the exemplary target-binding domains described herein or known in the art) bind specifically to a target selected from the group consisting of: CD16a, CD28, CD3, CD33, CD20, CD19, CD22, CD40, CD47, CD52, CD70, CD80, CD86, CD123, CD137, CD272, IL-1R, IL-1, VEGF, IL-6R, IL-4, IL-10, PDL-1, PDL-2, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, B7-H4, HVEM, EPCAM, BCMA, P-cadherin, CEACAM5, VISTA, a UL16-binding protein, HLA-DR, DLL4, TYRO3, AXL, MER, CD122, CD155, PDGF-DD, ILT3, ILT4, TIGIT, MHCII, LAG3, OX40, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

In some embodiments of any of the single-chain chimeric polypeptides or multi-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin, soluble cytokine protein, or soluble cell surface protein. Non-limiting examples of soluble interleukin proteins, soluble cytokine proteins, or soluble cell surface proteins include: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

In some embodiments of any of the single-chain chimeric polypeptides or multi-chain chimeric polypeptides described herein, one or more of the first target-binding domain (e.g., any of the exemplary target-binding domains described herein or known in the art), the second target-binding domain (e.g., any of the exemplary target-binding domains described herein or known in the art), and the one or more additional target-binding domains (e.g., any of the exemplary target-binding domains described herein or known in the art) is a soluble interleukin or cytokine receptor. Non-limiting examples of soluble interleukin receptors and soluble cytokine receptors include: a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

In some embodiments of any of the multi-chain chimeric polypeptides described herein, the first chimeric polypeptide further includes one or more (e.g., two, three, four, five, six, seven, eight, nine, or ten) additional target-binding domain(s) (e.g., any of the exemplary target-binding domains described herein or known in the art), where at least one of the one or more additional antigen-binding domain(s) is positioned between the linker domain (e.g., any of the exemplary linker domains described herein or known in the art) and the first domain of the pair of affinity domains (e.g., any of the exemplary first domains of any of the exemplary pairs of affinity domains described herein). In some embodiments, the first chimeric polypeptide of a multi-chain chimeric polypeptide can further include a linker sequence (e.g., any of the exemplary linker sequences described herein or known in the art) between the linker domain (e.g., any of the exemplary linker domains described herein) and the at least one of the one or more additional target-binding domain(s) (e.g., any of the exemplary target-binding domains described herein or known in the art), and/or a linker sequence (e.g., any of the exemplary linker sequences described herein or known in the art) between the at least one of the one or more additional target-binding domain(s) (e.g., any of the exemplary target-binding domains described herein or known in the art) and the first domain of the pair of affinity domains (e.g., any of the exemplary first domains described herein of any of the exemplary pairs of affinity domains described herein).

In some embodiments of any of the multi-chain chimeric polypeptides described herein, the first chimeric polypeptide further includes one or more (e.g., two, three, four, five, six, seven, eight, nine, or ten) additional target-binding domains at the N-terminal and/or C-terminal end of the first chimeric polypeptide. In some embodiments, at least one of the one or more additional target-binding domains (e.g., any of the exemplary target-binding domains described herein or known in the art) directly abuts the first domain of the pair of affinity domains (e.g., any of the exemplary first domains described herein of any of the exemplary pairs of affinity domains described herein) in the first chimeric polypeptide of a multi-chain chimeric polypeptide. In some embodiments, the first chimeric polypeptide of a multi-chain chimeric polypeptide further includes a linker sequence (e.g., any of the exemplary linker sequences described herein or known in the art) between the at least one of the one or more additional target-binding domains (e.g., any of the exemplary target-binding domains described herein or known in the art) and the first domain of the pair of affinity domains (e.g., any of the exemplary first domains described herein of any of the exemplary pairs of affinity domains described herein). In some embodiments, the at least one of the one or more additional target-binding domains (e.g., any of the exemplary target-binding domains described herein or known in the art) directly abuts the first target-binding domain (e.g., any of the exemplary target-binding domains described herein or known in the art) in the first chimeric polypeptide of a multi-chain chimeric polypeptide. In some embodiments, the first chimeric polypeptide of a multi-chain chimeric polypeptide further comprises a linker sequence (e.g., any of the exemplary linker sequences described herein or known in the art) between the at least one of the one or more additional target-binding domains (e.g., any of the exemplary target-binding domains described herein or known in the art) and the first target-binding domain (e.g., any of the exemplary target-binding domains described herein or known in the art).

In some embodiments of any of the multi-chain chimeric polypeptides described herein, at least one of the one or more additional target-binding domains (e.g., any of the exemplary target-binding domains described herein or known in the art) is disposed at the N- and/or C-terminus of the first chimeric polypeptide, and at least one of the one or more additional target-binding domains (e.g., any of the exemplary target-binding domains described herein or known in the art) is positioned between the linker domain (e.g., any of the exemplary linker domains described herein or known in the art) and the first domain of the pair of affinity domains (e.g., any of the exemplary first domains of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the N-terminus directly abuts the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide of a multi-chain chimeric polypeptide. In some embodiments, the first chimeric polypeptide of a multi-chain chimeric polypeptide further comprises a linker sequence (e.g., any of the linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one additional target-binding domain (e.g., any of the exemplary target-binding domains described herein or known in the art) of the one or more additional target-binding domains disposed at the C-terminus directly abuts the first target-binding domain (e.g., any of the exemplary target-binding domains described herein or known in the art) or the first domain of the pair of affinity domains (e.g., any of the exemplary first domains of any of the exemplary pairs of affinity domains described herein) in the first chimeric polypeptide of a multi-chain chimeric polypeptide. In some embodiments, the first chimeric polypeptide of a multi-chain chimeric polypeptide further includes a linker sequence (e.g., any of the exemplary linker sequences described herein or known in the art) disposed between the at least one additional target-binding domain (e.g., any of the exemplary target-binding domains described herein or known in the art) and the first target-binding domain (e.g., any of the exemplary target-binding domains described herein or known in the art) or the first domain of the pair of affinity domains (e.g., any of the exemplary first domains described herein of any of the exemplary pairs of affinity domains described herein) in the first chimeric polypeptide. In some embodiments, the at least one of the one or more additional target-binding domains (e.g., any of the exemplary target-binding domains described herein or known in the art) positioned between the linker domain (e.g., any of the exemplary linker domains described herein) and the first domain of the pair of affinity domains (e.g., any of the first domains described herein or any of the exemplary pairs of affinity domains described herein), directly abuts the linker domain and/or the first domain of the pair of affinity domains. In some embodiments, the first chimeric polypeptide of a multi-chain chimeric polypeptide further comprises a linker sequence (e.g., any of the exemplary linker sequences described herein or known in the art) disposed (i) between the linker domain (e.g., any of the exemplary linker domains described herein) and the at least one of the one or more additional target-binding domains (e.g., any of the exemplary target-binding domains described herein or known in the art) positioned between the linker domain (e.g., any of the exemplary linker domains described herein) and the first domain of the pair of affinity domains (e.g., any of the exemplary first domains of any of the exemplary pairs of affinity domains described herein), and/or (ii) between the first domain of the pair of affinity domains and the at least one of the one or more additional target-binding domains positioned between the linker domain and the first domain of the pair of affinity domains.

In some embodiments of any of the multi-chain chimeric polypeptides described herein, the second chimeric polypeptide further includes one or more (e.g., two, three, four, five, six, seven, eight, nine, or ten) additional target-binding domains (e.g., any of the exemplary target-binding domains described herein or known in the art) at the N-terminal end and/or the C-terminal end of the second chimeric polypeptide. In some embodiments, at least one of the one or more additional target-binding domains (e.g., any of the exemplary target-binding domains described herein or known in the art) directly abuts the second domain of the pair of affinity domains (e.g., any of the exemplary second domains of any of the exemplary pairs of affinity domains described herein) in the second chimeric polypeptide of a multi-chain chimeric polypeptide. In some embodiments, the second chimeric polypeptide of a multi-chain chimeric polypeptide further includes a linker sequence (e.g., any of the exemplary linker sequences described herein or known in the art) between at least one of the one or more additional target-binding domains (e.g., any of the exemplary target-binding domains described herein or known in the art) and the second domain of the pair of affinity domains (e.g., any of the second domains described herein of any of the exemplary pairs of affinity domains described herein) in the second chimeric polypeptide. In some embodiments, at least one of the one or more additional target-binding domains (e.g., any of the exemplary target-binding domains described herein or known in the art) directly abuts the second target-binding domain (e.g., any of the target-binding domains described herein or known in the art) in the second chimeric polypeptide of a multi-chain chimeric polypeptide. In some embodiments, the second chimeric polypeptide further includes a linker sequence (e.g., any of the exemplary linker sequences described herein or known in the art) between at least one of the one or more additional target-binding domains (e.g., any of the exemplary target binding domains described herein or known in the art) and the second target-binding domain (e.g., any of the exemplary target binding domains described herein or known in the art) in the second chimeric polypeptide.

In some embodiments of any of the multi-chain chimeric polypeptides described herein, two or more (e.g., three or more, four or more, five or more, six or more, seven or more, eight or more, nine or more, or ten or more) of the first target-binding domain, the second target-binding domain, and the one or more additional target-binding domains bind specifically to the same antigen. In some embodiments, two or more (e.g., three or more, four or more, five or more, six or more, seven or more, eight or more, nine or more, or ten or more) of the first target-binding domain, the second target-binding domain, and the one or more additional target-binding domains bind specifically to the same epitope. In some embodiments, two or more (e.g., three or more, four or more, five or more, six or more, seven or more, eight or more, nine or more, or ten or more) of the first target-binding domain, the second target-binding domain, and the one or more additional target-binding domains include the same amino acid sequence. In some embodiments, the first target-binding domain, the second target-binding domain, and the one or more additional target-binding domains each bind specifically to the same antigen. In some embodiments, the first target-binding domain, the second target-binding domain, and the one or more additional target-binding domains each bind specifically to the same epitope. In some embodiments, the first target-binding domain, the second target-binding domain, and the one or more additional target-binding domains each include the same amino acid sequence.

In some embodiments of any of the multi-chain chimeric polypeptides described herein, the first target-binding domain, the second target-binding domain, and the one or more additional target-binding domains bind specifically to different antigens. In some embodiments of any of the multi-chain chimeric polypeptides described herein, one or more (e.g., two or more, three or more, four or more, five or more, six or more, seven or more, eight or more, nine or more, or ten or more) of the first target-binding domain, the second target-binding domain, and the one or more target-binding domains is an antigen-binding domain. In some embodiments, the first target-binding domain, the second target-binding domain, and the one or more additional target-binding domains are each an antigen-binding domain (e.g., a scFv or a single-domain antibody).

Pairs of Affinity Domains

In some embodiments, a multi-chain chimeric polypeptide includes: 1) a first chimeric polypeptide that includes a first domain of a pair of affinity domains, and 2) a second chimeric polypeptide that includes a second domain of a pair of affinity domains such that the first chimeric polypeptide and the second chimeric polypeptide associate through the binding of the first domain and the second domain of the pair of affinity domains. In some embodiments, the pair of affinity domains is a sushi domain from an alpha chain of an IL-15 receptor (IL15Rα) (e.g., a human IL-15 receptor (IL-15Rα)) and a soluble IL-15 (e.g., a human soluble IL-15). A sushi domain, also known as a short consensus repeat or type 1 glycoprotein motif, is a common motif in protein-protein interaction. Sushi domains have been identified on a number of protein-binding molecules, including complement components C1r, C1s, factor H, and C2m, as well as the nonimmunologic molecules factor XIII and p2-glycoprotein. Atypical Sushi domain has approximately 60 amino acid residues and contains four cysteines (Ranganathan, Pac. Symp Biocomput. 2000:155-67). The first cysteine can form a disulfide bond with the third cysteine, and the second cysteine can form a disulfide bridge with the fourth cysteine. In some embodiments in which one member of the pair of affinity domains is a soluble IL-15, the soluble IL-15 has a D8N or D8A amino acid substitution. In some embodiments in which one member of the pair of affinity domains is an alpha chain of human IL-15 receptor (IL15Rα), the human IL15Rα is a mature full-length IL15Rα. In some embodiments, the pair of affinity domains is barnase and barnstar. In some embodiments, the pair of affinity domains is a PKA and an AKAP. In some embodiments, the pair of affinity domains is an adapter/docking tag module based on mutated RNase I fragments (Rossi, *Proc Natl Acad Sci USA.* 103:6841-6846, 2006; Sharkey et al., *Cancer Res.* 68:5282-5290, 2008; Rossi et al., *Trends Pharmacol Sci.* 33:474-481, 2012) or SNARE modules based on interactions of the proteins syntaxin, synaptotagmin, synaptobrevin, and SNAP25 (Deyev et al., *Nat Biotechnol.* 1486-1492, 2003).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains and the second domain of the pair of affinity domains bind to each other with a dissociation equilibrium constant ($K_D$) of less than $1\times10^{-7}$ M, less than $1\times10^{-8}$ M, less than $1\times10^{-9}$ M, less than $1\times10^{-10}$ M, less than $1\times10^{-11}$ M, less than $1\times10^{-12}$ M, or less than $1\times10^{-13}$ M. In some embodiments, the first domain of the pair of affinity domains and the second domain of the pair of affinity domains bind to each other with a $K_D$ of about $1\times10^{-4}$ M to about $1\times10^{-6}$ M, about $1\times10^{-5}$ M to about $1\times10^{-7}$ M, about $1\times10^{-6}$ M to about $1\times10^{-8}$ M, about $1\times10^{-7}$ M to about $1\times10^{-9}$ M, about $1\times10^{-8}$ M to about $1\times10^{-10}$ M, about $1\times10^{-9}$ M to about $1\times10^{-11}$ M, about $1\times10^{-10}$ M to about $1\times10^{-12}$ M, about $1\times10^{-11}$ M to about $1\times10^{-13}$ M, about $1\times10^{-4}$ M to about $1\times10^{-5}$ M, about $1\times10^{-5}$ M to about $1\times10^{-6}$ M, about $1\times10^{-6}$ M to about $1\times10^{-7}$ M, about $1\times10^{-7}$ M to about $1\times10^{-8}$ M, about $1\times10^{-8}$ M to about $1\times10^{-9}$ M, about $1\times10^{-9}$ M to about $1\times10^{-10}$ M, about $1\times10^{-10}$ M to about $1\times10^{-11}$ M, about $1\times10^{-11}$ M to about $1\times10^{-12}$ M, or about $1\times10^{-12}$ M to about $1\times10^{-13}$ M (inclusive). Any of a variety of different methods known in the art can be used to determine the $K_D$ value of the binding of the first domain of the pair of affinity domains and the second domain of the pair of affinity domains (e.g., an electrophoretic mobility shift assay, a filter binding assay, surface plasmon resonance, and a biomolecular binding kinetics assay, etc.).

In some embodiments, a first chimeric polypeptide of a multi-chain chimeric polypeptide includes a first domain of a pair of affinity domains and a second chimeric polypeptide of the multi-chain chimeric polypeptide includes a second domain of a pair of affinity domains, wherein the first domain of the pair of affinity domains, the second domain of the pair of affinity domains, or both is about 10 to 100 amino acids in length. For example, a first domain of a pair of affinity domains, a second domain of a pair of affinity domains, or both can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about to 45 amino acids in length, about 10 to 40 amino acids in length, about 10 to 35 amino acids in length, about 10 to 30 amino acids in length, about 10 to 25 amino acids in length, about 10 to amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a first domain of a pair of affinity domains, a second domain of a pair of affinity domains, or both is about 10, 15, 20, 25, 30, 35, 40, 45, 50, 55, 60, 65, 70, 75, 80, 85, 90, 95, or 100 amino acids in length.

In some embodiments, any of the first and/or second domains of a pair of affinity domains disclosed herein can include one or more additional amino acids (e.g., 1, 2, 3, 5, 6, 7, 8, 9, 10, or more amino acids) at its N-terminus and/or C-terminus, so long as the function of the first and/or second domains of a pair of affinity domains remains intact. For example, a sushi domain from an alpha chain of human IL-15 receptor (IL15Rα) can include one or more additional amino acids at the N-terminus and/or the C-terminus, while still retaining the ability to bind to a soluble IL-15. Additionally or alternatively, a soluble IL-15 can include one or more additional amino acids at the N-terminus and/or the C-terminus, while still retaining the ability to bind to a sushi domain from an alpha chain of human IL-15 receptor (IL15Rα).

A non-limiting example of a sushi domain from an alpha chain of IL-15 receptor alpha (IL15Rα) can include a sequence that is at least 70% identical, at least 75% identical, at least 80% identical, at least 85% identical, at least 90% identical, at least 95% identical, at least 99% identical, or 100% identical to ITCPPPMSVEHADIWVKSYSLYSRERYICNSGFKRKAGTSSLTECVLNKATNVAHWTTPS LKCIR (SEQ ID NO: 10). In some embodiments, a sushi domain from an alpha chain of IL15Rα can be encoded by a nucleic acid including

```
                                            (SEQ ID NO: 11)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG.
```

In some embodiments, a soluble IL-15 can include a sequence that is at least 70% identical, at least 75% identical, at least 80% identical, at least 85% identical, at least 90% identical, at least 95% identical, at least 99% identical, or 100% identical to NWVNVISDLKKIEDLIQ SMHIDATLYTESDVHPSCKVTAMKCFLLELQVISLESGDASIHD TVENLIILANNSLSSNGNVTESGCKECEELEEKNIKEFLQSFVHIVQMFINTS (SEQ ID NO: 39). In some embodiments, a soluble IL-15 can be encoded by a nucleic acid including the sequence of

```
                                           (SEQ ID NO: 110)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC.
```

Signal Sequence

In some embodiments, a single-chain chimeric polypeptide includes a signal sequence at its N-terminal end. As will be understood by those of ordinary skill in the art, a signal sequence is an amino acid sequence that is present at the N-terminus of a number of endogenously produced proteins that directs the protein to the secretory pathway (e.g., the protein is directed to reside in certain intracellular organelles, to reside in the cell membrane, or to be secreted from the cell). Signal sequences are heterogeneous and differ greatly in their primary amino acid sequences. However, signal sequences are typically 16 to 30 amino acids in length and include a hydrophilic, usually positively charged N-terminal region, a central hydrophobic domain, and a C-terminal region that contains the cleavage site for signal peptidase.

In some embodiments, a single-chain chimeric polypeptide includes a signal sequence having an amino acid sequence MKWVTFISLLFLFSSAYS (SEQ ID NO: 62). In some embodiments, a single chain chimeric polypeptide includes a signal sequence encoded by the nucleic acid sequence

```
                                            (SEQ ID NO: 63)
ATGAAATGGGTGACCTTTATTTCTTTACTGTTCCTCTTTAGCAGCGCCT

ACTCC,
```

-continued

```
                                            (SEQ ID NO: 64)
ATGAAGTGGGTCACATTTATCTCTTTACTGTTCCTCTTCTCCAGCGCCT

ACAGC,

or
                                            (SEQ ID NO: 65)
ATGAAATGGGTGACCTTTATTTCTTTACTGTTCCTCTTTAGCAGCGCCT

ACTCC.
```

In some embodiments, a single-chain chimeric polypeptide includes a signal sequence having an amino acid sequence MKCLLYLAFLFLGVNC (SEQ ID NO: 66). In some embodiments, a single-chain chimeric polypeptide includes a signal sequence having an amino acid sequence MGQIVTMFEALPHIIDEVINIVIIVLIIITSIKAVYNFATCGILALVSFLFLAGRSCG (SEQ ID NO: 67). In some embodiments, a single-chain chimeric polypeptide includes a signal sequence having an amino acid sequence MPNHQSGSPTGSSDLLLSGKKQRPHLALRRKRRREMRKINRKVRRMNLAPIKEKTAWQ HLQALISEAEEVLKTSQTPQNSLTLFLALLSVLGPPVTG (SEQ ID NO: 68). In some embodiments, a single-chain chimeric polypeptide includes a signal sequence having an amino acid sequence MDSKGSSQKGSRLLLLLVVSNLLLCQGVVS (SEQ ID NO: 69). Those of ordinary skill in the art will be aware of other appropriate signal sequences for use in a single-chain chimeric polypeptide.

In some embodiments, a single-chain chimeric polypeptide includes a signal sequence that is about 10 to 100 amino acids in length. For example, a signal sequence can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about to 45 amino acids in length, about 10 to 40 amino acids in length, about 10 to 35 amino acids in length, about 10 to 30 amino acids in length, about 10 to 25 amino acids in length, about 10 to amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a signal sequence is about 10, 15, 20, 25, 30, 35, 40, 45, 50, 55, 60, 65, 70, 75, 80, 85, 90, 95, or 100 amino acids in length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKWVTFISLLFLFSSAYS (SEQ ID NO: 62) can include one or more additional amino acids at the N-terminus or C-terminus, while still retaining the ability to direct the single-chain chimeric polypeptide to the secretory pathway.

In some embodiments, a single-chain chimeric polypeptide includes a signal sequence that directs the single-chain chimeric polypeptide into the extracellular space. Such embodiments are useful in producing single-chain chimeric polypeptides that are relatively easy to be isolated and/or purified.

In some embodiments, a multi-chain chimeric polypeptide includes a first chimeric polypeptide that includes a signal sequence at its N-terminal end. In some embodiments, a multi-chain chimeric polypeptide includes a second chimeric polypeptide that includes a signal sequence at its N-terminal end. In some embodiments, both the first chimeric polypeptide of a multi-chain chimeric polypeptide and a second chimeric polypeptide of the multi-chain chimeric polypeptide include a signal sequence. As will be understood by those of ordinary skill in the art, a signal sequence is an amino acid sequence that is present at the N-terminus of a number of endogenously produced proteins that directs the protein to the secretory pathway (e.g., the protein is directed to reside in certain intracellular organelles, to reside in the cell membrane, or to be secreted from the cell). Signal sequences are heterogeneous and differ greatly in their primary amino acid sequences. However, signal sequences are typically 16 to 30 amino acids in length and include a hydrophilic, usually positively charged N-terminal region, a central hydrophobic domain, and a C-terminal region that contains the cleavage site for signal peptidase.

In some embodiments, a first chimeric polypeptide of a multi-chain chimeric polypeptide, a second chimeric polypeptide of the multi-chain chimeric polypeptide, or both includes a signal sequence having an amino acid sequence MKWVTFISLLFLFSSAYS (SEQ ID NO: 62). In some embodiments, a first chimeric polypeptide of a multi-chain chimeric polypeptide, a second chimeric polypeptide of the multi-chain chimeric polypeptide, or both includes a signal sequence encoded by the nucleic acid sequence

```
                                        (SEQ ID NO: 63)
ATGAAATGGGTGACCTTTATTTCTTTACTGTTCCTCTTTAGCAGCGCCT

ACTCC,
                                        (SEQ ID NO: 64)
ATGAAGTGGGTCACATTTATCTCTTTACTGTTCCTCTTCTCCAGCGCCT

ACAGC,
or
                                        (SEQ ID NO: 65)
ATGAAATGGGTGACCTTTATTTCTTTACTGTTCCTCTTTAGCAGCGCCT

ACTCC.
```

In some embodiments, a first chimeric polypeptide of a multi-chain chimeric polypeptide, a second chimeric polypeptide of the multi-chain chimeric polypeptide, or both includes a signal sequence having an amino acid sequence MKCLLYLAFLFLGVNC (SEQ ID NO: 66). In some embodiments, a first chimeric polypeptide of a multi-chain chimeric polypeptide, a second chimeric polypeptide of the multi-chain chimeric polypeptide, or both includes a signal sequence having an amino acid sequence MGQIVTMFEALPHIIDEVINIVIIVLIIITSIKAVYNFATCGILALVSFLFLAGRSCG (SEQ ID NO: 67). In some embodiments, a first chimeric polypeptide of a multi-chain chimeric polypeptide, a second chimeric polypeptide of the multi-chain chimeric polypeptide, or both includes a signal sequence having an amino acid sequence MPNHQSGSPTGSSDLLLSGKKQRPHLALRRKRRREMRKINRKVRRMNLAPIKEKTAWQ HLQALISEAEEVLKTSQTPQNSLTLFLALLSVLGPPVTG (SEQ ID NO: 68). In some embodiments, a first chimeric polypeptide of a multi-chain chimeric polypeptide, a second chimeric polypeptide of the multi-chain chimeric polypeptide, or both includes a signal sequence having an amino acid sequence MDSKGSSQKGSRLLLLLVVSNLLLCQGVVS (SEQ ID NO: 69). Those of ordinary skill in the art will be aware of other appropriate signal sequences for use in a first chimeric polypeptide and/or a second chimeric polypeptide of multi-chain chimeric polypeptides described herein.

In some embodiments, a first chimeric polypeptide of a multi-chain chimeric polypeptide, a second chimeric polypeptide of the multi-chain chimeric polypeptide, or both includes a signal sequence that is about 10 to 100 amino acids in length. For example, a signal sequence can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about to 35 amino acids in length, about 10 to 30 amino acids in length, about 10 to 25 amino acids in length, about 10 to 20 amino acids in length, about 10 to 15 amino acids in length, about 20 to amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a signal sequence is about 10, 15, 20, 25, 30, 35, 40, 45, 50, 55, 60, 65, 70, 75, 80, 85, 90, 95, or 100 amino acids in length.

In some embodiments, any of the signal sequences disclosed herein can include one or more additional amino acids (e.g., 1, 2, 3, 5, 6, 7, 8, 9, 10, or more amino acids) at its N-terminus and/or C-terminus, so long as the function of the signal sequence remains intact. For example, a signal sequence having the amino acid sequence MKCLLYLAFLFLGVNC (SEQ ID NO: 66) can include one or more additional amino acids at the N-terminus or C-terminus, while still retaining the ability to direct a first chimeric polypeptide of a multi-chain chimeric polypeptide, a second chimeric polypeptide of the multi-chain chimeric polypeptide, or both to the secretory pathway.

In some embodiments, a first chimeric polypeptide of a multi-chain chimeric polypeptide, a second chimeric polypeptide of the multi-chain chimeric polypeptide, or both includes a signal sequence that directs the multi-chain chimeric polypeptide into the extracellular space. Such embodiments are useful in producing multi-chain chimeric polypeptides that are relatively easy to be isolated and/or purified.

Peptide Tags

In some embodiments, a single-chain chimeric polypeptide includes a peptide tag (e.g., at the N-terminal end or the C-terminal end of the single-chain chimeric polypeptide). In some embodiments, a single-chain chimeric polypeptide includes two or more peptide tags.

Exemplary peptide tags that can be included in a single-chain chimeric polypeptide include, without limitation, Avi-Tag (GLNDIFEAQKIEWHE; SEQ ID NO: 70), a calmodulin-tag (KRRWKKNFIAVSAANRFKKISSSGAL; SEQ ID NO: 71), a polyglutamate tag (EEEEEE; SEQ ID NO: 72), an E-tag (GAPVPYPDPLEPR; SEQ ID NO: 73), a FLAG-tag (DYKDDDDK; SEQ ID NO: 74), an HA-tag, a peptide from hemagglutinin (YPYDVPDYA; SEQ ID NO: 75), a his-tag (HHHHH (SEQ ID NO: 76); HHHHHH (SEQ ID NO: 77); HHHHHHH (SEQ ID NO: 78); HHHHHHHH (SEQ ID NO: 79); HHHHHHHHH (SEQ ID NO: 80); or HHHHHHHHHH (SEQ ID NO: 81)), a myc-tag (EQKLISEEDL; SEQ ID NO: 82), NE-tag (TKENPRSNQEESYDDNES; SEQ ID NO: 83), S-tag (KETAAAKFERQHMDS; SEQ ID NO: 84), SBP-tag (MDEKTTGWRGGHVVEGLAGELEQLRARLEHHPQGQREP; SEQ ID NO: 85), Softag 1 (SLAELLNAGLGGS; SEQ ID NO: 86), Softag 3 (TQDPSRVG; SEQ ID NO: 87), Spot-tag (PDRVRAVSHWSS; SEQ ID NO: 88), Strep-tag (WSHPQFEK; SEQ ID NO: 89), TC tag (CCPGCC; SEQ ID NO: 90), Ty tag (EVHTNQDPLD; SEQ ID NO: 91), V5 tag (GKPIPNPLLGLDST; SEQ ID NO: 92), VSV-tag (YTDIEMNRLGK; SEQ ID NO: 93), and Xpress tag (DLYDDDDK; SEQ ID NO: 94). In some embodiments, tissue factor protein is a peptide tag.

Peptide tags that can be included in a single-chain chimeric polypeptide can be used in any of a variety of applications related to the single-chain chimeric polypeptide. For example, a peptide tag can be used in the purification of a single-chain chimeric polypeptide. As one non-limiting example, a single-chain chimeric polypeptide can include a myc tag; and can be purified using an antibody that recognizes the myc tag(s). One non-limiting example of an antibody that recognizes a myc tag is 9E10, available from the non-commercial Developmental Studies Hybridoma Bank. As another non-limiting example, a single-chain chimeric polypeptide can include a histidine tag, and can be purified using a nickel or cobalt chelate. Those of ordinary skill in the art will be aware of other suitable tags and agent that bind those tags for use in purifying a single-chain chimeric polypeptide. In some embodiments, a peptide tag is removed from the single-chain chimeric polypeptide after purification. In some embodiments, a peptide tag is not removed from the single-chain chimeric polypeptide after purification.

Peptide tags that can be included in a single-chain chimeric polypeptide can be used, for example, in immunoprecipitation of the single-chain chimeric polypeptide, imaging of the single-chain chimeric polypeptide (e.g., via Western blotting, ELISA, flow cytometry, and/or immunocytochemistry), and/or solubilization of the single-chain chimeric polypeptide.

In some embodiments, a single-chain chimeric polypeptide includes a peptide tag that is about 10 to 100 amino acids in length. For example, a peptide tag can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about to 45 amino acids in length, about 10 to 40 amino acids in length, about 10 to 35 amino acids in length, about 10 to 30 amino acids in length, about 10 to 25 amino acids in length, about 10 to amino acids in length, about 10 to 15 amino acids in length, about 20 to 30 amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a peptide tag is about 10, 15, 20, 25, 30, 35, 40, 45, 50, 55, 60, 65, 70, 75, 80, 85, 90, 95, or 100 amino acids in length.

Peptide tags included in a single-chain chimeric polypeptide can be of any suitable length. For example, peptide tags can be 5, 6, 7, 8, 9, 10, 11, 12, 13, 14, 15, 16, 17, 18, 19, 20, or more amino acids in length. In embodiments in which a single-chain chimeric polypeptide includes two or more peptide tags, the two or more peptide tags can be of the same or different lengths. In some embodiments, any of the peptide tags disclosed herein may include one or more additional amino acids (e.g., 1, 2, 3, 5, 6, 7, 8, 9, 10, or more amino acids) at the N-terminus and/or C-terminus, so long as the function of the peptide tag remains intact. For example, a myc tag having the amino acid sequence EQKLISEEDL (SEQ ID NO: 82) can include one or more additional amino acids (e.g., at the N-terminus and/or the C-terminus of the peptide tag), while still retaining the ability to be bound by an antibody (e.g., 9E10).

In some embodiments, a multi-chain chimeric polypeptide includes a first chimeric polypeptide that includes a peptide tag (e.g., at the N-terminal end or the C-terminal end of the first chimeric polypeptide). In some embodiments, a multi-chain chimeric polypeptide includes a second chimeric polypeptide that includes a peptide tag (e.g., at the N-terminal end or the C-terminal end of the second chimeric polypeptide). In some embodiments, both the first chimeric polypeptide of a multi-chain chimeric polypeptide and a second chimeric polypeptide of the multi-chain chimeric polypeptide include a peptide tag. In some embodiments, a first chimeric polypeptide of a multi-chain chimeric polypeptide, a second chimeric polypeptide of the multi-chain chimeric polypeptide, or both include two or more peptide tags.

Exemplary peptide tags that can be included in a first chimeric polypeptide of a multi-chain chimeric polypeptide, a second chimeric polypeptide of the multi-chain chimeric polypeptide, or both include, without limitation, AviTag (GLNDIFEAQKIEWHE; SEQ ID NO: 70), a calmodulin-tag (KRRWKKNFIAVSAANRFKKISSSGAL; SEQ ID NO: 71), a polyglutamate tag (EEEEEE; SEQ ID NO: 72), an E-tag (GAPVPYPDPLEPR; SEQ ID NO: 73), a FLAG-tag (DYKDDDDK; SEQ ID NO: 74), an HA-tag, a peptide from hemagglutinin (YPYDVPDYA; SEQ ID NO: 75), a his-tag (HHHHH (SEQ ID NO: 76); HHHHHH (SEQ ID NO: 77); HHHII IHH (SEQ ID NO: 78); HHHHHHHH (SEQ ID NO: 79); HHHHHHHHH (SEQ ID NO: 80); or HHHHHHHHHH (SEQ ID NO: 81), a myc-tag (EQKLISEEDL; SEQ ID NO: 82), NE-tag (TKENPRSNQEESYDDNES; SEQ ID NO: 83), S-tag, (KETAAAKFERQHMD S; SEQ ID NO: 84), SBP-tag (MDEKTTGWRGGHVVEGLAGELEQLRARLEHHPQGQREP; SEQ ID NO: 85), Softag 1 (SLAELLNAGLGGS; SEQ ID NO: 86), Softag 3 (TQDPSRVG; SEQ ID NO: 87), Spot-tag (PDRVRAVSHWSS; SEQ ID NO: 88), Strep-tag (WSHPQFEK; SEQ ID NO: 89), TC tag (CCPGCC; SEQ ID NO: 90), Ty tag (EVHTNQDPLD; SEQ ID NO: 91), V5 tag (GKPIPNPLLGLDST; SEQ ID NO: 92), VSV-tag (YTDIEMNRLGK; SEQ ID NO: 93), and Xpress tag (DLYDDDDK; SEQ ID NO: 94). In some embodiments, tissue factor protein is a peptide tag.

Peptide tags that can be included in a first chimeric polypeptide of a multi-chain chimeric polypeptide, a second chimeric polypeptide of the multi-chain chimeric polypeptide, or both can be used in any of a variety of applications related to the multi-chain chimeric polypeptide. For example, a peptide tag can be used in the purification of a multi-chain chimeric polypeptide. As one non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both can include a myc tag; the multi-chain chimeric polypeptide that includes the myc-tagged first chimeric polypeptide, the myc-tagged second chimeric polypeptide, or both can be purified using an antibody that recognizes the myc tag(s). One non-limiting example of an antibody that recognizes a myc tag is 9E10, available from the non-commercial Developmental Studies Hybridoma Bank. As another non-limiting example, a first chimeric polypeptide of a multi-chain chimeric polypeptide (e.g., a recombinantly expressed first chimeric polypeptide), a second chimeric polypeptide of the multi-chain chimeric polypeptide (e.g., a recombinantly expressed second chimeric polypeptide), or both can include a histidine tag; the multi-chain chimeric polypeptide that includes the histidine-tagged first chimeric polypeptide, the histidine-tagged second chimeric polypeptide, or both can be purified using a nickel or cobalt chelate. Those of ordinary skill in the art will be aware of other suitable tags and agent that bind those tags for use in purifying multi-chain chimeric polypeptide. In some embodiments, a peptide tag is removed from the first chimeric polypeptide and/or the second chimeric polypeptide of the multi-chain chimeric polypeptide after purification. In some embodiments, a peptide tag is not removed from the first chimeric polypeptide and/or the second chimeric polypeptide of the multi-chain chimeric polypeptide after purification.

Peptide tags that can be included in a first chimeric polypeptide of a multi-chain chimeric polypeptide, a second chimeric polypeptide of the multi-chain chimeric polypeptide, or both can be used, for example, in immunoprecipitation of the multi-chain chimeric polypeptide, imaging of the multi-chain chimeric polypeptide (e.g., via Western blotting, ELISA, flow cytometry, and/or immunocytochemistry), and/or solubilization of the multi-chain chimeric polypeptide.

In some embodiments, a first chimeric polypeptide of a multi-chain chimeric polypeptide, a second chimeric polypeptide of the multi-chain chimeric polypeptide, or both includes a peptide tag that is about 10 to 100 amino acids in length. For example, a peptide tag can be about 10 to 100 amino acids in length, about 15 to 100 amino acids in length, about 20 to 100 amino acids in length, about 25 to 100 amino acids in length, about 30 to 100 amino acids in length, about 35 to 100 amino acids in length, about 40 to 100 amino acids in length, about 45 to 100 amino acids in length, about 50 to 100 amino acids in length, about 55 to 100 amino acids in length, about 60 to 100 amino acids in length, about 65 to 100 amino acids in length, about 70 to 100 amino acids in length, about 75 to 100 amino acids in length, about 80 to 100 amino acids in length, about 85 to 100 amino acids in length, about 90 to 100 amino acids in length, about 95 to 100 amino acids in length, about 10 to 95 amino acids in length, about 10 to 90 amino acids in length, about 10 to 85 amino acids in length, about 10 to 80 amino acids in length, about 10 to 75 amino acids in length, about 10 to 70 amino acids in length, about 10 to 65 amino acids in length, about 10 to 60 amino acids in length, about 10 to 55 amino acids in length, about 10 to 50 amino acids in length, about 10 to 45 amino acids in length, about 10 to 40 amino acids in length, about to 35 amino acids in length, about 10 to 30 amino acids in length, about 10 to 25 amino acids in length, about 10 to 20 amino acids in length, about 10 to 15 amino acids in length, about 20 to amino acids in length, about 30 to 40 amino acids in length, about 40 to 50 amino acids in length, about 50 to 60 amino acids in length, about 60 to 70 amino acids in length, about 70 to 80 amino acids in length, about 80 to 90 amino acids in length, about 90 to 100 amino acids in length, about 20 to 90 amino acids in length, about 30 to 80 amino acids in length, about 40 to 70 amino acids in length, about 50 to 60 amino acids in length, or any range in between. In some embodiments, a peptide tag is about 10, 15, 20, 25, 30, 35, 40, 45, 50, 55, 60, 65, 70, 75, 80, 85, 90, 95, or 100 amino acids in length.

Peptide tags included in a first chimeric polypeptide of a multi-chain chimeric polypeptide, a second chimeric polypeptide of the multi-chain chimeric polypeptide, or both can be of any suitable length. For example, peptide tags can be 5, 6, 7, 8, 9, 10, 11, 12, 13, 14, 15, 16, 17, 18, 19, 20, or more amino acids in length. In embodiments in which a multi-chain chimeric polypeptide includes two or more peptide tags, the two or more peptide tags can be of the same or different lengths. In some embodiments, any of the peptide tags disclosed herein may include one or more additional amino acids (e.g., 1, 2, 3, 5, 6, 7, 8, 9, 10, or more amino acids) at the N-terminus and/or C-terminus, so long as the function of the peptide tag remains intact. For example, a myc tag having the amino acid sequence EQKLISEEDL (SEQ ID NO: 82) can include one or more additional amino acids (e.g., at the N-terminus and/or the C-terminus of the peptide tag), while still retaining the ability to be bound by an antibody (e.g., 9E10).

Exemplary Embodiments of Single-Chain Chimeric Polypeptides—Type A

In some embodiments of any of the single-chain chimeric polypeptides described herein, the first target-binding domain and/or the second target-binding domain can independently bind specifically to CD3 (e.g., human CD3) or CD28 (e.g., human CD28). In some embodiments, the first target-binding domain binds specifically to CD3 (e.g., human CD3) and the second target-binding domain binds specifically to CD28 (e.g., human CD28). In some embodiments, the first target-binding domain binds specifically to CD28 (e.g., human CD28) and the second target-binding domain binds specifically to CD3 (e.g., human CD3).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, one or both of the first target-binding domain and the second target-binding domain is an antigen-binding domain. In some embodiments of these single-chain chimeric polypeptides, the first target-binding domain and the second target-binding domain are each an antigen-binding domain (e.g., any of the exemplary antigen-binding domains described herein). In some embodiments of these single-chain chimeric polypeptides, the antigen-binding domain includes a scFv or a single domain antibody.

A non-limiting example of an scFv that binds specifically to CD3 can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 20)
QIVLTQSPAMSASPGEKVTMTCSASSSVSYMNWYQQKSGTSPKRWIYDT

SKLASGVPAHFRGSGSGTSYSLTISGMEAEDAATYYCQQWSSNPFTFGS

GTKLEINRGGGGSGGGGSGGGGSQVQLQQSGAELARPGASVKMSCKASG

YTFTRYTMHWVKQRPGQGLEWIGYINPSRGYTNYNQKFKDKATLTTDKS

SSTAYMQLSSLTSEDSAVYYCARYYDDHYCLDYWGQGTTLTVSS.
```

In some embodiments, an scFv that binds specifically to CD3 can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 12)
CAGATCGTGCTGACCCAAAGCCCCGCCATCATGAGCGCTAGCCCCGGTG

AGAAGGTGACCATGACATGCTCCGCTTCCAGCTCCGTGTCCTACATGAA

CTGGTATCAGCAGAAAAGCGGAACCAGCCCCAAAAGGTGGATCTACGAC

ACCAGCAAGCTGGCCTCCGGAGTGCCCGCTCATTTCCGGGGCTCTGGAT

CCGGCACCAGCTACTCTTTAACCATTTCCGGCATGGAAGCTGAAGACGC

TGCCACCTACTATTGCCAGCAATGGAGCAGCAACCCCTTCACATTCGGA

TCTGGCACCAAGCTCGAAATCAATCGTGGAGGAGGTGGCAGCGGCGGCG

GTGGATCCGGCGGAGGAGGAAGCCAAGTTCAACTCCAGCAGAGCGGCGC

TGAACTGGCCCGGCCCGGCGCCTCCGTCAAGATGAGCTGCAAGGCTTCC

GGCTATACATTTACTCGTTACACAATGCATTGGGTCAAGCAGAGGCCCG

GTCAAGGTTTAGAGTGGATCGGATATATCAACCCTTCCCGGGGCTACAC

CAACTATAACCAAAAGTTCAAGGATAAAGCCACTTTAACCACTGACAAG

AGCTCCTCCACCGCCTACATGCAGCTGTCCTCTTTAACCAGCGAGGACT

CCGCTGTTTACTACTGCGCTAGGTATTACGACGACCACTACTGTTTAGA

CTATTGGGGACAAGGTACCACTTTAACCGTCAGCAGC.
```

A non-limiting example of an scFv that binds specifically to CD28 can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 26)
VQLQQSGPELVKPGASVKMSCKASGYTFTSYVIQWVKQKPGQGLEWIGS

INPYNDYTKYNEKFKGKATLTSDKSSITAYMEFSSLTSEDSALYYCARW

GDGNYWGRGTTLTVSSGGGGSGGGGSGGGGSDIEMTQSPAIMSASLGER

VTMTCTASSSVSSSYFHWYQQKPGSSPKLCIYSTSNLASGVPPRFSGSG

STSYSLTISSMEAEDAATYFCHQYHRSPTFGGGTKLETKR.
```

In some embodiments, an scFv that binds specifically to CD28 can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 13)
GTCCAGCTGCAGCAGAGCGGACCCGAACTCGTGAAACCCGGTGCTTCCG

TGAAAATGTCTTGTAAGGCCAGCGGATACACCTTCACCTCCTATGTGAT

CCAGTGGGTCAAACAGAAGCCCGGACAAGGTCTCGAGTGGATCGGCAGC

ATCAACCCTTACAACGACTATACCAAATACAACGAGAAGTTTAAGGGAA

AGGCTACTTTAACCTCCGACAAAAGCTCCATCACAGCCTACATGGAGTT

CAGCTCTTTAACATCCGAGGACAGCGCTCTGTACTATTGCGCCCGGTGG

GGCGACGGCAATTACTGGGGACGGGGCACAACACTGACCGTGAGCAGCG

GAGGCGGAGGCTCCGGCGGAGGCGGATCTGGCGGTGGCGGCTCCGACAT
```

-continued

CGAGATGACCCAGTCCCCCGCTATCATGTCCGCCTCTTTAGGCGAGCGG

GTCACAATGACTTGTACAGCCTCCTCCAGCGTCTCCTCCTCCTACTTCC

ATTGGTACCAACAGAAACCCGGAAGCTCCCCTAAACTGTGCATCTACAG

CACCAGCAATCTCGCCAGCGGCGTGCCCCCTAGGTTTTCCGGAAGCGGA

AGCACCAGCTACTCTTTAACCATCTCCTCCATGGAGGCTGAGGATGCCG

CCACCTACTTTTGTCACCAGTACCACCGGTCCCCCACCTTCGGAGGCGG

CACCAAACTGGAGACAAAGAGG.

In some embodiments of these single-chain chimeric polypeptides, the first target-binding domain and/or the second target-binding domain is a soluble receptor (e.g., a soluble CD28 receptor or a soluble CD3 receptor). In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 100)

QIVLTQSPAIMSASPGEKVTMTCSASSSVSYMNWYQQKSGTSPKRWIYD

TSKLASGVPAHFRGSGSGTSYSLTISGMEAEDAATYYCQQWSSNPFTFG

SGTKLEINRGGGGSGGGGSGGGGSQVQLQQSGAELARPGASVKMSCKAS

GYTFTRYTMEIWVKQRPGQGLEWIGYINPSRGYTNYNQKFKDKATLTTD

KSSSTAYMQLSSLTSEDSAVYYCARYYDDHYCLDYWGQGTTLTVSSSGT

TNTVAAYNLTWKSTNFKTILEWEPKPVNQVYTVQISTKSGDWKSKCFYT

TDTECDLTDEIVKDVKQTYLARVFSYPAGNVESTGSAGEPLYENSPEFT

PYLETNLGQPTIQSFEQVGTKVNVTVEDERTLVRRNNTFLSLRDVFGKD

LIYTLYYWKSSSSGKKTAKTNTNEFLIDVDKGENYCFSVQAVIPSRTVN

RKSTDSPVECMGQEKGEFREVQLQQSGPELVKPGASVKMSCKASGYTFT

SYVIQWVKQKPGQGLEWIGSINPYNDYTKYNEKFKGKATLTSDKSSITA

YMEFSSLTSEDSALYYCARWGDGNYWGRGTTLTVSSGGGGSGGGGSGGG

GSDIEMTQSPAIMSASLGERVTMTCTASSSVSSSYFHWYQQKPGSSPKL

CIYSTSNLASGVPPRFSGSGSGTSYSLTISSMEAEDAATYFCHQYHRSPT

FGGGTKLETKR.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 101)

CAGATCGTGCTGACCCAAAGCCCCGCCATCATGAGCGCTAGCCCCGGTG

AGAAGGTGACCATGACATGCTCCGCTTCCAGCTCCGTGTCCTACATGAA

-continued

CTGGTATCAGCAGAAAAGCGGAACCAGCCCCAAAAGGTGGATCTACGAC

ACCAGCAAGCTGGCCTCCGGAGTGCCCGCTCATTTCCGGGGCTCTGGAT

CCGGCACCAGCTACTCTTTAACCATTTCCGGCATGGAAGCTGAAGACGC

TGCCACCTACTATTGCCAGCAATGGAGCAGCAACCCCTTCACATTCGGA

TCTGGCACCAAGCTCGAAATCAATCGTGGAGGAGGTGGCAGCGGCGGCG

GTGGATCCGGCGGAGGAGGAAGCCAAGTTCAACTCCAGCAGAGCGGCGC

TGAACTGGCCCGGCCCGGCGCCTCCGTCAAGATGAGCTGCAAGGCTTCC

GGCTATACATTTACTCGTTACACAATGCATTGGGTCAAGCAGAGGCCCG

GTCAAGGTTTAGAGTGGATCGGATATATCAACCCTTCCCGGGGCTACAC

CAACTATAACCAAAAGTTCAAGGATAAAGCCACTTTAACCACTGACAAG

AGCTCCTCCACCGCCTACATGCAGCTGTCCTCTTTAACCAGCGAGGACT

CCGCTGTTTACTACTGCGCTAGGTATTACGACGACCACTACTGTTTAGA

CTATTGGGGACAAGGTACCACTTTAACCGTCAGCAGCTCCGGCACCACC

AATACCGTGGCCGCTTATAACCTCACATGGAAGAGCACCAACTTCAAGA

CAATTCTGGAATGGGAACCCAAGCCCGTCAATCAAGTTTACACCGTGCA

GATCTCCACCAAATCCGGAGACTGGAAGAGCAAGTGCTTCTACACAACA

GACACCGAGTGTGATTTAACCGACGAAATCGTCAAGGACGTCAAGCAAA

CCTATCTGGCTCGGGTCTTTTCCTACCCCGCTGGCAATGTCGAGTCCAC

CGGCTCCGCTGGCGAGCCTCTCTACGAGAATTCCCCCGAATTCACCCCT

TATTTAGAGACCAATTTAGGCCAGCCTACCATCCAGAGCTTCGAGCAAG

TTGGCACCAAGGTGAACGTCACCGTCGAGGATGAAAGGACTTTAGTGCG

GCGGAATAACACATTTTTATCCCTCCGGGATGTGTTCGGCAAAGACCTC

ATCTACACACTGTACTATTGGAAGTCCAGCTCCTCCGGCAAAAAGACCG

CTAAGACCAACACCAACGAGTTTTTAATTGACGTGGACAAAGGCGAGAA

CTACTGCTTCAGCGTGCAAGCCGTGATCCCTTCTCGTACCGTCAACCGG

AAGAGCACAGATTCCCCCGTTGAGTGCATGGGCCAAGAAAAGGGCGAGT

TCCGGGAGGTCCAGCTGCAGCAGAGCGGACCCGAACTCGTGAAACCCGG

TGCTTCCGTGAAAATGTCTTGTAAGGCCAGCGGATACACCTTCACCTCC

TATGTGATCCAGTGGGTCAAACAGAAGCCCGGACAAGGTCTCGAGTGGA

TCGGCAGCATCAACCCTTACAACGACTATACCAAATACAACGAGAAGTT

TAAGGGAAAGGCTACTTTAACCTCCGACAAAAGCTCCATCACAGCCTAC

ATGGAGTTCAGCTCTTTAACATCCGAGGACAGCGCTCTGTACTATTGCG

CCCGGTGGGGCGACGGCAATTACTGGGGACGGGGCACAACACTGACCGT

GAGCAGCGGAGGCGGAGGCTCCGGCGGAGGCGGATCTGGCGGTGGCGGC

TCCGACATCGAGATGACCCAGTCCCCCGCTATCATGTCCGCCTCTTTAG

GCGAGCGGGTCACAATGACTTGTACAGCCTCCTCCAGCGTCTCCTCCTC

CTACTTCCATTGGTACCAACAGAAACCCGGAAGCTCCCCTAAACTGTGC

ATCTACAGCACCAGCAATCTCGCCAGCGGCGTGCCCCCTAGGTTTTCCG

GAAGCGGAAGCACCAGCTACTCTTTAACCATCTCCTCCATGGAGGCTGA

GGATGCCGCCACCTACTTTTGTCACCAGTACCACCGGTCCCCCACCTTC

GGAGGCGGCACCAAACTGGAGACAAAGAGG.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 102)

MKWVTFISLLFLFSSAYSQIVLTQSPAIMSASPGEKVTMTCSASSSVSY

MNWYQQKSGTSPKRWIYDTSKLASGVPAHFRGSGSGTSYSLTISGMEAE

DAATYYCQQWSSNPFTFGSGTKLEINRGGGGSGGGGSGGGGSQVQLQQS

GAELARPGASVKMSCKASGYTFTRYTMHWVKQRPGQGLEWIGYINPSRG

YTNYNQKFKDKATLTTDKSSSTAYMQLSSLTSEDSAVYYCARYYDDHYC

LDYWGQGTTLTVSSSGTTNTVAAYNLTWKSTNFKTILEWEPKPVNQVYT

VQISTKSGDWKSKCFYTTDTECDLTDEIVKDVKQTYLARVFSYPAGNVE

STGSAGEPLYENSPEFTPYLETNLGQPTIQSFEQVGTKVNVTVEDERTL

VRRNNTFLSLRDVFGKDLIYTLYYWKSSSSGKKTAKTNTNEFLIDVDKG

ENYCFSVQAVIPSRTVNRKSTDSPVECMGQEKGEFREVQLQQSGPELVK

PGASVKMSCKASGYTFTSYVIQWVKQKPGQGLEWIGSINPYNDYTKYNE

KFKGKATLTSDKSSITAYMEFSSLTSEDSALYYCARWGDGNYWGRGTTL

TVSSGGGGSGGGGSGGGGSDIEMTQSPAIMSASLGERVTMTCTASSSVS

SSYFHWYQQKPGSSPKLCIYSTSNLASGVPPRFSGSGSTSYSLTISSME

AEDAATYFCHQYHRSPTFGGGTKLETKR.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 103)

ATGAAGTGGGTGACCTTCATCAGCTTATTATTTTTATTCAGCTCCGCCT

ATTCCCAGATCGTGCTGACCCAAAGCCCCGCCATCATGAGCGCTAGCCC

CGGTGAGAAGGTGACCATGACATGCTCCGCTTCCAGCTCCGTGTCCTAC

ATGAACTGGTATCAGCAGAAAAGCGGAACCAGCCCCAAAAGGTGGATCT

ACGACACCAGCAAGCTGGCCTCCGGAGTGCCCGCTCATTTCCGGGGCTC

TGGATCCGGCACCAGCTACTCTTTAACCATTTCCGGCATGGAAGCTGAA

GACGCTGCCACCTACTATTGCCAGCAATGGAGCAGCAACCCCTTCACAT

TCGGATCTGGCACCAAGCTCGAAATCAATCGTGGAGGAGGTGGCAGCGG

CGGCGGTGGATCCGGCGGAGGAGGAAGCCAAGTTCAACTCCAGCAGAGC

GGCGCTGAACTGGCCCGGCCCGGCGCCTCCGTCAAGATGAGCTGCAAGG

CTTCCGGCTATACATTTACTCGTTACACAATGCATTGGGTCAAGCAGAG

GCCCGGTCAAGGTTTAGAGTGGATCGGATATATCAACCCTTCCCGGGGC

TACACCAACTATAACCAAAAGTTCAAGGATAAAGCCACTTTAACCACTG

ACAAGAGCTCCTCCACCGCCTACATGCAGCTGTCCTCTTTAACCAGCGA

-continued

GGACTCCGCTGTTTACTACTGCGCTAGGTATTACGACGACCACTACTGT

TTAGACTATTGGGGACAAGGTACCACTTTAACCGTCAGCAGCTCCGGCA

CCACCAATACCGTGGCCGCTTATAACCTCACATGGAAGAGCACCAACTT

CAAGACAATTCTGGAATGGGAACCCAAGCCCGTCAATCAAGTTTACACC

GTGCAGATCTCCACCAAATCCGGAGACTGGAAGAGCAAGTGCTTCTACA

CAACAGACACCGAGTGTGATTTAACCGACGAAATCGTCAAGGACGTCAA

GCAAACCTATCTGGCTCGGGTCTTTTCCTACCCCGCTGGCAATGTCGAG

TCCACCGGCTCCGCTGGCGAGCCTCTCTACGAGAATTCCCCCGAATTCA

CCCCTTATTTAGAGACCAATTTAGGCCAGCCTACCATCCAGAGCTTCGA

GCAAGTTGGCACCAAGGTGAACGTCACCGTCGAGGATGAAAGGACTTTA

GTGCGGCGGAATAACACATTTTTATCCCTCCGGGATGTGTTCGGCAAAG

ACCTCATCTACACACTGTACTATTGGAAGTCCAGCTCCTCCGGCAAAAA

GACCGCTAAGACCAACACCAACGAGTTTTTAATTGACGTGGACAAAGGC

GAGAACTACTGCTTCAGCGTGCAAGCCGTGATCCCTTCTCGTACCGTCA

ACCGGAAGAGCACAGATTCCCCCGTTGAGTGCATGGGCCAAGAAAAGGG

CGAGTTCCGGGAGGTCCAGCTGCAGCAGAGCGGACCCGAACTCGTGAAA

CCCGGTGCTTCCGTGAAAATGTCTTGTAAGGCCAGCGGATACACCTTCA

CCTCCTATGTGATCCAGTGGGTCAAACAGAAGCCCGGACAAGGTCTCGA

GTGGATCGGCAGCATCAACCCTTACAACGACTATACCAAATACAACGAG

AAGTTTAAGGGAAAGGCTACTTTAACCTCCGACAAAAGCTCCATCACAG

CCTACATGGAGTTCAGCTCTTTAACATCCGAGGACAGCGCTCTGTACTA

TTGCGCCCGGTGGGGCGACGGCAATTACTGGGGACGGGGCACAACACTG

ACCGTGAGCAGCGGAGGCGGAGGCTCCGGCGGAGGCGGATCTGGCGGTG

GCGGCTCCGACATCGAGATGACCCAGTCCCCCGCTATCATGTCCGCCTC

TTTAGGCGAGCGGGTCACAATGACTTGTACAGCCTCCTCCAGCGTCTCC

TCCTCCTACTTCCATTGGTACCAACAGAAACCCGGAAGCTCCCCTAAAC

TGTGCATCTACAGCACCAGCAATCTCGCCAGCGGCGTGCCCCCTAGGTT

TTCCGGAAGCGGAAGCACCAGCTACTCTTTAACCATCTCCTCCATGGAG

GCTGAGGATGCCGCCACCTACTTTTGTCACCAGTACCACCGGTCCCCCA

CCTTCGGAGGCGGCACCAAACTGGAGACAAAGAGG.

Exemplary Embodiments of Single-Chain Chimeric Polypeptides—Type B

In some embodiments of any of the single-chain chimeric polypeptides described herein, the first target-binding domain and/or the second target-binding domain can independently bind specifically to an IL-2 receptor (e.g., human IL-2 receptor).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, the first target-binding domain and the second target-binding domain is a soluble human IL-2 protein. A non-limiting example of an IL-2 protein that binds specifically to an IL-2 receptor can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 28)
APTSSSTKKTQLQLEHLLLDLQMILNGINNYKNPKLTRMLTFKFYMPKK
ATELKHLQCLEEELKPLEEVLNLAQSKNFHLRPRDLISNINVIVLELKG
SETTFMCEYADETATIVEFLNRWITFCQSIISTLT.

In some embodiments, an IL-2 protein that binds specifically to an IL-2 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 104)
GCACCTACTTCAAGTTCTACAAAGAAAACACAGCTACAACTGGAGCATT
TACTGCTGGATTTACAGATGATTTTGAATGGAATTAATAATTACAAGAA
TCCCAAACTCACCAGGATGCTCACATTTAAGTTTTACATGCCCAAGAAG
GCCACAGAACTGAAACATCTTCAGTGTCTAGAAGAAGAACTCAAACCTC
TGGAGGAAGTGCTAAATTTAGCTCAAAGCAAAAACTTTCACTTAAGACC
CAGGGACTTAATCAGCAATATCAACGTAATAGTTCTGGAACTAAAGGGA
TCTGAAACAACATTCATGTGTGAATATGCTGATGAGACAGCAACCATTG
TAGAATTTCTGAACAGATGGATTACCTTTTGTCAAAGCATCATCTCAAC
ACTAACT.

In some embodiments, an IL-2 protein that binds specifically to an IL-2 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 105)
GCCCCCACCTCCTCCTCCACCAAGAAGACCCAGCTGCAGCTGGAGCATT
TACTGCTGGATTTACAGATGATTTTAAACGGCATCAACAACTACAAGAA
CCCCAAGCTGACTCGTATGCTGACCTTCAAGTTCTACATGCCCAAGAAG
GCCACCGAGCTGAAGCATTTACAGTGTTTAGAGGAGGAGCTGAAGCCCC
TCGAGGAGGTGCTGAATTTAGCCCAGTCCAAGAATTTCCATTTAAGGCC
CCGGGATTTAATCAGCAACATCAACGTGATCGTTTTAGAGCTGAAGGGC

-continued

TCCGAGACCACCTTCATGTGCGAGTACGCCGACGAGACCGCCACCATCG
TGGAGTTTTTAAATCGTTGGATCACCTTCTGCCAGTCCATCATCTCCAC
TTTAACC

In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 106)
APTSSSTKKTQLQLEHLLLDLQMILNGINNYKNPKLTRMLTFKFYMPKK
ATELKHLQCLEEELKPLEEVLNLAQSKNFHLRPRDLISNINVIVLELKG
SETTFMCEYADETATIVEFLNRWITFCQSIISTLTSGTTNTVAAYNLTW
KSTNFKTILEWEPKPVNQVYTVQISTKSGDWKSKCFYTTDTECDLTDEI
VKDVKQTYLARVFSYPAGNVESTGSAGEPLYENSPEFTPYLETNLGQPT
IQSFEQVGTKVNVTVEDERTLVRRNNTFLSLRDVFGKDLIYTLYYWKSS
SSGKKTAKTNTNEFLIDVDKGENYCFSVQAVIPSRTVNRKSTDSPVECM
GQEKGEFREAPTSSSTKKTQLQLEHLLLDLQMILNGINNYKNPKLTRML
TFKFYMPKKATELKHLQCLEEELKPLEEVLNLAQSKNFHLRPRDLISNI
NVIVLELKGSETTFMCEYADETATIVEFLNRWITFCQSIISTLT.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 107)
GCCCCCACCTCCTCCTCCACCAAGAAGACCCAGCTGCAGCTGGAGCATT
TACTGCTGGATTTACAGATGATTTTAAACGGCATCAACAACTACAAGAA
CCCCAAGCTGACTCGTATGCTGACCTTCAAGTTCTACATGCCCAAGAAG
GCCACCGAGCTGAAGCATTTACAGTGTTTAGAGGAGGAGCTGAAGCCCC
TCGAGGAGGTGCTGAATTTAGCCCAGTCCAAGAATTTCCATTTAAGGCC
CCGGGATTTAATCAGCAACATCAACGTGATCGTTTTAGAGCTGAAGGGC
TCCGAGACCACCTTCATGTGCGAGTACGCCGACGAGACCGCCACCATCG
TGGAGTTTTTAAATCGTTGGATCACCTTCTGCCAGTCCATCATCTCCAC
TTTAACCAGCGGCACAACCAACACAGTCGCTGCCTATAACCTCACTTGG
AAGAGCACCAACTTCAAAACCATCCTCGAATGGGAACCCAAACCCGTTA
ACCAAGTTTACACCGTGCAGATCAGCACCAAGTCCGGCGACTGGAAGTC
CAAATGTTTCTATACCACCGACACCGAGTGCGATCTCACCGATGAGATC
GTGAAAGATGTGAAACAGACCTACCTCGCCCGGGTGTTTAGCTACCCCG

-continued

```
CCGGCAATGTGGAGAGCACTGGTTCCGCTGGCGAGCCTTTATACGAGAA
CAGCCCCGAATTTACCCCTTACCTCGAGACCAATTTAGGACAGCCCACC
ATCCAAAGCTTTGAGCAAGTTGGCACAAAGGTGAATGTGACAGTGGAGG
ACGAGCGGACTTTAGTGCGGCGGAACAACACCTTTCTCAGCCTCCGGGA
TGTGTTCGGCAAAGATTTAATCTACACACTGTATTACTGGAAGTCCTCT
TCCTCCGGCAAGAAGACAGCTAAAACCAACACAAACGAGTTTTTAATCG
ACGTGGATAAAGGCGAAAACTACTGTTTCAGCGTGCAAGCTGTGATCCC
CTCCCGGACCGTGAATAGGAAAAGCACCGATAGCCCCGTTGAGTGCATG
GGCCAAGAAAAGGGCGAGTTCCGGGAGGCACCTACTTCAAGTTCTACAA
AGAAAACACAGCTACAACTGGAGCATTTACTGCTGGATTTACAGATGAT
TTTGAATGGAATTAATAATTACAAGAATCCCAAACTCACCAGGATGCTC
ACATTTAAGTTTTACATGCCCAAGAAGGCCACAGAACTGAAACATCTTC
AGTGTCTAGAAGAAGAACTCAAACCTCTGGAGGAAGTGCTAAATTTAGC
TCAAAGCAAAAACTTTCACTTAAGACCCAGGGACTTAATCAGCAATATC
AACGTAATAGTTCTGGAACTAAAGGGATCTGAAACAACATTCATGTGTG
AATATGCTGATGAGACAGCAACCATTGTAGAATTTCTGAACAGATGGAT
TACCTTTTGTCAAAGCATCATCTCAACACTAACT.
```

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 108)
MKWVTFISLLFLFSSAYSAPTSSSTKKTQLQLEHLLLDLQMILNGINNY
KNPKLTRMLTFKFYMPKKATELKHLQCLEEELKPLEEVLNLAQSKNFHL
RPRDLISNINVIVLELKGSETTFMCEYADETATIVEFLNRWITFCQSII
STLTSGTTNTVAAYNLTWKSTNFKTILEWEPKPVNQVYTVQISTKSGDW
KSKCFYTTDTECDLTDEIVKDVKQTYLARVFSYPAGNVESTGSAGEPLY
ENSPEFTPYLETNLGQPTIQSFEQVGTKVNVTVEDERTLVRRNNTFLSL
RDVFGKDLIYTLYYWKSSSSGKKTAKTNTNEFLIDVDKGENYCFSVQAV
IPSRTVNRKSTDSPVECMGQEKGEFREAPTSSSTKKTQLQLEHLLLDLQ
MILNGINNYKNPKLTRMLTFKFYMPKKATELKHLQCLEEELKPLEEVLN
LAQSKNFHLRPRDLISNINVIVLELKGSETTFMCEYADETATIVEFLNR
WITFCQSIISTLT.
```

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                            (SEQ ID NO: 109)
ATGAAGTGGGTGACCTTCATCAGCCTGCTGTTCCTGTTCTCCAGCGCCT
ACTCCGCCCCCACCTCCTCCTCCACCAAGAAGACCCAGCTGCAGCTGGA
GCATTTACTGCTGGATTTACAGATGATTTTAAACGGCATCAACAACTAC
AAGAACCCCAAGCTGACTCGTATGCTGACCTTCAAGTTCTACATGCCCA
AGAAGGCCACCGAGCTGAAGCATTTACAGTGTTTAGAGGAGGAGCTGAA
GCCCCTCGAGGAGGTGCTGAATTTAGCCCAGTCCAAGAATTTCCATTTA
AGGCCCCGGGATTTAATCAGCAACATCAACGTGATCGTTTTAGAGCTGA
AGGGCTCCGAGACCACCTTCATGTGCGAGTACGCCGACGAGACCGCCAC
CATCGTGGAGTTTTTAAATCGTTGGATCACCTTCTGCCAGTCCATCATC
TCCACTTTAACCAGCGGCACAACCAACACAGTCGCTGCCTATAACCTCA
CTTGGAAGAGCACCAACTTCAAAACCATCCTCGAATGGGAACCCAAACC
CGTTAACCAAGTTTACACCGTGCAGATCAGCACCAAGTCCGGCGACTGG
AAGTCCAAATGTTTCTATACCACCGACACCGAGTGCGATCTCACCGATG
AGATCGTGAAAGATGTGAAACAGACCTACCTCGCCCGGGTGTTTAGCTA
CCCCGCCGGCAATGTGGAGAGCACTGGTTCCGCTGGCGAGCCTTTATAC
GAGAACAGCCCCGAATTTACCCCTTACCTCGAGACCAATTTAGGACAGC
CCACCATCCAAAGCTTTGAGCAAGTTGGCACAAAGGTGAATGTGACAGT
GGAGGACGAGCGGACTTTAGTGCGGCGGAACAACACCTTTCTCAGCCTC
CGGGATGTGTTCGGCAAAGATTTAATCTACACACTGTATTACTGGAAGT
CCTCTTCCTCCGGCAAGAAGACAGCTAAAACCAACACAAACGAGTTTTT
AATCGACGTGGATAAAGGCGAAAACTACTGTTTCAGCGTGCAAGCTGTG
ATCCCCTCCCGGACCGTGAATAGGAAAAGCACCGATAGCCCCGTTGAGT
GCATGGGCCAAGAAAAGGGCGAGTTCCGGGAGGCACCTACTTCAAGTTC
TACAAAGAAAACACAGCTACAACTGGAGCATTTACTGCTGGATTTACAG
ATGATTTTGAATGGAATTAATAATTACAAGAATCCCAAACTCACCAGGA
TGCTCACATTTAAGTTTTACATGCCCAAGAAGGCCACAGAACTGAAACA
TCTTCAGTGTCTAGAAGAAGAACTCAAACCTCTGGAGGAAGTGCTAAAT
TTAGCTCAAAGCAAAAACTTTCACTTAAGACCCAGGGACTTAATCAGCA
ATATCAACGTAATAGTTCTGGAACTAAAGGGATCTGAAACAACATTCAT
GTGTGAATATGCTGATGAGACAGCAACCATTGTAGAATTTCTGAACAGA
TGGATTACCTTTTGTCAAAGCATCATCTCAACACTAACT.
```

Exemplary Embodiments of Single-Chain Chimeric Polypeptides—Type C

In some embodiments of any of the single-chain chimeric polypeptides described herein, the first target-binding domain and/or the second target-binding domain can independently bind specifically to an IL-15 receptor (e.g., a human IL-15 receptor).

In some embodiments of these single-chain chimeric polypeptides, the first target-binding domain and the soluble tissue factor domain directly abut each other. In some embodiments of these single-chain chimeric polypeptides, the single-chain chimeric polypeptide further includes a linker sequence (e.g., any of the exemplary linkers described herein) between the first target-binding domain and the soluble tissue factor domain.

In some embodiments of these single-chain chimeric polypeptides, the soluble tissue factor domain and the second target-binding domain directly abut each other. In some embodiments of these single-chain chimeric polypeptides, the single-chain chimeric polypeptide further includes a linker sequence (e.g., any of the exemplary linkers described herein) between the soluble tissue factor domain and the second target-binding domain.

In some embodiments of these single-chain chimeric polypeptides, the first target-binding domain and the second target-binding domain is a soluble human IL-15 protein. A non-limiting example of an IL-15 protein that binds specifically to an IL-15 receptor can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical)

```
                                          (SEQ ID NO: 39)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS.
```

In some embodiments, an IL-15 protein that binds specifically to an IL-15 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 111)
AACTGGGTGAACGTGATCAGCGATTTAAAGAAGATCGAGGATTTAATCC

AGAGCATGCACATCGACGCCACTCTGTACACTGAGAGCGACGTGCACCC

TAGCTGCAAGGTGACTGCCATGAAGTGCTTTTTACTGGAGCTGCAAGTT

ATCTCTTTAGAGAGCGGCGATGCCAGCATCCACGACACTGTGGAGAATT

TAATCATTTTAGCCAACAACTCTTTAAGCAGCAACGGCAACGTGACAGA

GAGCGGCTGCAAGGAGTGCGAGGAGCTGGAGGAGAAGAACATCAAGGAG

TTTTTACAGAGCTTCGTGCACATCGTGCAGATGTTCATCAACACTAGC.
```

In some embodiments, an IL-15 protein that binds specifically to an IL-15 receptor can be encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 110)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA
```

-continued

```
GTCCGGCTGCAAGGAGTGCGAAGAGCTGGAGGAGAAGAACATCAAGGAG

TTTCTGCAATCCTTTGTGCACATTGTCCAGATGTTCATCAATACCTCC.
```

In some embodiments of these single-chain chimeric polypeptides, the soluble tissue factor domain can be any of the exemplary soluble tissue factor domains described herein.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 112)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTSSGTTNTVAAYNLTWKSTNFKTILEWEPKPVNQV

YTVQISTKSGDWKSKCFYTTDTECDLTDEIVKDVKQTYLARVFSYPAGN

VESTGSAGEPLYENSPEFTPYLETNLGQPTIQSFEQVGTKVNVTVEDER

TLVRRNNTFLSLRDVFGKDLIYTLYYWKSSSSGKKTAKTNTNEFLIDVD

KGENYCFSVQAVIPSRTVNRKSTDSPVECMGQEKGEFRENWVNVISDLK

KIEDLIQSMHIDATLYTESDVHPSCKVTAMKCFLLELQVISLESGDASI

HDTVENLIILANNSLSSNGNVTESGCKECEELEEKNIKEFLQSFVHIVQ

MFINTS.
```

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 113)
AACTGGGTGAACGTGATCAGCGATTTAAAGAAGATCGAGGATTTAATCC

AGAGCATGCACATCGACGCCACTCTGTACACTGAGAGCGACGTGCACCC

TAGCTGCAAGGTGACTGCCATGAAGTGCTTTTTACTGGAGCTGCAAGTT

ATCTCTTTAGAGAGCGGCGATGCCAGCATCCACGACACTGTGGAGAATT

TAATCATTTTAGCCAACAACTCTTTAAGCAGCAACGGCAACGTGACAGA

GAGCGGCTGCAAGGAGTGCGAGGAGCTGGAGGAGAAGAACATCAAGGAG

TTTTTACAGAGCTTCGTGCACATCGTGCAGATGTTCATCAACACTAGCA

GCGGCACAACCAACACAGTCGCTGCCTATAACCTCACTTGGAAGAGCAC

CAACTTCAAAACCATCCTCGAATGGGAACCCAAACCCGTTAACCAAGTT

TACACCGTGCAGATCAGCACCAAGTCCGGCGACTGGAAGTCCAAATGTT

TCTATACCACCGACACCGAGTGCGATCTCACCGATGAGATCGTGAAAGA

TGTGAAACAGACCTACCTCGCCCGGGTGTTTAGCTACCCCGCCGGCAAT

GTGGAGAGCACTGGTTCCGCTGGCGAGCCTTTATACGAGAACAGCCCCG

AATTTACCCCTTACCTCGAGACCAATTTAGGACAGCCCACCATCCAAAG
```

-continued

CTTTGAGCAAGTTGGCACAAAGGTGAATGTGACAGTGGAGGACGAGCGG
ACTTTAGTGCGGCGGAACAACACCTTTCTCAGCCTCCGGGATGTGTTCG
GCAAAGATTTAATCTACACACTGTATTACTGGAAGTCCTCTTCCTCCGG
CAAGAAGACAGCTAAAACCAACACAAACGAGTTTTTAATCGACGTGGAT
AAAGGCGAAAACTACTGTTTCAGCGTGCAAGCTGTGATCCCCTCCCGGA
CCGTGAATAGGAAAAGCACCGATAGCCCCGTTGAGTGCATGGGCCAAGA
AAAGGGCGAGTTCCGGGAGAACTGGGTGAACGTCATCAGCGATTTAAAG
AAGATCGAAGATTTAATTCAGTCCATGCATATCGACGCCACTTTATACA
CAGAATCCGACGTGCACCCCTCTTGTAAGGTGACCGCCATGAAATGTTT
TTTACTGGAGCTGCAAGTTATCTCTTTAGAGAGCGGAGACGCTAGCATC
CACGACACCGTGGAGAATTTAATCATTTTAGCCAATAACTCTTTATCCA
GCAACGGCAACGTGACAGAGTCCGGCTGCAAGGAGTGCGAAGAGCTGGA
GGAGAAGAACATCAAGGAGTTTCTGCAATCCTTTGTGCACATTGTCCAG
ATGTTCATCAATACCTCC.

In some embodiments, a single-chain chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 114)
MKWVTFISLLFLFSSAYSNWVNVISDLKKIEDLIQSMHIDATLYTESDV
HPSCKVTAMKCFLLELQVISLESGDASIHDTVENLIILANNSLSSNGNV
TESGCKECEELEEKNIKEFLQSFVHIVQMFINTSSGTTNTVAAYNLTWK
STNFKTILEWEPKPVNQVYTVQISTKSGDWKSKCFYTTDTECDLTDEIV
KDVKQTYLARVFSYPAGNVESTGSAGEPLYENSPEFTPYLETNLGQPTI
QSFEQVGTKVNVTVEDERTLVRRNNTFLSLRDVFGKDLIYTLYYWKSSS
SGKKTAKTNTNEFLIDVDKGENYCFSVQAVIPSRTVNRKSTDSPVECMG
QEKGEFRENWVNVISDLKKIEDLIQSMHIDATLYTESDVHPSCKVTAMK
CFLLELQVISLESGDASIHDTVENLIILANNSLSSNGNVTESGCKECEE
LEEKNIKEFLQSFVHIVQMFINTS.

In some embodiments, a single-chain chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 115)
ATGAAGTGGGTGACCTTCATCAGCCTGCTGTTCCTGTTCTCCAGCGCCT
ACTCCAACTGGGTGAACGTGATCAGCGATTTAAAGAAGATCGAGGATTT
AATCCAGAGCATGCACATCGACGCCACTCTGTACACTGAGAGCGACGTG
CACCCTAGCTGCAAGGTGACTGCCATGAAGTGCTTTTTACTGGAGCTGC

-continued

AAGTTATCTCTTTAGAGAGCGGCGATGCCAGCATCCACGACACTGTGGA
GAATTTAATCATTTTAGCCAACAACTCTTTAAGCAGCAACGGCAACGTG
ACAGAGAGCGGCTGCAAGGAGTGCGAGGAGCTGGAGGAGAAGAACATCA
AGGAGTTTTTACAGAGCTTCGTGCACATCGTGCAGATGTTCATCAACAC
TAGCAGCGGCACAACCAACACAGTCGCTGCCTATAACCTCACTTGGAAG
AGCACCAACTTCAAAACCATCCTCGAATGGGAACCCAAACCCGTTAACC
AAGTTTACACCGTGCAGATCAGCACCAAGTCCGGCGACTGGAAGTCCAA
ATGTTTCTATACCACCGACACCGAGTGCGATCTCACCGATGAGATCGTG
AAAGATGTGAAACAGACCTACCTCGCCCGGGTGTTTAGCTACCCCGCCG
GCAATGTGGAGAGCACTGGTTCCGCTGGCGAGCCTTTATACGAGAACAG
CCCCGAATTTACCCCTTACCTCGAGACCAATTTAGGACAGCCCACCATC
CAAAGCTTTGAGCAAGTTGGCACAAAGGTGAATGTGACAGTGGAGGACG
AGCGGACTTTAGTGCGGCGGAACAACACCTTTCTCAGCCTCCGGGATGT
GTTCGGCAAAGATTTAATCTACACACTGTATTACTGGAAGTCCTCTTCC
TCCGGCAAGAAGACAGCTAAAACCAACACAAACGAGTTTTTAATCGACG
TGGATAAAGGCGAAAACTACTGTTTCAGCGTGCAAGCTGTGATCCCCTC
CCGGACCGTGAATAGGAAAAGCACCGATAGCCCCGTTGAGTGCATGGGC
CAAGAAAAGGGCGAGTTCCGGGAGAACTGGGTGAACGTCATCAGCGATT
TAAAGAAGATCGAAGATTTAATTCAGTCCATGCATATCGACGCCACTTT
ATACACAGAATCCGACGTGCACCCCTCTTGTAAGGTGACCGCCATGAAA
TGTTTTTTACTGGAGCTGCAAGTTATCTCTTTAGAGAGCGGAGACGCTA
GCATCCACGACACCGTGGAGAATTTAATCATTTTAGCCAATAACTCTTT
ATCCAGCAACGGCAACGTGACAGAGTCCGGCTGCAAGGAGTGCGAAGAG
CTGGAGGAGAAGAACATCAAGGAGTTTCTGCAATCCTTTGTGCACATTG
TCCAGATGTTCATCAATACCTCC.

Exemplary Multi-Chain Chimeric Polypeptides—Type A

In some embodiments of any of the multi-chain chimeric polypeptides described herein, the first target-binding domain and the second targeting-binding domain each independently bind specifically to a receptor of IL-18 or a receptor of IL-12. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is an agonistic antigen-binding domain. In some embodiments of these multi-chain chimeric polypeptides, the first target-binding domain and the second target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12.

In some embodiments of these multi-chain chimeric polypeptides, the first target-binding domain includes a soluble IL-18 (e.g., a soluble human IL-18).

In some embodiments of these multi-chain chimeric polypeptides, the soluble human IL-18 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 41)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNED.
```

In some embodiments of these multi-chain chimeric polypeptides, the soluble human IL-18 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 42)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT.
```

In some embodiments of these multi-chain chimeric polypeptides, the second target-binding domain includes a soluble IL-12 (e.g., a soluble human IL-12). In some embodiments of these multi-chain chimeric polypeptides, the soluble human IL-12 includes a sequence of soluble human IL-12β (p40) and a sequence of soluble human IL-12α (p35). In some embodiments of these multi-chain chimeric polypeptides, the soluble human IL-12 further includes a linker sequence (e.g., any of the exemplary linker sequences described herein) between the sequence of soluble IL-12β (p40) and the sequence of soluble human IL-12α (p35). In some examples of these multi-chain chimeric polypeptides, the linker sequence comprises

```
                                 (SEQ ID NO: 7)
GGGGSGGGGSGGGGS.
```

In some embodiments of these multi-chain chimeric polypeptides, the sequence of soluble human IL-12β (p40) comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 33)
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS.
```

In some embodiments of these multi-chain chimeric polypeptides, the soluble human IL-12P (p40) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 34)
ATTTGGGAACTGAAGAAGGACGTCTACGTGGTCGAACTGGACTGGTATC
CCGATGCTCCCGGCGAAATGGTGGTGCTCACTTGTGACACCCCCGAAGA
AGACGGCATCACTTGGACCCTCGATCAGAGCAGCGAGGTGCTGGGCTCC
GGAAAGACCCTCACAATCCAAGTTAAGGAGTTCGGAGACGCTGGCCAAT
ACACATGCCACAAGGGAGGCGAGGTGCTCAGCCATTCCTTATTATTATT
ACACAAGAAGGAAGACGGAATCTGGTCCACCGACATTTTAAAAGATCAG
AAGGAGCCCAAGAATAAGACCTTTTTAAGGTGTGAGGCCAAAAACTACA
GCGGTCGTTTCACTTGTTGGTGGCTGACCACCATTTCCACCGATTTAAC
CTTCTCCGTGAAAAGCAGCCGGGGAAGCTCCGACCCTCAAGGTGTGACA
TGTGGAGCCGCTACCCTCAGCGCTGAGAGGGTTCGTGGCGATAACAAGG
AATACGAGTACAGCGTGGAGTGCCAAGAAGATAGCGCTTGTCCCGCTGC
CGAAGAATCTTTACCCATTGAGGTGATGGTGGACGCCGTGCACAAACTC
AAGTACGAGAACTACACCTCCTCCTTCTTTATCCGGGACATCATTAAGC
CCGATCCTCCTAAGAATTTACAGCTGAAGCCTCTCAAAAATAGCCGGCA
AGTTGAGGTCTCTTGGGAATATCCCGACACTTGGAGCACACCCCACAGC
TACTTCTCTTTAACCTTTTGTGTGCAAGTTCAAGGTAAAAGCAAGCGGG
AGAAGAAAGACCGGGTGTTTACCGACAAAACCAGCGCCACCGTCATCTG
TCGGAAGAACGCCTCCATCAGCGTGAGGGCTCAAGATCGTTATTACTCC
AGCAGCTGGTCCGAGTGGGCCAGCGTGCCTTGTTCC.

In some embodiments of these multi-chain chimeric polypeptides, the soluble human IL-12a (p35) includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 35)
RNLPVATPDPGMFPCLEMSQNLLRAVSNMLQKARQTLEFYPCTSEEIDH
EDITKDKTSTVEACLPLELTKNESCLNSRETSFITNGSCLASRKTSFMM
ALCLSSIYEDLKMYQVEFKTMNAKLLMDPKRQIFLDQNMLAVIDELMQA
LNFNSETVPQKSSLEEPDFYKTKIKLCILLHAFRIRAVTIDRVMSYLNA
S.

In some embodiments of these multi-chain chimeric polypeptides, the soluble human IL-12α (p35) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 36)
CGTAACCTCCCCGTGGCTACCCCCGATCCCGGAATGTTCCCTTGTTTAC
ACCACAGCCAGAATTTACTGAGGGCCGTGAGCAACATGCTGCAGAAAGC
TAGGCAGACTTTAGAATTTTACCCTTGCACCAGCGAGGAGATCGACCAT

-continued

GAAGATATCACCAAGGACAAGACATCCACCGTGGAGGCTTGTTTACCTC
TGGAGCTGACAAAGAACGAGTCTTGTCTCAACTCTCGTGAAACCAGCTT
CATCACAAATGGCTCTTGTTTAGCTTCCCGGAAGACCTCCTTTATGATG
GCTTTATGCCTCAGCTCCATCTACGAGGATTTAAAGATGTACCAAGTGG
AGTTCAAGACCATGAACGCCAAGCTGCTCATGGACCCTAAACGGCAGAT
CTTTTTAGACCAGAACATGCTGGCTGTGATTGATGAGCTGATGCAAGCT
TTAAACTTCAACTCCGAGACCGTCCCTCAGAAGTCCTCCCTCGAGGAGC
CCGATTTTTACAAGACAAAGATCAAACTGTGCATTTTACTCCACGCCTT
TAGGATCCGGGCCGTGACCATTGACCGGGTCATGAGCTATTTAAACGCC
AGC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 116)
YFGKLESKLSVIRNLNDQVLFIDQGNRPLFEDMTDSDCRDNAPRTIFII
SMYKDSQPRGMAVTISVKCEKISTLSCENKIISFKEMNPPDNIKDTKSD
IIFFQRSVPGHDNKMQFESSSYEGYFLACEKERDLFKLILKKEDELGDR
SIMFTVQNEDSGTTNTVAAYNLTWKSTNFKTILEWEPKPVNQVYTVQIS
TKSGDWKSKCFYTTDTECDLTDEIVKDVKQTYLARVFSYPAGNVESTGS
AGEPLYENSPEFTPYLETNLGQPTIQSFEQVGTKVNVTVEDERTLVRRN
NTFLSLRDVFGKDLIYTLYYWKSSSSGKKTAKTNTNEFLIDVDKGENYC
FSVQAVIPSRTVNRKSTDSPVECMGQEKGEFRENWVNVISDLKKIEDLI
QSMHIDATLYTESDVHPSCKVTAMKCFLLELQVISLESGDASIHDTVEN
LIILANNSLSSNGNVTESGCKECEELEEKNIKEFLQSFVHIVQMFINT
S.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 117)
TACTTCGGCAAACTGGAATCCAAGCTGAGCGTGATCCGGAATTTAAACG
ACCAAGTTCTGTTTATCGATCAAGGTAACCGGCCTCTGTTCGAGGACAT
GACCGACTCCGATTGCCGGGACAATGCCCCCCGGACCATCTTCATTATC
TCCATGTACAAGGACAGCCAGCCCCGGGGCATGGCTGTGACAATTAGCG
TGAAGTGTGAGAAAATCAGCACTTTATCTTGTGAGAACAAGATCATCTC
CTTTAAGGAAATGAACCCCCCCGATAACATCAAGGACACCAAGTCCGAT
ATCATCTTCTTCCAGCGGTCCGTGCCCGGTCACGATAACAAGATGCAGT

-continued

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGATAGCGGCACAACCAACACAG

TCGCTGCCTATAACCTCACTTGGAAGAGCACCAACTTCAAAACCATCCT

CGAATGGGAACCCAAACCCGTTAACCAAGTTTACACCGTGCAGATCAGC

ACCAAGTCCGGCGACTGGAAGTCCAAATGTTTCTATACCACCGACACCG

AGTGCGATCTCACCGATGAGATCGTGAAAGATGTGAAACAGACCTACCT

CGCCCGGGTGTTTAGCTACCCCGCCGGCAATGTGGAGAGCACTGGTTCC

GCTGGCGAGCCTTTATACGAGAACAGCCCCGAATTTACCCCTTACCTCG

AGACCAATTTAGGACAGCCCACCATCCAAAGCTTTGAGCAAGTTGGCAC

AAAGGTGAATGTGACAGTGGAGGACGAGCGGACTTTAGTGCGGCGGAAC

AACACCTTTCTCAGCCTCCGGGATGTGTTCGGCAAAGATTTAATCTACA

CACTGTATTACTGGAAGTCCTCTTCCTCCGGCAAGAAGACAGCTAAAAC

CAACACAAACGAGTTTTTAATCGACGTGGATAAAGGCGAAAACTACTGT

TTCAGCGTGCAAGCTGTGATCCCCTCCCGGACCGTGAATAGGAAAAGCA

CCGATAGCCCCGTTGAGTGCATGGGCCAAGAAAAGGGCGAGTTCCGGGA

GAACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTACTGGAGCTGCAAGT

TATCTCTTTAGAGAGCGGAGACGCTAGCATCCACGACACCGTGGAGAAT

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTC

C.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 118)

MKWVTFISLLFLFSSAYSYFGKLESKLSVIRNLNDQVLFIDQGNRPLFE

DMTDSDCRDNAPRTIFIISMYKDSQPRGMAVTISVKCEKISTLSCENKI

ISFKEMNPPDNIKDTKSDIIFFQRSVPGHDNKMQFESSSYEGYFLACEK

ERDLFKLILKKEDELGDRSIMFTVQNEDSGTTNTVAAYNLTWKSTNFKT

ILEWEPKPVNQVYTVQISTKSGDWKSKCFYTTDTECDLTDEIVKDVKQT

YLARVFSYPAGNVESTGSAGEPLYENSPEFTPYLETNLGQPTIQSFEQV

GTKVNVTVEDERTLVRRNNTFLSLRDVFGKDLIYTLYYWKSSSSGKKTA

KTNTNEFLIDVDKGENYCFSVQAVIPSRTVNRKSTDSPVECMGQEKGEF

RENWVNVISDLKKIEDLIQSMHIDATLYTESDVHPSCKVTAMKCFLLEL

QVISLESGDASIHDTVENLIILANNSLSSNGNVTESGCKECEELEEKNI

KEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 119)

ATGAAGTGGGTCACATTTATCTCTTTACTGTTCCTCTTCTCCAGCGCCT

ACAGCTACTTCGGCAAACTGGAATCCAAGCTGAGCGTGATCCGGAATTT

AAACGACCAAGTTCTGTTTATCGATCAAGGTAACCGGCCTCTGTTCGAG

GACATGACCGACTCCGATTGCCGGGACAATGCCCCCCGGACCATCTTCA

TTATCTCCATGTACAAGGACAGCCAGCCCCGGGGCATGGCTGTGACAAT

TAGCGTGAAGTGTGAGAAAATCAGCACTTTATCTTGTGAGAACAAGATC

ATCTCCTTTAAGGAAATGAACCCCCCCGATAACATCAAGGACACCAAGT

CCGATATCATCTTCTTCCAGCGGTCCGTGCCCGGTCACGATAACAAGAT

GCAGTTCGAATCCTCCTCCTACGAGGGCTACTTTTTAGCTTGTGAAAAG

GAGAGGGATTTATTCAAGCTGATCCTCAAGAAGGAGGACGAGCTGGGCG

ATCGTTCCATCATGTTCACCGTCCAAAACGAGGATAGCGGCACAACCAA

CACAGTCGCTGCCTATAACCTCACTTGGAAGAGCACCAACTTCAAAACC

ATCCTCGAATGGGAACCCAAACCCGTTAACCAAGTTTACACCGTGCAGA

TCAGCACCAAGTCCGGCGACTGGAAGTCCAAATGTTTCTATACCACCGA

CACCGAGTGCGATCTCACCGATGAGATCGTGAAAGATGTGAAACAGACC

TACCTCGCCCGGGTGTTTAGCTACCCCGCCGGCAATGTGGAGAGCACTG

GTTCCGCTGGCGAGCCTTTATACGAGAACAGCCCCGAATTTACCCCTTA

CCTCGAGACCAATTTAGGACAGCCCACCATCCAAAGCTTTGAGCAAGTT

GGCACAAAGGTGAATGTGACAGTGGAGGACGAGCGGACTTTAGTGCGGC

GGAACAACACCTTTCTCAGCCTCCGGGATGTGTTCGGCAAAGATTTAAT

CTACACACTGTATTACTGGAAGTCCTCTTCCTCCGGCAAGAAGACAGCT

AAAACCAACACAAACGAGTTTTTAATCGACGTGGATAAAGGCGAAAACT

ACTGTTTCAGCGTGCAAGCTGTGATCCCCTCCCGGACCGTGAATAGGAA

AAGCACCGATAGCCCCGTTGAGTGCATGGGCCAAGAAAAGGGCGAGTTC

CGGGAGAACTGGGTGAACGTCATCAGCGATTTAAAGAAGATCGAAGATT

TAATTCAGTCCATGCATATCGACGCCACTTTATACACAGAATCCGACGT

GCACCCCTCTTGTAAGGTGACCGCCATGAAATGTTTTTACTGGAGCTG

CAAGTTATCTCTTTAGAGAGCGGAGACGCTAGCATCCACGACACCGTGG

AGAATTTAATCATTTTAGCCAATAACTCTTTATCCAGCAACGGCAACGT

GACAGAGTCCGGCTGCAAGGAGTGCGAAGAGCTGGAGGAGAAGAACATC

AAGGAGTTTCTGCAATCCTTTGTGCACATTGTCCAGATGTTCATCAATA

CCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 120)
IWELKKDVYVVELDWYPDAPGEMVVLTCDTPEEDGITWTLDQSSEVLGS
GKTLTIQVKEFGDAGQYTCHKGGEVLSHSLLLLHKKEDGIWSTDILKDQ
KEPKNKTFLRCEAKNYSGRFTCWWLTTISTDLTFSVKSSRGSSDPQGVT
CGAATLSAERVRGDNKEYEYSVECQEDSACPAAEESLPIEVMVDAVHKL
KYENYTSSFFIRDIIKPDPPKNLQLKPLKNSRQVEVSWEYPDTWSTPHS
YFSLTFCVQVQGKSKREKKDRVFTDKTSATVICRKNASISVRAQDRYYS
SSWSEWASVPCSGGGGSGGGGSGGGGSRNLPVATPDPGMFPCLHHSQNL
LRAVSNMLQKARQTLEFYPCTSEEIDHEDITKDKTSTVEACLPLELTKN
ESCLNSRETSFITNGSCLASRKTSFMMALCLSSIYEDLKMYQVEFKTMN
AKLLMDPKRQIFLDQNMLAVIDELMQALNFNSETVPQKSSLEEPDFYKT
KIKLCILLHAFRIRAVTIDRVMSYLNASITCPPPMSVEHADIWVKSYSL
YSRERYICNSGFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 121)
ATTTGGGAACTGAAGAAGGACGTCTACGTGGTCGAACTGGACTGGTATC
CCGATGCTCCCGGCGAAATGGTGGTGCTCACTTGTGACACCCCCGAAGA
AGACGGCATCACTTGGACCCTCGATCAGAGCAGCGAGGTGCTGGGCTCC
GGAAAGACCCTCACAATCCAAGTTAAGGAGTTCGGAGACGCTGGCCAAT
ACACATGCCACAAGGGAGGCGAGGTGCTCAGCCATTCCTTATTATTATT
ACACAAGAAGGAAGACGGAATCTGGTCCACCGACATTTTAAAAGATCAG
AAGGAGCCCAAGAATAAGACCTTTTTAAGGTGTGAGGCCAAAAACTACA
GCGGTCGTTTCACTTGTTGGTGGCTGACCACCATTTCCACCGATTTAAC
CTTCTCCGTGAAAAGCAGCCGGGGAAGCTCCGACCCTCAAGGTGTGACA
TGTGGAGCCGCTACCCTCAGCGCTGAGAGGGTTCGTGGCGATAACAAGG
AATACGAGTACAGCGTGGAGTGCCAAGAAGATAGCGCTTGTCCCGCTGC
CGAAGAATCTTTACCCATTGAGGTGATGGTGGACGCCGTGCACAAACTC
AAGTACGAGAACTACACCTCCTCCTTCTTTATCCGGGACATCATTAAGC
CCGATCCTCCTAAGAATTTACAGCTGAAGCCTCTCAAAAATAGCCGGCA
AGTTGAGGTCTCTTGGGAATATCCCGACACTTGGAGCACACCCCACAGC
TACTTCTCTTTAACCTTTTGTGTGCAAGTTCAAGGTAAAAGCAAGCGGG
AGAAGAAAGACCGGGTGTTTACCGACAAAACCAGCGCCACCGTCATCTG
TCGGAAGAACGCCTCCATCAGCGTGAGGGCTCAAGATCGTTATTACTCC
AGCAGCTGGTCCGAGTGGGCCAGCGTGCCTTGTTCCGGCGGTGGAGGAT
CCGGAGGAGGTGGCTCCGGCGGCGGAGGATCTCGTAACCTCCCCGTGGC

-continued

TACCCCCGATCCCGGAATGTTCCCTTGTTTACACCACAGCCAGAATTTA
CTGAGGGCCGTGAGCAACATGCTGCAGAAAGCTAGGCAGACTTTAGAAT
TTTACCCTTGCACCAGCGAGGAGATCGACCATGAAGATATCACCAAGGA
CAAGACATCCACCGTGGAGGCTTGTTTACCTCTGGAGCTGACAAAGAAC
GAGTCTTGTCTCAACTCTCGTGAAACCAGCTTCATCACAAATGGCTCTT
GTTTAGCTTCCCGGAAGACCTCCTTTATGATGGCTTTATGCCTCAGCTC
CATCTACGAGGATTTAAAGATGTACCAAGTGGAGTTCAAGACCATGAAC
GCCAAGCTGCTCATGGACCCTAAACGGCAGATCTTTTTAGACCAGAACA
TGCTGGCTGTGATTGATGAGCTGATGCAAGCTTTAAACTTCAACTCCGA
GACCGTCCCTCAGAAGTCCTCCCTCGAGGAGCCCGATTTTTACAAGACA
AAGATCAAACTGTGCATTTTACTCCACGCCTTTAGGATCCGGGCCGTGA
CCATTGACCGGGTCATGAGCTATTTAAACGCCAGCATTACATGCCCCCC
TCCCATGAGCGTGGAGCACGCCGACATCTGGGTGAAGAGCTATAGCCTC
TACAGCCGGGAGAGGTATATCTGTAACAGCGGCTTCAAGAGGAAGGCCG
GCACCAGCAGCCTCACCGAGTGCGTGCTGAATAAGGCTACCAACGTGGC
TCACTGGACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 122)
MKWVTFISLLFLFSSAYSIWELKKDVYVVELDWYPDAPGEMVVLTCDTP
EEDGITWTLDQSSEVLGSGKTLTIQVKEFGDAGQYTCHKGGEVLSHSLL
LLHKKEDGIWSTDILKDQKEPKNKTFLRCEAKNYSGRFTCWWLTTISTD
LTFSVKSSRGSSDPQGVTCGAATLSAERVRGDNKEYEYSVECQEDSACP
AAEESLPIEVMVDAVHKLKYENYTSSFFIRDIIKPDPPKNLQLKPLKNS
RQVEVSWEYPDTWSTPHSYFSLTFCVQVQGKSKREKKDRVFTDKTSATV
ICRKNASISVRAQDRYYSSSWSEWASVPCSGGGGSGGGGSGGGGSRNLP
VATPDPGMFPCLUESQNLLRAVSNMLQKARQTLEFYPCTSEEIDHEDIT
KDKTSTVEACLPLELTKNESCLNSRETSFITNGSCLASRKTSFMMALCL
SSIYEDLKMYQVEFKTMNAKLLMDPKRQIFLDQNMLAVIDELMQALNFN
SETVPQKSSLEEPDFYKTKIKLCILLHAFRIRAVTIDRVMSYLNASITC
PPPMSVEHADIWVKSYSLYSRERYICNSGFKRKAGTSSLTECVLNKATN
VAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 123)

```
ATGAAATGGGTGACCTTTATTTCTTTACTGTTCCTCTTTAGCAGCGCCT
ACTCCATTTGGGAACTGAAGAAGGACGTCTACGTGGTCGAACTGGACTG
GTATCCCGATGCTCCCGGCGAAATGGTGGTGCTCACTTGTGACACCCCC
GAAGAAGACGGCATCACTTGGACCCTCGATCAGAGCAGCGAGGTGCTGG
GCTCCGGAAAGACCCTCACAATCCAAGTTAAGGAGTTCGGAGACGCTGG
CCAATACACATGCCACAAGGGAGGCGAGGTGCTCAGCCATTCCTTATTA
TTATTACACAAGAAGGAAGACGGAATCTGGTCCACCGACATTTTAAAAG
ATCAGAAGGAGCCCAAGAATAAGACCTTTTTAAGGTGTGAGGCCAAAAA
CTACAGCGGTCGTTTCACTTGTTGGTGGCTGACCACCATTTCCACCGAT
TTAACCTTCTCCGTGAAAAGCAGCCGGGGAAGCTCCGACCCTCAAGGTG
TGACATGTGGAGCCGCTACCCTCAGCGCTGAGAGGGTTCGTGGCGATAA
CAAGGAATACGAGTACAGCGTGGAGTGCCAAGAAGATAGCGCTTGTCCC
GCTGCCGAAGAATCTTTACCCATTGAGGTGATGGTGGACGCCGTGCACA
AACTCAAGTACGAGAACTACACCTCCTCCTTCTTTATCCGGGACATCAT
TAAGCCCGATCCTCCTAAGAATTTACAGCTGAAGCCTCTCAAAAATAGC
CGGCAAGTTGAGGTCTCTTGGGAATATCCCGACACTTGGAGCACACCCC
ACAGCTACTTCTCTTTAACCTTTTGTGTGCAAGTTCAAGGTAAAAGCAA
GCGGGAGAAGAAAGACCGGGTGTTTACCGACAAAACCAGCGCCACCGTC
ATCTGTCGGAAGAACGCCTCCATCAGCGTGAGGGCTCAAGATCGTTATT
ACTCCAGCAGCTGGTCCGAGTGGGCCAGCGTGCCTTGTTCCGGCGGTGG
AGGATCCGGAGGAGGTGGCTCCGGCGGCGGAGGATCTCGTAACCTCCCC
GTGGCTACCCCCGATCCCGGAATGTTCCCTTGTTTACACCACAGCCAGA
ATTTACTGAGGGCCGTGAGCAACATGCTGCAGAAAGCTAGGCAGACTTT
AGAATTTTACCCTTGCACCAGCGAGGAGATCGACCATGAAGATATCACC
AAGGACAAGACATCCACCGTGGAGGCTTGTTTACCTCTGGAGCTGACAA
AGAACGAGTCTTGTCTCAACTCTCGTGAAACCAGCTTCATCACAAATGG
CTCTTGTTTAGCTTCCCGGAAGACCTCCTTTATGATGGCTTTATGCCTC
AGCTCCATCTACGAGGATTTAAAGATGTACCAAGTGGAGTTCAAGACCA
TGAACGCCAAGCTGCTCATGGACCCTAAACGGCAGATCTTTTTAGACCA
GAACATGCTGGCTGTGATTGATGAGCTGATGCAAGCTTTAAACTTCAAC
TCCGAGACCGTCCCTCAGAAGTCCTCCCTCGAGGAGCCCGATTTTTACA
AGACAAAGATCAAACTGTGCATTTTACTCCACGCCTTTAGGATCCGGGC
CGTGACCATTGACCGGGTCATGAGCTATTTAAACGCCAGCATTACATGC
CCCCCTCCCATGAGCGTGGAGCACGCCGACATCTGGGTGAAGAGCTATA
GCCTCTACAGCCGGGAGAGGTATATCTGTAACAGCGGCTTCAAGAGGAA
GGCCGGCACCAGCAGCCTCACCGAGTGCGTGCTGAATAAGGCTACCAAC
GTGGCTCACTGGACAACACCCTCTTTAAAGTGCATCCGG.
```

Exemplary Multi-Chain Chimeric Polypeptides—Type B

In some embodiments of any of the multi-chain chimeric polypeptides described herein, the first target-binding domain and the second targeting-binding domain each independently bind specifically to a receptor of IL-21 or to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble TGF-β receptor (e.g., a soluble TGF-β RII receptor). In some embodiments of these multi-chain chimeric polypeptides, the first target-binding domain and the second target-binding domain are each independently a soluble IL-21 or a soluble TGF-β receptor (e.g., a soluble TGF-β RII receptor). In some embodiments of these multi-chain chimeric polypeptides, the first target-binding domain and the second target-binding domain both bind specifically to a receptor of IL-21 or to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to TGF-β. In some embodiments of these multi-chain chimeric polypeptides, the first target-binding domain binds specifically to TGF-β, and the second target-binding domain bind specifically to a receptor for IL-21.

In some embodiments of these multi-chain chimeric polypeptides, the first target-binding domain includes a soluble IL-21 (e.g., a soluble human IL-21). In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 125)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC.

In some embodiments of these multi-chain chimeric polypeptides, the second target-binding domain includes a soluble TGF-β receptor (e.g., a soluble TGF-β RII receptor (e.g., a soluble human TGF-β RII receptor)). In some embodiments of these multi-chain chimeric polypeptides, the soluble human TGF-β RII includes a first sequence of soluble human TGF-β RII and a second sequence of soluble human TGF-βRII. In some embodiments of these multi-chain chimeric polypeptides, the soluble human TGF-β RII includes a linker disposed between the first sequence of soluble human TGF-β RII and the second sequence of soluble human TGF-βRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCACG

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT.

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCACA

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC.

In some embodiments of these multi-chain chimeric polypeptides, the soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 61)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCACG
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCACAATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGCTGCAGCAGCGACGAATGCAACGACAATATCATCTTTAGCGAGG
AATACAATACCAGCAACCCCGAC.

In some embodiments of these multi-chain chimeric polypeptides, the human TGFβRII receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 60)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 126)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS

-continued

YEKKPPKEFLERFKSLLQKMIHQHLSSRTHGSEDSSGTTNTVAAYNLTW
KSTNFKTILEWEPKPVNQVYTVQISTKSGDWKSKCFYTTDTECDLTDEI
VKDVKQTYLARVFSYPAGNVESTGSAGEPLYENSPEFTPYLETNLGQPT
IQSFEQVGTKVNVTVEDERTLVRRNNTFLSLRDVFGKDLIYTLYYWKSS
SSGKKTAKTNTNEFLIDVDKGENYCFSVQAVIPSRTVNRKSTDSPVECM
GQEKGEFRENWVNVISDLKKIEDLIQSMHIDATLYTESDVHPSCKVTAM
KCFLLELQVISLESGDASIHDTVENLIILANNSLSSNGNVTESGCKECE
ELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 127)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCCTCCGGCACCACCAATACCGTGGCCGCTTATAACCTCACATGG
AAGAGCACCAACTTCAAGACAATTCTGGAATGGGAACCCAAGCCCGTCA
ATCAAGTTTACACCGTGCAGATCTCCACCAAATCCGGAGACTGGAAGAG
CAAGTGCTTCTACACAACAGACACCGAGTGTGATTTAACCGACGAAATC
GTCAAGGACGTCAAGCAAACCTATCTGGCTCGGGTCTTTTCCTACCCCG
CTGGCAATGTCGAGTCCACCGGCTCCGCTGGCGAGCCTCTCTACGAGAA
TTCCCCCGAATTCACCCCTTATTTAGAGACCAATTTAGGCCAGCCTACC
ATCCAGAGCTTCGAGCAAGTTGGCACCAAGGTGAACGTCACCGTCGAGG
ATGAAAGGACTTTAGTGCGGCGGAATAACACATTTTTATCCCTCCGGGA
TGTGTTCGGCAAAGACCTCATCTACACACTGTACTATTGGAAGTCCAGC
TCCTCCGGCAAAAAGACCGCTAAGACCAACACCAACGAGTTTTTAATTG
ACGTGGACAAAGGCGAGAACTACTGCTTCAGCGTGCAAGCCGTGATCCC
TTCTCGTACCGTCAACCGGAAGAGCACAGATTCCCCCGTTGAGTGCATG
GGCCAAGAAAAGGGCGAGTTCCGGGAGAACTGGGTGAACGTCATCAGCG
ATTTAAAGAAGATCGAAGATTTAATTCAGTCCATGCATATCGACGCCAC
TTTATACACAGAATCCGACGTGCACCCCTCTTGTAAGGTGACCGCCATG
AAATGTTTTTTACTGGAGCTGCAAGTTATCTCTTTAGAGAGCGGAGACG
CTAGCATCCACGACACCGTGGAGAATTTAATCATTTTAGCCAATAACTC

-continued

TTTATCCAGCAACGGCAACGTGACAGAGTCCGGCTGCAAGGAGTGCGAA

GAGCTGGAGGAGAAGAACATCAAGGAGTTTCTGCAATCCTTTGTGCACA

TTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 128)
MKWVTFISLLFLFSSAYSQGQDRHMIRMRQLIDIVDQLKNYVNDLVPEF

LPAPEDVETNCEWSAFSCFQKAQLKSANTGNNERIINVSIKKLKRKPPS

TNAGRRQKHRLTCPSCDSYEKKPPKEFLERFKSLLQKMIHQHLSSRTHG

SEDSSGTTNTVAAYNLTWKSTNFKTILEWEPKPVNQVYTVQISTKSGDW

KSKCFYTTDTECDLTDEIVKDVKQTYLARVFSYPAGNVESTGSAGEPLY

ENSPEFTPYLETNLGQPTIQSFEQVGTKVNVTVEDERTLVRRNNTFLSL

RDVFGKDLIYTLYYWKSSSSGKKTAKTNTNEFLIDVDKGENYCFSVQAV

IPSRTVNRKSTDSPVECMGQEKGEFRENWVNVISDLKKIEDLIQSMHID

ATLYTESDVHPSCKVTAMKCFLLELQVISLESGDASIHDTVENLIILAN

NSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 129)
ATGAAGTGGGTGACCTTCATCAGCCTGCTGTTCCTGTTCTCCAGCGCCT

ACTCCCAGGGCCAGGACAGGCACATGATCCGGATGAGGCAGCTCATCGA

CATCGTCGACCAGCTGAAGAACTACGTGAACGACCTGGTGCCCGAGTTT

CTGCCTGCCCCCGAGGACGTGGAGACCAACTGCGAGTGGTCCGCCTTCT

CCTGCTTTCAGAAGGCCCAGCTGAAGTCCGCCAACACCGGCAACAACGA

GCGGATCATCAACGTGAGCATCAAGAAGCTGAAGCGGAAGCCTCCCTCC

ACAAACGCCGGCAGGAGGCAGAAGCACAGGCTGACCTGCCCCAGCTGTG

ACTCCTACGAGAAGAAGCCCCCCAAGGAGTTCCTGGAGAGGTTCAAGTC

CCTGCTGCAGAAGATGATCCATCAGCACCTGTCCTCCAGGACCCACGGC

TCCGAGGACTCCTCCGGCACCACCAATACCGTGGCCGCTTATAACCTCA

CATGGAAGAGCACCAACTTCAAGACAATTCTGGAATGGGAACCCAAGCC

CGTCAATCAAGTTTACACCGTGCAGATCTCCACCAAATCCGGAGACTGG

AAGAGCAAGTGCTTCTACACAACAGACACCGAGTGTGATTTAACCGACG

AAATCGTCAAGGACGTCAAGCAAACCTATCTGGCTCGGGTCTTTTCCTA

CCCCGCTGGCAATGTCGAGTCCACCGGCTCCGCTGGCGAGCCTCTCTAC

-continued

GAGAATTCCCCCGAATTCACCCCTTATTTAGAGACCAATTTAGGCCAGC

CTACCATCCAGAGCTTCGAGCAAGTTGGCACCAAGGTGAACGTCACCGT

CGAGGATGAAAGGACTTTAGTGCGGCGGAATAACACATTTTTATCCCTC

CGGGATGTGTTCGGCAAAGACCTCATCTACACACTGTACTATTGGAAGT

CCAGCTCCTCCGGCAAAAAGACCGCTAAGACCAACACCAACGAGTTTTT

AATTGACGTGGACAAAGGCGAGAACTACTGCTTCAGCGTGCAAGCCGTG

ATCCCTTCTCGTACCGTCAACCGGAAGAGCACAGATTCCCCCGTTGAGT

GCATGGGCCAAGAAAAGGGCGAGTTCCGGGAGAACTGGGTGAACGTCAT

CAGCGATTTAAAGAAGATCGAAGATTTAATTCAGTCCATGCATATCGAC

GCCACTTTATACACAGAATCCGACGTGCACCCCTCTTGTAAGGTGACCG

CCATGAAATGTTTTTTACTGGAGCTGCAAGTTATCTCTTTAGAGAGCGG

AGACGCTAGCATCCACGACACCGTGGAGAATTTAATCATTTTAGCCAAT

AACTCTTTATCCAGCAACGGCAACGTGACAGAGTCCGGCTGCAAGGAGT

GCGAAGAGCTGGAGGAGAAGAACATCAAGGAGTTTCTGCAATCCTTTGT

GCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 130)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDITCPPPM

SVEHADIWVKSYSLYSRERYICNSGFKRKAGTSSLTECVLNKATNVAHW

TTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 131)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCACG

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

-continued

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCACAATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACATCACGTGTCCTCCTCCTATG

TCCGTGGAACACGCAGACATCTGGGTCAAGAGCTACAGCTTGTACTCCA

GGGAGCGGTACATTTGTAACTCTGGTTTCAAGCGTAAAGCCGGCACGTC

CAGCCTGACGGAGTGCGTGTTGAACAAGGCCACGAATGTCGCCCACTGG

ACAACCCCCAGTCTCAAATGTATTAGA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 132)

MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDITCPPPMSVEHADIWVKSYSLYSRERYICNSGFKRKAG

TSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 133)

ACTCCATCCCCCCCCATGTGCAAAAGAGCGTGAACAACGATATGATCG

TGACCGACAACAACGGCGCCGTGAAGTTTCCCCAGCTCTGCAAGTTCTG

CGATGTCAGGTTCAGCACCTGCGATAATCAGAAGTCCTGCATGTCCAAC

TGCACGATCACCTCCATCTGCGAGAAGCCCCAAGAAGTGTGCGTGGCCG

-continued

TGTGGCGGAAAAATGACGAGAACATCACCCTGGAGACCGTGTGTCACGA

CCCCAAGCTCCCTTATCACGACTTCATTCTGGAGGACGCTGCCTCCCCC

AAATGCATCATGAAGGAGAAGAAGAAGCCCGGAGAGACCTTCTTTATGT

GTTCCTGTAGCAGCGACGAGTGTAACGACAACATCATCTTCAGCGAAGA

GTACAACACCAGCAACCCTGATGGAGGTGGCGGATCCGGAGGTGGAGGT

TCTGGTGGAGGTGGGAGTATTCCTCCCCACGTGCAGAAGAGCGTGAATA

ATGACATGATCGTGACCGATAACAATGGCGCCGTGAAATTTCCCCAGCT

GTGCAAATTCTGCGATGTGAGGTTTTCCACCTGCGACAACCAGAAGTCC

TGTATGAGCAACTGCACAATCACCTCCATCTGTGAGAAGCCTCAGGAGG

TGTGCGTGGCTGTCTGGCGGAAGAATGACGAGAATATCACCCTGGAAAC

CGTCTGCCACGATCCCAAGCTGCCCTACCACGATTTCATCCTGGAAGAC

GCCGCCAGCCCTAAGTGCATCATGAAAGAGAAAAAGAAGCCTGGCGAGA

CCTTTTTCATGTGCTCCTGCAGCAGCGACGAATGCAACGACAATATCAT

CTTTAGCGAGGAATACAATACCAGCAACCCCGACATCACGTGTCCTCCT

CCTATGTCCGTGGAACACGCAGACATCTGGGTCAAGAGCTACAGCTTGT

ACTCCAGGGAGCGGTACATTTGTAACTCTGGTTTCAAGCGTAAAGCCGG

CACGTCCAGCCTGACGGAGTGCGTGTTGAACAAGGCCACGAATGTCGCC

CACTGGACAACCCCCAGTCTCAAATGTATTAGA.

Exemplary Multi-Chain Chimeric Polypeptides—Type C

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the first target-binding domain includes a soluble IL-21 (e.g., a soluble human IL-21).

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 124)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 134)
CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT
```

-continued

```
TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCC.
```

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 125)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC.
```

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 135)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH.
```

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                        (SEQ ID NO: 136)
GATTGTGATATTGAAGGTAAAGATGGCAAACAATATGAGAGTGTTCTAA

TGGTCAGCATCGATCAATTATTGGACAGCATGAAAGAAATTGGTAGCAA

TTGCCTGAATAATGAATTTAACTTTTTTAAAAGACATATCTGTGATGCT

AATAAGGAAGGTATGTTTTTATTCCGTGCTGCTCGCAAGTTGAGGCAAT

TTCTTAAAATGAATAGCACTGGTGATTTTGATCTCCACTTATTAAAAGT

TTCAGAAGGCACAACAATACTGTTGAACTGCACTGGCCAGGTTAAAGGA
```

-continued

AGAAAACCAGCTGCCCTGGGTGAAGCCCAACCAACAAAGAGTTTGGAAG

AAAATAAATCTTTAAAGGAACAGAAAAAACTGAATGACTTGTGTTTCCT

AAAGAGACTATTACAAGAGATAAAAACTTGTTGGAATAAAATTTTGATG

GGCACTAAAGAACAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 126)

QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDSSGTTNTVAAYNLTW

KSTNFKTILEWEPKPVNQVYTVQISTKSGDWKSKCFYTTDTECDLTDEI

VKDVKQTYLARVFSYPAGNVESTGSAGEPLYENSPEFTPYLETNLGQPT

IQSFEQVGTKVNVTVEDERTLVRRNNTFLSLRDVFGKDLIYTLYYWKSS

SSGKKTAKTNTNEFLIDVDKGENYCFSVQAVIPSRTVNRKSTDSPVECM

GQEKGEFRENWVNVISDLKKIEDLIQSMHIDATLYTESDVHPSCKVTAM

KCFLLELQVISLESGDASIHDTVENLIILANNSLSSNGNVTESGCKECE

ELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 127)

CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCCTCAGGCACTACAAATACTGTGGCAGCATATAATTTAACTTGG

AAATCAACTAATTTCAAGACAATTTTGGAGTGGGAACCCAAACCCGTCA

ATCAAGTCTACACTGTTCAAATAAGCACTAAGTCAGGAGATTGGAAAAG

CAAATGCTTTTACACAACAGACACAGAGTGTGACCTCACCGACGAGATT

GTGAAGGATGTGAAGCAGACGTACTTGGCACGGGTCTTCTCCTACCCGG

CAGGGAATGTGGAGAGCACCGGTTCTGCTGGGGAGCCTCTGTATGAGAA

-continued

CTCCCCAGAGTTCACACCTTACCTGGAGACAAACCTCGGACAGCCAACA

ATTCAGAGTTTTGAACAGGTGGGAACAAAAGTGAATGTGACCGTAGAAG

ATGAACGGACTTTAGTCAGAAGGAACAACACTTTCCTAAGCCTCCGGGA

TGTTTTTGGCAAGGACTTAATTTATACACTTTATTATTGGAAATCTTCA

AGTTCAGGAAAGAAAACAGCCAAAACAAACACTAATGAGTTTTTGATTG

ATGTGGATAAAGGAGAAAACTACTGTTTCAGTGTTCAAGCAGTGATTCC

CTCCCGAACAGTTAACCGGAAGAGTACAGACAGCCCGGTAGAGTGTATG

GGCCAGGAGAAAGGGGAATTCAGAGAAAACTGGGTGAACGTCATCAGCG

ATTTAAAGAAGATCGAAGATTTAATTCAGTCCATGCATATCGACGCCAC

TTTATACACAGAATCCGACGTGCACCCCTCTTGTAAGGTGACCGCCATG

AAATGTTTTTTACTGGAGCTGCAAGTTATCTCTTTAGAGAGCGGAGACG

CTAGCATCCACGACACCGTGGAGAATTTAATCATTTTAGCCAATAACTC

TTTATCCAGCAACGGCAACGTGACAGAGTCCGGCTGCAAGGAGTGCGAA

GAGCTGGAGGAGAAGAACATCAAGGAGTTTCTGCAATCCTTTGTGCACA

TTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 128)

MGVKVLFALICIAVAEAQGQDRHMIRMRQLIDIVDQLKNYVNDLVPEFL

PAPEDVETNCEWSAFSCFQKAQLKSANTGNNERIINVSIKKLKRKPPST

NAGRRQKHRLTCPSCDSYEKKPPKEFLERFKSLLQKMIHQHLSSRTHGS

EDSSGTTNTVAAYNLTWKSTNFKTILEWEPKPVNQVYTVQISTKSGDWK

SKCFYTTDTECDLTDEIVKDVKQTYLARVFSYPAGNVESTGSAGEPLYE

NSPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAVI

PSRTVNRKSTDSPVECMGQEKGEFRENWVNVISDLKKIEDLIQSMHIDA

TLYTESDVHPSCKVTAMKCFLLELQVISLESGDASIHDTVENLIILANN

SLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 129)

ATGGGAGTGAAAGTTCTTTTTGCCCTTATTTGTATTGCTGTGGCCGAGG

CCCAAGGTCAAGATCGCCACATGATTAGAATGCGTCAACTTATAGATAT

TGTTGATCAGCTGAAAAATTATGTGAATGACTTGGTCCCTGAATTTCTG

CCAGCTCCAGAAGATGTAGAGACAAACTGTGAGTGGTCAGCTTTTTCCT

-continued

GTTTTCAGAAGGCCCAACTAAAGTCAGCAAATACAGGAAACAATGAAAG

GATAATCAATGTATCAATTAAAAAGCTGAAGAGGAAACCACCTTCCACA

AATGCAGGGAGAAGACAGAAACACAGACTAACATGCCCTTCATGTGATT

CTTATGAGAAAAAACCACCCAAAGAATTCCTAGAAAGATTCAAATCACT

TCTCCAAAAGATGATTCATCAGCATCTGTCCTCTAGAACACACGGAAGT

GAAGATTCCTCAGGCACTACAAATACTGTGGCAGCATATAATTTAACTT

GGAAATCAACTAATTTCAAGACAATTTTGGAGTGGGAACCCAAACCCGT

CAATCAAGTCTACACTGTTCAAATAAGCACTAAGTCAGGAGATTGGAAA

AGCAAATGCTTTTACACAACAGACACAGAGTGTGACCTCACCGACGAGA

TTGTGAAGGATGTGAAGCAGACGTACTTGGCACGGGTCTTCTCCTACCC

GGCAGGGAATGTGGAGAGCACCGGTTCTGCTGGGGAGCCTCTGTATGAG

AACTCCCCAGAGTTCACACCTTACCTGGAGACAAACCTCGGACAGCCAA

CAATTCAGAGTTTTGAACAGGTGGGAACAAAAGTGAATGTGACCGTAGA

AGATGAACGGACTTTAGTCAGAAGGAACAACACTTTCCTAAGCCTCCGG

GATGTTTTTGGCAAGGACTTAATTTATACACTTTATTATTGGAAATCTT

CAAGTTCAGGAAAGAAAACAGCCAAAACAAACACTAATGAGTTTTTGAT

TGATGTGGATAAAGGAGAAAACTACTGTTTCAGTGTTCAAGCAGTGATT

CCCTCCCGAACAGTTAACCGGAAGAGTACAGACAGCCCGGTAGAGTGTA

TGGGCCAGGAGAAAGGGGAATTCAGAGAAAACTGGGTGAACGTCATCAG

CGATTTAAAGAAGATCGAAGATTTAATTCAGTCCATGCATATCGACGCC

ACTTTATACACAGAATCCGACGTGCACCCCTCTTGTAAGGTGACCGCCA

TGAAATGTTTTTTACTGGAGCTGCAAGTTATCTCTTTAGAGAGCGGAGA

CGCTAGCATCCACGACACCGTGGAGAATTTAATCATTTTAGCCAATAAC

TCTTTATCCAGCAACGGCAACGTGACAGAGTCCGGCTGCAAGGAGTGCG

AAGAGCTGGAGGAGAAGAACATCAAGGAGTTTCTGCAATCCTTTGTGCA

CATTGTCCAGATGTTCATCAATACCTCC

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 137)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEHITCPPPMSVEHADIWVKSYSLYSRERYICNSGFKRKAGTSSLTE

CVLNKATNVAHWTTPSLKCIR

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 138)
GATTGTGATATTGAAGGTAAAGATGGCAAACAATATGAGAGTGTTCTAA

TGGTCAGCATCGATCAATTATTGGACAGCATGAAAGAAATTGGTAGCAA

TTGCCTGAATAATGAATTTAACTTTTTTAAAAGACATATCTGTGATGCT

AATAAGGAAGGTATGTTTTTATTCCGTGCTGCTCGCAAGTTGAGGCAAT

TTCTTAAAATGAATAGCACTGGTGATTTTGATCTCCACTTATTAAAAGT

TTCAGAAGGCACAACAATACTGTTGAACTGCACTGGCCAGGTTAAAGGA

AGAAAACCAGCTGCCCTGGGTGAAGCCCAACCAACAAAGAGTTTGGAAG

AAAATAAATCTTTAAAGGAACAGAAAAAACTGAATGACTTGTGTTTCCT

AAAGAGACTATTACAAGAGATAAAAACTTGTTGGAATAAAATTTTGATG

GGCACTAAAGAACACATCACGTGCCCTCCCCCCATGTCCGTGGAACACG

CAGACATCTGGGTCAAGAGCTACAGCTTGTACTCCAGGGAGCGGTACAT

TTGTAACTCTGGTTTCAAGCGTAAAGCCGGCACGTCCAGCCTGACGGAG

TGCGTGTTGAACAAGGCCACGAATGTCGCCCACTGGACAACCCCCAGTC

TCAAATGCATTAGA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 139)
MGVKVLFALICIAVAEADCDIEGKDGKQYESVLMVSIDQLLDSMKEIGS

NCLNNEFNFFKRHICDANKEGMFLFRAARKLRQFLKMNSTGDFDLHLLK

VSEGTTILLNCTGQVKGRKPAALGEAQPTKSLEENKSLKEQKKLNDLCF

LKRLLQEIKTCWNKILMGTKEHITCPPPMSVEHADIWVKSYSLYSRERY

ICNSGFKRKAGTSSLTECVLNKATNVAHWTTPSLKCIR

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least (SEQ ID NO: 140)
ATGGGAGTGAAAGTTCTTTTTGCCCTTATTTGTATTGCTGTGGCCGAGG

CCGATTGTGATATTGAAGGTAAAGATGGCAAACAATATGAGAGTGTTCT

AATGGTCAGCATCGATCAATTATTGGACAGCATGAAAGAAATTGGTAGC

AATTGCCTGAATAATGAATTTAACTTTTTTAAAAGACATATCTGTGATG

CTAATAAGGAAGGTATGTTTTTATTCCGTGCTGCTCGCAAGTTGAGGCA

ATTTCTTAAAATGAATAGCACTGGTGATTTTGATCTCCACTTATTAAAA

GTTTCAGAAGGCACAACAATACTGTTGAACTGCACTGGCCAGGTTAAAG

GAAGAAAACCAGCTGCCCTGGGTGAAGCCCAACCAACAAAGAGTTTGGA

-continued

AGAAAATAAATCTTTAAAGGAACAGAAAAAACTGAATGACTTGTGTTTC

CTAAAGAGACTATTACAAGAGATAAAAACTTGTTGGAATAAAATTTTGA

TGGGCACTAAAGAACACATCACGTGCCCTCCCCCCATGTCCGTGGAACA

CGCAGACATCTGGGTCAAGAGCTACAGCTTGTACTCCAGGGAGCGGTAC

ATTTGTAACTCTGGTTTCAAGCGTAAAGCCGGCACGTCCAGCCTGACGG

AGTGCGTGTTGAACAAGGCCACGAATGTCGCCCACTGGACAACCCCCAG

TCTCAAATGCATTAGA.

Exemplary Multi-Chain Chimeric Polypeptides—Type D

In some embodiments of any of the multi-chain chimeric polypeptides described herein, the first target-binding domain and the second targeting-binding domain each independently bind specifically to a receptor of IL-7 or a receptor of IL-21. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or both of the first target-binding domain and the second target-binding domain is a soluble IL-21 (e.g., a soluble human IL-21 polypeptide) or a soluble IL-7 (e.g., a soluble human IL-7 polypeptide). In some embodiments of these multi-chain chimeric polypeptides, the first target-binding domain and the second target-binding domain are each independently a soluble IL-21 or a soluble IL-7. In some embodiments of these multi-chain chimeric polypeptides, the first target-binding domain and the second target-binding domain both bind specifically to a receptor of IL-21 or a receptor of IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-21, and the second target-binding domain binds specifically to a receptor for IL-7. In some embodiments of these multi-chain chimeric polypeptides, the first target-binding domain binds specifically to a receptor for IL-7, and the second target-binding domain binds specifically to a receptor for IL-21.

In some embodiments of these multi-chain chimeric polypeptides, the soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 134)
CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 125)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

-continued

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC.

In some embodiments of these multi-chain chimeric polypeptides, the sequence of soluble human IL-7 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 135)

DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 136)

GATTGTGATATTGAAGGTAAAGATGGCAAACAATATGAGAGTGTTCTAA

TGGTCAGCATCGATCAATTATTGGACAGCATGAAAGAAATTGGTAGCAA

TTGCCTGAATAATGAATTTAACTTTTTTAAAAGACATATCTGTGATGCT

AATAAGGAAGGTATGTTTTTATTCCGTGCTGCTCGCAAGTTGAGGCAAT

TTCTTAAAATGAATAGCACTGGTGATTTTGATCTCCACTTATTAAAAGT

TTCAGAAGGCACAACAATACTGTTGAACTGCACTGGCCAGGTTAAAGGA

AGAAAACCAGCTGCCCTGGGTGAAGCCCAACCAACAAAGAGTTTGGAAG

AAAATAAATCTTTAAAGGAACAGAAAAAACTGAATGACTTGTGTTTCCT

AAAGAGACTATTACAAGAGATAAAAACTTGTTGGAATAAAATTTTGATG

GGCACTAAAGAACAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 141)

DCDIEGKDGKQYESVLMVSIDQLLDSMKEIGSNCLNNEFNEFKRHICDA

NKEGMFLFRAARKLRQFLKMNSTGDFDLHLLKVSEGTTILLNCTGQVKG

-continued

RKPAALGEAQPTKSLEENKSLKEQKKLNDLCFLKRLLQEIKTCWNKILM

GTKEHSGTTNTVAAYNLTWKSTNFKTILEWEPKPVNQVYTVQISTKSGD

WKSKCFYTTDTECDLTDEIVKDVKQTYLARVFSYPAGNVESTGSAGEPL

YENSPEFTPYLETNLGQPTIQSFEQVGTKVNVTVEDERTLVRRNNTFLS

LRDVEGKDLIYTLYYWKSSSSGKKTAKTNTNEFLIDVDKGENYCFSVQA

VIPSRTVNRKSTD SPVECMGQEKGEFRENWVNVISDLKKIEDLIQSMH

IDATLYTESDVHPSCKVTAMKCFLLELQVISLESGDASIHDTVENLIIL

ANNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 142)

GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCATAGCGGCACAACCAACACAGTCGCTGCCTATAACC

TCACTTGGAAGAGCACCAACTTCAAAACCATCCTCGAATGGGAACCCAA

ACCCGTTAACCAAGTTTACACCGTGCAGATCAGCACCAAGTCCGGCGAC

TGGAAGTCCAAATGTTTCTATACCACCGACACCGAGTGCGATCTCACCG

ATGAGATCGTGAAAGATGTGAAACAGACCTACCTCGCCCGGGTGTTTAG

CTACCCCGCCGGCAATGTGGAGAGCACTGGTTCCGCTGGCGAGCCTTTA

TACGAGAACAGCCCCGAATTTACCCCTTACCTCGAGACCAATTTAGGAC

AGCCCACCATCCAAAGCTTTGAGCAAGTTGGCACAAAGGTGAATGTGAC

AGTGGAGGACGAGCGGACTTTAGTGCGGCGGAACAACACCTTTCTCAGC

CTCCGGGATGTGTTCGGCAAAGATTTAATCTACACACTGTATTACTGGA

AGTCCTCTTCCTCCGGCAAGAAGACAGCTAAAACCAACACAAACGAGTT

TTTAATCGACGTGGATAAAGGCGAAAACTACTGTTTCAGCGTGCAAGCT

GTGATCCCCTCCCGGACCGTGAATAGGAAAAGCACCGATAGCCCCGTTG

AGTGCATGGGCCAAGAAAAGGGCGAGTTCCGGGAGAACTGGGTGAACGT

CATCAGCGATTTAAAGAAGATCGAAGATTTAATTCAGTCCATGCATATC

GACGCCACTTTATACACAGAATCCGACGTGCACCCCTCTTGTAAGGTGA

CCGCCATGAAATGTTTTTTACTGGAGCTGCAAGTTATCTCTTTAGAGAG

CGGAGACGCTAGCATCCACGACACCGTGGAGAATTTAATCATTTTAGCC

-continued

AATAACTCTTTATCCAGCAACGGCAACGTGACAGAGTCCGGCTGCAAGG

AGTGCGAAGAGCTGGAGGAGAAGAACATCAAGGAGTTTCTGCAATCCTT

TGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 143)

MKWVTFISLLFLFSSAYSDCDIEGKDGKQYESVLMVSIDQLLDSMKEIG

SNCLNNEFNFFKRHICDANKEGMFLFRAARKLRQFLKMNSTGDFDLHLL

KVSEGTTILLNCTGQVKGRKPAALGEAQPTKSLEENKSLKEQKKLNDLC

FLKRLLQEIKTCWNKILMGTKEHSGTTNTVAAYNLTWKSTNFKTILEWE

PKPVNQVYTVQISTKSGDWKSKCFYTTDTECDLTDEIVKDVKQTYLARV

FSYPAGNVESTGSAGEPLYENSPEFTPYLETNLGQPTIQSFEQVGTKVN

VTVEDERTLVRRNNTFLSLRDVFGKDLIYTLYYWKSSSSGKKTAKTNTN

EFLIDVDKGENYCFSVQAVIPSRTVNRKSTDSPVECMGQEKGEFRENWV

NVISDLKKIEDLIQSMHIDATLYTESDVHPSCKVTAMKCFLLELQVISL

ESGDASIHDTVENLIILANNSLSSNGNVTESGCKECEELEEKNIKEFLQ

SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 144)

ATGAAGTGGGTGACCTTCATCAGCCTGCTGTTCCTGTTCTCCAGCGCCT

ACTCCGATTGCGACATCGAGGGCAAGGACGGCAAGCAGTACGAGAGCGT

GCTGATGGTGTCCATCGACCAGCTGCTGGACAGCATGAAGGAGATCGGC

TCCAACTGCCTCAACAACGAGTTCAACTTCTTCAAGCGGCACATCTGCG

ACGCCAACAAGGAGGGCATGTTCCTGTTCAGGGCCGCCAGGAAACTGCG

GCAGTTCCTGAAGATGAACTCCACCGGCGACTTCGACCTGCACCTGCTG

AAGGTGTCCGAGGGCACCACCATCCTGCTGAACTGCACCGGACAGGTGA

AGGGCCGGAAACCTGCTGCTCTGGGAGAGGCCCAACCCACCAAGAGCCT

GGAGGAGAACAAGTCCCTGAAGGAGCAGAAGAAGCTGAACGACCTGTGC

TTCCTGAAGAGGCTGCTGCAGGAGATCAAGACCTGCTGGAACAAGATCC

TGATGGGCACCAAGGAGCATAGCGGCACAACCAACACAGTCGCTGCCTA

TAACCTCACTTGGAAGAGCACCAACTTCAAAACCATCCTCGAATGGGAA

CCCAAACCCGTTAACCAAGTTTACACCGTGCAGATCAGCACCAAGTCCG

GCGACTGGAAGTCCAAATGTTTCTATACCACCGACACCGAGTGCGATCT

-continued

CACCGATGAGATCGTGAAAGATGTGAAACAGACCTACCTCGCCCGGGTG

TTTAGCTACCCCGCCGGCAATGTGGAGAGCACTGGTTCCGCTGGCGAGC

CTTTATACGAGAACAGCCCCGAATTTACCCCTTACCTCGAGACCAATTT

AGGACAGCCCACCATCCAAAGCTTTGAGCAAGTTGGCACAAAGGTGAAT

GTGACAGTGGAGGACGAGCGGACTTTAGTGCGGCGGAACAACACCTTTC

TCAGCCTCCGGGATGTGTTCGGCAAAGATTTAATCTACACACTGTATTA

CTGGAAGTCCTCTTCCTCCGGCAAGAAGACAGCTAAAACCAACACAAAC

GAGTTTTTAATCGACGTGGATAAAGGCGAAAACTACTGTTTCAGCGTGC

AAGCTGTGATCCCCTCCCGGACCGTGAATAGGAAAAGCACCGATAGCCC

CGTTGAGTGCATGGGCCAAGAAAAGGGCGAGTTCCGGGAGAACTGGGTG

AACGTCATCAGCGATTTAAAGAAGATCGAAGATTTAATTCAGTCCATGC

ATATCGACGCCACTTTATACACAGAATCCGACGTGCACCCCTCTTGTAA

GGTGACCGCCATGAAATGTTTTTTACTGGAGCTGCAAGTTATCTCTTTA

GAGAGCGGAGACGCTAGCATCCACGACACCGTGGAGAATTTAATCATTT

TAGCCAATAACTCTTTATCCAGCAACGGCAACGTGACAGAGTCCGGCTG

CAAGGAGTGCGAAGAGCTGGAGGAGAAGAACATCAAGGAGTTTCTGCAA

TCCTTTGTGCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 145)

QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDSITCPPPMSVEHADI

WVKSYSLYSRERYICNSGFKRKAGTSSLTECVLNKATNVAHWTTPSLKC

IR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 146)

CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

-continued

```
TGCAGAAGATGATCCATCAGCACCTGTCCTCCAGGACCCACGGCTCCGA
GGACTCCATTACATGCCCCCCTCCCATGAGCGTGGAGCACGCCGACATC
TGGGTGAAGAGCTATAGCCTCTACAGCCGGGAGAGGTATATCTGTAACA
GCGGCTTCAAGAGGAAGGCCGGCACCAGCAGCCTCACCGAGTGCGTGCT
GAATAAGGCTACCAACGTGGCTCACTGGACAACACCCTCTTTAAAGTGC
ATCCGG.
```

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 147)
MKWVTFISLLFLFSSAYSQGQDRHMIRMRQLIDIVDQLKNYVNDLVPEF
LPAPEDVETNCEWSAFSCFQKAQLKSANTGNNERIINVSIKKLKRKPPS
TNAGRRQKHRLTCPSCDSYEKKPPKEFLERFKSLLQKMIHQHLSSRTHG
SEDSITCPPPMSVEHADIWVKSYSLYSRERYICNSGFKRKAGTSSLTEC
VLNKATNVAHWTTPSLKCIR.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 148)
ATGAAGTGGGTGACCTTCATCAGCCTGCTGTTCCTGTTCTCCAGCGCCT
ACTCCCAGGGCCAGGACAGGCACATGATCCGGATGAGGCAGCTCATCGA
CATCGTCGACCAGCTGAAGAACTACGTGAACGACCTGGTGCCCGAGTTT
CTGCCTGCCCCCGAGGACGTGGAGACCAACTGCGAGTGGTCCGCCTTCT
CCTGCTTTCAGAAGGCCCAGCTGAAGTCCGCCAACACCGGCAACAACGA
GCGGATCATCAACGTGAGCATCAAGAAGCTGAAGCGGAAGCCTCCCTCC
ACAAACGCCGGCAGGAGGCAGAAGCACAGGCTGACCTGCCCCAGCTGTG
ACTCCTACGAGAAGAAGCCCCCCAAGGAGTTCCTGGAGAGGTTCAAGTC
CCTGCTGCAGAAGATGATCCATCAGCACCTGTCCTCCAGGACCCACGGC
TCCGAGGACTCCATTACATGCCCCCCTCCCATGAGCGTGGAGCACGCCG
ACATCTGGGTGAAGAGCTATAGCCTCTACAGCCGGGAGAGGTATATCTG
TAACAGCGGCTTCAAGAGGAAGGCCGGCACCAGCAGCCTCACCGAGTGC
GTGCTGAATAAGGCTACCAACGTGGCTCACTGGACAACACCCTCTTTAA
AGTGCATCCGG.
```

Exemplary Multi-Chain Chimeric Polypeptides—Type E

In some embodiments of any of the multi-chain chimeric polypeptides described herein, the first target-binding domain and the second targeting-binding domain each independently bind specifically to a receptor for IL-18 (e.g., a soluble human IL-18), a receptor for IL-12 (e.g., a soluble human IL-12), or CD16 (e.g., an anti-CD16 scFv). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-12.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, one or both of the first target-binding domain and the second target-binding domain is a soluble IL-15 or a soluble IL-18. In some embodiments of these multi-chain chimeric polypeptides, the first target-binding domain and the second target-binding domain are each independently a soluble IL-15 or a soluble IL-18. In some embodiments of these multi-chain chimeric polypeptides, the first target-binding domain and the second target-binding domain both bind specifically to a receptor of IL-18 or a receptor of IL-12. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain binds specifically to a receptor for IL-12, and the second target-binding domain binds specifically to a receptor for IL-18. In some embodiments of these multi-chain chimeric polypeptides, the first target-binding domain binds specifically to a receptor for IL-18, and the second target-binding domain bind specifically to a receptor for IL-12. In some embodiments of these multi-chain chimeric polypeptides, the first target-binding domain binds specifically to CD16, and the second target-binding domain binds specifically to a receptor for IL-18. In some embodiments of these multi-chain chimeric polypeptides, the first target-binding domain binds specifically to a receptor for IL-18, and the second target-binding domain bind specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-18 (e.g., a soluble human IL-18).

In some embodiments of these multi-chain chimeric polypeptides, the soluble human IL-18 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 41)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNED.
```

In some embodiments of these multi-chain chimeric polypeptides, the soluble human IL-18 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 42)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT.
```

In some embodiments of these multi-chain chimeric polypeptides, the second target-binding domain includes a soluble IL-12 (e.g., a soluble human IL-12). In some embodiments of these multi-chain chimeric polypeptides, the soluble human IL-15 includes a sequence of soluble human IL-120 (p40) and a sequence of soluble human IL-12α (p35). In some embodiments of these multi-chain chimeric polypeptides, the soluble IL-15 (e.g., soluble human IL-15) further includes a linker sequence (e.g., any of the exemplary linker sequences described herein) between the sequence of soluble IL-120 (p40) and the sequence of soluble human IL-12α (p35). In some examples of these multi-chain chimeric polypeptides, the linker sequence comprises

```
                                         (SEQ ID NO: 7)
    GGGGSGGGGSGGGGS.
```

In some embodiments of these multi-chain chimeric polypeptides, the sequence of soluble human IL-120 (p40) comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 33)
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ
```

-continued

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS.

In some embodiments of these multi-chain chimeric polypeptides, the soluble human IL-120 (p40) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 34)
ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

AAGGAGCCCAAGAATAAGACCTTTTTAAGGTGTGAGGCCAAAAACTACA

GCGGTCGTTTCACTTGTTGGTGGCTGACCACCATTTCCACCGATTTAAC

CTTCTCCGTGAAAAGCAGCCGGGGAAGCTCCGACCCTCAAGGTGTGACA

TGTGGAGCCGCTACCCTCAGCGCTGAGAGGGTTCGTGGCGATAACAAGG

AATACGAGTACAGCGTGGAGTGCCAAGAAGATAGCGCTTGTCCCGCTGC

CGAAGAATCTTTACCCATTGAGGTGATGGTGGACGCCGTGCACAAACTC

AAGTACGAGAACTACACCTCCTCCTTCTTTATCCGGGACATCATTAAGC

CCGATCCTCCTAAGAATTTACAGCTGAAGCCTCTCAAAAATAGCCGGCA

AGTTGAGGTCTCTTGGGAATATCCCGACACTTGGAGCACACCCCACAGC

TACTTCTCTTTAACCTTTTGTGTGCAAGTTCAAGGTAAAAGCAAGCGGG

AGAAGAAAGACCGGGTGTTTACCGACAAAACCAGCGCCACCGTCATCTG

TCGGAAGAACGCCTCCATCAGCGTGAGGGCTCAAGATCGTTATTACTCC

AGCAGCTGGTCCGAGTGGGCCAGCGTGCCTTGTTCC.

In some embodiments of these multi-chain chimeric polypeptides, the soluble human IL-12a (p35) includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 35)
RNLPVATPDPGMFPCLHHSQNLLRAVSNMLQKARQTLEFYPCTSEEIDH

EDITKDKTSTVEACLPLELTKNESCLNSRETSFITNGSCLASRKTSFMM

-continued

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

S.

In some embodiments of these multi-chain chimeric polypeptides, the soluble human IL-12a (p35) is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 36)
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC.

In some embodiments of these multi-chain chimeric polypeptides, the additional target-binding domain includes an scFv that specifically binds to CD16 (e.g., an anti-CD16 scFv).

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 149)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 150)
TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

AACAACAGGCCCTCCGGCATCCCTGACAGGTTCTCCGGATCCTCCTCCG

GCAACACCGCCTCCCTGACCATCACAGGCGCTCAGGCCGAGGACGAGGC

TGACTACTACTGCAACTCCAGGGACTCCTCCGGCAACCATGTGGTGTTC

GGCGGCGGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 151)
EVQLVESGGGVVRPGGSLRLSCAASGFTFDDYGMSWVRQAPGKGLEWVS

GINWNGGSTGYADSVKGRFTISRDNAKNSLYLQMNSLRAEDTAVYYCAR

GRSLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 152)
GAGGTGCAGCTGGTGGAGTCCGGAGGAGGAGTGGTGAGGCCTGGAGGCT

CCCTGAGGCTGAGCTGTGCTGCCTCCGGCTTCACCTTCGACGACTACGG

CATGTCCTGGGTGAGGCAGGCTCCTGGAAAGGGCCTGGAGTGGGTGTCC

GGCATCAACTGGAACGGCGGATCCACCGGCTACGCCGATTCCGTGAAGG

GCAGGTTCACCATCAGCAGGGACAACGCCAAGAACTCCCTGTACCTGCA

GATGAACTCCCTGAGGGCCGAGGACACCGCCGTGTACTACTGCGCCAGG

GGCAGGTCCCTGCTGTTCGACTACTGGGGACAGGGCACCCTGGTGACCG

TGTCCAGG.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 116)
YFGKLESKLSVIRNLNQVLFIDQGNRPLFEDMTDSDCRDNAPRTIFIIS

MYKDSQPRGMAVTISVKCEKISTLSCENKIISFKEMNPPDNIKDTKSDI

IFFQRSVPGHDNKMQFESSSYEGYFLACEKERDLFKLILKKEDELGDRS

-continued

IMFTVQNEDSGTTNTVAAYNLTWKSTNFKTILEWEPKPVNQVYTVQIST

KSGDWKSKCFYTTDTECDLTDEIVKDVKQTYLARVFSYPAGNVESTGSA

GEPLYENSPEFTPYLETNLGQPTIQSFEQVGTKVNVTVEDERTLVRRNN

TFLSLRDVFGKDLIYTLYYWKSSSSGKKTAKTNTNEFLIDVDKGENYCF

SVQAVIPSRTVNRKSTDSPVECMGQEKGEFRENWVNVISDLKKIEDLIQ

SMHIDATLYTESDVHPSCKVTAMKCFLLELQVISLESGDASIHDTVENL

IILANNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 117)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGATAGCGGCACAACCAACACAG

TCGCTGCCTATAACCTCACTTGGAAGAGCACCAACTTCAAAACCATCCT

CGAATGGGAACCCAAACCCGTTAACCAAGTTTACACCGTGCAGATCAGC

ACCAAGTCCGGCGACTGGAAGTCCAAATGTTTCTATACCACCGACACCG

AGTGCGATCTCACCGATGAGATCGTGAAAGATGTGAAACAGACCTACCT

CGCCCGGGTGTTTAGCTACCCCGCCGGCAATGTGGAGAGCACTGGTTCC

GCTGGCGAGCCTTTATACGAGAACAGCCCCGAATTTACCCCTTACCTCG

AGACCAATTTAGGACAGCCCACCATCCAAAGCTTTGAGCAAGTTGGCAC

AAAGGTGAATGTGACAGTGGAGGACGAGCGGACTTTAGTGCGGCGGAAC

AACACCTTTCTCAGCCTCCGGGATGTGTTCGGCAAAGATTTAATCTACA

CACTGTATTACTGGAAGTCCTCTTCCTCCGGCAAGAAGACAGCTAAAAC

CAACACAAACGAGTTTTTAATCGACGTGGATAAAGGCGAAAACTACTGT

TTCAGCGTGCAAGCTGTGATCCCCTCCCGGACCGTGAATAGGAAAAGCA

CCGATAGCCCCGTTGAGTGCATGGGCCAAGAAAAGGGCGAGTTCCGGGA

GAACTGGGTGAACGTCATCAGCGATTTAAAGAAGATCGAAGATTTAATT

CAGTCCATGCATATCGACGCCACTTTATACACAGAATCCGACGTGCACC

CCTCTTGTAAGGTGACCGCCATGAAATGTTTTTTACTGGAGCTGCAAGT

TATCTCTTTAGAGAGCGGAGACGCTAGCATCCACGACACCGTGGAGAAT

-continued

TTAATCATTTTAGCCAATAACTCTTTATCCAGCAACGGCAACGTGACAG

AGTCCGGCTGCAAGGAGTGCGAAGAGCTGGAGGAGAAGAACATCAAGGA

GTTTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 118)

MKWVTFISLLFLFSSAYSYFGKLESKLSVIRNLNDQVLFIDQGNRPLFE

DMTDSDCRDNAPRTIFIISMYKDSQPRGMAVTISVKCEKISTLSCENKI

ISFKEMNPPDNIKDTKSDIIFFQRSVPGHDNKMQFESSSYEGYFLACEK

ERDLFKLILKKEDELGDRSIMFTVQNEDSGTTNTVAAYNLTWKSTNFKT

ILEWEPKPVNQVYTVQISTKSGDWKSKCFYTTDTECDLTDEIVKDVKQT

YLARVFSYPAGNVESTGSAGEPLYENSPEFTPYLETNLGQPTIQSFEQV

GTKVNVTVEDERTLVRRNNTFLSLRDVFGKDLIYTLYYWKSSSSGKKTA

KTNTNEFLIDVDKGENYCFSVQAVIPSRTVNRKSTDSPVECMGQEKGEF

RENWVNVISDLKKIEDLIQSMHIDATLYTESDVHPSCKVTAMKCFLLEL

QVISLESGDASIHDTVENLIILANNSLSSNGNVTESGCKECEELEEKNI

KEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 119)

ATGAAGTGGGTCACATTTATCTCTTTACTGTTCCTCTTCTCCAGCGCCT

ACAGCTACTTCGGCAAACTGGAATCCAAGCTGAGCGTGATCCGGAATTT

AAACGACCAAGTTCTGTTTATCGATCAAGGTAACCGGCCTCTGTTCGAG

GACATGACCGACTCCGATTGCCGGGACAATGCCCCCCGGACCATCTTCA

TTATCTCCATGTACAAGGACAGCCAGCCCCGGGGCATGGCTGTGACAAT

TAGCGTGAAGTGTGAGAAAATCAGCACTTTATCTTGTGAGAACAAGATC

ATCTCCTTTAAGGAAATGAACCCCCCCGATAACATCAAGGACACCAAGT

CCGATATCATCTTCTTCCAGCGGTCCGTGCCCGGTCACGATAACAAGAT

GCAGTTCGAATCCTCCTCCTACGAGGGCTACTTTTTAGCTTGTGAAAAG

GAGAGGGATTTATTCAAGCTGATCCTCAAGAAGGAGGACGAGCTGGGCG

ATCGTTCCATCATGTTCACCGTCCAAAACGAGGATAGCGGCACAACCAA

CACAGTCGCTGCCTATAACCTCACTTGGAAGAGCACCAACTTCAAAACC

ATCCTCGAATGGGAACCCAAACCCGTTAACCAAGTTTACACCGTGCAGA

TCAGCACCAAGTCCGGCGACTGGAAGTCCAAATGTTTCTATACCACCGA

CACCGAGTGCGATCTCACCGATGAGATCGTGAAAGATGTGAAACAGACC

-continued

TACCTCGCCCGGGTGTTTAGCTACCCCGCCGGCAATGTGGAGAGCACTG

GTTCCGCTGGCGAGCCTTTATACGAGAACAGCCCCGAATTTACCCCTTA

CCTCGAGACCAATTTAGGACAGCCCACCATCCAAAGCTTTGAGCAAGTT

GGCACAAAGGTGAATGTGACAGTGGAGGACGAGCGGACTTTAGTGCGGC

GGAACAACACCTTTCTCAGCCTCCGGGATGTGTTCGGCAAAGATTTAAT

CTACACACTGTATTACTGGAAGTCCTCTTCCTCCGGCAAGAAGACAGCT

AAAACCAACACAAACGAGTTTTTAATCGACGTGGATAAAGGCGAAAACT

ACTGTTTCAGCGTGCAAGCTGTGATCCCCTCCCGGACCGTGAATAGGAA

AAGCACCGATAGCCCCGTTGAGTGCATGGGCCAAGAAAAGGGCGAGTTC

CGGGAGAACTGGGTGAACGTCATCAGCGATTTAAAGAAGATCGAAGATT

TAATTCAGTCCATGCATATCGACGCCACTTTATACACAGAATCCGACGT

GCACCCCTCTTGTAAGGTGACCGCCATGAAATGTTTTTTACTGGAGCTG

CAAGTTATCTCTTTAGAGAGCGGAGACGCTAGCATCCACGACACCGTGG

AGAATTTAATCATTTTAGCCAATAACTCTTTATCCAGCAACGGCAACGT

GACAGAGTCCGGCTGCAAGGAGTGCGAAGAGCTGGAGGAGAAGAACATC

AAGGAGTTTCTGCAATCCTTTGTGCACATTGTCCAGATGTTCATCAATA

CCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 153)

IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCSGGGGSGGGGSGGGGSRNLPVATPDPGMFPCLHHSQNL

LRAVSNMLQKARQTLEFYPCTSEEIDHEDITKDKTSTVEACLPLELTKN

ESCLNSRETSFITNGSCLASRKTSFMMALCLSSIYEDLKMYQVEFKTMN

AKLLMDPKRQIFLDQNMLAVIDELMQALNFNSETVPQKSSLEEPDFYKT

KIKLCILLHAFRIRAVTIDRVMSYLNASITCPPPMSVEHADIWVKSYSL

YSRERYICNSGFKRKAGTSSLTECVLNKATNVAHWTTPSLKCIRSELTQ

DPAVSVALGQTVRITCQGDSLRSYYASWYQQKPGQAPVLVIYGKNNRPS

GIPDRFSGSSSGNTASLTITGAQAEDEADYYCNSRDSSGNHVVFGGGTK

LTVGHGGGGSGGGGSGGGGSEVQLVESGGGVVRPGGSLRLSCAASGFTF

DDYGMSWVRQAPGKGLEWVSGINWNGGSTGYADSVKGRFTISRDNAKNS

LYLQMNSLRAEDTAVYYCARGRSLLFDYWGQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 154)
ATTTGGGAACTGAAGAAGGACGTCTACGTGGTCGAACTGGACTGGTATC
CCGATGCTCCCGGCGAAATGGTGGTGCTCACTTGTGACACCCCCGAAGA
AGACGGCATCACTTGGACCCTCGATCAGAGCAGCGAGGTGCTGGGCTCC
GGAAAGACCCTCACAATCCAAGTTAAGGAGTTCGGAGACGCTGGCCAAT
ACACATGCCACAAGGGAGGCGAGGTGCTCAGCCATTCCTTATTATTATT
ACACAAGAAGGAAGACGGAATCTGGTCCACCGACATTTTAAAAGATCAG
AAGGAGCCCAAGAATAAGACCTTTTTAAGGTGTGAGGCCAAAAACTACA
GCGGTCGTTTCACTTGTTGGTGGCTGACCACCATTTCCACCGATTTAAC
CTTCTCCGTGAAAAGCAGCCGGGGAAGCTCCGACCCTCAAGGTGTGACA
TGTGGAGCCGCTACCCTCAGCGCTGAGAGGGTTCGTGGCGATAACAAGG
AATACGAGTACAGCGTGGAGTGCCAAGAAGATAGCGCTTGTCCCGCTGC
CGAAGAATCTTTACCCATTGAGGTGATGGTGGACGCCGTGCACAAACTC
AAGTACGAGAACTACACCTCCTCCTTCTTTATCCGGGACATCATTAAGC
CCGATCCTCCTAAGAATTTACAGCTGAAGCCTCTCAAAAATAGCCGGCA
AGTTGAGGTCTCTTGGGAATATCCCGACACTTGGAGCACACCCCACAGC
TACTTCTCTTTAACCTTTTGTGTGCAAGTTCAAGGTAAAAGCAAGCGGG
AGAAGAAAGACCGGGTGTTTACCGACAAAACCAGCGCCACCGTCATCTG
TCGGAAGAACGCCTCCATCAGCGTGAGGGCTCAAGATCGTTATTACTCC
AGCAGCTGGTCCGAGTGGGCCAGCGTGCCTTGTTCCGGCGGTGGAGGAT
CCGGAGGAGGTGGCTCCGGCGGCGGAGGATCTCGTAACCTCCCCGTGGC
TACCCCCGATCCCGGAATGTTCCCTTGTTTACACCACAGCCAGAATTTA
CTGAGGGCCGTGAGCAACATGCTGCAGAAAGCTAGGCAGACTTTAGAAT
TTTACCCTTGCACCAGCGAGGAGATCGACCATGAAGATATCACCAAGGA
CAAGACATCCACCGTGGAGGCTTGTTTACCTCTGGAGCTGACAAAGAAC
GAGTCTTGTCTCAACTCTCGTGAAACCAGCTTCATCACAAATGGCTCTT
GTTTAGCTTCCCGGAAGACCTCCTTTATGATGGCTTTATGCCTCAGCTC
CATCTACGAGGATTTAAAGATGTACCAAGTGGAGTTCAAGACCATGAAC
GCCAAGCTGCTCATGGACCCTAAACGGCAGATCTTTTTAGACCAGAACA
TGCTGGCTGTGATTGATGAGCTGATGCAAGCTTTAAACTTCAACTCCGA
GACCGTCCCTCAGAAGTCCTCCCTCGAGGAGCCCGATTTTTACAAGACA
AAGATCAAACTGTGCATTTTACTCCACGCCTTTAGGATCCGGGCCGTGA
CCATTGACCGGGTCATGAGCTATTTAAACGCCAGCATTACATGCCCCCC
TCCCATGAGCGTGGAGCACGCCGACATCTGGGTGAAGAGCTATAGCCTC
TACAGCCGGGAGAGGTATATCTGTAACAGCGGCTTCAAGAGGAAGGCCG
GCACCAGCAGCCTCACCGAGTGCGTGCTGAATAAGGCTACCAACGTGGC

-continued
TCACTGGACAACACCCTCTTTAAAGTGCATCCGGTCCGAGCTGACCCAG
GACCCTGCTGTGTCCGTGGCTCTGGGCCAGACCGTGAGGATCACCTGCC
AGGGCGACTCCCTGAGGTCCTACTACGCCTCCTGGTACCAGCAGAAGCC
CGGCCAGGCTCCTGTGCTGGTGATCTACGGCAAGAACAACAGGCCCTCC
GGCATCCCTGACAGGTTCTCCGGATCCTCCTCCGGCAACACCGCCTCCC
TGACCATCACAGGCGCTCAGGCCGAGGACGAGGCTGACTACTACTGCAA
CTCCAGGGACTCCTCCGGCAACCATGTGGTGTTCGGCGGCGGCACCAAG
CTGACCGTGGGCCATGGCGGCGGCGGCTCCGGAGGCGGCGGCAGCGGCG
GAGGAGGATCCGAGGTGCAGCTGGTGGAGTCCGGAGGAGGAGTGGTGAG
GCCTGGAGGCTCCCTGAGGCTGAGCTGTGCTGCCTCCGGCTTCACCTTC
GACGACTACGGCATGTCCTGGGTGAGGCAGGCTCCTGGAAAGGGCCTGG
AGTGGGTGTCCGGCATCAACTGGAACGGCGGATCCACCGGCTACGCCGA
TTCCGTGAAGGGCAGGTTCACCATCAGCAGGGACAACGCCAAGAACTCC
CTGTACCTGCAGATGAACTCCCTGAGGGCCGAGGACACCGCCGTGTACT
ACTGCGCCAGGGGCAGGTCCCTGCTGTTCGACTACTGGGGACAGGGCAC
CCTGGTGACCGTGTCCAGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 155)
MKWVTFISLLFLFSSAYSIWELKKDVYVVELDWYPDAPGEMVVLTCDTP
EEDGITWTLDQSSEVLGSGKTLTIQVKEFGDAGQYTCHKGGEVLSHSLL
LLHKKEDGIWSTDILKDQKEPKNKTFLRCEAKNYSGRFTCWWLTTISTD
LTFSVKSSRGSSDPQGVTCGAATLSAERVRGDNKEYEYSVECQEDSACP
AAEESLPIEVMVDAVHKLKYENYTSSFFIRDIIKPDPPKNLQLKPLKNS
RQVEVSWEYPDTWSTPHSYFSLTFCVQVQGKSKREKKDRVFTDKTSATV
ICRKNASISVRAQDRYYSSSWSEWASVPCSGGGGSGGGGSGGGGSRNLP
VATPDPGMFPCLHHSQNLLRAVSNMLQKARQTLEFYPCTSEEIDHEDIT
KDKTSTVEACLPLELTKNESCLNSRETSFITNGSCLASRKTSFMMALCL
SSIYEDLKMYQVEFKTMNAKLLMDPKRQIFLDQNMLAVIDELMQALNFN
SETVPQKSSLEEPDFYKTKIKLCILLHAFRIRAVTIDRVMSYLNASITC
PPPMSVEHADIWVKSYSLYSRERYICNSGFKRKAGTSSLTECVLNKATN
VAHWTTPSLKCIRSELTQDPAVSVALGQTVRITCQGDSLRSYYASWYQQ
KPGQAPVLVIYGKNNRPSGIPDRFSGSSSGNTASLTITGAQAEDEADYY
CNSRDSSGNHVVFGGGTKLTVGHGGGGSGGGGSGGGGSEVQLVESGGGV
VRPGGSLRLSCAASGFTFDDYGMSWVRQAPGKGLEWVSGINWNGGSTGY
ADSVKGRFTISRDNAKNSLYLQMNSLRAEDTAVYYCARGRSLLFDYWGQ
GTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 156)
ATGAAATGGGTGACCTTTATTTCTTTACTGTTCCTCTTTAGCAGCGCCT
ACTCCATTTGGGAACTGAAGAAGGACGTCTACGTGGTCGAACTGGACTG
GTATCCCGATGCTCCCGGCGAAATGGTGGTGCTCACTTGTGACACCCCC
GAAGAAGACGGCATCACTTGGACCCTCGATCAGAGCAGCGAGGTGCTGG
GCTCCGGAAAGACCCTCACAATCCAAGTTAAGGAGTTCGGAGACGCTGG
CCAATACACATGCCACAAGGGAGGCGAGGTGCTCAGCCATTCCTTATTA
TTATTACACAAGAAGGAAGACGGAATCTGGTCCACCGACATTTTAAAAG
ATCAGAAGGAGCCCAAGAATAAGACCTTTTTAAGGTGTGAGGCCAAAAA
CTACAGCGGTCGTTTCACTTGTTGGTGGCTGACCACCATTTCCACCGAT
TTAACCTTCTCCGTGAAAAGCAGCCGGGGAAGCTCCGACCCTCAAGGTG
TGACATGTGGAGCCGCTACCCTCAGCGCTGAGAGGGTTCGTGGCGATAA
CAAGGAATACGAGTACAGCGTGGAGTGCCAAGAAGATAGCGCTTGTCCC
GCTGCCGAAGAATCTTTACCCATTGAGGTGATGGTGGACGCCGTGCACA
AACTCAAGTACGAGAACTACACCTCCTCCTTCTTTATCCGGGACATCAT
TAAGCCCGATCCTCCTAAGAATTTACAGCTGAAGCCTCTCAAAAATAGC
CGGCAAGTTGAGGTCTCTTGGGAATATCCCGACACTTGGAGCACACCCC
ACAGCTACTTCTCTTTAACCTTTTGTGTGCAAGTTCAAGGTAAAAGCAA
GCGGGAGAAGAAAGACCGGGTGTTTACCGACAAAACCAGCGCCACCGTC
ATCTGTCGGAAGAACGCCTCCATCAGCGTGAGGGCTCAAGATCGTTATT
ACTCCAGCAGCTGGTCCGAGTGGGCCAGCGTGCCTTGTTCCGGCGGTGG
AGGATCCGGAGGAGGTGGCTCCGGCGGCGGAGGATCTCGTAACCTCCCC
GTGGCTACCCCCGATCCCGGAATGTTCCCTTGTTTACACCACAGCCAGA
ATTTACTGAGGGCCGTGAGCAACATGCTGCAGAAAGCTAGGCAGACTTT
AGAATTTTACCCTTGCACCAGCGAGGAGATCGACCATGAAGATATCACC
AAGGACAAGACATCCACCGTGGAGGCTTGTTTACCTCTGGAGCTGACAA
AGAACGAGTCTTGTCTCAACTCTCGTGAAACCAGCTTCATCACAAATGG
CTCTTGTTTAGCTTCCCGGAAGACCTCCTTTATGATGGCTTTATGCCTC
AGCTCCATCTACGAGGATTTAAAGATGTACCAAGTGGAGTTCAAGACCA
TGAACGCCAAGCTGCTCATGGACCCTAAACGGCAGATCTTTTTAGACCA
GAACATGCTGGCTGTGATTGATGAGCTGATGCAAGCTTTAAACTTCAAC
TCCGAGACCGTCCCTCAGAAGTCCTCCCTCGAGGAGCCCGATTTTTACA
AGACAAAGATCAAACTGTGCATTTTACTCCACGCCTTTAGGATCCGGGC
CGTGACCATTGACCGGGTCATGAGCTATTTAAACGCCAGCATTACATGC
CCCCCTCCCATGAGCGTGGAGCACGCCGACATCTGGGTGAAGAGCTATA
GCCTCTACAGCCGGGAGAGGTATATCTGTAACAGCGGCTTCAAGAGGAA
GGCCGGCACCAGCAGCCTCACCGAGTGCGTGCTGAATAAGGCTACCAAC
GTGGCTCACTGGACAACACCCTCTTTAAAGTGCATCCGGTCCGAGCTGA

-continued

CCCAGGACCCTGCTGTGTCCGTGGCTCTGGGCCAGACCGTGAGGATCAC
CTGCCAGGGCGACTCCCTGAGGTCCTACTACGCCTCCTGGTACCAGCAG
AAGCCCGGCCAGGCTCCTGTGCTGGTGATCTACGGCAAGAACAACAGGC
CCTCCGGCATCCCTGACAGGTTCTCCGGATCCTCCTCCGGCAACACCGC
CTCCCTGACCATCACAGGCGCTCAGGCCGAGGACGAGGCTGACTACTAC
TGCAACTCCAGGGACTCCTCCGGCAACCATGTGGTGTTCGGCGGCGGCA
CCAAGCTGACCGTGGGCCATGGCGGCGGCGGCTCCGGAGGCGGCGGCAG
CGGCGGAGGAGGATCCGAGGTGCAGCTGGTGGAGTCCGGAGGAGGAGTG
GTGAGGCCTGGAGGCTCCCTGAGGCTGAGCTGTGCTGCCTCCGGCTTCA
CCTTCGACGACTACGGCATGTCCTGGGTGAGGCAGGCTCCTGGAAAGGG
CCTGGAGTGGGTGTCCGGCATCAACTGGAACGGCGGATCCACCGGCTAC
GCCGATTCCGTGAAGGGCAGGTTCACCATCAGCAGGGACAACGCCAAGA
ACTCCCTGTACCTGCAGATGAACTCCCTGAGGGCCGAGGACACCGCCGT
GTACTACTGCGCCAGGGGCAGGTCCCTGCTGTTCGACTACTGGGGACAG
GGCACCCTGGTGACCGTGTCCAGG.

Exemplary Multi-Chain Chimeric Polypeptides—Type F

In some embodiments of any of the multi-chain chimeric polypeptides described herein, the first target-binding domain and the second targeting-binding domain each independently bind specifically to a receptor for IL-7 (e.g., a soluble human IL-7), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of any of the multi-chain chimeric polypeptides described herein, the first target-binding domain binds specifically to a receptor IL-7 and the second target-binding domain binds specifically to CD16 or a receptor for IL-21. In some embodiments of any of the multi-chain chimeric polypeptides described herein, the first target-binding domain includes a soluble IL-7 protein. In some embodiments of any of the multi-chain chimeric polypeptides described herein, the soluble IL-7 protein is a soluble human IL-7. In some embodiments of any of the multi-chain chimeric polypeptides described herein, the second antigen-binding domain includes a target-binding domain that binds specifically to CD16. In some embodiments of any of the multi-chain chimeric polypeptides described herein, the second target-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a soluble IL-7 (e.g., a soluble human IL-7).

In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 135)
DCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM
GTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 136)
GATTGTGATATTGAAGGTAAAGATGGCAAACAATATGAGAGTGTTCTAA
TGGTCAGCATCGATCAATTATTGGACAGCATGAAAGAAATTGGTAGCAA
TTGCCTGAATAATGAATTTAACTTTTTTAAAAGACATATCTGTGATGCT
AATAAGGAAGGTATGTTTTTATTCCGTGCTGCTCGCAAGTTGAGGCAAT
TTCTTAAAATGAATAGCACTGGTGATTTTGATCTCCACTTATTAAAAGT
TTCAGAAGGCACAACAATACTGTTGAACTGCACTGGCCAGGTTAAAGGA
AGAAAACCAGCTGCCCTGGGTGAAGCCCAACCAACAAAGAGTTTGGAAG
AAAATAAATCTTTAAAGGAACAGAAAAAACTGAATGACTTGTGTTTCCT

-continued

AAAGAGACTATTACAAGAGATAAAAACTTGTTGGAATAAAATTTTGATG

GGCACTAAAGAACAC.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)

GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT.

In some embodiments of these multi-chain chimeric polypeptides, the sequence of soluble human IL-21 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)

QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 134)

CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

-continued

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 125)

CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC

In some embodiments of these multi-chain chimeric polypeptides, the additional target-binding domain includes an scFv that specifically binds to CD16 (e.g., an anti-CD16 scFv).

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 149)

SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 150)

TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

AACAACAGGCCCTCCGGCATCCCTGACAGGTTCTCCGGATCCTCCTCCG

-continued

GCAACACCGCCTCCCTGACCATCACAGGCGCTCAGGCCGAGGACGAGGC

TGACTACTACTGCAACTCCAGGGACTCCTCCGGCAACCATGTGGTGTTC

GGCGGCGGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 151)

EVQLVESGGGVVRPGGSLRLSCAASGFTFDDYGMSWVRQAPGKGLEWVS

GMWNGGSTGYADSVKGRFTISRDNAKNSLYLQMNSLRAEDTAVYYCARG

RSLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 152)

GAGGTGCAGCTGGTGGAGTCCGGAGGAGGAGTGGTGAGGCCTGGAGGCT

CCCTGAGGCTGAGCTGTGCTGCCTCCGGCTTCACCTTCGACGACTACGG

CATGTCCTGGGTGAGGCAGGCTCCTGGAAAGGGCCTGGAGTGGGTGTCC

GGCATCAACTGGAACGGCGGATCCACCGGCTACGCCGATTCCGTGAAGG

GCAGGTTCACCATCAGCAGGGACAACGCCAAGAACTCCCTGTACCTGCA

GATGAACTCCCTGAGGGCCGAGGACACCGCCGTGTACTACTGCGCCAGG

GGCAGGTCCCTGCTGTTCGACTACTGGGGACAGGGCACCCTGGTGACCG

TGTCCAGG.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 141)

DCDIEGKDGKQYESVLMVSIDQLLDSMKEIGSNCLNNEFNEFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEHSGTTNTVAAYNLTWKSTNFKTILEWEPKPVNQVYTVQISTKSGD

WKSKCFYTTDTECDLTDEIVKDVKQTYLARVFSYPAGNVESTGSAGEPL

YENSPEFTPYLETNLGQPTIQSFEQVGTKVNVTVEDERTLVRRNNTFLS

LRDVFGKDLIYTLYYWKSSSSGKKTAKTNTNEFLIDVDKGENYCFSVQA

-continued

VIPSRTVNRKSTDSPVECMGQEKGEFRENWVNVISDLKKIEDLIQSMHI

DATLYTESDVHPSCKVTAMKCFLLELQVISLESGDASIHDTVENLIILA

NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 142)

GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCATAGCGGCACAACCAACACAGTCGCTGCCTATAACC

TCACTTGGAAGAGCACCAACTTCAAAACCATCCTCGAATGGGAACCCAA

ACCCGTTAACCAAGTTTACACCGTGCAGATCAGCACCAAGTCCGGCGAC

TGGAAGTCCAAATGTTTCTATACCACCGACACCGAGTGCGATCTCACCG

ATGAGATCGTGAAAGATGTGAAACAGACCTACCTCGCCCGGGTGTTTAG

CTACCCCGCCGGCAATGTGGAGAGCACTGGTTCCGCTGGCGAGCCTTTA

TACGAGAACAGCCCCGAATTTACCCCTTACCTCGAGACCAATTTAGGAC

AGCCCACCATCCAAAGCTTTGAGCAAGTTGGCACAAAGGTGAATGTGAC

AGTGGAGGACGAGCGGACTTTAGTGCGGCGGAACAACACCTTTCTCAGC

CTCCGGGATGTGTTCGGCAAAGATTTAATCTACACACTGTATTACTGGA

AGTCCTCTTCCTCCGGCAAGAAGACAGCTAAAACCAACACAAACGAGTT

TTTAATCGACGTGGATAAAGGCGAAAACTACTGTTTCAGCGTGCAAGCT

GTGATCCCCTCCCGGACCGTGAATAGGAAAAGCACCGATAGCCCCGTTG

AGTGCATGGGCCAAGAAAAGGGCGAGTTCCGGGAGAACTGGGTGAACGT

CATCAGCGATTTAAAGAAGATCGAAGATTTAATTCAGTCCATGCATATC

GACGCCACTTTATACACAGAATCCGACGTGCACCCCTCTTGTAAGGTGA

CCGCCATGAAATGTTTTTTACTGGAGCTGCAAGTTATCTCTTTAGAGAG

CGGAGACGCTAGCATCCACGACACCGTGGAGAATTTAATCATTTTAGCC

AATAACTCTTTATCCAGCAACGGCAACGTGACAGAGTCCGGCTGCAAGG

AGTGCGAAGAGCTGGAGGAGAAGAACATCAAGGAGTTTCTGCAATCCTT

TGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 143)
MKWVTFISLLFLFSSAYSDCDIEGKDGKQYESVLMVSIDQLLDSMKEIG
SNCLNNEFNEFKRHICDANKEGMELFRAARKLRQFLKMNSTGDFDLHLL
KVSEGTTILLNCTGQVKGRKPAALGEAQPTKSLEENKSLKEQKKLNDLC
FLKRLLQEIKTCWNKILMGTKEHSGTTNTVAAYNLTWKSTNEKTILEWE
PKPVNQVYTVQISTKSGDWKSKCEYTTDTECDLTDEIVKDVKQTYLARV
FSYPAGNVESTGSAGEPLYENSPEFTPYLETNLGQPTIQSFEQVGTKVN
VTVEDERTLVRRNNTELSLRDVEGKDLIYTLYYWKSSSSGKKTAKTNTN
EFLIDVDKGENYCFSVQAVIPSRTVNRKSTDSPVECMGQEKGEFRENWV
NVISDLKKIEDLIQSMHIDATLYTESDVHPSCKVTAMKCELLELQVISL
ESGDASIHDTVENLIILANNSLSSNGNVTESGCKECEELEEKNIKEFLQ
SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 144)
ATGAAGTGGGTGACCTTCATCAGCCTGCTGTTCCTGTTCTCCAGCGCCT
ACTCCGATTGCGACATCGAGGGCAAGGACGGCAAGCAGTACGAGAGCGT
GCTGATGGTGTCCATCGACCAGCTGCTGGACAGCATGAAGGAGATCGGC
TCCAACTGCCTCAACAACGAGTTCAACTTCTTCAAGCGGCACATCTGCG
ACGCCAACAAGGAGGGCATGTTCCTGTTCAGGGCCGCCAGGAAACTGCG
GCAGTTCCTGAAGATGAACTCCACCGGCGACTTCGACCTGCACCTGCTG
AAGGTGTCCGAGGGCACCACCATCCTGCTGAACTGCACCGGACAGGTGA
AGGGCCGGAAACCTGCTGCTCTGGGAGAGGCCCAACCCACCAAGAGCCT
GGAGGAGAACAAGTCCCTGAAGGAGCAGAAGAAGCTGAACGACCTGTGC
TTCCTGAAGAGGCTGCTGCAGGAGATCAAGACCTGCTGGAACAAGATCC
TGATGGGCACCAAGGAGCATAGCGGCACAACCAACACAGTCGCTGCCTA
TAACCTCACTTGGAAGAGCACCAACTTCAAAACCATCCTCGAATGGGAA
CCCAAACCCGTTAACCAAGTTTACACCGTGCAGATCAGCACCAAGTCCG
GCGACTGGAAGTCCAAATGTTTCTATACCACCGACACCGAGTGCGATCT
CACCGATGAGATCGTGAAAGATGTGAAACAGACCTACCTCGCCCGGGTG
TTTAGCTACCCCGCCGGCAATGTGGAGAGCACTGGTTCCGCTGGCGAGC
CTTTATACGAGAACAGCCCCGAATTTACCCCTTACCTCGAGACCAATTT
AGGACAGCCCACCATCCAAAGCTTTGAGCAAGTTGGCACAAAGGTGAAT
GTGACAGTGGAGGACGAGCGGACTTTAGTGCGGCGGAACAACACCTTTC
TCAGCCTCCGGGATGTGTTCGGCAAAGATTTAATCTACACACTGTATTA

-continued
CTGGAAGTCCTCTTCCTCCGGCAAGAAGACAGCTAAAACCAACACAAAC
GAGTTTTTAATCGACGTGGATAAAGGCGAAAACTACTGTTTCAGCGTGC
AAGCTGTGATCCCCTCCCGGACCGTGAATAGGAAAAGCACCGATAGCCC
CGTTGAGTGCATGGGCCAAGAAAAGGGCGAGTTCCGGGAGAACTGGGTG
AACGTCATCAGCGATTTAAAGAAGATCGAAGATTTAATTCAGTCCATGC
ATATCGACGCCACTTTATACACAGAATCCGACGTGCACCCCTCTTGTAA
GGTGACCGCCATGAAATGTTTTTTACTGGAGCTGCAAGTTATCTCTTTA
GAGAGCGGAGACGCTAGCATCCACGACACCGTGGAGAATTTAATCATTT
TAGCCAATAACTCTTTATCCAGCAACGGCAACGTGACAGAGTCCGGCTG
CAAGGAGTGCGAAGAGCTGGAGGAGAAGAACATCAAGGAGTTTCTGCAA
TCCTTTGTGCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 157)
SELTQDPAVSVALGQTVRITCQGDSLRSYYASWYQQKPGQAPVLVIYGK
NNRPSGIPDRFSGSSSGNTASLTITGAQAEDEADYYCNSRDSSGNHVVF
GGGTKLTVGHGGGGSGGGGSGGGGSEVQLVESGGGVVRPGGSLRLSCAA
SGFFDDYGMSWVRQAPGKGLEWVSGINWNGGSTGYADSVKGRFTISRDN
AKNSLYLQMNSLRAEDTAVYYCARGRSLLFDYWGQGTLVTVSRITCPPP
MSVEHADIWVKSYSLYSRERYICNSGFKRKAGTSSLTECVLNKATNVAH
WTTPSLKCIRQGQDRHMIRMRQLIDIVDQLKNYVNDLVPEFLPAPEDVE
TNCEWSAFSCFQKAQLKSANTGNNERIINVSIKKLKRKPPSTNAGRRQK
HRLTCPSCDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 158)
TCCGAGCTGACCCAGGACCCTGCTGTGTCCGTGGCTCTGGGCCAGACCG
TGAGGATCACCTGCCAGGGCGACTCCCTGAGGTCCTACTACGCCTCCTG
GTACCAGCAGAAGCCCGGCCAGGCTCCTGTGCTGGTGATCTACGGCAAG
AACAACAGGCCCTCCGGCATCCCTGACAGGTTCTCCGGATCCTCCTCCG
GCAACACCGCCTCCCTGACCATCACAGGCGCTCAGGCCGAGGACGAGGC
TGACTACTACTGCAACTCCAGGGACTCCTCCGGCAACCATGTGGTGTTC
GGCGGCGGCACCAAGCTGACCGTGGGCCATGGCGGCGGCGGCTCCGGAG
GCGGCGGCAGCGGCGGAGGAGGATCCGAGGTGCAGCTGGTGGAGTCCGG
AGGAGGAGTGGTGAGGCCTGGAGGCTCCCTGAGGCTGAGCTGTGCTGCC

-continued

TCCGGCTTCACCTTCGACGACTACGGCATGTCCTGGGTGAGGCAGGCTC

CTGGAAAGGGCCTGGAGTGGGTGTCCGGCATCAACTGGAACGGCGGATC

CACCGGCTACGCCGATTCCGTGAAGGGCAGGTTCACCATCAGCAGGGAC

AACGCCAAGAACTCCCTGTACCTGCAGATGAACTCCCTGAGGGCCGAGG

ACACCGCCGTGTACTACTGCGCCAGGGGCAGGTCCCTGCTGTTCGACTA

CTGGGGACAGGGCACCCTGGTGACCGTGTCCAGGATTACATGCCCCCCT

CCCATGAGCGTGGAGCACGCCGACATCTGGGTGAAGAGCTATAGCCTCT

ACAGCCGGGAGAGGTATATCTGTAACAGCGGCTTCAAGAGGAAGGCCGG

CACCAGCAGCCTCACCGAGTGCGTGCTGAATAAGGCTACCAACGTGGCT

CACTGGACAACACCCTCTTTAAAGTGCATCCGGCAGGGCCAGGACAGGC

ACATGATCCGGATGAGGCAGCTCATCGACATCGTCGACCAGCTGAAGAA

CTACGTGAACGACCTGGTGCCCGAGTTTCTGCCTGCCCCCGAGGACGTG

GAGACCAACTGCGAGTGGTCCGCCTTCTCCTGCTTTCAGAAGGCCCAGC

TGAAGTCCGCCAACACCGGCAACAACGAGCGGATCATCAACGTGAGCAT

CAAGAAGCTGAAGCGGAAGCCTCCCTCCACAAACGCCGGCAGGAGGCAG

AAGCACAGGCTGACCTGCCCCAGCTGTGACTCCTACGAGAAGAAGCCCC

CCAAGGAGTTCCTGGAGAGGTTCAAGTCCCTGCTGCAGAAGATGATCCA

TCAGCACCTGTCCTCCAGGACCCACGGCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 159)

MKWVTFISLLFLFSSAYSSELTQDPAVSVALGQTVRITCQGDSLRSYYA

SWYQQKPGQAPVLVIYGKNNRPSGIPDRFSGSSSGNTASLTITGAQAED

EADYYCNSRDSSGNHVVFGGGTKLTVGHGGGGSGGGGSGGGGSEVQLVE

SGGGVVRPGGSLRLSCAASGFTFDDYGMSWVRQAPGKGLEWVSGINWNG

GSTGYADSVKGRFTISRDNAKNSLYLQMNSLRAEDTAVYYCARGRSLLF

DYWGQGTLVTVSRITCPPPMSVEHADIWVKSYSLYSRERYICNSGFKRK

AGTSSLTECVLNKATNVAHWTTPSLKCIRQGQDRHMIRMIRQLIDIVDQ

LKNYVNDLVPEFLPAPEDVETNCEWSAFSCFQKAQLKSANTGNNERIIN

VSIKKLKRKPPSTNAGRRQKHRLTCPSCDSYEKKPPKEFLERFKSLLQK

MIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 160)

ATGAAGTGGGTGACCTTCATCAGCCTGCTGTTCCTGTTCTCCAGCGCCT

ACTCCTCCGAGCTGACCCAGGACCCTGCTGTGTCCGTGGCTCTGGGCCA

GACCGTGAGGATCACCTGCCAGGGCGACTCCCTGAGGTCCTACTACGCC

TCCTGGTACCAGCAGAAGCCCGGCCAGGCTCCTGTGCTGGTGATCTACG

GCAAGAACAACAGGCCCTCCGGCATCCCTGACAGGTTCTCCGGATCCTC

CTCCGGCAACACCGCCTCCCTGACCATCACAGGCGCTCAGGCCGAGGAC

GAGGCTGACTACTACTGCAACTCCAGGGACTCCTCCGGCAACCATGTGG

TGTTCGGCGGCGGCACCAAGCTGACCGTGGGCCATGGCGGCGGCGGCTC

CGGAGGCGGCGGCAGCGGCGGAGGAGGATCCGAGGTGCAGCTGGTGGAG

TCCGGAGGAGGAGTGGTGAGGCCTGGAGGCTCCCTGAGGCTGAGCTGTG

CTGCCTCCGGCTTCACCTTCGACGACTACGGCATGTCCTGGGTGAGGCA

GGCTCCTGGAAAGGGCCTGGAGTGGGTGTCCGGCATCAACTGGAACGGC

GGATCCACCGGCTACGCCGATTCCGTGAAGGGCAGGTTCACCATCAGCA

GGGACAACGCCAAGAACTCCCTGTACCTGCAGATGAACTCCCTGAGGGC

CGAGGACACCGCCGTGTACTACTGCGCCAGGGGCAGGTCCCTGCTGTTC

GACTACTGGGGACAGGGCACCCTGGTGACCGTGTCCAGGATTACATGCC

CCCCTCCCATGAGCGTGGAGCACGCCGACATCTGGGTGAAGAGCTATAG

CCTCTACAGCCGGGAGAGGTATATCTGTAACAGCGGCTTCAAGAGGAAG

GCCGGCACCAGCAGCCTCACCGAGTGCGTGCTGAATAAGGCTACCAACG

TGGCTCACTGGACAACACCCTCTTTAAAGTGCATCCGGCAGGGCCAGGA

CAGGCACATGATCCGGATGAGGCAGCTCATCGACATCGTCGACCAGCTG

AAGAACTACGTGAACGACCTGGTGCCCGAGTTTCTGCCTGCCCCCGAGGA

CGTGGAGACCAACTGCGAGTGGTCCGCCTTCTCCTGCTTTCAGAAGGCC

CAGCTGAAGTCCGCCAACACCGGCAACAACGAGCGGATCATCAACGTGA

GCATCAAGAAGCTGAAGCGGAAGCCTCCCTCCACAAACGCCGGCAGGAG

GCAGAAGCACAGGCTGACCTGCCCCAGCTGTGACTCCTACGAGAAGAAG

CCCCCCAAGGAGTTCCTGGAGAGGTTCAAGTCCCTGCTGCAGAAGATGA

TCCATCAGCACCTGTCCTCCAGGACCCACGGCTCCGAGGACTCC.

Exemplary Multi-Chain Chimeric Polypeptides—Type G

In some embodiments of any of the multi-chain chimeric polypeptides described herein, the first target-binding domain and the second targeting-binding domain each independently bind specifically to TGF-β (e.g., a human TGFβRII receptor), CD16 (e.g., an anti-CD16 scFv), or a receptor for IL-21 (e.g., a soluble human IL-21). In some embodiments of these multi-chain chimeric polypeptides described herein, the first chimeric polypeptide further includes the additional target-binding domain. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 or a receptor for IL-21.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional antigen-binding domain is an agonistic antigen-binding domain. In some embodiments of these multi-chain chimeric polypeptides, the first target-binding domain, the second target-binding domain, and the additional antigen-binding domain are each agonistic antigen-binding domains. In some embodiments of these multi-chain chimeric polypeptides, the antigen-binding domain includes a scFv or single-domain antibody.

In some embodiments of any of the multi-chain chimeric polypeptides described herein, the first target-binding domain and the second targeting-binding domain each independently bind specifically to TGF-β, CD16, or a receptor for IL-21. In some embodiments of any of the multi-chain chimeric polypeptides described herein, the first target-binding domain binds specifically to a TGF-β and the second target-binding domain binds specifically to CD16 or a receptor of IL-21. In some embodiments of any of the multi-chain chimeric polypeptides described herein, the first target-binding domain is a soluble TGF-β receptor. In some embodiments of any of the multi-chain chimeric polypeptides described herein, soluble TGF-β receptor is a soluble TGFβRII receptor. In some embodiments of any of the multi-chain chimeric polypeptides described herein, the second target-binding domain binds specifically to CD16. In some embodiments of any of the multi-chain chimeric polypeptides described herein, the second antigen-binding domain includes an antigen-binding domain that binds specifically to CD16. In some embodiments of any of the multi-chain chimeric polypeptides described herein, the second antigen-binding domain includes an scFv that binds specifically to CD16. In some embodiments of any of the multi-chain chimeric polypeptides described herein, the second target-binding domain binds specifically to a receptor for IL-21. In some embodiments of any of the multi-chain chimeric polypeptides described herein, the second target-binding domain includes a soluble IL-21. In some embodiments of any of the multi-chain chimeric polypeptides described herein, the second target-binding domain includes a soluble human IL-21. In some embodiments of any of the multi-chain chimeric polypeptides described herein, the second chimeric polypeptide further includes an additional target-binding domain that binds specifically to a receptor for IL-21. In some embodiments of any of the multi-chain chimeric polypeptides described herein, the additional target-binding domain includes a soluble IL-21. In some embodiments of any of the multi-chain chimeric polypeptides described herein, the soluble IL-21 is a soluble human IL-21. In some embodiments of any of the multi-chain chimeric polypeptides described herein, the second chimeric polypeptide further includes an additional target-binding domain that binds specifically to CD16.

In some embodiments of these multi-chain chimeric polypeptides, two or more of the first target-binding domain, the second target-binding domain, and the one or more additional target-binding domains bind specifically to the same antigen. In some embodiments, two or more of the first target-binding domain, the second target-binding domain, and the one or more additional target-binding domains bind specifically to the same epitope. In some embodiments, two or more of the first target-binding domain, the second target-binding domain, and the one or more additional target-binding domains comprise the same amino acid sequence.

In some embodiments of these multi-chain chimeric polypeptides, the first target-binding domain includes a TGFβRII receptor (e.g., a soluble human TGFβRII receptor). In some embodiments of these multi-chain chimeric polypeptides, the soluble human TGF-βRII includes a first sequence of soluble human TGF-β RII and a second sequence of soluble human TGF-β RII. In some embodiments of these multi-chain chimeric polypeptides, the soluble human TGF-βRII includes a linker disposed between the first sequence of soluble human TGF-β RII and the second sequence of soluble human TGF-β RII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 60)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD.

In some embodiments of these multi-chain chimeric polypeptides, the soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

-continued

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC.

In some embodiments of these multi-chain chimeric polypeptides, the sequence of soluble human IL-21 comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 134)
CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCC.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 125)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

-continued

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC.

In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 149)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 150)
TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

AACAACAGGCCCTCCGGCATCCCTGACAGGTTCTCCGGATCCTCCTCCG

GCAACACCGCCTCCCTGACCATCACAGGCGCTCAGGCCGAGGACGAGGC

TGACTACTACTGCAACTCCAGGGACTCCTCCGGCAACCATGTGGTGTTC

GGCGGCGGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 151)
EVQLVESGGGVVRPGGSLRLSCAASGFTFDDYGMSWVRQAPGKGLEWVS

GMWNGGSTGYADSVKGRFTISRDNAKNSLYLQMNSLRAEDTAVYYCARG

RSLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 152)

GAGGTGCAGCTGGTGGAGTCCGGAGGAGGAGTGGTGAGGCCTGGAGGCT
CCCTGAGGCTGAGCTGTGCTGCCTCCGGCTTCACCTTCGACGACTACGG
CATGTCCTGGGTGAGGCAGGCTCCTGGAAAGGGCCTGGAGTGGGTGTCC
GGCATCAACTGGAACGGCGGATCCACCGGCTACGCCGATTCCGTGAAGG
GCAGGTTCACCATCAGCAGGGACAACGCCAAGAACTCCCTGTACCTGCA
GATGAACTCCCTGAGGGCCGAGGACACCGCCGTGTACTACTGCGCCAGG
GGCAGGTCCCTGCTGTTCGACTACTGGGGACAGGGCACCCTGGTGACCG
TGTCCAGG.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)

IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPDSGTTNTV
AAYNLTWKSTNFKTILEWEPKPVNQVYTVQISTKSGDWKSKCFYTTDTE
CDLTDEIVKDVKQTYLARVFSYPAGNVESTGSAGEPLYENSPEFTPYLE
TNLGQPTIQSFEQVGTKVNVTVEDERTLVRRNNTFLSLRDVFGKDLIYT
LYYWKSSSSGKKTAKTNTNEFLIDVDKGENYCFSVQAVIPSRTVNRKST
DSPVECMGQEKGEFRENWVNVISDLKKIEDLIQSMHIDATLYTESDVHP
SCKVTAMKCFLLELQVISLESGDASIHDTVENLIILANNSLSSNGNVTE
SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)

ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA

-continued

GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGACAGCGGCACAACCAACACAGTC
GCTGCCTATAACCTCACTTGGAAGAGCACCAACTTCAAAACCATCCTCG
AATGGGAACCCAAACCCGTTAACCAAGTTTACACCGTGCAGATCAGCAC
CAAGTCCGGCGACTGGAAGTCCAAATGTTTCTATACCACCGACACCGAG
TGCGATCTCACCGATGAGATCGTGAAAGATGTGAAACAGACCTACCTCG
CCCGGGTGTTTAGCTACCCCGCCGGCAATGTGGAGAGCACTGGTTCCGC
TGGCGAGCCTTTATACGAGAACAGCCCCGAATTTACCCCTTACCTCGAG
ACCAATTTAGGACAGCCCACCATCCAAAGCTTTGAGCAAGTTGGCACAA
AGGTGAATGTGACAGTGGAGGACGAGCGGACTTTAGTGCGGCGGAACAA
CACCTTTCTCAGCCTCCGGGATGTGTTCGGCAAAGATTTAATCTACACA
CTGTATTACTGGAAGTCCTCTTCCTCCGGCAAGAAGACAGCTAAAACCA
ACACAAACGAGTTTTTAATCGACGTGGATAAAGGCGAAAACTACTGTTT
CAGCGTGCAAGCTGTGATCCCCTCCCGGACCGTGAATAGGAAAAGCACC
GATAGCCCCGTTGAGTGCATGGGCCAAGAAAAGGGCGAGTTCCGGGAGA
ACTGGGTGAACGTCATCAGCGATTTAAAGAAGATCGAAGATTTAATTCA
GTCCATGCATATCGACGCCACTTTATACACAGAATCCGACGTGCACCCC
TCTTGTAAGGTGACCGCCATGAAATGTTTTTTACTGGAGCTGCAAGTTA
TCTCTTTAGAGAGCGGAGACGCTAGCATCCACGACACCGTGGAGAATTT
AATCATTTTAGCCAATAACTCTTTATCCAGCAACGGCAACGTGACAGAG
TCCGGCTGCAAGGAGTGCGAAGAGCTGGAGGAGAAGAACATCAAGGAGT
TTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)

MKWVTFISLLFLFSSAYSIPPHVQKSVNNDMIVTDNNGAVKFPQLCKFC
DVRFSTCDNQKSCMSNCSITSICEKPQEVCVAVWRKNDENITLETVCHD

-continued

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDSGTTNTVAAYNLTWKSTNFKTILEWEPKPVNQVYTVQI

STKSGDWKSKCFYTTDTECDLTDEIVKDVKQTYLARVFSYPAGNVESTG

SAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENY

CFSVQAVIPSRTVNRKSTDSPVECMGQEKGEFRENWVNVISDLKKIEDL

IQSMHIDATLYTESDVHPSCKVTAMKCFLLELQVISLESGDASIHDTVE

NLIILANNSLSSNGNVTESGCKECEELEEKNIKEFLQSFVHIVQMFINT

S.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)

ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGCG

ATGTCAGGTTCAGCACCTGCGATAATCAGAAGTCCTGCATGTCCAACTGC

AGCATCACCTCCATCTGCGAGAAGCCCCAAGAAGTGTGCGTGGCCGTGTG

GCGGAAAAATGACGAGAACATCACCCTGGAGACCGTGTGTCACGACCCCA

AGCTCCCTTATCACGACTTCATTCTGGAGGACGCTGCCTCCCCCAAATGC

ATCATGAAGGAGAAGAAGAAGCCCGGAGAGACCTTCTTTATGTGTTCCTG

TAGCAGCGACGAGTGTAACGACAACATCATCTTCAGCGAAGAGTACAACA

CCAGCAACCCTGATGGAGGTGGCGGATCCGGAGGTGGAGGTTCTGGTGGA

GGTGGGAGTATTCCTCCCCACGTGCAGAAGAGCGTGAATAATGACATGAT

CGTGACCGATAACAATGGCGCCGTGAAATTTCCCCAGCTGTGCAAATTCT

GCGATGTGAGGTTTTCCACCTGCGACAACCAGAAGTCCTGTATGAGCAAC

TGCTCCATCACCTCCATCTGTGAGAAGCCTCAGGAGGTGTGCGTGGCTGT

CTGGCGGAAGAATGACGAGAATATCACCCTGGAAACCGTCTGCCACGATC

CCAAGCTGCCCTACCACGATTTCATCCTGGAAGACGCCGCCAGCCCTAAG

TGCATCATGAAAGAGAAAAAGAAGCCTGGCGAGACCTTTTTCATGTGCTC

CTGCAGCAGCGACGAATGCAACGACAATATCATCTTTAGCGAGGAATACA

ATACCAGCAACCCCGACAGCGGCACAACCAACACAGTCGCTGCCTATAAC

CTCACTTGGAAGAGCACCAACTTCAAAACCATCCTCGAATGGGAACCCAA

ACCCGTTAACCAAGTTTACACCGTGCAGATCAGCACCAAGTCCGGCGACT

GGAAGTCCAAATGTTTCTATACCACCGACACCGAGTGCGATCTCACCGAT

GAGATCGTGAAAGATGTGAAACAGACCTACCTCGCCCGGGTGTTTAGCTA

CCCCGCCGGCAATGTGGAGAGCACTGGTTCCGCTGGCGAGCCTTTATACG

AGAACAGCCCCGAATTTACCCCTTACCTCGAGACCAATTTAGGACAGCCC

ACCATCCAAAGCTTTGAGCAAGTTGGCACAAAGGTGAATGTGACAGTGGA

GGACGAGCGGACTTTAGTGCGGCGGAACAACACCTTTCTCAGCCTCCGGG

ATGTGTTCGGCAAAGATTTAATCTACACACTGTATTACTGGAAGTCCTCT

TCCTCCGGCAAGAAGACAGCTAAAACCAACACAAACGAGTTTTTAATCGA

CGTGGATAAAGGCGAAAACTACTGTTTCAGCGTGCAAGCTGTGATCCCCT

CCCGGACCGTGAATAGGAAAAGCACCGATAGCCCCGTTGAGTGCATGGGC

CAAGAAAAGGGCGAGTTCCGGGAGAACTGGGTGAACGTCATCAGCGATTT

AAAGAAGATCGAAGATTTAATTCAGTCCATGCATATCGACGCCACTTTAT

ACACAGAATCCGACGTGCACCCCTCTTGTAAGGTGACCGCCATGAAATGT

TTTTTACTGGAGCTGCAAGTTATCTCTTTAGAGAGCGGAGACGCTAGCAT

CCACGACACCGTGGAGAATTTAATCATTTTAGCCAATAACTCTTTATCCA

GCAACGGCAACGTGACAGAGTCCGGCTGCAAGGAGTGCGAAGAGCTGGAG

GAGAAGAACATCAAGGAGTTTCTGCAATCCTTTGTGCACATTGTCCAGAT

GTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 157)

SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGHGGGGSGGGGSGGGGSEVQLVESGGGVVRPGGSLRLSCAA

SGFTFDDYGMSWVRQAPGKGLEWVSGINWNGGSTGYADSVKGRFTISRD

NAKNSLYLQMNSLRAEDTAVYYCARGRSLLFDYWGQGTLVTVSRITCPP

PMSVEHADIWVKSYSLYSRERYICNSGFKRKAGTSSLTECVLNKATNVA

HWTTPSLKCIRQGQDRHMIRMRQLIDIVDQLKNYVNDLVPEFLPAPEDV

ETNCEWSAFSCFQKAQLKSANTGNNERIINVSIKKLKRKPPSTNAGRRQ

KHRLTCPSCDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 158)

TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

-continued

AACAACAGGCCCTCCGGCATCCCTGACAGGTTCTCCGGATCCTCCTCCG
GCAACACCGCCTCCCTGACCATCACAGGCGCTCAGGCCGAGGACGAGGC
TGACTACTACTGCAACTCCAGGGACTCCTCCGGCAACCATGTGGTGTTC
GGCGGCGGCACCAAGCTGACCGTGGGCCATGGCGGCGGCGGCTCCGGAG
GCGGCGGCAGCGGCGGAGGAGGATCCGAGGTGCAGCTGGTGGAGTCCGG
AGGAGGAGTGGTGAGGCCTGGAGGCTCCCTGAGGCTGAGCTGTGCTGCC
TCCGGCTTCACCTTCGACGACTACGGCATGTCCTGGGTGAGGCAGGCTC
CTGGAAAGGGCCTGGAGTGGGTGTCCGGCATCAACTGGAACGGCGGATC
CACCGGCTACGCCGATTCCGTGAAGGGCAGGTTCACCATCAGCAGGGAC
AACGCCAAGAACTCCCTGTACCTGCAGATGAACTCCCTGAGGGCCGAGG
ACACCGCCGTGTACTACTGCGCCAGGGGCAGGTCCCTGCTGTTCGACTA
CTGGGGACAGGGCACCCTGGTGACCGTGTCCAGGATTACATGCCCCCCT
CCCATGAGCGTGGAGCACGCCGACATCTGGGTGAAGAGCTATAGCCTCT
ACAGCCGGGAGAGGTATATCTGTAACAGCGGCTTCAAGAGGAAGGCCGG
CACCAGCAGCCTCACCGAGTGCGTGCTGAATAAGGCTACCAACGTGGCT
CACTGGACAACACCCTCTTTAAAGTGCATCCGGCAGGGCCAGGACAGGC
ACATGATCCGGATGAGGCAGCTCATCGACATCGTCGACCAGCTGAAGAA
CTACGTGAACGACCTGGTGCCCGAGTTTCTGCCTGCCCCCGAGGACGTG
GAGACCAACTGCGAGTGGTCCGCCTTCTCCTGCTTTCAGAAGGCCCAGC
TGAAGTCCGCCAACACCGGCAACAACGAGCGGATCATCAACGTGAGCAT
CAAGAAGCTGAAGCGGAAGCCTCCCTCCACAAACGCCGGCAGGAGGCAG
AAGCACAGGCTGACCTGCCCCAGCTGTGACTCCTACGAGAAGAAGCCCC
CCAAGGAGTTCCTGGAGAGGTTCAAGTCCCTGCTGCAGAAGATGATCCA
TCAGCACCTGTCCTCCAGGACCCACGGCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 159)
MKWVTFISLLFLFSSAYSSELTQDPAVSVALGQTVRITCQGDSLRSYYA
SWYQQKPGQAPVLVIYGKNNRPSGIPDRFSGSSSGNTASLTITGAQAED
EADYYCNSRDSSGNHVVFGGGTKLTVGHGGGGSGGGGSGGGGSEVQLVE
SGGGVVRPGGSLRLSCAASGFTFDDYGMSWVRQAPGKGLEWVSGINWNG
GSTGYADSVKGRFTISRDNAKNSLYLQMNSLRAEDTAVYYCARGRSLLF
DYWGQGTLVTVSRITCPPPMSVEHADIWVKSYSLYSRERYICNSGFKRK
AGTSSLTECVLNKATNVAHWTTPSLKCIRQGQDRHMIRMIRQLIDIVDQ
LKNYVNDLVPEFLPAPEDVETNCEWSAFSCFQKAQLKSANTGNNERIIN
VSIKKLKRKPPSTNAGRRQKHRLTCPSCDSYEKKPPKEFLERFKSLLQK
MIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 160)
ATGAAGTGGGTGACCTTCATCAGCCTGCTGTTCCTGTTCTCCAGCGCCT
ACTCCTCCGAGCTGACCCAGGACCCTGCTGTGTCCGTGGCTCTGGGCCA
GACCGTGAGGATCACCTGCCAGGGCGACTCCCTGAGGTCCTACTACGCC
TCCTGGTACCAGCAGAAGCCCGGCCAGGCTCCTGTGCTGGTGATCTACG
GCAAGAACAACAGGCCCTCCGGCATCCCTGACAGGTTCTCCGGATCCTC
CTCCGGCAACACCGCCTCCCTGACCATCACAGGCGCTCAGGCCGAGGAC
GAGGCTGACTACTACTGCAACTCCAGGGACTCCTCCGGCAACCATGTGG
TGTTCGGCGGCGGCACCAAGCTGACCGTGGGCCATGGCGGCGGCGGCTC
CGGAGGCGGCGGCAGCGGCGGAGGAGGATCCGAGGTGCAGCTGGTGGAG
TCCGGAGGAGGAGTGGTGAGGCCTGGAGGCTCCCTGAGGCTGAGCTGTG
CTGCCTCCGGCTTCACCTTCGACGACTACGGCATGTCCTGGGTGAGGCA
GGCTCCTGGAAAGGGCCTGGAGTGGGTGTCCGGCATCAACTGGAACGGC
GGATCCACCGGCTACGCCGATTCCGTGAAGGGCAGGTTCACCATCAGCA
GGGACAACGCCAAGAACTCCCTGTACCTGCAGATGAACTCCCTGAGGGC
CGAGGACACCGCCGTGTACTACTGCGCCAGGGGCAGGTCCCTGCTGTTC
GACTACTGGGGACAGGGCACCCTGGTGACCGTGTCCAGGATTACATGCC
CCCCTCCCATGAGCGTGGAGCACGCCGACATCTGGGTGAAGAGCTATAG
CCTCTACAGCCGGGAGAGGTATATCTGTAACAGCGGCTTCAAGAGGAAG
GCCGGCACCAGCAGCCTCACCGAGTGCGTGCTGAATAAGGCTACCAACG
TGGCTCACTGGACAACACCCTCTTTAAAGTGCATCCGGCAGGGCCAGGA
CAGGCACATGATCCGGATGAGGCAGCTCATCGACATCGTCGACCAGCTG
AAGAACTACGTGAACGACCTGGTGCCCGAGTTTCTGCCTGCCCCCGAGG
ACGTGGAGACCAACTGCGAGTGGTCCGCCTTCTCCTGCTTTCAGAAGGC
CCAGCTGAAGTCCGCCAACACCGGCAACAACGAGCGGATCATCAACGTG
AGCATCAAGAAGCTGAAGCGGAAGCCTCCCTCCACAAACGCCGGCAGGA
GGCAGAAGCACAGGCTGACCTGCCCCAGCTGTGACTCCTACGAGAAGAA
GCCCCCCAAGGAGTTCCTGGAGAGGTTCAAGTCCCTGCTGCAGAAGATG
ATCCATCAGCACCTGTCCTCCAGGACCCACGGCTCCGAGGACTCC.

Exemplary Multi-Chain Chimeric Polypeptides—Type H

In some embodiments of any of the multi-chain chimeric polypeptides described herein, the first target-binding domain and the second targeting-binding domain each independently bind specifically to a receptor of IL-7. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to a receptor for IL-7. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain include a soluble IL-7 (e.g., a soluble human IL-7). In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 135)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 141)
DCDIEGKDGKQYESVLMVSIDQLLDSMKEIGSNCLNNEFNEFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEHSGTTNTVAAYNLTWKSTNFKTILEWEPKPVNQVYTVQISTKSGD

WKSKCFYTTDTECDLTDEIVKDVKQTYLARVFSYPAGNVESTGSAGEPL

YENSPEFTPYLETNLGQPTIQSFEQVGTKVNVTVEDERTLVRRNNTFLS

LRDVEGKDLIYTLYYWKSSSSGKKTAKTNTNEFLIDVDKGENYCFSVQA

VIPSRTVNRKSTDSPVECMGQEKGEFRENWVNVISDLKKIEDLIQSMHI

DATLYTESDVHPSCKVTAMKCFLLELQVISLESGDASIHDTVENLIILA

NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 142)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

-continued

GAAGAGGCTGCTGCAGGAGATCAAGACCTGCTGGAACAAGATCCTGATG
GGCACCAAGGAGCATAGCGGCACAACCAACACAGTCGCTGCCTATAACC
TCACTTGGAAGAGCACCAACTTCAAAACCATCCTCGAATGGGAACCCAA
ACCCGTTAACCAAGTTTACACCGTGCAGATCAGCACCAAGTCCGGCGAC
TGGAAGTCCAAATGTTTCTATACCACCGACACCGAGTGCGATCTCACCG
ATGAGATCGTGAAAGATGTGAAACAGACCTACCTCGCCCGGGTGTTTAG
CTACCCCGCCGGCAATGTGGAGAGCACTGGTTCCGCTGGCGAGCCTTTA
TACGAGAACAGCCCCGAATTTACCCCTTACCTCGAGACCAATTTAGGAC
AGCCCACCATCCAAAGCTTTGAGCAAGTTGGCACAAAGGTGAATGTGAC
AGTGGAGGACGAGCGGACTTTAGTGCGGCGGAACAACACCTTTCTCAGC
CTCCGGGATGTGTTCGGCAAAGATTTAATCTACACACTGTATTACTGGA
AGTCCTCTTCCTCCGGCAAGAAGACAGCTAAAACCAACACAAACGAGTT
TTTAATCGACGTGGATAAAGGCGAAAACTACTGTTTCAGCGTGCAAGCT
GTGATCCCCTCCCGGACCGTGAATAGGAAAAGCACCGATAGCCCCGTTG
AGTGCATGGGCCAAGAAAAGGGCGAGTTCCGGGAGAACTGGGTGAACGT
CATCAGCGATTTAAAGAAGATCGAAGATTTAATTCAGTCCATGCATATC
GACGCCACTTTATACACAGAATCCGACGTGCACCCCTCTTGTAAGGTGA
CCGCCATGAAATGTTTTTTACTGGAGCTGCAAGTTATCTCTTTAGAGAG
CGGAGACGCTAGCATCCACGACACCGTGGAGAATTTAATCATTTTAGCC
AATAACTCTTTATCCAGCAACGGCAACGTGACAGAGTCCGGCTGCAAGG
AGTGCGAAGAGCTGGAGGAGAAGAACATCAAGGAGTTTCTGCAATCCTT
TGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 143)
MKWVTFISLLFLFSSAYSDCDIEGKDGKQYESVLMVSIDQLLDSMKEIG
SNCLNNEFNFFKRHICDANKEGMFLFRAARKLRQFLKMNSTGDFDLHLL
KVSEGTTILLNCTGQVKGRKPAALGEAQPTKSLEENKSLKEQKKLNDLC
FLKRLLQEIKTCWNKILMGTKEHSGTTNTVAAYNLTWKSTNFKTILEWE
PKPVNQVYTVQISTKSGDWKSKCFYTTDTECDLTDEIVKDVKQTYLARV
FSYPAGNVESTGSAGEPLYENSPEFTPYLETNLGQPTIQSFEQVGTKVN
VTVEDERTLVRRNNTFLSLRDVFGKDLIYTLYYWKSSSSGKKTAKTNTN
EFLIDVDKGENYCFSVQAVIPSRTVNRKSTDSPVECMGQEKGEFRENWV
NVISDLKKIEDLIQSMHIDATLYTESDVHPSCKVTAMKCFLLELQVISL
ESGDASIHDTVENLIILANNSLSSNGNVTESGCKECEELEEKNIKEFLQ
SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 144)
ATGAAGTGGGTGACCTTCATCAGCCTGCTGTTCCTGTTCTCCAGCGCCT
ACTCCGATTGCGACATCGAGGGCAAGGACGGCAAGCAGTACGAGAGCGT
GCTGATGGTGTCCATCGACCAGCTGCTGGACAGCATGAAGGAGATCGGC
TCCAACTGCCTCAACAACGAGTTCAACTTCTTCAAGCGGCACATCTGCG
ACGCCAACAAGGAGGGCATGTTCCTGTTCAGGGCCGCCAGGAAACTGCG
GCAGTTCCTGAAGATGAACTCCACCGGCGACTTCGACCTGCACCTGCTG
AAGGTGTCCGAGGGCACCACCATCCTGCTGAACTGCACCGGACAGGTGA
AGGGCCGGAAACCTGCTGCTCTGGGAGAGGCCCAACCCACCAAGAGCCT
GGAGGAGAACAAGTCCCTGAAGGAGCAGAAGAAGCTGAACGACCTGTGC
TTCCTGAAGAGGCTGCTGCAGGAGATCAAGACCTGCTGGAACAAGATCC
TGATGGGCACCAAGGAGCATAGCGGCACAACCAACACAGTCGCTGCCTA
TAACCTCACTTGGAAGAGCACCAACTTCAAAACCATCCTCGAATGGGAA
CCCAAACCCGTTAACCAAGTTTACACCGTGCAGATCAGCACCAAGTCCG
GCGACTGGAAGTCCAAATGTTTCTATACCACCGACACCGAGTGCGATCT
CACCGATGAGATCGTGAAAGATGTGAAACAGACCTACCTCGCCCGGGTG
TTTAGCTACCCCGCCGGCAATGTGGAGAGCACTGGTTCCGCTGGCGAGC
CTTTATACGAGAACAGCCCCGAATTTACCCCTTACCTCGAGACCAATTT
AGGACAGCCCACCATCCAAAGCTTTGAGCAAGTTGGCACAAAGGTGAAT
GTGACAGTGGAGGACGAGCGGACTTTAGTGCGGCGGAACAACACCTTTC
TCAGCCTCCGGGATGTGTTCGGCAAAGATTTAATCTACACACTGTATTA
CTGGAAGTCCTCTTCCTCCGGCAAGAAGACAGCTAAAACCAACACAAAC
GAGTTTTTAATCGACGTGGATAAAGGCGAAAACTACTGTTTCAGCGTGC
AAGCTGTGATCCCCTCCCGGACCGTGAATAGGAAAAGCACCGATAGCCC
CGTTGAGTGCATGGGCCAAGAAAAGGGCGAGTTCCGGGAGAACTGGGTG
AACGTCATCAGCGATTTAAAGAAGATCGAAGATTTAATTCAGTCCATGC
ATATCGACGCCACTTTATACACAGAATCCGACGTGCACCCCTCTTGTAA
GGTGACCGCCATGAAATGTTTTTTACTGGAGCTGCAAGTTATCTCTTTA
GAGAGCGGAGACGCTAGCATCCACGACACCGTGGAGAATTTAATCATTT
TAGCCAATAACTCTTTATCCAGCAACGGCAACGTGACAGAGTCCGGCTG
CAAGGAGTGCGAAGAGCTGGAGGAGAAGAACATCAAGGAGTTTCTGCAA
TCCTTTGTGCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 137)

DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEHITCPPPMSVEHADIWVKSYSLYSRERYICNSGFKRKAGTSSLTE

CVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 138)

GATTGTGATATTGAAGGTAAAGATGGCAAACAATATGAGAGTGTTCTAA

TGGTCAGCATCGATCAATTATTGGACAGCATGAAAGAAATTGGTAGCAA

TTGCCTGAATAATGAATTTAACTTTTTAAAAGACATATCTGTGATGCT

AATAAGGAAGGTATGTTTTTATTCCGTGCTGCTCGCAAGTTGAGGCAAT

TTCTTAAAATGAATAGCACTGGTGATTTTGATCTCCACTTATTAAAAGT

TTCAGAAGGCACAACAATACTGTTGAACTGCACTGGCCAGGTTAAAGGA

AGAAAACCAGCTGCCCTGGGTGAAGCCCAACCAACAAAGAGTTTGGAAG

AAAATAAATCTTTAAAGGAACAGAAAAAACTGAATGACTTGTGTTTCCT

AAAGAGACTATTACAAGAGATAAAAACTTGTTGGAATAAAATTTTGATG

GGCACTAAAGAACACATCACGTGCCCTCCCCCCATGTCCGTGGAACACG

CAGACATCTGGGTCAAGAGCTACAGCTTGTACTCCAGGGAGCGGTACAT

TTGTAACTCTGGTTTCAAGCGTAAAGCCGGCACGTCCAGCCTGACGGAG

TGCGTGTTGAACAAGGCCACGAATGTCGCCCACTGGACAACCCCCAGTC

TCAAATGCATTAGA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 139)

MKWVTFISLLFLFSSAYSDCDIEGKDGKQYESVLMVSIDQLLDSMKEIG

SNCLNNEFNFFKRHICDANKEGMFLFRAARKLRQFLKMNSTGDFDLHLL

KVSEGTTILLNCTGQVKGRKPAALGEAQPTKSLEENKSLKEQKKLNDLC

FLKRLLQEIKTCWNKILMGTKEHITCPPPMSVEHADIWVKSYSLYSRER

YICNSGFKRKAGTSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 140)

ATGAAGTGGGTGACCTTCATCAGCCTGCTGTTCCTGTTCTCCAGCGCCT

ACTCCGATTGCGACATCGAGGGCAAGGACGGCAAGCAGTACGAGAGCGT

GCTGATGGTGTCCATCGACCAGCTGCTGGACAGCATGAAGGAGATCGGC

TCCAACTGCCTCAACAACGAGTTCAACTTCTTCAAGCGGCACATCTGCG

ACGCCAACAAGGAGGGCATGTTCCTGTTCAGGGCCGCCAGGAAACTGCG

GCAGTTCCTGAAGATGAACTCCACCGGCGACTTCGACCTGCACCTGCTG

AAGGTGTCCGAGGGCACCACCATCCTGCTGAACTGCACCGGACAGGTGA

AGGGCCGGAAACCTGCTGCTCTGGGAGAGGCCCAACCCACCAAGAGCCT

GGAGGAGAACAAGTCCCTGAAGGAGCAGAAGAAGCTGAACGACCTGTGC

TTCCTGAAGAGGCTGCTGCAGGAGATCAAGACCTGCTGGAACAAGATCC

TGATGGGCACCAAGGAGCATATTACATGCCCCCCTCCCATGAGCGTGGA

GCACGCCGACATCTGGGTGAAGAGCTATAGCCTCTACAGCCGGGAGAGG

TATATCTGTAACAGCGGCTTCAAGAGGAAGGCCGGCACCAGCAGCCTCA

CCGAGTGCGTGCTGAATAAGGCTACCAACGTGGCTCACTGGACAACACC

CTCTTTAAAGTGCATCCGG.

Exemplary Multi-Chain Chimeric Polypeptides—Type I

In some embodiments of any of the multi-chain chimeric polypeptides described herein, the first target-binding domain and the second targeting-binding domain each independently bind specifically to TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain and the second target-binding domain each independently bind specifically to TGF-β. In some embodiments of these multi-chain chimeric polypeptides, the first target-binding domain and the second target-binding domain bind specifically to the same epitope. In some embodiments of these multi-chain chimeric polypeptides, the first target-binding domain and the second target-binding domain include the same amino acid sequence.

In some embodiments of these multi-chain chimeric polypeptides, the first target-binding domain and the second target-binding domain is a soluble TGF-β receptor (e.g., a soluble TGF-β RII receptor, e.g., a soluble human TGF-β RII). In some embodiments of these multi-chain chimeric polypeptides, the soluble human TGF-β RII includes a first sequence of soluble human TGF-βRII and a second sequence of soluble human TGF-β RII. In some embodiments of these multi-chain chimeric polypeptides, the soluble human TGF-βRII includes a linker disposed between the first sequence of soluble human TGF-β RII and the second sequence of soluble human TGF-β RII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPD.

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPD.

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGAT

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTGACCG
ATAACAATGGCGCCGTGAAATTTCCCCAGCTGTGCAAATTCTGCGATGT
GAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGC
GGAAGAATGACGAGAATATCACCCTGGAAACCGTCTGCCACGATCCCAA
GCTGCCCTACCACGATTTCATCCTGGAAGACGCCGCCAGCCCTAAGTGC
ATCATGAAAGAGAAAAAGAAGCCTGGCGAGACCTTTTTCATGTGCTCCT
GCAGCAGCGACGAATGCAACGACAATATCATCTTTAGCGAGGAATACAA
TACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 60)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDSGTTNTV

AAYNLTWKSTNFKTILEWEPKPVNQVYTVQISTKSGDWKSKCFYTTDTE

CDLTDEIVKDVKQTYLARVFSYPAGNVESTGSAGEPLYENSPEFTPYLE

TNLGQPTIQSFEQVGTKVNVTVEDERTLVRRNNTFLSLRDVFGKDLIYT

LYYWKSSSSGKKTAKTNTNEFLIDVDKGENYCFSVQAVIPSRTVNRKST

DSPVECMGQEKGEFRENWVNVISDLKKIEDLIQSMHIDATLYTESDVHP

SCKVTAMKCFLLELQVISLESGDASIHDTVENLIILANNSLSSNGNVTE

SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACAGCGGCACAACCAACACAGTC

GCTGCCTATAACCTCACTTGGAAGAGCACCAACTTCAAAACCATCCTCG

AATGGGAACCCAAACCCGTTAACCAAGTTTACACCGTGCAGATCAGCAC

CAAGTCCGGCGACTGGAAGTCCAAATGTTTCTATACCACCGACACCGAG

TGCGATCTCACCGATGAGATCGTGAAAGATGTGAAACAGACCTACCTCG

CCCGGGTGTTTAGCTACCCCGCCGGCAATGTGGAGAGCACTGGTTCCGC

TGGCGAGCCTTTATACGAGAACAGCCCCGAATTTACCCCTTACCTCGAG

ACCAATTTAGGACAGCCCACCATCCAAAGCTTTGAGCAAGTTGGCACAA

AGGTGAATGTGACAGTGGAGGACGAGCGGACTTTAGTGCGGCGGAACAA

CACCTTTCTCAGCCTCCGGGATGTGTTCGGCAAAGATTTAATCTACACA

CTGTATTACTGGAAGTCCTCTTCCTCCGGCAAGAAGACAGCTAAAACCA

ACACAAACGAGTTTTTAATCGACGTGGATAAAGGCGAAAACTACTGTTT

CAGCGTGCAAGCTGTGATCCCCTCCCGGACCGTGAATAGGAAAAGCACC

GATAGCCCCGTTGAGTGCATGGGCCAAGAAAAGGGCGAGTTCCGGGAGA

ACTGGGTGAACGTCATCAGCGATTTAAAGAAGATCGAAGATTTAATTCA

GTCCATGCATATCGACGCCACTTTATACACAGAATCCGACGTGCACCCC

TCTTGTAAGGTGACCGCCATGAAATGTTTTTTACTGGAGCTGCAAGTTA

TCTCTTTAGAGAGCGGAGACGCTAGCATCCACGACACCGTGGAGAATTT

AATCATTTTAGCCAATAACTCTTTATCCAGCAACGGCAACGTGACAGAG

-continued

TCCGGCTGCAAGGAGTGCGAAGAGCTGGAGGAGAAGAACATCAAGGAGT

TTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)

MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDSGTTNTVAAYNLTWKSTNFKTILEWEPKPVNQVYTVQI

STKSGDWKSKCFYTTDTECDLTDEIVKDVKQTYLARVFSYPAGNVESTG

SAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENY

CFSVQAVIPSRTVNRKSTDSPVECMGQEKGEFRENWVNVISDLKKIEDL

IQSMHIDATLYTESDVHPSCKVTAMKCFLLELQVISLESGDASIHDTVE

NLIILANNSLSSNGNVTESGCKECEELEEKNIKEFLQSFVHIVQMFINT

S.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)

ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

-continued

TGCAAATTCTGCGATGTGAGGTTTTCCACCTGCGACAACCAGAAGTCCT

GTATGAGCAACTGCTCCATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACAGCGGCACAACCAACA

CAGTCGCTGCCTATAACCTCACTTGGAAGAGCACCAACTTCAAAACCAT

CCTCGAATGGGAACCCAAACCCGTTAACCAAGTTTACACCGTGCAGATC

AGCACCAAGTCCGGCGACTGGAAGTCCAAATGTTTCTATACCACCGACA

CCGAGTGCGATCTCACCGATGAGATCGTGAAAGATGTGAAACAGACCTA

CCTCGCCCGGGTGTTTAGCTACCCCGCCGGCAATGTGGAGAGCACTGGT

TCCGCTGGCGAGCCTTTATACGAGAACAGCCCCGAATTTACCCCTTACC

TCGAGACCAATTTAGGACAGCCCACCATCCAAAGCTTTGAGCAAGTTGG

CACAAAGGTGAATGTGACAGTGGAGGACGAGCGGACTTTAGTGCGGCGG

AACAACACCTTTCTCAGCCTCCGGGATGTGTTCGGCAAAGATTTAATCT

ACACACTGTATTACTGGAAGTCCTCTTCCTCCGGCAAGAAGACAGCTAA

AACCAACACAAACGAGTTTTTAATCGACGTGGATAAAGGCGAAAACTAC

TGTTTCAGCGTGCAAGCTGTGATCCCCTCCCGGACCGTGAATAGGAAAA

GCACCGATAGCCCCGTTGAGTGCATGGGCCAAGAAAAGGGCGAGTTCCG

GGAGAACTGGGTGAACGTCATCAGCGATTTAAAGAAGATCGAAGATTTA

ATTCAGTCCATGCATATCGACGCCACTTTATACACAGAATCCGACGTGC

ACCCCTCTTGTAAGGTGACCGCCATGAAATGTTTTTTACTGGAGCTGCA

AGTTATCTCTTTAGAGAGCGGAGACGCTAGCATCCACGACACCGTGGAG

AATTTAATCATTTTAGCCAATAACTCTTTATCCAGCAACGGCAACGTGA

CAGAGTCCGGCTGCAAGGAGTGCGAAGAGCTGGAGGAGAAGAACATCAA

GGAGTTTCTGCAATCCTTTGTGCACATTGTCCAGATGTTCATCAATACC

TCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 130)

IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDITCPPPM

-continued

SVEHADIWVKSYSLYSRERYICNSGFKRKAGTSSLTECVLNKATNVAHW

TTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 131)

ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACATTACATGCCCCCCTCCCATG

AGCGTGGAGCACGCCGACATCTGGGTGAAGAGCTATAGCCTCTACAGCC

GGGAGAGGTATATCTGTAACAGCGGCTTCAAGAGGAAGGCCGGCACCAG

CAGCCTCACCGAGTGCGTGCTGAATAAGGCTACCAACGTGGCTCACTGG

ACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 132)

MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

-continued

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDITCPPPMSVEHADIWVKSYSLYSRERYICNSGFKRKAG

TSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 133)

ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCTCCATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACATTACATGCCCCCCTC

CCATGAGCGTGGAGCACGCCGACATCTGGGTGAAGAGCTATAGCCTCTA

CAGCCGGGAGAGGTATATCTGTAACAGCGGCTTCAAGAGGAAGGCCGGC

ACCAGCAGCCTCACCGAGTGCGTGCTGAATAAGGCTACCAACGTGGCTC

ACTGGACAACACCCTCTTTAAAGTGCATCCGG.

Exemplary Multi-Chain Chimeric Polypeptides—Type J

In some embodiments of any of the multi-chain chimeric polypeptides described herein, the first target-binding domain and the second targeting-binding domain each independently bind specifically to a receptor of IL-7, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments, the second chimeric polypeptide can include an additional target-binding domain. In some embodiments, the additional target-binding domain and the In some embodiments of these multi-chain chimeric polypeptides, one or more of the first target-binding domain, the second target-binding domain and the additional target-binding domain is an agonistic antigen-binding domain. In some embodiments of these multi-chain chimeric polypeptides, the first target-binding domain, the second target-binding domain, and the additional target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, the first target-binding domain binds specifically to a receptor for IL-7, and the second target-binding domain binds specifically to a receptor for IL-21 or a receptor for CD137L. In some embodiments, the additional target-binding domain binds specifically to a receptor for IL-21 or a receptor for CD137L.

In some embodiments of these multi-chain chimeric polypeptides, the first target-binding domain is a soluble IL-7 (e.g., a soluble human IL-7). In some embodiments of these multi-chain chimeric polypeptides, the soluble human IL-7 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 135)
```
DCDIEGKDGKQYESVLMVSIDQLLDSMKEIGSNCLNNEFNFFKRHICD
ANKEGMFLFRAARKLRQFLKMNSTGDFDLHLLKVSEGTTILLNCTGQV
KGRKPAALGEAQPTKSLEENKSLKEQKKLNDLCFLKRLLQEIKTCWNK
ILMGTKEH.
```

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)
```
GATTGCGACATCGAGGGCAAGGACGGCAAGCAGTACGAGAGCGTGCTGA
TGGTGTCCATCGACCAGCTGCTGGACAGCATGAAGGAGATCGGCTCCAA
CTGCCTCAACAACGAGTTCAACTTCTTCAAGCGGCACATCTGCGACGCC
AACAAGGAGGGCATGTTCCTGTTCAGGGCCGCCAGGAAACTGCGGCAGT
TCCTGAAGATGAACTCCACCGGCGACTTCGACCTGCACCTGCTGAAGGT
GTCCGAGGGCACCACCATCCTGCTGAACTGCACCGGACAGGTGAAGGGC
CGGAAACCTGCTGCTCTGGGAGAGGCCCAACCCACCAAGAGCCTGGAGG
AGAACAAGTCCCTGAAGGAGCAGAAGAAGCTGAACGACCTGTGCTTCCT
GAAGAGGCTGCTGCAGGAGATCAAGACCTGCTGGAACAAGATCCTGATG
GGCACCAAGGAGCAT.
```

In some embodiments of these multi-chain chimeric polypeptides, the second target-binding domain or the additional target-binding domain binds specifically to a receptor for IL-21. In some embodiments of these multi-chain chimeric polypeptides, the second target-binding domain or the additional target-binding domain is a soluble IL-21 (e.g., a soluble human IL-21).

In some embodiments of these multi-chain chimeric polypeptides, a soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS.

In some embodiments of these multi-chain chimeric polypeptides, a soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 125)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCC.

In some embodiments of these multi-chain chimeric polypeptides, the second target-binding domain binds specifically to a receptor for CD137L. In some embodiments of these multi-chain chimeric polypeptides, the second chimeric polypeptide further comprises an additional target-binding domain that binds specifically to a receptor for CD137L. In some embodiments of these multi-chain chimeric polypeptides, the second target-binding domain and/or the additional target-binding domain is a soluble CD137L (e.g., a soluble human CD137L).

In some embodiments of these multi-chain chimeric polypeptides, a soluble human CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 165)
REGPELSPDDPAGLLDLRQGMFAQLVAQNVLLIDGPLSWYSDPGLAGVS
LTGGLYKEDTKELVVAKAGVYYVFFQLELRRVVAGEGSGSVSLALHLQP
LRSAAGAAALALTVDLPPASSEARNSAFGFQGRLLHLSAGQRLGVHLHT
EARARHAWQLTQGATVLGLFRVTPEIPAGLPSPRSE.

In some embodiments of these multi-chain chimeric polypeptides, a soluble human CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 166)
CGCGAGGGTCCCGAGCTTTCGCCCGACGATCCCGCCGGCCTCTTGGACC
TGCGGCAGGGCATGTTTGCGCAGCTGGTGGCCCAAAATGTTCTGCTGAT
CGATGGGCCCCTGAGCTGGTACAGTGACCCAGGCCTGGCAGGCGTGTCC
CTGACGGGGGGCCTGAGCTACAAAGAGGACACGAAGGAGCTGGTGGTGG
CCAAGGCTGGAGTCTACTATGTCTTCTTTCAACTAGAGCTGCGGCGCGT
GGTGGCCGGCGAGGGCTCAGGCTCCGTTTCACTTGCGCTGCACCTGCAG
CCACTGCGCTCTGCTGCTGGGGCCGCCGCCCTGGCTTTGACCGTGGACC
TGCCACCCGCCTCCTCCGAGGCTCGGAACTCGGCCTTCGGTTTCCAGGG
CCGCTTGCTGCACCTGAGTGCCGGCCAGCGCCTGGGCGTCCATCTTCAC
ACTGAGGCCAGGGCACGCCATGCCTGGCAGCTTACCCAGGGCGCCACAG
TCTTGGGACTCTTCCGGGTGACCCCCGAAATCCCAGCCGGACTCCCTTC
ACCGAGGTCGGAA.

In some embodiments of these multi-chain chimeric polypeptides, a soluble human CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 167)
DPAGLLDLRQGMFAQLVAQNVLLIDGPLSWYSDPGLAGVSLTGGLSYKE
DTKELVVAKAGVYYVFFQLELRRVVAGEGSGSVSLALHLQPLRSAAGAA
ALALTVDLPPASSEARNSAFGFQGRLLHLSAGQRLGVHLHTEARARHAW
QLTQGATVLGLFRVTPEI.

In some embodiments of these multi-chain chimeric polypeptides, a soluble human CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 168)
GATCCCGCCGGCCTCTTGGACCTGCGGCAGGGCATGTTTGCGCAGCTGG
TGGCCCAAAATGTTCTGCTGATCGATGGGCCCCTGAGCTGGTACAGTGA
CCCAGGCCTGGCAGGCGTGTCCCTGACGGGGGGCCTGAGCTACAAAGAG
GACACGAAGGAGCTGGTGGTGGCCAAGGCTGGAGTCTACTATGTCTTCT
TTCAACTAGAGCTGCGGCGCGTGGTGGCCGGCGAGGGCTCAGGCTCCGT
TTCACTTGCGCTGCACCTGCAGCCACTGCGCTCTGCTGCTGGGGCCGCC
GCCCTGGCTTTGACCGTGGACCTGCCACCCGCCTCCTCCGAGGCTCGGA
ACTCGGCCTTCGGTTTCCAGGGCCGCTTGCTGCACCTGAGTGCCGGCCA
GCGCCTGGGCGTCCATCTTCACACTGAGGCCAGGGCACGCCATGCCTGG

-continued

CAGCTTACCCAGGGCGCCACAGTCTTGGGACTCTTCCGGGTGACCCCCG

AAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 141)
DCDIEGKDGKQYESVLMVSIDQLLDSMKEIGSNCLNNEFNEFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEHSGTTNTVAAYNLTWKSTNFKTILEWEPKPVNQVYTVQISTKSGD

WKSKCFYTTDTECDLTDEIVKDVKQTYLARVFSYPAGNVESTGSAGEPL

YENSPEFTPYLETNLGQPTIQSFEQVGTKVNVTVEDERTLVRRNNTFLS

LRDVEGKDLIYTLYYWKSSSSGKKTAKTNTNEFLIDVDKGENYCFSVQA

VIPSRTVNRKSTDSPVECMGQEKGEFRENWVNVISDLKKIEDLIQSMHI

DATLYTESDVHPSCKVTAMKCFLLELQVISLESGDASIHDTVENLIILA

NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 142)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCATAGCGGCACAACCAACACAGTCGCTGCCTATAACC

TCACTTGGAAGAGCACCAACTTCAAAACCATCCTCGAATGGGAACCCAA

ACCCGTTAACCAAGTTTACACCGTGCAGATCAGCACCAAGTCCGGCGAC

TGGAAGTCCAAATGTTTCTATACCACCGACACCGAGTGCGATCTCACCG

ATGAGATCGTGAAAGATGTGAAACAGACCTACCTCGCCCGGGTGTTTA

GCTACCCCGCCGGCAATGTGGAGAGCACTGGTTCCGCTGGCGAGCCTTT

ATACGAGAACAGCCCCGAATTTACCCCTTACCTCGAGACCAATTTAGGA

-continued

CAGCCCACCATCCAAAGCTTTGAGCAAGTTGGCACAAAGGTGAATGTGA

CAGTGGAGGACGAGCGGACTTTAGTGCGGCGGAACAACACCTTTCTCAG

CCTCCGGGATGTGTTCGGCAAAGATTTAATCTACACACTGTATTACTGG

AAGTCCTCTTCCTCCGGCAAGAAGACAGCTAAAACCAACACAAACGAGT

TTTTAATCGACGTGGATAAAGGCGAAAACTACTGTTTCAGCGTGCAAGC

TGTGATCCCCTCCCGGACCGTGAATAGGAAAAGCACCGATAGCCCCGTT

GAGTGCATGGGCCAAGAAAAGGGCGAGTTCCGGGAGAACTGGGTGAACG

TCATCAGCGATTTAAAGAAGATCGAAGATTTAATTCAGTCCATGCATAT

CGACGCCACTTTATACACAGAATCCGACGTGCACCCCTCTTGTAAGGTG

ACCGCCATGAAATGTTTTTTACTGGAGCTGCAAGTTATCTCTTTAGAGA

GCGGAGACGCTAGCATCCACGACACCGTGGAGAATTTAATCATTTTAGC

CAATAACTCTTTATCCAGCAACGGCAACGTGACAGAGTCCGGCTGCAAG

GAGTGCGAAGAGCTGGAGGAGAAGAACATCAAGGAGTTTCTGCAATCCT

TTGTGCACATTGTCCAGATGTTCATCAATACCTCC

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 143)
MKWVTFISLLFLFSSAYSDCDIEGKDGKQYESVLMVSIDQLLDSMKEIG

SNCLNNEFNFFKRHICDANKEGMFLFRAARKLRQFLKMNSTGDFDLHLL

KVSEGTTILLNCTGQVKGRKPAALGEAQPTKSLEENKSLKEQKKLNDLC

FLKRLLQEIKTCWNKILMGTKEHSGTTNTVAAYNLTWKSTNFKTILEWE

PKPVNQVYTVQISTKSGDWKSKCFYTTDTECDLTDEIVKDVKQTYLARV

FSYPAGNVESTGSAGEPLYENSPEFTPYLETNLGQPTIQSFEQVGTKVN

VTVEDERTLVRRNNTFLSLRDVFGKDLIYTLYYWKSSSSGKKTAKTNTN

EFLIDVDKGENYCFSVQAVIPSRTVNRKSTDSPVECMGQEKGEFRENWV

NVISDLKKIEDLIQSMHIDATLYTESDVHPSCKVTAMKCFLLELQVISL

ESGDASIHDTVENLIILANNSLSSNGNVTESGCKECEELEEKNIKEFLQ

SFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 144)
ATGAAGTGGGTGACCTTCATCAGCCTGCTGTTCCTGTTCTCCAGCGCCT

ACTCCGATTGCGACATCGAGGGCAAGGACGGCAAGCAGTACGAGAGCGT

GCTGATGGTGTCCATCGACCAGCTGCTGGACAGCATGAAGGAGATCGGC

TCCAACTGCCTCAACAACGAGTTCAACTTCTTCAAGCGGCACATCTGCG

-continued

ACGCCAACAAGGAGGGCATGTTCCTGTTCAGGGCCGCCAGGAAACTGCG

GCAGTTCCTGAAGATGAACTCCACCGGCGACTTCGACCTGCACCTGCTG

AAGGTGTCCGAGGGCACCACCATCCTGCTGAACTGCACCGGACAGGTGA

AGGGCCGGAAACCTGCTGCTCTGGGAGAGGCCCAACCCACCAAGAGCCT

GGAGGAGAACAAGTCCCTGAAGGAGCAGAAGAAGCTGAACGACCTGTGC

TTCCTGAAGAGGCTGCTGCAGGAGATCAAGACCTGCTGGAACAAGATCC

TGATGGGCACCAAGGAGCATAGCGGCACAACCAACACAGTCGCTGCCTA

TAACCTCACTTGGAAGAGCACCAACTTCAAAACCATCCTCGAATGGGAA

CCCAAACCCGTTAACCAAGTTTACACCGTGCAGATCAGCACCAAGTCCG

GCGACTGGAAGTCCAAATGTTTCTATACCACCGACACCGAGTGCGATCT

CACCGATGAGATCGTGAAAGATGTGAAACAGACCTACCTCGCCCGGGTG

TTTAGCTACCCCGCCGGCAATGTGGAGAGCACTGGTTCCGCTGGCGAGC

CTTTATACGAGAACAGCCCCGAATTTACCCCTTACCTCGAGACCAATTT

AGGACAGCCCACCATCCAAAGCTTTGAGCAAGTTGGCACAAAGGTGAAT

GTGACAGTGGAGGACGAGCGGACTTTAGTGCGGCGGAACAACACCTTTC

TCAGCCTCCGGGATGTGTTCGGCAAAGATTTAATCTACACACTGTATTA

CTGGAAGTCCTCTTCCTCCGGCAAGAAGACAGCTAAAACCAACACAAAC

GAGTTTTTAATCGACGTGGATAAAGGCGAAAACTACTGTTTCAGCGTGC

AAGCTGTGATCCCCTCCCGGACCGTGAATAGGAAAAGCACCGATAGCCC

CGTTGAGTGCATGGGCCAAGAAAAGGGCGAGTTCCGGGAGAACTGGGTG

AACGTCATCAGCGATTTAAAGAAGATCGAAGATTTAATTCAGTCCATGC

ATATCGACGCCACTTTATACACAGAATCCGACGTGCACCCCTCTTGTAA

GGTGACCGCCATGAAATGTTTTTTACTGGAGCTGCAAGTTATCTCTTTA

GAGAGCGGAGACGCTAGCATCCACGACACCGTGGAGAATTTAATCATTT

TAGCCAATAACTCTTTATCCAGCAACGGCAACGTGACAGAGTCCGGCTG

CAAGGAGTGCGAAGAGCTGGAGGAGAAGAACATCAAGGAGTTTCTGCAA

TCCTTTGTGCACATTGTCCAGATGTTCATCAATACCTCC

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 169)

QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDSITCPPPMSVEHADI

WVKSYSLYSRERYICNSGFKRKAGTSSLTECVLNKATNVAHWTTPSLKC

IRGGGGSGGGGSGGGGSREGPELSPDDPAGLLDLRQGMFAQLVAQNVLL

IDGPLSWYSDPGLAGVSLTGGLSYKEDTKELVVAKAGVYYVFFQLELRR

VVAGEGSGSVSLALHLQPLRSAAGAAALALTVDLPPASSEARNSAFGFQ

-continued

GRLLHLSAGQRLGVHLHTEARARHAWQLTQGATVLGLFRVTPEIPAGLP

SPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 170)

CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCCATTACATGCCCCCCTCCCATGAGCGTGGAGCACGCCGACATC

TGGGTGAAGAGCTATAGCCTCTACAGCCGGGAGAGGTATATCTGTAACA

GCGGCTTCAAGAGGAAGGCCGGCACCAGCAGCCTCACCGAGTGCGTGCT

GAATAAGGCTACCAACGTGGCTCACTGGACAACACCCTCTTTAAAGTGC

ATCCGGGGCGGTGGAGGATCCGGAGGAGGTGGCTCCGGCGGCGGAGGAT

CTCGCGAGGGTCCCGAGCTTTCGCCCGACGATCCCGCCGGCCTCTTGGA

CCTGCGGCAGGGCATGTTTGCGCAGCTGGTGGCCCAAAATGTTCTGCTG

ATCGATGGGCCCCTGAGCTGGTACAGTGACCCAGGCCTGGCAGGCGTGT

CCCTGACGGGGGGCCTGAGCTACAAAGAGGACACGAAGGAGCTGGTGGT

GGCCAAGGCTGGAGTCTACTATGTCTTCTTTCAACTAGAGCTGCGGCGC

GTGGTGGCCGGCGAGGGCTCAGGCTCCGTTTCACTTGCGCTGCACCTGC

AGCCACTGCGCTCTGCTGCTGGGGCCGCCGCCCTGGCTTTGACCGTGGA

CCTGCCACCCGCCTCCTCCGAGGCTCGGAACTCGGCCTTCGGTTTCCAG

GGCCGCTTGCTGCACCTGAGTGCCGGCCAGCGCCTGGGCGTCCATCTTC

ACACTGAGGCCAGGGCACGCCATGCCTGGCAGCTTACCCAGGGCGCCAC

AGTCTTGGGACTCTTCCGGGTGACCCCCGAAATCCCAGCCGGACTCCCT

TCACCGAGGTCGGAA.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 171)

MKWVTFISLLFLFSSAYSQGQDRHMIRMRQLIDIVDQLKNYVNDLVPEF

LPAPEDVETNCEWSAFSCFQKAQLKSANTGNNERIINVSIKKLKRKPPS

-continued

TNAGRRQKHRLTCPSCDSYEKKPPKEFLERFKSLLQKMIHQHLSSRTHG
SEDSITCPPPMSVEHADIWVKSYSLYSRERYICNSGFKRKAGTSSLTEC
VLNKATNVAHWTTPSLKCIRGGGGSGGGGSGGGGSREGPELSPDDPAGL
LDLRQGMFAQLVAQNVLLIDGPLSWYSDPGLAGVSLTGGLSYKEDTKEL
VVAKAGVYYVFFQLELRRVVAGEGSGSVSLALHLQPLRSAAGAAALALT
VDLPPASSEARNSAFGFQGRLLHLSAGQRLGVHLHTEARARHAWQLTQG
ATVLGLFRVTPEIPAGLPSPRSE

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 172)
ATGAAGTGGGTGACCTTCATCAGCCTGCTGTTCCTGTTCTCCAGCGCCT
ACTCCCAGGGCCAGGACAGGCACATGATCCGGATGAGGCAGCTCATCGA
CATCGTCGACCAGCTGAAGAACTACGTGAACGACCTGGTGCCCGAGTTT
CTGCCTGCCCCCGAGGACGTGGAGACCAACTGCGAGTGGTCCGCCTTCT
CCTGCTTTCAGAAGGCCCAGCTGAAGTCCGCCAACACCGGCAACAACGA
GCGGATCATCAACGTGAGCATCAAGAAGCTGAAGCGGAAGCCTCCCTCC
ACAAACGCCGGCAGGAGGCAGAAGCACAGGCTGACCTGCCCCAGCTGTG
ACTCCTACGAGAAGAAGCCCCCCAAGGAGTTCCTGGAGAGGTTCAAGTC
CCTGCTGCAGAAGATGATCCATCAGCACCTGTCCTCCAGGACCCACGGC
TCCGAGGACTCCATTACATGCCCCCCTCCCATGAGCGTGGAGCACGCCG
ACATCTGGGTGAAGAGCTATAGCCTCTACAGCCGGGAGAGGTATATCTG
TAACAGCGGCTTCAAGAGGAAGGCCGGCACCAGCAGCCTCACCGAGTGC
GTGCTGAATAAGGCTACCAACGTGGCTCACTGGACAACACCCTCTTTAA
AGTGCATCCGGGGCGGTGGAGGATCCGGAGGAGGTGGCTCCGGCGGCGG
AGGATCTCGCGAGGGTCCCGAGCTTTCGCCCGACGATCCCGCCGGCCTC
TTGGACCTGCGGCAGGGCATGTTTGCGCAGCTGGTGGCCCAAAATGTTC
TGCTGATCGATGGGCCCCTGAGCTGGTACAGTGACCCAGGCCTGGCAGG
CGTGTCCCTGACGGGGGGCCTGAGCTACAAAGAGGACACGAAGGAGCTG
GTGGTGGCCAAGGCTGGAGTCTACTATGTCTTCTTTCAACTAGAGCTGC
GGCGCGTGGTGGCCGGCGAGGGCTCAGGCTCCGTTTCACTTGCGCTGCA
CCTGCAGCCACTGCGCTCTGCTGCTGGGGCCGCCGCCCTGGCTTTGACC
GTGGACCTGCCACCCGCCTCCTCCGAGGCTCGGAACTCGGCCTTCGGTT
TCCAGGGCCGCTTGCTGCACCTGAGTGCCGGCCAGCGCCTGGGCGTCCA
TCTTCACACTGAGGCCAGGGCACGCCATGCCTGGCAGCTTACCCAGGGC
GCCACAGTCTTGGGACTCTTCCGGGTGACCCCCGAAATCCCAGCCGGAC
TCCCTTCACCGAGGTCGGAA.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 173)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDSITCPPPMSVEHADI
WVKSYSLYSRERYICNSGFKRKAGTSSLTECVLNKATNVAHWTTPSLKC
IRGGGGSGGGGSGGGGSDPAGLLDLRQGMFAQLVAQNVLLIDGPLSWYS
DPGLAGVSLTGGLSYKEDTKELVVAKAGVYYVFFQLELRRVVAGEGSGS
VSLALHLQPLRSAAGAAALALTVDLPPASSEARNSAFGFQGRLLHLSAG
QRLGVHLHTEARARHAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical at least 96% identical, at least 98% identical, at least 99% identical, or 100% identical) to:

(SEQ ID NO: 174)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCCATTACATGCCCCCCTCCCATGAGCGTGGAGCACGCCGACATC
TGGGTGAAGAGCTATAGCCTCTACAGCCGGGAGAGGTATATCTGTAACA
GCGGCTTCAAGAGGAAGGCCGGCACCAGCAGCCTCACCGAGTGCGTGCT
GAATAAGGCTACCAACGTGGCTCACTGGACAACACCCTCTTTAAAGTGC
ATCCGGGGCGGTGGAGGATCCGGAGGAGGTGGCTCCGGCGGCGGAGGAT
CTGATCCCGCCGGCCTCTTGGACCTGCGGCAGGGCATGTTTGCGCAGCT
GGTGGCCCAAAATGTTCTGCTGATCGATGGGCCCCTGAGCTGGTACAGT
GACCCAGGCCTGGCAGGCGTGTCCCTGACGGGGGGCCTGAGCTACAAAG
AGGACACGAAGGAGCTGGTGGTGGCCAAGGCTGGAGTCTACTATGTCTT
CTTTCAACTAGAGCTGCGGCGCGTGGTGGCCGGCGAGGGCTCAGGCTCC
GTTTCACTTGCGCTGCACCTGCAGCCACTGCGCTCTGCTGCTGGGGCCG
CCGCCCTGGCTTTGACCGTGGACCTGCCACCCGCCTCCTCCGAGGCTCG
GAACTCGGCCTTCGGTTTCCAGGGCCGCTTGCTGCACCTGAGTGCCGGC

-continued

```
CAGCGCCTGGGCGTCCATCTTCACACTGAGGCCAGGGCACGCCATGCCT

GGCAGCTTACCCAGGGCGCCACAGTCTTGGGACTCTTCCGGGTGACCCC

CGAAATC.
```

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 175)
MKWVTFISLLFLFSSAYSQGQDRHMIRMIRQLIDIVDQLKNYVNDLVPE

FLPAPEDVETNCEWSAFSCFQKAQLKSANTGNNERIINVSIKKLKRKPP

STNAGRRQKHRLTCPSCDSYEKKPPKEFLERFKSLLQKMIHQHLSSRTH

GSEDSITCPPPMSVEHADIWVKSYSLYSRERYICNSGFKRKAGTSSLTE

CVLNKATNVAHWTTPSLKCIRGGGGSGGGGSGGGGSDPAGLLDLRQGMF

AQLVAQNVLLIDGPLSWYSDPGLAGVSLTGGLSYKEDTKELVVAKAGVY

YVFFQLELRRVVAGEGSGSVSLALHLQPLRSAAGAAALALTVDLPPASS

EARNSAFGFQGRLLHLSAGQRLGVHLHTEARARHAWQLTQGATVLGLFR

VTPEI.
```

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 176)
ATGAAGTGGGTGACCTTCATCAGCCTGCTGTTCCTGTTCTCCAGCGCCT

ACTCCCAGGGCCAGGACAGGCACATGATCCGGATGAGGCAGCTCATCGA

CATCGTCGACCAGCTGAAGAACTACGTGAACGACCTGGTGCCCGAGTTT

CTGCCTGCCCCCGAGGACGTGGAGACCAACTGCGAGTGGTCCGCCTTCT

CCTGCTTTCAGAAGGCCCAGCTGAAGTCCGCCAACACCGGCAACAACGA

GCGGATCATCAACGTGAGCATCAAGAAGCTGAAGCGGAAGCCTCCCTCC

ACAAACGCCGGCAGGAGGCAGAAGCACAGGCTGACCTGCCCCAGCTGTG

ACTCCTACGAGAAGAAGCCCCCCAAGGAGTTCCTGGAGAGGTTCAAGTC

CCTGCTGCAGAAGATGATCCATCAGCACCTGTCCTCCAGGACCCACGGC

TCCGAGGACTCCATTACATGCCCCCCTCCCATGAGCGTGGAGCACGCCG

ACATCTGGGTGAAGAGCTATAGCCTCTACAGCCGGGAGAGGTATATCTG

TAACAGCGGCTTCAAGAGGAAGGCCGGCACCAGCAGCCTCACCGAGTGC

GTGCTGAATAAGGCTACCAACGTGGCTCACTGGACAACACCCTCTTTAA

AGTGCATCCGGGGCGGTGGAGGATCCGGAGGAGGTGGCTCCGGCGGCGG

AGGATCTGATCCCGCCGGCCTCTTGGACCTGCGGCAGGGCATGTTTGCG

CAGCTGGTGGCCCAAAATGTTCTGCTGATCGATGGGCCCCTGAGCTGGT
```

-continued

```
ACAGTGACCCAGGCCTGGCAGGCGTGTCCCTGACGGGGGGCCTGAGCTA

CAAAGAGGACACGAAGGAGCTGGTGGTGGCCAAGGCTGGAGTCTACTAT

GTCTTCTTTCAACTAGAGCTGCGGCGCGTGGTGGCCGGCGAGGGCTCAG

GCTCCGTTTCACTTGCGCTGCACCTGCAGCCACTGCGCTCTGCTGCTGG

GGCCGCCGCCCTGGCTTTGACCGTGGACCTGCCACCCGCCTCCTCCGAG

GCTCGGAACTCGGCCTTCGGTTTCCAGGGCCGCTTGCTGCACCTGAGTG

CCGGCCAGCGCCTGGGCGTCCATCTTCACACTGAGGCCAGGGCACGCCA

TGCCTGGCAGCTTACCCAGGGCGCCACAGTCTTGGGACTCTTCCGGGTG

ACCCCCGAAATC.
```

Exemplary Multi-Chain Chimeric Polypeptides—Type K

In some embodiments of any of the multi-chain chimeric polypeptides described herein, the first target-binding domain and the second targeting-binding domain each independently bind specifically to a receptor of IL-7 or TGF-β. In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to a receptor for IL-7, and the second target-binding domain binds specifically to TGF-β. In some embodiments of these multi-chain chimeric polypeptides, the first target-binding domain binds specifically to TGF-β, and the second target-binding domain binds specifically to a receptor for IL-7.

In some embodiments of these multi-chain chimeric polypeptides, the first target-binding domain includes a soluble IL-7 protein (e.g., a soluble human IL-7 protein). In some embodiments of these multi-chain chimeric polypeptides, the soluble human IL-7 protein includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 135)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH.

In some embodiments of these multi-chain chimeric polypeptides, the soluble human IL-7 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 197)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCGATGG

GCACCAAGGAGCAT.

In some embodiments of these multi-chain chimeric polypeptides, the second target-binding domain comprises a target-binding domain that binds specifically to TGF-β. In some embodiments of these multi-chain chimeric polypeptides, the second target-binding domain is a soluble TGF-β receptor (e.g., a soluble TGF-β RII receptor, e.g., a soluble human TGF-β RII receptor). In some embodiments of these multi-chain chimeric polypeptides, the soluble human TGF-β RII includes a first sequence of soluble human TGF-β RII and a second sequence of soluble human TGF-β RII. In some embodiments of these multi-chain chimeric polypeptides, the soluble human TGF-β RII includes a linker disposed between the first sequence of soluble human TGF-β RII and the second sequence of soluble human TGF—RII. In some examples of these multi-chain chimeric polypeptides, the linker includes the sequence (SEQ ID NO: 7)
GGGGSGGGGSGGGGS.

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical at least 99% identical or 100% identical to:

(SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCTCC

-continued

ATCACCTCCATCTGTGAGAAGCCTCAGGAGGTGTGCGTGGCTGTCTGGC
GGAAGAATGACGAGAATATCACCCTGGAAACCGTCTGCCACGATCCCAA
GCTGCCCTACCACGATTTCATCCTGGAAGACGCCGCCAGCCCTAAGTGC
ATCATGAAAGAGAAAAAGAAGCCTGGCGAGACCTTTTTCATGTGCTCCT
GCAGCAGCGACGAATGCAACGACAATATCATCTTTAGCGAGGAATACAA
TACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 60)
IPPHVQKSVNNDMIVTDNNGAVKFPQLCKFCDVRFSTCDNQKSMSNCSI
TSICEKPQEVCVAVWRKNDENITLETVCHDPKLPYHDFILEDAASPKCI
MKEKKKPGETFFMCSCSSDECNDNIIFSEEYNTSNPDGGGGSGGGGSGG
GGSIPPHVQKSVNNDMIVTDNNGAVKFPQLCKFCDVRFSTCDNQKSCMS
NCSITSICEKPQEVCVAVWRKNDENITLETVCHDPKLPYHDFILEDAAS
PKCIMKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGAC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 141)
DCDIEGKDGKQYESVLMVSIDQLLDSMKEIGSNCLNNEFNFFKRHICDA
NKEGMFLFRAARKLRQFLKMNSTGDFDLHLLKVSEGTTILLNCTGQVKG
RKPAALGEAQPTKSLEENKSLKEQKKLNDLCFLKRLLQEIKTCWNKILM
GTKEHSGTTNTVAAYNLTWKSTNFKTILEWEPKPVNQVYTVQISTKSGD
WKSKCFYTTDTECDLTDEIVKDVKQTYLARVFSYPAGNVESTGSAGEPL
YENSPEFTPYLETNLGQPTIQSFEQVGTKVNVTVEDERTLVRRNNTFLS
LRDVFGKDLIYTLYYWKSSSSGKKTAKTNTNEFLIDVDKGENYCFSVQA
VIPSRTVNRKSTDSPVECMGQEKGEFRENWVNVISDLKKIEDLIQSMHI
DATLYTESDVHPSCKVTAMKCFLLELQVISLESGDASIHDTVENLIILA
NNSLSSNGNVTESGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 142)
GATTGCGACATCGAGGGCAAGGACGGCAAGCAGTACGAGAGCGTGCTGA
TGGTGTCCATCGACCAGCTGCTGGACAGCATGAAGGAGATCGGCTCCAA
CTGCCTCAACAACGAGTTCAACTTCTTCAAGCGGCACATCTGCGACGCC
AACAAGGAGGGCATGTTCCTGTTCAGGGCCGCCAGGAAACTGCGGCAGT
TCCTGAAGATGAACTCCACCGGCGACTTCGACCTGCACCTGCTGAAGGT
GTCCGAGGGCACCACCATCCTGCTGAACTGCACCGGACAGGTGAAGGGC
CGGAAACCTGCTGCTCTGGGAGAGGCCCAACCCACCAAGAGCCTGGAGG
AGAACAAGTCCCTGAAGGAGCAGAAGAAGCTGAACGACCTGTGCTTCCT
GAAGAGGCTGCTGCAGGAGATCAAGACCTGCTGGAACAAGATCCTGATG
GGCACCAAGGAGCATAGCGGCACAACCAACACAGTCGCTGCCTATAACC
TCACTTGGAAGAGCACCAACTTCAAAACCATCCTCGAATGGGAACCCAA
ACCCGTTAACCAAGTTTACACCGTGCAGATCAGCACCAAGTCCGGCGAC
TGGAAGTCCAAATGTTTCTATACCACCGACACCGAGTGCGATCTCACCG
ATGAGATCGTGAAAGATGTGAAACAGACCTACCTCGCCCGGGTGTTTAG
CTACCCCGCCGGCAATGTGGAGAGCACTGGTTCCGCTGGCGAGCCTTTA
TACGAGAACAGCCCCGAATTTACCCCTTACCTCGAGACCAATTTAGGAC

-continued

AGCCCACCATCCAAAGCTTTGAGCAAGTTGGCACAAAGGTGAATGTGAC

AGTGGAGGACGAGCGGACTTTAGTGCGGCGGAACAACACCTTTCTCAGC

CTCCGGGATGTGTTCGGCAAAGATTTAATCTACACACTGTATTACTGGA

AGTCCTCTTCCTCCGGCAAGAAGACAGCTAAAACCAACACAAACGAGTT

TTTAATCGACGTGGATAAAGGCGAAAACTACTGTTTCAGCGTGCAAGCT

GTGATCCCCTCCCGGACCGTGAATAGGAAAAGCACCGATAGCCCCGTTG

AGTGCATGGGCCAAGAAAAGGGCGAGTTCCGGGAGAACTGGGTGAACGT

CATCAGCGATTTAAAGAAGATCGAAGATTTAATTCAGTCCATGCATATC

GACGCCACTTTATACACAGAATCCGACGTGCACCCCTCTTGTAAGGTGA

CCGCCATGAAATGTTTTTTACTGGAGCTGCAAGTTATCTCTTTAGAGAG

CGGAGACGCTAGCATCCACGACACCGTGGAGAATTTAATCATTTTAGCC

AATAACTCTTTATCCAGCAACGGCAACGTGACAGAGTCCGGCTGCAAGG

AGTGCGAAGAGCTGGAGGAGAAGAACATCAAGGAGTTTCTGCAATCCTT

TGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical to:

(SEQ ID NO: 143)

MKWVTFISLLFLFSSAYSDCDIEGKDGKQYESVLMVSDQLLDSMKEIGS

NCLNNEFNFFKRHICDANKEGMFLFRAARKLRQFLKMNSTGDFDLHLLK

VSEGTTILLNCTGQVKGRKPAALGEAQPTKSLEENKSLKEQKKLNDLCF

LKRLLQEIKTCWNKILMGTKEHSGTTNTVAAYNLTWKSTNFKTILEWEP

KPVNQVYTVQISTKSGDWKSKCFYTTDTECDLTDEIVKDVKQTYLARVF

SYPAGNVESTGSAGEPLYENSPEFTPYLETNLGQPTIQSFEQVGTKVNV

TVEDERTLVRRNNTFLSLRDVFGKDLIYTLYYWKSSSSGKKTAKTNTNE

FLIDVDKGENYCFSVQAVIPSRTVNRKSTDSPVECMGQEKGEFRENWVN

VISDLKKIEDLIQSMHIDATLYTESDVHPSCKVTAMKCFLLELQVISLE

SGDASIHDTVENLIILANNSLSSNGNVTESGCKECEELEEKNIKEFLQS

FVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 144)

ATGAAGTGGGTGACCTTCATCAGCCTGCTGTTCCTGTTCTCCAGCGCCT

ACTCCGATTGCGACATCGAGGGCAAGGACGGCAAGCAGTACGAGAGCGT

GCTGATGGTGTCCATCGACCAGCTGCTGGACAGCATGAAGGAGATCGGC

-continued

TCCAACTGCCTCAACAACGAGTTCAACTTCTTCAAGCGGCACATCTGCG

ACGCCAACAAGGAGGGCATGTTCCTGTTCAGGGCCGCCAGGAAACTGCG

GCAGTTCCTGAAGATGAACTCCACCGGCGACTTCGACCTGCACCTGCTG

AAGGTGTCCGAGGGCACCACCATCCTGCTGAACTGCACCGGACAGGTGA

AGGGCCGGAAACCTGCTGCTCTGGGAGAGGCCCAACCCACCAAGAGCCT

GGAGGAGAACAAGTCCCTGAAGGAGCAGAAGAAGCTGAACGACCTGTGC

TTCCTGAAGAGGCTGCTGCAGGAGATCAAGACCTGCTGGAACAAGATCC

TGATGGGCACCAAGGAGCATAGCGGCACAACCAACACAGTCGCTGCCTA

TAACCTCACTTGGAAGAGCACCAACTTCAAAACCATCCTCGAATGGGAA

CCCAAACCCGTTAACCAAGTTTACACCGTGCAGATCAGCACCAAGTCCG

GCGACTGGAAGTCCAAATGTTTCTATACCACCGACACCGAGTGCGATCT

CACCGATGAGATCGTGAAAGATGTGAAACAGACCTACCTCGCCCGGGTG

TTTAGCTACCCCGCCGGCAATGTGGAGAGCACTGGTTCCGCTGGCGAGC

CTTTATACGAGAACAGCCCCGAATTTACCCCTTACCTCGAGACCAATTT

AGGACAGCCCACCATCCAAAGCTTTGAGCAAGTTGGCACAAAGGTGAAT

GTGACAGTGGAGGACGAGCGGACTTTAGTGCGGCGGAACAACACCTTTC

TCAGCCTCCGGGATGTGTTCGGCAAAGATTTAATCTACACACTGTATTA

CTGGAAGTCCTCTTCCTCCGGCAAGAAGACAGCTAAAACCAACACAAAC

GAGTTTTTAATCGACGTGGATAAAGGCGAAAACTACTGTTTCAGCGTGC

AAGCTGTGATCCCCTCCCGGACCGTGAATAGGAAAAGCACCGATAGCCC

CGTTGAGTGCATGGGCCAAGAAAAGGGCGAGTTCCGGGAGAACTGGGTG

AACGTCATCAGCGATTTAAAGAAGATCGAAGATTTAATTCAGTCCATGC

ATATCGACGCCACTTTATACACAGAATCCGACGTGCACCCCTCTTGTAA

GGTGACCGCCATGAAATGTTTTTTACTGGAGCTGCAAGTTATCTCTTTA

GAGAGCGGAGACGCTAGCATCCACGACACCGTGGAGAATTTAATCATTT

TAGCCAATAACTCTTTATCCAGCAACGGCAACGTGACAGAGTCCGGCTG

CAAGGAGTGCGAAGAGCTGGAGGAGAAGAACATCAAGGAGTTTCTGCAA

TCCTTTGTGCACATTGTCCAGATGTTCATCAATACCTCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 130)

IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

-continued

SPKCIMKEKKKPGETFFMCSCSSDECNDNIIFSEEYNTSNPDITCPPPM

SVEHADIWVKSYSLYSRERYICNSGFKRKAGTSSLTECVLNKATNVAHW

TTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 131)

ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACATTACATGCCCCCCTCCCATG

AGCGTGGAGCACGCCGACATCTGGGTGAAGAGCTATAGCCTCTACAGCC

GGGAGAGGTATATCTGTAACAGCGGCTTCAAGAGGAAGGCCGGCACCAG

CAGCCTCACCGAGTGCGTGCTGAATAAGGCTACCAACGTGGCTCACTGG

ACAACACCCTCTTTAAAGTGCATCCGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least (SEQ ID NO: 132)

MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

-continued

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDITCPPPMSVEHADIWVKSYSLYSRERYICNSGFKRKAG

TSSLTECVLNKATNVAHWTTPSLKCIR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 133)

ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCTCCATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACATTACATGCCCCCCTC

CCATGAGCGTGGAGCACGCCGACATCTGGGTGAAGAGCTATAGCCTCTA

CAGCCGGGAGAGGTATATCTGTAACAGCGGCTTCAAGAGGAAGGCCGGC

ACCAGCAGCCTCACCGAGTGCGTGCTGAATAAGGCTACCAACGTGGCTC

ACTGGACAACACCCTCTTTAAAGTGCATCCGG.

Exemplary Multi-Chain Chimeric Polypeptides—Type L

In some embodiments of any of the multi-chain chimeric polypeptides described herein, the first target-binding domain and the second targeting-binding domain each independently bind specifically to TGF-β, a receptor of IL-21, or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a receptor for CD137L (e.g., a soluble CD137L, e.g., a soluble human CD137L).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, one or more of the first target-binding domain, the second target-binding domain and the additional target-binding domain is an agonistic antigen-binding domain. In some embodiments of these multi-chain chimeric polypeptides, the first target-binding domain, the second target-binding domain, and the additional target-binding domain are each agonistic antigen-binding domains. In some embodiments of these multi-chain chimeric polypeptides, the antigen-binding domain includes a scFv or single-domain antibody.

In some embodiments of these multi-chain chimeric polypeptides, the first target-binding domain binds specifically to TGF-β and the second target-binding domain binds specifically to a receptor for IL-21 or a receptor for CD137L.

In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGF-β RII includes a first sequence of soluble human TGF-β RII and a second sequence of soluble human TGF-β RII. In some embodiments of these multi-chain chimeric polypeptides, the soluble human TGF-β RII includes a linker disposed between the first sequence of soluble human TGF-β RII and the second sequence of soluble human TGF-β RII. In some examples of these multi-chain chimeric polypeptides, the linker includes the sequence (SEQ ID NO: 7)
GGGGSGGGGSGGGGS.

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNC

SITSICEKPQEVCVAVWRKNDENITLETVCHDPKLPYHDFILEDAASP

KCIMKEKKKPGETFFMCSCSSDECNDNIIFSEEYNTSNPD.

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSN

CSITSICEKPQEVCVAVWRKNDENITLETVCHDPKLPYHDFILEDAA

SPKCIMKEKKKPGETFFMCSCSSDECNDNIIFSEEYNTSNPD.

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATCCCCCCCCATGTGCAAAAGAGCGTGAACAACGATATGATCGTGA
CCGACAACAACGGCGCCGTGAAGTTTCCCCAGCTCTGCAAGTTCTG
CGATGTCAGGTTCAGCACCTGCGATAATCAGAAGTCCTGCATGTCC
AACTGCAGCATCACCTCCATCTGCGAGAAGCCCCAAGAAGTGTGCG
TGGCCGTGTGGCGGAAAAATGACGAGAACATCACCCTGGAGACCGT
GTGTCACGACCCCAAGCTCCCTTATCACGACTTCATTCTGGAGGAC
GCTGCCTCCCCCAAATGCATCATGAAGGAGAAGAAGAAGCCCGGAG
AGACCTTCTTTATGTGTTCCTGTAGCAGCGACGAGTGTAACGACAA
CATCATCTTCAGCGAAGAGTACAACACCAGCAACCCTGAT.

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTG
ACCGATAACAATGGCGCCGTGAAATTTCCCCAGCTGTGCAAATTC
TGCGATGTGAGGTTTTCCACCTGCGACAACCAGAAGTCCTGTATG
AGCAACTGCTCCATCACCTCCATCTGTGAGAAGCCTCAGGAGGTG
TGCGTGGCTGTCTGGCGGAAGAATGACGAGAATATCACCCTGGAA
ACCGTCTGCCACGATCCCAAGCTGCCCTACCACGATTTCATCCTG
GAAGACGCCGCCAGCCCTAAGTGCATCATGAAAGAGAAAAAGAAG
CCTGGCGAGACCTTTTTCATGTGCTCCTGCAGCAGCGACGAATGC
AACGACAATATCATCTTTAGCGAGGAATACAATACCAGCAACCCC
GAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 60)
IPPHVQKSVNNDMIVTDNNGAVKFPQLCKFCDVRFSTCDNQKSCM
SNCSITSICEKPQEVCVAVWRKNDENITLETVCHDPKLPYHDFIL
EDAASPKCIMKEKKKPGETFFMCSCSSDECNDNIIFSEEYNTSNP
DGGGGSGGGGSGGGGSIPPHVQKSVNNDMIVTDNNGAVKFPQLCK
FCDVRFSTCDNQKSCMSNCSITSICEKPQEVCVAVWRKNDENITL
ETVCHDPKLPYHDFILEDAASPKCIMKEKKKPGETFFMCSCSSDE
CNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
ATCCCCCCCCATGTGCAAAAGAGCGTGAACAACGATATGATCGT
GACCGACAACAACGGCGCCGTGAAGTTTCCCCAGCTCTGCAAGT
TCTGCGATGTCAGGTTCAGCACCTGCGATAATCAGAAGTCCTGC
ATGTCCAACTGCAGCATCACCTCCATCTGCGAGAAGCCCCAAGA
AGTGTGCGTGGCCGTGTGGCGGAAAAATGACGAGAACATCACCC
TGGAGACCGTGTGTCACGACCCCAAGCTCCCTTATCACGACTTC
ATTCTGGAGGACGCTGCCTCCCCCAAATGCATCATGAAGGAGAA
GAAGAAGCCCGGAGAGACCTTCTTTATGTGTTCCTGTAGCAGCG
ACGAGTGTAACGACAACATCATCTTCAGCGAAGAGTACAACACC
AGCAACCCTGATGGAGGTGGCGGATCCGGAGGTGGAGGTTCTGG
TGGAGGTGGGAGTATTCCTCCCCACGTGCAGAAGAGCGTGAATA
ATGACATGATCGTGACCGATAACAATGGCGCCGTGAAATTTCCC
CAGCTGTGCAAATTCTGCGATGTGAGGTTTTCCACCTGCGACAA
CCAGAAGTCCTGTATGAGCAACTGCTCCATCACCTCCATCTGTG
AGAAGCCTCAGGAGGTGTGCGTGGCTGTCTGGCGGAAGAATGAC
GAGAATATCACCCTGGAAACCGTCTGCCACGATCCCAAGCTGCC
CTACCACGATTTCATCCTGGAAGACGCCGCCAGCCCTAAGTGCA
TCATGAAAGAGAAAAAGAAGCCTGGCGAGACCTTTTTCATGTGC
TCCTGCAGCAGCGACGAATGCAACGACAATATCATCTTTAGCGA
GGAATACAATACCAGCAACCCCGAC.

In some embodiments of these multi-chain chimeric polypeptides, the second target-binding domain or the additional target-binding domain binds specifically to a receptor for IL-21. In some embodiments of these multi-chain chimeric polypeptides, the second target-binding domain or the additional target-binding domain includes a soluble IL-21 (e.g., a soluble human IL-21).

In some embodiments of these multi-chain chimeric polypeptides, a soluble human IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)
QGQDRHMIRMRQLIDIVDQLKNYVNDLVPEFLPAPEDVETNCEW
SAFSCFQKAQLKSANTGNNERIINVSIKKLKRKPPSTNAGRRQK
HRLTCPSCDSYEKKPPKEFLERFKSLLQKMIHQHLSSRTHGSED
S.

In some embodiments of these multi-chain chimeric polypeptides, the soluble human IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 125)
CAGGGCCAGGACAGGCACATGATCCGGATGAGGCAGCTCATCGA
CATCGTCGACCAGCTGAAGAACTACGTGAACGACCTGGTGCCCG
AGTTTCTGCCTGCCCCCGAGGACGTGGAGACCAACTGCGAGTGG
TCCGCCTTCTCCTGCTTTCAGAAGGCCCAGCTGAAGTCCGCCAA
CACCGGCAACAACGAGCGGATCATCAACGTGAGCATCAAGAAGC
TGAAGCGGAAGCCTCCCTCCACAAACGCCGGCAGGAGGCAGAAG
CACAGGCTGACCTGCCCCAGCTGTGACTCCTACGAGAAGAAGCC
CCCCAAGGAGTTCCTGGAGAGGTTCAAGTCCCTGCTGCAGAAGA
TGATCCATCAGCACCTGTCCTCCAGGACCCACGGCTCCGAGGAC
TCC.

In some embodiments of these multi-chain chimeric polypeptides, the second target-binding domain or the additional target-binding domain binds specifically to a receptor for CD137L. In some embodiments of these multi-chain chimeric polypeptides, the second target-binding domain and/or the additional target-binding domain includes a soluble CD137L (e.g., a soluble human CD137L).

In some embodiments of these multi-chain chimeric polypeptides, a soluble CD137L includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 165)
REGPELSPDDPAGLLDLRQGMFAQLVAQNVLLIDGPLSWYSDP
GLAGVSLTGGLSYKEDTKELVVAKAGVYYVFFQLELRRVVAGE
GSGSVSLALHLQPLRSAAGAAALALTVDLPPASSEARNSAFGF
QGRLLHLSAGQRLGVHLHTEARARHAWQLTQGATVLGLFRVTP
EIPAGLPSPRSE.

In some embodiments of these multi-chain chimeric polypeptides, a soluble CD137L is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 166)
CGCGAGGGTCCCGAGCTTTCGCCCGACGATCCCGCCGGCCTC
TTGGACCTGCGGCAGGGCATGTTTGCGCAGCTGGTGGCCCAA
AATGTTCTGCTGATCGATGGGCCCCTGAGCTGGTACAGTGAC
CCAGGCCTGGCAGGCGTGTCCCTGACGGGGGGCCTGAGCTAC
AAAGAGGACACGAAGGAGCTGGTGGTGGCCAAGGCTGGAGTC
TACTATGTCTTCTTTCAACTAGAGCTGCGGCGCGTGGTGGCC

-continued

GGCGAGGGCTCAGGCTCCGTTTCACTTGCGCTGCACCTGCAG
CCACTGCGCTCTGCTGCTGGGGCCGCCGCCCTGGCTTTGACC
GTGGACCTGCCACCCGCCTCCTCCGAGGCTCGGAACTCGGCC
TTCGGTTTCCAGGGCCGCTTGCTGCACCTGAGTGCCGGCCAG
CGCCTGGGCGTCCATCTTCACACTGAGGCCAGGGCACGCCAT
GCCTGGCAGCTTACCCAGGGCGCCACAGTCTTGGGACTCTTC
CGGGTGACCCCCGAAATCCCAGCCGGACTCCCTTCACCGAGG
TCGGAA.

In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 167)
DPAGLLDLRQGMFAQLVAQNVLLIDGPLSWYSDPGLAGVSLT
GGLSYKEDTKELVVAKAGVYYVFFQLELRRVVAGEGSGSVSL
ALHLQPLRSAAGAAALALTVDLPPASSEARNSAFGFQGRLLH
LSAGQRLGVHLHTEARARHAWQLTQGATVLGLFRVTPEI.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 168)
GATCCCGCCGGCCTCTTGGACCTGCGGCAGGGCATGTTTGCG
CAGCTGGTGGCCCAAAATGTTCTGCTGATCGATGGGCCCCTG
AGCTGGTACAGTGACCCAGGCCTGGCAGGCGTGTCCCTGACG
GGGGGCCTGAGCTACAAAGAGGACACGAAGGAGCTGGTGGTG
GCCAAGGCTGGAGTCTACTATGTCTTCTTTCAACTAGAGCTG
CGGCGCGTGGTGGCCGGCGAGGGCTCAGGCTCCGTTTCACTT
GCGCTGCACCTGCAGCCACTGCGCTCTGCTGCTGGGGCCGCC
GCCCTGGCTTTGACCGTGGACCTGCCACCCGCCTCCTCCGAG
GCTCGGAACTCGGCCTTCGGTTTCCAGGGCCGCTTGCTGCAC
CTGAGTGCCGGCCAGCGCCTGGGCGTCCATCTTCACACTGAG
GCCAGGGCACGCCATGCCTGGCAGCTTACCCAGGGCGCCACA
GTCTTGGGACTCTTCCGGGTGACCCCCGAAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)
IPPHVQKSVNNDMIVTDNNGAVKFPQLCKFCDVRFSTCDNQK
SCMSNCSITSICEKPQEVCVAVWRKNDENITLETVCHDPKLP
YHDFILEDAASPKCIMKEKKKPGETFFMCSCSSDECNDNIIF
SEEYNTSNPDGGGGSGGGGSGGGGSIPPHVQKSVNNDMIVTD
NNGAVKFPQLCKFCDVRFSTCDNQKSCMSNCSITSICEKPQE
VCVAVWRKNDENITLETVCHDPKLPYHDFILEDAASPKCIMK
EKKKPGETFFMCSCSSDECNDNIIFSEEYNTSNPDSGTTNTV
AAYNLTWKSTNFKTILEWEPKPVNQVYTVQISTKSGDWKSKC
FYTTDTECDLTDEIVKDVKQTYLARVFSYPAGNVESTGSAGE
PLYENSPEFTPYLETNLGQPTIQSFEQVGTKVNVTVEDERTL
VRRNNTFLSLRDVFGKDLIYTLYYWKSSSSGKKTAKTNTNEF
LIDVDKGENYCFSVQAVIPSRTVNRKSTDSPVECMGQEKGEF
RENWVNVISDLKKIEDLIQSMHIDATLYTESDVHPSCKVTAM
KCELLELQVISLESGDASIHDTVENLIILANNSLSSNGNVTE
SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)
ATCCCCCCCCATGTGCAAAAGAGCGTGAACAACGATATGATC
GTGACCGACAACAACGGCGCCGTGAAGTTTCCCCAGCTCTGC
AAGTTCTGCGATGTCAGGTTCAGCACCTGCGATAATCAGAAG
TCCTGCATGTCCAACTGCAGCATCACCTCCATCTGCGAGAAG
CCCCAAGAAGTGTGCGTGGCCGTGTGGCGGAAAAATGACGAG
AACATCACCCTGGAGACCGTGTGTCACGACCCCAAGCTCCCT
TATCACGACTTCATTCTGGAGGACGCTGCCTCCCCCAAATGC
ATCATGAAGGAGAAGAAGAAGCCCGGAGAGACCTTCTTTATG
TGTTCCTGTAGCAGCGACGAGTGTAACGACAACATCATCTTC
AGCGAAGAGTACAACACCAGCAACCCTGATGGAGGTGGCGGA
TCCGGAGGTGGAGGTTCTGGTGGAGGTGGGAGTATTCCTCCC
CACGTGCAGAAGAGCGTGAATAATGACATGATCGTGACCGAT
AACAATGGCGCCGTGAAATTTCCCCAGCTGTGCAAATTCTGC
GATGTGAGGTTTTCCACCTGCGACAACCAGAAGTCCTGTATG
AGCAACTGCTCCATCACCTCCATCTGTGAGAAGCCTCAGGAG
GTGTGCGTGGCTGTCTGGCGGAAGAATGACGAGAATATCACC
CTGGAAACCGTCTGCCACGATCCCAAGCTGCCCTACCACGAT
TTCATCCTGGAAGACGCCGCCAGCCCTAAGTGCATCATGAAA
GAGAAAAAGAAGCCTGGCGAGACCTTTTTCATGTGCTCCTGC

-continued

AGCAGCGACGAATGCAACGACAATATCATCTTTAGCGAGGAA
TACAATACCAGCAACCCCGACAGCGGCACAACCAACACAGTC
GCTGCCTATAACCTCACTTGGAAGAGCACCAACTTCAAAACC
ATCCTCGAATGGGAACCCAAACCCGTTAACCAAGTTTACACC
GTGCAGATCAGCACCAAGTCCGGCGACTGGAAGTCCAAATGT
TTCTATACCACCGACACCGAGTGCGATCTCACCGATGAGATC
GTGAAAGATGTGAAACAGACCTACCTCGCCCGGGTGTTTAGC
TACCCCGCCGGCAATGTGGAGAGCACTGGTTCCGCTGGCGAG
CCTTTATACGAGAACAGCCCCGAATTTACCCCTTACCTCGAG
ACCAATTTAGGACAGCCCACCATCCAAAGCTTTGAGCAAGTT
GGCACAAAGGTGAATGTGACAGTGGAGGACGAGCGGACTTTA
GTGCGGCGGAACAACACCTTTCTCAGCCTCCGGGATGTGTTC
GGCAAAGATTTAATCTACACACTGTATTACTGGAAGTCCTCT
TCCTCCGGCAAGAAGACAGCTAAAACCAACACAAACGAGTTT
TTAATCGACGTGGATAAAGGCGAAAACTACTGTTTCAGCGTG
CAAGCTGTGATCCCCTCCCGGACCGTGAATAGGAAAAGCACC
GATAGCCCCGTTGAGTGCATGGGCCAAGAAAAGGGCGAGTTC
CGGGAGAACTGGGTGAACGTCATCAGCGATTTAAAGAAGATC
GAAGATTTAATTCAGTCCATGCATATCGACGCCACTTTATAC
ACAGAATCCGACGTGCACCCCTCTTGTAAGGTGACCGCCATG
CAAGTTATCTCTTTAGAGAGCGGAGACGCTAGCATCCACGAC
AAATGTTTTTTACTGGAGCTGACCGTGGAGAATTTAATCATT
TTAGCCAATAACTCTTTATCCAGCAACGGCAACGTGACAGAG
TCCGGCTGCAAGGAGTGCGAAGAGCTGGAGGAGAAGAACATC
AAGGAGTTTCTGCAATCCTTTGTGCACATTGTCCAGATGTTC
ATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)
MKWVTFISLLFLFSSAYSIPPHVQKSVNNDMIVTDNNGAVKF
PQLCKFCDVRFSTCDNQKSCMSNCSITSICEKPQEVCVAVWR
KNDENITLETVCHDPKLPYHDFILEDAASPKCIMKEKKKPGE
TFFMCSCSSDECNDNIIFSEEYNTSNPDGGGGSGGGGSGGGG
SIPPHVQKSVNNDMIVTDNNGAVKFPQLCKFCDVRFSTCDNQ
KSCMSNCSITSICEKPQEVCVAVWRKNDENITLETVCHDPKL
PYHDFILEDAASPKCIMKEKKKPGETFFMCSCSSDECNDNII
FSEEYNTSNPDSGTTNTVAAYNLTWKSTNFKTILEWEPKPVN
QVYTVQISTKSGDWKSKCFYTTDTECDLTDEIVKDVKQTYLA

-continued

RVFSYPAGNVESTGSAGEPLYENSPEFTPYLETNLGQPTIQS
FEQVGTKVNVTVEDERTLVRRNNTFLSLRDVFGKDLIYTLYY
WKSSSSGKKTAKTNTNEFLIDVDKGENYCFSVQAVIPSRTVN
RKSTDSPVECMGQEKGEFRENWVNVISDLKKIEDLIQSMHID
ATLYTESDVHPSCKVTAMKCFLLELQVISLESGDASIHDTVE
NLIILANNSLSSNGNVTESGCKECEELEEKNIKEFLQSFVHI
VQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)
ATGAAGTGGGTGACCTTCATCAGCCTGCTGTTCCTGTTCTCCAGCGCCT
ACTCCATCCCCCCCCATGTGCAAAAGAGCGTGAACAACGATATGATCGT
GACCGACAACAACGGCGCCGTGAAGTTTCCCCAGCTCTGCAAGTTCTGC
GATGTCAGGTTCAGCACCTGCGATAATCAGAAGTCCTGCATGTCCAACT
GCAGCATCACCTCCATCTGCGAGAAGCCCCAAGAAGTGTGCGTGGCCGT
GTGGCGGAAAAATGACGAGAACATCACCCTGGAGACCGTGTGTCACGAC
CCCAAGCTCCCTTATCACGACTTCATTCTGGAGGACGCTGCCTCCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC
CTTTTTCATGTGCTCCTGCAGCAGCGACGAATGCAACGACAATATCATC
TTTAGCGAGGAATACAATACCAGCAACCCCGACAGCGGCACAACCAACA
CAGTCGCTGCCTATAACCTCACTTGGAAGAGCACCAACTTCAAAACCAT
CCTCGAATGGGAACCCAAACCCGTTAACCAAGTTTACACCGTGCAGATC
AGCACCAAGTCCGGCGACTGGAAGTCCAAATGTTTCTATACCACCGACA
CCGAGTGCGATCTCACCGATGAGATCGTGAAAGATGTGAAACAGACCTA
CCTCGCCCGGGTGTTTAGCTACCCCGCCGGCAATGTGGAGAGCACTGGT
TCCGCTGGCGAGCCTTTATACGAGAACAGCCCCGAATTTACCCCTTACC
TCGAGACCAATTTAGGACAGCCCACCATCCAAAGCTTTGAGCAAGTTGG
CACAAAGGTGAATGTGACAGTGGAGGACGAGCGGACTTTAGTGCGGCGG

-continued

AACAACACCTTTCTCAGCCTCCGGGATGTGTTCGGCAAAGATTTAATCT
ACACACTGTATTACTGGAAGTCCTCTTCCTCCGGCAAGAAGACAGCTAA
AACCAACACAAACGAGTTTTTAATCGACGTGGATAAAGGCGAAAACTAC
TGTTTCAGCGTGCAAGCTGTGATCCCCTCCCGGACCGTGAATAGGAAAA
GCACCGATAGCCCCGTTGAGTGCATGGGCCAAGAAAAGGGCGAGTTCCG
GGAGAACTGGGTGAACGTCATCAGCGATTTAAAGAAGATCGAAGATTTA
ATTCAGTCCATGCATATCGACGCCACTTTATACACAGAATCCGACGTGC
ACCCCTCTTGTAAGGTGACCGCCATGAAATGTTTTTTACTGGAGCTGCA
AGTTATCTCTTTAGAGAGCGGAGACGCTAGCATCCACGACACCGTGGAG
AATTTAATCATTTTAGCCAATAACTCTTTATCCAGCAACGGCAACGTGA
CAGAGTCCGGCTGCAAGGAGTGCGAAGAGCTGGAGGAGAAGAACATCAA
GGAGTTTCTGCAATCCTTTGTGCACATTGTCCAGATGTTCATCAATACC
TCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 169)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDSITCPPPMSVEHADI
WVKSYSLYSRERYICNSGFKRKAGTSSLTECVLNKATNVAHWTTPSLKC
IRGGGGSGGGGSGGGGSREGPELSPDDPAGLLDLRQGMFAQLVAQNVLL
IDGPLSWYSDPGLAGVSLTGGLSYKEDTKELVVAKAGVYYVFFQLELRR
VVAGEGSGSVSLALHLQPLRSAAGAAALALTVDLPPASSEARNSAFGFQ
GRLLHLSAGQRLGVHLHTEARARHAWQLTQGATVLGLFRVTPEIPAGLP
SPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 170)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC

-continued

TGCAGAAGATGATCCATCAGCACCTGTCCTCCAGGACCCACGGCTCCGA
GGACTCCATTACATGCCCCCCTCCCATGAGCGTGGAGCACGCCGACATC
TGGGTGAAGAGCTATAGCCTCTACAGCCGGGAGAGGTATATCTGTAACA
GCGGCTTCAAGAGGAAGGCCGGCACCAGCAGCCTCACCGAGTGCGTGCT
GAATAAGGCTACCAACGTGGCTCACTGGACAACACCCTCTTTAAAGTGC
ATCCGGGGCGGTGGAGGATCCGGAGGAGGTGGCTCCGGCGGCGGAGGAT
CTCGCGAGGGTCCCGAGCTTTCGCCCGACGATCCCGCCGGCCTCTTGGA
CCTGCGGCAGGGCATGTTTGCGCAGCTGGTGGCCCAAAATGTTCTGCTG
ATCGATGGGCCCCTGAGCTGGTACAGTGACCCAGGCCTGGCAGGCGTGT
CCCTGACGGGGGGCCTGAGCTACAAAGAGGACACGAAGGAGCTGGTGGT
GGCCAAGGCTGGAGTCTACTATGTCTTCTTTCAACTAGAGCTGCGGCGC
GTGGTGGCCGGCGAGGGCTCAGGCTCCGTTTCACTTGCGCTGCACCTGC
AGCCACTGCGCTCTGCTGCTGGGGCCGCCGCCCTGGCTTTGACCGTGGA
CCTGCCACCCGCCTCCTCCGAGGCTCGGAACTCGGCCTTCGGTTTCCAG
GGCCGCTTGCTGCACCTGAGTGCCGGCCAGCGCCTGGGCGTCCATCTTC
ACACTGAGGCCAGGGCACGCCATGCCTGGCAGCTTACCCAGGGCGCCAC
AGTCTTGGGACTCTTCCGGGTGACCCCCGAAATCCCAGCCGGACTCCCT
TCACCGAGGTCGGAA

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 171)
MKWVTFISLLFLFSSAYSQGQDRHMIRMRQLIDIVDQLKNYVNDLVPEF
LPAPEDVETNCEWSAFSCFQKAQLKSANTGNNERIINVSIKKLKRKPPS
TNAGRRQKHRLTCPSCDSYEKKPPKEFLERFKSLLQKMIHQHLSSRTHG
SEDSITCPPPMSVEHADIWVKSYSLYSRERYICNSGFKRKAGTSSLTEC
VLNKATNVAHWTTPSLKCIRGGGGSGGGGSGGGGSREGPELSPDDPAGL
LDLRQGMFAQLVAQNVLLIDGPLSWYSDPGLAGVSLTGGLSYKEDTKEL
VVAKAGVYYVFFQLELRRVVAGEGSGSVSLALHLQPLRSAAGAAALALT
VDLPPASSEARNSAFGFQGRLLHLSAGQRLGVHLHTEARARHAWQLTQG
ATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 172)
ATGAAGTGGGTGACCTTCATCAGCCTGCTGTTCCTGTTCTCCAGCGCCT
ACTCCCAGGGCCAGGACAGGCACATGATCCGGATGAGGCAGCTCATCGA
CATCGTCGACCAGCTGAAGAACTACGTGAACGACCTGGTGCCCGAGTTT
CTGCCTGCCCCCGAGGACGTGGAGACCAACTGCGAGTGGTCCGCCTTCT
CCTGCTTTCAGAAGGCCCAGCTGAAGTCCGCCAACACCGGCAACAACGA
GCGGATCATCAACGTGAGCATCAAGAAGCTGAAGCGGAAGCCTCCCTCC
ACAAACGCCGGCAGGAGGCAGAAGCACAGGCTGACCTGCCCCAGCTGTG
ACTCCTACGAGAAGAAGCCCCCCAAGGAGTTCCTGGAGAGGTTCAAGTC
CCTGCTGCAGAAGATGATCCATCAGCACCTGTCCTCCAGGACCCACGGC
TCCGAGGACTCCATTACATGCCCCCCTCCCATGAGCGTGGAGCACGCCG
ACATCTGGGTGAAGAGCTATAGCCTCTACAGCCGGGAGAGGTATATCTG
TAACAGCGGCTTCAAGAGGAAGGCCGGCACCAGCAGCCTCACCGAGTGC
GTGCTGAATAAGGCTACCAACGTGGCTCACTGGACAACACCCTCTTTAA
AGTGCATCCGGGGCGGTGGAGGATCCGGAGGAGGTGGCTCCGGCGGCGG
AGGATCTCGCGAGGGTCCCGAGCTTTCGCCCGACGATCCCGCCGGCCTC
TTGGACCTGCGGCAGGGCATGTTTGCGCAGCTGGTGGCCCAAAATGTTC
TGCTGATCGATGGGCCCCTGAGCTGGTACAGTGACCCAGGCCTGGCAGG
CGTGTCCCTGACGGGGGGCCTGAGCTACAAAGAGGACACGAAGGAGCTG
GTGGTGGCCAAGGCTGGAGTCTACTATGTCTTCTTTCAACTAGAGCTGC
GGCGCGTGGTGGCCGGCGAGGGCTCAGGCTCCGTTTCACTTGCGCTGCA
CCTGCAGCCACTGCGCTCTGCTGCTGGGGCCGCCGCCCTGGCTTTGACC
GTGGACCTGCCACCCGCCTCCTCCGAGGCTCGGAACTCGGCCTTCGGTT
TCCAGGGCCGCTTGCTGCACCTGAGTGCCGGCCAGCGCCTGGGCGTCCA
TCTTCACACTGAGGCCAGGGCACGCCATGCCTGGCAGCTTACCCAGGGC
GCCACAGTCTTGGGACTCTTCCGGGTGACCCCCGAAATCCCAGCCGGAC
TCCCTTCACCGAGGTCGGAA

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 173)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDSITCPPPMSVEHADI
WVKSYSLYSRERYICNSGFKRKAGTSSLTECVLNKATNVAHWTTPSLKC
IRGGGGSGGGGSGGGGSDPAGLLDLRQGMFAQLVAQNVLLIDGPLSWYS
DPGLAGVSLTGGLSYKEDTKELVVAKAGVYYVFFQLELRRVVAGEGSGS
VSLALHLQPLRSAAGAAALALTVDLPPASSEARNSAFGFQGRLLHLSAG
QRLGVHLHTEARARHAWQLTQGATVLGLFRVTPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 174)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCCATTACATGCCCCCCTCCCATGAGCGTGGAGCACGCCGACATC
TGGGTGAAGAGCTATAGCCTCTACAGCCGGGAGAGGTATATCTGTAACA
GCGGCTTCAAGAGGAAGGCCGGCACCAGCAGCCTCACCGAGTGCGTGCT
GAATAAGGCTACCAACGTGGCTCACTGGACAACACCCTCTTTAAAGTGC
ATCCGGGGCGGTGGAGGATCCGGAGGAGGTGGCTCCGGCGGCGGAGGAT
CTGATCCCGCCGGCCTCTTGGACCTGCGGCAGGGCATGTTTGCGCAGCT
GGTGGCCCAAAATGTTCTGCTGATCGATGGGCCCCTGAGCTGGTACAGT
GACCCAGGCCTGGCAGGCGTGTCCCTGACGGGGGGCCTGAGCTACAAAG
AGGACACGAAGGAGCTGGTGGTGGCCAAGGCTGGAGTCTACTATGTCTT
CTTTCAACTAGAGCTGCGGCGCGTGGTGGCCGGCGAGGGCTCAGGCTCC
GTTTCACTTGCGCTGCACCTGCAGCCACTGCGCTCTGCTGCTGGGGCCG
CCGCCCTGGCTTTGACCGTGGACCTGCCACCCGCCTCCTCCGAGGCTCG
GAACTCGGCCTTCGGTTTCCAGGGCCGCTTGCTGCACCTGAGTGCCGGC
CAGCGCCTGGGCGTCCATCTTCACACTGAGGCCAGGGCACGCCATGCCT
GGCAGCTTACCCAGGGCGCCACAGTCTTGGGACTCTTCCGGGTGACCCC
CGAAATC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 175)
MKWVTFISLLFLFSSAYSQGQDRHMIRMRQLIDIVDQLKNYVNDLVPEF
LPAPEDVETNCEWSAFSCFQKAQLKSANTGNNERIINVSIKKLKRKPPS
TNAGRRQKHRLTCPSCDSYEKKPPKEFLERFKSLLQKMIHQHLSSRTHG
SEDSITCPPPMSVEHADIWVKSYSLYSRERYICNSGFKRKAGTSSLTEC
VLNKATNVAHWTTPSLKCIRGGGGSGGGGSGGGGSDPAGLLDLRQGMFA

-continued

QLVAQNVLLIDGPLSWYSDPGLAGVSLTGGLSYKEDTKELVVAKAGVYY
VFFQLELRRVVAGEGSGSVSLALHLQPLRSAAGAAALALTVDLPPASSE
ARNSAFGFQGRLLHLSAGQRLGVHLHTEARARHAWQLTQGATVLGLFRV
TPEI.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 176)
ATGAAGTGGGTGACCTTCATCAGCCTGCTGTTCCTGTTCTCCAGCGCCT
ACTCCCAGGGCCAGGACAGGCACATGATCCGGATGAGGCAGCTCATCGA
CATCGTCGACCAGCTGAAGAACTACGTGAACGACCTGGTGCCCGAGTTT
CTGCCTGCCCCCGAGGACGTGGAGACCAACTGCGAGTGGTCCGCCTTCT
CCTGCTTTCAGAAGGCCCAGCTGAAGTCCGCCAACACCGGCAACAACGA
GCGGATCATCAACGTGAGCATCAAGAAGCTGAAGCGGAAGCCTCCCTCC
ACAAACGCCGGCAGGAGGCAGAAGCACAGGCTGACCTGCCCCAGCTGTG
ACTCCTACGAGAAGAAGCCCCCCAAGGAGTTCCTGGAGAGGTTCAAGTC
CCTGCTGCAGAAGATGATCCATCAGCACCTGTCCTCCAGGACCCACGGC
TCCGAGGACTCCATTACATGCCCCCCTCCCATGAGCGTGGAGCACGCCG
ACATCTGGGTGAAGAGCTATAGCCTCTACAGCCGGGAGAGGTATATCTG
TAACAGCGGCTTCAAGAGGAAGGCCGGCACCAGCAGCCTCACCGAGTGC
GTGCTGAATAAGGCTACCAACGTGGCTCACTGGACAACACCCTCTTTAA
AGTGCATCCGGGGCGGTGGAGGATCCGGAGGAGGTGGCTCCGGCGGCGG
AGGATCTGATCCCGCCGGCCTCTTGGACCTGCGGCAGGGCATGTTTGCG
CAGCTGGTGGCCCAAAATGTTCTGCTGATCGATGGGCCCCTGAGCTGGT
ACAGTGACCCAGGCCTGGCAGGCGTGTCCCTGACGGGGGGCCTGAGCTA
CAAAGAGGACACGAAGGAGCTGGTGGTGGCCAAGGCTGGAGTCTACTAT
GTCTTCTTTCAACTAGAGCTGCGGCGCGTGGTGGCCGGCGAGGGCTCAG
GCTCCGTTTCACTTGCGCTGCACCTGCAGCCACTGCGCTCTGCTGCTGG
GGCCGCCGCCCTGGCTTTGACCGTGGACCTGCCACCCGCCTCCTCCGAG
GCTCGGAACTCGGCCTTCGGTTTCCAGGGCCGCTTGCTGCACCTGAGTG
CCGGCCAGCGCCTGGGCGTCCATCTTCACACTGAGGCCAGGGCACGCCA
TGCCTGGCAGCTTACCCAGGGCGCCACAGTCTTGGGACTCTTCCGGGTG
ACCCCCGAAATC.

Exemplary Multi-Chain Chimeric Polypeptides—Type M

In some embodiments of any of the multi-chain chimeric polypeptides described herein, the first target-binding domain and the second targeting-binding domain each independently bind specifically to TGF-β or a receptor of IL-21. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor for IL-21 (e.g., a soluble IL-21, e.g., a soluble human IL-21) or a TGF-β (e.g., a soluble TGF-β receptor, e.g., a soluble TGFβRII receptor).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to TGF-β or a receptor for IL-21. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGF-β RII includes a first sequence of soluble human TGF-β RII and a second sequence of soluble human TGF-β RII. In some embodiments of these multi-chain chimeric polypeptides, the soluble human TGF-β RII includes a linker disposed between the first sequence of soluble human TGF-β RII and the second sequence of soluble human TGF-β RII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical at least 99% identical or 100% identical to:

```
                                         (SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.
```

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 58)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.
```

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                         (SEQ ID NO: 57)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC
```

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT.

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 59)

ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 60)

IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)

ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC.

In some embodiments of these multi-chain chimeric polypeptides, the second target-binding domain binds specifically to a receptor for IL-21. In some embodiments of these multi-chain chimeric polypeptides, the second target-binding domain includes a soluble IL-21 (e.g., a human soluble IL-21). In some embodiments of these multi-chain chimeric polypeptides, the soluble IL-21 includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 124)

QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS.

In some embodiments of these multi-chain chimeric polypeptides, the soluble IL-21 is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 125)

CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDSGTTNTV

AAYNLTWKSTNFKTILEWEPKPVNQVYTVQISTKSGDWKSKCFYTTDTE

CDLTDEIVKDVKQTYLARVFSYPAGNVESTGSAGEPLYENSPEFTPYLE

TNLGQPTIQSFEQVGTKVNVTVEDERTLVRRNNTFLSLRDVFGKDLIYT

LYYWKSSSSGKKTAKTNTNEFLIDVDKGENYCFSVQAVIPSRTVNRKST

DSPVECMGQEKGEFRENWVNVISDLKKIEDLIQSMHIDATLYTESDVHP

SCKVTAMKCFLLELQVISLESGDASIHDTVENLIILANNSLSSNGNVTE

SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACAGCGGCACAACCAACACAGTC

GCTGCCTATAACCTCACTTGGAAGAGCACCAACTTCAAAACCATCCTCG

AATGGGAACCCAAACCCGTTAACCAAGTTTACACCGTGCAGATCAGCAC

CAAGTCCGGCGACTGGAAGTCCAAATGTTTCTATACCACCGACACCGAG

TGCGATCTCACCGATGAGATCGTGAAAGATGTGAAACAGACCTACCTCG

CCCGGGTGTTTAGCTACCCCGCCGGCAATGTGGAGAGCACTGGTTCCGC

TGGCGAGCCTTTATACGAGAACAGCCCCGAATTTACCCCTTACCTCGAG

ACCAATTTAGGACAGCCCACCATCCAAAGCTTTGAGCAAGTTGGCACAA

AGGTGAATGTGACAGTGGAGGACGAGCGGACTTTAGTGCGGCGGAACAA

CACCTTTCTCAGCCTCCGGGATGTGTTCGGCAAAGATTTAATCTACACA

CTGTATTACTGGAAGTCCTCTTCCTCCGGCAAGAAGACAGCTAAAACCA

ACACAAACGAGTTTTTAATCGACGTGGATAAAGGCGAAAACTACTGTTT

CAGCGTGCAAGCTGTGATCCCCTCCCGGACCGTGAATAGGAAAAGCACC

GATAGCCCCGTTGAGTGCATGGGCCAAGAAAAGGGCGAGTTCCGGGAGA

ACTGGGTGAACGTCATCAGCGATTTAAAGAAGATCGAAGATTTAATTCA

GTCCATGCATATCGACGCCACTTTATACACAGAATCCGACGTGCACCCC

TCTTGTAAGGTGACCGCCATGAAATGTTTTTTACTGGAGCTGCAAGTTA

TCTCTTTAGAGAGCGGAGACGCTAGCATCCACGACACCGTGGAGAATTT

AATCATTTTAGCCAATAACTCTTTATCCAGCAACGGCAACGTGACAGAG

TCCGGCTGCAAGGAGTGCGAAGAGCTGGAGGAGAAGAACATCAAGGAGT

TTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)
MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDSGTTNTVAAYNLTWKSTNFKTILEWEPKPVNQVYTVQI

STKSGDWKSKCFYTTDTECDLTDEIVKDVKQTYLARVFSYPAGNVESTG

SAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENY

-continued

CFSVQAVIPSRTVNRKSTDSPVECMGQEKGEFRENWVNVISDLKKIEDL
IQSMHIDATLYTESDVHPSCKVTAMKCFLLELQVISLESGDASIHDTVE
NLIILANNSLSSNGNVTESGCKECEELEEKNIKEFLQSFVHIVQMFINT
S.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)
ATGAAGTGGGTGACCTTCATCAGCCTGCTGTTCCTGTTCTCCAGCGCCT
ACTCCATCCCCCCCCATGTGCAAAAGAGCGTGAACAACGATATGATCGT
GACCGACAACAACGGCGCCGTGAAGTTTCCCCAGCTCTGCAAGTTCTGC
GATGTCAGGTTCAGCACCTGCGATAATCAGAAGTCCTGCATGTCCAACT
GCAGCATCACCTCCATCTGCGAGAAGCCCCAAGAAGTGTGCGTGGCCGT
GTGGCGGAAAAATGACGAGAACATCACCCTGGAGACCGTGTGTCACGAC
CCCAAGCTCCCTTATCACGACTTCATTCTGGAGGACGCTGCCTCCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC
CTTTTTCATGTGCTCCTGCAGCAGCGACGAATGCAACGACAATATCATC
TTTAGCGAGGAATACAATACCAGCAACCCCGACAGCGGCACAACCAACA
CAGTCGCTGCCTATAACCTCACTTGGAAGAGCACCAACTTCAAAACCAT
CCTCGAATGGGAACCCAAACCCGTTAACCAAGTTTACACCGTGCAGATC
AGCACCAAGTCCGGCGACTGGAAGTCCAAATGTTTCTATACCACCGACA
CCGAGTGCGATCTCACCGATGAGATCGTGAAAGATGTGAAACAGACCTA
CCTCGCCCGGGTGTTTAGCTACCCCGCCGGCAATGTGGAGAGCACTGGT
TCCGCTGGCGAGCCTTTATACGAGAACAGCCCCGAATTTACCCCTTACC
TCGAGACCAATTTAGGACAGCCCACCATCCAAAGCTTTGAGCAAGTTGG
CACAAAGGTGAATGTGACAGTGGAGGACGAGCGGACTTTAGTGCGGCGG
AACAACACCTTTCTCAGCCTCCGGGATGTGTTCGGCAAAGATTTAATCT
ACACACTGTATTACTGGAAGTCCTCTTCCTCCGGCAAGAAGACAGCTAA
AACCAACACAAACGAGTTTTTAATCGACGTGGATAAAGGCGAAAACTAC

-continued

TGTTTCAGCGTGCAAGCTGTGATCCCCTCCCGGACCGTGAATAGGAAAA
GCACCGATAGCCCCGTTGAGTGCATGGGCCAAGAAAAGGGCGAGTTCCG
GGAGAACTGGGTGAACGTCATCAGCGATTTAAAGAAGATCGAAGATTTA
ATTCAGTCCATGCATATCGACGCCACTTTATACACAGAATCCGACGTGC
ACCCCTCTTGTAAGGTGACCGCCATGAAATGTTTTTTACTGGAGCTGCA
AGTTATCTCTTTAGAGAGCGGAGACGCTAGCATCCACGACACCGTGGAG
AATTTAATCATTTTAGCCAATAACTCTTTATCCAGCAACGGCAACGTGA
CAGAGTCCGGCTGCAAGGAGTGCGAAGAGCTGGAGGAGAAGAACATCAA
GGAGTTTCTGCAATCCTTTGTGCACATTGTCCAGATGTTCATCAATACC
TCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 177)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPDITCPPPM
SVEHADIWVKSYSLYSRERYICNSGFKRKAGTSSLTECVLNKATNVAHW
TTPSLKCIRQGQDRHMIRMRQLIDIVDQLKNYVNDLVPEFLPAPEDVET
NCEWSAFSCFQKAQLKSANTGNNERIINVSIKKLKRKPPSTNAGRRQKH
RLTCPSCDSYEKKPPKEFLERFKSLLQKMIHQHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 178)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT

-continued

GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGACATTACATGCCCCCCTCCCATG
AGCGTGGAGCACGCCGACATCTGGGTGAAGAGCTATAGCCTCTACAGCC
GGGAGAGGTATATCTGTAACAGCGGCTTCAAGAGGAAGGCCGGCACCAG
CAGCCTCACCGAGTGCGTGCTGAATAAGGCTACCAACGTGGCTCACTGG
ACAACACCCTCTTTAAAGTGCATCCGGCAGGGCCAGGACAGGCACATGA
TCCGGATGAGGCAGCTCATCGACATCGTCGACCAGCTGAAGAACTACGT
GAACGACCTGGTGCCCGAGTTTCTGCCTGCCCCCGAGGACGTGGAGACC
AACTGCGAGTGGTCCGCCTTCTCCTGCTTTCAGAAGGCCCAGCTGAAGT
CCGCCAACACCGGCAACAACGAGCGGATCATCAACGTGAGCATCAAGAA
GCTGAAGCGGAAGCCTCCCTCCACAAACGCCGGCAGGAGGCAGAAGCAC
AGGCTGACCTGCCCCAGCTGTGACTCCTACGAGAAGAAGCCCCCCAAGG
AGTTCCTGGAGAGGTTCAAGTCCCTGCTGCAGAAGATGATCCATCAGCA
CCTGTCCTCCAGGACCCACGGCTCCGAGGACTCC.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 179)
MKWVTFISLLFLFSSAYSIPPHVQKSVNNDMIVTDNNGAVKFPQLCKFC
DVRFSTCDNQKSCMSNCSITSICEKPQEVCVAVWRKNDENITLETVCHD
PKLPYHDFILEDAASPKCIMKEKKKPGETFFMCSCSSDECNDNIIFSEE
YNTSNPDGGGGSGGGGSGGGGSIPPHVQKSVNNDMIVTDNNGAVKFPQL
CKFCDVRFSTCDNQKSCMSNCSITSICEKPQEVCVAVWRKNDENITLET
VCHDPKLPYHDFILEDAASPKCIMKEKKKPGETFFMCSCSSDECNDNII
FSEEYNTSNPDITCPPPMSVEHADIWVKSYSLYSRERYICNSGFKRKAG
TSSLTECVLNKATNVAHWTTPSLKCIRQGQDRHMIRMRQLIDIVDQLKN
YVNDLVPEFLPAPEDVETNCEWSAFSCFQKAQLKSANTGNNERIINVSI
KKLKRKPPSTNAGRRQKHRLTCPSCDSYEKKPPKEFLERFKSLLQKMIH
QHLSSRTHGSEDS.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 180)
ATGAAGTGGGTGACCTTCATCAGCCTGCTGTTCCTGTTCTCCAGCGCCT
ACTCCATCCCCCCCCATGTGCAAAAGAGCGTGAACAACGATATGATCGT
GACCGACAACAACGGCGCCGTGAAGTTTCCCCAGCTCTGCAAGTTCTGC
GATGTCAGGTTCAGCACCTGCGATAATCAGAAGTCCTGCATGTCCAACT
GCAGCATCACCTCCATCTGCGAGAAGCCCCAAGAAGTGTGCGTGGCCGT
GTGGCGGAAAAATGACGAGAACATCACCCTGGAGACCGTGTGTCACGAC
CCCAAGCTCCCTTATCACGACTTCATTCTGGAGGACGCTGCCTCCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC
CTTTTTCATGTGCTCCTGCAGCAGCGACGAATGCAACGACAATATCATC
TTTAGCGAGGAATACAATACCAGCAACCCCGACATTACATGCCCCCCTC
CCATGAGCGTGGAGCACGCCGACATCTGGGTGAAGAGCTATAGCCTCTA
CAGCCGGGAGAGGTATATCTGTAACAGCGGCTTCAAGAGGAAGGCCGGC
ACCAGCAGCCTCACCGAGTGCGTGCTGAATAAGGCTACCAACGTGGCTC
ACTGGACAACACCCTCTTTAAAGTGCATCCGGCAGGGCCAGGACAGGCA
CATGATCCGGATGAGGCAGCTCATCGACATCGTCGACCAGCTGAAGAAC
TACGTGAACGACCTGGTGCCCGAGTTTCTGCCTGCCCCCGAGGACGTGG
AGACCAACTGCGAGTGGTCCGCCTTCTCCTGCTTTCAGAAGGCCCAGCT
GAAGTCCGCCAACACCGGCAACAACGAGCGGATCATCAACGTGAGCATC
AAGAAGCTGAAGCGGAAGCCTCCCTCCACAAACGCCGGCAGGAGGCAGA
AGCACAGGCTGACCTGCCCCAGCTGTGACTCCTACGAGAAGAAGCCCCC
CAAGGAGTTCCTGGAGAGGTTCAAGTCCCTGCTGCAGAAGATGATCCAT
CAGCACCTGTCCTCCAGGACCCACGGCTCCGAGGACTCC.

Exemplary Multi-Chain Chimeric Polypeptides—Type N

In some embodiments of any of the multi-chain chimeric polypeptides described herein, the first target-binding domain and the second targeting-binding domain each independently bind specifically to TGF-β or CD16. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to CD16 (e.g., an anti-CD16 scFv) or a TGF-β (e.g., a soluble TGF-β receptor, e.g., a soluble TGFβRII receptor).

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to TGF-β or CD16. In some embodiments of these multi-chain chimeric polypeptides, the first target-binding domain is a soluble TGF-β receptor (e.g., a soluble TGFβRII receptor, e.g., a soluble human TGFβRII receptor). In some embodiments of these multi-chain chimeric polypeptides, the soluble human TGF-β RII includes a first sequence of soluble human TGF-β RII and a second sequence of soluble human TGF-β RII. In some embodiments of these multi-chain chimeric polypeptides, the soluble human TGF-β RII includes a linker disposed between the first sequence of soluble human TGF-β RII and the second sequence of soluble human TGF-βRII. In some examples of these multi-chain chimeric polypeptides, the linker includes the sequence GGGGSGGGGSGGGGS (SEQ ID NO: 7).

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.
```

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 56)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD.
```

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

```
                                          (SEQ ID NO: 57)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC
```

-continued

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT.

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCTCC

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 60)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

-continued

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC.

In some embodiments of these multi-chain chimeric polypeptides, the second target-binding domain binds specifically to CD16. In some embodiments of these multi-chain chimeric polypeptides, the second target-binding domain includes an anti-CD16 scFv. In some embodiments of these multi-chain chimeric polypeptides, the scFv that binds specifically to CD16 includes a light chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 149)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGH.

In some embodiments of these multi-chain chimeric polypeptides, the scFv that binds specifically to CD16 is encoded by a light chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 150)
TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

AACAACAGGCCCTCCGGCATCCCTGACAGGTTCTCCGGATCCTCCTCCG

GCAACACCGCCTCCCTGACCATCACAGGCGCTCAGGCCGAGGACGAGGC

-continued

TGACTACTACTGCAACTCCAGGGACTCCTCCGGCAACCATGTGGTGTTC

GGCGGCGGCACCAAGCTGACCGTGGGCCAT.

In some embodiments of these multi-chain chimeric polypeptides, the scFv that binds specifically to CD16 includes a heavy chain variable domain that includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 151)
EVQLVESGGGVVRPGGSLRLSCAASGFTFDDYGMSWVRQAPGKGLEWVS

GINWNGGSTGYADSVKGRFTISRDNAKNSLYLQMNSLRAEDTAVYYCAR

GRSLLFDYWGQGTLVTVSR.

In some embodiments of these multi-chain chimeric polypeptides, the scFv that binds specifically to CD16 is encoded by a heavy chain variable domain sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 152)
GAGGTGCAGCTGGTGGAGTCCGGAGGAGGAGTGGTGAGGCCTGGAGGCT

CCCTGAGGCTGAGCTGTGCTGCCTCCGGCTTCACCTTCGACGACTACGG

CATGTCCTGGGTGAGGCAGGCTCCTGGAAAGGGCCTGGAGTGGGTGTCC

GGCATCAACTGGAACGGCGGATCCACCGGCTACGCCGATTCCGTGAAGG

GCAGGTTCACCATCAGCAGGGACAACGCCAAGAACTCCCTGTACCTGCA

GATGAACTCCCTGAGGGCCGAGGACACCGCCGTGTACTACTGCGCCAGG

GGCAGGTCCCTGCTGTTCGACTACTGGGGACAGGGCACCCTGGTGACCG

TGTCCAGG.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDSGTTNTV

AAYNLTWKSTNFKTILEWEPKPVNQVYTVQISTKSGDWKSKCFYTTDTE

CDLTDEIVKDVKQTYLARVFSYPAGNVESTGSAGEPLYENSPEFTPYLE

-continued

TNLGQPTIQSFEQVGTKVNVTVEDERTLVRRNNTFLSLRDVFGKDLIYT

LYYWKSSSSGKKTAKTNTNEFLIDVDKGENYCFSVQAVIPSRTVNRKST

DSPVECMGQEKGEFRENWVNVISDLKKIEDLIQSMHIDATLYTESDVHP

SCKVTAMKCFLLELQVISLESGDASIHDTVENLIILANNSLSSNGNVTE

SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGACAGCGGCACAACCAACACAGTC

GCTGCCTATAACCTCACTTGGAAGAGCACCAACTTCAAAACCATCCTCG

AATGGGAACCCAAACCCGTTAACCAAGTTTACACCGTGCAGATCAGCAC

CAAGTCCGGCGACTGGAAGTCCAAATGTTTCTATACCACCGACACCGAG

TGCGATCTCACCGATGAGATCGTGAAAGATGTGAAACAGACCTACCTCG

CCCGGGTGTTTAGCTACCCCGCCGGCAATGTGGAGAGCACTGGTTCCGC

TGGCGAGCCTTTATACGAGAACAGCCCCGAATTTACCCCTTACCTCGAG

ACCAATTTAGGACAGCCCACCATCCAAAGCTTTGAGCAAGTTGGCACAA

AGGTGAATGTGACAGTGGAGGACGAGCGGACTTTAGTGCGGCGGAACAA

CACCTTTCTCAGCCTCCGGGATGTGTTCGGCAAAGATTTAATCTACACA

CTGTATTACTGGAAGTCCTCTTCCTCCGGCAAGAAGACAGCTAAAACCA

ACACAAACGAGTTTTTAATCGACGTGGATAAAGGCGAAAACTACTGTTT

-continued

CAGCGTGCAAGCTGTGATCCCCTCCCGGACCGTGAATAGGAAAAGCACC

GATAGCCCCGTTGAGTGCATGGGCCAAGAAAAGGGCGAGTTCCGGGAGA

ACTGGGTGAACGTCATCAGCGATTTAAAGAAGATCGAAGATTTAATTCA

GTCCATGCATATCGACGCCACTTTATACACAGAATCCGACGTGCACCCC

TCTTGTAAGGTGACCGCCATGAAATGTTTTTTACTGGAGCTGCAAGTTA

TCTCTTTAGAGAGCGGAGACGCTAGCATCCACGACACCGTGGAGAATTT

AATCATTTTAGCCAATAACTCTTTATCCAGCAACGGCAACGTGACAGAG

TCCGGCTGCAAGGAGTGCGAAGAGCTGGAGGAGAAGAACATCAAGGAGT

TTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)

MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDSGTTNTVAAYNLTWKSTNFKTILEWEPKPVNQVYTVQI

STKSGDWKSKCFYTTDTECDLTDEIVKDVKQTYLARVFSYPAGNVESTG

SAGEPLYENSPEFTPYLETNLGQPTIQSFEQVGTKVNVTVEDERTLVRR

NNTFLSLRDVFGKDLIYTLYYWKSSSSGKKTAKTNTNEFLIDVDKGENY

CFSVQAVIPSRTVNRKSTDSPVECMGQEKGEFRENWVNVISDLKKIEDL

IQSMHIDATLYTESDVHPSCKVTAMKCFLLELQVISLESGDASIHDTVE

NLIILANNSLSSNGNVTESGCKECEELEEKNIKEFLQSFVHIVQMFINT

S.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)

ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

-continued

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCTCCATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACAGCGGCACAACCAACA

CAGTCGCTGCCTATAACCTCACTTGGAAGAGCACCAACTTCAAAACCAT

CCTCGAATGGGAACCCAAACCCGTTAACCAAGTTTACACCGTGCAGATC

AGCACCAAGTCCGGCGACTGGAAGTCCAAATGTTTCTATACCACCGACA

CCGAGTGCGATCTCACCGATGAGATCGTGAAAGATGTGAAACAGACCTA

CCTCGCCCGGGTGTTTAGCTACCCCGCCGGCAATGTGGAGAGCACTGGT

TCCGCTGGCGAGCCTTTATACGAGAACAGCCCCGAATTTACCCCTTACC

TCGAGACCAATTTAGGACAGCCCACCATCCAAAGCTTTGAGCAAGTTGG

CACAAAGGTGAATGTGACAGTGGAGGACGAGCGGACTTTAGTGCGGCGG

AACAACACCTTTCTCAGCCTCCGGGATGTGTTCGGCAAAGATTTAATCT

ACACACTGTATTACTGGAAGTCCTCTTCCTCCGGCAAGAAGACAGCTAA

AACCAACACAAACGAGTTTTTAATCGACGTGGATAAAGGCGAAAACTAC

TGTTTCAGCGTGCAAGCTGTGATCCCCTCCCGGACCGTGAATAGGAAAA

GCACCGATAGCCCCGTTGAGTGCATGGGCCAAGAAAAGGGCGAGTTCCG

GGAGAACTGGGTGAACGTCATCAGCGATTTAAAGAAGATCGAAGATTTA

ATTCAGTCCATGCATATCGACGCCACTTTATACACAGAATCCGACGTGC

ACCCCTCTTGTAAGGTGACCGCCATGAAATGTTTTTTACTGGAGCTGCA

AGTTATCTCTTTAGAGAGCGGAGACGCTAGCATCCACGACACCGTGGAG

AATTTAATCATTTTAGCCAATAACTCTTTATCCAGCAACGGCAACGTGA

CAGAGTCCGGCTGCAAGGAGTGCGAAGAGCTGGAGGAGAAGAACATCAA

GGAGTTTCTGCAATCCTTTGTGCACATTGTCCAGATGTTCATCAATACC

TCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 181)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPDITCPPPM
SVEHADIWVKSYSLYSRERYICNSGFKRKAGTSSLTECVLNKATNVAHW
TTPSLKCIRSELTQDPAVSVALGQTVRITCQGDSLRSYYASWYQQKPGQ
APVLVIYGKNNRPSGIPDRFSGSSSGNTASLTITGAQAEDEADYYCNSR
DSSGNHVVFGGGTKLTVGHGGGGSGGGGSGGGGSEVQLVESGGGVVRPG
GSLRLSCAASGFTFDDYGMSWVRQAPGKGLEWVSGINWNGGSTGYADSV
KGRFTISRDNAKNSLYLQMNSLRAEDTAVYYCARGRSLLFDYWGQGTLV
TVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 182)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGACATTACATGCCCCCCTCCCATG
AGCGTGGAGCACGCCGACATCTGGGTGAAGAGCTATAGCCTCTACAGCC
GGGAGAGGTATATCTGTAACAGCGGCTTCAAGAGGAAGGCCGGCACCAG
CAGCCTCACCGAGTGCGTGCTGAATAAGGCTACCAACGTGGCTCACTGG

-continued
ACAACACCCTCTTTAAAGTGCATCCGGTCCGAGCTGACCCAGGACCCTG
CTGTGTCCGTGGCTCTGGGCCAGACCGTGAGGATCACCTGCCAGGGCGA
CTCCCTGAGGTCCTACTACGCCTCCTGGTACCAGCAGAAGCCCGGCCAG
GCTCCTGTGCTGGTGATCTACGGCAAGAACAACAGGCCCTCCGGCATCC
CTGACAGGTTCTCCGGATCCTCCTCCGGCAACACCGCCTCCCTGACCAT
CACAGGCGCTCAGGCCGAGGACGAGGCTGACTACTACTGCAACTCCAGG
GACTCCTCCGGCAACCATGTGGTGTTCGGCGGCGGCACCAAGCTGACCG
TGGGCCATGGCGGCGGCGGCTCCGGAGGCGGCGGCAGCGGCGGAGGAGG
ATCCGAGGTGCAGCTGGTGGAGTCCGGAGGAGGAGTGGTGAGGCCTGGA
GGCTCCCTGAGGCTGAGCTGTGCTGCCTCCGGCTTCACCTTCGACGACT
ACGGCATGTCCTGGGTGAGGCAGGCTCCTGGAAAGGGCCTGGAGTGGGT
GTCCGGCATCAACTGGAACGGCGGATCCACCGGCTACGCCGATTCCGTG
AAGGGCAGGTTCACCATCAGCAGGGACAACGCCAAGAACTCCCTGTACC
TGCAGATGAACTCCCTGAGGGCCGAGGACACCGCCGTGTACTACTGCGC
CAGGGGCAGGTCCCTGCTGTTCGACTACTGGGGACAGGGCACCCTGGTG
ACCGTGTCCAGG.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical at least 96% identical, at least 98% identical, at least 99% identical, or 100% identical) to:

(SEQ ID NO: 183)
MKWVTFISLLFLFSSAYSIPPHVQKSVNNDMIVTDNNGAVKFPQLCKFC
DVRFSTCDNQKSCMSNCSITSICEKPQEVCVAVWRKNDENITLETVCHD
PKLPYHDFILEDAASPKCIMKEKKKPGETFFMCSCSSDECNDNIIFSEE
YNTSNPDGGGGSGGGGSGGGGSIPPHVQKSVNNDMIVTDNNGAVKFPQL
CKFCDVRFSTCDNQKSCMSNCSITSICEKPQEVCVAVWRKNDENITLET
VCHDPKLPYHDFILEDAASPKCIMKEKKKPGETFFMCSCSSDECNDNII
FSEEYNTSNPDITCPPPMSVEHADIWVKSYSLYSRERYICNSGFKRKAG
TSSLTECVLNKATNVAHWTTPSLKCIRSELTQDPAVSVALGQTVRITCQ
GDSLRSYYASWYQQKPGQAPVLVIYGKNNRPSGIPDRFSGSSSGNTASL
TITGAQAEDEADYYCNSRDSSGNHVVFGGGTKLTVGHGGGGSGGGGSGG
GGSEVQLVESGGGVVRPGGSLRLSCAASGFTFDDYGMSWVRQAPGKGLE
WVSGINWNGGSTGYADSVKGRFTISRDNAKNSLYLQMNSLRAEDTAVYY
CARGRSLLFDYWGQGTLVTVSR.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 184)

```
ATGAAGTGGGTGACCTTCATCAGCCTGCTGTTCCTGTTCTCCAGCGCCT
ACTCCATCCCCCCCCATGTGCAAAAGAGCGTGAACAACGATATGATCGT
GACCGACAACAACGGCGCCGTGAAGTTTCCCCAGCTCTGCAAGTTCTGC
GATGTCAGGTTCAGCACCTGCGATAATCAGAAGTCCTGCATGTCCAACT
GCAGCATCACCTCCATCTGCGAGAAGCCCCAAGAAGTGTGCGTGGCCGT
GTGGCGGAAAAATGACGAGAACATCACCCTGGAGACCGTGTGTCACGAC
CCCAAGCTCCCTTATCACGACTTCATTCTGGAGGACGCTGCCTCCCCCA
AATGCATCATGAAGGAGAAGAAGAAGCCCGGAGAGACCTTCTTTATGTG
TTCCTGTAGCAGCGACGAGTGTAACGACAACATCATCTTCAGCGAAGAG
TACAACACCAGCAACCCTGATGGAGGTGGCGGATCCGGAGGTGGAGGTT
CTGGTGGAGGTGGGAGTATTCCTCCCCACGTGCAGAAGAGCGTGAATAA
TGACATGATCGTGACCGATAACAATGGCGCCGTGAAATTTCCCCAGCTG
TGCAAATTCTGCGATGTGAGGTTTTCCACCTGCGACAACCAGAAGTCCT
GTATGAGCAACTGCTCCATCACCTCCATCTGTGAGAAGCCTCAGGAGGT
GTGCGTGGCTGTCTGGCGGAAGAATGACGAGAATATCACCCTGGAAACC
GTCTGCCACGATCCCAAGCTGCCCTACCACGATTTCATCCTGGAAGACG
CCGCCAGCCCTAAGTGCATCATGAAAGAGAAAAAGAAGCCTGGCGAGAC
CTTTTTCATGTGCTCCTGCAGCAGCGACGAATGCAACGACAATATCATC
TTTAGCGAGGAATACAATACCAGCAACCCCGACATTACATGCCCCCCTC
CCATGAGCGTGGAGCACGCCGACATCTGGGTGAAGAGCTATAGCCTCTA
CAGCCGGGAGAGGTATATCTGTAACAGCGGCTTCAAGAGGAAGGCCGGC
ACCAGCAGCCTCACCGAGTGCGTGCTGAATAAGGCTACCAACGTGGCTC
ACTGGACAACACCCTCTTTAAAGTGCATCCGGTCCGAGCTGACCCAGGA
CCCTGCTGTGTCCGTGGCTCTGGGCCAGACCGTGAGGATCACCTGCCAG
GGCGACTCCCTGAGGTCCTACTACGCCTCCTGGTACCAGCAGAAGCCCG
GCCAGGCTCCTGTGCTGGTGATCTACGGCAAGAACAACAGGCCCTCCGG
CATCCCTGACAGGTTCTCCGGATCCTCCTCCGGCAACACCGCCTCCCTG
ACCATCACAGGCGCTCAGGCCGAGGACGAGGCTGACTACTACTGCAACT
CCAGGGACTCCTCCGGCAACCATGTGGTGTTCGGCGGCGGCACCAAGCT
GACCGTGGGCCATGGCGGCGGCGGCTCCGGAGGCGGCGGCAGCGGCGGA
GGAGGATCCGAGGTGCAGCTGGTGGAGTCCGGAGGAGGAGTGGTGAGGC
CTGGAGGCTCCCTGAGGCTGAGCTGTGCTGCCTCCGGCTTCACCTTCGA
CGACTACGGCATGTCCTGGGTGAGGCAGGCTCCTGGAAAGGGCCTGGAG
TGGGTGTCCGGCATCAACTGGAACGGCGGATCCACCGGCTACGCCGATT
CCGTGAAGGGCAGGTTCACCATCAGCAGGGACAACGCCAAGAACTCCCT
GTACCTGCAGATGAACTCCCTGAGGGCCGAGGACACCGCCGTGTACTAC
TGCGCCAGGGGCAGGTCCCTGCTGTTCGACTACTGGGGACAGGGCACCC
TGGTGACCGTGTCCAGG.
```

Exemplary Multi-Chain Chimeric Polypeptides—Type O

In some embodiments of any of the multi-chain chimeric polypeptides described herein, the first target-binding domain and the second targeting-binding domain each independently bind specifically to TGF-β or a receptor of CD137L. In some embodiments of these multi-chain chimeric polypeptides described herein, the second chimeric polypeptide further includes the additional target-binding domain. In some embodiments of these multi-chain chimeric polypeptides described herein, the additional target-binding domain binds specifically to a receptor to TGF-β (e.g., a soluble TGF-β receptor, e.g., a soluble TGFβRII receptor) or CD137L.

In some examples of these multi-chain chimeric polypeptides, the first target-binding domain and the soluble tissue factor domain directly abut each other in the first chimeric polypeptide. In some examples of these multi-chain chimeric polypeptides, the first chimeric polypeptide further comprises a linker sequence (e.g., any of the exemplary linkers described herein) between the first target-binding domain and the soluble tissue factor domain in the first chimeric polypeptide.

In some embodiments of these multi-chain chimeric polypeptides, the soluble tissue factor domain and the first domain of the pair of affinity domains directly abut each other in the first chimeric polypeptide. In some embodiments of these multi-chain chimeric polypeptides, the first chimeric polypeptide further includes a linker sequence (e.g., any of the exemplary linkers described herein) between the soluble tissue factor domain and the first domain of the pair of affinity domains in the first chimeric polypeptide.

In some embodiments of these multi-chain chimeric polypeptides, the second domain of the pair of affinity domains and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the second target-binding domain in the second chimeric polypeptide.

In some embodiments, the second chimeric polypeptide further comprises one or more additional target-binding domains at the N-terminal end or the C-terminal end of the second chimeric polypeptide.

In some embodiments of these multi-chain chimeric polypeptides, the additional target-binding domain and the second domain of the pair of affinity domains directly abut each other in the second chimeric polypeptide. In some embodiments of these multi-chain chimeric polypeptides, the second chimeric polypeptide further includes a linker sequence (e.g., any of the exemplary linkers described herein) between the second domain of the pair of affinity domains and the additional target-binding domain in the second chimeric polypeptide.

In some embodiments of these multi-chain chimeric polypeptides, the additional target-binding domain and the second target-binding domain directly abut each other in the second chimeric polypeptide. In some embodiments of these multi-chain chimeric polypeptides, the second chimeric polypeptide further includes a linker sequence (e.g., any of the exemplary linkers described herein) between the second target-binding domain and the additional target-binding domain in the second chimeric polypeptide.

In some embodiments of these multi-chain chimeric polypeptides, the soluble tissue factor domain can be any of the exemplary soluble tissue factor domains described herein. In some embodiments of these multi-chain chimeric polypeptides, the pair of affinity domains can be any of the exemplary pairs of affinity domains described herein.

In some embodiments of these multi-chain chimeric polypeptides, the first target-binding domain binds specifically to TGF-β, and the second target-binding domain binds specifically to CD137L. In some embodiments of these multi-chain chimeric polypeptides, the first target-binding domain or the additional target-binding domain is a soluble TGF-β receptor (e.g., a soluble TGFβRII receptor, e.g., a soluble human TGFβRII receptor).

In some embodiments of these multi-chain chimeric polypeptides, the soluble human TGF-β RII includes a first sequence of soluble human TGF-β RII and a second sequence of soluble human TGF-β RII. In some embodiments of these multi-chain chimeric polypeptides, the soluble human TGF-β RII includes a linker disposed between the first sequence of soluble human TGF-β RII and the second sequence of soluble human TGF-β RII. In some examples of these multi-chain chimeric polypeptides, the linker includes the sequence (SEQ ID NO: 7)
GGGGSGGGGSGGGGS.

In some embodiments of these multi-chain chimeric polypeptides, the first sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPD.

In some embodiments of these multi-chain chimeric polypeptides, the second sequence of soluble human TGF-β RII receptor comprises a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 56)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPD.

In some embodiments of these multi-chain chimeric polypeptides, the first sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGAT.

In some embodiments of these multi-chain chimeric polypeptides, the second sequence of soluble human TGF-β RII receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 57)
ATTCCTCCCCACGTGCAGAAGAGCGTGAATAATGACATGATCGTGACCG
ATAACAATGGCGCCGTGAAATTTCCCCAGCTGTGCAAATTCTGCGATGT
GAGGTTTTCCACCTGCGACAACCAGAAGTCCTGTATGAGCAACTGCTCC
ATCACCTCCATCTGTGAGAAGCCTCAGGAGGTGTGCGTGGCTGTCTGGC
GGAAGAATGACGAGAATATCACCCTGGAAACCGTCTGCCACGATCCCAA
GCTGCCCTACCACGATTTCATCCTGGAAGACGCCGCCAGCCCTAAGTGC
ATCATGAAAGAGAAAAAGAAGCCTGGCGAGACCTTTTTCATGTGCTCCT
GCAGCAGCGACGAATGCAACGACAATATCATCTTTAGCGAGGAATACAA
TACCAGCAACCCCGAC.

In some embodiments of these multi-chain chimeric polypeptides, the soluble TGF-β receptor includes a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 60)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC
IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPD.

In some embodiments of these multi-chain chimeric polypeptides, the soluble TGF-β receptor is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 198)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
CTCCCTTATCACGACTTCATTCTGGAGGACGCTGCCTCCCCCAAATGCA
TCATGAAGGAGAAGAAGAAGCCCGGAGAGACCTTCTTTATGTGTTCCTG
TAGCAGCGACGAGTGTAACGACAACATCATCTTCAGCGAAGAGTACAAC
ACCAGCAACCCTGATGGAGGTGGCGGATCCGGAGGTGGAGGTTCTGGTG
GAGGTGGGAGTATTCCTCCCCACGTGCAGAAGAGCGTGAATAATGACAT
GATCGTGACCGATAACAATGGCGCCGTGAAATTTCCCCAGCTGTGCAAA
TTCTGCGATGTGAGGTTTTCCACCTGCGACAACCAGAAGTCCTGTATGA
GCAACTGCTCCATCACCTCCATCTGTGAGAAGCCTCAGGAGGTGTGCGT
GGCTGTCTGGCGGAAGAATGACGAGAATATCACCCTGGAAACCGTCTGC
CACGATCCCAAGCTGCCCTACCACGATTTCATCCTGGAAGACGCCGCCA
GCCCTAAGTGCATCATGAAAGAGAAAAAGAAGCCTGGCGAGACCTTTTT
CATGTGCTCCTGCAGCAGCGACGAATGCAACGACAATATCATCTTTAGC
GAGGAATACAATACCAGCAACCCCGAC.

In some embodiments of these multi-chain chimeric polypeptides, the second target-binding domain includes a soluble CD137L protein (e.g., a soluble human CD137L protein). In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 165)
REGPELSPDDPAGLLDLRQGMFAQLVAQNVLLIDGPLSWYSDPGLAGVS
LTGGLSYKEDTKELVVAKAGVYYVFFQLELRRVVAGEGSGSVSLALHLQ
PLRSAAGAAALALTVDLPPASSEARNSAFGFQGRLLHLSAGQRLGVHLH
TEARARHAWQLTQGATVLGLFRVTPEIPAGLPSPRSE.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 166)
CGCGAGGGTCCCGAGCTTTCGCCCGACGATCCCGCCGGCCTCTTGGACC
TGCGGCAGGGCATGTTTGCGCAGCTGGTGGCCCAAAATGTTCTGCTGAT
CGATGGGCCCCTGAGCTGGTACAGTGACCCAGGCCTGGCAGGCGTGTCC
CTGACGGGGGGCCTGAGCTACAAAGAGGACACGAAGGAGCTGGTGGTGG

-continued

CCAAGGCTGGAGTCTACTATGTCTTCTTTCAACTAGAGCTGCGGCGCGT
GGTGGCCGGCGAGGGCTCAGGCTCCGTTTCACTTGCGCTGCACCTGCAG
CCACTGCGCTCTGCTGCTGGGGCCGCCGCCCTGGCTTTGACCGTGGACC
TGCCACCCGCCTCCTCCGAGGCTCGGAACTCGGCCTTCGGTTTCCAGGG
CCGCTTGCTGCACCTGAGTGCCGGCCAGCGCCTGGGCGTCCATCTTCAC
ACTGAGGCCAGGGCACGCCATGCCTGGCAGCTTACCCAGGGCGCCACAG
TCTTGGGACTCTTCCGGGTGACCCCCGAAATCCCAGCCGGACTCCCTTC
ACCGAGGTCGGAA.

In some embodiments of these multi-chain chimeric polypeptides, a soluble human CD137L includes a sequence that is at least 80% identical (e.g., at least 85%, at least 90%, at least 95%, at least 96%, at least 97%, at least 98%, at least 99%, or 100% identical) to:

(SEQ ID NO: 167)
DPAGLLDLRQGMFAQLVAQNVLLIDGPLSWYSDPGLAGVSLTGGLSYKE
DTKELVVAKAGVYYVFFQLELRRVVAGEGSGSVSLALHLQPLRSAAGAA
ALALTVDLPPASSEARNSAFGFQGRLLHLSAGQRLGVHLHTEARARHAW
QLTQGATVLGLFRVTPEI.

In some embodiments of these multi-chain chimeric polypeptides, a soluble human CD137L is encoded by a sequence that is at least 80% identical (e.g., at least 85%, at least 90%, at least 95%, at least 96%, at least 97%, at least 98%, at least 99%, or 100% identical) to:

(SEQ ID NO: 168)
GATCCCGCCGGCCTCTTGGACCTGCGGCAGGGCATGTTTGCGCAGCTGG
TGGCCCAAAATGTTCTGCTGATCGATGGGCCCCTGAGCTGGTACAGTGA
CCCAGGCCTGGCAGGCGTGTCCCTGACGGGGGGCCTGAGCTACAAAGAG
GACACGAAGGAGCTGGTGGTGGCCAAGGCTGGAGTCTACTATGTCTTCT
TTCAACTAGAGCTGCGGCGCGTGGTGGCCGGCGAGGGCTCAGGCTCCGT
TTCACTTGCGCTGCACCTGCAGCCACTGCGCTCTGCTGCTGGGGCCGCC
GCCCTGGCTTTGACCGTGGACCTGCCACCCGCCTCCTCCGAGGCTCGGA
ACTCGGCCTTCGGTTTCCAGGGCCGCTTGCTGCACCTGAGTGCCGGCCA
GCGCCTGGGCGTCCATCTTCACACTGAGGCCAGGGCACGCCATGCCTGG
CAGCTTACCCAGGGCGCCACAGTCTTGGGACTCTTCCGGGTGACCCCCG
AAATC.

In some embodiments, the first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 161)
IPPHVQKSVNNDMIVTDNNGAVKFPQLCKFCDVRFSTCDNQKSCMSNCS
ITSICEKPQEVCVAVWRKNDENITLETVCHDPKLPYHDFILEDAASPKC

-continued

IMKEKKKPGETFFMCSCSSDECNDNIIFSEEYNTSNPDGGGGSGGGGSG
GGGSIPPHVQKSVNNDMIVTDNNGAVKFPQLCKFCDVRFSTCDNQKSCM
SNCSITSICEKPQEVCVAVWRKNDENITLETVCHDPKLPYHDFILEDAA
SPKCIMKEKKKPGETFFMCSCSSDECNDNIIFSEEYNTSNPDSGTTNTV
AAYNLTWKSTNFKTILEWEPKPVNQVYTVQISTKSGDWKSKCFYTTDTE
CDLTDEIVKDVKQTYLARVFSYPAGNVESTGSAGEPLYENSPEFTPYLE
TNLGQPTIQSFEQVGTKVNVTVEDERTLVRRNNTFLSLRDVFGKDLIYT
LYYWKSSSSGKKTAKTNTNEFLIDVDKGENYCFSVQAVIPSRTVNRKST
DSPVECMGQEKGEFRENWVNVISDLKKIEDLIQSMHIDATLYTESDVHP
SCKVTAMKCFLLELQVISLESGDASIHDTVENLIILANNSLSSNGNVTE
SGCKECEELEEKNIKEFLQSFVHIVQMFINTS.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 162)
ATCCCCCCCCATGTGCAAAAGAGCGTGAACAACGATATGATCGTGACCG
ACAACAACGGCGCCGTGAAGTTTCCCCAGCTCTGCAAGTTCTGCGATGT
CAGGTTCAGCACCTGCGATAATCAGAAGTCCTGCATGTCCAACTGCAGC
ATCACCTCCATCTGCGAGAAGCCCCAAGAAGTGTGCGTGGCCGTGTGGC
GGAAAAATGACGAGAACATCACCCTGGAGACCGTGTGTCACGACCCCAA
GCTCCCTTATCACGACTTCATTCTGGAGGACGCTGCCTCCCCCAAATGC
ATCATGAAGGAGAAGAAGAAGCCCGGAGAGACCTTCTTTATGTGTTCCT
GTAGCAGCGACGAGTGTAACGACAACATCATCTTCAGCGAAGAGTACAA
CACCAGCAACCCTGATGGAGGTGGCGGATCCGGAGGTGGAGGTTCTGGT
GGAGGTGGGAGTATTCCTCCCCACGTGCAGAAGAGCGTGAATAATGACA
TGATCGTGACCGATAACAATGGCGCCGTGAAATTTCCCCAGCTGTGCAA
ATTCTGCGATGTGAGGTTTTCCACCTGCGACAACCAGAAGTCCTGTATG
AGCAACTGCTCCATCACCTCCATCTGTGAGAAGCCTCAGGAGGTGTGCG
TGGCTGTCTGGCGGAAGAATGACGAGAATATCACCCTGGAAACCGTCTG
CCACGATCCCAAGCTGCCCTACCACGATTTCATCCTGGAAGACGCCGCC
AGCCCTAAGTGCATCATGAAAGAGAAAAAGAAGCCTGGCGAGACCTTTT
TCATGTGCTCCTGCAGCAGCGACGAATGCAACGACAATATCATCTTTAG
CGAGGAATACAATACCAGCAACCCCGACAGCGGCACAACCAACACAGTC
GCTGCCTATAACCTCACTTGGAAGAGCACCAACTTCAAAACCATCCTCG
AATGGGAACCCAAACCCGTTAACCAAGTTTACACCGTGCAGATCAGCAC
CAAGTCCGGCGACTGGAAGTCCAAATGTTTCTATACCACCGACACCGAG
TGCGATCTCACCGATGAGATCGTGAAAGATGTGAAACAGACCTACCTCG
CCCGGGTGTTTAGCTACCCCGCCGGCAATGTGGAGAGCACTGGTTCCGC
TGGCGAGCCTTTATACGAGAACAGCCCCGAATTTACCCCTTACCTCGAG

-continued

ACCAATTTAGGACAGCCCACCATCCAAAGCTTTGAGCAAGTTGGCACAA
AGGTGAATGTGACAGTGGAGGACGAGCGGACTTTAGTGCGGCGGAACAA
CACCTTTCTCAGCCTCCGGGATGTGTTCGGCAAAGATTTAATCTACACA
CTGTATTACTGGAAGTCCTCTTCCTCCGGCAAGAAGACAGCTAAAACCA
ACACAAACGAGTTTTTAATCGACGTGGATAAAGGCGAAAACTACTGTTT
CAGCGTGCAAGCTGTGATCCCCTCCCGGACCGTGAATAGGAAAAGCACC
GATAGCCCCGTTGAGTGCATGGGCCAAGAAAAGGGCGAGTTCCGGGAGA
ACTGGGTGAACGTCATCAGCGATTTAAAGAAGATCGAAGATTTAATTCA
GTCCATGCATATCGACGCCACTTTATACACAGAATCCGACGTGCACCCC
TCTTGTAAGGTGACCGCCATGAAATGTTTTTTACTGGAGCTGCAAGTTA
TCTCTTTAGAGAGCGGAGACGCTAGCATCCACGACACCGTGGAGAATTT
AATCATTTTAGCCAATAACTCTTTATCCAGCAACGGCAACGTGACAGAG
TCCGGCTGCAAGGAGTGCGAAGAGCTGGAGGAGAAGAACATCAAGGAGT
TTCTGCAATCCTTTGTGCACATTGTCCAGATGTTCATCAATACCTCC.

In some embodiments, a first chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 163)
MKWVTFISLLFLFSSAYSIPPHVQKSVNNDMIVTDNNGAVKFPQLCKFC
DVRFSTCDNQKSCMSNCSITSICEKPQEVCVAVWRKNDENITLETVCHD
PKLPYHDFILEDAASPKCIMKEKKKPGETFFMCSCSSDECNDNIIFSEE
YNTSNPDGGGGSGGGGSGGGGSIPPHVQKSVNNDMIVTDNNGAVKFPQL
CKFCDVRFSTCDNQKSCMSNCSITSICEKPQEVCVAVWRKNDENITLET
VCHDPKLPYHDFILEDAASPKCIMKEKKKPGETFFMCSCSSDECNDNII
FSEEYNTSNPDSGTTNTVAAYNLTWKSTNFKTILEWEPKPVNQVYTVQI
STKSGDWKSKCFYTTDTECDLTDEIVKDVKQTYLARVFSYPAGNVESTG
SAGEPLYENSPEFTPYLETNLGQPTIQSFEQVGTKVNVTVEDERTLVRR
NNTFLSLRDVFGKDLIYTLYYWKSSSSGKKTAKTNTNEFLIDVDKGENY
CFSVQAVIPSRTVNRKSTDSPVECMGQEKGEFRENWVNVISDLKKIEDL
IQSMHIDATLYTESDVHPSCKVTAMKCFLLELQVISLESGDASIHDTVE
NLIILANNSLSSNGNVTESGCKECEELEEKNIKEFLQSFVHIVQMFINT
S.

In some embodiments, a first chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 164)

ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCTCCATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACAGCGGCACAACCAACA

CAGTCGCTGCCTATAACCTCACTTGGAAGAGCACCAACTTCAAAACCAT

CCTCGAATGGGAACCCAAACCCGTTAACCAAGTTTACACCGTGCAGATC

AGCACCAAGTCCGGCGACTGGAAGTCCAAATGTTTCTATACCACCGACA

CCGAGTGCGATCTCACCGATGAGATCGTGAAAGATGTGAAACAGACCTA

CCTCGCCCGGGTGTTTAGCTACCCCGCCGGCAATGTGGAGAGCACTGGT

TCCGCTGGCGAGCCTTTATACGAGAACAGCCCCGAATTTACCCCTTACC

TCGAGACCAATTTAGGACAGCCCACCATCCAAAGCTTTGAGCAAGTTGG

CACAAAGGTGAATGTGACAGTGGAGGACGAGCGGACTTTAGTGCGGCGG

AACAACACCTTTCTCAGCCTCCGGGATGTGTTCGGCAAAGATTTAATCT

ACACACTGTATTACTGGAAGTCCTCTTCCTCCGGCAAGAAGACAGCTAA

AACCAACACAAACGAGTTTTTAATCGACGTGGATAAAGGCGAAAACTAC

TGTTTCAGCGTGCAAGCTGTGATCCCCTCCCGGACCGTGAATAGGAAAA

GCACCGATAGCCCCGTTGAGTGCATGGGCCAAGAAAAGGGCGAGTTCCG

GGAGAACTGGGTGAACGTCATCAGCGATTTAAAGAAGATCGAAGATTTA

ATTCAGTCCATGCATATCGACGCCACTTTATACACAGAATCCGACGTGC

ACCCCTCTTGTAAGGTGACCGCCATGAAATGTTTTTTACTGGAGCTGCA

AGTTATCTCTTTAGAGAGCGGAGACGCTAGCATCCACGACACCGTGGAG

AATTTAATCATTTTAGCCAATAACTCTTTATCCAGCAACGGCAACGTGA

CAGAGTCCGGCTGCAAGGAGTGCGAAGAGCTGGAGGAGAAGAACATCAA

GGAGTTTCTGCAATCCTTTGTGCACATTGTCCAGATGTTCATCAATACC

TCC.

In some embodiments, the second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 185)

IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPDITCPPPM

SVEHADIWVKSYSLYSRERYICNSGFKRKAGTSSLTECVLNKATNVAHW

TTPSLKCIRGGGGSGGGGSGGGGSREGPELSPDDPAGLLDLRQGMFAQL

VAQNVLLIDGPLSWYSDPGLAGVSLTGGLSYKEDTKELVVAKAGVYYVF

FQLELRRVVAGEGSGSVSLALHLQPLRSAAGAAALALTVDLPPASSEAR

NSAFGFQGRLLHLSAGQRLGVHLHTEARARHAWQLTQGATVLGLFRVTP

EIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 186)

ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

-continued

CGAGGAATACAATACCAGCAACCCCGACATTACATGCCCCCCTCCCATG

AGCGTGGAGCACGCCGACATCTGGGTGAAGAGCTATAGCCTCTACAGCC

GGGAGAGGTATATCTGTAACAGCGGCTTCAAGAGGAAGGCCGGCACCAG

CAGCCTCACCGAGTGCGTGCTGAATAAGGCTACCAACGTGGCTCACTGG

ACAACACCCTCTTTAAAGTGCATCCGGGGCGGTGGAGGATCCGGAGGAG

GTGGCTCCGGCGGCGGAGGATCTCGCGAGGGTCCCGAGCTTTCGCCCGA

CGATCCCGCCGGCCTCTTGGACCTGCGGCAGGGCATGTTTGCGCAGCTG

GTGGCCCAAAATGTTCTGCTGATCGATGGGCCCCTGAGCTGGTACAGTG

ACCCAGGCCTGGCAGGCGTGTCCCTGACGGGGGGCCTGAGCTACAAAGA

GGACACGAAGGAGCTGGTGGTGGCCAAGGCTGGAGTCTACTATGTCTTC

TTTCAACTAGAGCTGCGGCGCGTGGTGGCCGGCGAGGGCTCAGGCTCCG

TTTCACTTGCGCTGCACCTGCAGCCACTGCGCTCTGCTGCTGGGGCCGC

CGCCCTGGCTTTGACCGTGGACCTGCCACCCGCCTCCTCCGAGGCTCGG

AACTCGGCCTTCGGTTTCCAGGGCCGCTTGCTGCACCTGAGTGCCGGCC

AGCGCCTGGGCGTCCATCTTCACACTGAGGCCAGGGCACGCCATGCCTG

GCAGCTTACCCAGGGCGCCACAGTCTTGGGACTCTTCCGGGTGACCCCC

GAAATCCCAGCCGGACTCCCTTCACCGAGGTCGGAA.

In some embodiments, a second chimeric polypeptide can include a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 187)

MKWVTFISLLFLFSSAYSIPPHVQKSVNNDMIVTDNNGAVKFPQLCKFC

DVRFSTCDNQKSCMSNCSITSICEKPQEVCVAVWRKNDENITLETVCHD

PKLPYHDFILEDAASPKCIMKEKKKPGETFFMCSCSSDECNDNIIFSEE

YNTSNPDGGGGSGGGGSGGGGSIPPHVQKSVNNDMIVTDNNGAVKFPQL

CKFCDVRFSTCDNQKSCMSNCSITSICEKPQEVCVAVWRKNDENITLET

VCHDPKLPYHDFILEDAASPKCIMKEKKKPGETFFMCSCSSDECNDNII

FSEEYNTSNPDITCPPPMSVEHADIWVKSYSLYSRERYICNSGFKRKAG

TSSLTECVLNKATNVAHWTTPSLKCIRGGGGSGGGGSGGGGSREGPELS

PDDPAGLLDLRQGMFAQLVAQNVLLIDGPLSWYSDPGLAGVSLTGGLSY

KEDTKELVVAKAGVYYVFFQLELRRVVAGEGSGSVSLALHLQPLRSAAG

AAALALTVDLPPASSEARNSAFGFQGRLLHLSAGQRLGVHLHTEARARH

AWQLTQGATVLGLFRVTPEIPAGLPSPRSE.

In some embodiments, a second chimeric polypeptide is encoded by a sequence that is at least 80% identical (e.g., at least 82% identical, at least 84% identical, at least 86% identical, at least 88% identical, at least 90% identical, at least 92% identical, at least 94% identical, at least 96% identical, at least 98% identical, at least 99% identical, or 100% identical) to:

(SEQ ID NO: 188)

ATGAAGTGGGTGACCTTCATCAGCCTGCTGTTCCTGTTCTCCAGCGCCT

ACTCCATCCCCCCCCATGTGCAAAAGAGCGTGAACAACGATATGATCGT

GACCGACAACAACGGCGCCGTGAAGTTTCCCCAGCTCTGCAAGTTCTGC

GATGTCAGGTTCAGCACCTGCGATAATCAGAAGTCCTGCATGTCCAACT

GCAGCATCACCTCCATCTGCGAGAAGCCCCAAGAAGTGTGCGTGGCCGT

GTGGCGGAAAAATGACGAGAACATCACCCTGGAGACCGTGTGTCACGAC

CCCAAGCTCCCTTATCACGACTTCATTCTGGAGGACGCTGCCTCCCCCA

AATGCATCATGAAGGAGAAGAAGAAGCCCGGAGAGACCTTCTTTATGTG

TTCCTGTAGCAGCGACGAGTGTAACGACAACATCATCTTCAGCGAAGAG

TACAACACCAGCAACCCTGATGGAGGTGGCGGATCCGGAGGTGGAGGTT

CTGGTGGAGGTGGGAGTATTCCTCCCCACGTGCAGAAGAGCGTGAATAA

TGACATGATCGTGACCGATAACAATGGCGCCGTGAAATTTCCCCAGCTG

TGCAAATTCTGCGATGTGAGGTTTTCCACCTGCGACAACCAGAAGTCCT

GTATGAGCAACTGCTCCATCACCTCCATCTGTGAGAAGCCTCAGGAGGT

GTGCGTGGCTGTCTGGCGGAAGAATGACGAGAATATCACCCTGGAAACC

GTCTGCCACGATCCCAAGCTGCCCTACCACGATTTCATCCTGGAAGACG

CCGCCAGCCCTAAGTGCATCATGAAAGAGAAAAAGAAGCCTGGCGAGAC

CTTTTTCATGTGCTCCTGCAGCAGCGACGAATGCAACGACAATATCATC

TTTAGCGAGGAATACAATACCAGCAACCCCGACATTACATGCCCCCCTC

CCATGAGCGTGGAGCACGCCGACATCTGGGTGAAGAGCTATAGCCTCTA

CAGCCGGGAGAGGTATATCTGTAACAGCGGCTTCAAGAGGAAGGCCGGC

ACCAGCAGCCTCACCGAGTGCGTGCTGAATAAGGCTACCAACGTGGCTC

ACTGGACAACACCCTCTTTAAAGTGCATCCGGGGCGGTGGAGGATCCGG

AGGAGGTGGCTCCGGCGGCGGAGGATCTCGCGAGGGTCCCGAGCTTTCG

CCCGACGATCCCGCCGGCCTCTTGGACCTGCGGCAGGGCATGTTTGCGC

AGCTGGTGGCCCAAAATGTTCTGCTGATCGATGGGCCCCTGAGCTGGTA

CAGTGACCCAGGCCTGGCAGGCGTGTCCCTGACGGGGGGCCTGAGCTAC

AAAGAGGACACGAAGGAGCTGGTGGTGGCCAAGGCTGGAGTCTACTATG

TCTTCTTTCAACTAGAGCTGCGGCGCGTGGTGGCCGGCGAGGGCTCAGG

CTCCGTTTCACTTGCGCTGCACCTGCAGCCACTGCGCTCTGCTGCTGGG

GCCGCCGCCCTGGCTTTGACCGTGGACCTGCCACCCGCCTCCTCCGAGG

CTCGGAACTCGGCCTTCGGTTTCCAGGGCCGCTTGCTGCACCTGAGTGC

CGGCCAGCGCCTGGGCGTCCATCTTCACACTGAGGCCAGGGCACGCCAT

GCCTGGCAGCTTACCCAGGGCGCCACAGTCTTGGGACTCTTCCGGGTGA

CCCCCGAAATCCCAGCCGGACTCCCTTCACCGAGGTCGGAA.

Compositions/Kits

Also provided herein are compositions (e.g., pharmaceutical compositions) that include at least one of any of the single-chain chimeric polypeptides, multi-chain chimeric polypeptides, any of the cells, or any of the nucleic acids described herein. In some embodiments, the compositions include at least one of any of the single-chain chimeric polypeptides described herein. In some embodiments, the compositions include at least one of any of the multi-chain chimeric polypeptides described herein. In some embodiments, the compositions include any of the immune cells (e.g., any of the immune cells described herein, e.g., any of the immune cells produced using any of the methods described herein).

In some embodiments, the pharmaceutical compositions are formulated for different routes of administration (e.g., intravenous, subcutaneous). In some embodiments, the pharmaceutical compositions can include a pharmaceutically acceptable carrier (e.g., phosphate buffered saline).

Single or multiple administrations of pharmaceutical compositions can be given to a subject in need thereof depending on for example: the dosage and frequency as required and tolerated by the subject. The formulation should provide a sufficient quantity of active agent to effectively treat, prevent or ameliorate conditions, diseases or symptoms.

Also provided herein are kits that include any of the single-chain chimeric polypeptides, multi-chain chimeric polypeptides, compositions, nucleic acids, or cells (e.g., immune cells) described herein. In some embodiments, the kits can include instructions for performing any of the methods described herein. In some embodiments, the kits can include at least one dose of any of the pharmaceutical compositions described herein.

Also provided herein is an immune cell (e.g., an activated NK cell or T cell) produced by any of the methods described herein. Also provided herein are pharmaceutical compositions that include any of the activated immune cells (e.g., an activated NK cell or T cell) produced by any of the methods described herein. Also provided herein are kits that include any of the pharmaceutical compositions described herein that include any of the activated immune cells (e.g., an activated NK cell or T cell) produced by any of the methods described herein.

Also provided herein are kits that include (i) any of the single-chain chimeric polypeptides described herein, and (ii) any of the IgG1 antibody constructs described herein. Also provided herein are kits that include (ii) any of the multi-chain chimeric polypeptides described herein, and (ii) any of the IgG1 antibody constructs described herein. In some embodiments of any of the kits described herein, the kits further include instructions for performing any of the methods described herein.

Nucleic Acids/Vectors

Also provided herein are nucleic acids that encode any of the single-chain chimeric polypeptides described herein. Also provided herein are vectors that include any of the nucleic acids encoding any of the single-chain chimeric polypeptides described herein.

Also provided herein are nucleic acids that encode any of the multi-chain chimeric polypeptides described herein. In some embodiments, a first nucleic acid can encode the first chimeric polypeptide and a second nucleic acid can encode the second chimeric polypeptide. In some embodiments, a single nucleic acid can encode both the first chimeric polypeptide and the second chimeric polypeptide.

Also provided herein are vectors that include any of the nucleic acids encoding any of the multi-chain chimeric polypeptides described herein. In some embodiments, a first vector can include a nucleic acid encoding the first chimeric polypeptide and a second vector can include a nucleic acid encoding the second chimeric polypeptide. In some embodiments, a single vector can include a first nucleic acid encoding the first chimeric polypeptide and a second nucleic acid encoding the second chimeric polypeptide.

Also provided herein are nucleic acids that encode any of the IgG1 antibody constructs described herein.

Any of the vectors described herein can be an expression vector. For example, an expression vector can include a promoter sequence operably linked to the sequence encoding the single-chain chimeric polypeptide, or the first chimeric polypeptide and the second chimeric polypeptide of a multi-chain chimeric polypeptide.

Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, e.g., include sufficient cis-acting elements for expression; other elements for expression can be supplied by the host mammalian cell or in an in vitro expression system. Skilled practitioners will be capable of selecting suitable vectors and mammalian cells for making any of the single-chain chimeric polypeptides or multi-chain chimeric polypeptides described herein.

Cells

Also provided herein are cells (e.g., any of the exemplary cells described herein or known in the art) comprising any of the nucleic acids described herein that encode any of the single-chain chimeric polypeptides described herein.

Also provided herein are cells (e.g., any of the exemplary cells described herein or known in the art) that include any of the vectors described herein that encode any of the single-chain chimeric polypeptides described herein.

Also provided herein are cells (e.g., any of the exemplary cells described herein or known in the art) comprising any of the nucleic acids described herein that encode any of the multi-chain chimeric polypeptides described herein (e.g., encoding both the first and second chimeric polypeptides). Also provided herein are cells (e.g., any of the exemplary cells described herein or known in the art) comprising any of the nucleic acids described herein that encode any of the first chimeric polypeptides described herein. Also provided are cells (e.g., any of the exemplary cells described herein or known in the art) comprising any of the nucleic acids described herein that encode any of the second chimeric polypeptides described herein.

Also provided herein are cells (e.g., any of the exemplary cells described herein or known in the art) that include any of the vectors described herein that encode any of the multi-chain chimeric polypeptides described herein (e.g., encoding both the first and second chimeric polypeptides). Also provided herein are cells (e.g., any of the exemplary cells described herein or known in the art) that include any of the vectors described herein that encode any of the first chimeric polypeptides described herein. Also provided herein are cells (e.g., any of the exemplary cells described herein or known in the art) that include any of the vectors described herein that encode any of the second chimeric polypeptides described herein).

In some embodiments of any of the methods described herein, the cell can be a eukaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as Saccharomyces cerevisiae. In some embodiments, the eukaryotic cell is a higher eukaryote, such as mammalian, avian, plant, or insect cells. Non-limiting examples of mammalian cells include Chinese hamster ovary cells and human embryonic kidney cells (e.g., HEK293 cells).

Methods of introducing nucleic acids and expression vectors into a cell (e.g., a eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalefection, hydrodynamic delivery, magnetofection, viral transduction (e.g., adenoviral and lentiviral transduction), and nanoparticle transfection.

Methods of Producing Single-Chain and Multi-Chain Chimeric Polypeptides

Also provided herein are methods of producing any of the single-chain chimeric polypeptides described herein that include culturing any of the cells described herein in a culture medium under conditions sufficient to result in the production of the single-chain chimeric polypeptide; and recovering the single-chain chimeric polypeptide from the cell and/or the culture medium.

The recovery of the single-chain chimeric polypeptide from a culture medium or a cell (e.g., a eukaryotic cell) can be performed using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Also provided herein are single-chain chimeric polypeptides (e.g., any of the single-chain chimeric polypeptides described herein) produced by any of the methods described herein.

Also provided herein are methods of producing any of the multi-chain chimeric polypeptides described herein that include culturing any of the cells described herein in a culture medium under conditions sufficient to result in the production of the multi-chain chimeric polypeptide; and recovering the multi-chain chimeric polypeptide from the cell and/or the culture medium.

Also provided herein are method of producing any of the multi-chain chimeric polypeptides described herein that include: culturing any of cells described herein in a first culture medium under conditions sufficient to result in the production of the first chimeric polypeptide; recovering the first chimeric polypeptide from the cell and/or the first culture medium; culturing any of the cells described herein in a second culture medium under conditions sufficient to result in the production of the second chimeric polypeptide; recovering the second chimeric polypeptide from the cell and/or the second culture medium; and combining (e.g., mixing) the recovered first chimeric polypeptide and the recovered second chimeric polypeptide to form the multi-chain chimeric polypeptide (e.g., any of the multi-chain chimeric polypeptides described herein).

The recovery of the multi-chain chimeric polypeptide, the first chimeric polypeptide, or the second chimeric polypeptide from a cell (e.g., a eukaryotic cell) can be performed using techniques well-known in the art (e.g., ammonium sulfate precipitation, polyethylene glycol precipitation, ion-exchange chromatography (anion or cation), chromatography based on hydrophobic interaction, metal-affinity chromatography, ligand-affinity chromatography, and size exclusion chromatography).

Also provided herein are multi-chain chimeric polypeptides (e.g., any of the multi-chain chimeric polypeptides described herein), first chimeric polypeptides (e.g., any of the first chimeric polypeptides), or second chimeric polypeptides (e.g., any of the second chimeric polypeptides described herein) produced by any of the methods described herein. Methods of culturing cells are well known in the art. Cells can be maintained in vitro under conditions that favor proliferation, differentiation and growth. Briefly, cells can be cultured by contacting a cell (e.g., any cell) with a cell culture medium that includes the necessary growth factors and supplements to support cell viability and growth.

Methods of Promoting the Activation and Proliferation of an Immune Cell

Also provided herein are methods of promoting the activation and proliferation of an immune cell (e.g., an any of the exemplary immune cells described herein or known in the art) that include contacting an immune cell in a liquid culture medium including an effective amount of (i) any of the single-chain or multi-chain chimeric polypeptides described herein, and (ii) an IgG1 antibody construct that comprises at least one antigen-binding domain that binds specifically to the linker domain (e.g., a monoclonal or polyclonal human, mouse, rabbit, or goat IgG1 antibody that binds specifically to a linker domain or any of the other exemplary IgG1 antibody constructs described herein), under conditions that allow for the activation and proliferation of the immune cell.

In some embodiments of these methods, the IgG1 antibody construct includes at least one antigen-binding domain that binds specifically to the linker domain. In some embodiments of these methods, the IgG1 antibody construct is a monoclonal IgG1 antibody, where both of the antigen-binding domains in the monoclonal IgG1 antibody bind specifically to the linker domain. In some embodiments of these methods, the IgG1 antibody construct is a bispecific IgG1 antibody, where one of the two antigen-binding domains in the bispecific IgG1 antibody binds specifically to the linker domain.

In some embodiments of these methods, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days.

In some embodiments of any of the methods described herein, the liquid culture medium is a serum-free liquid culture medium. In some embodiments of any of the methods described herein, the liquid culture medium is a chemically-defined liquid culture medium.

In some embodiments of any of the methods described herein, the liquid culture medium includes the single-chain or multi-chain chimeric polypeptide and the IgG1 antibody construct at a molar ratio of about 0.5:1 to about 2:1 (e.g., about 0.8:1 to about 1.2:1).

In some embodiments of any of the methods described herein, the immune cell is selected from the group consisting of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments of any of the methods described herein, the immune cell is a T-cell or a natural killer cell.

In some embodiments of any of the methods described herein, the immune cell was previously obtained from a subject. Some embodiments of any of the methods described herein further include obtaining the immune cell from the subject prior to the contacting step.

In some embodiments of any of the methods described herein, the immune cell has previously been genetically modified to express a chimeric antigen receptor or a recombinant T-cell receptor.

Some embodiments of any of the methods described herein further includes, after the contacting step, introducing into the immune cell a nucleic acid encoding a chimeric antigen-receptor or a recombinant T-cell receptor.

Some embodiments of any of the methods described herein further include, before the contacting step, introducing into the immune cell a nucleic acid encoding a chimeric antigen-receptor or a recombinant T-cell receptor.

Some embodiments of any of the methods described herein further include, after the contacting step, isolating the immune cell.

In some embodiments of any of the methods described herein, after the contacting step, the immune cell has an increased level of expression or secretion of one or more proteins selected from the group consisting of: 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step.

Some embodiments of any of the methods described herein further include, after the contacting step, administering the immune cell to a subject in need thereof. In some embodiments of any of the methods described herein, the subject has been identified or diagnosed as having an age-related disease or condition. In some embodiments of any of the methods described herein, the age-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some embodiments of any of the methods described herein, the subject has been identified or diagnosed as having a cancer. In some embodiments of any of the methods described herein, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of any of the methods described herein, the subject has been diagnosed or identified as having an infectious disease. In some embodiments of any of the methods described herein, the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Also provided herein is an activated immune cell produced by any of the methods described herein. Also provided herein are pharmaceutical compositions that include any of the immune cells produced by any of the methods described herein. Also provided herein are kits that include any of the pharmaceutical compositions including any of the activated immune cells produced by any of the methods described herein.

Methods of Stimulating an Immune Cell

Also provided herein are methods of stimulating an immune cell (e.g., any of the exemplary immune cells described herein or known in the art) that include contacting an immune cell with an effective amount of any of the single-chain chimeric polypeptides or any of the multi-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell). In some examples, the contacting further includes contacting the immune cell with an effective amount of any of the IgG1 antibody constructs described herein.

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the single-chain chimeric polypeptide or multi-chain chimeric polypeptide is administered to a subject (e.g., a mammal, e.g., a human) in an amount sufficient to result in stimulation of an immune cell in the subject. In some embodiments of any of the methods, compositions, and kits described herein, the IgG1 antibody construct (e.g., any of the exemplary IgG1 antibody constructs described herein is administered to the subject in combination (e.g., simultaneously or sequentially) with administration of the single-chain chimeric polypeptide or multi-chain chimeric polypeptide (e.g., any of the single-chain chimeric polypeptides or multi-chain chimeric polypeptides described herein).

In some examples of any of the methods described herein, the immune cell can be an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

Some embodiments of these methods can further include, after the contacting step, introducing into the immune cell (e.g., any of the immune cells described herein) a nucleic acid encoding a chimeric antigen-receptor or a recombinant T-cell receptor. Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Activation of an immune cell can be determined using methods known in the art. For example, activation of an immune cell can be determined by detecting the levels of cytokines, chemokines that are secreted or cytotoxicity granules, activating receptors, and regulatory molecules that are upregulated upon activation of an immune cell. Non-limiting examples of cytokines and chemokines that are secreted or cytotoxicity granules, activating receptors, and regulatory molecules that are upregulated upon activation of an immune cell include: IL-2, interferon-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, perforin, TGFβ, STAT3, STAT4, STAT5, RORγT, FOXP3, GATA3, granzyme A, granzyme B, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ. The detection of these cytokines and chemokines can be performed using an immunoassay (e.g., an enzyme-linked immunosorbent assay). For example, activation of an immune cell can result in an increase of about 1% to about 800% (e.g., about 1% to about 750%, about 1% to about 700%, about 1% to about 650%, about 1% to about 600%, about 1% to about 550%, about 1% to about 500%, about 1% to about 4 50%, about 1% to about 400%, about 1% to about 3 50%, about 1% to about 300%, about 1% to about 280%, about 1% to about 260%, about 1% to about 240%, about 1% to about 220%, about 1% to about 200%, about 1% to about 180%, about 1% to about 160%, about 1% to about 140%, about 1% to about 120%, about 1% to about 100%, about 1% to about 90%, about 1% to about 80%, about 1% to about 70%, about 1% to about 60%, about 1% to about 50%, about 1% to about 45%, about 1% to about 40%, about 1% to about 35%, about 1% to about 30%, about 1% to about 25%, about 1% to about 20%, about 1% to about 15%, about 1% to about 10%, about 1% to about 5%, about 5% to about 800%, about 5% to about 7 50%, about 5% to about 700%, about 5% to about 650%, about 5% to about 600%, about 5% to about 550%, about 5% to about 500%, about 5% to about 450%, about 5% to about 400%, about 5% to about 3 50%, about 5% to about 300%, about 5% to about 280%, about 5% to about 260%, about 5% to about 240%, about 5% to about 220%, about 5% to about 200%, about 5% to about 180%, about 5% to about 160%, about 5% to about 140%, about 5% to about 120%, about 5% to about 100%, about 5% to about 90%, about 5% to about 80%, about 5% to about 70%, about 5% to about 60%, about 5% to about 50%, about 5% to about 45%, about 5% to about 40%, about 5% to about 35%, about 5% to about 30%, about 5% to about 25%, about 5% to about 20%, about 5% to about 15%, about 5% to about 10%, about 10% to about 800%, about 10% to about 7 50%, about 10% to about 700%, about 10% to about 6 50%, about 10% to about 600%, about 10% to about 550%, about 10% to about 500%, about 10% to about 4 50%, about 10% to about 400%, about 10% to about 3 50%, about 10% to about 300%, about 10% to about 280%, about 10% to about 260%, about 10% to about 240%, about 10% to about 220%, about 10% to about 200%, about 10% to about 180%, about 10% to about 160%, about 10% to about 140%, about 10% to about 120%, about 10% to about 100%, about 10% to about 90%, about 10% to about 80%, about 10% to about 70%, about 10% to about 60%, about 10% to about 50%, about 10% to about 45%, about 10% to about 40%, about 10% to about 35%, about 10% to about 30%, about 10% to about 25%, about 10% to about 20%, about 10% to about 15%, about 15% to about 800%, about 15% to about 7 50%, about 15% to about 700%, about 15% to about 6 50%, about 15% to about 600%, about 15% to about 550%, about 15% to about 500%, about 15% to about 4 50%, about 15% to about 400%, about 15% to about 3 50%, about 15% to about 300%, about 15% to about 280%, about 15% to about 260%, about 15% to about 240%, about 15% to about 220%, about 15% to about 200%, about 15% to about 180%, about 15% to about 160%, about 15% to about 140%, about 15% to about 120%, about 15% to about 100%, about 15% to about 90%, about 15% to about 80%, about 15% to about 70%, about 15% to about 60%, about 15% to about 50%, about 15% to about 45%, about 15% to about 40%, about 15% to about 35%, about 15% to about 30%, about 15% to about 25%, about 15% to about 20%, about 20% to about 800%, about 20% to about 750%, about 20% to about 700%, about 20% to about 650%, about 20% to about 600%, about 20% to about 550%, about 20% to about 500%, about 20% to about 450%, about 20% to about 400%, about 20% to about 3 50%, about 20% to about 300%, about 20% to about 280%, about 20% to about 260%, about 20% to about 240%, about 20% to about 220%, about 20% to about 200%, about 20% to about 180%, about 20% to about 160%, about 20% to about 140%, about 20% to about 120%, about 20% to about 100%, about 20% to about 90%, about 20% to about 80%, about 20% to about 70%, about 20% to about 60%, about 20% to about 50%, about 20% to about 45%, about 20% to about 40%, about 20% to about 35%, about 20% to about 30%, about 20% to about 25%, about 25% to about 800%, about 25% to about 750%, about 25% to about 700%, about 25% to about 650%, about 25% to about 600%, about 25% to about 550%, about 25% to about 500%, about 25% to about 450%, about 25% to about 400%, about 25% to about 3 50%, about 25% to about 300%, about 25% to about 280%, about 25% to about 260%, about 25% to about 240%, about 25% to about 220%, about 25% to about 200%, about 25% to about 180%, about 25% to about 160%, about 25% to about 140%, about 25% to about 120%, about 25% to about 100%, about 25% to about 90%, about 25% to about 80%, about 25% to about 70%, about 25% to about 60%, about 25% to about 50%, about 25% to about 45%, about 25% to about 40%, about 25% to about 35%, about 35% to about 800%, about 35% to about 7 50%, about 35% to about 700%, about 35% to about 6 50%, about 35% to about 600%, about 35% to about 550%, about 35% to about 500%, about 35% to about 4 50%, about 35% to about 400%, about 35% to about 3 50%, about 35% to about 300%, about 35% to about 280%, about 35% to about 260%, about 35% to about 240%, about 35% to about 220%, about 35% to about 200%, about 35% to about 180%, about 35% to about 160%, about 35% to about 140%, about 35% to about 120%, about 35% to about 100%, about 35% to about 90%, about 35% to about 80%, about 35% to about 70%, about 35% to about 60%, about 35% to about 50%, about 35% to about 45%, about 35% to about 40%, about 40% to about 800%, about 40% to about 7 50%, about 40% to about 700%, about 40% to about 650%, about 40% to about 600%, about 40% to about 550%, about 40% to about 500%, about 40% to about 450%, about 40% to about 400%, about 40% to about 350%, about 40% to about 300%, about 40% to about 280%, about 40% to about 260%, about 40% to about 240%, about 40% to about 220%, about 40% to about 200%, about 40% to about 180%, about 40% to about 160%, about 40% to about 140%, about 40% to about 120%, about 40% to about 100%, about 40% to about 90%, about 40% to about 80%, about 40% to about 70%, about 40% to about 60%, about 40% to about 50%, about 40% to about 45%, about 45% to about 800%, about 45% to about 750%, about 45% to about 700%, about 45% to about 650%, about 45% to about 600%, about 45% to about 550%, about 45% to about 500%, about 45% to about 450%, about 45% to about 400%, about 45% to about 350%, about 45% to about 300%, about 45% to about 280%, about 45% to about 260%, about 45% to about 240%, about 45% to about 220%, about 45% to about 200%, about 45% to about 180%, about 45% to about 160%, about 45% to about 140%, about 45% to about 120%, about 45% to about 100%, about 45% to about 90%, about 45% to about 80%, about 45% to about 70%, about 45% to about 60%, about 45% to about 50%, about 50% to about 800%, about 50% to about 750%, about 50% to about 700%, about 50% to about 650%, about 50% to about 600%, about 50% to about 550%, about 50% to about 500%, about 50% to about 450%, about 50% to about 400%, about 50% to about 350%, about 50% to about 300%, about 50% to about 280%, about 50% to about 260%, about 50% to about 240%, about 50% to about 220%, about 50% to about 200%, about 50% to about 180%, about 50% to about 160%, about 50% to about 140%, about 50% to about 120%, about 50% to about 100%, about 50% to about 90%, about 50% to about 80%, about 50% to about 70%, about 50% to about 60%, about 60% to about 800%, about 60% to about 750%, about 60% to about 700%, about 60% to about 650%, about 60% to about 600%, about 60% to about 550%, about 60% to about 500%, about 60% to about 450%, about 60% to about 400%, about 60% to about 350%, about 60% to about 300%, about 60% to about 280%, about 60% to about 260%, about 60% to about 240%, about 60% to about 220%, about 60% to about 200%, about 60% to about 180%, about 60% to about 160%, about 60% to about 140%, about 60% to about 120%, about 60% to about 100%, about 60% to about 90%, about 60% to about 80%, about 60% to about 70%, about 70% to about 800%, about 70% to about 750%, about 70% to about 700%, about 70% to about 650%, about 70% to about 600%, about 70% to about 550%, about 70% to about 500%, about 70% to about 450%, about 70% to about 400%, about 70% to about 350%, about 70% to about 300%, about 70% to about 280%, about 70% to about 260%, about 70% to about 240%, about 70% to about 220%, about 70% to about 200%, about 70% to about 180%, about 70% to about 160%, about 70% to about 140%, about 70% to about 120%, about 70% to about 100%, about 70% to about 90%, about 70% to about 80%, about 80% to about 800%, about 80% to about 750%, about 80% to about 700%, about 80% to about 650%, about 80% to about 600%, about 80% to about 550%, about 80% to about 500%, about 80% to about 450%, about 80% to about 400%, about 80% to about 350%, about 80% to about 300%, about 80% to about 280%, about 80% to about 260%, about 80% to about 240%, about 80% to about 220%, about 80% to about 200%, about 80% to about 180%, about 80% to about 160%, about 80% to about 140%, about 80% to about 120%, about 80% to about 100%, about 80% to about 90%, about 90% to about 800%, about 90% to about 750%, about 90% to about 700%, about 90% to about 650%, about 90% to about 600%, about 90% to about 550%, about 90% to about 500%, about 90% to about 450%, about 90% to about 400%, about 90% to about 350%, about 90% to about 300%, about 90% to about 280%, about 90% to about 260%, about 90% to about 240%, about 90% to about 220%, about 90% to about 200%, about 90% to about 180%, about 90% to about 160%, about 90% to about 140%, about 90% to about 120%, about 90% to about 100%, about 100% to about 800%, about 100% to about 750%, about 100% to about 700%, about 100% to about 650%, about 100% to about 600%, about 100% to about 550%, about 100% to about 500%, about 100% to about 450%, about 100% to about 400%, about 100% to about 350%, about 100% to about 300%, about 100% to about 280%, about 100% to about 260%, about 100% to about 240%, about 100% to about 220%, about 100% to about 200%, about 100% to about 180%, about 100% to about 160%, about 100% to about 140%, about 100% to about 120%, about 120% to about 800%, about 120% to about 750%, about 120% to about 700%, about 120% to about 650%, about 120% to about 600%, about 120% to about 550%, about 120% to about 500%, about 120% to about 450%, about 120% to about 400%, about 120% to about 350%, about 120% to about 300%, about 120% to about 280%, about 120% to about 260%, about 120% to about 240%, about 120% to about 220%, about 120% to about 200%, about 120% to about 180%, about 120% to about 160%, about 120% to about 140%, about 140% to about 800%, about 140% to about 750%, about 140% to about 700%, about 140% to about 650%, about 140% to about 600%, about 140% to about 550%, about 140% to about 500%, about 140% to about 450%, about 140% to about 400%, about 140% to about 350%, about 140% to about 300%, about 140% to about 280%, about 140% to about 260%, about 140% to about 240%, about 140% to about 220%, about 140% to about 200%, about 140% to about 180%, about 140% to about 160%, about 160% to about 800%, about 160% to about 750%, about 160% to about 700%, about 160% to about 650%, about 160% to about 600%, about 160% to about 550%, about 160% to about 500%, about 160% to about 450%, about 160% to about 400%, about 160% to about 350%, about 160% to about 300%, about 160% to about 280%, about 160% to about 260%, about 160% to about 240%, about 160% to about 220%, about 160% to about 200%, about 160% to about 180%, about 180% to about 800%, about 180% to about 750%, about 180% to about 700%, about 180% to about 650%, about 180% to about 600%, about 180% to about 550%, about 180% to about 500%, about 180% to about 450%, about 180% to about 400%, about 180% to about 350%, about 180% to about 300%, about 180% to about 280%, about 180% to about 260%, about 180% to about 240%, about 180% to about 220%, about 180% to about 200%, about 200% to about 800%, about 200% to about 750%, about 200% to about 700%, about 200% to about 650%, about 200% to about 600%, about 200% to about 550%, about 200% to about 500%, about 200% to about 450%, about 200% to about 400%, about 200% to about 350%, about 200% to about 300%, about 200% to about 280%, about 200% to about 260%, about 200% to about 240%, about 200% to about 220%, about 220% to about 800%, about 220% to about 750%, about 220% to about 700%, about 220% to about 650%, about 220% to about 600%, about 220% to about 550%, about 220% to about 500%, about 220% to about 450%, about 220% to about 400%, about 220% to about 350%, about 220% to about 300%, about 220% to about 280%, about 220% to about 260%, about 220% to about 240%, about 240% to about 800%, about 240% to about 750%, about 240% to about 700%, about 240% to about 650%, about 240% to about 600%, about 240% to about 550%, about 240% to about 500%, about 240% to about 450%, about 240% to about 400%, about 240% to about 350%, about 240% to about 300%, about 240% to about 280%, about 240% to about 260%, about 260% to about 800%, about 260% to about 750%, about 260% to about 700%, about 260% to about 650%, about 260% to about 600%, about 260% to about 550%, about 260% to about 500%, about 260% to about 450%, about 260% to about 400%, about 260% to about 350%, about 260% to about 300%, about 260% to about 280%, about 280% to about 800%, about 280% to about 750%, about 280% to about 700%, about 280% to about 650%, about 280% to about 600%, about 280% to about 550%, about 280% to about 500%, about 280% to about 450%, about 280% to about 400%, about 280% to about 350%, about 280% to about 300%, about 300% to about 800%, about 300% to about 750%, about 300% to about 700%, about 300% to about 650%, about 300% to about 600%, about 300% to about 550%, about 300% to about 500%, about 300% to about 450%, about 300% to about 400%, about 300% to about 350%, about 350% to about 800%, about 350% to about 750%, about 350% to about 700%, about 350% to about 650%, about 350% to about 600%, about 350% to about 550%, about 350% to about 500%, about 350% to about 450%, about 350% to about 400%, about 400% to about 800%, about 400% to about 750%, about 400% to about 700%, about 400% to about 650%, about 400% to about 600%, about 400% to about 550%, about 400% to about 500%, about 400% to about 450%, about 450% to about 800%, about 450% to about 750%, about 450% to about 700%, about 450% to about 650%, about 450% to about 600%, about 450% to about 550%, about 450% to about 500%, about 500% to about 800%, about 500% to about 750%, about 500% to about 700%, about 500% to about 650%, about 500% to about 600%, about 500% to about 550%, about 550% to about 800%, about 550% to about 750%, about 550% to about 700%, about 550% to about 650%, about 550% to about 600%, about 600% to about 800%, about 600% to about 750%, about 600% to about 700%, about 600% to about 650%, about 650% to about 800%, about 650% to about 750%, about 650% to about 700%, about 700% to about 800%, about 700% to about 750%, or about 750% to about 800%) of one or more of any of the cytokines, chemokines, cytotoxicity granules, activating receptors or regulatory molecules described herein (e.g., one or more of any of IL-2, interferon-γ, IL-1, TL-4, IL-5, TL-6, IL-7, IL-9, IL-10, IL-12, IL-13, IL-15, IL-17, IL-18, IL-22, TL-33, leukotriene B4, CCL5, TNFα, granzymes, perforin, TGFβ, STAT3, STAT4, STAT5, RORγT, FOXP3, and GATA3) (e.g., as compared to the level of the one or more cytokines and chemokines in a control not contacted with any of the single-chain chimeric polypeptides or any of the multi-chain chimeric polypeptides described herein).

Methods of Inducing or Increasing Proliferation of an Immune Cell

Also provided herein are methods of inducing or increasing proliferation of an immune cell (e.g., any of the exemplary immune cells described herein or known in the art) that include contacting an immune cell with an effective amount of any of the single-chain chimeric polypeptides or any of the multi-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell)). In some examples, the immune cell is further contacted in vitro with any of the IgG1 antibody constructs described herein in combination (e.g., simultaneously or sequentially) with contacting the immune cell in vitro with the single-chain chimeric polypeptide or multi-chain chimeric polypeptide (e.g., any of the single-chain chimeric polypeptides or multi-chain chimeric polypeptides described herein).

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the single-chain chimeric polypeptide or multi-chain chimeric polypeptide is administered to a subject (e.g., a mammal, e.g., a human) in an amount sufficient to result in stimulation of an immune cell in the subject. In such embodiments, the subject can further be administered any of the IgG1 antibody constructs described herein.

In some examples of any of the methods described herein, the immune cell can be an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

Some embodiments of these methods can further include, after the contacting step, introducing into the immune cell (e.g., any of the immune cells described herein) a nucleic acid encoding a chimeric antigen-receptor or a recombinant T-cell receptor. Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Detection of the proliferation of an immune cell can be performed using methods known in the art, e.g., cytometry (e.g., fluorescence-assisted flow cytometry), microscopy, and immunofluorescence microscopy, e.g., by comparing the rate of increase in the concentration of the immune cell in a sample not contacted with a single-chain chimeric polypeptide or a multi-chain chimeric polypeptide to the rate of increase in the concentration of the immune cell in a similar sample contacted with any of the single-chain chimeric polypeptides described herein or any of the multi-chain chimeric polypeptides described herein).

In other examples, the proliferation of an immune cell can be indirectly detected by detecting an increase in the level of one or more cytokines or chemokines secreted or cytotoxicity granules, activating receptors, regulatory molecules upregulated by proliferating immune cells (e.g., one or more of IL-2, IFN-γ, IL-1, IL-4, IL-5, IL-6, IL-7, IL-9, IL-10, IL-12, IL-13, IL-15, IL-17, IL-18, IL-22, IL-33, leukotriene B4, CCL5, TNFα, perforin, TGFβ, STAT3, RORγT, FOXP3, STAT6, GATA3, granzyme A, granzyme B, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ) (e.g., as compared to the level of the one or more cytokines and chemokines in a control not contacted with any of the single-chain chimeric polypeptides described herein).

In some embodiments, the methods provided herein can result in an increase (e.g., about 1% to about 800% increase, or any of the subranges of this range described herein) in the rate of increase in the concentration of the immune cell in a sample contacted with any of the single-chain chimeric polypeptides any of the multi-chain chimeric polypeptides described herein as compared to the rate of increase in a similar control sample not contacted with any of the single-chain chimeric polypeptides any of the multi-chain chimeric polypeptides described herein.

Methods of Inducing Differentiation of an Immune Cell

Also provided herein are method of inducing differentiation of an immune cell (e.g., any of the exemplary immune cells described herein or known in the art) into a memory or memory-like immune cell that include contacting an immune cell with an effective amount of any of the single-chain chimeric polypeptides or any of the multi-chain chimeric polypeptides described herein or any of the compositions (e.g., pharmaceutical compositions) described herein. In some examples, the immune cell is contacted in vitro (e.g., in a suitable liquid culture medium under conditions sufficient to result in stimulation of the immune cell). In some examples, the immune cell is further contacted in vitro with an effective amount of any of the IgG1 antibody constructs described herein.

In some examples, the immune cell has been previously obtained from a subject (e.g., a mammal, e.g., a human). Some embodiments of these methods further include obtaining the immune cell from the subject prior to the contacting step.

In some examples, the immune cell is contacted in vivo. In such embodiments, the single-chain chimeric polypeptide or multi-chain chimeric polypeptide is administered to a subject (e.g., a mammal, e.g., a human) in an amount sufficient to result in stimulation of an immune cell in the subject. In some examples, the immune cell is contacted in vivo with any of the IgG1 antibody constructs described herein in combination (e.g., simultaneously or sequentially) with contacting the immune cell in vivo with the single-chain chimeric polypeptide or multi-chain chimeric polypeptide (e.g., any of the single-chain chimeric polypeptides or any of the multi-chain chimeric polypeptides described herein).

In some examples of any of the methods described herein, the immune cell can be an immature thymocyte, a peripheral blood lymphocyte, a naïve T cell, a pluripotent Th cell precursor, a lymphoid progenitor cell, a Treg cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, or a natural killer cell, or a combination thereof.

In some examples, the immune cell has previously been genetically-modified to express a chimeric antigen receptor or a recombinant T-cell receptor. In some examples, the immune cell (e.g., any of the immune cells described herein) has previously been genetically-modified to express a co-stimulatory molecule (e.g., CD28).

Some embodiments of these methods can further include, after the contacting step, introducing into the immune cell (e.g., any of the immune cells described herein) a nucleic acid encoding a chimeric antigen-receptor or a recombinant T-cell receptor. Some embodiments of these methods can further include, after the contacting step, introducing into the immune cell (e.g., any of the immune cells described herein) a nucleic acid encoding a co-stimulatory molecule (e.g., CD28).

Some embodiments of these methods can further include administering a therapeutically effective amount of the immune cell to a subject in need thereof (e.g., any of the exemplary subjects described herein).

In some examples, the subject can be a subject identified or diagnosed as having an age-related disease or condition. Non-limiting examples of age-related diseases or disorders include: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples, the subject can be a subject that has been identified or diagnosed as having a cancer. Non-limiting examples of cancers include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples, the subject can be a subject that has been diagnosed or identified as having an infectious disease.

Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

In some examples, the immune cell is a NK cell, and the detection of a memory NK cell can include, e.g., the detection of the level of one or more of IL-12, IL-18, IL-33, STAT4, Zbtb32, DNAM-1, BIM, Noxa, SOCS1, BNIP3, BNIP3L, IFN-γ, TNFα, CXCL16, CXCR6, NKG2D, TRAIL, CD49, CD25, CD69, CD62L, Ly49D, CD49b, and Ly79H. A description of NK memory cells and methods of detecting the same is described in O'Sullivan et al., Immunity 43:634-645, 2015.

In some examples, the immune cell is a T cell, and the detection of memory T cells can include, e.g., the detection of the level of expression of one or more of CD45RO, CCR7, L-selectin (CD62L), CD44, CD45RA, integrin αeβ7, CD43, CD27, CD28, IL-7Rα, CD95, IL-2Rα, CXCR3, and LFA-1. In some examples, the immune cell is a B cell and the detection of memory B cells can include, e.g., the detection of the level of expression of CD27. Other types and markers of memory or memory-like immune cells are known in the art.

Methods of Treatment

Also provided herein are methods of treating a subject in need thereof (e.g., any of the exemplary subjects described herein or known in the art) that include administering to the subject a therapeutically effective amount of any of the single-chain chimeric polypeptides or any of the multi-chain chimeric polypeptides described herein or any of the compositions (e.g., pharmaceutical compositions) described herein. In some embodiments, a subject can further be administered a therapeutically effective amount of any of the IgG1 antibody constructs described herein.

In some embodiments of these methods, the subject has been identified or diagnosed as having a cancer. Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some embodiments, these methods can result in a reduction in the number, severity, or frequency of one or more symptoms of the cancer in the subject (e.g., as compared to the number, severity, or frequency of the one or more symptoms of the cancer in the subject prior to treatment). In some embodiments, these methods can result in a reduction (e.g., about 1% reduction to about 99% reduction, about 1% reduction to about 95% reduction, about 1% reduction to about 90% reduction, about 1% reduction to about 85% reduction, about 1% reduction to about 80% reduction, about 1% reduction to about 75% reduction, about 1% reduction to about 70% reduction, about 1% reduction to about 65% reduction, about 1% reduction to about 60% reduction, about 1% reduction to about 55% reduction, about 1% reduction to about 50% reduction, about 1% reduction to about 45% reduction, about 1% reduction to about 40% reduction, about 1% reduction to about 35% reduction, about 1% reduction to about 30% reduction, about 1% reduction to about 25% reduction, about 1% reduction to about 20% reduction, about 1% reduction to about 15% reduction, about 1% reduction to about 10% reduction, about 1% reduction to about 5% reduction, about 5% reduction to about 99% reduction, about 5% reduction to about 95% reduction, about 5% reduction to about 90% reduction, about 5% reduction to about 85% reduction, about 5% reduction to about 80% reduction, about 5% reduction to about 75% reduction, about 5% reduction to about 70% reduction, about 5% reduction to about 65% reduction, about 5% reduction to about 60% reduction, about 5% reduction to about 55% reduction, about 5% reduction to about 50% reduction, about 5% reduction to about 45% reduction, about 5% reduction to about 40% reduction, about 5% reduction to about 35% reduction, about 5% reduction to about 30% reduction, about 5% reduction to about 25% reduction, about 5% reduction to about 20% reduction, about 5% reduction to about 15% reduction, about 5% reduction to about 10% reduction, about 10% reduction to about 99% reduction, about 10% reduction to about 95% reduction, about 10% reduction to about 90% reduction, about 10% reduction to about 85% reduction, about 10% reduction to about 80% reduction, about 10% reduction to about 75% reduction, about 10% reduction to about 70% reduction, about 10% reduction to about 65% reduction, about 10% reduction to about 60% reduction, about 10% reduction to about 55% reduction, about 10% reduction to about 50% reduction, about 10% reduction to about 45% reduction, about 10% reduction to about 40% reduction, about 10% reduction to about 35% reduction, about 10% reduction to about 30% reduction, about 10% reduction to about 25% reduction, about 10% reduction to about 20% reduction, about 10% reduction to about 15% reduction, about 15% reduction to about 99% reduction, about 15% reduction to about 95% reduction, about 15% reduction to about 90% reduction, about 15% reduction to about 85% reduction, about 15% reduction to about 80% reduction, about 15% reduction to about 75% reduction, about 15% reduction to about 70% reduction, about 15% reduction to about 65% reduction, about 15% reduction to about 60% reduction, about 15% reduction to about 55% reduction, about 15% reduction to about 50% reduction, about 15% reduction to about 45% reduction, about 15% reduction to about 40% reduction, about 15% reduction to about 35% reduction, about 15% reduction to about 30% reduction, about 15% reduction to about 25% reduction, about 15% reduction to about 20% reduction, about 20% reduction to about 99% reduction, about 20% reduction to about 95% reduction, about 20% reduction to about 90% reduction, about 20% reduction to about 85% reduction, about 20% reduction to about 80% reduction, about 20% reduction to about 75% reduction, about 20% reduction to about 70% reduction, about 20% reduction to about 65% reduction, about 20% reduction to about 60% reduction, about 20% reduction to about 55% reduction, about 20% reduction to about 50% reduction, about 20% reduction to about 45% reduction, about 20% reduction to about 40% reduction, about 20% reduction to about 35% reduction, about 20% reduction to about 30% reduction, about 20% reduction to about 25% reduction, about 25% reduction to about 99% reduction, about 25% reduction to about 95% reduction, about 25% reduction to about 90% reduction, about 25% reduction to about 85% reduction, about 25% reduction to about 80% reduction, about 25% reduction to about 75% reduction, about 25% reduction to about 70% reduction, about 25% reduction to about 65% reduction, about 25% reduction to about 60% reduction, about 25% reduction to about 55% reduction, about 25% reduction to about 50% reduction, about 25% reduction to about 45% reduction, about 25% reduction to about 40% reduction, about 25% reduction to about 35% reduction, about 25% reduction to about 30% reduction, about 30% reduction to about 99% reduction, about 30% reduction to about 95% reduction, about 30% reduction to about 90% reduction, about 30% reduction to about 85% reduction, about 30% reduction to about 80% reduction, about 30% reduction to about 75% reduction, about 30% reduction to about 70% reduction, about 30% reduction to about 65% reduction, about 30% reduction to about 60% reduction, about 30% reduction to about 55% reduction, about 30% reduction to about 50% reduction, about 30% reduction to about 45% reduction, about 30% reduction to about 40% reduction, about 30% reduction to about 35% reduction, about 35% reduction to about 99% reduction, about 35% reduction to about 95% reduction, about 35% reduction to about 90% reduction, about 35% reduction to about 85% reduction, about 35% reduction to about 80% reduction, about 35% reduction to about 75% reduction, about 35% reduction to about 70% reduction, about 35% reduction to about 65% reduction, about 35% reduction to about 60% reduction, about 35% reduction to about 55% reduction, about 35% reduction to about 50% reduction, about 35% reduction to about 45% reduction, about 35% reduction to about 40% reduction, about 40% reduction to about 99% reduction, about 40% reduction to about 95% reduction, about 40% reduction to about 90% reduction, about 40% reduction to about 85% reduction, about 40% reduction to about 80% reduction, about 40% reduction to about 75% reduction, about 40% reduction to about 70% reduction, about 40% reduction to about 65% reduction, about 40% reduction to about 60% reduction, about 40% reduction to about 55% reduction, about 40% reduction to about 50% reduction, about 40% reduction to about 45% reduction, about 45% reduction to about 99% reduction, about 45% reduction to about 95% reduction, about 45% reduction to about 90% reduction, about 45% reduction to about 85% reduction, about 45% reduction to about 80% reduction, about 45% reduction to about 75% reduction, about 45% reduction to about 70% reduction, about 45% reduction to about 65% reduction, about 45% reduction to about 60% reduction, about 45% reduction to about 55% reduction, about 45% reduction to about 50% reduction, about 50% reduction to about 99% reduction, about 50% reduction to about 95% reduction, about 50% reduction to about 90% reduction, about 50% reduction to about 85% reduction, about 50% reduction to about 80% reduction, about 50% reduction to about 75% reduction, about 50% reduction to about 70% reduction, about 50% reduction to about 65% reduction, about 50% reduction to about 60% reduction, about 50% reduction to about 55% reduction, about 55% reduction to about 99% reduction, about 55% reduction to about 95% reduction, about 55% reduction to about 90% reduction, about 55% reduction to about 85% reduction, about 55% reduction to about 80% reduction, about 55% reduction to about 75% reduction, about 55% reduction to about 70% reduction, about 55% reduction to about 65% reduction, about 55% reduction to about 60% reduction, about 60% reduction to about 99% reduction, about 60% reduction to about 95% reduction, about 60% reduction to about 90% reduction, about 60% reduction to about 85% reduction, about 60% reduction to about 80% reduction, about 60% reduction to about 75% reduction, about 60% reduction to about 70% reduction, about 60% reduction to about 65% reduction, about 65% reduction to about 99% reduction, about 65% reduction to about 95% reduction, about 65% reduction to about 90% reduction, about 65% reduction to about 85% reduction, about 65% reduction to about 80% reduction, about 65% reduction to about 75% reduction, about 65% reduction to about 70% reduction, about 70% reduction to about 99% reduction, about 70% reduction to about 95% reduction, about 70% reduction to about 90% reduction, about 70% reduction to about 85% reduction, about 70% reduction to about 80% reduction, about 70% reduction to about 75% reduction, about 75% reduction to about 99% reduction, about 75% reduction to about 95% reduction, about 75% reduction to about 90% reduction, about 75% reduction to about 85% reduction, about 75% reduction to about 80% reduction, about 80% reduction to about 99% reduction, about 80% reduction to about 95% reduction, about 80% reduction to about 90% reduction, about 80% reduction to about 85% reduction, about 85% reduction to about 99% reduction, about 85% reduction to about 95% reduction, about 85% reduction to about 90% reduction, about 90% reduction to about 99% reduction, about 90% reduction to about 95% reduction, or about 95% reduction to about 99% reduction) in the volume of one or more solid tumors in the subject (e.g., as compared to the volume of the one or more solid tumors prior to treatment or at the start of treatment). In some embodiments, the these methods can reduce (e.g., about 1% reduction to about 99% reduction, or any of the subranges of this range described herein) the risk of developing a metastasis or developing one or more additional metastasis in a subject (e.g., as compared to the risk of developing a metastasis or developing one or more additional metastasis in a subject prior to treatment or in a similar subject or a population of subjects administered a different treatment).

In some examples of these methods, the subject has been identified or diagnosed as having an aging-related disease or condition. Non-limiting examples of aging-related diseases and conditions include Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples, these methods can result in a reduction in the number, severity, or frequency of one or more symptoms of the aging-related disease or condition in the subject (e.g., as compared to the number, severity, or frequency of the one or more symptoms of the aging-related disease or condition in the subject prior to treatment). In some examples, the methods can result in a decrease (e.g., about 1% decrease to about 99% decrease, an about 1% decrease to about 95% decrease, about 1% decrease to about 90% decrease, about 1% decrease to about 85% decrease, about 1% decrease to about 80% decrease, about 1% decrease to about 75% decrease, about 1% to about 70% decrease, about 1% decrease to about 65% decrease, about 1% decrease to about 60% decrease, about 1% decrease to about 55% decrease, about 1% decrease to about 50% decrease, about 1% decrease to about 45% decrease, about 1% decrease to about 40% decrease, about 1% decrease to about 35% decrease, about 1% decrease to about 30% decrease, about 1% decrease to about 25% decrease, about 1% decrease to about 20% decrease, about 1% decrease to about 15% decrease, about 1% decrease to about 10% decrease, about 1% decrease to about 5% decrease, about 5% decrease to about 99% decrease, an about 5% decrease to about 95% decrease, about 5% decrease to about 90% decrease, about 5% decrease to about 85% decrease, about 5% decrease to about 80% decrease, about 5% decrease to about 75% decrease, about 5% to about 70% decrease, about 5% decrease to about 65% decrease, about 5% decrease to about 60% decrease, about 5% decrease to about 55% decrease, about 5% decrease to about 50% decrease, about 5% decrease to about 45% decrease, about 5% decrease to about 40% decrease, about 5% decrease to about 35% decrease, about 5% decrease to about 30% decrease, about 5% decrease to about 25% decrease, about 5% decrease to about 20% decrease, about 5% decrease to about 15% decrease, about 5% decrease to about 10% decrease, about 10% decrease to about 99% decrease, an about 10% decrease to about 95% decrease, about 10% decrease to about 90% decrease, about 10% decrease to about 85% decrease, about 10% decrease to about 80% decrease, about 10% decrease to about 75% decrease, about 10% to about 70% decrease, about 10% decrease to about 65% decrease, about 10% decrease to about 60% decrease, about 10% decrease to about 55% decrease, about 10% decrease to about 50% decrease, about 10% decrease to about 45% decrease, about 10% decrease to about 40% decrease, about 10% decrease to about 35% decrease, about 10% decrease to about 30% decrease, about 10% decrease to about 25% decrease, about 10% decrease to about 20% decrease, about 10% decrease to about 15% decrease, about 15% decrease to about 99% decrease, an about 15% decrease to about 95% decrease, about 15% decrease to about 90% decrease, about 15% decrease to about 85% decrease, about 15% decrease to about 80% decrease, about 15% decrease to about 75% decrease, about 15% to about 70% decrease, about 15% decrease to about 65% decrease, about 15% decrease to about 60% decrease, about 15% decrease to about 55% decrease, about 15% decrease to about 50% decrease, about 15% decrease to about 45% decrease, about 15% decrease to about 40% decrease, about 15% decrease to about 35% decrease, about 15% decrease to about 30% decrease, about 15% decrease to about 25% decrease, about 15% decrease to about 20% decrease, about 20% decrease to about 99% decrease, an about 20% decrease to about 95% decrease, about 20% decrease to about 90% decrease, about 20% decrease to about 85% decrease, about 20% decrease to about 80% decrease, about 20% decrease to about 75% decrease, about 20% to about 70% decrease, about 20% decrease to about 65% decrease, about 20% decrease to about 60% decrease, about 20% decrease to about 55% decrease, about 20% decrease to about 50% decrease, about 20% decrease to about 45% decrease, about 20% decrease to about 40% decrease, about 20% decrease to about 35% decrease, about 20% decrease to about 30% decrease, about 20% decrease to about 25% decrease, about 25% decrease to about 99% decrease, an about 25% decrease to about 95% decrease, about 25% decrease to about 90% decrease, about 25% decrease to about 85% decrease, about 25% decrease to about 80% decrease, about 25% decrease to about 75% decrease, about 25% to about 70% decrease, about 25% decrease to about 65% decrease, about 25% decrease to about 60% decrease, about 25% decrease to about 55% decrease, about 25% decrease to about 50% decrease, about 25% decrease to about 45% decrease, about 25% decrease to about 40% decrease, about 25% decrease to about 35% decrease, about 25% decrease to about 30% decrease, about 30% decrease to about 99% decrease, an about 30% decrease to about 95% decrease, about 30% decrease to about 90% decrease, about 30% decrease to about 85% decrease, about 30% decrease to about 80% decrease, about 30% decrease to about 75% decrease, about 30% to about 70% decrease, about 30% decrease to about 65% decrease, about 30% decrease to about 60% decrease, about 30% decrease to about 55% decrease, about 30% decrease to about 50% decrease, about 30% decrease to about 45% decrease, about 30% decrease to about 40% decrease, about 30% decrease to about 35% decrease, about 35% decrease to about 99% decrease, an about 35% decrease to about 95% decrease, about 35% decrease to about 90% decrease, about 35% decrease to about 85% decrease, about 35% decrease to about 80% decrease, about 35% decrease to about 75% decrease, about 35% to about 70% decrease, about 35% decrease to about 65% decrease, about 35% decrease to about 60% decrease, about 35% decrease to about 55% decrease, about 35% decrease to about 50% decrease, about 35% decrease to about 45% decrease, about 35% decrease to about 40% decrease, about 40% decrease to about 99% decrease, an about 40% decrease to about 95% decrease, about 40% decrease to about 90% decrease, about 40% decrease to about 85% decrease, about 40% decrease to about 80% decrease, about 40% decrease to about 75% decrease, about 40% to about 70% decrease, about 40% decrease to about 65% decrease, about 40% decrease to about 60% decrease, about 40% decrease to about 55% decrease, about 40% decrease to about 50% decrease, about 40% decrease to about 45% decrease, about 45% decrease to about 99% decrease, an about 45% decrease to about 95% decrease, about 45% decrease to about 90% decrease, about 45% decrease to about 85% decrease, about 45% decrease to about 80% decrease, about 45% decrease to about 75% decrease, about 45% to about 70% decrease, about 45% decrease to about 65% decrease, about 45% decrease to about 60% decrease, about 45% decrease to about 55% decrease, about 45% decrease to about 50% decrease, about 50% decrease to about 99% decrease, an about 50% decrease to about 95% decrease, about 50% decrease to about 90% decrease, about 50% decrease to about 85% decrease, about 50% decrease to about 80% decrease, about 50% decrease to about 75% decrease, about 50% to about 70% decrease, about 50% decrease to about 65% decrease, about 50% decrease to about 60% decrease, about 50% decrease to about 55% decrease, about 55% decrease to about 99% decrease, an about 55% decrease to about 95% decrease, about 55% decrease to about 90% decrease, about 55% decrease to about 85% decrease, about 55% decrease to about 80% decrease, about 55% decrease to about 75% decrease, about 55% to about 70% decrease, about 55% decrease to about 65% decrease, about 55% decrease to about 60% decrease, about 60% decrease to about 99% decrease, an about 60% decrease to about 95% decrease, about 60% decrease to about 90% decrease, about 60% decrease to about 85% decrease, about 60% decrease to about 80% decrease, about 60% decrease to about 75% decrease, about 60% to about 70% decrease, about 60% decrease to about 65% decrease, about 65% decrease to about 99% decrease, an about 65% decrease to about 95% decrease, about 65% decrease to about 90% decrease, about 65% decrease to about 85% decrease, about 65% decrease to about 80% decrease, about 65% decrease to about 75% decrease, about 65% to about 70% decrease, about 70% decrease to about 99% decrease, an about 70% decrease to about 95% decrease, about 70% decrease to about 90% decrease, about 70% decrease to about 85% decrease, about 70% decrease to about 80% decrease, about 70% decrease to about 75% decrease, about 75% decrease to about 99% decrease, an about 75% decrease to about 95% decrease, about 75% decrease to about 90% decrease, about 75% decrease to about 85% decrease, about 75% decrease to about 80% decrease, about 80% decrease to about 99% decrease, an about 80% decrease to about 95% decrease, about 80% decrease to about 90% decrease, about 80% decrease to about 85% decrease, about 85% decrease to about 99% decrease, an about 85% decrease to about 95% decrease, about 85% decrease to about 90% decrease, about 90% decrease to about 99% decrease, an about 90% decrease to about 95% decrease, or about 95% decrease to about 99% decrease) in the number of senescent cells in the subject (e.g., a decrease in the number of senescent cells in one or more specific tissues involved and/or implicated in the aging-related disease or disorder in the subject), e.g., as compared to the number of senescent cells in the subject prior to treatment.

In some examples of these methods, the subject has been diagnosed or identified as having an infectious disease. Non-limiting examples of infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus. In some embodiments, these method can result in a decrease in the infectious titer (e.g., viral titer) in a subject (e.g., as compared to the infectious titer in the subject prior to treatment). In some embodiments, these methods can result in a reduction in the number, severity, or frequency of one or more symptoms of the infectious disease (e.g., viral infection) in the subject (e.g., as compared to the number, severity, or frequency of the one or more symptoms of the infectious disease in the subject prior to treatment).

The term "subject" refers to any mammal. In some embodiments, the subject or "subject in need of treatment" may be a canine (e.g., a dog), feline (e.g., a cat), equine (e.g., a horse), ovine, bovine, porcine, caprine, primate, e.g., a simian (e.g., a monkey (e.g., marmoset, baboon), or an ape (e.g., a gorilla, chimpanzee, orangutan, or gibbon) or a human; or rodent (e.g., a mouse, a guinea pig, a hamster, or a rat). In some embodiments, the subject or "subject in need of treatment" may be a non-human mammal, especially mammals that are conventionally used as models for demonstrating therapeutic efficacy in humans (e.g., murine, lapine, porcine, canine or primate animals) may be employed.

Methods of Killing a Cancer Cell, an Infected Cell, or a Senescent Cell

Also provided herein are methods of killing a cancer cell (e.g., any of the exemplary types of cancer described herein or known in the art), an infected cell (e.g., a cell infected with any of the exemplary viruses described herein or known in the art), or a senescent cell (e.g., a senescent cancer cell, a senescent fibroblast, or a senescent endothelial cell) in a subject in need thereof (e.g., any of the exemplary subjects described herein or known in the art) that include administering to the subject a therapeutically effective amount of any of the single-chain chimeric polypeptides or any of the multi-chain chimeric polypeptides described herein or any of the compositions (e.g., pharmaceutical compositions) described herein. In some embodiments, the subject can further be administered a therapeutically effective amount of any of the of IgG1 antibody constructs described herein.

In some embodiments of these methods, the subject has been identified or diagnosed as having a cancer. Non-limiting examples of cancer include: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. Non-limiting examples of aging-related diseases and conditions include Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. Non-limiting examples of an infectious disease include infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Senescent Cells

Senescence is a form of irreversible growth arrest accompanied by phenotypic changes, resistance to apoptosis and activation of damage-sensing signaling pathways. Cellular senescence was first described in cultured human fibroblast cells that lost their ability to proliferate, reaching permanent arrest after about 50 population doublings (referred to as the Hayflick limit). Senescence is considered a stress response that can be induced by a wide range of intrinsic and extrinsic insults, including oxidative and genotoxic stress, DNA damage, telomere attrition, oncogenic activation, mitochondrial dysfunction, or chemotherapeutic agents.

Senescent cells remain metabolically active and can influence the tissue hemostasis, disease and aging through their secretory phenotype. Senescence is considered as a physiologic process and is important in promoting wound healing, tissue homeostasis, regeneration, and fibrosis regulation. For instance, transient induction of senescent cells is observed during would healing and contributes to wound resolution. Perhaps one of the most important roles of senescence is its role in tumor suppression. However, the accumulation of senescent cells also drives aging and aging-related diseases and conditions. The senescent phenotype also can trigger chronic inflammatory responses and consequently augment chronic inflammatory conditions to promote tumor growth. The connection between senescence and aging was initially based on observations that senescent cells accumulate in aged tissue. The use of transgenic models has enabled the detection of senescent cells systematically in many age-related pathologies. Strategies to selectively eliminate senescent cells have demonstrated that senescent cells can indeed play a causal role in aging and related pathologies.

Senescent cells display important and unique properties which include changes in morphology, chromatin organization, gene expression, and metabolism. There are several biochemical and functional properties associated with cellular senescence, such as (i) increased expression of p16 and p21, inhibitors of cyclin-dependent kinases, (ii) presence of senescence-associated β-galactosidase, a marker of lysosomal activity, (iii) appearance of senescence-associated heterochromatin foci and downregulation of lamin B1 levels, (iv) resistance to apoptosis caused by an increased expression of anti-apoptotic BCL-family protein, and (v) upregulation of CD26 (DPP4), CD36 (Scavenger receptor), forkhead box 4 (FOXO4), and secretory carrier membrane protein 4 (SCAMP4). Senescent cells also express an inflammatory signature, the so-called senescence-associated secretory phenotype (SASP). Through SASP, the senescent cells produce a wide range of inflammatory cytokines (IL-6, IL-8), growth factors (TGF-β), chemokines (CCL-2), and matrix metalloproteinases (MMP-3, MMP-9) that operate in a cell-autonomous manner to reinforce senescence (autocrine effects) and communicate with and modify the microenvironment (paracrine effects). SASP factors can contribute to tumor suppression by triggering senescence surveillance, an immune-mediated clearance of senescent cells. However, chronic inflammation is also a known driver of tumorigenesis, and accumulating evidence indicates that chronic SASP can also boost cancer and aging-related diseases.

The secretion profile of senescent cells is context dependent. For instance, the mitochondrial dysfunction-associated senescence (MiDAS), induced by different mitochondrial dysfunction in human fibroblasts, led to the appearance of a SASP that was deficient in IL-1-dependent inflammatory factors. A decrease in the NAD+/NADH ratio activated AMPK signaling which induced MiDAS through the activation of p53. As a result, p53 inhibited NF-1κB signaling which is a crucial inducer of pro-inflammatory SASP. In contrast, the cellular senescence caused by persistent DNA damage in human cells induced an inflammatory SASP, which was dependent on the activation of ataxia-telangiectasia mutated (ATM) kinase but not on that of p53. In particular, the expression and secretion levels of IL-6 and IL-8 were increased. It was also demonstrated that cellular senescence caused by the ectopic expression p16INK4a and p21CIP1 induced the senescent phenotype in human fibroblasts without an inflammatory SASP indicating that the growth arrest itself did not stimulate SASP.

One of the most defining characteristics of senescence is stable growth arrest. This is achieved by two important pathways, the p16/Rb and the p53/p21, both of which are central in tumor suppression. DNA damage results in: (1) high deposition of γH2Ax (histone coding gene) and 53BP1 (involved in DNA damage response) in chromatin: this leads to activation of a kinase cascade eventually resulting in p53 activation, and (2) activation of p16INK4a and ARF (both encoded by CDKN2A) and P15INK4b (encoded by CDKN2B): p53 induces transcription of cyclin-dependent kinase inhibitor (p21) and along with both p161NK4a and p15INK4b block genes for cell cycle progression (CDK4 and CDK6). This eventually leads to hypophosphorylation of Retinoblastoma protein (Rb) and cell cycle arrest at the G1 phase.

Selectively killing senescent cells has been shown to significantly improve the health span of mice in the context of normal aging and ameliorates the consequences of age-related disease or cancer therapy (Ovadya, *J Clin Invest.* 128(4):1247-1254, 2018). In nature, the senescent cells are normally removed by the innate immune cells. Induction of senescence not only prevents the potential proliferation and transformation of damaged/altered cells, but also favors tissue repair through the production of SASP factors that function as chemoattractants mainly for Natural Killer (NK) cells (such as IL-15 and CCL2) and macrophages (such as CFS-1 and CCL2). These innate immune cells mediate the immunosurveillance mechanism for eliminating stressed cells. Senescent cells usually up-regulate the NK-cell activating receptor NKG2D and DNAM-1 ligands, which belong to a family of stress-inducible ligands: an important component of the frontline immune defense against infectious diseases and malignancies. Upon receptor activation, NK cells can then specifically induce the death of senescent cells through their cytolytic machinery. A role for NK cells in the immune surveillance of senescent cells has been pointed out in liver fibrosis (Sagiv, Oncogene 32(15): 1971-1977, 2013), hepatocellular carcinoma (Iannello, *J Exp Med* 210(10): 2057-2069, 2013), multiple myeloma (Soriani, *Blood* 113(15): 3503-3511, 2009), and glioma cells stressed by dysfunction of the mevalonate pathway (Ciaglia, *Int J Cancer* 142(1): 176-190, 2018). Endometrial cells undergo acute cellular senescence and do not differentiate into decidual cells. The differentiated decidual cells secrete IL-15 and thereby recruit uterine NK cells to target and eliminate the undifferentiated senescent cells thus helping to re-model and rejuvenate the endometrium (Brighton, *Elife* 6: e31274, 2017). With a similar mechanism, during liver fibrosis, p53-expressing senescent liver satellite cells skewed the polarization of resident Kupfer macrophages and freshly infiltrated macrophages toward the pro-inflammatory M1 phenotype, which display senolytic activity. F4/80$^+$ macrophages have been shown to play a key role in the clearance of mouse uterine senescent cells to maintain postpartum uterine function.

Senescent cells recruit NK cells by mainly upregulating ligands to NKG2D (expressed on NK cells), chemokines, and other SASP factors. In vivo models of liver fibrosis have shown effective clearance of senescent cells by activated NK cells (Krizhanovsky, *Cell* 134(4): 657-667, 2008). Studies have described various models to study senescence including liver fibrosis (Krizhanovsky, *Cell* 134(4): 657-667, 2008), osteoarthritis (Xu, *J Gerontol A Biol Sci Med Sci* 72(6): 780-785, 2017), and Parkinson's disease (Chinta, *Cell Rep* 22(4): 930-940, 2018). Animal models for studying senescent cells are described in: Krizhanovsky, Cell 134(4): 657-667, 2008; Baker, *Nature* 479(7372): 232-236, 2011; Farr, *Nat Med* 23(9): 1072-1079, 2017; Bourgeois, *FEBS Lett* 592(12): 2083-2097, 2018; Xu, *Nat Med* 24(8): 1246-1256, 2018).

Methods of Increasing Glucose Consumption of an Immune Cell

Also provided herein are methods of increasing the glucose consumption of an immune cell that include: contacting an immune cell (e.g., any of the immune cells described herein) in a liquid culture medium (e.g., any of the liquid culture media described herein) including an effective amount of (i) a single-chain chimeric polypeptide comprising a first target-binding domain, a linker domain, and a second target-binding domain (e.g., any of the single-chain chimeric polypeptides described herein), and optionally (ii) an IgG1 antibody construct that includes at least one antigen-binding domain that binds specifically to the linker domain (e.g., any of the exemplary IgG1 antibody constructs described herein), under conditions that allow for glucose consumption in the immune cell, where the first target-binding domain and the second target-binding domain are each independently selected from the group of: a soluble interleukin or cytokine protein, an antigen-binding domain, a soluble interleukin or cytokine receptor, and ligands of co-stimulatory molecules.

Also provided herein are methods of increasing the glucose consumption of an immune cell that include: contacting an immune cell in a liquid culture medium comprising (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains (e.g., any of the multi-chain chimeric polypeptides described herein); and (2) an effective amount of an IgG1 antibody construct including at least one antigen-binding domain that binds specifically to the linker domain, under conditions that allow for glucose consumption in the immune cell.

In some embodiments of any of the methods described herein, the increase in glucose consumption is compared to the level of glucose consumption in a similar immune cell not contacted with the single-chain chimeric polypeptide or the multi-chain chimeric polypeptide, and optionally the IgG1 antibody construct that includes at least one antigen-binding domain that binds specifically to the soluble tissue factor domain.

Non-limiting assays that can be used to detect glucose consumption include, e.g., assays that include the use of radiolabeled 3-O-methylglucose or radiolabeled 2-deoxyglucose, or an enzymatic, fluorometric assay for detecting 2-deoxyglucose. Additional examples of assays that can be used to detect glucose consumption are described in, e.g., Yamamoto et al., *Curr. Protoc. Pharmacol.*, Chapter 12, Unit 12.14.1-22, December 2011; Zou et al., *J. Biochem. Biophys. Methods* 64(3):207-215, September 2005; and MacKrell et al., *Diabetes* p. 1-9, published online on Mar. 13, 2012.

In some embodiments of these methods, the liquid culture medium includes the single-chain chimeric polypeptide or the multi-chain chimeric polypeptide, and the IgG1 antibody construct. In some examples of these methods, the IgG1 antibody construct is a monoclonal IgG1 antibody, where both of the antigen-binding domains in the monoclonal IgG1 antibody bind specifically to the soluble tissue factor domain. In some examples of these methods, the IgG1 antibody construct is a bispecific IgG1 antibody, where one of the two antigen-binding domains in the bispecific IgG1 antibody binds specifically to the soluble tissue factor domain.

In some embodiments of any of the methods described herein, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days).

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the single-chain chimeric polypeptide or the multi-chain chimeric polypeptide, and the IgG1 antibody construct at a molar ratio of about 0.5:1 to about 2:1 (e.g., about 0.8:1 to about 1.2:1).

In some embodiments of these methods, the immune cell is selected from the group of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments of any of the methods described herein, the immune cell is a T-cell or a natural killer cell.

In some examples of these methods, the immune cell was previously obtained from a subject. Some embodiments of these methods further include obtaining the immune cell from the subject prior to the contacting step. In some embodiments of these methods, the immune cell has previously been genetically modified to express a chimeric antigen receptor or a recombinant T-cell receptor. Some embodiments of these methods further include, after the contacting step, introducing into the immune cell a nucleic acid encoding a chimeric antigen-receptor or a recombinant T-cell receptor. Some embodiments of these methods further include, before the contacting step, introducing into the immune cell a nucleic acid encoding a chimeric antigen-receptor or a recombinant T-cell receptor. Some embodiments of these methods further include, after the contacting step, isolating the immune cell. Some embodiments of these methods further include, after the contacting step, administering the immune cell to a subject in need thereof.

In some examples of these methods, the subject has been identified or diagnosed as having an age-related disease or condition. In some examples of these methods, the age-related disease or condition is selected from the group of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MD), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Oxidative Phosphorylation of an Immune Cell

Also provided herein are methods of increasing the oxidative phosphorylation of an immune cell that include: contacting an immune cell (e.g., any of the immune cells described herein) in a liquid culture medium (e.g., any of the liquid culture media described herein) including an effective amount of (i) a single-chain chimeric polypeptide comprising a first target-binding domain, a linker domain, and a second target-binding domain (e.g., any of the exemplary single-chain chimeric polypeptides described herein), and optionally (ii) an IgG1 antibody construct that comprises at least one antigen-binding domain that binds specifically to the linker domain (e.g., any of the exemplary IgG1 antibody constructs described herein), under conditions that allow for oxidative phosphorylation in the immune cell, where the first target-binding domain and the second target-binding domain are each independently selected from the group of: a soluble interleukin or cytokine protein, an antigen-binding domain, a soluble interleukin or cytokine receptor, and ligands of co-stimulatory molecules.

Also provided herein are methods of increasing the oxidative phosphorylation of an immune cell that include: contacting an immune cell (e.g., any of the immune cells described herein) in a liquid culture medium (e.g., any of the liquid culture media described herein) comprising (1) an effective amount of a multi-chain chimeric polypeptide including: (a) a first chimeric polypeptide comprising: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains (e.g., any of the multi-chain chimeric polypeptides described herein); and (2) an effective amount of an IgG1 antibody construct including at least one antigen-binding domain that binds specifically to the linker domain (e.g., any of the exemplary IgG1 antibody constructs described herein), under conditions that allow for oxidative phosphorylation in the immune cell.

In some embodiments of any of the methods described herein, the increase in oxidative phosphorylation is compared to the level of oxidative phosphorylation in a similar immune cell not contacted with the single-chain chimeric polypeptide of the multi-chain chimeric polypeptide, and optionally the IgG1 antibody construct that includes at least one antigen-binding domain that binds specifically to the soluble tissue factor domain.

Non-limiting assays that can be used to detect oxidative phosphorylation include, e.g., immunofluorescent assays and colorimetric assays. A non-limiting commercial assay that can be used to determine the level of oxidative phosphorylation is MitoTox™ Complete OXPHOS Activity Assay (Abcam). Additional examples of assays that can be used to detect oxidative phosphorylation are described in, e.g., Chance et al., Nature 175:1120-1121, 1955; Pullman et al., *Science* 123(3208):1105-1107, 1956; Van Bergen et al., *Mitochondrion* 15:24-33, 2014; and Rocha et al., Sci. Rep. 5:15037, 2015.

In some embodiments of these methods, the liquid culture medium includes the single-chain chimeric polypeptide or the multi-chain chimeric polypeptide, and the IgG1 antibody construct. In some examples of these methods, the IgG1 antibody construct is a monoclonal IgG1 antibody, where both of the antigen-binding domains in the monoclonal IgG1 antibody bind specifically to the soluble tissue factor domain. In some examples of these methods, the IgG1 antibody construct is a bispecific IgG1 antibody, where one of the two antigen-binding domains in the bispecific IgG1 antibody binds specifically to the soluble tissue factor domain.

In some embodiments of any of the methods described herein, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days).

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the single-chain chimeric polypeptide or the multi-chain chimeric polypeptide, and the IgG1 antibody construct at a molar ratio of about 0.5:1 to about 2:1 (e.g., about 0.8:1 to about 1.2:1). In some embodiments of these methods, the immune cell is selected from the group of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments of any of the methods described herein, the immune cell is a T-cell or a natural killer cell.

In some examples of these methods, the immune cell was previously obtained from a subject. Some embodiments of these methods further include obtaining the immune cell from the subject prior to the contacting step. In some embodiments of these methods, the immune cell has previously been genetically modified to express a chimeric antigen receptor or a recombinant T-cell receptor. Some embodiments of these methods further include, after the contacting step, introducing into the immune cell a nucleic acid encoding a chimeric antigen-receptor or a recombinant T-cell receptor. Some embodiments of these methods further include, before the contacting step, introducing into the immune cell a nucleic acid encoding a chimeric antigen-receptor or a recombinant T-cell receptor. Some embodiments of these methods further include, after the contacting step, isolating the immune cell. Some embodiments of these methods further include, after the contacting step, administering the immune cell to a subject in need thereof.

In some examples of these methods, the subject has been identified or diagnosed as having an age-related disease or condition. In some examples of these methods, the age-related disease or condition is selected from the group of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma. In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Aerobic Glycolysis of an Immune Cell

Also provided herein are methods of increasing the aerobic glycolysis of an immune cell that include: contacting an immune cell (e.g., any of the immune cells described herein) in a liquid culture medium (e.g., any of the liquid culture media described herein) including an effective amount of (i) a single-chain chimeric polypeptide including a first target-binding domain, a linker domain, and a second target-binding domain (e.g., any of the single-chain chimeric polypeptides described herein), and optionally (ii) an IgG1 antibody construct that includes at least one antigen-binding domain that binds specifically to the linker domain (e.g., any of the exemplary IgG1 antibody constructs described herein), under conditions that allow for aerobic glycolysis in the immune cell, where the first target-binding domain and the second target-binding domain are each independently selected from the group of: a soluble interleukin or cytokine protein, an antigen-binding domain, a soluble interleukin or cytokine receptor, and ligands of co-stimulatory molecules.

Also provided herein are methods of increasing the aerobic glycolysis of an immune cell that include: contacting an immune cell (e.g., any of the immune cells described herein) in a liquid culture medium (e.g., any of the liquid culture media described herein) including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains (e.g., any of the multi-chain chimeric polypeptides described herein); and (2) an effective amount of an IgG1 antibody construct including at least one antigen-binding domain that binds specifically to the linker domain (e.g., any of the exemplary IgG1 antibody constructs described herein), under conditions that allow for aerobic glycolysis in the immune cell.

In some embodiments of any of the methods described herein, the increase in aerobic glycolysis is compared to the level of aerobic glycolysis in a similar immune cell not contacted with the single-chain chimeric polypeptide or the multi-chain chimeric polypeptide, and optionally the IgG1 antibody construct that includes at least one antigen-binding domain that binds specifically to the soluble tissue factor domain.

Non-limiting assays that can be used to detect aerobic glycolysis include, e.g., detection of ATP and/or $CO_2$ production, e.g., using gas chromatography/mass spectrometry, or extracellular acidification rate. Additional examples of assays that can be used to detect aerobic glycolysis are described in, e.g., Zhang et al., Bone 114:150-160, 2018; Zhao et al., *J. Breast Cancer* 21(2):112-123, 2018; Li et al., *Cell Comm. Signal.* 16(1):26, 2018; Cai et al., *J. Exp. Clin. Cancer Res.* 37(1):104, 2018; and Zhang et al., *Oncol. Rep.* 40(2):1156-1164, 2018.

In some embodiments of these methods, the liquid culture medium includes the single-chain chimeric polypeptide or the multi-chain chimeric polypeptide, and the IgG1 antibody construct. In some examples of these methods, the IgG1 antibody construct is a monoclonal IgG1 antibody, where both of the antigen-binding domains in the monoclonal IgG1 antibody bind specifically to the soluble tissue factor domain. In some examples of these methods, the IgG1 antibody construct is a bispecific IgG1 antibody, where one of the two antigen-binding domains in the bispecific IgG1 antibody binds specifically to the soluble tissue factor domain.

In some embodiments of any of the methods described herein, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days).

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the single-chain chimeric polypeptide or the multi-chain chimeric polypeptide, and the IgG1 antibody construct at a molar ratio of about 0.5:1 to about 2:1 (e.g., about 0.8:1 to about 1.2:1).

In some embodiments of these methods, the immune cell is selected from the group of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments of any of the methods described herein, the immune cell is a T-cell or a natural killer cell.

In some examples of these methods, the immune cell was previously obtained from a subject. Some embodiments of these methods further include obtaining the immune cell from the subject prior to the contacting step. In some embodiments of these methods, the immune cell has previously been genetically modified to express a chimeric antigen receptor or a recombinant T-cell receptor. Some embodiments of these methods further include, after the contacting step, introducing into the immune cell a nucleic acid encoding a chimeric antigen-receptor or a recombinant T-cell receptor. Some embodiments of these methods further include, before the contacting step, introducing into the immune cell a nucleic acid encoding a chimeric antigen-receptor or a recombinant T-cell receptor. Some embodiments of these methods further include, after the contacting step, isolating the immune cell. Some embodiments of these methods further include, after the contacting step, administering the immune cell to a subject in need thereof.

In some examples of these methods, the subject has been identified or diagnosed as having an age-related disease or condition. In some examples of these methods, the age-related disease or condition is selected from the group of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MD), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus. Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Extracellular Acidification Rate (ECAR) of an Immune Cell

Also provided herein are method of increasing the extracellular acidification rate (ECAR) of an immune cell that include: contacting an immune cell (e.g., any of the immune cells described herein) in a liquid culture medium (e.g., any of the liquid culture media described herein) including an effective amount of (i) a single-chain chimeric polypeptide including a first target-binding domain, a linker domain, and a second target-binding domain (e.g., any of the single-chain chimeric polypeptides described herein), and optionally (ii) an IgG1 antibody construct that includes at least one antigen-binding domain that binds specifically to the linker domain (e.g., any of the exemplary IgG1 antibody constructs described herein), under conditions that allow for extracellular acidification by the immune cell, where the first target-binding domain and the second target-binding domain are each independently selected from the group of: a soluble interleukin or cytokine protein, an antigen-binding domain, a soluble interleukin or cytokine receptor, and ligands of co-stimulatory molecules.

Also provided herein are methods of increasing the extracellular acidification rate (ECAR) of an immune cell that include: contacting an immune cell (e.g., any of the immune cells described herein) in a liquid culture medium (e.g., any of the liquid culture media described herein) including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains (e.g., any of the multi-chain chimeric polypeptides described herein); and (2) an effective amount of an IgG1 antibody construct including at least one antigen-binding domain that binds specifically to the linker domain (e.g., any of the exemplary IgG1 antibody constructs described herein), under conditions that allow for extracellular acidification by the immune cell.

In some embodiments of any of the methods described herein, the increase in extracellular acidification rate (ECAR) is compared to the level of extracellular acidification rate (ECAR) in a similar immune cell not contacted with the single-chain chimeric polypeptide or the multi-chain chimeric polypeptide, and optionally the IgG1 antibody construct that includes at least one antigen-binding domain that binds specifically to the soluble tissue factor domain.

Non-limiting commercial assays that can be used to detect extracellular acidification rate (ECAR) include, e.g., Glycolysis Assay (Extracellular Acidification Kit) (ab197244 or ab197245) (Abcam), MITO-ID® Extracellular pH Sensor Kit (ENZ-51048) (Enzo Life Sciences), and pH-Xtra™-Glycolysis Assay (Extracellular Acidification). Additional examples of assays that can be used to detect extracellular acidification rate (ECAR) are described in, e.g., Owicki et al., *Biosens. Bioelectron.* 7(4):255-272, 1992; Hynes et al., *Analytical Biochem.* 390(1):21-28, 2009; Trevani et al., *J. Immunol.* 162(8):4849-4857, 1999; and Mookerjee et al., *J. Vis. Exp.* 106:53464, 2015.

In some embodiments of these methods, the liquid culture medium includes the single-chain chimeric polypeptide or the multi-chain chimeric polypeptide, and the IgG1 antibody construct. In some examples of these methods, the IgG1 antibody construct is a monoclonal IgG1 antibody, where both of the antigen-binding domains in the monoclonal IgG1 antibody bind specifically to the soluble tissue factor domain. In some examples of these methods, the IgG1 antibody construct is a bispecific IgG1 antibody, where one of the two antigen-binding domains in the bispecific IgG1 antibody binds specifically to the soluble tissue factor domain.

In some embodiments of any of the methods described herein, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days).

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the single-chain chimeric polypeptide or the multi-chain chimeric polypeptide, and the IgG1 antibody construct at a molar ratio of about 0.5:1 to about 2:1 (e.g., about 0.8:1 to about 1.2:1).

In some embodiments of these methods, the immune cell is selected from the group of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a CD8+ T cell, a CD4+ T cell, a natural killer T cell, a mast cell, a macrophage, a neutrophil, a dendritic cell, a basophil, an eosinophil, and a natural killer cell. In some embodiments of any of the methods described herein, the immune cell is a T-cell or a natural killer cell.

In some examples of these methods, the immune cell was previously obtained from a subject. Some embodiments of these methods further include obtaining the immune cell from the subject prior to the contacting step. In some embodiments of these methods, the immune cell has previously been genetically modified to express a chimeric antigen receptor or a recombinant T-cell receptor. Some embodiments of these methods further include, after the contacting step, introducing into the immune cell a nucleic acid encoding a chimeric antigen-receptor or a recombinant T-cell receptor. Some embodiments of these methods further include, before the contacting step, introducing into the immune cell a nucleic acid encoding a chimeric antigen-receptor or a recombinant T-cell receptor. Some embodiments of these methods further include, after the contacting step, isolating the immune cell. Some embodiments of these methods further include, after the contacting step, administering the immune cell to a subject in need thereof.

In some examples of these methods, the subject has been identified or diagnosed as having an age-related disease or condition. In some examples of these methods, the age-related disease or condition is selected from the group of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CMIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Methods of Increasing Mitochondrial Oxygen Consumption Rate of an Immune Cell

Also provided herein are methods of increasing the mitochondrial oxygen consumption rate of an immune cell that include: contacting an immune cell (e.g., any of the immune cells described herein) in a liquid culture medium (e.g., any of the liquid culture media described herein) including an effective amount of (i) a single-chain chimeric polypeptide comprising a first target-binding domain, a linker domain, and a second target-binding domain (e.g., any of the single-chain chimeric polypeptides described herein), and optionally (ii) an IgG1 antibody construct that includes at least one antigen-binding domain that binds specifically to the linker domain (e.g., any of the exemplary IgG1 antibody constructs described herein), under conditions that allow for mitochondrial oxygen consumption rate by the immune cell, where the first target-binding domain and the second target-binding domain are each independently selected from the group of: a soluble interleukin or cytokine protein, an antigen-binding domain, a soluble interleukin or cytokine receptor, and ligands of co-stimulatory molecules.

Also provided herein are methods of increasing the mitochondrial oxygen consumption rate of an immune cell that include: contacting an immune cell (e.g., any of the immune cells described herein) in a liquid culture medium (e.g., any of the liquid culture media described herein) including (1) an effective amount of a multi-chain chimeric polypeptide including: (a) a first chimeric polypeptide including: (i) a first target-binding domain; (ii) a linker domain; and (iii) a first domain of a pair of affinity domains; (b) a second chimeric polypeptide including: (i) a second domain of a pair of affinity domains; and (ii) a second target-binding domain, where the first chimeric polypeptide and the second chimeric polypeptide associate through the binding of the first domain and the second domain of the pair of affinity domains (e.g., any of the multi-chain chimeric polypeptides described herein); and (2) an effective amount of an IgG1 antibody construct including at least one antigen-binding domain that binds specifically to the linker domain (e.g., any of the exemplary IgG1 antibody constructs described herein), under conditions that allow for mitochondrial oxygen consumption rate by the immune cell.

In some embodiments of any of the methods described herein, the increase in mitochondrial oxygen consumption rate is compared to the level of mitochondrial oxygen consumption rate in a similar immune cell not contacted with the single-chain chimeric polypeptide or the multi-chain chimeric polypeptide, and optionally the IgG1 antibody construct that includes at least one antigen-binding domain that binds specifically to the soluble tissue factor domain.

Non-limiting commercial assays that can be used to detect mitochondrial oxygen consumption rate include, e.g., assays that include the use of an electrode or a commercially available kit, e.g., Oxygen Consumption Rate Assay Kit (Cayman Chemical), the Seahorse assay (as described in Sakamuri et al., *Geroscience* 40(3):347-356, 2018). Additional examples of assays that can be used to detect mitochondrial oxygen consumption rate are described in, e.g., Li et al., *Mitochondrial Disorders*, pp. 63-72, December 2011; Kumagi et al., *Synapse* e22067, August 2018; Takahashi et al., *J. Physiol. Sci.* 67(6):731-737, 2017; and Iihoshi et al., *Toxicol. Lett.* 277:109-114, 2017.

In some embodiments of these methods, the liquid culture medium includes the single-chain chimeric polypeptide or the multi-chain chimeric polypeptide, and the IgG1 antibody construct. In some examples of these methods, the IgG1 antibody construct is a monoclonal IgG1 antibody, where both of the antigen-binding domains in the monoclonal IgG1 antibody bind specifically to the soluble tissue factor domain. In some examples of these methods, the IgG1 antibody construct is a bispecific IgG1 antibody, where one of the two antigen-binding domains in the bispecific IgG1 antibody binds specifically to the soluble tissue factor domain.

In some embodiments of any of the methods described herein, the contacting step is performed for a period of about 2 hours to about 20 days (e.g., about 2 hours to about 18 days, about 2 hours to about 16 days, about 2 hours to about 14 days, about 2 hours to about 12 days, about 2 hours to about 10 days, about 2 hours to about 8 days, about 2 hours to about 7 days, about 2 hours to about 6 days, about 2 hours to about 5 days, about 2 hours to about 4 days, about 2 hours to about 3 days, about 2 hours to about 2 days, about 2 hours to about 1 day, about 6 hours to about 18 days, about 6 hours to about 16 days, about 6 hours to about 14 days, about 6 hours to about 12 days, about 6 hours to about 10 days, about 6 hours to about 8 days, about 6 hours to about 7 days, about 6 hours to about 6 days, about 6 hours to about 5 days, about 6 hours to about 4 days, about 6 hours to about 3 days, about 6 hours to about 2 days, about 6 hours to about 1 day, about 12 hours to about 18 days, about 12 hours to about 16 days, about 12 hours to about 14 days, about 12 hours to about 12 days, about 12 hours to about 10 days, about 12 hours to about 8 days, about 12 hours to about 7 days, about 12 hours to about 6 days, about 12 hours to about 5 days, about 12 hours to about 4 days, about 12 hours to about 3 days, about 12 hours to about 2 days, about 12 hours to about 1 day, about 1 day to about 18 days, about 1 day to about 16 days, about 1 day to about 15 days, about 1 day to about 14 days, about 1 day to about 12 days, about 1 day to about 10 days, about 1 day to about 8 days, about 1 day to about 7 days, about 1 day to about 6 days, about 1 day to about 5 days, about 1 day to about 4 days, about 1 day to about 3 days, about 1 day to about 2 days, about 2 days to about 18 days, about 2 days to about 16 days, about 2 days to about 14 days, about 2 days to about 12 days, about 2 days to about 10 days, about 2 days to about 8 days, about 2 days to about 7 days, about 2 days to about 6 days, about 2 days to about 5 days, about 2 days to about 4 days, about 2 days to about 3 days, about 3 days to about 18 days, about 3 days to about 16 days, about 3 days to about 14 days, about 3 days to about 12 days, about 3 days to about 10 days, about 3 days to about 8 days, about 3 days to about 7 days, about 3 days to about 6 days, about 3 days to about 5 days, about 3 days to about 4 days, about 4 days to about 18 days, about 4 days to about 16 days, about 4 days to about 14 days, about 4 days to about 12 days, about 4 days to about 10 days, about 4 days to about 8 days, about 4 days to about 7 days, about 4 days to about 6 days, about 4 days to about 5 days, about 5 days to about 18 days, about 5 days to about 16 days, about 5 days to about 14 days, about 5 days to about 12 days, about 5 days to about 10 days, about 5 days to about 8 days, about 5 days to about 7 days, about 5 days to about 6 days, about 6 days to about 18 days, about 6 days to about 16 days, about 6 days to about 14 days, about 6 days to about 12 days, about 6 days to about 10 days, about 6 days to about 8 days, about 6 days to about 7 days, about 7 days to about 18 days, about 7 days to about 16 days, about 7 days to about 14 days, about 7 days to about 12 days, about 7 days to about 10 days, about 7 days to about 8 days, about 8 days to about 18 days, about 8 days to about 16 days, about 8 days to about 14 days, about 8 days to about 12 days, about 8 days to about 10 days, about 9 days to about 18 days, about 9 days to about 16 days, about 9 days to about 14 days, about 9 days to about 12 days, about 12 days to about 18 days, about 12 days to about 16 days, about 12 days to about 14 days, about 14 days to about 18 days, about 14 days to about 16 days, or about 16 days to about 18 days).

In some embodiments of these methods, the liquid culture medium can be a serum-free liquid culture medium. In some embodiments of these methods, the liquid culture medium can be a chemically-defined liquid culture medium. In other examples of these methods, the liquid culture medium includes serum.

In some examples of these methods, the liquid culture medium includes the single-chain chimeric polypeptide or the multi-chain chimeric polypeptide, and the IgG1 antibody construct at a molar ratio of about 0.5:1 to about 2:1 (e.g., about 0.8:1 to about 1.2:1).

In some embodiments of these methods, the immune cell is selected from the group of: an immature thymocyte, a peripheral blood lymphocyte, a naïve T cell, a pluripotent Th cell precursor, a lymphoid progenitor cell, a Treg cell, a memory T cell, a Th17 cell, a Th22 cell, a Th9 cell, a Th2 cell, a Th1 cell, a Th3 cell, γδ T cell, an αβ T cell, a tumor-infiltrating T cell, a $CD8^+$ T cell, a $CD4^+$ T cell, a natural killer T cell, a mast cell, a macrophage, a neutrophil, a dendritic cell, a basophil, an eosinophil, and a natural killer cell. In some embodiments of any of the methods described herein, the immune cell is a T-cell or a natural killer cell.

In some examples of these methods, the immune cell was previously obtained from a subject. Some embodiments of these methods further include obtaining the immune cell from the subject prior to the contacting step. In some embodiments of these methods, the immune cell has previously been genetically modified to express a chimeric antigen receptor or a recombinant T-cell receptor. Some embodiments of these methods further include, after the contacting step, introducing into the immune cell a nucleic acid encoding a chimeric antigen-receptor or a recombinant T-cell receptor. Some embodiments of these methods further include, before the contacting step, introducing into the immune cell a nucleic acid encoding a chimeric antigen-receptor or a recombinant T-cell receptor. Some embodiments of these methods further include, after the contacting step, isolating the immune cell. Some embodiments of these methods further include, after the contacting step, administering the immune cell to a subject in need thereof.

In some examples of these methods, the subject has been identified or diagnosed as having an age-related disease or condition. In some examples of these methods, the age-related disease or condition is selected from the group of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction. In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MD), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus. Also provided herein are activated immune cells produced by any of these methods. Also provided herein are pharmaceutical compositions that include any of the activated immune cells produced by any of these methods. Also provided herein are kits that include any of the pharmaceutical compositions described herein produced by any of the methods described herein.

Also provided herein are methods of killing a cancer cell, an infected cell, or a senescent cell in a subject in need thereof that include administering to the subject a therapeutically effective amount of any of the activated immune cells described herein produced by any of the methods described herein or any of the pharmaceutical compositions described herein.

In some examples of these methods, the subject has been identified or diagnosed as having a cancer. In some examples of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some examples of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Also provided herein are methods of treating a subject in need thereof that include administering to the subject a therapeutically effective amount of any of the activated immune cells described herein produced by any of the methods described herein or any of the pharmaceutical compositions described herein. In some examples of these methods, the subject has been identified or diagnosed as having a cancer. In some embodiments of these methods, the cancer is selected from the group of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

In some embodiments of these methods, the subject has been identified or diagnosed as having an aging-related disease or condition. In some examples of these methods, the aging-related disease or condition is selected from the group of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

In some examples of these methods, the subject has been diagnosed or identified as having an infectious disease. In some examples of these methods, the infectious disease is infection with human immunodeficiency virus, cytomegalovirus, adenovirus, coronavirus, rhinovirus, rotavirus, smallpox, herpes simplex virus, hepatitis B virus, hepatitis A virus, hepatitis C virus, papillomavirus, or influenza virus.

Additional Therapeutic Agents

Some embodiments of any of the methods described herein can further include administering to a subject (e.g., any of the subjects described herein) a therapeutically effective amount of one or more additional therapeutic agents. The one or more additional therapeutic agents can be administered to the subject at substantially the same time as a single-chain chimeric polypeptide (e.g., any of the single-chain chimeric polypeptides described herein), multi-chain chimeric polypeptides (e.g., any of the multi-chain chimeric polypeptides described herein), or an activated immune cell (e.g., an activated NK cell or an activated T cell) (e.g., administered as a single formulation or two or more formulations to the subject). In some embodiments, one or more additional therapeutic agents can be administered to the subject prior to administration of a single-chain chimeric polypeptide (e.g., any of the single-chain chimeric polypeptides described herein), multi-chain chimeric polypeptides (e.g., any of the multi-chain chimeric polypeptides described herein), or an activated immune cell (e.g., an activated NK cell or an activated T cell). In some embodiments, one or more additional therapeutic agents can be administered to the subject after administration of a single-chain chimeric polypeptide (e.g., any of the single-chain chimeric polypeptides described herein), multi-chain chimeric polypeptides (e.g., any of the multi-chain chimeric polypeptides described herein), or an activated immune cell (e.g., an activated NK cell or an activated T cell) to the subject.

Non-limiting examples of additional therapeutic agents include: anti-cancer drugs, activating receptor agonists, immune checkpoint inhibitors, agents for blocking HLA-specific inhibitory receptors, Glucogen Synthase Kinase (GSK) 3 inhibitors, and antibodies.

Non-limiting examples of anticancer drugs include anti-metabolic drugs (e.g., 5-fluorouracil (5-FU), 6-mercaptopurine (6-MP), capecitabine, cytarabine, floxuridine, fludarabine, gemcitabine, hydroxycarbamide, methotrexate, 6-thioguanine, cladribine, nelarabine, pentostatin, or pemetrexed), plant alkaloids (e.g., vinblastine, vincristine, vindesine, camptothecin, 9-methoxycamptothecin, coronaridine, taxol, naucleaorals, diprenylated indole alkaloid, montamine, schischkiniin, protoberberine, berberine, sanguinarine, chelerythrine, chelidonine, liriodenine, clivorine, β-carboline, antofine, tylophorine, cryptolepine, neocryptolepine, corynoline, sampangine, carbazole, crinamine, montanine, ellipticine, paclitaxel, docetaxel, etoposide, tenisopide, irinotecan, topotecan, or acridone alkaloids), proteasome inhibitors (e.g., lactacystin, disulfiram, epigallocatechin-3-gallate, marizomib (salinosporamide A), oprozomib (ONX-0912), delanzomib (CEP-18770), epoxomicin, MG132, beta-hydroxy beta-methylbutyrate, bortezomib, carfilzomib, or ixazomib), antitumor antibiotics (e.g., doxorubicin, daunorubicin, epirubicin, mitoxantrone, idarubicin, actinomycin, plicamycin, mitomycin, or bleomycin), histone deacetylase inhibitors (e.g., vorinostat, panobinostat, belinostat, givinostat, abexinostat, depsipeptide, entinostat, phenyl butyrate, valproic acid, trichostatin A, dacinostat, mocetinostat, pracinostat, nicotinamide, cambinol, tenovin 1, tenovin 6, sirtinol, ricolinostat, tefinostat, kevetrin, quisinostat, resminostat, tacedinaline, chidamide, or selisistat), tyrosine kinase inhibitors (e.g., axitinib, dasatinib, encorafinib, erlotinib, imatinib, nilotinib, pazopanib, and sunitinib), and chemotherapeutic agents (e.g., all-trans retinoic acid, azacitidine, azathioprine, doxifluridine, epothilone, hydroxyurea, imatinib, teniposide, tioguanine, valrubicin, vemurafenib, and lenalidomide). Additional examples of chemotherapeutic agents include alkylating agents, e.g., mechlorethamine, cyclophosphamide, chlorambucil, melphalan, ifosfamide, thiotepa, hexamethylmelamine, busulfan, altretamine, procarbazine, dacarbazine, temozolomide, carmustine, lumustine, streptozocin, carboplatin, cisplatin, and oxaliplatin.

Non-limiting examples of activating receptor agonists include any agonists for activating receptors which activate and enhance the cytotoxicity of NK cells, including anti-CD16 antibodies (e.g., anti-CD16/CD30 bispecific monoclonal antibody (BiMAb)) and Fc-based fusion proteins. Non-limiting examples of checkpoint inhibitors include anti-PD-1 antibodies (e.g., MEDIO680), anti-PD-L1 antibodies (e.g., BCD-135, BGB-A333, CBT-502, CK-301, CS1001, FAZ053, KN035, MDX-1105, MSB2311, SHR-1316, anti-PD-L1/CTLA-4 bispecific antibody KN046, anti-PD-L1/TGFβRII fusion protein M7824, anti-PD-L1/TIM-3 bispecific antibody LY3415244, atezolizumab, or avelumab), anti-TIM3 antibodies (e.g., TSR-022, Sym023, or MBG453) and anti-CTLA-4 antibodies (e.g., AGEN1884, MK-1308, or an anti-CTLA-4/OX40 bispecific antibody ATOR-1015). Non-limiting examples of agents for blocking HLA-specific inhibitory receptors include monalizumab (e.g., an anti-HLA-E NKG2A inhibitory receptor monoclonal antibody). Non-limiting examples of GSK3 inhibitor include tideglusib or CHIR99021. Non-limiting examples of antibodies that can be used as additional therapeutic agents include anti-CD26 antibodies (e.g., YS110), anti-CD36 antibodies, and any other antibody or antibody construct that can bind to and activate an Fc receptor (e.g., CD16) on a NK cell. In some embodiments, an additional therapeutic agent can be insulin or metformin.

EXAMPLES

The invention is further described in the following examples, which do not limit the scope of the invention described in the claims.

Example 1. Construction of Exemplary Multi-Chain Chimeric Polypeptides and Evaluation of Properties Thereof Two multi-chain chimeric polypeptides were generated and their properties were evaluated. Each of the two multi-chain chimeric polypeptides included a first chimeric polypeptide that included a soluble tissue factor domain covalently linked a first target-binding domain and a first domain of an affinity pair of domains. The second chimeric polypeptide in each of the two multi-chain chimeric polypeptides included a second domain of the affinity pair of domains, and a second target-binding domain.

Description of Logic Underlying Construction of Multi-Chain Chimeric Polypeptides Tissue Factor (TF) is a stable, transmembrane protein containing 236 amino acid residues. The truncated, recombinant 219-amino-acid extracellular domain of tissue factor is soluble and is known to be expressed at high levels in bacteria or mammalian cells. Without wishing to be bound to a particular theory, the applicants speculated that the 219-aa tissue factor could be used as a connector linker for creation of unique multi-chain chimeric polypeptides.

First chimeric polypeptides including soluble tissue factor domain were produced at high levels by CHO-K1 cells grown in fermentation broth. These first chimeric polypeptides were purified by an anti-tissue factor monoclonal antibody (mAb) coupled on a solid matrix. Notably, tissue factor contains binding sites for FVIIa and FX. The catalytic activity of the tissue factor-FVIIa complex for FX is approximately 1 million-fold lower when tissue factor is not anchored to a phospholipid bilayer. Thus, without wishing to be bound to a particular theory, applicants speculated that using the 219-aa extracellular domain of tissue factor without the transmembrane in construction of the first chimeric polypeptides may eliminate the pro-coagulation activity of tissue factor in the first chimeric polypeptides. In an effort to further reduce or eliminate the pro-coagulation activity of the 219-aa tissue factor, select mutations in tissue factor can be made, specifically at seven amino acid residues that are known to contribute to binding energy of the FVIIa binding site.

Characterization of Binding Interactions for Described Chimeric Polypeptides

To determine if the first and second chimeric polypeptides bind to each other to form multi-chain chimeric polypeptides, in vitro binding assays were performed. To determine if the first chimeric polypeptide comprising soluble tissue factor domain are recognized and bound by anti-TF mAb, in vitro binding assays were performed. Notably, the data indicated that the mutated tissue factor proteins are still recognized and selectively bound by the anti-TF mAb which is known to bind to the FX binding site on tissue factor. To determine if the first chimeric polypeptides comprising soluble tissue factor domain covalently linked to scFvs or cytokines (see FIG. 1 and FIG. 2) possess functional scFvs or cytokines, in vitro binding assays were performed. The data from the aforementioned assays were consistent with the purified first chimeric polypeptides having the expected biological activities (e.g., scFvs selectively bind expected target antigens or cytokines selectively bind expected receptors or binding proteins).

In addition, experiments performed using the two multi-chain chimeric polypeptides including a first and second chimeric polypeptide bound to each other demonstrate the expected target binding activity (e.g., the multi-chain chimeric polypeptide binds specifically to the target specifically recognized by the first target-binding domain and the target specifically recognized by the second target-binding domain).

Based on the aforementioned results, applicants concluded that the soluble tissue factor connecter linker provided or enabled appropriate display of the polypeptides encoding either scFvs, interleukins, cytokines, interleukin receptors, or cytokine receptors in three-dimensional space relative to soluble tissue factor domain and relative to one another such that each retained expected biological properties (and activities).

When both the first and second chimeric polypeptides were co-expressed, the heterodimeric complexes were secreted into the fermentation broths at high levels. The complexes were captured and readily purified by anti-TF mAb conjugated to a solid matrix using affinity chromatography. The first and second target-binding domains of these multi-chain chimeric polypeptides retained their expected biological activities as assayed by in vitro binding assays. Thus, the assembly of the multi-chain chimeric polypeptides provides the appropriate spatial display and folding of the domains for biological activities. Importantly, the spatial arrangement of the multi-chain chimeric polypeptides does not interfere with the FX binding site on tissue factor which enables the use of anti-TF mAb for affinity purification.

Characterization of Stability for Described Chimeric Polypeptides

Both purified multi-chain chimeric polypeptides are expected to be stable. These multi-chain chimeric polypeptides are structurally intact and expected to be fully biologically active when they are incubated in human serum at 37° C. for 72 hours.

Characterization of Propensity of Described Chimeric Polypeptides to Aggregate

Both purified multi-chain chimeric polypeptides are expected not to form aggregates when stored at 4° C. in PBS.

Characterization of Viscosity of Described Chimeric Polypeptides

Compositions including the multi-chain chimeric polypeptides are not expected to have any viscosity issues when formulated at a concentration as high as 50 mg/mL in PBS.

Discussion of Multi-Chain Chimeric Polypeptide Platform for Use in Selectively Binding Clinically Relevant Targets The data from our studies show that our platform technologies can be utilized to create molecules that could be fused to target-binding domains derived from antibodies, in any formats as discussed above, adhesion molecules, receptors, cytokines, chemokines etc. With the appropriate target-binding domain, the resulting multi-chain chimeric polypeptides could promote conjugation of various immune effector cells and mediate destruction of target cells, including cancer cells, virally-infected cells, or senescent cells. Other domains in the multi-chain chimeric polypeptides stimulate, activate, and attract the immune system for enhancing cytotoxicity of effector cells for the targeted cells.

Example 2: Creation of an IL-7/IL-15RαSu DNA Construct

In a non-limiting example, an IL-7/IL-15RαSu DNA construct was created (see FIG. 1). The human IL-7 sequence, human IL-15RαSu sequence, human IL-15 sequence, and human tissue factor 219 sequence were obtained from the UniProt website and DNA for these sequences was synthesized by Genewiz. A DNA construct was made linking the IL-7 sequence to the IL-15RαSu sequence. The final IL-7/IL-15RαSu DNA construct sequence was synthesized by Genewiz.

Example 3: Creation of an IL-21/TF/IL-15 DNA Construct

In a non-limiting example, an IL-21/TF/IL-15 construct was made (see FIG. 2) by linking the IL-21 sequence to the N-terminus coding region of tissue factor 219, and further linking the IL-21/TF construct with the N-terminus coding region of IL-15.

Example 4: Secretion of IL-7/IL-15RαSu and IL-21/TF/IL-15 Fusion Proteins

Figure 3:
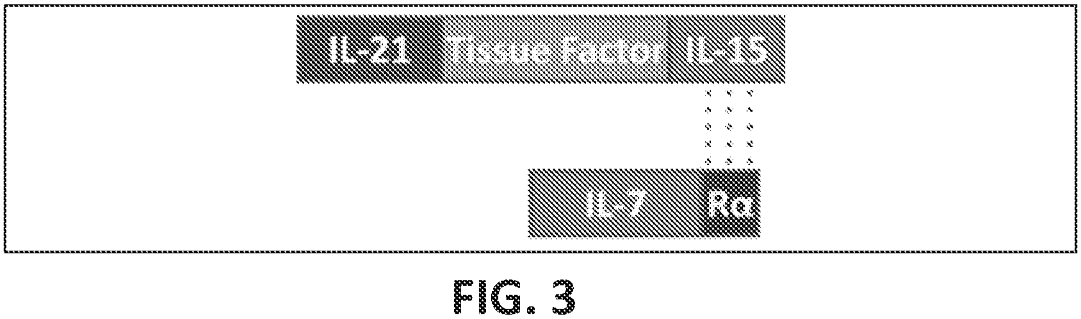
FIG. 3 shows a schematic diagram of the interaction between the exemplary IL-7/IL-15RαSu and IL-21/TF/IL-15 DNA constructs.
Figure 4:
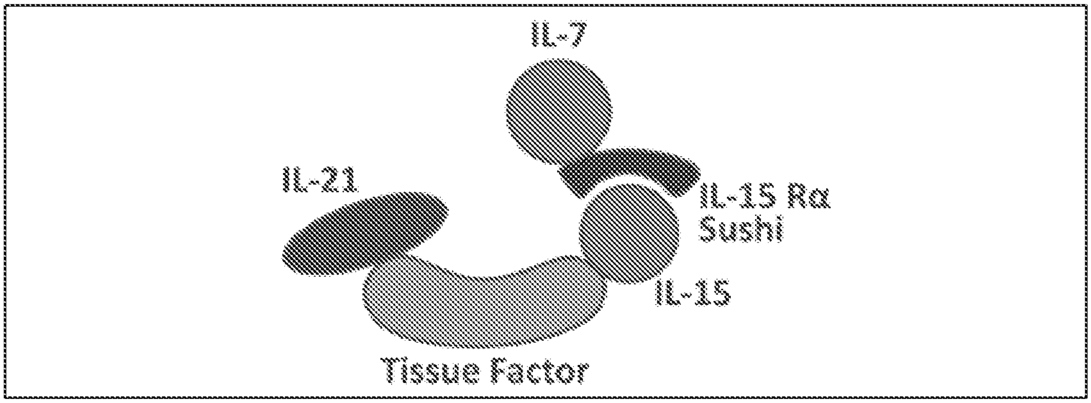
FIG. 4 shows a schematic diagram of the interaction between the exemplary IL-7/IL-15RαSu and IL-21/TF/IL-15 fusion proteins resulting in an IL-21/TF/IL-15:IL-7/IL-15RαSu complex (21t15-7s).

The IL-7/IL-15RαSu and IL-21/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-21/TF/IL-15:IL-7/IL-15RαSu protein complex (referred to as 21t15-7s, see FIGS. 3 and 4). The 21t15-7s protein was purified from CHO-K1 cell culture supernatant using anti-TF antibody affinity chromatography and size exclusion chromatography resulting in soluble (non-aggregated) protein complexes consisting of IL-7/IL-15RαSu and IL-21/TF/IL-15 fusion proteins.

In some cases, the leader (signal sequence) peptide is cleaved from the intact polypeptide to generate the mature form that may be soluble or secreted.

Example 5: Purification of 21t15-7s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Cell culture harvest of 21t15-7s was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was neutralized to pH 7.5-8.0 by adding 1M Tris base. The neutralized sample was then buffer exchanged into PBS using Amicon® centrifugal filters with a 30 KDa molecular weight cutoff. The buffer-exchanged protein sample was stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide and stored at 2-8° C.

Example 6: Creation of a TGF-βRII/IL-15RαSu DNA Construct

Figure 8:
FIG. 8 shows a schematic diagram of an exemplary TGF-βRII/IL-15RαSu DNA construct.

In a non-limiting example, a TGF-βRII/IL-15RαSu DNA construct was created (see FIG. 8). The human TGF-βRII sequence, human IL-15RαSu sequence, human IL-15 sequence, and human tissue factor 219 sequence were obtained from the UniProt website and DNA for these sequences was synthesized by Genewiz. A DNA construct was made linking the TGF-βRII sequences (separated by a linker) to the IL-15RαSu sequence. The final TGF-βRII/IL-15RαSu DNA construct sequence was synthesized by Genewiz.

Example 7: Creation of an IL-21/TF/IL-15 DNA Construct

Figure 9:
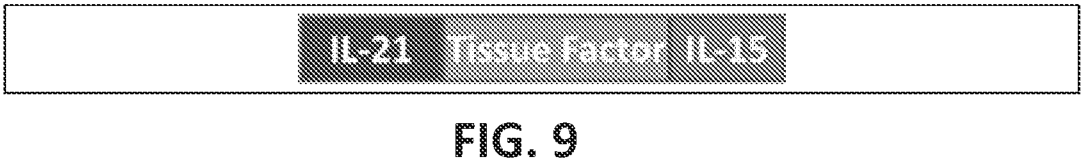
FIG. 9 shows a schematic diagram of an exemplary IL-21/TF/IL-15 DNA construct.

In a non-limiting example, an IL-21/TF/IL-15 construct was made (see FIG. 9) by linking the IL-21 sequence to the N-terminus coding region of tissue factor 219, and further linking the IL-21/TF construct with the N-terminus coding region of IL-15.

Example 8: Secretion of TGF-βRII/IL-15RαSu and IL-21/TF/IL-15 Fusion Proteins

The TGF-βRII/IL-15RαSu and IL-21/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-21/TF/IL-15: TGF-β RII/IL-15RαSu protein complex (referred to as 21t15-TGFRs, see FIGS. 10 and 11). The 21t15-TGFRs protein was purified from CHO-K1 cell culture supernatant using anti-TF antibody affinity chromatography and size exclusion chromatography resulting in soluble (non-aggregated) protein complexes consisting of TGF-β RII/IL-15RαSu and IL-21/TF/IL-15 fusion proteins.

Example 9: Size Exclusion Chromatography

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.7 mL/min. A capillary loop was used to inject 200 μL of 1 mg/mL of 7t15-21s complex onto the column. The injection was chased with 1.25 column volumes of PBS.

Example 10: SDS-PAGE of 21t15-7s and 21t15-TGFRs

To determine the purity and protein molecular weight, the purified 21t15-7s or 21t15-TGFRs protein sample were analyzed using 4-12% NuPage Bis-Tris protein gel SDS-PAGE. The gel will be stained with InstantBlue™ for about 30 min, followed by destaining overnight in purified water.

Example 11: Glycosylation of 21t15-7s and 21t15-TGFRs in CHO-K1 Cells

Glycosylation of 21t15-7s in CHO-K1 cells or 21t15-TGFRs in CHO-K1 cells were confirmed using the Protein Deglycosylation Mix II kit (New England Biolabs), according to the manufacturer's instructions.

Example 12: Recombinant Protein Quantitation of 21t15-7s and 21t15-TGFRs Complexes The 21t15-7s complex or the 21t15-TGFRs complex were detected and quantified using standard sandwich ELISA methods. Anti-human tissue factor antibody (IgG1) served as the capture antibody and biotinylated anti-human IL-21, IL-15, or IL-7 antibody (21t15-7s) or biotinylated anti-human IL-21, IL-15, or TGF-βRII antibody (21t15-TGFRs) served as the detection antibody. Tissue factor in purified 21t15-7s or 21t15-TGFRs protein complexes was detected using an anti-human tissue factor capture antibody, and anti-human tissue factor antibody (IgG1) detection antibody. The anti-TF ELISA will be compared to purified tissue factor at similar concentrations.

Figure 5:
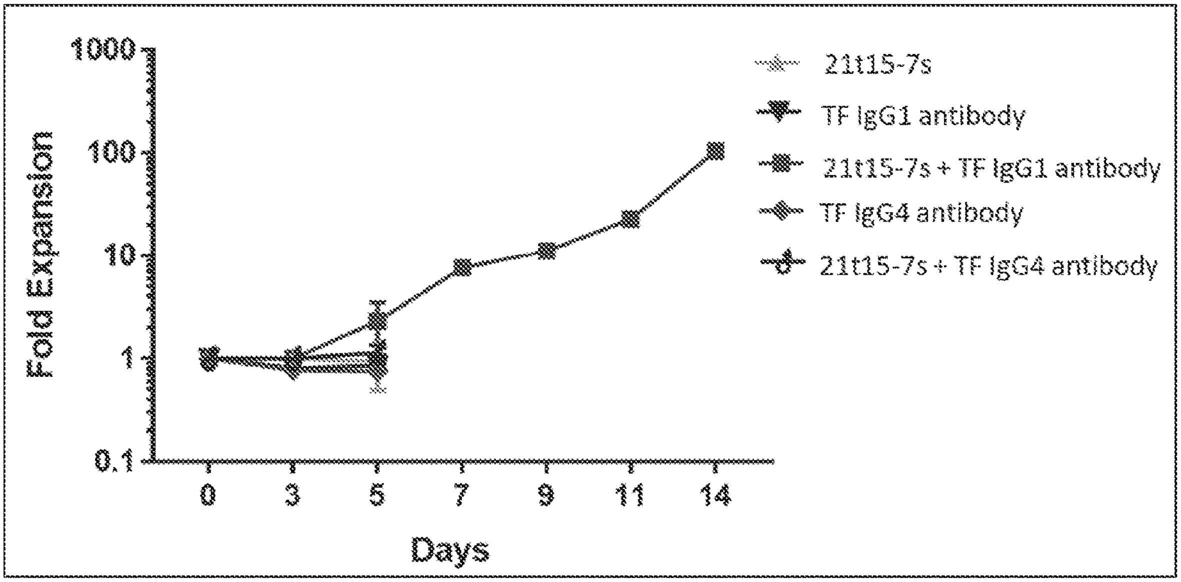
FIG. 5 shows the expansion of primary natural killer (NK) cells by stimulation with 21t15-7s+anti-TF IgG1 antibody.

Example 13: Expansion Capacity of Primary Natural Killer (NK) Cells by 21t15-7s Complex+Anti-TF IgG1 Antibody or 21t15-TGFRs Complex+Anti-TF IgG1 Antibody To assess the 21t15-7s complex's ability to expand primary natural killer (NK) cells, 21t15-7s complex and 21t15-7s complex+anti-TF IgG1 antibody was added to NK cells obtained from samples of fresh human leukocytes. Cells were stimulated with 50 nM of 21t15-7s complex with or without 25 nM of anti-TF IgG1 or anti-TF IgG4 antibody at 370 and 5% $CO_2$. Cells were maintained at concentration at $0.5\times10^6$/mL not exceeding $2.0\times10^6$/mL by counting every 48-72 hours and media was replenished with fresh stimulator. Cells stimulated with 21t15-7s complex or anti-TF IgG1 antibody or anti-TF IgG4 antibody or anti-TF IgG4+21t15-7s complex were maintained up to day 5. FIG. 5 shows expansion of primary NK cells upon incubation with 21t15-7s complex+anti-TF IgG1 antibody.

Figure 12:
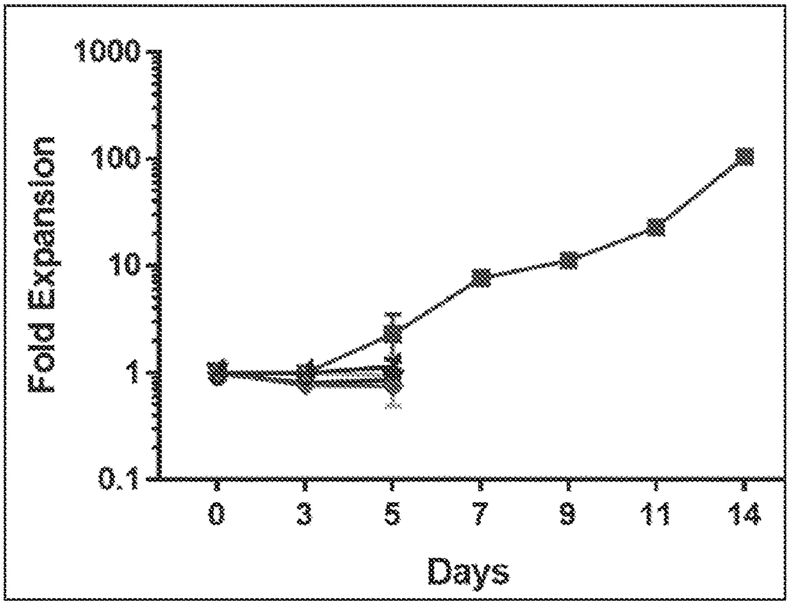
FIG. 12 shows the expansion of primary natural killer (NK) cells by stimulation with 21t15-TGFRs+anti-TF IgG1 antibody (dark line with squares) or primary NK cells contacted with 21t15-TGFRs alone, anti-TF IgG1 antibody, anti-TF IgG4 antibody, or with a combination of 21t15-TGFRs+anti-TF IgG4 antibody (all other data shown).
Figure 18:
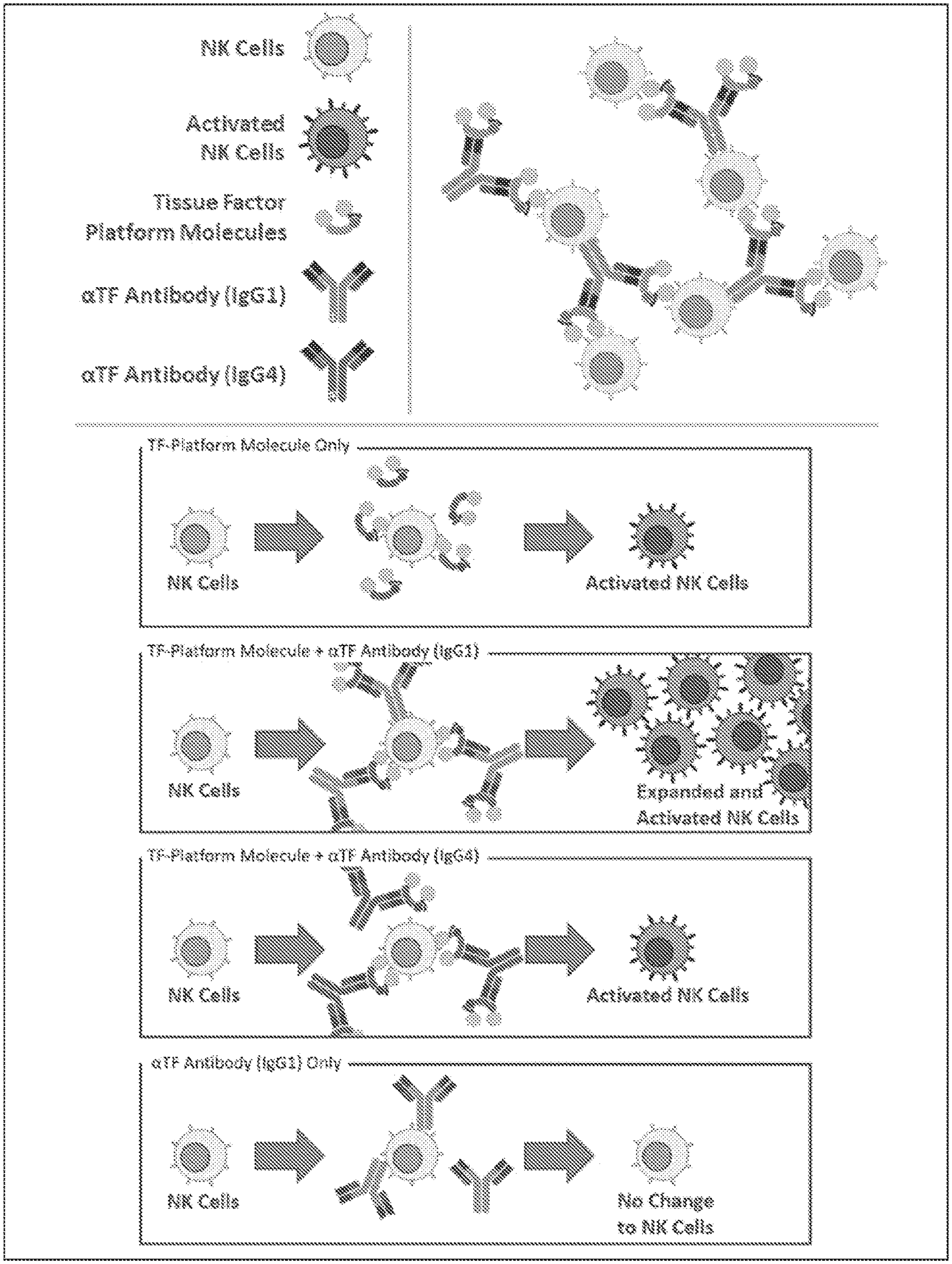
FIG. 18 shows in diagrammatic form the activation and expansion of primary natural killer (NK) cells by stimulation with 21t15-TGFRs+anti-TF IgG1 antibody.

To assess the 21t15-TGFRs complex's ability to expand primary natural killer (NK) cells, 21t15-TGFRs complex and 21t15-TGFRs complex+anti-TF IgG1 antibody was added to NK cells obtained from samples of fresh human leukocytes. Cells were stimulated with 50 nM of 21t15-TGFRs complex with or without 25 nM of anti-TF IgG1 or anti-TF IgG4 antibody at 37° C. and 5% $CO_2$. Cells were maintained at concentration at $0.5\times10^6$/mL not exceeding $2.0\times10^6$/mL by counting every 48-72 hours and media was replenished with fresh stimulator. Cells stimulated with 21t15-TGFRs complex or anti-TF IgG1 antibody or anti-TF IgG4 antibody or anti-TF IgG4+21t15-TGFRs complex were maintained up to day 5. FIG. 12 shows expansion of primary NK cells upon incubation with 21t15-TGFRs complex+anti-TF IgG1 antibody. FIG. 18 is a schematic summarizing these results.

Figure 6:
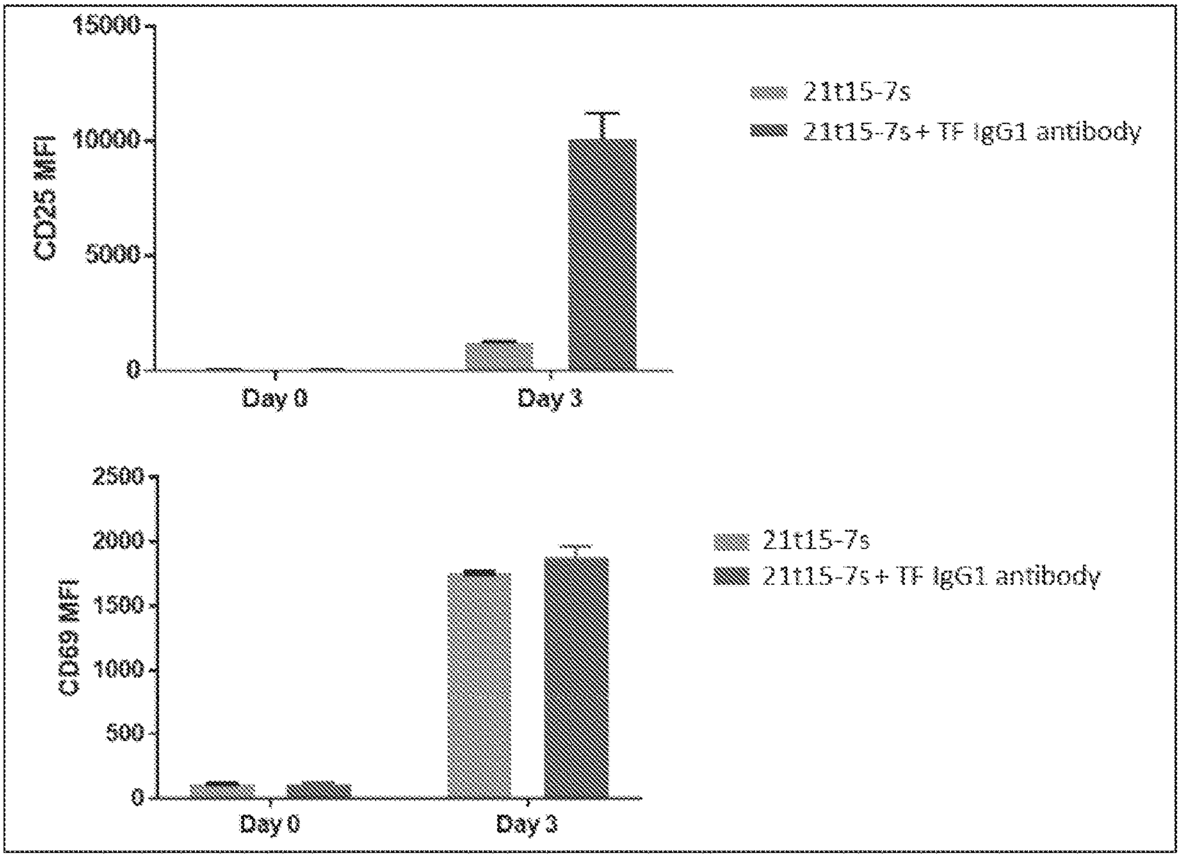
FIG. 6 shows activation of expanded primary NK cells, using CD25 MFI and CD69 MFI as markers of NK cell activation.

Example 14: Activation of Expanded NK Cells by the 21t15-7s Complex+Anti-TF IgG1 Antibody or the 21t15-TGFRs Complex+Anti-TF IgG1 Antibody Primary NK cells can be induced ex vivo following overnight stimulation of purified NK cells with 21t15-7s complex+anti-TF IgG1 antibody. Fresh human leukocytes were obtained from a blood bank and $CD56^+$ NK cells were isolated with the RosetteSep/human NK cell reagent (StemCell Technologies). The purity of NK cells was >80% and confirmed by staining with CD56-BV421 and CD16-BV510 specific antibodies (BioLegend). Cells were counted and resuspended in $1\times10^6$/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells were stimulated with 50 nM of 21t15-7s with or without 25 nM of TF IgG1 antibody at 37° C. and 5% $CO_2$. Cells were counted every 48-72 hours and maintained at a concentration of $0.5\times10^6$/mL to $2.0\times10^6$/mL until day 14. Media was periodically replenished with fresh stimulator. Cells were harvested and surface stained at day 3 with CD56-BV421, CD16-BV510, CD25-PE, CD69-APCFire750 specific antibodies (Biolegend and analyzed by Flow Cytometry-Celeste-BD Bioscience). FIG. 6 shows the activation markers CD25 MFI and CD69 MFI. The activation marker CD25 MFI increased with 21t15-7s complex+anti-TF IgG1 antibody stimulation, but not 21t15-7s complex stimulation. The activation marker CD69 MFI increased with both 21t15-7s complex+anti-TF IgG1 antibody and with 21t15-7s complex, alone.

Figure 13:
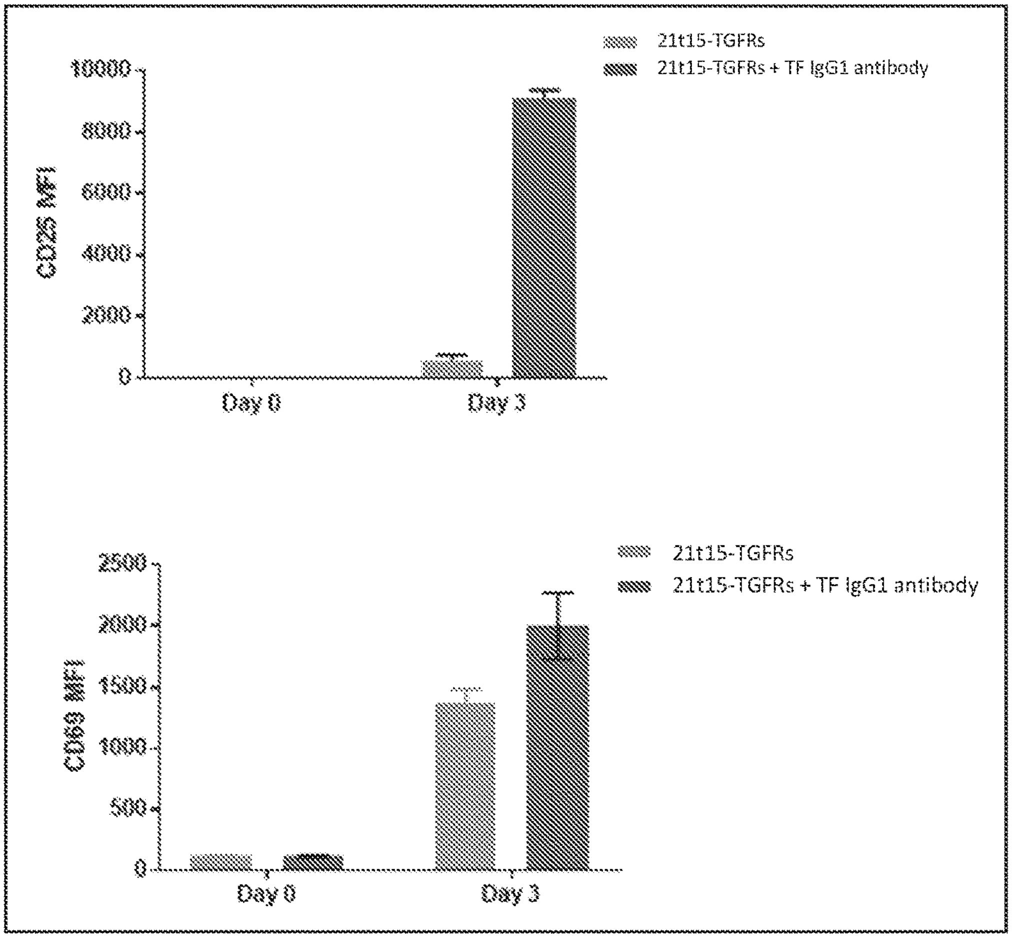
FIG. 13 shows activation of expanded primary NK cells, using CD25 MFI (top) and CD69 MFI (bottom) as markers of NK cell activation.

Primary NK cells can be induced ex vivo following overnight stimulation of purified NK cells with 21t15-TGFRs complex+anti-TF IgG1 antibody. Fresh human leukocytes were obtained from a blood bank and $CD56^+$ NK cells were isolated with the RosetteSep/human NK cell reagent (StemCell Technologies). The purity of NK cells was >80% and confirmed by staining with CD56-BV421 and CD16-BV510 specific antibodies (BioLegend). Cells were counted and resuspended in $1\times10^6$/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells were stimulated with 50 nM of 21t15-TGFRs with or without 25 nM of anti-TF IgG1 antibody at 37° C. and 5% C02. Cells were counted every 48-72 hours and maintained at a concentration of $0.5\times10^6$/mL to $2.0\times10^6$/mL until day 14. Media was periodically replenished with fresh stimulator. Cells were harvested and surface stained at day 3 with CD56-BV421, CD16-BV510, CD25-PE, CD69-APC-Fire750 specific antibodies (Biolegend and analyzed by Flow Cytometry-Celeste-BD Bioscience). FIG. 13 shows the activation markers CD25 MFI and CD69 MFI. The activation marker CD25 MFI increased with 21t15-TGFRs complex+anti-TF IgG1 antibody stimulation, but not 21t15-TGFRs complex stimulation. The activation marker CD69 MFI increased with both 21t15-TGFRs complex+anti-TF IgG1 antibody and with 21t15-TGFRs complex, alone.

Example 15: Cytotoxicity of NK Cells Against Human Tumor Cells

Figure 7:
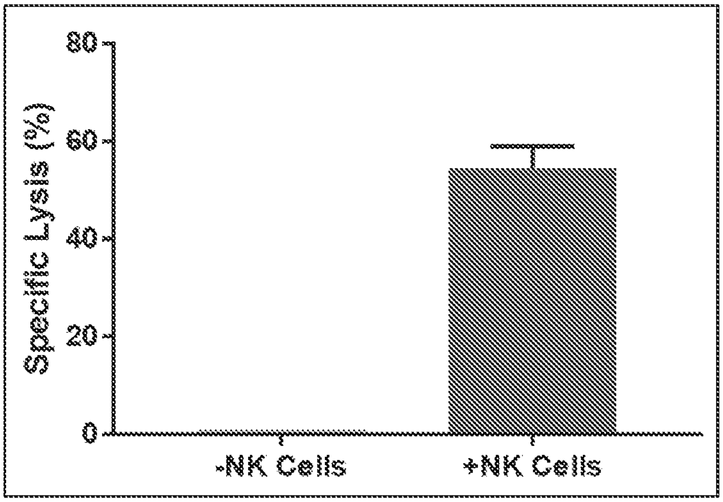
FIG. 7 shows cytotoxic activity of expanded NK cells against K562 human tumor cells, wherein NK cells stimulated with 21t15-7s+anti-TF IgG1 antibody demonstrate greater specific lysis of K562 cells than NK cells not stimulated with 21t15-7s+anti-TF IgG1 antibody.

Fresh human leukocytes were obtained from a blood bank. NK cells were isolated via negative selection using the RosetteSep/human NK cell reagent (StemCell Technologies). The purity of NK cells was >80% and confirmed by staining with CD56-BV421 and CD16-BV510 specific antibodies (BioLegend). Cells were counted and resuspended in $1\times10^6$/mL in a 24 well, flat bottom plate in 1 mL of complete media (RPMI 1640 (Gibco)), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies) and 10% FBS (Hyclone). Cells were stimulated with 21t15-7s 50 nM and 25 nM of anti-TF IgG1 antibody for up to 14 days at 37° C. and 5% $CO_2$. Cells were counted every 48-72 hours and maintained at a concentration of $0.5\times10^6$/mL to $2.0\times10^6$/mL until day 14. Media was periodically replenished with fresh stimulator. On day 14, cells were harvested and washed 2 times. K562 human tumor cells were harvested and labeled with Celltrace violet. Celltrace violet-labeled K562 cells were mixed with the in vitro expanded NK cells and incubated at 37° C. for 20 hours. The mixture was harvested and the percentage of dead K562 cells were determined by propidium iodide staining and flow cytometry. FIG. 7 shows increased specific lysis of K562 cells when incubated with expanded NK cells.

Example 16: Creation of an IL-21/IL-15RαSu DNA Construct

In a non-limiting example, an IL-21/IL-15RαSu DNA construct was created. The human IL-21 sequence and human IL-15RαSu sequence were obtained from the UniProt website and DNA for these sequences was synthesized by Genewiz. A DNA construct was made linking the IL-21 sequence to the IL-15RαSu sequence. The final IL-21/IL-15RαSu DNA construct sequence was synthesized by Genewiz. See FIG. 14.

Example 17: Creation of an IL-7/TF/IL-15 DNA Construct

Figure 15:
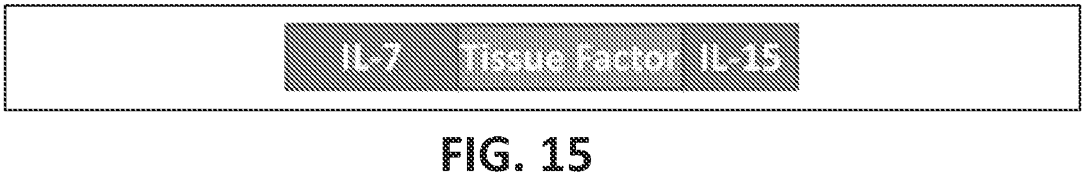
FIG. 15 shows a schematic diagram of an exemplary IL-7/TF/IL-15 DNA construct.

In a non-limiting example, an IL-7/TF/IL-15 construct was made by linking the IL-7 sequence to the N-terminus coding region of tissue factor 219, and further linking the IL-7/TF construct with the N-terminus coding region of IL-15. See FIG. 15.

Example 18: Creation of an IL-21/IL-15Rα Sushi DNA Construct

In a non-limiting example, a second chimeric polypeptide of IL-21/IL-15RαSu was generated. The human IL-21 and human IL-15Rα sushi sequences were obtained from the UniProt website and DNA for these sequences was synthesized by Genewiz. A DNA construct was made linking the IL-21 sequence to the IL-15Rα sushi sequence. The final IL-21/IL-15RαSu DNA construct sequence was synthesized by Genewiz.

Example 19: Creation of an IL-7/TF/IL-15 DNA Construct

In a non-limiting example, an exemplary first chimeric polypeptide of IL-7/TF/IL-15 was made by linking the IL-7 sequence to the N-terminus coding region of tissue factor 219, and further linking the IL-7/TF construct with the N-terminus coding region of IL-15. The nucleic acid sequence encoding the first chimeric polypeptide of IL-7/TF/IL-15 (including leader sequence), synthesized by Genewiz.

Example 20: Secretion of IL-21/IL-15RαSu and IL-7/TF/IL-15 Fusion Proteins

Figure 16:
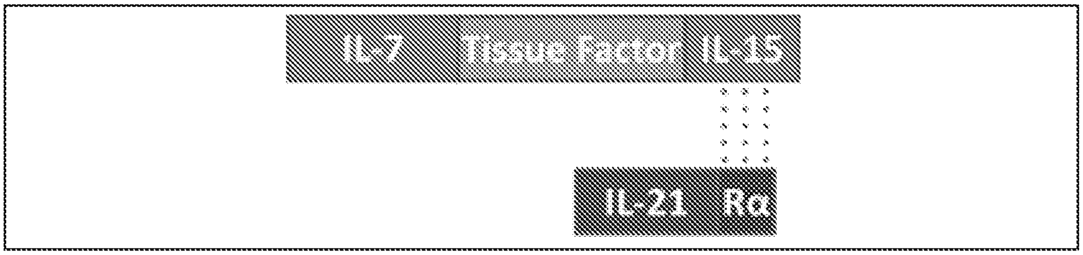
FIG. 16 shows a schematic diagram of the interaction between the exemplary IL-21/IL-15RαSu and IL-7/TF/IL-15 DNA constructs.
Figure 17:
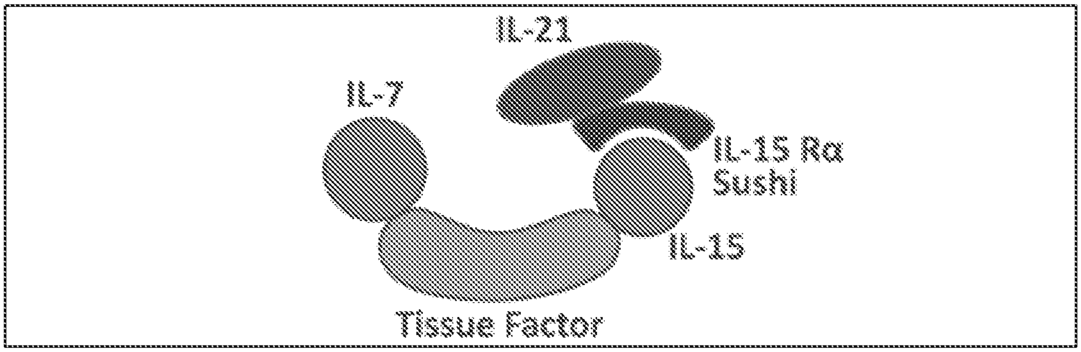
FIG. 17 shows a schematic diagram of the interaction between the exemplary IL-21/IL-15RαSu and IL-7/TF/IL-15 fusion proteins resulting in an IL-7/TF/IL-15:IL-21/IL-15RαSu complex (7t15-21s).

The IL-21/IL-15RαSu and IL-7/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-7/TF/IL-15:IL-21/IL-15RαSu protein complex (referred to as 7t15-21s). The 7t15-21s protein was purified from CHO-K1 cell culture supernatant using anti-TF antibody (IgG1) affinity chromatography and size exclusion chromatography resulting in soluble (non-aggregated) protein complexes consisting of IL-21/IL-15RαSu and IL-7/TF/IL-15 fusion proteins. See, FIGS. 16 and 17.

Figure 19:
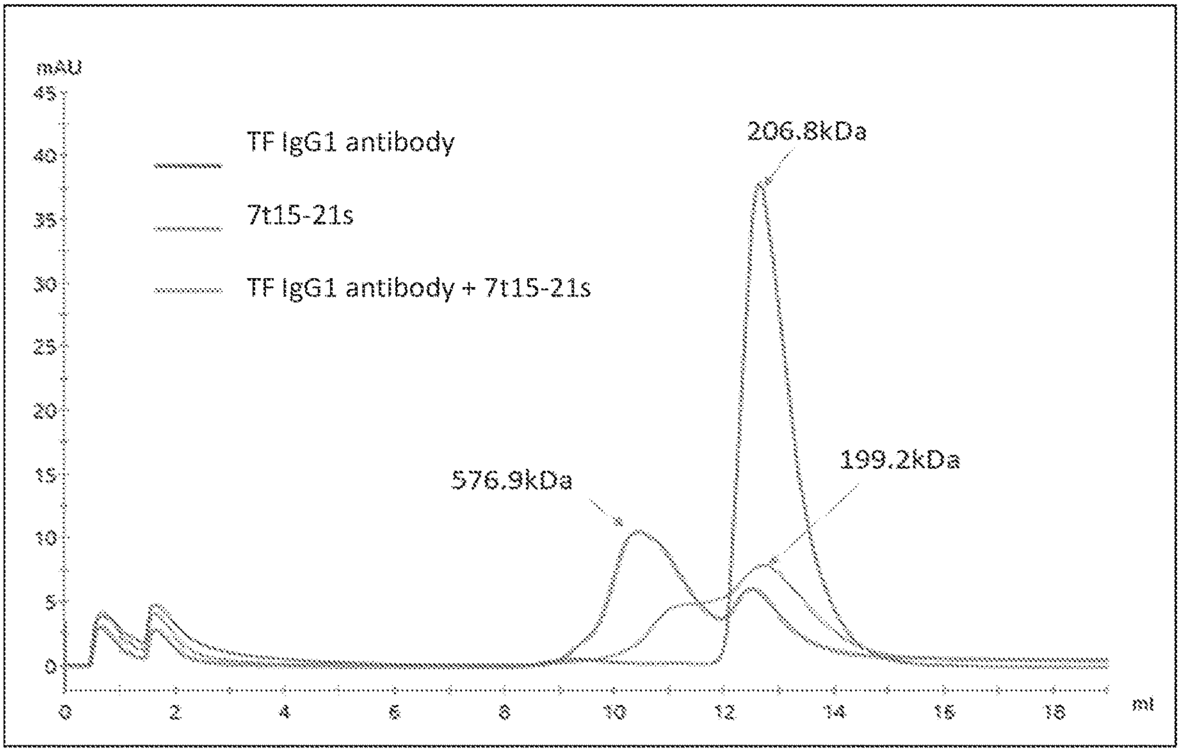
FIG. 19 shows size exclusion chromatography (SEC) profiles of anti-TF IgG1 antibody, 7t15-21s and the complex containing equal amounts of anti-TF IgG1 antibody and 7t15-21s.

Example 21: Analytical Size Exclusion Chromatography (SEC) Analysis of IL-21/IL-15RαSu and IL-7/TF/IL-15 Fusion Proteins To determine if anti-tissue factor monoclonal antibody and 7t15-21s can form an antibody-fusion-molecule complex, analytical size exclusion chromatography (SEC) was performed. A Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. Samples of the anti-TF mAb (1 mg/mL), 7t15-21s (1 mg/mL), and a mixture of combined at a 1:1 ratio, so the final concentration of each protein is 0.5 mg/mL) were in PBS. Each sample was injected into the Superdex 200 column using a capillary loop, and analyzed by SEC. The SEC chromatograph of each sample was shown in FIG. 19. The SEC results indicated that there are two protein peaks for 7t15-21s, likely representing a dimer (with an apparent molecular weight of 199.2 kDa) and a higher oligomer of 7t15-21s, and there is one peak (with an apparent molecular weight of 206.8 kDa) for the anti-TF mAb. However, as expected, a new protein peak with a higher molecular weight (with an apparent molecular weight of 576.9 kDa) was formed in the mixture sample containing the anti-TF mAb and 7t15-21s, indicating that the anti-TF mAb and 7t15-21s form an antibody-antigen complex through the binding of anti-TF mAb to TF in the fusion protein complex.

Example 22: Expansion Capacity of Primary Natural Killer (NK) Cells by 7t15-21s Complex+Anti-TF IgG1 Antibody To assess the 7t15-21s complex's ability to expand primary natural killer (NK) cells, 7t15-21s complex and 7t15-21s complex+anti-TF IgG1 antibody are added to NK cells obtained from samples of fresh human leukocytes. Cells are stimulated with 50 nM of 7t15-21s complex with or without 25 nM of anti-TF IgG1 or anti-TF IgG4 antibody at 37° C. and 5% C02. Cells are maintained at concentration at $0.5\times10^6$/mL not exceeding $2.0\times10^6$/mL by counting every 48-72 hours and media is replenished with fresh stimulator. Cells stimulated with 7t15-21s complex or anti-TF IgG1 antibody or anti-TF IgG4 antibody or anti-TF IgG4+7t15-21s complex are maintained up to day 5. Expansion of primary NK cells upon incubation with 21t15-7s complex+anti-TF IgG1 antibody is observed.

Example 23: Activation of Expanded NK Cells by the 7t15-21s Complex+Anti-TF IgG1 Antibody Primary NK cells are induced ex vivo following overnight stimulation of purified NK cells with 7t15-21s complex+TF IgG1 antibody. Fresh human leukocytes are obtained from a blood bank and $CD56^+$ NK cells are isolated with the RosetteSep/human NK cell reagent (StemCell Technologies). The purity of NK cells is >80% and is confirmed by staining with CD56-BV421 and CD16-BV510 specific antibodies (BioLegend). Cells are counted and resuspended in $1\times10^6$/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells are stimulated with 50 nM of 7t15-21s with or without 25 nM of anti-TF IgG1 antibody at 37° C. and 5% $CO_2$. Cells are counted every 48-72 hours and maintained at a concentration of $0.5\times10^6$/mL to $2.0\times10^6$/mL until day 14. Media is periodically replenished with fresh stimulator. Cells are harvested and surface stained at day 3 with CD56-BV421, CD16-BV510, CD25-PE, CD69-APCFire750 specific antibodies (Biolegend and analyzed by Flow Cytometry-Celeste-BD Bioscience). The activation marker CD25 MFI are observed to increase with 7t15-21s complex+anti-TF IgG1 antibody stimulation, but not 7t15-21s complex stimulation. The activation marker CD69 MFI is observed to increase with both 7t15-21s complex+anti-TF IgG1 antibody and with 7t15-21s complex, alone.

Example 24: Increase in Glucose Metabolism in NK Cells Using 7t15-21s and 21t15-7s in Combination with an Anti-TF IgG1 Antibody A set of experiments was performed to determine the effect of (1) 7t15-21s in combination with an anti-TF IgG1 antibody or (2) 21t15-7s in combination with an anti-TF IgG1 antibody on oxygen consumption rate (OCR) and extracellular acidification rate (ECAR) on NK cells purified from human blood. In these experiments, fresh human leukocytes were obtained from the blood bank and NK cells were isolated via negative selection using the RosetteSep/human NK cell reagent (StemCell Technologies). The purity of NK cells was >80% and confirmed by staining with CD56-BV421 and CD16-BV510 specific antibodies (BioLegend). The cells were counted and resuspended at a concentration of $1\times10^6$/mL in a 24-well flat-bottom plate in 1 mL of complete media (RPMI 1640 (Gibco) supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). The cells were stimulated with (1) 100 nM anti-TF IgG1 antibody, (2) 50 nM 7t15-21s and 100 nM anti-TF IgG1 antibody, or (3) 50 nM 21t15-7s and 100 nM anti-TF IgG1, for up to day 5 at 37° C., 5% C02. The cells were maintained at concentration at $0.5\times10^6$/mL not exceeding $2.0\times10^6$/mL until day 5 by counting every 48 hours and media was replenished with fresh stimulator. Extracellular flux assays on expanded NK cells were performed using a XFp Analyzer (Seahorse Bioscience). The harvested cells were washed and plated at $2.0\times10^5$ cells/well in at least duplicate for extracellular flux analysis of OCR (Oxygen Consumption Rate) and ECAR (Extracellular Acidification Rate).

Glycolysis stress tests were performed in Seahorse Media containing 2 mM of glutamine. The following were used during the assay: 10 mM glucose; 100 nM oligomycin; and 100 mM 2-deoxy-D-glycose (2DG).

Figure 20:
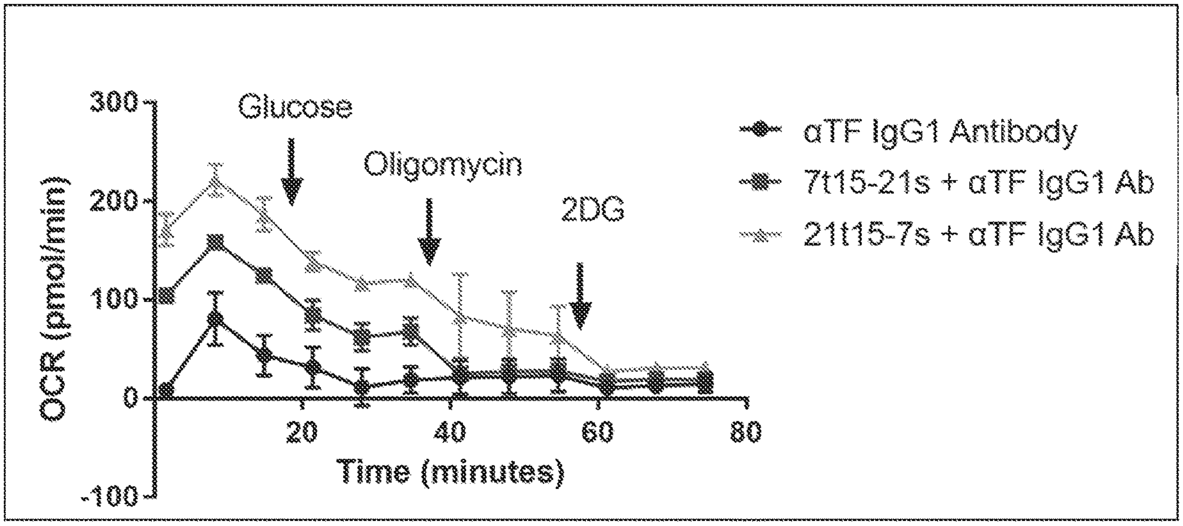
FIG. 20 is a graph showing the oxygen consumption rate (OCR) in pmoles/min for human NK cells isolated from blood ($1\times10^6$ cells/mL) and stimulated with (1) 50 nM anti-TF IgG1 (IgG1), (2) 100 nM 7t15-21s and 50 nM anti-TF IgG1, or (3) 100 nM 21t15-7s and 50 nM anti-TF IgG1 for up to 5 days at 37° C., 5% $CO_2$ in RPMI 1640 supplemented with 4 mM L-glutamine, penicillin, streptomycin, non-essential amino acids, sodium pyruvate, and 10% fetal bovine serum. Cells were maintained at a concentration of $0.5\times10^6$ cells/mL to $2.0\times10^6$ cells/mL until day 5. Glycolysis stress tests were performed in Seahorse media containing 2 mM glutamine. The drug concentrations used during the assay were as follows: 10 mM glucose, 100 nm oligomycin, and 100 mM 2-deoxy-D-glucose.
Figure 21:
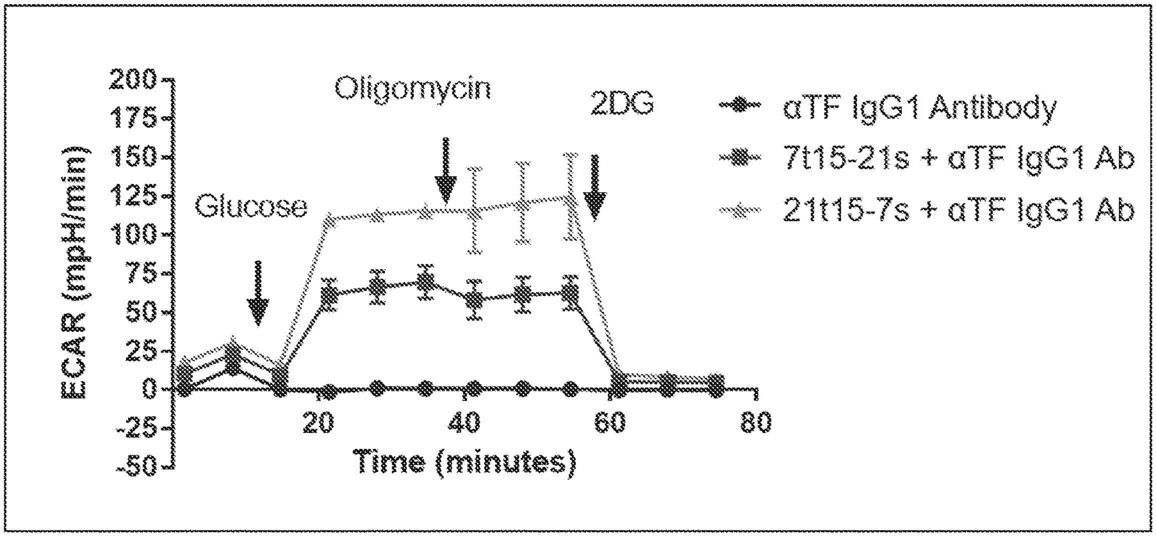
FIG. 21 is a graph showing the extracellular acidification rate (ECAR) in mpH/minute for human NK cells isolated from blood ($1\times10^6$ cells/mL) and stimulated with (1) 50 nM anti-TF IgG1 (IgG1), (2) 100 nM 7t15-21s and 50 nM anti-TF IgG1, or (3) 100 nM 21t15-7s and 50 nM anti-TF IgG1 for up to 5 days at 37° C., 5% $CO_2$ in RPMI 1640 supplemented with 4 mM L-glutamine, penicillin, streptomycin, non-essential amino acids, sodium pyruvate, and 10% fetal bovine serum. Cells were maintained at a concentration of $0.5\times10^6$ cells/mL to $2.0\times10^6$ cells/mL until day 5. Glycolysis stress tests were performed in Seahorse media containing 2 mM glutamine. The drug concentrations used during the assay were as follows: 10 mM glucose, 100 nm oligomycin, and 100 mM 2-deoxy-D-glucose.

The data show that the combinations of (1) 100 nM 7t15-21s and 50 nM anti-TF IgG1 antibody, and (2) 100 nM 21t15-7s and 50 nM anti-TF IgG1 result in a significant increase in oxygen consumption rate (FIG. 20) and extracellular acidification rate (ECAR) (FIG. 21).

Example 25: Increase in Glucose Metabolism in NK Cells Using 18t15-12s

Figure 22:
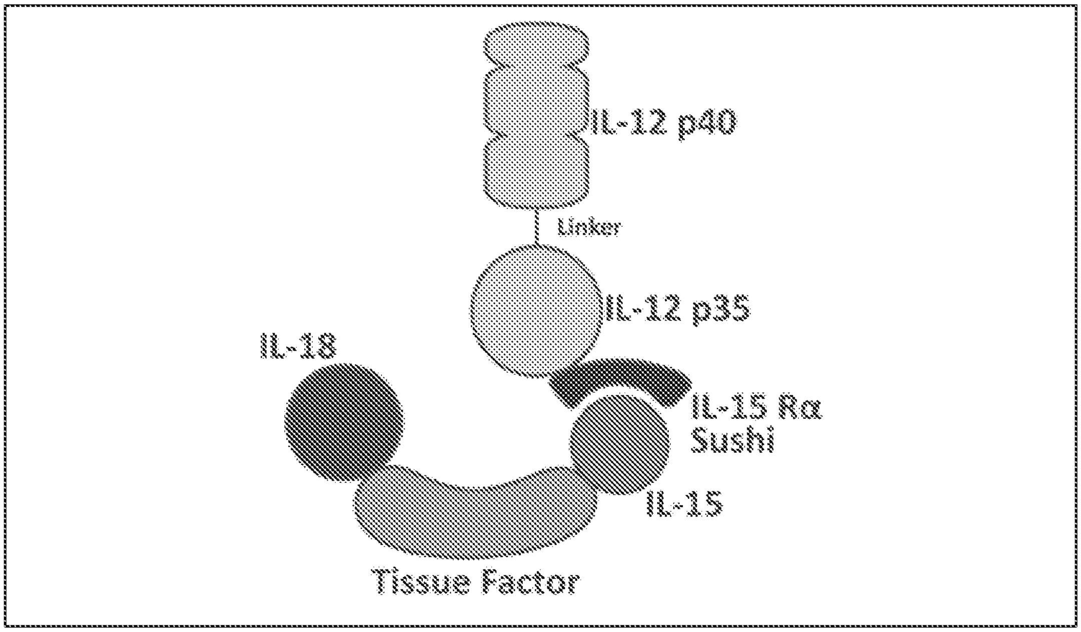
FIG. 22 is a schematic showing the structure of the 18t15-12s construct.

A set of experiments was performed to determine the effect of the construct of 18t15-12s (FIG. 22) on oxygen consumption rate and extracellular acidification rate (ECAR) on NK cells purified from human blood.

In these experiments, fresh human leukocytes were obtained from the blood bank from two different human donors and NK cells were isolated via negative selection using the RosetteSep/human NK cell reagent (StemCell Technologies). The purity of NK cells was >80% and confirmed by staining with CD56-BV421 and CD16-BV510 specific antibodies (BioLegend). The cells were counted and resuspended in $2\times10^6$/mL in 24-well, flat-bottom plates in 1 mL of complete media (RPMI 1640 (Gibco) supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies) and 10% FBS (Hyclone)). The cells were stimulated with either (1) media alone, (2) 100 nM 18t15-12s, or (3) mixture of single cytokines recombinant human IL-12 (0.25 μg), recombinant human IL-15 (1.25 μg), and recombinant human IL-18 (1.25 μg) overnight at 37° C., 5% $CO_2$. On the next day, the cells were harvested and extracellular flux assays on expanded NK cells were performed using a XFp Analyzer (Seahorse Bioscience). The harvested cells washed and plated $2.0\times10^5$ cells/well in at least duplicate for extracellular flux analysis of OCR (Oxygen Consumption Rate) and ECAR (Extracellular Acidification Rate). The glycolysis stress tests were performed in Seahorse Media contain 2 mM of glutamine. The following were used during the assay: 10 mM glucose; 100 nM oligomycin; and 100 mM 2-deoxy-D-glycose (2DG).

Figure 23:
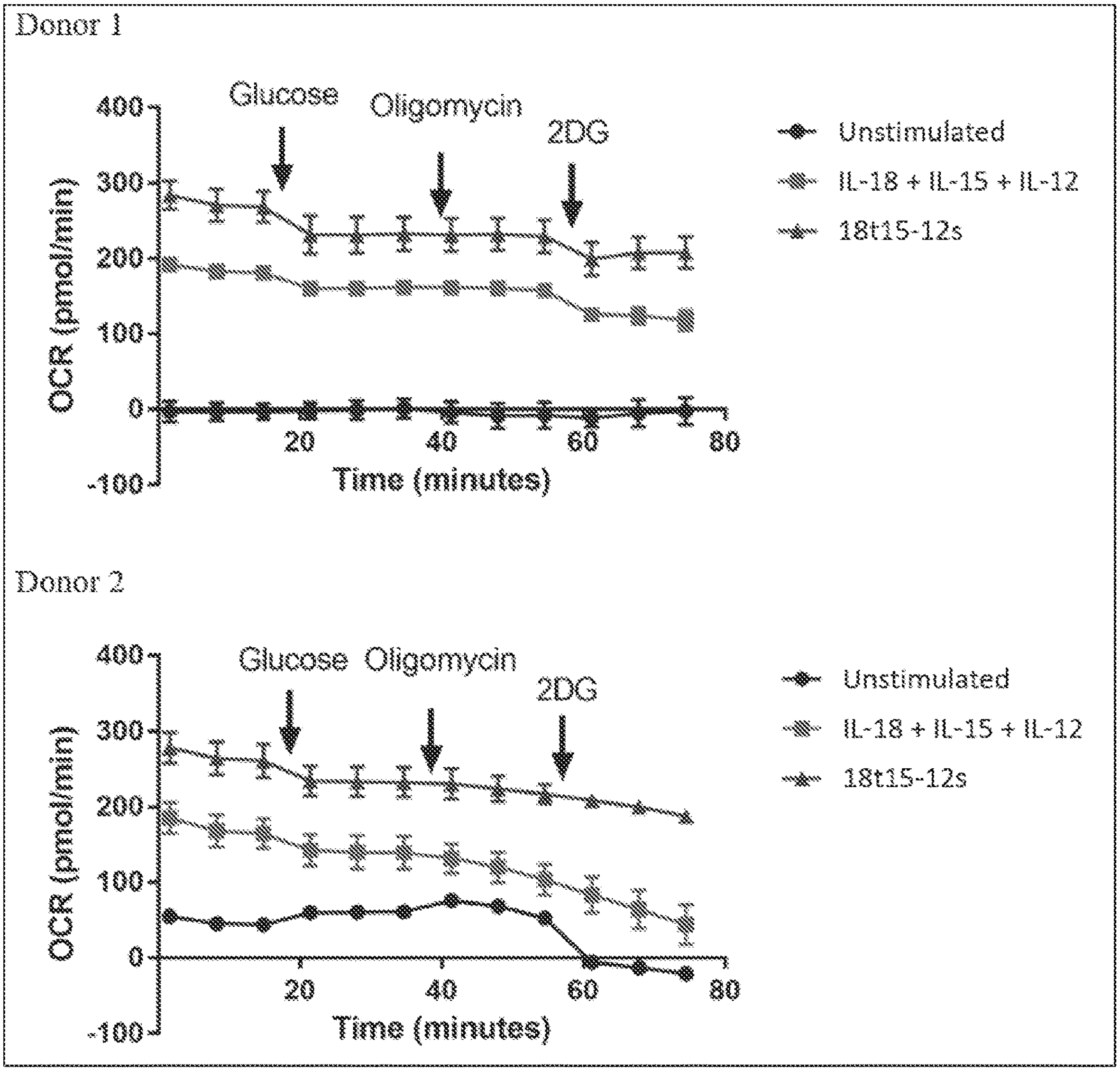
FIG. 23 are two graphs showing the oxygen consumption rate (OCR) in pmoles/min for human NK cells isolated from blood ($2\times10^6$ cells/mL) of two different donors. The isolated NK cells were left unstimulated or were stimulated with (1) 100 nM 18t15-12s ("1812") or a mixture of (2) recombinant human IL-12 (0.25 μg), recombinant human IL-15 (1.25 μg), and recombinant human IL-18 (1.25 μg) ("single cytokines"), overnight at 37° C., 5% $CO_2$ in RPMI 1640 supplemented with 4 mM L-glutamine, penicillin, streptomycin, non-essential amino acids, sodium pyruvate, and 10% fetal bovine serum. On the next day, the cells were harvested and extracellular flux assays on expanded NK cells were performed using a XFp Analyzer (Seahorse Bioscience). The harvested cells were washed and plated at $2.0\times10^5$ cells/well in at least duplicate for extracellular flux analysis of oxygen consumption rate. Glycolysis stress tests were performed in Seahorse Media contain 2 mM glutamine. Drug concentrations during the assay were: 10 mM glucose, 100 nM oligomycin, and 100 mM 2-deoxy-D-glucose.
Figure 24:
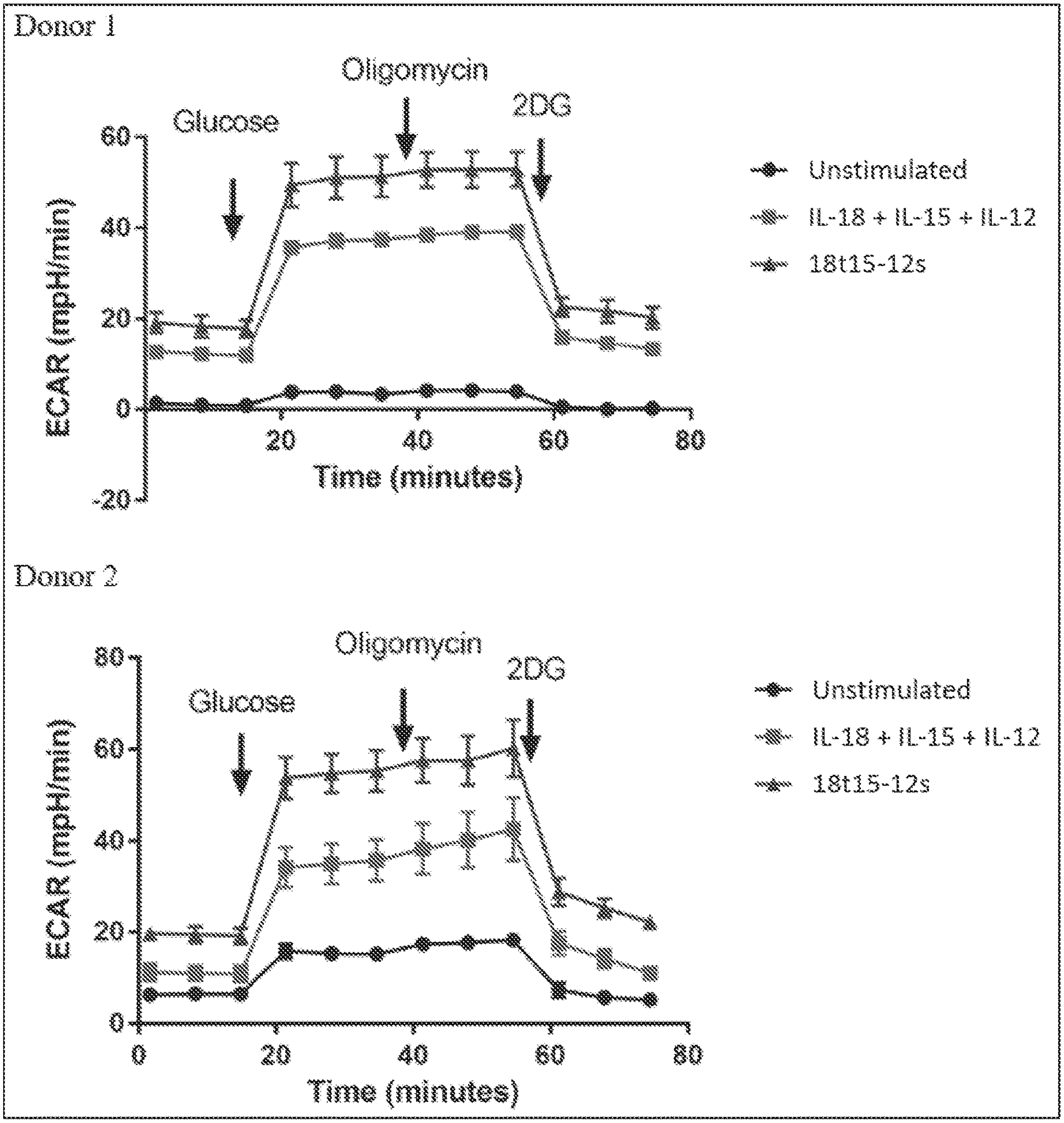
FIG. 24 are two graphs showing the extracellular acidification rate (ECAR) in mpH/minute for human NK cells isolated from blood ($2\times10^6$ cells/mL) of two different donors. The isolated NK cells were left unstimulated or were stimulated with (1) 100 nM 18t15-12s ("1812") or a mixture of (2) recombinant human IL-12 (0.25 μg), recombinant human IL-15 (1.25 μg), and recombinant human IL-18 (1.25 μg) ("single cytokines"), overnight at 37° C., 5% $CO_2$ in RPMI 1640 supplemented with 4 mM L-glutamine, penicillin, streptomycin, non-essential amino acids, sodium pyruvate, and 10% fetal bovine serum. On the next day, the cells were harvested and extracellular flux assays on expanded NK cells were performed using a XFp Analyzer (Seahorse Bioscience). The harvested cells were washed and plated at $2.0\times10^6$ cells/well in at least duplicate for extracellular flux analysis of extracellular flux analysis (ECAR). Glycolysis stress tests were performed in Seahorse Media contain 2 mM glutamine. Drug concentrations during the assay were: 10 mM glucose, 100 nM oligomycin, and 100 mM 2-deoxy-D-glucose.

The data show that the 18t15-12s results in significantly increased oxygen consumption rate (FIG. 23) and extracellular acidification rate (ECAR) as compared to the same cells activated with a combination of recombinant human IL-12, recombinant human IL-15, and recombinant human IL-18 (FIG. 24).

Example 26: Creation of an IL-12/IL-15RαSu DNA Construct

Figure 25:
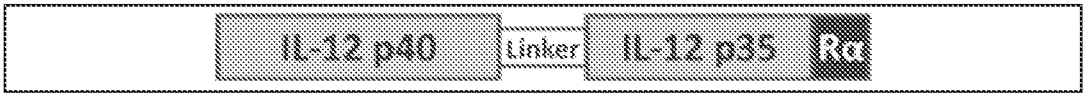
FIG. 25 shows a schematic diagram of an exemplary IL-12/IL-15RαSu DNA construct.

In a non-limiting example, an IL-12/IL-15RαSu DNA construct was created. (see FIG. 25) The human IL-12 subunit sequences, human IL-15RαSu sequence, human IL-15 sequence, human tissue factor 219 sequence, and human IL-18 sequence were obtained from the UniProt website and DNA for these sequences was synthesized by Genewiz. A DNA construct was made linking the IL-12 subunit beta (p40) to IL-12 subunit alpha (p35) with a GS (3) linker to generate a single chain version of IL-12 and then directly linking the IL-12 sequence to the IL-15RαSu sequence. The final IL-12/IL-15RαSu DNA construct sequence was synthesized by Genewiz.

The nucleic acid sequence of the IL12/IL-15RαSu construct (including signal peptide sequence) is as follows (SEQ ID NO: 123):

```
(Signal peptide)
ATGAAATGGGTGACCTTTATTTCTTTACTGTTCCTCTTTAGCAGCGCCT

ACTCC

(Human IL-12 subunit beta (p40))
ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC
```

-continued

```
GGAAAGACCCTCACAATCCAAGTTAAGGAGTTCGGAGACGCTGGCCAAT

CACATGCCACAAGGGAGGCGAGGTGCTCAGCCATTCCTTATTATTATTA

CACAAGAAGGAAGACGGAATCTGGTCCACCGACATTTTAAAAGATCAGA

AGGAGCCCAAGAATAAGACCTTTTTAAGGTGTGAGGCCAAAAACTACAG

CGGTCGTTTCACTTGTTGGTGGCTGACCACCATTTCCACCGATTTAACC

TTCTCCGTGAAAAGCAGCCGGGGAAGCTCCGACCCTCAAGGTGTGACAT

GTGGAGCCGCTACCCTCAGCGCTGAGAGGGTTCGTGGCGATAACAAGGA

ATACGAGTACAGCGTGGAGTGCCAAGAAGATAGCGCTTGTCCCGCTGCC

GAAGAATCTTTACCCATTGAGGTGATGGTGGACGCCGTGCACAAACTCA

AGTACGAGAACTACACCTCCTCCTTCTTTATCCGGGACATCATTAAGCC

CGATCCTCCTAAGAATTTACAGCTGAAGCCTCTCAAAAATAGCCGGCAA

GTTGAGGTCTCTTGGGAATATCCCGACACTTGGAGCACACCCCACAGCT

ACTTCTCTTTAACCTTTTGTGTGCAAGTTCAAGGTAAAAGCAAGCGGGA

GAAGAAAGACCGGGTGTTTACCGACAAAACCAGCGCCACCGTCATCTGT

CGGAAGAACGCCTCCATCAGCGTGAGGGCTCAAGATCGTTATTACTCCA

GCAGCTGGTCCGAGTGGGCCAGCGTGCCTTGTTCC

(Linker)
GGCGGTGGAGGATCCGGAGGAGGTGGCTCCGGCGGCGGAGGATCT

(Human IL-12 subunit alpha (p35))
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC

(Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG
```

Example 27: Creation of an IL-18/TF/IL-15 DNA Construct

Figure 26:
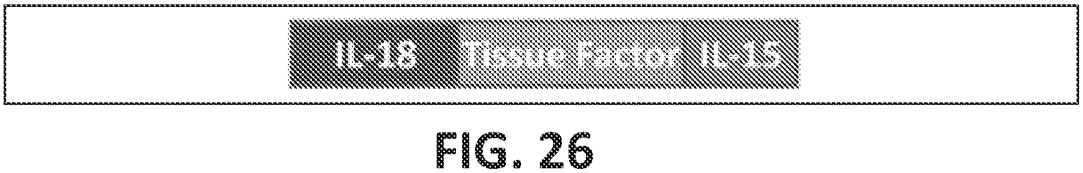
FIG. 26 shows a schematic diagram of an exemplary IL-18/TF/IL-15 DNA construct.

In a non-limiting example, an IL-18/TF/IL-15 construct was made (see FIG. 26) linking the IL-18 sequence to the N-terminus coding region of tissue factor 219, and further linking the IL-18/TF construct with the N-terminus coding region of IL-15. The nucleic acid sequence of the IL-18/TF/

IL-15 construct (including leader sequence), synthesized by Genewiz, is as follows (SEQ ID NO: 119):

```
(Signal peptide)
ATGAAGTGGGTCACATTTATCTCTTTACTGTTCCTCTTCTCCAGCGCCT

ACAGC

(Human IL-18)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT

(HumanTissueFactor219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG

(Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC
```

Example 28: Secretion of IL-12/IL-15RαSu and IL-18/TF/IL-15 Fusion Proteins

Figure 27:
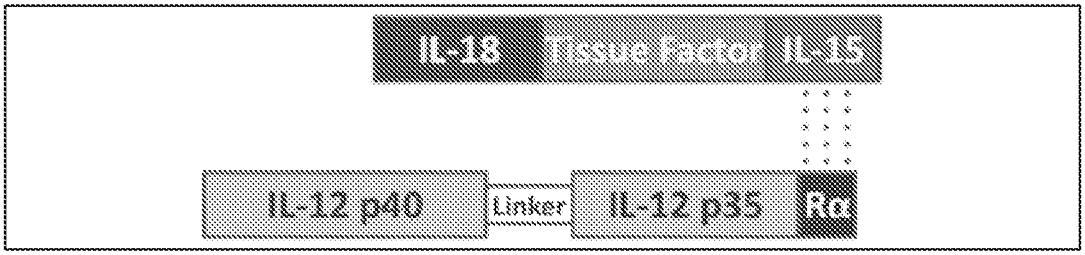
FIG. 27 shows a schematic diagram of the interaction between the exemplary IL-12/IL-15RαSu and IL-18/TF/IL-15 DNA constructs.
Figure 28:
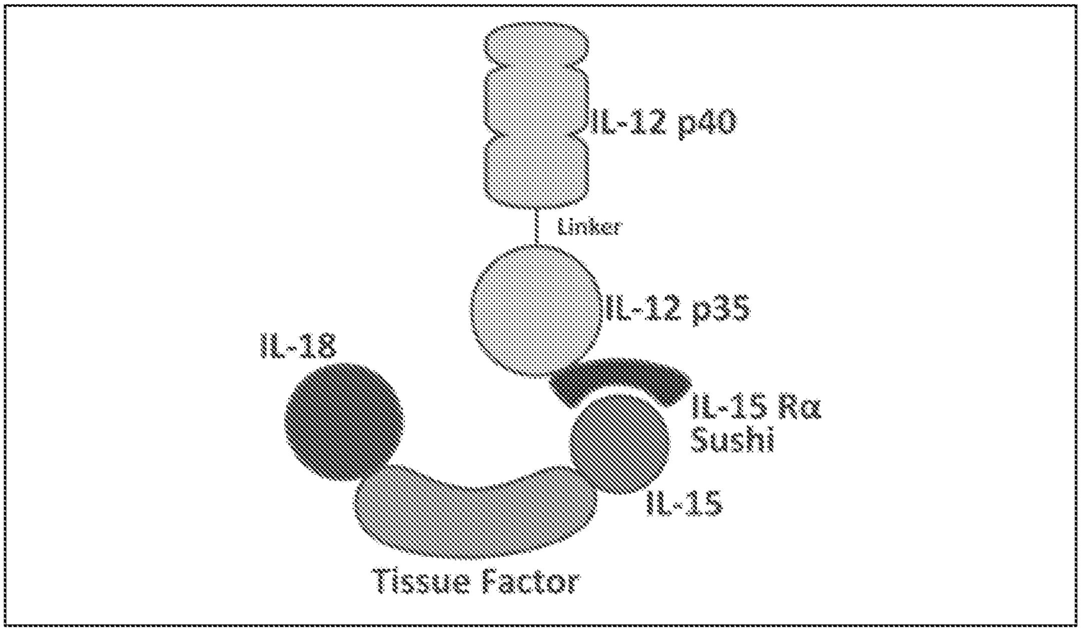
FIG. 28 shows a schematic diagram of the interaction between the exemplary IL-12/IL-15RαSu and IL-18/TF/IL-15 fusion proteins resulting in IL-18/TF/IL-15:IL-12/IL-15RαSu complex (18t15-12s).

The IL-12/IL-15RαSu and IL-18/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-18/TF/IL-15:IL-12/IL-15RαSu protein complex (referred to as 18t15-12s, see FIGS. 27 and 28). The 18t15-12s protein was purified from CHO-K1 cell culture supernatant using anti-TF antibody affinity chromatography and size exclusion chromatography resulting in soluble (non-aggregated) protein complexes consisting of IL-12/IL-15RαSu and IL-18/TF/IL-15 fusion proteins.

The amino acid sequence of the IL12/IL-15RαSu fusion protein (including signal peptide sequence) is as follows (SEQ ID NO: 122):

```
(Signal peptide)
MKWVTFISLLFLFSSAYS

(Human IL-12 subunit beta(p40))
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS

(Linker)
GGGGSGGGGSGGGGS

(Human IL-12 subunit alpha (p35))
RNLPVATPDPGMFPCLHHSQNLLRAVSNMLQKARQTLEFYPCTSEEIDH

EDITKDKTSTVEACLPLELTKNESCLNSRETSFITNGSCLASRKTSFMM

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

S

(Human IL-15R a sushi domain)
ITCPPPMSVEHADIWVKSYSLYSRERYICNSGFKRKAGTSSLTECVLNK

ATNVAHWTTPSLKCIR
```

The amino acid sequence of the IL-18/TF/IL-15 fusion protein (including signal peptide sequence) is as follows (SEQ ID NO: 118):

```
(Signal peptide)
MKWVTFISLLFLFSSAYS

(Human IL-18)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

TIFFQRSVPGHDNKMQFESSSYEGYFLACEKERDLFKLILKKEDELGDR

SIMFTVQNED

(Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF
```

-continued

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

In some cases, the leader (signal sequence) peptide is cleaved from the intact polypeptide to generate the mature form that may be soluble or secreted.

Example 29: Purification of 18t15-12s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Figure 29:
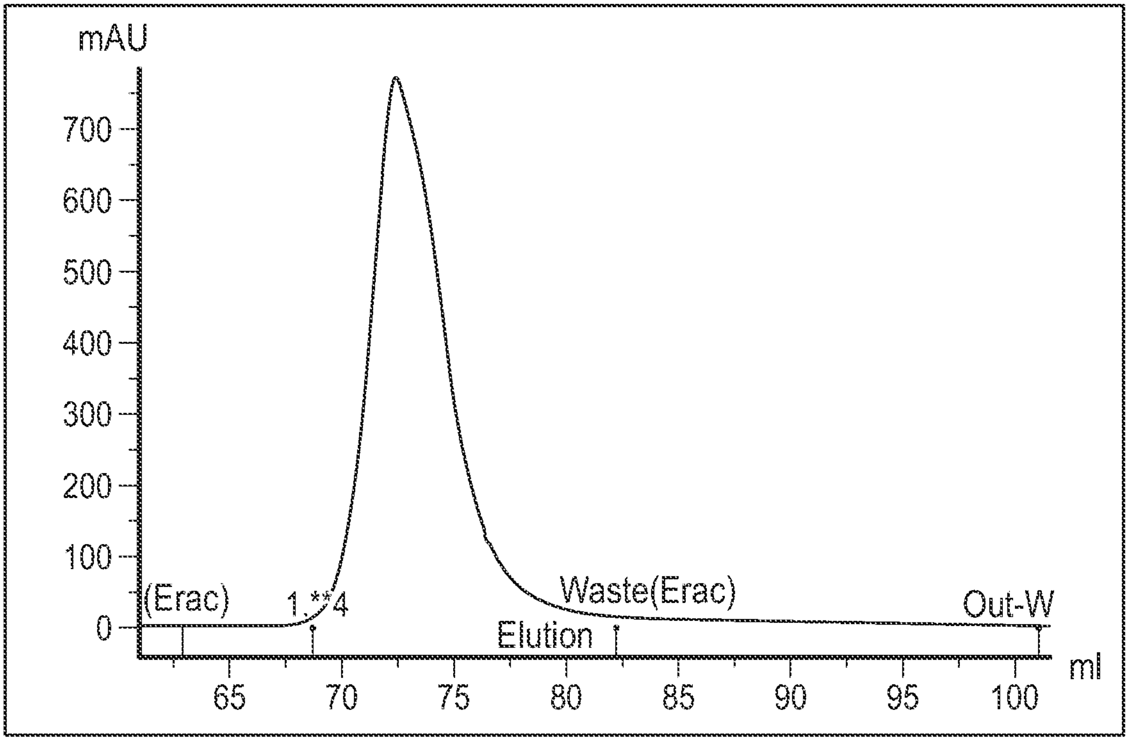
FIG. 29 shows a chromatograph of 18t15-12s purification elution from an anti-TF affinity column.

Cell culture harvest of 18t15-12s was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was neutralized to pH 7.5-8.0 by adding 1M Tris base. The neutralized sample was then buffer exchanged into PBS using Amicon® centrifugal filters with a 30 KDa molecular weight cutoff. FIG. 29 shows that the 18t15-12s complex binds the anti-TF antibody affinity column, wherein TF is an 18t15-12s binding partner. The buffer-exchanged protein sample is stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide and stored at 2-8° C.

Example 30: Size Exclusion Chromatography of 18t15-12s

Figure 30:
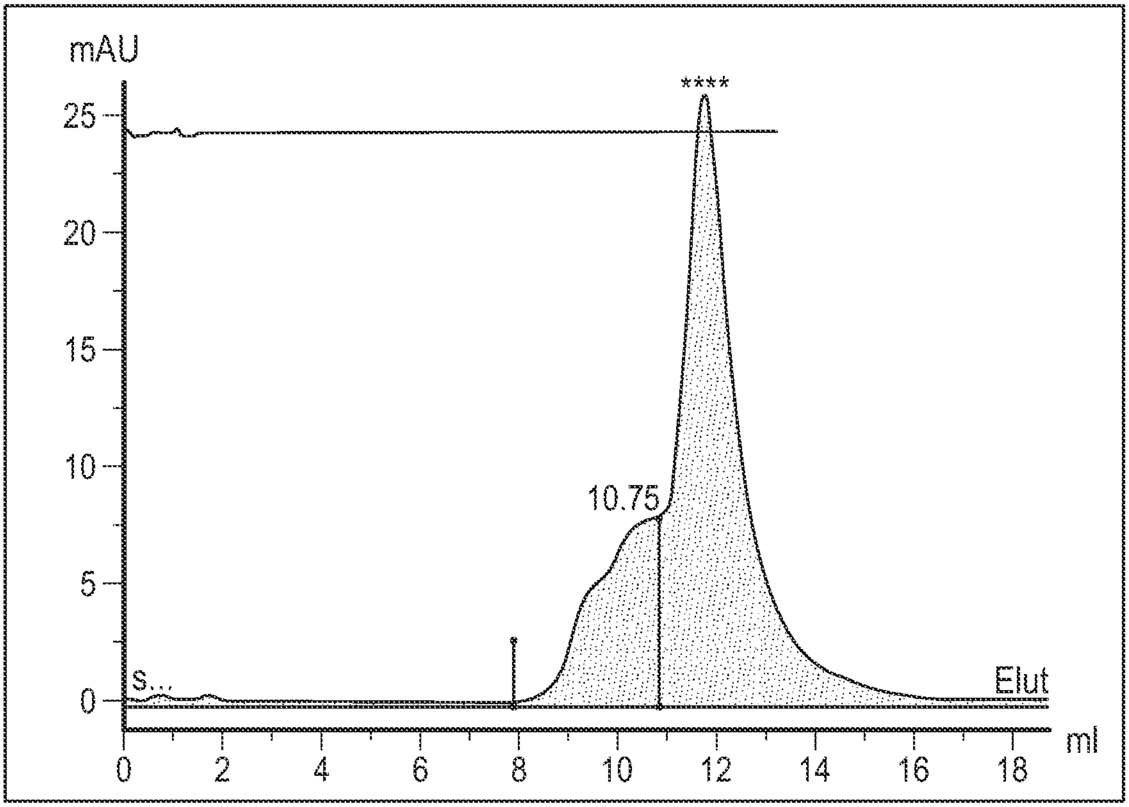
FIG. 30 shows an exemplary chromatographic profile of anti-TF antibody/SEC-purified 18t15-12s protein following elution on an analytical size exclusion column, demonstrating separation of monomeric multiprotein 18t15-12s complexes from protein aggregates.

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.8 mL/min. A capillary loop was used to inject 200 μL of 1 mg/mL of 18t15-12s complex onto the column. The injection was chased with 1.25 column volumes of PBS. The SEC chromatograph is shown in FIG. 30. There is a main 18t15-12s protein peak with a minor high molecular weight peak, likely due to differing degrees of glycosylation of 18t15-12s dimers or aggregates.

Example 31: SDS-PAGE of 18t15-12s

Figure 31:
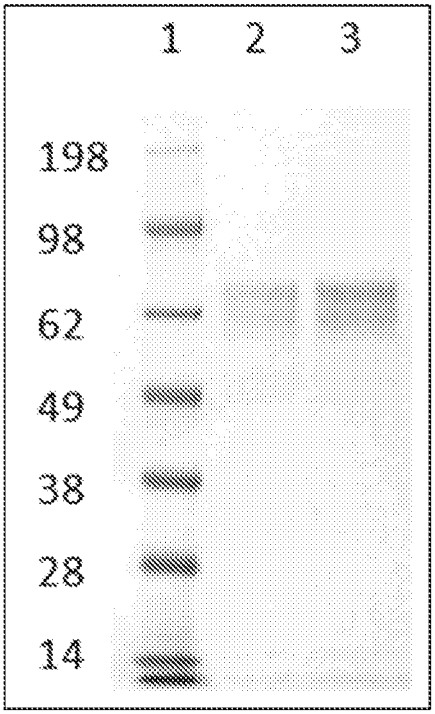
FIG. 31 shows an example of a 4-12% SDS-PAGE of the 18t15-12s complex following disulfide bond reduction. Lane 1: SeeBlue Plus2 marker; Lane 2: anti-TF antibody-purified 18t15-12s (0.5 μg); Lane 3: anti-TF antibody-purified 18t15-12s (1 μg).

To determine the purity and protein molecular weight, the purified 18t15-12s protein sample was analyzed using 4-12% NuPage Bis-Tris protein gel SDS-PAGE. The gel was stained with InstantBlue™ for about 30 min, followed by destaining overnight in purified water. FIG. 31 shows an example SDS gel of anti-TF antibody affinity purified 18t15-12s, with bands at the expected molecular weights (66 kDa and 56 kDa).

Example 32: Glycosylation of 18t15-12s in CHO-K1 Cells

Figure 32:
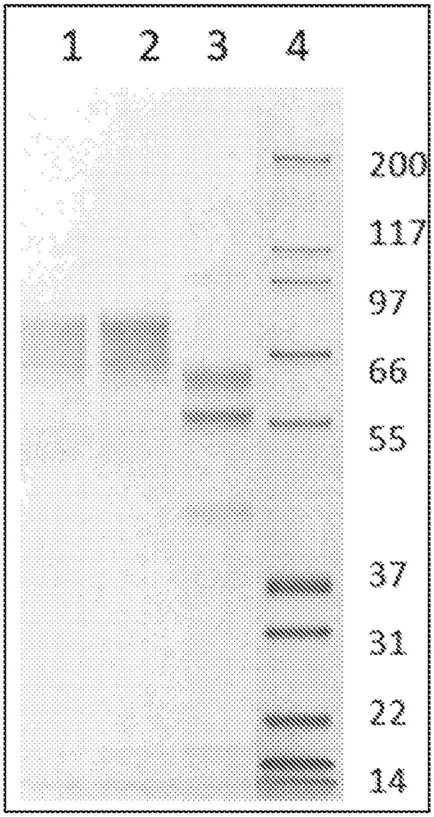
FIG. 32 shows SDS PAGE analysis of deglycosylated and non-deglycosylated 18t15-12s. Lane 1: anti-TF antibody-purified 18t15-12s (0.5 μg), non-deglycosylated; Lane 2: anti-TF antibody-purified 18t15-12s (1 μg), non-deglycosylated; Lane 3: 18t15-12s (1 μg), deglycosylated, Lane 4: Mark12 unstained maker.
Figure 33:
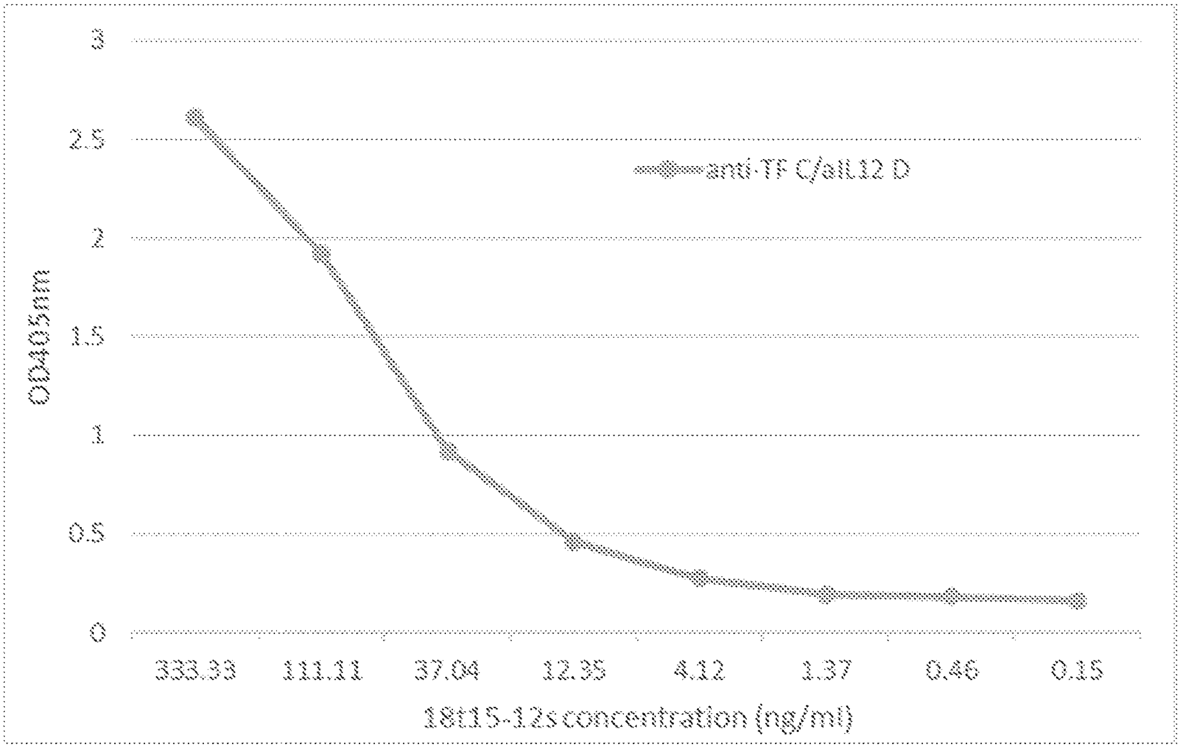
FIG. 33 shows a sandwich ELISA for the 18t15-12s complex, comprising an anti-human tissue factor capture antibody and a biotinylated anti-human IL-12 detection antibody (BAF 219).
Figure 34:
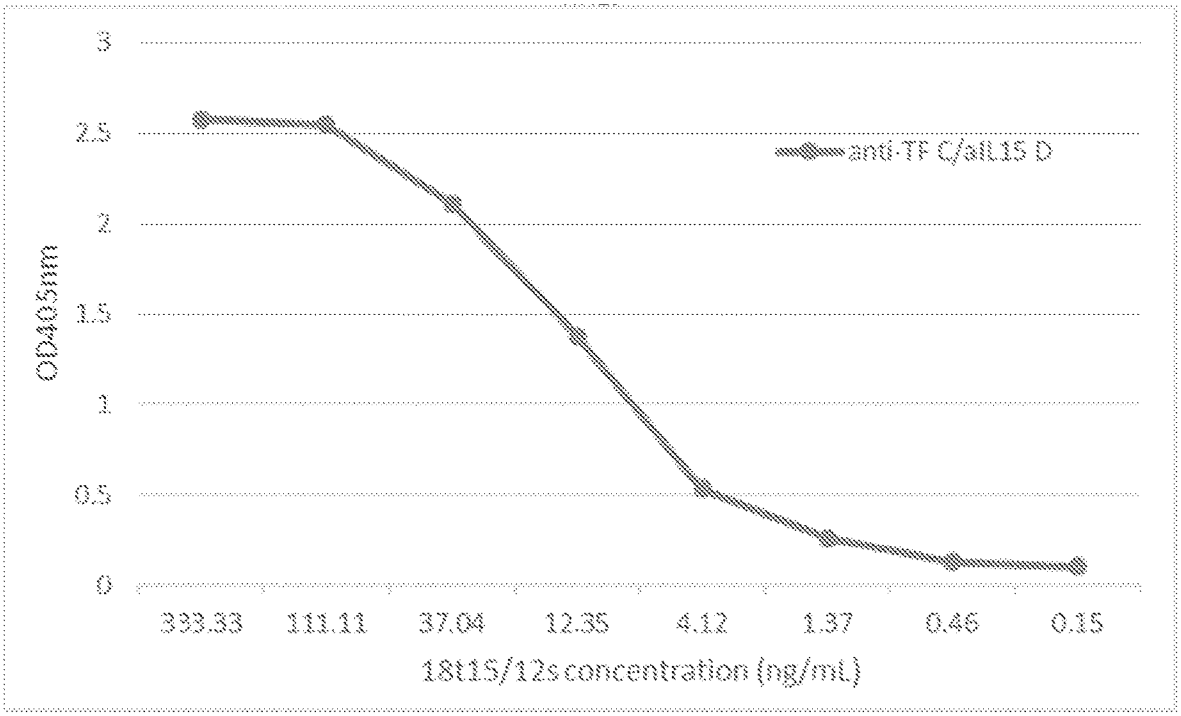
FIG. 34 shows a sandwich ELISA for the 18t15-12s complex, comprising an anti-human tissue factor capture antibody and a biotinylated anti-human IL-15 detection antibody (BAM 247).
Figure 35:
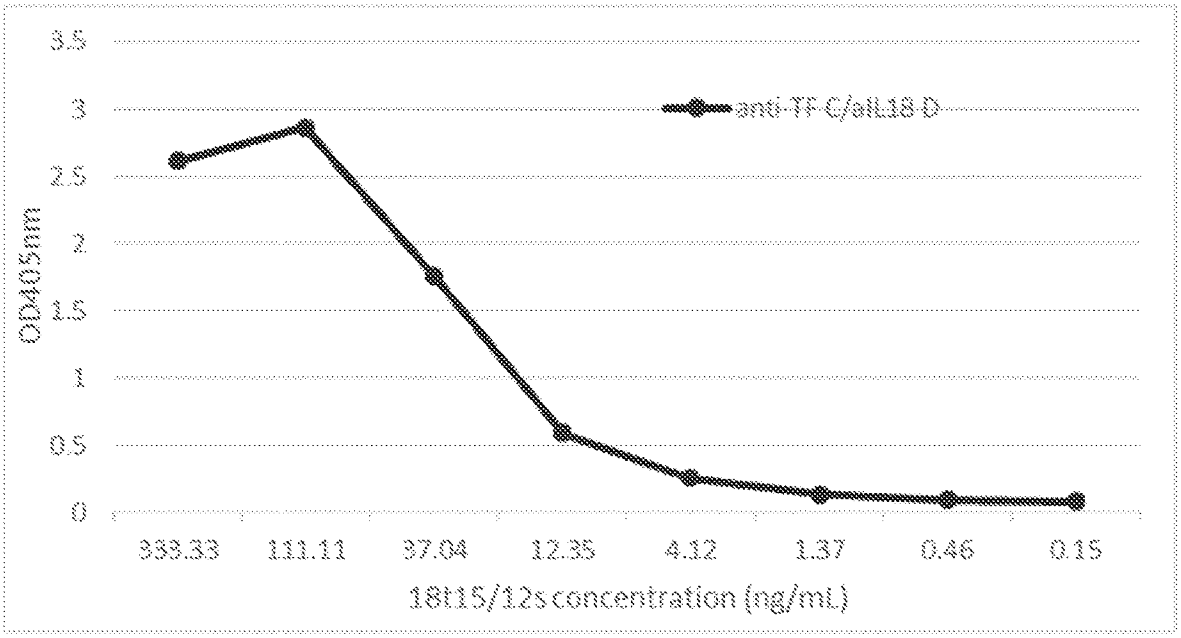
FIG. 35 shows a sandwich ELISA for the 18t15-12s complex, comprising an anti-human tissue factor capture antibody and a biotinylated anti-human IL-18 detection antibody (D045-6).
Figure 36:
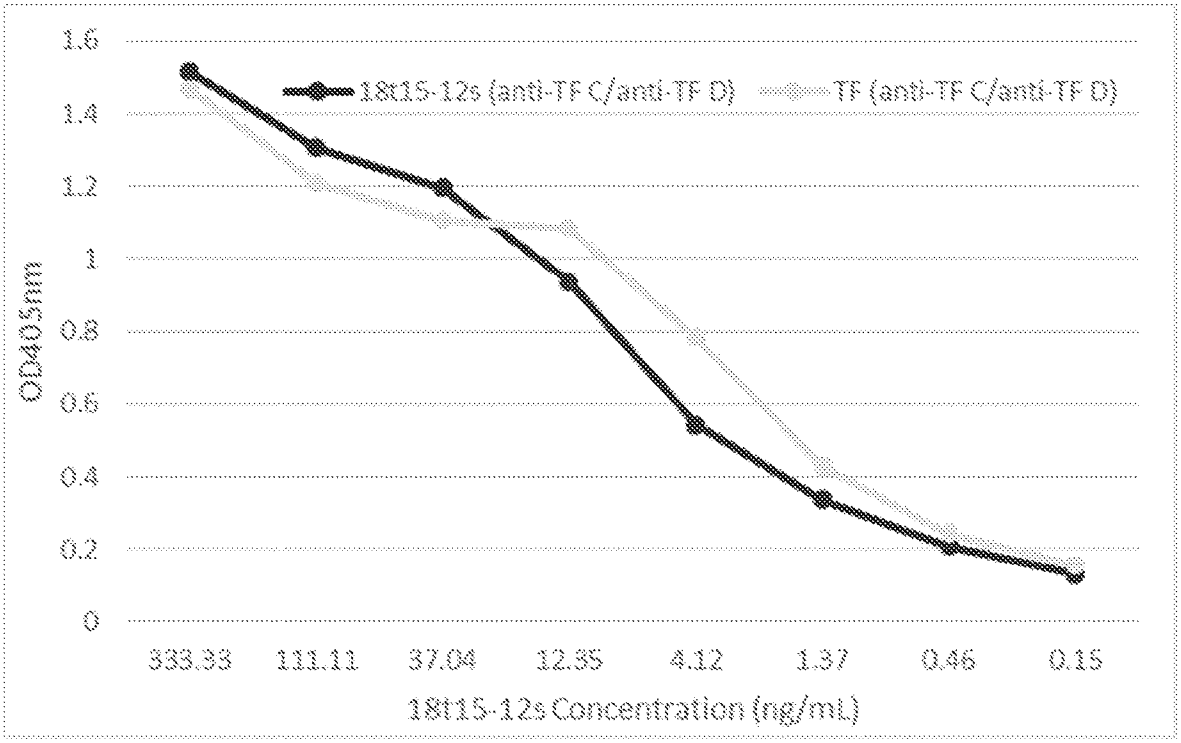
FIG. 36 shows a sandwich ELISA for the 18t15-12s complex, comprising an anti-human tissue factor (I43) capture antibody and an anti-human tissue factor detection antibody.
Figure 37:
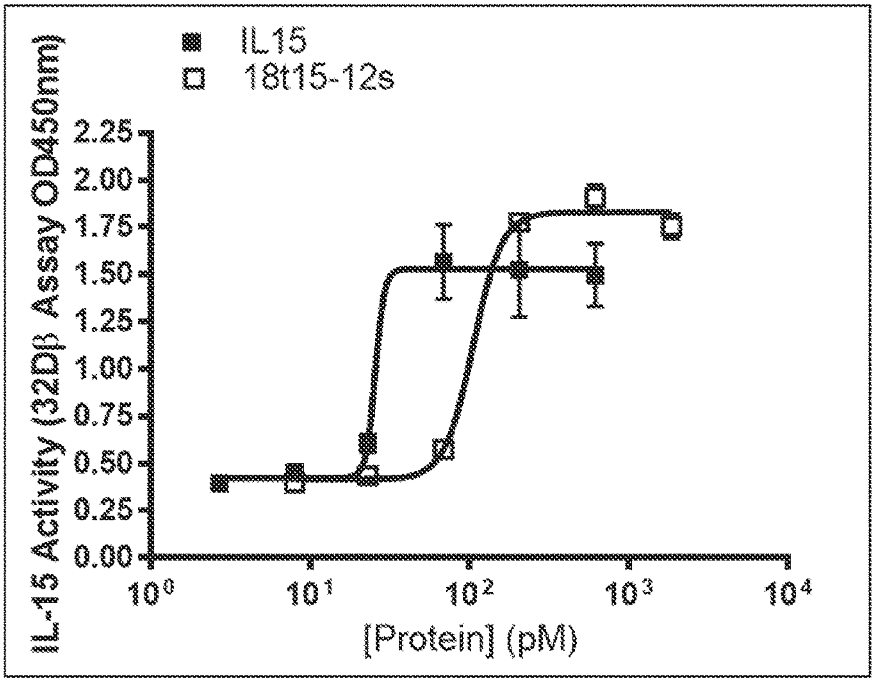
FIG. 37 shows proliferation of IL-15-dependent 32Dβ cells mediated by the 18t15-12s complex (open squares) and recombinant IL-15 (black squares).

Glycosylation of 18t15-12s in CHO-K1 cells was confirmed using the Protein Deglycosylation Mix II kit (New England Biolabs), according to the manufacturer's instructions. FIG. 32 shows an example SDS PAGE of deglycosylated and non-deglycosylated 18t15-12s. Deglycosylation reduces the molecular weight of 18t15-12s as seen in FIG. 32, lane 4.

Example 33: Recombinant Protein Quantitation of 18t15-12s Complexes

The 18t15-12s complex was detected and quantified using standard sandwich ELISA methods (see FIGS. 33-36). Anti-human tissue factor antibody served as the capture antibody and biotinylated anti-human IL-12, IL-15, or IL-18 antibody (BAF 219, BAM 247, D045-6, all R&D Systems) served as the detection antibody. Tissue factor in purified 18t15-12s protein complexes was also detected using an anti-human tissue factor capture antibody (I43), and anti-human tissue factor antibody detection antibody. The I43/anti-TF Ab ELISA was compared to purified tissue factor at similar concentrations.

Example 34: Immunostimulatory Capacity of the 18t15-12s Complex

To assess the IL-15 immunostimulatory activity of the 18t15-12s complex, increasing concentrations of 18t15-12s was added to 32Dβ cells (104 cell/well) in 200 μL IMDM: 10% FBS media. The 32Dβ cells were incubated for 3 days at 37° C. On the fourth day, WST-1 proliferation reagent (10 μL/well) was added and after 4 hours, absorbance was measured at 450 nm to determine cell proliferation based on cleavage of WST-1 to a soluble formazan dye. Bioactivity of human recombinant IL-15 was assessed as a positive control. As shown in FIG. 37, 18t15-12s demonstrated IL-15-dependent cell proliferation of 32Dβ cells. The 18t15-12s complex demonstrated reduced activity compared to human recombinant IL-15, possibly due to the linkage of IL-18 and tissue factor to the IL-15 domain.

Figure 38:
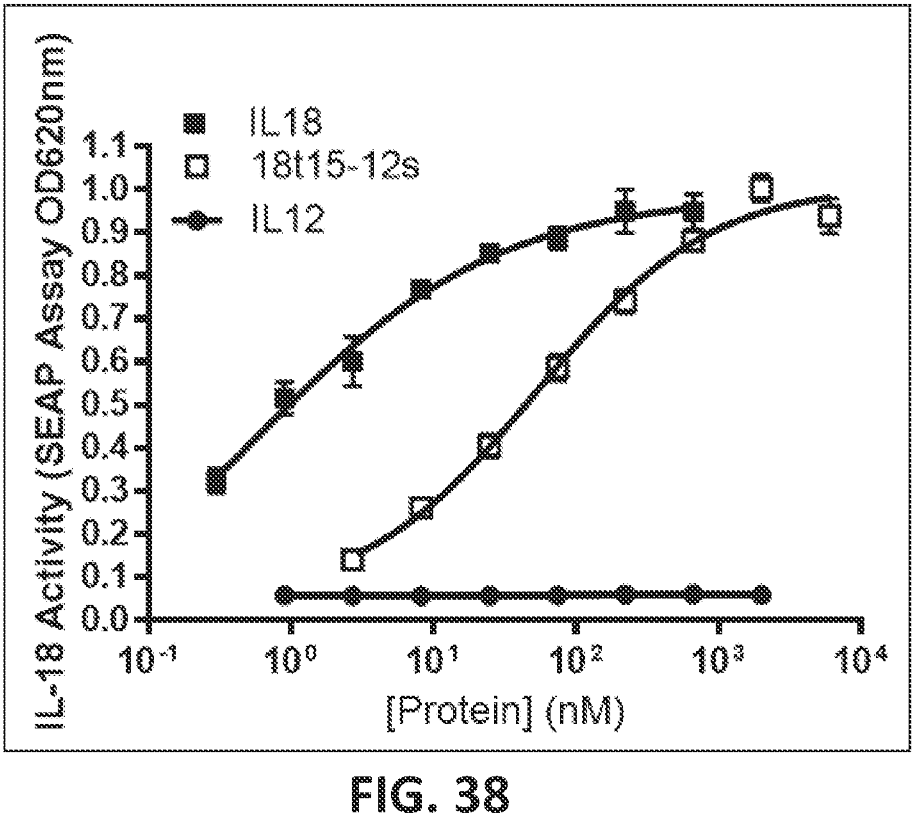
FIG. 38 shows biological activity of IL-18 within the 18t15-12s complex (open squares), where recombinant IL-18 (black squares) and recombinant IL-12 (black circles) serve as positive and negative controls, respectively.
Figure 39:
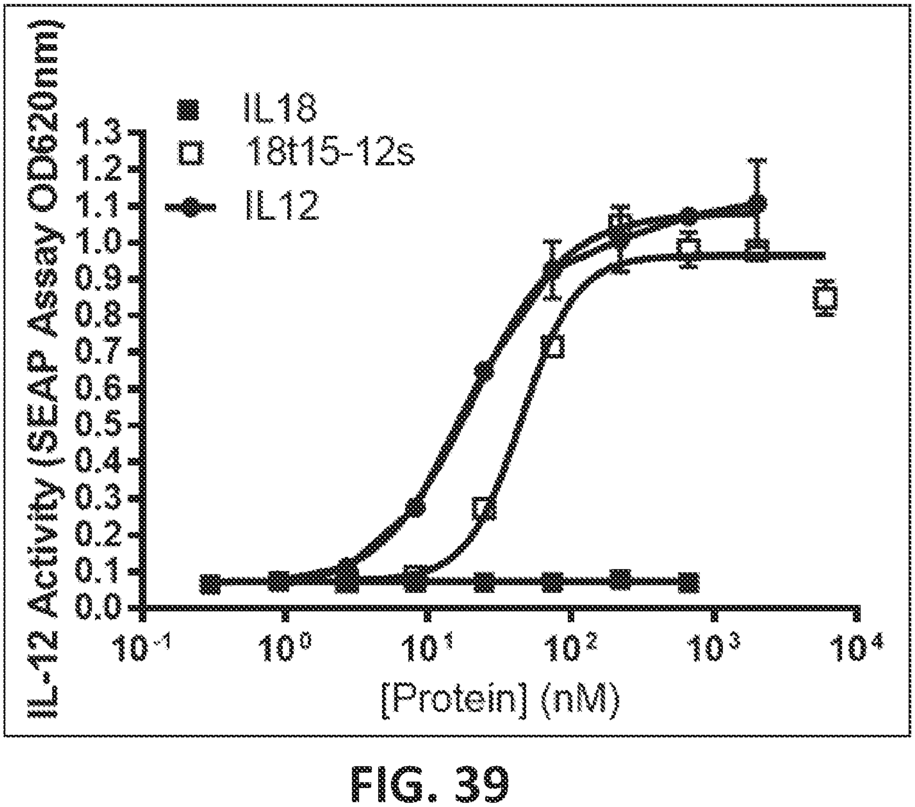
FIG. 39 shows biological activity of IL-12 within the 18t15-12s complex (open squares), where recombinant IL-12 (black circles) and recombinant IL-18 (open squares) serve as positive and negative controls, respectively.

In order to assess the individual activities of IL-12 and IL-18 in the 18t15-12s complex, 18t15-12s was added to HEK-Blue IL-12 and HEK-Blue IL-18 reporter cells ($5\times10^4$ cell/well; hkb-il12 and hkb-hmil18, InvivoGen) in 200 μL IMIDM: 10% heat-inactivated FBS media. Cells were incubated for overnight at 37° C. 20 μl of induced HEK-Blue IL-12 and HEK-Blue IL-18 reporter cell supernatant was added to 180 μl of QUANTI-Blue (InvivoGen), and incubated for 1-3 hours at 37° C. IL-12 or IL-18 activity was assessed by measuring absorbance at 620 nm. Human recombinant IL-12 or IL-18 was assessed as a positive or negative control. As shown in FIGS. 38 and 39, the each of the cytokine domains of the 18t15-12s complex retain specific biological activity. The activity of 18t15-12s was reduced compared to that of human recombinant IL-18 or IL-12, possibly due to linkage of IL-15 and tissue factor to the IL-18 domain and linkage of IL-12 to the IL-15Rα sushi domain.

Example 35: Induction of Cytokine-Induced Memory-Like NK Cells by the 18t15-12s Complex Cytokine-induced memory-like NK cells can be induced ex vivo following overnight stimulation of purified NK cells with saturating amounts of IL-12 (10 ng/mL), IL-15 (50 ng/mL), and IL-18 (50 ng/mL). These memory-like properties have been measured through expression of IL-2 receptor α (IL-2Rα, CD25), CD69 (and other activation markers), and increased IFN-γ production. To evaluate the ability of 18t15-12s complexes to promote generation of cytokine-induced memory-like NK cells, purified human NK cells (>95% $CD56^+$) were stimulated for 14-18 hours with 0.01 nM to 10000 nM of the 18t15-12s complex or a combination of individual cytokines (recombinant IL-12 (10 ng/mL), IL-18 (50 ng/mL), and IL-15 (50 ng/mL)). Cell-surface CD25 and CD 69 expression and intracellular IFN-γ levels were assessed by antibody-staining and flow cytometry.

Figure 40A:
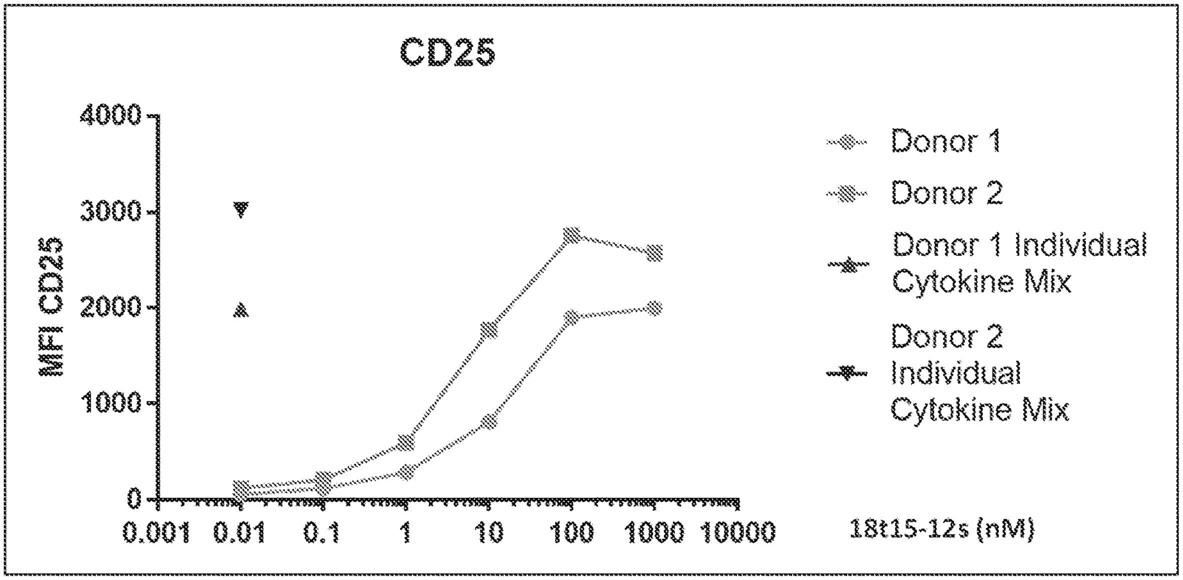
FIG. 40A shows a flow cytometry graph of cell-surface CD25 expression of NK cells induced by the 18t15-12s complex.
Figure 40B:
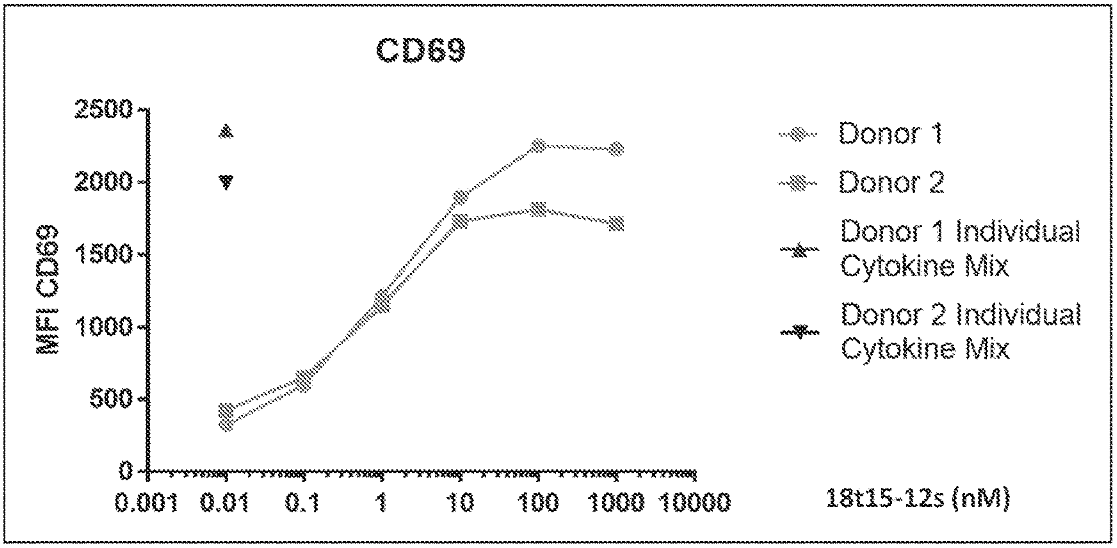
FIG. 40B shows a flow cytometry graph of cell-surface CD69 expression of NK cells induced by the 18t15-12s complex.

Fresh human leukocytes were obtained from a blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2\times10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either a mixture of cytokines hIL-12 (10 ng/mL) (Biolegend), hIL-18 (50 ng/mL) (R&D Systems) and hIL-15 (50 ng/mL) (NCI) or with 0.01 nM to 10000 nM of the 18t15-12s at 37° C., 5% $CO_2$ for 14-18 hrs. The cells were then harvested and surface stained with CD56-BV421, CD16-BV510, CD25-PE, CD69-APC-Fire750 specific antibodies (BioLegend) for 30 minutes. After staining, cells were washed (1500 RPM for 5 minutes at room temperature) in FACS buffer (1×PBS (Hyclone), with 0.5% BSA (EMD Millipore) and 0.001% sodium azide (Sigma)). After two washes, cells were analyzed using a BD FACSCelesta™ flow cytometer (Plotted Data-Mean Fluorescence Intensity, see FIGS. 40A and 40B).

Figure 41:
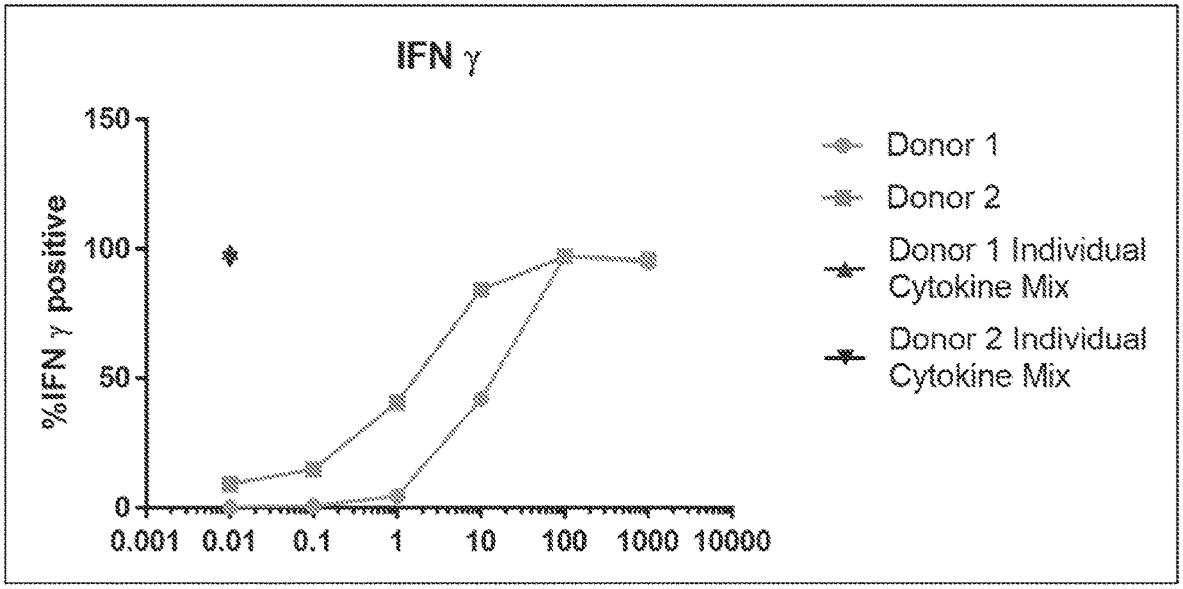
FIG. 41 shows a flow cytometry graph of intracellular interferon gamma expression of NK cells induced by the 18t15-12s complex.

Fresh human leukocytes were obtained from a blood bank and CD56+ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2\times10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either a cytokine mix of hIL-12 (10 ng/mL) (Biolegend), hIL-18 (50 ng/mL) (R&D), and hIL-15 (50 ng/mL) (NCI), or 0.01 nM to 10000 nM of the 18t15-12s complex at 37° C., 5% CO2 for 14-18 hrs. The cells were then treated with 10 μg/mL of Brefeldin A (Sigma) and 1× of Monensin (eBioscience) for 4 hrs before harvesting and staining for CD56-BV421, CD16-BV510, CD25-PE, CD69-APCFire750 for 30 minutes. After staining, cells were washed (1500 RPM for 5 minutes in room temperature) in FACS buffer (1×PBS (Hyclone), with 0.5% BSA (EMD Millipore) and 0.001% sodium azide (Sigma)) and fixed for 10 minutes at room temperature. After fixation, cells were washed (1500 RPM for 5 minutes in room temperature) in 1× permeabilized buffer (eBioscience) and stained with IFN-γ-PE Ab (Biolegend) for 30 minutes at room temperature. Cells were washed once again with 1× permeabilized buffer and then washed with FACS buffer. Cell pellets were resuspended in 300 μls of FACS buffer and analyzed using a BD FACSCelesta™ flow cytometer (Plotted % of IFN-γ Positive Cells, see FIG. 41).

Example 36: In Vitro Cytotoxicity of NK Cells Against Human Tumor Cells

Figure 42:
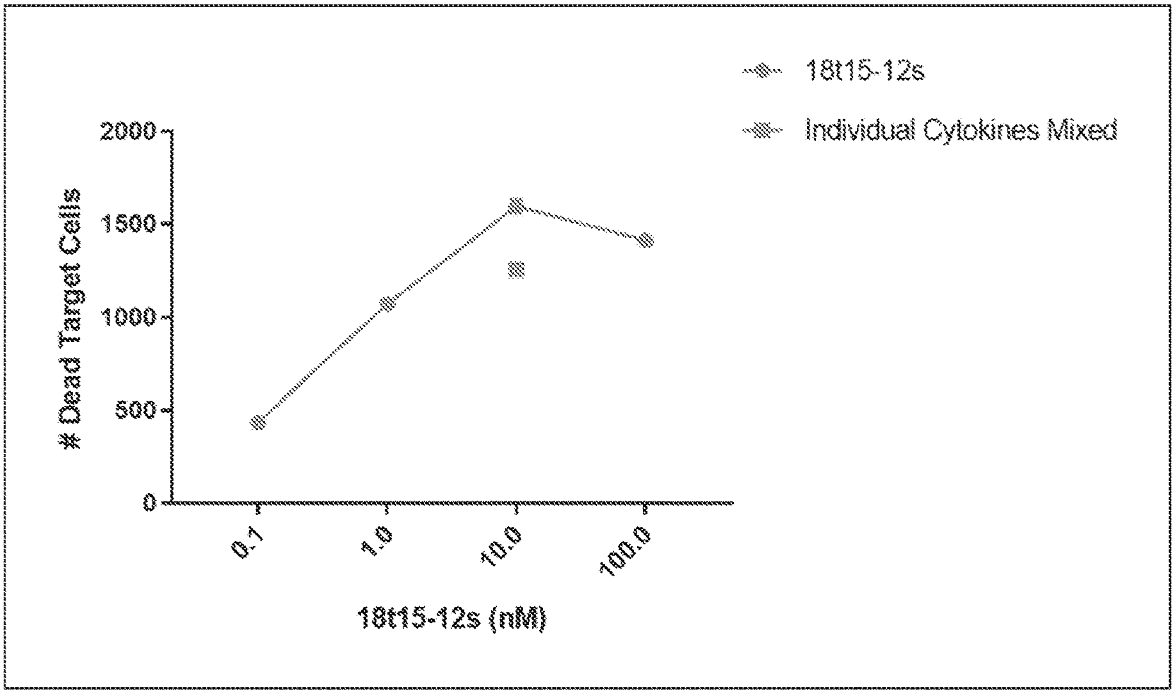
FIG. 42 shows a bar graph showing cytotoxicity of 18t15-12s induced human NK cells against K562. K562 cells (labeled with Celltrace violet) at 1×10^5/well and human NK cells (NK cells were isolated from human blood buffy coat with StemCell human NK cell purification kit) at 2×10^5/well were incubated with 18t15-12s in RPMI-10 for 20 hours. Cell mixtures were harvested, stained with propidium iodide (PI), and analyzed using a BD FACSCelesta™ flow cytometer. The graph represents duplicated samples.

Human myelogenous leukemia cells, K562 (CellTrace violet labelled), were incubated with purified human NK cells in the presence of increasing concentrations of the 18t15-12s complex or a mixture of cytokines as a control. After 20 hours, the cultures were harvested, stained with propidium iodide (PI), and assessed by flow cytometry. As shown in FIG. 42, the 18t15-12s complex induced human NK cytotoxicity against K562, at levels similar or greater than the cytokine mixture, wherein both the 18t15-12s complex and the cytokine mixture induced greater cytotoxicity than the medium control.

Figure 43:
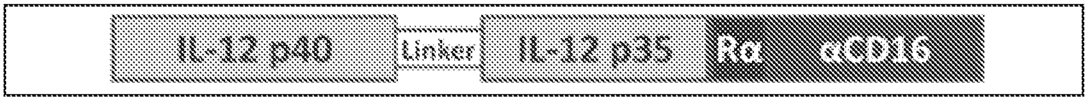
FIG. 43 shows a schematic diagram of an exemplary IL-12/IL-15RαSu/αCD16 DNA construct.

Example 37: Creation of IL-12/IL-15RαSu/αCD16scFv and IL-18/TF/IL-15 DNA Constructs In a non-limiting example, IL-12/IL-15RαSu/αCD16scFv and IL-18/TF/IL-15 DNA constructs were created (see FIG. 43). The human IL-12 subunit sequences, human IL-15RαSu sequence, human IL-15 sequence, human tissue factor 219 sequence, and human IL-18 sequence were synthesized by Genewiz. A DNA construct was made linking the IL-12 subunit beta (p40) to IL-12 subunit alpha (p35) with a GS (3) linker to generate a single chain version of IL-12, directly linking the IL-12 sequence to the IL-15RαSu sequence, and directly linking the IL-12/IL-15RαSu construct to the N-terminus coding region of αCD16scFv (referred as 18t15-12s16).

The nucleic acid sequence of the IL-12/IL-15RαSu/αCD16scFv construct is as follows (SEQ ID NO: 156):

```
(Signal peptide)
ATGAAATGGGTGACCTTTATTTCTTTACTGTTCCTCTTTAGCAGCGCCT

ACTCC

(Human IL-12 subunit beta (p40))
ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

AAGGAGCCCAAGAATAAGACCTTTTTAAGGTGTGAGGCCAAAAACTACA

GCGGTCGTTTCACTTGTTGGTGGCTGACCACCATTTCCACCGATTTAAC

CTTCTCCGTGAAAAGCAGCCGGGGAAGCTCCGACCCTCAAGGTGTGACA

TGTGGAGCCGCTACCCTCAGCGCTGAGAGGGTTCGTGGCGATAACAAGG

AATACGAGTACAGCGTGGAGTGCCAAGAAGATAGCGCTTGTCCCGCTGC

CGAAGAATCTTTACCCATTGAGGTGATGGTGGACGCCGTGCACAAACTC

AAGTACGAGAACTACACCTCCTCCTTCTTTATCCGGGACATCATTAAGC

CCGATCCTCCTAAGAATTTACAGCTGAAGCCTCTCAAAAATAGCCGGCA

AGTTGAGGTCTCTTGGGAATATCCCGACACTTGGAGCACACCCCACAGC
```

-continued

TACTTCTCTTTAACCTTTTGTGTGCAAGTTCAAGGTAAAAGCAAGCGGG

AGAAGAAAGACCGGGTGTTTACCGACAAAACCAGCGCCACCGTCATCTG

TCGGAAGAACGCCTCCATCAGCGTGAGGGCTCAAGATCGTTATTACTCC

AGCAGCTGGTCCGAGTGGGCCAGCGTGCCTTGTTCC (Linker)
GGCGGTGGAGGATCCGGAGGAGGTGGCTCCGGCGGCGGAGGATCT (Human IL-12 subunit alpha (p35))
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC (Human IL-15R a sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG (anti-Human CD16 light chain variable domain)
TCCGAGCTGACCCAGGACCCTGCTGTGTCCGTGGCTCTGGGCCAGACCG

TGAGGATCACCTGCCAGGGCGACTCCCTGAGGTCCTACTACGCCTCCTG

GTACCAGCAGAAGCCCGGCCAGGCTCCTGTGCTGGTGATCTACGGCAAG

AACAACAGGCCCTCCGGCATCCCTGACAGGTTCTCCGGATCCTCCTCCG

GCAACACCGCCTCCCTGACCATCACAGGCGCTCAGGCCGAGGACGAGGC

TGACTACTACTGCAACTCCAGGGACTCCTCCGGCAACCATGTGGTGTTC

GGCGGCGGCACCAAGCTGACCGTGGGCCAT (Linker)
GGCGGCGGCGGCTCCGGAGGCGGCGGCAGCGGCGGAGGAGGATCC (anti-Human CD16 heavy chain variable domain)
GAGGTGCAGCTGGTGGAGTCCGGAGGAGGAGTGGTGAGGCCTGGAGGCT

CCCTGAGGCTGAGCTGTGCTGCCTCCGGCTTCACCTTCGACGACTACGG

CATGTCCTGGGTGAGGCAGGCTCCTGGAAAGGGCCTGGAGTGGGTGTCC

GGCATCAACTGGAACGGCGGATCCACCGGCTACGCCGATTCCGTGAAGG

GCAGGTTCACCATCAGCAGGGACAACGCCAAGAACTCCCTGTACCTGCA

GATGAACTCCCTGAGGGCCGAGGACACCGCCGTGTACTACTGCGCCAGG

-continued

GGCAGGTCCCTGCTGTTCGACTACTGGGGACAGGGCACCCTGGTGACCG

TGTCCAGG

Figure 44:
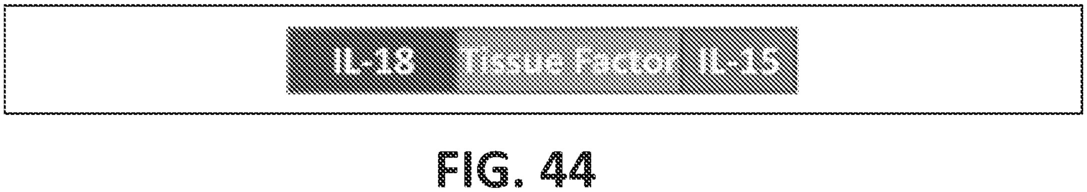
FIG. 44 shows a schematic diagram of an exemplary IL-18/TF/IL-15 DNA construct.

Constructs were also made linking the IL-18 sequence to the N-terminus coding region of tissue factor 219, and linking the IL-18/TF construct with the N-terminus coding region of IL-15 (see FIG. 44). The nucleic acid sequence of the IL-18/TF/IL-15 construct (including leader sequence) is as follows (SEQ ID NO: 119):

(Signal peptide)
ATGAAGTGGGTCACATTTATCTCTTTACTGTTCCTCTTCTCCAGCGCCT

ACAGC (Human IL-18)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT (Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

-continued

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

Figure 45:
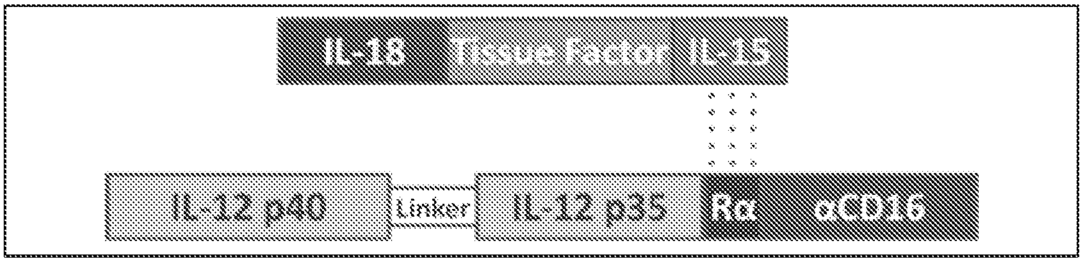
FIG. 45 shows a schematic diagram of the interaction between the exemplary IL-12/IL-15RαSu/αCD16scFv and IL-18/TF/IL-15 DNA constructs.
Figure 46:
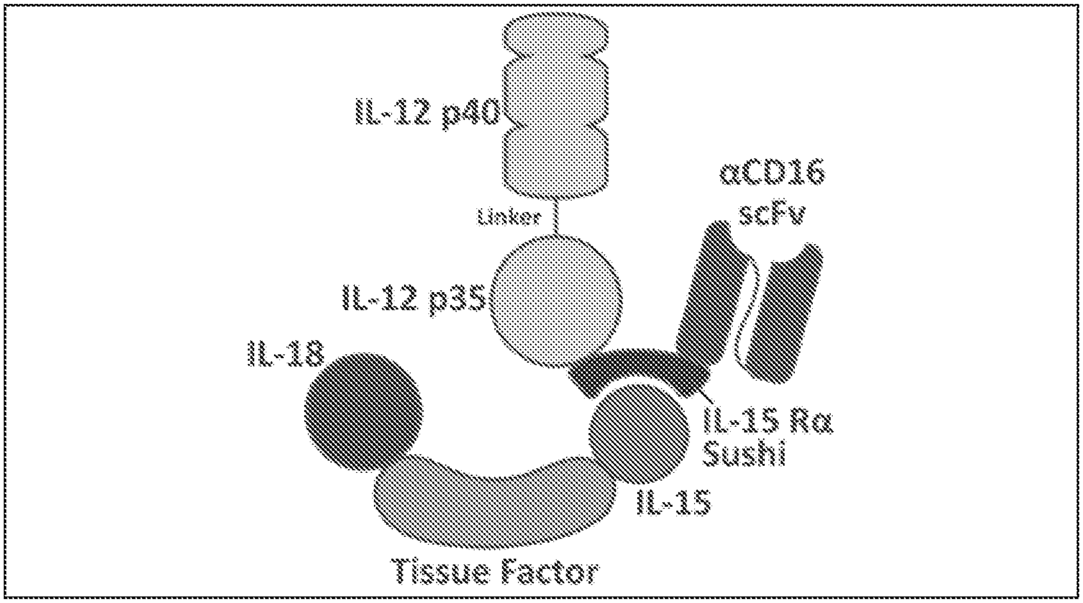
FIG. 46 shows a schematic diagram of an exemplary 18t15-12s/αCD16 protein complex.

Example 38: Secretion of IL-12/IL-15RαSu/αCD16scFv and IL-18/TF/IL-15 Fusion Proteins The IL-12/IL-15RαSu/αCD16scFv and IL-18/TF/IL-15 constructs were cloned into a pMSGV-1 modified retrovirus expression vector (Hughes, *Hum Gene Ther* 16:457-72, 2005, herein incorporated by reference), and the expression vector was transfected into CHO-K1 cells. Co-expression of the two constructs in CHO-K1 cells resulted in secretion of a soluble IL-18/TF/IL-15:IL-12/IL-15RαSu/αCD16scFv protein complex (referred to as 18t15-12s/αCD16). Co-expression of the two constructs in CHO-K1 cells resulted in secretion of the soluble IL-18/TF/IL-15:IL-12/IL-15RαSu/αCD16scFv protein complex (referred to as 18t15-12s/αCD16, see FIGS. 45 and 46), which can be purified by anti-TF antibody affinity and other chromatography methods. In some cases, the signal peptide is cleaved from the intact polypeptide to generate the mature form.

The amino acid sequence of the IL-12/IL-15RαSu/αCD16scFv fusion protein (including signal peptide sequence) is as follows (SEQ ID NO: 155):

(Signal peptide)
MKWVTFISLLFLFSSAYS (Human IL-12 subunit beta (p40))
IWELKKDVYVVELDWYPDAPGEMVVLTCDTPEEDGITWTLDQSSEVLGS

GKTLTIQVKEFGDAGQYTCHKGGEVLSHSLLLLHKKEDGIWSTDILKDQ

KEPKNKTFLRCEAKNYSGRFTCWWLTTISTDLTFSVKSSRGSSDPQGVT

CGAATLSAERVRGDNKEYEYSVECQEDSACPAAEESLPIEVMVDAVHKL

KYENYTSSFFIRDIIKPDPPKNLQLKPLKNSRQVEVSWEYPDTWSTPHS

YFSLTFCVQVQGKSKREKKDRVFTDKTSATVICRKNASISVRAQDRYYS

SSWSEWASVPCS (Linker)
GGGGSGGGGSGGGGS (Human IL-12 subunit alpha (p35))
RNLPVATPDPGMFPCLHHSQNLLRAVSNMLQKARQTLEFYPCTSEEIDH

EDITKDKTSTVEACLPLELTKNESCLNSRETSFITNGSCLASRKTSFMM

ALCLSSIYEDLKMYQVEFKTMNAKLLMDPKRQIFLDQNMLAVIDELMQA

LNFNSETVPQKSSLEEPDFYKTKIKLCILLHAFRIRAVTIDRVMSYLNA

S (Human IL-115R a sushi domain)
ITCPPPMSVEHADIWVKSYSLYSRERYICNSGFKRKAGTSSLTECVLNK

ATNVAHWTTPSLKCIR (anti-Human CD16 light chain variable domain)
SELTQDPAVSVALGQTVRITCQGDSLRSYYASWYQQKPGQAPVLVIYGK

NNRPSGIPDRFSGSSSGNTASLTITGAQAEDEADYYCNSRDSSGNHVVF

GGGTKLTVGH (Linker)
GGGGSGGGGSGGGGS

-continued (anti-Human CD16 heavy chain variable domain)
EVQLVESGGGVVRPGGSLRLSCAASGFTFDDYGMSWVRQAPGKGLEWVS

GINWNGGSTGYADSVKGRFTISRDNAKNSLYLQMNSLRAEDTAVYYCAR

GRSLLFDYWGQGTLVTVSR

The amino acid sequence of the IL-18/TF/IL-15 fusion protein (including leader sequence) is as follows (SEQ ID NO: 118):

(Signal peptide)
MKWVTFISLLFLFSSAYS (Human IL-18)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

IIFFQRSVPGHDNKMQFESSSYEGYFLACEKERDLFKLILKKEDELGDR

SIMFTVQNED (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQNIFINTS

Example 39: Creation of IL-18/IL-15RαSu and IL-12/TF/IL-15 DNA Constructs

In a non-limiting example, IL-18/IL-15RαSu and IL-12/TF/IL-15 DNA constructs were created. The human IL-18 subunit sequences, human IL-15RαSu sequence, human IL-12 sequence, human tissue factor 219 sequence, and human IL-15 sequence were synthesized by Genewiz. A DNA construct was made linking IL-18 directly to IL-15RαSu. An additional construct was also made linking IL-12 sequence to the N-terminus coding region of human tissue factor 219 form, and further linking the IL-12/TF construct to the N-terminus coding region of IL-15. As described above, a single-chain version of IL-12 (p40-linker-p35) was used.

The nucleic acid sequence of the IL-18/IL-15RαSu construct (including signal peptide sequence) is as follows (SEQ ID NO: 189):

(Signal peptide)
ATGAAGTGGGTCACATTTATCTCTTTACTGTTCCTCTTCTCCAGCGCCT

ACAGC (Human IL-18)
TACTTCGGCAAACTGGAATCCAAGCTGAGCGTGATCCGGAATTTAAACG

ACCAAGTTCTGTTTATCGATCAAGGTAACCGGCCTCTGTTCGAGGACAT

GACCGACTCCGATTGCCGGGACAATGCCCCCCGGACCATCTTCATTATC

-continued

TCCATGTACAAGGACAGCCAGCCCCGGGGCATGGCTGTGACAATTAGCG

TGAAGTGTGAGAAAATCAGCACTTTATCTTGTGAGAACAAGATCATCTC

CTTTAAGGAAATGAACCCCCCCGATAACATCAAGGACACCAAGTCCGAT

ATCATCTTCTTCCAGCGGTCCGTGCCCGGTCACGATAACAAGATGCAGT

TCGAATCCTCCTCCTACGAGGGCTACTTTTTAGCTTGTGAAAAGGAGAG

GGATTTATTCAAGCTGATCCTCAAGAAGGAGGACGAGCTGGGCGATCGT

TCCATCATGTTCACCGTCCAAAACGAGGAT (Human IL-115R a sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG

The nucleic acid sequence of the IL-12/TF/IL-15 construct (including leader sequence) is as follows (SEQ ID NO: 190):

(Signal peptide)
ATGAAATGGGTGACCTTTATTTCTTTACTGTTCCTCTTTAGCAGCGCCT

ACTCC (Human IL-12 subunit beta (p40))
ATTTGGGAACTGAAGAAGGACGTCTACGTGGTCGAACTGGACTGGTATC

CCGATGCTCCCGGCGAAATGGTGGTGCTCACTTGTGACACCCCCGAAGA

AGACGGCATCACTTGGACCCTCGATCAGAGCAGCGAGGTGCTGGGCTCC

GGAAAGACCCTCACAATCCAAGTTAAGGAGTTCGGAGACGCTGGCCAAT

ACACATGCCACAAGGGAGGCGAGGTGCTCAGCCATTCCTTATTATTATT

ACACAAGAAGGAAGACGGAATCTGGTCCACCGACATTTTAAAAGATCAG

AAGGAGCCCAAGAATAAGACCTTTTTAAGGTGTGAGGCCAAAAACTACA

GCGGTCGTTTCACTTGTTGGTGGCTGACCACCATTTCCACCGATTTAAC

CTTCTCCGTGAAAAGCAGCCGGGGAAGCTCCGACCCTCAAGGTGTGACA

TGTGGAGCCGCTACCCTCAGCGCTGAGAGGGTTCGTGGCGATAACAAGG

AATACGAGTACAGCGTGGAGTGCCAAGAAGATAGCGCTTGTCCCGCTGC

CGAAGAATCTTTACCCATTGAGGTGATGGTGGACGCCGTGCACAAACTC

AAGTACGAGAACTACACCTCCTCCTTCTTTATCCGGGACATCATTAAGC

CCGATCCTCCTAAGAATTTACAGCTGAAGCCTCTCAAAAATAGCCGGCA

AGTTGAGGTCTCTTGGGAATATCCCGACACTTGGAGCACACCCCACAGC

TACTTCTCTTTAACCTTTTGTGTGCAAGTTCAAGGTAAAAGCAAGCGGG

AGAAGAAAGACCGGGTGTTTACCGACAAAACCAGCGCCACCGTCATCTG

TCGGAAGAACGCCTCCATCAGCGTGAGGGCTCAAGATCGTTATTACTCC

AGCAGCTGGTCCGAGTGGGCCAGCGTGCCTTGTTCC (Linker)
GGCGGTGGAGGATCCGGAGGAGGTGGCTCCGGCGGCGGAGGATCT (Human IL-12 subunit alpha (p35))
CGTAACCTCCCCGTGGCTACCCCCGATCCCGGAATGTTCCCTTGTTTAC

ACCACAGCCAGAATTTACTGAGGGCCGTGAGCAACATGCTGCAGAAAGC

-continued

TAGGCAGACTTTAGAATTTTACCCTTGCACCAGCGAGGAGATCGACCAT

GAAGATATCACCAAGGACAAGACATCCACCGTGGAGGCTTGTTTACCTC

TGGAGCTGACAAAGAACGAGTCTTGTCTCAACTCTCGTGAAACCAGCTT

CATCACAAATGGCTCTTGTTTAGCTTCCCGGAAGACCTCCTTTATGATG

GCTTTATGCCTCAGCTCCATCTACGAGGATTTAAAGATGTACCAAGTGG

AGTTCAAGACCATGAACGCCAAGCTGCTCATGGACCCTAAACGGCAGAT

CTTTTTAGACCAGAACATGCTGGCTGTGATTGATGAGCTGATGCAAGCT

TTAAACTTCAACTCCGAGACCGTCCCTCAGAAGTCCTCCCTCGAGGAGC

CCGATTTTTACAAGACAAAGATCAAACTGTGCATTTTACTCCACGCCTT

TAGGATCCGGGCCGTGACCATTGACCGGGTCATGAGCTATTTAAACGCC

AGC (Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

Example 40: Secretion of IL-18/IL-15RαSu and IL-12/TF/IL-15 Fusion Proteins

The IL-18/IL-15RαSu and IL-12/TF/IL-15 constructs were cloned into a pMSGV-1 modified retrovirus expression vector (Hughes, *Hum Gene Ther* 16:457-72, 2005 herein incorporated by reference), and the expression vector was transfected into CHO-K1 cells. Co-expression of the two constructs in CHO-K1 cells resulted in secretion of a soluble IL-12/TF/IL-15:IL-18/IL-15RαSu protein complex (referred to as 12t15/s18), which can be purified by anti-TF antibody affinity and other chromatography methods.

The amino acid sequence of the IL-18/IL-15RαSu fusion protein (including signal peptide sequence) is as follows (SEQ ID NO: 191):

```
(Signal peptide)
MKWVTFISLLFLFSSAYS

(Human IL-18)
YFGKLESKLSVIRNLNDQVLFIDQGNRPLFEDMTDSDCRDNAPRTIFII

SMYKDSQPRGMAVTISVKCEKISTLSCENKIISFKEMNPPDNIKDTKSD

TIFFQRSVPGHDNKMQFESSSYEGYFLACEKERDLFKLILKKEDELGDR

SIMFTVQNED

(Human IL-115R a sushi domain)
ITCPPPMSVEHADIWVKSYSLYSRERYICNSGFKRKAGTSSLTECVLNK

ATNVAHWTTPSLKCIR
```

The amino acid sequence of the IL-12/TF/IL-15 fusion protein (including leader sequence) is as follows (SEQ ID NO: 192):

```
(Signal peptide)
MKWVTFISLLFLFSSAYS

(Human IL-12 subunit beta (p40))
IWELKKDVYVVELDWYPDAPGEMVVLTCDTPEEDGITWTLDQSSEVLG

SGKTLTIQVKEFGDAGQYTCHKGGEVLSHSLLLLHKKEDGIWSTDILK

DQKEPKNKTFLRCEAKNYSGRFTCWWLTTISTDLTFSVKSSRGSSDPQ

GVTCGAATLSAERVRGDNKEYEYSVECQEDSACPAAEESLPIEVMVDA

VHKLKYENYTSSFFIRDIIKPDPPKNLQLKPLKNSRQVEVSWEYPDTW

STPHSYFSLTFCVQVQGKSKREKKDRVFTDKTSATVICRKNASISVRA

QDRYYSSSWSEWASVPCS

(Linker)
GGGGSGGGGSGGGGS

(Human IL-12 subunit alpha (p35))
RNLPVATPDPGMFPCLUESQNLLRAVSNMLQKARQTLEFYPCTSEEID

HEDITKDKTSTVEACLPLELTKNESCLNSRETSFITNGSCLASRKTSF

MMALCLSSIYEDLKMYQVEFKTMNAKLLMDPKRQIFLDQNMLAVIDEL

MQALNFNSETVPQKSSLEEPDFYKTKIKLCILLHAFRIRAVTIDRVMS

YLNAS

(Human Tissue Factor 219)
SGTTNTVAAYNLTWKSTNFKTILEWEPKPVNQVYTVQISTKSGDWKSK

CFYTTDTECDLTDEIVKDVKQTYLARVFSYPAGNVESTGSAGEPLYEN

SPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAV

IPSRTVNRKSTDSPVECMGQEKGEFRE

(Human IL-15)
NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS
```

In some cases, the leader peptide is cleaved from the intact polypeptide to generate the mature form that may be soluble or secreted.

Example 41: Recombinant Protein Quantitation of the 18t15-12s16 Complex

Figure 47:
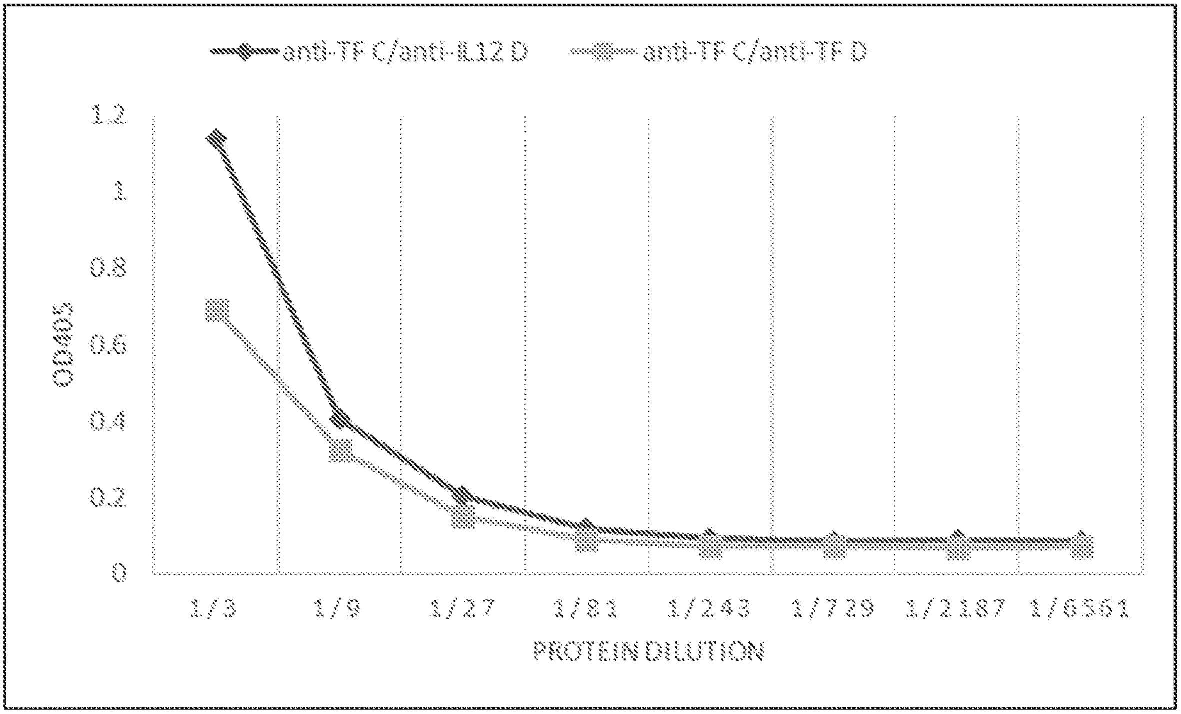
FIG. 47 shows a sandwich ELISA for the 18t15-12s16 complex, comprising an anti-human tissue factor capture antibody and a biotinylated anti-human IL-12 (dark line) or an anti-human tissue factor detection antibody (light line).

The 18t15-12s16 complex (comprising IL-12/IL-15RαSu/αCD16scFv; IL-18/TF/IL-15) was detected and quantified using standard sandwich ELISA methods (see FIG. 47). Anti-human tissue factor antibody/IL-2 or anti-TF antibody/IL-18 served as the capture antibody and biotinylated anti-human IL-12 or IL-18 antibody (BAF 219, D045-6, both R&D Systems) served as the detection antibody. Tissue factor was also detected using an anti-human tissue factor antibody (I43), and anti-human tissue factor antibody detection antibody.

Example 42: Creation of TGFβRII/IL-15RαSu and IL-21/TF/IL-15 DNA Constructs

Figure 48:
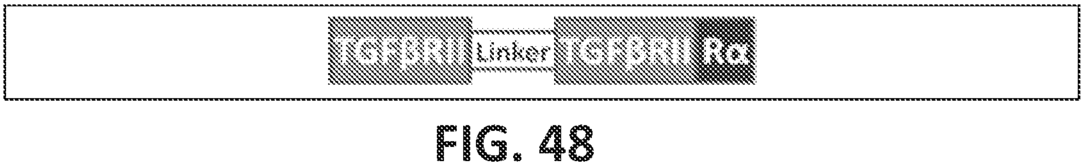
FIG. 48 shows a schematic diagram of an exemplary TGFβRII/IL-15RαSu DNA construct.

In a non-limiting example, a TGFβRII/IL-15RαSu DNA construct was created (see FIG. 48). The human TGFβRII dimer and human IL-21 sequences were obtained from the UniProt website and DNA for these sequences was synthesized by Genewiz. A DNA construct was made linking the TGFβRII to another TGFβRII with a linker to generate a single chain version of TGFβRII and then directly linking the TGFβRII single chain dimer sequence to the N-terminal coding region of IL-15RαSu.

The nucleic acid sequences of the TGFβRII/IL-15RαSu construct (including signal sequence) is as follows (SEQ ID NO: 133):

```
(Signal peptide)
ATGAAGTGGGTGACCTTCATCAGCCTGCTGTTCCTGTTCTCCAGCGCCT

ACTCC

(Human TGF βRII—1st fragment)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCACG

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT

(Linker)
GGAGGTGGCGGATCCGGAGGTGGAGGTTCTGGTGGAGGTGGGAGT

(Human TGF βRII—2nd fragment)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCACA

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT
```

GCAGCAGCGACGAATGCAACGACAATATCATCTTTAGCGAGGAATACAA

TACCAGCAACCCCGAC (Human IL-15R a sushi domain)
ATCACGTGTCCTCCTCCTATGTCCGTGGAACACGCAGACATCTGGGTCA

AGAGCTACAGCTTGTACTCCAGGGAGCGGTACATTTGTAACTCTGGTTT

CAAGCGTAAAGCCGGCACGTCCAGCCTGACGGAGTGCGTGTTGAACAAG

GCCACGAATGTCGCCCACTGGACAACCCCCAGTCTCAAATGTATTAGA

Figure 49:
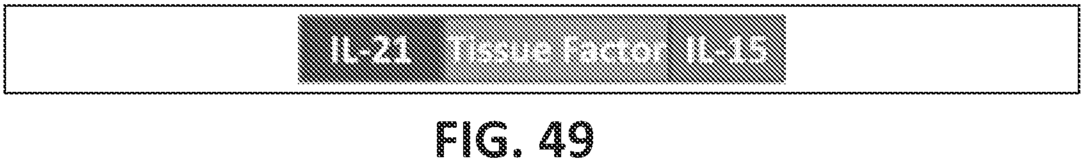
FIG. 49 shows a schematic diagram of an exemplary IL-21/TF/IL-15 construct.

Additionally, an IL-21/TF/IL-15 construct was made linking the IL-21 sequence to the N-terminus coding region of tissue factor 219, and further linking the IL-21/TF construct to the N-terminus coding region of IL-15 (see FIG. 49). The nucleic acid sequence of the IL-21/TF/IL-construct (including leader sequence) is as follows (SEQ ID NO: 129):

(Signal peptide)
ATGAAGTGGGTGACCTTCATCAGCCTGCTGTTCCTGTTCTCCAGCGCCT

ACTCC (Human IL-21)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC (Human Tissue Factor 219)
TCCGGCACCACCAATACCGTGGCCGCTTATAACCTCACATGGAAGAGCA

CCAACTTCAAGACAATTCTGGAATGGGAACCCAAGCCCGTCAATCAAGT

TTACACCGTGCAGATCTCCACCAAATCCGGAGACTGGAAGAGCAAGTGC

TTCTACACAACAGACACCGAGTGTGATTTAACCGACGAAATCGTCAAGG

ACGTCAAGCAAACCTATCTGGCTCGGGTCTTTTCCTACCCCGCTGGCAA

TGTCGAGTCCACCGGCTCCGCTGGCGAGCCTCTCTACGAGAATTCCCCC

GAATTCACCCCTTATTTAGAGACCAATTTAGGCCAGCCTACCATCCAGA

GCTTCGAGCAAGTTGGCACCAAGGTGAACGTCACCGTCGAGGATGAAAG

GACTTTAGTGCGGCGGAATAACACATTTTTATCCCTCCGGGATGTGTTC

GGCAAAGACCTCATCTACACACTGTACTATTGGAAGTCCAGCTCCTCCG

GCAAAAAGACCGCTAAGACCAACACCAACGAGTTTTTAATTGACGTGGA

CAAAGGCGAGAACTACTGCTTCAGCGTGCAAGCCGTGATCCCTTCTCGT

ACCGTCAACCGGAAGAGCACAGATTCCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

Figure 50:
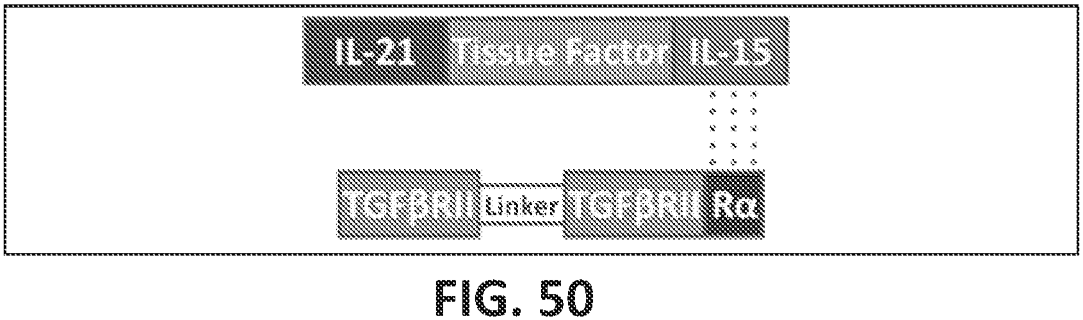
FIG. 50 shows a schematic diagram of the interaction between the exemplary IL-IL-21/TF/IL-15 and TGFβRII/IL-15RαSu constructs.
Figure 51:
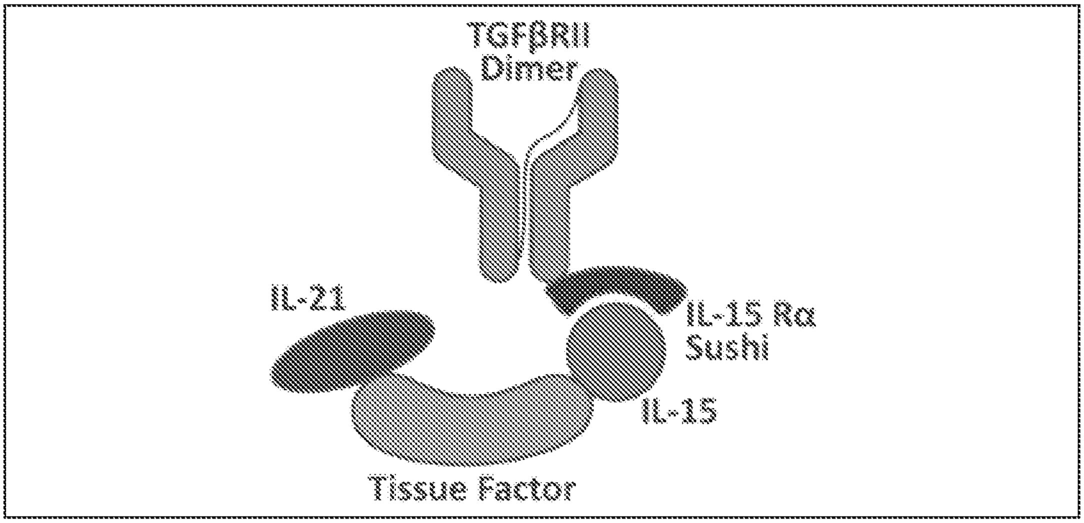
FIG. 51 shows a schematic diagram of the interaction between the exemplary TGFβRII/IL-15RαSu and IL-21/TF/IL-15 fusion proteins, resulting in an IL-21/TF/IL-15/TGFβRII/IL-15RαSu complex (21t15-TGFRs).

Example 43: Secretion of TGFβRII/IL-15RαSu and IL-21/TF/IL-15 Fusion Proteins The TGFβRII/IL-15RαSu and IL-21/TF/IL-15 DNA constructs were cloned into a pMSGV-1 modified retrovirus expression vector (as described in Hughes et al., *Hum Gene Ther* 16:457-72, 2005, herein incorporated by reference), and the expression vector was transfected into CHO-K1 cells. Co-expression of the two constructs in CHO-K1 cells resulted in secretion of the soluble IL-21/TF/IL-15: TGFβRII/IL-15RαSu protein complex (referred to as 21t15-TGFRs, see FIGS. 50 and 51). The 21t15-TGFRs complex was purified from CHO-K1 cell culture supernatant using anti-TF antibody affinity chromatography and other chromatography methods.

The amino acid sequence of the TGFβRII/IL-15RαSu construct (including signal peptide sequence) is as follows (SEQ ID NO: 132):

(Signal peptide)
MKWVTFISLLFLFSSAYS (Human TGF βRII-1st fragment)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD (Linker)
GGGGSGGGGSGGGGS (Human TGF βRII-2nd fragment)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNK

ATNVAHWTTPSLKCIR

The amino acid sequence of the mature IL-21/TF/IL-15fusion protein (including signal peptide sequence)is as follows (SEQ ID NO: 128):

(Signal peptide)
MKWVTFISLLFLFSSAYS (Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

-continued

```
EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE

(Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

In some cases, the leader peptide is cleaved from the intact polypeptide to generate a mature form that may be soluble or secreted.

Example 44: Purification of 21t15-TGFRs by Immunoaffinity Chromatography

An anti-TF antibody affinity column was connected to a GE Healthcare AKTA™ Avant protein purification system. The flow rate was 4 mL/min for all steps except the elution step, which was 2 mL/min.

Figure 52:
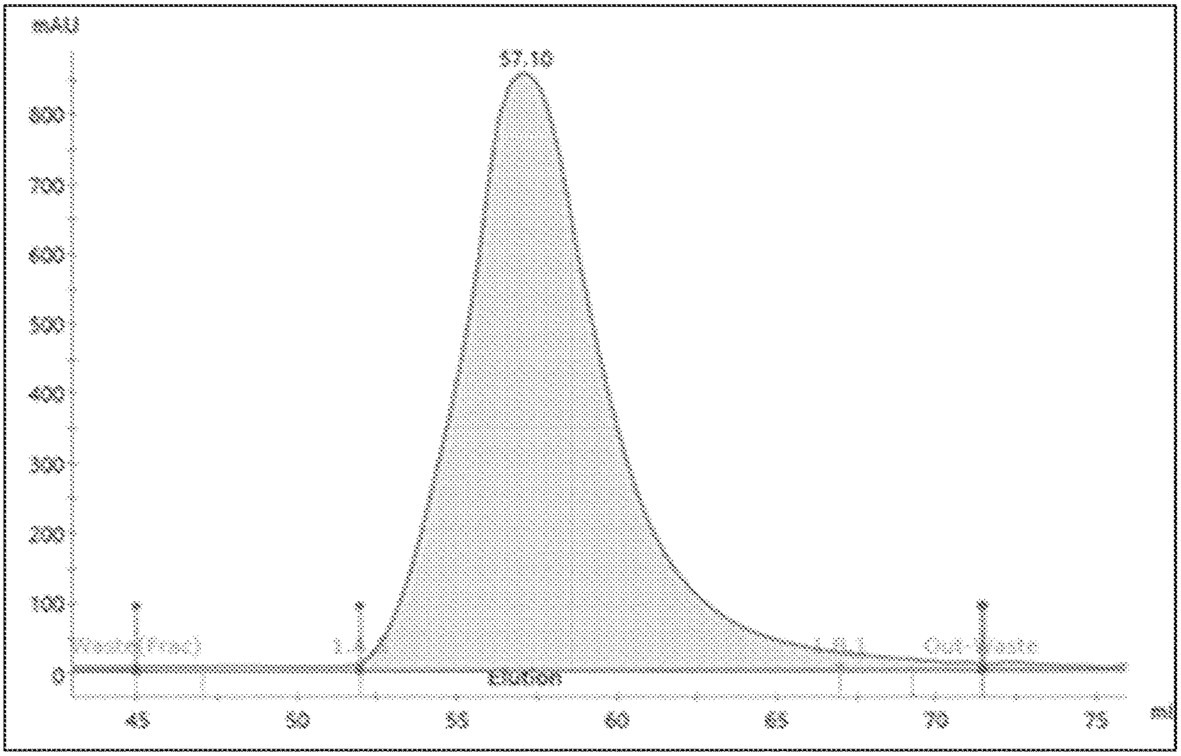
FIG. 52 shows a chromatograph of 21t15-TGFRs purification elution from an anti-TF antibody affinity column.

Cell culture harvest of 21t15-TGFRs was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was then neutralized to pH 7.5-8.0 by adding 1M Tris base. The neutralized sample was then buffer exchanged into PBS using Amicon® centrifugal filters with a 30 KDa molecular weight cutoff. FIG. 52 shows that the 21t15-TGFRs complex binds anti-TF antibody affinity column, wherein TF is a 21t15-TGFRs binding partner. The buffer-exchanged protein sample is stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide, and stored at 2-8° C.

Example 45: Size Exclusion Chromatography of 21t15-TGFRs

Figure 53:
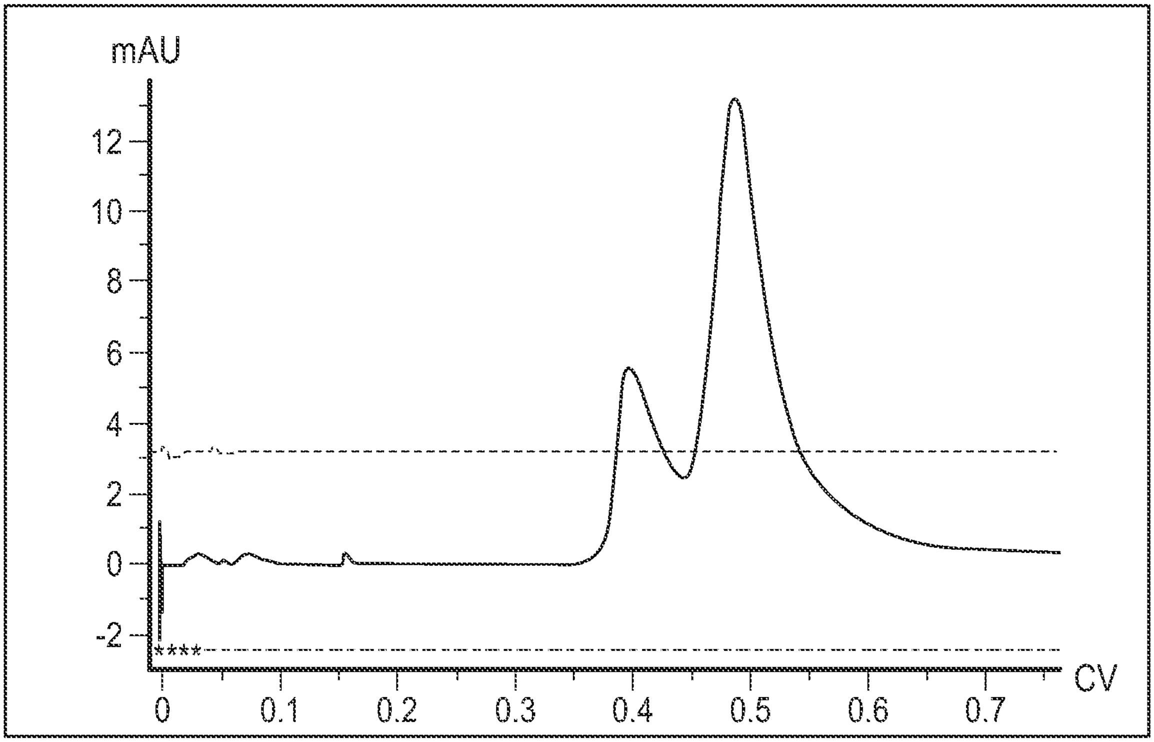
FIG. 53 shows an exemplary 21t15-TGFRs size exclusion chromatograph showing a main protein peak and a high molecular weight peak

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.8 mL/min. A capillary loop was used to inject 200 μL of 1 mg/mL of 21t15-TGFRs complex onto the column. The injection was then chased with 1.25 column volumes of PBS. The SEC chromatograph was shown in FIG. 53. There were two protein peaks, likely representing a monomer and dimer forms of 21t15-TGFRs.

Example 46: SDS-PAGE of 21t15-TGFRs

Figure 10:
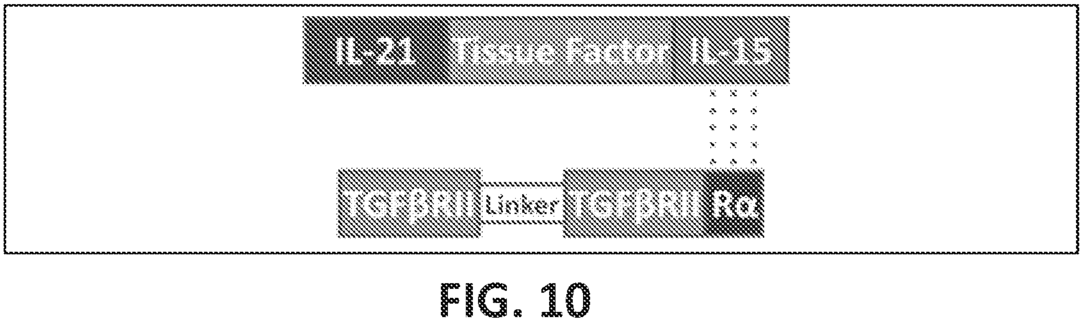
FIG. 10 shows a schematic diagram of the interaction between the exemplary TGF-βRII/IL-15RαSu and IL-21/TF/IL-15 DNA constructs.
Figure 11:
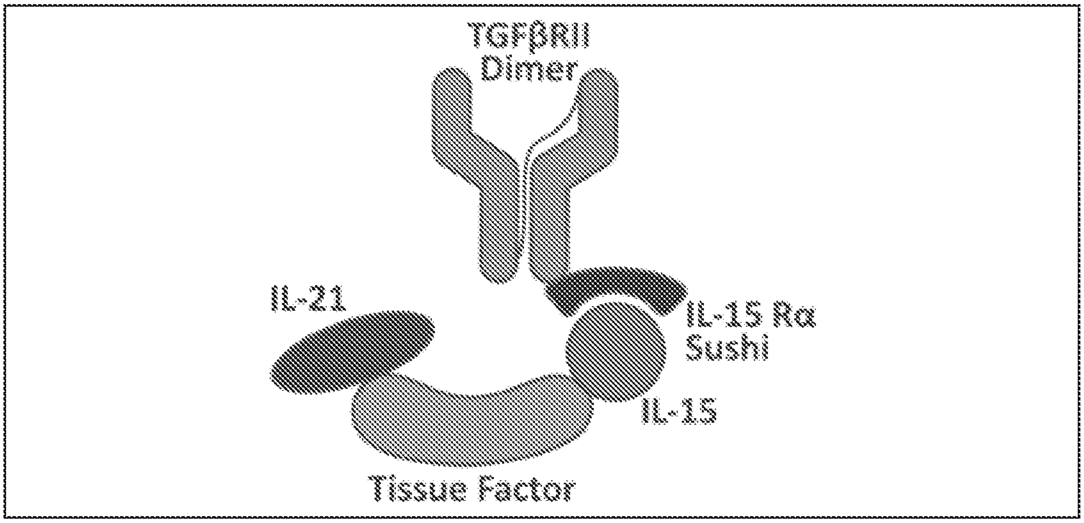
FIG. 11 shows a schematic diagram of the interaction between the exemplary TGF-βRII/IL-15RαSu and IL-21/TF/IL-15 fusion proteins resulting in an IL-21/TF/IL-15:TGF-βRII/IL-15RαSU complex (21t15-TGFRs).
Figure 54:
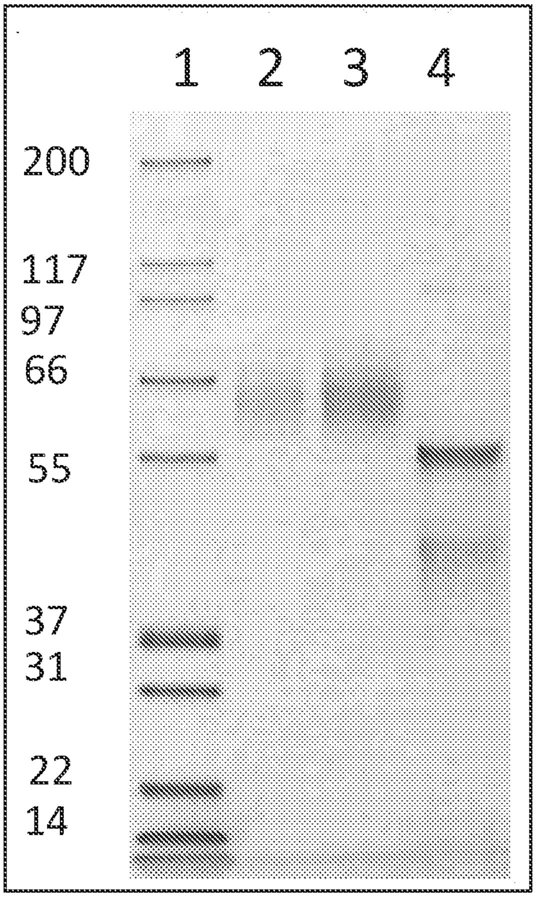
FIG. 54 shows an example of a 4-12% SDS-PAGE of the 21t15-TGFRs complex following disulfide bond reduction. Lane 1: Mark12 unstained marker (numbers on the left side indicate molecular weights in kDa); Lane 2: 21t15-TGFRs (0.5 μg); Lane 3: 21t15-TGFRs (1 μg); Lane 4: 21t15-TGFRs, deglycosylated (1 μg), wherein the MW was the expected size of 53 kDa and 39.08 kDa.
Figure 55:
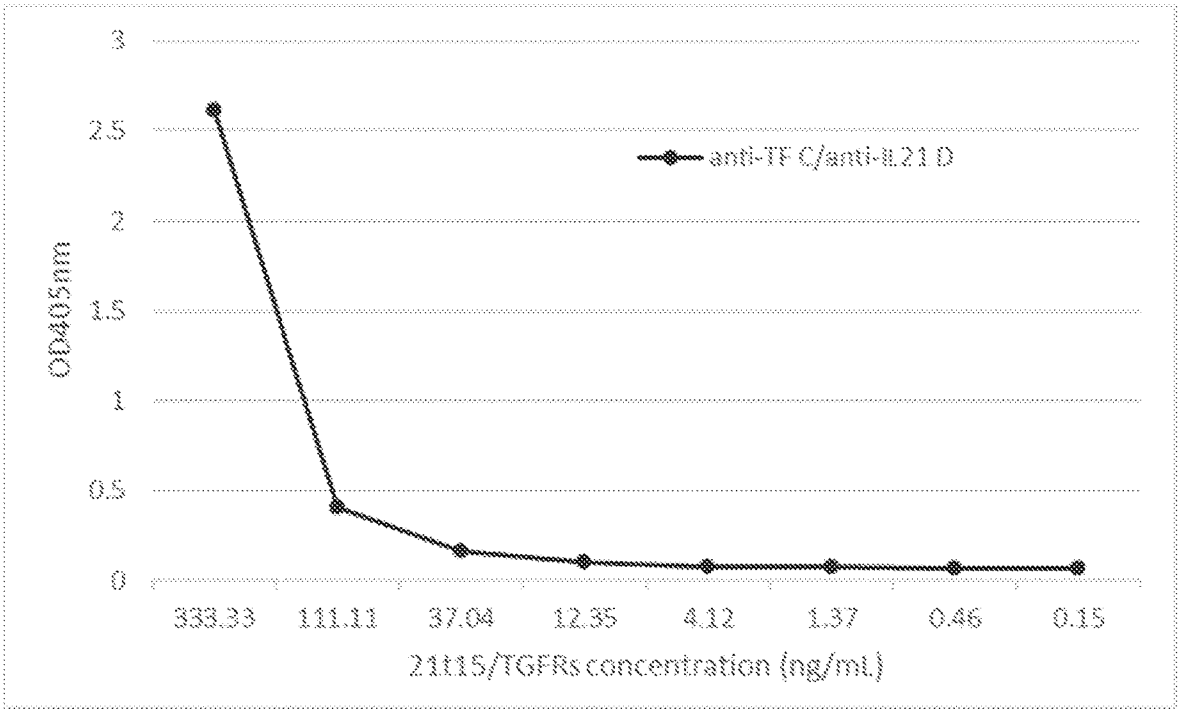
FIG. 55 shows a sandwich ELISA for the 21t15-TGFRs complex, comprising an anti-human tissue factor capture antibody and a biotinylated anti-human IL-21 detection antibody (13-7218-81, BioLegend).
Figure 56:
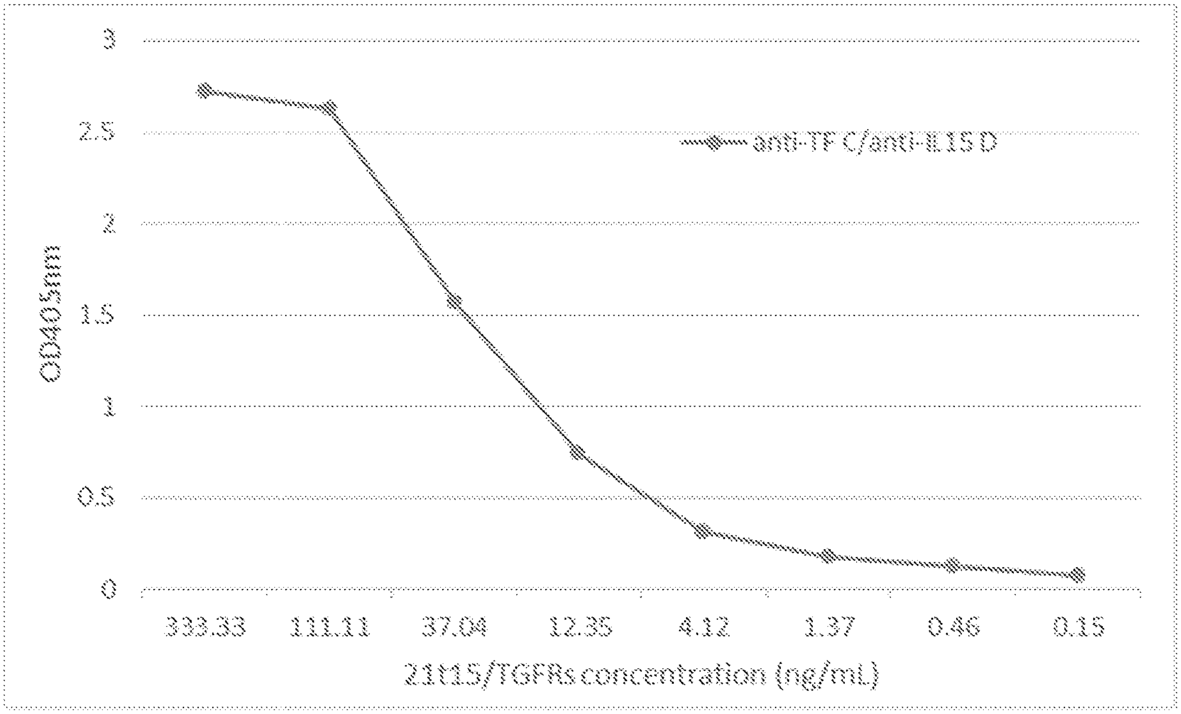
FIG. 56 shows a sandwich ELISA for the 21t15-TGFRs complex, comprising an anti-human tissue factor capture antibody and a biotinylated anti-human IL-15 detection antibody (BAM 247, R&D Systems).
Figure 57:
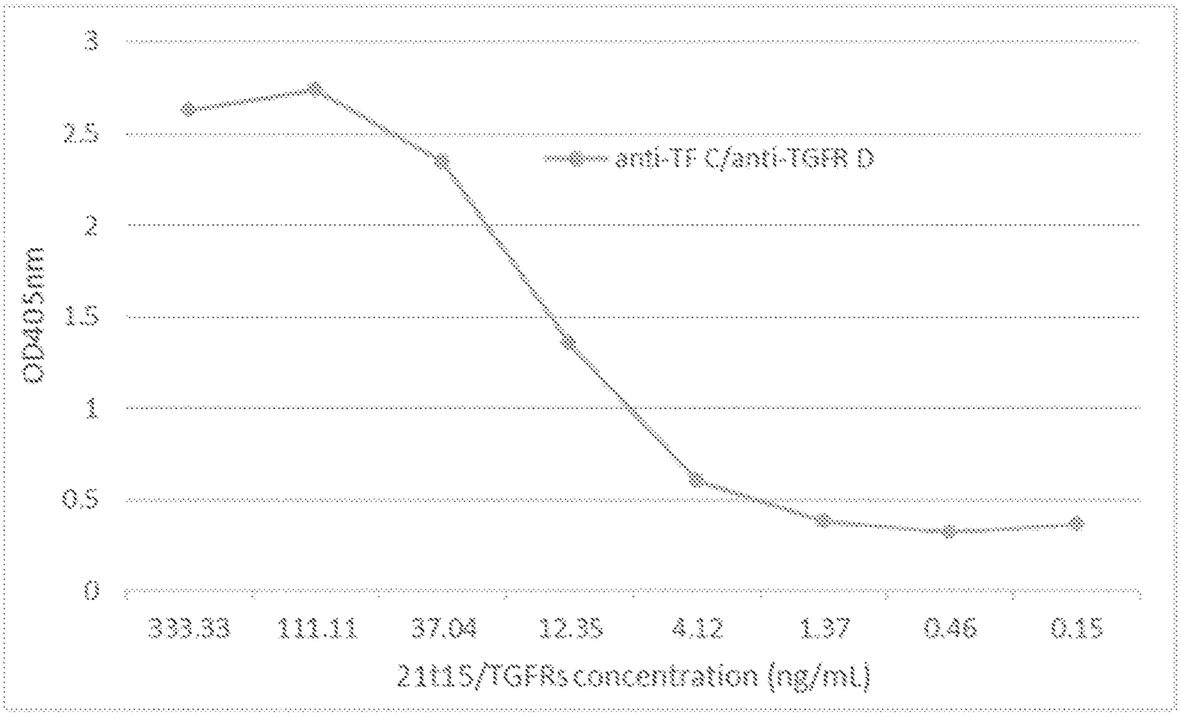
FIG. 57 shows a sandwich ELISA for the 21t15-TGFRs complex, comprising an anti-human tissue factor capture antibody and a biotinylated anti-human TGFβRII detection antibody (BAF241, R&D Systems).
Figure 58:
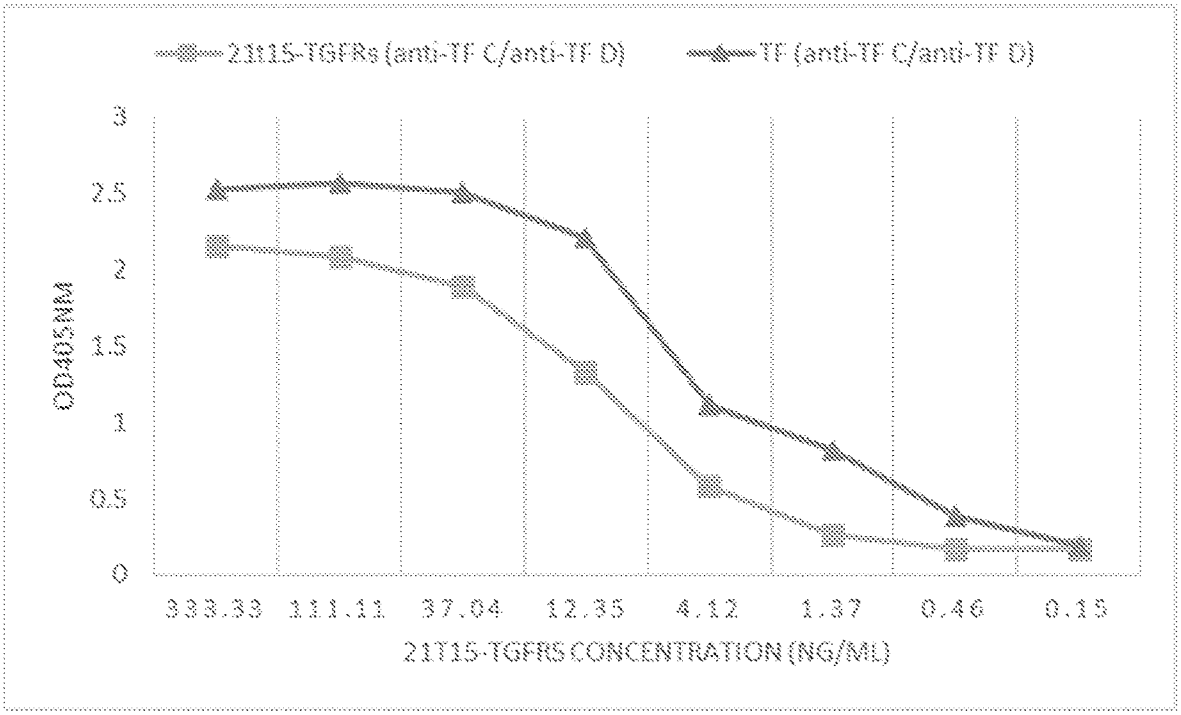
FIG. 58 shows a sandwich ELISA for the 21t15-TGFRs complex, comprising an anti-human tissue factor (I43) capture antibody and an anti-human tissue factor detection antibody.

To determine the purity and protein molecular weight, the purified 21t15-TGFRs complex protein sample was analyzed using 4-12% NuPage Bis-Tris protein gel SDS-PAGE under reduced conditions. The gel was stained with InstantBlue™ for about 30 min, followed by destaining overnight in purified water. FIG. 54 shows an example SDS gel of anti-TF antibody affinity purified 21t15-TGFRs, with bands at 39.08 kDa and 53 kDa. Glycosylation of 21t15-TGFRs in CHO cells was confirmed using the Protein Deglycosylation Mix II kit (New England Biolabs) and the manufacturer's instructions. FIG. 10 shows an example SDS PAGE of deglycosylated and non-deglycosylated 21t15-TGFRs. Deglycosylation reduces the molecular weight of 21t15-TGFRs, as seen in lane 4 of FIG. 54.

Example 47: Recombinant Protein Quantitation of 21t15-TGFRs Complexes

The 21t15-TGFRs complex was detected and quantified using standard sandwich ELISA methods (see FIGS. 55-59). Anti-human tissue factor antibody served as the capture antibody and biotinylated anti-human IL-21, IL-15, or TGFβRII served as the detection antibody. Tissue factor was also detected using an anti-human tissue factor capture antibody (I43), and anti-human tissue factor antibody detection antibody. The I43/anti-TF Ab ELISA was compared to purified tissue factor at similar concentrations.

Example 48: Immunostimulatory Capacity of the 21t15-TGFRs Complex

Figure 59:
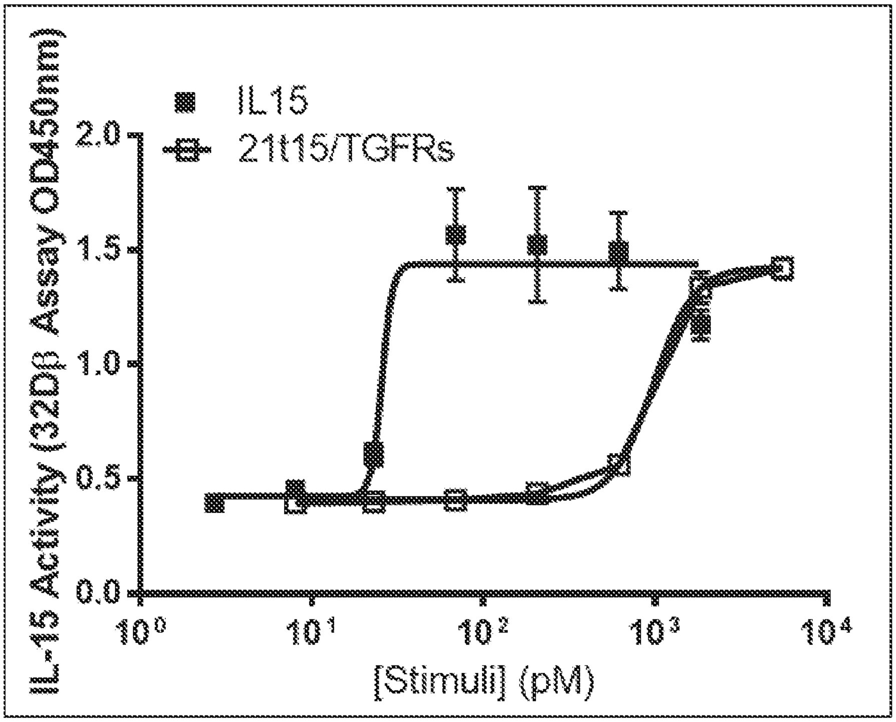
FIG. 59 shows IL-15-dependent proliferation of 32Dβ cells mediated by the 21t15-TGFRs complex (open squares) compared to IL-15 (black squares).

To assess the IL-15 immunostimulatory activity of the 21t15-TGFRs complexes, increasing concentrations of 21t15-TGFRs was added to 32Dβ cells ($10^4$ cell/well) in 200 μL IMDM: 10% FBS media and cells were incubated for 3 days at 37° C. On the fourth day, WST-1 proliferation reagent (10 μL/well) then was added and after 4 hours, absorbance was measured at 450 nm to determine cell proliferation based on cleavage of WST-1 to a soluble formazan dye. Bioactivity of the human recombinant IL-15 was assessed as a positive control. As shown in FIG. 59, 21*t*15-TGFRs demonstrated IL-15-dependent 32Dβ cell proliferation. The 21t15-TGFRs complex was reduced compared to that of human recombinant IL-15, possibly due to the linkage of IL-21 and tissue factor to the IL-15 domain.

Figure 60:
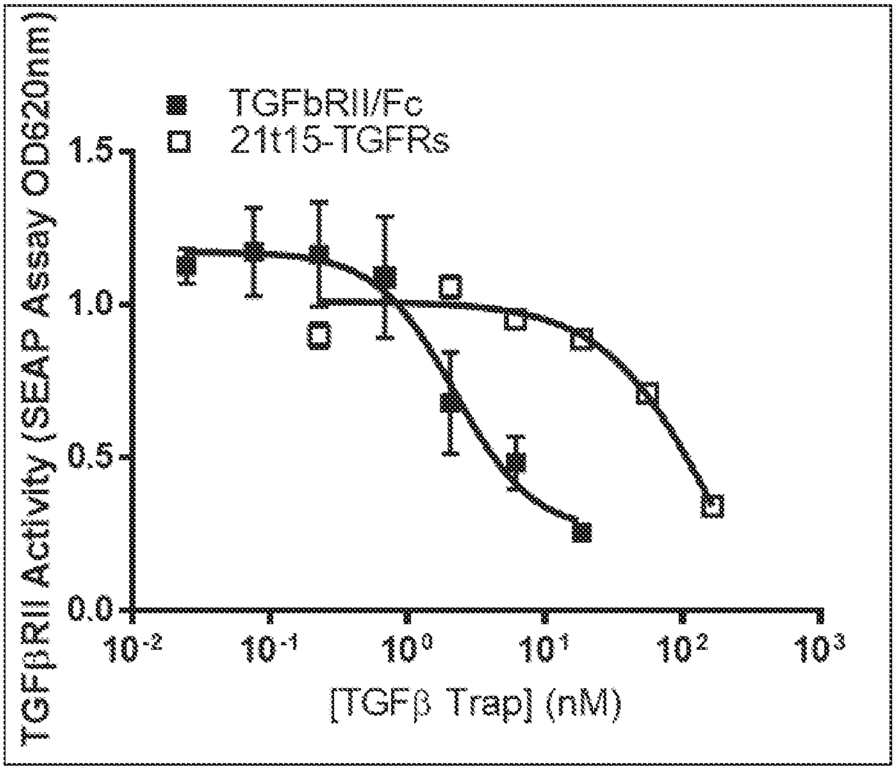
FIG. 60 shows biological activity of the TGFβRII domain within the 21t15-TGFRs complex (open squares). TGFβRII/Fc (black squares) served as a positive control.

Additionally, HEK-Blue TGFβ reporter cells (hkb-tgfb, InvivoGen) were used to measure the ability of 21t15-TGFRs to block TGFβ1 activity (FIG. 60). Increasing concentrations of 21t15-TGFRs were mixed with 0.1 nM of TGFβ1 and added to HEK-Blue TGFβ reporter cells (2.5×$10^4$ cell/well) in 200 μL IMDM: 10% heat-inactivated FBS media. Cells were incubated overnight at 37° C. The next day, 20 μl of induced HEK-Blue TGFβ reporter cell supernatant was added to 180 μl of QUANTI-Blue (InvivoGen) and incubated for 1-3 hours at 37° C. 21t15-TGFRs activity was assessed by measuring absorbance at 620 nm. Human recombinant TGFβRII/Fc activity was assessed as a positive control.

These results demonstrate that TGFβRII domain of the 21t15-TGFRs complex retains its ability to trap TGF (31. The ability of 21t15-TGFRs to block TGFβ1 activity was reduced compared to that of human recombinant TGFβRII/Fc, possibly due to the linkage of TGFβRII to the IL-15Rα sushi domain.

Example 49: Induction of Cytokine-Induced Memory-Like NK Cells by the 21t15-TGFRs Complex Cytokine-induced memory-like NK cells can be induced ex vivo following overnight stimulation of purified NK cells with saturating amounts of cytokines. These memory-like properties can be measured through expression of IL-2 receptor α (IL-2Rα, CD25), CD69 (and other activation markers), and increased IFN-γ production. To evaluate the ability of 21t15-TGFRs complexes to promote generation of cytokine-induced memory-like NK cells, purified human NK cells (>95% $CD56^+$) were stimulated for 14-18 hours with 1 nM to 100 nM of the 21t15-TGFRs complex. Cell-surface CD25 and CD 69 expression and intracellular IFN-γ levels were assessed by antibody-staining and flow cytometry.

Figure 61A:
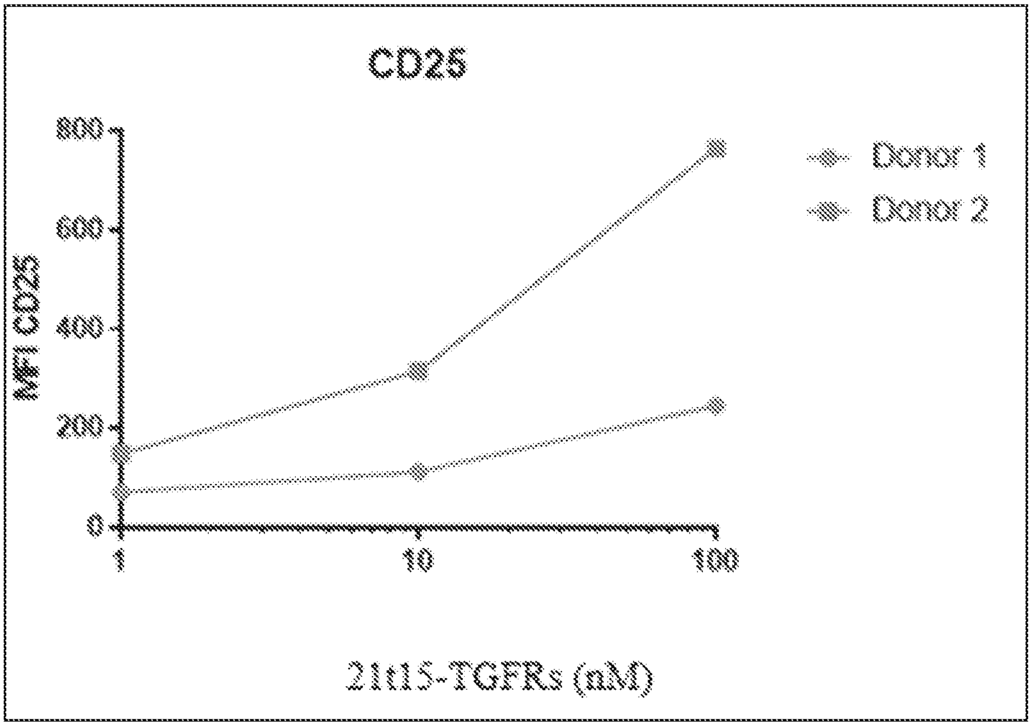
FIG. 61A shows a flow cytometry graph of cell-surface CD25 expression of NK cells induced by the 21t15-TGFRs complex.
Figure 61B:
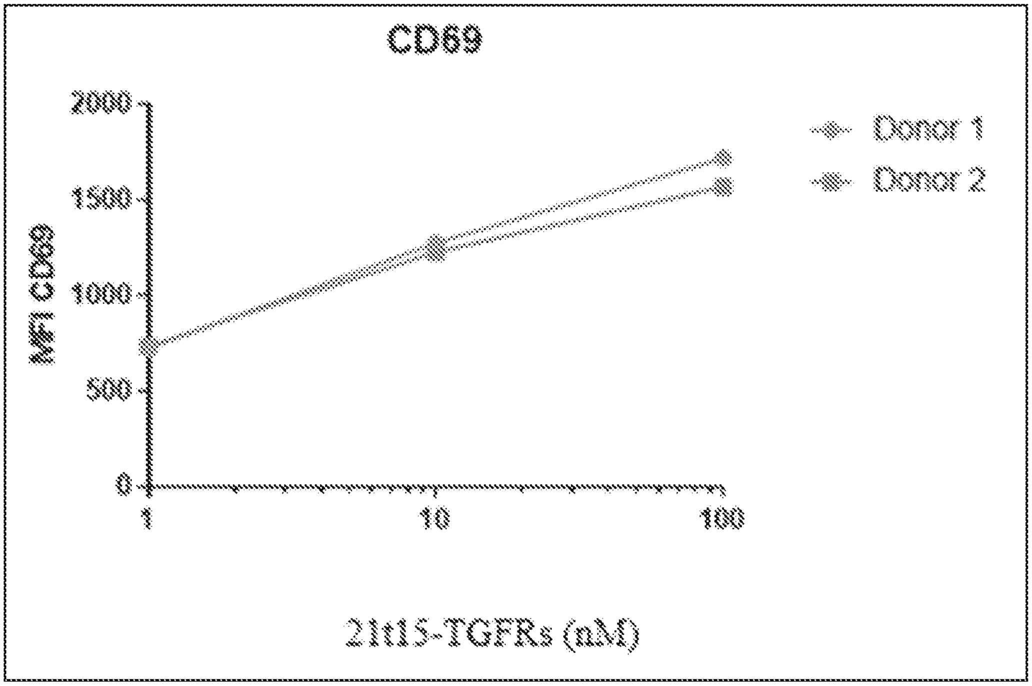
FIG. 61B shows a flow cytometry graph of cell-surface CD69 expression of NK cells induced by the 21t15-TGFRs complex.

Fresh human leukocytes were obtained from a blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 (BioLegend). Cells were counted and resuspended in $0.2\times10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-21 (50 ng/mL) (Biolegend) and hIL-15 (50 ng/mL) (NCI) or with 1 nM, 10 nM, or 100 nM 21t15-TGFRs complex overnight at 37° C., 5% $CO_2$ for 14-18 hrs. The cells were then harvested and surface stained for CD56-BV421, CD16-BV510, CD25-PE, CD69-APCFire750 for 30 minutes. After staining, cells were washed (1500 RPM for 5 minutes at room temperature) in FACS buffer (1×PBS (Hyclone) with 0.5% BSA (EMD Millipore) and 0.001% sodium azide (Sigma)). After two washes, cells were analyzed using a BD FACSCelesta™ flow cytometer (Plotted Data-Mean Fluorescence Intensity, see FIGS. 61A and 61B).

Figure 62:
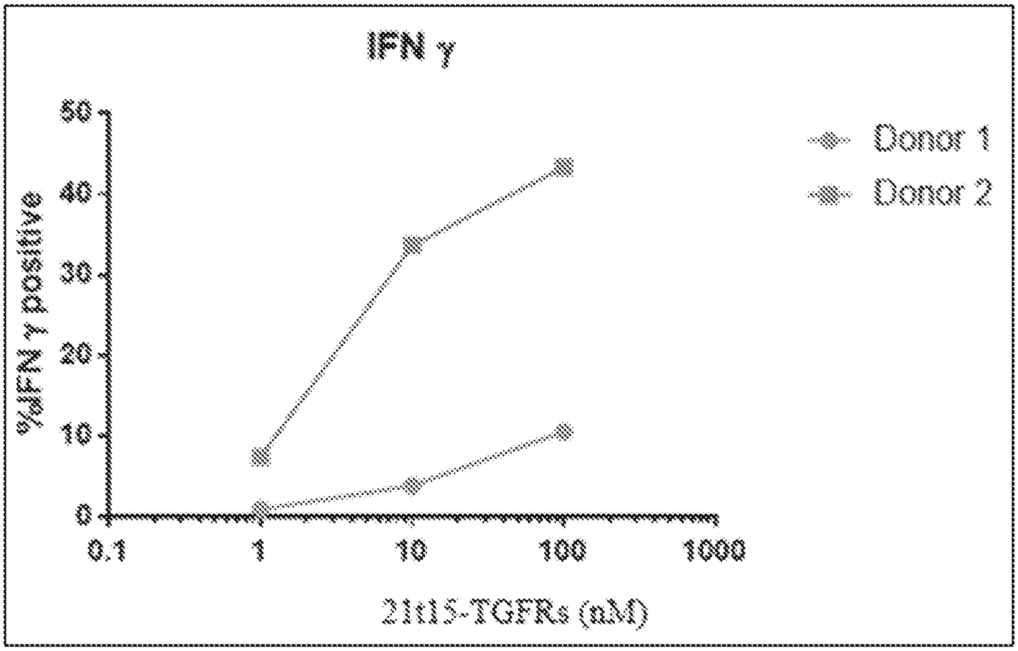
FIG. 62 shows a flow cytometry graph of intracellular interferon gamma expression of NK cells induced by the 21t15-TGFRs complex.

Fresh human leukocytes were obtained from a blood bank and $CD56^+$ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 specific antibodies (BioLegend). Cells were counted and resuspended in $0.2\times10^6$/mL in a 96 well flat bottom plate in 0.2 mL of complete media (RPMI 1640 (Gibco), supplemented with 2 mM L-glutamine (Thermo Life Technologies), penicillin (Thermo Life Technologies), streptomycin (Thermo Life Technologies), and 10% FBS (Hyclone)). Cells were stimulated with either mix-cytokines of hIL-21 (50 ng/mL) (Biolegend) and hIL-15 (50 ng/mL) (NCI) or with 1 nM, 10 nM, or 100 nM 21t15-TGFRs complex overnight at 37° C., 5% CO2 for 14-18 hrs. The cells were then treated with 10 μg/mL of Brefeldin A (Sigma) and 1× of Monensin (eBioscience) for 4 hrs. Cells were harvested and surface stained with CD56-BV421, CD16-BV510, CD25-PE, CD69-APCFire750 specific antibodies for 30 minutes. After staining, cells were washed (1500 RPM for 5 minutes at room temperature) in FACS buffer (1×PBS (Hyclone) with 0.5% BSA (EMD Millipore) and 0.001% sodium azide (Sigma)) and fixed for 10 minutes at room temperature. After fixation, cells were washed (1500 RPM for 5 minutes at room temperature) with 1× permeabilized buffer (eBioscience) and stained for intracellular IFN-γ-PE Ab (Biolegend) for 30 minutes at room temperature. Cells were washed once again with 1× permeabilized buffer and then washed with FACS buffer. Cell pellets were resuspended in 300 μls of FACS Buffer and analyzed using a BD FACSCelesta™ flow cytometer. (Plotted % of IFN-γ Positive Cells, see FIG. 62).

Example 50: In Vitro Cytotoxicity of NK Cells Against Human Tumor Cells

Figure 63:
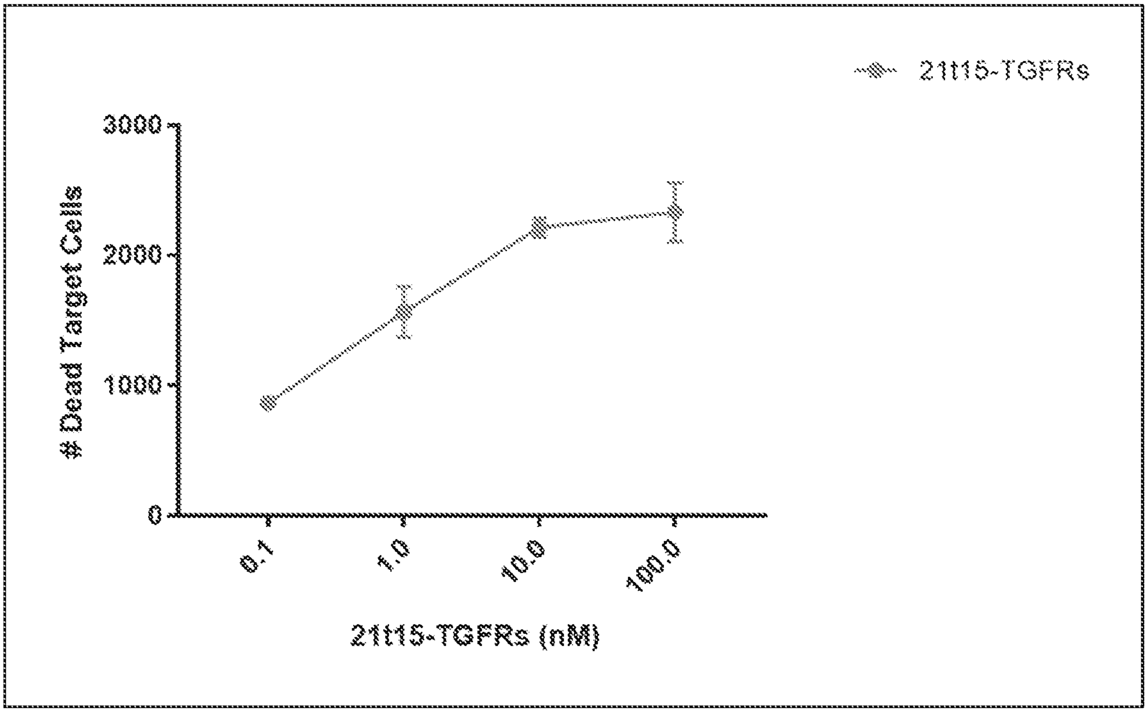
FIG. 63 shows a bar graph showing cytotoxicity of 21t15-TGFRs-induced human NK cells against K562. K562 cells (labeled with Celltrace violet) at 1×10^5/well and human NK cells (NK cells were isolated from human blood buffy coat with StemCell human NK cell purification kit) at 2×10^5/well were incubated with 18t15-12s in RPMI-10 for 20 hours. Cell mixtures were harvested, stained with propidium iodide (PI), and analyzed using a BD FACSCelesta™ flow cytometer. The graph represents duplicated samples.

K562 (CellTrace violet labelled), human myelogenous leukemia cells, were incubated with purified human NK cells (using StemCell human NK cell purification kit (E:T ratio; 2:1)) in the presence of increasing concentrations of the 21t15-TGFRs complex. After 20 hours, the cultures were harvested, stained with propidium iodide (PI), and assessed by flow cytometry. As shown in FIG. 63, the 21t15-TGFRs complex induced human NK cytotoxicity against K562, as compared to control.

Example 51: Creation of an IL-21/TF Mutant/IL-15 DNA Construct and Resulting Fusion Protein Complex with TGFβRII/IL-15RαSu In a non-limiting example, an IL-21/TF mutant/IL-15 DNA construct was made by linking IL-21 directly to the N-terminus coding region of a tissue factor 219 mutant, and further linking the IL-21/TF mutant to the N-terminus coding region of IL-15.

The nucleic acid sequence of the IL-21/TF mutant/IL-15 construct (including signal peptide sequence) is as follows (SEQ ID NO: 193, shaded nucleotides are mutant and the mutant codons are underlined):

```
(Signal sequence)
ATGAAGTGGGTGACCTTCATCAGCCTGCTGTTCCTGTTCTCCAGCGCCT

ACTCC

(Human IL-21)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC

(Human Tissue Factor 219 mutants)
TCCGGCACCACCAATACCGTGGCCGCTTATAACCTCACATGGAAGAGCA

CCAACTTCGCGACAGCTCTGGAATGGGAACCCAAGCCCGTCAATCAAGT

TTACACCGTGCAGATCTCCACCAAATCCGGAGACTGGAAGAGCAAGTGC

TTCTACACAACAGACACCGAGTGTGCTTTAACCGACGAAATCGTCAAGG

ACGTCAAGCAAACCTATCTGGCTCGGGTCTTTTCCTACCCCGCTGGCAA

TGTCGAGTCCACCGGCTCCGCTGGCGAGCCTCTCTACGAGAATTCCCCC

GAATTCACCCCTTATTTAGAGACCAATTTAGGCCAGCCTACCATCCAGA

GCTTCGAGCAAGTTGGCACCAAGGTGAACGTCACCGTCGAGGATGAAAG

GACTTTAGTGGCGCGGAATAACACAGCTTTATCCCTCCGGGATGTGTTC

GGCAAAGACCTCATCTACACACTGTACTATTGGAAGTCCAGCTCCTCCG

GCAAAAAGACCGCTAAGACCAACACCAACGAGTTTTTAATTGACGTGGA

CAAAGGCGAGAACTACTGCTTCAGCGTGCAAGCCGTGATCCCTTCTCGT

ACCGTCAACCGGAAGAGCACAGATTCCCCCGTTGAGTGCATGGGCCAAG

AAAAGGGCGAGTTCCGGGAG
```

-continued (Human IL-15)
AACTGGGTGAACGTCATCAGCGATTTAAAGAAGATCGAAGATTTAATTC
AGTCCATGCATATCGACGCCACTTTATACACAGAATCCGACGTGCACCC
CTCTTGTAAGGTGACCGCCATGAAATGTTTTTACTGGAGCTGCAAGTT
ATCTCTTTAGAGAGCGGAGACGCTAGCATCCACGACACCGTGGAGAATT
TAATCATTTTAGCCAATAACTCTTTATCCAGCAACGGCAACGTGACAGA
GTCCGGCTGCAAGGAGTGCGAAGAGCTGGAGGAGAAGAACATCAAGGAG
TTTCTGCAATCCTTTGTGCACATTGTCCAGATGTTCATCAATACCTCC The amino acid sequence of the IL-21/TF mutant/IL-15 construct (including signal peptide sequence) is as follows (SEQ ID NO: 194, substituted residues are shaded):

(Signal peptide)
MKWVTFISLLFLFSSAYS (Human IL-21)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS (Human Tissue Factor 219)
SGTTNTVAAYNLTWKSTNFATALEWEPKPVNQVYTVQISTKSGDWKSKC
FYTTDTECALTDEIVKDVKQTYLARVFSYPAGNVESTGSAGEPLYENSP
EFTPYLETNLGQPTIQSFEQVGTKVNVTVEDERTLVARNNTALSLRDVF
GKDLIYTLYYWKSSSSGKKTAKTNTNEFLIDVDKGENYCFSVQAVIPSR
TVNRKSTDSPVECMGQEKGEFRE (Human IL-15)
NWVNVISDLKKIEDLIQSMHIDATLYTESDVHPSCKVTAMKCFLLELQV
ISLESGDASIHDTVENLIILANNSLSSNGNVTESGCKECEELEEKNIKE
FLQSFVHIVQMFINTS In some cases, the leader peptide is cleaved from the intact polypeptide to generate a mature form that may be soluble or secreted.

In some embodiments, the IL-21/TF mutant/IL-15 DNA construct may be combined with an TGFβRII/IL-15RαSu DNA construct, transfected into cells using a retroviral vector as described above, and expressed as IL-21/TF mutant/IL-15 and TGFβRII/IL-15RαSu fusion proteins. The IL-15RαSu domain of the TGFβRII/IL-15RαSu fusion protein binds to the IL-15 domain of the IL-21/TF mutant/IL-15 fusion protein to create an IL-21/TF mutant/IL-15: TGFβRII/IL-15RαSu complex.

Example 52: Creation of IL-21/IL-15RαSu and TGFβRII/TF/IL-15 DNA Constructs and the Resulting Fusion Protein Complex In a non-limiting example, an IL-21/IL-15RαSu DNA construct was made by linking IL-21 directly to the IL-15RαSu subunit sequence. The nucleic acid sequence of the IL-21/IL-15RαSu construct (including signal sequence) is as follows (SEQ ID NO: 148):

(Signal sequence)
ATGAAGTGGGTGACCTTCATCAGCCTGCTGTTCCTGTTCTCCAGCGCCT
ACTCC (Human IL-21)
CAGGGCCAGGACAGGCACATGATCCGGATGAGGCAGCTCATCGACATCG
TCGACCAGCTGAAGAACTACGTGAACGACCTGGTGCCCGAGTTTCTGCC
TGCCCCCGAGGACGTGGAGACCAACTGCGAGTGGTCCGCCTTCTCCTGC
TTTCAGAAGGCCCAGCTGAAGTCCGCCAACACCGGCAACAACGAGCGGA
TCATCAACGTGAGCATCAAGAAGCTGAAGCGGAAGCCTCCCTCCACAAA
CGCCGGCAGGAGGCAGAAGCACAGGCTGACCTGCCCCAGCTGTGACTCC
TACGAGAAGAAGCCCCCCAAGGAGTTCCTGGAGAGGTTCAAGTCCCTGC
TGCAGAAGATGATCCATCAGCACCTGTCCTCCAGGACCCACGGCTCCGA
GGACTCC (Human IL-15R α sushi domain)
ATTACATGCCCCCCTCCCATGAGCGTGGAGCACGCCGACATCTGGGTGA
AGAGCTATAGCCTCTACAGCCGGGAGAGGTATATCTGTAACAGCGGCTT
CAAGAGGAAGGCCGGCACCAGCAGCCTCACCGAGTGCGTGCTGAATAAG
GCTACCAACGTGGCTCACTGGACAACACCCTCTTTAAAGTGCATCCGG The amino acid sequence of the IL-21/IL-15RαSu construct (including signal peptide sequence) is as follows (SEQ ID NO: 147):

(Signal peptide)
MKWVTFISLLFLFSSAYS (Human IL-21)
QGQDRHMIRMRQLIDIVDQLKNYVNDLVPEFLPAPEDVETNCEWSAFSC
FQKAQLKSANTGNNERIINVSIKKLKRKPPSTNAGRRQKHRLTCPSCDS
YEKKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLNK
ATNVAHWTTPSLKCIR In some cases, the leader peptide is cleaved from the intact polypeptide to generate a mature form that may be soluble or secreted.

In some embodiments, the IL-21/IL-15RαSu DNA construct may be combined with a TGFβRII/TF/IL-15 DNA construct, transfected into a retroviral vector as described above, and expressed as IL-21/IL-15RαSu and TGFβRII/TF/IL-15 fusion proteins. The IL-15RαSu domain of the IL-21/IL-15RαSu fusion protein binds to the IL-15 domain of the TGFβRII/TF/IL-15 fusion protein to create a TGFβRII/TF/IL-15:IL-21/IL-15RαSu complex.

The TGFβRII/TF/IL-15RαSu DNA construct was created by linking the TGFβRII sequence to the N-terminus coding region of human tissue factor 219 form, and then linking the TGFβRII/TF construct to the N-terminus coding region of IL-15. As described above, a single-chain version of TGFβRII (TGFβRII-linker-TGFβRII) was used. The nucleic acid sequence of the TGFβRII/TF/IL-15 construct (including leader sequence) is as follows (SEQ ID NO: 164):

(Signal peptide)
ATGAAGTGGGTGACCTTCATCAGCCTGCTGTTCCTGTTCTCCAGCGCCT

ACTCC (Human TGF βRII-1st fragment)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCACG

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGAT (Linker)
GGAGGTGGCGGATCCGGAGGTGGAGGTTCTGGTGGAGGTGGGAGT (Human TGF βRII-2nd fragment)
ATTCCTCCCCACGTGCAGAAGAGCGTGAATAATGACATGATCGTGACCG

ATAACAATGGCGCCGTGAAATTTCCCCAGCTGTGCAAATTCTGCGATGT

GAGGTTTTCCACCTGCGACAACCAGAAGTCCTGTATGAGCAACTGCACA

ATCACCTCCATCTGTGAGAAGCCTCAGGAGGTGTGCGTGGCTGTCTGGC

GGAAGAATGACGAGAATATCACCCTGGAAACCGTCTGCCACGATCCCAA

GCTGCCCTACCACGATTTCATCCTGGAAGACGCCGCCAGCCCTAAGTGC

ATCATGAAAGAGAAAAAGAAGCCTGGCGAGACCTTTTTCATGTGCTCCT

GCAGCAGCGACGAATGCAACGACAATATCATCTTTAGCGAGGAATACAA

TACCAGCAACCCCGAC (Human Tissue Factor 219)
TCCGGCACCACCAATACCGTGGCCGCTTATAACCTCACATGGAAGAGCA

CCAACTTCAAGACAATTCTGGAATGGGAACCCAAGCCCGTCAATCAAGT

TTACACCGTGCAGATCTCCACCAAATCCGGAGACTGGAAGAGCAAGTGC

TTCTACACAACAGACACCGAGTGTGATTTAACCGACGAAATCGTCAAGG

ACGTCAAGCAAACCTATCTGGCTCGGGTCTTTTCCTACCCCGCTGGCAA

TGTCGAGTCCACCGGCTCCGCTGGCGAGCCTCTCTACGAGAATTCCCCC

GAATTCACCCCTTATTTAGAGACCAATTTAGGCCAGCCTACCATCCAGA

GCTTCGAGCAAGTTGGCACCAAGGTGAACGTCACCGTCGAGGATGAAAG

GACTTTAGTGCGGCGGAATAACACATTTTTATCCCTCCGGGATGTGTTC

GGCAAAGACCTCATCTACACACTGTACTATTGGAAGTCCAGCTCCTCCG

GCAAAAAGACCGCTAAGACCAACACCAACGAGTTTTTAATTGACGTGGA

CAAAGGCGAGAACTACTGCTTCAGCGTGCAAGCCGTGATCCCTTCTCGT

ACCGTCAACCGGAAGAGCACAGATTCCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

-continued

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

The amino acid sequence of the TGFβRII/TF/IL-15 fusion protein (including signal peptide) is as follows (SEQ ID NO: 163):

(Signal peptide)
MKWVTFISLLFLFSSAYS (Human TGF βRII-1st fragment)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD (Linker)
GGGGSGGGGSGGGGS (Human TGF βRII-2nd fragment)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

Example 53. Production of an Exemplary Single-Chain Chimeric Polypeptides

Figure 64:
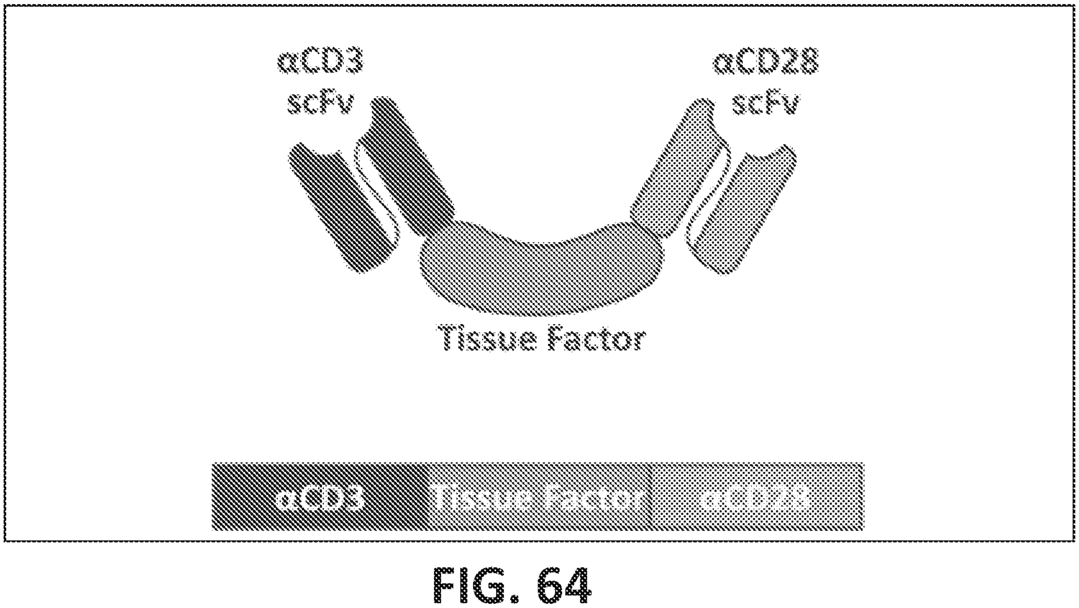
FIG. 64 are schematic diagrams of an exemplary αCD3scFv/TF/αCD28scFv single-chain chimeric polypeptide.

An exemplary single-chain chimeric polypeptide including a first target-binding domain that is an anti-CD3 scFv, a soluble human tissue factor domain, and a second target-binding domain that is an anti-CD28 scFv was generated (αCD3scFv/TF/αCD28scFv) (FIG. 64). The nucleic acid and amino acid sequences of this single-chain chimeric polypeptide are shown below.

Nucleic Acid Encoding Exemplary Single-Chain Chimeric Polypeptide (αCD3scFv/TF/αCD28scFv) (SEQ ID NO: 103)

(Signal peptide)
ATGAAGTGGGTGACCTTCATCAGCTTATTATTTTTATTCAGCTCCGCCT

ATTCC

-continued (αCD3 light chain variable region)
CAGATCGTGCTGACCCAAAGCCCCGCCATCATGAGCGCTAGCCCCGGTG

AGAAGGTGACCATGACATGCTCCGCTTCCAGCTCCGTGTCCTACATGAA

CTGGTATCAGCAGAAAAGCGGAACCAGCCCCAAAAGGTGGATCTACGAC

ACCAGCAAGCTGGCCTCCGGAGTGCCCGCTCATTTCCGGGGCTCTGGAT

CCGGCACCAGCTACTCTTTAACCATTCTATTGCGCCCGGTGGGGCGACG

GCAATTACTGGGGACGGGGCACAACACTGACCGTGAGCAGC (Linker)
GGAGGCGGAGGCTCCGGCGGAGGCGGATCTGGCGGTGGCGGCTCC (αCD28 light chain variable region)
GACATCGAGATGACCCAGTCCCCCGCTATCATGTCCGCCTCTTTAGGCG

AGCGGGTCACAATGACTTGTACAGCCTCCTCCAGCGTCTCCTCCTCCTA

CTTCCATTGGTACCAACAGAAACCCGGAAGCTCCCCTAAACTGTGCATC

TACAGCACCAGCAATCTCGCCAGCGGCGTGCCCCCTAGGTTTTCCGGAA

GCGGAAGCACCAGCTACTCTTTAACCATCTCCTCCATGGAGGCTGAGGA

TGCCGCCACCTACTTTTGTCACCAGTACCACCGGTCCCCCACCTTCGGA

GGCGGCACCAAACTGGAGACAAAGAGG

Exemplary Single-Chain Chimeric Polypeptide (αCD3scFv/TF/αCD28scFv) (SEQ ID NO: 102)

(Signal peptide)
MKWVTFISLLFLFSSAYS (αCD3 light chain variable region)
QIVLTQSPAIMSASPGEKVTMTCSASSSVSYMNWYQQKSGTSPKRWIYD

TSKLASGVPAHFRGSGSGTSYSLTISGMEAEDAATYYCQQWSSNPFTFG

SGTKLEINR (Linker)
GGGGSGGGGSGGGGS (αCD3 heavy chain variable region)
QVQLQQSGAELARPGASVKMSCKASGYTFTRYTMHWVKQRPGQGLEWIG

YINPSRGYTNYNQKFKDKATLTTDKSSSTAYMQLSSLTSEDSAVYYCAR

YYDDHYCLDYWGQGTTLTVSS (Human tissue factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (αCD28 light chain variable region)
VQLQQSGPELVKPGASVKMSCKASGYTFTSYVIQWVKQKPGQGLEWIGS

INPYNDYTKYNEKFKGKATLTSDKSSITAYMEFSSLTSEDSALYYCARW

GDGNYWGRGTTLTVSS (Linker)
GGGGSGGGGSGGGGS

-continued (αCD28 heavy chain variable region)
DIEMTQSPAIMSASLGERVTMTCTASSSVSSSYFHWYQQKPGSSPKLCI

YSTSNLASGVPPRFSGSGSGTSYSLTISSMEAEDAATYFCHQYHRSPTFG

GGTKLETKR

Figure 65:
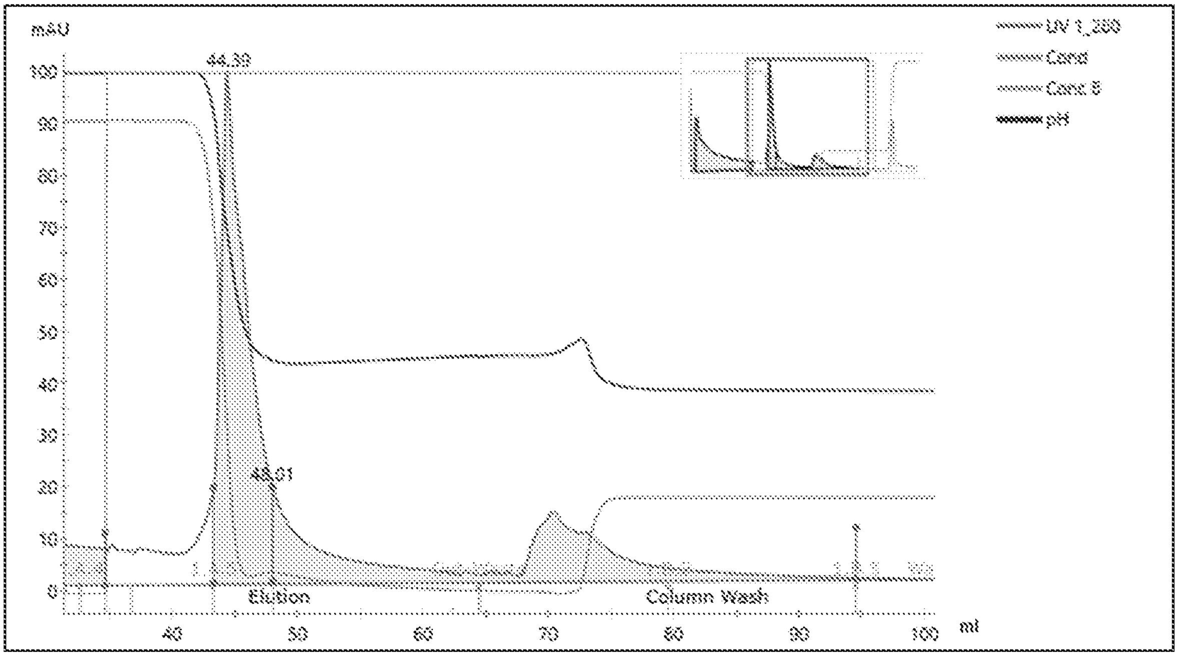
FIG. 65 is a chromatograph showing the elution of an exemplary αCD3scFv/TF/αCD28scFv single-chain chimeric polypeptide from an anti-tissue factor affinity column.

A second exemplary single-chain chimeric polypeptide including a first target-binding domain that is an anti-CD28 scFv, a soluble human tissue factor domain, and a second target-binding domain that is an anti-CD3 scFv was generated (αCD28scFv/TF/αCD3scFv) (FIG. 65). The nucleic acid and amino acid sequences of this single-chain chimeric polypeptide are shown below.

Nucleic Acid Encoding Exemplary Single-Chain Chimeric Polypeptide (αCD28scFv/TF/αCD3scFv) (SEQ ID NO: 195)

(Signal peptide)
ATGAAATGGGTCACCTTCATCTCTTTACTGTTTTTATTTAGCAGCGCCT

ACAGC (αCD28 light chain variable region)
GTGCAGCTGCAGCAGTCCGGACCCGAACTGGTCAAGCCCGGTGCCTCCG

TGAAAATGTCTTGTAAGGCTTCTGGCTACACCTTTACCTCCTACGTCAT

CCAATGGGTGAAGCAGAAGCCCGGTCAAGGTCTCGAGTGGATCGGCAGC

ATCAATCCCTACAACGATTACACCAAGTATAACGAAAAGTTTAAGGGCA

AGGCCACTCTGACAAGCGACAAGAGCTCCATTACCGCCTACATGGAGTT

TTCCTCTTTAACTTCTGAGGACTCCGCTTTATACTATTGCGCTCGTTGG

GGCGATGGCAATTATTGGGGCCGGGGAACTACTTTAACAGTGAGCTCC (Linker)
GGCGGCGGCGGAAGCGGAGGTGGAGGATCTGGCGGTGGAGGCAGC (αCD28 heavy chain variable region)
GACATCGAGATGACACAGTCCCCCGCTATCATGAGCGCCTCTTTAGGAG

AACGTGTGACCATGACTTGTACAGCTTCCTCCAGCGTGAGCAGCTCCTA

TTTCCACTGGTACCAGCAGAAACCCGGCTCCTCCCCTAAACTGTGTATC

TACTCCACAAGCAATTTAGCTAGCGGCGTGCCTCCTCGTTTTAGCGGCT

CCGGCAGCACCTCTTACTCTTTAACCATTAGCTCTATGGAGGCCGAAGA

TGCCGCCACATACTTTTGCCATCAGTACCACCGGTCCCCTACCTTTGGC

GGAGGCACAAAGCTGGAGACCAAGCGG (Human tissue factor 219 form)
AGCGGCACCACCAACACAGTGGCCGCCTACAATCTGACTTGGAAATCCA

CCAACTTCAAGACCATCCTCGAGTGGGAGCCCAAGCCCGTTAATCAAGT

TTATACCGTGCAGATTTCCACCAAGAGCGGCGACTGGAAATCCAAGTGC

TTCTATACCACAGACACCGAGTGCGATCTCACCGACGAGATCGTCAAAG

ACGTGAAGCAGACATATTTAGCTAGGGTGTTCTCCTACCCCGCTGGAAA

CGTGGAGAGCACCGGATCCGCTGGAGAGCCTTTATACGAGAACTCCCCC

GAATTCACCCCCTATCTGGAAACCAATTTAGGCCAGCCCACCATCCAGA

GCTTCGAACAAGTTGGCACAAAGGTGAACGTCACCGTCGAAGATGAGAG

GACTTTAGTGCGGAGGAACAATACATTTTTATCCTTACGTGACGTCTTC

GGCAAGGATTTAATCTACACACTGTATTACTGGAAGTCTAGCTCCTCCG

-continued

GCAAGAAGACCGCCAAGACCAATACCAACGAATTTTTAATTGACGTGGA

CAAGGGCGAGAACTACTGCTTCTCCGTGCAAGCTGTGATCCCCTCCCGG

ACAGTGAACCGGAAGTCCACCGACTCCCCCGTGGAGTGCATGGGCCAAG

AGAAGGGAGAGTTTCGTGAG (αCD3 light chain variable region)
CAGATCGTGCTGACCCAGTCCCCCGCTATTATGAGCGCTAGCCCCGGTG

AAAAGGTGACTATGACATGCAGCGCCAGCTCTTCCGTGAGCTACATGAA

CTGGTATCAGCAGAAGTCCGGCACCAGCCCTAAAAGGTGGATCTACGAC

ACCAGCAAGCTGGCCAGCGGCGTCCCCGCTCACTTTCGGGGCTCCGGCT

CCGGAACAAGCTACTCTCTGACCATCAGCGGCATGGAAGCCGAGGATGC

CGCTACCTATTACTGTCAGCAGTGGAGCTCCAACCCCTTCACCTTTGGA

TCCGGCACCAAGCTCGAGATTAATCGT (Linker)
GGAGGCGGAGGTAGCGGAGGAGGCGGATCCGGCGGTGGAGGTAGC (αCD3 heavy chain variable region)
CAAGTTCAGCTCCAGCAAAGCGGCGCCGAACTCGCTCGGCCCGGCGCTT

CCGTGAAGATGTCTTGTAAGGCCTCCGGCTATACCTTCACCCGGTACAC

AATGCACTGGGTCAAGCAACGGCCCGGTCAAGGTTTAGAGTGGATTGGC

TATATCAACCCCTCCCGGGGCTATACCAACTACAACCAGAAGTTCAAGG

ACAAAGCCACCCTCACCACCGACAAGTCCAGCAGCACCGCTTACATGCA

GCTGAGCTCTTTAACATCCGAGGATTCCGCCGTGTACTACTGCGCTCGG

TACTACGACGATCATTACTGCCTCGATTACTGGGGCCAAGGTACCACCT

TAACAGTCTCCTCC

Exemplary Single-Chain Chimeric Polypeptide (αCD28scFv/TF/αCD3scFv) (SEQ ID NO: 196)

(Signal peptide)
MKWVTFISLLFLFSSAYS (αCD28 light chain variable region)
VQLQQSGPELVKPGASVKMSCKASGYTFTSYVIQWVKQKPGQGLEWIGS

INPYNDYTKYNEKFKGKATLTSDKSSITAYMEFSSLTSEDSALYYCARW

GDGNYWGRGTTLTVSS (Linker)
GGGGSGGGGSGGGGS (αCD28 heavy chain variable region)
DIEMTQSPAIMSASLGERVTMTCTASSSVSSSYFHWYQQKPGSSPKLCI

YSTSNLASGVPPRFSGSGSTSYSLTISSMEAEDAATYFCHQYHRSPTFG

GGTKLETKR (Human tissue factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE

-continued (αCD3 light chain variable region)
QIVLTQSPAIMSASPGEKVTMTCSASSSVSYMNWYQQKSGTSPKRWIYD

TSKLASGVPAHFRGSGSGTSYSLTISGMEAEDAATYYCQQWSSNPFTFG

SGTKLEINR (Linker)
GGGGSGGGGSGGGGS (αCD3 heavy chain variable region)
QVQLQQSGAELARPGASVKMSCKASGYTFTRYTMHWVKQRPGQGLEWIG

YINPSRGYTNYNQKFKDKATLTTDKSSSTAYMQLSSLTSEDSAVYYCAR

YYDDHYCLDYWGQGTTLTVSS

The nucleic acid encoding αCD3scFv/TF/αCD28scFv was cloned into a modified retrovirus expression vectors as described previously (Hughes et al., *Hum Gene Ther* 16:457-72, 2005). The expression vector encoding αCD3scFv/TF/αCD28scFv was transfected into CHO-K1 cells. Expression of the expression vector in CHO-K1 cells allowed for secretion of the soluble αCD3scFv/TF/αCD28scFv single-chain chimeric polypeptide (referred to as 3t28), which can be purified by anti-TF antibody affinity and other chromatography methods.

An anti-tissue factor affinity column was used to purify the αCD3scFv/TF/αCD28scFv single-chain chimeric polypeptide. The anti-tissue factor affinity column was connected to a GE Healthcare AKTA Avant system. A flow rate of 4 mL/min was used for all steps except the elution step, which was 2 mL/min.

Cell culture harvest including αCD3scFv/TF/αCD28scFv single-chain chimeric polypeptide was adjusted to pH 7.4 with 1M Tris base and loaded onto the anti-TF antibody affinity column (described above) which was equilibrated with 5 column volumes of PBS. After sample loading, the column was washed with 5 column volumes PBS, followed by elution with 6 column volumes 0.1 M acetic acid, pH 2.9. An A280 elution peak was collected and then neutralized to pH 7.5-8.0 by adding 1 M Tris base. The neutralized sample was then buffer exchanged into PBS using Amicon centrifugal filters with a 30 kDa molecular weight cutoff. The data in FIG. 65 show that the anti-tissue factor affinity column can bind the αCD3scFv/TF/αCD28scFv single-chain chimeric polypeptide, which contains a human soluble tissue factor domain. The buffer-exchanged protein sample was stored at 2-8° C. for further biochemical analysis and biological activity testing.

After each elution, the anti-tissue factor affinity column was stripped using 6 column volumes of 0.1 M glycine, pH 2.5. The column was then neutralized using 10 column volumes of PBS, 0.05% $NaN_3$, and stored at 2-8° C.

Figure 66:
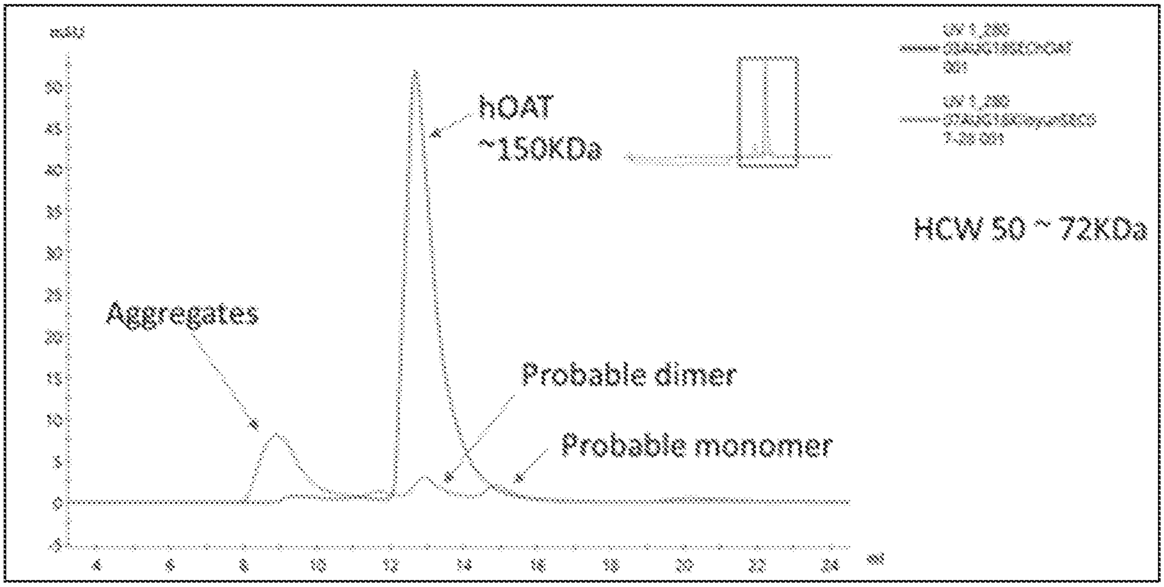
FIG. 66 is a chromatograph showing the elution of a Superdex 200 Increase 10/300 GL gel filtration column loaded with an exemplary αCD3scFv/TF/αCD28scFv single-chain chimeric polypeptide.

Analytical size exclusion chromatography (SEC) was performed on the αCD3scFv/TF/αCD28scFv single-chain chimeric polypeptide using a Superdex 200 Increase 10/300 GL gel filtration column (from GE Healthcare) connected to an AKTA Avant system (from GE Healthcare). The column was equilibrated with 2 column volumes of PBS. A flow rate of 0.8 mL/min was used. Two hundred pL of αCD3scFv/TF/αCD28scFv single-chain chimeric polypeptide (1 mg/mL) was injected onto the column using a capillary loop. After injection of the single-chain chimeric polypeptide, 1.25 column volumes of PBS were flowed into the column. The SEC chromatograph is shown in FIG. 66. The data show that there are 3 protein peaks, likely representing a monomer and dimer or other different forms of the αCD3scFv/TF/αCD28scFv single-chain chimeric polypeptide.

Figure 67:
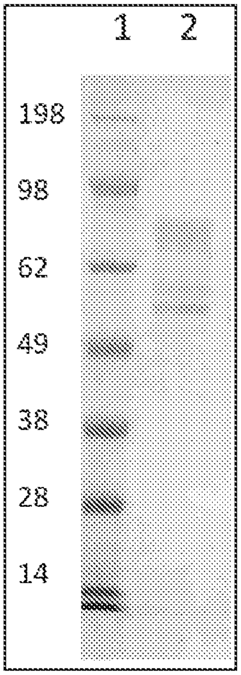
FIG. 67 is a sodium dodecyl sulfate polyacrylamide gel (4-12% NuPage Bis-Tris gel) of an exemplary αCD3scFv/TF/αCD28scFv single-chain chimeric polypeptide purified using an anti-tissue factor affinity column.

To determine the purity and protein molecular weight of the αCD3scFv/TF/αCD28scFv single-chain chimeric polypeptide, the purified αCD3scFv/TF/αCD28scFv protein sample from anti-tissue factor affinity column was analyzed by standard sodium dodecyl sulfate polyacrylamide gel (4-12% NuPage Bis-Tris gel) electrophoresis (SDS-PAGE) method under reduced conditions. The gel was stained with InstantBlue for about 30 minutes and destained overnight with purified water. FIG. 67 shows the SDS gel of the αCD3scFv/TF/αCD28scFv single-chain chimeric polypeptide purified using an anti-tissue factor affinity column. The results show that the purified αCD3scFv/TF/αCD28scFv single-chain chimeric polypeptide has the expected molecular weight (72 kDa) in reduced SDS gel.

Figure 68:
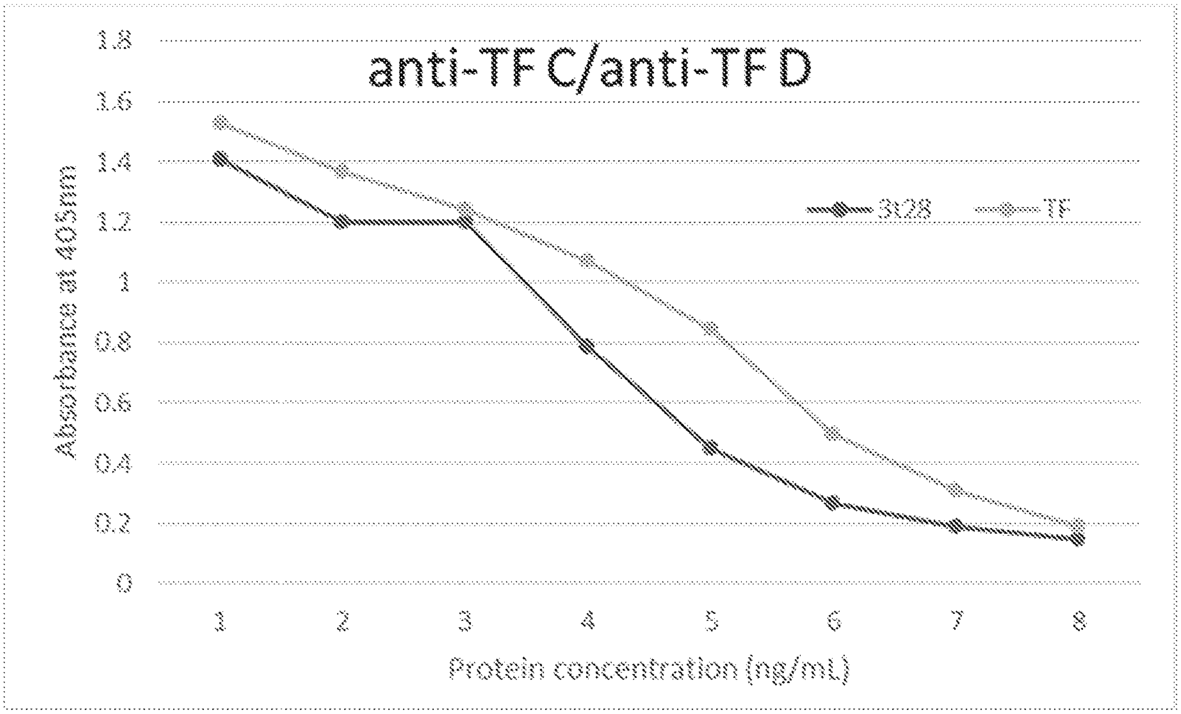
FIG. 68 is a graph showing the ELISA quantitation of an exemplary αCD3scFv/TF/αCD28scFv single-chain chimeric polypeptide performed using the methods described in Example 53. Purified tissue factor was used as the control.

Example 54. Functional Characterization of αCD3scFv/TF/αCD28scFv Single-Chain Chimeric Polypeptide ELISA-based methods confirmed the formation of the αCD3scFv/TF/αCD28scFv single-chain chimeric polypeptide. The αCD3scFv/TF/αCD28scFv single-chain chimeric polypeptide was detected using an anti-TF antibody (I43)/anti-TF antibody-specific ELISA with a capture antibody, anti-human tissue factor antibody (I43), and a detection antibody, anti-TF antibody (FIG. 68). A purified tissue factor protein with a similar concentration was used as a control.

Figure 69:
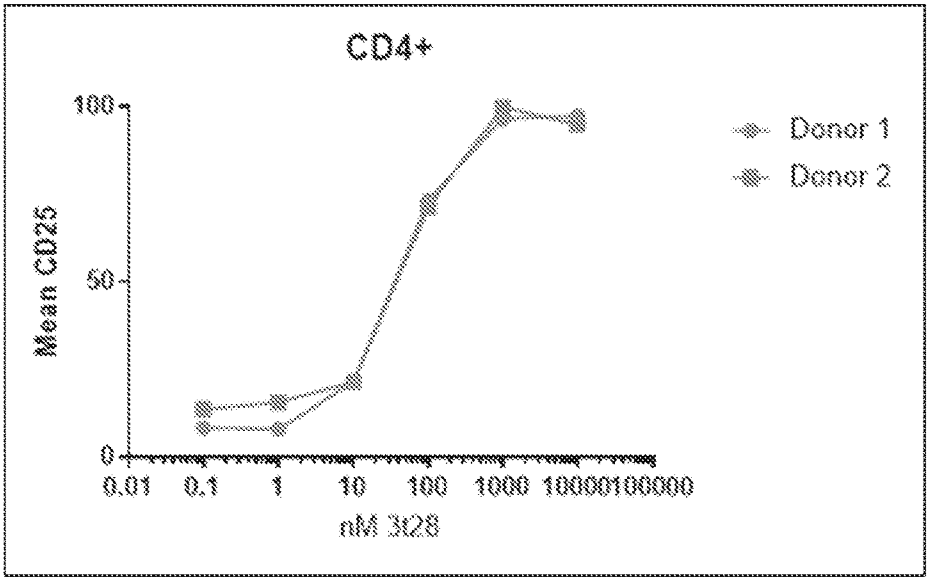
FIG. 69 is a graph showing the ability of an exemplary αCD3scFv/TF/αCD28scFv single-chain chimeric polypeptide to stimulate CD25 expression in CD4+ T-cells isolated from blood from two donors. The experiments were performed as described in Example 54.
Figure 70:
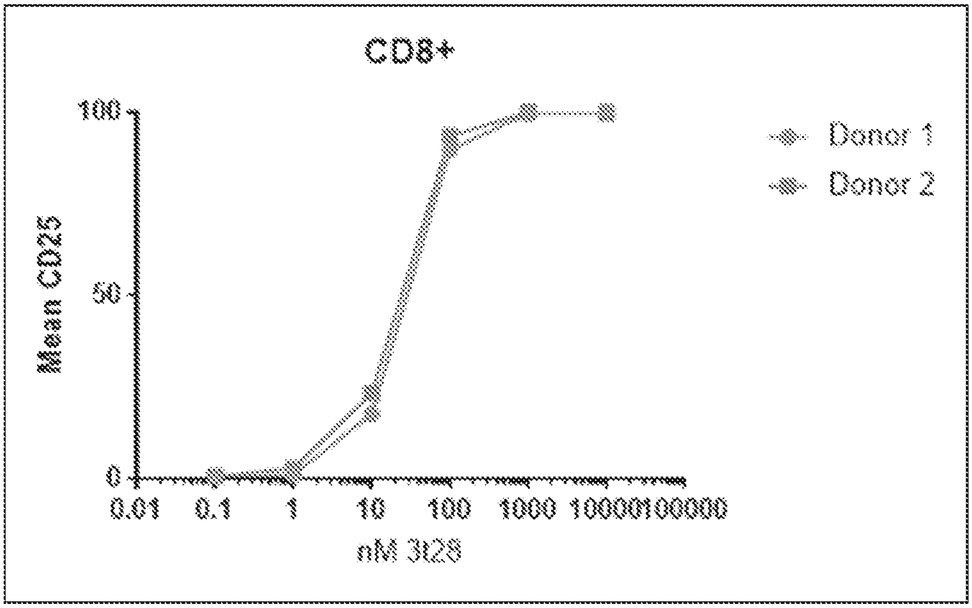
FIG. 70 is a graph showing the ability of an exemplary αCD3scFv/TF/αCD28scFv single-chain chimeric polypeptide to stimulate CD25 expression in CD8+ T-cells isolated from blood from two donors. The experiments were performed as described in Example 54.
Figure 71:
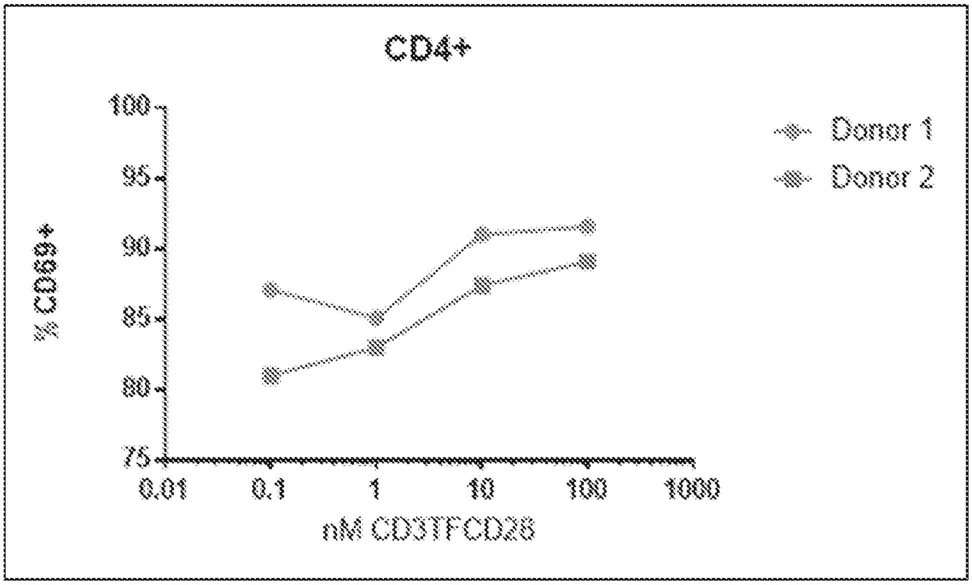
FIG. 71 is a graph showing the ability of an exemplary αCD3scFv/TF/αCD28scFv single-chain chimeric polypeptide to stimulate CD69 expression in CD4+ T-cells isolated from blood from two donors. The experiments were performed as described in Example 54.

A further in vitro experiment was performed to determine whether the αCD3scFv/TF/αCD28scFv single-chain chimeric polypeptide is capable of activating human peripheral blood mononuclear cells (PBMCs). Fresh human leukocytes were obtained from the blood bank and peripheral blood mononuclear cells (PBMC) were isolated using density gradient Histopaque (Sigma). The cells were counted and resuspended in $0.2\times10^6$/mL in a 96-well flat bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with αCD3scFv/TF/αCD28scFv single-chain chimeric polypeptide from 0.01 nM to 1000 nM for 3 days at 37° C., 5% $CO_2$. After 72 hours, the cells were harvested and surface stained for CD4-488, CD8-PerCP Cy5.5, CD25-BV421, CD69-APCFire750, CD62L-PE Cy7, and CD44-PE specific antibodies (Biolegend) for 30 minutes. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were resuspended in 300 μL of FACS buffer and analyzed by Flow Cytometry (Celesta-BD Bioscience). The data in FIGS. 69 and 70 show that the αCD3scFv/TF/αCD28scFv single-chain chimeric polypeptide is able to stimulate both $CD8^+$ and $CD4^+$ T-cells. A further experiment was performed, in which PBMCs isolated from blood using Histopaque (Sigma) were counted and resuspended in $0.2\times10^6$/mL in a 96-well flat bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were then stimulated with the αCD3scFv/TF/αCD28scFv single-chain chimeric polypeptide from 0.01 nM to 1000 nM for 3 days at 37° C., 5% $CO_2$. After 72 hours, the cells were harvested and surface stained for CD4-488, CD8-PerCP Cy5.5, CD25-BV421, CD69-APCFire750, CD62L-PE Cy7, and CD44-PE (Biolegend) for 30 minutes. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were resuspended in 300 μL of FACS buffer and analyzed by Flow Cytometry (Celesta-BD Bioscience). The data again show that the αCD3scFv/TF/αCD28scFv single-chain chimeric polypeptide was able to stimulate activation of $CD4^+$ T cells (FIG. 71).

Example 55. Construction of Exemplary Multi-Chain Chimeric Polypeptides and Evaluation of Properties Thereof Two multi-chain chimeric polypeptides were generated and their properties were evaluated. Each of the two multi-chain chimeric polypeptides included a first chimeric polypeptide that included a soluble tissue factor domain covalently linked a first target-binding domain and a first domain of an affinity pair of domains. The second chimeric polypeptide in each of the two multi-chain chimeric polypeptides included a second domain of the affinity pair of domains, and a second target-binding domain.

Description of Logic Underlying Construction of Multi-Chain Chimeric Polypeptides Tissue Factor (TF) is a stable, transmembrane protein containing 236 amino acid residues. The truncated, recombinant 219-amino-acid extracellular domain of tissue factor is soluble and is known to be expressed at high levels in bacteria or mammalian cells. Without wishing to be bound to a particular theory, the applicants speculated that the 219-aa tissue factor could be used as a connector linker for creation of unique multi-chain chimeric polypeptides.

First chimeric polypeptides including soluble tissue factor domain were produced at high levels by CHO-K1 cells grown in fermentation broth. These first chimeric polypeptides were purified by an anti-tissue factor monoclonal antibody (mAb) coupled on a solid matrix. Notably, tissue factor contains binding sites for FVIIa and FX. The catalytic activity of the tissue factor-FVIIa complex for FX is approximately 1 million-fold lower when tissue factor is not anchored to a phospholipid bilayer. Thus, without wishing to be bound to a particular theory, applicants speculated that using the 219-aa extracellular domain of tissue factor without the transmembrane in construction of the first chimeric polypeptides may eliminate the pro-coagulation activity of tissue factor in the first chimeric polypeptides. In an effort to further reduce or eliminate the pro-coagulation activity of the 219-aa tissue factor, select mutations in tissue factor can be made, specifically at seven amino acid residues that are known to contribute to binding energy of the FVIIa binding site.

Characterization of Binding Interactions for Described Chimeric Polypeptides

To determine if the first and second chimeric polypeptides bind to each other to form multi-chain chimeric polypeptides, in vitro binding assays were performed. To determine if the first chimeric polypeptide comprising soluble tissue factor domain are recognized and bound by anti-TF mAb, in vitro binding assays were performed. Notably, the data indicated that the mutated tissue factor proteins are still recognized and selectively bound by the anti-TF mAb which is known to bind to the FX binding site on tissue factor. To determine if the first chimeric polypeptides comprising soluble tissue factor domain covalently linked to scFvs or cytokines (see FIG. 72 and FIG. 73) possess functional scFvs or cytokines, in vitro binding assays were performed. The data from the aforementioned assays were consistent with the purified first chimeric polypeptides having the expected biological activities (e.g., scFvs selectively bind expected target antigens or cytokines selectively bind expected receptors or binding proteins).

In addition, experiments performed using the two multi-chain chimeric polypeptides including a first and second chimeric polypeptide bound to each other demonstrate the expected target binding activity (e.g., the multi-chain chimeric polypeptide binds specifically to the target specifically recognized by the first target-binding domain and the target specifically recognized by the second target-binding domain).

Based on the aforementioned results, applicants concluded that the soluble tissue factor connecter linker provided or enabled appropriate display of the polypeptides encoding either scFvs, interleukins, cytokines, interleukin receptors, or cytokine receptors in three-dimensional space relative to soluble tissue factor domain and relative to one another such that each retained expected biological properties (and activities).

When both the first and second chimeric polypeptides were co-expressed, the heterodimeric complexes were secreted into the fermentation broths at high levels. The complexes were captured and readily purified by anti-TF mAb conjugated to a solid matrix using affinity chromatography. The first and second target-binding domains of these multi-chain chimeric polypeptides retained their expected biological activities as assayed by in vitro binding assays. Thus, the assembly of the multi-chain chimeric polypeptides provides the appropriate spatial display and folding of the domains for biological activities. Importantly, the spatial arrangement of the multi-chain chimeric polypeptides does not interfere with the FX binding site on tissue factor which enables the use of anti-TF mAb for affinity purification.

Characterization of Stability for Described Chimeric Polypeptides

Both purified multi-chain chimeric polypeptides are expected to be stable. These multi-chain chimeric polypeptides are structurally intact and expected to be fully biologically active when they are incubated in human serum at 37° C. for 72 hours.

Characterization of Propensity of Described Chimeric Polypeptides to Aggregate

Both purified multi-chain chimeric polypeptides are expected not to form aggregates when stored at 4° C. in PBS.

Characterization of Viscosity of Described Chimeric Polypeptides

Compositions including the multi-chain chimeric polypeptides are not expected to have any viscosity issues when formulated at a concentration as high as 50 mg/mL in PBS.

Discussion of Multi-Chain Chimeric Polypeptide Platform for Use in Selectively Binding Clinically Relevant Targets The data from our studies show that our platform technologies can be utilized to create molecules that could be fused to target-binding domains derived from antibodies, in any formats as discussed above, adhesion molecules, receptors, cytokines, chemokines etc. With the appropriate target-binding domain, the resulting multi-chain chimeric polypeptides could promote conjugation of various immune effector cells and mediate destruction of target cells, including cancer cells, virally-infected cells, or senescent cells. Other domains in the multi-chain chimeric polypeptides stimulate, activate, and attract the immune system for enhancing cytotoxicity of effector cells for the targeted cells.

Example 56: Creation of an IL-7/IL-15RαSu DNA Construct

Figure 72:
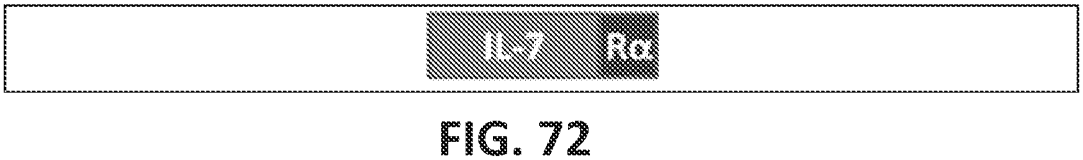
FIG. 72 shows a schematic diagram of an exemplary IL-7/IL-15RαSu DNA construct.
Figure 73:
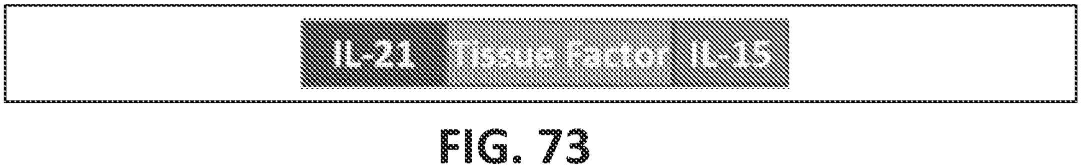
FIG. 73 shows a schematic diagram of an exemplary IL-21/TF/IL-15 DNA construct.

In a non-limiting example, an IL-7/IL-15RαSu DNA construct was created (see FIG. 72). The human IL-7 sequence, human IL-15RαSu sequence, human IL-15 sequence, and human tissue factor 219 sequence were obtained from the UniProt website and DNA for these sequences was synthesized by Genewiz. A DNA construct was made linking the IL-7 sequence to the IL-15RαSu sequence. The final IL-7/IL-15RαSu DNA construct sequence was synthesized by Genewiz.

The nucleic acid sequence encoding the second chimeric polypeptide of IL-7/IL-15RαSu construct (including signal peptide sequence) is as follows (SEQ ID NO: 140):

```
GATTGTGATATTGAAGGTAAAGATGGCAAACAATATGAGAGTGTTCTAA

TGGTCAGCATCGATCAATTATTGGACAGCATGAAAGAAATTGGTAGCAA

TTGCCTGAATAATGAATTTAACTTTTTTAAAAGACATATCTGTGATGCT

AATAAGGAAGGTATGTTTTTATTCCGTGCTGCTCGCAAGTTGAGGCAAT

TTCTTAAAATGAATAGCACTGGTGATTTTGATCTCCACTTATTAAAAGT

TTCAGAAGGCACAACAATACTGTTGAACTGCACTGGCCAGGTTAAAGGA

AGAAAACCAGCTGCCCTGGGTGAAGCCCAACCAACAAAGAGTTTGGAAG

AAAATAAATCTTTAAAGGAACAGAAAAAACTGAATGACTTGTGTTTCCT

AAAGAGACTATTACAAGAGATAAAAACTTGTTGGAATAAAATTTTGATG

GGCACTAAAGAACAC

(Human IL-15R α sushi domain)
ATCACGTGCCCTCCCCCCATGTCCGTGGAACACGCAGACATCTGGGTCA

AGAGCTACAGCTTGTACTCCAGGGAGCGGTACATTTGTAACTCTGGTTT

CAAGCGTAAAGCCGGCACGTCCAGCCTGACGGAGTGCGTGTTGAACAAG

GCCACGAATGTCGCCCACTGGACAACCCCCAGTCTCAAATGCATTAGA
```

The second chimeric polypeptide of IL-7/IL-15RαSu construct (including signal peptide sequence) is as follows (SEQ ID NO: 139):

```
(Signal peptide)
MKWVTFISLLFLFSSAYS

(Human IL-7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH

(Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE
```

-continued

```
(Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

Example 57: Creation of an IL-21/TF/IL-15 DNA Construct

In a non-limiting example, an IL-21/TF/IL-15 construct was made (see FIG. 73) by linking the IL-21 sequence to the N-terminus coding region of tissue factor 219, and further linking the IL-21/TF construct with the N-terminus coding region of IL-15.

The nucleic acid sequence encoding the first chimeric polypeptide of IL-21/TF/IL-15 construct (including leader sequence), synthesized by Genewiz, is as follows (SEQ ID NO: 129):

```
(Signal peptide)
ATGGGAGTGAAAGTTCTTTTTGCCCTTATTTGTATTGCTGTGGCCGAGG

CC

(Human IL-21 fragment)
CAAGGTCAAGATCGCCACATGATTAGAATGCGTCAACTTATAGATATTG

TTGATCAGCTGAAAAATTATGTGAATGACTTGGTCCCTGAATTTCTGCC

AGCTCCAGAAGATGTAGAGACAAACTGTGAGTGGTCAGCTTTTTCCTGT

TTTCAGAAGGCCCAACTAAAGTCAGCAAATACAGGAAACAATGAAAGGA

TAATCAATGTATCAATTAAAAAGCTGAAGAGGAAACCACCTTCCACAAA

TGCAGGGAGAAGACAGAAACACAGACTAACATGCCCTTCATGTGATTCT

TATGAGAAAAAACCACCCAAAGAATTCCTAGAAAGATTCAAATCACTTC

TCCAAAAGATGATTCATCAGCATCTGTCCTCTAGAACACACGGAAGTGA

AGATTCC

(Human Tissue Factor 219)
TCAGGCACTACAAATACTGTGGCAGCATATAATTTAACTTGGAAATCAA

CTAATTTCAAGACAATTTTGGAGTGGGAACCCAAACCCGTCAATCAAGT

CTACACTGTTCAAATAAGCACTAAGTCAGGAGATTGGAAAAGCAAATGC

TTTTACACAACAGACACAGAGTGTGACCTCACCGACGAGATTGTGAAGG

ATGTGAAGCAGACGTACTTGGCACGGGTCTTCTCCTACCCGGCAGGGAA

TGTGGAGAGCACCGGTTCTGCTGGGGAGCCTCTGTATGAGAACTCCCCA

GAGTTCACACCTTACCTGGAGACAAACCTCGGACAGCCAACAATTCAGA

GTTTTGAACAGGTGGGAACAAAAGTGAATGTGACCGTAGAAGATGAACG

GACTTTAGTCAGAAGGAACAACACTTTCCTAAGCCTCCGGGATGTTTTT

GGCAAGGACTTAATTTATACACTTTATTATTGGAAATCTTCAAGTTCAG

GAAAGAAAACAGCCAAAACAAACACTAATGAGTTTTTGATTGATGTGGA

TAAAGGAGAAAACTACTGTTTCAGTGTTCAAGCAGTGATTCCCTCCCGA

ACAGTTAACCGGAAGAGTACAGACAGCCCGGTAGAGTGTATGGGCCAGG

AGAAAGGGGAATTCAGAGAA
```

-continued

```
(Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC
```

The first chimeric polypeptide of IL-21/TF/IL-15 construct including leader sequence is SEQ ID NO: 128:

```
(Signal peptide)
MGVKVLFALICIAVAEA

(Human IL-21)
QGQDRHMIRMRQLIDIVDQLKNYVNDLVPEFLPAPEDVETNCEWSAFS

CFQKAQLKSANTGNNERIINVSIKKLKRKPPSTNAGRRQKHRLTCPSC

DSYEKKPPKEFLERFKSLLQKMIHQHLSSRTHGSEDS

(Human Tissue Factor 219)
SGTTNTVAAYNLTWKSTNFKTILEWEPKPVNQVYTVQISTKSGDWKSK

CFYTTDTECDLTDEIVKDVKQTYLARVFSYPAGNVESTGSAGEPLYEN

SPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAV

IPSRTVNRKSTDSPVECMGQEKGEFRE

(Human IL-15)
NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS
```

Example 58: Secretion of IL-7/IL-15RαSu and IL-21/TF/IL-15 Fusion Proteins

Figure 74:
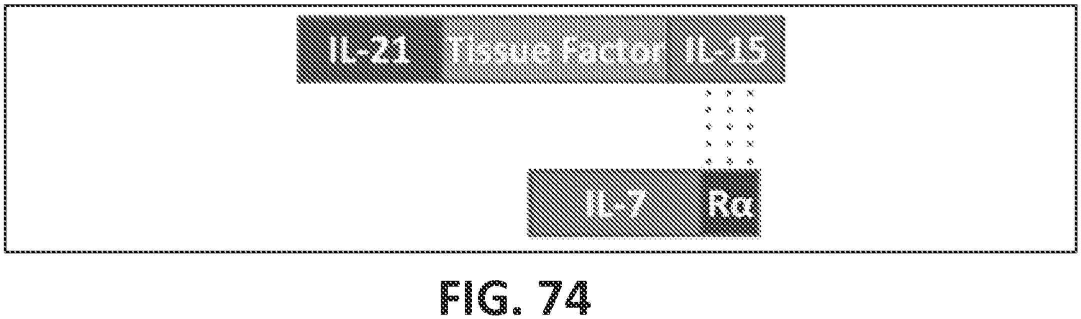
FIG. 74 shows a schematic diagram of the interaction between the exemplary IL-7/IL-15RαSu and IL-21/TF/IL-15 DNA constructs.
Figure 75:
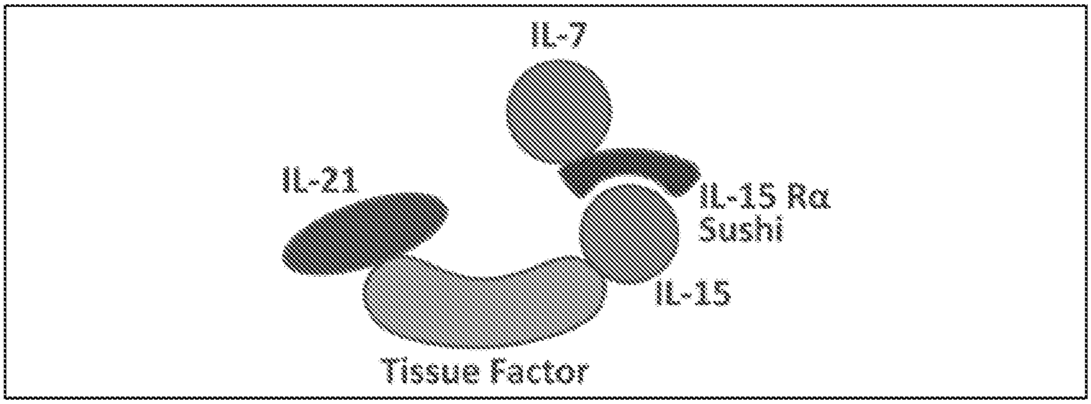
FIG. 75 shows a schematic diagram of the interaction between the exemplary IL-7/IL-15RαSu and IL-21/TF/IL-15 fusion proteins resulting in an IL-21/TF/IL-15:IL-7/IL-15RαSu complex (21t15-7s).

The IL-7/IL-15RαSu and IL-21/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-21/TF/IL-15:IL-7/IL-15RαSu protein complex (referred to as 21t15-7s, see FIGS. 74 and 75). The 21t15-7s protein was purified from CHO-K1 cell culture supernatant using anti-TF antibody affinity chromatography and size exclusion chromatography resulting in soluble (non-aggregated) protein complexes consisting of IL-7/IL-15RαSu and IL-21/TF/IL-15 fusion proteins.

In some cases, the leader (signal sequence) peptide is cleaved from the intact polypeptide to generate the mature form that may be soluble or secreted.

Example 59: Purification of 21t15-7s by Immunoaffinity Chromatography

An anti-TF antibody affinity column was connected to a GE Healthcare™ AKTA Avant protein purification system. The flow rate was 4 mL/min for all steps except the elution step, which was 2 mL/min.

Cell culture harvest of 21t15-7s was adjusted to pH 7.4 with 1M Tris base and loaded onto the anti-TF antibody affinity column equilibrated with 5 column volumes of PBS. After loading the sample, the column was washed with 5 column volumes PBS, followed by elution with 6 column volumes 0.1M acetic acid, pH 2.9. Absorbance at 280 nm was collected and then the sample was neutralized to pH 7.5-8.0 by adding 1M Tris base. The neutralized sample was then buffer exchanged into PBS using Amicon® centrifugal filters with a 30 KDa molecular weight cutoff. The buffer-exchanged protein sample was stored at 2-8° C. for further biochemical analysis and biological activity testing.

After each elution, the anti-TF antibody affinity column was then stripped using 6 column volumes 0.1M glycine, pH 2.5. The column was then neutralized using 10 column volumes PBS, 0.05% sodium azide and stored at 2-8° C.

Example 60: Creation of a TGF-βRII/IL-15RαSu DNA Construct

Figure 76:
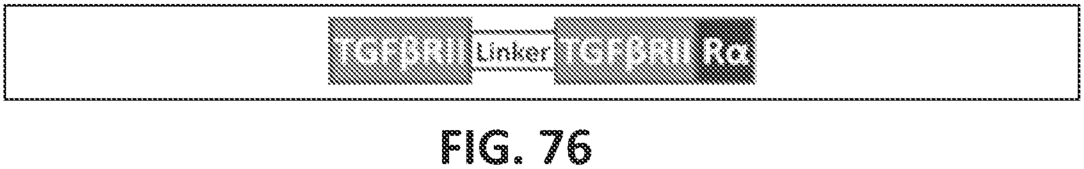
FIG. 76 shows a schematic diagram of an exemplary TGF-βRII/IL-15RαSu DNA construct.

In a non-limiting example, a TGF-βRII/IL-15RαSu DNA construct was created (see FIG. 76). The human TGF-βRII sequence, human IL-15RαSu sequence, human IL-15 sequence, and human tissue factor 219 sequence were obtained from the UniProt website and DNA for these sequences was synthesized by Genewiz. A DNA construct was made linking the TGF-βRII sequences (separated by a linker) to the IL-15RαSu sequence. The final TGF-βRII/IL-15RαSu DNA construct sequence was synthesized by Genewiz.

Example 61: Creation of an IL-21/TF/IL-15 DNA Construct

Figure 77:
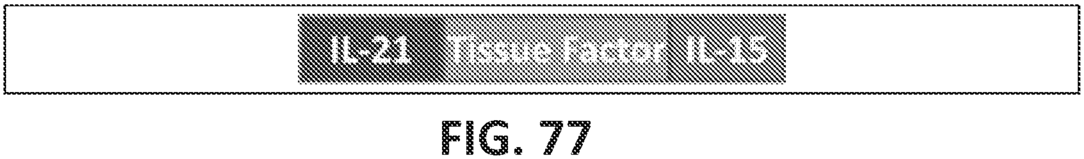
FIG. 77 shows a schematic diagram of an exemplary IL-21/TF/IL-15 DNA construct.

In a non-limiting example, an IL-21/TF/IL-15 construct was made (see FIG. 77) by linking the IL-21 sequence to the N-terminus coding region of tissue factor 219, and further linking the IL-21/TF construct with the N-terminus coding region of IL-15.

Figure 78:
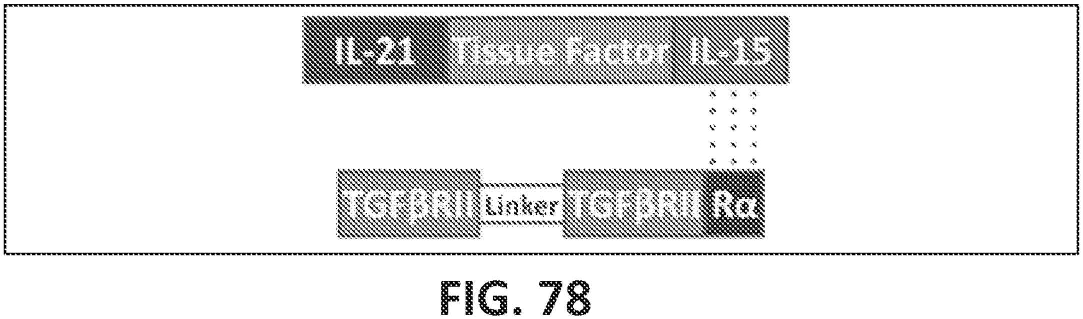
FIG. 78 shows a schematic diagram of the interaction between the exemplary TGF-β RII/IL-15RαSu and IL-21/TF/IL-15 DNA constructs.
Figure 79:
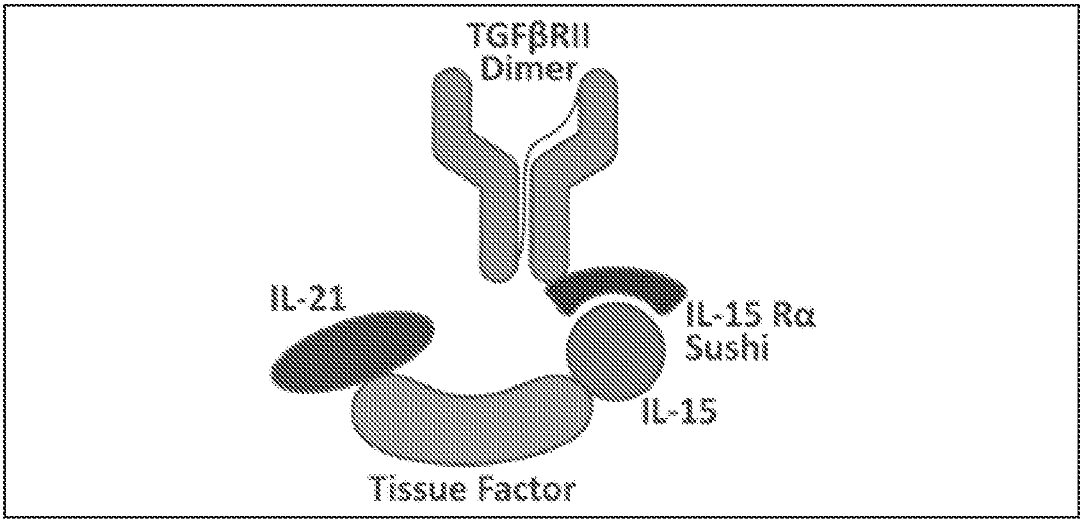
FIG. 79 shows a schematic diagram of the interaction between the exemplary TGF-βRII/IL-15RαSu and IL-21/TF/IL-15 fusion proteins resulting in an IL-21/TF/IL-15:TGF-βRII/IL-15RαSU complex (21t15-TGFRs).

Example 62: Secretion of TGF-βRII/IL-15RαSu and IL-21/TF/IL-15 Fusion Proteins The TGF-βRII/IL-15RαSu and IL-21/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-21/TF/IL-15:TGF-βRII/IL-15RαSu protein complex (referred to as 21t15-TGFRs, see FIGS. 78 and 79). The 21t15-TGFRs protein was purified from CHO-K1 cell culture supernatant using anti-TF antibody affinity chromatography and size exclusion chromatography resulting in soluble (non-aggregated) protein complexes consisting of TGF-βRII/IL-15RαSu and IL-21/TF/IL-15 fusion proteins.

Example 63: Size Exclusion Chromatography

A GE Healthcare Superdex® 200 Increase 10/300 GL gel filtration column was connected to a GE Healthcare AKTA™ Avant protein purification system. The column was equilibrated with 2 column volumes of PBS. The flow rate was 0.7 mL/min. A capillary loop was used to inject 200 μL of 1 mg/mL of 7t15-21s complex onto the column. The injection was chased with 1.25 column volumes of PBS.

Example 64: SDS-PAGE of 21t15-7s and 21t15-TGFRs

To determine the purity and protein molecular weight, the purified 21t15-7s or 21t15-TGFRs protein sample were analyzed using 4-12% NuPage Bis-Tris protein gel SDS-PAGE. The gel will be stained with InstantBlue™ for about 30 min, followed by destaining overnight in purified water.

Example 65: Glycosylation of 21t15-7s and 21t15-TGFRs in CHO-K1 Cells

Glycosylation of 21t15-7s in CHO-K1 cells or 21t15-TGFRs in CHO-K1 cells were confirmed using the Protein Deglycosylation Mix II kit (New England Biolabs), according to the manufacturer's instructions.

Example 66: Recombinant Protein Quantitation of 21t15-7s and 21t15-TGFRs Complexes The 21t15-7s complex or the 21t15-TGFRs complex were detected and quantified using standard sandwich ELISA methods. Anti-human tissue factor antibody (IgG1) served as the capture antibody and biotinylated anti-human IL-21, IL-15, or IL-7 antibody (21t15-7s) or biotinylated anti-human IL-21, IL-15, or TGF-βRII antibody (21t15-TGFRs) served as the detection antibody. Tissue factor in purified 21t15-7s or 21t15-TGFRs protein complexes was detected using an anti-human tissue factor capture antibody, and anti-human tissue factor antibody (IgG1) detection antibody. The anti-TF ELISA will be compared to purified tissue factor at similar concentrations.

Example 67: Creation of an IL-21/IL-15RαSu DNA Construct

Figure 80:
FIG. 80 shows a schematic diagram of an exemplary IL-21/IL-15RαSu DNA construct.

In a non-limiting example, an IL-21/IL-15RαSu DNA construct was created. The human IL-21 sequence and human IL-15RαSu sequence were obtained from the UniProt website and DNA for these sequences was synthesized by Genewiz. A DNA construct was made linking the IL-21 sequence to the IL-15RαSu sequence. The final IL-21/IL-15RαSu DNA construct sequence was synthesized by Genewiz. See FIG. 80.

Example 68: Creation of an IL-7/TF/IL-15 DNA Construct

Figure 81:
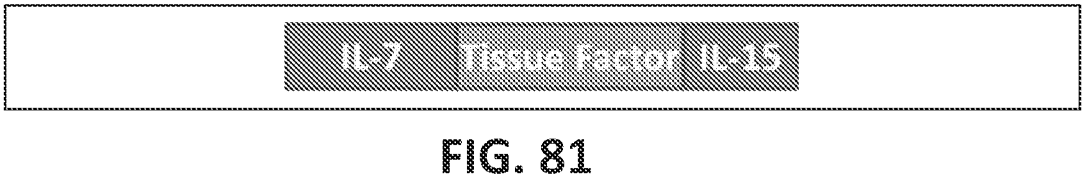
FIG. 81 shows a schematic diagram of an exemplary IL-7/TF/IL-15 DNA construct.

In a non-limiting example, an IL-7/TF/IL-15 construct was made by linking the IL-7 sequence to the N-terminus coding region of tissue factor 219, and further linking the IL-7/TF construct with the N-terminus coding region of IL-15. See FIG. 81.

Example 69: Creation of an IL-21/IL-15Rα Sushi DNA Construct

In a non-limiting example, a second chimeric polypeptide of IL-21/IL-15RαSu was generated. The human IL-21 and human IL-15Rα sushi sequences were obtained from the UniProt website and DNA for these sequences was synthesized by Genewiz. A DNA construct was made linking the IL-21 sequence to the IL-15Rα sushi sequence. The final IL-21/IL-15RαSu DNA construct sequence was synthesized by Genewiz.

The nucleic acid sequence encoding the second chimeric polypeptide of IL-21/IL-15RαSu domain (including leader sequence), synthesized by Genewiz, is as follows (SEQ ID NO: 148):

```
(Signal peptide)
ATGAAGTGGGTGACCTTCATCAGCCTGCTGTTCCTGTTCTCCAGCGCC

TACTCC

(Human IL-21)
CAGGGCCAGGACAGGCACATGATCCGGATGAGGCAGCTCATCGACATC

GTCGACCAGCTGAAGAACTACGTGAACGACCTGGTGCCCGAGTTTCTG

CCTGCCCCCGAGGACGTGGAGACCAACTGCGAGTGGTCCGCCTTCTCC

TGCTTTCAGAAGGCCCAGCTGAAGTCCGCCAACACCGGCAACAACGAG

CGGATCATCAACGTGAGCATCAAGAAGCTGAAGCGGAAGCCTCCCTCC

ACAAACGCCGGCAGGAGGCAGAAGCACAGGCTGACCTGCCCCAGCTGT

GACTCCTACGAGAAGAAGCCCCCCAAGGAGTTCCTGGAGAGGTTCAAG

TCCCTGCTGCAGAAGATGATCCATCAGCACCTGTCCTCCAGGACCCAC

GGCTCCGAGGACTCC

(Human IL-15R α sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGC

TTCAAGAGGAAGGCCGGCACCAGCAGCCTCACCGAGTGCGTGCTGAAT

AAGGCTACCAACGTGGCTCACTGGACAACACCCTCTTTAAAGTGCATC

CGG
```

The second chimeric polypeptide of IL-21/IL-15Rα sushi domain (including leader sequence) is as follows (SEQ ID NO: 147):

```
(Signal Sequence)
MKWVTFISLLFLFSSAYS

(Human IL-21)
QGQDRHMIRMRQLIDIVDQLKNYVNDLVPEFLPAPEDVETNCEWSAFS

CFQKAQLKSANTGNNERIINVSIKKLKRKPPSTNAGRRQKHRLTCPSC

DSYEKKPPKEFLERFKSLLQKMIHQHLSSRTHGSEDS

(Human IL-15Rα sushi domain)
ITCPPPMSVEHADIWVKSYSLYSRERYICNSGFKRKAGTSSLTECVLN

KATNVAHWTTPSLKCIR
```

Example 70: Creation of an IL-7/TF/IL-15 DNA Construct

In a non-limiting example, an exemplary first chimeric polypeptide of IL-7/TF/IL-15 was made by linking the IL-7 sequence to the N-terminus coding region of tissue factor 219, and further linking the IL-7/TF construct with the N-terminus coding region of IL-15. The nucleic acid sequence encoding the first chimeric polypeptide of IL-7/TF/IL-15 (including leader sequence), synthesized by Genewiz, is as follows (SEQ ID NO: 144):

```
(Signal peptide)
ATGAAGTGGGTGACCTTCATCAGCCTGCTGTTCCTGTTCTCCAGCGCC

TACTCC

(Human IL-7 fragment)
GATTGCGACATCGAGGGCAAGGACGGCAAGCAGTACGAGAGCGTGCTG

ATGGTGTCCATCGACCAGCTGCTGGACAGCATGAAGGAGATCGGCTCC

AACTGCCTCAACAACGAGTTCAACTTCTTCAAGCGGCACATCTGCGAC

GCCAACAAGGAGGGCATGTTCCTGTTCAGGGCCGCCAGGAAACTGCGG

CAGTTCCTGAAGATGAACTCCACCGGCGACTTCGACCTGCACCTGCTG

AAGGTGTCCGAGGGCACCACCATCCTGCTGAACTGCACCGGACAGGTG

AAGGGCCGGAAACCTGCTGCTCTGGGAGAGGCCCAACCCACCAAGAGC

CTGGAGGAGAACAAGTCCCTGAAGGAGCAGAAGAAGCTGAACGACCTG

TGCTTCCTGAAGAGGCTGCTGCAGGAGATCAAGACCTGCTGGAACAAG

ATCCTGATGGGCACCAAGGAGCAT

(Human Tissue Factor 219)
AGCGGCACAACCAACACAGTCGCTGCCTATAACCTCACTTGGAAGAGC

ACCAACTTCAAAACCATCCTCGAATGGGAACCCAAACCCGTTAACCAA

GTTTACACCGTGCAGATCAGCACCAAGTCCGGCGACTGGAAGTCCAAA

TGTTTCTATACCACCGACACCGAGTGCGATCTCACCGATGAGATCGTG

AAAGATGTGAAACAGACCTACCTCGCCCGGGTGTTTAGCTACCCCGCC

GGCAATGTGGAGAGCACTGGTTCCGCTGGCGAGCCTTTATACGAGAAC

AGCCCCGAATTTACCCCTTACCTCGAGACCAATTTAGGACAGCCCACC

ATCCAAAGCTTTGAGCAAGTTGGCACAAAGGTGAATGTGACAGTGGAG

GACGAGCGGACTTTAGTGCGGCGGAACAACACCTTTCTCAGCCTCCGG

GATGTGTTCGGCAAAGATTTAATCTACACACTGTATTACTGGAAGTCC

TCTTCCTCCGGCAAGAAGACAGCTAAAACCAACACAAACGAGTTTTTA

ATCGACGTGGATAAAGGCGAAAACTACTGTTTCAGCGTGCAAGCTGTG

ATCCCCTCCCGGACCGTGAATAGGAAAAGCACCGATAGCCCCGTTGAG

TGCATGGGCCAAGAAAAGGGCGAGTTCCGGGAG

(Human IL-15)
AACTGGGTGAACGTCATCAGCGATTTAAAGAAGATCGAAGATTTAATT

CAGTCCATGCATATCGACGCCACTTTATACACAGAATCCGACGTGCAC

CCCTCTTGTAAGGTGACCGCCATGAAATGTTTTTTACTGGAGCTGCAA

GTTATCTCTTTAGAGAGCGGAGACGCTAGCATCCACGACACCGTGGAG

AATTTAATCATTTTAGCCAATAACTCTTTATCCAGCAACGGCAACGTG

ACAGAGTCCGGCTGCAAGGAGTGCGAAGAGCTGGAGGAGAAGAACATC

AAGGAGTTTCTGCAATCCTTTGTGCACATTGTCCAGATGTTCATCAAT

ACCTCC
```

The first chimeric polypeptide of IL-7/TF/IL-15 (including leader sequence), is as follows (SEQ ID NO: 143):

```
(Signal peptide)
MKWVTFISLLFLFSSAYS

(Human IL-7)
DCDIEGKDGKQYESVLMVSIDQLLDSMKEIGSNCLNNEFNFFKRHICD

ANKEGMFLFRAARKLRQFLKMNSTGDFDLHLLKVSEGTTILLNCTGQV

KGRKPAALGEAQPTKSLEENKSLKEQKKLNDLCFLKRLLQEIKTCWNK

ILMGTKEH

(Human Tissue Factor 219)
SGTTNTVAAYNLTWKSTNFKTILEWEPKPVNQVYTVQISTKSGDWKSK

CFYTTDTECDLTDEIVKDVKQTYLARVFSYPAGNVESTGSAGEPLYEN

SPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAV

IPSRTVNRKSTDSPVECMGQEKGEFRE

(Human IL-15)
NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS
```

Example 71: Secretion of IL-21/IL-15RαSu and IL-7/TF/IL-15 Fusion Proteins

Figure 82:
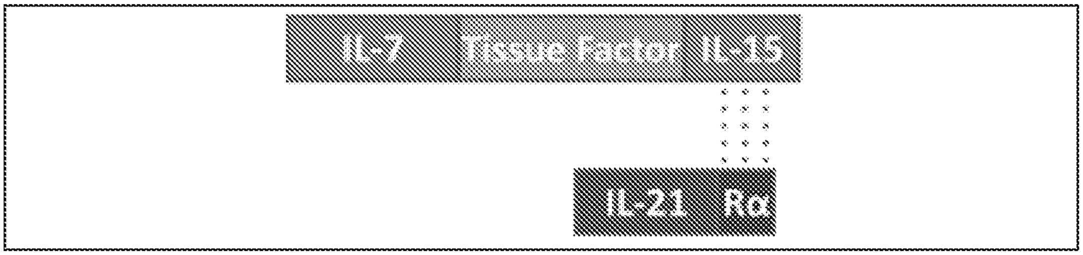
FIG. 82 shows a schematic diagram of the interaction between the exemplary IL-21/IL-15RαSu and IL-7/TF/IL-15 DNA constructs.
Figure 83:
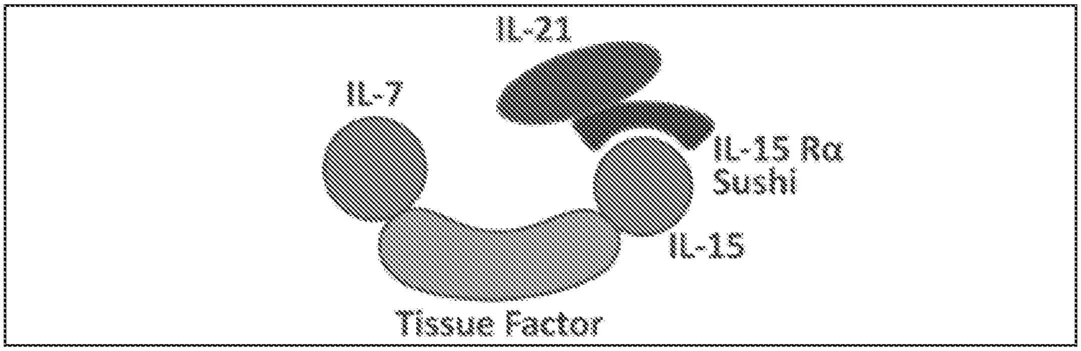
FIG. 83 shows a schematic diagram of the interaction between the exemplary IL-21/IL-15RαSu and IL-7/TF/IL-15 fusion proteins resulting in an IL-7/TF/IL-15:IL-21/IL-15RαSU complex (7t15-21s).

The IL-21/IL-15RαSu and IL-7/TF/IL-15 DNA constructs were cloned into a pMSGV-1 modified retrovirus expression vector (as described by Hughes, *Hum Gene Ther* 16:457-72, 2005, hereby incorporated by reference), and the expression vector was transfected into CHO-K1 cells. Co-expression of the two constructs in CHO-K1 cells allowed for formation and secretion of a soluble IL-7/TF/IL-15:IL-21/IL-15RαSu protein complex (referred to as 7t15-21s). The 7t15-21s protein was purified from CHO-K1 cell culture supernatant using anti-TF antibody (IgG1) affinity chromatography and size exclusion chromatography resulting in soluble (non-aggregated) protein complexes consisting of IL-21/IL-15RαSu and IL-7/TF/IL-15 fusion proteins. See, FIGS. 82 and 83.

Figure 84:
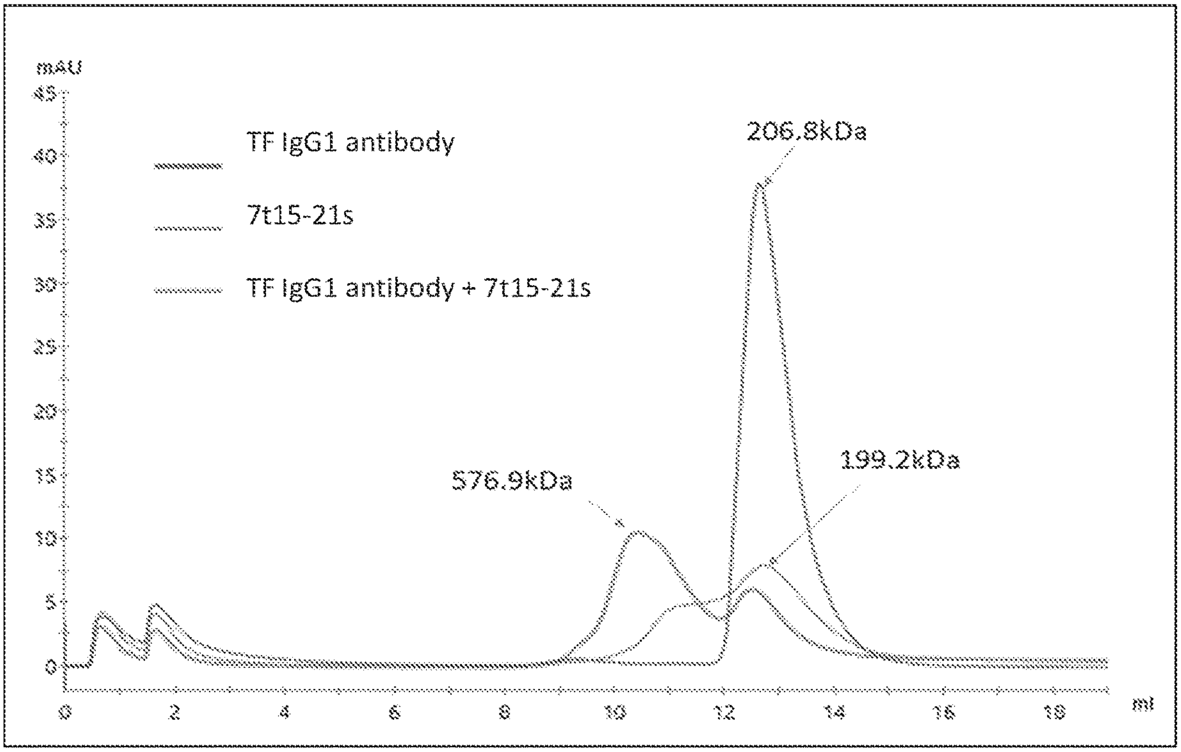
FIG. 84 shows size exclusion chromatography (SEC) profiles of anti-TF IgG1 antibody, 7t15-21s and the complex containing equal amounts of anti-TF IgG1 antibody and 7t15-21s.

Example 72: Analytical Size Exclusion Chromatography (SEC) Analysis of IL-21/IL-15RαSu and IL-7/TF/IL-15 Fusion Proteins To determine if anti-tissue factor monoclonal antibody and 7t15-21s can form an antibody-fusion-molecule complex, analytical size exclusion chromatography (SEC) was performed. A Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. Samples of the anti-TF mAb (1 mg/mL), 7t15-21s (1 mg/mL), and a mixture of combined at a 1:1 ratio, so the final concentration of each protein is 0.5 mg/mL) were in PBS. Each sample was injected into the Superdex 200 column using a capillary loop, and analyzed by SEC. The SEC chromatograph of each sample was shown in FIG. 84. The SEC results indicated that there are two protein peaks for 7t15-21s, likely representing a dimer (with an apparent molecular weight of 199.2 kDa) and a higher oligomer of 7t15-21s, and there is one peak (with an apparent molecular weight of 206.8 kDa) for the anti-TF mAb. However, as expected, a new protein peak with a higher molecular weight (with an apparent molecular weight of 576.9 kDa) was formed in the mixture sample containing the anti-TF mAb and 7t15-21s, indicating that the anti-TF mAb and 7t15-21s form an antibody-antigen complex through the binding of anti-TF mAb to TF in the fusion protein complex.

Example 73: Expansion Capacity of Primary Natural Killer (NK) Cells by 7t15-21s Complex+Anti-TF IgG1 Antibody To assess the 7t15-21s complex's ability to expand primary natural killer (NK) cells, 7t15-21s complex and 7t15-21s complex+anti-TF IgG1 antibody are added to NK cells obtained from samples of fresh human leukocytes. Cells are stimulated with 50 nM of 7t15-21s complex with or without 25 nM of anti-TF IgG1 or anti-TF IgG4 antibody at 37° C. and 5% $CO_2$. Cells are maintained at concentration at $0.5\times10^6$/mL not exceeding $2.0\times10^6$/mL by counting every 48-72 hours and media is replenished with fresh stimulator. Cells stimulated with 7t15-21s complex or anti-TF IgG1 antibody or anti-TF IgG4 antibody or anti-TF IgG4+7t15-21s complex are maintained up to day 5. Expansion of primary NK cells upon incubation with 21t15-7s complex+anti-TF IgG1 antibody is observed.

Example 74: Activation of Expanded NK Cells by the 7t15-21s Complex+Anti-TF IgG1 Antibody Primary NK cells are induced ex vivo following overnight stimulation of purified NK cells with 7t15-21s complex+anti-TF IgG1 antibody. Fresh human leukocytes are obtained from a blood bank and $CD56^+$ NK cells are isolated with the RosetteSep/human NK cell reagent (StemCell Technologies). The purity of NK cells is >80% and is confirmed by staining with CD56-BV421 and CD16-BV510 specific antibodies (BioLegend). Cells are counted and resuspended in $1\times10^6$/mL in a 24 well flat bottom plate in 1 mL of complete media (RPMI 1640 (Gibco), supplemented with 4 mM L-glutamine (Thermo Life Technologies), penicillin (Thermo Life Technologies), streptomycin (Thermo Life Technologies), non-essential amino acid (Thermo Life Technologies), sodium pyruvate (Thermo Life Technologies), and 10% FBS (Hyclone)). Cells are stimulated with 50 nM of 7t15-21s with or without 25 nM of anti-TF IgG1 antibody at 37° C. and 5% $CO_2$. Cells are counted every 48-72 hours and maintained at a concentration of $0.5\times10^6$/mL to $2.0\times10^6$/mL until day 14. Media is periodically replenished with fresh stimulator. Cells are harvested and surface stained at day 3 with CD56-BV421, CD16-BV510, CD25-PE, CD69-APCFire750 specific antibodies (Biolegend and analyzed by Flow Cytometry-Celeste-BD Bioscience). The activation marker CD25 MFI are observed to increase with 7t15-21s complex+anti-TF IgG1 antibody stimulation, but not 7t15-21s complex stimulation. The activation marker CD69 MFI is observed to increase with both 7t15-21s complex+anti-TF IgG1 antibody and with 7t15-21s complex, alone.

Example 75: 7t15-16s21 Fusion Protein Generation and Characterization

Figure 85:
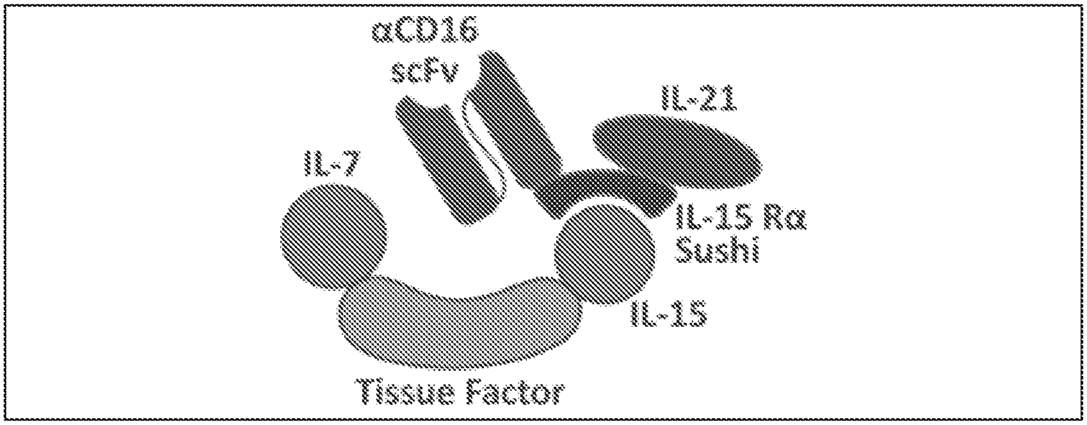
FIG. 85 shows a schematic of the 7t15-16s21 construct.
Figure 86:
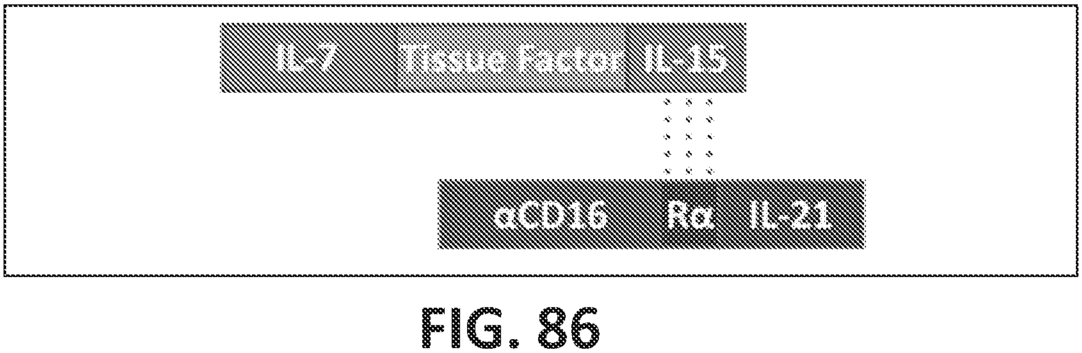
FIG. 86 shows an additional schematic of the 7t15-16s21 construct.

A fusion protein complex was generated comprising of anti-CD16scFv/IL-15RαSu/IL-21 and IL-7/TF/IL-15 fusion proteins. The human IL-7 and IL-21 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15. See, FIGS. 85 and 86.

The nucleic acid and protein sequences of a construct comprising IL-7 linked to the N-terminus of tissue factor 219 following with the N-terminus of IL-15 are shown below.

The nucleic acid sequence of the IL-7/TF/IL-15 construct (including signal peptide sequence) is as follows:

```
(Signal peptide)
ATGAAGTGGGTGACCTTCATCAGCCTGCTGTTCCTGTTCTCCAGCGCC

TACTCC

(Human IL-7)
GATTGCGACATCGAGGGCAAGGACGGCAAGCAGTACGAGAGCGTGCTG

ATGGTGTCCATCGACCAGCTGCTGGACAGCATGAAGGAGATCGGCTCC

AACTGCCTCAACAACGAGTTCAACTTCTTCAAGCGGCACATCTGCGAC

GCCAACAAGGAGGGCATGTTCCTGTTCAGGGCCGCCAGGAAACTGCGG

CAGTTCCTGAAGATGAACTCCACCGGCGACTTCGACCTGCACCTGCTG

AAGGTGTCCGAGGGCACCACCATCCTGCTGAACTGCACCGGACAGGTG

AAGGGCCGGAAACCTGCTGCTCTGGGAGAGGCCCAACCCACCAAGAGC

CTGGAGGAGAACAAGTCCCTGAAGGAGCAGAAGAAGCTGAACGACCTG

TGCTTCCTGAAGAGGCTGCTGCAGGAGATCAAGACCTGCTGGAACAAG

ATCCTGATGGGCACCAAGGAGCAT

(Human Tissue Factor 219)
AGCGGCACAACCAACACAGTCGCTGCCTATAACCTCACTTGGAAGAGC

ACCAACTTCAAAACCATCCTCGAATGGGAACCCAAACCCGTTAACCAA

GTTTACACCGTGCAGATCAGCACCAAGTCCGGCGACTGGAAGTCCAAA

TGTTTCTATACCACCGACACCGAGTGCGATCTCACCGATGAGATCGTG

AAAGATGTGAAACAGACCTACCTCGCCCGGGTGTTTAGCTACCCCGCC

GGCAATGTGGAGAGCACTGGTTCCGCTGGCGAGCCTTTATACGAGAAC

AGCCCCGAATTTACCCCTTACCTCGAGACCAATTTAGGACAGCCCACC

ATCCAAAGCTTTGAGCAAGTTGGCACAAAGGTGAATGTGACAGTGGAG

GACGAGCGGACTTTAGTGCGGCGGAACAACACCTTTCTCAGCCTCCGG

GATGTGTTCGGCAAAGATTTAATCTACACACTGTATTACTGGAAGTCC

TCTTCCTCCGGCAAGAAGACAGCTAAAACCAACACAAACGAGTTTTTA

ATCGACGTGGATAAAGGCGAAAACTACTGTTTCAGCGTGCAAGCTGTG

ATCCCCTCCCGGACCGTGAATAGGAAAAGCACCGATAGCCCCGTTGAG

TGCATGGGCCAAGAAAAGGGCGAGTTCCGGGAG

(Human IL-15)
AACTGGGTGAACGTCATCAGCGATTTAAAGAAGATCGAAGATTTAATT

CAGTCCATGCATATCGACGCCACTTTATACACAGAATCCGACGTGCAC

CCCTCTTGTAAGGTGACCGCCATGAAATGTTTTTTACTGGAGCTGCAA

GTTATCTCTTTAGAGAGCGGAGACGCTAGCATCCACGACACCGTGGAG

AATTTAATCATTTTAGCCAATAACTCTTTATCCAGCAACGGCAACGTG
```

-continued

```
ACAGAGTCCGGCTGCAAGGAGTGCGAAGAGCTGGAGGAGAAGAACATC

AAGGAGTTTCTGCAATCCTTTGTGCACATTGTCCAGATGTTCATCAAT

ACCTCC
```

The amino acid sequence of IL-7/TF/IL-15 fusion protein (including the leader sequence) is as follows:

```
(Signal peptide)
MKWVTFISLLFLFSSAYS

(Human IL-7)
DCDIEGKDGKQYESVLMVSIDQLLDSMKEIGSNCLNNEFNFFKRHICD

ANKEGMFLFRAARKLRQFLKMNSTGDFDLHLLKVSEGTTILLNCTGQV

KGRKPAALGEAQPTKSLEENKSLKEQKKLNDLCFLKRLLQEIKTCWNK

ILMGTKEH

(Human Tissue Factor 219)
SGTTNTVAAYNLTWKSTNFKTILEWEPKPVNQVYTVQISTKSGDWKSK

CFYTTDTECDLTDEIVKDVKQTYLARVFSYPAGNVESTGSAGEPLYEN

SPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAV

IPSRTVNRKSTDSPVECMGQEKGEFRE

(Human IL-15)
NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS
```

Constructs were also made by linking the anti-CD16scFv sequence to the N-terminus coding region of IL-15RαSu chain followed by the N-terminus coding region of IL-21 which was synthesized by Genewiz. The nucleic acid and protein sequences of a construct comprising the anti-CD16scFv linked to the N-terminus of TL-15RαSu chain followed by the N-terminus coding region of IL-21 are shown below.

The nucleic acid sequence of the anti-CD16SscFv/IL-15 RαSu/IL-21 construct (including signal peptide sequence) is as follows:

```
(Signal peptide)
ATGAAGTGGGTGACCTTCATCAGCCTGCTGTTCCTGTTCTCCAGCGCC

TACTCC

((Anti-human CD16scFv)
TCCGAGCTGACCCAGGACCCTGCTGTGTCCGTGGCTCTGGGCCAGACC

GTGAGGATCACCTGCCAGGGCGACTCCCTGAGGTCCTACTACGCCTCC

TGGTACCAGCAGAAGCCCGGCCAGGCTCCTGTGCTGGTGATCTACGGC

AAGAACAACAGGCCCTCCGGCATCCCTGACAGGTTCTCCGGATCCTCC

TCCGGCAACACCGCCTCCCTGACCATCACAGGCGCTCAGGCCGAGGAC

GAGGCTGACTACTACTGCAACTCCAGGGACTCCTCCGGCAACCATGTG

GTGTTCGGCGGCGGCACCAAGCTGACCGTGGGCCATGGCGGCGGCGGC

TCCGGAGGCGGCGGCAGCGGCGGAGGAGGATCCGAGGTGCAGCTGGTG

GAGTCCGGAGGAGGAGTGGTGAGGCCTGGAGGCTCCCTGAGGCTGAGC
```

-continued

```
TGTGCTGCCTCCGGCTTCACCTTCGACGACTACGGCATGTCCTGGGTG

AGGCAGGCTCCTGGAAAGGGCCTGGAGTGGGTGTCCGGCATCAACTGG

AACGGCGGATCCACCGGCTACGCCGATTCCGTGAAGGGCAGGTTCACC

ATCAGCAGGGACAACGCCAAGAACTCCCTGTACCTGCAGATGAACTCC

CTGAGGGCCGAGGACACCGCCGTGTACTACTGCGCCAGGGGCAGGTCC

CTGCTGTTCGACTACTGGGGACAGGGCACCCTGGTGACCGTGTCCAGG

(Human IL-15R α sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGC

TTCAAGAGGAAGGCCGGCACCAGCAGCCTCACCGAGTGCGTGCTGAAT

AAGGCTACCAACGTGGCTCACTGGACAACACCCTCTTTAAAGTGCATC

CGG

(Human IL-21)
CAGGGCCAGGACAGGCACATGATCCGGATGAGGCAGCTCATCGACATC

GTCGACCAGCTGAAGAACTACGTGAACGACCTGGTGCCCGAGTTTCTG

CCTGCCCCCGAGGACGTGGAGACCAACTGCGAGTGGTCCGCCTTCTCC

TGCTTTCAGAAGGCCCAGCTGAAGTCCGCCAACACCGGCAACAACGAG

CGGATCATCAACGTGAGCATCAAGAAGCTGAAGCGGAAGCCTCCCTCC

ACAAACGCCGGCAGGAGGCAGAAGCACAGGCTGACCTGCCCCAGCTGT

GACTCCTACGAGAAGAAGCCCCCCAAGGAGTTCCTGGAGAGGTTCAAG

TCCCTGCTGCAGAAGATGATCCATCAGCACCTGTCCTCCAGGACCCAC

GGCTCCGAGGACTCC
```

The amino acid sequence of the anti-CD16scFv/IL-15RαSu/IL-21 construct (including signal peptide sequence) is as follows:

```
(Signal peptide)
MKWVTFISLLFLFSSAYS

(Anti-human CD16scFv)
SELTQDPAVSVALGQTVRITCQGDSLRSYYASWYQQKPGQAPVLVIYG

KNNRPSGIPDRFSGSSSGNTASLTITGAQAEDEADYYCNSRDSSGNHV

VFGGGTKLTVGHGGGGSGGGGSGGGGSEVQLVESGGGVVRPGGSLRLS

CAASGFTFDDYGMSWVRQAPGKGLEWVSGINWNGGSTGYADSVKGRFT

ISRDNAKNSLYLQMNSLRAEDTAVYYCARGRSLLFDYWGQGTLVTVSR

(Human IL-15R α sushi domain)
ITCPPPMSVEHADIWVKSYSLYSRERYICNSGFKRKAGTSSLTECVLN

KATNVAHWTTPSLKCIR

(Human IL-21)
QGQDRHMIRMRQLIDIVDQLKNYVNDLVPEFLPAPEDVETNCEWSAFS

CFQKAQLKSANTGNNERIINVSIKKLKRKPPSTNAGRRQKHRLTCPSC

DSYEKKPPKEFLERFKSLLQKMIHQHLSSRTHGSEDS
```

In some cases, the leader peptide is cleaved from the intact polypeptide to generate the mature form that may be soluble or secreted.

The anti-CD16scFv/IL-15RαSu/IL-21 and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15:anti-CD16scFv/IL-15RαSu/IL-21 protein complex (referred to as 7t15-16s21), which can be purified by anti-TF antibody-based affinity and other chromatography methods.

Binding of 7t15-16s21 to CHO Cells Expressing Human CD16b

Figure 87A:
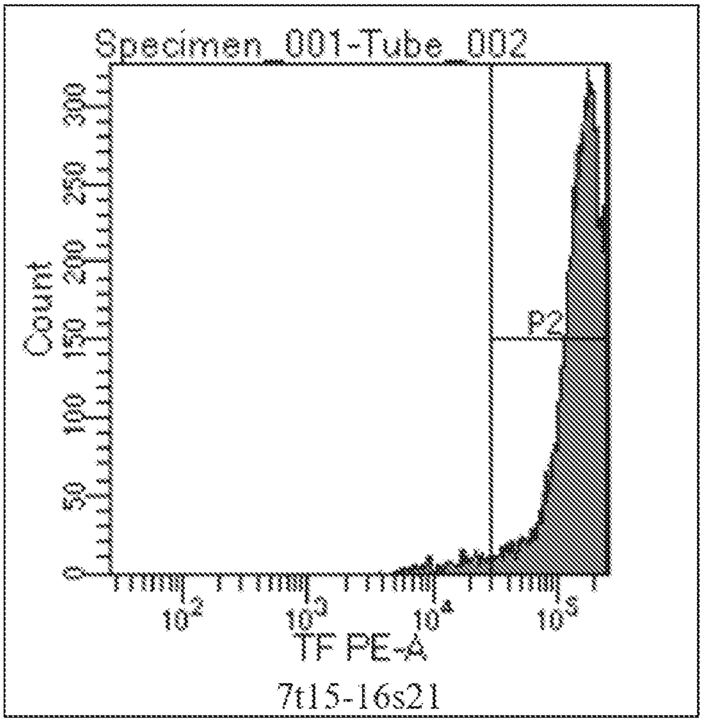
FIGS. 87A and 87B are graphs showing binding of 7t15-16s21 to CHO cells expressing human CD16b as compared to a control protein.
Figure 87B:
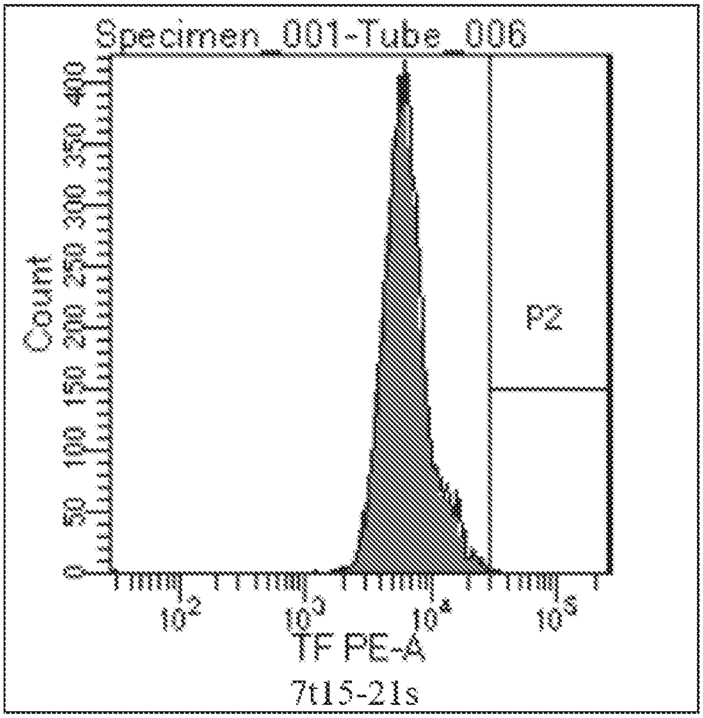

CHO cells were transfected with human CD16b in a pMC plasmid and selected with 10 μg/mL of blasticidin for 10 days. The CHO cells stably expressing CD16b were stained with 1.2 μg/mL of 7t15-16s21 (containing anti-human CD16 scFv) or 18t15-12s (does not contain anti-human CD16 scFv) as a negative control, and then stained with biotinylated anti-human tissue factor and PE conjugated streptavidin. Only anti-human CD16scFv containing 7t15-16s21 stained the cells as shown in FIG. 87A. 18t15-12s did not stain the CHO cells expressing human CD16b as showed in FIG. 87B.

Detection of IL-15, IL-21, and IL-7 in 7t15-16s21 Using ELISA

Figure 88A:
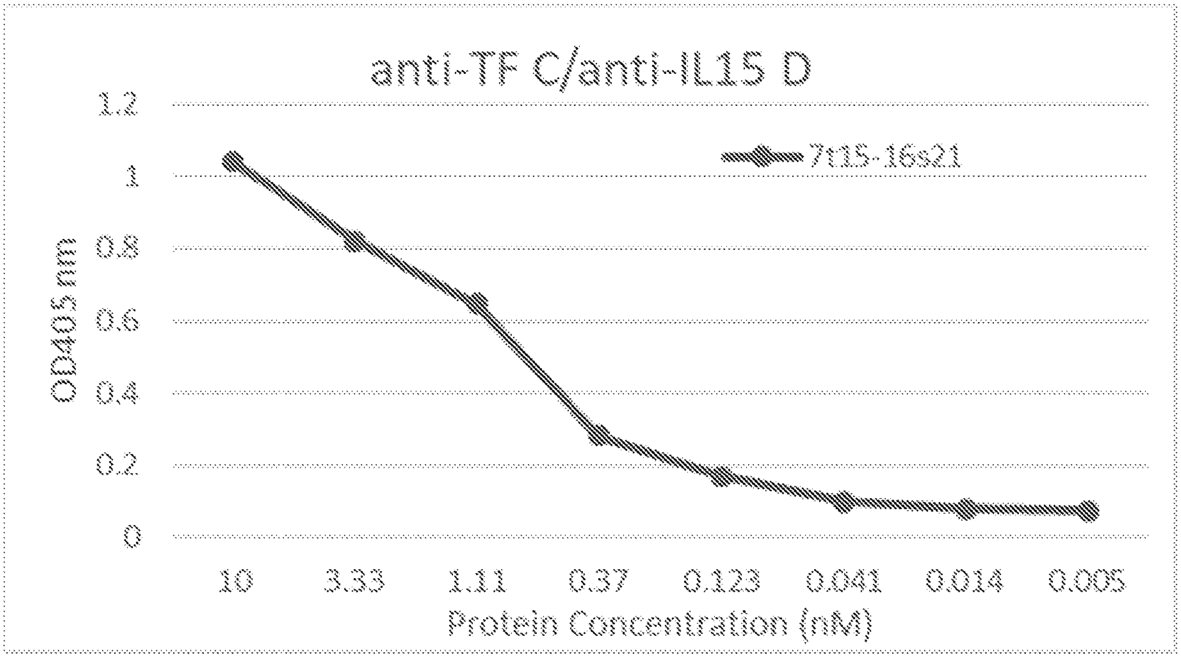
FIGS. 88A-88C are results from ELISA experiments using antibodies against IL-15, IL-21, and IL-7 in detecting 7t15-16s21.
Figure 88B:
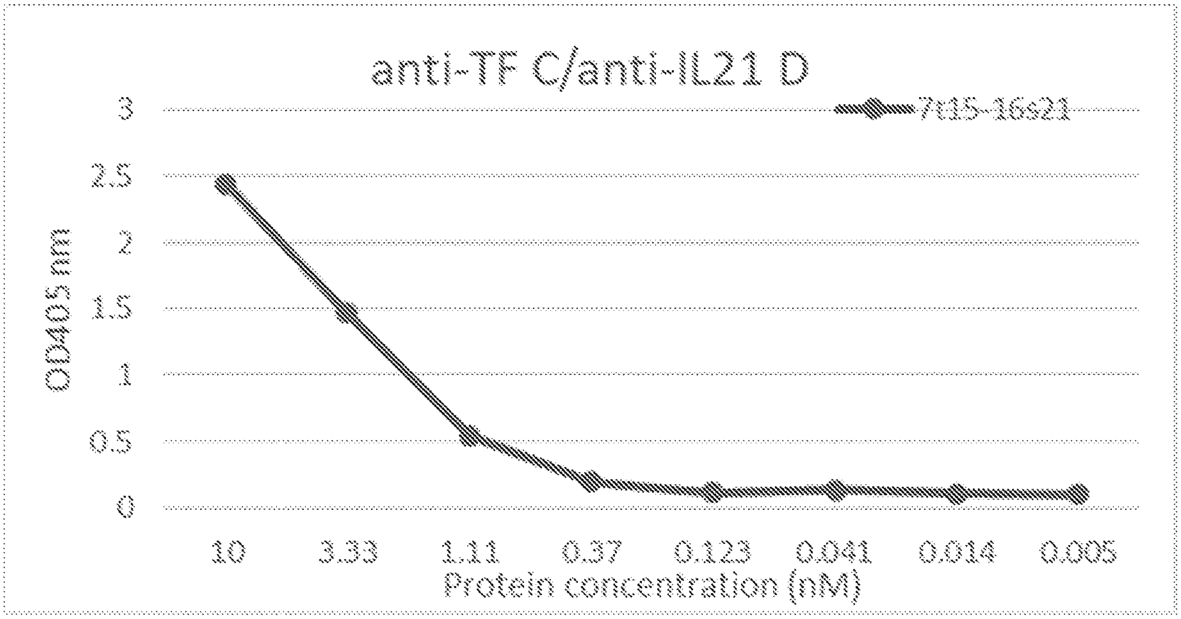
Figure 88C:
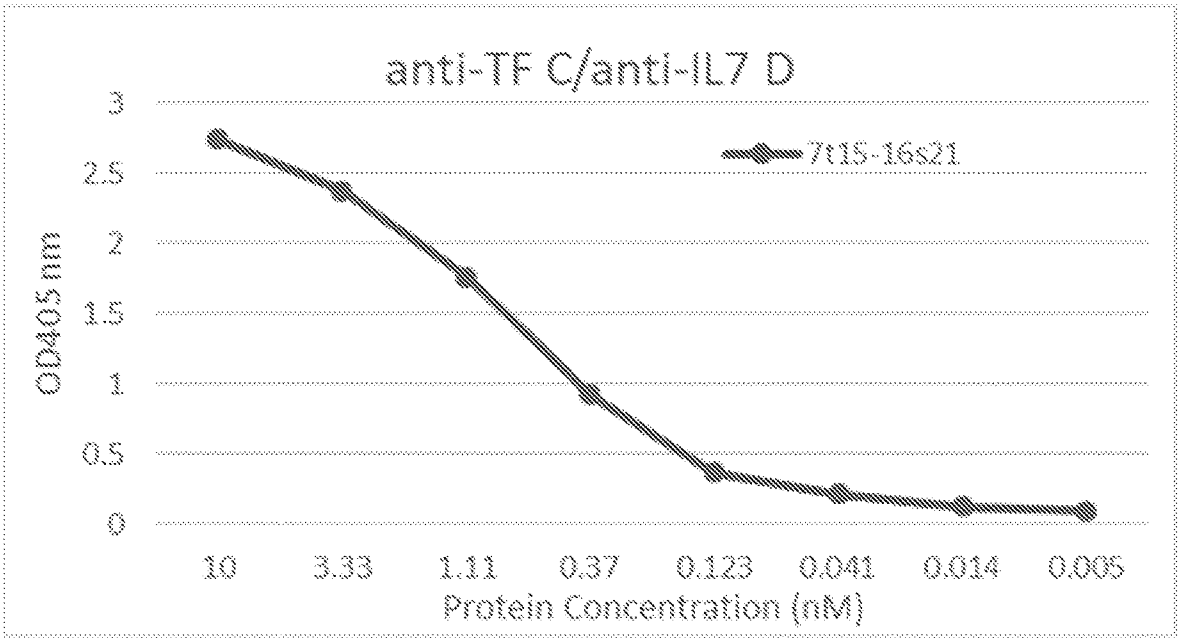

A 96-well plate was coated with 100 μL (8 μg/mL) of anti-TF antibody in R5 (coating buffer) and incubated at room temperature (RT) for 2 hrs. The plates were washed 3 times and blocked with 100 μL of 1% BSA in PBS. Serial dilution of 7t15-16s21 (at a 1:3 ratio) were added to the wells, and incubated at RT for 60 min. Following 3 washes, 50 ng/mL of biotinylated-anti-IL15 antibody (BAM247, R&D Systems), 500 ng/mL of biotinylated-anti-IL-21 antibody (13-7218-81, R&D Systems), or 500 ng/mL of biotinylated-anti-IL-7 antibody (506602, R&D Systems) was added to the wells and incubated at RT for 60 min. The plate was washed 3 times, and incubated with 0.25 μg/mL of HRP-SA (Jackson ImmunoResearch) at 100 μL per well for 30 min at RT, followed by 4 washes and incubation with 100 μl of ABTS for 2 mins at RT. Absorbance was read at 405 nm. As shown in FIGS. 88A-88C, the IL-15, IL-21, and IL-7 domains in 7t15-16s21 were detected by the individual antibodies.

Figure 89:
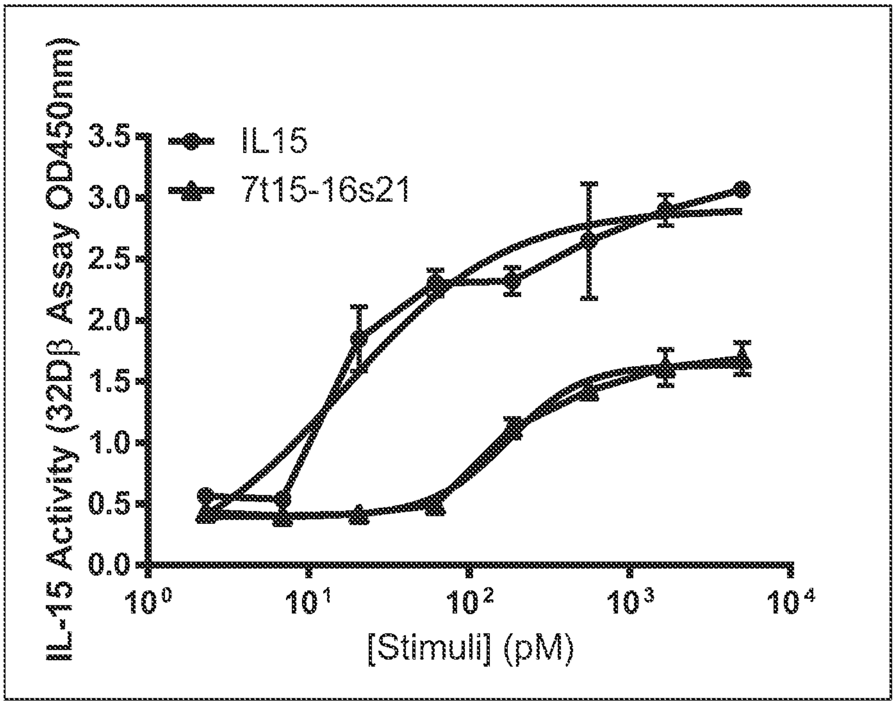
FIG. 89 shows results of the 32Dβ cell proliferation assay with 7t15-16s21 or recombinant IL-15.

The IL-15 in 7t15-16s21 Promotes IL-2Rβ and Common γ Chain Containing 32Dβ Cell Proliferation To analyze the activity of IL-15 in 7t15-16s21, the IL-15 activity of 7t15-16s21 was compared to recombinant IL-15 using 32Dβ cells that express IL2β and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted 7t15-16s21 or IL-15 were added to the cells (FIG. 89). Cells were incubated in a $CO_2$ incubator at 37° C. for 3 days. Cell proliferation was detected by adding 10 μl of WST1 to each well on day 3 and incubating for an additional 3 hours in a $CO_2$ incubator at 37° C. The absorbance at 450 nm was measured by analyzing the amount of formazan dye produced. As shown in FIG. 5, 7t15-16s21 and IL-15 promoted 32Dβ cell proliferation, with the $EC_{50}$ of 7t15-16s21 and IL-15 being 172.2 pM and 16.63 pM, respectively.

Purification Elution Chromatograph of 7t15-16s21 from Anti-TF Affinity Column

Figure 90:
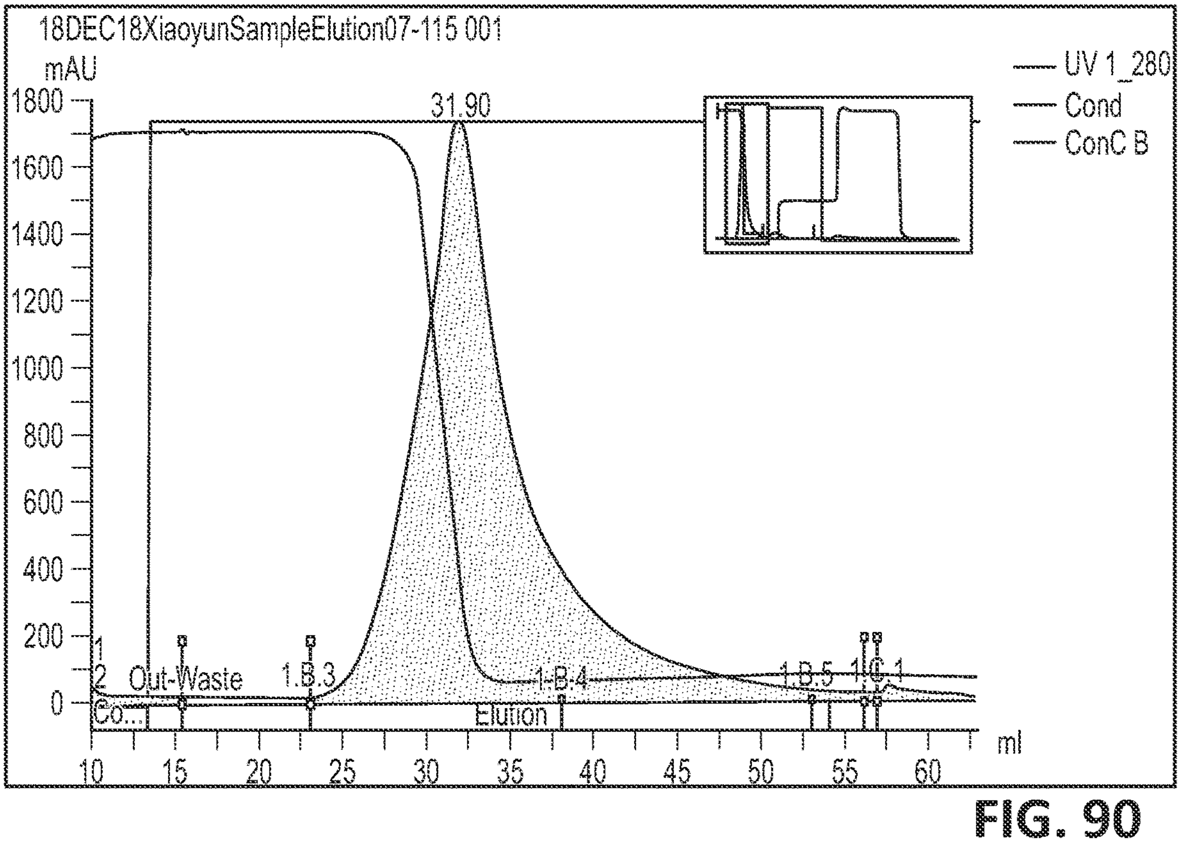
FIG. 90 is a line graph showing the chromatographic profile of 7t15-16s21 protein containing cell culture supernatant following binding and elution on anti-TF antibody resin.

7t15-16s21 harvested from cell culture was loaded onto the anti-TF affinity column equilibrated with 5 column volumes of PBS. The column was then washed with 5 column volumes of PBS, followed by elution with 6 column volumes of 0.1M acetic acid (pH 2.9). A280 elution peak was collected and neutralized to pH 7.5-8.0 with 1M Tris base. The neutralized sample was buffer exchanged into PBS using Amicon centrifugal filters with a 30 KDa molecular weight cutoff. FIG. 90 is a line graph showing the chromatographic profile of 7t15-16s21 protein containing cell culture supernatant following binding and elution on anti-TF antibody resin. As shown in FIG. 90, the anti-TF antibody affinity column bound 7t15-16s21 which contains TF. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of 7t15-16s21

Figure 91:
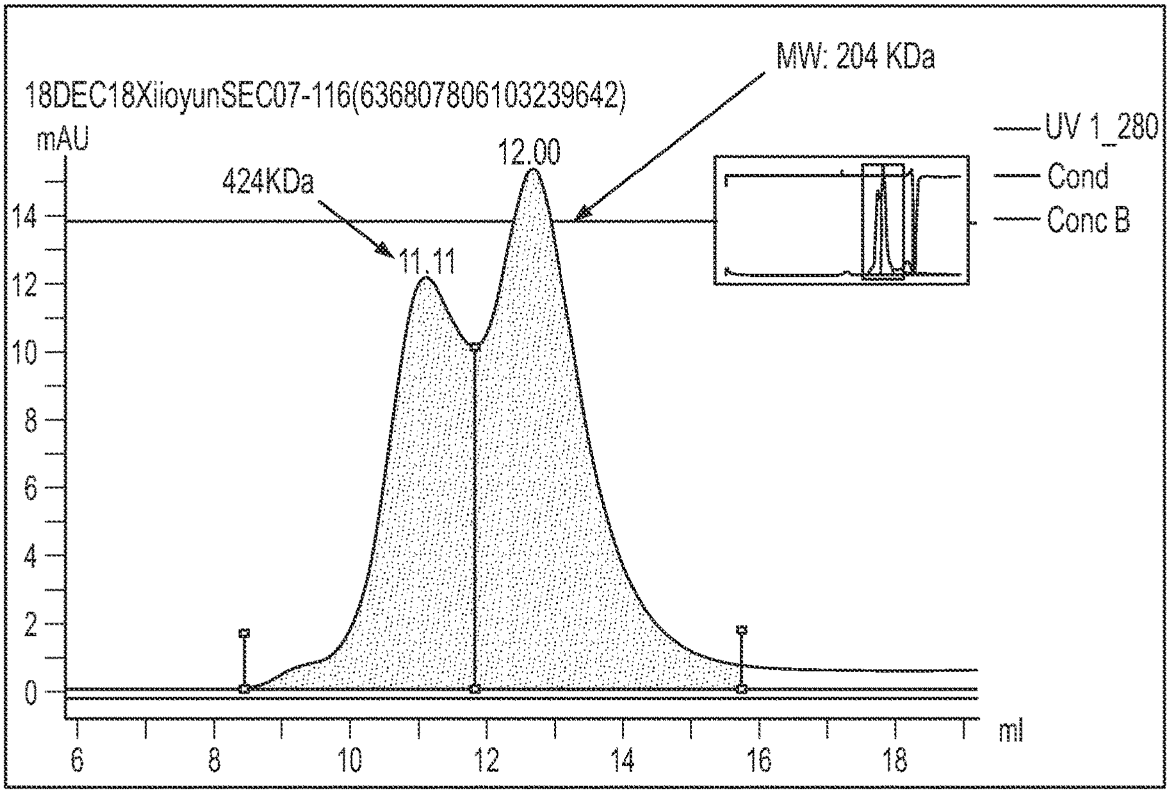
FIG. 91 shows the analytical SEC Profile of 7t15-16s21.

To perform size exclusion chromatography (SEC) analysis for 7t15-16s21, a Superdex 200 Increase 10/300 GL gel filtration column (GE Healthcare) connected to an AKTA Avant system (GE Healthcare) was used. The column was equilibrated with 2 column volumes of PBS. The flow rate was 0.7 mL/min. A sample containing 7t15-16s21 in PBS was injected into the Superdex 200 column using a capillary loop, and analyzed by SEC. As shown in FIG. 91, the SEC results showed two protein peaks for 7t15-16s21.

Example 76: TGFRt15-16s21 Fusion Protein Generation and Characterization

Figure 92:
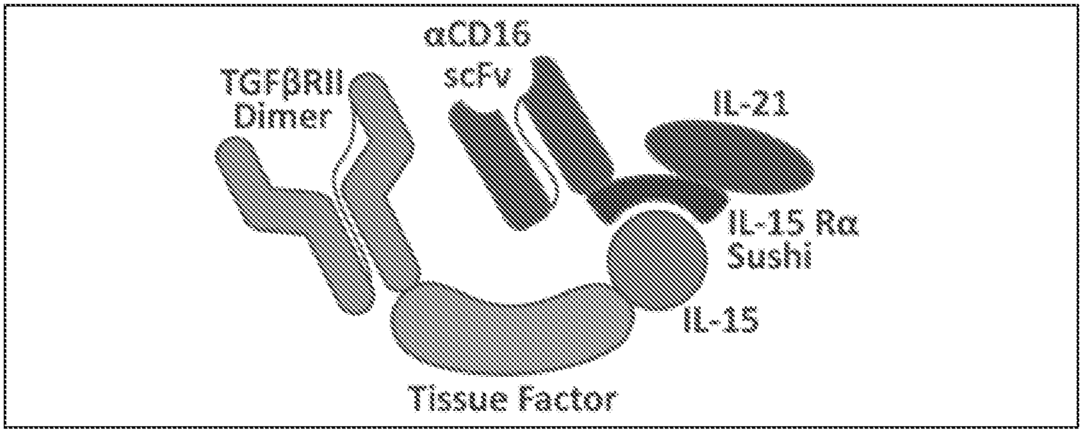
FIG. 92 shows a schematic of the TGFRt15-16s21 construct.
Figure 93:
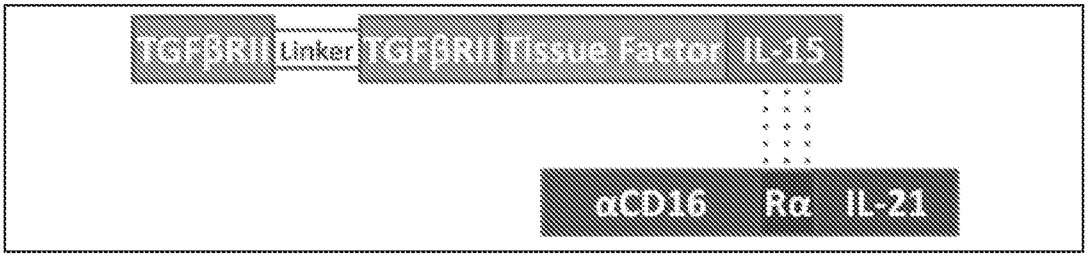
FIG. 93 shows an additional schematic of the TGFRt15-16s21 construct.

A fusion protein complex was generated comprising anti-human CD16scFv/IL-15RαSu/IL21 and TGFβ Receptor II/TF/IL-15 fusion proteins (FIGS. 92 and 93). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the two TGFβ Receptor II/TF/IL-15 construct (including signal peptide sequence) is as follows:

```
(Signal peptide)
ATGAAGTGGGTGACCTTCATCAGCCTGCTGTTCCTGTTCTCCAGCGCC

TACTCC

(Two Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

AGCATCACCTCCATCTGCGAGAAGCCCCAAGAAGTGTGCGTGGCCGTG
```

-continued

```
TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCTCCATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGAC

(Human Tissue Factor 219)
AGCGGCACAACCAACACAGTCGCTGCCTATAACCTCACTTGGAAGAGC

ACCAACTTCAAAACCATCCTCGAATGGGAACCCAAACCCGTTAACCAA

GTTTACACCGTGCAGATCAGCACCAAGTCCGGCGACTGGAAGTCCAAA

TGTTTCTATACCACCGACACCGAGTGCGATCTCACCGATGAGATCGTG

AAAGATGTGAAACAGACCTACCTCGCCCGGGTGTTTAGCTACCCCGCC

GGCAATGTGGAGAGCACTGGTTCCGCTGGCGAGCCTTTATACGAGAAC

AGCCCCGAATTTACCCCTTACCTCGAGACCAATTTAGGACAGCCCACC

ATCCAAAGCTTTGAGCAAGTTGGCACAAAGGTGAATGTGACAGTGGAG

GACGAGCGGACTTTAGTGCGGCGGAACAACACCTTTCTCAGCCTCCGG

GATGTGTTCGGCAAAGATTTAATCTACACACTGTATTACTGGAAGTCC

TCTTCCTCCGGCAAGAAGACAGCTAAAACCAACACAAACGAGTTTTTA

ATCGACGTGGATAAAGGCGAAAACTACTGTTTCAGCGTGCAAGCTGTG

ATCCCCTCCCGGACCGTGAATAGGAAAAGCACCGATAGCCCCGTTGAG

TGCATGGGCCAAGAAAAGGGCGAGTTCCGGGAG

(Human IL-15)
AACTGGGTGAACGTCATCAGCGATTTAAAGAAGATCGAAGATTTAATT

CAGTCCATGCATATCGACGCCACTTTATACACAGAATCCGACGTGCAC

CCCTCTTGTAAGGTGACCGCCATGAAATGTTTTTTACTGGAGCTGCAA

GTTATCTCTTTAGAGAGCGGAGACGCTAGCATCCACGACACCGTGGAG

AATTTAATCATTTTAGCCAATAACTCTTTATCCAGCAACGGCAACGTG

ACAGAGTCCGGCTGCAAGGAGTGCGAAGAGCTGGAGGAGAAGAACATC

AAGGAGTTTCTGCAATCCTTTGTGCACATTGTCCAGATGTTCATCAAT

ACCTCC
```

The amino acid sequence of TGFβ Receptor II/TF/IL-15 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNC

SITSICEKPQEVCVAVWRKNDENITLETVCHDPKLPYHDFILEDAASP

KCIMKEKKKPGETFFMCSCSSDECNDNIIFSEEYNTSNPDGGGGSGGG

GSGGGGSIPPHVQKSVNNDMIVTDNNGAVKFPQLCKFCDVRFSTCDNQ

KSCMSNCSITSICEKPQEVCVAVWRKNDENITLETVCHDPKLPYHDFI

LEDAASPKCIMKEKKKPGETFFMCSCSSDECNDNIIFSEEYNTSNPD

(Human Tissue Factor 219)
SGTTNTVAAYNLTWKSTNFKTILEWEPKPVNQVYTVQISTKSGDWKS

KCFYTTDTECDLTDEIVKDVKQTYLARVFSYPAGNVESTGSAGEPLY

ENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFS

VQAVIPSRTVNRKSTDSPVECMGQEKGEFRE

(Human IL-15)
NWVNVISDLKKIEDLIQSMHIDATLYTESDVHPSCKVTAMKCFLLEL

QVISLESGDASIHDTVENLIILANNSLSSNGNVTESGCKECEELEEK

NIKEFLQSFVHIVQMFINTS
```

Constructs were also made by attaching anti-human CD16scFv directly linking to the N-terminus coding region of IL-15RαSu chain followed by the N-terminus coding region of IL-21 which was synthesized by Genewiz. The nucleic acid and protein sequences of a construct comprising the anti-human CD16scFv linked to the N-terminus of IL-15RαSu followed by the N-terminus coding region of IL-21 are shown below.

The nucleic acid sequence of the anti-CD16scFv/IL-15 RαSu/IL-21 construct (including signal peptide sequence) is as follows:

```
(Signal peptide)
ATGAAGTGGGTGACCTTCATCAGCCTGCTGTTCCTGTTCTCCAGCGC

CTACTCC

(Anti-human CD16scFv)
TCCGAGCTGACCCAGGACCCTGCTGTGTCCGTGGCTCTGGGCCAGAC

CGTGAGGATCACCTGCCAGGGCGACTCCCTGAGGTCCTACTACGCCT

CCTGGTACCAGCAGAAGCCCGGCCAGGCTCCTGTGCTGGTGATCTAC

GGCAAGAACAACAGGCCCTCCGGCATCCCTGACAGGTTCTCCGGATC

CTCCTCCGGCAACACCGCCTCCCTGACCATCACAGGCGCTCAGGCCG

AGGACGAGGCTGACTACTACTGCAACTCCAGGGACTCCTCCGGCAAC

CATGTGGTGTTCGGCGGCGGCACCAAGCTGACCGTGGGCCATGGCGG

CGGCGGCTCCGGAGGCGGCGGCAGCGGCGGAGGAGGATCCGAGGTGC

AGCTGGTGGAGTCCGGAGGAGGAGTGGTGAGGCCTGGAGGCTCCCTG

AGGCTGAGCTGTGCTGCCTCCGGCTTCACCTTCGACGACTACGGCAT

GTCCTGGGTGAGGCAGGCTCCTGGAAAGGGCCTGGAGTGGGTGTCCG
```

-continued

```
GCATCAACTGGAACGGCGGATCCACCGGCTACGCCGATTCCGTGAAG

GGCAGGTTCACCATCAGCAGGGACAACGCCAAGAACTCCCTGTACCT

GCAGATGAACTCCCTGAGGGCCGAGGACACCGCCGTGTACTACTGCG

CCAGGGGCAGGTCCCTGCTGTTCGACTACTGGGGACAGGGCACCCTG

GTGACCGTGTCCAGG

(Human IL-15R α sushi domain)
ATTACATGCCCCCCTCCCATGAGCGTGGAGCACGCCGACATCTGGGT

GAAGAGCTATAGCCTCTACAGCCGGGAGAGGTATATCTGTAACAGCG

GCTTCAAGAGGAAGGCCGGCACCAGCAGCCTCACCGAGTGCGTGCTG

AATAAGGCTACCAACGTGGCTCACTGGACAACACCCTCTTTAAAGTG

CATCCGG

(Human IL-21)
CAGGGCCAGGACAGGCACATGATCCGGATGAGGCAGCTCATCGACAT

CGTCGACCAGCTGAAGAACTACGTGAACGACCTGGTGCCCGAGTTTC

TGCCTGCCCCCGAGGACGTGGAGACCAACTGCGAGTGGTCCGCCTTC

TCCTGCTTTCAGAAGGCCCAGCTGAAGTCCGCCAACACCGGCAACAA

CGAGCGGATCATCAACGTGAGCATCAAGAAGCTGAAGCGGAAGCCTC

CCTCCACAAACGCCGGCAGGAGGCAGAAGCACAGGCTGACCTGCCCC

AGCTGTGACTCCTACGAGAAGAAGCCCCCCAAGGAGTTCCTGGAGAG

GTTCAAGTCCCTGCTGCAGAAGATGATCCATCAGCACCTGTCCTCCA

GGACCCACGGCTCCGAGGACTCC
```

The amino acid sequence of the anti-CD16scFv/IL-15RαSu/IL-21 construct (including signal peptide sequence) is as follows:

```
(Signal peptide)
MKWVTFISLLFLFSSAYS

(Anti-human CD16scFv)
SELTQDPAVSVALGQTVRITCQGDSLRSYYASWYQQKPGQAPVLVIY

GKNNRPSGIPDRFSGSSSGNTASLTITGAQAEDEADYYCNSRDSSGN

HVVFGGGTKLTVGHGGGGSGGGGSGGGGSEVQLVESGGGVVRPGGSL

RLSCAASGFTFDDYGMSWVRQAPGKGLEWVSGINWNGGSTGYADSVK

GRFTISRDNAKNSLYLQMNSLRAEDTAVYYCARGRSLLFDYWGQGTL

VTVSR

(Human IL-15R α sushi domain)
ITCPPPMSVEHADIWVKSYSLYSRERYICNSGFKRKAGTSSLTECVL

NKATNVAHWTTPSLKCIR

(Human IL-21)
QGQDRHMIRMRQLIDIVDQLKNYVNDLVPEFLPAPEDVETNCEWSAF

SCFQKAQLKSANTGNNERIINVSIKKLKRKPPSTNAGRRQKHRLTCP

SCDSYEKKPPKEFLERFKSLLQKMIHQHLSSRTHGSEDS
```

In some cases, the leader peptide is cleaved from the intact polypeptide to generate the mature form that may be soluble or secreted.

The anti-CD16scFv/IL-15RαSu/IL-21 and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:CD16scFv/IL-15RαSu/IL-21 protein complex (referred to as TGFRt15-16s21), which can be purified by anti-TF antibody-based affinity and other chromatography methods.

Interaction Between TGFRt15-16s21 and CHO Cells Expressing Human CD16b

Figure 94A:
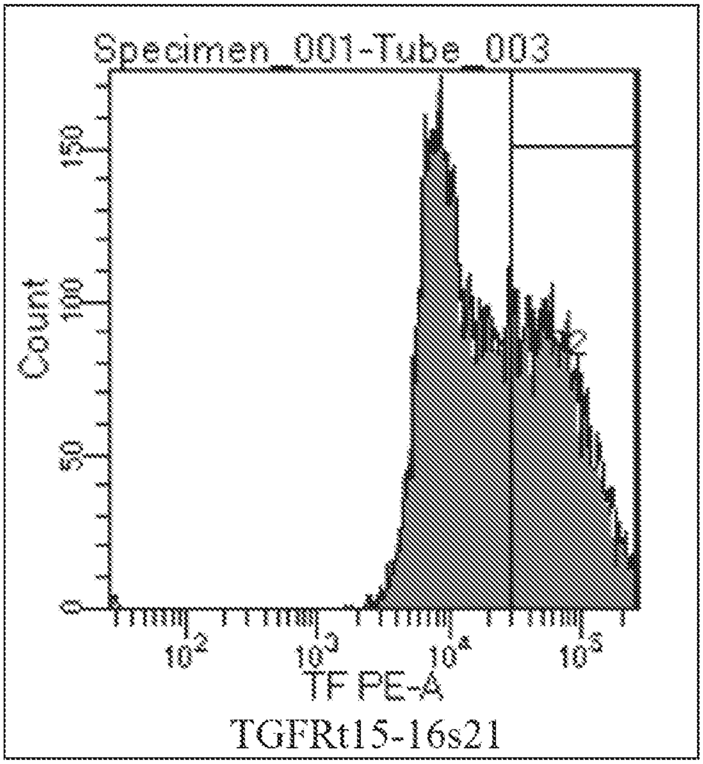
FIGS. 94A and 94B show binding affinity of TGFRt15-16s21 and 7t15-21s with CHO cells expressing human CD16b.
Figure 94B:
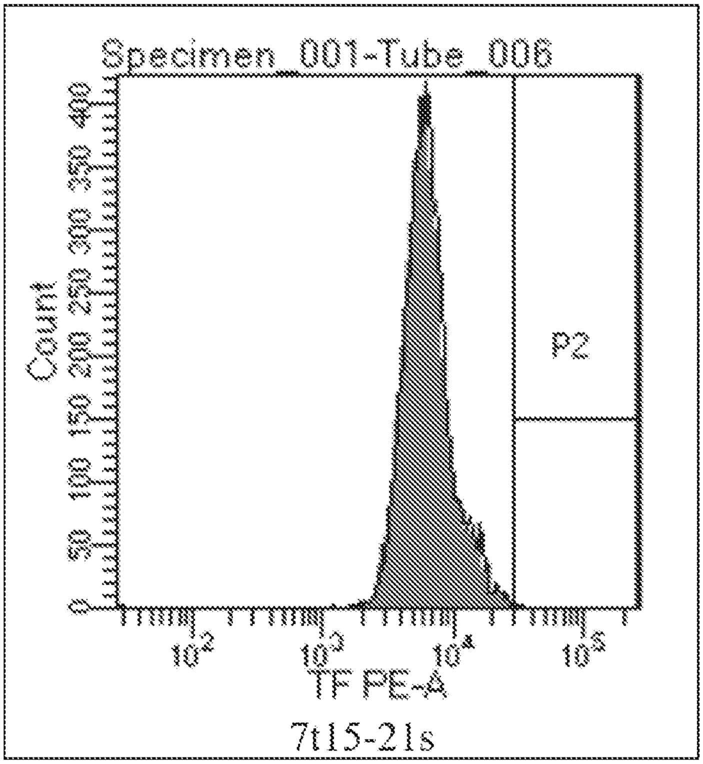

CHO cells were transfected with human CD16b in a pMC plasmid and selected with 10 μg/mL of blasticidin for 10 days. Cells stably expressing CD16b were stained with 1.2 μg/mL of TGFRt15-16s21 (containing anti-human CD16 scFv) or 7t15-21s (no anti-human CD16 scFv) as a negative control, and with biotinylated anti-human tissue factor antibody and PE conjugated streptavidin. As shown in FIGS. 94A and 94B, TGFRt15-16s21, which contains anti-human CD16scFv, showed positive binding, while 7t15-21s did not show binding.

Effect of TGFRt15-16s21 on TGFβ Activity in HEK-Blue TGFβ Cells

Figure 95:
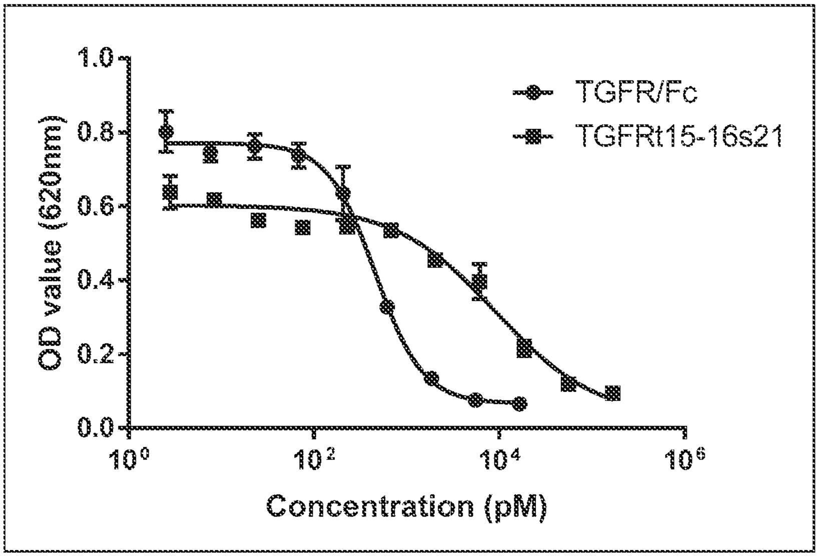
FIG. 95 shows results of TGFβ1 inhibition by TGFRt15-16s21 and TGFR-Fc.

To evaluate the activity of TGFβRII in TGFRt15-16s21, the effect of TGFRt15-16s21 on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μl cells were added to each well ($2.5\times10^4$ cells/well) and followed with 50 μL 0.1 nM TGFβ1 (R&D systems). TGFRt15-16s21 or TGFR-Fc (R&D Systems) prepared at a 1:3 serial dilution was then added to the plate to reach a total volume of 200 μL. After 24 hrs of incubation at 37° C., 40 μL of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. The IC50 of each protein sample was calculated with GraphPad Prism 7.04. The IC50 of TGFRt15-16s21 and TGFR-Fc were 9127 pM and 460.6 pM respectively. These results showed that the TGFβRII domain in TGFRt15-16s21 was able to block the activity of TGFβ-1 in HEK-Blue TGFβ cells. See, FIG. 95.

Figure 96:
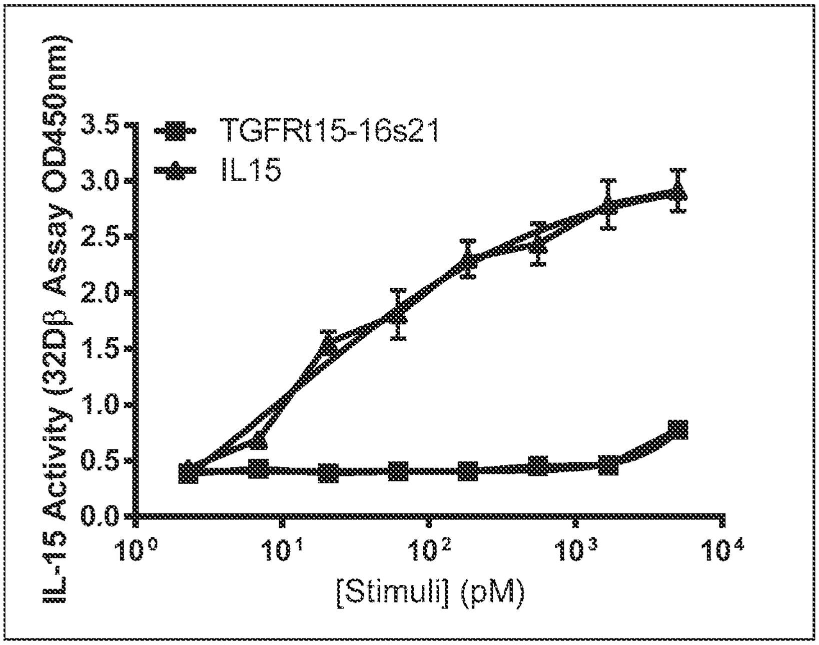
FIG. 96 shows results of 32Dβ cell proliferation assay with TGFRt15-16s21 or recombinant IL-15.

The IL-15 in TGFRt15-16s21 Promotes IL-2Rβ and Common γ Chain Containing 32Dβ Cell Proliferation To analyze the activity of IL-15 in TGFRt15-16s21, the IL-15 activity of TGFRt15-16s21 was compared to recombinant IL-15 using 32Dβ cells that express IL2RP and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted TGFRt15-16s21 or IL-15 were added to the cells (FIG. 96). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The absorbance at 450 nm was measured by analyzing the amount of formazan dye produced. As shown in FIG. 96, TGFRt15-16s21 and IL-15 promoted 32Dβ cell proliferation, with the $EC_{50}$ of TGFRt15-16s21 and IL-15 being 51298 pM and 10.63 pM, respectively.

Detection of IL-15, IL-21, and TGFβRII in TGFRt15-16s21 Using ELISA

Figure 97A:
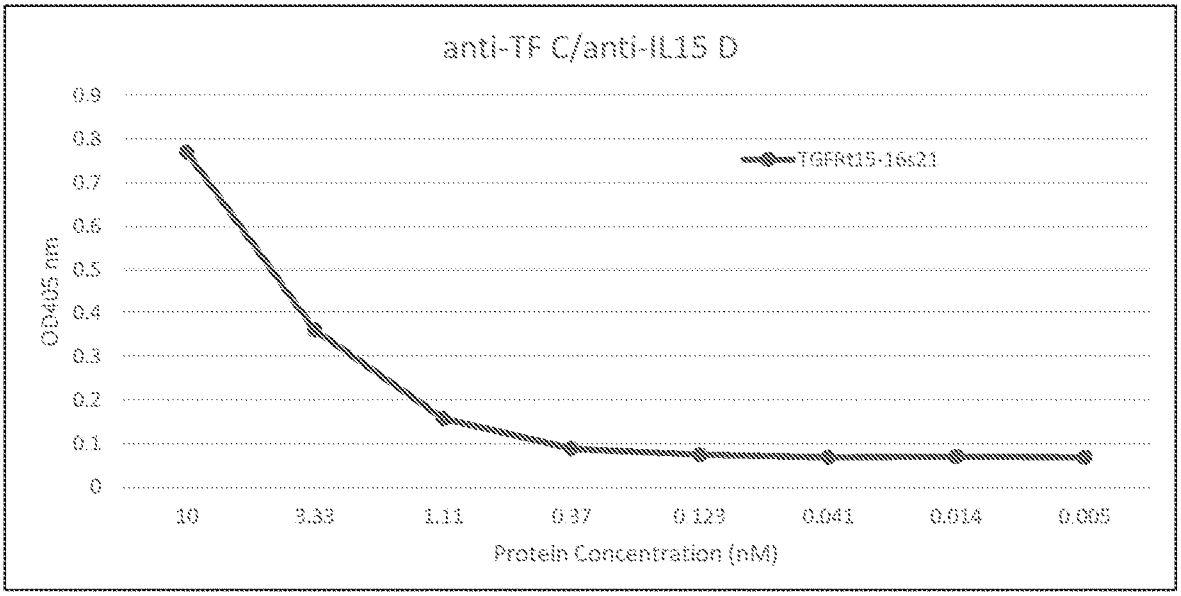
FIGS. 97A-97C show results of detecting IL-15, IL-21, and TGFβRII in TGFRt15-16s21 with corresponding antibodies using ELISA.
Figure 97B:
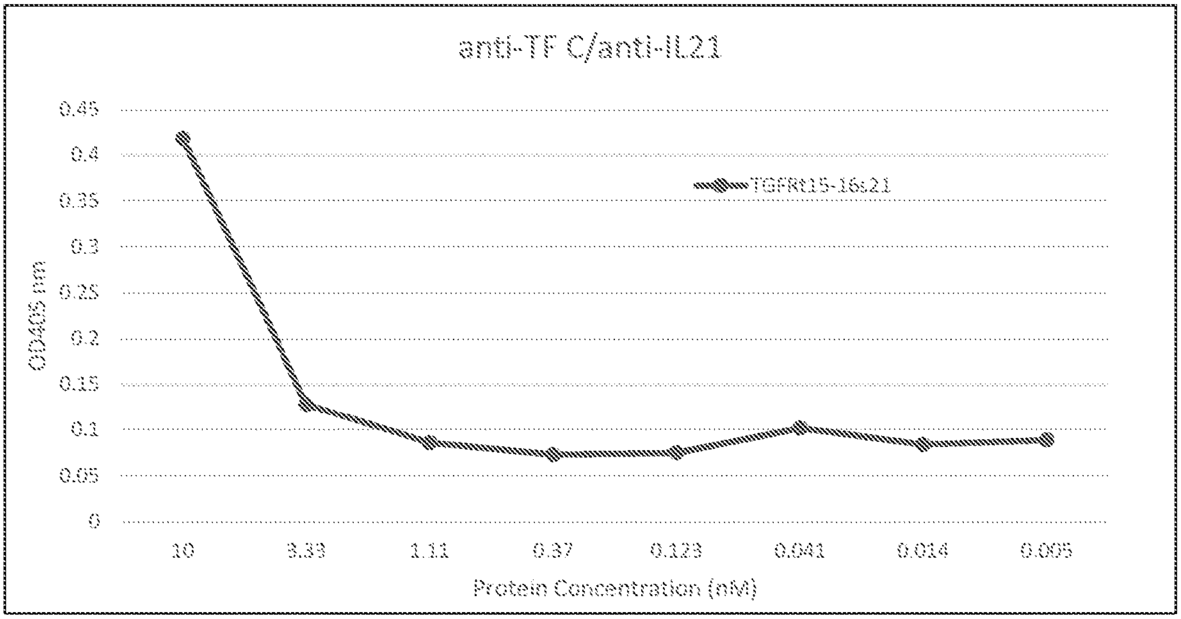
Figure 97C:
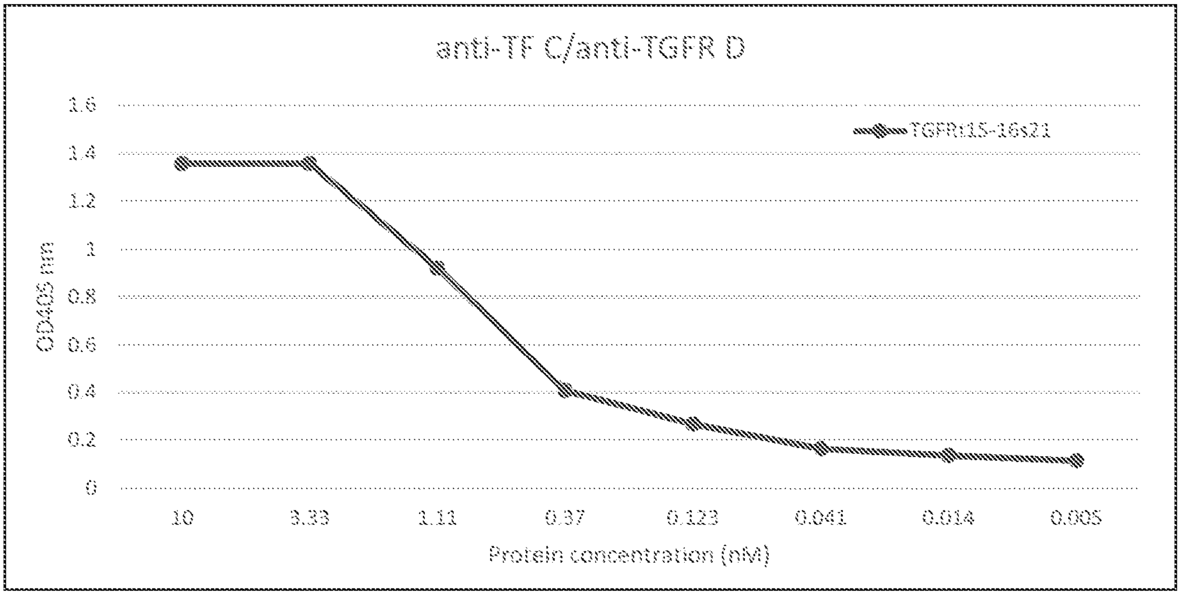

A 96-well plate was coated with 100 μL (8 μg/mL) of anti-TF antibody in R5 (coating buffer) and incubated at room temperature (RT) for 2 hrs. The plates were washed 3 times and blocked with 100 μL of 1% BSA in PBS. TGFRt15-16s21 serially diluted at a 1:3 ratio was added and incubated at RT for 60 min. Following three washes, 50 ng/mL of biotinylated-anti-IL-15 antibody (BAM247, R&D Systems), 500 ng/mL of biotinylated-anti-IL-21 antibody (13-7218-81, R&D Systems), or 200 ng/mL of biotinylated-anti-TGFβRII antibody (BAF241, R&D Systems) was applied per well, and incubated at RT for 60 min. Following three washes, incubation with 0.25 μg/mL of HRP-SA (Jackson ImmunoResearch at 100 μL per well for 30 min at RT was carried out, followed by 4 washes and incubation with 100 μL of ABTS for 2 mins at RT. Absorbance was read at 405 nm. As shown in FIGS. 97A-97C, the IL-15, IL-21, and TGFβRII domains in TGFRt15-16s21 were detected by the respective antibodies.

Figure 14:
FIG. 14 shows a schematic diagram of an exemplary IL-21/IL-15RαSu DNA construct.

Purification Elution Chromatograph of TGFRt15-16s21 Using Anti-TF Antibody Affinity Column TGFRt15-16s21 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 14, the anti-TF antibody affinity column bound to TGFRt15-16s21 which contains tissue factor as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE of TGFRt15-16s21

Figure 98:
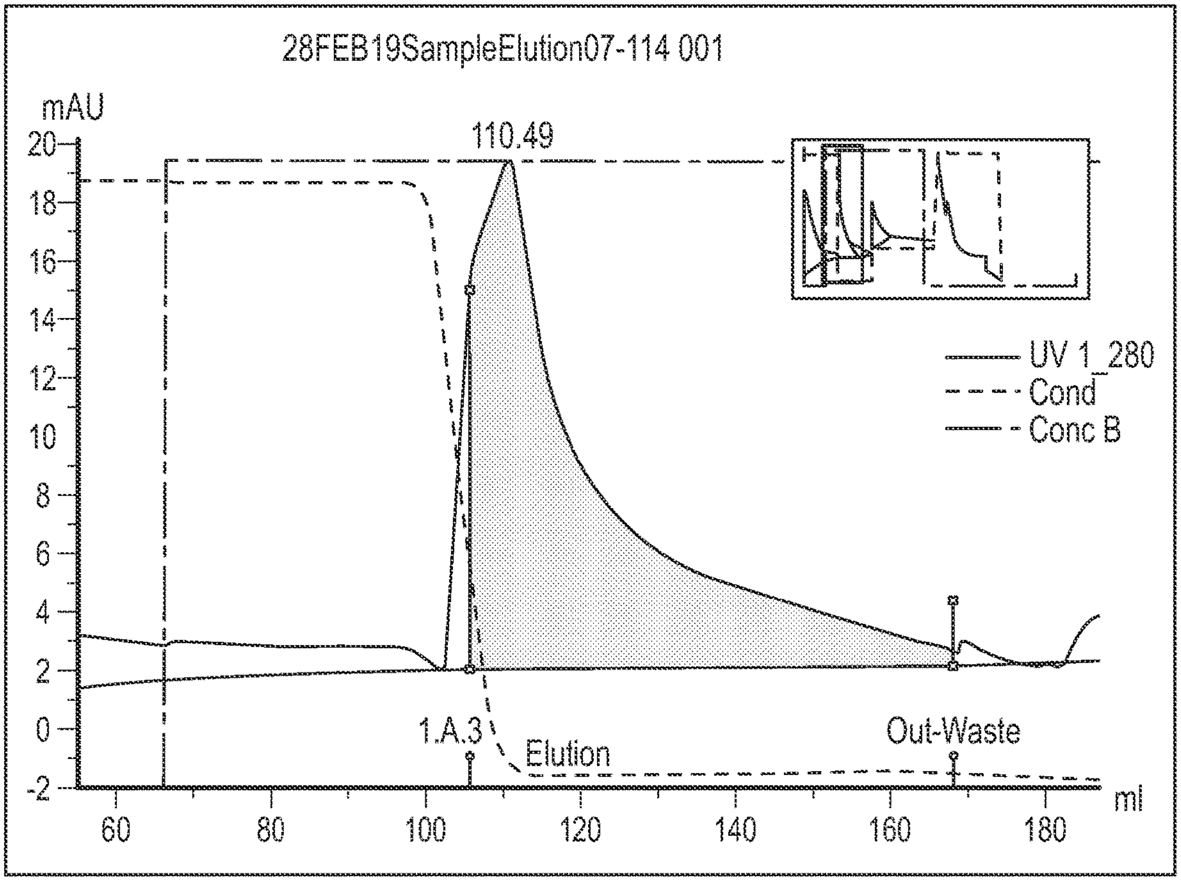
FIG. 98 is a line graph showing the chromatographic profile of TGFRt15-16s21 protein containing cell culture supernatant following binding and elution on anti-TF antibody resin.

To determine the purity and molecular weight of the TGFRt15-16s21 protein, protein sample purified with anti-TF antibody affinity column (FIG. 98) was analyzed by sodium dodecyl sulfate polyacrylamide gel (4-12% NuPage Bis-Tris gel) electrophoresis (SDS-PAGE) under reduced condition. After electrophoresis, the gel was stained with InstantBlue for about 30 min, followed by destaining overnight in purified water.

Figure 99:
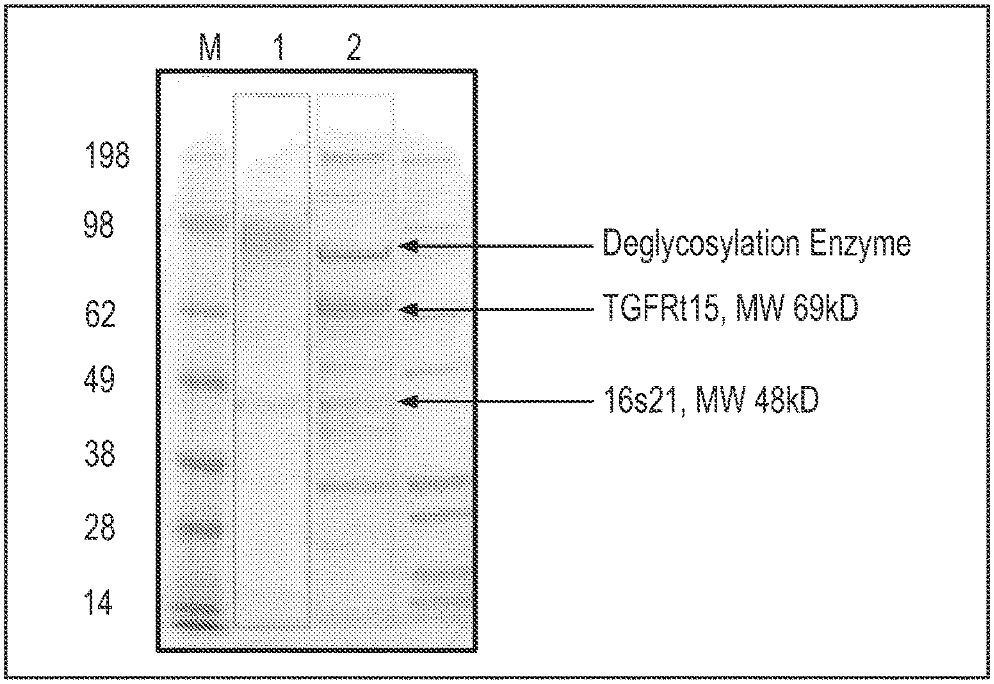
FIG. 99 shows results of a reduced SDS-PAGE analysis of TGFRt15-16s21.

To verify that the TGFRt15-16s21 protein undergoes glycosylation after translation in CHO cells, a deglycosylation experiment was conducted using the Protein Deglycosylation Mix II kit from New England Biolabs according to the manufacturer's instructions. FIG. 99 shows results from the reduced SDS-PAGE analysis of the sample in non-deglycosylated (lane 1 in red outline) and deglycosylated (lane 2 in yellow outline) state. The results showed that the TGFRt15-16s21 protein is glycosylated when expressed in CHO cells. After deglycosylation, the purified sample showed expected molecular weights (69 kDa and 48 kDa) in the reduced SDS gel. Lane M was loaded with 10 μL of SeeBlue Plus2 Prestained Standard.

Example 77: 7t15-7s Fusion Protein Generation and Characterization

A fusion protein complex was generated comprising IL-7/TF/IL-15 and IL-7/IL-15RαSu fusion proteins. The human IL-7, tissue factor 219, and IL-15 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15.

The nucleic acid and protein sequences of a construct comprising IL-7 linked to the N-terminus of tissue factor 219 following with the N-terminus of IL-15 are shown below.

The nucleic acid sequence of 7t15 construct (including signal peptide sequence) is as

```
(Signal peptide)
ATGAAGTGGGTGACCTTCATCAGCCTGCTGTTCCTGTTCTCCAGCGC

CTACTCC

(Human IL7)
GATTGCGACATCGAGGGCAAGGACGGCAAGCAGTACGAGAGCGTGCT

GATGGTGTCCATCGACCAGCTGCTGGACAGCATGAAGGAGATCGGCT

CCAACTGCCTCAACAACGAGTTCAACTTCTTCAAGCGGCACATCTGC

GACGCCAACAAGGAGGGCATGTTCCTGTTCAGGGCCGCCAGGAAACT

GCGGCAGTTCCTGAAGATGAACTCCACCGGCGACTTCGACCTGCACC

TGCTGAAGGTGTCCGAGGGCACCACCATCCTGCTGAACTGCACCGGA

CAGGTGAAGGGCCGGAAACCTGCTGCTCTGGGAGAGGCCCAACCCAC

CAAGAGCCTGGAGGAGAACAAGTCCCTGAAGGAGCAGAAGAAGCTGA

ACGACCTGTGCTTCCTGAAGAGGCTGCTGCAGGAGATCAAGACCTGC

TGGAACAAGATCCTGATGGGCACCAAGGAGCAT

(Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACC

AAGTTTACACCGTGCAGATCAGCACCAAGTCCGGCGACTGGAAGTCC

AAATGTTTCTATACCACCGACACCGAGTGCGATCTCACCGATGAGAT

CGTGAAAGATGTGAAACAGACCTACCTCGCCCGGGTGTTTAGCTACC

CCGCCGGCAATGTGGAGAGCACTGGTTCCGCTGGCGAGCCTTTATAC

GAGAACAGCCCCGAATTTACCCCTTACCTCGAGACCAATTTAGGACA

GCCCACCATCCAAAGCTTTGAGCAAGTTGGCACAAAGGTGAATGTGA

CAGTGGAGGACGAGCGGACTTTAGTGCGGCGGAACAACACCTTTCTC

AGCCTCCGGGATGTGTTCGGCAAAGATTTAATCTACACACTGTATTA

CTGGAAGTCCTCTTCCTCCGGCAAGAAGACAGCTAAAACCAACACAA

ACGAGTTTTTAATCGACGTGGATAAAGGCGAAAACTACTGTTTCAGC

GTGCAAGCTGTGATCCCCTCCCGGACCGTGAATAGGAAAAGCACCGA

TAGCCCCGTTGAGTGCATGGGCCAAGAAAAGGGCGAGTTCCGGGAG
```

-continued

```
(Human IL-15)
AACTGGGTGAACGTCATCAGCGATTTAAAGAAGATCGAAGATTTAAT

TCAGTCCATGCATATCGACGCCACTTTATACACAGAATCCGACGTGC

ACCCCTCTTGTAAGGTGACCGCCATGAAATGTTTTTTACTGGAGCTG

CAAGTTATCTCTTTAGAGAGCGGAGACGCTAGCATCCACGACACCGT

GGAGAATTTAATCATTTTAGCCAATAACTCTTTATCCAGCAACGGCA

ACGTGACAGAGTCCGGCTGCAAGGAGTGCGAAGAGCTGGAGGAGAAG

AACATCAAGGAGTTTCTGCAATCCTTTGTGCACATTGTCCAGATGTT

CATCAATACCTCC
```

The amino acid sequence of 7t15 fusion protein (including the leader sequence) is as follows:

```
(Signal peptide)
MKWVTFISLLFLFSSAYS

(Human IL7)
DCDIEGKDGKQYESVLMVSIDQLLDSMKEIGSNCLNNEFNFFKRHICD

ANKEGMFLFRAARKLRQFLKMNSTGDFDLHLLKVSEGTTILLNCTGQV

KGRKPAALGEAQPTKSLEENKSLKEQKKLNDLCFLKRLLQEIKTCWNK

ILMGTKEH

(Human Tissue Factor 219)
SGTTNTVAAYNLTWKSTNFKTILEWEPKPVNQVYTVQISTKSGDWKSK

CFYTTDTECDLTDEIVKDVKQTYLARVFSYPAGNVESTGSAGEPLYEN

SPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAV

IPSRTVNRKSTDSPVECMGQEKGEFRE

(Human IL-15)
NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS
```

Constructs were also made by linking the IL-7 sequence to the N-terminus coding region of IL-15RαSu chain which was synthesized by Genewiz. The nucleic acid and protein sequences of a construct comprising the TL-7 linked to the N-terminus of IL-15RαSu chain are shown below.

The nucleic acid sequence of 7s construct (including signal peptide sequence) is as follows:

```
(Signal peptide)
ATGAAGTGGGTGACCTTCATCAGCCTGCTGTTCCTGTTCTCCAGCGCC

TACTCC

(Human IL7)
GATTGCGACATCGAGGGCAAGGACGGCAAGCAGTACGAGAGCGTGCTG

ATGGTGTCCATCGACCAGCTGCTGGACAGCATGAAGGAGATCGGCTCC

AACTGCCTCAACAACGAGTTCAACTTCTTCAAGCGGCACATCTGCGAC

GCCAACAAGGAGGGCATGTTCCTGTTCAGGGCCGCCAGGAAACTGCGG

CAGTTCCTGAAGATGAACTCCACCGGCGACTTCGACCTGCACCTGCTG

AAGGTGTCCGAGGGCACCACCATCCTGCTGAACTGCACCGGACAGGTG
```

-continued

AAGGGCCGGAAACCTGCTGCTCTGGGAGAGGCCCAACCCACCAAGAGC

CTGGAGGAGAACAAGTCCCTGAAGGAGCAGAAGAAGCTGAACGACCTG

TGCTTCCTGAAGAGGCTGCTGCAGGAGATCAAGACCTGCTGGAACAAG

ATCCTGATGGGCACCAAGGAGCAT (Human IL-15R α sushi domain)
ATTACATGCCCCCCTCCCATGAGCGTGGAGCACGCCGACATCTGGGTG

AAGAGCTATAGCCTCTACAGCCGGGAGAGGTATATCTGTAACAGCGGC

TTCAAGAGGAAGGCCGGCACCAGCAGCCTCACCGAGTGCGTGCTGAAT

AAGGCTACCAACGTGGCTCACTGGACAACACCCTCTTTAAAGTGCATC

CGG

The amino acid sequence of 7s fusion protein (including the leader sequence) is as follows:

(Signal peptide)
MKWVTFISLLFLFSSAYS (Human IL7)
DCDIEGKDGKQYESVLMVSIDQLLDSMKEIGSNCLNNEFNFFKRHICD

ANKEGMFLFRAARKLRQFLKMNSTGDFDLHLLKVSEGTTILLNCTGQV

KGRKPAALGEAQPTKSLEENKSLKEQKKLNDLCFLKRLLQEIKTCWNK

ILMGTKEH (Human IL-15R α sushi domain)
ITCPPPMSVEHADIWVKSYSLYSRERYICNSGFKRKAGTSSLTECVLN

KATNVAHWTTPSLKCIR

Figure 100:
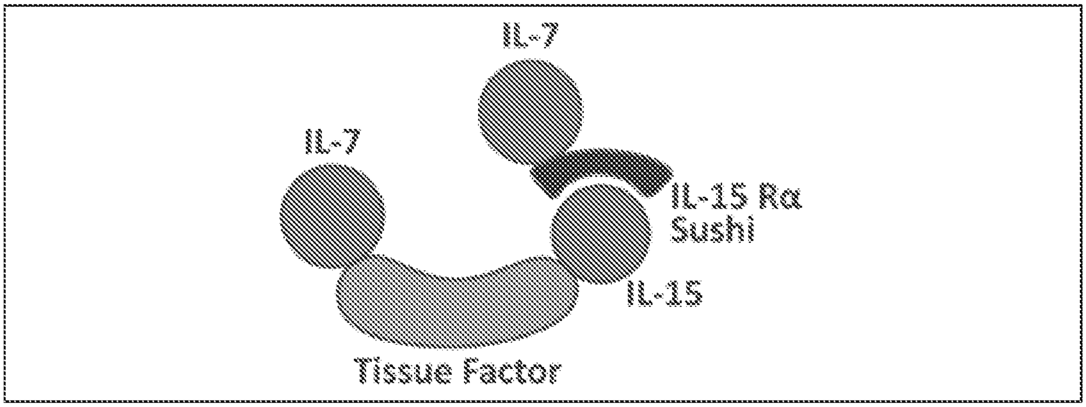
FIG. 100 shows a schematic of the 7t15-7s construct.
Figure 101:
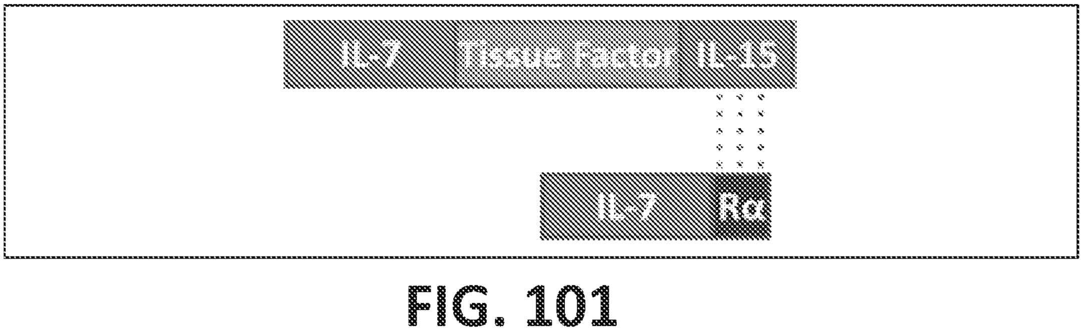
FIG. 101 shows an additional schematic of the 7t15-7s construct.

The IL-7/TF/IL-15 and IL-7/IL-15RαSu constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. Hum Gene Ther 2005; 16:457-72), and the expression vectors were transfected into CHO-K1 cells. Co-expression of the two constructs in CHO-K1 cells allowed for formation and secretion of the soluble IL-7/TF/IL-15:IL-7/IL-15RαSu protein complex (referred to as 7t15-7s), which can be purified by anti-TF antibody affinity and other chromatography methods. See, FIGS. 100 and 101.

Figure 102:
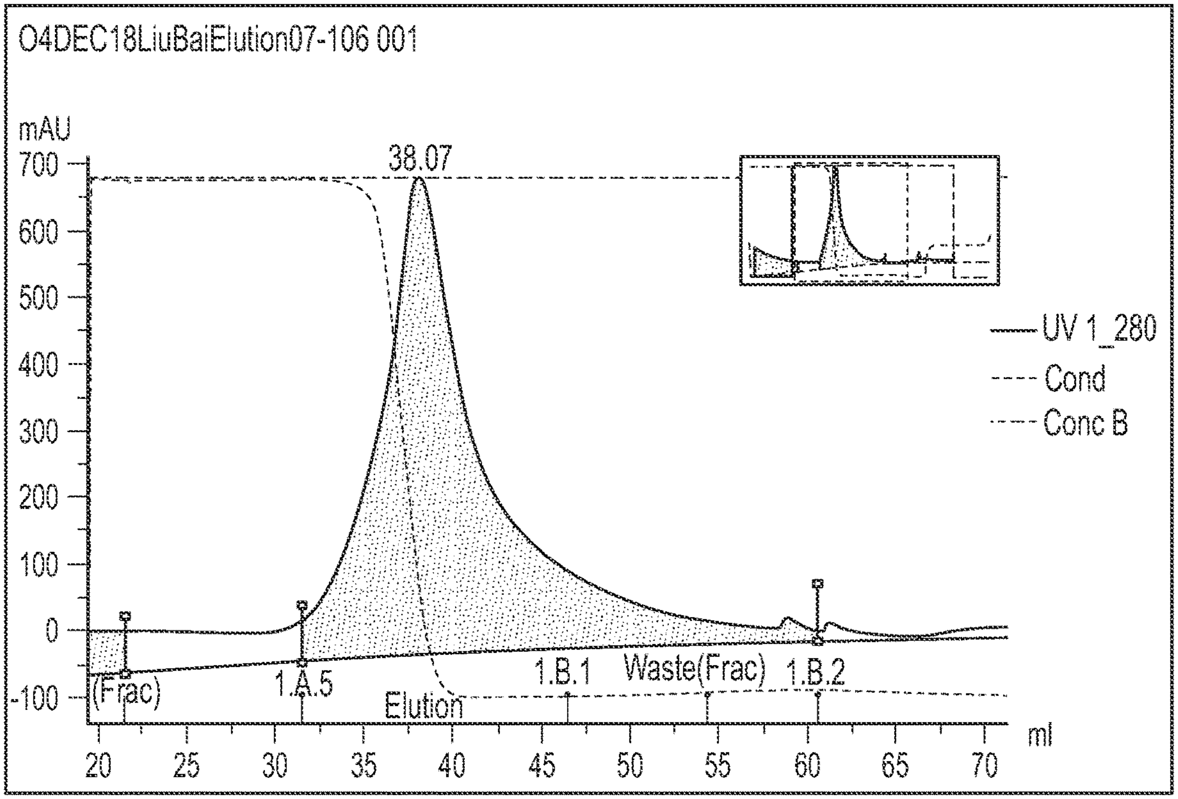
FIG. 102 is a line graph showing the chromatographic profile of 7t15-7s protein containing cell culture supernatant following binding and elution on anti-TF antibody resin.

Purification Elution Chromatograph of 7t15-7s Using Anti-TF Antibody Affinity Column 7t15-7s harvested from cell culture was loaded onto the anti-TF antibody affinity column equilibrated with 5 column volumes of PBS. After sample loading, the column was washed with column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a KDa molecular weight cutoff. As shown in FIG. 102, the anti-TF antibody affinity column bound to 7t15-7s which contains tissue factor (TF) as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except the elution step, which was 2 mL/min.

Immunostimulation of 7t15-7s in C57BL 6 Mice

7t15-7s is a multi-chain polypeptide (a type A multi-chain polypeptide described herein) that includes the first polypeptide that is a soluble fusion of human IL-7, human tissue factor 219 fragment and human IL-15 (7t15), and the second polypeptide that is a soluble fusion of human IL-7 and sushi domain of human IL-15 receptor alpha chain (7s).

Figure 103:
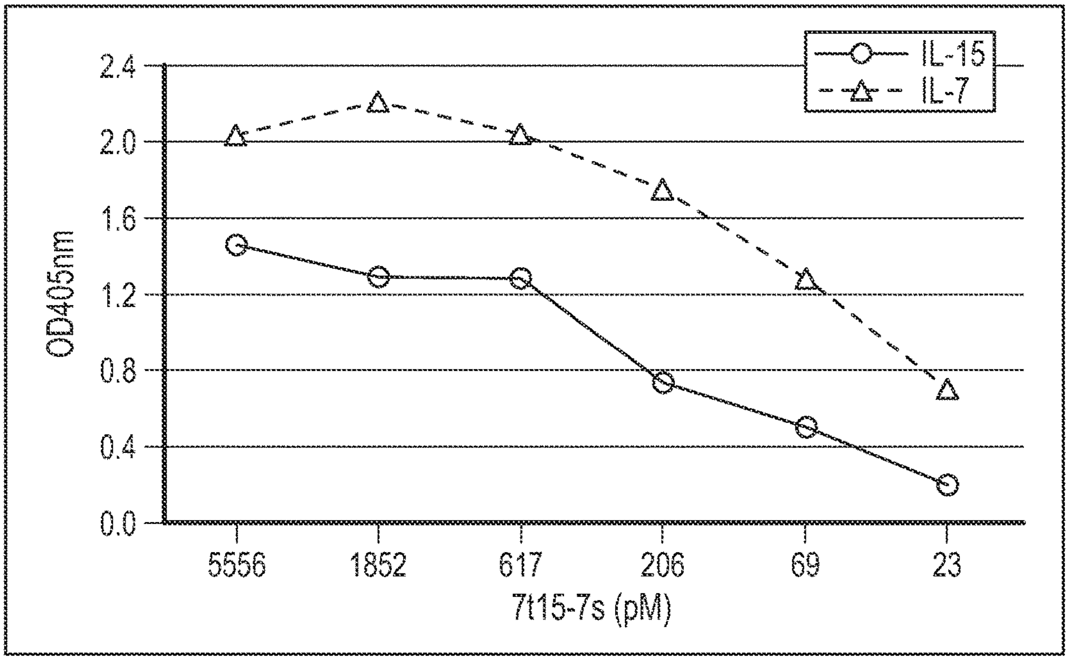
FIG. 103 shows detection of TF, IL-15 and IL-7 in 7t15-7s using ELISA.
Figure 104A:
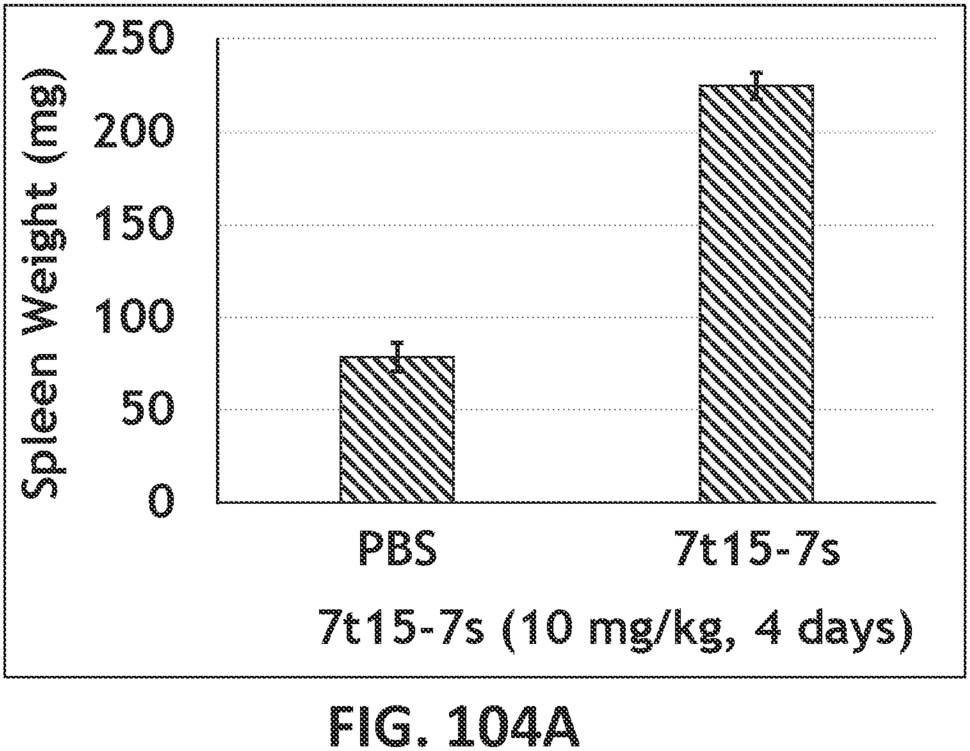
FIGS. 104A and 104B show spleen weight and the percentages of immune cell types in 7t15-7s-treated and control-treated mice.
Figure 104B:
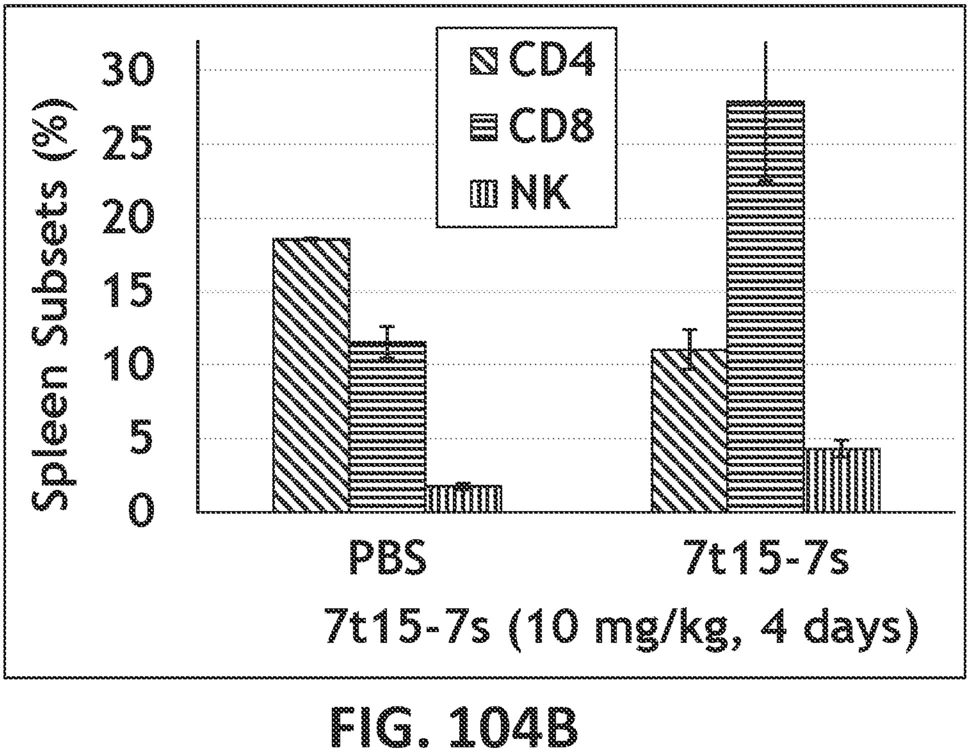

CHO cells were co-transfected with the IL7-TF-IL15 (7t15) and IL7-IL15Rα sushi domain (7s) vectors. The 7t15-7s complex was purified from the transfected CHO cell culture supernatant. The IL-7, IL-15 and tissue factor (TF) components were demonstrated in the complex by ELISA as shown in FIG. 103. A humanized anti-TF monoclonal antibody was used as the capture antibody to determine TF in 7t15-7s, and biotinylated anti-human IL-15 antibody (R&D systems) and biotinylated anti-human IL-7 antibody (R&D Systems) were used as the detection antibodies to respectively detect IL-15 and IL-7 in 7t15-7s, followed by peroxidase conjugated streptavidin (Jackson ImmunoResearch Lab) and ABTS substrate (Surmodics IVD, Inc.). 7t15-7s was subcutaneously injected into C57BL/6 mice at 10 mg/kg to determine the immunostimulatory activity of 7t15-7s in vivo. C57BL/6 mice subcutaneously treated with PBS were used as control. The mouse spleens were collected and weighed day 4 post treatment. Single splenocytes suspensions were prepared, and with fluorochrome-conjugated anti-CD4, anti-CD8, and anti-NK1.1 antibodies and the percentage of $CD4^+$ T cells, CD8+ T cells, and NK cells was analyzed by flow cytometry. The results showed that 7t15-7s was effective at expanding splenocytes based on spleen weight (FIG. 104A) and specifically, the percentages of $CD8^+$ T cells and NK cells were higher compared to control-treated mice (FIG. 104B).

Example 78: TGFRt15-TGFRs Fusion Protein Generation and Characterization

A fusion protein complex was generated comprising of TGFβ Receptor II/IL-15RαSu and TGFβ Receptor II/TF/IL-15 fusion proteins. The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the two TGFβ Receptor II/TF/IL-15 construct (including signal peptide sequence) is as follows:

(Signal peptide)
ATGAAGTGGGTGACCTTCATCAGCCTGCTGTTCCTGTTCTCCAGCGCC

TACTCC (Two Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

AGCATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCTCCATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGAC (Human Tissue Factor 219)
AGCGGCACAACCAACACAGTCGCTGCCTATAACCTCACTTGGAAGAGC

ACCAACTTCAAAACCATCCTCGAATGGGAACCCAAACCCGTTAACCAA

GTTTACACCGTGCAGATCAGCACCAAGTCCGGCGACTGGAAGTCCAAA

TGTTTCTATACCACCGACACCGAGTGCGATCTCACCGATGAGATCGTG

AAAGATGTGAAACAGACCTACCTCGCCCGGGTGTTTAGCTACCCCGCC

GGCAATGTGGAGAGCACTGGTTCCGCTGGCGAGCCTTTATACGAGAAC

AGCCCCGAATTTACCCCTTACCTCGAGACCAATTTAGGACAGCCCACC

ATCCAAAGCTTTGAGCAAGTTGGCACAAAGGTGAATGTGACAGTGGAG

GACGAGCGGACTTTAGTGCGGCGGAACAACACCTTTCTCAGCCTCCGG

GATGTGTTCGGCAAAGATTTAATCTACACACTGTATTACTGGAAGTCC

TCTTCCTCCGGCAAGAAGACAGCTAAAACCAACACAAACGAGTTTTTA

ATCGACGTGGATAAAGGCGAAAACTACTGTTTCAGCGTGCAAGCTGTG

ATCCCCTCCCGGACCGTGAATAGGAAAAGCACCGATAGCCCCGTTGAG

TGCATGGGCCAAGAAAAGGGCGAGTTCCGGGAG (Human IL-15)
AACTGGGTGAACGTCATCAGCGATTTAAAGAAGATCGAAGATTTAATT

CAGTCCATGCATATCGACGCCACTTTATACACAGAATCCGACGTGCAC

CCCTCTTGTAAGGTGACCGCCATGAAATGTTTTTTACTGGAGCTGCAA

GTTATCTCTTTAGAGAGCGGAGACGCTAGCATCCACGACACCGTGGAG

AATTTAATCATTTTAGCCAATAACTCTTTATCCAGCAACGGCAACGTG

ACAGAGTCCGGCTGCAAGGAGTGCGAAGAGCTGGAGGAGAAGAACATC

AAGGAGTTTCTGCAATCCTTTGTGCACATTGTCCAGATGTTCATCAAT

ACCTCC

The amino acid sequence of TGFβ Receptor II/TF/IL-15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNC

SITSICEKPQEVCVAVWRKNDENITLETVCHDPKLPYHDFILEDAASP

KCIMKEKKKPGETFFMCSCSSDECNDNIIFSEEYNTSNPDGGGGSGGG

GSGGGGSIPPHVQKSVNNDMIVTDNNGAVKFPQLCKFCDVRFSTCDNQ

KSCMSNCSITSICEKPQEVCVAVWRKNDENITLETVCHDPKLPYHDFI

LEDAASPKCIMKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSK

CFYTTDTECDLTDEIVKDVKQTYLARVFSYPAGNVESTGSAGEPLYEN

SPEFTPYLETNLGQPTIQSFEQVGTKVNVTVEDERTLVRRNNTFLSLR

DVFGKDLIYTLYYWKSSSSGKKTAKTNTNEFLIDVDKGENYCFSVQAV

IPSRTVNRKSTDSPVECMGQEKGEFRE (Human IL-15)
NWVNVISDLKKIEDLIQSMHIDATLYTESDVHPSCKVTAMKCFLLELQ

VISLESGDASIHDTVENLIILANNSLSSNGNVTESGCKECEELEEKNI

KEFLQSFVHIVQMFINTS

Constructs were also made by attaching two TGFβ Receptor II directly to the IL-15RαSu chain which was synthesized by Genewiz. The nucleic acid and protein sequences of a construct comprising the TGFβ Receptor II linked to the N-terminus of IL-15RαSu are shown below.

The nucleic acid sequence of the TGFβ Receptor II/IL-15 RαSu construct (including signal peptide sequence) is as follows:

(Signal peptide)
ATGAAGTGGGTGACCTTCATCAGCCTGCTGTTCCTGTTCTCCAGCGCC

TACTCC (Two human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

AGCATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

-continued

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCTCCATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGAC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG

The amino acid sequence of the two TGFβ Receptor II/IL-15RαSu construct (including signal peptide sequence) is as follows:

(Signal peptide)
MKWVTFISLLFLFSSAYS (Two human TGFβ Receptor II extra-cellular domains)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD (Human IL-15R a sushi domain)
ITCPPPMSVEHADIWVKSYSLYSRERYICNSGFKRKAGTSSLTECVLNK

ATNVAHWTTPSLKCIR

In some cases, the leader peptide is cleaved from the intact polypeptide to generate the mature form that may be soluble or secreted.

Figure 105:
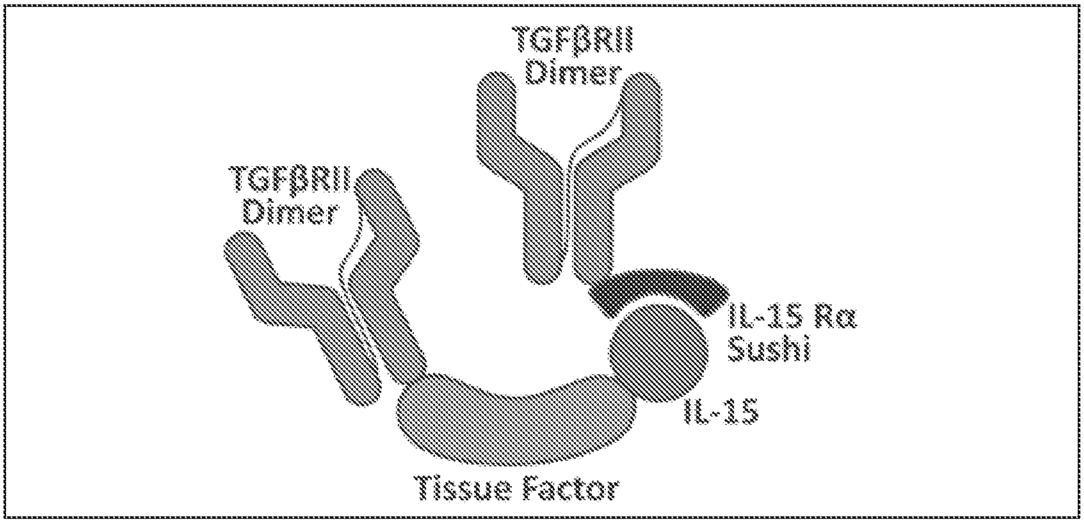
FIG. 105 shows a schematic of the TGFRt15-TGFRs construct.
Figure 106:
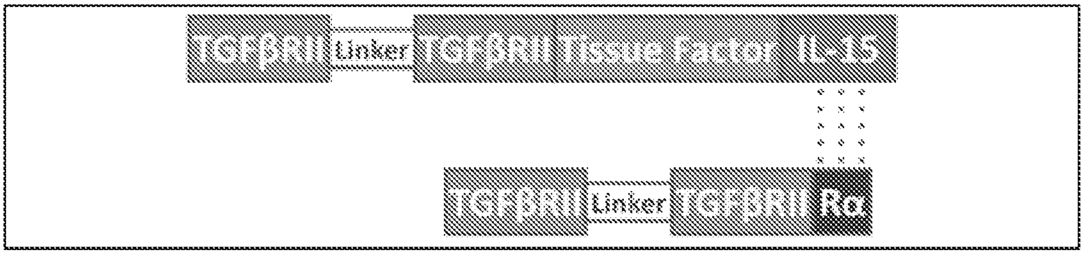
FIG. 106 shows an additional schematic of the TGFRt15-TGFRs construct.

The TGFβR/IL-15RαSu and TGFβR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFβR/TF/IL-15:TGFβR/IL-15RαSu protein complex (referred to as TGFRt15-TGFRs), which can be purified by anti-TF antibody affinity and other chromatography methods. See, FIGS. 105 and 106.

Effect of TGFRt15-TGFRs on TGFβ Activity in HEK-Blue TGFβ Cells

Figure 107:
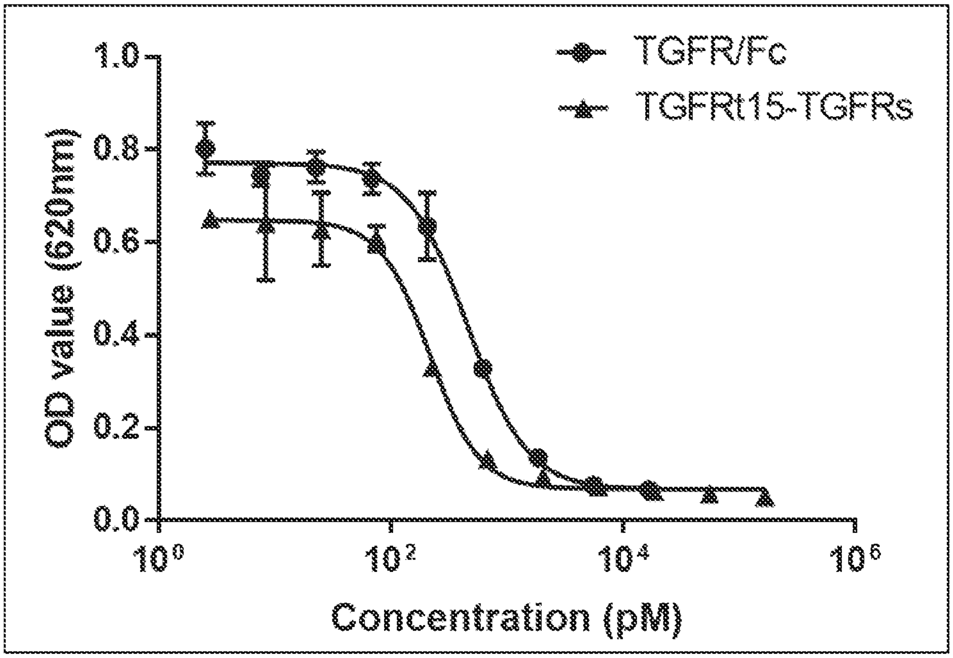
FIG. 107 shows results of TGFβ1 inhibition by TGFRt15-TGFRs and TGFR-Fc.

To evaluate the activity of TGFβRII in TGFRt15-TGFRs, the effect of TGFRt15-16s21 on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μL cells were added to each well ($2.5\times10^4$ cells/well) and followed with 50 μL 0.1 nM TGFβ1 (R&D systems). TGFRt15-16s21 or TGFR-Fc (R&D Systems) prepared at a 1:3 serial dilution was then added to the plate to reach a total volume of 200 μL. After 24 hrs of incubation at 37° C., 40 μL of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. See, FIG. 107. The IC50 of each protein sample was calculated with GraphPad Prism 7.04. The IC50 of TGFRt15-TGFRs and TGFR-Fc were 216.9 pM and 460.6 pM respectively. These results showed that the TGFβRII domain in TGFRt15-TGFRs was able to block the activity of TGFβ1 in HEK-Blue TGFβ cells.

Figure 108:
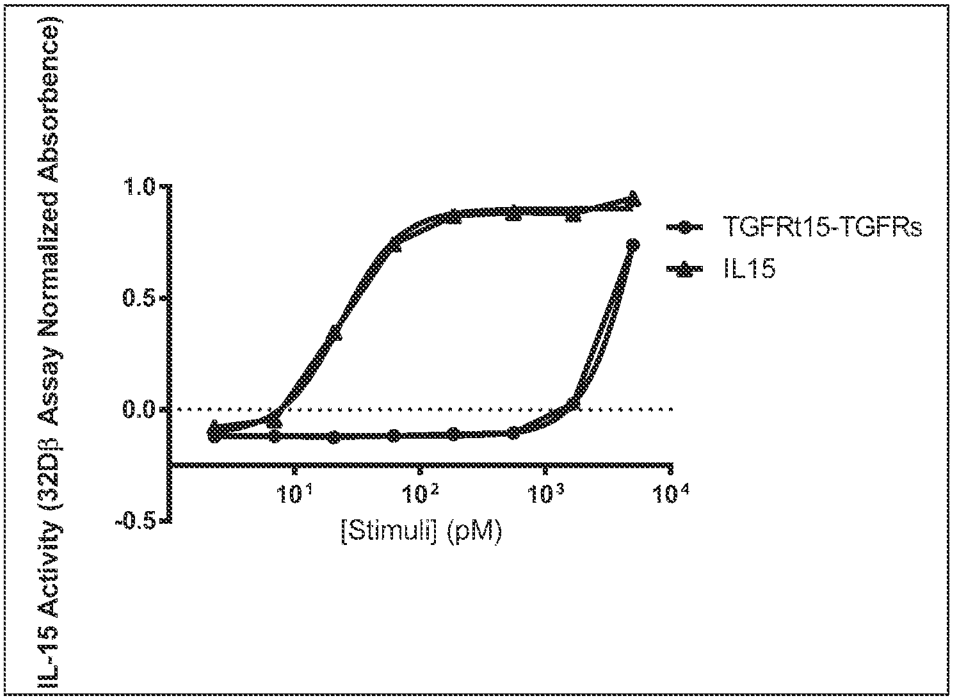
FIG. 108 shows results of 32Dβ cell proliferation assay with TGFRt15-TGFRs or recombinant IL-15

The IL-15 in TGFRt15-TGFRs Promotes IL-2Rβ and Common γ Chain Containing 32Dβ Cell Proliferation To evaluate the activity of IL-15 in TGFRt15-TGFRs, the IL-15 activity of TGFRt15-TGFRs was compared to recombinant IL-15 using 32Dβ cells that express IL2β and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted TGFRt15-TGFRs or IL-15 were added to the cells (FIG. 108). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The absorbance at 450 nm was measured by analyzing the amount of formazan dye produced. As shown in FIG. 108, TGFRt15-TGFRs and IL-15 promoted 32Dβ cell proliferation, with the $EC_{50}$ of TGFRt15-16s21 and IL-15 being 1901 pM and 10.63 pM, respectively.

Figure 109A:
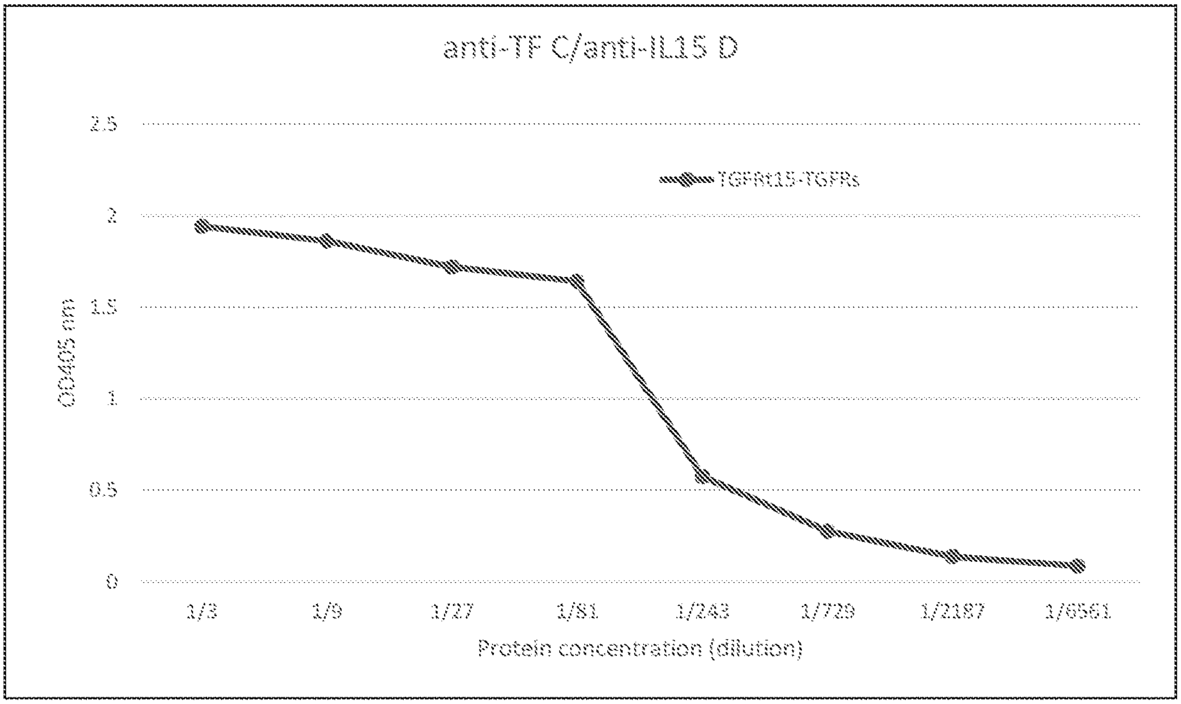
FIGS. 109A and 109B show results of detecting IL-15 and TGFβRII in TGFRt15-TGFRs with corresponding antibodies using ELISA.
Figure 109B:
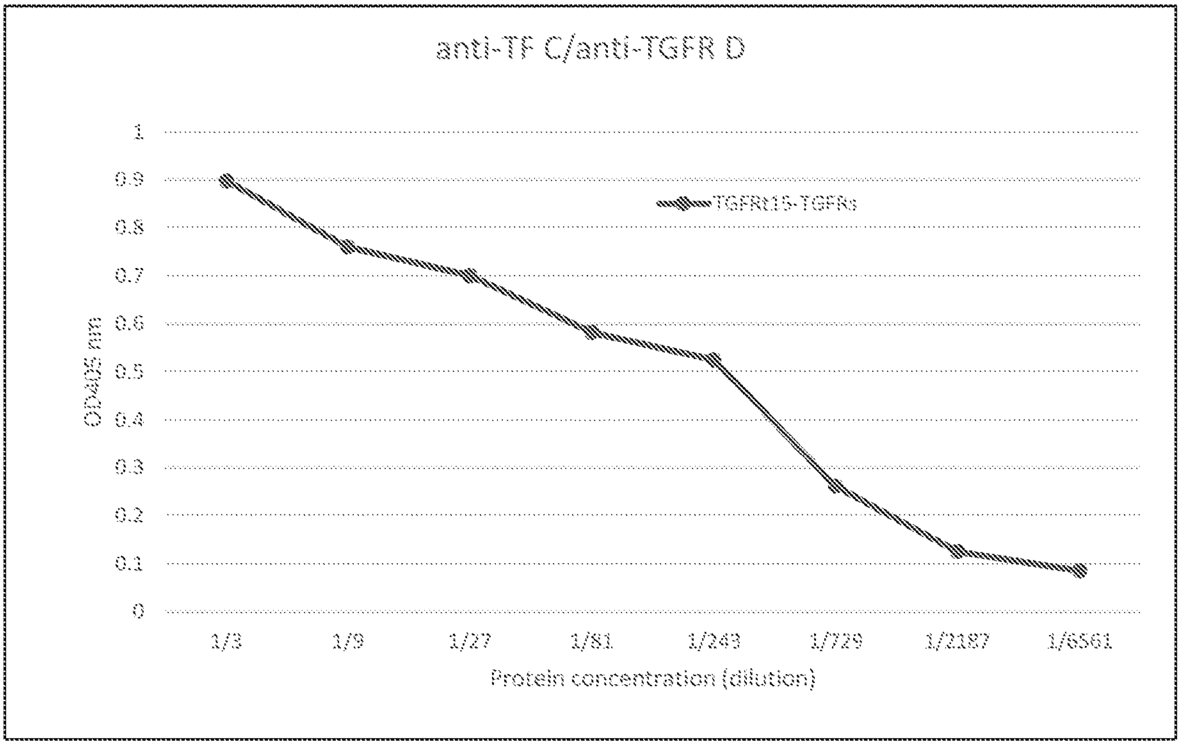
Figure 110:
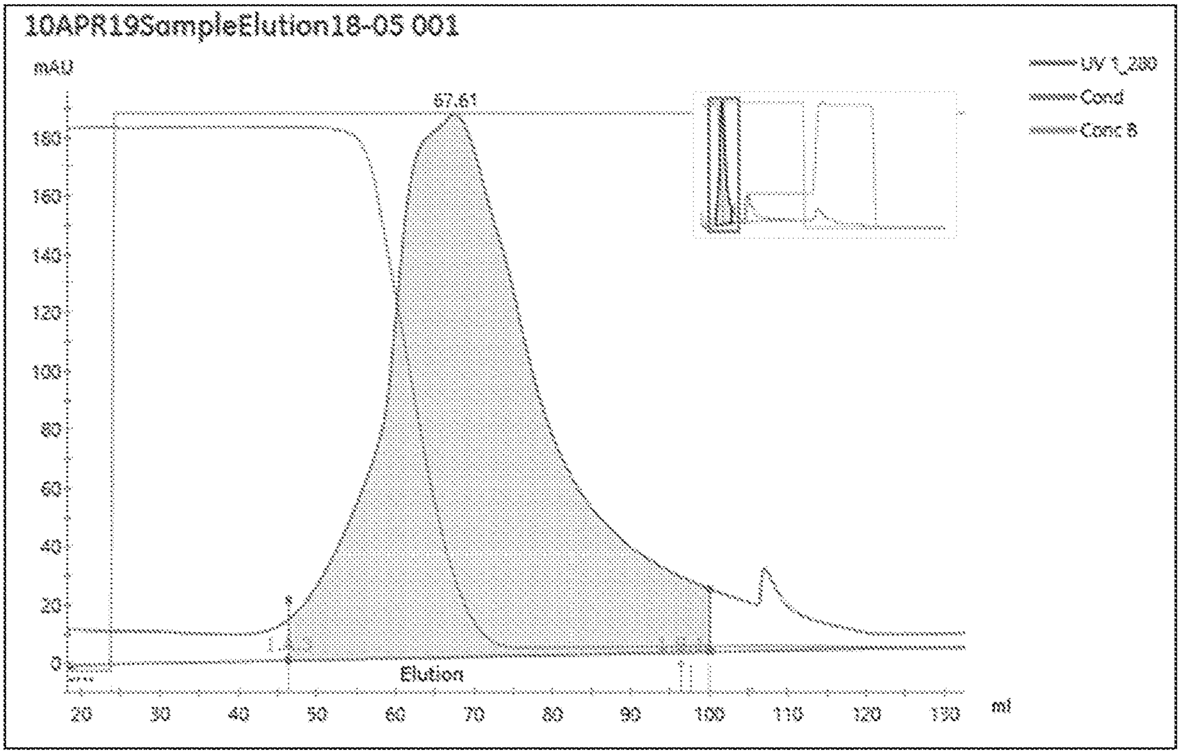
FIG. 110 is a line graph showing the chromatographic profile of TGFRt15-TGFRs protein containing cell culture supernatant following binding and elution on anti-TF antibody resin.

Detection of IL-15 and TGFβRII Domains in TGFRt15-TGFRs with Corresponding Antibodies Using ELISA A 96-well plate was coated with 100 μL (8 μg/mL) of anti-TF antibody in R5 (coating buffer) and incubated at room temperature (RT) for 2 hrs. The plates were washed 3 times and blocked with 100 μL of 1% BSA in PBS. TGFRt15-TGFRs was added at a 1:3 serial dilution, and incubated at RT for 60 min. After 3 washes, 50 ng/mL of biotinylated-anti-IL-15 antibody (BAM247, R&D Systems), or 200 ng/mL of biotinylated-anti-TGFβRII antibody (BAF241, R&D Systems) was added to the wells and incubated at RT for 60 min. Next the plates were washed 3 times, and 0.25 μg/mL of HRP-SA (Jackson ImmunoResearch) at 100 μL per well was added and incubated for 30 min at RT, followed by 4 washes and incubation with 100 μL of ABTS for 2 mins at RT. Absorbance at 405 nm was read. As shown in FIGS. 109A and 109B, the IL-15 and TGFβRII domains in TGFRt15-TGFRs were detected by the individual antibodies.

Purification Elution Chromatograph of TGFRt15-TGFRs from Anti-TF Antibody Affinity Column TGFRt15-TGFRs harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG.

110, the anti-TF antibody affinity column bound to TGFRt15-TGFRs which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of TGFRt15-TGFRs

Figure 111:
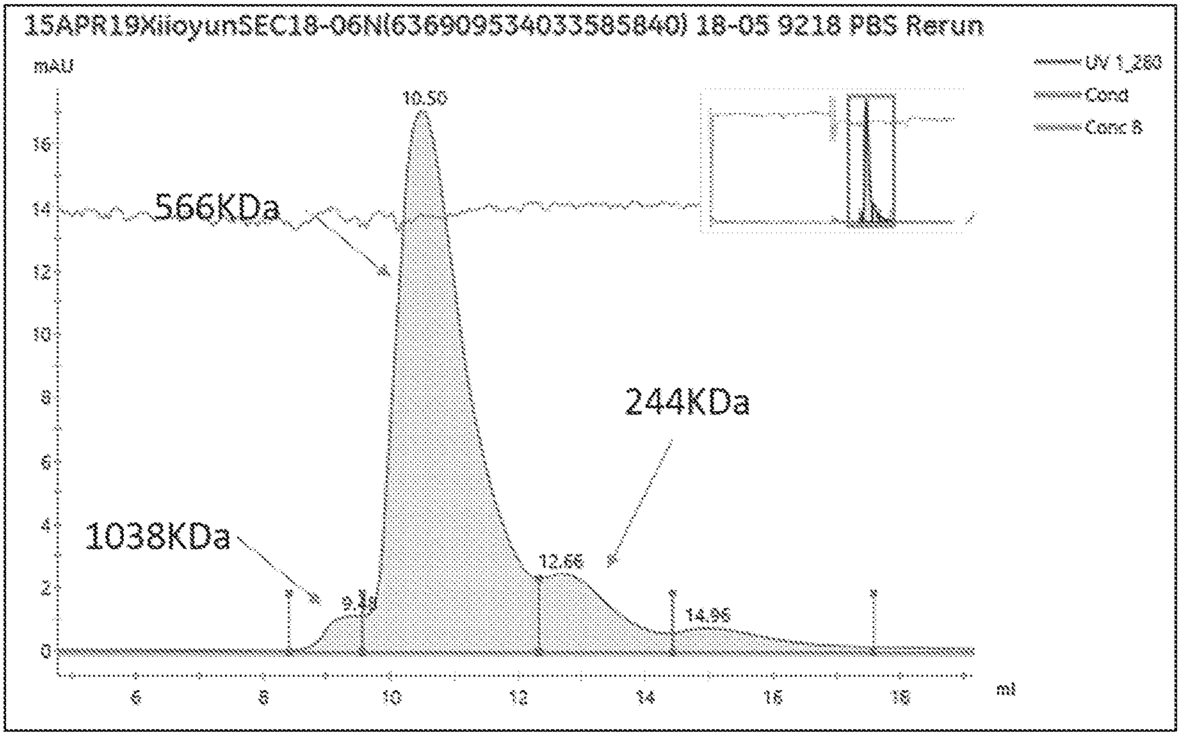
FIG. 111 shows the analytical SEC profile of TGFRt15-TGFRs.

A Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. A sample containing TGFRt15-TGFRs in PBS was injected into the Superdex 200 column using a capillary loop, and analyzed by SEC. The SEC chromatograph of the sample is shown in FIG. 111. The SEC results showed four protein peaks for TGFRt15-TGFRs Reduced SDS-PAGE Analysis of TGFRt15-TGFRs To determine the purity and molecular weight of the TGFRt15-TGFRs protein, protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

Figure 112:
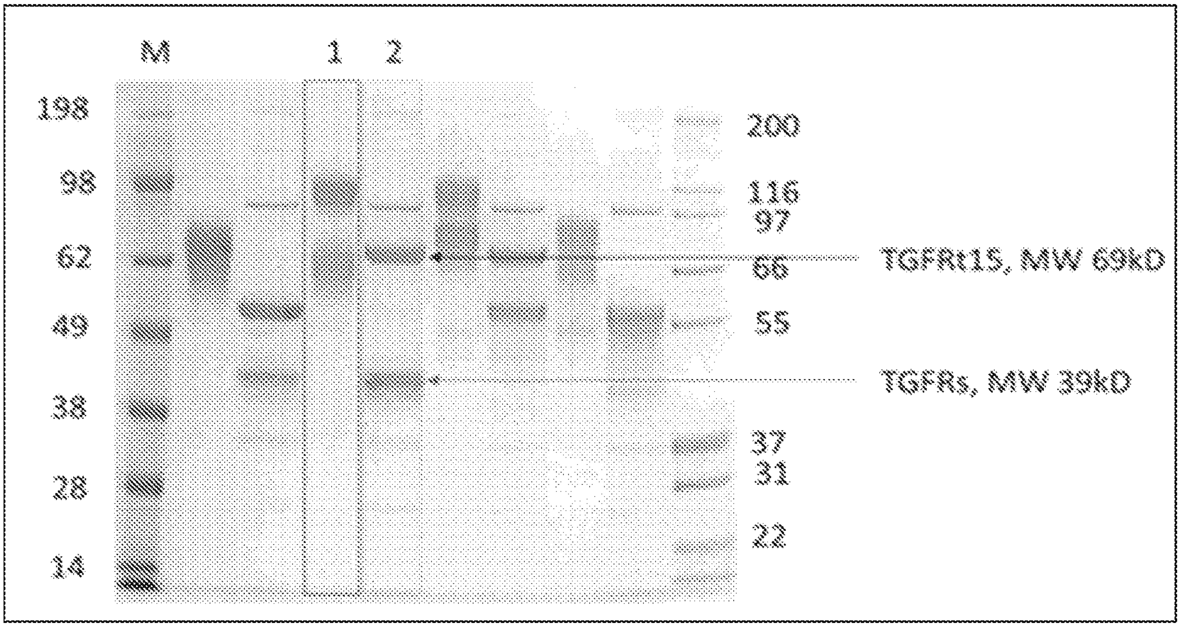
FIG. 112 shows TGFRt15-TGFRs before and after deglycosylation as analyzed by reduced SDS-PAGE.

To verify that the TGFRt15-TGFRs protein undergoes glycosylation after translation in CHO cells, a deglycosylation experiment was conducted using the Protein Deglycosylation Mix II kit from New England Biolabs and the manufacturer's instructions. FIG. 112 shows the reduced SDS-PAGE analysis of the sample in non-deglycosylated (lane 1 in red outline) and deglycosylated (lane 2 in yellow outline) state. The results showed that the TGFRt15-TGFRs protein is glycosylated when expressed in CHO cells. After deglycosylation, the purified sample showed expected molecular weights (69 kDa and 39 kDa) in the reduced SDS gel. Lane M was loaded with 10 ul of SeeBlue Plus2 Prestained Standard.

Immunostimulatory Activity of TGFRt15-TGFRs in C57BL 6 Mice

TGFRt15-TGFRs is a multi-chain polypeptide (a type A multi-chain polypeptide described herein) that includes a first polypeptide that is a soluble fusion of two TGFβRII domains, human tissue factor 219 fragment and human IL-15, and the second polypeptide that is a soluble fusion of two TGFβRII domains and sushi domain of human IL-15 receptor alpha chain.

Figure 113A:
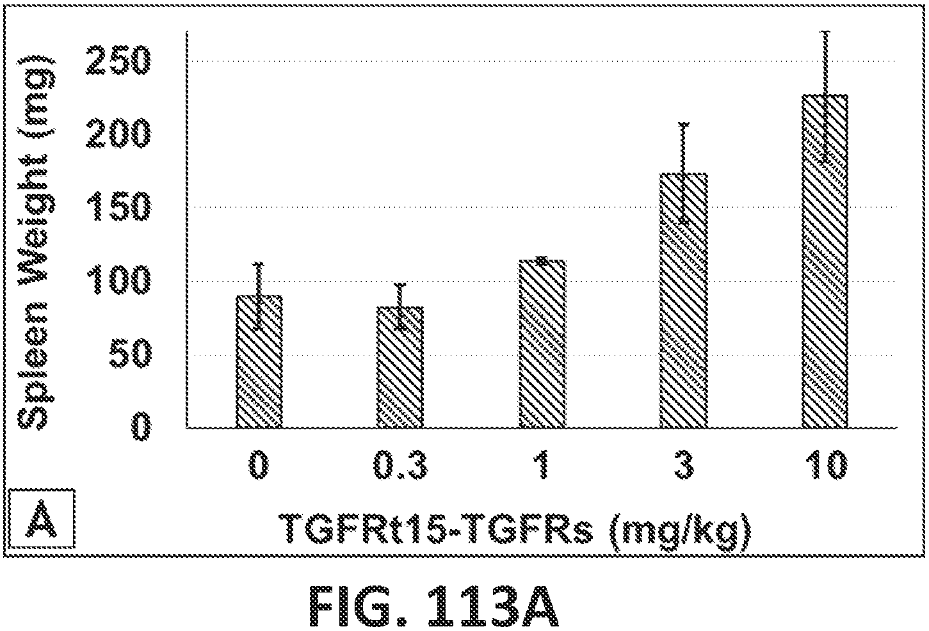
FIGS. 113A and 113B show spleen weight and the percentages of immune cell types in TGFRt15-TGFRs-treated and control-treated mice.
Figure 113B:
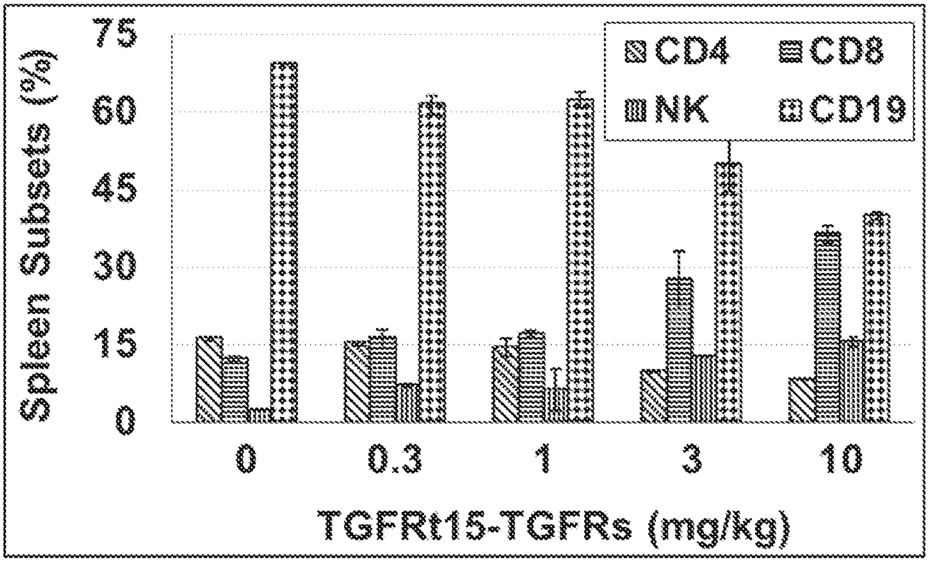

Wild type C57BL/6 mice were treated subcutaneously with either control solution or with TGFRt15-TGFRs at a dosage of 0.3 mg/kg, 1 mg/kg, 3 mg/kg, or 10 mg/kg. Four days after treatment, spleen weight and the percentages of various immune cell types present in the spleen were evaluated. As shown in FIG. 113A, the spleen weight in mice treated with TGFRt15-TGFRs increased with increasing dosage of TGFRt15-TGFRs. Moreover, the spleen weight in mice treated with 1 mg/kg, 3 mg/kg, and 10 mg/kg of TGFRt15-TGFRs were higher as compared to mice treated with the control solution, respectively. In addition, the percentages of $CD4^+$ T cells, $CD8^+$ T cells, NK cells, and $CD19^+$ B cells present in the spleen of control-treated and TGFRt15-TGFRs-treated mice were evaluated. As shown in FIG. 113B, in the spleens of mice treated with TGFRt15-TGFRs, the percentages of CD8+ T cells and NK cells both increased with increasing dosage of TGFRt15-TGFRs. Specifically, the percentages of $CD8^+$ T cells were higher in mice treated with 0.3 mg/kg, 3 mg/kg, and 10 mg/kg of TGFRt15-TGFRs compared to control-treated mice, and the percentages of NK cells were higher in mice treated with 0.3 mg/kg, 1 mg/kg, 3 mg/kg, and 10 mg/kg of TGFRt15-TGFRs compared to control-treated mice. These results demonstrate that TGFRt15-TGFRs is able to stimulate immune cells in the spleen, in particular $CD8^+$ T cells and NK cells.

The pharmacokinetics of TGFRt15-TGFRs molecules were evaluated in wild type C57BL/6 mice. The mice were treated subcutaneously with TGFRt15-TGFRs at a dosage of 3 mg/kg. The mouse blood was drained from tail vein at various time points and the serum was prepared. The TGFRt15-TGFRs concentrations in mouse serum was determined with ELISA (capture: anti-human tissue factor antibody; detection: biotinylated anti-human TGFβ receptor antibody and followed by peroxidase conjugated streptavidin and ABTS substrate). The results showed that the half-life of TGFRt15-TGFRs was 12.66 hours in C57BL/6 mice.

Figure 114A:
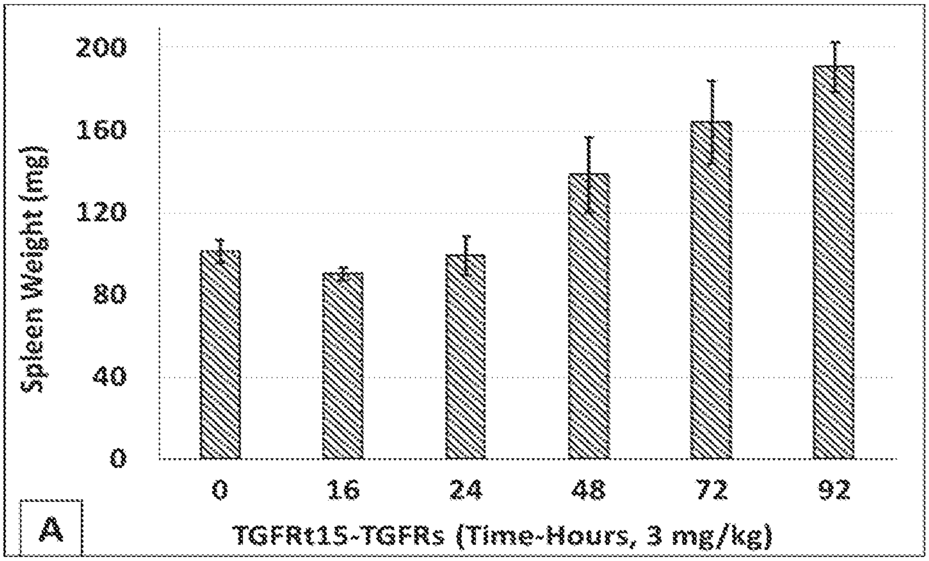
FIGS. 114A and 114B show the spleen weight and immunostimulation over 92 hours in mice treated with TGFRt15-TGFRs.
Figure 114B:
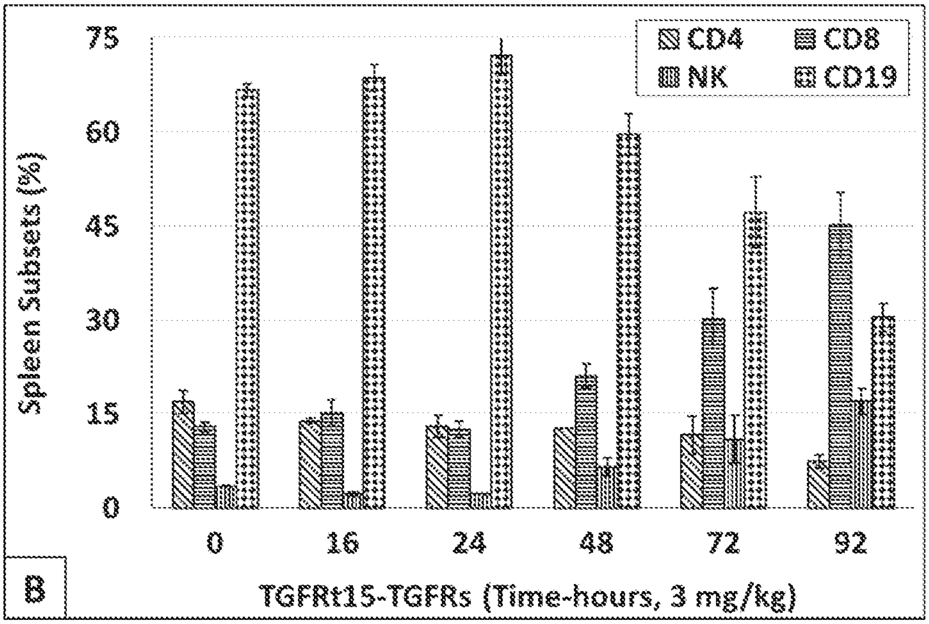

The mouse splenocytes were prepared in order to evaluate the immunostimulatory activity of TGFRt15-TGFRs over time in mice. As shown in FIG. 114A, the spleen weight in mice treated with TGFRt15-TGFRs increased 48 hours posttreatment and continued to increase over time. In addition, the percentages of $CD4^+$ T cells, $CD8^+$ T cells, NK cells, and $CD19^+$ B cells present in the spleen of control-treated and TGFRt15-TGFRs-treated mice were evaluated. As shown in FIG. 114B, in the spleens of mice treated with TGFRt15-TGFRs, the percentages of $CD8^+$ T cells and NK cells both increased at 48 hours after treatment and were higher and higher overtime after the single dose treatment. These results further demonstrate that TGFRt15-TGFRs is able to stimulate immune cells in the spleen, in particular CD8+ T cells and NK cells.

Figure 115A:
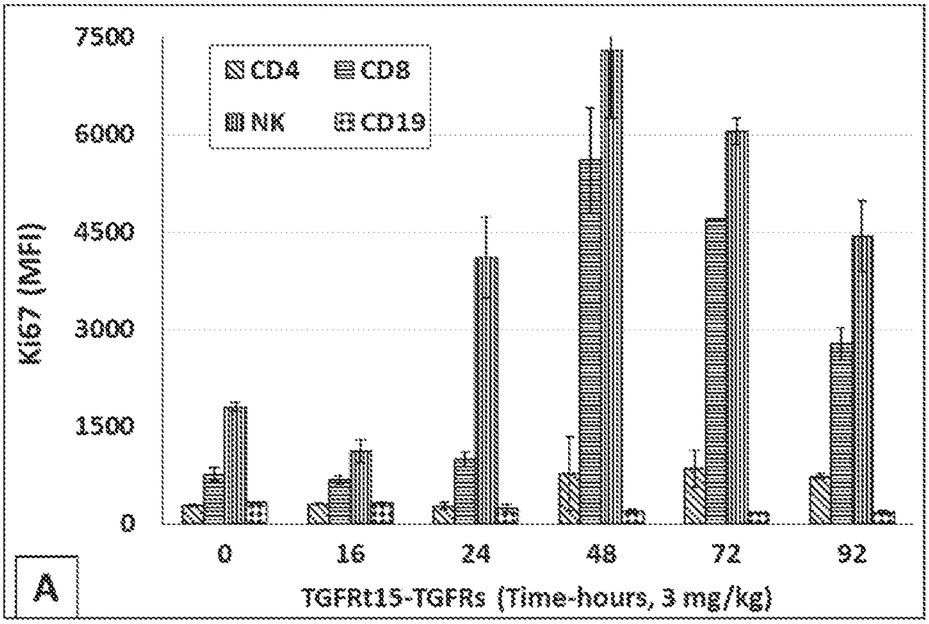
FIG. 115A shows spleen weight in mice treated with 7t15-7s as compared to PBS control.
Figure 115B:
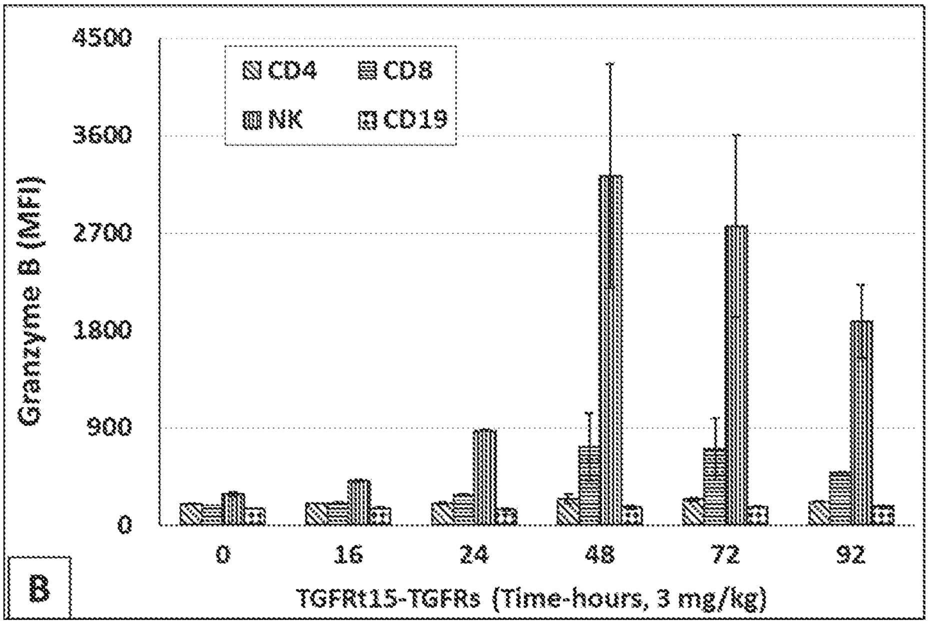
FIG. 115B shows the percentage of CD4+ T cells, CD8+ T cells, and NK cells in mice treated with 7t15-7s as compared to PBS control.

Furthermore, the dynamic proliferation of immune cells based on Ki67 expression of splenocytes and cytotoxicity potential based on granzyme B expression were evaluated in splenocytes isolated from mice following a single dose (3 mg/kg) of TGFRt15-TGFRs. As shown in FIGS. 115A and 115B, in the spleens of mice treated with TGFRt15-TGFRs, the expression of Ki67 and granzyme B by NK cells increased at 24 hours after treatment and its expression of $CD8^+$ T cells and NK cells both increased at 48 hours and later time points after the single dose treatment. These results demonstrate that TGFRt15-TGFRs not only increases the numbers of $CD8^+$ T cells and NK cells but also enhance the cytotoxicity of these cells. The single dose treatment of TGFRt15-TGFRs led CD8+ T cells and NK cells to proliferate for at least 4 days.

Figure 116:
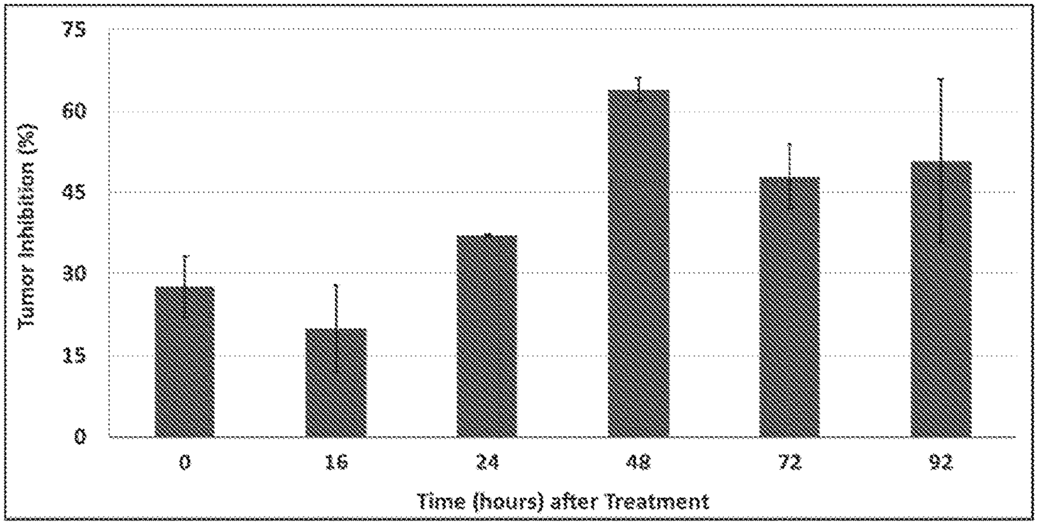
FIG. 116 shows enhancement of cytotoxicity of splenocytes by TGFRt15-TGFRs in C57BL/6 Mice.

The cytotoxicity of the splenocytes from TGFRt15-TGFRs-treated mice against tumor cells was also evaluated. Mouse Moloney leukemia cells (Yac-1) were labeled with CellTrace Violet and were used as tumor target cells. Splenocytes were prepared from TGFRt15-TGFRs (3 mg/kg)-treated mouse spleens at various time points post treatment and were used as effector cells. The target cells were mixed with effector cells at an E:T ratio=10:1 and incubated at 37° C. for 20 hours. Target cell viability was assessed by analysis of propidium iodide positive, violet-labeled Yac-1 cells using flow cytometry. Percentage of Yac-1 tumor inhibition was calculated using the formula, (1-[viable Yac-1 cell number in experimental sample]/[viable Yac-1 cell number in the sample without splenocytes])×100. As shown in FIG. 116, splenocytes from TGFRt15-TGFRs-treated mice had stronger cytotoxicity against Yac-1 cells than the control mouse splenocytes.

Tumor Size Analysis in Response to Chemotherapy and/or TGFRt15-TGFRs

Figure 117:
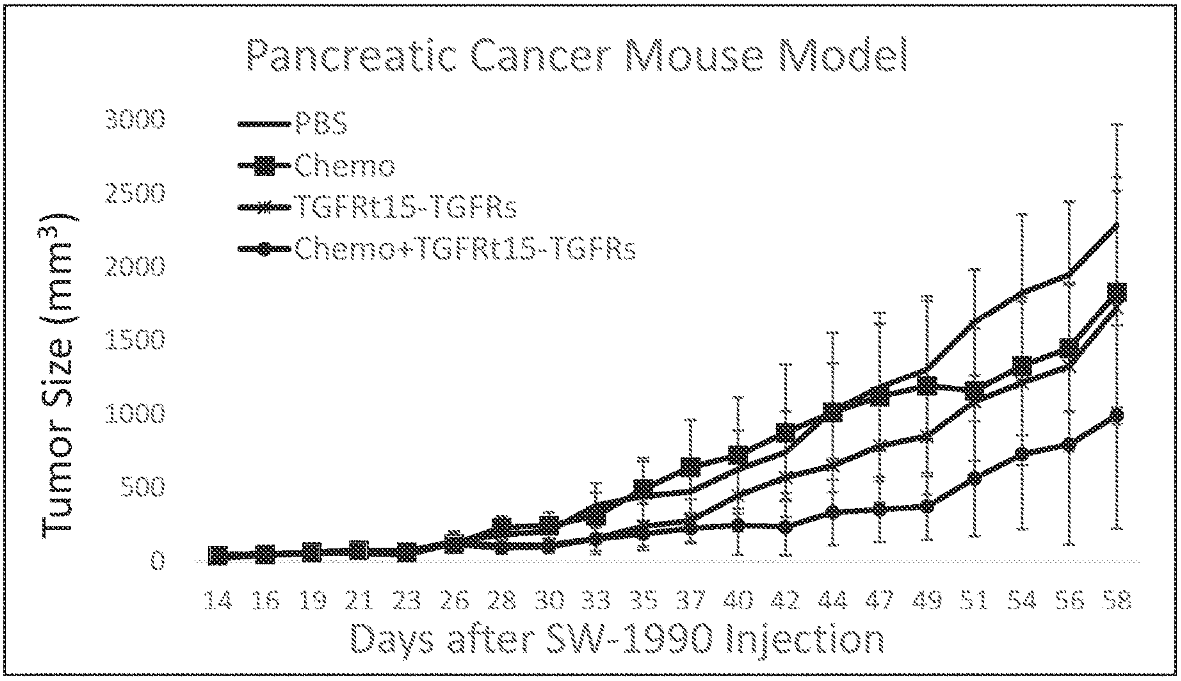
FIG. 117 shows changes in tumor size in response to PBS treatment, chemotherapy alone, TGFRt15-TGFRs alone, or chemotherapy and TGFRt15-TGFRs combination, in a pancreatic cancer mouse model.

Pancreatic cancer cells (SW1990, ATCC® CRL-2172) were subcutaneously (s.c.) injected into C57BL/6 scid mice (The Jackson Laboratory, 001913, $2\times10^6$ cells/mouse, in 100 μL HBSS) to establish the pancreatic cancer mouse model. Two weeks after tumor cell injection, chemotherapy was initiated in these mice intraperitoneally with a combination of Abraxane (Celgene, 68817-134, 5 mg/kg, i.p.) and Gemcitabine (Sigma Aldrich, G6423, 40 mg/kg, i.p.), followed by immunotherapy with TGFRt15-TGFRs (3 mg/kg, s.c.) in 2 days. The procedure above was considered one treatment cycle and was repeated for another 3 cycles (1 cycle/week). Control groups were set up as the SW1990-injected mice that received PBS, chemotherapy (Gemcitabine and Abraxane), or TGFRt15-TGFRs alone. Along with the treatment cycles, tumor size of each animal was measured and recorded every other day, until the termination of the experiment 2 months after the SW1990 cells were injected. Measurement of the tumor volumes were analyzed by group and the results indicated that the animals receiving a combination of chemotherapy and TGFRt15-TGFRs had significantly smaller tumors comparing to the PBS group, whereas neither chemotherapy nor TGFRt15-TGFRs therapy alone work as sufficiently as the combination (FIG. 117).

In Vitro Senescent B16F10 Melanoma Model

Figure 118:
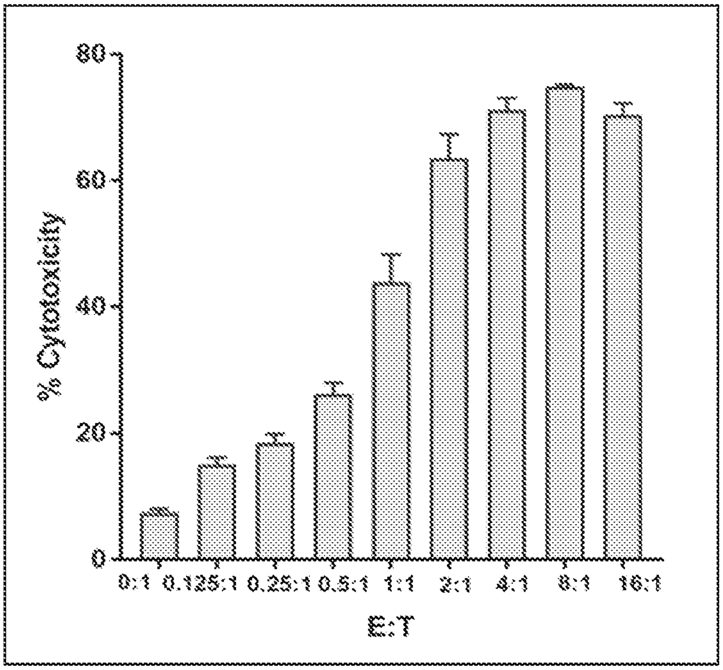
FIG. 118 shows the cytotoxicity of NK cells isolated from mice treated with TGFRt15-TGFRs.

Next, in vitro killing of senescent B16F10 melanoma cells by activated mouse NK cells was evaluated. B16F10 senescence cells (B16F10-SNC) cells were labelled with CellTrace violet and incubated for 16 hrs with different E:T ratio of in vitro 2t2-activated mouse NK cells (isolated from spleen of C57BL/6 mice injected with TGFRt15-TGFRs 10 mg/kg for 4 days). The cells were trypsinized, washed and resuspended in complete media containing propidium iodide (PI) solution. The cytotoxicity was assessed by flow cytometry (FIG. 118).

In Vivo Efficacy of TGFRt15-TGFRs in a Melanoma Mouse Model

Figure 119A:
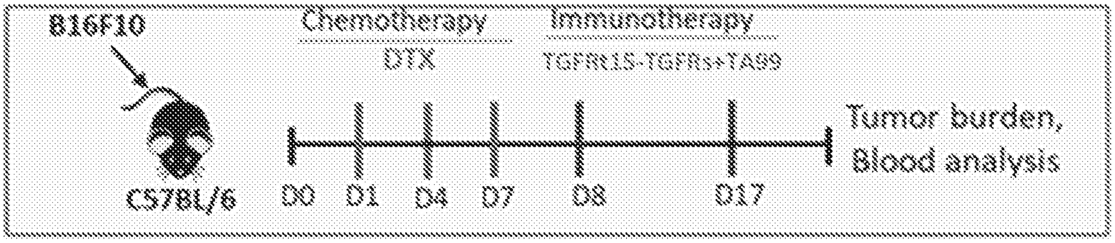
FIGS. 119A-119E show results of the in vivo efficacy of TGFRt15-TGFRs in a melanoma mouse model.
Figure 119B:
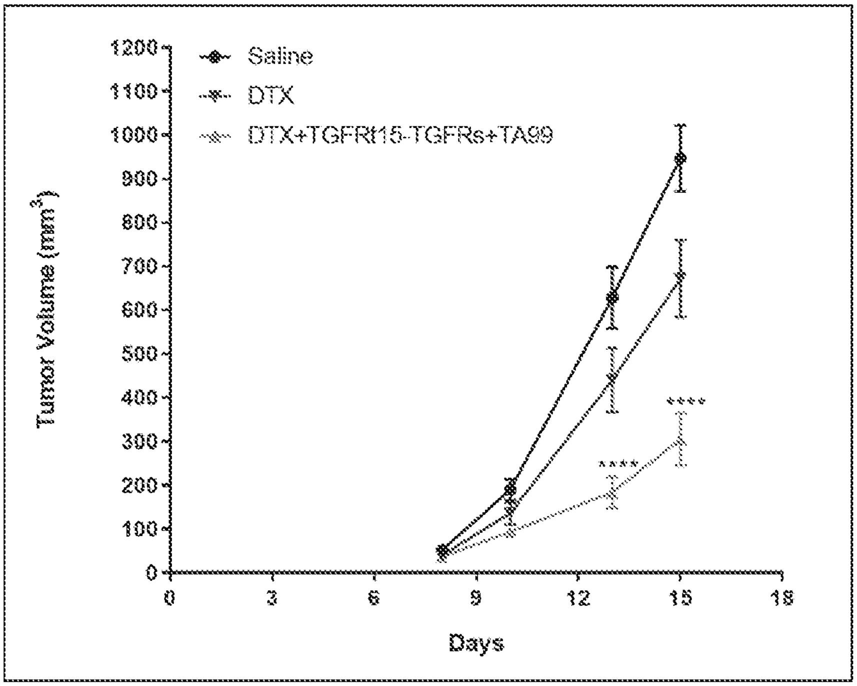
Figure 119C:
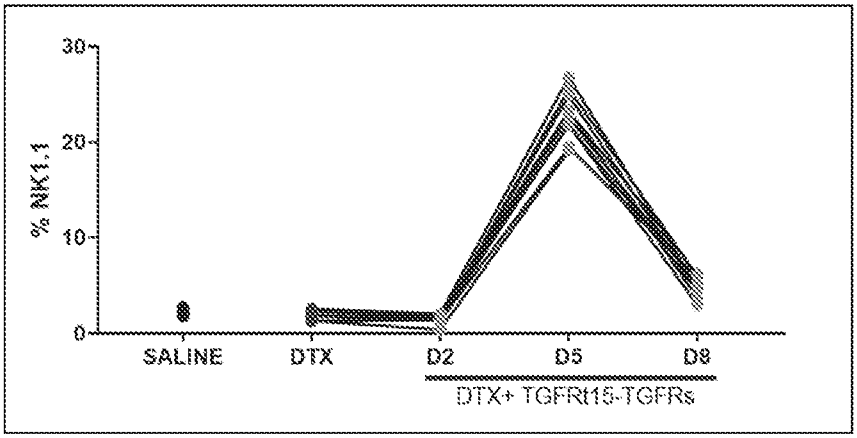
Figure 119D:
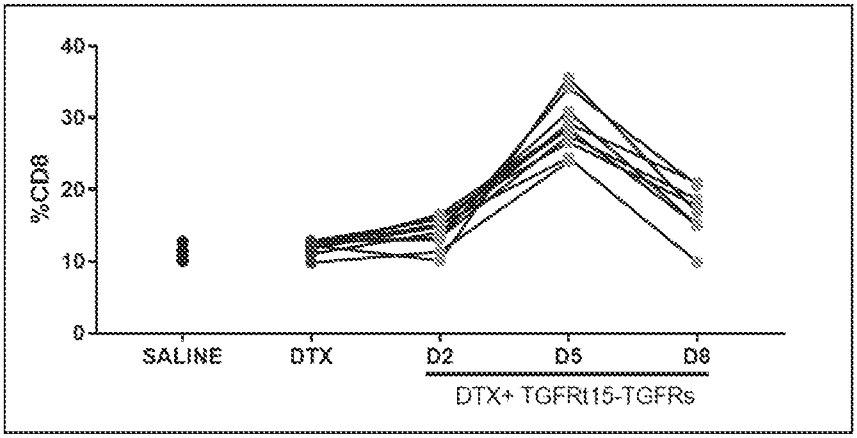
Figure 119E:
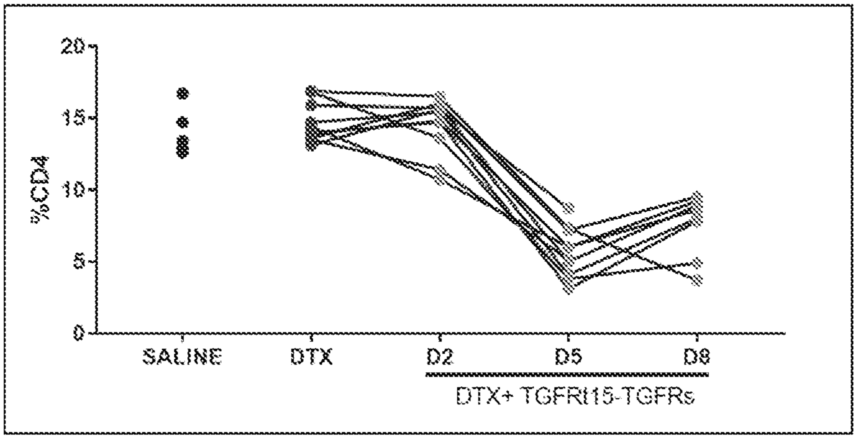

Next, the in vivo efficacy of TGFRt15-TGFRs in a melanoma mouse model was evaluated using a combination treatment containing TGFRt15-TGFRs. FIG. 119A shows a schematic of the treatment regimen. C57BL/6 mice were subcutaneously injected with $0.5\times10^6$ B16F10 melanoma cells, and treated with three doses of chemotherapy docetaxel (10 mg/kg) at day 1, day 4 and day 7 followed by treatment with a single dose of a combination immunotherapy of TGFRt15-TGFRs (3 mg/kg)+TA99 (200 μg) (anti-Trp1 antibody). As shown in FIG. 119B, tumor growth was monitored by caliper measurement, and tumor volume was calculated using the formula $V=(L\times W^2)/2$, where L is the largest tumor diameter and W is the perpendicular tumor diameter (N=10, ****p<0.001, Multiple t test analyses). Next, peripheral blood analysis of immune cell subsets in B16F10 tumor model was carried out. Blood was drawn from submandibular vein pre-immunotherapy and post-immunotherapy treatment at days 2, 5 and 8. The RBCs were lysed in ACK lysis buffer and the lymphocytes were washed and stained with fluorescently labelled anti-NK1.1, anti-CD8 and anti-CD4 antibodies. The cells were analyzed by Flow Cytometry (Celesta-BD Bioscience).

Example 79: 7t15-21s137L (Long Version) Fusion Protein Creation and Characterization A fusion protein complex was generated comprising of IL-21/IL-15RαSu/CD137L and IL-7/TF/IL-15 fusion proteins. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of the 7t15 construct (including signal peptide sequence) is as

```
(Signal peptide)
ATGAAGTGGGTGACCTTCATCAGCCTGCTGTTCCTGTTCTCCAGCGCCT

ACTCC

(Human IL7)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT

(Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG
```

-continued (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

The amino acid sequence of 7t15 fusion protein (including the leader sequence) is as follows:

(Signal peptide)
MKWVTFISLLFLFSSAYS (Human IL7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

The nucleic acid and protein sequences of the 21s137L are shown below. The nucleic acid sequence of the 21s137L construct (including signal peptide sequence) is as follows:

(Signal peptide)
ATGAAGTGGGTGACCTTCATCAGCCTGCTGTTCCTGTTCTCCAGCGCCT

ACTCC (Human IL-21)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC

-continued (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGAC

CTGCGGCAGGGCATGTTTGCGCAGCTGGTGGCCCAAAATGTTCTGCTG

ATCGATGGGCCCCTGAGCTGGTACAGTGACCCAGGCCTGGCAGGCGTG

TCCCTGACGGGGGGCCTGAGCTACAAAGAGGACACGAAGGAGCTGGTG

GTGGCCAAGGCTGGAGTCTACTATGTCTTCTTTCAACTAGAGCTGCGG

CGCGTGGTGGCCGGCGAGGGCTCAGGCTCCGTTTCACTTGCGCTGCAC

CTGCAGCCACTGCGCTCTGCTGCTGGGGCCGCCGCCCTGGCTTTGACC

GTGGACCTGCCACCCGCCTCCTCCGAGGCTCGGAACTCGGCCTTCGGT

TTCCAGGGCCGCTTGCTGCACCTGAGTGCCGGCCAGCGCCTGGGCGTC

CATCTTCACACTGAGGCCAGGGCACGCCATGCCTGGCAGCTTACCCAG

GGCGCCACAGTCTTGGGACTCTTCCGGGTGACCCCCGAAATCCCAGCC

GGACTCCCTTCACCGAGGTCGGAA

The amino acid sequence of 21s137L fusion protein (including the leader sequence) is as follows:

(Signal peptide)
MKWVTFISLLFLFSSAYS (Human IL-21)
QGQDRHMIRMRQLIDIVDQLKNYVNDLVPEFLPAPEDVETNCEWSAFS

CFQKAQLKSANTGNNERIINVSIKKLKRKPPSTNAGRRQKHRLTCPSC

DSYEKKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLN

KATNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGV

SLTGGLSYKEDTKELVVAKAGVYYVFFQLELRRVVAGEGSGSVSLALH

LQPLRSAAGAAALALTVDLPPASSEARNSAFGFQGRLLHLSAGQRLGV

HLHTEARARHAWQLTQGATVLGLFRVTPEIPAGLPSPRSE

In some cases, the leader peptide is cleaved from the intact polypeptide to generate the mature form that may be soluble or secreted.

The IL-21/IL-15RαSu/CD137L and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. Hum Gene Ther 2005; 16:457-72), and the expression vectors were transfected into CHO-K1 cells. Co-expression of the two constructs in CHO-K1 cells allowed for formation and secretion of the soluble IL-7/TF/IL-15: IL-21/IL-15RαSu/CD137L protein complex (referred to as 7t15-21s137L), which can be purified by anti-TF antibody affinity and other chromatography methods.

Figure 120:
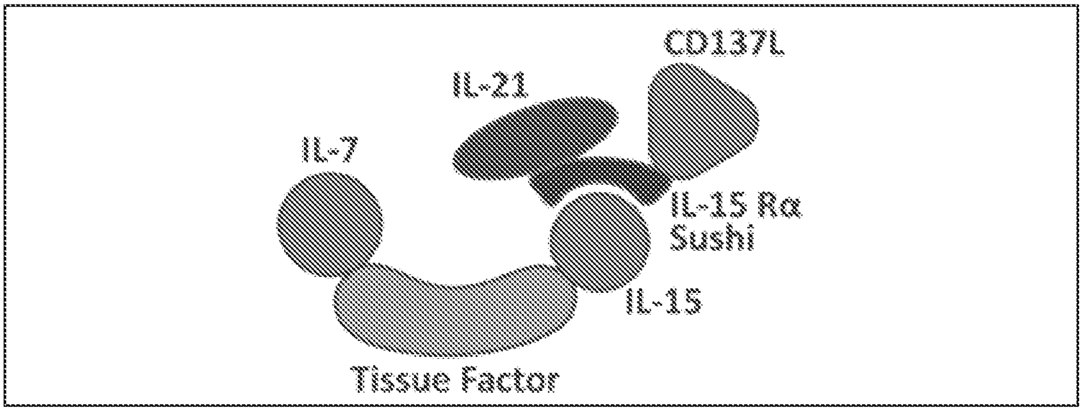
FIG. 120 shows a schematic of the 7t15-21s137L (long version) construct.
Figure 121:
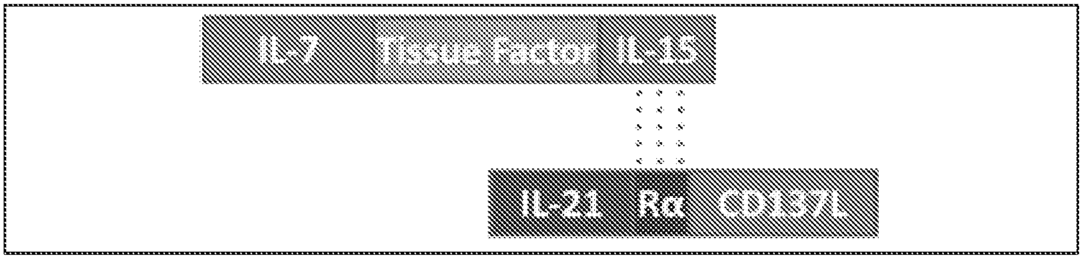
FIG. 121 shows an additional schematic of the 7t15-21s137L (long version) construct.
Figure 122:
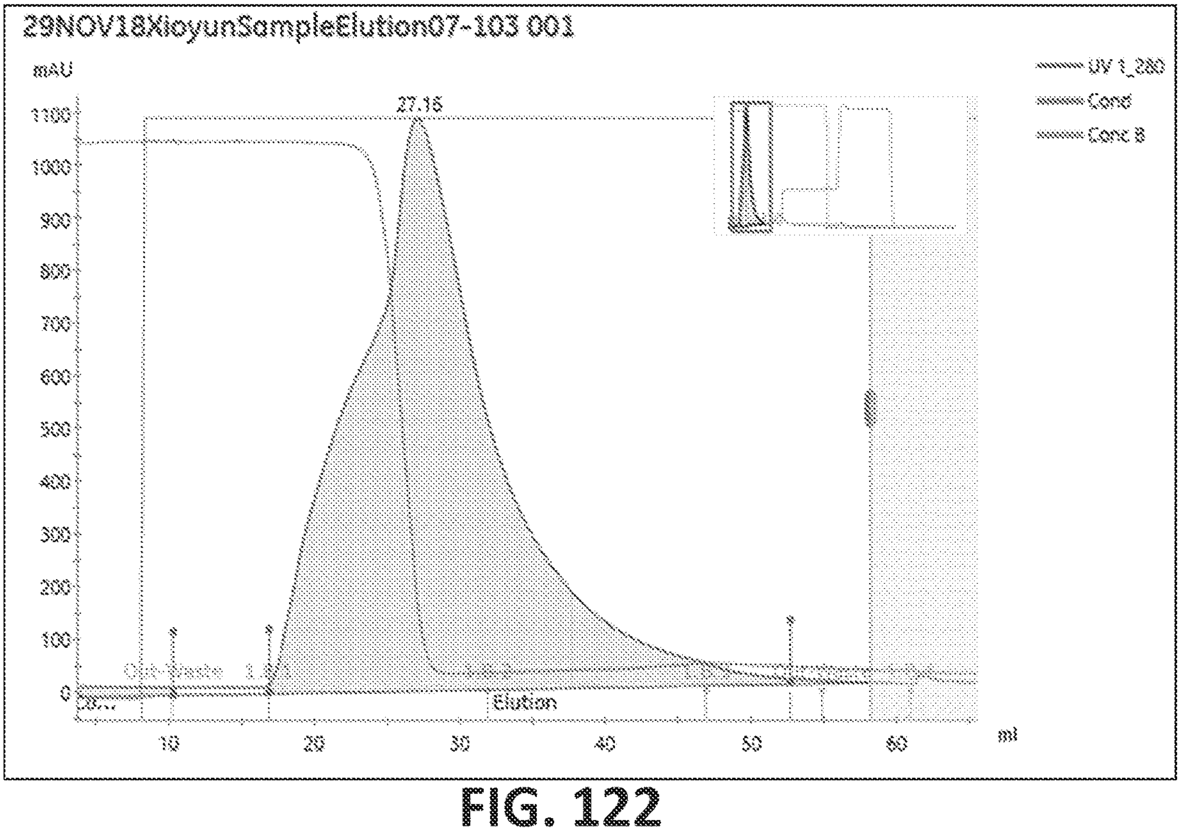
Figure 123:
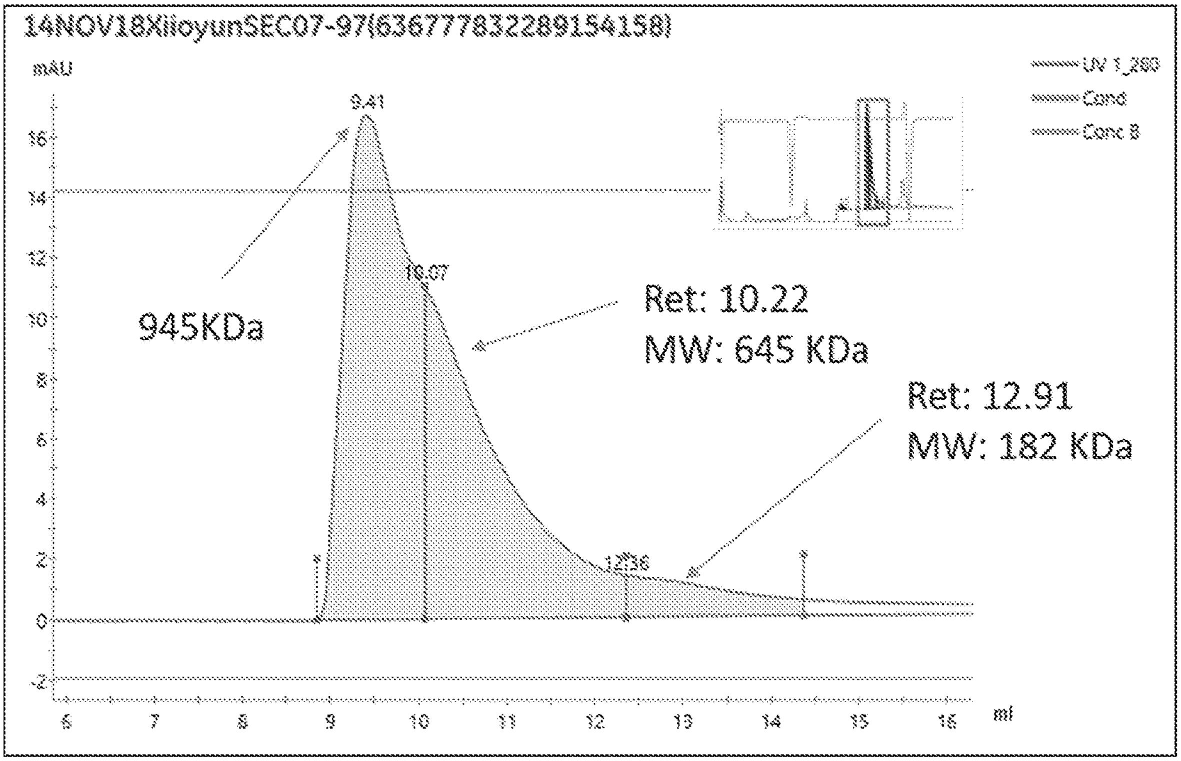
Figure 124:
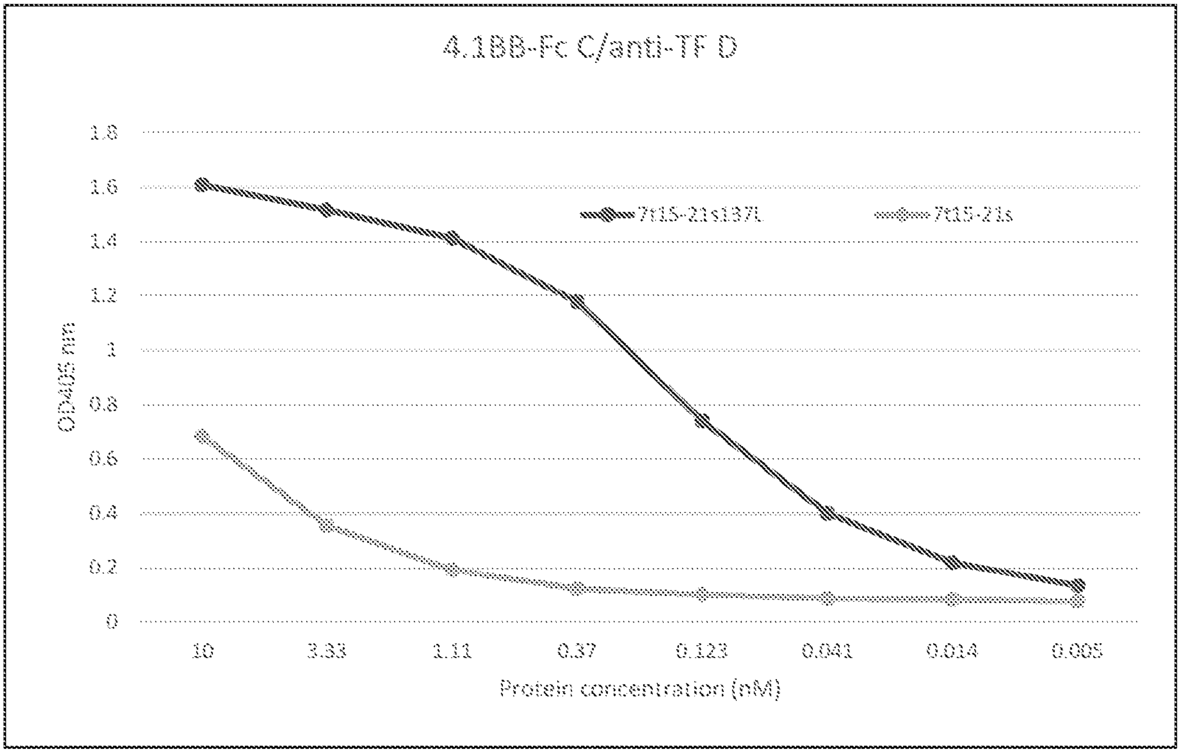

Purification Elution Chromatograph of 7t15-21s137L Using Anti-TF Antibody Affinity Column 7t15-21s137L (FIGS. 120 and 121) harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 122, the anti-TF antibody affinity column bound to 7t15-21s137L which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min. FIG. 123 shows the analytical SEC profile of 7t15-21s137L.

Example 80: 7t15-21s137L (Short Version) Fusion Protein Generation and Characterization A fusion protein complex was generated comprising of IL-21/IL-15RαSu/CD137L and IL-7/TF/IL-15 fusion proteins. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of 7t15 construct (including signal peptide sequence) is as

```
(Signal peptide)
ATGAAGTGGGTGACCTTCATCAGCCTGCTGTTCCTGTTCTCCAGCGCC

TACTCC

(Human IL7)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT
```

-continued

```
(Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG

(Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC
```

The amino acid sequence of 7t15 fusion protein (including the leader sequence) is as follows:

```
(Signal peptide)
MKWVTFISLLFLFSSAYS

(Human IL7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH

(Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE

(Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS
```

The nucleic acid and protein sequences of the 21s137L (short version) are shown below. The nucleic acid sequence of 21s137L (short version) construct (including signal peptide sequence) is as follows:

```
(Signal peptide)
ATGAAGTGGGTGACCTTCATCAGCCTGCTGTTCCTGTTCTCCAGCGCCT

ACTCC

(Human IL-21)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC

(Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG

((G4S)3 linker)
GGCGGTGGAGGATCCGGAGGAGGTGGCTCCGGCGGCGGAGGATCT

(Human CD137 Ligand short version)
GATCCCGCCGGCCTCTTGGACCTGCGGCAGGGCATGTTTGCGCAGCTGG

TGGCCCAAAATGTTCTGCTGATCGATGGGCCCCTGAGCTGGTACAGTGA

CCCAGGCCTGGCAGGCGTGTCCCTGACGGGGGGCCTGAGCTACAAAGAG

GACACGAAGGAGCTGGTGGTGGCCAAGGCTGGAGTCTACTATGTCTTCT

TTCAACTAGAGCTGCGGCGCGTGGTGGCCGGCGAGGGCTCAGGCTCCGT

TTCACTTGCGCTGCACCTGCAGCCACTGCGCTCTGCTGCTGGGGCCGCC

GCCCTGGCTTTGACCGTGGACCTGCCACCCGCCTCCTCCGAGGCTCGGA

ACTCGGCCTTCGGTTTCCAGGGCCGCTTGCTGCACCTGAGTGCCGGCCA

GCGCCTGGGCGTCCATCTTCACACTGAGGCCAGGGCACGCCATGCCTGG

CAGCTTACCCAGGGCGCCACAGTCTTGGGACTCTTCCGGGTGACCCCCG

AAATC
```

The amino acid sequence of the 21s137L (short version) construct (including signal peptide sequence) is as follows:

```
(Signal peptide)
MKWVTFISLLFLFSSAYS

(Human IL-21)
QGQDRHMIRMRQLIDIVDQLKNYVNDLVPEFLPAPEDVETNCEWSAFSC

FQKAQLKSANTGNNERIINVSIKKLKRKPPSTNAGRRQKHRLTCPSCDS

YEKKPPKEFLERFKSLLQKMIHQHLSSRTHGSEDS
```

-continued

```
(Human IL-15R α sushi domain)
ITCPPPMSVEHADIWVKSYSLYSRERYICNSGFKRKAGTSSLTECVLNK

ATNVAHWTTPSLKCIR

((G4S)3 linker)
GGGGSGGGGSGGGGS

(Human CD137 Ligand short version)
DPAGLLDLRQGMFAQLVAQNVLLIDGPLSWYSDPGLAGVSLTGGLSYKE

DTKELVVAKAGVYYVFFQLELRRVVAGEGSGSVSLALHLQPLRSAAGAA

ALALTVDLPPASSEARNSAFGFQGRLLHLSAGQRLGVHLHTEARARHAW

QLTQGATVLGLFRVTPEI
```

The IL-21/IL-15RαSu/CD137L (short version) and IL-7/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble IL-7/TF/IL-15: IL-21/IL-15RαSu/CD137L protein complex (referred to as 7t15-21s137L (short version)), which can be purified by anti-TF antibody affinity and other chromatography methods.

Binding of 7t15-21s137L (Short Version) to CD137 (4.1BB)

On day 1, a 96-well plate was coated with 100 μL (2.5 μg/mL) of GAH IgG Fe (G-102-C, R&D Systems) in R5 (coating buffer) or R5 only and incubated at 4° C., overnight. On day 2, the plates were washed three times and blocked with 300 μL of 1% BSA in PBS at 37° C. for 2 hrs. 10 ng/mL of 4.1BB/Fc (838-4B, R&D Systems) was added at 100 μL/well and incubated for 2 hrs at RT. After three washes, the 7t15-21s137L or 7t15-21s serially diluted at a 1:3 ratio (starting at 10 nM), and incubated at 4° C. overnight. On day 3, following 3 washes, 300 ng/mL of biotinylated-anti-hTF antibody (BAF2339, R&D Systems) was added at 100 μL per well and incubated at RT for 2 hrs. The plate was then washed three times and incubated with 0.25 μg/mL of HRP-SA (Jackson ImmuneResearch) at 100 μL per well for 30 min, followed by 3 washes and incubation with 100 μL of ABTS for 2 mins at RT. Absorbance was read at 405 nm. As shown in FIG. 124, 7t15-21s137L (short version) showed significant interaction with 4.1BB/Fc (blue line) as compared to 7t15-21s.

Detection of IL-15, IL-21, and IL-7 in 7t15-21s137L (Short Version) with ELISA

A 96-well plate was coated with 100 μL (8 μg/mL) of anti-TF antibody in R5 (coating buffer) and incubated at RT for 2 hrs. The plates were washed 3 times and blocked with 100 μL of 1% BSA in PBS. 7t15-21s137L (short version), serially diluted at a 1:3 ratio was added, and incubated at RT for 60 min. After three washes, 50 ng/mL of biotinylated-anti-IL15 antibody (BAM247, R&D Systems), 500 ng/mL of biotinylated-anti-IL21 antibody (13-7218-81, R&D Systems), or 500 ng/mL of biotinylated-anti-IL7 antibody (506602, R&D Systems) was added to the wells and incubated at RT for 60 min. After three washes and incubation with 0.25 μg/mL of RP-SA (Jackson ImmunoResearch) at 100 μL per well was carried out for 30 min at RT, followed by four washes and incubation with 100 μL of ABTS for 2 mins at RT. Absorbance was read at 405 nm. As shown in FIGS. 125A-125C, the IL-15, IL-21, and IL-7 domains in 7t15-21s137L (short version) were detected by the respective antibodies.

The IL-15 in 7t15-1s137L (Short Version) Promotes IL2Rαβγ Containing CTLL2 Cell Proliferation To evaluate the IL-15 activity of 7t15-21s137L (short version), 7t15-21s137L (short version) was compared with recombinant TL15 in promoting proliferation of IL2Rαβγ expressing CTLL2 cells. IL-15-dependent CTLL2 cells were washed 5 times with IMDM-10% FBS and seeded to the wells at $2\times10^4$ cells/well. Serially diluted 7t15-21s137L (short version) or IL-15 were added to the cells (FIG. 126). Cells were incubated in a $CO_2$ incubator at 37° C. for 3 days. Cell proliferation was detected by adding 10 μL of WST1 to each well on day 3 and incubated for an additional 3 hours in a $CO_2$ incubator at 37° C. The amount of formazan dye produced was analyzed by measuring the absorbance at 450 nm. As shown in FIG. 126, 7t15-21s137L (short version) and IL-15 promoted CTLL2 cell proliferation. The $EC_{50}$ of 7t15-21s137L (short version) and IL-15 was 55.91 pM and 6.22 pM. respectively.

The IL-21 in 7t15-1s137L (Short Version) Promotes IL21R Containing B9 Cell Proliferation To evaluate the IL-21 activity of 7t15-21s137L (short version), 7t15-21s137L (short version) was compared with recombinant IL-21 in promoting proliferation of IL-21R expressing B9 cells. IL-21R containing B9 cells were washed 5 times with RPMI-10% FBS and seeded to the wells at $1\times10^4$ cells/well. Serially diluted 7t15-21s137L (short version) or IL-21 were added to the cells (FIG. 127). Cells were incubated in a $CO_2$ incubator at 37° C. for 5 days. Cell proliferation was detected by adding 10 μL of WST1 to each well on day 5 and incubated for an additional 4 hours in a $CO_2$ incubator at 37° C. The amount of formazan dye produced was analyzed by measuring the absorbance at 450 nm. As shown in FIG. 127, 7t15-21s137L (short version) and IL-21 promoted B9 cell proliferation. The $EC_{50}$ of 7t15-21s137L (short version) and IL-21 was 104.1 nM and 72.55 nM. respectively.

Example 86: 7t15-TGFRs Fusion Protein Generation and Characterization

A fusion protein complex was generated comprising of TGFβ Receptor II/IL-15RαSu and IL-7/TF/IL-15 fusion proteins (FIGS. 128 and 129). The human TGFβ Receptor II (Ile24-Asp159), tissue factor 219, IL-15, and IL-7 sequences were obtained from the UniProt website and DNA for these sequences was synthesized by Genewiz. Specifically, a construct was made linking the IL-7 sequence to the N-terminus coding region of tissue factor 219 followed by the N-terminus coding region of IL-15. The nucleic acid and protein sequences of a construct comprising IL-7 linked to the N-terminus of tissue factor 219 following with the N-terminus of IL-15 are shown below.

The nucleic acid sequence of the 7t15 construct (including signal peptide sequence) is as follows:

```
(Signal peptide)
ATGAAGTGGGTGACCTTCATCAGCCTGCTGTTCCTGTTCTCCAGCGCCT

ACTCC
```

-continued

```
(Human IL7)
GATTGCGACATCGAGGGCAAGGACGGCAAGCAGTACGAGAGCGTGCTGA

TGGTGTCCATCGACCAGCTGCTGGACAGCATGAAGGAGATCGGCTCCAA

CTGCCTCAACAACGAGTTCAACTTCTTCAAGCGGCACATCTGCGACGCC

AACAAGGAGGGCATGTTCCTGTTCAGGGCCGCCAGGAAACTGCGGCAGT

TCCTGAAGATGAACTCCACCGGCGACTTCGACCTGCACCTGCTGAAGGT

GTCCGAGGGCACCACCATCCTGCTGAACTGCACCGGACAGGTGAAGGGC

CGGAAACCTGCTGCTCTGGGAGAGGCCCAACCCACCAAGAGCCTGGAGG

AGAACAAGTCCCTGAAGGAGCAGAAGAAGCTGAACGACCTGTGCTTCCT

GAAGAGGCTGCTGCAGGAGATCAAGACCTGCTGGAACAAGATCCTGATG

GGCACCAAGGAGCAT

(Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG

(Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC
```

The amino acid sequence of 7t15 fusion protein (including the leader sequence) is as follows:

```
(Signal peptide)
MKWVTFISLLFLFSSAYS

(Human IL7)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG
```

-continued

RKPAALGEAQPTKSLEENKSLKEQKKLNDLCFLKRLLQEIKTCWNKILM

GTKEH (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

Constructs were also made by attaching two TGFβ Receptor II directly to the IL-15RαSu chain which was synthesized by Genewiz. The nucleic acid and protein sequences of a construct comprising the TGFβ Receptor II linked to the N-terminus of IL-15RαSu are shown below.

The nucleic acid sequence of the TGFRs construct (including signal peptide sequence) is as follows:

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

-continued

CAAGAGGAAGGCCGGCACCAGCAGCCTCACCGAGTGCGTGCTGAATAAG

GCTACCAACGTGGCTCACTGGACAACACCCTCTTTAAAGTGCATCCGG

The amino acid sequence of TGFRs fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVLNK

ATNVAHWTTPSLKCIR

Effect of 7t15-TGFRs on TGFβ Activity in HEK-Blue TGFβ Cells

To evaluate the activity of TGFβR in 7t15-TGFRs, the effect of 7t15-TGFRs on the activity of TGFβ1 in HEK-Blue TGFβ cells was analyzed. HEK-Blue TGFβ cells (Invivogen) were washed twice with pre-warmed PBS and resuspended in the testing medium (DMEM, 10% heat-inactivated FCS, 1× glutamine, 1× anti-anti, and 2× glutamine) at $5\times10^5$ cells/mL. In a flat-bottom 96-well plate, 50 μL cells were added to each well ($2.5\times10^4$ cells/well) and followed with 50 μL 0.1 nM TGFβ1 (R&D systems). 7t15-TGFRs or TGFR-Fc (R&D Systems) prepared at al: 3 serial dilution was then added to the plate to reach a total volume of 200 μL. After 24 hrs of incubation at 37° C., 40 μL of induced HEK-Blue TGFβ cell supernatant was added to 160 μL pre-warmed QUANTI-Blue (Invivogen) in a flat-bottom 96-well plate, and incubated at 37° C. for 1-3 hrs. The OD values were then determined using a plate reader (Multiscan Sky) at 620-655 nM. See, FIG. 130. The IC50 of each protein sample was calculated with GraphPad Prism 7.04. The IC50 of 7t15-TGFRs and TGFR-Fc were 1142 pM and 558.6 pM respectively. These results showed that the TGFβR in 7t15-TGFRs was able to block the activity of TGFβ1 in HEK-Blue TGFβ cells.

Detection of IL-15, TGFβRII, and IL-7 in 7t15-TGFRs with ELISA

A 96-well plate was coated with 100 μL (8 μg/mL) of anti-TF antibody in R5 (coating buffer) and incubated at room temperature (RT) for 2 hrs. The plates were washed three times and blocked with 100 μL of 1% BSA in PBS. Serial dilution of 7t15-TGFRs (1:3 ratio) was added, and incubated at RT for 60 mins. After 3 washes, 50 ng/mL of biotinylated-anti-IL-15 antibody (BAM247, R&D Systems), 200 ng/mL of biotinylated-anti-TGFbRII antibody (BAF241, R&D Systems), or 500 ng/mL of biotinylated-anti-IL-7 antibody (506602, R&D Systems) was added and incubated at RT for 60 min. Following three washes, incubation with 0.25 μg/mL of HRP-SA (Jackson ImmunoResearch) at 100 μL per well was carried out for 30 min at RT, followed by 4 washes and incubation with 100 μL of ABTS for 2 mins at RT. Absorbance was read at 405 nm. As shown in FIGS. 131A-131C, the IL-15, TGFR, and IL-7 in 7t15-TGFRs were detected by the respective antibodies.

The IL-15 in 7t15-TGFRs Promotes IL-2Rβ and Common γ Chain Containing 32Dβ Cell Proliferation To evaluate the activity of IL-15 in 7t15-TGFRs, 7t15-TGFRs was compared to recombinant IL-15 using 32Dβ cells that express IL2β and common γ chain, and evaluating their effects on promoting cell proliferation. IL-15 dependent 32Dβ cells were washed 5 times with IMDM-10% FBS and seeded in the wells at $2\times10^4$ cells/well. Serially-diluted 7t15-TGFRs or IL-15 were added to the cells (FIG. 132). Cells were incubated in a $CO_2$ incubator at 37° C. for 3 days. Cell proliferation was detected by adding 10 μL of WST1 to each well on day 3 and incubating for an additional 3 hours in a $CO_2$ incubator at 37° C. The amount of formazan dye produced was analyzed by measuring the absorbance at 450 nm. As shown in FIG. 132, 7*t*15-TGFRs and IL-15 promoted 32Dβ cell proliferation, with the $EC_{50}$ of 7t15-TGFRs and IL-15 being 126 nM and 16.63 pM, respectively.

Purification Elution Chromatograph of 7t15-TGFRs Using Anti-TF Antibody Affinity Column 7t15-TGFRs harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 133, the anti-TF antibody affinity column can bind 7t15-TGFRs which contains TF as a fusion partner of 7t15-TGFRs. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE Analysis of 7t15-TGFRs

To determine the purity and molecular weight of the protein, 7t15-TGFRs protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water. To verify that the 7t15-TGFRs protein undergoes glycosylation after translation in CHO cells, a deglycosylation experiment was conducted using the Protein Deglycosylation Mix II kit from New England Biolabs and the manufacturer's instructions. FIG. 134 shows reduced SDS-PAGE analysis of the sample in non-deglycosylated (lane 1 in red outline) and deglycosylated (lane 2 in yellow outline) state. These results showed that the protein is glycosylated when it is expressed in CHO cells. After deglycosylation, the purified sample showed expected molecular weights (55 kDa and 39 kDa) in reduced SDS gel. Lane M was loaded with 10 ul of SeeBlue Plus2 Prestained Standard.

Characterization of 7t15-TGFRs

7t15-TGFRs is a multi-chain polypeptide (a type A multi-chain polypeptide described herein) that includes the first polypeptide that is a soluble fusion of human IL-7, human tissue factor 219 fragment and human IL-15 (7t15), and the second polypeptide that is a soluble fusion of single chain two TGFβRII domains and sushi domain of human IL-15 receptor alpha chain (TGFRs).

CHO cells were co-transfected with 7t15 and TGFRs vectors. The 7t15-TGFRs complex was purified from the transfected CHO cell culture supernatant. The IL-7, IL-15, TGFβ receptor and tissue factor (TF) components were demonstrated in the complex by ELISA as shown in FIG. 135. A humanized anti-TF monoclonal antibody was used as the capture antibody to determine TF in 7t15-TGFRs, and biotinylated antibodies against human IL-15 antibody (R&D systems), human IL-7 (Biolegend), anti-TGFβ receptor (R&D Systems) were used as the detection antibodies to respectively determine IL-7, IL-15 and TGFβ receptor in 7t15-TGFRs. Peroxidase conjugated streptavidin (Jackson ImmunoResearch Lab) and ABTS substrate (Surmodics IVD, Inc.) were then used to detect the bound biotinylated antibodies. The results were analyzed by ELISA (FIG. 135).

In Vivo Characterization of 7t15-TGFRs in C57BL 6 Mice

To determine the immunostimulatory activity of 7t15-TGFRs in vivo, C57BL/6 mice were subcutaneously treated with control solution (PBS) or 7t15-TGFRs at 0.3, 1, 3 and 10 mg/kg. The treated mice were euthanized. The mouse spleens were collected and weighed day 4 post treatment. Single splenocyte suspensions were prepared and stained with fluorochrome-conjugated anti-CD4, anti-CD8, and anti-NK1.1 antibodies and the percentage of $CD4^+$ T cells, CD8+ T cells, and NK cells was analyzed by flow cytometry. The results showed that 7t15-TGFRs was effective at expanding splenocytes based on spleen weight (FIG. 136A), especially at 1-10 mg/kg. The percentages of $CD8^+$ T cells and NK cells were higher compared to control-treated mice (FIG. 136B) at all doses tested.

CD44 Expression of $CD4^+$ and $CD8^+$ T Cells

It has been known that IL-15 induces CD44 expression on T cells and development of memory T cells. CD44 expression of $CD4^+$ and $CD8^+$ T cells in the 7t15-TGFRs treated mice were assessed. C57BL/6 mice were subcutaneously treated with 7t15-TGFRs. The splenocytes were stained with fluorochrome-conjugated anti-CD4, anti-CD8 and anti-CD44 monoclonal antibodies for immunocyte subsets. The percentages of $CD4^+CD44^{high}$ T cells of total $CD4^+$ T cells and $CD8^+CD44^{high}$ T cells of total $CD8^+$ T cells were analyzed by flow cytometry. As shown in FIGS. 137A and 137B, 7*t*15-TGFRs significantly activated $CD4^+$ and $CD8^+$ T cells to differentiate into memory T cells.

Furthermore, the dynamic proliferation of immune cells based on Ki67 expression of splenocytes and cytotoxicity potential based on granzyme B expression of the splenocytes induced by 7t15-TGFRs after the single dose treatment of mouse were also evaluated. C57BL/6 mice were subcutaneously treated with 7t15-TGFRs at 3 mg/kg. The treated mice were euthanized and the splenocytes were prepared. The prepared splenocytes were stained with fluorochrome-conjugated anti-CD4, anti-CD8, and anti-NK1.1 (NK) antibodies for immunocyte subsets and then intracellularly stained with anti-Ki67 antibody for cell proliferation and anti-granzyme B antibody for cytotoxic marker. The mean fluorescent intensity (MFI) of Ki67 and granzyme B of corresponding immunocyte subsets was analyzed by flow cytometry. As shown in FIGS. 138A and 138B, in the spleens of mice treated with 7t15-TGFRs, the expression of Ki67 and granzyme B by $CD8^+$ T cells and NK cells increased compared with PBS control treatment. These results demonstrate that 7t15-TGFRs is not only to increase numbers of $CD8^+$ T cells and NK cells but also enhance potential cytotoxicity of these cells.

Additionally, cytotoxicity of the mouse splenocytes against tumor cells was also evaluated. Mouse Yac-1 cells were labeled with CellTrace Violet and used as tumor target cells. The splenocytes were prepared from 7t15-TGFRs-treated mice and used as effector cells. The target cells were mixed with effector cells at E:T ratio=10:1 in RPMI-10 medium with or without 7t15-TGFRs at 100 nM and incubated at 37° C. for 20 hours. Target Yac-1 cell inhibition was assessed by analysis of viable violet-labeled Yac-1 cells using flow cytometry. Percentage of Yac-1 inhibition was calculated using a formula, (1-viable Yac-1 cell number in experimental sample/viable Yac-1 cell number in the sample without splenocytes)×100. As shown in FIG. 139, 7*t*15-TGFRs-treated mouse splenocytes had stronger cytotoxicity against Yac-1 cells than the control mouse splenocytes and addition of 7t15-TGFRs during cytotoxic assay further enhanced cytotoxicity of splenocytes against Yac-1 target cells.

Example 81: TGFRt15-21s137L Fusion Protein Generation and Characterization

A fusion protein complex was generated comprising IL-21/IL-15RαSu/CD137L and TGFβ Receptor II/TF/IL-15 fusion proteins. The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGCCT

ACTCC

(Human TGFβ Receptor II fragments)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG
```

-continued

```
CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC

(Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG

(Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC
```

The amino acid sequence of TGFRt15 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD

(Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF
```

-continued

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

The nucleic acid and protein sequences of the 21s137L are shown below. The nucleic acid sequence of the 21s137L construct (including signal peptide sequence) is as follows:

(Signal peptide)
ATGAAGTGGGTGACCTTCATCAGCCTGCTGTTCCTGTTCTCCAGCGCCT

ACTCC (Human IL-21)
CAGGGCCAGGACAGGCACATGATCCGGATGAGGCAGCTCATCGACATCG

TCGACCAGCTGAAGAACTACGTGAACGACCTGGTGCCCGAGTTTCTGCC

TGCCCCCGAGGACGTGGAGACCAACTGCGAGTGGTCCGCCTTCTCCTGC

TTTCAGAAGGCCCAGCTGAAGTCCGCCAACACCGGCAACAACGAGCGGA

TCATCAACGTGAGCATCAAGAAGCTGAAGCGGAAGCCTCCCTCCACAAA

CGCCGGCAGGAGGCAGAAGCACAGGCTGACCTGCCCCAGCTGTGACTCC

TACGAGAAGAAGCCCCCCAAGGAGTTCCTGGAGAGGTTCAAGTCCCTGC

TGCAGAAGATGATCCATCAGCACCTGTCCTCCAGGACCCACGGCTCCGA

GGACTCC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGAC

CTGCGGCAGGGCATGTTTGCGCAGCTGGTGGCCCAAAATGTTCTGCTG

ATCGATGGGCCCCTGAGCTGGTACAGTGACCCAGGCCTGGCAGGCGTG

TCCCTGACGGGGGGCCTGAGCTACAAAGAGGACACGAAGGAGCTGGTG

GTGGCCAAGGCTGGAGTCTACTATGTCTTCTTTCAACTAGAGCTGCGG

CGCGTGGTGGCCGGCGAGGGCTCAGGCTCCGTTTCACTTGCGCTGCAC

CTGCAGCCACTGCGCTCTGCTGCTGGGGCCGCCGCCCTGGCTTTGACC

GTGGACCTGCCACCCGCCTCCTCCGAGGCTCGGAACTCGGCCTTCGGT

TTCCAGGGCCGCTTGCTGCACCTGAGTGCCGGCCAGCGCCTGGGCGTC

CATCTTCACACTGAGGCCAGGGCACGCCATGCCTGGCAGCTTACCCAG

GGCGCCACAGTCTTGGGACTCTTCCGGGTGACCCCCGAAATCCCAGCC

GGACTCCCTTCACCGAGGTCGGAA

The amino acid sequence of 21s137L fusion protein (including the leader sequence) is as (Signal peptide)
MKWVTFISLLFLFSSAYS (Human IL-21)
QGQDRHMIRMRQLIDIVDQLKNYVNDLVPEFLPAPEDVETNCEWSAFS

CFQKAQLKSANTGNNERIINVSIKKLKRKPPSTNAGRRQKHRLTCPSC

DSYEKKPPKEFLERFKSLLQKMIHQHLSSRTHGSEDS (Human IL-15R α sushi domain)
ITCPPPMSVEHADIWVKSYSLYSRERYICNSGFKRKAGTSSLTECVLN

KATNVAHWTTPSLKCIR ((G4S)3 linker)
GGGGSGGGGSGGGGS (Human CD137L)
REGPELSPDDPAGLLDLRQGMFAQLVAQNVLLIDGPLSWYSDPGLAGV

SLTGGLSYKEDTKELVVAKAGVYYVFFQLELRRVVAGEGSGSVSLALH

LQPLRSAAGAAALALTVDLPPASSEARNSAFGFQGRLLHLSAGQRLGV

HLHTEARARHAWQLTQGATVLGLFRVTPEIPAGLPSPRSE

In some cases, the leader peptide is cleaved from the intact polypeptide to generate the mature form that may be soluble or secreted.

The IL-21/IL-15RαSu/CD137L and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15: IL-21/IL-15RαSu/CD137L protein complex (referred to as TGFRt15-21s137L), which can be purified by anti-TF antibody affinity and other chromatography methods. See, FIGS. 140 and 141.

Purification Elution Chromatograph of TGFRt15-21s137L Using Anti-TF Antibody Affinity Column TGFRt15-21s137L harvest from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 142, the anti-TF antibody affinity column bound to TGFRt15-21s137L which contains TF as a fusion partner of TGFRt15-21s137L. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Example 82: TGFRt15-TGFRs21 Fusion Protein Generation and Characterization

A fusion protein complex was generated comprising of TGFβ Receptor II/IL-15RαSu/IL-21 and TGFβ Receptor II/TF/IL-15 fusion proteins. The human TGFβ Receptor II (Ile24-Asp159), tissue factor 219, IL-21, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGCC

TACTCC

(Human TGFβ Receptor II fragments)
ATCCCCCCCCATGTGCAAAAGAGCGTGAACAACGATATGATCGTGACC

GACAACAACGGCGCCGTGAAGTTTCCCCAGCTCTGCAAGTTCTGCGAT

GTCAGGTTCAGCACCTGCGATAATCAGAAGTCCTGCATGTCCAACTGC

AGCATCACCTCCATCTGCGAGAAGCCCCAAGAAGTGTGCGTGGCCGTG

TGGCGGAAAAATGACGAGAACATCACCCTGGAGACCGTGTGTCACGAC

CCCAAGCTCCCTTATCACGACTTCATTCTGGAGGACGCTGCCTCCCCC

AAATGCATCATGAAGGAGAAGAAGAAGCCCGGAGAGACCTTCTTTATG

TGTTCCTGTAGCAGCGACGAGTGTAACGACAACATCATCTTCAGCGAA

GAGTACAACACCAGCAACCCTGATGGAGGTGGCGGATCCGGAGGTGGA

GGTTCTGGTGGAGGTGGGAGTATTCCTCCCCACGTGCAGAAGAGCGTG

AATAATGACATGATCGTGACCGATAACAATGGCGCCGTGAAATTTCCC

CAGCTGTGCAAATTCTGCGATGTGAGGTTTTCCACCTGCGACAACCAG

AAGTCCTGTATGAGCAACTGCTCCATCACCTCCATCTGTGAGAAGCCT

CAGGAGGTGTGCGTGGCTGTCTGGCGGAAGAATGACGAGAATATCACC

CTGGAAACCGTCTGCCACGATCCCAAGCTGCCCTACCACGATTTCATC

CTGGAAGACGCCGCCAGCCCTAAGTGCATCATGAAAGAGAAAAAGAAG

CCTGGCGAGACCTTTTTCATGTGCTCCTGCAGCAGCGACGAATGCAAC

GACAATATCATCTTTAGCGAGGAATACAATACCAGCAACCCCGAC

(Human Tissue Factor 219)
AGCGGCACAACCAACACAGTCGCTGCCTATAACCTCACTTGGAAGAGC

ACCAACTTCAAAACCATCCTCGAATGGGAACCCAAACCCGTTAACCAA

GTTTACACCGTGCAGATCAGCACCAAGTCCGGCGACTGGAAGTCCAAA

TGTTTCTATACCACCGACACCGAGTGCGATCTCACCGATGAGATCGTG

AAAGATGTGAAACAGACCTACCTCGCCCGGGTGTTTAGCTACCCCGCC

GGCAATGTGGAGAGCACTGGTTCCGCTGGCGAGCCTTTATACGAGAAC
```

-continued

```
AGCCCCGAATTTACCCCTTACCTCGAGACCAATTTAGGACAGCCCACC

ATCCAAAGCTTTGAGCAAGTTGGCACAAAGGTGAATGTGACAGTGGAG

GACGAGCGGACTTTAGTGCGGCGGAACAACACCTTTCTCAGCCTCCGG

GATGTGTTCGGCAAAGATTTAATCTACACACTGTATTACTGGAAGTCC

TCTTCCTCCGGCAAGAAGACAGCTAAAACCAACACAAACGAGTTTTTA

ATCGACGTGGATAAAGGCGAAAACTACTGTTTCAGCGTGCAAGCTGTG

ATCCCCTCCCGGACCGTGAATAGGAAAAGCACCGATAGCCCCGTTGAG

TGCATGGGCCAAGAAAAGGGCGAGTTCCGGGAG

(Human IL-15)
AACTGGGTGAACGTCATCAGCGATTTAAAGAAGATCGAAGATTTAATT

CAGTCCATGCATATCGACGCCACTTTATACACAGAATCCGACGTGCAC

CCCTCTTGTAAGGTGACCGCCATGAAATGTTTTTTACTGGAGCTGCAA

GTTATCTCTTTAGAGAGCGGAGACGCTAGCATCCACGACACCGTGGAG

AATTTAATCATTTTAGCCAATAACTCTTTATCCAGCAACGGCAACGTG

ACAGAGTCCGGCTGCAAGGAGTGCGAAGAGCTGGAGGAGAAGAACATC

AAGGAGTTTCTGCAATCCTTTGTGCACATTGTCCAGATGTTCATCAAT

ACCTCC
```

The amino acid sequence of TGFRt15 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSNC

SITSICEKPQEVCVAVWRKNDENITLETVCHDPKLPYHDFILEDAASP

KCIMKEKKKPGETFFMCSCSSDECNDNIIFSEEYNTSNPDGGGGSGGG

GSGGGGSIPPHVQKSVNNDMIVTDNNGAVKFPQLCKFCDVRFSTCDNQ

KSCMSNCSITSICEKPQEVCVAVWRKNDENITLETVCHDPKLPYHDFI

LEDAASPKCIMKEKKKPGETFFMCSCSSDECNDNIIFSEEYNTSNPD

(Human Tissue Factor 219)
SGTTNTVAAYNLTWKSTNFKTILEWEPKPVNQVYTVQISTKSGDWKS

KCFYTTDTECDLTDEIVKDVKQTYLARVFSYPAGNVESTGSAGEPLY

ENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFS

VQAVIPSRTVNRKSTDSPVECMGQEKGEFRE

(Human IL-15)
NWVNVISDLKKIEDLIQSMHIDATLYTESDVHPSCKVTAMKCFLLEL

QVISLESGDASIHDTVENLIILANNSLSSNGNVTESGCKECEELEEK

NIKEFLQSFVHIVQMFINTS
```

Constructs were also made by attaching two TGFβ Receptor II directly to the IL-15RαSu chain, followed by the N-terminus coding region of IL-21, which was synthesized by Genewiz. The nucleic acid and protein sequences of a construct comprising the TGFβ Receptor II linked to the N-terminus of IL-15RαSu following with the N-terminus of IL-21 are shown below.

The nucleic acid sequence of the TGFRs21 construct (including signal peptide sequence) is as follows:

```
(Signal peptide)
ATGAAGTGGGTGACCTTCATCAGCCTGCTGTTCCTGTTCTCCAGCGC

CTACTCC

(Human TGFβ Receptor II fragments)
ATCCCCCCCCATGTGCAAAAGAGCGTGAACAACGATATGATCGTGAC

CGACAACAACGGCGCCGTGAAGTTTCCCCAGCTCTGCAAGTTCTGCG

ATGTCAGGTTCAGCACCTGCGATAATCAGAAGTCCTGCATGTCCAAC

TGCAGCATCACCTCCATCTGCGAGAAGCCCCAAGAAGTGTGCGTGGC

CGTGTGGCGGAAAAATGACGAGAACATCACCCTGGAGACCGTGTGTC

ACGACCCCAAGCTCCCTTATCACGACTTCATTCTGGAGGACGCTGCC

TCCCCCAAATGCATCATGAAGGAGAAGAAGAAGCCCGGAGAGACCTT

CTTTATGTGTTCCTGTAGCAGCGACGAGTGTAACGACAACATCATCT

TCAGCGAAGAGTACAACACCAGCAACCCTGATGGAGGTGGCGGATCC

GGAGGTGGAGGTTCTGGTGGAGGTGGGAGTATTCCTCCCCACGTGCA

GAAGAGCGTGAATAATGACATGATCGTGACCGATAACAATGGCGCCG

TGAAATTTCCCCAGCTGTGCAAATTCTGCGATGTGAGGTTTTCCACC

TGCGACAACCAGAAGTCCTGTATGAGCAACTGCTCCATCACCTCCAT

CTGTGAGAAGCCTCAGGAGGTGTGCGTGGCTGTCTGGCGGAAGAATG

ACGAGAATATCACCCTGGAAACCGTCTGCCACGATCCCAAGCTGCCC

TACCACGATTTCATCCTGGAAGACGCCGCCAGCCCTAAGTGCATCAT

GAAAGAGAAAAAGAAGCCTGGCGAGACCTTTTTCATGTGCTCCTGCA

GCAGCGACGAATGCAACGACAATATCATCTTTAGCGAGGAATACAAT

ACCAGCAACCCCGAC

(Human IL-15R α sushi domain)
ATTACATGCCCCCCTCCCATGAGCGTGGAGCACGCCGACATCTGGGT

GAAGAGCTATAGCCTCTACAGCCGGGAGAGGTATATCTGTAACAGCG

GCTTCAAGAGGAAGGCCGGCACCAGCAGCCTCACCGAGTGCGTGCTG

AATAAGGCTACCAACGTGGCTCACTGGACAACACCCTCTTTAAAGTG

CATCCGG

(Human IL-21)
CAGGGCCAGGACAGGCACATGATCCGGATGAGGCAGCTCATCGACAT

CGTCGACCAGCTGAAGAACTACGTGAACGACCTGGTGCCCGAGTTTC

TGCCTGCCCCCGAGGACGTGGAGACCAACTGCGAGTGGTCCGCCTTC

TCCTGCTTTCAGAAGGCCCAGCTGAAGTCCGCCAACACCGGCAACAA

CGAGCGGATCATCAACGTGAGCATCAAGAAGCTGAAGCGGAAGCCTC

CCTCCACAAACGCCGGCAGGAGGCAGAAGCACAGGCTGACCTGCCCC

AGCTGTGACTCCTACGAGAAGAAGCCCCCCAAGGAGTTCCTGGAGAG

GTTCAAGTCCCTGCTGCAGAAGATGATCCATCAGCACCTGTCCTCCA

GGACCCACGGCTCCGAGGACTCC
```

The amino acid sequence of TGFRs21 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSN

CSITSICEKPQEVCVAVWRKNDENITLETVCHDPKLPYHDFILEDAA

SPKCIMKEKKKPGETFFMCSCSSDECNDNIIFSEEYNTSNPDGGGGS

GGGGSGGGGSIPPHVQKSVNNDMIVTDNNGAVKFPQLCKFCDVRFST

CDNQKSCMSNCSITSICEKPQEVCVAVWRKNDENITLETVCHDPKLP

YHDFILEDAASPKCIMKEKKKPGETFFMCSCSSDECNDNIIFSEEYN

TSNPD

(Human IL-15R α sushi domain)
ITCPPPMSVEHADIWVKSYSLYSRERYICNSGFKRKAGTSSLTECVL

NKATNVAHWTTPSLKCIR

(Human IL-21)
QGQDRHMIRMRQLIDIVDQLKNYVNDLVPEFLPAPEDVETNCEWSAF

SCFQKAQLKSANTGNNERIINVSIKKLKRKPPSTNAGRRQKHRLTCP

SCDSYEKKPPKEFLERFKSLLQKMIHQHLSSRTHGSEDS
```

In some cases, the leader peptide is cleaved from the intact polypeptide to generate the mature form that may be soluble or secreted.

The TGFR/IL-15RαSu/IL-21 and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/IL-21 protein complex (referred to as TGFRt15-TGFRs21), which can be purified by anti-TF antibody affinity and other chromatography methods. See, FIGS. 143 and 144.

Purification Elution Chromatograph of TGFRt15-TGFRs21 Using Anti-TF Antibody Affinity Column TGFRt15-TGFRs21 harvested from cell culture was loaded onto the anti-TF antibody affinity column equilibrated with 5 column volumes of PBS. After sample loading, the column was washed with 5 column volumes of PBS, followed by elution with 6 column volumes of 0.1M acetic acid (pH 2.9). A280 elution peak was collected and then neutralized to pH 7.5-8.0 with 1M Tris base. The neutralized sample was then buffer exchanged into PBS using Amicon centrifugal filters with a 30 KDa molecular weight cutoff. As shown in FIG. 145, the anti-TF antibody affinity column bound to TGFRt15-TGFRs21 which contains TF as a fusion partner. The buffer-exchanged protein sample was stored at 2-8° C. for further biochemical analyses and biological activity tests. After each elution, the anti-TF antibody affinity column was stripped using 6 column volumes of 0.1M glycine (pH 2.5). The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE Analysis of TGFRt15-TGFRs21

To determine the purity and molecular weight of the protein, TGFRt15-TGFRs21 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the TGFRt15-TGFRs21 protein undergoes glycosylation after translation in CHO cells, a deglycosylation experiment was conducted using the Protein Deglycosylation Mix II kit from New England Biolabs and the manufacturer's instructions. FIG. 146 shows the reduced SDS-PAGE analysis of the sample in non-deglycosylated (lane 1 in red outline) and deglycosylated (lane 2 in yellow outline) state. It is clear that the protein is glycosylated when it is expressed in CHO cells. After deglycosylation, the purified sample showed expected molecular weights (69 kDa and 55 kDa) in reduced SDS gel. Lane M was loaded with 10 ul of SeeBlue Plus2 Prestained Standard.

Immunostimulation of TGFRt15-TGFRs21 in C57BL 6 Mice

TGFRt15-TGFRs21 is a multi-chain polypeptide (a type A multi-chain polypeptide described herein) that includes the first polypeptide that is a soluble fusion of single chain two TGFβRII domains, human tissue factor 219 fragment and human IL-15 (TGFRt15), and the second polypeptide that is a soluble fusion of single chain two TGFβRII domains, sushi domain of human IL-15 receptor alpha chain and human IL-21 (TGFRs21).

CHO cells were co-transfected with TGFRt15 and TGFRs21 vectors. The TGFRt15-TGFRs21 complex was purified from the transfected CHO cell culture supernatant. The TGFβ receptor, IL-15, IL-21 and tissue factor (TF) components were demonstrated in the complex by ELISA as shown in FIGS. 147A and 147B. A humanized anti-TF monoclonal antibody was used as the capture antibody to determine TF in TGFRt15-TGFRs21, biotinylated anti-human IL-15 antibody (R&D systems), biotinylated anti-human TGFβ receptor antibody (R&D systems, and biotinylated anti-human IL-21 antibody (R&D Systems) were used as the detection antibodies to respectively determine IL-15, TGFβ receptor, and IL-21 in TGFRt15-TGFRs21. For detection, peroxidase conjugated streptavidin (Jackson ImmunoResearch Lab) and ABTS were used.

Wild type C57BL/6 mice were treated subcutaneously with either control solution (PBS) or with TGFRt15-TGFRs21 at 3 mg/kg. Four days after treatment, spleen weight and the percentages of various immune cell types present in the spleen were evaluated. As shown in FIG. 148A, the percentages of $CD4^+$ T cells, $CD8^+$ T cells, and NK cells present in the spleen of control-treated and TGFRt15-TGFRs21-treated mice were evaluated. The dynamic proliferation of immune cells based on Ki67 expression after TGFRt15-TGFRs21 treatment was also evaluated. The splenocytes were stained with fluorochrome-conjugated anti-CD4, anti-CD8, and anti-NK1.1 (NK) antibodies and then intracellularly stained with anti-Ki67 antibody. The percentage of $CD4^+$ T cells, $CD8^+$ T cells, and NK cells and the mean fluorescent intensity (MFI) of Ki67 of corresponding immunocyte subsets were analyzed by flow cytometry (FIGS. 148A and 148B). Furthermore, cytotoxicity potential based on granzyme B expression of the splenocytes induced by TGFRt15-TGFRs21 after the single dose treatment of mouse was also evaluated. As shown in FIG. 149, in the spleens of mice treated with TGFRt15-TGFRs21, the expression of granzyme B by NK cells increased after treatment. The splenocytes from TGFRt15-TGFRs21-treated mice were stained with fluorochrome-conjugated anti-CD4, anti-CD8, and anti-NK1.1 (NK) antibodies and then intracellularly stained with anti-granzyme B antibody. The mean fluorescent intensity (MFI) of granzyme B of corresponding immunocyte subsets was analyzed by flow cytometry (FIG. 149).

As shown in FIG. 148A, in the spleens of mice treated with TGFRt15-TGFRs21, the percentages of $CD8^+$ T cells and NK cells both increased on day 4 after a single TGFRt15-TGFRs21 treatment. These results demonstrate that TGFRt15-TGFRs21 is able to induce immune cells to proliferate in mouse spleen, in particular $CD8^+$ T cells and NK cells.

Additionally, cytotoxicity of the mouse splenocytes against tumor cells was also evaluated. Mouse Yac-1 cells were labeled with CellTrace Violet and used as tumor target cells. The splenocytes were prepared from TGFRt15-TGFRs21-treated mice and used as effector cells. The target cells were mixed with effector cells at E:T ratio=10:1 in RPMI-10 medium with or without TGFRt15-TGFRs21 at 100 nM and incubated at 37° C. for 24 hours. Target Yac-1 cell inhibition was assessed by analysis of viable violet-labeled Yac-1 cells using flow cytometry. Percentage of Yac-1 inhibition was calculated using a formula, (1-[viable Yac-1 cell number in experimental sample]/[viable Yac-1 cell number in the sample without splenocytes])×100. As shown in FIG. 150, TGFRt15-TGFRs21-treated mouse splenocytes had stronger cytotoxicity against Yac-1 cells than the control mouse cells in the presence of TGFRt15-TGFRs21 during cytotoxic assay (shown in legend of FIG. 150).

Example 83: TGFRt15-TGFRs16 Fusion Protein Generation

A fusion protein complex was generated comprising of TGFβ Receptor II/IL-15RαSu/anti-CD16scFv and TGFβ Receptor II/TF/IL-15 fusion proteins (See, FIGS. 151 and 152). The human TGFβ Receptor II (Ile24-Asp159), tissue factor 219, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGC

CTACTCC

(Human TGFβ Receptor II fragments)
ATCCCCCCCCATGTGCAAAAGAGCGTGAACAACGATATGATCGTGAC

CGACAACAACGGCGCCGTGAAGTTTCCCCAGCTCTGCAAGTTCTGCG

ATGTCAGGTTCAGCACCTGCGATAATCAGAAGTCCTGCATGTCCAAC
```

-continued

```
TGCAGCATCACCTCCATCTGCGAGAAGCCCCAAGAAGTGTGCGTGGC
CGTGTGGCGGAAAAATGACGAGAACATCACCCTGGAGACCGTGTGTC
ACGACCCCAAGCTCCCTTATCACGACTTCATTCTGGAGGACGCTGCC
TCCCCCAAATGCATCATGAAGGAGAAGAAGAAGCCCGGAGAGACCTT
CTTTATGTGTTCCTGTAGCAGCGACGAGTGTAACGACAACATCATCT
TCAGCGAAGAGTACAACACCAGCAACCCTGATGGAGGTGGCGGATCC
GGAGGTGGAGGTTCTGGTGGAGGTGGGAGTATTCCTCCCCACGTGCA
GAAGAGCGTGAATAATGACATGATCGTGACCGATAACAATGGCGCCG
TGAAATTTCCCCAGCTGTGCAAATTCTGCGATGTGAGGTTTTCCACC
TGCGACAACCAGAAGTCCTGTATGAGCAACTGCTCCATCACCTCCAT
CTGTGAGAAGCCTCAGGAGGTGTGCGTGGCTGTCTGGCGGAAGAATG
ACGAGAATATCACCCTGGAAACCGTCTGCCACGATCCCAAGCTGCCC
TACCACGATTTCATCCTGGAAGACGCCGCCAGCCCTAAGTGCATCAT
GAAAGAGAAAAAGAAGCCTGGCGAGACCTTTTTCATGTGCTCCTGCA
GCAGCGACGAATGCAACGACAATATCATCTTTAGCGAGGAATACAAT
ACCAGCAACCCCGAC

(Human Tissue Factor 219)
AGCGGCACAACCAACACAGTCGCTGCCTATAACCTCACTTGGAAGAG
CACCAACTTCAAAACCATCCTCGAATGGGAACCCAAACCCGTTAACC
AAGTTTACACCGTGCAGATCAGCACCAAGTCCGGCGACTGGAAGTCC
AAATGTTTCTATACCACCGACACCGAGTGCGATCTCACCGATGAGAT
CGTGAAAGATGTGAAACAGACCTACCTCGCCCGGGTGTTTAGCTACC
CCGCCGGCAATGTGGAGAGCACTGGTTCCGCTGGCGAGCCTTTATAC
GAGAACAGCCCCGAATTTACCCCTTACCTCGAGACCAATTTAGGACA
GCCCACCATCCAAAGCTTTGAGCAAGTTGGCACAAAGGTGAATGTGA
CAGTGGAGGACGAGCGGACTTTAGTGCGGCGGAACAACACCTTTCTC
AGCCTCCGGGATGTGTTCGGCAAACATTTAATCTACACACTGTATTA
CTGGAAGTCCTCTTCCTCCGGCAAGAAGACAGCTAAAACCAACACAA
ACGAGTTTTTAATCGACGTGGATAAAGGCGAAAACTACTGTTTCAGC
GTGCAAGCTGTGATCCCCTCCCGGACCGTGAATAGGAAAAGCACCGA
TAGCCCCGTTGAGTGCATGGGCCAAGAAAAGGGCGAGTTCCGGGAG

(Human IL-15)
AACTGGGTGAACGTCATCAGCGATTTAAAGAAGATCGAAGATTTAAT
TCAGTCCATGCATATCGACGCCACTTTATACACAGAATCCGACGTGC
ACCCCTCTTGTAAGGTGACCGCCATGAAATGTTTTTTACTGGAGCTG
CAAGTTATCTCTTTAGAGAGCGGAGACGCTAGCATCCACGACACCGT
GGAGAATTTAATCATTTTAGCCAATAACTCTTTATCCAGCAACGGCA
ACGTGACAGAGTCCGGCTGCAAGGAGTGCGAAGAGCTGGAGGAGAAG
AACATCAAGGAGTTTCTGCAATCCTTTGTGCACATTGTCCAGATGTT
CATCAATACCTCC
```

The amino acid sequence of TGFRt15 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSN
CSITSICEKPQEVCVAVWRKNDENITLETVCHDPKLPYHDFILEDAA
SPKCIMKEKKKPGETFFMCSCSSDECNDNIIFSEEYNTSNPDGGGGS
GGGGSGGGGSIPPHVQKSVNNDMIVTDNNGAVKFPQLCKFCDVRFST
CDNQKSCMSNCSITSICEKPQEVCVAVWRKNDENITLETVCHDPKLP
YHDFILEDAASPKCIMKEKKKPGETFFMCSCSSDECNDNIIFSEEYN
TSNPD

(Human Tissue Factor 219)
SGTTNTVAAYNLTWKSTNFKTILEWEPKPVNQVYTVQISTKSGDWKS
KCFYTTDTECDLTDEIVKDVKQTYLARVFSYPAGNVESTGSAGEPLY
ENSPEFTPYLETNLGQPTIQSFEQVGTKVNVTVEDERTLVRRNNTFL
SLRDVFGKDLIYTLYYWKSSSSGKKTAKTNTNEFLIDVDKGENYCFS
VQAVIPSRTVNRKSTDSPVECMGQEKGEFRE

(Human IL-15)
NWVNVISDLKKIEDLIQSMHIDATLYTESDVHPSCKVTAMKCFLLEL
QVISLESGDASIHDTVENLIILANNSLSSNGNVTESGCKECEELEEK
NIKEFLQSFVHIVQMFINTS
```

Constructs were also made by attaching two TGFβ Receptor II directly to the IL-15RαSu chain, followed by the anti-CD16scFv sequence, which was synthesized by Genewiz. The nucleic acid and protein sequences of a construct comprising the TGFβ Receptor II linked to the N-terminus of IL-15RαSu following with the anti-CD16scFv sequence are shown below.

The nucleic acid sequence of the TGFRs16 construct (including signal peptide sequence) is as follows:

```
(Signal peptide)
ATGAAGTGGGTGACCTTCATCAGCCTGCTGTTCCTGTTCTCCAGCGC
CTACTCC

(Human TGFβ Receptor II fragments)
ATCCCCCCCCATGTGCAAAAGAGCGTGAACAACGATATGATCGTGAC
CGACAACAACGGCGCCGTGAAGTTTCCCCAGCTCTGCAAGTTCTGCG
ATGTCAGGTTCAGCACCTGCGATAATCAGAAGTCCTGCATGTCCAAC
TGCAGCATCACCTCCATCTGCGAGAAGCCCCAAGAAGTGTGCGTGGC
CGTGTGGCGGAAAAATGACGAGAACATCACCCTGGAGACCGTGTGTC
ACGACCCCAAGCTCCCTTATCACGACTTCATTCTGGAGGACGCTGCC
TCCCCCAAATGCATCATGAAGGAGAAGAAGAAGCCCGGAGAGACCTT
CTTTATGTGTTCCTGTAGCAGCGACGAGTGTAACGACAACATCATCT
TCAGCGAAGAGTACAACACCAGCAACCCTGATGGAGGTGGCGGATCC
GGAGGTGGAGGTTCTGGTGGAGGTGGGAGTATTCCTCCCCACGTGCA
GAAGAGCGTGAATAATGACATGATCGTGACCGATAACAATGGCGCCG
```

-continued

```
TGAAATTTCCCCAGCTGTGCAAATTCTGCGATGTGAGGTTTTCCACC

TGCGACAACCAGAAGTCCTGTATGAGCAACTGCTCCATCACCTCCAT

CTGTGAGAAGCCTCAGGAGGTGTGCGTGGCTGTCTGGCGGAAGAATG

ACGAGAATATCACCCTGGAAACCGTCTGCCACGATCCCAAGCTGCCC

TACCACGATTTCATCCTGGAAGACGCCGCCAGCCCTAAGTGCATCAT

GAAAGAGAAAAAGAAGCCTGGCGAGACCTTTTTCATGTGCTCCTGCA

GCAGCGACGAATGCAACGACAATATCATCTTTAGCGAGGAATACAAT

ACCAGCAACCCCGAC

(Human IL-15R α sushi domain)
ATTACATGCCCCCCTCCCATGAGCGTGGAGCACGCCGACATCTGGGT

GAAGAGCTATAGCCTCTACAGCCGGGAGAGGTATATCTGTAACAGCG

GCTTCAAGAGGAAGGCCGGCACCAGCAGCCTCACCGAGTGCGTGCTG

AATAAGGCTACCAACGTGGCTCACTGGACAACACCCTCTTTAAAGTG

CATCCGG

(Anti-human CD16scFv)
TCCGAGCTGACCCAGGACCCTGCTGTGTCCGTGGCTCTGGGCCAGAC

CGTGAGGATCACCTGCCAGGGCGACTCCCTGAGGTCCTACTACGCCT

CCTGGTACCAGCAGAAGCCCGGCCAGGCTCCTGTGCTGGTGATCTAC

GGCAAGAACAACAGGCCCTCCGGCATCCCTGACAGGTTCTCCGGATC

CTCCTCCGGCAACACCGCCTCCCTGACCATCACAGGCGCTCAGGCCG

AGGACGAGGCTGACTACTACTGCAACTCCAGGGACTCCTCCGGCAAC

CATGTGGTGTTCGGCGGCGGCACCAAGCTGACCGTGGGCCATGGCGG

CGGCGGCTCCGGAGGCGGCGGCAGCGGCGGAGGAGGATCCGAGGTGC

AGCTGGTGGAGTCCGGAGGAGGAGTGGTGAGGCCTGGAGGCTCCCTG

AGGCTGAGCTGTGCTGCCTCCGGCTTCACCTTCGACGACTACGGCAT

GTCCTGGGTGAGGCAGGCTCCTGGAAAGGGCCTGGAGTGGGTGTCCG

GCATCAACTGGAACGGCGGATCCACCGGCTACGCCGATTCCGTGAAG

GGCAGGTTCACCATCAGCAGGGACAACGCCAAGAACTCCCTGTACCT

GCAGATGAACTCCCTGAGGGCCGAGGACACCGCCGTGTACTACTGCG

CCAGGGGCAGGTCCCTGCTGTTCGACTACTGGGGACAGGGCACCCTG

GTGACCGTGTCCAGG
```

The amino acid sequence of TGFRs16 fusion protein (including the leader sequence) is as follows:

```
(Signal peptide)
MKWVTFISLLFLFSSAYS

(Human TGFβ Receptor II)
IPPHVQKSVNNDMIVTDNNGAVKFPQLCKFCDVRFSTCDNQKSCMSN

CSITSICEKPQEVCVAVWRKNDENITLETVCHDPKLPYHDFILEDAA

SPKCIMKEKKKPGETFFMCSCSSDECNDNIIFSEEYNTSNPDGGGGS

GGGGSGGGGSIPPHVQKSVNNDMIVTDNNGAVKFPQLCKFCDVRFST
```

-continued

```
CDNQKSCMSNCSITSICEKPQEVCVAVWRKNDENITLETVCHDPKLP

YHDFILEDAASPKCIMKEKKKPGETFFMCSCSSDECNDNIIFSEEYN

TSNPD

(Human IL-15R α sushi domain)
ITCPPPMSVEHADIWVKSYSLYSRERYICNSGFKRKAGTSSLTECVL

NKATNVAHWTTPSLKCIR

(Anti-human CD16scFv)
SELTQDPAVSVALGQTVRITCQGDSLRSYYASWYQQKPGQAPVLVIY

GKNNRPSGIPDRFSGSSSGNTASLTITGAQAEDEADYYCNSRDSSGN

HVVFGGGTKLTVGHGGGGSGGGGSGGGGSEVQLVESGGGVVRPGGSL

RLSCAASGFTFDDYGMSWVRQAPGKGLEWVSGINWNGGSTGYADSVK

GRFTISRDNAKNSLYLQMNSLRAEDTAVYYCARGRSLLFDYWGQGTL

VTVSR
```

In some cases, the leader peptide is cleaved from the intact polypeptide to generate the mature form that may be soluble or secreted.

The TGFR/IL-15RαSu/anti-CD16scFv and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. *Hum Gene Ther* 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/anti-CD16scFv protein complex (referred to as TGFRt15-TGFRs16), which can be purified by anti-TF antibody affinity and other chromatography methods.

Example 84: The TGFRt15-TGFRs137L Fusion Protein Generation

A fusion protein complex was generated comprising of TGFβ Receptor II/IL-15RαSu/CD137L and TGFβ Receptor II/TF/IL-15 fusion proteins (see, FIGS. 153 and 154). The human TGFβ Receptor II (Ile24-Asp159), tissue factor 219, CD137L, and IL-15 sequences were obtained from the UniProt website and DNA for these sequences was synthesized by Genewiz. Specifically, a construct was made linking two TGFβ Receptor II sequences with a G4S(3) linker to generate a single chain version of TGFβ Receptor II and then directly linking to the N-terminus coding region of tissue factor 219 followed by the N-terminus coding region of IL-15.

The nucleic acid and protein sequences of a construct comprising two TGFβ Receptor II linked to the N-terminus of tissue factor 219 following with the N-terminus of IL-15 are shown below.

The nucleic acid sequence of the TGFRt15 construct (including signal peptide sequence) is as follows:

```
(Signal peptide)
ATGAAGTGGGTGACCTTCATCAGCCTGCTGTTCCTGTTCTCCAGCGCCT

ACTCC
```

-continued (Human TGFβ Receptor II fragments)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC (Human Tissue Factor 219)
AGCGGCACAACCAACACAGTCGCTGCCTATAACCTCACTTGGAAGAGCA

CCAACTTCAAAACCATCCTCGAATGGGAACCCAAACCCGTTAACCAAGT

TTACACCGTGCAGATCAGCACCAAGTCCGGCGACTGGAAGTCCAAATGT

TTCTATACCACCGACACCGAGTGCGATCTCACCGATGAGATCGTGAAAG

ATGTGAAACAGACCTACCTCGCCCGGGTGTTTAGCTACCCCGCCGGCAA

TGTGGAGAGCACTGGTTCCGCTGGCGAGCCTTTATACGAGAACAGCCCC

GAATTTACCCCTTACCTCGAGACCAATTTAGGACAGCCCACCATCCAAA

GCTTTGAGCAAGTTGGCACAAAGGTGAATGTGACAGTGGAGGACGAGCG

GACTTTAGTGCGGCGGAACAACACCTTTCTCAGCCTCCGGGATGTGTTC

GGCAAAGATTTAATCTACACACTGTATTACTGGAAGTCCTCTTCCTCCG

GCAAGAAGACAGCTAAAACCAACACAAACGAGTTTTTAATCGACGTGGA

TAAAGGCGAAAACTACTGTTTCAGCGTGCAAGCTGTGATCCCCTCCCGG

ACCGTGAATAGGAAAAGCACCGATAGCCCCGTTGAGTGCATGGGCCAAG

AAAAGGGCGAGTTCCGGGAG (Human IL-15)
AACTGGGTGAACGTCATCAGCGATTTAAAGAAGATCGAAGATTTAATTC

AGTCCATGCATATCGACGCCACTTTATACACAGAATCCGACGTGCACCC

CTCTTGTAAGGTGACCGCCATGAAATGTTTTTTACTGGAGCTGCAAGTT

ATCTCTTTAGAGAGCGGAGACGCTAGCATCCACGACACCGTGGAGAATT

TAATCATTTTAGCCAATAACTCTTTATCCAGCAACGGCAACGTGACAGA

GTCCGGCTGCAAGGAGTGCGAAGAGCTGGAGGAGAAGAACATCAAGGAG

TTTCTGCAATCCTTTGTGCACATTGTCCAGATGTTCATCAATACCTCC

The amino acid sequence of TGFRt15 fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNCS

ITSICEKPQEVCVAVWRKNDENITLETVCHDPKLPYHDFILEDAASPKC

IMKEKKKPGETFFMCSCSSDECNDNIIFSEEYNTSNPDGGGGSGGGGSG

GGGSIPPHVQKSVNNDMIVTDNNGAVKFPQLCKFCDVRFSTCDNQKSCM

SNCSITSICEKPQEVCVAVWRKNDENITLETVCHDPKLPYHDFILEDAA

SPKCIMKEKKKPGETFFMCSCSSDECNDNIIFSEEYNTSNPD (Human Tissue Factor 219)
SGTTNTVAAYNLTWKSTNFKTILEWEPKPVNQVYTVQISTKSGDWKSKC

FYTTDTECDLTDEIVKDVKQTYLARVFSYPAGNVESTGSAGEPLYENSP

EFTPYLETNLGQPTIQSFEQVGTKVNVTVEDERTLVRRNNTFLSLRDVF

GKDLIYTLYYWKSSSSGKKTAKTNTNEFLIDVDKGENYCFSVQAVIPSR

TVNRKSTDSPVECMGQEKGEFRE (Human IL-15)
NWVNVISDLKKIEDLIQSMHIDATLYTESDVHPSCKVTAMKCFLLELQV

ISLESGDASIHDTVENLIILANNSLSSNGNVTESGCKECEELEEKNIKE

FLQSFVHIVQMFINTS

Constructs were also made by attaching two TGFβ Receptor II directly to the IL-15RαSu chain, followed by a (G4S)3 linker and the CD137L sequence, which was synthesized by Genewiz. The nucleic acid and protein sequences of a construct comprising the TGFβ Receptor II linked to the N-terminus of IL-15RαSu following with a (G4S)3 linker and the CD137L sequence are shown below.

The nucleic acid sequence of the TGFRs137L construct (including signal peptide sequence) is as follows:

(Signal peptide)
ATGAAGTGGGTGACCTTCATCAGCCTGCTGTTCCTGTTCTCCAGCGCCT

ACTCC (Human TGFβ Receptor II fragments)
ATCCCCCCCCATGTGCAAAAGAGCGTGAACAACGATATGATCGTGACCG

ACAACAACGGCGCCGTGAAGTTTCCCCAGCTCTGCAAGTTCTGCGATGT

CAGGTTCAGCACCTGCGATAATCAGAAGTCCTGCATGTCCAACTGCAGC

ATCACCTCCATCTGCGAGAAGCCCCAAGAAGTGTGCGTGGCCGTGTGGC

GGAAAAATGACGAGAACATCACCCTGGAGACCGTGTGTCACGACCCCAA

GCTCCCTTATCACGACTTCATTCTGGAGGACGCTGCCTCCCCCAAATGC

ATCATGAAGGAGAAGAAGAAGCCCGGAGAGACCTTCTTTATGTGTTCCT

GTAGCAGCGACGAGTGTAACGACAACATCATCTTCAGCGAAGAGTACAA

CACCAGCAACCCTGATGGAGGTGGCGGATCCGGAGGTGGAGGTTCTGGT

GGAGGTGGGAGTATTCCTCCCCACGTGCAGAAGAGCGTGAATAATGACA

TGATCGTGACCGATAACAATGGCGCCGTGAAATTTCCCCAGCTGTGCAA

ATTCTGCGATGTGAGGTTTTCCACCTGCGACAACCAGAAGTCCTGTATG

-continued

AGCAACTGCTCCATCACCTCCATCTGTGAGAAGCCTCAGGAGGTGTGCG

TGGCTGTCTGGCGGAAGAATGACGAGAATATCACCCTGGAAACCGTCTG

CCACGATCCCAAGCTGCCCTACCACGATTTCATCCTGGAAGACGCCGCC

AGCCCTAAGTGCATCATGAAAGAGAAAAAGAAGCCTGGCGAGACCTTTT

TCATGTGCTCCTGCAGCAGCGACGAATGCAACGACAATATCATCTTTAG

CGAGGAATACAATACCAGCAACCCCGAC (Human IL-15R α sushi domain)
ATTACATGCCCCCCTCCCATGAGCGTGGAGCACGCCGACATCTGGGTGA

AGAGCTATAGCCTCTACAGCCGGGAGAGGTATATCTGTAACAGCGGCTT

CAAGAGGAAGGCCGGCACCAGCAGCCTCACCGAGTGCGTGCTGAATAAG

GCTACCAACGTGGCTCACTGGACAACACCCTCTTTAAAGTGCATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGAC

CTGCGGCAGGGCATGTTTGCGCAGCTGGTGGCCCAAAATGTTCTGCTG

ATCGATGGGCCCCTGAGCTGGTACAGTGACCCAGGCCTGGCAGGCGTG

TCCCTGACGGGGGGCCTGAGCTACAAAGAGGACACGAAGGAGCTGGTG

GTGGCCAAGGCTGGAGTCTACTATGTCTTCTTTCAACTAGAGCTGCGG

CGCGTGGTGGCCGGCGAGGGCTCAGGCTCCGTTTCACTTGCGCTGCAC

CTGCAGCCACTGCGCTCTGCTGCTGGGGCCGCCGCCCTGGCTTTGACC

GTGGACCTGCCACCCGCCTCCTCCGAGGCTCGGAACTCGGCCTTCGGT

TTCCAGGGCCGCTTGCTGCACCTGAGTGCCGGCCAGCGCCTGGGCGTC

CATCTTCACACTGAGGCCAGGGCACGCCATGCCTGGCAGCTTACCCAG

GGCGCCACAGTCTTGGGACTCTTCCGGGTGACCCCCGAAATCCCAGCC

GGACTCCCTTCACCGAGGTCGGAA

The amino acid sequence of TGFRs137L fusion protein (including the leader sequence) is as follows:

(Signal peptide)
MKWVTFISLLFLFSSAYS (Human TGFβ Receptor II)
IPPHVQKSVNNDMIVTDNNGAVKFPQLCKFCDVRFSTCDNQKSCMSNC

SITSICEKPQEVCVAVWRKNDENITLETVCHDPKLPYHDFILEDAASP

KCIMKEKKKPGETFFMCSCSSDECNDNIIFSEEYNTSNPDGGGGSGGG

GSGGGGSIPPHVQKSVNNDMIVTDNNGAVKFPQLCKFCDVRFSTCDNQ

KSCMSNCSITSICEKPQEVCVAVWRKNDENITLETVCHDPKLPYHDFI

LEDAASPKCIMKEKKKPGETFFMCSCSSDECNDNIIFSEEYNTSNPD (Human IL-15R α sushi domain)
ITCPPPMSVEHADIWVKSYSLYSRERYICNSGFKRKAGTSSLTECVL

NKATNVAHWTTPSLKCIR ((G4S)3 linker)
GGGGSGGGGSGGGGS

-continued (Human CD137L)
REGPELSPDDPAGLLDLRQGMFAQLVAQNVLLIDGPLSWYSDPGLAG

VSLTGGLSYKEDTKELVVAKAGVYYVFFQLELRRVVAGEGSGSVSLA

LHLQPLRSAAGAAALALTVDLPPASSEARNSAFGFQGRLLHLSAGQR

LGVHLHTEARARHAWQLTQGATVLGLFRVTPEIPAGLPSPRSE

In some cases, the leader peptide is cleaved from the intact polypeptide to generate the mature form that may be soluble or secreted.

The TGFR/IL-15RαSu/CD137L and TGFR/TF/IL-15 constructs were cloned into a modified retrovirus expression vectors as described previously (Hughes M S, Yu Y Y, Dudley M E, Zheng Z, Robbins P F, Li Y, et al. Transfer of a TCR gene derived from a patient with a marked antitumor response conveys highly active T-cell effector functions. Hum Gene Ther 2005; 16:457-72), and the expression vectors were transfected into CHO-K1 cells. Co-expression of the two constructs in CHO-K1 cells allowed for formation and secretion of the soluble TGFR/TF/IL-15:TGFR/IL-15RαSu/CD137L protein complex (referred to as TGFRt15-TGFRs137L), which can be purified by anti-TF antibody affinity and other chromatography methods.

Example 85. Production and Characterization of the Exemplary Single-Chain Chimeric Polypeptide 2t2

An exemplary single-chain chimeric polypeptide including a first target-binding domain that binds to an IL-2 receptor, a soluble human tissue factor domain, and a second target-binding domain that binds to an IL-2 receptor was generated (IL-2/TF/IL-2, or 2t2) (FIG. 155). The nucleic acid and amino acid sequences of this single-chain chimeric polypeptide are shown below.

Nucleic Acid Encoding Exemplary Single-Chain Chimeric Polypeptide (IL-2/TF/IL-2) (SEQ ID NO: 109)

(Signal peptide)
ATGAAGTGGGTGACCTTCATCAGCCTGCTGTTCCTGTTCTCCAGCGC

CTACTCC (First IL-2 fragment)
GCCCCCACCTCCTCCTCCACCAAGAAGACCCAGCTGCAGCTGGAGCA

TTTACTGCTGGATTTACAGATGATTTTAAACGGCATCAACAACTACA

AGAACCCCAAGCTGACTCGTATGCTGACCTTCAAGTTCTACATGCCC

AAGAAGGCCACCGAGCTGAAGCATTTACAGTGTTTAGAGGAGGAGCT

GAAGCCCCTCGAGGAGGTGCTGAATTTAGCCCAGTCCAAGAATTTCC

ATTTAAGGCCCCGGGATTTAATCAGCAACATCAACGTGATCGTTTTA

GAGCTGAAGGGCTCCGAGACCACCTTCATGTGCGAGTACGCCGACGA

GACCGCCACCATCGTGGAGTTTTTAAATCGTTGGATCACCTTCTGCC

AGTCCATCATCTCCACTTTAACC (Human tissue factor 219 form)
AGCGGCACAACCAACACAGTCGCTGCCTATAACCTCACTTGGAAGAG

CACCAACTTCAAAACCATCCTCGAATGGGAACCCAAACCCGTTAACC

AAGTTTACACCGTGCAGATCAGCACCAAGTCCGGCGACTGGAAGTCC

AAATGTTTCTATACCACCGACACCGAGTGCGATCTCACCGATGAGAT

-continued

```
CGTGAAAGATGTGAAACAGACCTACCTCGCCCGGGTGTTTAGCTACC

CCGCCGGCAATGTGGAGAGCACTGGTTCCGCTGGCGAGCCTTTATAC

GAGAACAGCCCCGAATTTACCCCTTACCTCGAGACCAATTTAGGACA

GCCCACCATCCAAAGCTTTGAGCAAGTTGGCACAAAGGTGAATGTGA

CAGTGGAGGACGAGCGGACTTTAGTGCGGCGGAACAACACCTTTCTC

AGCCTCCGGGATGTGTTCGGCAAAGATTTAATCTACACACTGTATTA

CTGGAAGTCCTCTTCCTCCGGCAAGAAGACAGCTAAAACCAACACAA

ACGAGTTTTTAATCGACGTGGATAAAGGCGAAAACTACTGTTTCAGC

GTGCAAGCTGTGATCCCCTCCCGGACCGTGAATAGGAAAAGCACCGA

TAGCCCCGTTGAGTGCATGGGCCAAGAAAAGGGCGAGTTCCGGGAG

(Second IL-2 fragment)
GCACCTACTTCAAGTTCTACAAAGAAAACACAGCTACAACTGGAGCA

TTTACTGCTGGATTTACAGATGATTTTGAATGGAATTAATAATTACA

AGAATCCCAAACTCACCAGGATGCTCACATTTAAGTTTTACATGCCC

AAGAAGGCCACAGAACTGAAACATCTTCAGTGTCTAGAAGAAGAACT

CAAACCTCTGGAGGAAGTGCTAAATTTAGCTCAAAGCAAAAACTTTC

ACTTAAGACCCAGGGACTTAATCAGCAATATCAACGTAATAGTTCTG

GAACTAAAGGGATCTGAAACAACATTCATGTGTGAATATGCTGATGA

GACAGCAACCATTGTAGAATTTCTGAACAGATGGATTACCTTTTGTC

AAAGCATCATCTCAACACTAACT
```

Exemplary Single-Chain Chimeric Polypeptide (IL-2/TF/IL-2) (SEQ ID NO: 108)

```
(Signal peptide)
MKWVTFISLLFLFSSAYS

(Human IL-2)
APTSSSTKKTQLQLEHLLLDLQMILNGINNYKNPKLTRMLTFKFYMP

KKATELKHLQCLEEELKPLEEVLNLAQSKNFHLRPRDLISNINVIVL

ELKGSETTFMCEYADETATIVEFLNRWITFCQSIISTLT

(Human Tissue Factor 219)
SGTTNTVAAYNLTWKSTNFKTILEWEPKPVNQVYTVQISTKSGDWKS

KCFYTTDTECDLTDEIVKDVKQTYLARVFSYPAGNVESTGSAGEPLY

ENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFS

VQAVISRTVNRKSTDSPVECMGQEKGEFRE

(Human IL-2)
APTSSSTKKTQLQLEHLLLDLQMILNGINNYKNPKLTRMLTFKFYMP

KKATELKHLQCLEEELKPLEEVLNLAQSKNFHLRPRDLISNINVIVL

ELKGSETTFMCEYADETATIVEFLNRWITFCQSIISTLT
```

The nucleic acid encoding IL-2/TF/IL-2 was cloned into a modified retrovirus expression vector as described previously (Hughes et al., *Hum Gene Ther* 16:457-72, 2005). The expression vector encoding IL-2/TF/IL-2 was transfected into CHO-K1 cells. Expression of the expression vector in CHO-K1 cells allowed for secretion of the soluble IL-2/TF/IL-2 single-chain chimeric polypeptide (referred to as 2t2), which can be purified by anti-TF antibody affinity and other chromatography methods.

IL-2 and 2t2 Promoted IL-2R8 and Common γ Chain Containing 32D8 Cell Proliferation in a Similar Manner To evaluate the IL-2 activity of 2t2, 2t2 was compared with recombinant IL-2 for promoting proliferation of 32Dβ cells that express IL-2RP and common γ chain. IL-2 dependent 32Dβ cells were washed 5 times with IMDM-10% FBS and seeded to the wells at $2\times10^4$ cells/well. Serial dilutions of 2t2 or IL-2 were added to the cells (FIG. 156). Cells were incubated in a $CO_2$ incubator at 37° C. for 3 days. Cell proliferation was detected by adding 10 μl of WST1 to each well on day 3 and incubating for an additional 3 hours in a $CO_2$ incubator at 37° C. The amount of formazan dye produced was analyzed by measuring the absorbance at 450 nm. As shown in FIG. 156, 2t2 and IL-2 activated 32Dβ cells in a similar manner. The $EC_{50}$ of 2t2 and IL-2 was 158.1 pM and 140 pM. respectively.

2t2 Showed Improved Ability to Promote IL-2Rαβγ Containing CTLL-2 Cell Proliferation as Compared to IL-2

To evaluate the IL-2 activity of 2t2, 2t2 was compared with recombinant IL-2 for promoting proliferation of CTLL-2 cells that express IL-2Rα, IL-2RP and common γ chain. IL-2 dependent CTLL-2 cells were washed 5 times with IMDM-10% FBS and seeded to the wells at $2\times10^4$ cells/well. Serial dilutions of 2t2 or IL-2 were added to the cells (FIG. 157). Cells were incubated in a $CO_2$ incubator at 37° C. for 3 days. Cell proliferation was detected by adding 10 μl of WST1 to each well in the day 3 and incubating for an additional 3 hours in a $CO_2$ incubator at 37° C. The amount of formazan dye produced was analyzed by measuring the absorbance at 450 nm. As shown in FIG. 157, 2*t*2 promoted CTLL-2 cell proliferation 4-5-fold stronger than IL-2. The $EC_{50}$ of 2t2 was 123.2 pM and IL-2 was 548.2 pM.

2t2 Suppressed the Increase of the Highfat-Induced Hyperglycemia in $ApoE^{-/-}$ Mice Six-week-old female $ApoE^{-/-}$ mice (Jackson Lab) were fed with standard chow diet or high diet fat containing 21% fat, 0.15% cholesterol, 34.1% sucrose, 19.5% casein, and 15% starch (TD88137, Harlan Laboratories) and maintained in the standard conditions. At week 7, mice fed with high fat diet were randomly assigned into the control group and treatment group. Mice then received either 2t2 (treatment group) or PBS (chow diet group and control group) per subcutaneous injection at a dosage of 3 mg/kg. Three days post dosing, the mice were fasted overnight, and blood samples were collected through retro-orbital venous plexus puncture. Overnight fasting glucose levels were measured using a OneTouch Glucometer. As shown in FIG. 158, the results showed that 2t2 injection effectively suppresses the increase of glucose levels in $ApoE^{-/-}$ mice.

2t2 Significantly Upregulate the Ratio of $CD4^+CD25^+$ $FoxP3^+$ T Regulatory (Treg) Cells in Blood Lymphocytes Six-week-old female $ApoE^{-/-}$ mice (Jackson Lab) were fed with standard chow diet or high diet fat containing 21% fat, 0.15% cholesterol, 34.1% sucrose, 19.5% casein, and 15% starch (TD88137, Harlan Laboratories) and maintained in the standard conditions. At week 7, mice fed with the high fat diet were randomly assigned into control group and treatment group. Mice then received either 2t2 (treatment group) or PBS (chow diet group and control group) per subcutaneous injection at a dosage of 3 mg/kg. Three days after the dosing, overnight fasting blood samples were collected through retro-orbital venous plexus puncture and incubated with ACK lysing buffer (Thermo Fisher Scientific) at 37° C. for 5 minutes. Samples were then resuspended in FACS buffer (1×PBS (Hyclone) with 0.5% BSA (EMD Millipore) and 0.001% sodium azide (Sigma)) and surface stained with FITC-anti-CD4 and APC-anti-CD25 antibodies (BioLegend) for 30 minutes. Surface-stained samples were further fixed and premetallized with Fix/Perm buffer (BioLegend) and intracellular stained with PE-anti-Foxp3 antibody (BioLegend). After staining, cells were washed twice with FACs buffer followed by centrifugation at 1500 RPM for 5 minutes at room temperature. The cells were analyzed by flow cytometry (Celesta-BD Bioscience). As shown in FIG. 159, 2t2 treatment significantly increased Treg populations in blood lymphocytes (3.5%±0.32) compared to the untreated groups (0.4% 0.16 for chow diet group and 0.46%±0.09 for high fat diet group).

Purification Elution Chromatograph of 2t2 from Anti-TF Antibody Affinity Column

2t2 harvested from cell culture was loaded onto the anti-TF antibody affinity column equilibrated with 5 column volumes of PBS. After sample loading, the column was washed with column volumes of PBS, followed by elution with 6 column volumes of 0.1M acetic acid, pH 2.9. A280 elution peak was collected and then neutralized to pH 7.5-8.0 with 1M Tris base. The neutralized sample was then buffer exchanged into PBS using Amicon centrifugal filters with a kDa molecular weight cutoff. As shown in FIG. 160, the anti-TF antibody affinity column bound to 2t2 which contains TF as a fusion domain. The buffer-exchanged protein sample was stored at 2-8° C. for further biochemical analyses and biological activity tests. After each elution, the anti-TF antibody affinity column was stripped using 6 column volumes of 0.1M glycine, pH 2.5. The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Analytical Size Exclusion Chromatography (SEC) Analysis of 2t2

To analyze 2t2 using analytical size exclusion chromatography (SEC), a Superdex 200 Increase 10/300 GL gel filtration column (from GE Healthcare) was connected to an AKTA Avant system (from GE Healthcare). The column was equilibrated with 2 column volumes of PBS. The flow rate was 0.7 mL/min. A sample containing 2t2 in PBS was injected into the Superdex 200 column using a capillary loop, and analyzed by SEC. The SEC chromatograph of the sample is shown in FIG. 161. The SEC results indicated two protein peaks for 2t2.

Reduced SDS-PAGE of 2t2

To determine the purity and molecular weight of the protein, 2t2 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the 2t2 protein undergoes glycosylation after translation in CHO cells, a deglycosylation experiment was conducted using the Protein Deglycosylation Mix II kit from New England Biolabs according to the manufacturer's instructions. FIGS. 162A and 162B show the reduced SDS-PAGE analysis of the sample in non-deglycosylated (lane 1 in red outline) and deglycosylated (lane 2 in yellow outline) state. The results show that the 2t2 protein is glycosylated when expressed in CHO cells. After deglycosylation, the purified sample ran with expected molecular weights (56 kDa) in reduced SDS gel. Lane M was loaded with 10 μL of SeeBlue Plus2 Prestained Standard.

In Vivo Characterization of 2t2

2t2 was subcutaneously injected into C57BL/6 mice at various doses to determine the immunostimulatory activity of 2t2 in vivo. Mice were subcutaneously treated with control solution (PBS) or 2t2 at 0.1, 0.4, 2 and 10 mg/kg. The treated mice were euthanized day 3 post treatment. The mouse spleens were collected and weighed day 3 post treatment. Single splenocyte suspensions were prepared, and the prepared splenocytes were stained for $CD4^+$ T cells, $CD8^+$ T cells and NK cells (with fluorochrome-conjugated anti-CD4, -CD8, and -NK1.1 antibodies), and analyzed by flow cytometry. The results showed that 2t2 was effective at expanding splenocytes based on spleen weight (FIG. 163A) especially at 0.1-10 mg/kg. The percentage of $CD8^+$ T cells were higher compared to control-treated mice (FIG. 163B) at 2 and 10 mg/kg. The percentage of NK cells were higher compared to control-treated mice (FIG. 163B) at all doses tested.

It has been known that IL-2 upregulates CD25 expression by immunocytes. We therefore accessed CD25 expression of $CD4^+$ T cells, $CD8^+$ T cells and NK cells in the 2t2 treated mice. C57BL/6 mice were subcutaneously treated with 2t2 as described in the paragraph above. The splenocytes were stained with fluorochrome-conjugated anti-CD4, -CD8, -CD25 and -NK1.1 monoclonal antibodies. The CD25 expression (MFI) of splenocyte subsets was analyzed by flow cytometry. As shown in FIG. 164, at the doses and time points tested, 2t2 significantly upregulated CD25 expression by $CD4^+$ T cells but not $CD8^+$ T cells or NK cells.

The pharmacokinetics of 2t2 in C57BL/6 mice were also investigated. 2t2 was subcutaneously injected into C57BL/6 mice at 1 mg/kg. The mouse blood was drawn from tail vein at various time points as shown in FIG. 165 and the serum was prepared. 2t2 concentrations were determined with ELISA (Capture: anti-tissue factor antibody; Detection: biotinylated anti-human IL-2 antibody followed by SA-IRP and ABTS substrate). The half-life of 2t2 was 1.83 hours calculated with PK Solutions 2.0 (Summit Research Services).

2t2 Attenuated the Formation of Highfat-Induced Atherosclerotic Plaques in $ApoE^{-/-}$ Mice Six-week-old female $ApoE^{-/-}$ mice (The Jackson Laboratory) were fed with standard chow diet or high diet fat (21% fat, 0.15% cholesterol, 34.1% sucrose, 19.5% casein, and 15% starch) (TD88137, Harlan Laboratories) and maintained in the standard conditions. At week 7, mice fed with high fat diet (HFD) were randomly assigned into control group and treatment group. Mice were then administrated either 2t2 (treatment group) or PBS (chow diet group and control group) subcutaneously at a dosage of 3 mg/kg weekly for 4 weeks. At week 12, all mice were euthanized by isoflurane. Aortas were collected, opened longitudinally and stained with Sudan IV solution (0.5%) using enface method. The percentage of plaque area (red color as shown in FIG. 166A) relative to total aorta area was then quantified with Image J software. FIG. 166A shows a representative view of atherosclerotic plaques from each group. FIG. 166B shows the results of quantitative analysis of atherosclerotic plaques of each group. The percentage of plaque areas in control group (HF Diet) was much higher than the treatment group (HFD+2t2), being 10.28% vs 4.68%.

2t2 Suppresses the Progression of Type 2 Diabetes.

Male BKS.Cg-Dock7$^{m}$+/+Lepr$^{db}$/J (db/db (Jackson Lab)) mice were fed with standard chow diet and received drinking water ad libitum. At the age of six weeks, mice were randomly assigned into control group and treatment group. The treatment group received 2t2 by subcutaneous injection at 3 mg/kg bi-weekly, while control group received vehicle (PBS) only.

Overnight fasting glucose levels were measure weekly using a OneTouch Glucometer. The results showed that 2t2 effectively suppressed the increase of glucose levels in BKS.Cg-Dock7$^{m}$+/+Lepr$^{db}$/J mice (FIG. 167).

2t2 Significantly Upregulates the Ratio of $CD4^{+}CD25^{+}$ $FoxP3^{+}$ T Regulatory Cells in Blood Lymphocytes after the First Injection Male BKS.Cg-Dock7$^{m}$+/+Lepr$^{db}$/J (db/db) (The Jackson Laboratory) mice were fed with standard chow diet and received drinking water ad libitum. At the age of six weeks, mice were randomly assigned into control group and treatment group. The treatment group received 2t2 by subcutaneous injection at 3 mg/kg bi-weekly, while the control group received vehicle (PBS) only. Four days after the first drug injection, overnight fasting blood samples were collected and incubated with ACK lysing buffer (Thermo Fisher Scientific) at 37° C. for 5 minutes. Samples were then resuspended in FACS buffer (1×PBS (Hyclone) with 0.5% BSA (EMD Millipore) and 0.001% sodium azide (Sigma)) and surface stained with FITC-anti-CD4 and APC-anti-CD25 antibodies (BioLegend) for 30 minutes. Surface-stained samples were further fixed and premetallized with Fix/Perm buffer (BioLegend) and intracellular stained with PE-anti-Foxp3 antibody (BioLegend). After staining, cells were washed twice with FACs buffer and were analyzed by flow cytometry (Celesta-BD Bioscience). The percentage of $CD4^{+}CD25^{+}FoxP3^{+}$ Tregs in blood lymphocytes were measured. As shown in FIG. 168, the results showed that 2t2 significantly upregulated the ratio of Tregs in blood lymphocytes. * $p<0.05$.

Example 86. Production and Characterization of the Exemplary Single-Chain Chimeric Polypeptide 15t15

A second exemplary single-chain chimeric polypeptide including a first target-binding domain that binds to an IL-15 receptor, a soluble human tissue factor domain, and a second target-binding domain that binds to an IL-15 receptor was generated (IL-15/TF/IL-15 or 15t15) (FIG. 169). The nucleic acid and amino acid sequences of this single-chain chimeric polypeptide are shown below.

Nucleic Acid Encoding Exemplary Single-Chain Chimeric Polypeptide (IL-15/TF/IL-15) (SEQ ID NO: 115)

```
(Signal peptide)
ATGAAGTGGGTGACCTTCATCAGCCTGCTGTTCCTGTTCTCCAGCGC

CTACTCC

(First IL-15 fragment)
AACTGGGTGAACGTGATCAGCGATTTAAAGAAGATCGAGGATTTAAT

CCAGAGCATGCACATCGACGCCACTCTGTACACTGAGAGCGACGTGC

ACCCTAGCTGCAAGGTGACTGCCATGAAGTGCTTTTTACTGGAGCTG

CAAGTTATCTCTTTAGAGAGCGGCGATGCCAGCATCCACGACACTGT

GGAGAATTTAATCATTTTAGCCAACAACTCTTTAAGCAGCAACGGCA

ACGTGACAGAGAGCGGCTGCAAGGAGTGCGAGGAGCTGGAGGAGAAG

AACATCAAGGAGTTTTTACAGAGCTTCGTGCACATCGTGCAGATGTT

CATCAACACTAGC
```

-continued

```
(Human tissue factor 219 form)
AGCGGCACAACCAACACAGTCGCTGCCTATAACCTCACTTGGAAGAG

CACCAACTTCAAAACCATCCTCGAATGGGAACCCAAACCCGTTAACC

AAGTTTACACCGTGCAGATCAGCACCAAGTCCGGCGACTGGAAGTCC

AAATGTTTCTATACCACCGACACCGAGTGCGATCTCACCGATGAGAT

CGTGAAAGATGTGAAACAGACCTACCTCGCCCGGGTGTTTAGCTACC

CCGCCGGCAATGTGGAGAGCACTGGTTCCGCTGGCGAGCCTTTATAC

GAGAACAGCCCCGAATTTACCCCTTACCTCGAGACCAATTTAGGACA

GCCCACCATCCAAAGCTTTGAGCAAGTTGGCACAAAGGTGAATGTGA

CAGTGGAGGACGAGCGGACTTTAGTGCGGCGGAACAACACCTTTCTC

AGCCTCCGGGATGTGTTCGGCAAAGATTTAATCTACACACTGTATTA

CTGGAAGTCCTCTTCCTCCGGCAAGAAGACAGCTAAAACCAACACAA

ACGAGTTTTTAATCGACGTGGATAAAGGCGAAAACTACTGTTTCAGC

GTGCAAGCTGTGATCCCCTCCCGGACCGTGAATAGGAAAAGCACCGA

TAGCCCCGTTGAGTGCATGGGCCAAGAAAAGGGCGAGTTCCGGGAG

(Second IL-15 fragment)
AACTGGGTGAACGTCATCAGCGATTTAAAGAAGATCGAAGATTTAAT

TCAGTCCATGCATATCGACGCCACTTTATACACAGAATCCGACGTGC

ACCCCTCTTGTAAGGTGACCGCCATGAAATGTTTTTTACTGGAGCTG

CAAGTTATCTCTTTAGAGAGCGGAGACGCTAGCATCCACGACACCGT

GGAGAATTTAATCATTTTAGCCAATAACTCTTTATCCAGCAACGGCA

ACGTGACAGAGTCCGGCTGCAAGGAGTGCGAAGAGCTGGAGGAGAAG

AACATCAAGGAGTTTCTGCAATCCTTTGTGCACATTGTCCAGATGTT

CATCAATACCTCC
```

Exemplary Single-Chain Chimeric Polypeptide (IL-15/TF/IL-15) (SEQ ID NO: 114)

```
(Signal peptide)
MKWVTFISLLFLFSSAYS

(Human IL-15)
NWVNVISDLKKIEDLIQSMHIDATLYTESDVHPSCKVTAMKCFLLEL

QVISLESGDASIHDTVENLIILANNSLSSNGNVTESGCKECEELEEK

NIKEFLQSFVHIVQMFINTS

(Human Tissue Factor 219)
SGTTNTVAAYNLTWKSTNFKTILEWEPKPVNQVYTVQISTKSGDWKS

KCFYTTDTECDLTDEIVKDVKQTYLARVFSYPAGNVESTGSAGEPLY

ENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFS

VQAVIPSRTVNRKSTDSPVECMGQEKGEFRE

(Human IL-15)
NWVNVISDLKKIEDLIQSMHIDATLYTESDVHPSCKVTAMKCFLLEL

QVISLESGDASIHDTVENLIILANNSLSSNGNVTESGCKECEELEEK

NIKEFLQSFVHIVQMFINTS
```

The nucleic acid encoding IL-15/TF/IL-15 was cloned into a modified retrovirus expression vector as described previously (Hughes et al., *Hum Gene Ther* 16:457-72, 2005). The expression vector encoding IL-15/TF/IL-15 was transfected into CHO-K1 cells. Expression of the expression vector in CHO-K1 cells allowed for secretion of the soluble IL-15/TF/IL-15 single-chain chimeric polypeptide (referred to as 15t15), which can be purified by anti-TF antibody affinity and other chromatography methods.

15t15 Promotes IL-2R8 and Common γ Chain Containing 32D8 Cell Proliferation

IL-15 activity of 15t15 was compared with recombinant IL-15 in IL2RP and common γ chain expressed 32Dβ cells. IL-15 dependent 32Dβ cells were washed five times with IMDM-10% FBS and seeded to the wells at $2\times10^4$ cells/well. Serial dilutions of 15t15 or IL-15 were added to the cells (FIG. 170). Cells were incubated in a $CO_2$ incubator at 37° C. for 3 days. Cell proliferation was detected by adding 10 μl of WST1 to each well in the day 3 and incubating for an additional 3 hours in a $CO_2$ incubator at 37° C. The amount of formazan dye produced was analyzed by measuring the absorbance at 450 nm. As shown in FIG. 170, 15t15 promoted 32Dβ cell proliferation less efficiently as compared to IL-15. The $EC_{50}$ of 15t15 and IL-15 was 161.4 pM and 1.6 pM, respectively.

Purification Elution Chromatograph of 15t15 from Anti-TF Antibody Affinity Column 15t15 harvested from cell culture was loaded onto the anti-TF antibody affinity column equilibrated with 5 column volumes of PBS. After sample loading, the column was washed with column volumes of PBS, followed by elution with 6 column volumes of 0.1M acetic acid, pH 2.9. A280 elution peak was collected and then neutralized to pH 7.5-8.0 with 1M Tris base. The neutralized sample was then buffer exchanged into PBS using Amicon centrifugal filters with a kDa molecular weight cutoff. As shown in FIG. 171, the anti-TF antibody affinity column bound to 15t15 which contains TF as a fusion domain. The buffer-exchanged protein sample was stored at 2-8° C. for further biochemical analyses and biological activity tests. After each elution, the anti-TF antibody affinity column was stripped using 6 column volumes of 0.1M glycine, pH 2.5. The column was then neutralized using 5 column volumes of PBS, and 7 column volumes of 20% ethanol for storage. The anti-TF antibody affinity column was connected to a GE Healthcare AKTA Avant system. The flow rate was 4 mL/min for all steps except for the elution step, which was 2 mL/min.

Reduced SDS-PAGE of 15t15

To determine the purity and molecular weight of the protein, 15t15 protein sample purified with anti-TF antibody affinity column was analyzed by sodium dodecyl sulfate polyacrylamide gel (4-12% NuPage Bis-Tris gel) electrophoresis (SDS-PAGE) method under reduced condition. After electrophoresis, the gel was stained with InstantBlue for about 30 min, followed by destaining overnight in purified water.

To verify that the 15t15 protein undergoes glycosylation after translation in CHO cells, a deglycosylation experiment was conducted using the Protein Deglycosylation Mix II kit from New England Biolabs and the manufacturer's instructions. FIGS. 172A and 172B show the reduced SDS-PAGE analysis of the sample in non-deglycosylated (lane 1 in red outline) and deglycosylated (lane 2 in yellow outline) state. The results showed that the 15t15 protein is glycosylated when expressed in CHO cells. After deglycosylation, the purified sample ran with expected molecular weights (50 kDa) in reduced SDS gel. Lane M was loaded with 10 μL of SeeBlue Plus2 Prestained Standard.

Example 87: Stimulation of NK Cells In Vitro by Multi-Chain Chimeric Polypeptide Constructs Alone or in Combination with an Anti-TF Antibody A set of experiments was performed to assess the changes in surface phenotype of NK cells after stimulation with 18t15-12s, 18t15-12s16, and 7t15-21s+anti-TF antibody. In these experiments, fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended at $0.2\times10^6$/mL in a 96-well flat-bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 18t15-12s (100 nM); 18t15-12s16 (100 nM); a mixture of single cytokines rhIL15 (50 ng/mL) (Miltenyi), rhIL18 (50 ng/mL) (Invivogen), and rhIL-12 (10 ng/mL) (Peprotech); 7t15-21s+anti-TF antibody (100 nM-50 nM); 7t15-21s (100 nM); or anti-TF antibody (50 nM) at 37° C. and 5% $CO_2$ for 16 hours. The next day, the cells were harvested and surface stained for 30 minutes for CD56, CD16, CD25, CD69, CD27, CD62L, NKp30, and NKp44. After surface staining, the cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIG. 173 shows that overnight incubation of purified NK cells with 18t15-12s, 18t15-12s16, and 7t15-21s+anti-TF antibody resulted in an increase in the percentage of cells expressing CD25, CD69, NKp44, and NKp30 activation markers and a decrease in the percentage of cells expressing CD62L. All activation marker data is from $CD56^+$ gated lymphocytes.

A set of experiments was performed to assess changes in the surface phenotype of lymphocyte populations after stimulation with 18t15-12s, 18t15-12s16, and 7t15-21s. In these experiments, fresh human leukocytes were obtained from the blood bank. Peripheral blood lymphocytes were isolated with the Ficoll-PAQUE Plus (GE Healthcare) density gradient media. The cells were counted and resuspended at $0.2\times10^6$/mL in a 96-well flat-bottom plate in 0.2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 18t15-12s (100 nM); 18t15-12s16 (100 nM), a mixture of single cytokines rhIL15 (50 ng/mL) (Miltenyi), rhIL18 (50 ng/mL) (Invivogen), and rhIL-12 (10 ng/mL) (Peprotech); 7t15-21s (100 nM)+anti-TF antibody (50 nM); 7t15-21s (100 nM); or anti-TF antibody (50 nM) at 37° C. and 5% $CO_2$ for 16 hours. The next day, the cells were harvested and surface stained for 30 minutes for CD4 or CD8, CD62L, and CD69. After surface staining, cells were washed (1500 RPM for 5 minutes at room temperature) in FACS buffer (1×PBS (Hyclone) with 0.5% BSA (EMD Millipore) and 0.001% sodium azide (Sigma)). After two washes, the cells were analyzed by flow cytometry (Celesta-BD Bioscience). FIG. 174 shows that overnight incubation of purified lymphocyte populations (CD4 and CD8 T cells)

with 18t15-12s, 18t15-12s16, or 7t15-21s+anti-TF antibody resulted in an increase in the percentage of CD8 and CD4 T cells expressing CD69. Additionally, incubation with 7t15-21s+anti-TF antibody resulted in an increase in the percentage of CD8 and CD4 T cells expressing CD62L (FIG. 174).

Example 88: Induction of Proliferation of NK Cells In Vitro by 7t15-21s and Anti-TF Antibody A set of experiments was performed to determine the effect of 7t15-21s or the combination of 7t15-21s+anti-TF antibody on immune cell proliferation. In these experiments, fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APC-Fire750 antibodies (BioLegend). The cells were counted and resuspended in $2\times10^6$/mL in a 24 well flat bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 7t15-21s (100 nM), 7t15-21s+anti-TF antibody (IgG1 Ab, 50 nM) or 7t15-21s (100 nM)+anti-TF antibody IgG4 (50 nM) for 5 days. After every 2 days, the cells were resuspended at $2\times10^6$/mL with fresh media with the multi-chain chimeric polypeptides and in some instances, the anti-TF antibodies described mentioned above. After 5 days, cells were counted using trypan blue to access the fold-expansion (Data shown for 3 healthy donors). FIG. 175 shows 7t15-21s+anti-TF antibody treatment provided a greater fold-increase in NK cell expansion than treatment with 7t15-21s alone or 7t15-21s+anti-TF antibody IgG4.

A set of experiments was performed to determine NK proliferation following treatment with the combination of 7t15-21s+anti-TF antibody. In these experiments, fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended in $2\times10^6$/mL in a 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 7t15-21s (100 nM) and anti-TF antibody (50 nM) for up to 15 days. After every 2 days, cells were resuspended at $2\times10^6$/mL with fresh media containing 100 nM 7t15-21s and 50 nM of anti-TF antibody. As the volume of the cultures increased, the cells were transferred to higher volume flasks. At the indicated time points, the cells were counted using trypan blue to access the fold-expansion (data shown for 1 healthy donor). FIG. 176 shows that 7t15-21s+anti-TF antibody treatment provided a >200-fold increase in NK cell expansion over 2 weeks in culture.

A set of experiments was performed to determine changes in the cell surface phenotype of NK cells expanded following treatment with 7t15-21s+anti-TF antibody. In these experiments, fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended in $2\times10^6$/mL in a 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 7t15-21s (100 nM) and anti-TF antibody (50 nM) for 15 days. After every 2 days, the cells were resuspended at $2\times10^6$/mL with fresh media containing 100 nM 7t15-21s and 50 nM of anti-TF antibody. As the volume of the cultures increased, the cells were transferred to higher volume flasks. To assess the change in the phenotype of NK cells, expanded cells were stained with antibodies for cell-surface CD56, CD16, CD25, CD69, CD62L, and CD57 (BioLegend). After surface staining, the cells were washed (1500 RPM for 5 minutes at room temperature) in FACS buffer (1×PBS (Hyclone) with 0.5% BSA (EID Millipore) and 0.001% sodium azide (Sigma)). After two washes, the cells were analyzed by flow cytometry (Celesta-BD Bioscience). The cell surface phenotype of NK cells on Day 0 and Day 15 were compared. FIG. 177 shows that incubation of NK cells with 7t15-21s+anti-TF antibody resulted in an increase in the percentage of $CD16^+CD56^+$ NK cells expressing CD25 and CD69, and a decrease in the percentage of $CD16^+CD56^+$ NK cells expressing CD62L and CD57.

Example 89: Induction of Proliferation of Immune Cells In Vivo

A set of experiments was performed to determine the effect 7t15-21s+anti-TF antibody-expanded NK cells in NSG mice following treatment with 7t15-21s, TGFRt15-TGFRs, and 2t2. In these experiments, fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APCFire750 antibodies (BioLegend). The cells were counted and resuspended in $2\times10^6$/mL in a 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with: 7t15-21s (100 nM) and anti-TF antibody (50 nM) for 15 days. After every 2 days, the cells were resuspended at $2\times10^6$/mL with fresh media containing 100 nM 7t15-21s and 50 nM of anti-TF antibody. As the volume of the cultures increased, the cells were transferred to higher volume flasks. The cells were counted using trypan blue to access the fold-expansion. 7t15-21s+anti-TF antibody-expanded NK cells were washed three times in warm HBSS Buffer (Hyclone) at 1000 RPM for 10 minutes at room temperature. The 7t15-21s+anti-TF antibody-expanded-NK cells were resuspended in $10\times10^6$/0.2 mL HBSS buffer and injected intravenously into the tail vein of NSG mice (NOD scid gamma mouse) (Jackson Laboratories). The transferred NK cells were supported every 48 hours with either 7t15-21s (10 ng/dose, i.p.), TGFRt15-TGFRs (10 ng/dose, i.p.) or 2t2 (10 ng/dose, i.p.) for up to 21 days. Engraftment and persistence of the human 7t15-21s+anti-TF antibody-expanded NK cells were measured every week in blood staining for hCD45, mCD45, hCD56, hCD3, and hCD16 antibodies by flow cytometry (Celesta-BD Bioscience) (Data represent 3 mice per group). FIG. 178 indicates that treatment of mice bearing adoptively-transferred 7t15-21s+ anti-TF antibody-expanded NK cells with 7t15-21s-, TGFRt15-TGFRs-, or 2t2-induced expansion and persistence of the adoptively transferred NK cells compared to control treated mice.

Example 90: NK-Mediated Cytotoxicity Following Treatment with Multi-Chain Construct+Anti-TF Antibody A set of experiments was performed to determine the effective killing of chemical-induced senescent human fibroblasts by 7t15-21s+anti-TF antibody-expanded NK cells. In these experiments, human lung fibroblasts (IMR-90 and WI-38) were treated with doxorubicin (0.8 μM) for 48 hours. The cells were rested for 48 hours and then treated with doxorubicin (0.8 μM) again for 48 hours. Doxorubicin-containing culture medium was changed and the cells were rested in culture medium for 7 days. FIG. 179A shows beta galactosidase staining confirming senescence induction. NK cells isolated from healthy donors were expanded as follows: NK cells were treated with 7t15-21s (100 nM) and anti-TF antibody (50 nM) for 15 days. After every 2 days, cells were resuspended at $2\times10^6$/mL with fresh media containing 100 nM of 7t15-21s and 50 nM of anti-TF antibody. As the volume of the cultures increased, the cells were transferred to higher volume flasks. The cells were counted using trypan blue to access the fold-expansion. On the day of experiment, the target cells were trypsinized, labeled with Cell Trace Violet (CTV), and added to expanded NK cells at an Effector (NK):Target ratio (ET) of 4:1. The cell mixture was incubated for 20 hours. Non-senescent target fibroblast cells and untreated senescent human fibroblasts were included as controls. After incubation, the cells were trypsinized, washed, and resuspended in Propidium Iodide (PI) solution. The cytotoxicity of the 7t15-21s+anti-TF antibody-expanded NK cells against the chemical-induced senescent human fibroblasts was accessed by flow cytometry based on PI staining of the CTV-labeled cells. FIG. 179B shows percent of dead ($PI^+$) target cells for non-senescent cells (left two bars) and for senescent cells (right two bars). The results demonstrate that 7t15-21s expanded human NK cells effectively kill non-senescent and senescent cells (FIG. 179B).

A set of experiments was performed to assess the effective killing of UV-induced senescent human fibroblasts by 7t15-21s+anti-TF antibody-expanded NK cells. In these experiments, human foreskin fibroblasts (HFF) were grown in 48-well plates ($0.1\times10^6$ cells/well) overnight and treated with ultraviolet (UV) B light (3250J/$m^2$) twice a day for 5 days. The culture medium was changed every 3 days. After UV exposure, the cells were kept for 2 days, trypsinized, and transferred to T175 flask. After 4 days, the cells were trypsinized and beta galactosidase staining and gene expression (senescence markers and NK ligand) analysis was performed to confirm induction of senescence. FIG. 180A shows beta galactosidase staining confirming the induction of senescence. FIG. 180B shows gene expression for senescence markers and an NK ligand, which further confirm the induction of senescence.

To assess killing of UV-induced senescent human fibroblasts, NK cells isolated from healthy donors were expanded as follows: NK cells were treated with 7t15-21s (100 nM) and anti-TF antibody (50 nM) for 15 days. After every 2 days, the cells were resuspended at $2\times10^6$/mL with fresh media containing 100 nM of 7t15-21s and 50 nM of anti-TF antibody. As the volume of the cultures increased, the cells were transferred to higher volume flasks. The cells were counted using trypan blue to access the fold-expansion. On the day of experiment, target cells (UV-induced senescent human fibroblasts) were trypsinized, labeled with Cell Trace Violet (CTV), and added to expanded NK cells at an Effector (NK):Target (HFF) ratio of 4:1. The cell mixture was incubated for 10 hours. Untreated target cells were included as a control. After incubation, the cells were trypsinized, washed, and resuspended in propidium iodide (PI) solution and analyzed by flow cytometry. FIG. 180C shows the percentage of dead (PI+) target cells for non-senescent cells (two left bars) and for senescent cells (two right bars). The results demonstrate that 7t15-21s-expanded human NK cells effectively kill non-senescent and senescent cells.

Example 91: Activation and Proliferation of NK Cells In Vitro

Fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APC-Fire750 antibodies (BioLegend). The cells were counted and resuspended at $2\times10^6$/mL in 24-well flat-bottom plates in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone).

The cells were stimulated with the following molecules: 7t15-21s (100 nM), 7t15-21s (100 nM)+anti-TF antibody (IgG1 Ab, 50 nM), or 7t15-21s (100 nM)+anti-TF antibody (IgG4 Ab, 50 nM) for 5 days. After every 2 days, the cells were resuspended at $2\times10^6$/mL with fresh media with the supplemented molecules. After 5 days, the cells were counted using trypan blue to access the fold-expansion (data shown for 3 healthy donors). The results showed that the 7t15-21s+anti-TF antibody (IgG1) treatment provided a greater fold increase in NK cell expansion than treatment with 7t15-21s alone or with 7t15-21s+anti-TF antibody (IgG4) (FIG. 181).

Fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APC-Fire750 antibodies (BioLegend). The cells were counted and resuspended at $2\times10^6$/mL in 24-well flat-bottom plate in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone). The cells were stimulated with either 7t15-21s (100 nM) and anti-TF antibody (IgG1) (50 nM), or with 7t15-21s137L short version (41BBs) (100 nM) and anti-TF antibody (IgG1) (50 nM) for up to 13 days. After every 2 days, the cells were resuspended at $2\times10^6$/mL with fresh media with supplemented molecules. As the volume of the cultures increased, the cells were transferred to higher volume flasks. At the indicated time points as shown in FIG. 182, the cells were counted using trypan blue to assess the fold-expansion (data shown for 3 healthy donors). The results showed that the 7t15-21s+anti-TF antibody (IgG1) treatment provided a >30-fold increase in NK cell expansion over 13 days in culture (FIG. 182).

Example 92: Treatment of a Subject Having a Cancer

Daudi tumor cells (Human Burkitt's lymphoma) (ATCC) were cultured in complete media (RPMI 1640 (Gibco)

supplemented with 2 mM L-glutamine (Thermo Life Technologies), penicillin (Thermo Life Technologies), streptomycin (Thermo Life Technologies), and 10% FBS (Hyclone)). Daudi cells were washed three times in warm HBSS Buffer (Hyclone) at 1000 RPM for 10 minutes at room temperature. The cells were resuspended in $10\times10^6$/0.2 mL HBSS buffer and injected intravenously into the tail vein of NSG mice (NOD scid gamma mouse) (The Jackson Laboratory). After day 10, bone marrow was harvested from untreated NSG mice to evaluate tumor cell engraftment. Engraftment of Daudi cells in bone marrow was verified by flow cytometry (Celesta-BD Bioscience) using PE-conjugated anti-human HLA-DR antibody (BioLegend).

Fresh human leukocytes were obtained from the blood bank and $CD56^+$ NK cells were isolated with the RosetteSep/human NK cell reagent (StemCell Technologies). The purity of NK cells was >90% and confirmed by staining with CD56-BV421, CD16-BV510, CD25-PE, and CD69-APC-Fire750 antibodies (BioLegend). The cells were counted and resuspended at $2\times10^6$/mL in 24-well flat-bottom plates in 2 mL of complete media (RPMI 1640 (Gibco) supplemented with 2 mM L-glutamine (Thermo Life Technologies), penicillin (Thermo Life Technologies), streptomycin (Thermo Life Technologies), and 10% FBS (Hyclone)). The cells were stimulated with 7t15-21s (100 nM) and anti-TF antibody (IgG1) (50 nM) for 15 days. After every 2 days, the cells were resuspended at $2\times10^6$/mL with fresh media with supplemented molecules. As the volume of the cultures increased, the cells were transferred to higher volume flasks. The cells were counted using trypan blue to assess the fold-expansion.

The 7t15-21s+anti-TF antibody (IgG1)-expanded NK cells were washed three times in warm HBSS Buffer (Hyclone) at 1000 RPM for 10 minutes at room temperature. The NK cells were resuspended in $10\times10^6$/0.2 mL HBSS buffer and injected intravenously into the tail vein of NSG mice bearing Daudi tumors on day 10. The transferred NK cells were supported every 48 hours with 2t2 (10 ng/dose, i.p.) for up to 7 days. After day 7 post-NK cell transfer, the percentage of HLA-DR+Daudi cells in the bone marrow was determined by flow cytometry. The data show that adoptive transfer of the 7t15-21s+anti-TF antibody (IgG1)-expanded NK cells resulted in a decrease in Daudi tumor cells in the bone marrow of NSG mice (FIG. 183).

Example 93: Improvement of the Texture and/or Appearance and/or Hair

The $ApoE^{-/-}$ mice were fed with chow diet (shown as "CD" in FIG. 184A) or Western diet (shown as "WD" in FIGS. 184B-E) from Day 0. On Day 44 (Week 7), the mice were administrated subcutaneously with PBS (FIGS. 184A and 184B), 3 mg/kg of TGFRt15-TGFRs (FIG. 184C), 2t2 (FIG. 195D), or anti-TF antibody (IgG4) (FIG. 184E). The pictures were taken one week after treatment on Day 51 (Week 8). Compared to the PBS control group (FIG. 184B), the skin texture was significantly improved in mice fed with a Western diet and treated with 2t2 or TGFRt15-TGFRs (FIGS. 184C and 184D).

Example 94: Tissue Factor Coagulation Assays Following Treatment with Single-Chain or Multi-Chain Chimeric Polypeptides A set of experiments was performed to assess blood coagulation following treatment with single-chain or multi-chain chimeric polypeptides. To initiate the blood coagulation cascade pathway, tissue factor (TF) binds to Factor VIIa (FVIIa) to form a TF/FVIIa complex. The TF/FVIIa complex then binds Factor X (FX) and converts FX to FXa.

Factor VIIa (FVIIa) Activity Assay

One assay to measure blood coagulation involves measuring Factor VIIa (FVIIa) activity. This type of assay requires the presence of tissue factor and calcium. The TF/FVIIa complex activity can be measured by a small substrate or by a natural protein substrate, for example, Factor X (FX). When FX is used as a substrate, phospholipids are also required for TF/FVIIa activity. In this assay, FVIIa activity is determined with FVIIa-specific chromogenic substrate S-2288 (Diapharma, West Chester, OH). The color change of the S-2288 substrate can be measured spectrophotometrically and is proportional to the proteolytic activity of FVIIa (e.g., the TF/FVIIa complex).

In these experiments, the FVIIa activity of the following groups were compared: the 219-amino acid extracellular domain of tissue factor domain ($TF_{219}$), a multi-chain chimeric polypeptide with a wild-type tissue factor domain, and a multi-chain chimeric polypeptide with a mutant tissue factor domain. The chimeric polypeptides containing mutant tissue factor molecules were constructed with mutations to the TF domain at amino acid sites: Lys20, Ile22, Asp58, Arg135, and Phe140.

In order to assess activity of FVIIa, FVIIa, and $TF_{219}$ or a $TF_{219}$-containing multi-chain chimeric polypeptide were mixed at an equal molar concentration (10 nM) in all wells of a 96-well ELISA plate in a total volume of 70 μL. After incubation for 10 minutes at 37° C., 10 μL of 8 mM 5-2288 substrate was added to start the reaction. The incubation was then kept at 37° C. for 20 minutes. Finally, color change was monitored by reading absorbance at 405 nm. The OD values of different TF/VIIa complexes are shown in Table 1 and Table 2. Table 1 shows a comparison of $TF_{219}$, 21t15-21s wild-type (WT) and 21t15-21s mutant (Mut). Table 2 shows a comparison of TF219,21t15-TGFRs wild-type (WT), and 21t15-TGFRs mutant (Mut). These data show that TF219-containing multi-chain chimeric polypeptides (e.g., 21t15-21s-WT, 21t15-21s-Mut, 21t15-TGFRS-WT, and 21t15-TGFRS-Mut) have lower FVIIa activity than TF219 when the chromogenic S-2288 was used as a substrate. Notably, the multi-chain chimeric polypeptides containing TF219 mutations showed much lower FVIIa activity when compared to multi-chain chimeric polypeptides containing wild type TF219.

TABLE 1

| FVIIa activity | |
|---|---|
| Molecule | OD value at 405 nm |
| $TF_{219}$ | 0.307 |
| 21t15/21S-WT | 0.136 |
| 21t15/21S-Mut | 0.095 |

WT: wild type of $TF_{219}$,

Mut: $TF_{219}$ containing mutations.

TABLE 2

| FVIIa activity | |
|---|---|
| Molecule | OD value at 405 nm |
| $TF_{219}$ | 0.345 |
| 21t15/TGFRS-WT | 0.227 |
| 21t15/TGFRS-Mut | 0.100 |

WT: wild type of $TF_{219}$,
Mut: $TF_{219}$ containing mutations.

Factor X (FX) Activation Assay

An additional assay to measure blood coagulation involves measuring activation of Factor X (FX). Briefly, TF/VIIa activates blood coagulation Factor X (FX) to Factor Xa (FXa) in the presence of calcium and phospholipids. $TF_{243}$, which contains the transmembrane domain of TF, has much higher activity in activating FX to FXa than $TF_{219}$, which does not contain the transmembrane domain. TF/VIIa dependent activation of FX is determined by measuring FXa activity using an FXa-specific chromogenic substrate S-2765 (Diapharma, West Chester, OH). The color change of S-2765 can be monitored spectrophotometrically and is proportional to the proteolytic activity of FXa.

In these experiments, FX activation with a multi-chain chimeric polypeptide (18t15-12s, mouse (m)21t15, 21t15-TGFRs, and 21t15-7s) was compared with a positive control (Innovin) or $TF_{219}$. $TF_{219}$ (or $TF_{219}$-containing multi-chain chimeric polypeptides)/FVIIa complexes were mixed at an equal molar concentration (0.1 nM each) in a volume of 50 μL in round bottom wells of a 96-well ELISA plate, after which 10 μL of 180 nM FX was added. After 15 minutes of incubation at 37° C., during which time FX was converted to FXa, 8 μL of 0.5 M EDTA (which chelates calcium and thus terminates FX activation by TF/VIIa) was added to each well to stop FX activation. Next, 10 μL of 3.2 mM S-2765 substrate was added to the reaction mixture. Immediately, the plate absorbance was measured at 405 nm and was recorded as the absorbance at time 0. The plate was then incubated for 10-20 minutes at 37° C. The color change was monitored by reading absorbance at 405 nm following the incubation. Results of FX activation as measured by FXa activity using chromogenic substrate S-2765 are shown in FIG. 185. In this experiment, Innovin, which is a commercial prothrombin reagent containing lipidated recombinant human $TF_{243}$, was used as a positive control for FX activation. Innovin was reconstituted with purified water to about 10 nM of $TF_{243}$. Next, 0.1 nM TF/VIIa complex was made by mixing an equal volume of 0.2 nM of FVIIa with 0.2 nM of Innovin. Innovin demonstrated very potent FX activation activity, while $TF_{219}$ and $TF_{219}$-containing multi-chain chimeric polypeptides had very low FX activation activity, confirming that $TF_{219}$ is not active in a TF/FVIIa complex for activating natural substrate FX in vivo.

Prothrombin Time Test

A third assay to measure blood coagulation is the prothrombin time (PT) test, which measures blood clotting activity. Here, the PT test was performed using commercially available normal human plasma (Ci-Trol Coagulation Control, Level I). For a standard PT test, clot reactions were initiated by addition of Innovin, a lipidated recombinant human $TF_{243}$, in the presence of calcium. Clotting time was monitored and reported by STart PT analyzer (Diagnostica Stago, Parsippany, N.J.). PT assays were started by injecting 0.2 mL of various dilutions of Innovin diluted in PT assay buffer (50 mM Tris-HCl, pH 7.5, 14.6 mM $CaCl_2$), 0.1% BSA) into cuvettes containing 0.1 mL of normal human plasma prewarmed at 37° C. In the PT assay, shorter PT time (clotting time) indicates a higher TF-dependent clotting activity while longer PT (clotting time) means lower TF-dependent clotting activity.

As seen in FIG. 186, addition of different amounts of Innovin (e.g., Innovin reconstituted with purified water equivalent to 10 nM of lipidated recombinant human $TF_{243}$ was considered to be 100% Innovin) to the PT assay demonstrated a dose-response relationship, where lower concentrations of $TF_{243}$ resulted in a longer PT time (lower clotting activity). For example, 0.001% Innovin had a PT time greater than 110 seconds, which was almost the same as buffer alone.

In another experiment, the PT test was conducted on $TF_{219}$ and multi-chain chimeric polypeptides including: 18t15-12s, 7t15-21s, 21t15-TGFRs-WT, and 21t15-TGFRs-Mut. FIG. 187 show that $TF_{219}$ and $TF_{219}$-containing multi-chain chimeric polypeptides (at a concentration of 100 nM) had prolonged PT times indicating extremely low or no clotting activity.

Studies were also conducted to evaluate whether incubating the multi-chain chimeric polypeptides in the presence of other cells carrying receptors for the cytokine components of the multi-chain chimeric polypeptide (32Dβ or human PBMCs) would affect the clotting time in the PT assay. To examine whether cells that express IL-15 receptor (32Dβ cells) or IL-15 and IL-21 receptors (PBMCs) would bind IL-15-containing multi-chain chimeric polypeptides to mimic natural TF as a cellular FVIIa receptor, $TF_{219}$-containing multi-chain chimeric polypeptides (at a concentration of 100 nM for each molecule) were diluted in the PT assay buffer and preincubated with 32Dβ cells (at $2\times10^5$ cells/mL) or PBMC (at $1\times10^5$ cells/mL) for 20-30 minutes at room temperature. The PT assay was then conducted as described above. FIGS. 188 and 189 shows that $TF_{219}$ and $TF_{219}$-containing multi-chain chimeric polypeptides mixed with 32Dβ cells (FIG. 188) or PBMC (FIG. 189) at a final concentration of 100 nM had prolonged PT times similar to 0.001-0.01% Innovin (equivalent to 0.1 pM to 1.0 pM of $TF_{243}$). Expressed in percentage of relative $TF_{243}$ activity, $TF_{219}$-containing multi-chain chimeric polypeptides had 100,000 to 1,000,000 times lower TF dependent clotting activity when compared to Innovin. This demonstrated that $TF_{219}$-containing multi-chain chimeric polypeptides had extremely low or no TF-dependent clotting activity, even while the molecules were bound to an intact cell membrane surface, such as 32Dβ or PBMCs.

Example 95: Characterization of 7t15-21s137L (Long Version)

The nucleic acid sequence of the 7t15 construct (including signal peptide sequence) is as follows (SEQ ID NO: 144):

```
(Signal peptide)
ATGAAGTGGGTGACCTTCATCAGCCTGCTGTTCCTGTTCTCCAGCGC

CTACTCC

(Human IL7)
GATTGCGACATCGAGGGCAAGGACGGCAAGCAGTACGAGAGCGTGCT

GATGGTGTCCATCGACCAGCTGCTGGACAGCATGAAGGAGATCGGCT

CCAACTGCCTCAACAACGAGTTCAACTTCTTCAAGCGGCACATCTGC

GACGCCAACAAGGAGGGCATGTTCCTGTTCAGGGCCGCCAGGAAACT
```

-continued

GCGGCAGTTCCTGAAGATGAACTCCACCGGCGACTTCGACCTGCACC

TGCTGAAGGTGTCCGAGGGCACCACCATCCTGCTGAACTGCACCGGA

CAGGTGAAGGGCCGGAAACCTGCTGCTCTGGGAGAGGCCCAACCCAC

CAAGAGCCTGGAGGAGAACAAGTCCCTGAAGGAGCAGAAGAAGCTGA

ACGACCTGTGCTTCCTGAAGAGGCTGCTGCAGGAGATCAAGACCTGC

TGGAACAAGATCCTGATGGGCACCAAGGAGCAT (Human Tissue Factor 219)
AGCGGCACAACCAACACAGTCGCTGCCTATAACCTCACTTGGAAGAG

CACCAACTTCAAAACCATCCTCGAATGGGAACCCAAACCCGTTAACC

AAGTTTACACCGTGCAGATCAGCACCAAGTCCGGCGACTGGAAGTCC

AAATGTTTCTATACCACCGACACCGAGTGCGATCTCACCGATGAGAT

CGTGAAAGATGTGAAACAGACCTACCTCGCCCGGGTGTTTAGCTACC

CCGCCGGCAATGTGGAGAGCACTGGTTCCGCTGGCGAGCCTTTATAC

GAGAACAGCCCCGAATTTACCCCTTACCTCGAGACCAATTTAGGACA

GCCCACCATCCAAAGCTTTGAGCAAGTTGGCACAAAGGTGAATGTGA

CAGTGGAGGACGAGCGGACTTTAGTGCGGCGGAACAACACCTTTCTC

AGCCTCCGGGATGTGTTCGGCAAAGATTTAATCTACACACTGTATTA

CTGGAAGTCCTCTTCCTCCGGCAAGAAGACAGCTAAAACCAACACAA

ACGAGTTTTTAATCGACGTGGATAAAGGCGAAAACTACTGTTTCAGC

GTGCAAGCTGTGATCCCCTCCCGGACCGTGAATAGGAAAAGCACCGA

TAGCCCCGTTGAGTGCATGGGCCAAGAAAAGGGCGAGTTCCGGGAG (Human IL-15)
AACTGGGTGAACGTCATCAGCGATTTAAAGAAGATCGAAGATTTAAT

TCAGTCCATGCATATCGACGCCACTTTATACACAGAATCCGACGTGC

ACCCCTCTTGTAAGGTGACCGCCATGAAATGTTTTTTACTGGAGCTG

CAAGTTATCTCTTTAGAGAGCGGAGACGCTAGCATCCACGACACCGT

GGAGAATTTAATCATTTTAGCCAATAACTCTTTATCCAGCAACGGCA

ACGTGACAGAGTCCGGCTGCAAGGAGTGCGAAGAGCTGGAGGAGAAG

AACATCAAGGAGTTTCTGCAATCCTTTGTGCACATTGTCCAGATGTT

CATCAATACCTCC

The amino acid sequence of 7t15 fusion protein (including the leader sequence) is as follows (SEQ ID NO: 143):

(Signal peptide)
MKWVTFISLLFLFSSAYS (Human IL7)
DCDIEGKDGKQYESVLMVSIDQLLDSMKEIGSNCLNNEFNFFKRHIC

DANKEGMFLFRAARKLRQFLKMNSTGDFDLHLLKVSEGTTILLNCTG

QVKGRKPAALGEAQPTKSLEENKSLKEQKKLNDLCFLKRLLQEIKTC

WNKILMGTKEH (Human Tissue Factor 219)
SGTTNTVAAYNLTWKSTNFKTILEWEPKPVNQVYTVQISTKSGDWKS

KCFYTTDTECDLTDEIVKDVKQTYLARVFSYPAGNVESTGSAGEPLY

-continued

ENSPEFTPYLETNLGQPTIQSFEQVGTKVNVTVEDERTLVRRNNTFL

SLRDVFGKDLIYTLYYWKSSSSGKKTAKTNTNEFLIDVDKGENYCFS

VQAVIPSRTVNRKSTDSPVECMGQEKGEFRE (Human IL-15)
NWVNVISDLKKIEDLIQSMHIDATLYTESDVHPSCKVTAMKCFLLEL

QVISLESGDASIHDTVENLIILANNSLSSNGNVTESGCKECEELEEK

NIKEFLQSFVHIVQMFINTS

The nucleic acid sequence of the 21s137L construct (including signal peptide sequence) is as follows (SEQ ID NO: 172):

(Signal peptide)
ATGAAGTGGGTGACCTTCATCAGCCTGCTGTTCCTGTTCTCCAGCGC

CTACTCC (Human IL-21)
CAGGGCCAGGACAGGCACATGATCCGGATGAGGCAGCTCATCGACAT

CGTCGACCAGCTGAAGAACTACGTGAACGACCTGGTGCCCGAGTTTC

TGCCTGCCCCCGAGGACGTGGAGACCAACTGCGAGTGGTCCGCCTTC

TCCTGCTTTCAGAAGGCCCAGCTGAAGTCCGCCAACACCGGCAACAA

CGAGCGGATCATCAACGTGAGCATCAAGAAGCTGAAGCGGAAGCCTC

CCTCCACAAACGCCGGCAGGAGGCAGAAGCACAGGCTGACCTGCCCC

AGCTGTGACTCCTACGAGAAGAAGCCCCCCAAGGAGTTCCTGGAGAG

GTTCAAGTCCCTGCTGCAGAAGATGATCCATCAGCACCTGTCCTCCA

GGACCCACGGCTCCGAGGACTCC (Human IL-15R α sushi domain)
ATTACATGCCCCCCTCCCATGAGCGTGGAGCACGCCGACATCTGGGT

GAAGAGCTATAGCCTCTACAGCCGGGAGAGGTATATCTGTAACAGCG

GCTTCAAGAGGAAGGCCGGCACCAGCAGCCTCACCGAGTGCGTGCTG

AATAAGGCTACCAACGTGGCTCACTGGACAACACCCTCTTTAAAGTG

CATCCGG ((G4S)3 linker)
GGCGGTGGAGGATCCGGAGGAGGTGGCTCCGGCGGCGGAGGATCT (Human CD137L)
CGCGAGGGTCCCGAGCTTTCGCCCGACGATCCCGCCGGCCTCTTGGA

CCTGCGGCAGGGCATGTTTGCGCAGCTGGTGGCCCAAAATGTTCTGC

TGATCGATGGGCCCCTGAGCTGGTACAGTGACCCAGGCCTGGCAGGC

GTGTCCCTGACGGGGGGCCTGAGCTACAAAGAGGACACGAAGGAGCT

GGTGGTGGCCAAGGCTGGAGTCTACTATGTCTTCTTTCAACTAGAGC

TGCGGCGCGTGGTGGCCGGCGAGGGCTCAGGCTCCGTTTCACTTGCG

CTGCACCTGCAGCCACTGCGCTCTGCTGCTGGGGCCGCCGCCCTGGC

TTTGACCGTGGACCTGCCACCCGCCTCCTCCGAGGCTCGGAACTCGG

CCTTCGGTTTCCAGGGCCGCTTGCTGCACCTGAGTGCCGGCCAGCGC

CTGGGCGTCCATCTTCACACTGAGGCCAGGGCACGCCATGCCTGGCA

GCTTACCCAGGGCGCCACAGTCTTGGGACTCTTCCGGGTGACCCCCG

AAATCCCAGCCGGACTCCCTTCACCGAGGTCGGAA

The amino acid sequence of 21s137L fusion protein (including the leader sequence) is as follows (SEQ ID NO: 171):

```
(Signal peptide)
MKWVTFISLLFLFSSAYS

(Human IL-21)
QGQDRHMIRMRQLIDIVDQLKNYVNDLVPEFLPAPEDVETNCEWSAF

SCFQKAQLKSANTGNNERIINVSIKKLKRKPPSTNAGRRQKHRLTCP

SCDSYEKKPPKEFLERFKSLLQKMIHQHLSSRTHGSEDS

(Human IL-15R α sushi domain)
ITCPPPMSVEHADIWVKSYSLYSRERYICNSGFKRKAGTSSLTECVL

NKATNVAHWTTPSLKCIR

((G4S)3 linker)
GGGGSGGGGSGGGGS

(Human CD137L)
REGPELSPDDPAGLLDLRQGMFAQLVAQNVLLIDGPLSWYSDPGLAG

VSLTGGLSYKEDTKELVVAKAGVYYVFFQLELRRVVAGEGSGSVSLA

LHLQPLRSAAGAAALALTVDLPPASSEARNSAFGFQGRLLHLSAGQR

LGVHLHTEARARHAWQLTQGATVLGLFRVTPEIPAGLPSPRSE
```

The following experiment was conducted to evaluate whether the CD137L portion in 7t15-21s137L was intact to bind to CD137 (4.1BB). On day 1, a 96-well plate was coated with 100 μL (2.5 μg/mL) of GAH IgG Fc (G-102-C, R&D Systems) in R5 (coating buffer), overnight. On day 2, the plates were washed three times and blocked with 300 μL of 1% BSA in PBS at 37° C. for 2 hrs. 10 ng/ml of 4.1BB/Fc (838-4B, R&D Systems) was added at 100 μl/well for 2 hrs at room temperature. Following three washes, 7t15-21s137L (long version) or 7t15-21s137Ls (short version) was added starting at 10 nM, or recombinant human 4.1BBL starting at 180 ng/mL, with ⅓ dilution, followed by incubation at 4° C. overnight. On day 3, the plates were washed three times, and 500 ng/mL of biotinylate-goat anti-human 4.1BBL (BAF2295, R&D Systems) was applied at 100 μL per well, followed by incubation at RT for 2 hrs. The plates were washed three times, and incubated with 0.25 μg/mL of HRP-SA (Jackson ImmuneResearch) at 100 μL per well for 30 min. The plates were then washed three times, and incubated with 100 μL of ABTS for 2 mins at RT. The results were read at 405 nm. As shown in FIG. 190, both 7t15-21s137L (long version) and 7t15-21s137L (short version) could interact with 4.1BB/Fc (dark diamond and gray square) compared to the recombinant human 4.1BB ligand (rhCD137L, light gray star). 7t15-21s137L (long version) (dark diamond) interacted better with 4.1BB/Fc as compared to 7t15-21s137L (short version) (gray square).

The following experiments were conducted to evaluate whether the components IL7, IL21, IL15, and 4.1BBL in 7t15-21s137L (long version) were intact to be detected by the individual antibody using ELISA. A 96-well plate was coated with 100 μL (4 μg/mL) of anti-TF (human IgG1) in R5 (coating buffer) and incubated at RT for 2 hrs. The plates were washed three times, and blocked with 100 μL of 1% BSA in PBS. Purified 7t15-21s137L (long version) was added starting at 10 nM, and at ⅓ dilution, followed by incubation at RT for 60 min. The plates were washed three times, and 500 ng/mL of biotinylate-anti-IL7 (506602, R&D Systems), 500 ng/mL of biotinylate-anti-IL21 (13-7218-81, R&D Systems), 50 ng/mL of biotinylate-anti-IL15 (BAM247, R&D Systems), or 500 ng/ml of biotinylate-goat anti-human 4.1BBL (BAF2295, R&D Systems) was added per well and incubated at room temperature for 60 min. The plates were washed three times and incubated with 0.25 μg/mL of HRP-SA (Jackson ImmunoResearch) at 100 μL per well for 30 min at RT. The plates were washed four times, and incubated with 100 μL of ABTS for 2 mins at room temperature. The absorbance results were read at 405 nm. As shown in FIG. 191A-191D, the components including IL7, IL21, IL15, and 4.1BBL in 7t15-21s137L (long version) were detected by the individual antibodies.

The following experiment was conducted to evaluate the activity of IL15 in 7t15-21s137L (long version) and 7t15-21s137L (short version). The ability of 7t15-21s137L (long version) and 7t15-21s137L (short version) to promote proliferation of IL2Rαβγ-expressing CTLL2 cells was compared with that of recombinant IL15. IL15 dependent CTLL2 cells were washed five times with IMDM-10% FBS and seeded to the wells at $2\times10^4$ cells/well. Serially diluted 7t15-21s137L (long version), 7t15-21s137L (short version), or IL15 were added to the cells. Cells were incubated in a $CO_2$ incubator at 37° C. for 3 days. Cell proliferation was detected by adding 20 μL of PrestoBlue (A13261, ThermoFisher) to each well on day 3 and incubated for an additional 4 hours in a $CO_2$ incubator at 37° C. Raw absorbance at 570-610 nm was read in a micro-titer plate reader. As shown in FIG. 192, 7t15-21s137L (long version), 7t15-21s137L (short version), and IL15 all promoted CTLL2 cell proliferation. The $EC_{50}$ of 7t15-21s137L (long version), 7t15-21s137L (short version), and IL15 is 51.19 pM, 55.75 pM, and 4.947 pM, respectively.

Example 96: Induction of Treg Cells by 2t2

The peripheral blood mononuclear cells (PBMC) of a heathy donor (Donor 163) were isolated from 5 mL of whole blood buffy coats by Ficoll Paque Plus (GE17144003). The PBMC were then lysed with ACK to remove red blood cells. Cells were washed with IMDM-10% FBS and counted. $1.8\times10^6$ cells (100 μL/tube) were seeded to the flow tubes and incubated with 50 L of descending 2t2 or IL2 (15000, 1500, 150, 15, 1.5, 0.15, or 0 pM) and 50 pLof pre-staining antibodies (anti-CD8-BV605 and anti-CD127-AF647). Cells were incubated for 30 min at 37° C. in water bath. 200 μL of pre-warmed BD Phosflow Fix Buffer I (Cat #557870, Becton Dickinson Biosciences) was added for 10 min at 37° C. in water bath to stop the stimulation. Cells ($4.5\times10^5$ cells/100 μL) were transferred to a V-shape 96-well plate and were spun down followed by permeabilization with 100 μL of −20° C. pre-cooled BD Phosflow Perm Buffer III (Cat #BD Biosciences) for 30 min on ice. The cells were then extensively washed ×2 with 200 μL of FACS buffer and stained with a panel of fluorescent antibodies (anti-CD25-PE, CD4-PerCP-Cy5.5, CD56-BV421, CD45RA-PE-Cy7 and pSTAT5a-AF488) to distinguish between different lymphocyte subpopulations and evaluate the pSTAT5a status. Cells were spun down and resuspended in 200 μL of FACS buffer for FACSCelesta analysis. As sown in Figure C1A, 6 pM of 2t2 was sufficient to induce the phosphorylation of Stat5a in $CD4^+CD25^-$ $T_{reg}$ cells while 43.11 pM of IL-2 was required to induce phosphorylation of Stat5a in the same population of lymphocytes. In contrast, 2t2 was less active (FIG. 193B) or equally active (FIG. 193C) as compared to IL2 in inducing phosphorylation of Stat5a in $CD4^+CD25^-$ $T_{con}$ and $CD8^+$ $T_{con}$ cells. These results suggest that 2t2 is superior as compared to IL2 in activating $T_{reg}$ in human PBMC, and that 2t2 demonstrates increased $T_{reg}$ selectivity compared to IL-2 in human blood lymphocyte pStat5a responses.

Example 97: Differentiation of the Immune Cell into a Memory-Like Immune Cell

Fresh human leukocytes were obtained from the blood bank and $CD56^{+}$ NK cells were isolated with the RosetteSep/human NK cell reagent (StemCell Technologies). The purity of NK cells was >70% and confirmed by staining with CD56-BV421, CD16-BV510, CD25-PE, CD69-APC-Fire750 (BioLegend). The cells were counted and resuspended at a density of $2\times10^{6}$ cells/mL in RPMI 1640 medium (Gibco) supplemented with 2 mM L-glutamine (Thermo Life Technologies), antibiotics (penicillin, 10,000 units/mL; streptomycin, 10,000 μg/mL; Thermo Life Technologies), and 10% FBS (Hyclone). The cells (1 mL) were transferred into a 24-well flat bottom plate, and subjected to either: no treatment, or expanded with 7t15-21s+anti-tissue factor (TF)-antibody (IgG1) (50 nM) for 14 days with medium. The cells were replenished with fresh 7t15-21s+ anti-TF-antibody (IgG1) (50 nM) to keep the cell density at approximately $1\times10^{6}$ cells/mL.

Unexpanded NK cells to treatment groups were used as positive controls for full DNA methylation levels (Data not shown). NK cells were pelleted ($1\times10^{6}$), and genomic DNA (nDNA) isolated using the QIAamp UCP DNA Micro Kit (Qiagen). 500 ng of purified nDNA was subjected to sodium bisulfite treatment using the EZ DNA Methylation-Direct kit (Zymo Research) according to the manufacturer's protocol. Bisulfite treatment introduces methylation-dependent changes in the DNA with demethylated cytosines being converted into uracil, whereas methylated cytosines remain unchanged. The bisulfite-treated nDNA (10-50 ng) was used as template to PCR amplify a 228 bp region of the IFNγ promoter containing two CpG sites (CpG −186 and CpG −54, position relative to the transcription start site, TSS), known to be heavily regulated by DNA methylation in T cells, using the Pyromark PCR kit (Qiagen) with the forward primer IFNG127F (5'-ATGGTATAGGTGGGTATAATGG-3') (SEQ ID NO: 30) and the biotinylated reverse primer IFNG355R-bio (biotin-5'-CAATATACTACACCTCCTCTAACTAC-3') (SEQ ID NO: 43) (GENEWIZ). The PCR conditions were 15 min at 95° C., 48 cycles of 30 sec at 95° C., 30 sec at 56° C., 60 sec at 72° C. followed by 10 min at 72° C. The integrity and quality of the PCR amplified products were visualized on a 1.2% TAE agarose gel. The DNA methylation status of these two CpG sites was determined by pyrosequencing, which is the gold standard technique to quantitatively measure DNA methylation at single CpG-site. Pyrosequencing reactions were performed at Johns Hopkins University Genetic Resources Core Facility using the DNA sequencing primers C186-IFNG135F (5'-GGTGGGTATAATGGG-3') (SEQ ID NO: 14) and C54-IFNG261F (5'-ATTATTTTATTTTAAAAAATTTGTG-3') (SEQ ID NO: 15), specific to the CpG sites −186 and −54, respectively. Commercially available non-methylated and methylated DNA (Zymo Research) were used as controls for DNA methylation. The methylation percentages of the two CpG sites (−186 and −54) were pooled for each treatment. The percent difference in DNA methylation was calculated relative to the levels of DNA methylation at the two CpG sites observed in unexposed NK cells.

Analysis of the DNA methylation status of these two IFNγ CpG sites revealed higher levels of DNA demethylation in NK cells supported by 7t15-21s+anti-TF-antibody compared to unexposed NK cells (FIG. 194). These 7t15-21s+ anti-TF-antibody supported NK cells exhibited 47.70%+ 11.76 difference in DNA methylation (i.e., demethylation) compared to unexposed NK cells. The DNA methylation levels of these two IFNγ CpG sites correlated with increased expression of IFNγ following treatment with 7t15-21s+anti-TF-antibody. These data suggest that long-term exposure of NK cells (14 days expansion in culture) with a combination regimen of 7t15-21s+anti-TF-antibody is able to induce DNA demethylation of the two hypomethylated IFNγ CpG sites (−186 and −54) and that 7t15-21s+anti-TF-antibody (IgG1) can epigenetically reprogram gene expression of IFNγ via DNA demethylation of CpG sites leading to interconversion of NK cells into innate immune memory NK cells.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Exemplary Embodiments

Embodiment A1. A single-chain chimeric polypeptide comprising:

(i) a first target-binding domain;

(ii) a soluble tissue factor domain; and (iii) a second target-binding domain.

Embodiment A2. The single-chain chimeric polypeptide of embodiment A1, wherein the first target-binding domain and the soluble tissue factor domain directly abut each other.

Embodiment A3. The single-chain chimeric polypeptide of embodiment A1, wherein the single-chain chimeric polypeptide further comprises a linker sequence between the first target-binding domain and the soluble tissue factor domain.

Embodiment A4. The single-chain chimeric polypeptide of any one of embodiments A1-A3, wherein the soluble tissue factor domain and the second target-binding domain directly abut each other.

Embodiment A5. The single-chain chimeric polypeptide of any one of embodiments A1-A3, wherein the single-chain chimeric polypeptide further comprises a linker sequence between the soluble tissue factor domain and the second target-binding domain.

Embodiment A6. The single-chain chimeric polypeptide of embodiment A1, wherein the first target-binding domain and the second target-binding domain directly abut each other.

Embodiment A7. The single-chain chimeric polypeptide of embodiment A1, wherein the single-chain chimeric polypeptide further comprises a linker sequence between the first target-binding domain and the second target-binding domain.

Embodiment A8. The single-chain chimeric polypeptide of embodiment A6 or A7, wherein the second target-binding domain and the soluble tissue factor domain directly abut each other.

Embodiment A9. The single-chain chimeric polypeptide of embodiment A6 or A7, wherein the single-chain chimeric polypeptide further comprises a linker sequence between the second target-binding domain and the soluble tissue factor domain.

Embodiment A10. The single-chain chimeric polypeptide of any one of embodiments A1-A9, wherein the first target-binding domain and the second target-binding domain bind specifically to the same antigen.

Embodiment A11. The single-chain chimeric polypeptide of embodiment A10, wherein the first target-binding domain and the second target-binding domain bind specifically to the same epitope.

Embodiment A12. The single-chain chimeric polypeptide of embodiment A11, wherein the first target-binding domain and the second target-binding domain comprise the same amino acid sequence.

Embodiment A13. The single-chain chimeric polypeptide of any one of embodiments A1-A9, wherein the first target-binding domain and the second target-binding domain bind specifically to different antigens.

Embodiment A14. The single-chain chimeric polypeptide of any one of embodiments A1-A13, wherein one or both of the first target-binding domain and the second target-binding domain is an antigen-binding domain.

Embodiment A15. The single-chain chimeric polypeptide of embodiment A14, wherein the first target-binding domain and the second target-binding domain are each an antigen-binding domain.

Embodiment A16. The single-chain chimeric polypeptide of embodiment A13, wherein antigen-binding domain comprises a scFv or a single domain antibody.

Embodiment A17. The single-chain chimeric polypeptide of any one of embodiments A1-A16, wherein one or both of the first target-binding domain and the second target-binding domain bind to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-D, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment A18. The single-chain chimeric polypeptide of any one of embodiments A1-A16, wherein one or both of the first target-binding domain and the second target-binding domain is a soluble interleukin, soluble cytokine protein, or soluble cell surface protein.

Embodiment A19. The single-chain chimeric polypeptide of embodiment A18, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-D, SCF, FLT3L, MICA, MICB, and a ULP16-binding protein.

Embodiment A20. The single-chain chimeric polypeptide of any one of embodiments A1-A16, wherein one or both of the first target-binding domain and the second target-binding domain is a soluble interleukin, soluble cytokine receptor, or soluble cell surface receptor.

Embodiment A21. The single-chain chimeric polypeptide of embodiment A20, wherein the soluble interleukin receptor, soluble cytokine receptor, or soluble cell surface receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment A22. The single-chain chimeric polypeptide of any one of embodiments A1-A21, wherein the soluble tissue factor domain is a soluble human tissue factor domain.

Embodiment A23. The single-chain chimeric polypeptide of embodiment A22, wherein the soluble human tissue factor domain comprises a sequence that is at least 80% identical to SEQ ID NO: 1.

Embodiment A24. The single-chain chimeric polypeptide of embodiment A23, wherein the soluble human tissue factor domain comprises a sequence that is at least 90% identical to SEQ ID NO: 1.

Embodiment A25. The single-chain chimeric polypeptide of embodiment A24, wherein the soluble human tissue factor domain comprises a sequence that is at least 95% identical to SEQ ID NO: 1.

Embodiment A26. The single-chain chimeric polypeptide of any one of embodiments A22-A25, wherein the soluble human tissue factor domain does not comprise one or more of:

- a lysine at an amino acid position that corresponds to amino acid position 20 of mature wildtype human tissue factor protein;
- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;
- a tyrosine at an amino acid position that corresponds to amino acid position 94 of mature wildtype human tissue factor protein;
- an arginine at an amino acid position that corresponds to amino acid position 135 of mature wildtype human tissue factor protein; and
- a phenylalanine at an amino acid position that corresponds to amino acid position 140 of mature wildtype human tissue factor protein.

Embodiment A27. The single-chain chimeric polypeptide of embodiment A26, wherein the soluble human tissue factor domain does not comprise any of.

- a lysine at an amino acid position that corresponds to amino acid position 20 of mature wildtype human tissue factor protein;
- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment A28. The single-chain chimeric polypeptide of any one of embodiments A1-A27, wherein the soluble tissue factor domain is not capable of binding Factor VIIa.

Embodiment A29. The single-chain chimeric polypeptide of any one of embodiments A1-A28, wherein the soluble tissue factor domain does not convert inactive Factor X into Factor Xa.

Embodiment A30. The single-chain chimeric polypeptide of any one of embodiments A1-A29, wherein the single-chain chimeric polypeptide does not stimulate blood coagulation in a mammal.

Embodiment A31. The single-chain chimeric polypeptide of any one of embodiments A1-A30, wherein the single-chain chimeric polypeptide further comprises one or more additional target-binding domains at its N- and/or C-terminus.

Embodiment A32. The single-chain chimeric polypeptide of embodiment A31, wherein the single-chain chimeric polypeptide comprises one or more additional target-binding domains at its N-terminus.

Embodiment A33. The single-chain chimeric polypeptide of embodiment A32, wherein one or more additional target-binding domains directly abuts the first target-binding domain, the second target-binding domain, or the soluble tissue factor domain.

Embodiment A34. The single-chain chimeric polypeptide of embodiment A33, wherein the single-chain chimeric polypeptide further comprises a linker sequence between one of the at least one additional target-binding domains and the first target-binding domain, the second target-binding domain, or the soluble tissue factor domain.

Embodiment A35. The single-chain chimeric polypeptide of embodiment A31, wherein the single-chain chimeric polypeptide comprises one or more additional target-binding domains at its C-terminus.

Embodiment A36. The single-chain chimeric polypeptide of embodiment A35, wherein one of the one or more additional target-binding domains directly abuts the first target-binding domain, the second target-binding domain, or the soluble tissue factor domain.

Embodiment A37. The single-chain chimeric polypeptide of embodiment A35, wherein the single-chain chimeric polypeptide further comprises a linker sequence between one of the at least one additional target-binding domains and the first target-binding domain, the second target-binding domain, or the soluble tissue factor domain.

Embodiment A38. The single-chain chimeric polypeptide of embodiment A31, wherein the single-chain chimeric polypeptide comprises one or more additional target binding domains at its N-terminus and the C-terminus.

Embodiment A39. The single-chain chimeric polypeptide of embodiment A38, wherein one of the one or more additional antigen binding domains at the N-terminus directly abuts the first target-binding domain, the second target-binding domain, or the soluble tissue factor domain.

Embodiment A40. The single-chain chimeric polypeptide of embodiment A38, wherein the single-chain chimeric polypeptide further comprises a linker sequence between one of the one or more additional antigen-binding domains at the N-terminus and the first target-binding domain, the second target-binding domain, or the soluble tissue factor domain.

Embodiment A41. The single-chain chimeric polypeptide of embodiment A38, wherein one of the one or more additional antigen binding domains at the C-terminus directly abuts the first target-binding domain, the second target-binding domain, or the soluble tissue factor domain.

Embodiment A42. The single-chain chimeric polypeptide of embodiment A38, wherein the single-chain chimeric polypeptide further comprises a linker sequence between one of the one or more additional antigen-binding domains at the C-terminus and the first target-binding domain, the second target-binding domain, or the soluble tissue factor domain.

Embodiment A43. The single-chain chimeric polypeptide of any one of embodiments A31-A42, wherein two or more of the first target-binding domain, the second target-binding domain, and the one or more additional target-binding domains bind specifically to the same antigen.

Embodiment A44. The single-chain chimeric polypeptide of embodiment A43, wherein two or more of the first target-binding domain, the second target-binding domain, and the one or more additional target-binding domains bind specifically to the same epitope.

Embodiment A45. The single-chain chimeric polypeptide of embodiment A44, wherein two or more of the first target-binding domain, the second target-binding domain, and the one or more additional target-binding domains comprise the same amino acid sequence.

Embodiment A46. The single-chain chimeric polypeptide of embodiment A43, wherein the first target-binding domain, the second target-binding domain, and the one or more additional target-binding domains each bind specifically to the same antigen.

Embodiment A47. The single-chain chimeric polypeptide of embodiment A46, wherein the first target-binding domain, the second target-binding domain, and the one or more additional target-binding domains each bind specifically to the same epitope.

Embodiment A48. The single-chain chimeric polypeptide of embodiment A47, wherein the first target-binding domain, the second target-binding domain, and the one or more additional target-binding domains each comprise the same amino acid sequence.

Embodiment A49. The single-chain chimeric polypeptide of any one of embodiments A31-A42, wherein the first target-binding domain, the second target-binding domain, and the one or more additional target-binding domains bind specifically to different antigens.

Embodiment A50. The single-chain chimeric polypeptide of any one of embodiments A31-A49, wherein one or more of the first target-binding domain, the second target-binding domain, and the one or more target-binding domains is an antigen-binding domain.

Embodiment A51. The single-chain chimeric polypeptide of embodiment A50, wherein the first target-binding domain, the second target-binding domain, and the one or more additional target-binding domains are each an antigen-binding domain.

Embodiment A52. The single-chain chimeric polypeptide of embodiment A51, wherein antigen-binding domain comprises a scFv or a single domain antibody.

Embodiment A53. The single-chain chimeric polypeptide of any one of embodiments A31-A52, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-D, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment A54. The single-chain chimeric polypeptide of any one of embodiments A31-A52, wherein one or more of the first target-binding domain, the second target-binding domain, and the one or more additional target-binding domains is a soluble interleukin, soluble cytokine protein, or soluble cell surface protein.

Embodiment A55. The single-chain chimeric polypeptide of embodiment A54, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-D, SCF, FLT3L, MICA, MICB, and a ULP16-binding protein.

Embodiment A56. The single-chain chimeric polypeptide of any one of embodiments A31-A52, wherein one or more of the first target-binding domain, the second target-binding domain, and the one or more additional target-binding domains is a soluble interleukin receptor, soluble cytokine receptor, or soluble cell surface receptor.

Embodiment A57. The single-chain chimeric polypeptide of embodiment A56, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment A58. The single-chain chimeric polypeptide of any one of embodiments A1-A57, wherein the single-chain chimeric polypeptide further comprises a signal sequence at its N-terminal end.

Embodiment A59. The single-chain chimeric polypeptide of any one of embodiments A1-A58, wherein the single-chain chimeric polypeptide further comprises a peptide tag positioned at the N-terminal end or the C-terminal end of the single-chain chimeric polypeptide.

Embodiment A60. A composition comprising any of the single-chain chimeric polypeptides of embodiments A1-A59.

Embodiment A61. The composition of embodiment A60, wherein the composition is a pharmaceutical composition.

Embodiment A62. A kit comprising at least one dose of the composition of embodiment A60 or A61.

Embodiment A63. Nucleic acid encoding any of the single-chain chimeric polypeptides of any one of embodiments A1-A59.

Embodiment A64. A vector comprising the nucleic acid of embodiment A63.

Embodiment A65. The vector of embodiment A64, wherein the vector is an expression vector.

Embodiment A66. A cell comprising the nucleic acid of embodiment A63 or the vector of embodiment A64 or A65.

Embodiment A67. A method of producing a single-chain chimeric polypeptide, the method comprising:

culturing the cell of embodiment A66 in a culture medium under conditions sufficient to result in the production of the single-chain chimeric polypeptide; and recovering the single-chain chimeric polypeptide from the cell and/or the culture medium.

Embodiment A68. A single-chain chimeric polypeptide produced by the method of embodiment A67.

Embodiment A69. The single-chain chimeric polypeptide of embodiment A26, wherein the soluble human tissue factor domain comprises a sequence that is at least 80% identical to SEQ ID NO: 5.

Embodiment A70. The single-chain chimeric polypeptide of embodiment A69, wherein the soluble human tissue factor domain comprises a sequence that is at least 90% identical to SEQ ID NO: 5.

Embodiment A71. The single-chain chimeric polypeptide of embodiment A70, wherein the soluble human tissue factor domain comprises a sequence that is at least 95% identical to SEQ ID NO: 5.

Embodiment A72. The single-chain chimeric polypeptide of embodiment A71, wherein the soluble human tissue factor domain comprises a sequence that is 100% identical to SEQ ID NO: 5.

Embodiment A73. The single-chain chimeric polypeptide of embodiment A26, wherein the soluble human tissue factor domain comprises a sequence that is at least 80% identical to SEQ ID NO: 6.

Embodiment A74. The single-chain chimeric polypeptide of embodiment A73, wherein the soluble human tissue factor domain comprises a sequence that is at least 90% identical to SEQ ID NO: 6.

Embodiment A75. The single-chain chimeric polypeptide of embodiment A74, wherein the soluble human tissue factor domain comprises a sequence that is at least 95% identical to SEQ ID NO: 6.

Embodiment A76. The single-chain chimeric polypeptide of embodiment A75, wherein the soluble human tissue factor domain comprises a sequence that is 100% identical to SEQ ID NO: 6.

Embodiment B1. A single-chain chimeric polypeptide comprising:

(i) a first target-binding domain;

(ii) a soluble tissue factor domain; and (iii) a second target-binding domain, wherein:

the first target-binding domain and the second target-binding domain each specifically bind to an IL-2 receptor; or the first target-binding domain and the second target-binding domain each specifically bind to an IL-15 receptor.

Embodiment B2. The single-chain chimeric polypeptide of embodiment B1, wherein the first target-binding domain and the soluble tissue factor domain directly abut each other.

Embodiment B3. The single-chain chimeric polypeptide of embodiment B1, wherein the single-chain chimeric polypeptide further comprises a linker sequence between the first target-binding domain and the soluble tissue factor domain.

Embodiment B4. The single-chain chimeric polypeptide of any one of embodiments B1-B3, wherein the soluble tissue factor domain and the second target-binding domain directly abut each other.

Embodiment B5. The single-chain chimeric polypeptide of any one of embodiments B1-B3, wherein the single-chain chimeric polypeptide further comprises a linker sequence between the soluble tissue factor domain and the second target-binding domain.

Embodiment B6. The single-chain chimeric polypeptide of embodiment B1, wherein the first target-binding domain and the second target-binding domain directly abut each other.

Embodiment B7. The single-chain chimeric polypeptide of embodiment B1, wherein the single-chain chimeric polypeptide further comprises a linker sequence between the first target-binding domain and the second target-binding domain.

Embodiment B8. The single-chain chimeric polypeptide of embodiment B6 or B7, wherein the second target-binding domain and the soluble tissue factor domain directly abut each other.

Embodiment B9. The single-chain chimeric polypeptide of embodiment B6 or B7, wherein the single-chain chimeric polypeptide further comprises a linker sequence between the second target-binding domain and the soluble tissue factor domain.

Embodiment B10. The single-chain chimeric polypeptide of any one of embodiments B1-B9, wherein both the first target-binding domain and the second target-binding domain is a soluble interleukin protein.

Embodiment B11. The single-chain chimeric polypeptide of embodiment B10, wherein the first target-binding domain and the second target-binding domain is a soluble IL-2 protein.

Embodiment B12. The single-chain chimeric polypeptide of embodiment B11, wherein the soluble IL-2 protein is a soluble human IL-2 protein.

Embodiment B13. The single-chain chimeric polypeptide of embodiment B12, wherein the soluble human IL-2 protein comprises SEQ ID NO: 28.

Embodiment B14. The single-chain chimeric polypeptide of embodiment B10, wherein the first target-binding domain and the second target-binding domain is a soluble IL-15 protein.

Embodiment B15. The single-chain chimeric polypeptide of embodiment B14, wherein the soluble IL-15 protein is a soluble human IL-15 protein.

Embodiment B16. The single-chain chimeric polypeptide of embodiment B15, wherein the soluble human IL-15 protein comprises SEQ ID NO: 39.

Embodiment B17. The single-chain chimeric polypeptide of any one of embodiments B1-B16, wherein the soluble tissue factor domain is a soluble human tissue factor domain.

Embodiment B18. The single-chain chimeric polypeptide of embodiment B17, wherein the soluble human tissue factor domain comprises a sequence that is at least 80% identical to SEQ ID NO: 1.

Embodiment B19. The single-chain chimeric polypeptide of embodiment B18, wherein the soluble human tissue factor domain comprises a sequence that is at least 90% identical to SEQ ID NO: 1.

Embodiment B20. The single-chain chimeric polypeptide of embodiment B19, wherein the soluble human tissue factor domain comprises a sequence that is at least 95% identical to SEQ ID NO: 1.

Embodiment B21. The single-chain chimeric polypeptide of any one of embodiments B17-B20, wherein the soluble human tissue factor domain does not comprise one or more of: a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment B22. The single-chain chimeric polypeptide of embodiment B21, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment B23. The single-chain chimeric polypeptide of any one of embodiments B1-B22, wherein the soluble tissue factor domain is not capable of binding Factor VIIa.

Embodiment B24. The single-chain chimeric polypeptide of any one of embodiments B1-B23, wherein the soluble tissue factor domain does not convert inactive Factor X into Factor Xa.

Embodiment B25. The single-chain chimeric polypeptide of any one of embodiments B1-B24, wherein the single-chain chimeric polypeptide does not stimulate blood coagulation in a mammal.

Embodiment B26. The single-chain chimeric polypeptide of any one of embodiments B1-B25, wherein the single-chain chimeric polypeptide further comprises one or more additional target-binding domains at its N- and/or C-terminus.

Embodiment B27. The single-chain chimeric polypeptide of embodiment B26, wherein the single-chain chimeric polypeptide comprises one or more additional target-binding domains at its N-terminus.

Embodiment B28. The single-chain chimeric polypeptide of embodiment B27, wherein one or more additional target-binding domains directly abuts the first target-binding domain, the second target-binding domain, or the soluble tissue factor domain.

Embodiment B29. The single-chain chimeric polypeptide of embodiment B28, wherein the single-chain chimeric polypeptide further comprises a linker sequence between one of the at least one additional target-binding domains and the first target-binding domain, the second target-binding domain, or the soluble tissue factor domain.

Embodiment B30. The single-chain chimeric polypeptide of embodiment B26, wherein the single-chain chimeric polypeptide comprises one or more additional target-binding domains at its C-terminus.

Embodiment B31. The single-chain chimeric polypeptide of embodiment B30, wherein one of the one or more additional target-binding domains directly abuts the first target-binding domain, the second target-binding domain, or the soluble tissue factor domain.

Embodiment B32. The single-chain chimeric polypeptide of embodiment B30, wherein the single-chain chimeric polypeptide further comprises a linker sequence between one of the at least one additional target-binding domains and the first target-binding domain, the second target-binding domain, or the soluble tissue factor domain.

Embodiment B33. The single-chain chimeric polypeptide of embodiment B26, wherein the single-chain chimeric polypeptide comprises one or more additional target binding domains at its N-terminus and the C-terminus.

Embodiment B34. The single-chain chimeric polypeptide of embodiment B33, wherein one of the one or more additional antigen binding domains at the N-terminus directly abuts the first target-binding domain, the second target-binding domain, or the soluble tissue factor domain.

Embodiment B35. The single-chain chimeric polypeptide of embodiment B33, wherein the single-chain chimeric polypeptide further comprises a linker sequence between one of the one or more additional antigen-binding domains at the N-terminus and the first target-binding domain, the second target-binding domain, or the soluble tissue factor domain.

Embodiment B36. The single-chain chimeric polypeptide of embodiment B33, wherein one of the one or more additional antigen binding domains at the C-terminus directly abuts the first target-binding domain, the second target-binding domain, or the soluble tissue factor domain.

Embodiment B37. The single-chain chimeric polypeptide of embodiment B33, wherein the single-chain chimeric polypeptide further comprises a linker sequence between one of the one or more additional antigen-binding domains at the C-terminus and the first target-binding domain, the second target-binding domain, or the soluble tissue factor domain.

Embodiment B38. The single-chain chimeric polypeptide of any one of embodiments B26-B37, wherein each of the first target-binding domain, the second target-binding domain, and the one or more additional target-binding domains bind specifically to an IL-2 receptor or an IL-receptor.

Embodiment B39. The single-chain chimeric polypeptide of embodiment B38, wherein each of the first target-binding domain, the second target-binding domain, and the one or more additional target-binding domains comprise the same amino acid sequence.

Embodiment B40. The single-chain chimeric polypeptide of any one of embodiments B26-B37, wherein the one or more additional target-binding domains is an antigen-binding domain.

Embodiment B41. The single-chain chimeric polypeptide of embodiment B40, wherein the antigen-binding domain comprises a scFv or a single domain antibody.

Embodiment B42. The single-chain chimeric polypeptide of any one of embodiments B26-B37, B40, and B41, wherein the one or more additional target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment B43. The single-chain chimeric polypeptide of any one of embodiments B6-B37, B40, and B41, wherein the one or more additional target-binding domains is a soluble interleukin or cytokine protein.

Embodiment B44. The single-chain chimeric polypeptide of embodiment B43, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, and SCF.

Embodiment B45. The single-chain chimeric polypeptide of any one of embodiments B6-B37, B40, and B41, wherein the one or more additional target-binding domains is a soluble interleukin or cytokine receptor.

Embodiment B46. The single-chain chimeric polypeptide of embodiment B45, wherein the soluble receptor is a soluble TGF-β receptor II (TGF-βRII) and a soluble TGF-βRIII.

Embodiment B47. The single-chain chimeric polypeptide of any one of embodiments B1-B46, wherein the single-chain chimeric polypeptide further comprises a signal sequence at its N-terminal end.

Embodiment B48. The single-chain chimeric polypeptide of any one of embodiments B1-B47, wherein the single-chain chimeric polypeptide further comprises a peptide tag positioned at the N-terminal end or the C-terminal end of the single-chain chimeric polypeptide.

Embodiment B49. A composition comprising any of the single-chain chimeric polypeptides of embodiments B1-B48.

Embodiment B50. The composition of embodiment B49, wherein the composition is a pharmaceutical composition.

Embodiment B51. A kit comprising at least one dose of the composition of embodiment B49 or B50.

Embodiment B52. A nucleic acid encoding any of the single-chain chimeric polypeptides of any one of embodiments B1-B48.

Embodiment B53. A vector comprising the nucleic acid of embodiment B52.

Embodiment B54. The vector of embodiment B53, wherein the vector is an expression vector.

Embodiment B55. A cell comprising the nucleic acid of embodiment B52 or the vector of embodiment B53 or B54.

Embodiment B56. A method of producing a single-chain chimeric polypeptide, the method comprising:

culturing the cell of embodiment B55 in a culture medium under conditions sufficient to result in the production of the single-chain chimeric polypeptide; and recovering the single-chain chimeric polypeptide from the cell and/or the culture medium.

Embodiment B57. A single-chain chimeric polypeptide produced by the method of embodiment B56.

Embodiment B58. The single-chain chimeric polypeptide of embodiment B21, wherein the soluble human tissue factor domain comprises a sequence that is at least 80% identical to SEQ ID NO: 5.

Embodiment B59. The single-chain chimeric polypeptide of embodiment B58, wherein the soluble human tissue factor domain comprises a sequence that is at least 90% identical to SEQ ID NO: 5.

Embodiment B60. The single-chain chimeric polypeptide of embodiment B59, wherein the soluble human tissue factor domain comprises a sequence that is at least 95% identical to SEQ ID NO: 5.

Embodiment B61. The single-chain chimeric polypeptide of embodiment B60, wherein the soluble human tissue factor domain comprises a sequence that is 100% identical to SEQ ID NO: 5.

Embodiment B62. The single-chain chimeric polypeptide of embodiment B21, wherein the soluble human tissue factor domain comprises a sequence that is at least 80% identical to SEQ ID NO: 6.

Embodiment B63. The single-chain chimeric polypeptide of embodiment B62, wherein the soluble human tissue factor domain comprises a sequence that is at least 90% identical to SEQ ID NO: 6.

Embodiment B64. The single-chain chimeric polypeptide of embodiment B63, wherein the soluble human tissue factor domain comprises a sequence that is at least 95% identical to SEQ ID NO: 6.

Embodiment B65. The single-chain chimeric polypeptide of embodiment B64, wherein the soluble human tissue factor domain comprises a sequence that is 100% identical to SEQ ID NO: 6.

Embodiment C1. A multi-chain chimeric polypeptide comprising:

(a) a first chimeric polypeptide comprising:

(i) a first target-binding domain;

(ii) a soluble tissue factor domain; and (iii) a first domain of a pair of affinity domains;

(b) a second chimeric polypeptide comprising:

(i) a second domain of a pair of affinity domains; and (ii) a second target-binding domain, wherein the first chimeric polypeptide and the second chimeric polypeptide associate through the binding of the first domain and the second domain of the pair of affinity domains.

Embodiment C2. The multi-chain chimeric polypeptide of embodiment C1, wherein the first target-binding domain and the soluble tissue factor domain directly abut each other in the first chimeric polypeptide.

Embodiment C3. The multi-chain chimeric polypeptide of embodiment C1, wherein the first chimeric polypeptide further comprises a linker sequence between the first target-binding domain and the soluble tissue factor domain in the first chimeric polypeptide.

Embodiment C4. The multi-chain chimeric polypeptide of any one of embodiments C1-C3, wherein the soluble tissue factor domain and the first domain of the pair of affinity domains directly abut each other in the first chimeric polypeptide.

Embodiment C5. The multi-chain chimeric polypeptide of any one of embodiments C1-C3, wherein the first chimeric polypeptide further comprises a linker sequence between the soluble tissue factor domain and the first domain of the pair of affinity domains in the first chimeric polypeptide.

Embodiment C6. The multi-chain chimeric polypeptide of any one of embodiments C1-C5, wherein the second domain of the pair of affinity domains and the second target-binding domain directly abut each other in the second chimeric polypeptide.

Embodiment C7. The multi-chain chimeric polypeptide of any one of embodiments C1-C5, wherein second chimeric polypeptide further comprises a linker sequence between the second domain of the pair of affinity domains and the second target-binding domain in the second chimeric polypeptide.

Embodiment C8. The multi-chain chimeric polypeptide of any one of embodiments C1-C7, wherein the first target-binding domain and the second target-binding domain bind specifically to the same antigen.

Embodiment C9. The multi-chain chimeric polypeptide of embodiment C8, wherein the first target-binding domain and the second target-binding domain bind specifically to the same epitope.

Embodiment C10. The multi-chain chimeric polypeptide of embodiment C9, wherein the first target-binding domain and the second target-binding domain comprise the same amino acid sequence.

Embodiment C11. The multi-chain chimeric polypeptide of any one of embodiments C1-C7, wherein the first target-binding domain and the second target-binding domain bind specifically to different antigens.

Embodiment C12. The multi-chain chimeric polypeptide of any one of embodiments C1-C11, wherein one or both of the first target-binding domain and the second target-binding domain is an antigen-binding domain.

Embodiment C13. The multi-chain chimeric polypeptide of embodiment C12, wherein the first target-binding domain and the second target-binding domain are each antigen-binding domains.

Embodiment C14. The multi-chain chimeric polypeptide of embodiment C12 or C13, wherein antigen-binding domain comprises a scFv or a single domain antibody.

Embodiment C15. The multi-chain chimeric polypeptide of any one of embodiments C1-C14, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF- βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment C16. The multi-chain chimeric polypeptide of any one of embodiments C1-C14, wherein one or both of the first target-binding domain and the second target-binding domain is a soluble interleukin or cytokine protein.

Embodiment C17. The multi-chain chimeric polypeptide of embodiment C16, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment C18. The multi-chain chimeric polypeptide of any one of embodiments C1-C14, wherein one or both of the first target-binding domain and the second target-binding domain is a soluble interleukin receptor, a soluble cytokine receptor, or a soluble cell surface receptor.

Embodiment C19. The multi-chain chimeric polypeptide of embodiment C18, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment C20. The multi-chain chimeric polypeptide of any one of embodiments C1-C19, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment C21. The multi-chain chimeric polypeptide of embodiment C20, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment C22. The multi-chain chimeric polypeptide of any one of embodiments C1-C19, wherein the first chimeric polypeptide further comprises one or more additional target-binding domains at the N-terminal and/or C-terminal end of the first chimeric polypeptide.

Embodiment C23. The multi-chain chimeric polypeptide of embodiment C22, wherein at least one of the one or more additional target-binding domains directly abuts the first domain of the pair of affinity domains in the first chimeric polypeptide.

Embodiment C24. The multi-chain chimeric polypeptide of embodiment C22, wherein the first chimeric polypeptide further comprises a linker sequence between the at least one of the one or more additional target-binding domains and the first domain of the pair of affinity domains.

Embodiment C25. The multi-chain chimeric polypeptide of embodiment C22, wherein the at least one of the one or more additional target-binding domains directly abuts the first target-binding domain in the first chimeric polypeptide.

Embodiment C26. The multi-chain chimeric polypeptide of embodiment C22, wherein the first chimeric polypeptide further comprises a linker sequence between the at least one of the one or more additional target-binding domains and the first target-binding domain.

Embodiment C27. The multi-chain chimeric polypeptide of embodiment C22, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment C28. The multi-chain chimeric polypeptide of embodiment C27, wherein the at least one additional target-binding domain of the one or more additional target-binding domains disposed at the N-terminus directly abuts the first target-binding domain or the first domain of the pair of affinity domains in the first chimeric polypeptide.

Embodiment C29. The multi-chain chimeric polypeptide of embodiment C27, wherein the first chimeric polypeptide further comprises a linker sequence disposed between the at least one additional target-binding domain and the first target-binding domain or the first domain of the pair of affinity domains in the first chimeric polypeptide.

Embodiment C30. The multi-chain chimeric polypeptide of embodiment C27, wherein the at least one additional target-binding domain of the one or more additional target-binding domains disposed at the C-terminus directly abuts the first target-binding domain or the first domain of the pair of affinity domains in the first chimeric polypeptide.

Embodiment C31. The multi-chain chimeric polypeptide of embodiment C27, wherein the first chimeric polypeptide further comprises a linker sequence disposed between the at least one additional target-binding domain and the first target-binding domain or the first domain of the pair of affinity domains in the first chimeric polypeptide.

Embodiment C32. The multi-chain chimeric polypeptide of embodiment C27, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment C33. The multi-chain chimeric polypeptide of embodiment C27, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment C34. The multi-chain chimeric polypeptide of any one of embodiments C1-C33, wherein the second chimeric polypeptide further comprises one or more additional target-binding domains at the N-terminal end or the C-terminal end of the second chimeric polypeptide.

Embodiment C35. The multi-chain chimeric polypeptide of embodiment C34, wherein at least one of the one or more additional target-binding domains directly abuts the second domain of the pair of affinity domains in the second chimeric polypeptide.

Embodiment C36. The multi-chain chimeric polypeptide of embodiment C34, wherein the second chimeric polypeptide further comprises a linker sequence between at least one of the one or more additional target-binding domains and the second domain of the pair of affinity domains in the second chimeric polypeptide.

Embodiment C37. The multi-chain chimeric polypeptide of embodiment C34, wherein at least one of the one or more additional target-binding domains directly abuts the second target-binding domain in the second chimeric polypeptide.

Embodiment C38. The multi-chain chimeric polypeptide of embodiment C34, wherein the second chimeric polypeptide further comprises a linker sequence between at least one of the one or more additional target-binding domains and the second target-binding domain in the second chimeric polypeptide.

Embodiment C39. The multi-chain chimeric polypeptide of any one of embodiments C20-C38, wherein two or more of the first target-binding domain, the second target-binding domain, and the one or more additional target-binding domains bind specifically to the same antigen.

Embodiment C40. The multi-chain chimeric polypeptide of embodiment C39, wherein two or more of the first target-binding domain, the second target-binding domain, and the one or more additional target-binding domains bind specifically to the same epitope.

Embodiment C41. The multi-chain chimeric polypeptide of embodiment C40, wherein two or more of the first target-binding domain, the second target-binding domain, and the one or more additional target-binding domains comprise the same amino acid sequence.

Embodiment C42. The multi-chain chimeric polypeptide of embodiment C39, wherein the first target-binding domain, the second target-binding domain, and the one or more additional target-binding domains each bind specifically to the same antigen.

Embodiment C43. The multi-chain chimeric polypeptide of embodiment C42, wherein the first target-binding domain, the second target-binding domain, and the one or more additional target-binding domains each bind specifically to the same epitope.

Embodiment C44. The multi-chain chimeric polypeptide of embodiment C43, wherein the first target-binding domain, the second target-binding domain, and the one or more additional target-binding domains each comprise the same amino acid sequence.

Embodiment C45. The multi-chain chimeric polypeptide of any one of embodiments C20-C38, wherein the first target-binding domain, the second target-binding domain, and the one or more additional target-binding domains bind specifically to different antigens.

Embodiment C46. The multi-chain chimeric polypeptide of any one of embodiments C20-C45, wherein one or more of the first target-binding domain, the second target-binding domain, and the one or more target-binding domains is an antigen-binding domain.

Embodiment C47. The multi-chain chimeric polypeptide of embodiment C46, wherein the first target-binding domain, the second target-binding domain, and the one or more additional target-binding domains are each an antigen-binding domain.

Embodiment C48. The multi-chain chimeric polypeptide of embodiment C47, wherein antigen-binding domain comprises a scFv.

Embodiment C49. The multi-chain chimeric polypeptide of any one of embodiments C20-C48, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment C50. The multi-chain chimeric polypeptide of any one of embodiments C20-C48, wherein one or more of the first target-binding domain, the second target-binding domain, and the one or more additional target-binding domains is a soluble interleukin, a soluble cytokine protein, or a soluble cell surface protein.

Embodiment C51. The multi-chain chimeric polypeptide of embodiment C50, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment C52. The multi-chain chimeric polypeptide of any one of embodiments C20-C48, wherein one or more of the first target-binding domain, the second target-binding domain, and the one or more additional target-binding domains is a soluble interleukin receptor, a soluble cytokine receptor, or a soluble cell surface receptor.

Embodiment C53. The multi-chain chimeric polypeptide of embodiment C52, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment C54. The multi-chain chimeric polypeptide of any one of embodiments C1-C53, wherein the first chimeric polypeptide further comprises a peptide tag at the N-terminal end or the C-terminal end of the first chimeric polypeptide.

Embodiment C55. The multi-chain chimeric polypeptide of any one of embodiments C1-C53, wherein the second chimeric polypeptide further comprises a peptide tag at the N-terminal end or the C-terminal end of the second chimeric polypeptide.

Embodiment C56. The multi-chain chimeric polypeptide of any one of embodiments C1-C55, wherein the soluble tissue factor domain is a soluble human tissue factor domain.

Embodiment C57. The multi-chain chimeric polypeptide of embodiment C56, wherein the soluble human tissue factor domain comprises a sequence that is at least 80% identical to SEQ ID NO: 1.

Embodiment C58. The multi-chain chimeric polypeptide of embodiment C57, wherein the soluble human tissue factor domain comprises a sequence that is at least 90% identical to SEQ ID NO: 1.

Embodiment C59. The multi-chain chimeric polypeptide of embodiment C58, wherein the soluble human tissue factor domain comprises a sequence that is at least 95% identical to SEQ ID NO: 1.

Embodiment C60. The multi-chain chimeric polypeptide of any one of embodiments C56-C59, wherein the soluble human tissue factor domain does not comprise one or more of:

- a lysine at an amino acid position that corresponds to amino acid position 20 of mature wildtype human tissue factor protein;
- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;
- a tyrosine at an amino acid position that corresponds to amino acid position 94 of mature wildtype human tissue factor protein;
- an arginine at an amino acid position that corresponds to amino acid position 135 of mature wildtype human tissue factor protein; and
- a phenylalanine at an amino acid position that corresponds to amino acid position 140 of mature wildtype human tissue factor protein.

Embodiment C61. The multi-chain chimeric polypeptide of embodiment C60, wherein the soluble human tissue factor domain does not comprise any of:

- a lysine at an amino acid position that corresponds to amino acid position 20 of mature wildtype human tissue factor protein;
- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;
- a tyrosine at an amino acid position that corresponds to amino acid position 94 of mature wildtype human tissue factor protein;
- an arginine at an amino acid position that corresponds to amino acid position 135 of mature wildtype human tissue factor protein; and
- a phenylalanine at an amino acid position that corresponds to amino acid position 140 of mature wildtype human tissue factor protein.

Embodiment C62. The multi-chain chimeric polypeptide of any one of embodiments C1-C61, wherein the soluble tissue factor domain is not capable of binding to Factor VIIa.

Embodiment C63. The multi-chain chimeric polypeptide of any one of embodiments C1-C62, wherein the soluble tissue factor domain does not convert inactive Factor X into Factor Xa.

Embodiment C64. The multi-chain chimeric polypeptide of any one of embodiments C1-C63, wherein the multi-chain chimeric polypeptide does not stimulate blood coagulation in a mammal.

Embodiment C65. The multi-chain chimeric polypeptide of any one of embodiments C1-C64, wherein the pair of affinity domains is a sushi domain from an alpha chain of human IL-15 receptor (IL15Rα) and a soluble IL-15.

Embodiment C66. The multi-chain chimeric polypeptide of embodiment C65, wherein the soluble IL15 has a D8N or D8A amino acid substitution.

Embodiment C67. The multi-chain chimeric polypeptide of embodiment C65 or C66, wherein the human IL15Rα is a mature full-length IL15Rα.

Embodiment C68. The multi-chain chimeric polypeptide of any one of embodiments C1-C64, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment C69. The multi-chain chimeric polypeptide of any one of embodiments C1-C68, wherein the first chimeric polypeptide and/or the second chimeric polypeptide further comprises a signal sequence at its N-terminal end.

Embodiment C70. A composition comprising any of the multi-chain chimeric polypeptides of embodiments C1-C69.

Embodiment C71. The composition of embodiment C70, wherein the composition is a pharmaceutical composition.

Embodiment C72. A kit comprising at least one dose of the composition of embodiment C70 or C71.

Embodiment C73. Nucleic acid encoding any of the multi-chain chimeric polypeptides of any one of embodiments C1-C69.

Embodiment C74. A vector comprising the nucleic acid of embodiment C73.

Embodiment C75. The vector of embodiment C74, wherein the vector is an expression vector.

Embodiment C76. A cell comprising the nucleic acid of embodiment C73 or the vector of embodiment C74 or C75.

Embodiment C77. A method of producing a multi-chain chimeric polypeptide, the method comprising:

- culturing the cell of embodiment C76 in a culture medium under conditions sufficient to result in the production of the multi-chain chimeric polypeptide; and
- recovering the multi-chain chimeric polypeptide from the cell and/or the culture medium.

Embodiment C78. A multi-chain chimeric polypeptide produced by the method of embodiment C77.

Embodiment C79. The multi-chain chimeric polypeptide of embodiment A56, wherein the soluble human tissue factor domain comprises a sequence that is at least 80% identical to SEQ ID NO: 5.

Embodiment C80. The multi-chain chimeric polypeptide of embodiment C79, wherein the soluble human tissue factor domain comprises a sequence that is at least 90% identical to SEQ ID NO: 5.

Embodiment C81. The multi-chain chimeric polypeptide of embodiment C80, wherein the soluble human tissue factor domain comprises a sequence that is at least 95% identical to SEQ ID NO: 5.

Embodiment C82. The multi-chain chimeric polypeptide of embodiment C81, wherein the soluble human tissue factor domain comprises a sequence that is 100% identical to SEQ ID NO: 5.

Embodiment C83. The multi-chain chimeric polypeptide of embodiment C56, wherein the soluble human tissue factor domain comprises a sequence that is at least 80% identical to SEQ ID NO: 6.

Embodiment C84. The multi-chain chimeric polypeptide of embodiment C83, wherein the soluble human tissue factor domain comprises a sequence that is at least 90% identical to SEQ ID NO: 6.

Embodiment C85. The multi-chain chimeric polypeptide of embodiment C84, wherein the soluble human tissue factor domain comprises a sequence that is at least 95% identical to SEQ ID NO: 6.

Embodiment C86. The multi-chain chimeric polypeptide of embodiment C85, wherein the soluble human tissue factor domain comprises a sequence that is 100% identical to SEQ ID NO: 6.

Embodiment D1. A multi-chain chimeric polypeptide comprising:

(a) a first chimeric polypeptide comprising:
 (i) a first target-binding domain;
 (ii) a soluble tissue factor domain; and
 (iii) a first domain of a pair of affinity domains;
(b) a second chimeric polypeptide comprising:
 (i) a second domain of a pair of affinity domains; and
 (ii) a second target-binding domain, wherein:

the first chimeric polypeptide and the second chimeric polypeptide associate through the binding of the first domain and the second domain of the pair of affinity domains;

the first target-binding domain and the second targeting-binding domain each independently bind specifically to a receptor of IL-18 or a receptor of IL-12.

Embodiment D2. The multi-chain chimeric polypeptide of embodiment D1, wherein the first target-binding domain and the soluble tissue factor domain directly abut each other in the first chimeric polypeptide.

Embodiment D3. The multi-chain chimeric polypeptide of embodiment D1, wherein the first chimeric polypeptide further comprises a linker sequence between the first target-binding domain and the soluble tissue factor domain in the first chimeric polypeptide.

Embodiment D4. The multi-chain chimeric polypeptide of any one of embodiments D1-D3, wherein the soluble tissue factor domain and the first domain of the pair of affinity domains directly abut each other in the first chimeric polypeptide.

Embodiment D5. The multi-chain chimeric polypeptide of any one of embodiments D1-D3, wherein the first chimeric polypeptide further comprises a linker sequence between the soluble tissue factor domain and the first domain of the pair of affinity domains in the first chimeric polypeptide.

Embodiment D6. The multi-chain chimeric polypeptide of any one of embodiments D1-D5, wherein the second domain of the pair of affinity domains and the second target-binding domain directly abut each other in the second chimeric polypeptide.

Embodiment D7. The multi-chain chimeric polypeptide of any one of embodiments D1-D5, wherein second chimeric polypeptide further comprises a linker sequence between the second domain of the pair of affinity domains and the second target-binding domain in the second chimeric polypeptide.

Embodiment D8. The multi-chain chimeric polypeptide of any one of embodiments D1-D7, wherein the soluble tissue factor domain is a soluble human tissue factor domain.

Embodiment D9. The multi-chain chimeric polypeptide of embodiment D8, wherein the soluble human tissue factor domain comprises a sequence that is at least 80% identical to SEQ ID NO: 1.

Embodiment D10. The multi-chain chimeric polypeptide of embodiment D9, wherein the soluble human tissue factor domain comprises a sequence that is at least 90% identical to SEQ ID NO: 1.

Embodiment D11. The multi-chain chimeric polypeptide of embodiment D10, wherein the soluble human tissue factor domain comprises a sequence that is at least 95% identical to SEQ ID NO: 1.

Embodiment D12. The multi-chain chimeric polypeptide of any one of embodiments D8-D11, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment D13. The multi-chain chimeric polypeptide of embodiment D12, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment D14. The multi-chain chimeric polypeptide of any one of embodiments D1-D13, wherein the soluble tissue factor domain is not capable of binding to Factor VIIa.

Embodiment D15. The multi-chain chimeric polypeptide of any one of embodiments D1-D14, wherein the soluble tissue factor domain does not convert inactive Factor X into Factor Xa.

Embodiment D16. The multi-chain chimeric polypeptide of any one of embodiments D1-D15, wherein the multi-chain chimeric polypeptide does not stimulate blood coagulation in a mammal.

Embodiment D17. The multi-chain chimeric polypeptide of any one of embodiments D1-D16, wherein the first chimeric polypeptide further comprises a peptide tag at the N-terminal end or the C-terminal end of the first chimeric polypeptide.

Embodiment D18. The multi-chain chimeric polypeptide of any one of embodiments D1-D17, wherein the second chimeric polypeptide further comprises a peptide tag at the N-terminal end or the C-terminal end of the second chimeric polypeptide.

Embodiment D19. The multi-chain chimeric polypeptide of any one of embodiments D1-D18, wherein the first chimeric polypeptide and/or the second chimeric polypeptide further comprises a signal sequence at its N-terminal end.

Embodiment D20. The multi-chain chimeric polypeptide of embodiment D19, wherein the signal sequence comprises SEQ ID NO: 62.

Embodiment D21. The multi-chain chimeric polypeptide of embodiment D20, wherein the signal sequence is SEQ ID NO: 62.

Embodiment D22. The multi-chain chimeric polypeptide of any one of embodiments D1-D21, wherein the pair of affinity domains is a sushi domain from an alpha chain of human IL-15 receptor (IL15Rα) and a soluble IL-15.

Embodiment D23. The multi-chain chimeric polypeptide of embodiment D22, wherein the soluble IL-15 has a D8N or D8A amino acid substitution.

Embodiment D24. The multi-chain chimeric polypeptide of embodiment D22, wherein the soluble IL-15 comprises a sequence that is 80% identical to SEQ ID NO: 39.

Embodiment D25. The multi-chain chimeric polypeptide of embodiment D24, wherein the soluble IL-15 comprises a sequence that is 90% identical to SEQ ID NO: 39.

Embodiment D26. The multi-chain chimeric polypeptide of embodiment D25, wherein the soluble IL-15 comprises a sequence that is 95% identical to SEQ ID NO: 39.

Embodiment D27. The multi-chain chimeric polypeptide of embodiment D26, wherein the soluble IL-15 comprises SEQ ID NO: 39.

Embodiment D28. The multi-chain chimeric polypeptide of any one of embodiments D22-D27, wherein the sushi domain of IL15Rα comprises a sushi domain from human IL15Rα.

Embodiment D29. The multi-chain chimeric polypeptide of embodiment D28, wherein the sushi domain from human IL15Rα comprises a sequence that is 80% identical to SEQ ID NO: 10.

Embodiment D30. The multi-chain chimeric polypeptide of embodiment D29, wherein the sushi domain from human IL15Rα comprises a sequence that is 90% identical to SEQ ID NO: 10.

Embodiment D31. The multi-chain chimeric polypeptide of embodiment D30, wherein the sushi domain from human IL15Rα comprises a sequence that is 95% identical to SEQ ID NO: 10.

Embodiment D32. The multi-chain chimeric polypeptide of embodiment D31, wherein the sushi domain from human IL15Rα comprises SEQ ID NO: 10.

Embodiment D33. The multi-chain chimeric polypeptide of embodiment D28, wherein the sushi domain from human IL15Rα is a mature full-length IL15Rα.

Embodiment D34. The multi-chain chimeric polypeptide of any one of embodiments D1-D21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment D35. The multi-chain chimeric polypeptide of any one of embodiments D1-D34, wherein one or both of the first target-binding domain and the second target-binding domain is an agonistic antigen-binding domain.

Embodiment D36. The multi-chain chimeric polypeptide of embodiment D35, wherein the first target-binding domain and the second target-binding domain are each agonistic antigen-binding domains.

Embodiment D37. The multi-chain chimeric polypeptide of embodiment D35 or D36, wherein antigen-binding domain comprises a scFv or single-domain antibody.

Embodiment D38. The multi-chain chimeric polypeptide of any one of embodiments D1-D34, wherein one or both of the first target-binding domain and the second target-binding domain is a soluble IL-15 or a soluble IL-18.

Embodiment D39. The multi-chain chimeric polypeptide of embodiment D38, wherein the first target-binding domain and the second target-binding domain are each independently a soluble IL-15 or a soluble IL-18.

Embodiment D40. The multi-chain chimeric polypeptide of any one of embodiments D1-D39, wherein the first target-binding domain and the second target-binding domain both bind specifically to a receptor of IL-18 or a receptor of IL-12.

Embodiment D41. The multi-chain chimeric polypeptide of embodiment B40, wherein the first target-binding domain and the second target-binding domain bind specifically to the same epitope.

Embodiment D42. The multi-chain chimeric polypeptide of embodiment D41, wherein the first target-binding domain and the second target-binding domain comprise the same amino acid sequence.

Embodiment D43. The multi-chain chimeric polypeptide of any one of embodiments D1-D39, wherein the first target-binding domain binds specifically to a receptor for IL-12, and the second target-binding domain binds specifically to a receptor for IL-18.

Embodiment D44. The multi-chain chimeric polypeptide of any one of embodiments D1-D39, wherein the first target-binding domain binds specifically to a receptor for IL-18, and the second target-binding domain bind specifically to a receptor for IL-12.

Embodiment D45. The multi-chain chimeric polypeptide of embodiment D44, wherein the first target-binding domain comprises a soluble IL-18.

Embodiment D46. The multi-chain chimeric polypeptide of embodiment D45, wherein the soluble IL-18 is a soluble human IL-18.

Embodiment D47. The multi-chain chimeric polypeptide of embodiment D46, wherein the soluble human IL-18 comprises a sequence at least 80% identical to SEQ ID NO: 41.

Embodiment D48. The multi-chain chimeric polypeptide of embodiment D47, wherein the soluble human IL-18 comprises a sequence at least 90% identical to SEQ ID NO: 41.

Embodiment D49. The multi-chain chimeric polypeptide of embodiment D48, wherein the soluble human IL-18 comprises a sequence at least 95% identical to SEQ ID NO: 41.

Embodiment D50. The multi-chain chimeric polypeptide of embodiment D49, wherein the soluble human IL-18 comprises a sequence of SEQ ID NO: 41.

Embodiment D51. The multi-chain chimeric polypeptide of any one of embodiments D44-D50, wherein the second target-binding domain comprises a soluble IL-12.

Embodiment D52. The multi-chain chimeric polypeptide of embodiment D51, wherein the soluble IL-18 is a soluble human IL-12.

Embodiment D53. The multi-chain chimeric polypeptide of embodiment D52, wherein the soluble human IL-15 comprises a sequence of soluble human IL-120 (p40) and a sequence of soluble human IL-12α (p35).

Embodiment D54. The multi-chain chimeric polypeptide of embodiment D53, wherein the soluble human IL-15 further comprises a linker sequence between the sequence of soluble IL-12 (p40) and the sequence of soluble human IL-12α (p35).

Embodiment D55. The multi-chain chimeric polypeptide of embodiment D54, wherein the linker sequence comprises SEQ ID NO: 7.

Embodiment D56. The multi-chain chimeric polypeptide of any one of embodiments D53-D55, wherein the sequence of soluble human IL-120 (p40) comprises a sequence that is at least 80% identical to SEQ ID NO: 33.

Embodiment D57. The multi-chain chimeric polypeptide of embodiment D56, wherein the sequence of soluble human IL-120 (p40) comprises a sequence that is at least 90% identical to SEQ ID NO: 33.

Embodiment D58. The multi-chain chimeric polypeptide of embodiment D57, wherein the sequence of soluble human IL-120 (p40) comprises a sequence that is at least 95% identical to SEQ ID NO: 33.

Embodiment D59. The multi-chain chimeric polypeptide of embodiment D58, wherein the sequence of soluble human IL-120 (p40) comprises SEQ ID NO: 33.

Embodiment D60. The multi-chain chimeric polypeptide of any one of embodiments D53-D59, wherein the sequence of soluble human IL-12α (p35) comprises a sequence that is at least 80% identical to SEQ ID NO: 35.

Embodiment D61. The multi-chain chimeric polypeptide of embodiment D60, wherein the sequence of soluble human IL-12α (p35) comprises a sequence that is at least 90% identical to SEQ ID NO: 35.

Embodiment D62. The mule-chain chimeric polypeptide of embodiment D61, wherein the sequence of soluble human IL-12α (p35) comprises a sequence that is at least 95% identical to SEQ ID NO: 35.

Embodiment D63. The multi-chain chimeric polypeptide of embodiment D62, wherein the sequence of soluble human IL-12α (p35) comprises SEQ ID NO: 35.

Embodiment D64. The multi-chain chimeric polypeptide of embodiment D1, wherein the first chimeric polypeptide comprises a sequence that is at least 80% identical to SEQ ID NO: 116.

Embodiment D65. The multi-chain chimeric polypeptide of embodiment D64, wherein the first chimeric polypeptide comprises a sequence that is at least 90% identical to SEQ ID NO: 116.

Embodiment D66. The multi-chain chimeric polypeptide of embodiment D65, wherein the first chimeric polypeptide comprises a sequence that is at least 95% identical to SEQ ID NO: 116.

Embodiment D67. The multi-chain chimeric polypeptide of embodiment D66, wherein the first chimeric polypeptide comprises SEQ ID NO: 116.

Embodiment D68. The multi-chain chimeric polypeptide of embodiment D67, wherein the first chimeric polypeptide comprises SEQ ID NO: 118.

Embodiment D69. The multi-chain chimeric polypeptide of any one of embodiments D1 and D64-D68, wherein the second chimeric polypeptide comprises a sequence that is at least 80% identical to SEQ ID NO: 120.

Embodiment D70. The multi-chain chimeric polypeptide of embodiment D69, wherein the second chimeric polypeptide comprises a sequence that is at least 90% identical to SEQ ID NO: 120.

Embodiment D71. The multi-chain chimeric polypeptide of embodiment D70, wherein the second chimeric polypeptide comprises a sequence that is at least 95% identical to SEQ ID NO: 120.

Embodiment D72. The multi-chain chimeric polypeptide of embodiment D71, wherein the second chimeric polypeptide comprises SEQ ID NO: 120.

Embodiment D73. The multi-chain chimeric polypeptide of embodiment D72, wherein the second chimeric polypeptide comprises SEQ ID NO: 122.

Embodiment D74. The multi-chain chimeric polypeptide of any one of embodiments D1-D63, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment D75. The multi-chain chimeric polypeptide of embodiment D74, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment D76. The multi-chain chimeric polypeptide of any one of embodiments D1-D63, wherein the first chimeric polypeptide further comprises one or more additional target-binding domains at the N-terminal and/or C-terminal end of the first chimeric polypeptide.

Embodiment D77. The multi-chain chimeric polypeptide of embodiment D76, wherein at least one of the one or more additional target-binding domains directly abuts the first domain of the pair of affinity domains in the first chimeric polypeptide.

Embodiment D78. The multi-chain chimeric polypeptide of embodiment D76, wherein the first chimeric polypeptide further comprises a linker sequence between the at least one of the one or more additional target-binding domains and the first domain of the pair of affinity domains.

Embodiment D79. The multi-chain chimeric polypeptide of embodiment D76, wherein the at least one of the one or more additional target-binding domains directly abuts the first target-binding domain in the first chimeric polypeptide.

Embodiment D80. The multi-chain chimeric polypeptide of embodiment D76, wherein the first chimeric polypeptide further comprises a linker sequence between the at least one of the one or more additional target-binding domains and the first target-binding domain.

Embodiment D81. The multi-chain chimeric polypeptide of embodiment D76, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment D82. The multi-chain chimeric polypeptide of embodiment D81, wherein the at least one additional target-binding domain of the one or more additional target-binding domains disposed at the N-terminus directly abuts the first target-binding domain or the first domain of the pair of affinity domains in the first chimeric polypeptide.

Embodiment D83. The multi-chain chimeric polypeptide of embodiment D81, wherein the first chimeric polypeptide further comprises a linker sequence disposed between the at least one additional target-binding domain and the first target-binding domain or the first domain of the pair of affinity domains in the first chimeric polypeptide.

Embodiment D84. The multi-chain chimeric polypeptide of embodiment D81, wherein the at least one additional target-binding domain of the one or more additional target-binding domains disposed at the C-terminus directly abuts the first target-binding domain or the first domain of the pair of affinity domains in the first chimeric polypeptide.

Embodiment D85. The multi-chain chimeric polypeptide of embodiment D81, wherein the first chimeric polypeptide further comprises a linker sequence disposed between the at least one additional target-binding domain and the first target-binding domain or the first domain of the pair of affinity domains in the first chimeric polypeptide.

Embodiment D86. The multi-chain chimeric polypeptide of embodiment D81, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment D87. The multi-chain chimeric polypeptide of embodiment D81, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment D88. The multi-chain chimeric polypeptide of any one of embodiments D1-D63 and D74-D87, wherein the second chimeric polypeptide further comprises one or more additional target-binding domains at the N-terminal end or the C-terminal end of the second chimeric polypeptide.

Embodiment D89. The multi-chain chimeric polypeptide of embodiment D88, wherein at least one of the one or more additional target-binding domains directly abuts the second domain of the pair of affinity domains in the second chimeric polypeptide.

Embodiment D90. The multi-chain chimeric polypeptide of embodiment D88, wherein the second chimeric polypeptide further comprises a linker sequence between at least one of the one or more additional target-binding domains and the second domain of the pair of affinity domains in the second chimeric polypeptide.

Embodiment D91. The multi-chain chimeric polypeptide of embodiment D88, wherein at least one of the one or more additional target-binding domains directly abuts the second target-binding domain in the second chimeric polypeptide.

Embodiment D92. The multi-chain chimeric polypeptide of embodiment D88, wherein the second chimeric polypeptide further comprises a linker sequence between at least one of the one or more additional target-binding domains and the second target-binding domain in the second chimeric polypeptide.

Embodiment D93. The multi-chain chimeric polypeptide of any one of embodiments D74-D92, wherein two or more of the first target-binding domain, the second target-binding domain, and the one or more additional target-binding domains bind specifically to the same antigen.

Embodiment D94. The multi-chain chimeric polypeptide of embodiment D93, wherein two or more of the first target-binding domain, the second target-binding domain, and the one or more additional target-binding domains bind specifically to the same epitope.

Embodiment D95. The multi-chain chimeric polypeptide of embodiment D94, wherein two or more of the first target-binding domain, the second target-binding domain, and the one or more additional target-binding domains comprise the same amino acid sequence.

Embodiment D96. The multi-chain chimeric polypeptide of any one of embodiments D74-D92, wherein the first target-binding domain, the second target-binding domain, and the one or more additional target-binding domains bind specifically to different antigens.

Embodiment D97. The multi-chain chimeric polypeptide of any one of embodiments D74-D96, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment D98. The multi-chain chimeric polypeptide of any one of embodiments D74-D96, wherein the one or more additional target-binding domains is a soluble interleukin, soluble cytokine protein, or soluble cell surface protein.

Embodiment D99. The multi-chain chimeric polypeptide of embodiment D98, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment D100. The multi-chain chimeric polypeptide of any one of embodiments D74-D96, wherein the one or more additional target-binding domains is a soluble interleukin receptor, soluble cytokine receptor, or soluble cell surface receptor.

Embodiment D101. The multi-chain chimeric polypeptide of embodiment D100, wherein the soluble receptor is a soluble TGF-β receptor II (TGF-β RII), a soluble TGF-βRIII, a soluble NKG2D, a soluble NKP30, a soluble NKp44, a soluble NKp46, a soluble DNAM-1, a scMHCI, a scMHCII, a scTCR, a soluble CD155, a soluble CD122, or a soluble CD28.

Embodiment D102. A composition comprising any of the multi-chain chimeric polypeptides of embodiments D1-D101.

Embodiment D103. The composition of embodiment D102, wherein the composition is a pharmaceutical composition.

Embodiment D104. A kit comprising at least one dose of the composition of embodiment D102 or D103.

Embodiment D105. Nucleic acid encoding any of the multi-chain chimeric polypeptides of any one of embodiments D1-D101.

Embodiment D106. A vector comprising the nucleic acid of embodiment D105.

Embodiment D107. The vector of embodiment D106, wherein the vector is an expression vector.

Embodiment D108. A cell comprising the nucleic acid of embodiment D105 or the vector of embodiment D106 or D107.

Embodiment D109. A method of producing a multi-chain chimeric polypeptide, the method comprising:

culturing the cell of embodiment D108 in a culture medium under conditions sufficient to result in the production of the multi-chain chimeric polypeptide; and recovering the multi-chain chimeric polypeptide from the cell and/or the culture medium.

Embodiment D 110. A multi-chain chimeric polypeptide produced by the method of embodiment D109.

Embodiment D111. The multi-chain chimeric polypeptide of embodiment D8, wherein the soluble human tissue factor domain comprises a sequence that is at least 80% identical to SEQ ID NO: 5.

Embodiment D112. The multi-chain chimeric polypeptide of embodiment D111, wherein the soluble human tissue factor domain comprises a sequence that is at least 90% identical to SEQ ID NO: 5.

Embodiment D113. The multi-chain chimeric polypeptide of embodiment D112, wherein the soluble human tissue factor domain comprises a sequence that is at least 95% identical to SEQ ID NO: 5.

Embodiment D114. The multi-chain chimeric polypeptide of embodiment D113, wherein the soluble human tissue factor domain comprises a sequence that is 100% identical to SEQ ID NO: 5.

Embodiment D115. The multi-chain chimeric polypeptide of embodiment D8, wherein the soluble human tissue factor domain comprises a sequence that is at least 80% identical to SEQ ID NO: 6.

Embodiment D116. The multi-chain chimeric polypeptide of embodiment D115, wherein the soluble human tissue factor domain comprises a sequence that is at least 90% identical to SEQ ID NO: 6.

Embodiment D117. The multi-chain chimeric polypeptide of embodiment D116, wherein the soluble human tissue factor domain comprises a sequence that is at least 95% identical to SEQ ID NO: 6.

Embodiment D118. The multi-chain chimeric polypeptide of embodiment D117, wherein the soluble human tissue factor domain comprises a sequence that is 100% identical to SEQ ID NO: 6.

Embodiment E1. A multi-chain chimeric polypeptide comprising:

(a) a first chimeric polypeptide comprising:
  (i) a first target-binding domain;
  (ii) a soluble tissue factor domain; and
  (iii) a first domain of a pair of affinity domains;
(b) a second chimeric polypeptide comprising:
  (i) a second domain of a pair of affinity domains; and
  (ii) a second target-binding domain, wherein:

the first chimeric polypeptide and the second chimeric polypeptide associate through the binding of the first domain and the second domain of the pair of affinity domains; and the first target-binding domain and the second targeting-binding domain each independently bind specifically to a receptor of IL-21 or a ligand of tumor growth factor receptor βRII (TGFβRII).

Embodiment E2. The multi-chain chimeric polypeptide of embodiment E1, wherein the first target-binding domain and the soluble tissue factor domain directly abut each other in the first chimeric polypeptide.

Embodiment E3. The multi-chain chimeric polypeptide of embodiments E1, wherein the first chimeric polypeptide further comprises a linker sequence between the first target-binding domain and the soluble tissue factor domain in the first chimeric polypeptide.

Embodiment E4. The multi-chain chimeric polypeptide of any one of embodiments E1-E3, wherein the soluble tissue factor domain and the first domain of the pair of affinity domains directly abut each other in the first chimeric polypeptide.

Embodiment E5. The multi-chain chimeric polypeptide of any one of embodiments E1-E3, wherein the first chimeric polypeptide further comprises a linker sequence between the soluble tissue factor domain and the first domain of the pair of affinity domains in the first chimeric polypeptide.

Embodiment E6. The multi-chain chimeric polypeptide of any one of embodiments E1-E5, wherein the second domain of the pair of affinity domains and the second target-binding domain directly abut each other in the second chimeric polypeptide.

Embodiment E7. The multi-chain chimeric polypeptide of any one of embodiments E1-E5, wherein second chimeric polypeptide further comprises a linker sequence between the second domain of the pair of affinity domains and the second target-binding domain in the second chimeric polypeptide.

Embodiment E8. The multi-chain chimeric polypeptide of any one of embodiments E1-E7, wherein the soluble tissue factor domain is a soluble human tissue factor domain.

Embodiment E9. The multi-chain chimeric polypeptide of embodiment E8, wherein the soluble human tissue factor domain comprises a sequence that is at least 80% identical to SEQ ID NO: 1.

Embodiment E10. The multi-chain chimeric polypeptide of embodiment E9, wherein the soluble human tissue factor domain comprises a sequence that is at least 90% identical to SEQ ID NO: 1.

Embodiment E11. The multi-chain chimeric polypeptide of embodiment E10, wherein the soluble human tissue factor domain comprises a sequence that is at least 95% identical to SEQ ID NO: 1.

Embodiment E12. The multi-chain chimeric polypeptide of any one of embodiments E8-E11, wherein the soluble human tissue factor domain does not comprise one or more of a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment E13. The multi-chain chimeric polypeptide of embodiment E12, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment E14. The multi-chain chimeric polypeptide of any one of embodiments E1-E13, wherein the soluble tissue factor domain is not capable of binding to Factor VIIa.

Embodiment E15. The multi-chain chimeric polypeptide of any one of embodiments E1-E14, wherein the soluble tissue factor domain does not convert inactive Factor X into Factor Xa.

Embodiment E16. The multi-chain chimeric polypeptide of any one of embodiments E1-E15, wherein the multi-chain chimeric polypeptide does not stimulate blood coagulation in a mammal.

Embodiment E17. The multi-chain chimeric polypeptide of any one of embodiments E1-E16, wherein the first chimeric polypeptide further comprises a peptide tag at the N-terminal end or the C-terminal end of the first chimeric polypeptide.

Embodiment E18. The multi-chain chimeric polypeptide of any one of embodiments E1-E17, wherein the second chimeric polypeptide further comprises a peptide tag at the N-terminal end or the C-terminal end of the second chimeric polypeptide.

Embodiment E19. The multi-chain chimeric polypeptide of any one of embodiments E1-E18, wherein the first chimeric polypeptide and/or the second chimeric polypeptide further comprises a signal sequence at its N-terminal end.

Embodiment E20. The multi-chain chimeric polypeptide of embodiment E19, wherein the signal sequence comprises SEQ ID NO: 62.

Embodiment E21. The multi-chain chimeric polypeptide of embodiment E20, wherein the signal sequence is SEQ ID NO: 62.

Embodiment E22. The multi-chain chimeric polypeptide of any one of embodiments E1-E21, wherein the pair of affinity domains is a sushi domain from an alpha chain of human IL-15 receptor (IL15Rα and a soluble IL-15.

Embodiment E23. The multi-chain chimeric polypeptide of embodiment E22, wherein the soluble IL-15 has a D8N or D8A amino acid substitution.

Embodiment E24. The multi-chain chimeric polypeptide of embodiment E22, wherein the soluble IL-15 comprises a sequence that is 80% identical to SEQ ID NO: 39.

Embodiment E25. The multi-chain chimeric polypeptide of embodiment E24, wherein the soluble IL-15 comprises a sequence that is 90% identical to SEQ ID NO: 39.

Embodiment E26. The multi-chain chimeric polypeptide of embodiment E25, wherein the soluble IL-15 comprises a sequence that is 95% identical to SEQ ID NO: 39.

Embodiment E27. The multi-chain chimeric polypeptide of embodiment E26, wherein the soluble IL-15 comprises SEQ ID NO: 39.

Embodiment E28. The multi-chain chimeric polypeptide of any one of embodiments E22-E27, wherein the sushi domain of IL15Rα comprises a sushi domain from human IL15Rα.

Embodiment E29. The multi-chain chimeric polypeptide of embodiment E28, wherein the sushi domain from human IL15Rα comprises a sequence that is 80% identical to SEQ ID NO: 10.

Embodiment E30. The multi-chain chimeric polypeptide of embodiment E29, wherein the sushi domain from human IL15Rα comprises a sequence that is 90% identical to SEQ ID NO: 10.

Embodiment E31. The multi-chain chimeric polypeptide of embodiment E30, wherein the sushi domain from human IL15Rα comprises a sequence that is 95% identical to SEQ ID NO: 10.

Embodiment E32. The multi-chain chimeric polypeptide of embodiment E31, wherein the sushi domain from human IL15Rα comprises SEQ ID NO: 10.

Embodiment E33. The multi-chain chimeric polypeptide of embodiment E28, wherein the sushi domain from human IL15Rα is a mature full-length IL15Rα.

Embodiment E34. The multi-chain chimeric polypeptide of any one of embodiments E1-E21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment E35. The multi-chain chimeric polypeptide of any one of embodiments E1-E34, wherein one or both of the first target-binding domain and the second target-binding domain is an antigen-binding domain.

Embodiment E36. The multi-chain chimeric polypeptide of embodiment E35, wherein the first target-binding domain and the second target-binding domain are antigen-binding domains.

Embodiment E37. The multi-chain chimeric polypeptide of embodiment E35 or E36, wherein antigen-binding domain comprises a scFv or single-domain antibody.

Embodiment E38. The multi-chain chimeric polypeptide of any one of embodiments E1-E34, wherein one or both of the first target-binding domain and the second target-binding domain is a soluble IL-21 or a soluble TGFβRII.

Embodiment E39. The multi-chain chimeric polypeptide of any one of embodiments E1-E38, wherein the first target-binding domain and the second target-binding domain both bind specifically to a receptor of IL-21 or a ligand of TGFβRII.

Embodiment E40. The multi-chain chimeric polypeptide of embodiment E39, wherein the first target-binding domain and the second target-binding domain bind specifically to the same epitope.

Embodiment E41. The multi-chain chimeric polypeptide of embodiment E40, wherein the first target-binding domain and the second target-binding domain comprise the same amino acid sequence.

Embodiment E42. The multi-chain chimeric polypeptide of any one of embodiments E1-E38, wherein the first target-binding domain binds specifically to a ligand of TGFβRII, and the second target-binding domain binds specifically to a receptor for IL-21.

Embodiment E43. The multi-chain chimeric polypeptide of any one of embodiments E1-E38, wherein the first target-binding domain binds specifically to a receptor for IL-21, and the second target-binding domain bind specifically to a ligand of TGFβRII.

Embodiment E44. The multi-chain chimeric polypeptide of embodiment E43, wherein the first target-binding domain comprises a soluble IL-21.

Embodiment E45. The multi-chain chimeric polypeptide of embodiment E44, wherein the soluble IL-21 is a soluble human IL-21.

Embodiment E46. The multi-chain chimeric polypeptide of embodiment E45, wherein the soluble human IL-21 comprises a sequence at least 80% identical to SEQ ID NO: 124.

Embodiment E47. The multi-chain chimeric polypeptide of embodiment E46, wherein the soluble human IL-21 comprises a sequence at least 90% identical to SEQ ID NO: 124.

Embodiment E48. The multi-chain chimeric polypeptide of embodiment E47, wherein the soluble human IL-21 comprises a sequence at least 95% identical to SEQ ID NO: 124.

Embodiment E49. The multi-chain chimeric polypeptide of embodiment E48, wherein the soluble human IL-21 comprises a sequence of SEQ ID NO: 124.

Embodiment E50. The multi-chain chimeric polypeptide of any one of embodiments E43-E49, wherein the second target-binding domain comprises a soluble TGFβRII.

Embodiment E51. The multi-chain chimeric polypeptide of embodiment E50, wherein the soluble TGFβRII is a soluble human TGFβRII.

Embodiment E52. The multi-chain chimeric polypeptide of embodiment E51, wherein the soluble human TGFβRII comprises a first sequence of soluble human TGFβRII and a second sequence of soluble human TGFβRII.

Embodiment E53. The multi-chain chimeric polypeptide of embodiment E52, wherein the soluble human TGFβRII further comprises a linker sequence between the first sequence of soluble human TGFβRII and the second sequence of soluble human TGFβRII.

Embodiment E54. The multi-chain chimeric polypeptide of embodiment E53, wherein the linker sequence comprises SEQ ID NO: 7.

Embodiment E55. The multi-chain chimeric polypeptide of any one of embodiments E52-E54, wherein the first sequence of soluble human TGFβRII comprises a sequence that is at least 80% identical to SEQ ID NO: 56.

Embodiment E56. The multi-chain chimeric polypeptide of embodiment E55, wherein the first sequence of soluble human TGFβRII comprises a sequence that is at least 90% identical to SEQ ID NO: 56.

Embodiment E57. The multi-chain chimeric polypeptide of embodiment E56, wherein the first sequence of soluble human TGFβRII comprises a sequence that is at least 95% identical to SEQ ID NO: 56.

Embodiment E58. The multi-chain chimeric polypeptide of embodiment E57, wherein the first sequence of soluble human TGFβRII comprises SEQ ID NO: 56.

Embodiment E59. The multi-chain chimeric polypeptide of any one of embodiments E52-E58, wherein the second sequence of soluble human TGFβRII comprises a sequence that is at least 80% identical to SEQ ID NO: 56.

Embodiment E60. The multi-chain chimeric polypeptide of embodiment E59, wherein the second sequence of soluble human TGFβRII comprises a sequence that is at least 90% identical to SEQ ID NO: 56.

Embodiment E61. The mule-chain chimeric polypeptide of embodiment E60, wherein the second sequence of soluble human TGFβRII comprises a sequence that is at least 95% identical to SEQ ID NO: 56.

Embodiment E62. The multi-chain chimeric polypeptide of embodiment E61, wherein the second sequence of soluble human TGFβRII comprises SEQ ID NO: 56.

Embodiment E63. The multi-chain chimeric polypeptide of embodiment E1, wherein the first chimeric polypeptide comprises a sequence that is at least 80% identical to SEQ ID NO: 126.

Embodiment E64. The multi-chain chimeric polypeptide of embodiment E63, wherein the first chimeric polypeptide comprises a sequence that is at least 90% identical to SEQ ID NO: 126.

Embodiment E65. The multi-chain chimeric polypeptide of embodiment E64, wherein the first chimeric polypeptide comprises a sequence that is at least 95% identical to SEQ ID NO: 126.

Embodiment E66. The multi-chain chimeric polypeptide of embodiment E65, wherein the first chimeric polypeptide comprises SEQ ID NO: 126.

Embodiment E67. The multi-chain chimeric polypeptide of embodiment E66, wherein the first chimeric polypeptide comprises SEQ ID NO: 128.

Embodiment E68. The multi-chain chimeric polypeptide of any one of embodiments E1 and E63-E67, wherein the second chimeric polypeptide comprises a sequence that is at least 80% identical to SEQ ID NO: 130.

Embodiment E69. The multi-chain chimeric polypeptide of embodiment E68, wherein the second chimeric polypeptide comprises a sequence that is at least 90% identical to SEQ ID NO: 130.

Embodiment E70. The multi-chain chimeric polypeptide of embodiment E69, wherein the second chimeric polypeptide comprises a sequence that is at least 95% identical to SEQ ID NO: 130.

Embodiment E71. The multi-chain chimeric polypeptide of embodiment E70, wherein the second chimeric polypeptide comprises SEQ ID NO: 130.

Embodiment E72. The multi-chain chimeric polypeptide of embodiment E71, wherein the second chimeric polypeptide comprises SEQ ID NO: 132.

Embodiment E73. The multi-chain chimeric polypeptide of any one of embodiments E1-E62, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment E74. The multi-chain chimeric polypeptide of embodiment E73, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment E75. The multi-chain chimeric polypeptide of any one of embodiments E1-E62, wherein the first chimeric polypeptide further comprises one or more additional target-binding domains at the N-terminal and/or C-terminal end of the first chimeric polypeptide.

Embodiment E76. The multi-chain chimeric polypeptide of embodiment E75, wherein at least one of the one or more additional target-binding domains directly abuts the first domain of the pair of affinity domains in the first chimeric polypeptide.

Embodiment E77. The multi-chain chimeric polypeptide of embodiment E75, wherein the first chimeric polypeptide further comprises a linker sequence between the at least one of the one or more additional target-binding domains and the first domain of the pair of affinity domains.

Embodiment E78. The multi-chain chimeric polypeptide of embodiment E75, wherein the at least one of the one or more additional target-binding domains directly abuts the first target-binding domain in the first chimeric polypeptide.

Embodiment E79. The multi-chain chimeric polypeptide of embodiment E75, wherein the first chimeric polypeptide further comprises a linker sequence between the at least one of the one or more additional target-binding domains and the first target-binding domain.

Embodiment E80. The multi-chain chimeric polypeptide of embodiment E75, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment E81. The multi-chain chimeric polypeptide of embodiment E80, wherein the at least one additional target-binding domain of the one or more additional target-binding domains disposed at the N-terminus directly abuts the first target-binding domain or the first domain of the pair of affinity domains in the first chimeric polypeptide.

Embodiment E82. The multi-chain chimeric polypeptide of embodiment E80, wherein the first chimeric polypeptide further comprises a linker sequence disposed between the at least one additional target-binding domain and the first target-binding domain or the first domain of the pair of affinity domains in the first chimeric polypeptide.

Embodiment E83. The multi-chain chimeric polypeptide of embodiment E80, wherein the at least one additional target-binding domain of the one or more additional target-binding domains disposed at the C-terminus directly abuts the first target-binding domain or the first domain of the pair of affinity domains in the first chimeric polypeptide.

Embodiment E84. The multi-chain chimeric polypeptide of embodiment E80, wherein the first chimeric polypeptide further comprises a linker sequence disposed between the at least one additional target-binding domain and the first target-binding domain or the first domain of the pair of affinity domains in the first chimeric polypeptide.

Embodiment E85. The multi-chain chimeric polypeptide of embodiment E80, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment E86. The multi-chain chimeric polypeptide of embodiment E80, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment E87. The multi-chain chimeric polypeptide of any one of embodiments E1-E62 and E73-E86, wherein the second chimeric polypeptide further comprises one or more additional target-binding domains at the N-terminal end or the C-terminal end of the second chimeric polypeptide.

Embodiment E88. The multi-chain chimeric polypeptide of embodiment E87, wherein at least one of the one or more additional target-binding domains directly abuts the second domain of the pair of affinity domains in the second chimeric polypeptide.

Embodiment E89. The multi-chain chimeric polypeptide of embodiment E87, wherein the second chimeric polypeptide further comprises a linker sequence between at least one of the one or more additional target-binding domains and the second domain of the pair of affinity domains in the second chimeric polypeptide.

Embodiment E90. The multi-chain chimeric polypeptide of embodiment E87, wherein at least one of the one or more additional target-binding domains directly abuts the second target-binding domain in the second chimeric polypeptide.

Embodiment E91. The multi-chain chimeric polypeptide of embodiment E87, wherein the second chimeric polypeptide further comprises a linker sequence between at least one of the one or more additional target-binding domains and the second target-binding domain in the second chimeric polypeptide.

Embodiment E92. The multi-chain chimeric polypeptide of any one of embodiments E73-E91, wherein two or more of the first target-binding domain, the second target-binding domain, and the one or more additional target-binding domains bind specifically to the same antigen.

Embodiment E93. The multi-chain chimeric polypeptide of embodiment E92, wherein two or more of the first target-binding domain, the second target-binding domain, and the one or more additional target-binding domains bind specifically to the same epitope.

Embodiment E94. The multi-chain chimeric polypeptide of embodiment E93, wherein two or more of the first target-binding domain, the second target-binding domain, and the one or more additional target-binding domains comprise the same amino acid sequence.

Embodiment E95. The multi-chain chimeric polypeptide of any one of embodiments E73-E91, wherein the first target-binding domain, the second target-binding domain, and the one or more additional target-binding domains bind specifically to different antigens.

Embodiment E96. The multi-chain chimeric polypeptide of any one of embodiments E73-E95, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-D, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment E97. The multi-chain chimeric polypeptide of any one of embodiments E73-E95, wherein the one or more additional target-binding domains is a soluble interleukin, soluble cytokine protein, or soluble cell surface protein.

Embodiment E98. The multi-chain chimeric polypeptide of embodiment E97, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment E99. The multi-chain chimeric polypeptide of any one of embodiments E73-E95, wherein the one or more additional target-binding domains is a soluble interleukin or cytokine receptor.

Embodiment E100. The multi-chain chimeric polypeptide of embodiment E99, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment E101. A composition comprising any of the multi-chain chimeric polypeptides of embodiments E1-E100.

Embodiment E102. The composition of embodiment E101, wherein the composition is a pharmaceutical composition.

Embodiment E103. A kit comprising at least one dose of the composition of embodiment E101 or E102.

Embodiment E104. Nucleic acid encoding any of the multi-chain chimeric polypeptides of any one of embodiments E1-E100.

Embodiment E105. A vector comprising the nucleic acid of embodiment E104.

Embodiment E106. The vector of embodiment E105, wherein the vector is an expression vector.

Embodiment E107. A cell comprising the nucleic acid of embodiment C161 or the vector of embodiment E105 or E106.

Embodiment E108. A method of producing a multi-chain chimeric polypeptide, the method comprising:

culturing the cell of embodiment E107 in a culture medium under conditions sufficient to result in the production of the multi-chain chimeric polypeptide; and recovering the multi-chain chimeric polypeptide from the cell and/or the culture medium.

Embodiment E109. A multi-chain chimeric polypeptide produced by the method of embodiment E108.

Embodiment E110. The multi-chain chimeric polypeptide of embodiment E12, wherein the soluble human tissue factor domain comprises a sequence that is at least 80% identical to SEQ ID NO: 5.

Embodiment E111. The multi-chain chimeric polypeptide of embodiment E110, wherein the soluble human tissue factor domain comprises a sequence that is at least 90% identical to SEQ ID NO: 5.

Embodiment E112. The multi-chain chimeric polypeptide of embodiment E111, wherein the soluble human tissue factor domain comprises a sequence that is at least 95% identical to SEQ ID NO: 5.

Embodiment E113. The multi-chain chimeric polypeptide of embodiment E112, wherein the soluble human tissue factor domain comprises a sequence that is 100% identical to SEQ ID NO: 5.

Embodiment E114. The multi-chain chimeric polypeptide of embodiment E12, wherein the soluble human tissue factor domain comprises a sequence that is at least 80% identical to SEQ ID NO: 6.

Embodiment E115. The multi-chain chimeric polypeptide of embodiment E114, wherein the soluble human tissue factor domain comprises a sequence that is at least 90% identical to SEQ ID NO: 6.

Embodiment E116. The multi-chain chimeric polypeptide of embodiment E115, wherein the soluble human tissue factor domain comprises a sequence that is at least 95% identical to SEQ ID NO: 6.

Embodiment E117. The multi-chain chimeric polypeptide of embodiment E116, wherein the soluble human tissue factor domain comprises a sequence that is 100% identical to SEQ ID NO: 6.

Embodiment F1. A multi-chain chimeric polypeptide comprising:

(c) a first chimeric polypeptide comprising:

(i) a first target-binding domain;

(ii) a soluble tissue factor domain; and (iii) a first domain of a pair of affinity domains;

(d) a second chimeric polypeptide comprising:

(i) a second domain of a pair of affinity domains; and (ii) a second target-binding domain, wherein:

the first chimeric polypeptide and the second chimeric polypeptide associate through the binding of the first domain and the second domain of the pair of affinity domains;

the first target-binding domain and the second targeting-binding domain each independently bind specifically to a receptor of IL-21 or a receptor of IL-7.

Embodiment F2. The multi-chain chimeric polypeptide of embodiment F1, wherein the first target-binding domain and the soluble tissue factor domain directly abut each other in the first chimeric polypeptide.

Embodiment F3. The multi-chain chimeric polypeptide of embodiment F1, wherein the first chimeric polypeptide further comprises a linker sequence between the first target-binding domain and the soluble tissue factor domain in the first chimeric polypeptide.

Embodiment F4. The multi-chain chimeric polypeptide of any one of embodiments F1-F3, wherein the soluble tissue factor domain and the first domain of the pair of affinity domains directly abut each other in the first chimeric polypeptide.

Embodiment F5. The multi-chain chimeric polypeptide of any one of embodiments F1-F3, wherein the first chimeric polypeptide further comprises a linker sequence between the soluble tissue factor domain and the first domain of the pair of affinity domains in the first chimeric polypeptide.

Embodiment F6. The multi-chain chimeric polypeptide of any one of embodiments F1-F5, wherein the second domain of the pair of affinity domains and the second target-binding domain directly abut each other in the second chimeric polypeptide.

Embodiment F7. The multi-chain chimeric polypeptide of any one of embodiments F1-F5, wherein second chimeric polypeptide further comprises a linker sequence between the second domain of the pair of affinity domains and the second target-binding domain in the second chimeric polypeptide.

Embodiment F8. The multi-chain chimeric polypeptide of any one of embodiments F1-F7, wherein the soluble tissue factor domain is a soluble human tissue factor domain.

Embodiment F9. The multi-chain chimeric polypeptide of embodiment F8, wherein the soluble human tissue factor domain comprises a sequence that is at least 80% identical to SEQ ID NO: 1.

Embodiment F10. The multi-chain chimeric polypeptide of embodiment F9, wherein the soluble human tissue factor domain comprises a sequence that is at least 90% identical to SEQ ID NO: 1.

Embodiment F11. The multi-chain chimeric polypeptide of embodiment F10, wherein the soluble human tissue factor domain comprises a sequence that is at least 95% identical to SEQ ID NO: 1.

Embodiment F12. The multi-chain chimeric polypeptide of embodiment F11, wherein the soluble human tissue factor domain comprises SEQ ID NO: 1.

Embodiment F13. The multi-chain chimeric polypeptide of embodiment F8, wherein the soluble human tissue factor domain comprises a sequence that is at least 80% identical to SEQ ID NO: 5.

Embodiment F14. The multi-chain chimeric polypeptide of embodiment F13, wherein the soluble human tissue factor domain comprises a sequence that is at least 90% identical to SEQ ID NO: 5.

Embodiment F15. The multi-chain chimeric polypeptide of embodiment F14, wherein the soluble human tissue factor domain comprises a sequence that is at least 95% identical to SEQ ID NO: 5.

Embodiment F16. The multi-chain chimeric polypeptide of embodiment F15, wherein the soluble human tissue factor domain comprises SEQ ID NO: 5.

Embodiment F17. The multi-chain chimeric polypeptide of embodiment F8, wherein the soluble human tissue factor domain comprises a sequence that is at least 80% identical to SEQ ID NO: 6.

Embodiment F18. The multi-chain chimeric polypeptide of embodiment F17, wherein the soluble human tissue factor domain comprises a sequence that is at least 90% identical to SEQ ID NO: 6.

Embodiment F19. The multi-chain chimeric polypeptide of embodiment F18, wherein the soluble human tissue factor domain comprises a sequence that is at least 95% identical to SEQ ID NO: 6.

Embodiment F20. The multi-chain chimeric polypeptide of embodiment F19, wherein the soluble human tissue factor domain comprises SEQ ID NO: 6.

Embodiment F21. The multi-chain chimeric polypeptide of any one of embodiments F8-F11, F13-F15, and F17-F19, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment F22. The multi-chain chimeric polypeptide of embodiment F21, wherein the soluble human tissue factor domain does not comprise any of.

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment F23. The multi-chain chimeric polypeptide of any one of embodiments F1-F22, wherein the soluble tissue factor domain is not capable of binding to Factor VIIa.

Embodiment F24. The multi-chain chimeric polypeptide of any one of embodiments F1-F23, wherein the soluble tissue factor domain does not convert inactive Factor X into Factor Xa.

Embodiment F25. The multi-chain chimeric polypeptide of any one of embodiments F1-F24, wherein the multi-chain chimeric polypeptide does not stimulate blood coagulation in a mammal.

Embodiment F26. The multi-chain chimeric polypeptide of any one of embodiments F1-F25, wherein the first chimeric polypeptide further comprises a peptide tag at the N-terminal end or the C-terminal end of the first chimeric polypeptide.

Embodiment F27. The multi-chain chimeric polypeptide of any one of embodiments F1-F26, wherein the second chimeric polypeptide further comprises a peptide tag at the N-terminal end or the C-terminal end of the second chimeric polypeptide.

Embodiment F28. The multi-chain chimeric polypeptide of any one of embodiments F1-F27, wherein the first chimeric polypeptide and/or the second chimeric polypeptide further comprises a signal sequence at its N-terminal end.

Embodiment F29. The multi-chain chimeric polypeptide of embodiment F28, wherein the signal sequence comprises SEQ ID NO: 62.

Embodiment F30. The multi-chain chimeric polypeptide of embodiment F28, wherein the signal sequence is SEQ ID NO: 44.

Embodiment F31. The multi-chain chimeric polypeptide of any one of embodiments F1-F30, wherein the pair of affinity domains is a sushi domain from an alpha chain of human IL-15 receptor (IL15Rα) and a soluble IL-15.

Embodiment F32. The multi-chain chimeric polypeptide of embodiment F31, wherein the soluble IL-15 has a D8N or D8A amino acid substitution.

Embodiment F33. The multi-chain chimeric polypeptide of embodiment F31, wherein the soluble IL-15 comprises a sequence that is at least 80% identical to SEQ ID NO: 39.

Embodiment F34. The multi-chain chimeric polypeptide of embodiment F33, wherein the soluble IL-15 comprises a sequence that is at least 90% identical to SEQ ID NO: 39.

Embodiment F35. The multi-chain chimeric polypeptide of embodiment F34, wherein the soluble IL-15 comprises a sequence that is at least 95% identical to SEQ ID NO: 39.

Embodiment F36. The multi-chain chimeric polypeptide of embodiment F35, wherein the soluble IL-15 comprises SEQ ID NO: 39.

Embodiment F37. The multi-chain chimeric polypeptide of any one of embodiments F31-F36, wherein the sushi domain of IL15Rα comprises a sushi domain from human IL15Rα.

Embodiment F38. The multi-chain chimeric polypeptide of embodiment F37, wherein the sushi domain from human IL15Rα comprises a sequence that is at least 80% identical to SEQ ID NO: 10.

Embodiment F39. The multi-chain chimeric polypeptide of embodiment F38, wherein the sushi domain from human IL15Rα comprises a sequence that is at least 90% identical to SEQ ID NO: 10.

Embodiment F40. The multi-chain chimeric polypeptide of embodiment F39, wherein the sushi domain from human IL15Rα comprises a sequence that is at least 95% identical to SEQ ID NO: 10.

Embodiment F41. The multi-chain chimeric polypeptide of embodiment F40, wherein the sushi domain from human IL15Rα comprises SEQ ID NO: 10.

Embodiment F42. The multi-chain chimeric polypeptide of embodiment F37, wherein the sushi domain from human IL15Rα is a mature full-length IL15Rα.

Embodiment F43. The multi-chain chimeric polypeptide of any one of embodiments F1-F30, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment F44. The multi-chain chimeric polypeptide of any one of embodiments F1-F43, wherein one or both of the first target-binding domain and the second target-binding domain is an agonistic antigen-binding domain.

Embodiment F45. The multi-chain chimeric polypeptide of embodiment F44, wherein the first target-binding domain and the second target-binding domain are each agonistic antigen-binding domains.

Embodiment F46. The multi-chain chimeric polypeptide of embodiment F44 or F45, wherein antigen-binding domain comprises a scFv or single-domain antibody.

Embodiment F47. The multi-chain chimeric polypeptide of any one of embodiments F1-F43, wherein one or both of the first target-binding domain and the second target-binding domain is a soluble IL-21 or a soluble IL-7.

Embodiment F48. The multi-chain chimeric polypeptide of embodiment F47, wherein the first target-binding domain and the second target-binding domain are each independently a soluble IL-21 or a soluble IL-7.

Embodiment F49. The multi-chain chimeric polypeptide of any one of embodiments F1-F48, wherein the first target-binding domain and the second target-binding domain both bind specifically to a receptor of IL-21 or a receptor of IL-7.

Embodiment F50. The multi-chain chimeric polypeptide of embodiment F49, wherein the first target-binding domain and the second target-binding domain bind specifically to the same epitope.

Embodiment F51. The multi-chain chimeric polypeptide of embodiment F50, wherein the first target-binding domain and the second target-binding domain comprise the same amino acid sequence.

Embodiment F52. The multi-chain chimeric polypeptide of any one of embodiments F1-F48, wherein the first target-binding domain binds specifically to a receptor for IL-21, and the second target-binding domain binds specifically to a receptor for IL-7.

Embodiment F53. The multi-chain chimeric polypeptide of any one of embodiments F1-F48, wherein the first target-binding domain binds specifically to a receptor for IL-7, and the second target-binding domain bind specifically to a receptor for IL-21.

Embodiment F54. The multi-chain chimeric polypeptide of embodiment F53, wherein the first target-binding domain comprises a soluble IL-21.

Embodiment F55. The multi-chain chimeric polypeptide of embodiment F54, wherein the soluble IL-21 is a soluble human IL-21.

Embodiment F56. The multi-chain chimeric polypeptide of embodiment F55, wherein the soluble human IL-21 comprises a sequence at least 80% identical to SEQ ID NO: 124.

Embodiment F57. The multi-chain chimeric polypeptide of embodiment F56, wherein the soluble human IL-21 comprises a sequence at least 90% identical to SEQ ID NO: 124.

Embodiment F58. The multi-chain chimeric polypeptide of embodiment F57, wherein the soluble human IL-21 comprises a sequence at least 95% identical to SEQ ID NO: 124.

Embodiment F59. The multi-chain chimeric polypeptide of embodiment F58, wherein the soluble human IL-21 comprises a sequence of SEQ ID NO: 124.

Embodiment F60. The multi-chain chimeric polypeptide of any one of embodiments F53-F59, wherein the second target-binding domain comprises a soluble IL-7.

Embodiment F61. The multi-chain chimeric polypeptide of embodiment F60, wherein the soluble IL-7 is a soluble human IL-7.

Embodiment F62. The multi-chain chimeric polypeptide of embodiment F61, wherein the soluble human IL-7 comprises a sequence at least 80% identical to SEQ ID NO: 135.

Embodiment F63. The multi-chain chimeric polypeptide of embodiment F62, wherein the soluble human IL-7 comprises a sequence at least 90% identical to SEQ ID NO: 135.

Embodiment F64. The multi-chain chimeric polypeptide of embodiment F63, wherein the soluble human IL-7 comprises a sequence at least 95% identical to SEQ ID NO: 135.

Embodiment F65. The multi-chain chimeric polypeptide of embodiment F64, wherein the soluble human IL-7 comprises a sequence of SEQ ID NO: 135.

Embodiment F66. The multi-chain chimeric polypeptide of embodiment F1, wherein the first chimeric polypeptide comprises a sequence that is at least 80% identical to SEQ ID NO: 141.

Embodiment F67. The multi-chain chimeric polypeptide of embodiment F66, wherein the first chimeric polypeptide comprises a sequence that is at least 90% identical to SEQ ID NO: 141.

Embodiment F68. The multi-chain chimeric polypeptide of embodiment F67, wherein the first chimeric polypeptide comprises a sequence that is at least 95% identical to SEQ ID NO: 141.

Embodiment F69. The multi-chain chimeric polypeptide of embodiment F68, wherein the first chimeric polypeptide comprises SEQ ID NO: 141.

Embodiment F70. The multi-chain chimeric polypeptide of embodiment F69, wherein the first chimeric polypeptide comprises SEQ ID NO: 143.

Embodiment F71. The multi-chain chimeric polypeptide of any one of embodiments F1 and F66-F70, wherein the second chimeric polypeptide comprises a sequence that is at least 80% identical to SEQ ID NO: 145.

Embodiment F72. The multi-chain chimeric polypeptide of embodiment F71, wherein the second chimeric polypeptide comprises a sequence that is at least 90% identical to SEQ ID NO: 145.

Embodiment F73. The multi-chain chimeric polypeptide of embodiment F72, wherein the second chimeric polypeptide comprises a sequence that is at least 95% identical to SEQ ID NO: 145.

Embodiment F74. The multi-chain chimeric polypeptide of embodiment F73, wherein the second chimeric polypeptide comprises SEQ ID NO: 145.

Embodiment F75. The multi-chain chimeric polypeptide of embodiment F74, wherein the second chimeric polypeptide comprises SEQ ID NO: 147.

Embodiment F76. The multi-chain chimeric polypeptide of embodiment F1, wherein the first chimeric polypeptide comprises a sequence that is at least 80% identical to SEQ ID NO: 126.

Embodiment F77. The multi-chain chimeric polypeptide of embodiment F76, wherein the first chimeric polypeptide comprises a sequence that is at least 90% identical to SEQ ID NO: 126.

Embodiment F78. The multi-chain chimeric polypeptide of embodiment F77, wherein the first chimeric polypeptide comprises a sequence that is at least 95% identical to SEQ ID NO: 126.

Embodiment F79. The multi-chain chimeric polypeptide of embodiment F68, wherein the first chimeric polypeptide comprises SEQ ID NO: 126.

Embodiment F80. The multi-chain chimeric polypeptide of embodiment F69, wherein the first chimeric polypeptide comprises SEQ ID NO: 128.

Embodiment F81. The multi-chain chimeric polypeptide of any one of embodiments F1 and F76-F80, wherein the second chimeric polypeptide comprises a sequence that is at least 80% identical to SEQ ID NO: 137.

Embodiment F82. The multi-chain chimeric polypeptide of embodiment F81, wherein the second chimeric polypeptide comprises a sequence that is at least 90% identical to SEQ ID NO: 137.

Embodiment F83. The multi-chain chimeric polypeptide of embodiment F82, wherein the second chimeric polypeptide comprises a sequence that is at least 95% identical to SEQ ID NO: 137.

Embodiment F84. The multi-chain chimeric polypeptide of embodiment F83, wherein the second chimeric polypeptide comprises SEQ ID NO: 137.

Embodiment F85. The multi-chain chimeric polypeptide of embodiment F84, wherein the second chimeric polypeptide comprises SEQ ID NO: 139.

Embodiment F86. The multi-chain chimeric polypeptide of any one of embodiments F1-F65, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment F87. The multi-chain chimeric polypeptide of embodiment F86, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment F88. The multi-chain chimeric polypeptide of any one of embodiments F1-F65, wherein the first chimeric polypeptide further comprises one or more additional target-binding domains at the N-terminal and/or C-terminal end of the first chimeric polypeptide.

Embodiment F89. The multi-chain chimeric polypeptide of embodiment F88, wherein at least one of the one or more additional target-binding domains directly abuts the first domain of the pair of affinity domains in the first chimeric polypeptide.

Embodiment F90. The multi-chain chimeric polypeptide of embodiment F88, wherein the first chimeric polypeptide further comprises a linker sequence between the at least one of the one or more additional target-binding domains and the first domain of the pair of affinity domains.

Embodiment F91. The multi-chain chimeric polypeptide of embodiment F88, wherein the at least one of the one or more additional target-binding domains directly abuts the first target-binding domain in the first chimeric polypeptide.

Embodiment F92. The multi-chain chimeric polypeptide of embodiment F88, wherein the first chimeric polypeptide further comprises a linker sequence between the at least one of the one or more additional target-binding domains and the first target-binding domain.

Embodiment F93. The multi-chain chimeric polypeptide of embodiment F88, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment F94. The multi-chain chimeric polypeptide of embodiment F93, wherein the at least one additional target-binding domain of the one or more additional target-binding domains disposed at the N-terminus directly abuts the first target-binding domain or the first domain of the pair of affinity domains in the first chimeric polypeptide.

Embodiment F95. The multi-chain chimeric polypeptide of embodiment F93, wherein the first chimeric polypeptide further comprises a linker sequence disposed between the at least one additional target-binding domain and the first target-binding domain or the first domain of the pair of affinity domains in the first chimeric polypeptide.

Embodiment F96. The multi-chain chimeric polypeptide of embodiment F93, wherein the at least one additional target-binding domain of the one or more additional target-binding domains disposed at the C-terminus directly abuts the first target-binding domain or the first domain of the pair of affinity domains in the first chimeric polypeptide.

Embodiment F97. The multi-chain chimeric polypeptide of embodiment F93, wherein the first chimeric polypeptide further comprises a linker sequence disposed between the at least one additional target-binding domain and the first target-binding domain or the first domain of the pair of affinity domains in the first chimeric polypeptide.

Embodiment F98. The multi-chain chimeric polypeptide of embodiment F93, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment F99. The multi-chain chimeric polypeptide of embodiment F93, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment F100. The multi-chain chimeric polypeptide of any one of embodiments F1-F65 and F86-F99, wherein the second chimeric polypeptide further comprises one or more additional target-binding domains at the N-terminal end or the C-terminal end of the second chimeric polypeptide.

Embodiment F101. The multi-chain chimeric polypeptide of embodiment F100, wherein at least one of the one or more additional target-binding domains directly abuts the second domain of the pair of affinity domains in the second chimeric polypeptide.

Embodiment F102. The multi-chain chimeric polypeptide of embodiment F100, wherein the second chimeric polypeptide further comprises a linker sequence between at least one of the one or more additional target-binding domains and the second domain of the pair of affinity domains in the second chimeric polypeptide.

Embodiment F103. The multi-chain chimeric polypeptide of embodiment F100, wherein at least one of the one or more additional target-binding domains directly abuts the second target-binding domain in the second chimeric polypeptide.

Embodiment F104. The multi-chain chimeric polypeptide of embodiment F100, wherein the second chimeric polypeptide further comprises a linker sequence between at least one of the one or more additional target-binding domains and the second target-binding domain in the second chimeric polypeptide.

Embodiment F105. The multi-chain chimeric polypeptide of any one of embodiments F86-F104, wherein two or more of the first target-binding domain, the second target-binding domain, and the one or more additional target-binding domains bind specifically to the same antigen.

Embodiment F106. The multi-chain chimeric polypeptide of embodiment F105, wherein two or more of the first target-binding domain, the second target-binding domain, and the one or more additional target-binding domains bind specifically to the same epitope.

Embodiment F107. The multi-chain chimeric polypeptide of embodiment F106, wherein two or more of the first target-binding domain, the second target-binding domain, and the one or more additional target-binding domains comprise the same amino acid sequence.

Embodiment F108. The multi-chain chimeric polypeptide of any one of embodiments F86-F104, wherein the first target-binding domain, the second target-binding domain, and the one or more additional target-binding domains bind specifically to different antigens.

Embodiment F109. The multi-chain chimeric polypeptide of any one of embodiments F86-F108, wherein the one or more additional antigen-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, and a receptor for CD28.

Embodiment F110. The multi-chain chimeric polypeptide of any one of embodiments F86-F108, wherein the one or more additional target-binding domains is a soluble interleukin, soluble cytokine protein, or soluble cell surface protein.

Embodiment F111. The multi-chain chimeric polypeptide of embodiment F110, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment F112. The multi-chain chimeric polypeptide of any one of embodiments F86-F108, wherein the one or more additional target-binding domains is a soluble interleukin receptor, soluble cytokine receptor, or soluble cell surface receptor.

Embodiment F113. The multi-chain chimeric polypeptide of embodiment F112, wherein the soluble receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, or a soluble CD28.

Embodiment F114. A composition comprising any of the multi-chain chimeric polypeptides of embodiments F1-F113.

Embodiment F115. The composition of embodiment F114, wherein the composition is a pharmaceutical composition.

Embodiment F116. A kit comprising at least one dose of the composition of embodiment F114 or F115.

Embodiment F117. Nucleic acid encoding any of the multi-chain chimeric polypeptides of any one of embodiments F1-F113.

Embodiment F118. A vector comprising the nucleic acid of embodiment F117.

Embodiment F119. The vector of embodiment F118, wherein the vector is an expression vector.

Embodiment F120. A cell comprising the nucleic acid of embodiment F117 or the vector of embodiment F118 or F119.

Embodiment F121. A method of producing a multi-chain chimeric polypeptide, the method comprising:

culturing the cell of embodiment F120 in a culture medium under conditions sufficient to result in the production of the multi-chain chimeric polypeptide; and recovering the multi-chain chimeric polypeptide from the cell and/or the culture medium.

Embodiment F122. A multi-chain chimeric polypeptide produced by the method of embodiment F121.

Embodiment G1. A multi-chain chimeric polypeptide comprising:

(e) a first chimeric polypeptide comprising:
 (i) a first target-binding domain;
 (ii) a soluble tissue factor domain; and
 (iii) a first domain of a pair of affinity domains;
(f) a second chimeric polypeptide comprising:
 (i) a second domain of a pair of affinity domains; and
 (ii) a second target-binding domain, wherein:

the first chimeric polypeptide and the second chimeric polypeptide associate through the binding of the first domain and the second domain of the pair of affinity domains; and the first target-binding domain and the second targeting-binding domain each independently bind specifically to: a receptor for IL-7, CD16, a receptor for IL-21, TGF-β, or a receptor for CD137L.

Embodiment G2. The multi-chain chimeric polypeptide of embodiment G1, wherein the first target-binding domain and the soluble tissue factor domain directly abut each other in the first chimeric polypeptide.

Embodiment G3. The multi-chain chimeric polypeptide of embodiment G1, wherein the first chimeric polypeptide further comprises a linker sequence between the first target-binding domain and the soluble tissue factor domain in the first chimeric polypeptide.

Embodiment G4. The multi-chain chimeric polypeptide of any one of embodiments G1-G3, wherein the soluble tissue factor domain and the first domain of the pair of affinity domains directly abut each other in the first chimeric polypeptide.

Embodiment G5. The multi-chain chimeric polypeptide of any one of embodiments G1-G3, wherein the first chimeric polypeptide further comprises a linker sequence between the soluble tissue factor domain and the first domain of the pair of affinity domains in the first chimeric polypeptide.

Embodiment G6. The multi-chain chimeric polypeptide of any one of embodiments G1-G5, wherein the second domain of the pair of affinity domains and the second target-binding domain directly abut each other in the second chimeric polypeptide.

Embodiment G7. The multi-chain chimeric polypeptide of any one of embodiments G1-G5, wherein second chimeric polypeptide further comprises a linker sequence between the second domain of the pair of affinity domains and the second target-binding domain in the second chimeric polypeptide.

Embodiment G8. The multi-chain chimeric polypeptide of any one of embodiments G1-G7, wherein the soluble tissue factor domain is a soluble human tissue factor domain.

Embodiment G9. The multi-chain chimeric polypeptide of embodiment G8, wherein the soluble human tissue factor domain comprises a sequence that is at least 80% identical to SEQ ID NO: 1.

Embodiment G10. The multi-chain chimeric polypeptide of embodiment G9, wherein the soluble human tissue factor domain comprises a sequence that is at least 90% identical to SEQ ID NO: 1.

Embodiment G11. The multi-chain chimeric polypeptide of embodiment G10, wherein the soluble human tissue factor domain comprises a sequence that is at least 95% identical to SEQ ID NO: 1.

Embodiment G12. The multi-chain chimeric polypeptide of any one of embodiments G8-G11, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment G13. The multi-chain chimeric polypeptide of embodiment G12, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;
an aspartic acid at an amino acid position that corresponds to amino acid position 58 of mature wildtype human tissue factor protein;
a tyrosine at an amino acid position that corresponds to amino acid position 94 of mature wildtype human tissue factor protein;
an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment G14. The multi-chain chimeric polypeptide of any one of embodiments G1-G13, wherein the soluble tissue factor domain is not capable of binding to Factor VIIa.

Embodiment G15. The multi-chain chimeric polypeptide of any one of embodiments G1-G14, wherein the soluble tissue factor domain does not convert inactive Factor X into Factor Xa.

Embodiment G16. The multi-chain chimeric polypeptide of any one of embodiments G1-G15, wherein the multi-chain chimeric polypeptide does not stimulate blood coagulation in a mammal.

Embodiment G17. The multi-chain chimeric polypeptide of any one of embodiments G1-G16, wherein the first chimeric polypeptide further comprises a peptide tag at the N-terminal end or the C-terminal end of the first chimeric polypeptide.

Embodiment G18. The multi-chain chimeric polypeptide of any one of embodiments G1-G17, wherein the second chimeric polypeptide further comprises a peptide tag at the N-terminal end or the C-terminal end of the second chimeric polypeptide.

Embodiment G19. The multi-chain chimeric polypeptide of any one of embodiments G1-G18, wherein the first chimeric polypeptide and/or the second chimeric polypeptide further comprises a signal sequence at its N-terminal end.

Embodiment G20. The multi-chain chimeric polypeptide of embodiment G19, wherein the signal sequence comprises SEQ ID NO: 62.

Embodiment G21. The multi-chain chimeric polypeptide of embodiment G20, wherein the signal sequence is SEQ ID NO: 62.

Embodiment G22. The multi-chain chimeric polypeptide of any one of embodiments G1-G21, wherein the pair of affinity domains is a sushi domain from an alpha chain of human IL-15 receptor (IL15Rα) and a soluble IL-15.

Embodiment G23. The multi-chain chimeric polypeptide of embodiment G22, wherein the soluble IL-15 has a D8N or D8A amino acid substitution.

Embodiment G24. The multi-chain chimeric polypeptide of embodiment G22, wherein the soluble IL-15 comprises a sequence that is 80% identical to SEQ ID NO: 39.

Embodiment G25. The multi-chain chimeric polypeptide of embodiment G24, wherein the soluble IL-15 comprises a sequence that is 90% identical to SEQ ID NO: 39.

Embodiment G26. The multi-chain chimeric polypeptide of embodiment G25, wherein the soluble IL-15 comprises a sequence that is 95% identical to SEQ ID NO: 39.

Embodiment G27. The multi-chain chimeric polypeptide of embodiment G26, wherein the soluble IL-15 comprises SEQ ID NO: 39.

Embodiment G28. The multi-chain chimeric polypeptide of any one of embodiments G22-G27, wherein the sushi domain of IL15Rα comprises a sushi domain from human IL15Rα.

Embodiment G29. The multi-chain chimeric polypeptide of embodiment G28, wherein the sushi domain from human IL15Rα comprises a sequence that is 80% identical to SEQ ID NO: 10.

Embodiment G30. The multi-chain chimeric polypeptide of embodiment G29, wherein the sushi domain from human IL15Rα comprises a sequence that is 90% identical to SEQ ID NO: 10.

Embodiment G31. The multi-chain chimeric polypeptide of embodiment G30, wherein the sushi domain from human IL15Rα comprises a sequence that is 95% identical to SEQ ID NO: 10.

Embodiment G32. The multi-chain chimeric polypeptide of embodiment G31, wherein the sushi domain from human IL15Rα comprises SEQ ID NO: 10.

Embodiment G33. The multi-chain chimeric polypeptide of embodiment G28, wherein the sushi domain from human IL15Rα is a mature full-length IL15Rα.

Embodiment G34. The multi-chain chimeric polypeptide of any one of embodiments G1-G21, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment G35. The multi-chain chimeric polypeptide of any one of embodiments G1-G34, wherein the first target-binding domain and the second targeting-binding domain each independently bind specifically to a receptor for IL-7, CD16, or a receptor for IL-21.

Embodiment G36. The multi-chain chimeric polypeptide of embodiment G35, wherein the first target-binding domain binds specifically to a receptor IL-7 and the second target-binding domain binds specifically to CD16 or a receptor for IL-21.

Embodiment G37. The multi-chain chimeric polypeptide of embodiment G36, wherein the first target-binding domain comprises a soluble IL-7 protein.

Embodiment G38. The multi-chain chimeric polypeptide of embodiment G37, wherein the soluble IL-7 protein is a soluble human IL-7.

Embodiment G39. The multi-chain chimeric polypeptide of any one of embodiments G36-G38, wherein the second antigen-binding domain comprises an antigen-binding domain that binds specifically to CD16.

Embodiment G40. The multi-chain chimeric polypeptide of embodiment G39, wherein the second antigen-binding domain comprises an scFv that binds specifically to CD16.

Embodiment G41. The multi-chain chimeric polypeptide of any one of embodiments G36-G38, wherein the second antigen-binding domain bind specifically to a receptor for IL-21.

Embodiment G42. The multi-chain chimeric polypeptide of embodiment G41, wherein the second antigen-binding domain comprises a soluble IL-21.

Embodiment G43. The multi-chain chimeric polypeptide of embodiment G42, wherein the soluble IL-21 is a soluble human IL-21.

Embodiment G44. The multi-chain chimeric polypeptide of any one of embodiments G36-G40, wherein the second chimeric polypeptide further comprises an additional target-binding domain that binds specifically to a receptor for IL-21.

Embodiment G45. The multi-chain chimeric polypeptide of embodiment G44, wherein the additional target-binding domain comprises a soluble IL-21.

Embodiment G46. The multi-chain chimeric polypeptide of embodiment G45, wherein the soluble IL-21 is a soluble human IL-12.

Embodiment G47. The multi-chain chimeric polypeptide of any one of embodiments G1-G34, wherein the first target-binding domain and the second targeting-binding domain each independently bind specifically to TGF-β, CD16, or a receptor for IL-21.

Embodiment G48. The multi-chain chimeric polypeptide of embodiment G47, wherein the first target-binding domain binds specifically to a TGF-β and the second target-binding domain binds specifically to CD16 or a receptor of IL-21.

Embodiment G49. The multi-specific chimeric polypeptide of embodiment G48, wherein the first target-binding domain is a soluble TGF-β receptor.

Embodiment G50. The multi-specific chimeric polypeptide of embodiment G49, wherein soluble TGF-β receptor is a soluble TGFβRII receptor.

Embodiment G51. The multi-specific chimeric polypeptide of any one of embodiments G48-G50, wherein the second target-binding domain binds specifically to CD16.

Embodiment G52. The multi-specific chimeric polypeptide of embodiment G51, wherein the second antigen-binding domain comprises an antigen-binding domain that binds specifically to CD16.

Embodiment G53. The multi-chain chimeric polypeptide of embodiment G52, wherein the second antigen-binding domain comprises an scFv that binds specifically to CD16.

Embodiment G54. The multi-chain chimeric polypeptide of any one of embodiments G48-G50, wherein the second target-binding domain binds specifically to a receptor for IL-21.

Embodiment G55. The multi-chain chimeric polypeptide of embodiment G54, wherein the second target-binding domain comprises a soluble IL-21.

Embodiment G56. The multi-chain chimeric polypeptide of embodiment G55, wherein the second target-binding domain comprises a soluble human IL-21.

Embodiment G57. The multi-chain chimeric polypeptide of any one of embodiments G48-G53, wherein the second chimeric polypeptide further comprises an additional target-binding domain that binds specifically to a receptor for IL-21.

Embodiment G58. The multi-chain chimeric polypeptide of embodiment G57, wherein the additional target-binding domain comprises a soluble IL-21.

Embodiment G59. The multi-chain chimeric polypeptide of embodiment G58, wherein the soluble IL-21 is a soluble human IL-21.

Embodiment G60. The multi-chain chimeric polypeptide of any one of embodiments G1-G34, wherein the first target-binding domain and the second target-binding domain each independently bind specifically to a receptor for IL-7.

Embodiment G61. The multi-chain chimeric polypeptide of embodiment G60, wherein the first target-binding domain and the second target-binding domain include a soluble IL-7.

Embodiment G62. The multi-chain chimeric polypeptide of embodiment G61, wherein the soluble IL-7 is a soluble human IL-7.

Embodiment G63. The multi-chain chimeric polypeptide of any one of embodiments G1-G34, wherein the first target-binding domain and the second target-binding domain each independently bind specifically to TGF-β.

Embodiment G64. The multi-specific chimeric polypeptide of embodiment G63, wherein the first target-binding domain and the second target-binding domain is a soluble TGF-β receptor.

Embodiment G65. The multi-specific chimeric polypeptide of embodiment G64, wherein the soluble TGF-β receptor is a soluble TGFβRII receptor.

Embodiment G66. The multi-specific chimeric polypeptide of any one of embodiments G1-G34, wherein the first target-binding domain and the second targeting-binding domain each independently bind specifically to a receptor for IL-7, a receptor for IL-21, or a receptor for CD137L.

Embodiment G67. The multi-chain chimeric polypeptide of embodiment G66, wherein the first target-binding domain binds specifically to a receptor for IL-7 and the second target-binding domain binds specifically to a receptor for IL-21 or a receptor for CD137L.

Embodiment G68. The multi-specific chimeric polypeptide of embodiment G67, wherein the first target-binding domain is a soluble IL-7.

Embodiment G69. The multi-specific chimeric polypeptide of embodiment G68, wherein the soluble TL-7 is a soluble human IL-7.

Embodiment G70. The multi-chain chimeric polypeptide of any one of embodiments G67-G69, wherein the second target-binding domain binds specifically to a receptor for IL-21.

Embodiment G71. The multi-chain chimeric polypeptide of embodiment G70, wherein the second target-binding domain is a soluble IL-21.

Embodiment G72. The multi-chain chimeric polypeptide of embodiment G71, wherein the soluble IL-21 is a soluble human IL-21.

Embodiment G73. The multi-chain chimeric polypeptide of any one of embodiments G67-G69, wherein the second antigen-binding domain binds specifically to a receptor for CD137L.

Embodiment G74. The multi-chain chimeric polypeptide of embodiment G73, wherein the second antigen-binding domain is a soluble CD137L.

Embodiment G75. The multi-chain chimeric polypeptide of embodiment G74, wherein the soluble CD137L is a soluble human CD137L.

Embodiment G76. The multi-chain chimeric polypeptide of any one of embodiments G67-G72, wherein the second chimeric polypeptide further comprises an additional target-binding domain that binds specifically to a receptor for CD137L.

Embodiment G77. The multi-chain chimeric polypeptide of embodiment G76, wherein the additional target-binding domain comprises a soluble CD137L.

Embodiment G78. The multi-chain chimeric polypeptide of embodiment G77, wherein the soluble CD137L is a soluble human CD137L.

Embodiment G79. The multi-chain chimeric polypeptide of any one of embodiments G1-G34, wherein the first target-binding domain and the second targeting-binding domain each independently bind specifically to a receptor for IL-7 or TGF-β.

Embodiment G80. The multi-chain chimeric polypeptide of embodiment G79, wherein the first target-binding domain binds specifically to a receptor IL-7 and the second target-binding domain binds specifically to TGF-β.

Embodiment G81. The multi-chain chimeric polypeptide of embodiment G80, wherein the first target-binding domain comprises a soluble IL-7 protein.

Embodiment G82. The multi-chain chimeric polypeptide of embodiment G81, wherein the soluble IL-7 protein is a soluble human IL-7.

Embodiment G83. The multi-chain chimeric polypeptide of any one of embodiments G80-G82, wherein the second antigen-binding domain comprises an antigen-binding domain that binds specifically to TGF-β.

Embodiment G84. The multi-specific chimeric polypeptide of embodiment G83, wherein the second target-binding domain is a soluble TGF-β receptor.

Embodiment G85. The multi-specific chimeric polypeptide of embodiment G84, wherein the soluble TGF-β receptor is a soluble TGFβRII receptor.

Embodiment G86. The multi-chain chimeric polypeptide of any one of embodiments G1-G34, wherein the first target-binding domain and the second targeting-binding domain each independently bind specifically to TGF-β, a receptor for IL-21, or a receptor for CD137L. Embodiment G87. The multi-chain chimeric polypeptide of embodiment G86, wherein the first target-binding domain binds specifically to a TGF-β and the second target-binding domain binds specifically to a receptor for IL-21 or a receptor for CD137L.

Embodiment G88. The multi-specific chimeric polypeptide of embodiment G87, wherein the first target-binding domain is a soluble TGF-β receptor.

Embodiment G89. The multi-specific chimeric polypeptide of embodiment G88, wherein the soluble TGF-β receptor is a soluble TGFβRII receptor.

Embodiment G90. The multi-specific chimeric polypeptide of any one of embodiments G87-G89, wherein the second target-binding domain binds specifically to a receptor for IL-21.

Embodiment G91. The multi-chain chimeric polypeptide of embodiment G90, wherein the second target-binding domain comprises a soluble IL-21.

Embodiment G92. The multi-chain chimeric polypeptide of embodiment G91, wherein the second target-binding domain comprises a soluble human IL-21.

Embodiment G93. The multi-specific chimeric polypeptide of any one of embodiments G87-G89, wherein the second target-binding domain binds specifically to a receptor for CD137L.

Embodiment G94. The multi-chain chimeric polypeptide of embodiment G93, wherein the second target-binding domain comprises a soluble CD137L.

Embodiment G95. The multi-chain chimeric polypeptide of embodiment G94, wherein the second target-binding domain comprises a soluble human CD137L.

Embodiment G96. The multi-chain chimeric polypeptide of any one of embodiments G87-G92, wherein the second chimeric polypeptide further comprises an additional target-binding domain that binds specifically to a receptor for CD137L.

Embodiment G97. The multi-chain chimeric polypeptide of embodiment G96, wherein the additional target-binding domain comprises a soluble CD137L.

Embodiment G98. The multi-chain chimeric polypeptide of embodiment G97, wherein the soluble CD137L is a soluble human CD137L.

Embodiment G99. The multi-chain chimeric polypeptide of any one of embodiments G1-G34, wherein the first target-binding domain and the second targeting-binding domain each independently bind specifically to TGF-β or a receptor for IL-21.

Embodiment G100. The multi-chain chimeric polypeptide of embodiment G99, wherein the first target-binding domain binds specifically to a TGF-β and the second target-binding domain binds specifically to TGF-β or a receptor for IL-21.

Embodiment G101. The multi-specific chimeric polypeptide of embodiment G100, wherein the first target-binding domain is a soluble TGF-β receptor.

Embodiment G102. The multi-specific chimeric polypeptide of embodiment G101, wherein the soluble TGF-β receptor is a soluble TGFβRII receptor.

Embodiment G103. The multi-specific chimeric polypeptide of any one of embodiments G100-G102, wherein the second target-binding domain binds specifically to a receptor for IL-21.

Embodiment G104. The multi-chain chimeric polypeptide of embodiment G103, wherein the second target-binding domain comprises a soluble IL-21.

Embodiment G105. The multi-chain chimeric polypeptide of embodiment G104, wherein the second target-binding domain comprises a soluble human IL-21.

Embodiment G106. The multi-specific chimeric polypeptide of any one of embodiments G100-G102, wherein the second target-binding domain binds specifically to TGF-β.

Embodiment G107. The multi-specific chimeric polypeptide of embodiment G106, wherein the first target-binding domain is a soluble TGF-β receptor.

Embodiment G108. The multi-specific chimeric polypeptide of embodiment G107, wherein the soluble TGF-β receptor is a soluble TGFβRII receptor.

Embodiment G109. The multi-specific chimeric polypeptide of any one of embodiments G100-G105, wherein the second polypeptide further comprises an additional target-binding domain that binds specifically to TGF-β.

Embodiment G110. The multi-specific chimeric polypeptide of embodiment G109, wherein the first target-binding domain is a soluble TGF-β receptor.

Embodiment G111. The multi-specific chimeric polypeptide of embodiment G110, wherein the soluble TGF-β receptor is a soluble TGFβRII receptor.

Embodiment G112. The multi-chain chimeric polypeptide of any one of embodiments G1-G34, wherein the first target-binding domain and the second targeting-binding domain each independently bind specifically to TGF-β or IL-16.

Embodiment G113. The multi-chain chimeric polypeptide of embodiment G112, wherein the first target-binding domain binds specifically to a TGF-β and the second target-binding domain binds specifically to TGF-β or IL-16.

Embodiment G114. The multi-specific chimeric polypeptide of embodiment G113, wherein the first target-binding domain is a soluble TGF-β receptor.

Embodiment G115. The multi-specific chimeric polypeptide of embodiment G114, wherein the soluble TGF-β receptor is a soluble TGFβRII receptor.

Embodiment G116. The multi-specific chimeric polypeptide of any one of embodiments G113-G115, wherein the second target-binding domain binds specifically to IL-16.

Embodiment G117. The multi-specific chimeric polypeptide of embodiment G116, wherein the second antigen-binding domain comprises an antigen-binding domain that binds specifically to CD16.

Embodiment G118. The multi-chain chimeric polypeptide of embodiment G117, wherein the second antigen-binding domain comprises an scFv that binds specifically to CD16.

Embodiment G119. The multi-specific chimeric polypeptide of any one of embodiments G113-G115, wherein the second target-binding domain binds specifically to TGF-β.

Embodiment G120. The multi-specific chimeric polypeptide of embodiment G119, wherein the first target-binding domain is a soluble TGF-β receptor.

Embodiment G121. The multi-specific chimeric polypeptide of embodiment G120, wherein the soluble TGF-β receptor is a soluble TGFβRII receptor.

Embodiment G122. The multi-specific chimeric polypeptide of any one of embodiments G113-G118, wherein the second chimeric polypeptide further comprises an additional target-binding domain that binds specifically to TGF-β.

Embodiment G123. The multi-specific chimeric polypeptide of embodiment G122, wherein the first target-binding domain is a soluble TGF-β receptor.

Embodiment G124. The multi-specific chimeric polypeptide of embodiment G123, wherein the soluble TGF-β receptor is a soluble TGFβRII receptor.

Embodiment G125. The multi-chain chimeric polypeptide of any one of embodiments G1-G34, wherein the first target-binding domain and the second targeting-binding domain each independently bind specifically to a TGF-β or a receptor for CD137L.

Embodiment G126. The multi-chain chimeric polypeptide of embodiment G125, wherein the first target-binding domain binds specifically to TGF-β and the second target-binding domain binds specifically to a receptor for CD137L.

Embodiment G127. The multi-specific chimeric polypeptide of embodiment G126, wherein the first target-binding domain is a soluble TGF-β receptor.

Embodiment G128. The multi-specific chimeric polypeptide of embodiment G127, wherein the soluble TGF-β receptor is a soluble TGFβRII receptor.

Embodiment G129. The multi-chain chimeric polypeptide of embodiment G128, wherein the second target-binding domain comprises a soluble CD137L protein.

Embodiment G130. The multi-chain chimeric polypeptide of embodiment G129, wherein the soluble CD137L protein is a soluble human CD137L.

Embodiment G131. The multi-chain chimeric polypeptide of any one of embodiments G126-G130, wherein the second chimeric polypeptide further comprises an additional target-binding domain that binds specifically to TGF-β.

Embodiment G132. The multi-specific chimeric polypeptide of embodiment G131, wherein the additional target-binding domain is a soluble TGF-β receptor.

Embodiment G133. The multi-specific chimeric polypeptide of embodiment G132, wherein the soluble TGF-β receptor is a soluble TGFβRII receptor.

Embodiment G134. The multi-chain chimeric polypeptide of embodiment G1, wherein the first chimeric polypeptide comprises a sequence that is at least 80% identical to SEQ ID NO: 141.

Embodiment G135. The multi-chain chimeric polypeptide of embodiment G134, wherein the first chimeric polypeptide comprises a sequence that is at least 90% identical to SEQ ID NO: 141.

Embodiment G136. The multi-chain chimeric polypeptide of embodiment G135, wherein the first chimeric polypeptide comprises a sequence that is at least 95% identical to SEQ ID NO: 141.

Embodiment G137. The multi-chain chimeric polypeptide of embodiment G136, wherein the first chimeric polypeptide comprises SEQ ID NO: 141.

Embodiment G138. The multi-chain chimeric polypeptide of embodiment G137, wherein the first chimeric polypeptide comprises SEQ ID NO: 143.

Embodiment G139. The multi-chain chimeric polypeptide of any one of embodiments G1 and G134-G138, wherein the second chimeric polypeptide comprises a sequence that is at least 80% identical to SEQ ID NO: 157.

Embodiment G140. The multi-chain chimeric polypeptide of embodiment G139, wherein the second chimeric polypeptide comprises a sequence that is at least 90% identical to SEQ ID NO: 157.

Embodiment G141. The multi-chain chimeric polypeptide of embodiment G140, wherein the second chimeric polypeptide comprises a sequence that is at least 95% identical to SEQ ID NO: 157.

Embodiment G142. The multi-chain chimeric polypeptide of embodiment G141, wherein the second chimeric polypeptide comprises SEQ ID NO: 157.

Embodiment G143. The multi-chain chimeric polypeptide of embodiment G142, wherein the second chimeric polypeptide comprises SEQ ID NO: 159.

Embodiment G144. The multi-chain chimeric polypeptide of embodiment G1, wherein the first chimeric polypeptide comprises a sequence that is at least 80% identical to SEQ ID NO: 161.

Embodiment G145. The multi-chain chimeric polypeptide of embodiment G144, wherein the first chimeric polypeptide comprises a sequence that is at least 90% identical to SEQ ID NO: 161.

Embodiment G146. The multi-chain chimeric polypeptide of embodiment G145, wherein the first chimeric polypeptide comprises a sequence that is at least 95% identical to SEQ ID NO: 161.

Embodiment G147. The multi-chain chimeric polypeptide of embodiment G146, wherein the first chimeric polypeptide comprises SEQ ID NO: 161.

Embodiment G148. The multi-chain chimeric polypeptide of embodiment G147, wherein the first chimeric polypeptide comprises SEQ ID NO: 163.

Embodiment G149. The multi-chain chimeric polypeptide of any one of embodiments G1 and G144-G148, wherein the second chimeric polypeptide comprises a sequence that is at least 80% identical to SEQ ID NO: 157.

Embodiment G150. The multi-chain chimeric polypeptide of embodiment G149, wherein the second chimeric polypeptide comprises a sequence that is at least 90% identical to SEQ ID NO: 157.

Embodiment G151. The multi-chain chimeric polypeptide of embodiment G150, wherein the second chimeric polypeptide comprises a sequence that is at least 95% identical to SEQ ID NO: 157.

Embodiment G152. The multi-chain chimeric polypeptide of embodiment G151, wherein the second chimeric polypeptide comprises SEQ ID NO: 157.

Embodiment G153. The multi-chain chimeric polypeptide of embodiment G152, wherein the second chimeric polypeptide comprises SEQ ID NO: 159.

Embodiment G154. The multi-chain chimeric polypeptide of embodiment G1, wherein the first chimeric polypeptide comprises a sequence that is at least 80% identical to SEQ ID NO: 141.

Embodiment G155. The multi-chain chimeric polypeptide of embodiment G154, wherein the first chimeric polypeptide comprises a sequence that is at least 90% identical to SEQ ID NO: 141.

Embodiment G156. The multi-chain chimeric polypeptide of embodiment G155, wherein the first chimeric polypeptide comprises a sequence that is at least 95% identical to SEQ ID NO: 141.

Embodiment G157. The multi-chain chimeric polypeptide of embodiment G156, wherein the first chimeric polypeptide comprises SEQ ID NO: 141.

Embodiment G158. The multi-chain chimeric polypeptide of embodiment G157, wherein the first chimeric polypeptide comprises SEQ ID NO: 143.

Embodiment G159. The multi-chain chimeric polypeptide of any one of embodiments G1 and G154-G158, wherein the second chimeric polypeptide comprises a sequence that is at least 80% identical to SEQ ID NO: 137.

Embodiment G160. The multi-chain chimeric polypeptide of embodiment G159, wherein the second chimeric polypeptide comprises a sequence that is at least 90% identical to SEQ ID NO: 137.

Embodiment G161. The multi-chain chimeric polypeptide of embodiment G160, wherein the second chimeric polypeptide comprises a sequence that is at least 95% identical to SEQ ID NO: 137.

Embodiment G162. The multi-chain chimeric polypeptide of embodiment G161, wherein the second chimeric polypeptide comprises SEQ ID NO: 137.

Embodiment G163. The multi-chain chimeric polypeptide of embodiment G162, wherein the second chimeric polypeptide comprises SEQ ID NO: 139.

Embodiment G164. The multi-chain chimeric polypeptide of embodiment G1, wherein the first chimeric polypeptide comprises a sequence that is at least 80% identical to SEQ ID NO: 161.

Embodiment G165. The multi-chain chimeric polypeptide of embodiment G164, wherein the first chimeric polypeptide comprises a sequence that is at least 90% identical to SEQ ID NO: 161.

Embodiment G166. The multi-chain chimeric polypeptide of embodiment G165, wherein the first chimeric polypeptide comprises a sequence that is at least 95% identical to SEQ ID NO: 161.

Embodiment G167. The multi-chain chimeric polypeptide of embodiment G166, wherein the first chimeric polypeptide comprises SEQ ID NO: 161.

Embodiment G168. The multi-chain chimeric polypeptide of embodiment G167, wherein the first chimeric polypeptide comprises SEQ ID NO: 163.

Embodiment G169. The multi-chain chimeric polypeptide of any one of embodiments G1 and G164-G168, wherein the second chimeric polypeptide comprises a sequence that is at least 80% identical to SEQ ID NO: 130.

Embodiment G170. The multi-chain chimeric polypeptide of embodiment G169, wherein the second chimeric polypeptide comprises a sequence that is at least 90% identical to SEQ ID NO: 130.

Embodiment G171. The multi-chain chimeric polypeptide of embodiment G170, wherein the second chimeric polypeptide comprises a sequence that is at least 95% identical to SEQ ID NO: 130.

Embodiment G172. The multi-chain chimeric polypeptide of embodiment G171, wherein the second chimeric polypeptide comprises SEQ ID NO: 130.

Embodiment G173. The multi-chain chimeric polypeptide of embodiment G172, wherein the second chimeric polypeptide comprises SEQ ID NO: 132.

Embodiment G174. The multi-chain chimeric polypeptide of embodiment G1, wherein the first chimeric polypeptide comprises a sequence that is at least 80% identical to SEQ ID NO: 141.

Embodiment G175. The multi-chain chimeric polypeptide of embodiment G174, wherein the first chimeric polypeptide comprises a sequence that is at least 90% identical to SEQ ID NO: 141.

Embodiment G176. The multi-chain chimeric polypeptide of embodiment G175, wherein the first chimeric polypeptide comprises a sequence that is at least 95% identical to SEQ ID NO: 141.

Embodiment G177. The multi-chain chimeric polypeptide of embodiment G176, wherein the first chimeric polypeptide comprises SEQ ID NO: 141.

Embodiment G178. The multi-chain chimeric polypeptide of embodiment G177, wherein the first chimeric polypeptide comprises SEQ ID NO: 143.

Embodiment G179. The multi-chain chimeric polypeptide of any one of embodiments G1 and G174-G178, wherein the second chimeric polypeptide comprises a sequence that is at least 80% identical to SEQ ID NO: 169.

Embodiment G180. The multi-chain chimeric polypeptide of embodiment G179, wherein the second chimeric polypeptide comprises a sequence that is at least 90% identical to SEQ ID NO: 169.

Embodiment G181. The multi-chain chimeric polypeptide of embodiment G180, wherein the second chimeric polypeptide comprises a sequence that is at least 95% identical to SEQ ID NO: 169.

Embodiment G182. The multi-chain chimeric polypeptide of embodiment G181, wherein the second chimeric polypeptide comprises SEQ ID NO: 169.

Embodiment G183. The multi-chain chimeric polypeptide of embodiment G182, wherein the second chimeric polypeptide comprises SEQ ID NO: 171.

Embodiment G184. The multi-chain chimeric polypeptide of embodiment G1, wherein the first chimeric polypeptide comprises a sequence that is at least 80% identical to SEQ ID NO: Embodiment G185. The multi-chain chimeric polypeptide of embodiment G184, wherein the first chimeric polypeptide comprises a sequence that is at least 90% identical to SEQ ID NO: 141.

Embodiment G186. The multi-chain chimeric polypeptide of embodiment G185, wherein the first chimeric polypeptide comprises a sequence that is at least 95% identical to SEQ ID NO: 141.

Embodiment G187. The multi-chain chimeric polypeptide of embodiment G186, wherein the first chimeric polypeptide comprises SEQ ID NO: 141.

Embodiment G188. The multi-chain chimeric polypeptide of embodiment G187, wherein the first chimeric polypeptide comprises SEQ ID NO: 143.

Embodiment G189. The multi-chain chimeric polypeptide of any one of embodiments G1 and G184-G188, wherein the second chimeric polypeptide comprises a sequence that is at least 80% identical to SEQ ID NO: 173.

Embodiment G190. The multi-chain chimeric polypeptide of embodiment G189, wherein the second chimeric polypeptide comprises a sequence that is at least 90% identical to SEQ ID NO: 173.

Embodiment G191. The multi-chain chimeric polypeptide of embodiment G190, wherein the second chimeric polypeptide comprises a sequence that is at least 95% identical to SEQ ID NO: 173.

Embodiment G192. The multi-chain chimeric polypeptide of embodiment G191, wherein the second chimeric polypeptide comprises SEQ ID NO: 173.

Embodiment G193. The multi-chain chimeric polypeptide of embodiment G192, wherein the second chimeric polypeptide comprises SEQ ID NO: 175.

Embodiment G194. The multi-chain chimeric polypeptide of embodiment G1, wherein the first chimeric polypeptide comprises a sequence that is at least 80% identical to SEQ ID NO: 141.

Embodiment G195. The multi-chain chimeric polypeptide of embodiment G194, wherein the first chimeric polypeptide comprises a sequence that is at least 90% identical to SEQ ID NO: 141.

Embodiment G196. The multi-chain chimeric polypeptide of embodiment G195, wherein the first chimeric polypeptide comprises a sequence that is at least 95% identical to SEQ ID NO: 141.

Embodiment G197. The multi-chain chimeric polypeptide of embodiment G196, wherein the first chimeric polypeptide comprises SEQ ID NO: 141.

Embodiment G198. The multi-chain chimeric polypeptide of embodiment G197, wherein the first chimeric polypeptide comprises SEQ ID NO: 143.

Embodiment G199. The multi-chain chimeric polypeptide of any one of embodiments G1 and G194-G198, wherein the second chimeric polypeptide comprises a sequence that is at least 80% identical to SEQ ID NO: 129.

Embodiment G200. The multi-chain chimeric polypeptide of embodiment G199, wherein the second chimeric polypeptide comprises a sequence that is at least 90% identical to SEQ ID NO: 130.

Embodiment G201. The multi-chain chimeric polypeptide of embodiment G200, wherein the second chimeric polypeptide comprises a sequence that is at least 95% identical to SEQ ID NO: 130.

Embodiment G202. The multi-chain chimeric polypeptide of embodiment G201, wherein the second chimeric polypeptide comprises SEQ ID NO: 130.

Embodiment G203. The multi-chain chimeric polypeptide of embodiment G202, wherein the second chimeric polypeptide comprises SEQ ID NO: 132.

Embodiment G204. The multi-chain chimeric polypeptide of embodiment G1, wherein the first chimeric polypeptide comprises a sequence that is at least 80% identical to SEQ ID NO: 161.

Embodiment G205. The multi-chain chimeric polypeptide of embodiment G204, wherein the first chimeric polypeptide comprises a sequence that is at least 90% identical to SEQ ID NO: 161.

Embodiment G206. The multi-chain chimeric polypeptide of embodiment G205, wherein the first chimeric polypeptide comprises a sequence that is at least 95% identical to SEQ ID NO: 161.

Embodiment G207. The multi-chain chimeric polypeptide of embodiment G206, wherein the first chimeric polypeptide comprises SEQ ID NO: 161.

Embodiment G208. The multi-chain chimeric polypeptide of embodiment G207, wherein the first chimeric polypeptide comprises SEQ ID NO: 163.

Embodiment G209. The multi-chain chimeric polypeptide of any one of embodiments G1 and G204-G208, wherein the second chimeric polypeptide comprises a sequence that is at least 80% identical to SEQ ID NO: 169.

Embodiment G210. The multi-chain chimeric polypeptide of embodiment G209, wherein the second chimeric polypeptide comprises a sequence that is at least 90% identical to SEQ ID NO: 169.

Embodiment G211. The multi-chain chimeric polypeptide of embodiment G210, wherein the second chimeric polypeptide comprises a sequence that is at least 95% identical to SEQ ID NO: 169.

Embodiment G212. The multi-chain chimeric polypeptide of embodiment G211, wherein the second chimeric polypeptide comprises SEQ ID NO: 169.

Embodiment G213. The multi-chain chimeric polypeptide of embodiment G212, wherein the second chimeric polypeptide comprises SEQ ID NO: 171.

Embodiment G214. The multi-chain chimeric polypeptide of embodiment G1, wherein the first chimeric polypeptide comprises a sequence that is at least 80% identical to SEQ ID NO: 161.

Embodiment G215. The multi-chain chimeric polypeptide of embodiment G214, wherein the first chimeric polypeptide comprises a sequence that is at least 90% identical to SEQ ID NO: 161.

Embodiment G216. The multi-chain chimeric polypeptide of embodiment G215, wherein the first chimeric polypeptide comprises a sequence that is at least 95% identical to SEQ ID NO: 161.

Embodiment G217. The multi-chain chimeric polypeptide of embodiment GE216, wherein the first chimeric polypeptide comprises SEQ ID NO: 161.

Embodiment G218. The multi-chain chimeric polypeptide of embodiment G217, wherein the first chimeric polypeptide comprises SEQ ID NO: 163.

Embodiment G219. The multi-chain chimeric polypeptide of any one of embodiments G1 and G214-G218, wherein the second chimeric polypeptide comprises a sequence that is at least 80% identical to SEQ ID NO: 177.

Embodiment G220. The multi-chain chimeric polypeptide of embodiment G219, wherein the second chimeric polypeptide comprises a sequence that is at least 90% identical to SEQ ID NO: 177.

Embodiment G221. The multi-chain chimeric polypeptide of embodiment G220, wherein the second chimeric polypeptide comprises a sequence that is at least 95% identical to SEQ ID NO: 177.

Embodiment G222. The multi-chain chimeric polypeptide of embodiment G221, wherein the second chimeric polypeptide comprises SEQ ID NO: 177.

Embodiment G223. The multi-chain chimeric polypeptide of embodiment G222, wherein the second chimeric polypeptide comprises SEQ ID NO: 179.

Embodiment G224. The multi-chain chimeric polypeptide of embodiment G1, wherein the first chimeric polypeptide comprises a sequence that is at least 80% identical to SEQ ID NO: 161.

Embodiment G225. The multi-chain chimeric polypeptide of embodiment G224, wherein the first chimeric polypeptide comprises a sequence that is at least 90% identical to SEQ ID NO: 161.

Embodiment G226. The multi-chain chimeric polypeptide of embodiment G225, wherein the first chimeric polypeptide comprises a sequence that is at least 95% identical to SEQ ID NO: 161.

Embodiment G227. The multi-chain chimeric polypeptide of embodiment G226, wherein the first chimeric polypeptide comprises SEQ ID NO: 161.

Embodiment G228. The multi-chain chimeric polypeptide of embodiment G227, wherein the first chimeric polypeptide comprises SEQ ID NO: 163.

Embodiment G229. The multi-chain chimeric polypeptide of any one of embodiments G1 and G224-G228, wherein the second chimeric polypeptide comprises a sequence that is at least 80% identical to SEQ ID NO: 181.

Embodiment G230. The multi-chain chimeric polypeptide of embodiment G229, wherein the second chimeric polypeptide comprises a sequence that is at least 90% identical to SEQ ID NO: 181.

Embodiment G231. The multi-chain chimeric polypeptide of embodiment G230, wherein the second chimeric polypeptide comprises a sequence that is at least 95% identical to SEQ ID NO: 181.

Embodiment G232. The multi-chain chimeric polypeptide of embodiment G231, wherein the second chimeric polypeptide comprises SEQ ID NO: 181.

Embodiment G233. The multi-chain chimeric polypeptide of embodiment G232, wherein the second chimeric polypeptide comprises SEQ ID NO: 183.

Embodiment G234. The multi-chain chimeric polypeptide of embodiment G1, wherein the first chimeric polypeptide comprises a sequence that is at least 80% identical to SEQ ID NO: 161.

Embodiment G235. The multi-chain chimeric polypeptide of embodiment G234, wherein the first chimeric polypeptide comprises a sequence that is at least 90% identical to SEQ ID NO: 161.

Embodiment G236. The multi-chain chimeric polypeptide of embodiment G235, wherein the first chimeric polypeptide comprises a sequence that is at least 95% identical to SEQ ID NO: 161.

Embodiment G237. The multi-chain chimeric polypeptide of embodiment G236, wherein the first chimeric polypeptide comprises SEQ ID NO: 161.

Embodiment G238. The multi-chain chimeric polypeptide of embodiment G237, wherein the first chimeric polypeptide comprises SEQ ID NO: 163.

Embodiment G239. The multi-chain chimeric polypeptide of any one of embodiments G1 and G234-G238, wherein the second chimeric polypeptide comprises a sequence that is at least 80% identical to SEQ ID NO: 185 Embodiment G240. The multi-chain chimeric polypeptide of embodiment G239, wherein the second chimeric polypeptide comprises a sequence that is at least 90% identical to SEQ ID NO: 185.

Embodiment G241. The multi-chain chimeric polypeptide of embodiment G240, wherein the second chimeric polypeptide comprises a sequence that is at least 95% identical to SEQ ID NO: 185.

Embodiment G242. The multi-chain chimeric polypeptide of embodiment G241, wherein the second chimeric polypeptide comprises SEQ ID NO: 185.

Embodiment G243. The multi-chain chimeric polypeptide of embodiment G242, wherein the second chimeric polypeptide comprises SEQ ID NO: 187.

Embodiment G244. The multi-chain chimeric polypeptide of any one of embodiments G1-G133, wherein the first chimeric polypeptide further comprises one or more additional target-binding domain(s), where at least one of the one or more additional antigen-binding domain(s) is positioned between the soluble tissue factor domain and the first domain of the pair of affinity domains.

Embodiment G245. The multi-chain chimeric polypeptide of embodiment G244, wherein the first chimeric polypeptide further comprises a linker sequence between the soluble tissue factor domain and the at least one of the one or more additional antigen-binding domain(s), and/or a linker sequence between the at least one of the one or more additional antigen-binding domain(s) and the first domain of the pair of affinity domains.

Embodiment G246. The multi-chain chimeric polypeptide of any one of embodiments G1-G133, wherein the first chimeric polypeptide further comprises one or more additional target-binding domains at the N-terminal and/or C-terminal end of the first chimeric polypeptide.

Embodiment G247. The multi-chain chimeric polypeptide of embodiment G246, wherein at least one of the one or more additional target-binding domains directly abuts the first domain of the pair of affinity domains in the first chimeric polypeptide.

Embodiment G248. The multi-chain chimeric polypeptide of embodiment G246, wherein the first chimeric polypeptide further comprises a linker sequence between the at least one of the one or more additional target-binding domains and the first domain of the pair of affinity domains.

Embodiment G249. The multi-chain chimeric polypeptide of embodiment G246, wherein the at least one of the one or more additional target-binding domains directly abuts the first target-binding domain in the first chimeric polypeptide.

Embodiment G250. The multi-chain chimeric polypeptide of embodiment G246, wherein the first chimeric polypeptide further comprises a linker sequence between the at least one of the one or more additional target-binding domains and the first target-binding domain.

Embodiment G251. The multi-chain chimeric polypeptide of embodiment G246, wherein at least one of the one or more additional target-binding domains is disposed at the N- and/or C-terminus of the first chimeric polypeptide, and at least one of the one or more additional target-binding domains is positioned between the soluble tissue factor domain and the first domain of the pair of affinity domains in the first chimeric polypeptide.

Embodiment G252. The multi-chain chimeric polypeptide of embodiment G251, wherein the at least one additional target-binding domain of the one or more additional target-binding domains disposed at the N-terminus directly abuts the first target-binding domain or the first domain of the pair of affinity domains in the first chimeric polypeptide.

Embodiment G253. The multi-chain chimeric polypeptide of embodiment G251, wherein the first chimeric polypeptide further comprises a linker sequence disposed between the at least one additional target-binding domain and the first target-binding domain or the first domain of the pair of affinity domains in the first chimeric polypeptide.

Embodiment G254. The multi-chain chimeric polypeptide of embodiment G251, wherein the at least one additional target-binding domain of the one or more additional target-binding domains disposed at the C-terminus directly abuts the first target-binding domain or the first domain of the pair of affinity domains in the first chimeric polypeptide.

Embodiment G255. The multi-chain chimeric polypeptide of embodiment G251, wherein the first chimeric polypeptide further comprises a linker sequence disposed between the at least one additional target-binding domain and the first target-binding domain or the first domain of the pair of affinity domains in the first chimeric polypeptide.

Embodiment G256. The multi-chain chimeric polypeptide of embodiment G251, wherein the at least one of the one or more additional target-binding domains positioned between the soluble tissue factor domain and the first domain of the pair of affinity domains, directly abuts the soluble tissue factor domain and/or the first domain of the pair of affinity domains.

Embodiment G257. The multi-chain chimeric polypeptide of embodiment G251, wherein the first chimeric polypeptide further comprises a linker sequence disposed (i) between the soluble tissue factor domain and the at least one of the one or more additional target-binding domains positioned between the soluble tissue factor domain and the first domain of the pair of affinity domains, and/or (ii) between the first domain of the pair of affinity domains and the at least one of the one or more additional target-binding domains positioned between the soluble tissue factor domain and the first domain of the pair of affinity domains.

Embodiment G258. The multi-chain chimeric polypeptide of any one of embodiments G44-G46, G57-G59, G76-G78, G96-G98, G109-G111, G122-G124, and G131-G133, wherein the second chimeric polypeptide further comprises the additional target-binding domain at the N-terminal end or the C-terminal end of the second chimeric polypeptide.

Embodiment G259. The multi-chain chimeric polypeptide of embodiment G258, wherein the additional target-binding domain directly abuts the second domain of the pair of affinity domains in the second chimeric polypeptide.

Embodiment G260. The multi-chain chimeric polypeptide of embodiment G258, wherein the second chimeric polypeptide further comprises a linker sequence between the additional target-binding domain and the second domain of the pair of affinity domains in the second chimeric polypeptide.

Embodiment G261. The multi-chain chimeric polypeptide of embodiment G258, wherein the additional target-binding domain directly abuts the second target-binding domain in the second chimeric polypeptide.

Embodiment G262. The multi-chain chimeric polypeptide of embodiment G258, wherein the second chimeric polypeptide further comprises a linker sequence between the additional target-binding domain and the second target-binding domain in the second chimeric polypeptide.

Embodiment G263. A composition comprising any of the multi-chain chimeric polypeptides of embodiments G1-G262.

Embodiment G264. The composition of embodiment G263, wherein the composition is a pharmaceutical composition.

Embodiment G265. A kit comprising at least one dose of the composition of embodiment G263 or G264.

Embodiment G266. Nucleic acid encoding any of the multi-chain chimeric polypeptides of any one of embodiments G1-G262.

Embodiment G267. A vector comprising the nucleic acid of embodiment G266.

Embodiment G268. The vector of embodiment G267, wherein the vector is an expression vector.

Embodiment G269. A cell comprising the nucleic acid of embodiment G266 or the vector of embodiment G267 or G268.

Embodiment G270. A method of producing a multi-chain chimeric polypeptide, the method comprising:

culturing the cell of embodiment G269 in a culture medium under conditions sufficient to result in the production of the multi-chain chimeric polypeptide; and recovering the multi-chain chimeric polypeptide from the cell and/or the culture medium.

Embodiment G271. A multi-chain chimeric polypeptide produced by the method of embodiment G327.

Embodiment G272. The multi-chain chimeric polypeptide of embodiment G8, wherein the soluble human tissue factor domain comprises a sequence that is at least 80% identical to SEQ ID NO: 5.

Embodiment G273. The multi-chain chimeric polypeptide of embodiment G272, wherein the soluble human tissue factor domain comprises a sequence that is at least 90% identical to SEQ ID NO: 5.

Embodiment G274. The multi-chain chimeric polypeptide of embodiment G273, wherein the soluble human tissue factor domain comprises a sequence that is at least 95% identical to SEQ ID NO: 5.

Embodiment G275. The multi-chain chimeric polypeptide of embodiment G274, wherein the soluble human tissue factor domain comprises a sequence that is 100% identical to SEQ ID NO: 5.

Embodiment G276. The multi-chain chimeric polypeptide of embodiment G8, wherein the soluble human tissue factor domain comprises a sequence that is at least 80% identical to SEQ ID NO: 6.

Embodiment G277. The multi-chain chimeric polypeptide of embodiment G276, wherein the soluble human tissue factor domain comprises a sequence that is at least 90% identical to SEQ ID NO: 6.

Embodiment G278. The multi-chain chimeric polypeptide of embodiment G277, wherein the soluble human tissue factor domain comprises a sequence that is at least 95% identical to SEQ ID NO: 6.

Embodiment G279. The multi-chain chimeric polypeptide of embodiment G279, wherein the soluble human tissue factor domain comprises a sequence that is 100% identical to SEQ ID NO: 6.

Embodiment H1. A method of promoting the activation and proliferation of a natural killer cell or a T cell, the method comprising:

contacting a natural killer cell or a T cell in a liquid culture medium comprising an effective amount of (i) a single-chain chimeric polypeptide comprising a first target-binding domain, a linker domain, and a second target-binding domain, and (ii) an IgG1 antibody construct that comprises at least one antigen-binding domain that binds specifically to the linker domain, under conditions that allow for the activation and proliferation of the natural killer cell or the T cell, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules.

Embodiment H2. The method of embodiment H1, wherein the first target-binding domain and the linker domain directly abut each other.

Embodiment H3. The method of embodiment H1, wherein the single-chain chimeric polypeptide further comprises a linker sequence between the first target-binding domain and the linker domain.

Embodiment H4. The method of any one of embodiments H1-H3, wherein the linker domain and the second target-binding domain directly abut each other.

Embodiment H5. The method of any one of embodiments H1-H3, wherein the single-chain chimeric polypeptide further comprises a linker sequence between the linker domain and the second target-binding domain.

Embodiment H6. The method of embodiment H1, wherein the first target-binding domain and the second target-binding domain directly abut each other.

Embodiment H7. The method of embodiment H1, wherein the single-chain chimeric polypeptide further comprises a linker sequence between the first target-binding domain and the second target-binding domain.

Embodiment H8. The method of embodiment H6 or H7, wherein the second target-binding domain and the linker domain directly abut each other.

Embodiment H9. The method of embodiment H6 or H7, wherein the single-chain chimeric polypeptide further comprises a linker sequence between the second target-binding domain and the linker domain.

Embodiment H10. The method of any one of embodiments H1-H9, wherein the first target-binding domain and the second target-binding domain bind specifically to the same antigen.

Embodiment H11. The method of embodiment H10, wherein the first target-binding domain and the second target-binding domain bind specifically to the same epitope.

Embodiment H12. The method of embodiment H11, wherein the first target-binding domain and the second target-binding domain comprise the same amino acid sequence.

Embodiment H13. The method of any one of embodiments H1-H9, wherein the first target-binding domain and the second target-binding domain bind specifically to different antigens.

Embodiment H14. The method of any one of embodiments H1-H13, wherein one or both of the first target-binding domain and the second target-binding domain is an antigen-binding domain.

Embodiment H15. The method of embodiment H14, wherein the first target-binding domain and the second target-binding domain are each an antigen-binding domain.

Embodiment H16. The method of embodiment H14 or H15, wherein antigen-binding domain comprises a scFv or a single domain antibody.

Embodiment H17. The method of any one of embodiments H1-H16, wherein one or both of the first target-binding domain and the second target-binding domain bind to a target selected from the group consisting of: CD16a, CD28, CD3, CD33, CD20, CD19, CD22, CD52, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H18. The method of any one of embodiments H1-H16, wherein one or both of the first target-binding domain and the second target-binding domain is a soluble interleukin, soluble cytokine protein, or soluble cell surface protein.

Embodiment H19. The method of embodiment H18, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H20. The method of any one of embodiments H1-H16, wherein one or both of the first target-binding domain and the second target-binding domain is a soluble interleukin receptor, soluble cytokine receptor, or soluble cell surface receptor.

Embodiment H21. The method of embodiment H20, wherein the soluble interleukin receptor, soluble cytokine receptor, or soluble cell surface receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment H22. The method of any one of embodiments H1-H21, wherein the linker domain is a soluble tissue factor domain.

Embodiment H23. The method of embodiment H22, wherein the soluble tissue factor domain is a soluble human tissue factor domain.

Embodiment H24. The method of embodiment H23, wherein the soluble human tissue factor domain comprises a sequence that is at least 80% identical to SEQ ID NO: 1.

Embodiment H25. The method of embodiment H24, wherein the soluble human tissue factor domain comprises a sequence that is at least 90% identical to SEQ ID NO: 1.

Embodiment H26. The method of embodiment H25, wherein the soluble human tissue factor domain comprises a sequence that is at least 95% identical to SEQ ID NO: 1.

Embodiment H27. The method of any one of embodiments H23-H26, wherein the soluble human tissue factor domain does not comprise one or more of:

- a lysine at an amino acid position that corresponds to amino acid position 20 of mature wildtype human tissue factor protein;
- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;
- a tyrosine at an amino acid position that corresponds to amino acid position 94 of mature wildtype human tissue factor protein;
- an arginine at an amino acid position that corresponds to amino acid position 135 of mature wildtype human tissue factor protein; and
- a phenylalanine at an amino acid position that corresponds to amino acid position 140 of mature wildtype human tissue factor protein.

Embodiment H28. The method of embodiment H27, wherein the soluble human tissue factor domain does not comprise any of:

- a lysine at an amino acid position that corresponds to amino acid position 20 of mature wildtype human tissue factor protein;
- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;
- a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H29. The method of any one of embodiments H22-H28, wherein the soluble tissue factor domain is not capable of binding Factor VIIa.

Embodiment H30. The method of any one of embodiments H22-H29, wherein the soluble tissue factor domain does not convert inactive Factor X into Factor Xa.

Embodiment H31. The method of any one of embodiments H22-H30, wherein the single-chain chimeric polypeptide does not stimulate blood coagulation in a mammal.

Embodiment H32. The method of any one of embodiments H22-H31, wherein the IgG1 antibody construct comprises at least one antigen-binding domain that binds specifically to the soluble tissue factor domain.

Embodiment H33. The method of any one of embodiments H1-H21, wherein the linker domain is selected from the group consisting of: a kappa chain and a lambda chain.

Embodiment H34. The method of any one of embodiments H1-H33, wherein the IgG1 antibody construct is a monoclonal IgG1 antibody, where both of the antigen-binding domains in the monoclonal IgG1 antibody bind specifically to the linker domain.

Embodiment H35. The method of any one of embodiments H1-H33, wherein the IgG1 antibody construct is a bispecific IgG1 antibody, where one of the two antigen-binding domains in the bispecific IgG1 antibody binds specifically to the linker domain.

Embodiment H36. The method of any one of embodiments H1-H35, wherein the single-chain chimeric polypeptide further comprises one or more additional target-binding domains at its N- and/or C-terminus.

Embodiment H37. The method of embodiment H36, wherein the single-chain chimeric polypeptide comprises one or more additional target-binding domains at its N-terminus.

Embodiment H38. The method of embodiment H37, wherein one or more additional target-binding domains directly abuts the first target-binding domain, the second target-binding domain, or the linker domain.

Embodiment H39. The method of embodiment H38, wherein the single-chain chimeric polypeptide further comprises a linker sequence between one of the at least one additional target-binding domains and the first target-binding domain, the second target-binding domain, or the linker domain.

Embodiment H40. The method of embodiment H36, wherein the single-chain chimeric polypeptide comprises one or more additional target-binding domains at its C-terminus.

Embodiment H41. The method of embodiment H40, wherein one of the one or more additional target-binding domains directly abuts the first target-binding domain, the second target-binding domain, or the linker domain.

Embodiment H42. The method of embodiment H40, wherein the single-chain chimeric polypeptide further comprises a linker sequence between one of the at least one additional target-binding domains and the first target-binding domain, the second target-binding domain, or the linker domain.

Embodiment H43. The method of embodiment H36, wherein the single-chain chimeric polypeptide comprises one or more additional target binding domains at its N-terminus and the C-terminus.

Embodiment H44. The method of embodiment H43, wherein one of the one or more additional target-binding domains at the N-terminus directly abuts the first target-binding domain, the second target-binding domain, or the linker domain.

Embodiment H45. The method of embodiment H43, wherein the single-chain chimeric polypeptide further comprises a linker sequence between one of the one or more additional target-binding domains at the N-terminus and the first target-binding domain, the second target-binding domain, or the linker domain.

Embodiment H46. The method of embodiment H43, wherein one of the one or more additional target-binding domains at the C-terminus directly abuts the first target-binding domain, the second target-binding domain, or the linker domain.

Embodiment H47. The method of embodiment H43, wherein the single-chain chimeric polypeptide further comprises a linker sequence between one of the one or more additional target-binding domains at the C-terminus and the first target-binding domain, the second target-binding domain, or the linker domain.

Embodiment H48. The method of any one of embodiments H36-H47, wherein two or more of the first target-binding domain, the second target-binding domain, and the one or more additional target-binding domains bind specifically to the same antigen.

Embodiment H49. The method of embodiment H48, wherein two or more of the first target-binding domain, the second target-binding domain, and the one or more additional target-binding domains bind specifically to the same epitope.

Embodiment H50. The method of embodiment H49, wherein two or more of the first target-binding domain, the second target-binding domain, and the one or more additional target-binding domains comprise the same amino acid sequence.

Embodiment H51. The method of embodiment H48, wherein the first target-binding domain, the second target-binding domain, and the one or more additional target-binding domains each bind specifically to the same antigen.

Embodiment H52. The method of embodiment H51, wherein the first target-binding domain, the second target-binding domain, and the one or more additional target-binding domains each bind specifically to the same epitope.

Embodiment H53. The method of embodiment H52, wherein the first target-binding domain, the second target-binding domain, and the one or more additional target-binding domains each comprise the same amino acid sequence.

Embodiment H54. The method of any one of embodiments H36-H47, wherein the first target-binding domain, the second target-binding domain, and the one or more additional target-binding domains bind specifically to different antigens.

Embodiment H55. The method of any one of embodiments H36-H54, wherein one or more of the first target-binding domain, the second target-binding domain, and the one or more target-binding domains is an antigen-binding domain.

Embodiment H56. The method of embodiment H55, wherein the first target-binding domain, the second target-binding domain, and the one or more additional target-binding domains are each an antigen-binding domain.

Embodiment H57. The method of embodiment H55 or H56, wherein the antigen-binding domain comprises a scFv or a single domain antibody.

Embodiment H58. The method of any one of embodiments H36-H57, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H59. The method of any one of embodiments H36-H57, wherein one or more of the first target-binding domain, the second target-binding domain, and the one or more additional target-binding domains is a soluble interleukin, soluble cytokine protein, or soluble cell surface protein.

Embodiment H60. The method of embodiment H59, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H61. The method of any one of embodiments H36-H57, wherein one or more of the first target-binding domain, the second target-binding domain, and the one or more additional target-binding domains is a soluble interleukin receptor, soluble cytokine receptor, or soluble cell surface receptor.

Embodiment H62. The method of embodiment H61, wherein the soluble interleukin receptor, soluble cytokine receptor, or soluble cell surface receptor is a soluble TGF-β receptor II (TGF-βRII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment H63. The method of any one of embodiments H36-H57, wherein one or more of the first target-binding domain, the second target-binding domain, and the one or more additional target-binding domains is a ligand of a co-stimulatory molecule.

Embodiment H64. The method of embodiment H63, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H65. The method of any one of embodiments H1-H64, wherein the single-chain chimeric polypeptide further comprises a peptide tag positioned at the N-terminal end or the C-terminal end of the single-chain chimeric polypeptide.

Embodiment H66. The method of any one of embodiments H1-H65, wherein the contacting step is performed for a period of about 2 hours to about 20 days.

Embodiment H67. The method of embodiment H66, wherein the contacting step is performed for a period of about 1 day to about 15 days.

Embodiment H68. The method of any one of embodiments H1-H67, wherein the liquid culture medium is a serum-free liquid culture medium.

Embodiment H69. The method of any one of embodiments H1-H67, wherein the liquid culture medium is a chemically-defined liquid culture medium.

Embodiment H70. The method of any one of embodiments H1-H69, wherein the liquid culture medium comprises the single-chain chimeric polypeptide and the IgG1 antibody construct at a molar ratio of about 0.5:1 to about 2:1.

Embodiment H71. The method of embodiment H70, wherein the liquid culture medium comprises the single-chain chimeric polypeptide and the IgG1 antibody construct at a molar ratio of about 0.8:1 to about 1.2:1.

Embodiment H72. The method of any one of embodiments H1-H71, wherein the NK cell or T cell was previously obtained from a subject.

Embodiment H73. The method of embodiment H72, wherein the method further comprises obtaining the NK cell or T cell from the subject prior to the contacting step.

Embodiment H74. The method of any one of embodiments H1-H73, wherein the NK cell or T cell has previously been genetically modified to express a chimeric antigen receptor or a recombinant T-cell receptor.

Embodiment H75. The method of any one of embodiments H1-H73, wherein the method further comprises, after the contacting step, introducing into the NK cell or the T cell a nucleic acid encoding a chimeric antigen-receptor or a recombinant T-cell receptor.

Embodiment H76. The method of any one of embodiments H1-H73, wherein the method further comprises, before the contacting step, introducing into the NK cell or the T cell a nucleic acid encoding a chimeric antigen-receptor or a recombinant T-cell receptor.

Embodiment H77. The method of any one of embodiments H1-H76, wherein the method further comprises, after the contacting step, isolating the NK cell or the T cell.

Embodiment H78. The method of any one of embodiments H1-H77, wherein after the contacting step, the NK cell or the T cell has an increased level of expression or secretion of one or more proteins selected from the group consisting of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step.

Embodiment H79. The method of any one of embodiments H1-H78, wherein the method further comprises, after the contacting step, administering the NK cell or the T cell to a subject in need thereof.

Embodiment H80. The method of embodiment H79, wherein the subject has been identified or diagnosed as having an age-related disease or condition.

Embodiment H81. The method of embodiment H80, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H82. The method of embodiment H79, wherein the subject has been identified or diagnosed as having a cancer.

Embodiment H83. The method of embodiment H82, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H84. The method of embodiment H79, wherein the subject has been diagnosed or identified as having an infectious disease.

Embodiment H85. The method of embodiment H84, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment H86. An activated NK cell or T cell produced by the method of any one of embodiments H1-H78.

Embodiment H87. A pharmaceutical composition comprising the activated NK cell or the activated T cell of embodiment H86.

Embodiment H88. A kit comprising a pharmaceutical composition comprising the activated NK cell or the activated T cell of embodiment H86.

Embodiment H89. A method of killing a cancer cell, an infected cell, or a senescent cell in a subject in need thereof, the method comprising administering to the subject a therapeutically effective amount of the activated NK cell or the activated T cell of embodiment H86 or the pharmaceutical composition of embodiment H87.

Embodiment H90. The method of embodiment H89, wherein the subject has been identified or diagnosed as having a cancer.

Embodiment H91. The method of embodiment H90, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CMIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H92. The method of embodiment H89, wherein the subject has been identified or diagnosed as having an aging-related disease or condition.

Embodiment H93. The method of embodiment H92, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H94. A method of treating a subject in need thereof, the method comprising administering to the subject a therapeutically effective amount of the activated NK cell or the activated T cell of embodiment H86 or the pharmaceutical composition of embodiment H87.

Embodiment H95. The method of embodiment H94, wherein the subject has been identified or diagnosed as having a cancer.

Embodiment H96. The method of embodiment H95, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H97. The method of embodiment H94, wherein the subject has been identified or diagnosed as having an aging-related disease or condition.

Embodiment H98. The method of embodiment H97, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H99. The method of embodiment H94, wherein the subject has been diagnosed or identified as having an infectious disease.

Embodiment H100. The method of embodiment H99, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment H101. A kit comprising:

(i) a single-chain chimeric polypeptide comprising a first target-binding domain, a linker domain, and a second target-binding domain, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules; and (ii) an IgG1 antibody construct comprising at least one antigen-binding domain that binds specifically to the linker domain.

Embodiment H102. The kit of embodiment H101, wherein the first target-binding domain and the linker domain directly abut each other.

Embodiment H103. The kit of embodiment H101, wherein the single-chain chimeric polypeptide further comprises a linker sequence between the first target-binding domain and the linker domain.

Embodiment H104. The kit of any one of embodiments H101-H103, wherein the linker domain and the second target-binding domain directly abut each other.

Embodiment H105. The kit of any one of embodiments H101-H103, wherein the single-chain chimeric polypeptide further comprises a linker sequence between the linker domain and the second target-binding domain.

Embodiment H106. The kit of embodiment H101, wherein the first target-binding domain and the second target-binding domain directly abut each other.

Embodiment H107. The kit of embodiment H101, wherein the single-chain chimeric polypeptide further comprises a linker sequence between the first target-binding domain and the second target-binding domain.

Embodiment H108. The kit of embodiment H106 or H107, wherein the second target-binding domain and the linker domain directly abut each other.

Embodiment H109. The kit of embodiment H106 or H107, wherein the single-chain chimeric polypeptide further comprises a linker sequence between the second target-binding domain and the linker domain.

Embodiment H110. The kit of any one of embodiments H101-H109, wherein the first target-binding domain and the second target-binding domain bind specifically to the same antigen.

Embodiment H111. The kit of embodiment H110, wherein the first target-binding domain and the second target-binding domain bind specifically to the same epitope.

Embodiment H112. The kit of embodiment H111, wherein the first target-binding domain and the second target-binding domain comprise the same amino acid sequence.

Embodiment H113. The kit of any one of embodiments H101-H109, wherein the first target-binding domain and the second target-binding domain bind specifically to different antigens.

Embodiment H114. The kit of any one of embodiments H101-H113, wherein one or both of the first target-binding domain and the second target-binding domain is an antigen-binding domain.

Embodiment H115. The kit of embodiment H114, wherein the first target-binding domain and the second target-binding domain are each an antigen-binding domain.

Embodiment H116. The kit of embodiment H114 or H115, wherein the antigen-binding domain comprises a scFv or a single domain antibody.

Embodiment H117. The kit of any one of embodiments H101-H116, wherein one or both of the first target-binding domain and the second target-binding domain bind to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H118. The kit of any one of embodiments H101-H116, wherein one or both of the first target-binding domain and the second target-binding domain is a soluble interleukin, soluble cytokine protein, or soluble cell surface protein.

Embodiment H119. The kit of embodiment H118, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H120. The kit of any one of embodiments H101-H116, wherein one or both of the first target-binding domain and the second target-binding domain is a soluble interleukin or cytokine receptor.

Embodiment H121. The kit of embodiment H120, wherein the soluble interleukin or cytokine receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment H122. The kit of any one of embodiments H101-H121, wherein the linker domain is a soluble tissue factor domain.

Embodiment H123. The kit of embodiment H122, wherein the soluble tissue factor domain is a soluble human tissue factor domain.

Embodiment H124. The kit of embodiment H123, wherein the soluble human tissue factor domain comprises a sequence that is at least 80% identical to SEQ ID NO: 1.

Embodiment H125. The kit of embodiment H124, wherein the soluble human tissue factor domain comprises a sequence that is at least 90% identical to SEQ ID NO: 1.

Embodiment H126. The kit of embodiment H125, wherein the soluble human tissue factor domain comprises a sequence that is at least 95% identical to SEQ ID NO: 1.

Embodiment H127. The kit of any one of embodiments H123-H126, wherein the soluble human tissue factor domain does not comprise one or more of:

- a lysine at an amino acid position that corresponds to amino acid position 20 of mature wildtype human tissue factor protein;
- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;
- a tyrosine at an amino acid position that corresponds to amino acid position 94 of mature wildtype human tissue factor protein;
- an arginine at an amino acid position that corresponds to amino acid position 135 of mature wildtype human tissue factor protein; and
- a phenylalanine at an amino acid position that corresponds to amino acid position 140 of mature wildtype human tissue factor protein.

Embodiment H128. The kit of embodiment H127, wherein the soluble human tissue factor domain does not comprise any of:

- a lysine at an amino acid position that corresponds to amino acid position 20 of mature wildtype human tissue factor protein;
- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;
- a tyrosine at an amino acid position that corresponds to amino acid position 94 of mature wildtype human tissue factor protein;
- an arginine at an amino acid position that corresponds to amino acid position 135 of mature wildtype human tissue factor protein; and
- a phenylalanine at an amino acid position that corresponds to amino acid position 140 of mature wildtype human tissue factor protein.

Embodiment H129. The kit of any one of embodiments H122-H128, wherein the soluble tissue factor domain is not capable of binding Factor VIIa.

Embodiment H130. The kit of any one of embodiments H122-H129, wherein the soluble tissue factor domain does not convert inactive Factor X into Factor Xa.

Embodiment H131. The kit of any one of embodiments H122-H130, wherein the single-chain chimeric polypeptide does not stimulate blood coagulation in a mammal.

Embodiment H132. The kit of any one of embodiments H122-H131, wherein the IgG1 antibody construct comprises at least one antigen-binding domain that binds specifically to the soluble tissue factor domain.

Embodiment H133. The kit of any one of embodiments H101-H121, wherein the linker domain is selected from the group consisting of: a kappa chain and a lambda chain.

Embodiment H134. The kit of any one of embodiments H101-H133, wherein the IgG1 antibody construct is a monoclonal IgG1 antibody, where both antigen-binding domains in the monoclonal IgG1 antibody bind specifically to the linker domain.

Embodiment H135. The kit of any one of embodiments H101-H133, wherein the IgG1 antibody construct is a bispecific IgG1 antibody, where one of the two antigen-binding domains in the bispecific IgG1 antibody binds specifically to the linker domain.

Embodiment H136. The kit of any one of embodiments H101-H135, wherein the single-chain chimeric polypeptide further comprises one or more additional target-binding domains at its N- and/or C-terminus.

Embodiment H137. The kit of embodiment H136, wherein the single-chain chimeric polypeptide comprises one or more additional target-binding domains at its N-terminus.

Embodiment H138. The kit of embodiment H137, wherein one or more additional target-binding domains directly abuts the first target-binding domain, the second target-binding domain, or the linker domain.

Embodiment H139. The kit of embodiment H138, wherein the single-chain chimeric polypeptide further comprises a linker sequence between one of the at least one additional target-binding domains and the first target-binding domain, the second target-binding domain, or the linker domain.

Embodiment H140. The kit of embodiment H136, wherein the single-chain chimeric polypeptide comprises one or more additional target-binding domains at its C-terminus.

Embodiment H141. The kit of embodiment H140, wherein one of the one or more additional target-binding domains directly abuts the first target-binding domain, the second target-binding domain, or the linker domain.

Embodiment H142. The kit of embodiment H140, wherein the single-chain chimeric polypeptide further comprises a linker sequence between one of the at least one additional target-binding domains and the first target-binding domain, the second target-binding domain, or the linker domain.

Embodiment H143. The kit of embodiment H136, wherein the single-chain chimeric polypeptide comprises one or more additional target binding domains at its N-terminus and the C-terminus.

Embodiment H144. The kit of embodiment H143, wherein one of the one or more additional target-binding domains at the N-terminus directly abuts the first target-binding domain, the second target-binding domain, or the linker domain.

Embodiment H145. The kit of embodiment H143, wherein the single-chain chimeric polypeptide further comprises a linker sequence between one of the one or more additional target-binding domains at the N-terminus and the first target-binding domain, the second target-binding domain, or the linker domain.

Embodiment H146. The kit of embodiment H143, wherein one of the one or more additional target-binding domains at the C-terminus directly abuts the first target-binding domain, the second target-binding domain, or the linker domain.

Embodiment H147. The kit of embodiment H143, wherein the single-chain chimeric polypeptide further comprises a linker sequence between one of the one or more additional target-binding domains at the C-terminus and the first target-binding domain, the second target-binding domain, or the linker domain.

Embodiment H148. The kit of any one of embodiments H136-H147, wherein two or more of the first target-binding domain, the second target-binding domain, and the one or more additional target-binding domains bind specifically to the same antigen.

Embodiment H149. The kit of embodiment H148, wherein two or more of the first target-binding domain, the second target-binding domain, and the one or more additional target-binding domains bind specifically to the same epitope.

Embodiment H150. The kit of embodiment H149, wherein two or more of the first target-binding domain, the second target-binding domain, and the one or more additional target-binding domains comprise the same amino acid sequence.

Embodiment H151. The kit of embodiment H148, wherein the first target-binding domain, the second target-binding domain, and the one or more additional target-binding domains each bind specifically to the same antigen.

Embodiment H152. The kit of embodiment H151, wherein the first target-binding domain, the second target-binding domain, and the one or more additional target-binding domains each bind specifically to the same epitope.

Embodiment H153. The kit of embodiment H152, wherein the first target-binding domain, the second target-binding domain, and the one or more additional target-binding domains each comprise the same amino acid sequence.

Embodiment H154. The kit of any one of embodiments H136-H147, wherein the first target-binding domain, the second target-binding domain, and the one or more additional target-binding domains bind specifically to different antigens.

Embodiment H155. The kit of any one of embodiments H136-H154, wherein one or more of the first target-binding domain, the second target-binding domain, and the one or more target-binding domains is an antigen-binding domain.

Embodiment H156. The kit of embodiment H155, wherein the first target-binding domain, the second target-binding domain, and the one or more additional target-binding domains are each an antigen-binding domain.

Embodiment H157. The kit of embodiment H155 or H156, wherein the antigen-binding domain comprises a scFv or a single domain antibody.

Embodiment H158. The kit of any one of embodiments H136-H157, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, IGF-1R, MUC4AC, MUCSAC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H159. The kit of any one of embodiments H136-H157, wherein one or more of the first target-binding domain, the second target-binding domain, and the one or more additional target-binding domains is a soluble interleukin, soluble cytokine protein, or soluble cell surface protein.

Embodiment H160. The kit of embodiment H159, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H161. The kit of any one of embodiments H136-H157, wherein one or more of the first target-binding domain, the second target-binding domain, and the one or more additional target-binding domains is a soluble interleukin or cytokine receptor.

Embodiment H162. The kit of embodiment H161, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment H163. The method of any one of embodiments H136-H162, wherein one or both of the first target-binding domain and the second target-binding domain is a ligand of a co-stimulatory molecule.

Embodiment H164. The kit of embodiment H163, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H165. The kit of any one of embodiments H101-H164, wherein the single-chain chimeric polypeptide further comprises a peptide tag positioned at the N-terminal end or the C-terminal end of the single-chain chimeric polypeptide.

Embodiment H166. A method of promoting the activation and proliferation of a natural killer cell or a T cell, the method comprising:

contacting a natural killer cell or a T cell in a liquid culture medium comprising:

(1) an effective amount of a multi-chain chimeric polypeptide comprising:

(c) a first chimeric polypeptide comprising:

(i) a first target-binding domain;

(ii) a linker domain; and (iii) a first domain of a pair of affinity domains;

(d) a second chimeric polypeptide comprising:

(i) a second domain of a pair of affinity domains; and (ii) a second target-binding domain, wherein the first chimeric polypeptide and the second chimeric polypeptide associate through the binding of the first domain and the second domain of the pair of affinity domains; and (2) an effective amount of an IgG1 antibody construct comprising at least one antigen-binding domain that binds specifically to the linker domain, under conditions that allow for the activation and proliferation of the natural killer cell or the T cell.

Embodiment H167. The method of embodiment H166, wherein the first target-binding domain and the linker domain directly abut each other in the first chimeric polypeptide.

Embodiment H168. The method of embodiment H166, wherein the first chimeric polypeptide further comprises a linker sequence between the first target-binding domain and the linker domain in the first chimeric polypeptide.

Embodiment H169. The method of any one of embodiments H166-H168, wherein the linker domain and the first domain of the pair of affinity domains directly abut each other in the first chimeric polypeptide.

Embodiment H170. The method of any one of embodiments H166-H168, wherein the first chimeric polypeptide further comprises a linker sequence between the linker domain and the first domain of the pair of affinity domains in the first chimeric polypeptide.

Embodiment H171. The method of any one of embodiments H166-H170, wherein the second domain of the pair of affinity domains and the second target-binding domain directly abut each other in the second chimeric polypeptide.

Embodiment H172. The method of any one of embodiments H166-H170, wherein the second chimeric polypeptide further comprises a linker sequence between the second domain of the pair of affinity domains and the second target-binding domain in the second chimeric polypeptide.

Embodiment H173. The method of any one of embodiments H166-H172, wherein the first target-binding domain and the second target-binding domain bind specifically to the same antigen.

Embodiment H174. The method of embodiment H173, wherein the first target-binding domain and the second target-binding domain bind specifically to the same epitope.

Embodiment H175. The method of embodiment H174, wherein the first target-binding domain and the second target-binding domain comprise the same amino acid sequence.

Embodiment H176. The method of any one of embodiments H166-H172, wherein the first target-binding domain and the second target-binding domain bind specifically to different antigens.

Embodiment H177. The method of any one of embodiments H166-H176, wherein one or both of the first target-binding domain and the second target-binding domain is an antigen-binding domain.

Embodiment H178. The method of embodiment H177, wherein the first target-binding domain and the second target-binding domain are each antigen-binding domains.

Embodiment H179. The method of embodiment H177 or H178, wherein the antigen-binding domain comprises a scFv or a single domain antibody.

Embodiment H180. The method of any one of embodiments H166-H179, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H181. The method of any one of embodiments H166-H179, wherein one or both of the first target-binding domain and the second target-binding domain is a soluble interleukin, soluble cytokine protein, or soluble cell surface protein.

Embodiment H182. The method of embodiment H181, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H183. The method of any one of embodiments H166-H179, wherein one or both of the first target-binding domain and the second target-binding domain is a soluble interleukin or cytokine receptor.

Embodiment H184. The method of embodiment H183, wherein the soluble receptor is a soluble TGF-β receptor II (TGF-β RII), a soluble TGF-βRIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment H185. The method of any one of embodiments H166-H184, wherein the first chimeric polypeptide further comprises one or more additional target-binding domain(s), where at least one of the one or more target-binding domain(s) is positioned between the linker domain and the first domain of the pair of affinity domains.

Embodiment H186. The method of embodiment H185, wherein the first chimeric polypeptide further comprises a linker sequence between the linker domain and the at least one of the one or more target antigen-binding domain(s), and/or a linker sequence between the at least one of the one or more target antigen-binding domain(s) and the first domain of the pair of affinity domains.

Embodiment H187. The method of any one of embodiments H166-H184, wherein the first chimeric polypeptide further comprises one or more additional target-binding domains at the N-terminal and/or C-terminal end of the first chimeric polypeptide.

Embodiment H188. The method of embodiment H187, wherein at least one of the one or more additional target-binding domains directly abuts the first domain of the pair of affinity domains in the first chimeric polypeptide.

Embodiment H189. The method of embodiment H187, wherein the first chimeric polypeptide further comprises a linker sequence between the at least one of the one or more additional target-binding domains and the first domain of the pair of affinity domains.

Embodiment H190. The method of embodiment H187, wherein the at least one of the one or more additional target-binding domains directly abuts the first target-binding domain in the first chimeric polypeptide.

Embodiment H191. The method of embodiment H187, wherein the first chimeric polypeptide further comprises a linker sequence between the at least one of the one or more additional target-binding domains and the first target-binding domain.

Embodiment H192. The method of embodiment H187, wherein at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide.

Embodiment H193. The method of embodiment H192, wherein the at least one additional target-binding domain of the one or more additional target-binding domains disposed at the N-terminus directly abuts the first target-binding domain or the first domain of the pair of affinity domains in the first chimeric polypeptide.

Embodiment H194. The method of embodiment H192, wherein the first chimeric polypeptide further comprises a linker sequence disposed between the at least one additional target-binding domain and the first target-binding domain or the first domain of the pair of affinity domains in the first chimeric polypeptide.

Embodiment H195. The method of embodiment H192, wherein the at least one additional target-binding domain of the one or more additional target-binding domains disposed at the C-terminus directly abuts the first target-binding domain or the first domain of the pair of affinity domains in the first chimeric polypeptide.

Embodiment H196. The method of embodiment H192, wherein the first chimeric polypeptide further comprises a linker sequence disposed between the at least one additional target-binding domain and the first target-binding domain or the first domain of the pair of affinity domains in the first chimeric polypeptide.

Embodiment H197. The method of embodiment H192, wherein the at least one of the one or more additional target-binding domains positioned between the linker domain and the first domain of the pair of affinity domains, directly abuts the linker domain and/or the first domain of the pair of affinity domains.

Embodiment H198. The method of embodiment H192, wherein the first chimeric polypeptide further comprises a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

Embodiment H199. The method of any one of embodiments H166-H198, wherein the second chimeric polypeptide further comprises one or more additional target-binding domains at the N-terminal end and/or the C-terminal end of the second chimeric polypeptide.

Embodiment H200. The method of embodiment H199, wherein at least one of the one or more additional target-binding domains directly abuts the second domain of the pair of affinity domains in the second chimeric polypeptide.

Embodiment H201. The method of embodiment H199, wherein the second chimeric polypeptide further comprises a linker sequence between at least one of the one or more additional target-binding domains and the second domain of the pair of affinity domains in the second chimeric polypeptide.

Embodiment H202. The method of embodiment H199, wherein at least one of the one or more additional target-binding domains directly abuts the second target-binding domain in the second chimeric polypeptide.

Embodiment H203. The method of embodiment H199, wherein the second chimeric polypeptide further comprises a linker sequence between at least one of the one or more additional target-binding domains and the second target-binding domain in the second chimeric polypeptide.

Embodiment H204. The method of any one of embodiments H185-H203, wherein two or more of the first target-binding domain, the second target-binding domain, and the one or more additional target-binding domains bind specifically to the same antigen.

Embodiment H205. The method of embodiment H204, wherein two or more of the first target-binding domain, the second target-binding domain, and the one or more additional target-binding domains bind specifically to the same epitope.

Embodiment H206. The method of embodiment H205, wherein two or more of the first target-binding domain, the second target-binding domain, and the one or more additional target-binding domains comprise the same amino acid sequence.

Embodiment H207. The method of embodiment H204, wherein the first target-binding domain, the second target-binding domain, and the one or more additional target-binding domains each bind specifically to the same antigen.

Embodiment H208. The method of embodiment H207, wherein the first target-binding domain, the second target-binding domain, and the one or more additional target-binding domains each bind specifically to the same epitope.

Embodiment H209. The method of embodiment H208, wherein the first target-binding domain, the second target-binding domain, and the one or more additional target-binding domains each comprise the same amino acid sequence.

Embodiment H210. The method of any one of embodiments H185-H203, wherein the first target-binding domain, the second target-binding domain, and the one or more additional target-binding domains bind specifically to different antigens.

Embodiment H211. The method of any one of embodiments H185-H210, wherein one or more of the first target-binding domain, the second target-binding domain, and the one or more target-binding domains is an antigen-binding domain.

Embodiment H212. The method of embodiment H211, wherein the first target-binding domain, the second target-binding domain, and the one or more additional target-binding domains are each an antigen-binding domain.

Embodiment H213. The method of embodiment H211 or H212, wherein the antigen-binding domain comprises a scFv.

Embodiment H214. The method of any one of embodiments H185-H213, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment H215. The method of any one of embodiments H185-H213, wherein one or more of the first target-binding domain, the second target-binding domain, and the one or more additional target-binding domains is a soluble interleukin, soluble cytokine protein, or soluble cell surface protein.

Embodiment H216. The method of embodiment H215, wherein the soluble interleukin. soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H217. The method of any one of embodiments H185-H213, wherein one or more of the first target-binding domain, the second target-binding domain, and the one or more additional target-binding domains is a soluble interleukin or cytokine receptor.

Embodiment H218. The method of embodiment H217, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment H219. The method of any one of embodiments H166-H218, wherein the first chimeric polypeptide further comprises a peptide tag at the N-terminal end or the C-terminal end of the first chimeric polypeptide.

Embodiment H220. The method of any one of embodiments H166-H218, wherein the second chimeric polypeptide further comprises a peptide tag at the N-terminal end or the C-terminal end of the second chimeric polypeptide.

Embodiment H221. The method of any one of embodiments H166-H220, wherein the linker domain is a soluble tissue factor domain.

Embodiment H222. The method of embodiment H221, wherein the soluble tissue factor domain is a soluble human tissue factor domain.

Embodiment H223. The method of embodiment H222, wherein the soluble human tissue factor domain comprises a sequence that is at least 80% identical to SEQ ID NO: 1.

Embodiment H224. The method of embodiment H223, wherein the soluble human tissue factor domain comprises a sequence that is at least 90% identical to SEQ ID NO: 1.

Embodiment H225. The method of embodiment H224, wherein the soluble human tissue factor domain comprises a sequence that is at least 95% identical to SEQ ID NO: 1.

Embodiment H226. The method of any one of embodiments H222-H225, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H227. The method of embodiment H226, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H228. The method of any one of embodiments H221-H227, wherein the soluble tissue factor domain is not capable of binding to Factor VIIa.

Embodiment H229. The method of any one of embodiments H221-H228, wherein the soluble tissue factor domain does not convert inactive Factor X into Factor Xa.

Embodiment H230. The method of any one of embodiments H221-H229, wherein the multi-chain chimeric polypeptide does not stimulate blood coagulation in a mammal.

Embodiment H231. The method of any one of embodiments H221-H230, wherein the IgG1 antibody construct comprises at least one antigen-binding domain that binds specifically to the soluble tissue factor domain.

Embodiment H232. The method of any one of embodiments H166-H220, wherein the linker domain is selected from the group consisting of: a kappa chain and a lambda chain.

Embodiment H233. The method of any one of embodiments H166-H232, wherein the IgG1 antibody construct is a monoclonal IgG1 antibody, where both antigen-binding domains in the monoclonal IgG1 antibody bind specifically to the linker domain.

Embodiment H234. The method of any one of embodiments H166-H232, wherein the IgG1 antibody construct is a bispecific IgG1 antibody, where one of the two antigen-binding domains in the bispecific IgG1 antibody binds specifically to the linker domain.

Embodiment H235. The method of any one of embodiments H166-H234, wherein the pair of affinity domains is a sushi domain from an alpha chain of human IL-15 receptor (IL15Rα) and a soluble IL-15.

Embodiment H236. The method of embodiment H235, wherein the soluble IL15 has a D8N or D8A amino acid substitution.

Embodiment H237. The method of embodiment H235 or H236, wherein the human IL15Rα is a mature full-length IL15Rα.

Embodiment H238. The method of any one of embodiments H166-H234, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment H239. The method of any one of embodiments H166-H238, wherein the first chimeric polypeptide and/or the second chimeric polypeptide further comprises a signal sequence at its N-terminal end.

Embodiment H240. The method of any one of embodiments H166-H238, wherein the first chimeric polypeptide and/or the second chimeric polypeptide lacks a signal sequence at its N-terminal end.

Embodiment H241. The method of any one of embodiments H166-H240, wherein the contacting step is performed for a period of about 2 hours to about 20 days.

Embodiment H242. The method of embodiment H241, wherein the contacting step is performed for a period of about 1 day to about 15 days.

Embodiment H243. The method of any one of embodiments H166-H242, wherein the liquid culture medium is a serum-free liquid culture medium.

Embodiment H244. The method of any one of embodiments H166-H242, wherein the liquid culture medium is a chemically-defined liquid culture medium.

Embodiment H245. The method of any one of embodiments H166-H244, wherein the liquid culture medium comprises the multi-chain chimeric polypeptide and the IgG1 antibody construct at a molar ratio of about 0.5:1 to about 2:1.

Embodiment H246. The method of embodiment H245, wherein the liquid culture medium comprises the multi-chain chimeric polypeptide and the IgG1 antibody construct at a molar ratio of about 0.8:1 to about 1.2:1.

Embodiment H247. The method of any one of embodiments H166-H246, wherein the NK cell or T cell was previously obtained from a subject.

Embodiment H248. The method of embodiment H247, wherein the method further comprises obtaining the NK cell or T cell from the subject prior to the contacting step.

Embodiment H249. The method of any one of embodiments H166-H248, wherein the NK cell or T cell has previously been genetically modified to express a chimeric antigen receptor or a recombinant T-cell receptor.

Embodiment H250. The method of any one of embodiments H166-H248, wherein the method further comprises, after the contacting step, introducing into the NK cell or the T cell a nucleic acid encoding a chimeric antigen-receptor or a recombinant T-cell receptor.

Embodiment H251. The method of any one of embodiments H166-H248, wherein the method further comprises, before the contacting step, introducing into the NK cell or the T cell a nucleic acid encoding a chimeric antigen-receptor or a recombinant T-cell receptor.

Embodiment H252. The method of any one of embodiments H166-H251, wherein the method further comprises, after the contacting step, isolating the NK cell or the T cell.

Embodiment H253. The method of any one of embodiments H166-H252, wherein after the contacting step, the NK cell or the T cell has an increased level of expression or secretion of one or more proteins selected from the group consisting of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step.

Embodiment H254. The method of any one of embodiments H166-H253, wherein the method further comprises, after the contacting step, administering the NK cell or the T cell to a subject in need thereof.

Embodiment H255. The method of embodiment H254, wherein the subject has been identified or diagnosed as having an age-related disease or condition.

Embodiment H256. The method of embodiment H255, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H257. The method of embodiment H254, wherein the subject has been identified or diagnosed as having a cancer.

Embodiment H258. The method of embodiment H257, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H259. The method of embodiment H254, wherein the subject has been diagnosed or identified as having an infectious disease.

Embodiment H260. The method of embodiment H259, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment H261. An activated NK cell or T cell produced by the method of any one of embodiments H166-H253.

Embodiment H262. A pharmaceutical composition comprising the activated NK cell or the activated T cell of embodiment H261.

Embodiment H263. A kit comprising a pharmaceutical composition comprising the activated NK cell or the activated T cell of embodiment H261.

Embodiment H264. A method of killing a cancer cell, an infected cell, or a senescent cell in a subject in need thereof, the method comprising administering to the subject a therapeutically effective amount of the activated NK cell or the activated T cell of embodiment H261 or the pharmaceutical composition of embodiment H262.

Embodiment H265. The method of embodiment H264, wherein the subject has been identified or diagnosed as having a cancer.

Embodiment H266. The method of embodiment H265, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H267. The method of embodiment H264, wherein the subject has been identified or diagnosed as having an aging-related disease or condition.

Embodiment H268. The method of embodiment H267, wherein the aging-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Embodiment H269. A method of treating a subject in need thereof, the method comprising administering to the subject a therapeutically effective amount of the activated NK cell or the activated T cell of embodiment H261 or the pharmaceutical composition of embodiment H262.

Embodiment H270. The method of embodiment H269, wherein the subject has been identified or diagnosed as having a cancer.

Embodiment H271. The method of embodiment H270, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H272. The method of embodiment H269, wherein the subject has been identified or diagnosed as having an aging-related disease or condition.

Embodiment H273. The method of embodiment H272, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H274. The method of embodiment H269, wherein the subject has been diagnosed or identified as having an infectious disease.

Embodiment H275. The method of embodiment H274, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment H276. A kit comprising:

(1) a multi-chain chimeric polypeptide comprising:

(a) a first chimeric polypeptide comprising:

(i) a first target-binding domain;

(ii) a linker domain; and (iii) a first domain of a pair of affinity domains;

(b) a second chimeric polypeptide comprising:

(i) a second domain of a pair of affinity domains; and (ii) a second target-binding domain, wherein the first chimeric polypeptide and the second chimeric polypeptide associate through the binding of the first domain and the second domain of the pair of affinity domains; and (2) an effective amount of an IgG1 antibody that comprises at least one antigen-binding domain that binds specifically to the linker domain.

Embodiment H277. The kit of embodiment H276, wherein the first target-binding domain and the linker domain directly abut each other in the first chimeric polypeptide.

Embodiment H278. The kit of embodiment H276, wherein the first chimeric polypeptide further comprises a linker sequence between the first target-binding domain and the linker domain in the first chimeric polypeptide.

Embodiment H279. The kit of any one of embodiments H276-H278, wherein the linker domain and the first domain of the pair of affinity domains directly abut each other in the first chimeric polypeptide.

Embodiment H280. The kit of any one of embodiments H276-H278, wherein the first chimeric polypeptide further comprises a linker sequence between the linker domain and the first domain of the pair of affinity domains in the first chimeric polypeptide.

Embodiment H281. The kit of any one of embodiments H276-H280, wherein the second domain of the pair of affinity domains and the second target-binding domain directly abut each other in the second chimeric polypeptide.

Embodiment H282. The kit of any one of embodiments H276-H280, wherein the second chimeric polypeptide further comprises a linker sequence between the second domain of the pair of affinity domains and the second target-binding domain in the second chimeric polypeptide.

Embodiment H283. The kit of any one of embodiments H276-H282, wherein the first target-binding domain and the second target-binding domain bind specifically to the same antigen.

Embodiment H284. The kit of embodiment H283, wherein the first target-binding domain and the second target-binding domain bind specifically to the same epitope.

Embodiment H285. The kit of embodiment H284, wherein the first target-binding domain and the second target-binding domain comprise the same amino acid sequence.

Embodiment H286. The kit of any one of embodiments H276-H282, wherein the first target-binding domain and the second target-binding domain bind specifically to different antigens.

Embodiment H287. The kit of any one of embodiments H276-H286, wherein one or both of the first target-binding domain and the second target-binding domain is an antigen-binding domain.

Embodiment H288. The kit of embodiment H287, wherein the first target-binding domain and the second target-binding domain are each antigen-binding domains.

Embodiment H289. The kit of embodiment H287 or H288, wherein the antigen-binding domain comprises a scFv or a single domain antibody.

Embodiment H290. The kit of any one of embodiments H276-H289, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H291. The kit of any one of embodiments H276-H289, wherein one or both of the first target-binding domain and the second target-binding domain is a soluble interleukin, soluble cytokine protein, or soluble cell surface protein.

Embodiment H292. The kit of embodiment H291, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H293. The kit of any one of embodiments H276-H289, wherein one or both of the first target-binding domain and the second target-binding domain is a soluble interleukin or cytokine receptor.

Embodiment H294. The kit of embodiment H293, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment H295. The kit of any one of embodiments H276-H294, wherein the first chimeric polypeptide further comprises one or more additional target-binding domain(s), where at least one of the one or more target-binding domain(s) is positioned between the linker domain and the first domain of the pair of affinity domains.

Embodiment H296. The kit of embodiment H295, wherein the first chimeric polypeptide further comprises a linker sequence between the linker domain and the at least one of the one or more target antigen-binding domain(s), and/or a linker sequence between the at least one of the one or more target antigen-binding domain(s) and the first domain of the pair of affinity domains.

Embodiment H297. The kit of any one of embodiments H276-H294, wherein the first chimeric polypeptide further comprises one or more additional target-binding domains at the N-terminal and/or C-terminal end of the first chimeric polypeptide.

Embodiment H298. The kit of embodiment H297, wherein at least one of the one or more additional target-binding domains directly abuts the first domain of the pair of affinity domains in the first chimeric polypeptide.

Embodiment H299. The kit of embodiment H297, wherein the first chimeric polypeptide further comprises a linker sequence between the at least one of the one or more additional target-binding domains and the first domain of the pair of affinity domains.

Embodiment H300. The kit of embodiment H297, wherein the at least one of the one or more additional target-binding domains directly abuts the first target-binding domain in the first chimeric polypeptide.

Embodiment H301. The kit of embodiment H297, wherein the first chimeric polypeptide further comprises a linker sequence between the at least one of the one or more additional target-binding domains and the first target-binding domain.

Embodiment H302. The kit of embodiment H297, wherein at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide.

Embodiment H303. The kit of embodiment H302, wherein the at least one additional target-binding domain of the one or more additional target-binding domains disposed at the N-terminus directly abuts the first target-binding domain or the first domain of the pair of affinity domains in the first chimeric polypeptide.

Embodiment H304. The kit of embodiment H302, wherein the first chimeric polypeptide further comprises a linker sequence disposed between the at least one additional target-binding domain and the first target-binding domain or the first domain of the pair of affinity domains in the first chimeric polypeptide.

Embodiment H305. The kit of embodiment H302, wherein the at least one additional target-binding domain of the one or more additional target-binding domains disposed at the C-terminus directly abuts the first target-binding domain or the first domain of the pair of affinity domains in the first chimeric polypeptide.

Embodiment H306. The kit of embodiment H302, wherein the first chimeric polypeptide further comprises a linker sequence disposed between the at least one additional target-binding domain and the first target-binding domain or the first domain of the pair of affinity domains in the first chimeric polypeptide.

Embodiment H307. The kit of embodiment H302, wherein the at least one of the one or more additional target-binding domains positioned between the linker domain and the first domain of the pair of affinity domains, directly abuts the linker domain and/or the first domain of the pair of affinity domains.

Embodiment H308. The kit of embodiment H302, wherein the first chimeric polypeptide further comprises a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

Embodiment H309. The kit of any one of embodiments H276-H308, wherein the second chimeric polypeptide further comprises one or more additional target-binding domains at the N-terminal end or the C-terminal end of the second chimeric polypeptide.

Embodiment H310. The kit of embodiment H309, wherein at least one of the one or more additional target-binding domains directly abuts the second domain of the pair of affinity domains in the second chimeric polypeptide.

Embodiment H311. The kit of embodiment H309, wherein the second chimeric polypeptide further comprises a linker sequence between at least one of the one or more additional target-binding domains and the second domain of the pair of affinity domains in the second chimeric polypeptide.

Embodiment H312. The kit of embodiment H309, wherein at least one of the one or more additional target-binding domains directly abuts the second target-binding domain in the second chimeric polypeptide.

Embodiment H313. The kit of embodiment H309, wherein the second chimeric polypeptide further comprises a linker sequence between at least one of the one or more additional target-binding domains and the second target-binding domain in the second chimeric polypeptide.

Embodiment H314. The kit of any one of embodiments H295-H313, wherein two or more of the first target-binding domain, the second target-binding domain, and the one or more additional target-binding domains bind specifically to the same antigen.

Embodiment H315. The kit of embodiment H314, wherein two or more of the first target-binding domain, the second target-binding domain, and the one or more additional target-binding domains bind specifically to the same epitope.

Embodiment H316. The kit of embodiment H315, wherein two or more of the first target-binding domain, the second target-binding domain, and the one or more additional target-binding domains comprise the same amino acid sequence.

Embodiment H317. The kit of embodiment H314, wherein the first target-binding domain, the second target-binding domain, and the one or more additional target-binding domains each bind specifically to the same antigen.

Embodiment H318. The kit of embodiment H317, wherein the first target-binding domain, the second target-binding domain, and the one or more additional target-binding domains each bind specifically to the same epitope.

Embodiment H319. The kit of embodiment H318, wherein the first target-binding domain, the second target-binding domain, and the one or more additional target-binding domains each comprise the same amino acid sequence.

Embodiment H320. The kit of any one of embodiments H295-H313, wherein the first target-binding domain, the second target-binding domain, and the one or more additional target-binding domains bind specifically to different antigens.

Embodiment H321. The kit of any one of embodiments H295-H320, wherein one or more of the first target-binding domain, the second target-binding domain, and the one or more target-binding domains is an antigen-binding domain.

Embodiment H322. The kit of embodiment H321, wherein the first target-binding domain, the second target-binding domain, and the one or more additional target-binding domains are each an antigen-binding domain.

Embodiment H323. The kit of embodiment H321 or H322, wherein the antigen-binding domain comprises a scFv.

Embodiment H324. The kit of any one of embodiments H295-H323, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-β receptor III (TGF-βRIII), a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment H325. The kit of any one of embodiments H295-H323, wherein one or more of the first target-binding domain, the second target-binding domain, and the one or more additional target-binding domains is a soluble interleukin, soluble cytokine protein, or soluble cell surface protein.

Embodiment H326. The kit of embodiment H325, wherein the soluble interleukin or cytokine protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H327. The kit of any one of embodiments H295-H323, wherein one or more of the first target-binding domain, the second target-binding domain, and the one or more additional target-binding domains is a soluble interleukin or cytokine receptor.

Embodiment H328. The kit of embodiment H327, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment H329. The kit of any one of embodiments H295-H328, wherein one or both of the first target-binding domain and the second target-binding domain is a ligand of a co-stimulatory molecule.

Embodiment H330. The kit of embodiment H329, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H331. The kit of any one of embodiments H276-H330, wherein the linker domain is a soluble tissue factor domain.

Embodiment H332. The kit of embodiment H331, wherein the soluble tissue factor domain is a soluble human tissue factor domain.

Embodiment H333. The kit of embodiment H332, wherein the soluble human tissue factor domain comprises a sequence that is at least 80% identical to SEQ ID NO: 1.

Embodiment H334. The kit of embodiment H333, wherein the soluble human tissue factor domain comprises a sequence that is at least 90% identical to SEQ ID NO: 1.

Embodiment H335. The kit of embodiment H334, wherein the soluble human tissue factor domain comprises a sequence that is at least 95% identical to SEQ ID NO: 1.

Embodiment H336. The kit of any one of embodiments H332-H335, wherein the soluble human tissue factor domain does not comprise one or more of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H337. The kit of embodiment H336, wherein the soluble human tissue factor domain does not comprise any of:

a lysine at an amino acid position that corresponds to amino acid position 20 of mature wildtype human tissue factor protein;

an isoleucine at an amino acid position that corresponds to amino acid position 22 of mature wildtype human tissue factor protein;

a tryptophan at an amino acid position that corresponds to amino acid position 45 of mature wildtype human tissue factor protein;

an aspartic acid at an amino acid position that corresponds to amino acid position 58 of mature wildtype human tissue factor protein;

a tyrosine at an amino acid position that corresponds to amino acid position 94 of mature wildtype human tissue factor protein;

an arginine at an amino acid position that corresponds to amino acid position 135 of mature wildtype human tissue factor protein; and a phenylalanine at an amino acid position that corresponds to amino acid position 140 of mature wildtype human tissue factor protein.

Embodiment H338. The kit of any one of embodiments H331-H337, wherein the soluble tissue factor domain is not capable of binding to Factor VIIa.

Embodiment H339. The kit of any one of embodiments H331-H338, wherein the soluble tissue factor domain does not convert inactive Factor X into Factor Xa.

Embodiment H340. The kit of any one of embodiments H331-H339, wherein the multi-chain chimeric polypeptide does not stimulate blood coagulation in a mammal.

Embodiment H341. The kit of any one of embodiments H331-H340, wherein the IgG1 antibody construct comprises at least one antigen-binding domain that binds specifically to the soluble tissue factor domain.

Embodiment H342. The kit of any one of embodiments H276-H330, wherein the linker domain is selected from the group consisting of: a kappa chain and a lambda chain.

Embodiment H343. The kit of any one of embodiments H276-H342, wherein the IgG1 antibody construct is a monoclonal IgG1 antibody, where both antigen-binding domains in the monoclonal IgG1 antibody bind specifically to the linker domain.

Embodiment H344. The kit of any one of embodiments H276-H342, wherein the IgG1 antibody construct is a bispecific IgG1 antibody, where one of the two antigen-binding domains in the bispecific IgG1 antibody binds specifically to the linker domain.

Embodiment H345. The kit of any one of embodiments H276-H344, wherein the pair of affinity domains is a sushi domain from an alpha chain of human IL-15 receptor (IL15Rα) and a soluble IL-15.

Embodiment H346. The kit of embodiment H345, wherein the soluble IL15 has a D8N or D8A amino acid substitution.

Embodiment H347. The kit of embodiment H345 or H346, wherein the human IL15Rα is a mature full-length IL15Rα.

Embodiment H348. The kit of any one of embodiments H276-H344, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment H349. The kit of any one of embodiments H276-H348, wherein the first chimeric polypeptide and/or the second chimeric polypeptide further comprises a signal sequence at its N-terminal end.

Embodiment H350. The kit of any one of embodiments H276-H348, wherein the first chimeric polypeptide and/or the second chimeric polypeptide lacks a signal sequence at its N-terminal end.

Embodiment H351. The method of any one of embodiments H1-H16, wherein one or both of the first target-binding domain and the second target-binding domain is a ligand of a co-stimulatory molecule.

Embodiment H352. The method of embodiment H351, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H353. The method of any one of embodiments H1-H62, wherein the single-chain chimeric polypeptide further comprises a signal sequence at its N-terminal end.

Embodiment H354. The method of any one of embodiments H1-H62, wherein the single-chain chimeric polypeptide lacks a signal sequence at its N-terminal end.

Embodiment H355. The kit of any one of embodiments H101-H162, wherein the single-chain chimeric polypeptide further comprises a signal sequence at its N-terminal end.

Embodiment H356. The kit of any one of embodiments H101-H162, wherein the single-chain chimeric polypeptide lacks a signal sequence at its N-terminal end.

Embodiment H357. The method of any one of embodiments H166-H179, wherein one or both of the first target-binding domain and the second target-binding domain is a ligand of a co-stimulatory molecule.

Embodiment H358. The method of embodiment H357, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H359. The method of any one of embodiments H185-H217, wherein one or both of the first target-binding domain and the second target-binding domain is a ligand of a co-stimulatory molecule.

Embodiment H360. The method of embodiment H359, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H361. The kit of any one of embodiments H276-H294, wherein one or both of the first target-binding domain and the second target-binding domain is a ligand of a co-stimulatory molecule.

Embodiment H362. The kit of embodiment H361 wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H363. The kit of any one of embodiments H276-H330, wherein the first chimeric polypeptide further comprises a peptide tag at the N-terminal end or the C-terminal end of the first chimeric polypeptide.

Embodiment H364. The kit of any one of embodiments H276-H328, wherein the second chimeric polypeptide further comprises a peptide tag at the N-terminal end or the C-terminal end of the second chimeric polypeptide.

Embodiment H365. A method of increasing the glucose consumption of an immune cell, the method comprising:

contacting an immune cell in a liquid culture medium comprising an effective amount of (i) a single-chain chimeric polypeptide comprising a first target-binding domain, a linker domain, and a second target-binding domain, and optionally (ii) an IgG1 antibody construct that comprises at least one antigen-binding domain that binds specifically to the linker domain, under conditions that allow for glucose consumption in the immune cell, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules.

Embodiment H366. A method of increasing the oxidative phosphorylation of an immune cell, the method comprising:

contacting an immune cell in a liquid culture medium comprising an effective amount of (i) a single-chain chimeric polypeptide comprising a first target-binding domain, a linker domain, and a second target-binding domain, and optionally (ii) an IgG1 antibody construct that comprises at least one antigen-binding domain that binds specifically to the linker domain, under conditions that allow for oxidative phosphorylation in the immune cell, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules.

Embodiment H367. A method of increasing the aerobic glycolysis of an immune cell, the method comprising:

contacting an immune cell in a liquid culture medium comprising an effective amount of (i) a single-chain chimeric polypeptide comprising a first target-binding domain, a linker domain, and a second target-binding domain, and optionally (ii) an IgG1 antibody construct that comprises at least one antigen-binding domain that binds specifically to the linker domain, under conditions that allow for aerobic glycolysis in the immune cell, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules.

Embodiment H368. A method of increasing the extracellular acidification rate (ECAR) of an immune cell, the method comprising:

contacting an immune cell in a liquid culture medium comprising an effective amount of (i) a single-chain chimeric polypeptide comprising a first target-binding domain, a linker domain, and a second target-binding domain, and optionally (ii) an IgG1 antibody construct that comprises at least one antigen-binding domain that binds specifically to the linker domain, under conditions that allow for extracellular acidification by the immune cell, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules.

Embodiment H369. A method of increasing the mitochondrial oxygen consumption rate of an immune cell, the method comprising:

contacting an immune cell in a liquid culture medium comprising an effective amount of (i) a single-chain chimeric polypeptide comprising a first target-binding domain, a linker domain, and a second target-binding domain, and optionally (ii) an IgG1 antibody construct that comprises at least one antigen-binding domain that binds specifically to the linker domain, under conditions that allow for mitochondrial oxygen consumption rate by the immune cell, wherein the first target-binding domain and the second target-binding domain are each independently selected from the group consisting of: a soluble interleukin or cytokine protein, an antigen-binding domain, a soluble interleukin or cytokine receptor, and ligands of co-stimulatory molecules.

Embodiment H370. The method of any one of embodiments H365-H369, wherein the liquid culture medium comprises the single-chain chimeric polypeptide and the IgG1 antibody construct.

Embodiment H371. The method of embodiment H370, wherein the IgG1 antibody construct is a monoclonal IgG1 antibody, where both of the antigen-binding domains in the monoclonal IgG1 antibody bind specifically to the linker domain.

Embodiment H372. The method of embodiment H370, wherein the IgG1 antibody construct is a bispecific IgG1 antibody, where one of the two antigen-binding domains in the bispecific IgG1 antibody binds specifically to the linker domain.

Embodiment H373. The method of any one of embodiments H365-H372, wherein the contacting step is performed for a period of about 2 hours to about 20 days.

Embodiment H374. The method of embodiment H373, wherein the contacting step is performed for a period of about 1 day to about 15 days.

Embodiment H375. The method of any one of embodiments H365-H374, wherein the liquid culture medium is a serum-free liquid culture medium.

Embodiment H376. The method of any one of embodiments H365-H374, wherein the liquid culture medium is a chemically-defined liquid culture medium.

Embodiment H377. The method of any one of embodiments H365-H374, wherein the liquid culture medium comprises serum.

Embodiment H378. The method of any one of embodiments H365-H377, wherein the liquid culture medium comprises the single-chain chimeric polypeptide and the IgG1 antibody construct at a molar ratio of about 0.5:1 to about 2:1.

Embodiment H379. The method of embodiment H378, wherein the liquid culture medium comprises the single-chain chimeric polypeptide and the IgG1 antibody construct at a molar ratio of about 0.8:1 to about 1.2:1.

Embodiment H380. The method of any one of embodiments H365-H379, wherein the first target-binding domain and the linker domain directly abut each other.

Embodiment H381. The method of any one of embodiments H365-H379, wherein the single-chain chimeric polypeptide further comprises a linker sequence between the first target-binding domain and the linker domain.

Embodiment H382. The method of any one of embodiments H365-H381, wherein the linker domain and the second target-binding domain directly abut each other.

Embodiment H383. The method of any one of embodiments H365-H381, wherein the single-chain chimeric polypeptide further comprises a linker sequence between the linker domain and the second target-binding domain.

Embodiment H384. The method of any one of embodiments H365-H379, wherein the first target-binding domain and the second target-binding domain directly abut each other.

Embodiment H385. The method of any one of embodiments H365-H379, wherein the single-chain chimeric polypeptide further comprises a linker sequence between the first target-binding domain and the second target-binding domain.

Embodiment H386. The method of embodiment H384 or H385, wherein the second target-binding domain and the linker domain directly abut each other.

Embodiment H387. The method of embodiment H384 or H385, wherein the single-chain chimeric polypeptide further comprises a linker sequence between the second target-binding domain and the linker domain.

Embodiment H388. The method of any one of embodiments H365-H387, wherein the first target-binding domain and the second target-binding domain bind specifically to the same antigen.

Embodiment H389. The method of embodiment H388, wherein the first target-binding domain and the second target-binding domain bind specifically to the same epitope.

Embodiment H390. The method of embodiment H389, wherein the first target-binding domain and the second target-binding domain comprise the same amino acid sequence.

Embodiment H391. The method of any one of embodiments H365-H387, wherein the first target-binding domain and the second target-binding domain bind specifically to different antigens.

Embodiment H392. The method of any one of embodiments H365-H391, wherein one or both of the first target-binding domain and the second target-binding domain is an antigen-binding domain.

Embodiment H393. The method of embodiment H392, wherein the first target-binding domain and the second target-binding domain are each an antigen-binding domain.

Embodiment H394. The method of embodiment H392 or H393, wherein antigen-binding domain comprises a scFv or a single domain antibody.

Embodiment H395. The method of any one of embodiments H365-H394, wherein one or both of the first target-binding domain and the second target-binding domain bind to a target selected from the group consisting of: CD16a, CD28, CD3, CD33, CD20, CD19, CD22, CD52, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H396. The method of any one of embodiments H365-H394, wherein one or both of the first target-binding domain and the second target-binding domain is a soluble interleukin, soluble cytokine protein, or soluble cell surface protein.

Embodiment H397. The method of embodiment H396, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H398. The method of any one of embodiments H365-H394, wherein one or both of the first target-binding domain and the second target-binding domain is a soluble interleukin or cytokine receptor.

Embodiment H399. The method of embodiment H398, wherein the soluble interleukin or cytokine receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment H400. The method of any one of embodiments H365-H399, wherein the linker domain is a soluble tissue factor domain.

Embodiment H401. The method of embodiment H400, wherein the soluble tissue factor domain is a soluble human tissue factor domain.

Embodiment H402. The method of embodiment H401, wherein the soluble human tissue factor domain comprises a sequence that is at least 80% identical to SEQ ID NO: 1.

Embodiment H403. The method of embodiment H402, wherein the soluble human tissue factor domain comprises a sequence that is at least 90% identical to SEQ ID NO: 1.

Embodiment H404. The method of embodiment H403, wherein the soluble human tissue factor domain comprises a sequence that is at least 95% identical to SEQ ID NO: 1.

Embodiment H405. The method of any one of embodiments H401-H404, wherein the soluble human tissue factor domain does not comprise one or more of:

- a lysine at an amino acid position that corresponds to amino acid position 20 of mature wildtype human tissue factor protein;
- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;
- a tyrosine at an amino acid position that corresponds to amino acid position 94 of mature wildtype human tissue factor protein;
- an arginine at an amino acid position that corresponds to amino acid position 135 of mature wildtype human tissue factor protein; and
- a phenylalanine at an amino acid position that corresponds to amino acid position 140 of mature wildtype human tissue factor protein.

Embodiment H406. The method of embodiment H405, wherein the soluble human tissue factor domain does not comprise any of:

- a lysine at an amino acid position that corresponds to amino acid position 20 of mature wildtype human tissue factor protein;
- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;
- a tyrosine at an amino acid position that corresponds to amino acid position 94 of mature wildtype human tissue factor protein;
- an arginine at an amino acid position that corresponds to amino acid position 135 of mature wildtype human tissue factor protein; and
- a phenylalanine at an amino acid position that corresponds to amino acid position 140 of mature wildtype human tissue factor protein.

Embodiment H407. The method of any one of embodiments H400-H406, wherein the soluble tissue factor domain is not capable of binding Factor VIIa.

Embodiment H408. The method of any one of embodiments H400-H407, wherein the soluble tissue factor domain does not convert inactive Factor X into Factor Xa.

Embodiment H409. The method of any one of embodiments H400-H408, wherein the single-chain chimeric polypeptide does not stimulate blood coagulation in a mammal.

Embodiment H410. The method of any one of embodiments H400-H409, wherein the IgG1 antibody construct comprises at least one antigen-binding domain that binds specifically to the soluble tissue factor domain.

Embodiment H411. The method of any one of embodiments H365-H399, wherein the linker domain is selected from the group consisting of: a kappa chain and a lambda chain.

Embodiment H412. The method of any one of embodiments H365-H411, wherein the IgG1 antibody construct is a monoclonal IgG1 antibody, where both of the antigen-binding domains in the monoclonal IgG1 antibody bind specifically to the linker domain.

Embodiment H413. The method of any one of embodiments H365-H411, wherein the IgG1 antibody construct is a bispecific IgG1 antibody, where one of the two antigen-binding domains in the bispecific IgG1 antibody binds specifically to the linker domain.

Embodiment H414. The method of any one of embodiments H365-H413, wherein the single-chain chimeric polypeptide further comprises one or more additional target-binding domains at its N- and/or C-terminus.

Embodiment H415. The method of embodiment H414, wherein the single-chain chimeric polypeptide comprises one or more additional target-binding domains at its N-terminus.

Embodiment H416. The method of embodiment H415, wherein one or more additional target-binding domains directly abuts the first target-binding domain, the second target-binding domain, or the linker domain.

Embodiment H417. The method of embodiment H416, wherein the single-chain chimeric polypeptide further comprises a linker sequence between one of the at least one additional target-binding domains and the first target-binding domain, the second target-binding domain, or the linker domain.

Embodiment H418. The method of embodiment H414, wherein the single-chain chimeric polypeptide comprises one or more additional target-binding domains at its C-terminus.

Embodiment H419. The method of embodiment H418, wherein one of the one or more additional target-binding domains directly abuts the first target-binding domain, the second target-binding domain, or the linker domain.

Embodiment H420. The method of embodiment H418, wherein the single-chain chimeric polypeptide further comprises a linker sequence between one of the at least one additional target-binding domains and the first target-binding domain, the second target-binding domain, or the linker domain.

Embodiment H421. The method of embodiment H414, wherein the single-chain chimeric polypeptide comprises one or more additional target binding domains at its N-terminus and the C-terminus.

Embodiment H422. The method of embodiment H421, wherein one of the one or more additional target-binding domains at the N-terminus directly abuts the first target-binding domain, the second target-binding domain, or the linker domain.

Embodiment H423. The method of embodiment H421, wherein the single-chain chimeric polypeptide further comprises a linker sequence between one of the one or more additional target-binding domains at the N-terminus and the first target-binding domain, the second target-binding domain, or the linker domain.

Embodiment H424. The method of embodiment H421, wherein one of the one or more additional target-binding domains at the C-terminus directly abuts the first target-binding domain, the second target-binding domain, or the linker domain.

Embodiment H425. The method of embodiment H421, wherein the single-chain chimeric polypeptide further comprises a linker sequence between one of the one or more additional target-binding domains at the C-terminus and the first target-binding domain, the second target-binding domain, or the linker domain.

Embodiment H426. The method of any one of embodiments H414-H425, wherein two or more of the first target-binding domain, the second target-binding domain, and the one or more additional target-binding domains bind specifically to the same antigen.

Embodiment H427. The method of embodiment H426, wherein two or more of the first target-binding domain, the second target-binding domain, and the one or more additional target-binding domains bind specifically to the same epitope.

Embodiment H428. The method of embodiment H427, wherein two or more of the first target-binding domain, the second target-binding domain, and the one or more additional target-binding domains comprise the same amino acid sequence.

Embodiment H429. The method of embodiment H426, wherein the first target-binding domain, the second target-binding domain, and the one or more additional target-binding domains each bind specifically to the same antigen.

Embodiment H430. The method of embodiment H429, wherein the first target-binding domain, the second target-binding domain, and the one or more additional target-binding domains each bind specifically to the same epitope.

Embodiment H431. The method of embodiment H430, wherein the first target-binding domain, the second target-binding domain, and the one or more additional target-binding domains each comprise the same amino acid sequence.

Embodiment H432. The method of any one of embodiments H414-H425, wherein the first target-binding domain, the second target-binding domain, and the one or more additional target-binding domains bind specifically to different antigens.

Embodiment H433. The method of any one of embodiments H414-H432, wherein one or more of the first target-binding domain, the second target-binding domain, and the one or more target-binding domains is an antigen-binding domain.

Embodiment H434. The method of embodiment H433, wherein the first target-binding domain, the second target-binding domain, and the one or more additional target-binding domains are each an antigen-binding domain.

Embodiment H435. The method of embodiment H433 or H434, wherein the antigen-binding domain comprises a scFv or a single domain antibody.

Embodiment H436. The method of any one of embodiments H414-H435, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-βRII), a ligand of TGF-βRIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H437. The method of any one of embodiments H414-H432, wherein one or more of the first target-binding domain, the second target-binding domain, and the one or more additional target-binding domains is a soluble interleukin, soluble cytokine protein, or soluble cell surface protein.

Embodiment H438. The method of embodiment H437, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H439. The method of any one of embodiments H414-H432, wherein one or more of the first target-binding domain, the second target-binding domain, and the one or more additional target-binding domains is a soluble interleukin or cytokine receptor.

Embodiment H440. The method of embodiment H439, wherein the soluble interleukin or cytokine receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment H441. The method of any one of embodiments H414-H432, wherein one or more of the first target-binding domain, the second target-binding domain, and the one or more additional target-binding domains is a ligand of a co-stimulatory molecule.

Embodiment H442. The method of embodiment H441, wherein the ligand of a co-stimulatory molecule is a soluble CD80, CD86, CD40, ICOSL, CD70, OX40L, 4-1BBL, GITRL, LIGHT, TIM3, TIM4, ICAM1, LFA3, CD1d, or LLT-1.

Embodiment H443. The method of any one of embodiments H365-H442, wherein the single-chain chimeric polypeptide further comprises a peptide tag positioned at the N-terminal end or the C-terminal end of the single-chain chimeric polypeptide.

Embodiment H444. The method of any one of embodiments H365-H443, wherein the NK cell or T cell was previously obtained from a subject.

Embodiment H445. The method of embodiment H444, wherein the method further comprises obtaining the NK cell or T cell from the subject prior to the contacting step.

Embodiment H446. The method of any one of embodiments H365-H445, wherein the immune cell has previously been genetically modified to express a chimeric antigen receptor or a recombinant T-cell receptor.

Embodiment H447. The method of any one of embodiments H365-H445, wherein the method further comprises, after the contacting step, introducing into the immune cell a nucleic acid encoding a chimeric antigen-receptor or a recombinant T-cell receptor.

Embodiment H448. The method of any one of embodiments H365-H445, wherein the method further comprises, before the contacting step, introducing into the immune cell a nucleic acid encoding a chimeric antigen-receptor or a recombinant T-cell receptor.

Embodiment H449. The method of any one of embodiments H365-H448, wherein the method further comprises, after the contacting step, isolating the immune cell.

Embodiment H450. The method of any one of embodiments H365-H449, wherein after the contacting step, the immune cell has an increased level of expression or secretion of one or more proteins selected from the group consisting of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step.

Embodiment H451. The method of any one of embodiments H365-H450, wherein the method further comprises, after the contacting step, administering the immune cell to a subject in need thereof.

Embodiment H452. The method of embodiment H451, wherein the subject has been identified or diagnosed as having an age-related disease or condition.

Embodiment H453. The method of embodiment H452, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H454. The method of embodiment H451, wherein the subject has been identified or diagnosed as having a cancer.

Embodiment H455. The method of embodiment H454, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H456. The method of embodiment H451, wherein the subject has been diagnosed or identified as having an infectious disease.

Embodiment H457. The method of embodiment H456, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment H458. An activated immune cell produced by the method of any one of embodiments H365-H450.

Embodiment H459. A pharmaceutical composition comprising the activated immune cell of embodiment H458.

Embodiment H460. A kit comprising a pharmaceutical composition comprising the activated immune cell of embodiment H458.

Embodiment H461. A method of killing a cancer cell, an infected cell, or a senescent cell in a subject in need thereof, the method comprising administering to the subject a therapeutically effective amount of the activated immune cell of embodiment H458 or the pharmaceutical composition of embodiment H459.

Embodiment H462. The method of embodiment H461, wherein the subject has been identified or diagnosed as having a cancer.

Embodiment H463. The method of embodiment H462, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H464. The method of embodiment H462, wherein the subject has been identified or diagnosed as having an aging-related disease or condition.

Embodiment H465. The method of embodiment H464, wherein the aging-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H466. A method of treating a subject in need thereof, the method comprising administering to the subject a therapeutically effective amount of the activated immune cell of embodiment H458 or the pharmaceutical composition of embodiment H459.

Embodiment H467. The method of embodiment H466, wherein the subject has been identified or diagnosed as having a cancer.

Embodiment H468. The method of embodiment H467, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CMIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H469. The method of embodiment H466, wherein the subject has been identified or diagnosed as having an aging-related disease or condition.

Embodiment H470. The method of embodiment H469, wherein the aging-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H471. The method of embodiment H466, wherein the subject has been diagnosed or identified as having an infectious disease.

Embodiment H472. The method of embodiment H471, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, or influenza virus.

Embodiment H473. A method of increasing the glucose consumption of an immune cell, the method comprising:

contacting an immune cell in a liquid culture medium comprising (1) an effective amount of a multi-chain chimeric polypeptide comprising:

(a) a first chimeric polypeptide comprising:

(i) a first target-binding domain;

(ii) a linker domain; and (iii) a first domain of a pair of affinity domains;

(b) a second chimeric polypeptide comprising:
(i) a second domain of a pair of affinity domains; and
(ii) a second target-binding domain,
wherein the first chimeric polypeptide and the second chimeric polypeptide associate through the binding of the first domain and the second domain of the pair of affinity domains; and
(2) an effective amount of an IgG1 antibody construct comprising at least one antigen-binding domain that binds specifically to the linker domain, under conditions that allow for glucose consumption in the immune cell.

Embodiment H474. A method of increasing the oxidative phosphorylation of an immune cell, the method comprising:
contacting an immune cell in a liquid culture medium comprising (1) an effective amount of a multi-chain chimeric polypeptide comprising:
(a) a first chimeric polypeptide comprising:
(i) a first target-binding domain;
(ii) a linker domain; and
(iii) a first domain of a pair of affinity domains;
(b) a second chimeric polypeptide comprising:
(i) a second domain of a pair of affinity domains; and
(ii) a second target-binding domain,
wherein the first chimeric polypeptide and the second chimeric polypeptide associate through the binding of the first domain and the second domain of the pair of affinity domains; and
(2) an effective amount of an IgG1 antibody construct comprising at least one antigen-binding domain that binds specifically to the linker domain, under conditions that allow for oxidative phosphorylation in the immune cell.

Embodiment H475. A method of increasing the aerobic glycolysis of an immune cell, the method comprising:
contacting an immune cell in a liquid culture medium comprising (1) an effective amount of a multi-chain chimeric polypeptide comprising:
(a) a first chimeric polypeptide comprising:
(i) a first target-binding domain;
(ii) a linker domain; and
(iii) a first domain of a pair of affinity domains;
(b) a second chimeric polypeptide comprising:
(i) a second domain of a pair of affinity domains; and
(ii) a second target-binding domain,
wherein the first chimeric polypeptide and the second chimeric polypeptide associate through the binding of the first domain and the second domain of the pair of affinity domains; and
(2) an effective amount of an IgG1 antibody construct comprising at least one antigen-binding domain that binds specifically to the linker domain, under conditions that allow for aerobic glycolysis in the immune cell.

Embodiment H476. A method of increasing the extracellular acidification rate (ECAR) of an immune cell, the method comprising:
contacting an immune cell in a liquid culture medium comprising (1) an effective amount of a multi-chain chimeric polypeptide comprising:
(a) a first chimeric polypeptide comprising:
(i) a first target-binding domain;
(ii) a linker domain; and
(iii) a first domain of a pair of affinity domains;
(b) a second chimeric polypeptide comprising:
(i) a second domain of a pair of affinity domains; and
(ii) a second target-binding domain,
wherein the first chimeric polypeptide and the second chimeric polypeptide associate through the binding of the first domain and the second domain of the pair of affinity domains; and
(2) an effective amount of an IgG1 antibody construct comprising at least one antigen-binding domain that binds specifically to the linker domain, under conditions that allow for extracellular acidification by the immune cell.

Embodiment H477. A method of increasing the mitochondrial oxygen consumption rate of an immune cell, the method comprising:
contacting an immune cell in a liquid culture medium comprising (1) an effective amount of a multi-chain chimeric polypeptide comprising:
(a) a first chimeric polypeptide comprising:
(i) a first target-binding domain;
(ii) a linker domain; and
(iii) a first domain of a pair of affinity domains;
(b) a second chimeric polypeptide comprising:
(i) a second domain of a pair of affinity domains; and
(ii) a second target-binding domain,
wherein the first chimeric polypeptide and the second chimeric polypeptide associate through the binding of the first domain and the second domain of the pair of affinity domains; and
(2) an effective amount of an IgG1 antibody construct comprising at least one antigen-binding domain that binds specifically to the linker domain, under conditions that allow for mitochondrial oxygen consumption rate by the immune cell.

Embodiment H478. The method of any one of embodiments H473-H477, wherein the liquid culture medium comprises the single-chain chimeric polypeptide and the IgG1 antibody construct.

Embodiment H479. The method of embodiment H478, wherein the IgG1 antibody construct is a monoclonal IgG1 antibody, where both of the antigen-binding domains in the monoclonal IgG1 antibody bind specifically to the linker domain.

Embodiment H480. The method of embodiment H478, wherein the IgG1 antibody construct is a bispecific IgG1 antibody, where one of the two antigen-binding domains in the bispecific IgG1 antibody binds specifically to the linker domain.

Embodiment H481. The method of any one of embodiments H473-H480, wherein the contacting step is performed for a period of about 2 hours to about 20 days.

Embodiment H482. The method of embodiment H481, wherein the contacting step is performed for a period of about 1 day to about 15 days.

Embodiment H483. The method of any one of embodiments H473-H482, wherein the liquid culture medium is a serum-free liquid culture medium.

Embodiment H484. The method of any one of embodiments H473-H482, wherein the liquid culture medium is a chemically-defined liquid culture medium.

Embodiment H485. The method of any one of embodiments H473-H482, wherein the liquid culture medium comprises serum.

Embodiment H486. The method of any one of embodiments H473-H485, wherein the liquid culture medium comprises the single-chain chimeric polypeptide and the IgG1 antibody construct at a molar ratio of about 0.5:1 to about 2:1.

Embodiment H487. The method of embodiment H486, wherein the liquid culture medium comprises the single-chain chimeric polypeptide and the IgG1 antibody construct at a molar ratio of about 0.8:1 to about 1.2:1.

Embodiment H488. The method of any one of embodiments H473-H487, wherein the first target-binding domain and the linker domain directly abut each other in the first chimeric polypeptide.

Embodiment H489. The method of any one of embodiments H473-H487, wherein the first chimeric polypeptide further comprises a linker sequence between the first target-binding domain and the linker domain in the first chimeric polypeptide.

Embodiment H490. The method of any one of embodiments H473-H489, wherein the linker domain and the first domain of the pair of affinity domains directly abut each other in the first chimeric polypeptide.

Embodiment H491. The method of any one of embodiments H473-H489, wherein the first chimeric polypeptide further comprises a linker sequence between the linker domain and the first domain of the pair of affinity domains in the first chimeric polypeptide.

Embodiment H492. The method of any one of embodiments H473-H491, wherein the second domain of the pair of affinity domains and the second target-binding domain directly abut each other in the second chimeric polypeptide.

Embodiment H493. The method of any one of embodiments H473-H491, wherein the second chimeric polypeptide further comprises a linker sequence between the second domain of the pair of affinity domains and the second target-binding domain in the second chimeric polypeptide.

Embodiment H494. The method of any one of embodiments H473-H493, wherein the first target-binding domain and the second target-binding domain bind specifically to the same antigen.

Embodiment H495. The method of embodiment H494, wherein the first target-binding domain and the second target-binding domain bind specifically to the same epitope.

Embodiment H496. The method of embodiment H495, wherein the first target-binding domain and the second target-binding domain comprise the same amino acid sequence.

Embodiment H497. The method of any one of embodiments H473-H493, wherein the first target-binding domain and the second target-binding domain bind specifically to different antigens.

Embodiment H498. The method of any one of embodiments H473-H497, wherein one or both of the first target-binding domain and the second target-binding domain is an antigen-binding domain.

Embodiment H499. The method of embodiment H498, wherein the first target-binding domain and the second target-binding domain are each antigen-binding domains.

Embodiment H500. The method of embodiment H498 or H499, wherein the antigen-binding domain comprises a scFv or a single domain antibody.

Embodiment H501. The method of any one of embodiments H473-H500, wherein one or both of the first target-binding domain and the second target-binding domain bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD28.

Embodiment H502. The method of any one of embodiments H473-H497, wherein one or both of the first target-binding domain and the second target-binding domain is a soluble interleukin, soluble cytokine protein, or soluble cell surface protein.

Embodiment H503. The method of embodiment H502, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H504. The method of any one of embodiments H473-H497, wherein one or both of the first target-binding domain and the second target-binding domain is a soluble interleukin or cytokine receptor.

Embodiment H505. The method of embodiment H504, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, or a soluble CD28.

Embodiment H506. The method of any one of embodiments H473-H505, wherein the first chimeric polypeptide further comprises one or more additional target-binding domain(s), where at least one of the one or more target-binding domain(s) is positioned between the linker domain and the first domain of the pair of affinity domains.

Embodiment H507. The method of embodiment H506, wherein the first chimeric polypeptide further comprises a linker sequence between the linker domain and the at least one of the one or more target antigen-binding domain(s), and/or a linker sequence between the at least one of the one or more target antigen-binding domain(s) and the first domain of the pair of affinity domains.

Embodiment H508. The method of any one of embodiments H473-H505, wherein the first chimeric polypeptide further comprises one or more additional target-binding domains at the N-terminal and/or C-terminal end of the first chimeric polypeptide.

Embodiment H509. The method of embodiment H508, wherein at least one of the one or more additional target-binding domains directly abuts the first domain of the pair of affinity domains in the first chimeric polypeptide.

Embodiment H510. The method of embodiment H508, wherein the first chimeric polypeptide further comprises a linker sequence between the at least one of the one or more additional target-binding domains and the first domain of the pair of affinity domains.

Embodiment H511. The method of embodiment H508, wherein the at least one of the one or more additional target-binding domains directly abuts the first target-binding domain in the first chimeric polypeptide.

Embodiment H512. The method of embodiment H508, wherein the first chimeric polypeptide further comprises a linker sequence between the at least one of the one or more additional target-binding domains and the first target-binding domain.

Embodiment H513. The method of embodiment H508, wherein at least one of the one or more additional target-binding domains is disposed at the N- and/or C-terminus of the first chimeric polypeptide, and at least one of the one or more additional target-binding domains is positioned between the linker domain and the first domain of the pair of affinity domains in the first chimeric polypeptide.

Embodiment H514. The method of embodiment H513, wherein the at least one additional target-binding domain of the one or more additional target-binding domains disposed at the N-terminus directly abuts the first target-binding domain or the first domain of the pair of affinity domains in the first chimeric polypeptide.

Embodiment H515. The method of embodiment H513, wherein the first chimeric polypeptide further comprises a linker sequence disposed between the at least one additional target-binding domain and the first target-binding domain or the first domain of the pair of affinity domains in the first chimeric polypeptide.

Embodiment H516. The method of embodiment H513, wherein the at least one additional target-binding domain of the one or more additional target-binding domains disposed at the C-terminus directly abuts the first target-binding domain or the first domain of the pair of affinity domains in the first chimeric polypeptide.

Embodiment H517. The method of embodiment H513, wherein the first chimeric polypeptide further comprises a linker sequence disposed between the at least one additional target-binding domain and the first target-binding domain or the first domain of the pair of affinity domains in the first chimeric polypeptide.

Embodiment H518. The method of embodiment H513, wherein the at least one of the one or more additional target-binding domains positioned between the linker domain and the first domain of the pair of affinity domains, directly abuts the linker domain and/or the first domain of the pair of affinity domains.

Embodiment H519. The method of embodiment H513, wherein the first chimeric polypeptide further comprises a linker sequence disposed (i) between the linker domain and the at least one of the one or more additional target-binding domains positioned between the linker domain and the first domain of the pair of affinity domains, and/or (ii) between the first domain of the pair of affinity domains and the at least one of the one or more additional target-binding domains positioned between the linker domain and the first domain of the pair of affinity domains.

Embodiment H520. The method of any one of embodiments H473-H519, wherein the second chimeric polypeptide further comprises one or more additional target-binding domains at the N-terminal end and/or the C-terminal end of the second chimeric polypeptide.

Embodiment H521. The method of embodiment H520, wherein at least one of the one or more additional target-binding domains directly abuts the second domain of the pair of affinity domains in the second chimeric polypeptide.

Embodiment H522. The method of embodiment H520, wherein the second chimeric polypeptide further comprises a linker sequence between at least one of the one or more additional target-binding domains and the second domain of the pair of affinity domains in the second chimeric polypeptide.

Embodiment H523. The method of embodiment H520, wherein at least one of the one or more additional target-binding domains directly abuts the second target-binding domain in the second chimeric polypeptide.

Embodiment H524. The method of embodiment H520, wherein the second chimeric polypeptide further comprises a linker sequence between at least one of the one or more additional target-binding domains and the second target-binding domain in the second chimeric polypeptide.

Embodiment H525. The method of any one of embodiments H506-H524, wherein two or more of the first target-binding domain, the second target-binding domain, and the one or more additional target-binding domains bind specifically to the same antigen.

Embodiment H526. The method of embodiment H525, wherein two or more of the first target-binding domain, the second target-binding domain, and the one or more additional target-binding domains bind specifically to the same epitope.

Embodiment H527. The method of embodiment H526, wherein two or more of the first target-binding domain, the second target-binding domain, and the one or more additional target-binding domains comprise the same amino acid sequence.

Embodiment H528. The method of embodiment H525, wherein the first target-binding domain, the second target-binding domain, and the one or more additional target-binding domains each bind specifically to the same antigen.

Embodiment H529. The method of embodiment H528, wherein the first target-binding domain, the second target-binding domain, and the one or more additional target-binding domains each bind specifically to the same epitope.

Embodiment H530. The method of embodiment H529, wherein the first target-binding domain, the second target-binding domain, and the one or more additional target-binding domains each comprise the same amino acid sequence.

Embodiment H531. The method of any one of embodiments H506-H524, wherein the first target-binding domain, the second target-binding domain, and the one or more additional target-binding domains bind specifically to different antigens.

Embodiment H532. The method of any one of embodiments H506-H531, wherein one or more of the first target-binding domain, the second target-binding domain, and the one or more target-binding domains is an antigen-binding domain.

Embodiment H533. The method of embodiment H532, wherein the first target-binding domain, the second target-binding domain, and the one or more additional target-binding domains are each an antigen-binding domain.

Embodiment H534. The method of embodiment H532 or H533, wherein the antigen-binding domain comprises a scFv.

Embodiment H535. The method of any one of embodiments H506-H534, wherein one or more of the first target-binding domain, the second target-binding domain, and the one or more target-binding domains bind specifically to a target selected from the group consisting of: CD16a, CD28, CD3, CD33, CD20, CD19, CD22, CD123, IL-1R, IL-1, VEGF, IL-6R, IL-4, IL-10, PDL-1, TIGIT, PD-1, TIM3, CTLA4, MICA, MICB, IL-6, IL-8, TNFα, CD26a, CD36, ULBP2, CD30, CD200, CD80, CD86, PD-L2, B7-H4, HVEM, ILT3, ILT4, TIGIT, MHCII, LAG3, CD272, VISTA, CD137, CD40, CD47, CD70, OX40, IGF-1R, MUC4AC, MUC5AC, Trop-2, CMET, EGFR, HER1, HER2, HER3, PSMA, CEA, B7H3, EPCAM, BCMA, P-cadherin, CEACAM5, a UL16-binding protein, HLA-DR, DLL4, TYRO3, AXL, MER, CD122, CD155, PDGF-DD, a ligand of TGF-β receptor II (TGF-β RII), a ligand of TGF-β RIII, a ligand of DNAM-1, a ligand of NKp46, a ligand of NKp44, a ligand of NKG2D, a ligand of NKp30, a ligand for a scMHCI, a ligand for a scMHCII, a ligand for a scTCR, a receptor for IL-1, a receptor for IL-2, a receptor for IL-3, a receptor for IL-7, a receptor for IL-8, a receptor for IL-10, a receptor for IL-12, a receptor for IL-15, a receptor for IL-17, a receptor for IL-18, a receptor for IL-21, a receptor for PDGF-DD, a receptor for stem cell factor (SCF), a receptor for stem cell-like tyrosine kinase 3 ligand (FLT3L), a receptor for MICA, a receptor for MICB, a receptor for a ULP16-binding protein, a receptor for CD155, a receptor for CD122, and a receptor for CD3, and a receptor for CD28.

Embodiment H536. The method of any one of embodiments H506-H534, wherein one or more of the first target-binding domain, the second target-binding domain, and the one or more additional target-binding domains is a soluble interleukin, soluble cytokine protein, or soluble cell surface protein.

Embodiment H537. The method of embodiment H536, wherein the soluble interleukin, soluble cytokine protein, or soluble cell surface protein is selected from the group consisting of: IL-1, IL-2, IL-3, IL-7, IL-8, IL-10, IL-12, IL-15, IL-17, IL-18, IL-21, PDGF-DD, SCF, FLT3L, MICA, MICB, and a ULP16-binding protein.

Embodiment H538. The method of any one of embodiments H506-H534, wherein one or more of the first target-binding domain, the second target-binding domain, and the one or more additional target-binding domains is a soluble interleukin or cytokine receptor.

Embodiment H539. The method of embodiment H538, wherein the soluble receptor is a soluble TGF-β receptor II (TGF-β RII), a soluble TGF-β RIII, a soluble NKG2D, a soluble NKp30, a soluble NKp44, a soluble NKp46, a soluble DNAM-1, a scMHCI, a scMHCII, a scTCR, a soluble CD155, a soluble CD122, a soluble CD3, or a soluble CD28.

Embodiment H540. The method of any one of embodiments H473-H539, wherein the first chimeric polypeptide further comprises a peptide tag at the N-terminal end or the C-terminal end of the first chimeric polypeptide.

Embodiment H541. The method of any one of embodiments H473-H539, wherein the second chimeric polypeptide further comprises a peptide tag at the N-terminal end or the C-terminal end of the second chimeric polypeptide.

Embodiment H542. The method of any one of embodiments H473-H541, wherein the linker domain is a soluble tissue factor domain.

Embodiment H543. The method of embodiment H542, wherein the soluble tissue factor domain is a soluble human tissue factor domain.

Embodiment H544. The method of embodiment H543, wherein the soluble human tissue factor domain comprises a sequence that is at least 80% identical to SEQ ID NO: 1.

Embodiment H545. The method of embodiment H544, wherein the soluble human tissue factor domain comprises a sequence that is at least 90% identical to SEQ ID NO: 1.

Embodiment H546. The method of embodiment H545, wherein the soluble human tissue factor domain comprises a sequence that is at least 95% identical to SEQ ID NO: 1.

Embodiment H547. The method of any one of embodiments H543-H546, wherein the soluble human tissue factor domain does not comprise one or more of:

- a lysine at an amino acid position that corresponds to amino acid position 20 of mature wildtype human tissue factor protein;
- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;
- a tyrosine at an amino acid position that corresponds to amino acid position 94 of mature wildtype human tissue factor protein;
- an arginine at an amino acid position that corresponds to amino acid position 135 of mature wildtype human tissue factor protein; and
- a phenylalanine at an amino acid position that corresponds to amino acid position 140 of mature wildtype human tissue factor protein.

Embodiment H548. The method of embodiment H547, wherein the soluble human tissue factor domain does not comprise any of: a lysine at an amino acid position that corresponds to amino acid position 20 of mature wildtype human tissue factor protein;

- an isoleucine at an amino acid position that corresponds to amino acid position 22 of mature wildtype human tissue factor protein;
- a tryptophan at an amino acid position that corresponds to amino acid position 45 of mature wildtype human tissue factor protein;
- an aspartic acid at an amino acid position that corresponds to amino acid position 58 of mature wildtype human tissue factor protein;
- a tyrosine at an amino acid position that corresponds to amino acid position 94 of mature wildtype human tissue factor protein;
- an arginine at an amino acid position that corresponds to amino acid position 135 of mature wildtype human tissue factor protein; and
- a phenylalanine at an amino acid position that corresponds to amino acid position 140 of mature wildtype human tissue factor protein.

Embodiment H549. The method of any one of embodiments H542-H548, wherein the soluble tissue factor domain is not capable of binding to Factor VIIa.

Embodiment H550. The method of any one of embodiments H542-H549, wherein the soluble tissue factor domain does not convert inactive Factor X into Factor Xa.

Embodiment H551. The method of any one of embodiments H542-H550, wherein the multi-chain chimeric polypeptide does not stimulate blood coagulation in a mammal.

Embodiment H552. The method of any one of embodiments H542-H551, wherein the IgG1 antibody construct comprises at least one antigen-binding domain that binds specifically to the soluble tissue factor domain.

Embodiment H553. The method of any one of embodiments H473-H541, wherein the linker domain is selected from the group consisting of: a kappa chain and a lambda chain.

Embodiment H554. The method of any one of embodiments H473-H553, wherein the IgG1 antibody construct is a monoclonal IgG1 antibody, where both antigen-binding domains in the monoclonal IgG1 antibody bind specifically to the linker domain.

Embodiment H555. The method of any one of embodiments H473-H553, wherein the IgG1 antibody construct is a bispecific IgG1 antibody, where one of the two antigen-binding domains in the bispecific IgG1 antibody binds specifically to the linker domain.

Embodiment H556. The method of any one of embodiments H473-H555, wherein the pair of affinity domains is a sushi domain from an alpha chain of human IL-15 receptor (IL15Rα) and a soluble IL-15.

Embodiment H557. The method of embodiment H556, wherein the soluble IL15 has a D8N or D8A amino acid substitution.

Embodiment H558. The method of embodiment H556 or H557, wherein the human IL15Rα is a mature full-length IL15Rα.

Embodiment H559. The method of any one of embodiments H473-H555, wherein the pair of affinity domains is selected from the group consisting of: barnase and barnstar, a PKA and an AKAP, adapter/docking tag modules based on mutated RNase I fragments, and SNARE modules based on interactions of the proteins syntaxin, synaptotagmin, synaptobrevin, and SNAP25.

Embodiment H560. The method of any one of embodiments H473-H559, wherein the first chimeric polypeptide and/or the second chimeric polypeptide further comprises a signal sequence at its N-terminal end.

Embodiment H561. The method of any one of embodiments H473-H559, wherein the first chimeric polypeptide and/or the second chimeric polypeptide lacks a signal sequence at its N-terminal end.

Embodiment H562. The method of any one of embodiments H473-H561, wherein the immune cell was previously obtained from a subject.

Embodiment H563. The method of embodiment H562, wherein the method further comprises obtaining the immune cell from the subject prior to the contacting step.

Embodiment H564. The method of any one of embodiments H473-H563, wherein the immune cell has previously been genetically modified to express a chimeric antigen receptor or a recombinant T-cell receptor.

Embodiment H565. The method of any one of embodiments H473-H563, wherein the method further comprises, after the contacting step, introducing into the immune cell a nucleic acid encoding a chimeric antigen-receptor or a recombinant T-cell receptor.

Embodiment H566. The method of any one of embodiments H473-H563, wherein the method further comprises, before the contacting step, introducing into the immune cell a nucleic acid encoding a chimeric antigen-receptor or a recombinant T-cell receptor.

Embodiment H567. The method of any one of embodiments H473-H566, wherein the method further comprises, after the contacting step, isolating the immune cell.

Embodiment H568. The method of any one of embodiments H473-H567, wherein after the contacting step, the immune cell has an increased level of expression or secretion of one or more proteins selected from the group consisting of: TNF-α, IFN-γ, granzyme A, granzyme B, perforin, 2B4, CD8, CD11a, CD16, CD25, CD27, CD48, CD49d, CD54, CD56, CD58, CD62L, CD69, CD70, CD94, CD137, CD158a, CD158b, CD158e, CD178, CD226, CD253, NKG2A, NKG2C, NKG2D, LIR-1, LILR-B1, KIR2DL1, KIR3DL1, KIR2DL2, KIR2DL3, CXCR3, NKp30, NKp44, NKp46, NKG2D, DNAM-1, NKG2A, TRAIL, FasL, CXCR3, CXCR4, LTB, MX1, BAX, TNF-α, and IFN-γ as compared to the level of expression or secretion of the one or more proteins prior to the contacting step.

Embodiment H569. The method of any one of embodiments H473-H568, wherein the method further comprises, after the contacting step, administering the immune cell to a subject in need thereof.

Embodiment H570. The method of embodiment H569, wherein the subject has been identified or diagnosed as having an age-related disease or condition.

Embodiment H571. The method of embodiment H570, wherein the age-related disease or condition is selected from the group consisting of: Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H572. The method of embodiment H569, wherein the subject has been identified or diagnosed as having a cancer.

Embodiment H573. The method of embodiment H572, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H574. The method of embodiment H569, wherein the subject has been diagnosed or identified as having an infectious disease.

Embodiment H575. The method of embodiment H574, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

Embodiment H576. An activated immune cell produced by the method of any one of embodiments H473-H568.

Embodiment H577. A pharmaceutical composition comprising the activated cell of embodiment H576.

Embodiment H578. A kit comprising a pharmaceutical composition comprising the activated immune cell of embodiment H261.

Embodiment H579. A method of killing a cancer cell, an infected cell, or a senescent cell in a subject in need thereof, the method comprising administering to the subject a therapeutically effective amount of the activated immune cell of embodiment H576 or the pharmaceutical composition of embodiment H577.

Embodiment H580. The method of embodiment H579, wherein the subject has been identified or diagnosed as having a cancer.

Embodiment H581. The method of embodiment H580, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CMIL), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H582. The method of embodiment H579, wherein the subject has been identified or diagnosed as having an aging-related disease or condition.

Embodiment H583. The method of embodiment H582, wherein the aging-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction Embodiment H584. A method of treating a subject in need thereof, the method comprising administering to the subject a therapeutically effective amount of the activated immune cell of embodiment H576 or the pharmaceutical composition of embodiment H577.

Embodiment H585. The method of embodiment H584, wherein the subject has been identified or diagnosed as having a cancer.

Embodiment H586. The method of embodiment H585, wherein the cancer is selected from the group consisting of: solid tumor, hematological tumor, sarcoma, osteosarcoma, glioblastoma, neuroblastoma, melanoma, rhabdomyosarcoma, Ewing sarcoma, osteosarcoma, B-cell neoplasms, multiple myeloma, B-cell lymphoma, B-cell non-Hodgkin's lymphoma, Hodgkin's lymphoma, chronic lymphocytic leukemia (CLL), acute myeloid leukemia (AML), chronic myeloid leukemia (CML), acute lymphocytic leukemia (ALL), myelodysplastic syndromes (MDS), cutaneous T-cell lymphoma, retinoblastoma, stomach cancer, urothelial carcinoma, lung cancer, renal cell carcinoma, gastric and esophageal cancer, pancreatic cancer, prostate cancer, breast cancer, colorectal cancer, ovarian cancer, non-small cell lung carcinoma, squamous cell head and neck carcinoma, endometrial cancer, cervical cancer, liver cancer, and hepatocellular carcinoma.

Embodiment H587. The method of embodiment H584, wherein the subject has been identified or diagnosed as having an aging-related disease or condition.

Embodiment H588. The method of embodiment H587, wherein the aging-related disease or condition is selected from the group consisting of. Alzheimer's disease, aneurysm, cystic fibrosis, fibrosis in pancreatitis, glaucoma, hypertension, idiopathic pulmonary fibrosis, inflammatory bowel disease, intervertebral disc degeneration, macular degeneration, osteoarthritis, type 2 diabetes mellitus, adipose atrophy, lipodystrophy, atherosclerosis, cataracts, COPD, idiopathic pulmonary fibrosis, kidney transplant failure, liver fibrosis, loss of bone mass, myocardial infarction, sarcopenia, wound healing, alopecia, cardiomyocyte hypertrophy, osteoarthritis, Parkinson's disease, age-associated loss of lung tissue elasticity, macular degeneration, cachexia, glomerulosclerosis, liver cirrhosis, NAFLD, osteoporosis, amyotrophic lateral sclerosis, Huntington's disease, spinocerebellar ataxia, multiple sclerosis, and renal dysfunction.

Embodiment H589. The method of embodiment H584, wherein the subject has been diagnosed or identified as having an infectious disease.

Embodiment H590. The method of embodiment H589, wherein the infectious disease is infection with human immunodeficiency virus, cytomegalovirus, adenovirus, coronavirus, rhinovirus, rotavirus, smallpox, herpes simplex virus, hepatitis B virus, hepatitis A virus, and hepatitis C virus, papillomavirus, and influenza virus.

What is claimed is:

1. A method of activating or inducing differentiation or expansion of a memory T cell, the method comprising contacting a memory T cell with a liquid culture medium comprising:

(1) an effective amount of a multi-chain chimeric polypeptide comprising:

(a) a first chimeric polypeptide comprising:

(i) a first target-binding domain;

(ii) a soluble tissue factor domain comprising a sequence that is at least 90% identical to SEQ ID NO: 1; and (iii) a first domain of a pair of affinity domains comprising a sequence that is at least 90% identical to SEQ ID NO: 39;

(b) a second chimeric polypeptide comprising:

(i) a second domain of the pair of affinity domains comprising a sequence that is at least 90% identical to SEQ ID NO: 10; and (ii) a second target-binding domain, wherein the first chimeric polypeptide and the second chimeric polypeptide associate through the binding of the first domain and the second domain of the pair of affinity domains; and wherein:

(A) the first target-binding domain comprises a sequence that is at least 90% identical to SEQ ID NO: 135 and the second target-binding domain comprises a sequence that is at least 90% identical to SEQ ID NO: 124;

(B) the first target-binding domain comprises a sequence that is at least 90% identical to SEQ ID NO: 124 and the second target-binding domain comprises a sequence that is at least 90% identical to SEQ ID NO: 135;

(C) the first target-binding domain comprises a sequence that is at least 90% identical to SEQ ID NO: 124 and the second target-binding domain comprises a sequence that is at least 90% identical to SEQ ID NO: 60; or (D) the first target-binding domain comprises a sequence that is at least 90% identical to SEQ ID NO: 60 and the second target-binding domain comprises a sequence that is at least 90% identical to SEQ ID NO: 60; and (2) an effective amount of an IgG1 antibody construct comprising at least one antigen-binding domain that binds specifically to the soluble tissue factor domain.

2. The method of claim 1, wherein the immune cell was previously obtained from a subject.

3. The method of claim 1, wherein the memory T cell is a peripheral blood memory T cell selected from the group consisting of: a Th17 cell, a Th22 cell, a Th9 cell, a Th2 cell, a Th1 cell, a Th3 cell, a λδ T cell, an Iϑ T cell, a tumor-infiltrating T cell, an effector T cell, a $CD8^+$ T cell, and a $CD4^+$ T cell.

4. The method of claim 1, wherein the memory T cell has previously been genetically modified to express a chimeric antigen receptor or a recombinant T cell receptor.

5. The method of claim 1, wherein the method further comprises, after the contacting step, introducing into the memory T cell a nucleic acid encoding a chimeric antigen receptor or a recombinant T cell receptor.

6. The method of claim 1, wherein the first target-binding domain and the soluble tissue factor domain directly abut each other in the first chimeric polypeptide.

7. The method of claim 1, wherein the first chimeric polypeptide further comprises a linker sequence between the first target-binding domain and the soluble tissue factor domain in the first chimeric polypeptide.

8. The method of claim 1, wherein the soluble tissue factor domain and the first domain of the pair of affinity domains directly abut each other in the first chimeric polypeptide.

9. The method of claim 1, wherein the first chimeric polypeptide further comprises a linker sequence between the soluble tissue factor domain and the first domain of the pair of affinity domains in the first chimeric polypeptide.

10. The method of claim 1, wherein the second domain of the pair of affinity domains and the second target-binding domain directly abut each other in the second chimeric polypeptide.

11. The method of claim 1, wherein the second chimeric polypeptide further comprises a linker sequence between the second domain of the pair of affinity domains and the second target-binding domain in the second chimeric polypeptide.

12. The method of claim 1, wherein the soluble tissue factor domain is a soluble human tissue factor domain.

13. The method of claim 1, wherein the soluble tissue factor domain does not stimulate blood coagulation.

14. The method of claim 1, wherein the multi-chain chimeric polypeptide does not stimulate blood coagulation.

15. The method of claim 1, wherein the contacting step is performed for a period of about 2 hours to about 20 days.

16. The method of claim 1, wherein the liquid culture medium comprises the multi-chain chimeric polypeptide and the IgG1 antibody construct at a molar ratio of about 0.5:1 to about 2:1.

17. The method of claim 1, wherein:

the first target-binding domain comprises a sequence that is at least 90% identical to SEQ ID NO: 135;

the soluble tissue factor domain comprises a sequence that is at least 90% identical to SEQ ID NO: 1;

the first domain of the pair of affinity domains comprises a sequence that is at least 90% identical to SEQ ID NO: 39;

the second domain of the pair of affinity domains comprises a sequence that is at least 90% identical to SEQ ID NO: 10; and the second target-binding domain comprises a sequence that is at least 90% identical to SEQ ID NO: 124.

18. The method of claim 1, wherein:

the first target-binding domain comprises a sequence that is at least 95% identical to SEQ ID NO: 135;

the soluble tissue factor domain comprises a sequence that is at least 95% identical to SEQ ID NO: 1;

the first domain of the pair of affinity domains comprises a sequence that is at least 95% identical to SEQ ID NO: 39;

the second domain of the pair of affinity domains comprises a sequence that is at least 95% identical to SEQ ID NO: 10; and the second target-binding domain comprises a sequence that is at least 95% identical to SEQ ID NO: 124.

19. The method of claim 1, wherein:

the first target-binding domain comprises SEQ ID NO: 135;

the soluble tissue factor domain comprises SEQ ID NO: 1;

the first domain of the pair of affinity domains comprises SEQ ID NO: 39;

the second domain of the pair of affinity domains comprises SEQ ID NO: 10; and the second target-binding domain comprises SEQ ID NO: 124.

20. The method of claim 1, wherein:
the first chimeric polypeptide comprises a sequence at least 90% identical to SEQ ID NO: 141; and
the second chimeric polypeptide comprises a sequence at least 90% identical to SEQ ID NO: 145.

21. The method of claim 1, wherein:
the first chimeric polypeptide comprises a sequence at least 95% identical to SEQ ID NO: 141; and
the second chimeric polypeptide comprises a sequence at least 95% identical to SEQ ID NO: 145.

22. The method of claim 1, wherein:
the first chimeric polypeptide comprises SEQ ID NO: 141; and
the second chimeric polypeptide comprises SEQ ID NO: 145.

23. The method of claim 1, wherein:
the first target-binding domain comprises a sequence that is at least 90% identical to SEQ ID NO: 124;
the soluble tissue factor domain comprises a sequence that is at least 90% identical to SEQ ID NO: 1;
the first domain of the pair of affinity domains comprises a sequence that is at least 90% identical to SEQ ID NO: 39;
the second domain of the pair of affinity domains comprises a sequence that is at least 90% identical to SEQ ID NO: 10; and
the second target-binding domain comprises a sequence that is at least 90% identical to SEQ ID NO: 135.

24. The method of claim 1, wherein:
the first target-binding domain comprises a sequence that is at least 95% identical to SEQ ID NO: 124;
the soluble tissue factor domain comprises a sequence that is at least 95% identical to SEQ ID NO: 1;
the first domain of the pair of affinity domains comprises a sequence that is at least 95% identical to SEQ ID NO: 39;
the second domain of the pair of affinity domains comprises a sequence that is at least 95% identical to SEQ ID NO: 10; and
the second target-binding domain comprises a sequence that is at least 95% identical to SEQ ID NO: 135.

25. The method of claim 1, wherein:
the first target-binding domain comprises SEQ ID NO: 124;
the soluble tissue factor domain comprises SEQ ID NO: 1;
the first domain of the pair of affinity domains comprises SEQ ID NO: 39;
the second domain of the pair of affinity domains comprises SEQ ID NO: 10; and
the second target-binding domain comprises SEQ ID NO: 135.

26. The method of claim 1, wherein:
the first chimeric polypeptide comprises a sequence that is at least 90% identical to SEQ ID NO: 126; and
the second chimeric polypeptide comprises a sequence that is at least 90% identical to SEQ ID NO: 137.

27. The method of claim 1, wherein:
the first chimeric polypeptide comprises a sequence that is at least 95% identical to SEQ ID NO: 126; and
the second chimeric polypeptide comprises a sequence that is at least 95% identical to SEQ ID NO: 137.

28. The method of claim 1, wherein:
the first chimeric polypeptide comprises SEQ ID NO: 126; and
the second chimeric polypeptide comprises SEQ ID NO: 137.

29. The method of claim 1, wherein:
the first target-binding domain comprises a sequence that is at least 90% identical to SEQ ID NO: 124;
the soluble tissue factor domain comprises a sequence that is at least 90% identical to SEQ ID NO: 1;
the first domain of the pair of affinity domains comprises a sequence that is at least 90% identical to SEQ ID NO: 39;
the second domain of the pair of affinity domains comprises a sequence that is at least 90% identical to SEQ ID NO: 10; and
the second target-binding domain comprises a sequence that is at least 90% identical to SEQ ID NO: 60.

30. The method of claim 1, wherein:
the first target-binding domain comprises a sequence that is at least 95% identical to SEQ ID NO: 124;
the soluble tissue factor domain comprises a sequence that is at least 95% identical to SEQ ID NO: 1;
the first domain of the pair of affinity domains comprises a sequence that is at least 95% identical to SEQ ID NO: 39;
the second domain of the pair of affinity domains comprises a sequence that is at least 95% identical to SEQ ID NO: 10; and
the second target-binding domain comprises a sequence that is at least 95% identical to SEQ ID NO: 60.

31. The method of claim 1, wherein:
the first target-binding domain comprises SEQ ID NO: 124;
the soluble tissue factor domain comprises SEQ ID NO: 1;
the first domain of the pair of affinity domains comprises SEQ ID NO: 39;
the second domain of the pair of affinity domains comprises SEQ ID NO: 10; and
the second target-binding domain comprises SEQ ID NO: 60.

32. The method of claim 1, wherein:
the first chimeric polypeptide comprises a sequence that is at least 90% identical to SEQ ID NO: 126; and
the second chimeric polypeptide comprises a sequence that is at least 90% identical to SEQ ID NO: 132.

33. The method of claim 1, wherein:
the first chimeric polypeptide comprises a sequence that is at least 95% identical to SEQ ID NO: 126; and
the second chimeric polypeptide comprises a sequence that is at least 95% identical to SEQ ID NO: 132.

34. The method of claim 1, wherein:
the first chimeric polypeptide comprises SEQ ID NO: 126; and
the second chimeric polypeptide comprises SEQ ID NO: 132.

35. The method of claim 1, wherein:
the first target-binding domain comprises a sequence that is at least 90% identical to SEQ ID NO: 60;
the soluble tissue factor domain comprises a sequence that is at least 90% identical to SEQ ID NO: 1;
the first domain of the pair of affinity domains comprises a sequence that is at least 90% identical to SEQ ID NO: 39;
the second domain of the pair of affinity domains comprises a sequence that is at least 90% identical to SEQ ID NO: 10; and
the second target-binding domain comprises a sequence that is at least 90% identical to SEQ ID NO: 60.

36. The method of claim 1, wherein:

the first target-binding domain comprises a sequence that is at least 95% identical to SEQ ID NO: 160;

the soluble tissue factor domain comprises a sequence that is at least 95% identical to SEQ ID NO: 1;

the first domain of the pair of affinity domains comprises a sequence that is at least 95% identical to SEQ ID NO: 39;

the second domain of the pair of affinity domains comprises a sequence that is at least 95% identical to SEQ ID NO: 10; and the second target-binding domain comprises a sequence that is at least 95% identical to SEQ ID NO: 60.

37. The method of claim 1, wherein:

the first target-binding domain comprises SEQ ID NO: 60;

the soluble tissue factor domain comprises SEQ ID NO: 1;

the first domain of the pair of affinity domains comprises SEQ ID NO: 39;

the second domain of the pair of affinity domains comprises SEQ ID NO: 10; and the second target-binding domain comprises SEQ ID NO: 60.

38. The method of claim 1, wherein:

the first chimeric polypeptide comprises a sequence that is at least 90% identical to SEQ ID NO: 161; and the second chimeric polypeptide comprises a sequence that is at least 90% identical to SEQ ID NO: 130.

39. The method of claim 1, wherein:

the first chimeric polypeptide comprises a sequence that is at least 95% identical to SEQ ID NO: 161; and the second chimeric polypeptide comprises a sequence that is at least 95% identical to SEQ ID NO: 130.

40. The method of claim 1, wherein:

the first chimeric polypeptide comprises SEQ ID NO: 161; and the second chimeric polypeptide comprises SEQ ID NO: 130.

* * * * *